(12) United States Patent
Giese et al.

(10) Patent No.: US 11,208,400 B2
(45) Date of Patent: Dec. 28, 2021

(54) SUBSTITUTED 6-(1H-PYRAZOL-1-YL)PYRIMIDIN-4-AMINE DERIVATIVES AND USES THEREOF

(71) Applicants: Bayer Aktiengesellschaft, Leverkusen (DE); Bayer Pharma Aktiengesellschaft, Berlin (DE)

(72) Inventors: Anja Giese, Berlin (DE); Jürgen Klar, Wuppertal (DE); Alexander Helmut Michael Ehrmann, Cambridge, MA (US); Jens Willwacher, Biberach an der Riß (DE); David Engel, Wuppertal (DE); Andre Philippe Dieskau, Wuppertal (DE); Antje Kahnert, Wuppertal (DE); Alexey Gromov, Erkrath (DE); Carsten Schmeck, Mülheim (DE); Niels Lindner, Wuppertal (DE); Thomas Müller, Langenfeld (DE); Anna Lena Andreevski, Solingen (DE); Jan Dreher, Wuppertal (DE); Karl Collins, Düsseldorf (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/341,410

(22) PCT Filed: Oct. 9, 2017

(86) PCT No.: PCT/EP2017/075630
§ 371 (c)(1),
(2) Date: Apr. 11, 2019

(87) PCT Pub. No.: WO2018/069222
PCT Pub. Date: Apr. 19, 2018

(65) Prior Publication Data
US 2020/0055842 A1    Feb. 20, 2020

(30) Foreign Application Priority Data
Oct. 14, 2016   (EP) .................................... 16193953

(51) Int. Cl.
| | | |
|---|---|---|
| *C07D 403/14* | (2006.01) | |
| *C07D 401/14* | (2006.01) | |
| *C07D 405/14* | (2006.01) | |
| *C07D 413/14* | (2006.01) | |
| *C07D 487/04* | (2006.01) | |

(52) U.S. Cl.
CPC ......... *C07D 403/14* (2013.01); *C07D 401/14* (2013.01); *C07D 405/14* (2013.01); *C07D 413/14* (2013.01); *C07D 487/04* (2013.01)

(58) Field of Classification Search
CPC .. C07D 403/14; C07D 471/04; C07D 487/04; C07D 413/14; A61K 31/506; A61K 31/5377
See application file for complete search history.

(56) References Cited

U.S. PATENT DOCUMENTS

| | | | |
|---|---|---|---|
| 6,355,823 B1 | 3/2002 | Peerce | |
| 6,693,102 B2 | 2/2004 | Stasch | |
| 7,705,043 B2 | 4/2010 | Alonso-alija | |
| 7,781,470 B2 | 8/2010 | Alonso-alija | |
| 8,580,778 B2 | 11/2013 | Jeske | |
| 8,796,324 B2 | 8/2014 | Bruggemeier | |
| 9,096,592 B2 | 8/2015 | Follmann | |
| 9,163,017 B2 | 10/2015 | Degoey | |
| 9,216,978 B2 | 12/2015 | Follmann | |
| 9,687,476 B2 | 6/2017 | Fürstner | |
| 9,993,476 B2 | 6/2018 | Follmann | |
| 2004/0176446 A1 | 9/2004 | Alonso-Alija et al. | |
| 2009/0269420 A1 | 10/2009 | Jeske | |
| 2013/0267548 A1 | 10/2013 | Follmann | |

FOREIGN PATENT DOCUMENTS

| | | |
|---|---|---|
| DE | 10200802011 A1 | 10/2009 |
| EP | 1465638 B1 | 5/2007 |
| EP | 1815860 B1 | 4/2010 |
| EP | 1841760 B1 | 8/2011 |
| MX | 2010010324 A | 11/2010 |
| WO | WO0006568 A1 | 2/2000 |
| WO | WO0006569 A1 | 2/2000 |
| WO | WO0119355 A2 | 3/2001 |

(Continued)

OTHER PUBLICATIONS

Isakova, T. et al. (2011) "Fibroblast Growth Factor 23 and Risks of Mortality and End-Stage Renal Disease in Patients with Chronic Kidney Disease," JAMA 305(23): 2432-2439.

(Continued)

*Primary Examiner* — Deepak R Rao
(74) *Attorney, Agent, or Firm* — Morrison & Foerster LLP

(57) ABSTRACT

The present invention covers substituted 6-(1H-pyrazol-1-yl)pyrimidin-4-amine compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular for the treatment and/or prophylaxis of cardiovascular and renal diseases, as a sole agent or in combination with other active ingredients.

17 Claims, No Drawings

(56) References Cited

FOREIGN PATENT DOCUMENTS

| | | |
|---|---|---|
| WO | WO0119776 A2 | 3/2001 |
| WO | WO0119778 A1 | 3/2001 |
| WO | WO0119780 A2 | 3/2001 |
| WO | WO0242301 A1 | 5/2002 |
| WO | WO02070462 A1 | 9/2002 |
| WO | WO02070510 A2 | 9/2002 |
| WO | WO03095451 A1 | 11/2003 |
| WO | WO2010105770 A1 | 9/2010 |
| WO | WO2011104322 A1 | 9/2011 |
| WO | WO2011147809 A1 | 12/2011 |
| WO | WO2012003405 A1 | 1/2012 |
| WO | WO2012006473 A1 | 1/2012 |
| WO | WO2012006474 A2 | 1/2012 |
| WO | WO2012006477 A1 | 1/2012 |
| WO | WO2012028647 A1 | 3/2012 |
| WO | WO2012054110 A2 | 4/2012 |
| WO | WO2012059549 A1 | 5/2012 |
| WO | WO2012004258 A9 | 6/2012 |
| WO | WO2013062065 A1 | 5/2013 |
| WO | WO2013082756 A1 | 6/2013 |
| WO | WO2014152716 A1 | 9/2014 |
| WO | WO2014181287 A1 | 11/2014 |
| WO | WO2016057278 A1 | 4/2016 |
| WO | WO2016071212 A1 | 5/2016 |
| WO | WO2016082751 A1 | 6/2016 |
| WO | 2018069490 A1 | 4/2018 |
| WO | 2018069892 A1 | 4/2018 |
| WO | 2018069907 A1 | 4/2018 |

OTHER PUBLICATIONS

Biber, J. et al. (2013). "Phostphate Transporters and Their Function," Annu. Rev. Physiol. 75: 535-550.

Bruno, N.C. et al. (2013). "Design and preparation of new palladium precatalysts for C—C and C—N cross-coupling reactions," Chem. Sci. 4: 916-920.

Evenepoel, P. et al. (2016). "Dietary phosphorus restriction in predialysis chronic kidney disease: time for a cease-fire?," Kidney International 89: 21-23.

Forster, I.C., et al. (2013). "Phosphate transporters of the SLC20 and SLC34 families," Molecular Aspects of Medicine 34: 386-395.

Gattineni, J. et al. (2009). "FGF23 decreases renal NaPi-2a and NaPi-2c expression and induces hypophosphatemia in vivo predominantly via FGF receptor 1," Am J Physiol Renal Physiol 297: F282-F291.

Hassan, J. et al. (2002). "Aryl-Aryl Bond Formation One Century after the Discovery of the Ullmann Reaction," Chem. Rev. 102:1359-1469.

International Search Report dated Nov. 17, 2017 for PCT Application No. PCT/EP2017/075630, filed Oct. 9, 2017, 15 pages.

Neven, E. et al. (2016). "Can Intestinal Phosphate Binding or Inhibition of Hydroxyapatite Growth in the Vascular Wall Halt the Progression of Established Aortic Calcification in Chronic Kidney Disease?," Vascular Calcification 99: 525-534.

Ridge, D.N. et al. (1979). "Potential Antiarthritic Agents. 2. Benzoylacetonitriles and β-Aminocinnamonitriles," Journal of Medicinal Chemistry 22(11): 1385-1389.

Spasovski, G. (2015). "Advances in pharmacotherapy for hyperphosphatemia in renal disease," Expert Opin. Pharmacother. 16(17): 2589-2599.

Tenenhouse, H.S., et al. (2003). "Disorders of Renal Tubular Phosphate Transport," J Am Soc Nephrol 14: 240-247.

Wu, H. et al. (2013). "Assay development of inducible human renal phosphate transporter Npt2A (SLC34A1) in Flp-In-Trex-HEK293 cells," European Journal of Pharmacology 721: 332-340.

Ohnishi, M. et al. (2009). "In Vivo Genetic Evidence for Suppressing Vascular and Soft-Tissue Calcification Through the Reduction of Serum Phosphate Levels, Even in the Presence of High Serum Calcium and 1,25-Dihydroxyvitamin D Levels," Circ Cardiovasc Genet, pp. 583-590, and supplemental material 6 pages.

SUBSTITUTED 6-(1H-PYRAZOL-1-YL)PYRIMIDIN-4-AMINE DERIVATIVES AND USES THEREOF

CROSS REFERENCE TO RELATED APPLICATIONS

This application is a national stage application under 35 U.S.C. § 371 of International Application No. PCT/EP2017/075630, filed internationally on Oct. 9, 2017, which claims the benefit of European Application No. 16193953.3, filed Oct. 14, 2016.

The present invention covers substituted 6-(1H-pyrazol-1-yl)pyrimidin-4-amine compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular for the treatment and/or prophylaxis of cardiovascular and renal diseases, as a sole agent or in combination with other active ingredients.

BACKGROUND

Vascular calcification is one of the major life-threatening complications in patients with chronic kidney disease (CKD) (Neven at al Calcif Tissue Int (2016), 99:525-534). With CKD progression renal function declines, so called uremic toxins are retained and as consequence plasma levels of inorganic phosphate (Pi) and other plasma components are subsequently increased.

This is the origin of hyperphosphatemia which per se has been identified as an independent risk factor being responsible for further rapid decline of kidney function. A large body of evidence directly links hyperphosphatemia with adverse renal and cardiovascular outcomes. In addition patients with CKD are known to develop Pi imbalance and the uprgulation of phosphaturic hormones regulating renal phosphate excretion like FGF23. FGF23 can be detected early on in the plasma of CKD patients. Elevated FGF23 levels are associated with an increased cardiovascular risk in CKD patients (Isakova JAMA 2011). Therefore controlling phosphate metabolism in patients with chronic kidney disease has been a major therapeutic challenge for nephrologists for decades (Evenepoel P. Kidney International 2016, 21-23).

The current treatment of hyperphosphatemia is summarized in the Kidney Disease improving global outcome (KDIGO)-CKD-Mineral and Bone Disorders (MBD) guidelines. The choice of the phosphate binder used is recommended to be individualized for each patient considering the CKD stage, presents or absence of other components of CKD-mineral and bone disorders, concomitant therapies and side-effect profile of each drug. Currently available phosphate binders can be roughly divided in different subclasses. Aluminium hydroxide and calcium based binders (CBB) like calcium acetate and calcium carbonate represent the first generation of phosphate binders. However, their adverse effects like bone and central nervous system toxicity for aluminium hydroxide and hypercalcemia in up to 50% of the patient using CBBs, respectively, limited the use of these types of phosphate binders. Non-calcium based binders (NCBBs) like e.g. sevelamer hydrochloride and sevelamer carbonate, Lanthanum and lanthanum carbonate and magnesium based binders are commonly used to treat hyperphosphatemia. Also combinations of low dose CBBs and NCBBs, new phosphate binding agents like colestilan, iron-containing phosphate binders, inhibitors of the intestinal and renal proximal tubule sodium-phosphate co-transporter like niacin or nicotinamide or other inhibitors like tenapanor (NHE3 inhibitor) are used to treat hyperphosphatemia (Spasovski Expert Opinion 2015, 2589-2599).

Recently, a large body of in vivo and in vitro studies has shown that fibroblast growth factor-23 (FGF23) in addition to calcitriol, calcidiol, parathyroid hormone (PTH) is a key regulator of phosphate homeostasis and therefore might be a good target to address hyperphosphatemia (Gattineni Am J Physiol Renal Physiol 2009, F282-F291).

Although hyperphosphatemia is characterized by high plasma levels of inorganic phosphate (Pi), inorganic phosphate is fundamental to cellular function and skeletal mineralization. Normal Pi intake in the adult human is in the range of 800 to 1600 mg/day. Approximately 65% to 75% of ingested Pi is absorbed in the small intestine, regardless of the level of Pi intake, and hormonal regulation of this process plays only a minor role in normal Pi homeostasis. Most of the absorbed Pi is excreted in the urine. This means that Pi homeostasis and plasma Pi concentration depend primarily on renal mechanisms that regulate tubular Pi transport. (Tenenhouse H. S. Annu. Rev. Nutr. 2005, 240-247)

In general, members of two families of SLC proteins (SLC20 and SLC34) act as $Na^+$-dependent, secondary-active co-transporters to transport Pi across cell membranes. The SLC34 proteins are expressed in specific organs important for Pi homeostasis: NaPi-IIa (SLC34A1) and NaPi-IIc (SLC34A3) fulfill essential roles in Pi reabsorption in the kidney proximal tubule and NaPi-IIb (SLC34A2) mediates Pi absorption in the gut. The SLC20 proteins, PiT-1 (SLC20A1), PiT-2 (SLC20A2) are expressed ubiquitously in all tissues and although generally considered as "housekeeping" transport proteins, the discovery of tissue-specific activity, regulatory pathways and gene-related pathophysiologies, is redefining their importance (Foster et al. Molecular Aspects of Medicine 2013, 386-395)

Npt2a was identified as the most prominent Pi transporter within the kidney and thereby being involved in the regulation of the Pi excretion (Biber et al Annu. Rev. Physiol. 2013, 535-550). Therefore Np2ta inhibitors may have the potential to address cardiovascular (CV)-mortality and CV-morbidity by altering vascular calcification and plasma phosphate levels.

Npt2a inhibitors provide a novel approach to address vascular calcification in patients with chronic kidney disease and/or in patients with arterial hypertension, cardiac hypertrophy, ischemic heart disease, peripheral arterial disease and retinopathy.

Compounds that are inhibitors of the intestinal sodium-dependent phosphate transport Npt2b are described in WO2012/006473, in WO2012/006474, in WO2012/006477, in WO2012/054110, in WO2013/062065, in EP1465638, in EP1815860, in U.S. Pat. No. 6,355,823, in WO2016/082751 and in WO2013/082756.

Substituted Pyrimidines are disclosed e.g. in U.S. Pat. No. 9,163,017 B2 for the treatment of Hepatitis C, in WO2014152716 A1 for the treatment and prevention of viral infections, in EP1841760B1 as kinase modulators for the treatment of cancer and in WO2014181287A1 to treat inflammatory diseases, autoimmune disorders and other related disorders.

However, the state of the art does not describe the 6-(1H-pyrazol-1-yl)pyrimidin-4-amine compounds of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively reduce plasma phosphate levels and increase urinary Pi excretion due to their Npt2a inhibition potential. Moreover the compounds of the present invention have surprisingly been found to effectively inhibit vascular calcification and to reduce FGF-23 and parathyroid hormone levels significantly by inhibiting Npt2a and may therefore be used for the treatment or prophylaxis of diseases and/or conditions associated with hyperphosphatemia, patients with disbalanced phosphate homeostasis, elevated plasma FGF23 levels, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

DESCRIPTION OF THE INVENTION

The invention provides compounds of the formula

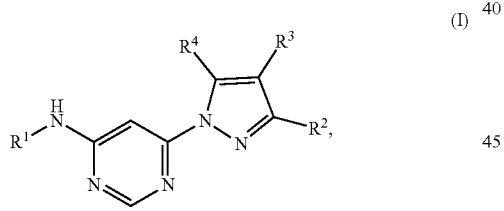

(I)

in which
$R^1$ represents a group of the formula

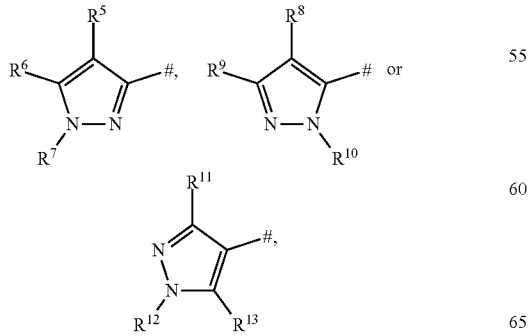

in which
# represents the point of attachment to the amino group,
$R^5$ represents a group selected from a halogen atom, cyano, $(C_1-C_4)$-alkyl, $(C_1-C_4)$-alkoxy, $(C_3-C_6)$-cycloalkyl, 4- to 6-membered heterocycle and $(C_1-C_4)$-alkylcarbonyl,
  wherein said $(C_1-C_4)$-alkyl is optionally substituted, identically or differently, with one or two groups selected from —$NR^{14}R^{15}$, $(C_1-C_4)$-alkoxy and cyclopropyl and optionally up to five fluorine atoms,
    wherein said cyclopropyl is optionally substituted with up to four fluorine atoms,
  wherein
  $R^{14}$ represents a hydrogen atom or $(C_1-C_4)$-alkyl,
  $R^{15}$ represents a hydrogen atom or $(C_1-C_4)$-alkyl,
  or
  $R^{14}$ and $R^{15}$ together with the nitrogen atom they are attached form a 4- to 5-membered heterocycle
    wherein said 4- to 5-membered heterocycle is optionally substituted, identically or differently, with one, two or three groups selected from $(C_1-C_4)$-alkyl trifluormethyl, difluoromethyl and optionally up to five fluorine atoms,
  wherein said $(C_1-C_4)$-alkoxy is optionally substituted with up to three fluorine atoms,
  wherein said 4- to 6-membered heterocycle is optionally substituted, identically or differently, with one or two groups selected from $(C_1-C_4)$-alkyl and optionally up to five fluorine atoms,
  wherein said $(C_3-C_6)$-cycloalkyl is optionally substituted, identically or differently, with one or two groups selected from $(C_1-C_4)$-alkyl and optionally up to five fluorine atoms,
$R^6$ represents 6-membered heteroaryl, 2-oxopyridin-1(2H)-yl, a 4- to 8-membered heterocycle or $(C_4-C_8)$-cycloalkyl,
or
represents a group of the formula

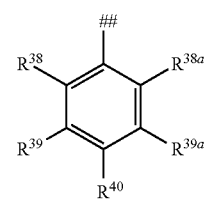

in which
## represents the point of attachment to the pyrazole ring,
$R^{38}$ represents a hydrogen atom, halogen or methyl,
$R^{38a}$ represents a hydrogen atom, halogen or methyl,
$R^{39}$ represents a hydrogen atom, cyano, fluorine or $(C_1-C_4)$-alkylsulfanyl,
$R^{39a}$ represents a hydrogen atom, cyano, fluorine or $(C_1-C_4)$-alkylsulfanyl,
$R^{40}$ represents a hydrogen atom, halogen, cyano, hydroxy, —$(CH_2)_nNR^{16}R^{17}$, $(C_1-C_4)$-alkyl, $(C_1-C_4)$-alkoxy or $(C_1-C_4)$-alkoxycarbonyl,
  wherein said $(C_1-C_4)$-alkyl is optionally substituted with cyano and optionally with up to five fluorine atoms,
  wherein said $(C_1-C_4)$-alkoxy is optionally substituted with up to five fluorine atoms, wherein
n represents 0 or 1,
$R^{16}$ represents a hydrogen atom or $(C_1-C_4)$-alkyl,
    wherein said $(C_1-C_4)$-alkyl is optionally substituted with up to five fluorine atoms,
$R^{17}$ represents a hydrogen atom or $(C_1-C_4)$-alkyl,
    wherein said $(C_1-C_4)$-alkyl is optionally substituted with up to five fluorine atoms,
or
$R^{16}$ and $R^{17}$ together with the nitrogen atom they are attached form a 4- to 8-membered heterocycle
    wherein said 4- to 8-membered heterocycle is optionally substituted, identically or differently, with one, two or three groups selected from $(C_1-C_4)$-alkyl and optionally up to five fluorine atoms,
wherein said 6-membered heteroaryl group is optionally substituted, identically or differently, with one or two groups selected from a halogen atom, cyano, $(C_1-C_4)$-alkyl, and $(C_1-C_4)$-alkoxy,
    wherein said $(C_1-C_4)$-alkyl is optionally substituted with up to five fluorine atoms,
    wherein said $(C_1-C_4)$-alkoxy is optionally substituted with up to three fluorine atoms,
wherein said 2-oxopyridin-1(2H)-yl is optionally substituted, identically or differently, with one or two groups selected from a halogen atom, cyano, $(C_1-C_4)$-alkyl and $(C_1-C_4)$-alkoxy,
    wherein said $(C_1-C_4)$-alkyl is optionally substituted with up to five fluorine atoms,
    wherein said $(C_1-C_4)$-alkoxy is optionally substituted with up to three fluorine atoms,
wherein said 4- to 8-membered heterocycle is optionally substituted, identically or differently, with one, two or three groups selected from $(C_1-C_4)$-alkyl, cyano, $(C_1-C_4)$-alkoxycarbonyl and optionally up to five fluorine atoms,
    wherein said $(C_1-C_4)$-alkyl is optionally substituted with up to five fluorine atoms,
    wherein said $(C_4-C_8)$-cycloalkyl is optionally substituted, identically or differently, with one or two groups selected from $(C_1-C_4)$-alkyl, cyano and optionally up to five fluorine atoms,
    wherein said $(C_1-C_4)$-alkyl is optionally substituted with $(C_3-C_6)$-cycloalkyl and optionally up to five fluorine atoms,
$R^7$ represents a hydrogen atom, $(C_1-C_4)$-alkyl, a phenyl group, a 5- to 6-membered heteroaryl group or $(C_1-C_4)$-alkylsulfonyl,
    wherein any phenyl group and any 5- to 6-membered heteroaryl are each optionally substituted, identically or differently, with one, two or three groups selected from a halogen atom, $(C_1-C_4)$-alkyl, trifluoromethyl, $(C_1-C_4)$-alkoxy and trifluoromethoxy,
    wherein said $(C_1-C_4)$-alkyl is optionally substituted with a group selected from $(C_3-C_6)$-cycloalkyl, 4- to 6-membered heterocycle, hydroxy, —NR$^{20}$R$^{21}$, $(C_1-C_4)$-alkoxy or benzyloxy and optionally with up to five fluorine atoms,
        wherein said $(C_3-C_6)$-cycloalkyl is optionally substituted, identically or differently, with one or two groups selected from $(C_1-C_4)$-alkyl, hydroxy and up to five fluorine atoms,
        wherein said 4- to 6-membered heterocycle is optionally substituted, identically or differently, with one or two groups selected from $(C_1-C_4)$-alkyl and optionally up to five fluorine atoms,
and
wherein
$R^{20}$ represents a hydrogen atom or $(C_1-C_4)$-alkyl,
$R^{21}$ represents a hydrogen atom or $(C_1-C_4)$-alkyl,
or
$R^{20}$ and $R^{21}$ together with the nitrogen atom they are attached form a 4- to 6-membered heterocycle
    wherein said 4- to 6-membered heterocycle is optionally substituted, identically or differently, with one, two or three groups selected from $(C_1-C_4)$-alkyl and optionally up to five fluorine atoms,
with the proviso that if $R^5$ is $(C_1-C_4)$-alkoxy then $R^7$ is different from hydrogen,
with the proviso that if $R^6$ is 6-membered heteroaryl then $R^7$ is different from hydrogen,
with the proviso that if $R^6$ is 2-oxopyridin-1(2H)-yl then $R^7$ is different from hydrogen,
with the proviso that if $R^6$ is a 4- to 8-membered heterocycle then $R^7$ is different from hydrogen,
$R^8$ represents a group selected from a halogen atom, cyano, $(C_1-C_4)$-alkyl, $(C_1-C_4)$-alkoxy, $(C_3-C_6)$-cycloalkyl, 4- to 6-membered heterocycle, $(C_1-C_4)$-alkylcarbonyl and a phenyl group,
    wherein said $(C_1-C_4)$-alkyl is optionally substituted, identically or differently, with one or two groups selected from —NR$^{22}$R$^{23}$ $(C_1-C_4)$-alkoxy and cyclopropyl and optionally up to five fluorine atoms,
        wherein said cyclopropyl is optionally substituted with up to four fluorine atoms,
        wherein said $(C_1-C_4)$-alkoxy is optionally substituted with up to five fluorine atoms,
    wherein
    $R^{22}$ represents a hydrogen atom or $(C_1-C_4)$-alkyl,
    $R^{23}$ represents a hydrogen atom or $(C_1-C_4)$-alkyl,
    or
    $R^{22}$ and $R^{23}$ together with the nitrogen atom they are attached form a 4- to 6-membered heterocycle
        wherein said 4- to 6-membered heterocycle is optionally substituted, identically or differently, with one, two or three groups selected from $(C_1-C_4)$-alkyl and optionally up to five fluorine atoms,
    wherein said $(C_1-C_4)$-alkoxy is optionally substituted with up to five fluorine atoms,
    wherein said $(C_3-C_6)$-cycloalkyl is optionally substituted, identically or differently, with one or two groups selected from $(C_1-C_4)$-alkyl and optionally up to five fluorine atoms,
    wherein said 4- to 6-membered heterocycle is optionally substituted, identically or differently, with one or two groups selected from $(C_1-C_4)$-alkyl and optionally up to five fluorine atoms,
and
wherein said phenyl group is optionally substituted, identically or differently, with one, two or three groups selected from a halogen atom, cyano, $(C_1-C_4)$-alkyl, trifluoromethyl, $(C_1-C_4)$-alkoxy and trifluoromethoxy,
$R^9$ represents 6-membered heteroaryl, 2-oxopyridin-1(2H)-yl, $(C_3-C_8)$-cycloalkyl, a 4- to 8-membered heterocycle or $(C_1-C_4)$-alkyl, or
represents a group of the formula

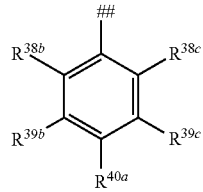

in which
## represents the point of attachment to the pyrazole ring,
$R^{38b}$ represents a hydrogen atom, halogen or methyl,
$R^{38c}$ represents a hydrogen atom, halogen or methyl,
$R^{39b}$ represents a hydrogen atom, cyano, fluorine or $(C_1\text{-}C_4)$-alkylsulfanyl,
$R^{39c}$ represents a hydrogen atom, cyano, fluorine or $(C_1\text{-}C_4)$-alkylsulfanyl,
$R^{40a}$ represents a hydrogen atom, halogen, cyano, hydroxy, $-(CH_2)_n NR^{16a}R^{17a}$, $(C_1\text{-}C_4)$-alkyl, $(C_1\text{-}C_4)$-alkoxy, $(C_1\text{-}C_4)$-alkoxycarbonyl, a 4- to 6-membered heterocycle, cyclopropyl or cyclobutyl,
  wherein said $(C_1\text{-}C_4)$-alkyl is optionally substituted with cyano and optionally with up to five fluorine atoms,
  wherein said $(C_1\text{-}C_4)$-alkoxy is optionally substituted with up to five fluorine atoms,
  wherein said 4- to 6-membered heterocycle is optionally substituted, identically or differently, with one, two or three groups selected from $(C_1\text{-}C_4)$-alkyl and optionally up to five fluorine atoms,
  wherein
  n represents 0 or 1,
  $R^{16a}$ represents a hydrogen atom or $(C_1\text{-}C_4)$-alkyl,
    wherein said $(C_1\text{-}C_4)$-alkyl is optionally substituted with up to five fluorine atoms,
  $R^{17a}$ represents a hydrogen atom or $(C_1\text{-}C_4)$-alkyl,
    wherein said $(C_1\text{-}C_4)$-alkyl is optionally substituted with up to five fluorine atoms,
  or
  $R^{16a}$ and $R^{17a}$ together with the nitrogen atom they are attached form a 4- to 8-membered heterocycle
    wherein said 4- to 8-membered heterocycle is optionally substituted, identically or differently, with one, two or three groups selected from $(C_1\text{-}C_4)$-alkyl and optionally up to five fluorine atoms,
  wherein said $(C_1\text{-}C_4)$-alkyl is optionally substituted with up to five fluorine atoms,
wherein said 6-membered heteroaryl group is optionally substituted, identically or differently, with one or two groups selected from a halogen atom, cyano, $(C_1\text{-}C_4)$-alkyl, and $(C_1\text{-}C_4)$-alkoxy,
  wherein said $(C_1\text{-}C_4)$-alkyl is optionally substituted with up to five fluorine atoms,
  wherein said $(C_1\text{-}C_4)$-alkoxy is optionally substituted with up to three fluorine atoms,
wherein said 2-oxopyridin-1(2H)-yl is optionally substituted, identically or differently, with one or two groups selected from a halogen atom, cyano, $(C_1\text{-}C_4)$-alkyl, and $(C_1\text{-}C_4)$-alkoxy,
  wherein said $(C_1\text{-}C_4)$-alkyl is optionally substituted with up to five fluorine atoms,
  wherein said $(C_1\text{-}C_4)$-alkoxy is optionally substituted with up to three fluorine atoms,
  wherein said $(C_3\text{-}C_8)$-cycloalkyl is optionally substituted, identically or differently, with one or two groups selected from $(C_1\text{-}C_4)$-alkyl, cyano and optionally up to five fluorine atoms,
    wherein said $(C_1\text{-}C_4)$-alkyl is optionally substituted with $(C_3\text{-}C_6)$-cycloalkyl and optionally up to five fluorine atoms,
  wherein said 4- to 8-membered heterocycle is optionally substituted identically or differently, with one or two groups selected from $(C_1\text{-}C_4)$-alkyl, cyano, $(C_1\text{-}C_4)$-alkoxycarbonyl and optionally up to five fluorine atoms,
    wherein said $(C_1\text{-}C_4)$-alkyl is optionally substituted with up to five fluorine atoms,
$R^{10}$ represents a hydrogen atom, $(C_1\text{-}C_4)$-alkyl, $(C_3\text{-}C_5)$-cycloalkyl, $(C_1\text{-}C_4)$-alkoxycarbonyl, mono-$(C_1\text{-}C_4)$-alkylamino, a phenyl group or a 5- to 6-membered heteroaryl group,
  wherein any phenyl group and any 5- to 6-membered heteroaryl are each optionally substituted, identically or differently, with one, two or three groups selected from a halogen atom, $(C_1\text{-}C_4)$-alkyl, trifluoromethyl, $(C_1\text{-}C_4)$-alkoxy and trifluoromethoxy,
  wherein said $(C_1\text{-}C_4)$-alkyl is optionally substituted with a group selected from $(C_3\text{-}C_6)$-cycloalkyl, 5-membered heteroaryl, $-NR^{28}R^{29}$, $(C_1\text{-}C_4)$-alkoxy or benzyloxy and optionally with up to five fluorine atoms and is optionally additionally substituted with hydroxy,
    wherein said $(C_3\text{-}C_6)$-cycloalkyl is optionally substituted, identically or differently, with hydroxy or one or two groups $(C_1\text{-}C_4)$-alkyl and optionally up to five fluorine atoms,
    and
    wherein
    $R^{28}$ represents a hydrogen atom or $(C_1\text{-}C_4)$-alkyl,
    $R^{29}$ represents a hydrogen atom or $(C_1\text{-}C_4)$-alkyl,
    or
    $R^{28}$ and $R^{29}$ together with the nitrogen atom they are attached form a 4- to 6-membered heterocycle
      wherein said 4- to 6-membered heterocycle is optionally substituted, identically or differently, with one, two or three groups selected from $(C_1\text{-}C_4)$-alkyl and optionally up to five fluorine atoms,
    wherein said 5-membered heteroaryl is optionally substituted with $(C_1\text{-}C_4)$-alkyl,
with the proviso that if $R^9$ is 6-membered heterorayl then $R^{10}$ is different from hydrogen,
with the proviso that if $R^9$ is 2-oxopyridin-1 (2H)-yl then $R^{10}$ is different from hydrogen,
with the proviso that if $R^9$ is a 4- to 8-membered heterocycle then $R^{10}$ is different from hydrogen,
with the proviso that if $R^8$ is $(C_1\text{-}C_4)$-alkoxy then $R^{10}$ is different from hydrogen,
$R^{11}$ represents a group selected from a hydrogen atom, a fluorine atom, a chlorine atom, $(C_1\text{-}C_4)$-alkyl and cyclopropyl,
  wherein said $(C_1\text{-}C_4)$-alkyl is optionally substituted with cyclopropyl and optionally up to five fluorine atoms,
$R^{12}$ represents a 6-membered heteroaryl group, 2-oxopyridin-1(2H)-yl, $(C_4\text{-}C_8)$-cycloalkyl or $(C_1\text{-}C_4)$- alkyl,
or
represents a group of the formula

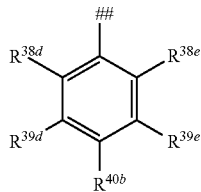

in which
## represents the point of attachment to the pyrazole ring,
$R^{38d}$ represents a hydrogen atom, halogen or methyl,
$R^{38e}$ represents a hydrogen atom, halogen or methyl,
$R^{39d}$ represents a hydrogen atom, cyano, fluorine or $(C_1-C_4)$-alkylsulfanyl,
$R^{39e}$ represents a hydrogen atom, cyano, fluorine or $(C_1-C_4)$-alkylsulfanyl,
$R^{40b}$ represents a hydrogen atom, halogen, cyano, hydroxy, —$(CH_2)_n NR^{16a}R^{17a}$, $(C_1-C_4)$-alkyl, $(C_1-C_4)$-alkoxy, $(C_1-C_4)$-alkoxycarbonyl, a 4- to 6-membered heterocycle, cyclopropyl or cyclobutyl,
wherein said $(C_1-C_4)$-alkyl is optionally substituted with cyano and optionally with up to five fluorine atoms,
wherein said $(C_1-C_4)$-alkoxy is optionally substituted with up to five fluorine atoms,
wherein said 4- to 6-membered heterocycle is optionally substituted, identically or differently, with one, two or three groups selected from $(C_1-C_4)$-alkyl and optionally up to five fluorine atoms,
wherein
n represents 0 or 1,
$R^{16a}$ represents a hydrogen atom or $(C_1-C_4)$-alkyl,
wherein said $(C_1-C_4)$-alkyl is optionally substituted with up to five fluorine atoms,
$R^{17a}$ represents a hydrogen atom or $(C_1-C_4)$-alkyl,
wherein said $(C_1-C_4)$-alkyl is optionally substituted with up to five fluorine atoms,
or
$R^{16a}$ and $R^{17a}$ together with the nitrogen atom they are attached form a 4- to 8-membered heterocycle,
wherein said 4- to 8-membered heterocycle is optionally substituted, identically or differently, with one, two or three groups selected from $(C_1-C_4)$-alkyl and optionally up to five fluorine atoms,
wherein said 6-membered heteroaryl group is optionally substituted, identically or differently, with one or two groups selected from a halogen atom, cyano, $(C_1-C_4)$-alkyl, and $(C_1-C_4)$-alkoxy,
wherein said $(C_1-C_4)$-alkyl is optionally substituted with up to five fluorine atoms,
wherein said $(C_1-C_4)$-alkoxy is optionally substituted with up to three fluorine atoms,
wherein said 2-oxopyridin-1(2H)-yl is optionally substituted, identically or differently, with one or two groups selected from a halogen atom, cyano, $(C_1-C_4)$-alkyl, and $(C_1-C_4)$-alkoxy,
wherein said $(C_1-C_4)$-alkyl is optionally substituted with up to five fluorine atoms,
wherein said $(C_1-C_4)$-alkoxy is optionally substituted with up to three fluorine atoms,
wherein said $(C_4-C_8)$-cycloalkyl is optionally substituted, identically or differently, with one or two groups selected from $(C_1-C_4)$-alkyl or cyano and optionally up to five fluorine atoms,
$R^{13}$ represents a group selected from a hydrogen atom, a fluorine atom, a chlorine atom, $(C_1-C_4)$-alkyl and cyclopropyl,
wherein said $(C_1-C_4)$-alkyl is optionally substituted with cyclopropyl and up to five fluorine atoms,
$R^2$ represents a group selected from a hydrogen atom, $(C_1-C_4)$-alkyl, $(C_3-C_6)$-cycloalkyl and $(C_1-C_4)$-alkoxycarbonyl,
wherein said $(C_1-C_4)$-alkyl is optionally substituted, identically or differently, with one or two groups selected from hydroxy, $(C_1-C_4)$-alkoxy, cyclopropyl and optionally up to five fluorine atoms,
$R^3$ represents a group selected from a hydrogen atom, a halogen atom, cyano, hydroxy, nitro, amino, mono-$(C_1-C_4)$-alkylamino, di-$(C_1-C_4)$-alkylamino, $(C_1-C_4)$-alkylsulfanyl, $(C_1-C_4)$-alkylsulfinyl, $(C_1-C_4)$-alkylsulfonyl, $(C_1-C_6)$-alkyl, $(C_1-C_4)$-alkoxy, $(C_3-C_6)$-cycloalkyl, 4- to 6-membered heterocycle, 5- to 6-membered heteroaryl, —$(CH_2)_q C(=O)$—$NR^{34}R^{35}$, —O—$C(=O)$—$NR^{36}R^{37}$, —O—$C(=O)$—$OR^{37a}$, —NH—$C(=O)$—$NR^{36}R^{37}$, —$N(CH_3)$—$C(=O)$—$NR^{36}R^{37}$, —NH—$C(=O)$—$OR^{37a}$, —$N(CH_3)$—$C(=O)$—$OR^{37a}$—NH—$C(=O)$—$R^{37}$, —$N(CH_3)$—$C(=O)$—$R^{37}$, $(C_1-C_4)$-alkylcarbonyl, $(C_1-C_4)$-alkylcarbonyloxy and $(C_1-C_4)$-alkoxycarbonyl,
wherein said $(C_1-C_6)$-alkyl is optionally substituted, identically or differently, with one or two groups selected from hydroxy, amino, mono-$(C_1-C_4)$-alkylamino, di-$(C_1-C_4)$-alkylamino, cyano, $(C_1-C_4)$-alkoxy, 4- to 6-membered heterocycle, $(C_1-C_4)$-alkoxycarbonyl and cyclopropyl and optionally up to six fluorine atoms,
wherein said 4- to 6-membered heterocycle is optionally substituted with $(C_1-C_4)$-alkyl or cyclopropyl and optionally up to two fluorine atoms,
wherein said $(C_1-C_4)$-alkoxy is optionally substituted with cyano, cyclopropyl and optionally up to five fluorine atoms,
wherein said $(C_1-C_4)$-alkyl of mono-$(C_1-C_4)$-alkylamino is optionally substituted with cyano, cyclopropyl and optionally up to five fluorine atoms,
wherein said di-$(C_1-C_4)$-alkylamino is optionally substituted with cyano, cyclopropyl and optionally up to five fluorine atoms,
wherein said $(C_3-C_6)$-cycloalkyl is optionally substituted, identically or differently, with one or two groups selected from $(C_1-C_4)$-alkyl, $(C_1-C_4)$-alkoxy, hydroxy and cyclopropyl and optionally up to five fluorine atoms,
wherein said 4- to 6-membered heterocycle is optionally substituted, identically or differently, with one or two groups selected from $(C_1-C_4)$-alkyl, trifluoromethyl, difluoromethyl, $(C_1-C_4)$-alkoxy, $(C_1-C_4)$-alkoxycarbonyl, mono-$(C_1-C_4)$-alkylaminocarbonyl, di-$(C_1-C_4)$-alkylaminocarbonyl, $(C_1-C_4)$-alkylcarbonyl, hydroxy and cyclopropyl and optionally up to five fluorine atoms,
wherein said 5- to 6-membered heteroaryl is optionally substituted, identically or differently, with one or two groups selected from $(C_1-C_4)$-alkyl, $(C_1-C_4)$-alkoxy, and cyclopropyl and optionally up to five fluorine atoms, wherein
q represents 0 or 1,
$R^{34}$ represents a hydrogen atom or $(C_1-C_4)$-alkyl,
$R^{35}$ represents a hydrogen atom, $(C_1-C_4)$-alkyl or phenyl,
or
$R^{34}$ and $R^{35}$ together with the nitrogen atom they are attached form a 4- to 7-membered heterocyclyl ring
wherein said 4- to 7-membered heterocyclyl ring is optionally substituted, identically or differently, with one, two or three groups selected from a fluorine atom, hydroxy, $(C_1-C_4)$-alkyl, $(C_1-C_4)$-alkoxy, cyclopropyl, difluoromethyl, trifluoromethyl and trifluoromethoxy,
wherein
$R^{36}$ represents a hydrogen atom or methyl,
$R^{37}$ represents a hydrogen atom, methyl, difluoromethyl, trifluoromethyl or cyclopropyl,
$R^{37a}$ represents methyl, difluoromethyl, trifluoromethyl or cyclopropyl,
with the proviso that if $R^3$ is —$(CH_2)_qC(=O)$—$NR^{34}R^{35}$, —O—C(=O)—$NR^{36}R^{37}$, —O—C(=O)—$OR^{37a}$, —N(CH$_3$)—C(=O)—$NR^{36}R^{37}$, —NH—C(=O)—$OR^{37a}$, —NH—C(=O)—$NR^{36}R^{37}$, —N(CH$_3$)—C(=O)—$OR^{37a}$—NH—C(=O)—$R^{37}$ or —N(CH$_3$)—C(=O)—$R^{37}$, then $R^7$ and $R^{10}$ are different from hydrogen,
with the proviso that if $R^3$ is cyano then $R^2$ and $R^4$ are different from hydrogen,
with the proviso that if $R^3$ is cyano then $R^6$ and $R^9$ are different from 6-membered heteroaryl,
or
$R^2$ and $R^3$ together with the carbon atoms they are attached form a 4- to 6-membered carbocycle, a 4- to 7-membered azaheterocycle, a 4- to 7-membered oxaheterocycle, a 5- to 6-membered heteroaryl group or a phenyl ring,
wherein said 4- to 7-membered azaheterocycle is optionally substituted, identically or differently, with one or two groups selected from hydroxy, oxo, $(C_1-C_4)$-alkyl, trifluoromethyl, $(C_1-C_4)$-alkylcarbonyl and $(C_1-C_4)$-alkoxycarbonyl and optionally up to five fluorine atoms,
wherein said 4- to 7-membered oxaheterocycle is optionally substituted, identically or differently, with one or two groups selected from hydroxy, oxo, $(C_1-C_4)$-alkyl, trifluoromethyl, $(C_1-C_4)$-alkylcarbonyl and $(C_1-C_4)$-alkoxycarbonyl and optionally up to five fluorine atoms,
wherein said 4- to 6-membered carbocycle is optionally substituted, identically or differently, with one or two groups selected from hydroxy, oxo, amino, mono-$(C_1-C_4)$-alkylamino, di-$(C_1-C_4)$-alkylamino, $(C_1-C_4)$-alkyl, trifluoromethyl, $(C_1-C_4)$-alkylcarbonyl and $(C_1-C_4)$-alkoxycarbonyl and optionally up to five fluorine atoms,
and
wherein any phenyl group and any 5- to 6-membered heteroaryl group are each optionally substituted, identically or differently, with one, two or three groups selected from a halogen atom, $(C_1-C_4)$-alkyl, trifluoromethyl, $(C_1-C_4)$-alkoxy and trifluoromethoxy,
with the proviso that if $R^2$ and $R^3$ together with the carbon atoms they are attached form a 4- to 7-membered azaheterocycle with a non-substituted nitrogen atom which is not directly attached to the pyrazole, then $R^7$ and $R^{10}$ are different from hydrogen,
with the proviso that if $R^7$ and $R^{10}$ are hydrogen then the nitrogen atom of the 4- to 7-membered azaheterocycle formed by $R^2$ and $R^3$ together with the carbon atoms they are attached to is substituted with $(C_1-C_4)$-alkyl or $(C_1-C_4)$-alkoxycarbonyl,
$R^4$ represents a group selected from a hydrogen atom, $(C_1-C_4)$-alkyl, $(C_3-C_6)$-cycloalkyl and $(C_1-C_4)$-alkoxycarbonyl and hydroxy,
wherein said $(C_1-C_4)$-alkyl is optionally substituted, identically or differently, with one or two groups selected from hydroxy, $(C_1-C_4)$-alkoxy and cyclopropyl and optionally up to five fluorine atoms,
or
$R^3$ and $R^4$ together with the carbon atoms they are attached form a 4- to 6-membered carbocycle, a 4- to 7-membered heterocycle, a 5- to 6-membered heteroaryl group or a phenyl ring,
wherein said 4- to 7-membered heterocycle is optionally substituted, identically or differently, with one or two groups selected from a fluorine atom, hydroxy, oxo, $(C_1-C_4)$-alkyl, trifluoromethyl, $(C_1-C_4)$-alkylcarbonyl and $(C_1-C_4)$-alkoxycarbonyl and optionally up to five fluorine atoms,
wherein said 4- to 6-membered carbocycle is optionally substituted, identically or differently, with one or two groups selected from a fluorine atom, hydroxy, oxo, $(C_1-C_4)$-alkyl, trifluoromethyl, $(C_1-C_4)$-alkylcarbonyl and $(C_1-C_4)$-alkoxycarbonyl and optionally up to five fluorine atoms,
and
wherein any phenyl group and any 5- to 6-membered heteroaryl group are each optionally substituted, identically or differently, with one, two or three groups selected from a halogen atom, $(C_1-C_4)$-alkyl, trifluoromethyl, $(C_1-C_4)$-alkoxy and trifluoromethoxy,
with the proviso that if $R^3$ and $R^4$ together with the carbon atoms they are attached form a 4- to 7-membered heterocycle with a non-substituted nitrogen atom which is not directly attached to the pyrazole, then $R^7$ and $R^{10}$ is different from hydrogen,
with the proviso that if $R^7$ and $R^{10}$ are hydrogen then the nitrogen atom of the 4- to 7-membered heterocycle formed by $R^3$ and $R^4$ together with the carbon atoms they are attached to is substituted with $(C_1-C_4)$-alkyl or $(C_1-C_4)$-alkoxycarbonyl,
or a stereoisomer, a tautomer, an N-oxide, a hydrate, a solvate, or a salt thereof, or a mixture of same.

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon atom or heteroatom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents.

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom, even more particularly fluorine or chlorine.

The term "$C_1$-$C_4$-alkyl" and "$C_1$-$C_6$-alkyl" means a linear or branched, saturated, monovalent hydrocarbon group having 1, 2, 3, or 4 carbon atoms, and 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "($C_1$-$C_4$)-alkylsulfanyl" means a linear or branched, saturated, monovalent group of formula ($C_1$-$C_6$-alkyl)-S—, in which the term "$C_1$-$C_4$-alkyl" is as defined supra, e.g. a methylsulfanyl, ethylsulfanyl, propylsulfanyl, isopropylsulfanyl, butylsulfanyl, sec-butylsulfanyl, isobutylsulfanyl, tert-butylsulfanyl group.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy, tert-butoxy, or an isomer thereof.

The term "$C_3$-$C_6$-cycloalkyl" and "$C_5$-$C_6$-cycloalkyl" means a saturated, monovalent, mono- or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl group, or a bicyclic hydrocarbon ring. The term "3- to 6-membered cycloalkyl" is equivalent to a "$C_3$-$C_6$-cycloalkyl", Thus a "4-membered cycloalkyl group" has the same meaning as a "$C_4$-cycloalkyl group".

The terms "($C_3$-$C_6$)-cycloalkyl" and "$C_3$-$C_8$-cycloalkyl" mean a saturated, monovalent, mono- or bicyclic hydrocarbon ring which contains 3, 4, 5, 6, 7 or 8 carbon atoms ("$C_3$-$C_8$-cycloalkyl"). Said $C_3$-$C_8$-cycloalkyl group is for example, a monocyclic hydrocarbon ring, e.g. a cyclopropyl, cyclobutyl, cyclopentyl, cyclohexyl, cycloheptyl or cyclooctyl group, or a bicyclic hydrocarbon ring, e.g. a bicyclo [4.2.0]octyl or octahydropentalenyl.

The term "3- to 6-membered heterocycle", "4-membered heterocycle", "4- to 6-membered heterocycle", "5- to 6-membered heterocycle", "3- to 8-membered heterocycle" and 4- to 8-membered heterocycle means a monocyclic, saturated heterocycle with 3 to 8, 4 to 8, 3 to 6, 4 to 6 or 4 or 5 or 6, ring atoms in total, respectively, which contains one or two identical or different ring heteroatoms from the series N, S or O, it being possible for said heterocycloalkyl group to be attached to the rest of the molecule via any one of the carbon atoms. A heterocycloalkyl group which contains at least one ring nitrogen atom may be named aza-heterocyloalkyl, respectively a heterocycloalkyl group which contains at least one ring oxygen atom may be named oxa-heterocyloalkyl. In particular, an aza-heterocyloalkyl group contains only ring nitrogen atoms and an oxa-heterocyloalkyl group contains only ring oxygen atoms.

Said heterocycle, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

The terms "azaheterocyclyl" and "azaheterocycle" in the context of the invention mean a monocyclic or bicyclic, saturated or partly unsaturated heterocycle which has the particular number of ring atoms specified, contains a nitrogen atom and may additionally contain one or two further ring heteroatom(s) from the group of N, O, S, SO and/or $SO_2$, and is joined via a ring nitrogen atom. Preferred examples include: pyrrolidinyl, pyrazolidinyl, piperidinyl, piperazinyl, morpholinyl, thiomorpholinyl, 1,1-dioxothiomorpholinyl, hexahydroazepinyl, hexahydro-1,4-diazepinyl, 1,2,3,4-tetrahydroisoquinolinyl, 1,2,3,4-tetrahydroquinolinyl, indolinyl, 8-azabicyclo[3.2.1]octanyl, 9-azabicyclo [3.3.1]nonanyl, 3-azabicyclo[4.1.0]heptanyl and quinuclidinyl.

The terms "oxaheterocyclyl" and "oxaheterocycle" in the context of the invention mean a monocyclic or bicyclic, saturated or partly unsaturated heterocycle which has the particular number of ring atoms specified, contains an oxygen atom and may additionally contain one or two further ring heteroatom(s) from the group of N, O, S, SO and/or $SO_2$, The term "5- to 6-membered heteroaryl", "5-membered heteroaryl" and "6-membered heteroaryl" means a monovalent, monocyclic aromatic ring with 5 to 6, or 5 or 6, ring atoms in total, respectively, 5 or 6 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thia-diazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl.

mono-($C_1$-$C_4$)-alkylamino in the context of the invention means an amino group with one straight-chain or branched alkyl substituent which contains 1, 2, 3 or 4 carbon atoms, such as: methylamino, ethylamino, n-propylamino, isopropylamino, n-butylamino, and tert-butylamino, for example.

di-($C_1$-$C_4$)-alkylamino in the context of the invention means an amino group with two identical or different straight-chain or branched alkyl substituents which each contain 1, 2, 3 or 4 carbon atoms, such as: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, and N-tert-butyl-N-methylamino, for example.

($C_1$-$C_4$)-Alkylcarbonyl in the context of the invention means a straight-chain or branched alkyl group having 1, 2, 3 or 4 carbon atoms which is bound to the rest of the molecule via a carbonyl group [—C(=O)—], such as: acetyl, propionyl, n-butyryl, isobutyryl, n-pentanoyl, and pivaloyl, for example.

($C_1$-$C_4$)-Alkoxycarbonyl in the context of the invention means a straight-chain or branched alkoxy group having 1, 2, 3 or 4 carbon atoms which is bound to the rest of the molecule via a carbonyl group [—C(=O)—], such as: methoxycarbonyl, ethoxycarbonyl, n-propoxycarbonyl, isopropoxycarbonyl, n-butoxycarbonyl, and tert-butoxycarbonyl, for example.

mono-($C_1$-$C_4$)-alkylaminocarbonyl in the context of the invention means an amino group which is bound to the rest of the molecule via a carbonyl group [—C(=O)—] and which has one straight-chain or branched alkyl substituent having 1, 2, 3 or 4 carbon atoms, such as: methylaminocarbonyl, ethylaminocarbonyl, n-propylaminocarbonyl, isopropylaminocarbonyl, n-butylaminocarbonyl, and tert-butylaminocarbonyl, for example.

di-($C_1$-$C_4$)-alkylaminocarbonyl in the context of the invention means an amino group which is bound to the rest of the molecule via a carbonyl group [—C(=O)—] and which has two identical or different straight-chain or branched alkyl substituents having in each case 1, 2, 3 or 4 carbon atoms, such as: N,N-dimethylaminocarbonyl, N,N-diethylaminocarbonyl, N-ethyl-N-methylaminocarbonyl, N-methyl-N-n-propylaminocarbonyl, N-isopropyl-N-methylaminocarbonyl, N,N-diisopropylaminocarbonyl, N-n-butyl-N-methylaminocarbonyl, and N-tert-butyl-N-methylaminocarbonyl, for example.

An oxo substituent in the context of the invention means an oxygen atom, which is bound to a carbon atom via a double bond In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_4$", as used in the present text, e.g. in the context of the definition of "$C_1$-$C_4$-alkyl", "$C_1$-$C_4$-alkoxy", " or "$C_1$-$C_4$-alkylsulfanyl", means an alkyl group having a finite number of carbon atoms of 1 to 4, i.e. 1, 2, 3, or 4 carbon atoms.

The term "$C_1$-$C_6$", as used in the present text, e.g. in the context of the definition of "$C_1$-$C_6$-alkyl", means an alkyl group having a finite number of carbon atoms of 1 to 6, i.e. 1, 2, 3, 4, 5 or 6 carbon atoms.

Further, as used herein, the term "$C_3$-$C_6$", as used in the present text, e.g. in the context of the definition of "$C_3$-$C_6$-cycloalkyl", means a cycloalkyl group having a finite number of carbon atoms of 3 to 6, i.e. 3, 4, 5 or 6 carbon atoms.

Further, as used herein, the term "$C_3$-$C_8$", as used in the present text, e.g. in the context of the definition of "$C_3$-$C_8$-cycloalkyl", means a cycloalkyl group having a finite number of carbon atoms of 3 to 8, i.e. 3, 4, 5, 6, 7 or 8 carbon atoms.

When a range of values is given, said range encompasses each value and sub-range within said range.

For example:

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_1$-$C_3$" encompasses $C_1$, $C_2$, $C_3$, $C_1$-$C_3$, $C_1$-$C_2$, and $C_2$-$C_3$;

"$C_2$-$C_4$" encompasses $C_2$, $C_3$, $C_4$, $C_2$-$C_4$, $C_2$-$C_3$, and $C_3$-$C_4$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy (mesyl(ate), Ms), [(trifluoromethyl)sulfonyl]oxy (triflyl/(ate), Tf), [(nonafluoro-butyl)sulfonyl]oxy (nonaflate, Nf), (phenylsulfonyl)oxy, [(4-methylphenyl)sulfonyl]oxy, [(4-bromo-phenyl)sulfonyl]oxy, [(4-nitrophenyl)sulfonyl]oxy, [(2-nitrophenyl)sulfonyl]oxy, [(4-isopropylphenyl)-sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron Letters, 2011, 52, 3865) is a rapid route for incorporation of deuterium. Metal catalysts (i.e. Pd, Pt, and Rh) in the presence of deuterium gas can be used to directly exchange deuterium for hydrogen in functional groups containing hydrocarbons (J. G. Atkinson et al., U.S. Pat. No. 3,966,781). A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844, 1989; P. J. Reider et al., J. Org. Chem. 52, 3326-3334, 1987; M. Jarman et al., Carcinogenesis 16(4), 683-688, 1995; J. Atzrodt et al., Angew. Chem., Int. Ed. 2007, 46, 7744; K. Matoishi et al., Chem. Commun. 2000, 1519-1520; K. Kassahun et al., WO2012/112363.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490; A. Streitwieser et al., J. Am. Chem. Soc., 1963, 85, 2759;], basicity [C. L. Perrin et al., J. Am. Chem. Soc., 2005, 127, 9641; C. L. Perrin, et al., J. Am. Chem. Soc., 2003, 125, 15008; C. L. Perrin in Advances in Physical Organic Chemistry, 44, 144], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102; D. J. Kushner et al., Can. J. Physiol. Pharmacol., 1999, 77, 79). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

In another embodiment the present invention concerns a deuterium-containing compound of general formula (I) having 1, 2, 3 or 4 deuterium atoms, particularly with 1, 2 or 3 deuterium atoms.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains an imidazopyridine moiety as a heteroaryl group for example can exist as a 1H tautomer, or a 3H tautomer, or even a mixture in any amount of the two tautomers, namely:

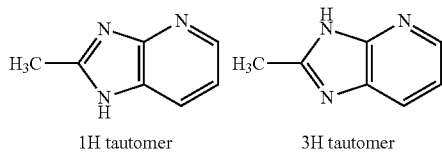

1H tautomer       3H tautomer

Moreover, in the course of the synthesis of the 1H-pyrazole group the 1H-pyrazol-3-yl tautomer as well as its tautomer 1H-pyrazol-5-yl tautomer are formed.

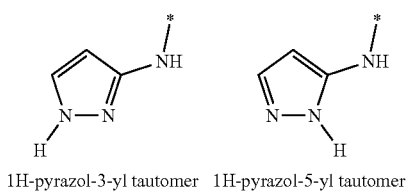 [SMILES: *Nc1cc[nH]n1 ; *Nc1ccn[nH]1]

1H-pyrazol-3-yl tautomer    1H-pyrazol-5-yl tautomer

The present invention includes all possible tautomers of the compounds of the present invention as single tautomers, or as any mixture of said tautomers, in any ratio.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt, in particular as a free acid. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

In accordance with a preferred embodiment of the first aspect, the present invention covers a pharmaceutically acceptable salt of compounds of general formula (I), (I-C), supra, which is an alkali metal salt, in particular a sodium or potassium salt, or an ammonium salt derived from an organic tertiary amine, in particular choline.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF$_3$COOH", "x Na", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

As used herein, the term "in vivo hydrolysable ester" means an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, it being possible for said esters to be formed at any carboxy group in the compounds of the present invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl include acetoxymethoxy and 2,2-dimethyl-propionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

Preference is given to compounds of the formula (I) in which $R^1$ represents a group of the formula

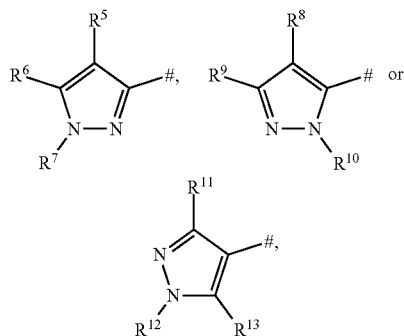

in which
# represents the point of attachment to the amino group,
$R^5$ represents a group selected from fluorine, chlorine, cyano, ($C_1$-$C_4$)-alkyl, methoxy, ethoxy, ($C_3$-$C_5$)-cycloalkyl, methylcarbonyl and ethylcarbonyl,
  wherein said ($C_1$-$C_4$)-alkyl is optionally substituted, identically or differently, with one or two groups selected from —NR$^{14}$R$^{15}$, methoxy, ethoxy, difluoromethoxy, trifluoromethoxy and cyclopropyl and optionally up to five fluorine atoms,
    wherein said cyclopropyl is optionally substituted with up to four fluorine atoms,
  wherein
  $R^{14}$ represents a hydrogen atom or ($C_1$-$C_4$)-alkyl,
  $R^{15}$ represents a hydrogen atom or ($C_1$-$C_4$)-alkyl,
  or
  $R^{14}$ and $R^{15}$ together with the nitrogen atom they are attached form a 4- to 5-membered heterocycle
    wherein said 4- to 5-membered heterocycle is optionally substituted, identically or differently, with one or two groups selected from ($C_1$-$C_4$)-alkyl, trifluormethyl, difluoromethyl and optionally up to five fluorine atoms,
  wherein said methoxy and ethoxy are optionally substituted with up to three fluorine atoms,
  wherein said ($C_3$-$C_5$)-cycloalkyl is optionally substituted with up to four fluorine atoms,
$R^6$ represents pyridyl, pyrimidyl, 2-oxopyridin-1(2H)-yl, ($C_5$-$C_8$)-cycloalkyl or a 6- to 8-membered heterocycle or
represents a group of the formula

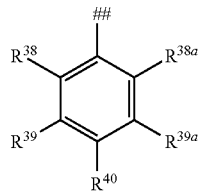

in which
## represents the point of attachment to the pyrazole ring,
$R^{38}$ represents a hydrogen atom, halogen or methyl,
$R^{38a}$ represents a hydrogen atom, halogen or methyl,
$R^{39}$ represents a hydrogen atom, cyano, fluorine or $(C_1-C_4)$-alkylsulfanyl,
$R^{39a}$ represents a hydrogen atom, cyano, fluorine or $(C_1-C_4)$-alkylsulfanyl,
$R^{40}$ represents a hydrogen atom, fluorine, chlorine, cyano, hydroxy, —$(CH_2)_nNR^{16}R^{17}$, $(C_1-C_3)$-alkyl, $(C_1-C_3)$-alkoxy or $(C_1-C_4)$-alkoxycarbonyl,
wherein said $(C_1-C_3)$-alkyl is optionally substituted with cyano and optionally with up to five fluorine atoms,
wherein said $(C_1-C_3)$-alkoxy is optionally substituted with up to five fluorine atoms,
wherein
n represents 0 or 1,
$R^{16}$ represents a hydrogen atom or $(C_1-C_4)$-alkyl,
$R^{17}$ represents a hydrogen atom or $(C_1-C_4)$-alkyl,
or
$R^{16}$ and $R^{17}$ together with the nitrogen atom they are attached form a 4- to 6-membered heterocycle
wherein said 4- to 6-membered heterocycle is optionally substituted, identically or differently, with one, two or three groups selected from $(C_1-C_4)$-alkyl and optionally up to five fluorine atoms,
wherein said pyridyl and pyrimidyl are optionally substituted, identically or differently, with one or two groups selected from a halogen atom, cyano, methyl, ethyl, methoxy and ethoxy,
wherein said $(C_1-C_4)$-alkyl is optionally substituted with up to five fluorine atoms,
wherein said methoxy and ethoxy are optionally substituted with up to three fluorine atoms,
wherein said 2-oxopyridin-1(2H)-yl is optionally substituted, identically or differently, with one or two groups selected from fluorine, cyano, methyl, ethyl, methoxy and ethoxy,
wherein said methyl and ethyl are optionally substituted with up to three fluorine atoms,
wherein said methoxy and ethoxy are optionally substituted with up to three fluorine atoms,
wherein said 6- to 8-membered heterocycle is optionally substituted, identically or differently, with one or two groups selected from $(C_1-C_4)$-alkyl, cyano, $(C_1-C_4)$-alkoxycarbonyl and optionally up to five fluorine atoms,
wherein said $(C_1-C_4)$-alkyl is optionally substituted with up to three fluorine atoms,
wherein said $(C_5-C_8)$-cycloalkyl is optionally substituted, identically or differently, with one or two groups selected from $(C_1-C_4)$-alkyl and cyano, and optionally up to five fluorine atoms,
wherein said $(C_1-C_4)$-alkyl is optionally substituted with up to three fluorine atoms,
$R^7$ represents a hydrogen atom, $(C_1-C_4)$-alkyl, methylsulfonyl or ethylsulfonyl,
wherein said $(C_1-C_4)$-alkyl is optionally substituted with a group selected from $(C_3-C_6)$-cycloalkyl, hydroxy, —$NR^{20}R^{21}$, methoxy, ethoxy or benzyloxy and optionally with up to five fluorine atoms,
wherein said $(C_3-C_6)$-cycloalkyl is optionally substituted with hydroxy and optionally up to four fluorine atoms,
and
wherein
$R^{20}$ represents a hydrogen atom or $(C_1-C_4)$-alkyl,
$R^{21}$ represents a hydrogen atom or $(C_1-C_4)$-alkyl,
with the proviso that if $R^5$ is methoxy or ethoxy then $R^7$ is different from hydrogen,
with the proviso that if $R^6$ is pyridyl or pyrimidyl then $R^7$ is different from hydrogen,
with the proviso that if $R^6$ is 2-oxopyridin-1(2H)-yl then $R^7$ is different from hydrogen,
with the proviso that if $R^6$ is a 6- to 8-membered heterocycle then $R^7$ is different from hydrogen,
$R^8$ represents a group selected from fluorine, chlorine, cyano, $(C_1-C_4)$-alkyl, methoxy, ethoxy, methylcarbonyl, ethylcarbonyl and $(C_3-C_5)$-cycloalkyl,
wherein said $(C_1-C_4)$-alkyl is optionally substituted with methoxy, —$NR^{22}R^{23}$ and cyclopropyl and optionally up to five fluorine atoms,
wherein said cyclopropyl is optionally substituted with up to four fluorine atoms
wherein said methoxy is optionally substituted with up to three fluorine atoms,
wherein
$R^{22}$ represents a hydrogen atom or $(C_1-C_4)$-alkyl,
$R^{23}$ represents a hydrogen atom or $(C_1-C_4)$-alkyl,
or
$R^{22}$ and $R^{23}$ together with the nitrogen atom they are attached form a 4- to 6-membered heterocycle
wherein said 4- to 6-membered heterocycle is optionally substituted, identically or differently, with one, two or three groups selected from $(C_1-C_4)$-alkyl and optionally up to five fluorine atoms,
wherein said methoxy and ethoxy are optionally substituted with up to three fluorine atoms,
and
wherein said $(C_3-C_5)$-cycloalkyl is optionally substituted with up to four fluorine atoms,
$R^9$ represents pyridyl, pyrimidyl, 2-oxopyridin-1(2H)-yl, $(C_5-C_8)$-cycloalkyl or a 6- to 8-membered heterocycle or $(C_1-C_4)$-alkyl,
or
represents a group of the formula

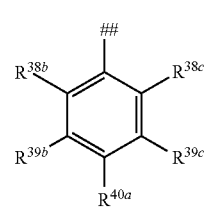

in which ## represents the point of attachment to the pyrazole ring, $R^{38b}$ represents a hydrogen atom, halogen or methyl, $R^{38c}$ represents a hydrogen atom, halogen or methyl, $R^{39b}$ represents a hydrogen atom, cyano, fluorine or $(C_1-C_4)$-alkylsulfanyl, $R^{39c}$ represents a hydrogen atom, cyano, fluorine or $(C_1-C_4)$-alkylsulfanyl, $R^{40a}$ represents a hydrogen atom, fluorine, chlorine, cyano, hydroxy, —$(CH_2)_nNR^{16a}R^{17a}$, $(C_1-C_3)$-alkyl, $(C_1-C_3)$-alkoxy, $(C_1-C_4)$-alkoxycarbonyl, a 4- to 6-membered heterocycle, cyclopropyl or cyclobutyl, wherein said $(C_1-C_3)$-alkyl is optionally substituted with cyano and optionally with up to five fluorine atoms, wherein said $(C_1-C_3)$-alkoxy is optionally substituted with up to five fluorine atoms, wherein said 4- to 6-membered heterocycle is optionally substituted, identically or differently, with one, two or three groups selected from $(C_1-C_4)$-alkyl and optionally up to five fluorine atoms, wherein n represents 0 or 1, $R^{16a}$ represents a hydrogen atom or $(C_1-C_4)$-alkyl, $R^{17a}$ represents a hydrogen atom or $(C_1-C_4)$-alkyl, or $R^{16a}$ and $R^{17a}$ together with the nitrogen atom they are attached form a 4- to 6-membered heterocycle wherein said 4- to 6-membered heterocycle is optionally substituted, identically or differently, with one, two or three groups selected from $(C_1-C_4)$-alkyl and optionally up to five fluorine atoms, wherein said $(C_1-C_4)$-alkyl is optionally substituted with up to five fluorine atoms, wherein said pyridyl and pyrimidyl are optionally substituted, identically or differently, with one or two groups selected from a halogen atom, cyano, methyl, ethyl, methoxy and ethoxy, wherein said methyl and ethyl is optionally substituted with up to three fluorine atoms, wherein said methoxy and ethoxy are optionally substituted with up to three fluorine atoms, wherein said 2-oxopyridin-1(2H)-yl is optionally substituted, identically or differently, with one or two groups selected from fluorine, cyano, methyl, ethyl, methoxy and ethoxy, wherein said methyl and ethyl are optionally substituted with up to three fluorine atoms, wherein said methoxy and ethoxy are optionally substituted with up to three fluorine atoms, wherein said 6- to 8-membered heterocycle is optionally substituted, identically or differently, with one or two groups selected from methyl, ethyl, cyano and $(C_1-C_4)$-alkoxycarbonyl and optionally up to five fluorine atoms, wherein said methyl is optionally substituted with up to three fluorine atoms, wherein said $(C_5-C_8)$-cycloalkyl is optionally substituted, identically or differently, with one or two groups selected from methyl, ethyl and cyano, and optionally up to five fluorine atoms, wherein said methyl is optionally substituted with up to three fluorine atoms, $R^{10}$ represents a hydrogen atom, $(C_1-C_4)$-alkyl or $(C_3-C_6)$-cycloalkyl, wherein said $(C_1-C_4)$-alkyl is optionally substituted with a group selected from $(C_3-C_6)$-cycloalkyl, 2-methyl-2H-tetrazol-5-yl, 1-methyl-1H-tetrazol-5-yl, —$NR^{28}R^{29}$, methoxy, ethoxy or benzyloxy and optionally with up to five fluorine atoms optionally with up to five fluorine atoms and is optionally additionally substituted with hydroxy, wherein said $(C_3-C_6)$-cycloalkyl is optionally substituted with up to four fluorine atoms, and wherein $R^{28}$ represents a hydrogen atom or $(C_1-C_4)$-alkyl, $R^{29}$ represents a hydrogen atom or $(C_1-C_4)$-alkyl, with the proviso that if $R^9$ is pyridyl or pyrimidyl then $R^{10}$ is different from hydrogen, with the proviso that if $R^9$ is 2-oxopyridin-1 (2H)-yl then $R^{10}$ is different from hydrogen, with the proviso that if $R^9$ is a 6- to 8-membered heterocycle then $R^{10}$ is different from hydrogen, with the proviso that if $R^8$ is methoxy or ethoxy then $R^0$ is different from hydrogen, $R^{11}$ represents a group selected from a hydrogen atom, $(C_1-C_4)$-alkyl and cyclopropyl, wherein said $(C_1-C_4)$-alkyl is optionally substituted with cyclopropyl and optionally with up to five fluorine atoms, $R^{12}$ represents pyridyl or 2-oxopyridin-1(2H)-yl, or represents a group of the formula

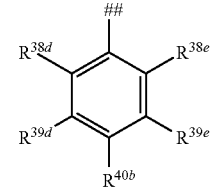

in which ## represents the point of attachment to the pyrazole ring, $R^{38d}$ represents a hydrogen atom, fluorine or methyl, $R^{38e}$ represents a hydrogen atom, fluorine or methyl, $R^{39d}$ represents a hydrogen atom, cyano or fluorine, $R^{39e}$ represents a hydrogen atom, $R^{40b}$ represents a hydrogen atom, fluorine, chlorine, cyano, hydroxy, methyl, trifluoromethyl, methoxy, trifluoromethoxy or methoxycarbonyl, wherein said pyridyl is optionally substituted, identically or differently, with one or two groups selected from fluorine, cyano, methyl and methoxy, wherein said methyl is optionally substituted with up to three fluorine atoms, wherein said methoxy is optionally substituted with up to three fluorine atoms, wherein said 2-oxopyridin-1(2H)-yl is optionally substituted, identically or differently, with one or two groups selected from fluorine, cyano, methyl and methoxy, wherein said methyl is optionally substituted with up to three fluorine atoms, wherein said methoxy is optionally substituted with up to three fluorine atoms, $R^{13}$ represents a group selected from a hydrogen atom, $(C_1-C_4)$-alkyl and cyclopropyl, wherein said $(C_1-C_4)$-alkyl is optionally substituted with cyclopropyl and optionally with up to five fluorine atoms, $R^2$ represents a group selected from a hydrogen atom, $(C_1-C_4)$-alkyl, cyclopropyl, methoxycarbonyl and ethoxycarbonyl, wherein said $(C_1-C_4)$-alkyl is optionally substituted, identically or differently, with one or two groups selected from hydroxy, methoxy, ethoxy, cyclopropyl and optionally up to five fluorine atoms, $R^3$ represents a group selected from a hydrogen atom, fluorine, chlorine, bromine, cyano, hydroxy, nitro, amino, mono-$(C_1-C_4)$-alkylamino, di-$(C_1-C_4)$-alkylamino, $(C_1-C_4)$-alkylsulfanyl, $(C_1-C_4)$-alkylsulfinyl, $(C_1-C_4)$-alkylsulfonyl, $(C_1-C_6)$-alkyl, $(C_1-C_4)$-alkoxy, —O—C(=O)—$NR^{36}R^{37}$, —O—C(=O)—$OR^{37a}$, —NH—C(=O)—$NR^{36}R^{37}$, —N($CH_3$)—C(=O)—$NR^{36}R^{37}$, —NH—C(=O)—$OR^{37a}$, —N($CH_3$)—C(=O)—$OR^{37a}$—NH—C(=O)—$R^{37}$, —N($CH_3$)—C(=O)—$R^{37}$, $(C_3-C_5)$-cycloalkyl, 4- to 6-membered heterocycle, 5- to 6-membered heteroaryl, —$(CH_2)_q$—C(=O)—$NR^{34}R^{35}$, methylcarbonyl, ethylcarbonyl, $(C_1-C_4)$-alkylcarbonyloxy and $(C_1-C_4)$-alkoxycarbonyl, wherein said $(C_1-C_6)$-alkyl is optionally substituted, identically or differently, with one or two groups selected from hydroxy, amino, mono-$(C_1-C_4)$-alkylamino, di-$(C_1-C_4)$-alkylamino, cyano, methoxy, ethoxy, methoxycarbonyl, ethoxycarbony, 4- to 6-membered heterocycle and cyclopropyl and optionally up to five fluorine atoms, wherein said 4- to 6-membered heterocycle is optionally substituted with methyl, ethyl or cyclopropyl and optionally up to two fluorine atoms, wherein said $(C_1-C_4)$-alkoxy is optionally substituted with cyano, cyclopropyl and optionally up to five fluorine atoms, wherein said $(C_3-C_5)$-cycloalkyl is optionally substituted with hydroxyl, methoxy, ethoxy and optionally up to four fluorine atoms, wherein said 4- to 6-membered heterocycle is optionally substituted with hydroxyl, trifluoromethyl, methoxy, ethoxy and optionally up to four fluorine atoms, wherein said 5- to 6-membered heteroaryl is optionally substituted, identically or differently, with one or two groups selected from methyl, ethyl and methoxy and optionally up to four fluorine atoms, wherein q is 0, $R^{34}$ represents a hydrogen atom or $(C_1-C_4)$-alkyl, $R^{35}$ represents a hydrogen atom or $(C_1-C_4)$-alkyl, or $R^{34}$ and $R^{35}$ together with the nitrogen atom they are attached form a 4- to 7-membered heterocycle, wherein said 4- to 7-membered heterocycle ring is optionally substituted, identically or differently, with one, two or three groups selected from a fluorine atom, hydroxy, methyl, ethyl, methoxy, ethoxy, cyclopropyl, difluoromethyl, trifluoromethyl and trifluoromethoxy, wherein $R^{36}$ represents a hydrogen atom or methyl, $R^{37}$ represents a hydrogen atom, methyl, difluoromethyl, trifluoromethyl or cyclopropyl, $R^{37a}$ represents methyl, difluoromethyl, trifluoromethyl or cyclopropyl, with the proviso that if $R^3$ is —$(CH_2)_q$C(=O)—$NR^{34}R^{35}$, —O—C(=O)—$NR^{36}R^{37}$, —O—C(=O)—$OR^{37a}$, —N($CH_3$)—C(=O)—$NR^{36}R^{37}$, —NH—C(=O)—$OR^{37a}$, —NH—C(=O)—$NR^{36}R^{37}$, —N($CH_3$)—C(=O)—$OR^{37a}$, —NH—C(=O)—$R^{37}$ or —N($CH_3$)—C(=O)—$R^{37}$, then $R^7$ and $R^{10}$ are different from hydrogen, with the proviso that if $R^3$ is cyano then $R^2$ and $R^4$ are different from hydrogen, with the proviso that if $R^3$ is cyano then $R^6$ and $R^9$ are different from 6-membered heteroaryl, or $R^2$ and $R^3$ together with the carbon atoms they are attached form a 5- to 6-membered carbocycle, a 5- to 7-membered azaheterocycle, a 5- to 7-membered oxaheterocycle, a 5- to 6-membered heteroaryl group or a phenyl ring, wherein said 5- to 7-membered azaheterocycle is optionally substituted, identically or differently, with one or two groups selected from oxo, methyl, ethyl, propyl, trifluoromethyl and $(C_1-C_4)$-alkoxycarbonyl and optionally up to four fluorine atoms, wherein said 5- to 7-membered oxaheterocycle is optionally substituted, identically or differently, with one or two groups selected from oxo, methyl, ethyl, trifluoromethyl and $(C_1-C_4)$-alkoxycarbonyl and optionally up to four fluorine atoms, wherein said 5- to 6-membered carbocycle is optionally substituted, identically or differently, with one or two groups selected from hydroxy, oxo, amino, mono-$(C_1-C_4)$-alkylamino, di-$(C_1-C_4)$-alkylamino, methyl, ethyl, trifluoromethyl and $(C_1-C_4)$-alkoxycarbonyl and optionally up to four fluorine atoms, and wherein any phenyl group and any 5- to 6-membered heteroaryl group are each optionally substituted, identically or differently, with one or two groups selected from fluorine, chlorine, methyl, ethyl, trifluoromethyl, methoxy and trifluoromethoxy, with the proviso that if $R^2$ and $R^3$ together with the carbon atoms they are attached to form a 5- to 7-membered azaheterocycle with a non-substituted nitrogen atom which is not directly attached to the pyrazole, then $R^7$ and $R^{10}$ are different from hydrogen, with the proviso that if $R^7$ and $R^{10}$ are hydrogen then the nitrogen atom of the 5- to 7-membered azaheterocycle formed by $R^2$ and $R^3$ together with the carbon atoms they are attached to is substituted with methyl, ethyl or $(C_1-C_4)$-alkoxycarbonyl, $R^4$ represents a group selected from a hydrogen atom, $(C_1-C_4)$-alkyl, cyclopropyl, methoxycarbonyl, ethoxycarbonyl and hydroxy, wherein said $(C_1-C_4)$-alkyl is optionally substituted, identically or differently, with one or two groups selected from hydroxy, methoxy and cyclopropyl and optionally up to five fluorine atoms, or $R^3$ and $R^4$ together with the carbon atoms they are attached form a 5- to 6-membered carbocycle, a 5- to 7-membered heterocycle, a 5- to 6-membered heteroaryl group or a phenyl ring, wherein said 5- to 7-membered heterocycle is optionally substituted, identically or differently, with one or two groups selected from oxo, methyl, ethyl, propyl trifluoromethyl and $(C_1-C_4)$-alkoxycarbonyl and optionally up to four fluorine atoms, wherein said 5- to 6-membered carbocycle is optionally substituted, identically or differently, with one or two groups selected from oxo, hydroxyl, methyl, ethyl, trifluoromethyl and $(C_1-C_4)$-alkoxycarbonyl and optionally up to four fluorine atoms, and
wherein any phenyl group and any 5- to 6-membered heteroaryl group are each optionally substituted, identically or differently, with one or two groups selected from fluorine, chlorine, methyl, ethyl, trifluoromethyl, methoxy and trifluoromethoxy, with the proviso that if $R^3$ and $R^4$ together with the carbon atoms they are attached form a 5- to 7-membered heterocycle with a non-substituted nitrogen atom which is not directly attached to the pyrazole, then $R^7$ and $R^{10}$ is different from hydrogen, with the proviso that if $R^7$ and $R^{10}$ are hydrogen then the nitrogen atom of the 5- to 7-membered heterocycle formed by $R^3$ and $R^4$ together with the carbon atoms they are attached to is substituted with methyl, ethyl or $(C_1-C_4)$-alkoxycarbonyl, or a stereoisomer, a tautomer, an N-oxide, a hydrate, a solvate, or a salt thereof, or a mixture of same.

Preference is given to compounds of the formula (I) in which:

$R^1$ represents a group of the formula

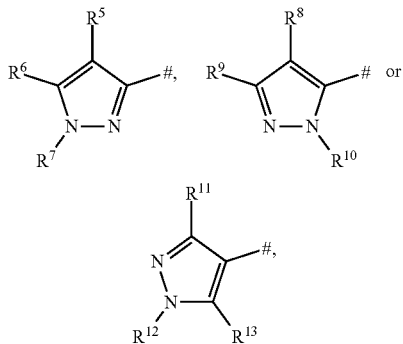

in which

\# represents the point of attachment to the amino group, $R^5$ represents a group selected from chlorine, $(C_1-C_4)$-alkyl, methoxy, ethoxy and $(C_3-C_5)$-cycloalkyl,
  wherein said $(C_1-C_4)$-alkyl is optionally substituted with a group selected from methoxy, difluoromethoxy, trifluoromethoxy, —$NR^{14}R^{15}$, cyclopropyl or optionally with up to three fluorine atoms,
  wherein
  $R^{14}$ represents $(C_1-C_4)$-alkyl,
  $R^{15}$ represents $(C_1-C_4)$-alkyl,
  or
  $R^{14}$ and $R^{15}$ together with the nitrogen atom they are attached form a 4- to 6-membered heterocycle
    wherein said 4- to 6-membered heterocycle is optionally substituted with methyl or trifluoromethyl or optionally with up to four fluorine atoms,
  wherein said methoxy and ethoxy are optionally substituted with up to three fluorine atoms,
  wherein said $(C_3-C_5)$-cycloalkyl is optionally substituted with up to four fluorine atoms, $R^6$ represents pyridyl or $(C_5-C_8)$-cycloalkyl,
or
represents a group of the formula

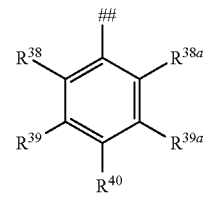

in which

\#\# represents the point of attachment to the pyrazole ring, $R^{38}$ represents a hydrogen atom, methyl or fluorine,
$R^{38a}$ represents a hydrogen atom,
$R^{39}$ represents a hydrogen atom, cyano or fluorine,
$R^{39a}$ represents a hydrogen atom, cyano, fluorine or methylsulfanyl,
$R^{40}$ represents a hydrogen atom, fluorine, chlorine, cyano, hydroxy, —$(CH_2)_nNR^{16}R^{17}$, methyl, methoxy, ethoxy, difluoromethoxy, trifluoromethoxy, methoxycarbonyl or ethoxycarbonyl,
  wherein said methyl is optionally substituted with cyano or optionally with up to three fluorine atoms,
  wherein
  n represents 0,
  $R^{16}$ represents a hydrogen atom or $(C_1-C_4)$-alkyl,
  $R^{17}$ represents $(C_1-C_4)$-alkyl,
wherein said pyridyl is optionally substituted, identically or differently, with one or two groups selected from fluorine, cyano, methyl, methoxy and ethoxy,
  wherein said methyl is optionally substituted with up to three fluorine atoms,
  wherein said methoxy is optionally substituted with up to three fluorine atoms,
wherein said $(C_5-C_8)$-cycloalkyl is optionally substituted, identically or differently, with one or two groups selected from $(C_1-C_4)$-alkyl and cyano, or optionally with up to five fluorine atoms,
  wherein said $(C_1-C_4)$-alkyl is optionally substituted with up to three fluorine atoms, $R^7$ represents a hydrogen atom or $(C_1-C_4)$-alkyl,
  wherein said $(C_1-C_4)$-alkyl is optionally substituted with $(C_3-C_6)$-cycloalkyl, methoxy or ethoxy or optionally with up to three fluorine atoms,
with the proviso that if $R^5$ is methoxy, ethoxy, difluoromethoxy or trifluoromethoxy then $R^7$ is different from hydrogen,
with the proviso that if $R^6$ is pyridyl then $R^7$ is different from hydrogen, $R^8$ represents a group selected from chlorine, $(C_1-C_4)$-alkyl, methoxy, ethoxy and $(C_3-C_5)$-cycloalkyl,
  wherein said $(C_1-C_4)$-alkyl is optionally substituted with a group selected from methoxy —$NR^{22}R^{23}$, cyclopropyl or optionally with up to three fluorine atoms,
  wherein said methoxy is optionally substituted with up to three fluorine atoms,
  wherein
  $R^{22}$ represents $(C_1-C_4)$-alkyl,
  $R^{23}$ represents $(C_1-C_4)$-alkyl,
  wherein said methoxy and ethoxy are optionally substituted with up to three fluorine atoms,
  and
  wherein said $(C_3-C_5)$-cycloalkyl is optionally substituted with up to four fluorine atoms, $R^9$ represents pyridyl or $(C_5-C_8)$-cycloalkyl,
or
represents a group of the formula

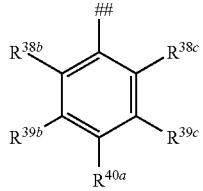

in which
## represents the point of attachment to the pyrazole ring,
$R^{38b}$ represents a hydrogen atom, methyl or fluorine,
$R^{38c}$ represents a hydrogen atom or fluorine,
$R^{39b}$ represents a hydrogen atom, cyano or fluorine,
$R^{39c}$ represents a hydrogen atom, cyano or fluorine,
$R^{40a}$ represents a hydrogen atom, fluorine, chlorine, cyano, hydroxy, $-(CH_2)_n NR^{16a}R^{17a}$, methyl, methoxy, ethoxy, difluoromethoxy, trifluoromethoxy, methoxycarbonyl or ethoxycarbonyl, a 4- to 6-membered heterocycle, cyclopropyl or cyclobutyl,
  wherein said methyl is optionally substituted with cyano or optionally with up to three fluorine atoms,
  wherein
  n represents 0,
  $R^{16a}$ represents a hydrogen atom,
  $R^{17a}$ represents $(C_1-C_4)$-alkyl,
  wherein said 4- to 6-membered heterocycle is optionally substituted, with methyl or optionally with up to five fluorine atoms,
  wherein said pyridyl is optionally substituted, identically or differently, with one or two groups selected from fluorine, cyano, methyl, methoxy and ethoxy,
  wherein said methyl is optionally substituted with up to three fluorine atoms,
  wherein said methoxy and ethoxy are optionally substituted with up to three fluorine atoms,
  wherein said $(C_5-C_8)$-cycloalkyl is optionally substituted, identically or differently, with one or two groups selected from methyl, ethyl, cyano or optionally with up to five fluorine atoms,
  wherein said methyl is optionally substituted with up to three fluorine atoms,
$R^{10}$ represents a hydrogen atom, $(C_1-C_4)$-alkyl or cyclopropyl,
  wherein said $(C_1-C_4)$-alkyl is optionally substituted with a group selected from $(C_3-C_6)$-cycloalkyl, methoxy, ethoxy, 2-methyl-2H-tetrazol-5-yl, 1-methyl-1H-tetrazol-5-yl, $-NR^{28}R^{29}$ or optionally with up to three fluorine atoms and is optionally additionally substituted with hydroxy,
  wherein said $(C_3-C_6)$-cycloalkyl is optionally substituted with up to four fluorine atoms,
  and
  wherein
  $R^{28}$ represents a hydrogen atom or $(C_1-C_4)$-alkyl,
  $R^{29}$ represents $(C_1-C_4)$-alkyl,
with the proviso that if $R^9$ is pyridyl then $R^{10}$ is different from hydrogen,
with the proviso that if $R^8$ is methoxy, ethoxy, difluoromethoxy or trifluoromethoxy then $R^{10}$ is different from hydrogen,
$R^{11}$ represents cyclopropyl, methyl or ethyl,
  wherein said methyl or ethyl are optionally substituted with cyclopropyl or optionally with up to three fluorine atoms,
$R^{12}$ represents a group of the formula

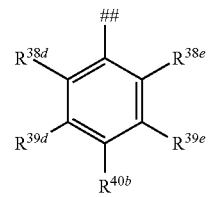

in which
## represents the point of attachment to the pyrazole ring,
$R^{38d}$ represents a hydrogen atom or fluorine,
$R^{38e}$ represents a hydrogen atom,
$R^{39d}$ represents a hydrogen atom or fluorine,
$R^{39e}$ represents a hydrogen atom,
$R^{40b}$ represents a hydrogen atom, fluorine, chlorine or cyano,
$R^{13}$ represents a group selected from a hydrogen atom, methyl and cyclopropyl,
  wherein said methyl is optionally substituted with cyclopropyl or optionally with up to three fluorine atoms,
$R^2$ represents a hydrogen atom or methyl,
  wherein said methyl is optionally substituted with up to three fluorine atoms,
$R^3$ represents a group selected from a hydrogen atom, fluorine, chlorine, bromine, cyano, hydroxy, nitro, amino, mono-$(C_1-C_4)$-alkylamino, di-$(C_1-C_4)$-alkylamino, methylsulfanyl, ethylsulfanyl, methylsulfinyl, ethylsulfinyl, methylsulfonyl, ethylsulfonyl, $-O-C(=O)-OR^{37a}$, $-NH-C(=O)-NR^{36}R^{37}$, $-N(CH_3)-C(=O)-NR^{36}R^{37}$, $-NH-C(=O)-OR^{37a}$, $(C_1-C_4)$-alkyl, methoxy, ethoxy, $(C_3-C_5)$-cycloalkyl, 4- to 6-membered heterocycle, 5-membered heteroaryl, $-(CH_2)_q-C(=O)-NR^{34}R^{35}$, methoxycarbonyl and ethoxycarbonyl,
  wherein said $(C_1-C_4)$-alkyl is optionally substituted, identically or differently, with one or two groups selected from hydroxy, cyano, methoxy, ethoxy, methoxycarbonyl, ethoxycarbonyl, methylamino, ethylamino, dimethylamino, diethylamino, a 4- to 6-membered heterocycle and cyclopropyl and optionally up to three fluorine atoms,
    wherein said 4- to 6-membered heterocycle is optionally substituted with methyl, ethyl or cyclopropyl and optionally up to two fluorine atoms,
  wherein said methoxy and ethoxy are optionally substituted with cyano, cyclopropyl or optionally up to three fluorine atoms,
  wherein said $(C_3-C_5)$-cycloalkyl is optionally substituted with hydroxy or optionally with up to four fluorine atoms,
  wherein said 4- to 6-membered heterocycle is optionally substituted with hydroxyl or trifluoromethyl or optionally with up to four fluorine atoms, wherein said 5-membered heteroaryl is optionally substituted, identically or differently, with one or two groups selected from methyl and methoxy
wherein
q is 0,
$R^{34}$ represents a hydrogen atom or $(C_1-C_4)$-alkyl,
$R^{35}$ represents $(C_1-C_4)$-alkyl,
or
$R^{34}$ and $R^{35}$ together with the nitrogen atom they are attached form a 4- to 6-membered heterocycle ring
  wherein said 4- to 6-membered heterocycle ring is optionally substituted, identically or differently, with one or two groups selected from a fluorine atom, methyl, difluoromethyl, trifluoromethyl and trifluoromethoxy,
wherein
$R^{36}$ represents a hydrogen atom or methyl,
$R^{37}$ represents a hydrogen atom, methyl, difluoromethyl, trifluoromethyl or cyclopropyl,
$R^{37a}$ represents methyl, difluoromethyl, trifluoromethyl or cyclopropyl,
with the proviso that if $R^3$ is —$(CH_2)_qC(=O)$—$NR^{34}R^{35}$, —O—C(=O)—$OR^{37a}$, —NH—C(=O)—$NR^{36}R^{37}$, —N(CH_3)—C(=O)—$NR^{36}R^{37}$ or —NH—C(=O)—$OR^{37a}$, then $R^7$ and $R^{10}$ are different from hydrogen,
with the proviso that if $R^3$ is cyano then $R^2$ and $R^4$ are different from hydrogen,
with the proviso that if $R^3$ is cyano then $R^6$ and $R^9$ are different from pyridyl or pyrimidyl,
or
$R^2$ and $R^3$ together with the carbon atoms they are attached form a 4- to 6-membered carbocycle, a 5- to 6-membered azaheterocycle, a 5- to 6-membered oxaheterocycle, a 6-membered heteroaryl group or a phenyl ring,
wherein said phenyl group is optionally substituted, identically or differently, with one or two groups selected from fluorine, chlorine, methyl, trifluoromethyl, methoxy and trifluoromethoxy,
wherein said 5- to 6-membered carbocycle is optionally substituted, identically or differently, with one or two groups selected from hydroxy, oxo, methyl, ethyl, trifluoromethyl and $(C_1-C_4)$-alkoxycarbonyl or optionally with up to four fluorine atoms,
wherein said 5- to 6-membered azaheterocycle is optionally substituted with oxo, methyl, ethyl, propyl, trifluoromethyl, tert.-butoxycarbonyl or optionally with up to four fluorine atoms,
wherein said 5- to 6-membered oxaheterocycle is optionally substituted with oxo, methyl, ethyl, trifluoromethyl, methoxycarbonyl and ethoxycarbonyl or optionally with up to four fluorine atoms,
with the proviso that if $R^2$ and $R^3$ together with the carbon atoms they are attached to form a 5- to 6-membered azaheterocycle with a non-substituted nitrogen atom which is not directly attached to the pyrazole, then $R^7$ and $R^{10}$ are different from hydrogen,
with the proviso that if $R^7$ and $R^{10}$ are hydrogen then the nitrogen atom of the 5- to 6-membered azaheterocycle formed by $R^2$ and $R^3$ together with the carbon atoms they are attached to is substituted with methyl, ethyl, methoxycarbonyl or ethoxycarbonyl,
$R^4$ represents a group selected from a hydrogen atom, $(C_1-C_4)$-alkyl, cyclopropyl, methoxycarbonyl, ethoxycarbonyl and hydroxy,
  wherein said $(C_1-C_4)$-alkyl is optionally substituted with a group selected from hydroxy, methoxy and cyclopropyl or optionally with up to three fluorine atoms,
or
$R^3$ and $R^4$ together with the carbon atoms they are attached form a 5- to 6-membered carbocycle, a 5- to 6-membered heterocycle, a 6-membered heteroaryl group or a phenyl ring,
  wherein said 5- to 6-membered heterocycle is optionally substituted, identically or differently, with one or two groups selected from oxo, methyl, ethyl, propyl, trifluoromethyl, methoxycarbonyl, ethoxycarbonyl, tert.-butoxycarbonyl or optionally with up to four fluorine atoms,
  wherein said 5- to 6-membered carbocycle is optionally substituted, identically or differently, with one or two groups selected from oxo, hydroxy, methyl, ethyl, trifluoromethyl methoxycarbonyl and ethoxycarbonyl or optionally with up to four fluorine atoms,
  and
  wherein any phenyl group and any 6-membered heteroaryl group are each optionally substituted, identically or differently, with one or two groups selected from fluorine, chlorine, methyl, ethyl, trifluoromethyl, methoxy and trifluoromethoxy,
with the proviso that if $R^3$ and $R^4$ together with the carbon atoms they are attached form a 5- to 6-membered heterocycle with a non-substituted nitrogen atom which is not directly attached to the pyrazole, then $R^7$ and $R^{10}$ is different from hydrogen,
with the proviso that if $R^7$ and $R^{10}$ are hydrogen then the nitrogen atom of the 5- to 6-membered heterocycle formed by $R^3$ and $R^4$ together with the carbon atoms they are attached to is substituted with methyl, ethyl, methoxycarbonyl or ethoxycarbonyl,
or a stereoisomer, a tautomer, an N-oxide, a hydrate, a solvate, or a salt thereof, or a mixture of same.

Preference is given to compounds of the formula (I) in which:

$R^1$ represents a group of the formula

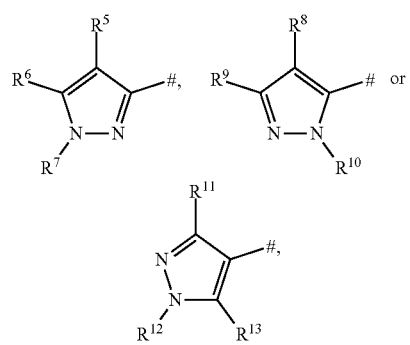

in which
# represents the point of attachment to the amino group,
$R^5$ represents a group selected from chlorine, methyl, ethyl, methoxy or cyclopropyl,
  wherein said methyl and ethyl are optionally substituted with methoxy or optionally with up to three fluorine atoms,
  wherein said methoxy is optionally substituted with up to three fluorine atoms,
$R^6$ represents 5-fluoropyridin-2-yl, 6-trifluoromethylpyridin-3-yl or cyclohexyl, or
represents a group of the formula

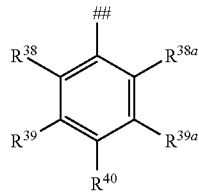

in which
## represents the point of attachment to the pyrazole ring,
$R^{38}$ represents a hydrogen atom or fluorine,
$R^{38a}$ represents a hydrogen atom,
$R^{39}$ represents a hydrogen atom,
$R^{39a}$ represents a hydrogen atom or cyano,
$R^{40}$ represents a hydrogen atom, fluorine, chlorine, cyano, methyl, difluoromethyl, trifluoromethyl, methoxy, ethoxy, difluoromethoxy, trifluoromethoxy, methoxycarbonyl or ethoxycarbonyl,
$R^7$ represents a hydrogen atom, methyl, ethyl, cyclopropylmethyl, 2-cyclopropylethyl or 2,2-difluoroethyl,
with the proviso that if $R^5$ is methoxy, difluoromethoxy or trifluoromethoxy then $R^7$ is different from hydrogen,
with the proviso that if $R^6$ is 2-pyridinyl then $R^7$ is different from hydrogen,
$R^8$ represents a group selected from chlorine, methyl, ethyl, methoxy and cylcopropyl,
$R^9$ represents pyridyl or 4-cyanopentacyclo[4.2.0.0$^{2,5}$.0$^{3,8}$.0$^{4,7}$]octan-1-yl,
or
represents a group of the formula


in which
## represents the point of attachment to the pyrazole ring,
$R^{38b}$ represents a hydrogen atom or fluorine,
$R^{38c}$ represents a hydrogen atom,
$R^{39b}$ represents a hydrogen atom,
$R^{39c}$ represents a hydrogen atom,
$R^{40a}$ represents a hydrogen atom, fluorine, chlorine, cyano, methyl, difluoromethyl, trifluoromethyl, methylamino, methoxy, difluoromethoxy, trifluoromethoxy or cyclopropyl,
wherein said pyridyl is optionally substituted with fluorine, methyl, difluoromethyl, trifluoromethyl or methoxy,
$R^{10}$ represents a hydrogen atom, methyl, ethyl, 2,2-difluoroethyl, cyclopropylmethyl, cyclobutylmethyl, 2-cyclopropylethyl, 2-cyclopropyl-2-hydroxypropyl, 2-cyclopropyl-2-hydroxyethyl, 2-methoxyethyl, or cyclopropyl,
wherein said methyl and ethyl are optionally substituted with a group selected from cyclopropyl, methoxy or optionally up to three fluorine atoms and is optionally additionally substituted with hydroxy,
with the proviso that if $R^9$ is pyridyl then $R^{10}$ is different from hydrogen,
with the proviso that if $R^8$ is methoxy then $R^{10}$ is different from hydrogen,
$R^{11}$ represents methyl,
$R^{12}$ represents a group of the formula

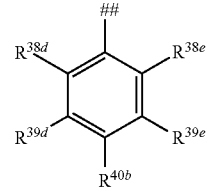

in which
## represents the point of attachment to the pyrazole ring,
$R^{38d}$ represents a hydrogen atom,
$R^{38e}$ represents a hydrogen atom,
$R^{39d}$ represents a hydrogen atom,
$R^{39e}$ represents a hydrogen atom,
$R^{40b}$ represents fluorine or cyano,
$R^{13}$ represents a group selected from a hydrogen atom or methyl,
$R^2$ represents a hydrogen atom, methyl or difluoromethyl,
$R^3$ represents a group selected from a hydrogen atom, fluorine, chlorine, bromine, cyano, hydroxy, nitro, amino, ethylamino, dimethylamino, —O—C(=O)—NR$^{36}$R$^{37}$, —O—C(=O)—OR$^{37a}$, —NH—C(=O)—OR$^{37a}$, (C$_1$-C$_4$)-alkyl, methoxy, cyclopropyl, cyclobutyl, 4-membered heterocycle, 1,3,4-oxadiazol-2-yl, 2-(trifluoromethyl)-1,3-dioxolan-2-yl, —(CH$_2$)$_q$—C(=O)—NR$^{34}$R$^{35}$, methoxycarbonyl and ethoxycarbonyl,
wherein said (C$_1$-C$_4$)-alkyl is optionally substituted, identically or differently, with one or two groups selected from hydroxy, methoxy, methoxycarbonyl, ethoxycarbonyl, dimethylamino, a 4-membered azaheterocycle and cyclopropyl and optionally up to three fluorine atoms,
wherein said 4-membered azaheterocycle is optionally substituted with up to two fluorine atoms,
wherein said methoxy is optionally substituted with cyano, cyclopropyl and optionally up to three fluorine atoms,
wherein said cyclopropyl and cyclobutyl are optionally substituted with hydroxy,
wherein said 4-membered heterocycle is optionally substituted with hydroxy,
wherein said 1,3,4-oxadiazol-2-yl is optionally substituted with methyl,
wherein
q is 0,
$R^{34}$ represents methyl,
$R^{35}$ represents methyl,
or
$R^{34}$ and $R^{35}$ together with the nitrogen atom they are attached form a 4- to 6-membered heterocycle ring
wherein said 4- to 6-membered heterocycle ring is optionally substituted, identically or differently, with one or two groups selected from a fluorine atom, methyl, difluoromethyl and trifluoromethyl,
wherein
$R^{36}$ represents a methyl atom,
$R^{37}$ represents a hydrogen atom or methyl, $R^{37a}$ represents methyl, with the proviso that if $R^3$ is —(CH$_2$)$_q$C(=O)—NR$^{34}$R$^{35}$ O—C(=O)—NR$^{36}$R$^{37}$, —O—C(=O)—OR$^{37a}$ or —NH—C(=O)—OR$^{37a}$, then $R^7$ and $R^{10}$ are different from hydrogen, with the proviso that if $R^3$ is cyano then $R^2$ and $R^4$ are different from hydrogen, with the proviso that if $R^3$ is cyano then $R^6$ and $R^9$ are different from pyridyl, or $R^2$ and $R^3$ together with the carbon atoms they are attached form a 5- to 6-membered carbocycle, a pyrrolidinyl, a pyridyl or a phenyl ring, wherein said 5- to 6-membered carbocycle is optionally substituted, identically or differently, with one or two groups selected from oxo, methyl, trifluoromethyl and hydroxy, wherein said pyrrolidinyl is substituted with propyl or tert.-butoxycarbonyl, $R^4$ represents a group selected from a hydrogen atom, methyl, 2-hydroxypropan-2-yl, fluoromethyl, difluoromethyl, methoxycarbonyl, ethoxycarbonyl and hydroxy, or $R^3$ and $R^4$ together with the carbon atoms they are attached form a 5- to 6-membered carbocycle, a pyrrolidinyl ring or a piperidinyl ring, a pyridyl group or a phenyl ring, wherein said pyrrolidinyl ring is substituted with propyl or tert-butoxycarbonyl, wherein said piperidinyl ring is substituted with propyl or tert-butoxycarbonyl, wherein said 5- to 6-membered carbocycle is optionally substituted, identically or differently, with one or two groups selected from oxo, hydroxy and methyl, or a stereoisomer, a tautomer, an N-oxide, a hydrate, a solvate, or a salt thereof, or a mixture of same.

Preference is also given to compounds of the formula (I) in which $R^1$ represents a group of the formula

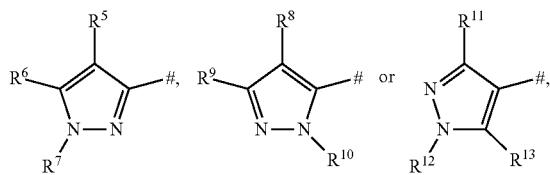

in which # represents the point of attachment to the amino group, $R^5$ represents a group selected from a halogen atom, cyano, (C$_1$-C$_4$)-alkyl, (C$_1$-C$_4$)-alkoxy, (C$_3$-C$_6$)-cycloalkyl, 3- to 6-membered heterocycle and (C$_1$-C$_4$)-alkylcarbonyl, wherein said (C$_1$-C$_4$)-alkyl is optionally substituted, identically or differently, with one or two groups selected from hydroxy, —NR$^{14}$R$^{15}$, (C$_1$-C$_4$)-alkoxy and cyclopropyl and optionally up to five fluorine atoms, wherein said cyclopropyl is optionally substituted with up to four fluorine atoms, wherein $R^{14}$ represents a hydrogen atom or (C$_1$-C$_4$)-alkyl, $R^{15}$ represents a hydrogen atom or (C$_1$-C$_4$)-alkyl, or $R^{14}$ and $R^{15}$ together with the nitrogen atom they are attached form a 3- to 6-membered heterocycle wherein said 3- to 6-membered heterocycle is optionally substituted, identically or differently, with one, two or three groups selected from (C$_1$-C$_4$)-alkyl and optionally up to five fluorine atoms, wherein said 3- to 6-membered heterocycle is optionally substituted, identically or differently, with one or two groups selected from (C$_1$-C$_4$)-alkyl and up to five fluorine atoms, wherein said 3- to 6-membered heterocycle is optionally substituted, identically or differently, with one or two groups selected from (C$_1$-C$_4$)-alkyl and optionally up to five fluorine atoms, wherein said (C$_3$-C$_6$)-cycloalkyl is optionally substituted, identically or differently, with one or two groups selected from (C$_1$-C$_4$)-alkyl and optionally up to five fluorine atoms, $R^6$ represents a phenyl group or (C$_4$-C$_6$)-cycloalkyl, wherein said phenyl group is optionally substituted, identically or differently, with one, two or three groups selected from a halogen atom, cyano, hydroxy, —(CH$_2$)$_n$NR$^{16}$R$^{17}$, (C$_1$-C$_4$)-alkyl, (C$_1$-C$_4$)-alkoxy, (C$_1$-C$_4$)-alkoxycarbonyl and —C(=O)—NR$^{18}$R$^{19}$, wherein said (C$_1$-C$_4$)-alkyl is optionally substituted with cyano and optionally with up to five fluorine atoms, wherein said (C$_1$-C$_4$)-alkoxy is optionally substituted with up to five fluorine atoms, wherein n represents 0 or 1, $R^{16}$ represents a hydrogen atom or (C$_1$-C$_4$)-alkyl, wherein said (C$_1$-C$_4$)-alkyl is optionally substituted with up to five fluorine atoms, $R^{17}$ represents a hydrogen atom or (C$_1$-C$_4$)-alkyl, wherein said (C$_1$-C$_4$)-alkyl is optionally substituted with up to five fluorine atoms, or $R^{16}$ and $R^{17}$ together with the nitrogen atom they are attached form a 3- to 8-membered heterocycle wherein said 3- to 8-membered heterocycle is optionally substituted, identically or differently, with one, two or three groups selected from (C$_1$-C$_4$)-alkyl and optionally up to five fluorine atoms, wherein $R^{18}$ represents a hydrogen atom or (C$_1$-C$_4$)-alkyl, $R^{19}$ represents a hydrogen atom or (C$_1$-C$_4$)-alkyl, or $R^{18}$ and $R^{19}$ together with the nitrogen atom they are attached form a 3- to 8-membered heterocycle wherein said 3- to 8-membered heterocycle is optionally substituted, identically or differently, with one, two or three groups selected from (C$_1$-C$_4$)-alkyl and optionally up to five fluorine atoms, wherein said (C$_4$-C$_6$)-cycloalkyl is optionally substituted, identically or differently, with one or two groups selected from (C$_1$-C$_4$)-alkyl and optionally up to five fluorine atoms, wherein said (C$_1$-C$_4$)-alkyl is optionally substituted with (C$_3$-C$_6$)-cycloalkyl and optionally up to five fluorine atoms, $R^7$ represents a hydrogen atom, (C$_1$-C$_4$)-alkyl, a phenyl group, a 5- to 6-membered heteroaryl group or (C$_1$-C$_4$)-alkylsulfonyl, wherein any phenyl group and any 5- to 6-membered heteroaryl are each optionally substituted, identically or differently, with one, two or three groups selected from a halogen atom, (C$_1$-C$_4$)-alkyl, trifluoromethyl, (C$_1$-C$_4$)-alkoxy and trifluoromethoxy, wherein said (C$_1$-C$_4$)-alkyl is optionally substituted with a group selected from (C$_3$-C$_6$)-cycloalkyl, 4- to 6-membered heterocycle, —NR$^{20}$R$^{21}$, (C$_1$-C$_4$)-alkoxy or benzyloxy and optionally with up to five fluorine atoms, wherein said (C$_3$-C$_6$)-cycloalkyl is optionally substituted, identically or differently, with one or two groups selected from (C$_1$-C$_4$)-alkyl and up to five fluorine atoms, wherein said 4- to 6-membered heterocycle is optionally substituted, identically or differently, with one or two groups selected from $(C_1-C_4)$-alkyl and optionally up to five fluorine atoms,
and
wherein
$R^{20}$ represents a hydrogen atom or $(C_1-C_4)$-alkyl,
$R^{21}$ represents a hydrogen atom or $(C_1-C_4)$-alkyl,
or
$R^{20}$ and $R^{21}$ together with the nitrogen atom they are attached form a 3- to 6-membered heterocycle
wherein said 3- to 6-membered heterocycle is optionally substituted, identically or differently, with one, two or three groups selected from $(C_1-C_4)$-alkyl and optionally up to five fluorine atoms,
$R^8$ represents a group selected from a halogen atom, cyano, $(C_1-C_4)$-alkyl, $(C_3-C_6)$-cycloalkyl, 3- to 6-membered heterocycle, $(C_1-C_4)$-alkylcarbonyl and a phenyl group,
wherein said $(C_1-C_4)$-alkyl is optionally substituted, identically or differently, with one or two groups selected from hydroxy, —$NR^{22}R^{23}$ $(C_1-C_4)$-alkoxy and cyclopropyl and optionally up to five fluorine atoms,
   wherein said cyclopropyl is optionally substituted with up to four fluorine atoms
wherein
$R^{22}$ represents a hydrogen atom or $(C_1-C_4)$-alkyl,
$R^{23}$ represents a hydrogen atom or $(C_1-C_4)$-alkyl,
or
$R^{22}$ and $R^{23}$ together with the nitrogen atom they are attached form a 3- to 6-membered heterocycle
wherein said 3- to 6-membered heterocycle is optionally substituted, identically or differently, with one, two or three groups selected from $(C_1-C_4)$-alkyl and optionally up to five fluorine atoms,
wherein said $(C_3-C_6)$-cycloalkyl is optionally substituted, identically or differently, with one or two groups selected from $(C_1-C_4)$-alkyl and optionally up to five fluorine atoms,
wherein said 3- to 6-membered heterocycle is optionally substituted, identically or differently, with one or two groups selected from $(C_1-C_4)$-alkyl and optionally up to five fluorine atoms,
and
wherein said phenyl group is optionally substituted, identically or differently, with one, two or three groups selected from a halogen atom, cyano, $(C_1-C_4)$-alkyl, trifluoromethyl, $(C_1-C_4)$-alkoxy and trifluoromethoxy,
$R^9$ represents a phenyl group, $(C_4-C_6)$-cycloalkyl or $(C_1-C_4)$-alkyl,
wherein said $(C_1-C_4)$-alkyl is optionally substituted with up to five fluorine atoms,
wherein said phenyl group is optionally substituted, identically or differently, with one, two or three groups selected from a halogen atom, cyano, hydroxy, —$(CH_2)_mNR^{24}R^{25}$, $(C_1-C_4)$-alkyl, $(C_1-C_4)$-alkoxy, $(C_1-C_4)$-alkoxycarbonyl and —$C(=O)$—$NR^{26}R^{27}$,
wherein said $(C_1-C_4)$-alkyl is optionally substituted with cyano and optionally with up to five fluorine atoms,
wherein said $(C_1-C_4)$-alkoxy is optionally substituted with up to five fluorine atoms,
wherein
m represents 0 or 1,
$R^{24}$ represents a hydrogen atom or $(C_1-C_4)$-alkyl,
wherein said $(C_1-C_4)$-alkyl is optionally substituted with up to five fluorine atoms,
$R^{25}$ represents a hydrogen atom or $(C_1-C_4)$-alkyl,
wherein said $(C_1-C_4)$-alkyl is optionally substituted with up to five fluorine atoms,
or
$R^{24}$ and $R^{25}$ together with the nitrogen atom they are attached form a 3- to 6-membered heterocycle
wherein said 3- to 6-membered heterocycle is optionally substituted, identically or differently, with one, two or three groups selected from $(C_1-C_4)$-alkyl and optionally up to five fluorine atoms,
wherein
$R^{26}$ represents a hydrogen atom or $(C_1-C_4)$-alkyl,
$R^{27}$ represents a hydrogen atom or $(C_1-C_4)$-alkyl,
or
$R^{26}$ and $R^{27}$ together with the nitrogen atom they are attached form a 3- to 8-membered heterocycle
wherein said 3- to 8-membered heterocycle is optionally substituted, identically or differently, with one, two or three groups selected from $(C_1-C_4)$-alkyl and optionally up to five fluorine atoms,
wherein said $(C_4-C_6)$-cycloalkyl is optionally substituted, identically or differently, with one or two groups selected from $(C_1-C_4)$-alkyl and optionally up to five fluorine atoms,
wherein said $(C_1-C_4)$-alkyl is optionally substituted with $(C_3-C_6)$-cycloalkyl and optionally up to five fluorine atoms,
$R^{10}$ represents a hydrogen atom, $(C_1-C_4)$-alkyl, $(C_3-C_5)$-cycloalkyl a phenyl group or a 5- to 6-membered heteroaryl group,
wherein any phenyl group and any 5- to 6-membered heteroaryl are each optionally substituted, identically or differently, with one, two or three groups selected from a halogen atom, $(C_1-C_4)$-alkyl, trifluoromethyl, $(C_1-C_4)$-alkoxy and trifluoromethoxy,
wherein said $(C_1-C_4)$-alkyl is optionally substituted with a group selected from $(C_3-C_6)$-cycloalkyl, 3- to 6-membered heterocycle, —$NR^{28}R^{29}$, $(C_1-C_4)$-alkoxy or benzyloxy and optionally with up to five fluorine atoms,
wherein said $(C_3-C_6)$-cycloalkyl is optionally substituted, identically or differently, with one or two groups selected from $(C_1-C_4)$-alkyl and optionally up to five fluorine atoms,
wherein said 3- to 6-membered heterocycle is optionally substituted, identically or differently, with one or two groups selected from $(C_1-C_4)$-alkyl and optionally up to five fluorine atoms,
and
wherein
$R^{28}$ represents a hydrogen atom or $(C_1-C_4)$-alkyl,
$R^{29}$ represents a hydrogen atom or $(C_1-C_4)$-alkyl,
or
$R^{28}$ and $R^{29}$ together with the nitrogen atom they are attached form a 3- to 6-membered heterocycle
wherein said 3- to 6-membered heterocycle is optionally substituted, identically or differently, with one, two or three groups selected from $(C_1-C_4)$-alkyl and optionally up to five fluorine atoms,
$R^{11}$ represents a group selected from a hydrogen atom, a fluorine atom, a chlorine atom, $(C_1-C_4)$-alkyl and cyclopropyl,
wherein said $(C_1-C_4)$-alkyl is optionally substituted with up to five fluorine atoms,
$R^{12}$ represents a phenyl group, a 5- to 6-membered heteroaryl group, $(C_4-C_6)$-cycloalkyl or $(C_1-C_4)$-alkyl,
wherein said phenyl group is optionally substituted, identically or differently, with one, two or three groups selected from a halogen atom, cyano, hydroxy, —$(CH_2)_pNR^{30}R^{31}$, $(C_1-C_4)$-alkyl, trifluoromethyl, $(C_1-C_4)$-alkoxy, trifluoromethoxy, $(C_1-C_4)$-alkoxycarbonyl and —$C(=O)$—$NR^{32}R^{33}$ wherein said $(C_4-C_6)$-cycloalkyl is optionally substituted, identically or differently, with one or two groups selected from $(C_1-C_4)$-alkyl and optionally up to five fluorine atoms,
wherein
p represents 0 or 1,
$R^{30}$ represents a hydrogen atom or $(C_1-C_4)$-alkyl,
wherein said $(C_1-C_4)$-alkyl is optionally substituted with up to five fluorine atoms,
$R^{31}$ represents a hydrogen atom or $(C_1-C_4)$-alkyl,
wherein said $(C_1-C_4)$-alkyl is optionally substituted with up to five fluorine atoms,
or
$R^{30}$ and $R^{31}$ together with the nitrogen atom they are attached form a 3- to 6-membered heterocycle
wherein said 3- to 6-membered heterocycle is optionally substituted, identically or differently, with one,
two or three groups selected from $(C_1-C_4)$-alkyl and optionally up to five fluorine atoms,
wherein
$R^{32}$ represents a hydrogen atom or $(C_1-C_4)$-alkyl,
$R^{33}$ represents a hydrogen atom or $(C_1-C_4)$-alkyl,
or
$R^{32}$ and $R^{33}$ together with the nitrogen atom they are attached form a 3- to 8-membered heterocycle
wherein said 3- to 8-membered heterocycle is optionally substituted, identically or differently, with one, two or three groups selected from $(C_1-C_4)$-alkyl and optionally up to five fluorine atoms,
$R^{13}$ represents a group selected from a hydrogen atom, a fluorine atom, a chlorine atom, $(C_1-C_4)$-alkyl and cyclopropyl,
wherein said $(C_1-C_4)$-alkyl is optionally substituted with up to five fluorine atoms,
$R^2$ represents a group selected from a hydrogen atom, $(C_1-C_4)$-alkyl, $(C_3-C_6)$-cycloalkyl and $(C_1-C_4)$-alkoxycarbonyl,
wherein said $(C_1-C_4)$-alkyl is optionally substituted, identically or differently, with one or two groups selected from hydroxy, $(C_1-C_4)$-alkoxy, cyclopropyl and optionally up to five fluorine atoms,
$R^3$ represents a group selected from a hydrogen atom, a halogen atom, cyano, $(C_1-C_6)$-alkyl, $(C_3-C_6)$-cycloalkyl, 3- to 6-membered heterocycle, 5- to 6-membered heteroaryl, —$(CH_2)_qC(=O)$—$NR^{34}R^{34}R^{35}$ $(C_1-C_4)$-alkylcarbonyl and $(C_1-C_4)$-alkoxycarbonyl,
wherein said $(C_1-C_6)$-alkyl is optionally substituted, identically or differently, with one or two groups selected from hydroxy, cyano, $(C_1-C_4)$-alkoxy, $(C_1-C_4)$-alkoxycarbonyl and cyclopropyl and optionally up to five fluorine atoms,
wherein said $(C_3-C_6)$-cycloalkyl is optionally substituted, identically or differently, with one or two groups selected from $(C_1-C_4)$-alkyl, $(C_1-C_4)$-alkoxy, and cyclopropyl and optionally up to five fluorine atoms,
wherein said 3- to 6-membered heterocycle is optionally substituted, identically or differently, with one or two groups selected from $(C_1-C_4)$-alkyl, $(C_1-C_4)$-alkoxy, and cyclopropyl and optionally up to five fluorine atoms,
wherein said 5- to 6-membered heteroaryl is optionally substituted, identically or differently, with one or two groups selected from $(C_1-C_4)$-alkyl, $(C_1-C_4)$-alkoxy, and cyclopropyl and optionally up to five fluorine atoms,
wherein
q represents 0 or 1,
$R^{34}$ represents a hydrogen atom or $(C_1-C_4)$-alkyl,
$R^{35}$ represents a hydrogen atom, $(C_1-C_4)$-alkyl or phenyl,
or
$R^{34}$ and $R^{35}$ together with the nitrogen atom they are attached form a 3- to 7-membered heterocyclyl ring
wherein said 3- to 7-membered heterocyclyl ring is optionally substituted, identically or differently, with one, two or three groups selected from a fluorine atom, hydroxy, $(C_1-C_4)$-alkyl, $(C_1-C_4)$-alkoxy, cyclopropyl, difluoromethyl, trifluoromethyl and trifluoromethoxy,
or
$R^2$ and $R^3$ together with the carbon atoms they are attached form a 4- to 6-membered carbocycle, a 4- to 7-membered heterocycle, a 5- to 6-membered heteroaryl group or a phenyl ring,
wherein said 4- to 7-membered heterocycle is optionally substituted, identically or differently, with one or two groups selected from a fluorine atom, hydroxy, oxo, $(C_1-C_4)$-alkyl, trifluoromethyl, $(C_1-C_4)$-alkylcarbonyl and $(C_1-C_4)$-alkoxycarbonyl and optionally up to five fluorine atoms,
wherein said 4- to 6-membered carbocycle is optionally substituted, identically or differently, with one or two groups selected from a fluorine atom, hydroxy, oxo, $(C_1-C_4)$-alkyl, trifluoromethyl, $(C_1-C_4)$-alkylcarbonyl and $(C_1-C_4)$-alkoxycarbonyl and optionally up to five fluorine atoms,
and
wherein any phenyl group and any 5- to 6-membered heteroaryl group are each optionally substituted, identically or differently, with one, two or three groups selected from a halogen atom, $(C_1-C_4)$-alkyl, trifluoromethyl, $(C_1-C_4)$-alkoxy and trifluoromethoxy,
$R^4$ represents a group selected from a hydrogen atom, $(C_1-C_4)$-alkyl, $(C_3-C_6)$-cycloalkyl and $(C_1-C_4)$-alkoxycarbonyl and hydroxy,
wherein said $(C_1-C_4)$-alkyl is optionally substituted, identically or differently, with one or two groups selected from hydroxy, $(C_1-C_4)$-alkoxy and cyclopropyl and optionally up to five fluorine atoms,
$R^3$ and $R^4$ together with the carbon atoms they are attached form a 4- to 6-membered carbocycle, a 4- to 7-membered heterocycle, a 5- to 6-membered heteroaryl group or a phenyl ring,
wherein said 4- to 7-membered heterocycle is optionally substituted, identically or differently, with one or two groups selected from a fluorine atom, hydroxy, oxo, $(C_1-C_4)$-alkyl, trifluoromethyl, $(C_1-C_4)$-alkylcarbonyl and $(C_1-C_4)$-alkoxycarbonyl and optionally up to five fluorine atoms,
wherein said 4- to 6-membered carbocycle is optionally substituted, identically or differently, with one or two groups selected from a fluorine atom, hydroxy, oxo, $(C_1-C_4)$-alkyl, trifluoromethyl, $(C_1-C_4)$-alkylcarbonyl and $(C_1-C_4)$-alkoxycarbonyl and optionally up to five fluorine atoms,
and
wherein any phenyl group and any 5- to 6-membered heteroaryl group are each optionally substituted, identically or differently, with one, two or three groups selected from a halogen atom, $(C_1-C_4)$-alkyl, trifluoromethyl, $(C_1-C_4)$-alkoxy and trifluoromethoxy,
or a stereoisomer, a tautomer, an N-oxide, a hydrate, a solvate, or a salt thereof, or a mixture of same.

Preference is also given to compounds of the formula (I) in which
R¹ represents a group of the formula

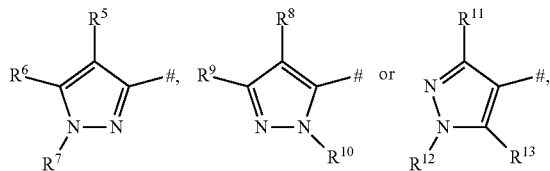

in which
# represents the point of attachment to the amino group,
R⁵ represents a group selected from fluorine, chlorine, cyano, (C₁-C₄)-alkyl, methoxy, ethoxy, (C₃-C₅)-cycloalkyl, 4- to 6-membered heterocycle, methylcarbonyl and ethylcarbonyl,
wherein said (C₁-C₄)-alkyl is optionally substituted, identically or differently, with one or two groups selected from hydroxy, —NR¹⁴R¹⁵, methoxy, ethoxy and cyclopropyl and optionally up to five fluorine atoms,
  wherein said cyclopropyl is optionally substituted with up to four fluorine atoms,
wherein
R¹⁴ represents a hydrogen atom or (C₁-C₄)-alkyl,
R¹⁵ represents a hydrogen atom or (C₁-C₄)-alkyl,
or
R¹⁴ and R¹⁵ together with the nitrogen atom they are attached form a 3- to 6-membered heterocycle
wherein said 3- to 6-membered heterocycle is optionally substituted, identically or differently, with one, two or three groups selected from (C₁-C₄)-alkyl and optionally up to five fluorine atoms,
wherein said (C₃-C₅)-cycloalkyl is optionally substituted with up to four fluorine atoms,
wherein said 4- to 6-membered heterocycle is optionally substituted up to four fluorine atoms,
R⁶ represents a phenyl group or cyclohexyl,
wherein said phenyl group is optionally substituted, identically or differently, with one, two or three groups selected from fluorine, chlorine, —(CH₂)ᵣCN, hydroxy, —NR¹⁶R¹⁷, (C₁-C₃)-alkyl, (C₁-C₃)-alkoxy, methoxycarbonyl, ethoxycarbonyl and —C(=O)—NR¹⁸R¹⁹
wherein said (C₁-C₃)-alkyl is optionally substituted with up to three fluorine atoms,
wherein said (C₁-C₃)-alkoxy is optionally substituted with up to three fluorine atoms,
wherein
r represents 0 or 1,
R¹⁶ represents a hydrogen atom or (C₁-C₄)-alkyl,
R¹⁷ represents a hydrogen atom or (C₁-C₄)-alkyl,
or
R¹⁶ and R¹⁷ together with the nitrogen atom they are attached form a 3- to 6-membered heterocycle
wherein said 3- to 6-membered heterocycle is optionally substituted, identically or differently, with one, two or three groups selected from (C₁-C₄)-alkyl and optionally up to four fluorine atoms,
wherein
R¹⁸ represents a hydrogen atom or (C₁-C₄)-alkyl,
R¹⁹ represents a hydrogen atom or (C₁-C₄)-alkyl,
or
R¹⁸ and R¹⁹ together with the nitrogen atom they are attached form a 3- to 8-membered heterocycle
wherein said 3- to 8-membered heterocycle is optionally substituted, identically or differently, with one, two or three groups selected from (C₁-C₄)-alkyl and optionally up to four fluorine atoms,
wherein said cyclohexyl is optionally substituted, identically or differently, with one or two groups selected from (C₁-C₄)-alkyl and optionally up to four fluorine atoms,
R⁷ represents a hydrogen atom, (C₁-C₄)-alkyl, (C₃-C₅)-cycloalkyl, methylsulfonyl or ethylsulfonyl,
wherein said (C₁-C₄)-alkyl is optionally substituted with a group selected from (C₃-C₆)-cycloalkyl, 4- to 6-membered heterocycle, —NR²⁰R²¹, methoxy, ethoxy or benzyloxy and optionally with up to five fluorine atoms,
wherein said (C₃-C₆)-cycloalkyl is optionally substituted with up to four fluorine atoms,
wherein said 4- to 6-membered heterocycle is optionally substituted, identically or differently, with one or two groups selected from (C₁-C₄)-alkyl and optionally up to five fluorine atoms,
and
wherein
R²⁰ represents a hydrogen atom or (C₁-C₄)-alkyl,
R²¹ represents a hydrogen atom or (C₁-C₄)-alkyl,
or
R²⁰ and R²¹ together with the nitrogen atom they are attached form a 3- to 6-membered heterocycle
wherein said 3- to 6-membered heterocycle is optionally substituted, identically or differently, with one, two or three groups selected from (C₁-C₄)-alkyl and optionally up to five fluorine atoms,
R⁸ represents a group selected from fluorine, chlorine, cyano, (C₁-C₄)-alkyl, methoxy, ethoxy, (C₃-C₅)-cycloalkyl, 4- to 6-membered heterocycle and a phenyl group,
wherein said (C₁-C₄)-alkyl is optionally substituted with hydroxy, methoxy, —NR²²R²³ and cyclopropyl and optionally up to five fluorine atoms,
  wherein said cyclopropyl is optionally substituted with up to four fluorine atoms
wherein
R²² represents a hydrogen atom or (C₁-C₄)-alkyl,
R²³ represents a hydrogen atom or (C₁-C₄)-alkyl,
or
R²² and R²³ together with the nitrogen atom they are attached form a 3- to 6-membered heterocycle
wherein said 3- to 6-membered heterocycle is optionally substituted, identically or differently, with one, two or three groups selected from (C₁-C₄)-alkyl and optionally up to five fluorine atoms,
wherein said (C₃-C₅)-cycloalkyl is optionally substituted with up to four fluorine atoms,
wherein said 4- to 6-membered heterocycle is optionally substituted up to four fluorine atoms,
and
wherein said phenyl group is optionally substituted with fluorine, chlorine, cyano, methyl, trifluoromethyl, methoxy and trifluoromethoxy,
R⁹ represents a phenyl group, cyclohexyl or (C₁-C₄)-alkyl,
wherein said (C₁-C₄)-alkyl is optionally substituted with up to five fluorine atoms,
wherein said phenyl group is optionally substituted, identically or differently, with one, two or three groups selected from fluorine, chlorine, (CH₂)ₜCN, hydroxy, —NR²⁴R²⁵, (C₁-C₃)-alkyl, (C₁-C₃)-alkoxy, trifluoromethoxy, methoxycarbonyl, ethoxycarbonyl and —C(=O)—NR²⁶R²⁷
  wherein
  t represents 0 or 1, wherein said $(C_1-C_3)$-alkyl is optionally substituted with up to three fluorine atoms, wherein said $(C_1-C_3)$-alkoxy is optionally substituted with up to three fluorine atoms, wherein $R^{24}$ represents a hydrogen atom or $(C_1-C_4)$-alkyl, $R^{25}$ represents a hydrogen atom or $(C_1-C_4)$-alkyl, or $R^{24}$ and $R^{25}$ together with the nitrogen atom they are attached form a 3- to 6-membered heterocycle wherein said 3- to 6-membered heterocycle is optionally substituted, identically or differently, with one, two or three groups selected from $(C_1-C_4)$-alkyl and optionally up to five fluorine atoms, wherein $R^{26}$ represents a hydrogen atom or $(C_1-C_4)$-alkyl, $R^{27}$ represents a hydrogen atom or $(C_1-C_4)$-alkyl, or $R^{26}$ and $R^{27}$ together with the nitrogen atom they are attached form a 3- to 5-membered heterocycle wherein said 3- to 5-membered heterocycle is optionally substituted, identically or differently, with one, two or three groups selected from $(C_1-C_4)$-alkyl and optionally up to five fluorine atoms, wherein said cyclohexyl is optionally substituted, identically or differently, with one or two groups selected from $(C_1-C_4)$-alkyl and optionally up to five fluorine atoms, $R^{10}$ represents a hydrogen atom, $(C_1-C_4)$-alkyl or $(C_3-C_5)$-cycloalkyl, wherein said $(C_1-C_4)$-alkyl is optionally substituted with a group selected from $(C_3-C_6)$-cycloalkyl, 4- to 6-membered heterocycle, —NR$^{28}$R$^{29}$, methoxy, ethoxy or benzyloxy and optionally with up to five fluorine atoms, wherein said $(C_3-C_6)$-cycloalkyl is optionally substituted with up to four fluorine atoms, wherein said 4- to 6-membered heterocycle is optionally substituted with up to four fluorine atoms, and wherein $R^{28}$ represents a hydrogen atom or $(C_1-C_4)$-alkyl, $R^{29}$ represents a hydrogen atom or $(C_1-C_4)$-alkyl, or $R^{28}$ and $R^{29}$ together with the nitrogen atom they are attached form a 3- to 6-membered heterocycle wherein said 3- to 6-membered heterocycle is optionally substituted, identically or differently, with one, two or three groups selected from $(C_1-C_4)$-alkyl and optionally up to five fluorine atoms, $R^{11}$ represents a group selected from a hydrogen atom, $(C_1-C_4)$-alkyl and cyclopropyl, wherein said $(C_1-C_4)$-alkyl is optionally substituted with up to five fluorine atoms, $R^{12}$ represents a phenyl group, wherein said phenyl group is optionally substituted, identically or differently, with one or two groups selected from fluorine, chlorine, cyano, methyl, trifluoromethyl, methoxy, trifluoromethoxy and methoxycarbonyl, $R^{13}$ represents a group selected from a hydrogen atom, $(C_1-C_4)$-alkyl and cyclopropyl, wherein said $(C_1-C_4)$-alkyl is optionally substituted with up to five fluorine atoms, $R^2$ represents a group selected from a hydrogen atom, $(C_1-C_4)$-alkyl, cyclopropyl, methoxycarbonyl and ethoxycarbonyl, wherein said $(C_1-C_4)$-alkyl is optionally substituted, identically or differently, with one or two groups selected from hydroxy, methoxy, ethoxy, cyclopropyl and optionally up to five fluorine atoms, $R^3$ represents a group selected from a hydrogen atom, fluorine, chlorine, cyano, $(C_1-C_6)$-alkyl, $(C_3-C_5)$-cycloalkyl, 4- to 6-membered heterocycle, 5- to 6-membered heteroaryl, —C(=O)—NR$^{34}$R$^{35}$ methylcarbonyl, ethylcarbonyl and $(C_1-C_4)$-alkoxycarbonyl, wherein said $(C_1-C_6)$-alkyl is optionally substituted, identically or differently, with one or two groups selected from hydroxy, cyano, methoxy, ethoxy, methoxycarbonyl, ethoxycarbonyl and cyclopropyl and optionally up to five fluorine atoms, wherein said $(C_3-C_6)$-cycloalkyl is optionally substituted with up to four fluorine atoms, wherein said 3- to 6-membered heterocycle is optionally substituted with up to four fluorine atoms, wherein said 5- to 6-membered heteroaryl is optionally substituted, identically or differently, with one or two groups selected from methyl, ethyl and methoxy and optionally up to four fluorine atoms, wherein $R^{34}$ represents a hydrogen atom or $(C_1-C_4)$-alkyl, $R^{35}$ represents a hydrogen atom or $(C_1-C_4)$-alkyl, or $R^{34}$ and $R^{35}$ together with the nitrogen atom they are attached form a $(C_3-C_7)$-heterocyclyl ring wherein said $(C_3-C_7)$-heterocyclyl ring is optionally substituted, identically or differently, with one, two or three groups selected from a fluorine atom, hydroxy, methyl, ethyl, methoxy, ethoxy, cyclopropyl, difluoromethyl, trifluoromethyl and trifluoromethoxy, or $R^2$ and $R^3$ together with the carbon atoms they are attached form a 4- to 6-membered carbocycle, a 4- to 7-membered heterocycle, a 5- to 6-membered heteroaryl group or a phenyl ring, wherein said 4- to 7-membered heterocycle is optionally substituted, identically or differently, with one or two groups selected from oxo, methyl, ethyl, trifluoromethyl and $(C_1-C_4)$-alkoxycarbonyl and optionally up to four fluorine atoms, wherein said 4- to 6-membered carbocycle is optionally substituted, identically or differently, with one or two groups selected from oxo, methyl, ethyl, trifluoromethyl and $(C_1-C_4)$-alkoxycarbonyl and optionally up to four fluorine atoms, and wherein any phenyl group and any 5- to 6-membered heteroaryl group are each optionally substituted, identically or differently, with one or two groups selected from fluorine, chlorine, methyl, ethyl, trifluoromethyl, methoxy and trifluoromethoxy, $R^4$ represents a group selected from a hydrogen atom, $(C_1-C_4)$-alkyl, cyclopropyl, methoxycarbonyl, ethoxycarbonyl and hydroxy, wherein said $(C_1-C_4)$-alkyl is optionally substituted, identically or differently, with one or two groups selected from hydroxy, methoxy and cyclopropyl and optionally up to five fluorine atoms, or $R^3$ and $R^4$ together with the carbon atoms they are attached form a 4- to 6-membered carbocycle, a 4- to 7-membered heterocycle, a 5- to 6-membered heteroaryl group or a phenyl ring, wherein said 4- to 7-membered heterocycle is optionally substituted, identically or differently, with one or two groups selected from oxo, methyl, ethyl, trifluoromethyl and ($C_1$-$C_4$)-alkoxycarbonyl and optionally up to four fluorine atoms,
wherein said 4- to 6-membered carbocycle is optionally substituted, identically or differently, with one or two groups selected from oxo, hydroxyl, methyl, ethyl, trifluoromethyl and ($C_1$-$C_4$)-alkoxycarbonyl and optionally up to four fluorine atoms,
and
wherein any phenyl group and any 5- to 6-membered heteroaryl group are each optionally substituted, identically or differently, with one or two groups selected from fluorine, chlorine, methyl, ethyl, trifluoromethyl, methoxy and trifluoromethoxy,
or a stereoisomer, a tautomer, an N-oxide, a hydrate, a solvate, or a salt thereof, or a mixture of same.

Preference is also given to compounds of the formula (I) in which:
$R^1$ represents a group of the formula

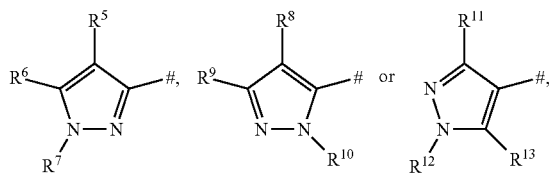

in which
# represents the point of attachment to the amino group,
$R^5$ represents a group selected from chlorine, ($C_1$-$C_4$)-alkyl, methoxy, ethoxy, ($C_3$-$C_5$)-cycloalkyl and 4- to 6-membered heterocycle,
wherein said ($C_1$-$C_4$)-alkyl is optionally substituted with a group selected from methoxy, —$NR^{14}R^{15}$, cyclopropyl and optionally up to three fluorine atoms,
wherein
$R^{14}$ represents ($C_1$-$C_4$)-alkyl,
$R^{15}$ represents ($C_1$-$C_4$)-alkyl,
or
$R^{14}$ and $R^{15}$ together with the nitrogen atom they are attached form a 3- to 6-membered heterocycle
wherein said ($C_3$-$C_5$)-cycloalkyl is optionally substituted with up to four fluorine atoms, wherein said 4- to 6-membered heterocycle is optionally substituted up to four fluorine atoms,
$R^6$ represents a phenyl group,
wherein said phenyl group is optionally substituted, identically or differently, with one or two groups selected from fluorine, chlorine, cyano, hydroxy, —$NR^{16}R^{17}$, methyl, methoxy, ethoxy, trifluoromethoxy, methoxycarbonyl, ethoxycarbonyl and —C(=O)—$NR^{18}R^{19}$,
wherein said methyl is optionally substituted with up to three fluorine atoms,
wherein
$R^{16}$ represents ($C_1$-$C_4$)-alkyl,
$R^{17}$ represents ($C_1$-$C_4$)-alkyl,
or
$R^{16}$ and $R^{17}$ together with the nitrogen atom they are attached form a 3- to 6-membered heterocycle
wherein said 3- to 6-membered heterocycle is optionally substituted, identically or differently, with one, two or three groups selected from ($C_1$-$C_4$)-alkyl and optionally up to four fluorine atoms,
wherein
$R^{18}$ represents ($C_1$-$C_4$)-alkyl,
$R^{19}$ represents ($C_1$-$C_4$)-alkyl,
or
$R^{18}$ and $R^{19}$ together with the nitrogen atom they are attached form a 3- to 6-membered heterocycle
wherein said 3- to 6-membered heterocycle is optionally substituted, identically or differently, with one, two or three groups selected from ($C_1$-$C_4$)-alkyl and optionally up to four fluorine atoms,
$R^7$ represents a hydrogen atom or ($C_1$-$C_4$)-alkyl,
wherein said ($C_1$-$C_4$)-alkyl is optionally substituted with a group selected from ($C_3$-$C_6$)-cycloalkyl, 4- to 6-membered heterocycle, —$NR^{20}R^{21}$ and optionally with up to three fluorine atoms,
wherein said 4- to 6-membered heterocycle is optionally substituted, identically or differently, with one or two groups selected from ($C_1$-$C_4$)-alkyl and optionally up to five fluorine atoms,
and
wherein
$R^{20}$ represents a hydrogen atom or ($C_1$-$C_4$)-alkyl,
$R^{21}$ represents a hydrogen atom or ($C_1$-$C_4$)-alkyl,
or
$R^{20}$ and $R^{21}$ together with the nitrogen atom they are attached form a 3- to 6-membered heterocycle
wherein said 3- to 6-membered heterocycle is optionally substituted, identically or differently, with one, two or three groups selected from ($C_1$-$C_4$)-alkyl and optionally up to five fluorine atoms,
$R^8$ represents a group selected from chlorine, ($C_1$-$C_4$)-alkyl, methoxy, ethoxy, ($C_3$-$C_6$)-cycloalkyl and 4- to 6-membered heterocycle,
wherein said ($C_1$-$C_4$)-alkyl is optionally substituted with a group selected from methoxy —$NR^{22}R^{23}$, cyclopropyl and optionally up to three fluorine atoms,
wherein
$R^{22}$ represents ($C_1$-$C_4$)-alkyl,
$R^{23}$ represents ($C_1$-$C_4$)-alkyl,
or
$R^{22}$ and $R^{23}$ together with the nitrogen atom they are attached form a 3- to 6-membered heterocycle
wherein said ($C_3$-$C_6$)-cycloalkyl is optionally substituted with up to four fluorine atoms,
wherein said 4- to 6-membered heterocycle is optionally substituted up to four fluorine atoms,
$R^9$ represents a phenyl group,
wherein said phenyl group is optionally substituted, identically or differently, with one or two groups selected from fluorine, chlorine, cyano, hydroxy, —$NR^{24}R^{25}$, methyl, methoxy, ethoxy, trifluoromethoxy, methoxycarbonyl, ethoxycarbonyl and —C(=O)—$NR^{26}R^{27}$
wherein said methyl is optionally substituted with up to three fluorine atoms,
wherein
$R^{24}$ represents ($C_1$-$C_4$)-alkyl,
$R^{25}$ represents ($C_1$-$C_4$)-alkyl,
or
$R^{24}$ and $R^{25}$ together with the nitrogen atom they are attached form a 3- to 6-membered heterocycle
wherein said 3- to 6-membered heterocycle is optionally substituted, identically or differently, with one, two or three groups selected from ($C_1$-$C_4$)-alkyl and optionally up to five fluorine atoms,
wherein
$R^{26}$ represents ($C_1$-$C_4$)-alkyl,
$R^{27}$ represents ($C_1$-$C_4$)-alkyl, or
$R^{26}$ and $R^{27}$ together with the nitrogen atom they are attached form a 3- to 5-membered heterocycle wherein said 3- to 5-membered heterocycle is optionally substituted, identically or differently, with one, two or three groups selected from $(C_1-C_4)$-alkyl and optionally up to five fluorine atoms, $R^{10}$ represents a hydrogen atom, $(C_1-C_4)$-alkyl or cyclopropyl, wherein said $(C_1-C_4)$-alkyl is optionally substituted with a group selected from $(C_3-C_6)$-cycloalkyl, 4- to 6-membered heterocycle, —NR$^{28}$R$^{29}$ and optionally with up to three fluorine atoms, wherein said $(C_3-C_6)$-cycloalkyl is optionally substituted with up to four fluorine atoms, wherein said 4- to 6-membered heterocycle is optionally substituted with up to four fluorine atoms, and wherein
$R^{28}$ represents a hydrogen atom or $(C_1-C_4)$-alkyl,
$R^{29}$ represents $(C_1-C_4)$-alkyl,
or
$R^{28}$ and $R^{29}$ together with the nitrogen atom they are attached form a 3- to 6-membered heterocycle
wherein said 3- to 6-membered heterocycle is optionally substituted, identically or differently, with one, two or three groups selected from $(C_1-C_4)$-alkyl and optionally up to five fluorine atoms, $R^{11}$ represents cyclopropyl or methyl,
wherein said methyl is optionally substituted with up to three fluorine atoms, $R^{12}$ represents a phenyl group,
wherein said phenyl group is optionally substituted, identically or differently, with one or two groups selected from fluorine, chlorine or cyano, $R^{13}$ represents a group selected from a hydrogen atom, methyl and cyclopropyl,
wherein said methyl is optionally substituted with up to three fluorine atoms, $R^2$ represents a hydrogen atom or methyl,
wherein said methyl is optionally substituted with up to three fluorine atoms, $R^3$ represents a group selected from a hydrogen atom, fluorine, chlorine, cyano, $(C_1-C_4)$-alkyl, $(C_3-C_5)$-cycloalkyl, 4- to 6-membered heterocycle, 5- to 6-membered heteroaryl, —C(=O)—NR$^{34}$R$^{35}$ methoxycarbonyl and ethoxycarbonyl, wherein said $(C_1-C_4)$-alkyl is optionally substituted with a group selected from hydroxy, cyano, methoxy, ethoxy, methoxycarbonyl, ethoxycarbonyl and cyclopropyl and optionally up to five fluorine atoms, wherein said $(C_3-C_5)$-cycloalkyl is optionally substituted with up to four fluorine atoms, wherein said 3- to 6-membered heterocycle is optionally substituted with up to four fluorine atoms, wherein said 5- to 6-membered heteroaryl is optionally substituted, identically or differently, with one or two groups selected from methyl, ethyl and methoxy and optionally up to three fluorine atoms, wherein
$R^{34}$ represents a hydrogen atom or $(C_1-C_4)$-alkyl,
$R^{35}$ represents $(C_1-C_4)$-alkyl,
or
$R^{34}$ and $R^{35}$ together with the nitrogen atom they are attached form a 3- to 6-membered heterocycle ring
wherein said 3- to 6-membered heterocycle ring is optionally substituted, identically or differently, with one or two groups selected from a fluorine atom, methyl, difluoromethyl, trifluoromethyl and trifluoromethoxy, or
$R^2$ and $R^3$ together with the carbon atoms they are attached form a phenyl or a 4- to 6-membered carbocycle, wherein said phenyl group is optionally substituted, identically or differently, with one or two groups selected from fluorine, chlorine, methyl, trifluoromethyl, methoxy and trifluoromethoxy, wherein said 4- to 6-membered carbocycle is optionally substituted, identically or differently, with one or two groups selected from oxo, methyl, ethyl, trifluoromethyl and $(C_1-C_4)$-alkoxycarbonyl and optionally up to four fluorine atoms, $R^4$ represents a group selected from a hydrogen atom, $(C_1-C_4)$-alkyl, hydroxy and cyclopropyl, wherein said $(C_1-C_4)$-alkyl is optionally substituted with a group selected from hydroxy, methoxy and cyclopropyl and optionally up to five fluorine atoms, or
$R^3$ and $R^4$ together with the carbon atoms they are attached form a 4- to 6-membered carbocycle, a 4- to 6-membered heterocycle, a 5- to 6-membered heteroaryl group or a phenyl ring, wherein said 4- to 6-membered heterocycle is optionally substituted, identically or differently, with one or two groups selected from oxo, methyl, ethyl, trifluoromethyl and $(C_1-C_4)$-alkoxycarbonyl and optionally up to four fluorine atoms, wherein said 4- to 6-membered carbocycle is optionally substituted, identically or differently, with one or two groups selected from oxo, hydroxyl, methyl, ethyl, trifluoromethyl and $(C_1-C_4)$-alkoxycarbonyl and optionally up to four fluorine atoms, and
wherein any phenyl group and any 5- to 6-membered heteroaryl group are each optionally substituted, identically or differently, with one or two groups selected from fluorine, chlorine, methyl, ethyl, trifluoromethyl, methoxy and trifluoromethoxy, or a stereoisomer, a tautomer, an N-oxide, a hydrate, a solvate, or a salt thereof, or a mixture of same.

Preference is also given to compounds of the formula (I) in which,
$R^1$ represents a group of the formula in which
# represents the point of attachment to the amino group,
$R^5$ represents a group selected from chlorine, methyl, ethyl, methoxy and cyclopropyl
wherein said methyl is optionally substituted with a group selected from methoxy and cyclopropyl and optionally up to three fluorine atoms,
$R^6$ represents a phenyl group,
wherein said phenyl group is optionally substituted, identically or differently, with one or two groups selected from fluorine, chlorine, cyano, methyl, methoxy, ethoxy, trifluoromethoxy, methoxycarbonyl and ethoxycarbonyl, wherein said methyl is optionally substituted with up to three fluorine atoms,
$R^7$ represents a hydrogen atom, methyl, ethyl or cyclopropyl,
wherein said methyl and ethyl are optionally substituted with cyclopropyl and optionally with up to three fluorine atoms,
$R^8$ represents a group selected from chlorine, methyl, ethyl, methoxy and cyclopropyl,
wherein said methyl is optionally substituted with a group selected from methoxy and cyclopropyl and optionally up to three fluorine atoms,
$R^9$ represents a phenyl group,
wherein said phenyl group is optionally substituted, identically or differently, with one or two groups selected from fluorine, chlorine, cyano, methyl, methoxy, ethoxy, trifluoromethoxy, methoxycarbonyl and ethoxycarbonyl,
wherein said methyl is optionally substituted with up to three fluorine atoms,
$R^{10}$ represents a hydrogen atom, methyl, ethyl or cyclopropyl,
wherein said methyl and ethyl are optionally substituted with cyclopropyl and optionally with up to three fluorine atoms,
$R^{11}$ represents cyclopropyl or methyl,
wherein said methyl is optionally substituted with up to three fluorine atoms,
$R^{12}$ represents a phenyl group,
wherein said phenyl group is optionally substituted, identically or differently, with one or two groups selected from fluorine, chlorine or cyano,
$R^{13}$ represents a group selected from a hydrogen atom, methyl and cyclopropyl,
wherein said methyl is optionally substituted with up to three fluorine atoms,
$R^2$ represents a hydrogen atom or methyl,
$R^3$ represents a group selected from a hydrogen atom, fluorine, chlorine, cyano, ($C_1$-$C_4$)-alkyl, cyclopropyl, 4- to 6-membered heterocycle, 5- to 6-membered heteroaryl, —C(=O)—NR$^{34}$R$^{35}$, methoxycarbonyl and ethoxycarbonyl,
wherein said ($C_1$-$C_4$)-alkyl is optionally substituted with a group selected from hydroxy, ethoxycarbonyl and cyclopropyl and optionally up to three fluorine atoms,
wherein said 5- to 6-membered heteroaryl is optionally substituted, identically or differently, with one or two groups selected from methyl, ethyl and methoxy and optionally up to two fluorine atoms,
wherein
$R^{34}$ represents a hydrogen atom, methyl or ethyl,
$R^{35}$ represents methyl or ethyl,
or
$R^{34}$ and $R^{35}$ together with the nitrogen atom they are attached form a 4- to 6-membered heterocycle ring
wherein said 4- to 6-membered heterocycle ring is optionally substituted, identically or differently, with one or two groups selected from a fluorine atom, methyl, difluoromethyl and trifluoromethyl,
or
$R^2$ and $R^3$ together with the carbon atoms they are attached form a phenyl or a 5- to 6-membered carbocycle,
wherein said phenyl group is optionally substituted with one or two fluorine atoms,
wherein said 5- to 6-membered carbocycle is optionally substituted, with up to four fluorine atoms,
$R^4$ represents a group selected from a hydrogen atom, methyl and cyclopropyl, wherein said methyl is optionally substituted with up to three fluorine atoms,
or
$R^3$ and $R^4$ together with the carbon atoms they are attached form a 5- to 6-membered carbocycle, a 4- to 6-membered heterocycle, a 5- to 6-membered heteroaryl group or a phenyl ring,
wherein said 4- to 6-membered heterocycle is optionally substituted, identically or differently, with ($C_1$-$C_4$)-alkoxycarbonyl and optionally up to four fluorine atoms,
wherein said 4- to 6-membered carbocycle is optionally substituted with up to four fluorine atoms, and
wherein any phenyl group and any 5- to 6-membered heteroaryl group are each optionally substituted with one or two fluorine atoms,
or a stereoisomer, a tautomer, an N-oxide, a hydrate, a solvate, or a salt thereof, or a mixture of same.

Preference is also given to compounds of the formula (I) in which
$R^1$ represents a group of the formula

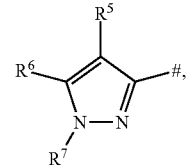

in which
# represents the point of attachment to the amino group,
$R^5$ represents a group selected from chlorine, methyl, ethyl, methoxy or cyclopropyl,
    wherein said methyl and ethyl are optionally substituted with methoxy or optionally with up to three fluorine atoms,
    wherein said methoxy is optionally substituted with up to three fluorine atoms,
$R^6$ represents 5-fluoropyridin-2-yl, 6-trifluoromethylpyridin-3-yl or cyclohexyl,
or
represents a group of the formula

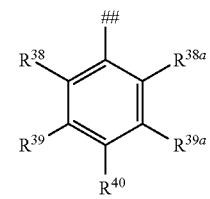

in which
## represents the point of attachment to the pyrazole ring,
$R^{38}$ represents a hydrogen atom or fluorine,
$R^{38a}$ represents a hydrogen atom,
$R^{39}$ represents a hydrogen atom,
$R^{39a}$ represents a hydrogen atom or cyano,
$R^{40}$ represents a hydrogen atom, fluorine, chlorine, cyano, methyl, difluoromethyl, trifluoromethyl, methoxy, ethoxy, difluoromethoxy, trifluoromethoxy, methoxycarbonyl or ethoxycarbonyl,
$R^7$ represents a hydrogen atom, methyl, ethyl, cyclopropylmethyl, 2-cyclopropylethyl or 2,2-difluoroethyl, with the proviso that if $R^5$ is methoxy, difluoromethoxy or trifluoromethoxy then $R^7$ is different from hydrogen, with the proviso that if $R^6$ is 2-pyridinyl then $R^7$ is different from hydrogen, and stereoisomers, tautomers, hydrates, solvates, and salts thereof, and mixtures of same.

Preference is also given to compounds of the formula (I) in which $R^1$ represents a group of the formula

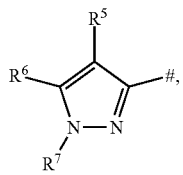

in which

\# represents the point of attachment to the amino group, $R^5$ represents a group selected from chlorine, methyl, ethyl, methoxy or cyclopropyl,
  wherein said methyl and ethyl are optionally substituted with methoxy or optionally with up to three fluorine atoms,
  wherein said methoxy is optionally substituted with up to three fluorine atoms, $R^6$ represents 5-fluoropyridin-2-yl, 6-trifluoromethylpyridin-3-yl or cyclohexyl,
  or
  represents a group of the formula

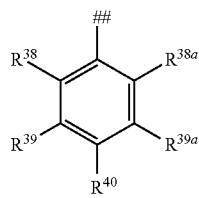

in which

\#\# represents the point of attachment to the pyrazole ring, $R^{38}$ represents a hydrogen atom, $R^{38a}$ represents a hydrogen atom, $R^{39}$ represents a hydrogen atom, $R^{39a}$ represents a hydrogen atom, $R^{40}$ represents a hydrogen atom, fluorine, chlorine, cyano, methyl, difluoromethyl, trifluoromethyl, methoxy, ethoxy, difluoromethoxy, trifluoromethoxy, methoxycarbonyl or ethoxycarbonyl, $R^7$ represents a hydrogen atom, methyl, ethyl, cyclopropylmethyl, 2-cyclopropylethyl or 2,2-difluoroethyl, with the proviso that if $R^5$ is methoxy, difluoromethoxy or trifluoromethoxy then $R^7$ is different from hydrogen, with the proviso that if $R^6$ represents 5-fluoropyridin-2-yl or 6-trifluoromethylpyridin-3-yl then $R^7$ is different from hydrogen, and stereoisomers, tautomers, hydrates, solvates, and salts thereof, and mixtures of same.

Preference is also given to compounds of the formula (I) in which $R^5$ represents methyl, ethyl or methoxy and stereoisomers, tautomers, hydrates, solvates, and salts thereof, and mixtures of same.

Preference is also given to compounds of the formula (I) in which $R^1$ represents group of the formula,

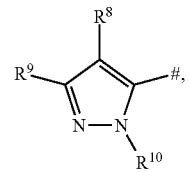

$R^8$ represents a group selected from chlorine, methyl, ethyl, methoxy and cylcopropyl, $R^9$ represents pyridyl or 4-cyanopentacyclo[4.2.0.0$^{2,5}$.0$^{3,8}$.0$^{4,7}$]octan-1-yl,
  or
  represents a group of the formula

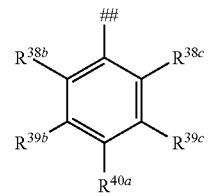

in which

\#\# represents the point of attachment to the pyrazole ring, $R^{38b}$ represents a hydrogen atom or fluorine, $R^{38c}$ represents a hydrogen atom, $R^{39b}$ represents a hydrogen atom, $R^{39c}$ represents a hydrogen atom, $R^{40a}$ represents a hydrogen atom, fluorine, chlorine, cyano, methyl, difluoromethyl, trifluoromethyl, methylamino, methoxy, difluoromethoxy, trifluoromethoxy or cyclopropyl, wherein said pyridyl is optionally substituted with fluorine, methyl, difluoromethyl, trifluoromethyl or methoxy, $R^{10}$ represents a hydrogen atom, methyl, ethyl, 2,2-difluoroethyl, cyclopropylmethyl, cyclobutylmethyl, 2-cyclopropylethyl, 2-cyclopropyl-2-hydroxypropyl, 2-cyclopropyl-2-hydroxyethyl, 2-methoxyethyl, or cyclopropyl, wherein said methyl and ethyl are optionally substituted with a group selected from cyclopropyl, methoxy or optionally up to three fluorine atoms and is optionally additionally substituted with hydroxy, with the proviso that if $R^9$ is pyridyl then $R^{10}$ is different from hydrogen, with the proviso that if $R^8$ is methoxy then $R^{10}$ is different from hydrogen, and stereoisomers, tautomers, hydrates, solvates, and salts thereof, and mixtures of same.

Preference is also given to compounds of the formula (I) in which

R$^1$ represents group of the formula,

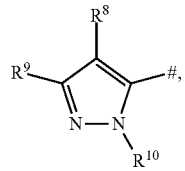

R$^8$ represents a group selected from chlorine, methyl, ethyl, methoxy and cylcopropyl, R$^9$ represents pyridyl or 4-cyanopentacyclo[4.2.0.0$^{2,5}$.0$^{3,8}$.0$^{4,7}$]octan-1-yl, or represents a group of the formula

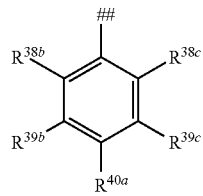

in which ## represents the point of attachment to the pyrazole ring,

R$^{38b}$ represents a hydrogen atom,

R$^{38c}$ represents a hydrogen atom,

R$^{39b}$ represents a hydrogen atom,

R$^{39c}$ represents a hydrogen atom,

R$^{40a}$ represents a hydrogen atom, fluorine, chlorine, cyano, methyl, difluoromethyl, trifluoromethyl, methylamino, methoxy, difluoromethoxy, trifluoromethoxy or cyclopropyl, wherein said pyridyl is optionally substituted with fluorine, methyl, difluoromethyl, trifluoromethyl or methoxy, R$^{10}$ represents a hydrogen atom, methyl, ethyl, 2,2-difluoroethyl, cyclopropylmethyl, cyclobutylmethyl, 2-cyclopropylethyl, 2-cyclopropyl-2-hydroxypropyl, 2-cyclopropyl-2-hydroxyethyl, 2-methoxyethyl, or cyclopropyl, wherein said methyl and ethyl are optionally substituted with a group selected from cyclopropyl, methoxy or optionally up to three fluorine atoms and is optionally additionally substituted with hydroxy, with the proviso that if R$^9$ is pyridyl then R$^{10}$ is different from hydrogen, with the proviso that if R$^8$ is methoxy then R$^{10}$ is different from hydrogen, and stereoisomers, tautomers, hydrates, solvates, and salts thereof, and mixtures of same.

Preference is also given to compounds of the formula (I) in which

R$^1$ represents group of the formula,

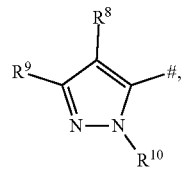

R$^8$ represents a group selected from methyl, ethyl or methoxy, and stereoisomers, tautomers, hydrates, solvates, and salts thereof, and mixtures of same.

Preference is also given to compounds of the formula (I) in which

R$^9$ represents pyridyl wherein said pyridyl is optionally substituted with fluorine, methyl, difluoromethyl, trifluoromethyl or methoxy, and stereoisomers, tautomers, hydrates, solvates, and salts thereof, and mixtures of same.

Preference is also given to compounds of the formula (I) in which

R$^9$ represents 4-cyanopentacyclo[4.2.0.0$^{2,5}$.0$^{3,8}$.0$^{4,7}$]octan-1-yl, and stereoisomers, tautomers, hydrates, solvates, and salts thereof, and mixtures of same.

Preference is also given to compounds of the formula (I) in which

R$^1$ represents group of the formula,

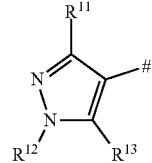

R$^{11}$ represents methyl,

R$^{12}$ represents a group of the formula

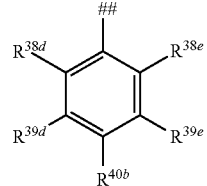

in which ## represents the point of attachment to the pyrazole ring,

R$^{38d}$ represents a hydrogen atom,

R$^{38e}$ represents a hydrogen atom,

R$^{39d}$ represents a hydrogen atom,

R$^{39e}$ represents a hydrogen atom,

R$^{40b}$ represents fluorine or cyano,

R$^{13}$ represents a group selected from a hydrogen atom or methyl, and stereoisomers, tautomers, hydrates, solvates, and salts thereof, and mixtures of same.

Preference is also given to compounds of the formula (I) in which $R^2$ represents a hydrogen atom, methyl or difluoromethyl,
and stereoisomers, tautomers, hydrates, solvates, and salts thereof, and mixtures of same.

Preference is also given to compounds of the formula (I) in which
$R^3$ represents a group selected from a hydrogen atom, fluorine, chlorine, bromine, cyano, hydroxy, nitro, amino, ethylamino, dimethylamino, —O—C(=O)—NR$^{36}$R$^{37}$, —O—C(=O)—OR$^{37a}$, —NH—C(=O)—OR$^{37a}$, ($C_1$-$C_4$)-alkyl, methoxy, cyclopropyl, cyclobutyl, 4-membered heterocycle, 1,3,4-oxadiazol-2-yl, 2-(trifluoromethyl)-1,3-dioxolan-2-yl, —(CH$_2$)$_q$—C(=O)—NR$^{34}$R$^{35}$, methoxycarbonyl and ethoxycarbonyl,
  wherein said ($C_1$-$C_4$)-alkyl is optionally substituted, identically or differently, with one or two groups selected from hydroxy, methoxy, methoxycarbonyl, ethoxycarbonyl, dimethylamino, a 4-membered azaheterocycle and cyclopropyl and optionally up to three fluorine atoms,
    wherein said 4-membered azaheterocycle is optionally substituted with up to two fluorine atoms,
  wherein said methoxy is optionally substituted with cyano, cyclopropyl and optionally up to three fluorine atoms,
  wherein said cyclopropyl and cyclobutyl are optionally substituted with hydroxy,
  wherein said 4-membered heterocycle is optionally substituted with hydroxy,
  wherein said 1,3,4-oxadiazol-2-yl is optionally substituted with methyl,
  wherein
  q is 0,
  $R^{34}$ represents methyl,
  $R^{35}$ represents methyl,
  or
  $R^{34}$ and $R^{35}$ together with the nitrogen atom they are attached form a 4- to 6-membered heterocycle ring
    wherein said 4- to 6-membered heterocycle ring is optionally substituted, identically or differently, with one or two groups selected from a fluorine atom, methyl, difluoromethyl and trifluoromethyl,
  wherein
  $R^{36}$ represents a methyl atom,
  $R^{37}$ represents a hydrogen atom or methyl,
  $R^{37a}$ represents methyl,
and stereoisomers, tautomers, hydrates, solvates, and salts thereof, and mixtures of same.

Preference is also given to compounds of the formula (I) in which
$R^2$ and $R^3$ together with the carbon atoms they are attached form a 5- to 6-membered carbocycle, a pyrrolidinyl, a pyridyl or a phenyl ring,
wherein said 5- to 6-membered carbocycle is optionally substituted, identically or differently, with one
or two groups selected from oxo, methyl, trifluoromethyl and hydroxy,
wherein said pyrrolidinyl is substituted with propyl or tert.-butoxycarbonyl,
and stereoisomers, tautomers, hydrates, solvates, and salts thereof, and mixtures of same.

Preference is also given to compounds of the formula (I) in which
$R^4$ represents a group selected from a hydrogen atom, methyl, 2-hydroxypropan-2-yl, fluoromethyl, difluoromethyl, methoxycarbonyl, ethoxycarbonyl and hydroxy,
and stereoisomers, tautomers, hydrates, solvates, and salts thereof, and mixtures of same.

Preference is also given to compounds of the formula (I) in which
$R^3$ and $R^4$ together with the carbon atoms they are attached form a 5- to 6-membered carbocycle, a pyrrolidinyl ring or a piperidinyl ring, a pyridyl group or a phenyl ring,
  wherein said pyrrolidinyl ring is substituted with propyl or tert-butoxycarbonyl,
  wherein said piperidinyl ring is substituted with propyl or tert-butoxycarbonyl,
  wherein said 5- to 6-membered carbocycle is optionally substituted, identically or differently, with one or two groups selected from oxo, hydroxy and methyl,
and stereoisomers, tautomers, hydrates, solvates, and salts thereof, and mixtures of same.

Preference is also given to compounds of the formula (I) in which
$R^1$ represents group of the formula,

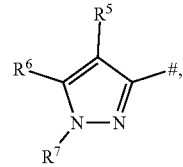

in which
# represents the point of attachment to the amino group,
$R^5$ represents a group selected from chlorine, methyl, ethyl, methoxy and cyclopropyl
  wherein said methyl is optionally substituted with a group selected from methoxy and cyclopropyl and optionally up to three fluorine atoms,
$R^6$ represents a phenyl group,
  wherein said phenyl group is optionally substituted, identically or differently, with one or two groups selected from fluorine, chlorine, cyano, methyl, methoxy, ethoxy, trifluoromethoxy, methoxycarbonyl and ethoxycarbonyl,
  wherein said methyl is optionally substituted with up to three fluorine atoms,
$R^7$ represents a hydrogen atom, methyl, ethyl or cyclopropyl,
  wherein said methyl and ethyl are optionally substituted with cyclopropyl and optionally with up to three fluorine atoms,
and stereoisomers, tautomers, hydrates, solvates, and salts thereof, and mixtures of same.

Preference is also given to compounds of the formula (I) in which
$R^1$ represents group of the formula,

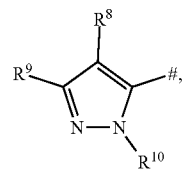

in which
# represents the point of attachment to the amino group,
$R^8$ represents a group selected from chlorine, methyl, ethyl, methoxy and cyclopropyl,
  wherein said methyl is optionally substituted with a group selected from methoxy and cyclopropyl and optionally up to three fluorine atoms, $R^9$ represents a phenyl group,
wherein said phenyl group is optionally substituted, identically or differently, with one or two groups selected from fluorine, chlorine, cyano, methyl, methoxy, ethoxy, trifluoromethoxy, methoxycarbonyl and ethoxycarbonyl,
wherein said methyl is optionally substituted with up to three fluorine atoms,
$R^{10}$ represents a hydrogen atom, methyl, ethyl or cyclopropyl,
wherein said methyl and ethyl are optionally substituted with cyclopropyl and optionally with up to three fluorine atoms,
and stereoisomers, tautomers, hydrates, solvates, and salts thereof, and mixtures of same.

Preference is also given to compounds of the formula (I) in which
$R^1$ represents group of the formula,

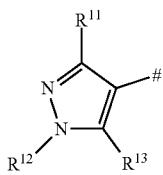

in which
# represents the point of attachment to the amino group,
$R^{11}$ represents cyclopropyl or methyl,
wherein said methyl is optionally substituted with up to three fluorine atoms,
$R^{12}$ represents a phenyl group,
wherein said phenyl group is optionally substituted, identically or differently, with one or two groups selected from fluorine, chlorine or cyano,
$R^{13}$ represents a group selected from a hydrogen atom, methyl and cyclopropyl,
wherein said methyl is optionally substituted with up to three fluorine atoms,
and stereoisomers, tautomers, hydrates, solvates, and salts thereof, and mixtures of same.

Preference is also given to compounds of the formula (I) in which
$R^2$ represents methyl,
and stereoisomers, tautomers, hydrates, solvates, and salts thereof, and mixtures of same.

Preference is also given to compounds of the formula (I) in which
$R^2$ represents a hydrogen atom,
and stereoisomers, tautomers, hydrates, solvates, and salts thereof, and mixtures of same.

Preference is also given to compounds of the formula (I) in which
$R^3$ represents a group selected from a hydrogen atom, fluorine, chlorine, cyano, $(C_1-C_4)$-alkyl, cyclopropyl, 4- to 6-membered heterocycle, 5- to 6-membered heteroaryl, —C(=O)—$NR^{34}R^{35}$, methoxycarbonyl and ethoxycarbonyl,
wherein said $(C_1-C_4)$-alkyl is optionally substituted with a group selected from hydroxy, ethoxycarbonyl and cyclopropyl and optionally up to three fluorine atoms,
wherein said 5- to 6-membered heteroaryl is optionally substituted, identically or differently, with one or two groups selected from methyl, ethyl and methoxy and optionally up to two fluorine atoms,
wherein
$R^{34}$ represents a hydrogen atom, methyl or ethyl,
$R^{35}$ represents methyl or ethyl,
or
$R^{34}$ and $R^{35}$ together with the nitrogen atom they are attached form a 4- to 6-membered heterocycle ring
wherein said 4- to 6-membered heterocycle ring is optionally substituted, identically or differently, with one or two groups selected from a fluorine atom, methyl, difluoromethyl and trifluoromethyl,
and stereoisomers, tautomers, hydrates, solvates, and salts thereof, and mixtures of same.

Preference is also given to compounds of the formula (I) in which
$R^3$ represents a group selected from a hydrogen atom, chlorine, cyano, $(C_1-C_4)$-alkyl, —C(=O)—$NR^{34}R^{35}$ and ethoxycarbonyl,
wherein said $(C_1-C_4)$-alkyl is optionally substituted with a group selected from hydroxyl and ethoxycarbonyl and optionally up to three fluorine atoms,
wherein
$R^{34}$ represents methyl or ethyl,
$R^{35}$ represents methyl or ethyl,
or
$R^{34}$ and $R^{35}$ together with the nitrogen atom they are attached form a 4- to 6-membered heterocycle ring
wherein said 4- to 6-membered heterocycle ring is optionally substituted, identically or differently, with one or two groups selected from a fluorine atom, methyl, difluoromethyl and trifluoromethyl,
and stereoisomers, tautomers, hydrates, solvates, and salts thereof, and mixtures of same.

Preference is also given to compounds of the formula (I) in which
$R^3$ represents a hydrogen atom,
and stereoisomers, tautomers, hydrates, solvates, and salts thereof, and mixtures of same.

Preference is also given to compounds of the formula (I) in which
$R^3$ represents chlorine,
and stereoisomers, tautomers, hydrates, solvates, and salts thereof, and mixtures of same.

Preference is also given to compounds of the formula (I) in which
$R^2$ and $R^3$ together with the carbon atoms they are attached form a phenyl or a 5- to 6-membered carbocycle,
wherein said phenyl group is optionally substituted with one or two fluorine atoms,
wherein said 5- to 6-membered carbocycle is optionally substituted, with up to four fluorine atoms,
and stereoisomers, tautomers, hydrates, solvates, and salts thereof, and mixtures of same.

Preference is also given to compounds of the formula (I) in which
$R^2$ and $R^3$ together with the carbon atoms they are attached form a phenyl or a 5- to 6-membered carbocycle,
and stereoisomers, tautomers, hydrates, solvates, and salts thereof, and mixtures of same.

Preference is also given to compounds of the formula (I) in which
$R^4$ represents a group selected from a hydrogen atom, methyl and cyclopropyl,
wherein said methyl is optionally substituted with up to three fluorine atoms,
and stereoisomers, tautomers, hydrates, solvates, and salts thereof, and mixtures of same.

Preference is also given to compounds of the formula (I) in which $R^4$ represents methyl,
wherein said methyl is optionally substituted with up to three fluorine atoms,
and stereoisomers, tautomers, hydrates, solvates, and salts thereof, and mixtures of same.

Preference is also given to compounds of the formula (I) in which
$R^4$ represents methyl,
and stereoisomers, tautomers, hydrates, solvates, and salts thereof, and mixtures of same.

Preference is also given to compounds of the formula (I) in which
$R^3$ and $R^4$ together with the carbon atoms they are attached form a 5- to 6-membered carbocycle, a 4- to 6-membered heterocycle, a 5- to 6-membered heteroaryl group or a phenyl ring,
wherein said 4- to 6-membered heterocycle is optionally substituted, identically or differently, with $(C_1\text{-}C_4)$-alkoxycarbonyl and optionally up to four fluorine atoms,
wherein said 4- to 6-membered carbocycle is optionally substituted with up to four fluorine atoms, and
wherein any phenyl group and any 5- to 6-membered heteroaryl group are each optionally substituted with one or two fluorine atoms,
and stereoisomers, tautomers, hydrates, solvates, and salts thereof, and mixtures of same.

Preference is also given to compounds of the formula (I) in which
$R^3$ and $R^4$ together with the carbon atoms they are attached form a 5- to 6-membered carbocycle, a 4- to 6-membered heterocycle or a phenyl ring,
wherein said 4- to 6-membered heterocycle is optionally substituted, identically or differently, with $(C_1\text{-}C_4)$-alkoxycarbonyl and optionally up to four fluorine atoms,
wherein said 4- to 6-membered carbocycle is optionally substituted with up to four fluorine atoms, and
wherein any phenyl group and any 5- to 6-membered heteroaryl group are each optionally substituted with one or two fluorine atoms,
and stereoisomers, tautomers, hydrates, solvates, and salts thereof, and mixtures of same.

Preference is also given to compounds of the formula (I) in which
$R^3$ and $R^4$ together with the carbon atoms they are attached form a 5- to 6-membered carbocycle, a 4- to 6-membered heterocycle or a phenyl ring,
wherein said 4- to 6-membered heterocycle is optionally substituted with $(C_1\text{-}C_4)$-alkoxycarbonyl,
and stereoisomers, tautomers, hydrates, solvates, and salts thereof, and mixtures of same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers the compounds of general formula (I) which are disclosed in the Example Section of this text, infra.

In accordance with a second aspect, the present invention covers methods of preparing compounds of general formula (I) as defined supra, said methods comprising the step [A] of allowing an intermediate compound of general formula (II-A), (II-B) or (II-C):

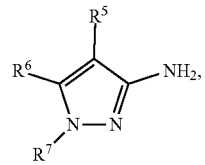

(II-A)

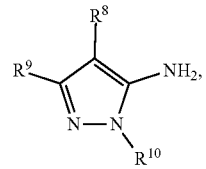

(II-B)

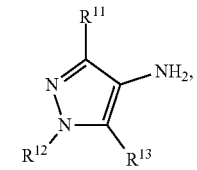

(II-C)

in which $R^5$, $R^6$, $R^7$, $R^8$, $R^9$, $R^{10}$, $R^1$, $R^{12}$ and $R^{13}$ are as defined for the compound of general formula (I) as defined supra,
to react in the presence of sodium iodide and a suitable base, with 4,6-dichloropyrimidine (III),
or
to react in the presence of a suitable Broenstedt acid or Lewis acid with 4,6-dichloropyrimidine (III),
or
to react in the presence of a suitable base with 4,6-dichloropyrimidine (III),
or
to react in the presence of a suitable base and in the presence of a suitable catalyst, in particular a suitable palladium catalyst, and a suitable ligand with 4,6-dichloropyrimidine (III),

(III)

thereby giving a compound of general formula (IV-A), (IV-B) and (IV-C), respectively:

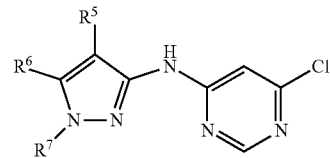

(IV-A)

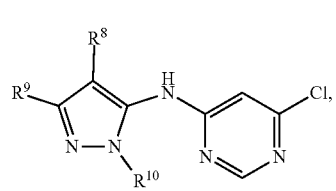

(IV-B)

-continued

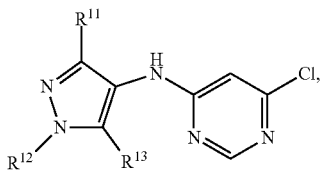
(IV-C)

in which R⁵, R⁶, R⁷, R⁸, R⁹, R¹⁰, R¹¹, R¹² and R¹³ are as defined for the compound of general formula (I) as defined supra, which is allowed to react in the presence of a suitable base and where appropriate in the presence of a suitable catalyst, in particular a suitable palladium catalyst, with a pyrazole of general formula (V),

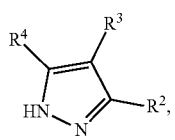
(V)

in which R², R³ and R⁴ are as defined for the compound of general formula (I) as defined supra, thereby giving a compound of general formula (I-A), (I-B) and (I-C), respectively.

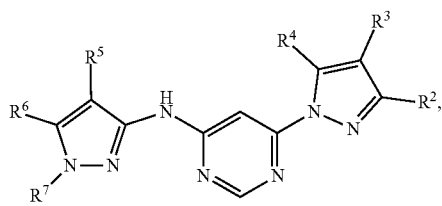
(I-A)

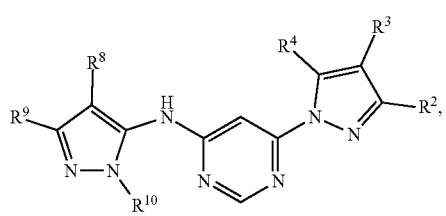
(I-B)

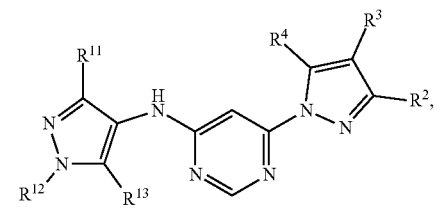
(I-C)

in which R², R³, R⁴, R⁵, R⁶, R⁷, R⁸, R⁹, R¹⁰, R¹¹, R¹² and R¹³ are as defined for the compound of general formula (I) as defined supra, then optionally converting said compound into solvates, salts and/or solvates of such salts using the corresponding (i) solvents and/or (ii) bases or acids.

or

[B] of allowing an intermediate compound of general formula (IV-A), (IV-B) or (IV-C):

(IV-A)

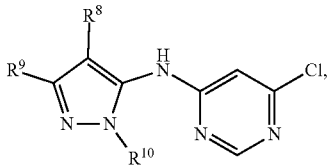
(IV-B)

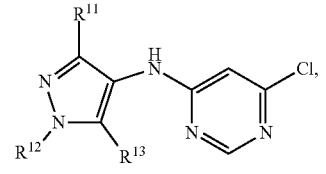
(IV-C)

in which R⁵, R⁶, R⁷, R⁸, R⁹, R¹⁰, R¹¹, R¹² and R¹³ are as defined for the compound of general formula (I) as defined supra, to react in the presence of a hydrazine equivalent, in particular hydrazine monohydrate, thereby giving a compound of general formula (V-A), (V-B) and (V-C), respectively,

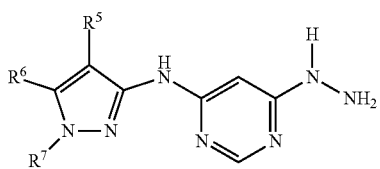
(V-A)

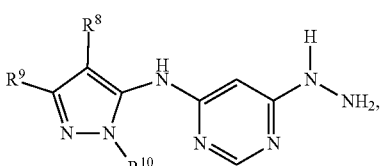
(V-B)

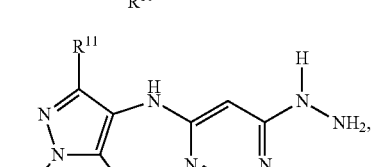
(V-C)

which is allowed to react in the presence of a 1,3 dicarbonyl compound of general formula (VI),

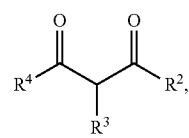
(VI)

in which $R^2$, $R^3$ and $R^4$ are as defined for the compound of general formula (I) as defined supra,
thereby giving a compound of general formula (I-A), (I-B) and (I-C), respectively,

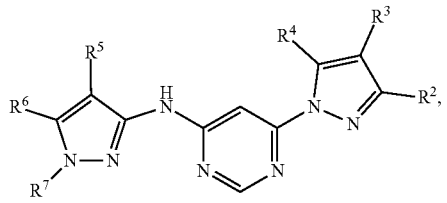
(I-A)

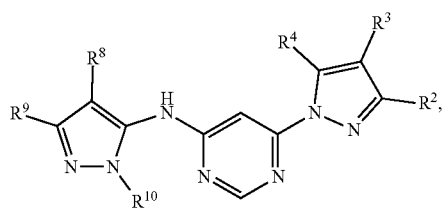
(I-B)

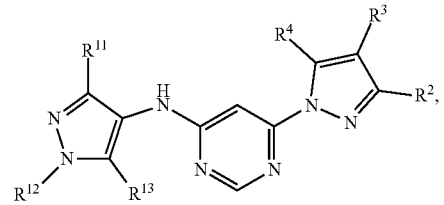
(I-C)

in which $R^2$, $R^3$, $R^4$, $R^5$, $R^6$, $R^7$, $R^8$, $R^9$, $R^{10}$, $R^{11}$, $R^{12}$ and $R^{13}$ are as defined for the compound of general formula (I) as defined supra,
then optionally converting said compound into solvates, salts and/or solvates of such salts using the corresponding (i) solvents and/or (ii) bases or acids.
or
[C] of allowing an intermediate compound of general formula (IV-A), (IV-B) or (IV-C):

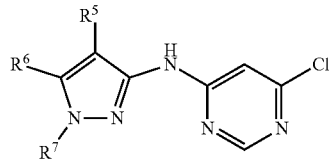
(IV-A)

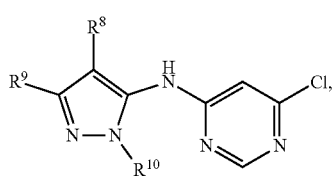
(IV-B)

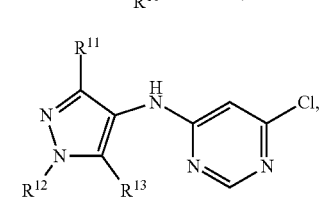
(IV-C)

in which $R^5$, $R^6$, $R^7$, $R^8$, $R^9$, $R^{10}$, $R^{11}$, $R^{12}$ and $R^{13}$ are as defined for the compound of general formula (I) as defined supra,
to react in the presence of a hydrazine equivalent, in particular hydrazine monohydrate,
thereby giving a compound of general formula (V-A), (V-B) and (V-C), respectively,

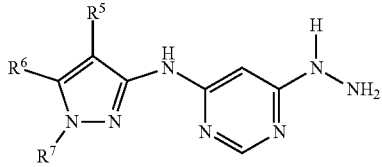
(V-A)

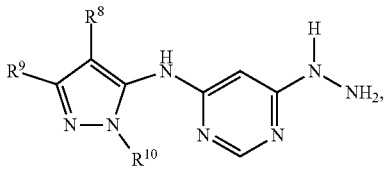
(V-B)

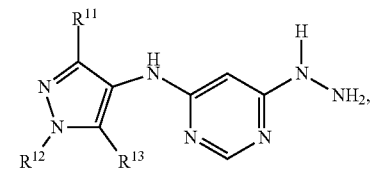
(V-C)

which is allowed to react in the presence of a 1,3 dicarbonyl compound of general formula (VII),

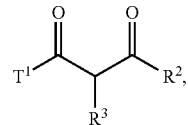
(VII)

in which $R^2$ and $R^3$ are as defined for the compound of general formula (I) as defined supra, and
$T^1$ represents methoxy or ethoxy,
thereby giving a compound of general formula (I-D), (I-E) and (I-F), respectively,

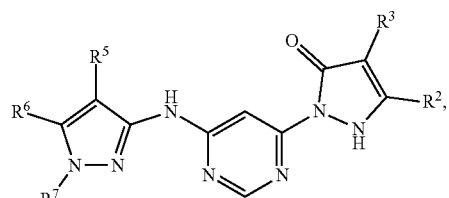
(I-D)

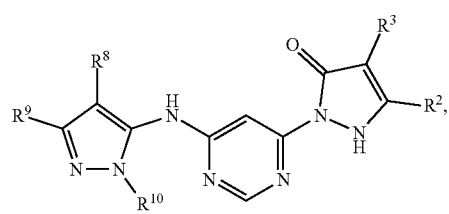
(I-E)

(I-F)

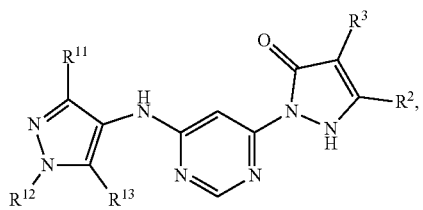

in which R², R³, R⁴, R⁵, R⁶, R⁷, R⁸, R⁹, R¹⁰, R¹¹, R¹² and R¹³ are as defined for the compound of general formula (I) as defined supra,
then optionally converting said compound into solvates, salts and/or solvates of such salts using the corresponding (i) solvents and/or (ii) bases or acids.

[D] of allowing an intermediate compound of general formula (VIII):

(VIII)

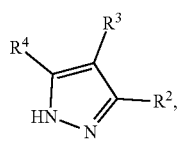

in which R², R³ and R⁴ are as defined for the compound of general formula (I) as defined supra,
to react in the presence of a suitable base with 4,6-dichloropyrimidine (III), (III)

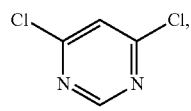

thereby giving a compound of general formula (IX), (IX)

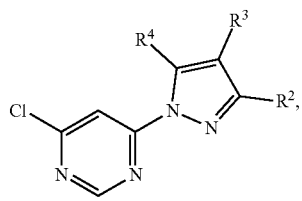

in which R¹, R², R³ and R⁴ are as defined for the compound of general formula (I) as defined supra,
which is allowed to react
b) in the presence of a suitable Broenstedt acid or Lewis acid with an intermediate compound of general formula (II-A), (II-B) or (II-C),
or
c) in the presence of a suitable base with an intermediate compound of general formula (II-A), (II-B) or (II-C),
or
d) in the presence of a suitable base and in the presence of a suitable catalyst, in particular a suitable palladium catalyst, and a suitable ligand with an intermediate compound of general formula (II-A), (II-B) or (II-C), (II-A)

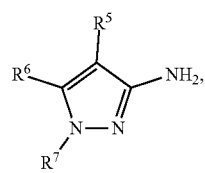

(II-B)

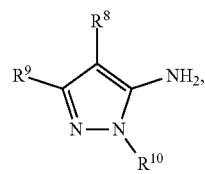

(II-C)

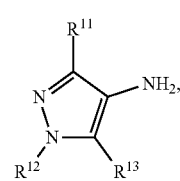

in which R⁵, R⁶, R⁷, R⁸, R⁹, R¹⁰, R¹¹, R¹² and R¹³ are as defined for the compound of general formula (I) as defined supra, and
thereby giving a compound of general formula (I-A), (I-B) and (I-C), respectively, (I-A)

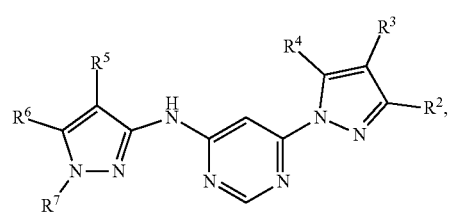

(I-B)

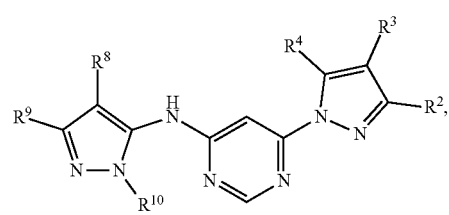

(I-C)

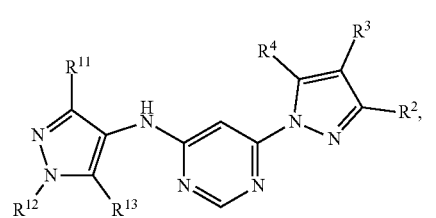

in which R², R³, R⁵, R⁶, R⁷, R⁸, R⁹, R¹⁰, R¹¹, R¹² and R¹³ are as defined for the compound of general formula (I) as defined supra,
then optionally converting said compound into solvates, salts and/or solvates of such salts using the corresponding (i) solvents and/or (ii) bases or acids.

or

[E] of allowing 4,6-dichloropyrimidine (III),

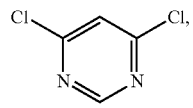
(III)

to react with a hydrazine equivalent, in particular hydrazine monohydrate, thereby giving a compound of general formula (X),

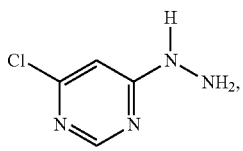
(X)

which is allowed to react in the presence of a 1,3 dicarbonyl compound of general formula (VI),

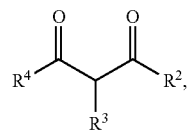
(VI)

in which $R^2$, $R^3$ and $R^4$ are as defined for the compound of general formula (I) as defined supra, thereby giving a compound of general formula (VII),

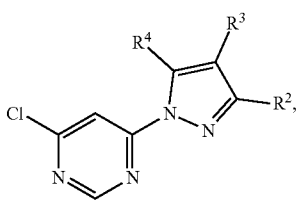
(IX)

in which $R^1$, $R^2$, $R^3$ and $R^4$ are as defined for the compound of general formula (I) as defined supra, which is allowed to react b) in the presence of a suitable Broenstedt acid with an intermediate compound of general formula (II-A), (II-B) or (II-C), or c) in the presence of a suitable base with an intermediate compound of general formula (II-A), (II-B) or (II-C), or d) in the presence of a suitable base and in the presence of a suitable catalyst, in particular a suitable palladium catalyst, and a suitable ligand with an intermediate compound of general formula (II-A), (II-B) or (II-C),

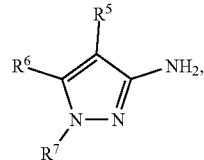
(II-A)

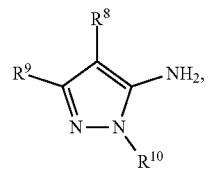
(II-B)

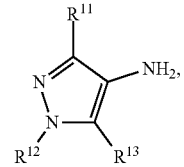
(II-C)

in which $R^5$, $R^6$, $R^7$, $R^8$, $R^9$, $R^{10}$, $R^{11}$, $R^{12}$ and $R^{13}$ are as defined for the compound of general formula (I) as defined supra, and thereby giving a compound of general formula (I-A), (I-B) and (I-C), respectively, (I-A)

(I-B)

(I-C)

in which $R^2$, $R^3$, $R^4$, $R^5$, $R^6$, $R^7$, $R^8$, $R^9$, $R^{10}$, $R^{11}$, $R^{12}$ and $R^{13}$ are as defined for the compound of general formula (I) as defined supra, then optionally converting said compound into solvates, salts and/or solvates of such salts using the corresponding (i) solvents and/or (ii) bases or acids.

or
[F] of allowing compound of general formula (IX),

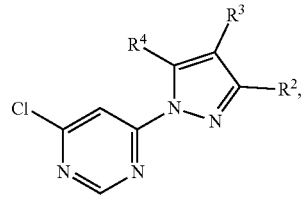
(IX)

in which $R^2$, $R^3$ and $R^4$ are as defined for the compound of general formula (I) as defined supra,
which is allowed to react
b) in the presence of a suitable Broenstedt acid or a suitable base with an intermediate compound of general formula (X), or
c) in the presence of a suitable base with an intermediate compound of general formula (X) or
d) in the presence of a suitable base and in the presence of a suitable catalyst, in particular a suitable palladium catalyst, and a suitable ligand with an intermediate compound of general formula (X),

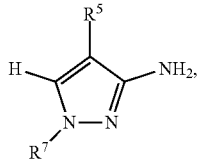
(X)

in which $R^5$, and $R^7$ are as defined for the compound of general formula (I) as defined supra, and
thereby giving a compound of general formula (XI),

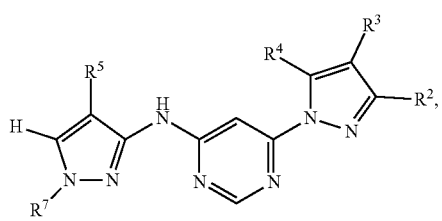
(XI)

in which $R^2$, $R^3$, $R^4$, $R^5$ and $R^7$ are as defined for the compound of general formula (I) as defined supra,
which is allowed to react in the presence of a suitable base and in the presence of a suitable palladium catalyst with a compound of general formula (XII), $$R^6-X,$$ (XII)

in which $R^6$ is as defined for the compound of general formula (I) as defined supra, and
X is chlorine, bromine, iodine or triflate,
thereby giving a compound of general formula (I-A),

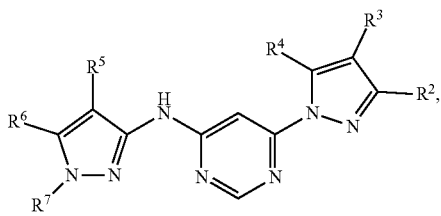
(I-A)

in which $R^2$, $R^3$, $R^4$, $R^5$, $R^6$ and $R^7$ are as defined for the compound of general formula (I) as defined supra,
then optionally converting said compound into solvates, salts and/or solvates of such salts using the corresponding (i) solvents and/or (ii) bases or acids.

The compounds of the formulae (I-A), (I-B), (I-C), (I-D), (I-E) and (I-F) form a subset of the compounds of the formula (I) according to the invention.

The compounds of the formulae (II-A), (II-B), (II-C), (III), (V), (VI), (VII) and (VIII) are commercially available, known from the literature or can be prepared analogously to processes known from the literature.

The preparation processes described can be illustrated in an exemplary manner by the synthesis schemes below (Schemes 1 to 3):

Scheme 1:

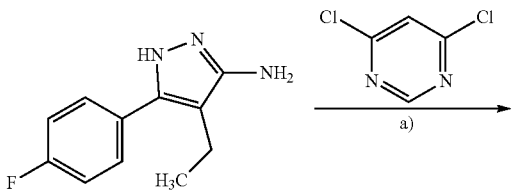

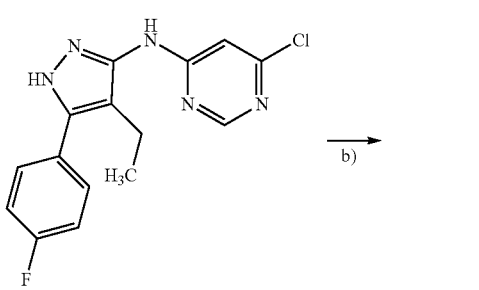

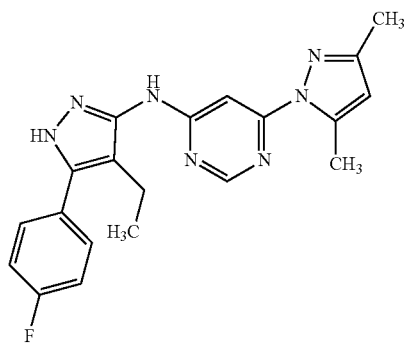

[a]: NaI, DIPEA, DMF, 80° C.; b): DBU, NMP, 190° C.].
Scheme 2:
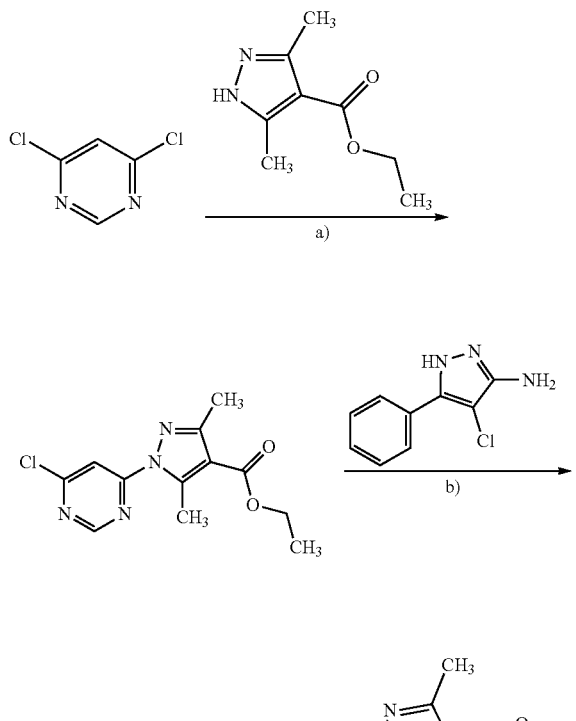
[a]: Cs₂CO₃, DMF, r.t.; b): Pd₂(dba)₃, Xantphos, NaOPh, dioxane, 80° C.].
Scheme 3:
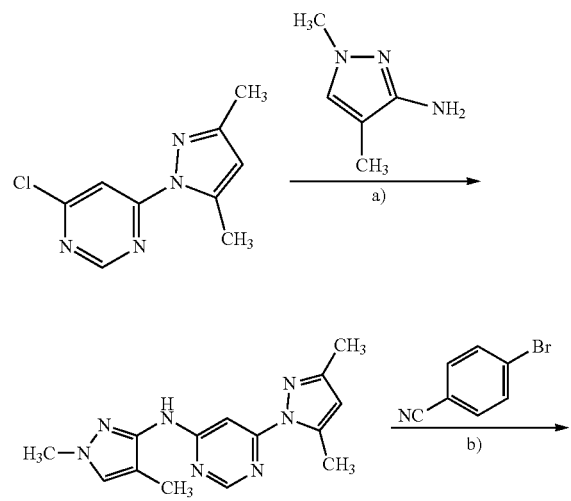
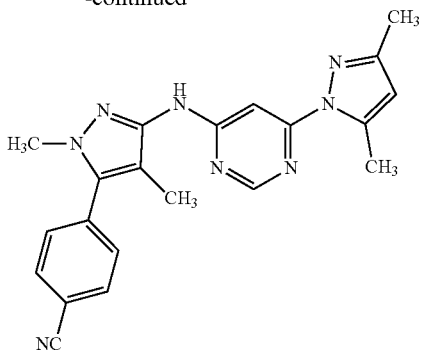
a): Pd₂(dba)₃, Xantphos, NaOPh, dioxane, 80° C.; b): PdCl(C₃H₅)dppb, KOAc, DMAc, 150° C.
Further preparation processes used for preparing compounds of the present invention can be illustrated in an exemplary manner by the synthesis schemes below (Schemes 8 to 13):
Scheme 8:
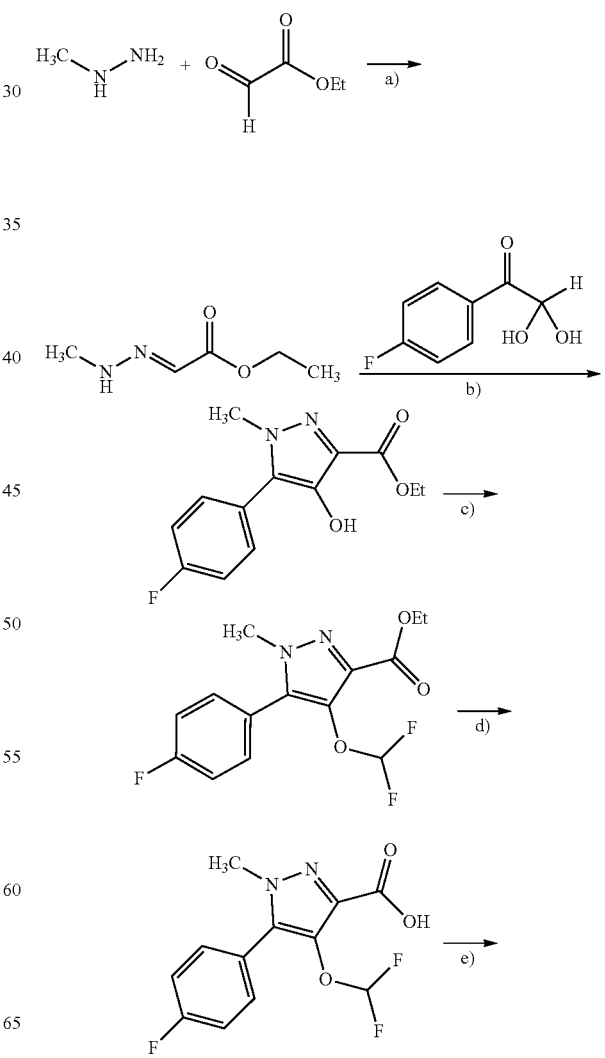

-continued

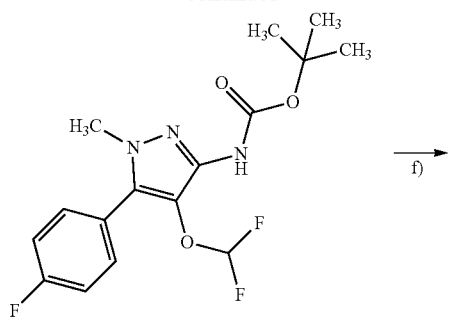

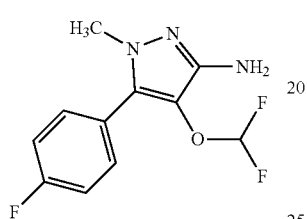

a): THF, 0° C. to rt; b): MgSO₄, n-Butylacetate AcOH, 0° C. to 110° C.; c): diethyl [bromo(difluoro)methyl]phosphonate, KOH, MeCN/H₂O, −20° C.; d): NaOH, THF, MeOH, H₂O, rt; e): diphenylphosporyl azide, NEt₃, t-BuOH, Toluene, rt to 80° C.; f): TFA, CH₂Cl₂, rt. 3

Scheme 9:

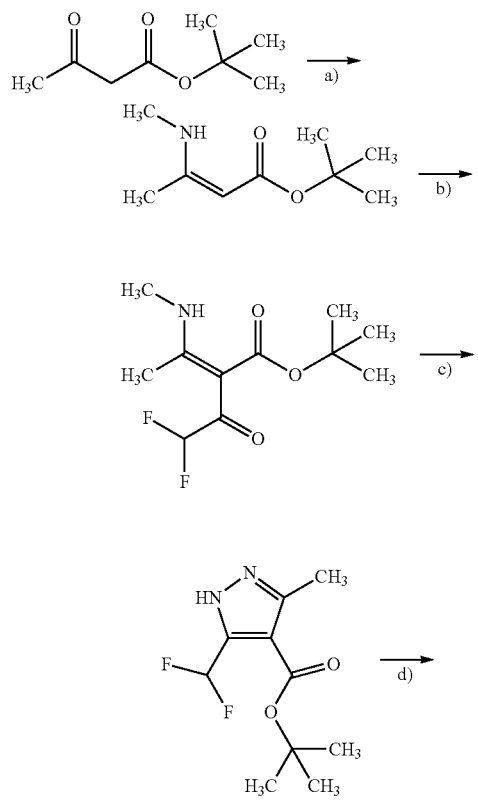

-continued

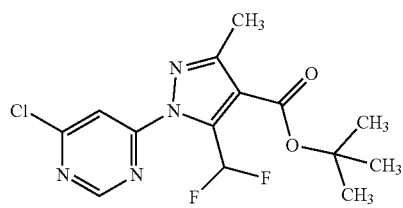

a): aq. Methylamine solution, SiO₂; b): difluoroacetic anhydride, NEt₃, MTBE, 0° C. to rt; c): hydrazine monohydrate, MeOH, −20° C. to rt; d): 4,6-dichloropyrimidine, Cs₂CO₃, DMF Scheme 10:

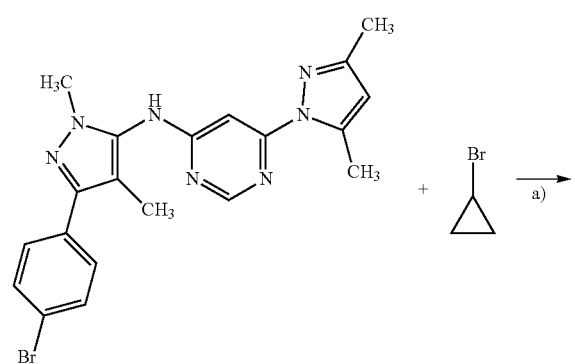

a): Nickel (II) chloride dimethoxyethane adduct, 4,4'-di-tert-butyl-2,2'-bipyridine, Ir(F₂(CF3)ppy]₂(dtbbpy)PF₆, tris(trimethyl)silane, LiOH, dimethoxyethane, two 34 W blue LEDs.

Scheme 11:

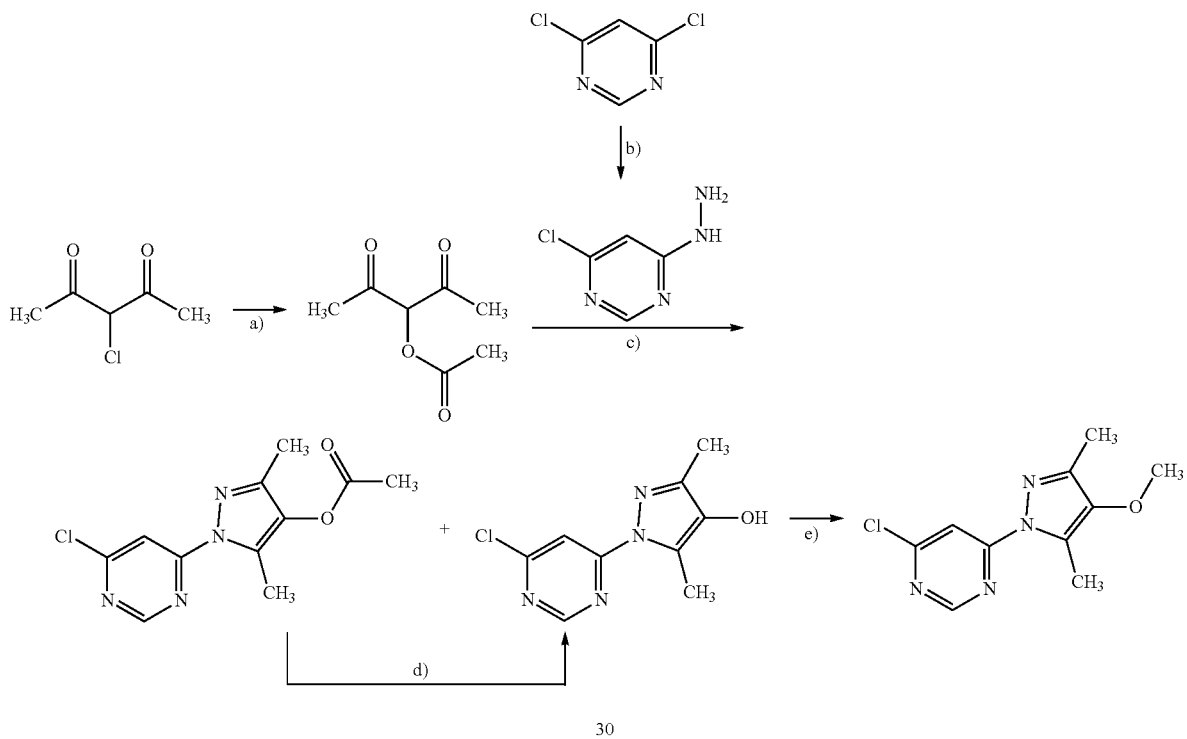

a): NaOAc, DMSO, rt; b) L: hydrazine monohydrate, EtOH, rt; c): (6-chloropyrimidin-4-yl)hydrazine, EtOH, reflux; d): $K_2CO_3$, MeOH, 0° C.; e): $Cs_2CO_3$, MeI, DMF, rt.

Scheme 12:

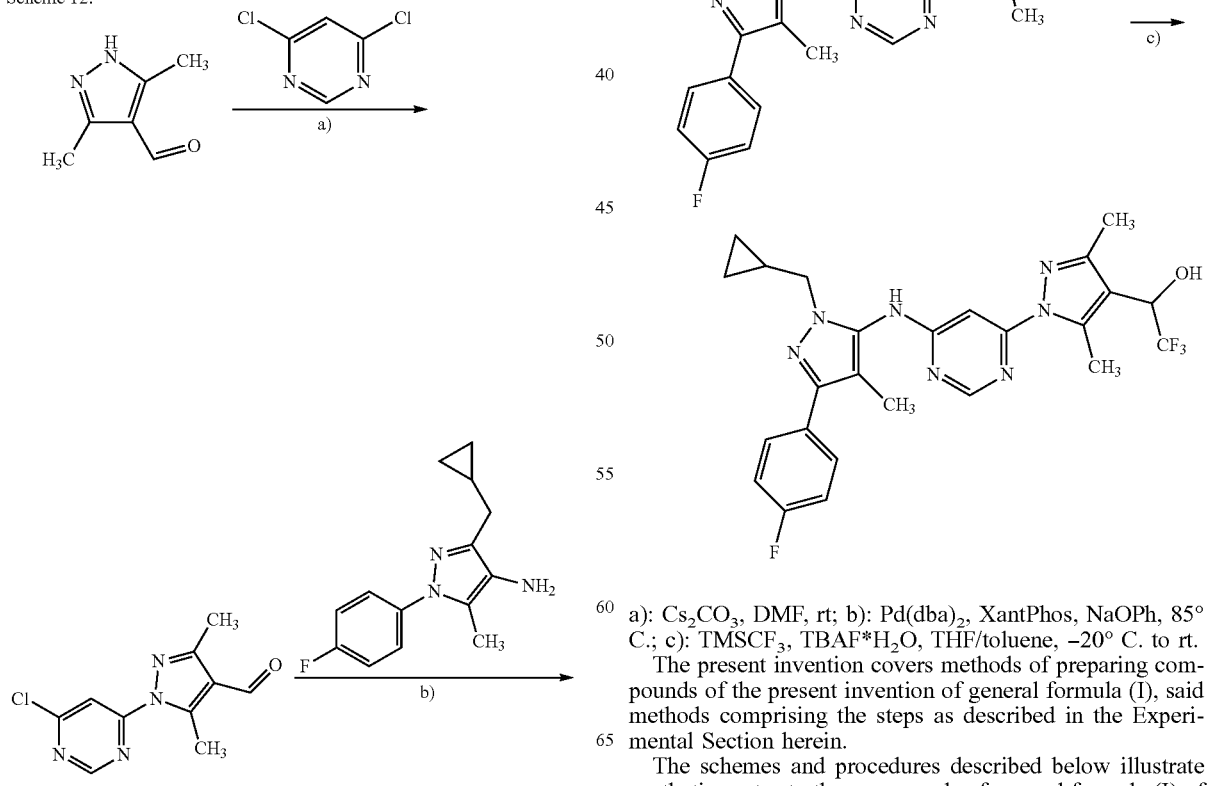

a): $Cs_2CO_3$, DMF, rt; b): Pd(dba)$_2$, XantPhos, NaOPh, 85° C.; c): TMSCF$_3$, TBAF*H$_2$O, THF/toluene, −20° C. to rt.

The present invention covers methods of preparing compounds of the present invention of general formula (I), said methods comprising the steps as described in the Experimental Section herein.

The schemes and procedures described below illustrate synthetic routes to the compounds of general formula (I) of the invention and are not intended to be limiting. It is clear to the person skilled in the art that the order of transformations as exemplified in schemes 1, 2, 3 and 4 can be modified in various ways. The order of transformations exemplified in these schemes is therefore not intended to be limiting.

In addition, interconversion of any of the substituents, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^A$, $T^1$, Q, and X can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T.W. Greene and P.G.M. Wuts in Protective Groups in Organic Synthesis, $3^{rd}$ edition, Wiley 1999). Specific examples are described in the subsequent paragraphs.

Suitable bases for the process step (II-A), (II-B) or (II-C)+(III)→(IV-A), (IV-B) or (IV-C) and (II-A), (II-B) or (II-C)+(IX)→(I-A), (I-B) or (I-C), when using approach a) or c) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, if appropriate with addition of an alkali metal iodide, for example sodium iodide or potassium iodide, alkali alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using N,N-diisopropylethylamine.

Suitable Broensted acids for the process step (II-A), (II-B) or (II-C)+(III)→(IV-A), (IV-B) or (IV-C) and (II-A), (II-B) or (II-C)+(IX)→(I-A), (I-B) or (I-C), when using approach b) are aqueous hydrochloric acid, hydrobromic acid, hydrochloric acid in dioxane, acetic acid, trifluoroacetic acid, difluoroacetic, p-toluene sulfonic acid, camphor sulfonic acid, methane sulfonic acid, perchloric acid, sulfuric acid, phosphoric acid. Preference is given to hydrochloric acid. Suitable A Lewis acid for this process step is tin chloride.

Suitable bases for the process step (II-A), (II-B) or (II-C)+(III)→(IV-A), (IV-B) or (IV-C) and (II-A), (II-B) or (II-C)+(IX)→(I-A), (I-B) or (I-C), and (IX)+(X)→(XI) when using approach d) and for the process step (IV-A), (IV-B) or (IV-C)+(V)→(I-A), (I-B) or (I-C), and for the process step (VIII)+(III)→(IX) are for example, alkali metal or alkaline earth metal carbonates such as lithium carbonate, sodium carbonate, potassium carbonate, calcium carbonate or caesium carbonate, alkali metal or alkaline earth metal hydroxides such as sodium hydroxide, potassium hydroxide or barium hydroxide, alkali metal or alkaline earth metal phosphates such as potassium phosphate, alkali metal alkoxides such as sodium tert-butoxide or potassium tert-butoxide and sodium methoxide, alkali metal phenoxides such as sodium phenoxide, amides such as sodium amide, lithium bis(trimethylsilyl)amide, sodium bis(trimethylsilyl)amide or potassium bis(trimethylsilyl)amide or lithium diisopropylamide or organic amines such as 1,5-diazabicyclo[4.3.0]non-5-ene (DBN), 1,8-diazabicyclo[5.4.0]undec-7-ene (DBU); preference is given to sodium phenoxide, caesium carbonate, potassium carbonate, sodium tert-butoxide or potassium tert-butoxide or lithium bis(trimethylsilyl)amide.

Suitable inert solvents for the process step (II-A), (II-B) or (II-C)+(III)→(IV-A), (IV-B) or (IV-C) and (IX)+(X)→(XI) for example, when using approach a), b, c) are, aromatic hydrocarbons such as benzene, toluene or xylene, ethers such as diethyl ether, diisopropyl ether, methyl tert-butyl ether, 1,2-dimethoxyethane, bis-(2-methoxyethyl) ether, tetrahydrofuran or 1,4-dioxane, or dipolar aprotic solvents such as acetonitrile, N,N-dimethylformamide (DMF), N,N-dimethylacetamide (DMA), dimethyl sulfoxide (DMSO), N,N'-dimethylpropyleneurea (DMPU), N-methylpyrrolidinone (NMP) or pyridine. It is also possible to use mixtures of the solvents mentioned, optionally also in a mixture with water. Preference is given to using dimethylformamide in a), N-methylpyrrolidinone in b).

Suitable inert solvents for the process step (II-A), (II-B) or (II-C)+(III)→(IV-A), (IV-B) or (IV-C) when using approach d) and for the process step (IV-A), (IV-B) or (IV-C)+(V)→(I-A), (I-B) or (I-C) and for the process steps (IX)+(X)→(XI), (XI)+(XII)→(I-A) and (VIII)+(III)→(IX) are for example, ethers such as 1,4-dioxane, tetrahydrofuran, 2-methyltetrahydrofuran, diethyl ether, di-n-butylether, glycol dimethyl ether or diethylene glycol dimethyl ether, alcohols such as tert-butanol or amyl alcohols or other solvents such as dimethylformamide (DMF), dimethyl sulphoxide (DMSO), dimethylacetamide (DMA), toluene or acetonitrile, or mixtures of the solvents mentioned; preference is given to dimethylformamide, tert-butanol, 1,4-dioxane or toluene.

Suitable Palladium catalysts for the process step (II-A), (II-B) or (II-C)+(III)→(IV-A), (IV-B) or (IV-C) when using approach d) and for the process step (IV-A), (IV-B) or (IV-C)+(V)→(I-A), (I-B) or (I-C) and for the process steps (VIII)+(III)→(IX), (IX)+(X)→(XI) and (XI)+(XII)→(I-A) are, for example, palladium on activated carbon, palladium (II) acetate, bis(dibenzylideneacetone)palladium(0), tetrakis (triphenylphosphine)palladium(0), bis(triphenyl-phosphine) palladium(II) chloride, bis(acetonitrile)palladium(II) chloride and [1,1'-bis(diphenylphosphino)ferrocene]dichloropalladium(II) and the corresponding dichloromethane complex, optionally in conjunction with additional phosphane ligands, for example 1,4-Bis(diphenylphosphino)butane-palladium(II) chloride (Pd(dppb)Cl$_2$); Dichloro[1,3-bis (diphenylphosphino)propane]palladium(II) (Pd(dppp)Cl$_2$), [1,1'-Bis(diphenyl-phosphino)ferrocene]dichloropalladiu (Pd(dppf)Cl$_2$, 2,2'-bis(diphenylphosphino)-1,1'-binaphthyl (BINAP), (2-biphenyl)di-tert-butylphosphine, dicyclohexyl [2',4',6'-tris(1-methylethyl)biphenyl-2-yl]phosphane (XPhos), bis(2-phenylphosphinophenyl) ether (DPEphos) or 4,5-bis(diphenylphosphino)-9,9-dimethylxanthene (Xantphos) [cf., for example, Hassan J. et al., Chem. Rev. 2002, 102, 1359-1469], 2-(dicyclohexylphosphine)-3,6-dimethoxy-2',4',6'-triisopropyl-1,1'-biphenyl (BrettPhos), 2-dicyclohexylphosphino-2',6'-dimethoxybiphenyl (SPhos), 2-dicyclohexylphosphino-2',6'-diisopropoxybiphenyl (RuPhos), 2-(di-t-butylphosphino)-3-methoxy-6-methyl-2',4',6'-tri-i-propyl-1,1'-biphenyl (RockPhos) and 2-di-tert-butylphosphino-2',4',6'-triisopropylbiphenyl (tert-ButylXPhos). It is furthermore possible to use appropriate precatalysts such as chloro-[2-(dicyclohexylphosphine)-3,6-dimethoxy-2',4',6'- triisopropyl-1,1'-biphenyl][2-(2-aminoethyl)-phenyl]palladium(II) (BrettPhos precatalyst) [cf., for example, S. L. Buchwald et al., Chem. Sci. 2013, 4, 916], optionally in combination with additional phosphane ligands such as 2-(dicyclohexylphosphine)-3,6-dimethoxy-2',4',6'-triisopropyl-1,1'-biphenyl (BrettPhos); preference is given to bis(dibenzylideneacetone)palladium(0) in combination with 4,5-bis(diphenylphosphino)-9,9-dimethylxanthene (Xantphos) and chloro-[2-(dicyclohexylphosphine)-3,6-dimethoxy-2',4',6'-triisopropyl-1,1'-biphenyl][2-(2-aminoethyl)phenyl]-palladium(II) (BrettPhos precatalyst) or a mixture of chloro-[2-(dicyclohexylphosphine)-3,6-dimethoxy-2',4',6'-triisopropyl-1,1'-biphenyl][2-(2-aminoethyl)phenyl]palladium(II) (BrettPhos precatalyst) and 2-(dicyclohexylphosphine)-3,6-dimethoxy-2',4',6'-triisopropyl-1,1'-biphenyl (BrettPhos).

The process steps (II-A), (II-B) or (II-C)+(III)→(IV-A), (IV-B) or (IV-C) and (IX)+(X)→(XI) are generally carried out when using approach a) in a temperature range of from −10° C. to +220° C., preferably in a) from +60° C. to +100° C., at atmospheric pressure; in b) and c) from +60° C. to +220° C.; in d)+10° C. to +150° C. However, it is also possible to carry out the reaction at reduced or at elevated pressure (for example at from 0.5 to 5 bar). It may optionally be advantageous to carry out the reaction with microwave irradiation.

The process step (IV-A), (IV-B) or (IV-C)+(V)→(I-A), (I-B) or (I-C) and the process step (VIII)+(III)→(IX) are generally carried out in a temperature range of from −10° C. to +220° C., preferably in a) from +60° C. to +150° C. However, it is also possible to carry out the reaction at reduced or at elevated pressure (for example at from 0.5 to 5 bar). It may optionally be advantageous to carry out the reaction with microwave irradiation.

The process step (XI)+(XII)→(I-A) is generally carried out in a temperature range of from −20° C. to +250° C., preferably in a) from +80° C. to +150° C. However, it is also possible to carry out the reaction at reduced or at elevated pressure (for example at from 0.5 to 5 bar). It may optionally be advantageous to carry out the reaction with microwave irradiation.

Suitable inert solvents for the process step (II-A), (II-B) or (II-C)+hydrazine or hydrazine equivalent→(V-A), (V-B) or (V-C) and (IV-A), (IV-B) or (IV-C)+hydrazine or hydrazine equivalent→(V-A), (V-B) or (V-C) and (III)+hydrazine or hydrazine equivalent→(X) are ethers such as 1,4-dioxane, tetrahydrofuran, 2-methyltetrahydrofuran, diethyl ether, di-n-butylether, glycol dimethyl ether or diethylene glycol dimethyl ether, alcohols such as tert-butanol or amyl alcohols or other solvents such as dimethylformamide (DMF), dimethyl sulphoxide (DMSO), dimethylacetamide (DMA), toluene or acetonitrile, or mixtures of the solvents mentioned; preference is given to dimethylformamide, tert-butanol, 1,4-dioxane or toluene.

The process step (II-A), (II-B) or (II-C)+hydrazine or hydrazine equivalent→(V-A), (V-B) or (V-C) and (IV-A), (IV-B) or (IV-C)+hydrazine or hydrazine equivalent→(V-A), (V-B) or (V-C) and (III)+hydrazine or hydrazine equivalent→(X) is generally carried out in a temperature range of from −20° C. to +250° C., preferably in from +50° C. to +120° C., at atmospheric pressure. However, it is also possible to carry out the reaction at reduced or at elevated pressure (for example at from 0.5 to 5 bar). It may optionally be advantageous to carry out the reaction with microwave irradiation.

Suitable inert solvents for the process step (V-A), (V-B) or (V-C)+(VII)→(I-A), (I-B) or (I-C) and (V-A), (V-B) or (V-C)+(VI)→(I-D), (I-E) or (I-F) and (X)+(VI)→(IX) are ethers such as 1,4-dioxane, tetrahydrofuran, 2-methyltetrahydrofuran, diethyl ether, di-n-butylether, glycol dimethyl ether or diethylene glycol dimethyl ether, alcohols such as tert-butanol or amyl alcohols or other solvents such as dimethylformamide (DMF), dimethyl sulphoxide (DMSO), dimethylacetamide (DMA), toluene or acetonitrile, or mixtures of the solvents mentioned; preference is given to ethanol.

The process step (V-A), (V-B) or (V-C)+(VI)→(I-A), (I-B) or (I-C) and (V-A), (V-B) or (V-C)+(VI)→(I-D), (I-E) or (I-F) and (X)+(VI)→(IX) is generally carried out in a temperature range of from −20° C. to +250° C., preferably in from +50° C. to +120° C., at atmospheric pressure. However, it is also possible to carry out the reaction at reduced or at elevated pressure (for example at from 0.5 to 5 bar). It may optionally be advantageous to carry out the reaction with microwave irradiation.

The compounds of the formula (II-A) and (II-B) are known from the literature or can be prepared by reacting a compound of the formula (XIII),

(XIII)

in which $R^6$ is as defined for the compound of general formula (I) as defined supra, and in which $R^9$ is as defined for the compound of general formula (I) as defined supra, and $T^2$ represents chlorine, methoxy, ethoxy or phenoxy in the presence of a suitable base, with a compound of general formula (XIV),

(XIV)

thereby giving a compound of general formula (XV),

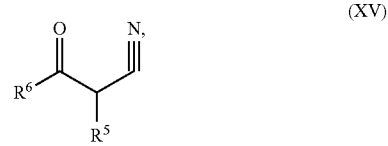

(XV)

in which $R^6$ and $R^6$ are as defined for the compound of general formula (I) as defined supra, which is allowed

[G] to react with a hydrazine equivalent, in particular hydrazine monohydrate, thereby giving a compound of general formula (II-A1),

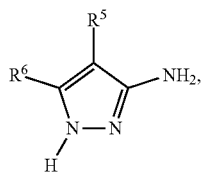
(II-A1)

in which $R^6$ and $R^6$ are as defined for the compound of general formula (I) as defined supra, or

[H] to react in the presence of a suitable base with dimethyl sulfate thereby giving a compound of general formula (XVI),

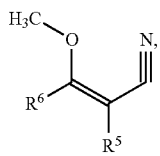
(XVI)

in which $R^6$ and $R^6$ are as defined for the compound of general formula (I) as defined supra, which is then allowed to react with a hydrazine equivalent, in particular hydrazine monohydrate, thereby giving a compound of general formula (II-A1),

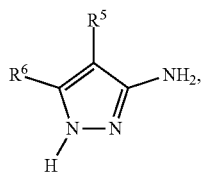
(II-A1)

in which $R^6$ and $R^6$ are as defined for the compound of general formula (I) as defined supra, which is then allowed to react with a compound of general formula (XVII),

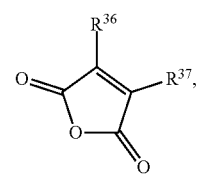
(XVII)

in which $R^{36}$ and $R^{37}$ are methyl or preferably form a phenyl ring together with the atoms they are attached to, thereby giving a compound of general formula (XVIII-1),

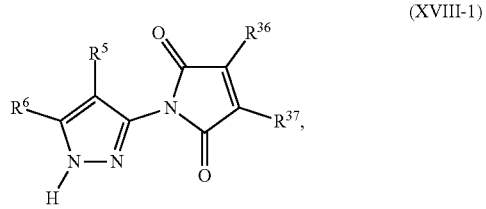
(XVIII-1)

in which $R^5$ and $R^6$ are as defined for the compound of general formula (I) as defined supra, and $R^{36}$ and $R^{37}$ are methyl or preferably form a phenyl ring together with the atoms they are attached to, which is then in the presence of a suitable base allowed to react with a compound of general formula (XIX),

(XIX)

$R^7-X$, in which $R^7$ is as defined for the compound of general formula (I) as defined supra, and X represents a suitable leaving group, in particular chlorine, bromine, iodine, mesylate, triflate or tosylate, thereby giving a compound of general formula (XX-1),

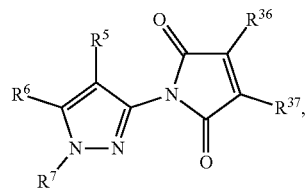
(XX-1)

in which $R^5$, $R^6$ and $R^6$ are as defined for the compound of general formula (I) as defined supra, and $R^{36}$ and $R^{37}$ are methyl or preferably form a phenyl ring together with the atoms they are attached to, which is the allowed to react with a hydrazine equivalent, in particular hydrazine monohydrate.

In the process steps (XV)+hydrazine or hydrazine equivalent→(II-A1) and (XVI)+hydrazine or hydrazine equivalent→(II-A1) the corresponding tautomere (II-B1)

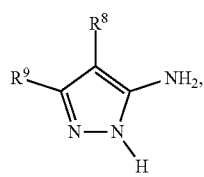
(II-B1)

in which $R^9$ and $R^8$ are as defined for the compound of general formula (I) as defined supra, given that $R^6$ is $R^9$ and $R^5$ is $R^8$ is also formed as a person skilled in the art would expect. As a consequence the tautomeres of (XX-1) and (XVIII-1) which are (XVIII-2) and (XX-2), respectively, are formed in the following process steps.

(XVIII-2)
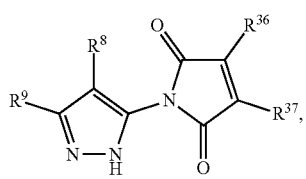
(XX-2)
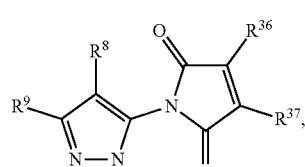
in which R⁹ and R⁸ are as defined for the compound of general formula (I) as defined supra, given that $R^6$ is $R^9$ and $R^5$ is $R^8$
The process described is illustrated in an exemplary manner by the schemes below (Scheme 4-6):
Scheme 4:
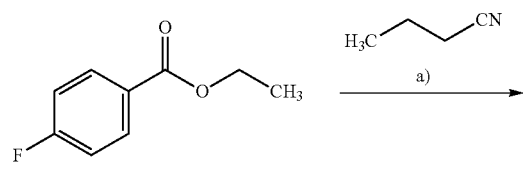
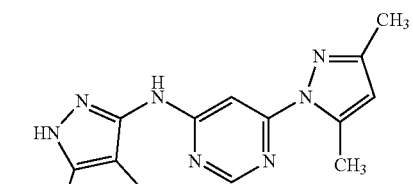
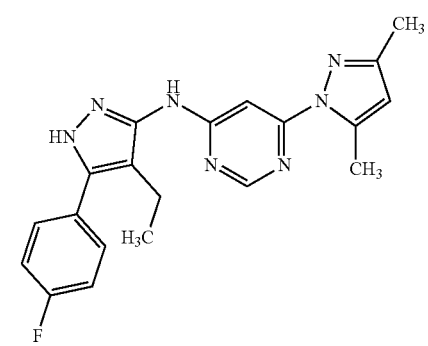
[a]: LiHMDS, THF, r.t.; b): Hydrazine Monohydrate, EtOH, reflux; c): NaI, DIPEA, DMF, 80° C.; d): DBU, NMP, 190° C.].
Scheme 5:
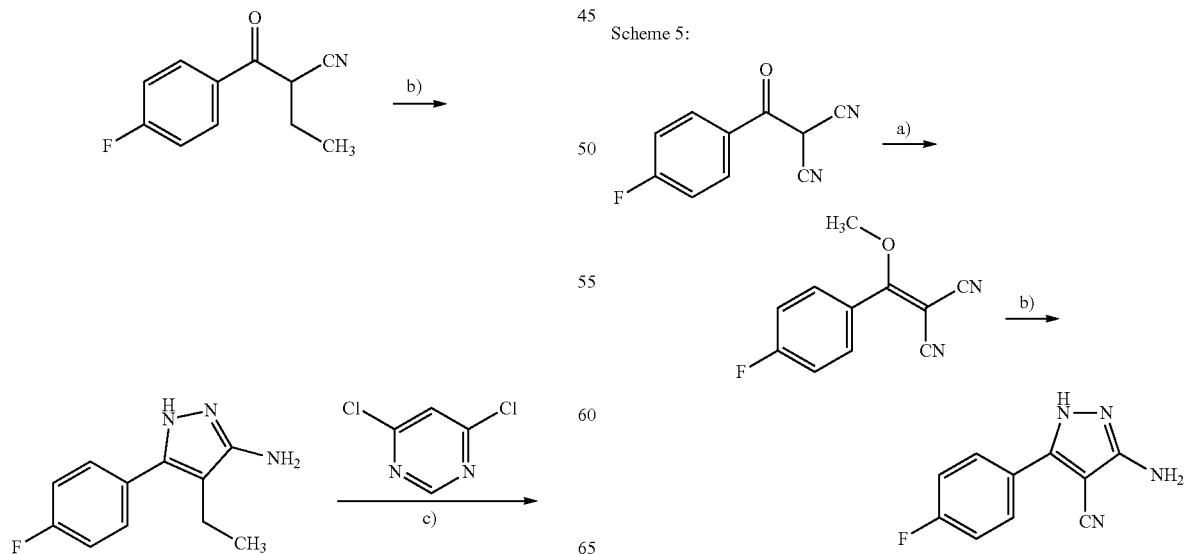

[a]: Dimethyl sulfate, dioaxne/water, NaHCO₃, reflux b): Hydrazine Monohydrate, 2-propanol, reflux].

Scheme 6:

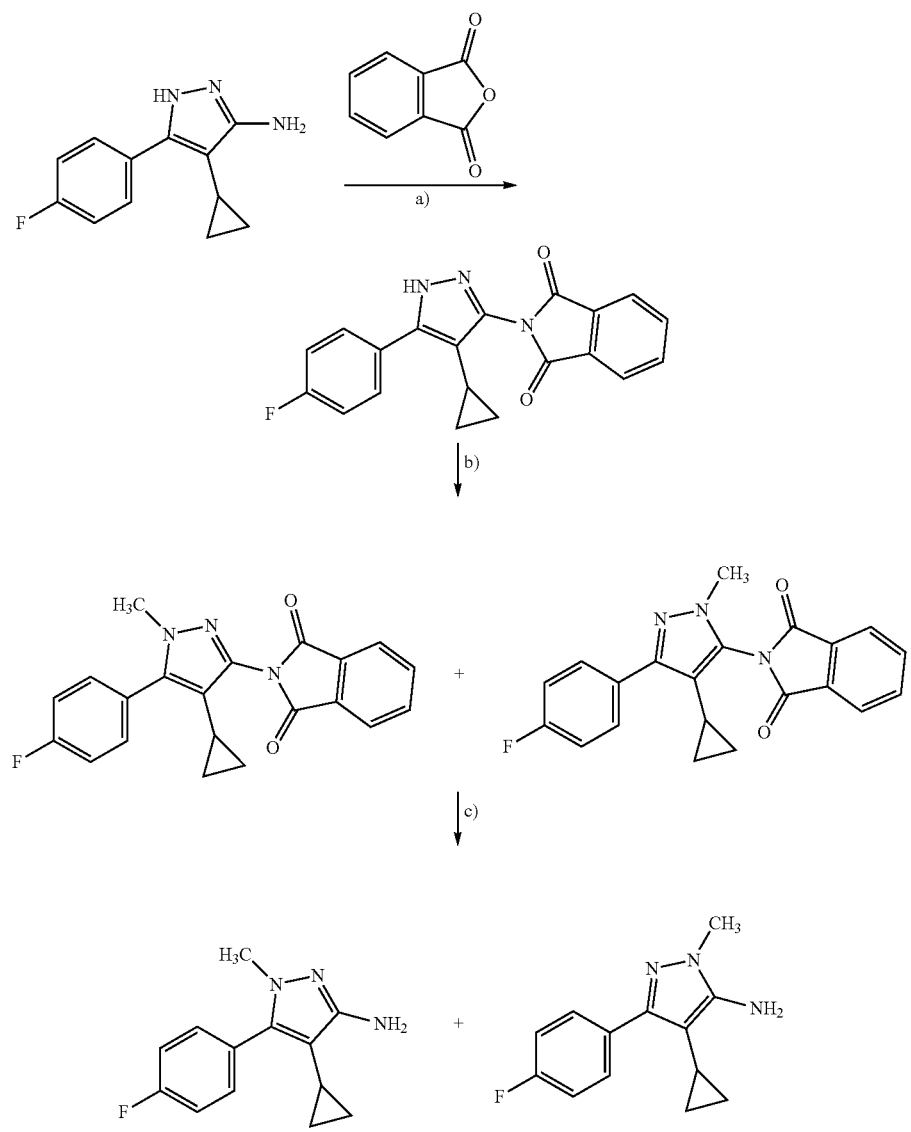

[a]: AcOH, reflux; b): MeI, K₂CO₃, DMF, r.t. c): Hydrazine Monohydrate, EtOH, 80° C.].

The compounds of the formula (II-C) are known from the literature or can be prepared by reacting a compound of the formula (XXI),

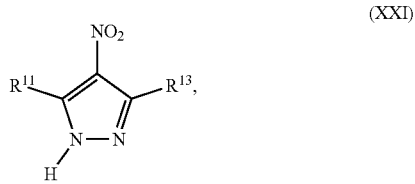
(XXI)

in which $R^{11}$ and $R^{13}$ are as defined for the compound of general formula (I) as defined supra, in the presence of a suitable base and in the presence of a suitable copper salt with a compound of general formula (XXII),

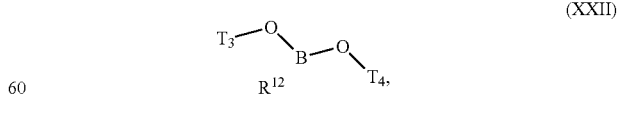
(XXII)

in which $R^{12}$ is as defined for the compound of general formula (I) as defined supra, and $T^3$ and $T^4$ are defined as hydrogen, methyl or they form a 4,4,5,5-tetramethyl-1,3,2-dioxaborolane ring together with the atoms they are attached to.

thereby giving a compound of general formula (XXIII),

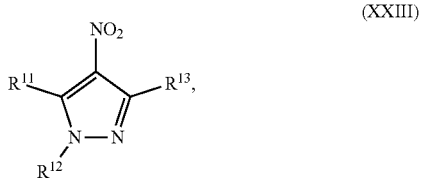

(XXIII)

in which $R^{11}$, $R^{12}$ and $R^{13}$ are as defined for the compound of general formula (I) as defined supra,
which is then hydrogenated in the presence of iron and hydrochloric acid, hydrogen/palladium, iron and ammonium chloride, hydrogen/platinum dioxide or acetic acid/zinc.

The compounds of the formulae (XIII), (XIV), (XV), (XVII), (XIX), (XXI) and (XXII) are commercially available, known from the literature or can be prepared analogously to processes known from the literature.

The process described is illustrated in an exemplary manner by the scheme below (Scheme 7):

Scheme 7:

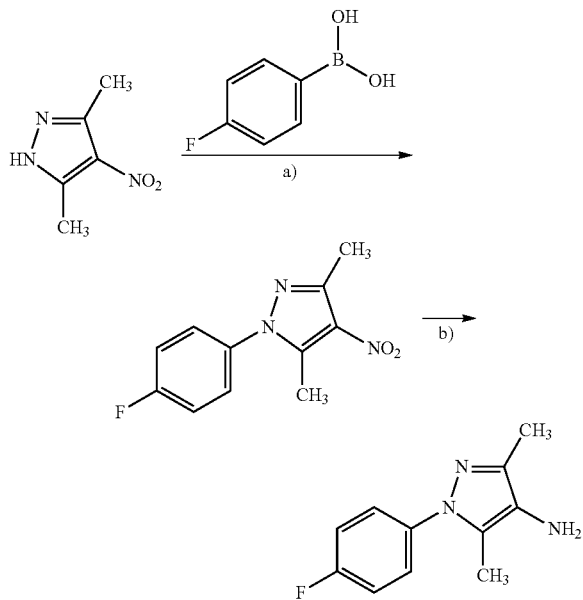

[a): Cu(OAc)$_2$, pyridine, DCM, molecular sieves, r.t.; b): Fe, HCl, MeOH, reflux].

Starting materials are either commercially available or can be prepared according to procedures available from the public domain, as understandable to the person skilled in the art. Specific examples are described in the Experimental Section.

Suitable inert solvents for the process step (XIII)+(XIV)→(XV) for example, are aromatic hydrocarbons such as benzene, toluene or xylene, ethers such as diethyl ether, diisopropyl ether, methyl tert-butyl ether, 1,2-dimethoxyethane, bis-(2-methoxyethyl) ether, tetrahydrofurane or 1,4-dioxane. It is also possible to use mixtures of the solvents mentioned, optionally also in a mixture with water. Preference is given to using tetrahydrofurane in a) ethanol in b).

Suitable bases for the process step (XIII)+(XIV)→(XV) are for example, alkali metal or alkaline earth metal carbonates such as lithium carbonate, sodium carbonate, potassium carbonate, calcium carbonate or caesium carbonate, alkali metal or alkaline earth metal hydroxides such as sodium hydroxide, potassium hydroxide or barium hydroxide, alkali metal or alkaline earth metal phosphates such as potassium phosphate, alkali metal alkoxides such as sodium tert-butoxide or potassium tert-butoxide and sodium methoxide, alkali metal phenoxides such as sodium phenoxide, amides such as sodium amide, lithium bis(trimethylsilyl)amide, sodium bis(trimethylsilyl)amide or potassium bis(trimethylsilyl)amide or lithium diisopropylamide or organic amines such as 1,5-diazabicyclo[4.3.0]non-5-ene (DBN), 1,8-diazabicyclo[5.4.0]undec-7-ene (DBU); preference is given to lithium bis(trimethylsilyl)amide.

The process (XIII)+(XIV)→(XV) is generally carried out in a temperature range of from −80° C. to +220° C., preferably in a) from 0° C. to +60° C.

Suitable inert solvents for the process steps (XV)+hydrazine or hydrazine equivalent→(II-A1), (XVI)+hydrazine or hydrazine equivalent→(II-A1) and (XX)+hydrazine or hydrazine equivalent→(II-A) are ethers such as 1,4-dioxane, tetrahydrofuran, 2-methyltetrahydrofuran, diethyl ether, di-n-butylether, glycol dimethyl ether or diethylene glycol dimethyl ether, alcohols such as methanol, ethanol, 2-propanol, tert-butanol or amyl alcohols or other solvents such as dimethylformamide (DMF), dimethyl sulphoxide (DMSO), dimethylacetamide (DMA), toluene or acetonitrile, or mixtures of the solvents mentioned; preference is given to ethanol and 2-propanol.

The process steps (XV)+hydrazine or hydrazine equivalent→(II-A1), (XVI)+hydrazine or hydrazine equivalent→(II-A1) and (XX-1)+hydrazine or hydrazine equivalent→(II-A) are generally carried out in a temperature range of from −20° C. to the respective boiling point of the solvent, preferably in from +50° C. to +120° C., at atmospheric pressure. However, it is also possible to carry out the reaction at reduced or at elevated pressure (for example at from 0.5 to 5 bar). It may optionally be advantageous to carry out the reaction with microwave irradiation.

Suitable inert solvents for the process step (XV)→(XVI) are, aromatic hydrocarbons such as benzene, toluene or xylene, ethers such as diethyl ether, diisopropyl ether, methyl tert-butyl ether, 1,2-dimethoxyethane, bis-(2-methoxyethyl) ether, tetrahydrofuran or 1,4-dioxane, or dipolar aprotic solvents such as acetonitrile, N,N-dimethylformamide (DMF), N,N-dimethylacetamide (DMA), dimethyl sulfoxide (DMSO), N,N'-dimethylpropyleneurea (DMPU), N-methylpyrrolidinone (NMP) or pyridine. It is also possible to use mixtures of the solvents mentioned, optionally also in a mixture with water. Preference is given to using 1,4-dioxane or a mixture of 1,4-dioxane and water.

Suitable bases for the process step (XV)→(XVI) are for example, alkali metal or alkaline earth metal carbonates such as lithium carbonate, sodium carbonate, sodium hydrogen carbonate, potassium carbonate, potassium hydrogen carbonate, calcium carbonate, calcium hydrogen carbonate, or caesium carbonate, alkali metal or alkaline earth metal hydroxides such as sodium hydroxide, potassium hydroxide or barium hydroxide, alkali metal or alkaline earth metal phosphates such as potassium phosphate, alkali metal alkoxides such as sodium tert-butoxide or potassium tert-butoxide and sodium methoxide, alkali metal phenoxides such as sodium phenoxide, amides such as sodium amide, lithium bis(trimethylsilyl)amide, sodium bis(trimethylsilyl)amide or potassium bis(trimethylsilyl)amide or lithium diisopropylamide or organic amines such as 1,5-diazabicyclo[4.3.0]non-5-ene (DBN), 1,8-diazabicyclo[5.4.0]undec-7-ene (DBU); preference is given to sodium hydrogen carbonate.

The process step (XV)→(XVI) is generally carried out in a temperature range of from −20° C. to the respective boiling point of the solvent, preferably in from +50° C. to the respective boiling point of the solvent, at atmospheric pressure. However, it is also possible to carry out the reaction at reduced or at elevated pressure (for example at from 0.5 to 5 bar). It may optionally be advantageous to carry out the reaction with microwave irradiation.

Suitable inert solvents for the process steps (II-A1)+(XVII)→(XVIII) are acids like acetic acid, ethers such as 1,4-dioxane, tetrahydrofuran, 2-methyltetrahydrofuran, diethyl ether, di-n-butylether, glycol dimethyl ether or diethylene glycol dimethyl ether, alcohols such as tert-butanol or amyl alcohols or other solvents such as dimethylformamide (DMF), dimethyl sulphoxide (DMSO), dimethylacetamide (DMA), toluene or acetonitrile, or mixtures of the solvents mentioned; preference is given to acetic acid.

The process step (II-A1)+(XVII)→(XVIII-1) is generally carried out in a temperature range of from −20° C. to the respective boiling point of the solvent, preferably in from +50° C. to +150° C., at atmospheric pressure. However, it is also possible to carry out the reaction at reduced or at elevated pressure (for example at from 0.5 to 5 bar). It may optionally be advantageous to carry out the reaction with microwave irradiation.

Inert solvents for the process step (XVIII-1)+(XIX)→(XX-1) are, for example, halogenated hydrocarbons such as dichloromethane, trichloromethane, carbon tetrachloride, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP) or pyridine. It is also possible to use mixtures of the solvents mentioned. Preference is given to using dimethylformamide or dimethyl sulphoxide.

Suitable bases for the process step (XVIII-1)+(XIX)→(XX-1) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, if appropriate with addition of an alkali metal iodide, for example sodium iodide or potassium iodide, alkali alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate, caesium carbonate or sodium methoxide.

The reaction is generally carried out in a temperature range of from 0° C. to +120° C., preferably at from +20° C. to +80° C., if appropriate in a microwave. The reaction can be carried out at atmospheric, elevated or reduced pressure (for example from 0.5 to 5 bar).

Suitable inert solvents for the process step (XXI)+(XXII)→(XXIII) are, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using dichloromethane.

Suitable bases for the process step (XXI)+(XXII)→(XXIII) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, if appropriate with addition of an alkali metal iodide, for example sodium iodide or potassium iodide, alkali alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using pyridine Suitable copper salts for the process step (XXI)+(XXII)→(XXIII) are copper(II) acetate, copper(I) oxide/oxygen, copper(I) iodide/oxygen, iron and palladium, copper(II) bis(trifluoromethanesulfonate) Preference is given to using copper acetate copper acetate.

The reaction is generally carried out in a temperature range of from 0° C. to the respective boiling point of the solvent, preferably from +20° C. to +80° C., if appropriate in a microwave. The reaction can be carried out at atmospheric, elevated or reduced pressure (for example from 0.5 to 5 bar).

Suitable inert solvents for the process steps (XXIII)→(II-C) are ethers such as 1,4-dioxane, tetrahydrofuran, 2-methyltetrahydrofuran, diethyl ether, di-n-butylether, glycol dimethyl ether or diethylene glycol dimethyl ether, alcohols such as tert-butanol or amyl alcohols or other solvents such as dimethylformamide (DMF), dimethyl sulphoxide (DMSO), dimethylacetamide (DMA), toluene or acetonitrile, or mixtures of the solvents mentioned; preference is given to acetic acid.

The reaction is generally carried out in a temperature range of from 0° C. to the respective boiling point of the solvent, preferably from +20° C. to +100° C., if appropriate in a microwave. The reaction can be carried out at atmospheric, elevated or reduced pressure (for example from 0.5 to 5 bar).

Further compounds according to the invention can optionally also be prepared by converting functional groups of individual substituents, in particular those listed under $R^1$, starting with the compounds of the formula (I) obtained by the above processes. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action which could not have been predicted. Compounds of the present invention have surprisingly been found to effectively reduce plasma phosphate levels and increase urinary Pi excretion due to their Npt2a inhibition potential. Moreover the compounds of the present invention have surprisingly been found to effectively inhibit vascular calcification and to reduce FGF-23 and parathyroid hormone levels significantly by inhibiting Npt2a. It is possible therefore that said compounds can be used for the treatment or prophylaxis of diseases, preferably soft tissue calcification disorders in humans and animals.

Compounds of the present invention can be utilized to prevent and/or treat diseases and/or conditions associated with hyperphosphatemia, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve. This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder.

The present invention also provides methods of treating diseases and/or conditions associated with hyperphosphatemia, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

These disorders have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as soft tissue calcification, e.g. chronic kidney disease associated calcification, non-chronic kidney disease associated calcification, and any associated condition.

In accordance with a further aspect, the present invention covers compounds of general formula (I), as described supra, or stereoisomers, tautomers, hydrates, solvates, and salts thereof, particularly pharmaceutically acceptable salts thereof, or mixtures of same, for use in the treatment and/or prophylaxis of diseases.

In accordance with a further embodiment, the present invention covers compounds of general formula (I), as described supra, or stereoisomers, tautomers, hydrates, solvates, and salts thereof, particularly pharmaceutically acceptable salts thereof, or mixtures of same, for use in the treatment and/or prophylaxis of diseases and/or conditions associated with hyperphosphatemia, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

The pharmaceutical activity of the compounds according to the invention can be explained by their activity as Npt2a Inhibitors.

In accordance with a further aspect, the present invention covers the use of compounds of general formula (I), as described supra, or stereoisomers, tautomers, hydrates, solvates, and salts thereof, particularly pharmaceutically acceptable salts thereof, or mixtures of same, for the treatment and/or prophylaxis of diseases, in particular diseases and/or conditions associated with hyperphosphatemia, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

In accordance with a further aspect, the present invention covers the use of compounds of general formula (I), as described supra, or stereoisomers, tautomers, hydrates, solvates, and salts thereof, particularly pharmaceutically acceptable salts thereof, or mixtures of same, in a method of treatment and/or prophylaxis of diseases, in particular diseases and/or conditions associated with hyperphosphatemia, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

In accordance with a further aspect, the present invention covers the use of a compound of general formula (I), as described supra, or stereoisomers, tautomers, hydrates, solvates, and salts thereof, particularly pharmaceutically acceptable salts thereof, or mixtures of same, for the preparation of a pharmaceutical composition, preferably a medicament, for the treatment and/or prophylaxis of diseases, in diseases and/or conditions associated with hyperphosphatemia, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

In accordance with a further aspect, the present invention covers a method of treatment and/or prophylaxis of diseases, in diseases and/or conditions associated with hyperphosphatemia, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve, using an effective amount of a compound of general formula (I), as described supra, or stereoisomers, tautomers, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients, in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

The compounds of general formula (I), as described supra, or stereoisomers, tautomers, hydrates, solvates, and salts thereof, particularly pharmaceutically acceptable salts thereof, or mixtures of same, are suitable for the treatment and/or prophylaxis of diseases and/or conditions associated with hyperphosphatemia, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve. The compounds of general formula (I), as described supra, or stereoisomers, tautomers, hydrates, solvates, and salts thereof, particularly pharmaceutically acceptable salts thereof, or mixtures of same, are also suitable for the treatment and/or prophylaxis of chronic kidney disease (CKD). The compounds of general formula (I), as described supra, or stereoisomers, tautomers, hydrates, solvates, and salts thereof, particularly pharmaceutically acceptable salts thereof, or mixtures of same, are also suitable for the treatment and/or prophylaxis of soft tissue calcification disorders. The compounds of general formula (I), as described supra, or stereoisomers, tautomers, hydrates, solvates, and salts thereof, particularly pharmaceutically acceptable salts thereof, or mixtures of same, are also suitable for the treatment and/or prophylaxis of chronic kidney disease associated calcification disorders and non-chronic kidney disease associated calcification disorders.

The compounds of general formula (I), as described supra, or stereoisomers, tautomers, hydrates, solvates, and salts thereof, particularly pharmaceutically acceptable salts thereof, or mixtures of same, are suitable for the treatment and/or prophylaxis of cardiovascular and of renal disorders, in particular of diseases and/or conditions associated with hyperphosphatemia, soft tissue calcification, chronic kidney disease (CKD), soft tissue calcification, in particular chronic kidney disease associated calcification and non-chronic kidney disease associated calcification, and also of chronic renal disease.

Within the meaning of the present invention, the term renal insufficiency comprises both acute and chronic manifestations of renal insufficiency, and also underlying or related renal disorders such as diabetic and non-diabetic nephropathies, hypertensive nephropathies, ischaemic renal disorders, renal hypoperfusion, intradialytic hypotension, obstructive uropathy, renal stenoses, glomerulopathies, glomerulonephritis (such as, for example, primary glomerulonephritides; minimal change glomerulonephritis (lipoid-nephrosis); membranous glomerulonephritis; focal segmental glomerulosclerosis (FSGS); membrane-proliferative glomerulonephritis; crescentic glomerulonephritis; mesangioproliferative glomerulonephritis (IgA nephritis, Berger's disease); post-infectious glomerulonephritis; secondary glomerulonephritides: diabetes mellitus, lupus erythematosus, amyloidosis, Goodpasture syndrome, Wegener granulomatosis, Henoch-Schönlein purpura, microscopic polyangiitis, acute glomerulonephritis, pyelonephritis (for example as a result of: urolithiasis, benign prostate hyperplasia, diabetes, malformations, abuse of analgesics, Crohn's disease), glomerulosclerosis, arteriolonecrose of the kidney, tubulointerstitial diseases, nephropathic disorders such as primary and congenital or acquired renal disorder, Alport syndrome, nephritis, immunological kidney disorders such as kidney transplant rejection and immunocomplex-induced renal disorders, nephropathy induced by toxic substances, nephropathy induced by contrast agents, diabetic and non-diabetic nephropathy, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or the need for dialysis. The present invention also comprises the use of the compounds according to the invention for the treatment and/or prophylaxis of sequelae of renal insufficiency, for example pulmonary oedema, heart failure, uremia, anemia, electrolyte disturbances (for example hypercalemia, hyponatremia) and disturbances in bone and carbohydrate metabolism.

The compounds of general formula (I), as described supra, or stereoisomers, tautomers, hydrates, solvates, and salts thereof, particularly pharmaceutically acceptable salts thereof, or mixtures of same, can also be used for the treatment and/or prophylaxis of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

The compounds of general formula (I), as described supra, or stereoisomers, tautomers, hydrates, solvates, and salts thereof, particularly pharmaceutically acceptable salts thereof, or mixtures of same, can also be used for the treatment and/or prophylaxis of metabolic syndrome, hypertension, resistant hypertension, acute and chronic heart failure, coronary heart disease, stable and unstable angina pectoris, peripheral and cardiac vascular disorders, for treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for treatment and/or prophylaxis of erectile dysfunction and female sexual dysfunction.

The compounds of general formula (I), as described supra, or stereoisomers, tautomers, hydrates, solvates, and salts thereof, particularly pharmaceutically acceptable salts thereof, or mixtures of same, can also be used for the treatment and/or prophylaxis of pulmonary arterial hypertension (PAH) and other forms of pulmonary hypertension (PH) including left-heart disease, thromboembolisms (CTEPH), sarcoidosis, COPD or pulmonary fibrosis-associated pulmonary hypertension, chronic-obstructive pulmonary disease (COPD).

Due to their activity and selectivity profile, the compounds of general formula (I), as described supra, or stereoisomers, tautomers, hydrates, solvates, and salts thereof, particularly pharmaceutically acceptable salts thereof, or mixtures of same, are believed to be particularly suitable for the treatment and/or prevention preeclampsia, peripheral arterial disease (PAD) and coronary microvascular dysfunction (CMD), Raynaud's syndrome, dysmenorrhea, glaucoma, diabetic retinopathy, proliferative vitroretinopathy and disorders of the connective tissue (for example sarcoidosisdiabetic, inflammatory or hypertensive nephropaties, fibrotic disorders, cardiac insufficiency, angina pectoris, hypertension, ischemias, vascular disorders, thromboembolic disorders, erectile dysfunction, dementia and Alzheimer.

The compounds of general formula (I), as described supra, or stereoisomers, tautomers, hydrates, solvates, and salts thereof, particularly pharmaceutically acceptable salts thereof, or mixtures of same, are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems.

The compounds of general formula (I), as described supra, or stereoisomers, tautomers, hydrates, solvates, and salts thereof, particularly pharmaceutically acceptable salts thereof, or mixtures of same, are furthermore also suitable for controlling cerebral blood flow and thus represent effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be used for controlling states of pain and tinnitus.

The present invention further provides a method for treatment and/or prophylaxis of disorders, in particular the disorders mentioned above, using an effective amount of at least one of the compounds according to the invention.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of diseases and/or conditions associated with hyperphosphatemia, chronic kidney disease (CKD), soft tissue calcification, chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

An embodiment of the invention are pharmaceutical compositions comprising at least one compound of formula (I) according to the invention, preferably together with at least one inert, non-toxic, pharmaceutically suitable auxiliary, and the use of these pharmaceutical compositions for the above cited purposes.

Particularly, the present invention covers a pharmaceutical combination, which comprises:
one or more first active ingredients, in particular compounds of general formula (I) as defined supra, and one or more further active ingredients, in particular for the treatment and/or prophylaxis of diseases and/or conditions associated with hyperphosphatemia, chronic kidney disease (CKD), soft tissue calcification, chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known agents of the same indication treatment group, such as agents used for the treatment and/or prophylaxis of diseases and/or conditions associated with hyperphosphatemia, elevated plasma FGF23 levels, chronic kidney disease (CKD), soft tissue calcification, chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

The inventive compounds can be employed alone or, if required, in combination with other active ingredients. The present invention further provides medicaments comprising at least one of the inventive compounds and one or more further active ingredients, especially for treatment and/or prophylaxis of the aforementioned disorders. Preferred examples of suitable active ingredient combinations include:
organic nitrates and NO donors, for example sodium nitroprusside, nitroglycerin, isosorbide mononitrate, isosorbide dinitrate, molsidomine or SIN-1, and inhaled NO;
compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil, tadalafil, udenafil, desantafil, avanafil, mirodenafil, lodenafil or PF-00489791;
antithrombotic agents, by way of example and with preference from the group of the platelet aggregation inhibitors, the anticoagulants or the profibrinolytic substances;
hypotensive active ingredients, by way of example and with preference from the group of the calcium antagonists, angiotensin AII antagonists, ACE inhibitors, NEP-inhibitors, vasopeptidase-inhibitors, endothelin antagonists, renin inhibitors, alpha-receptor blockers, beta-receptor blockers, mineralocorticoid receptor antagonists, rho-kinase-inhibitors and the diuretics;

antiarrhythmic agents, by way of example and with preference from the group of sodium channel blocker, beta-receptor blocker, potassium channel blocker, calcium antagonists, If-channel blocker, digitalis, parasympatholytics (vagoliytics), sympathomimetics and other antiarrhythmics as adenosin, adenosine receptor agonists as well as vernakalant;

positive-inotrop agents, by way of example cardiac glycoside (Dogoxin), beta-adrenergic and dopaminergic agonists, such as isoprenalin, adrenalin, noradrenalin, dopamin or dobutamin;

vasopressin-rezeptor-antagonists, by way of example and with preference from the group of conivaptan, tolvaptan, lixivaptan, mozavaptan, satavaptan, SR-121463, RWJ 676070 or BAY 86-8050, as well as the compounds described in WO 2010/105770, WO2011/104322 and WO 2016/071212;

active ingredients which alter lipid metabolism, for example and with preference from the group of the thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

bronchodilatory agents, for example and with preference from the group of the beta-adrenergic rezeptor-agonists, such as, by way of example and preferably, albuterol, isoproterenol, metaproterenol, terbutalin, formoterol or salmeterol, or from the group of the anticholinergics, such as, by way of example and preferably, ipratropiumbromid;

anti-inflammatory agents, for example and with preference from the group of the glucocorticoids, such as, by way of example and preferably, prednison, prednisolon, methylprednisolon, triamcinolon, dexamethason, beclomethason, betamethason, flunisolid, budesonid or fluticason as well as the non-steroidal anti-inflammatory agents (NSAIDs), by way of example and preferably, acetyl salicylic acid (aspirin), ibuprofen and naproxen, 5-amino salicylic acid-derivates, leukotriene-antagonists, TNF-alpha-inhibitors and chemokin-receptor antagonists, such as CCR1, 2 and/or 5 inhibitors;

agents that inhibit the signal transductions cascade, for example and with preference from the group of the kinase inhibitors, by way of example and preferably, from the group of the tyrosine kinase- and/or serine/threonine kinase inhibitors;

agents, that inhibit the degradation and modification of the extracellular matrix, for example and with preference from the group of the inhibitors of the matrix-metalloproteases (MMPs), by way of example and preferably, inhibitors of chymasee, stromelysine, collagenases, gelatinases and aggrecanases (with preference from the group of MMP-1, MMP-3, MMP-8, MMP-9, MMP-10, MMP-11 and MMP-13) as well as of the metallo-elastase (MMP-12) and neutrophil-elastase (HNE), as for example sivelestat or DX-890;

agents, that block the bindung of serotonin to its receptor, for example and with preference antagonists of the $5-HT_{2b}$-receptor;

organic nitrates and NO-donators, for example and with preference sodium nitroprussid, nitroglycerine, isosorbid mononitrate, isosorbid dinitrate, molsidomine or SIN-1, as well as inhaled NO;

NO-independent, but heme-dependent stimulators of the soluble guanylate cyclase, for example and with preference the compounds described in WO 00/06568, WO 00/06569, WO 02/42301, WO 03/095451, WO 2011/147809, WO 2012/004258, WO 2012/028647 and WO 2012/059549;

NO-independent and heme-independent activators of the soluble guanylate cyclase, for example and with preference the compounds described in WO 01/19355, WO 01/19776, WO 01/19778, WO 01/19780, WO 02/070462 and WO 02/070510 beschriebenen Verbindungen;

agents, that stimulates the synthesis of cGMP, wie beispielsweise sGC Modulatoren, for example and with preference riociguat, cinaciguat, vericiguat or BAY 1101042;

prostacyclin-analogs, for example and with preference iloprost, beraprost, treprostinil or epoprostenol;

agents, that inhibit soulble epoxidhydrolase (sEH), for example and with preference N,N'-Dicyclohexyl urea, 12-(3-Adamantan-1-yl-ureido)-dodecanic acid or 1-Adamantan-1-yl-3-{5-[2-(2-ethoxyethoxy)ethoxy]pentyl}-urea;

agents that interact with glucose metabolism, for example and with preference insuline, biguanide, thiazolidinedione, sulfonyl urea, acarbose, DPP4 inhibitors, GLP-1 analogs or SGLT-1 inhibitors;

natriuretic peptides, for example and with preference atrial natriuretic peptide (ANP), natriuretic peptide type B (BNP, Nesiritid) natriuretic peptide type C (CNP) or urodilatin;

activators of the cardiac myosin, for example and with preference omecamtiv mecarbil (CK-1827452);

calcium-sensitizers, for example and with preference levosimendan;

agents that affect the energy metabolism of the heart, for example and with preference etomoxir, dichloroacetat, ranolazine or trimetazidine, full or partial adenosine A1 receptor agonists such as GS-9667 (formerly known as CVT-3619), capadenoson, neladenoson and BAY 1067197;

agents that affect the heart rate, for example and with preference ivabradin;

Antithrombotic agents are preferably understood to mean compounds from the group of the platelet aggregation inhibitors, the anticoagulants or the profibrinolytic substances.

In a preferred embodiment of the invention, the inventive compounds are administered in combination with a platelet aggregation inhibitor, by way of example and with preference aspirin, clopidogrel, prasugrel, ticagrelor, ticlopidin or dipyridamole.

In a preferred embodiment of the invention, the inventive compounds are administered in combination with a thrombin inhibitor, by way of example and with preference ximelagatran, dabigatran, melagatran, bivalirudin or clexane.

In a preferred embodiment of the invention, the inventive compounds are administered in combination with a GPIIb/IIIa antagonist such as, by way of example and with preference, tirofiban or abciximab.

In a preferred embodiment of the invention, the inventive compounds are administered in combination with a factor Xa inhibitor, by way of example and with preference rivaroxaban (BAY 59-7939), DU-176b, apixaban, betrixaban, otamixaban, fidexaban, razaxaban, letaxaban, eribaxaban, fondaparinux, idraparinux, PMD-3112, darexaban (YM-150), KFA-1982, EMD-503982, MCM-17, MLN-1021, DX 9065a, DPC 906, JTV 803, SSR-126512 or SSR-128428.

In a preferred embodiment of the invention, the inventive compounds are administered in combination with heparin or with a low molecular weight (LMW) heparin derivative.

In a preferred embodiment of the invention, the inventive compounds are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, rho-kinase inhibitors and the diuretics.

In a preferred embodiment of the invention, the inventive compounds are administered in combination with a calcium antagonist, by way of example and with preference nifedipine, amlodipine, verapamil or diltiazem.

In a preferred embodiment of the invention, the inventive compounds are administered in combination with an alpha-1-receptor blocker, by way of example and with preference prazosin.

In a preferred embodiment of the invention, the inventive compounds are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, by way of example and with preference losartan, candesartan, valsartan, telmisartan or embusartan or a dual angiotensin AII antagonist/neprilysin-inhibitor, by way of example and with preference LCZ696 (valsartan/sacubitril).

In a preferred embodiment of the invention, the inventive compounds are administered in combination with an ACE inhibitor, by way of example and with preference enalapril, captopril, lisinopril, ramipril, delapril, fosinopril, quinopril, perindopril or trandopril.

In a preferred embodiment of the invention, the inventive compounds are administered in combination with an endothelin antagonist, by way of example and with preference bosentan, darusentan, ambrisentan or sitaxsentan.

In a preferred embodiment of the invention, the inventive compounds are administered in combination with a renin inhibitor, by way of example and with preference aliskiren, SPP-600 or SPP-800.

In a preferred embodiment of the invention, the inventive compounds are administered in combination with a mineralocorticoid receptor antagonist, by way of example and with preference spironolactone or eplerenone.

In a preferred embodiment of the invention, the inventive compounds are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the inventive compounds are administered in combination with a CETP inhibitor, by way of example and with preference dalcetrapib, anacetrapib, torcetrapib (CP-529 414), JJT-705 or CETP vaccine (Avant).

In a preferred embodiment of the invention, the inventive compounds are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the inventive compounds are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the inventive compounds are administered in combination with a squalene synthesis inhibitor, by way of example and with preference BMS-188494 or TAK-475.

In a preferred embodiment of the invention, the inventive compounds are administered in combination with an ACAT inhibitor, by way of example and with preference avasimibe, melinamide, pactimibe, eflucimibe or SMP-797.

In a preferred embodiment of the invention, the inventive compounds are administered in combination with an MTP inhibitor, by way of example and with preference implitapide, BMS-201038, R-103757 or JTT-130.

In a preferred embodiment of the invention, the inventive compounds are administered in combination with a PPAR-gamma agonist, by way of example and with preference pioglitazone or rosiglitazone.

In a preferred embodiment of the invention, the inventive compounds are administered in combination with a PPAR-delta agonist, by way of example and with preference GW 501516 or BAY 68-5042.

In a preferred embodiment of the invention, the inventive compounds are administered in combination with a cholesterol absorption inhibitor, by way of example and with preference ezetimibe, tiqueside or pamaqueside.

In a preferred embodiment of the invention, the inventive compounds are administered in combination with a lipase inhibitor, a preferred example being orlistat.

In a preferred embodiment of the invention, the inventive compounds are administered in combination with a polymeric bile acid adsorbent, by way of example and with preference cholestyramine, colestipol, colesolvam, CholestaGel or colestimide.

In a preferred embodiment of the invention, the inventive compounds are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the inventive compounds are administered in combination with a lipoprotein(a) antagonist, by way of example and with preference, gemcabene calcium (CI-1027) or nicotinic acid.

In a preferred embodiment of the invention, the inventive compounds are administered in combination with a lipoprotein(a) antagonist, by way of example and with preference, gemcabene calcium (CI-1027) or nicotinic acid.

In a preferred embodiment of the invention, the inventive compounds are administered in combination with sGC modulators, by way of example and with preference, riociguat, cinaciguat or vericiguat.

In a preferred embodiment of the invention, the inventive compounds are administered in combination with an agent affecting the glucose metabolism, by way of example and with preference, insuline, a sulfonyl urea, acarbose, DPP4 inhibitors, GLP-1 analogs or SGLT-1 inhibitors.

In a preferred embodiment of the invention, the compounds according to the invention are administered in combination with a TGFbeta antagonist, by way of example and with preference pirfenidone or fresolimumab.

In a preferred embodiment of the invention, the compounds according to the invention are administered in combination with a CCR2 antagonist, by way of example and with preference CCX-140.

In a preferred embodiment of the invention, the compounds according to the invention are administered in combination with a TNFalpha antagonist, by way of example and with preference adalimumab.

In a preferred embodiment of the invention, the compounds according to the invention are administered in combination with a galectin-3 inhibitor, by way of example and with preference GCS-100.

In a preferred embodiment of the invention, the compounds according to the invention are administered in combination with a Nrf-2 inhibitor, by way of example and with preference bardoxolone In a preferred embodiment of the invention, the compounds according to the invention are administered in combination with a BMP-7 agonist, by way of example and with preference THR-184.

In a preferred embodiment of the invention, the compounds according to the invention are administered in combination with a NOX1/4 inhibitor, by way of example and with preference GKT-137831.

In a preferred embodiment of the invention, the compounds according to the invention are administered in combination with a medicament which affects the vitamin D metabolism, by way of example and with preference calcitriol, alfacalcidol, doxercalciferol, maxacalcitol, paricalcitol, cholecalciferol or paracalcitol.

In a preferred embodiment of the invention, the compounds according to the invention are administered in combination with a cytostatic agent, by way of example and with preference cyclophosphamide.

In a preferred embodiment of the invention, the compounds according to the invention are administered in combination with an immunosuppressive agent, by way of example and with preference ciclosporin.

In a preferred embodiment of the invention, the compounds according to the invention are administered in combination with a phosphate binder, by way of example and with preference colestilan, sevelamer hydrochloride and sevelamer carbonate, Lanthanum and lanthanum carbonate.

In a preferred embodiment of the invention, the compounds according to the invention are administered in combination with renal proximal tubule sodium-phosphate co-transporter, by way of example and with preference, niacin or nicotinamide.

In a preferred embodiment of the invention, the compounds according to the invention are administered in combination with a calcimimetic for therapy of hyperparathyroidism.

In a preferred embodiment of the invention, the compounds according to the invention are administered in combination with agents for iron deficit therapy, by way of example and with preference iron products.

In a preferred embodiment of the invention, the compounds according to the invention are administered in combination with agents for the therapy of hyperurikaemia, by way of example and with preference allopurinol or rasburicase.

In a preferred embodiment of the invention, the compounds according to the invention are administered in combination with glycoprotein hormone for the therapy of anaemia, by way of example and with preference erythropoietin.

In a preferred embodiment of the invention, the compounds according to the invention are administered in combination with biologics for immune therapy, by way of example and with preference abatacept, rituximab, eculizumab or belimumab.

In a preferred embodiment of the invention, the compounds according to the invention are administered in combination with vasopressin antagonists (group of the vaptanes) for the treatment of heart failure, by way of example and with preference tolvaptan, conivaptan, lixivaptan, mozavaptan, satavaptan or relcovaptan.

In a preferred embodiment of the invention, the compounds according to the invention are administered in combination with Jak inhibitors, by way of example and with preference ruxolitinib, tofacitinib, baricitinib, CYT387, GSK2586184, lestaurtinib, pacritinib (SB1518) or TG101348.

In a preferred embodiment of the invention, the compounds according to the invention are administered in combination with prostacyclin analogs for therapy of microthrombi.

In a preferred embodiment of the invention, the compounds according to the invention are administered in combination with an alkali therapy, by way of example and with preference sodium bicarbonate.

In a preferred embodiment of the invention, the compounds according to the invention are administered in combination with an mTOR inhibitor, by way of example and with preference everolimus or rapamycin.

In a preferred embodiment of the invention, the compounds according to the invention are administered in combination with an NHE3 inhibitor, by way of example and with preference AZD 1722 or tenapanor.

In a preferred embodiment of the invention, the compounds according to the invention are administered in combination with an eNOS modulator, by way of example and with preference sapropterin.

In a preferred embodiment of the invention, the compounds according to the invention are administered in combination with a CTGF inhibitor, by way of example and with preference FG-3019.

In a particular preferred embodiment of the invention, the inventive compounds are administered in combination with one or more further agents selected from the group of the hypotensive active compounds, of the antiinflammatory agents/immunosuppressive agents, the phosphate binders, the sodium-phosphate co-transporters, NHE3 inhibitors, antiarrhythmic agents, agents that alter lipid metabolism and/or the active compounds which modulate vitamin D metabolism.

Based upon standard laboratory techniques known to evaluate compounds useful for the treatment of diseases and/or conditions associated with hyperphosphatemia, chronic kidney disease (CKD), chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 50 mg/kg body weight per day, and more preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight. The average daily oral dosage regimen will preferably be from 0.01 to 30 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Nevertheless, it may optionally be necessary to deviate from the stated amounts, namely depending on body weight, route of administration, individual response to the active substance, type of preparation and time point or interval when application takes place. Thus, in some cases it may be sufficient to use less than the aforementioned minimum amount, whereas in other cases the stated upper limit must be exceeded. When applying larger amounts, it may be advisable to distribute these in several individual doses throughout the day.

According to a further embodiment, the compounds of formula (I) according to the invention are administered orally once or twice or three times a day. According to a further embodiment, the compounds of formula (I) according to the invention are administered orally once or twice a day. According to a further embodiment, the compounds of formula (I) according to the invention are administered orally once a day. For the oral administration, a rapid release or a modified release dosage form may be used.

EXPERIMENTAL SECTION

The following table 1 lists the abbreviations used in this paragraph and in the Examples section as far as they are not explained within the text body. Other abbreviations have their meanings customary per se to the skilled person.

TABLE 1

| Abbreviation | Meaning |
| --- | --- |
| DBU | 1,8-diazabicycloundec-7-ene |
| dichloromethane | dichloromethane |
| DMSO | dimethyl sulfoxide |
| EDTA | ethylenediaminetetraacetic acid |
| MTBE | methyl tert-butyl ether |
| NMR | nuclear magnetic resonance |
| NMP | N-Methyl-2-pyrrolidone |
| DMF | N,N-dimethylformamide |
| MS | mass spectroscopy |
| $R_t$ | retention time |
| HPLC, LC | high performance liquid chromatography |
| h | hour |
| min | minute |
| ppm | chemical shift $\delta$ in parts per million |
| s | singlet |
| d | doublet |
| dd | doublet of doublet |
| m | multiplet |
| ESI | electrospray ionisation |
| phosphazen-base P(2)-Et | 1-Ethyl-2,2,4,4,4-pentakis(dimethylamino)-2$\lambda$5,4$\lambda$5-catenadi(phosphazene) |
| pos | positive |
| neg | negative |
| DAD | Diode Array Detector |
| m/z | mass-to-charge ratio (in mass spectrum) |
| TFA | trifluoroacetic acid |
| THF | tetrahydrofuran |
| tBuBrettPhos Pd G3 | [(2-Di-tert-butylphosphino-3,6-dimethoxy-2',4',6'-triisopropyl-1,1'-biphenyl)-2-(2'-amino-1,1'-biphenyl)]palladium(II) methanesulfonate |
| SFC | supercritical fluid chromatography |
| XantPhos | 4,5-Bis(diphenylphosphino)-9,9-dimethylxanthene |

Other abbreviations not specified herein have their meanings customary to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

NMR peak forms are stated as they appear in the spectra, possible higher order effects have not been considered.

The $^1$H-NMR data of selected compounds are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\delta_2$ (intensity$_2$), ..., $\delta_i$ (intensity$_i$), ..., $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures).

In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash NH2 silica gel in combination with a Isolera autopurifier (Biotage) and eluents such as gradients of e.g. hexane/EE or dichloromethane/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated in vacuum" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be construed as limiting the scope of the invention in any manner. All publications mentioned herein are incorporated by reference in their entirety.

Methods

Preparative HPLC

Methods for purifications by preparative HPLC given in the subsequent specific experimental descriptions refer (unless otherwise noted) to the following conditions:

Method 1: Instrument: Waters Prep LC/MS System, Column: XBridge C18 5 μm 100×30 mm; Eluent A: water, eluent B: acetonitrile, eluent C: 2% aqueous ammonia solution, eluent D: acetonitrile/water 80/20. flow: 80 ml/min, room temperature, detection wavelength 200-400 nm, At-column injection; gradient: 0-2 min 59% eluent A, 29% eluent B, 2-10 min 59 to 29% eluent A, 29 to 59% eluent B, 10-12 min 0% eluent A, 88% eluent B, eluent C and D constantly 6% each over the whole run-time.

Method 2: Instrument: Waters Prep LC/MS System, Column: XBridge C18 5 μm 100×30 mm; Eluent A: water, eluent B: acetonitrile, eluent C: 2% aqueous formic acid solution, eluent D: acetonitrile/water 80/20. flow: 80 ml/min, room temperature, detection wavelength 200-400 nm, At-column injection; gradient: 0-2 min 59% eluent A, 29% eluent B, 2-10 min 59 to 29% eluent A, 29 to 59% eluent B, 10-12 min 0% eluent A, 88% eluent B, eluent C and D constantly 6% each over the whole run-time.

Method 3: Instrument: Waters Prep LC/MS System, column: Phenomenex Kinetex C18 5 μm 100×30 mm; eluent A: water, eluent B: acetonitrile, eluent C: 2% aqueous formic acid in water, eluent D: acetonitrile/water 80/20. flow: 80 ml/min, room temperature, detection wavelength 200-400 nm, At-Column injection; gradient: 0-2 min 59% eluent A, 29% eluent B, 2-10 min 59 to 29% eluent A, 29 to 59% eluent B, 10-12 min 0% eluent A, 88% eluent B, eluent C and D constantly 6% each over the whole run-time.

Method 4: Instrument: Waters Prep LC/MS System, column: Phenomenex Kinetex C18 5 μm 100×30 mm; eluent A: water, eluent B: acetonitrile, eluent C: 2% aqueous formic acid in water, eluent D: acetonitrile/water 80/20. flow: 80 ml/min, room temperature, detection wavelength 200-400 nm, At-Column injection; gradient: 0-2 min 49% eluent A, 39% eluent B, 2-10 min 49 to 19% eluent A, 39 to 69% eluent B, 10-12 min 0% eluent A, 88% eluent B, eluent C and D constantly 6% each over the whole run-time.

Method 5: Instrument: Waters Prep LC/MS System, column: Phenomenex Kinetex C18 5 μm 100×30 mm; eluent A: water, eluent B: acetonitrile, eluent C: 2% aqueous formic acid in water, eluent D: acetonitrile/water 80/20. flow: 80 ml/min, room temperature, detection wavelength 200-400 nm, At-Column injection; gradient: 0-2 min 29% eluent A, 59% eluent B, 2-10 min 29 to 0% eluent A, 59 to 88% eluent B, 10-12 min 0% eluent A, 88% eluent B, eluent C and D constantly 6% each over the whole run-time.

Method 6: Instrument: Waters Prep LC/MS System, Column: XBridge C18 5 μm 100×30 mm; Eluent A: water, eluent B: acetonitrile, eluent C: 2% aqueous ammonia solution, eluent D: acetonitrile/water 80/20. flow: 80 ml/min, room temperature, detection wavelength 200-400 nm, At-column injection; gradient: 0-2 min 49% eluent A, 39% eluent B, 2-10 min 49 to 39% eluent A, 39 to 49% eluent B, 10-12 min 0% eluent A, 88% eluent B, eluent C and D constantly 6% each over the whole run-time.

Method 7: Instrument: Waters Prep LC/MS System, column: Phenomenex Kinetex C18 5 μm 100×30 mm; eluent A: water, eluent B: acetonitrile, eluent C: 2% aqueous formic acid in water, eluent D: acetonitrile/water 80/20. flow: 80 ml/min, room temperature, detection wavelength 200-400 nm, At-Column injection; gradient: 0-2 min 69% eluent A, 19% eluent B, 2-10 min 69 to 39% eluent A, 19 to 49% eluent B, 10-12 min 0% eluent A, 88% eluent B, eluent C and D constantly 6% each over the whole run-time.

Method 8: Instrument: Waters Prep LC/MS System, Column: XBridge C18 5 μm 100×30 mm; Eluent A: water, eluent B: acetonitrile, eluent C: 2% aqueous ammonia solution, eluent D: acetonitrile/water 80/20. flow: 80 ml/min, room temperature, detection wavelength 200-400 nm, At-column injection; gradient: 0-2 min 29% eluent A, 59% eluent B, 2-10 min 29 to 0% eluent A, 59 to 88% eluent B, 10-12 min 0% eluent A, 88% eluent B, eluent C and D constantly 6% each over the whole run-time.

Method 17: Instrument: Waters Prep LC/MS System, Column: XBridge C18 5 μm 100×30 mm; Eluent A: water, eluent B: acetonitrile, eluent C: 2% aqueous ammonia solution, eluent D: acetonitrile/water 80/20. flow: 80 ml/min, room temperature, detection wavelength 200-400 nm, At-column injection; gradient: 0-2 min 69% eluent A, 19% eluent B, 2-10 min 69 to 19% eluent A, 19 to 69% eluent B, 10-12 min 0% eluent A, 88% eluent B, eluent C and D constantly 6% each over the whole run-time.

Method 18: Instrument: Waters Prep LC/MS System, Column: XBridge C18 5 μm 100×30 mm; Eluent A: water, eluent B: acetonitrile, eluent C: 2% aqueous ammonia solution, eluent D: acetonitrile/water 80/20. flow: 80 ml/min, room temperature, detection wavelength 200-400 nm, At-column injection; gradient: 0-2 min 79% eluent A, 9% eluent B, 2-10 min 79 to 49% eluent A, 9 to 39% eluent B, 10-12 min 0% eluent A, 88% eluent B, eluent C and D constantly 6% each over the whole run-time.

Method 19: Instrument: Knauer Azura, column: Chromatorex C18 10 μm, 125 mm×40 mm; eluent A: water, eluent B: acetonitrile; flow: 100 ml/min; room temperature, wavelength 210 nm, gradient: 0-3 min 20% eluent B, 3-21 min 20% eluent B to 95% eluent B, 21-24 min 95% eluent B, 24-25 min 95% eluent B to 20% eluent B, 25-27.5 min 20% eluent B.

Method 20: Instrument: Waters Prep LC/MS System, column: Daicel Chiralpak IF 5 μm, 250 mm×20 mm; eluent: ethanol; flow: 15 ml/min; temperature 70 C, wavelength 220 nm; gradient: 0-15 min 100% ethanol.

Analytical HPLC/LC/MS

LC-MS-data given in the subsequent specific experimental descriptions refer (unless otherwise noted) to the following conditions:

Method 9: Instrument: Waters ACQUITY SQD UPLC System; Column: Waters Acquity UPLC HSS T3 1.8μ 50×1 mm; eluent A: 1 l water+0.25 ml 99% ige formic acid, eluent B: 1 l acetonitrile+0.25 ml 99% formic acid; gradient: 0.0 min 90% A→1.2 min 5% A→2.0 min 5% A temperature: 50° C.; flow: 0.40 ml/min; UV-detection: 208-400 nm.

Method 10: Instrument: Thermo Scientific FT-MS; Instrument UHPLC+: Thermo Scientific UltiMate 3000; column: Waters, HSST3, 2.1×75 mm, C18 1.8 μm; eluent A: 1 l water+0.01% formic acid; eluent B: 1 l acetonitrile+0.01% formic acid; gradient: 0.0 min 10% B→2.5 min 95% B→3.5 min 95% B; temperature: 50° C.; flow: 0.90 ml/min; UV-detection: 210 nm/optimal Integration Path 210-300 nm.

Method 11: Instrument: Agilent MS Quad 6150; HPLC: Agilent 1290; column: Waters Acquity UPLC HSS T3 1.8 50×2.1 mm; eluent A: 1 l water+0.25 ml 99% formic acid, eluent B: 1 l acetonitrile+0.25 ml 99% ige formic acid; gradient: 0.0 min 90% A→0.3 min 90% A→1.7 min 5% A→3.0 min 5% A temperature: 50° C.; flow: 1.20 ml/min; UV-detection: 205-305 nm.

Method 12: Instrument MS: ThermoFisherScientific LTQ-Orbitrap-XL; type HPLC: Agilent 1200SL; column: Agilent, POROSHELL 120, 3×150 mm, SB-C18 2.7 μm; eluent A: 1 l water+0.1% TFA; eluent B: 1 l acetonitrile+0.1% TFA; gradient: 0.0 min 2% B→0.3 min 2% B→5.0 min 95% B→10.0 min 95% B; temperature: 40° C.; flow: 0.75 ml/min; UV-detection: 210 nm.

Method 13: Instrument: Waters Acquity UPLCMS SingleQuad; column: Acquity UPLC BEH C18 1.7 m, 50×2.1 mm; eluent A: water+0.1 Vol-% TFA (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 14: Instrument: Waters ACQUITY SQD UPLC System; column: Waters Acquity UPLC HSS T3 1.8 50×1 mm; eluent A: 1 l water+0.25 ml formic acid (99%), eluent B: 1 l acetonitrile+0.25 ml formic acid (99%); gradient: 0.0 min 95% A→6.0 min 5% A→7.5 min 5% A temperature: 50° C.; flow: 0.35 ml/min; UV-detection: 210-400 nm.

Method 16: Instrument: Waters Single Quad MS System; Instrument Waters UPLC Acquity; Säule: Waters BEH C18 1.7 μm 50×2.1 mm; Eluent A: 1 l Water+1.0 mL (25% Ammonia)/L, Eluent B: 1 l Acetonitril; Gradient: 0.0 min 92% A→0.1 min 92% A→1.8 min 5% A→3.5 min 5% A; Often: 50° C.; Flow: 0.45 mL/min; UV-Detection: 210 nm (208-400 nm).

Method 21: Instrument: Waters Single Quad MS System; Instrument Waters UPLC Acquity; column: Waters BEH C18 1.7 μm 50×2.1 mm; Eluent A: 1 l Water+1.0 mL (25% ammonia)/L, Eluent B: 1 l acetonitrile; gradient: 0.0 min 92% A→0.1 min 92% A→1.8 min 5% A→3.5 min 5% A; temperature: 50° C.; flow: 0.45 mL/min; UV-detection: 210 nm (208-400 nm).

GC-MS

GC-MS-data given in the subsequent specific experimental descriptions refer (unless otherwise noted) to the following conditions:

Method 15: Instrument: Thermo Scientific DSQII, Thermo Scientific Trace GC Ultra; column: Restek RTX-35MS, 15 m×200 m×0.33 m; constant flow with helium: 1.20 ml/min; temperature: 60° C.; Inlet: 220° C.; gradient: 60° C., 30° C./min→300° C. (3.33 min hold).

Synthetic Intermediates

Intermediate 1

4-chloro-6-(3,5-dimethyl-1H-pyrazol-1-yl)pyrimidine

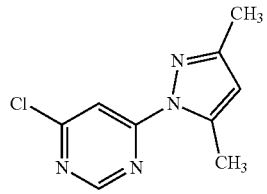

A solution of 4,6-dichloropyrimidine (10.0 g, 67.1 mmol) and 3,5-dimethyl-1H-pyrazole (6.45 g, 67.1 mmol) in DMF (42 mL) was treated with caesium carbonate (21.9 g, 67.1 mmol). The resulting mixture was stirred overnight at room temperature. The mixture was poured into 700 mL water, the resulting precipitate was collected by filtration, washed with water and dried to yield 4.8 g (34% yield) of the desired compound.

LC-MS (method 9): Rt=0.97 min; MS (ESIpos): m/z=209 [M+H]⁺

¹H-NMR (400 MHz, DMSO-d₆) δ [ppm]: −0.016 (0.62), 2.218 (16.00), 2.654 (13.00), 6.259 (2.71), 7.886 (2.77), 8.891 (2.48).

Intermediate 2

2-(4-fluorobenzoyl)butanenitrile

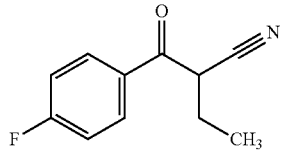

A solution of butyronitrile (3.8 mL, 43 mmol) in THF (100 mL) was treated with lithium bis(trimethylsilyl)amide (1M in THF; 130 mL, 1.0 M, 130 mmol) at 30° C. Afterwards ethyl 4-fluorobenzoate (19 ml, 130 mmol) was added dropwise. The resulting mixture was stirred for 1 hour. The reaction was quenched by the addition of water and extracted once with MTBE. The aqueous phase was acidified with aqueous hydrochloric acid to pH 2 and subsequently extracted three times with dichloromethane. The combined organic phases were washed over sodium sulphate and the solvent was removed under reduced pressure to yield the crude desired product (8.31 g, 79% yield) which was used in the next step without any further purification.

LC-MS (method 9): R$_t$=0.87 min; MS (ESIneg): m/z=190 [M−H]⁻

¹H-NMR (400 MHz, DMSO-d6) δ [ppm]: 1.008 (7.45), 1.026 (16.00), 1.045 (8.04), 1.069 (1.74), 1.088 (3.54), 1.106 (1.75), 1.164 (0.61), 1.182 (1.20), 1.199 (0.61), 1.783 (0.97), 1.801 (1.56), 1.818 (1.97), 1.837 (2.21), 1.855 (1.41), 1.920 (0.42), 1.939 (1.38), 1.952 (1.59), 1.957 (1.80), 1.971 (1.79), 1.995 (2.77), 2.005 (0.87), 2.281 (0.58), 2.300 (1.71), 2.318 (1.65), 2.337 (0.54), 3.346 (0.47), 4.028 (0.54), 4.046

(0.53), 5.147 (2.40), 5.160 (2.72), 5.167 (2.73), 5.180 (2.35), 7.295 (0.92), 7.299 (0.88), 7.317 (1.89), 7.339 (1.13), 7.410 (3.19), 7.433 (6.51), 7.455 (3.58), 7.599 (1.03), 7.613 (1.18), 7.621 (1.07), 7.634 (0.92), 7.998 (0.45), 8.013 (0.52), 8.020 (0.48), 8.034 (0.46), 8.109 (4.31), 8.114 (2.38), 8.123 (4.89), 8.131 (4.74), 8.145 (4.13), 10.860 (0.97).

Intermediate 3

4-ethyl-5-(4-fluorophenyl)-1H-pyrazol-3-amine

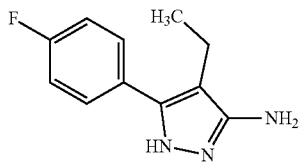

A solution of 2-(4-fluorobenzoyl)butanenitrile (6.50 g, 34.0 mmol) in ethanol (80 mL) was treated with hydrazine hydrate (1:1) (2.0 ml, 41 mmol). The mixture was refluxed for 3 hours. After cooling to room temperature the mixture was poured into sodium hydrogen carbonate solution (1M). Ethanol was removed under reduced pressure, the resulting precipitate was collected by filtration, washed with water and dried to yield 5.68 g (81% yield) of the desired product.

LC-MS (method 9): $R_t$=0.62 min; MS (ESIpos): m/z=206 [M+H]$^+$ $^1$H-NMR (400 MHz, DMSO-d$_6$) δ [ppm]: 1.014 (7.35), 1.032 (16.00), 1.051 (7.67), 2.388 (2.65), 2.407 (7.99), 2.425 (7.79), 2.444 (2.46), 3.327 (5.49), 4.487 (1.85), 7.238 (2.73), 7.260 (5.64), 7.282 (3.26), 7.495 (3.91), 7.509 (4.88), 7.515 (4.60), 7.529 (3.35), 11.519 (2.77).

Intermediate 4 ethyl 1-(6-chloropyrimidin-4-yl)-3,5-dimethyl-1H-pyrazole-4-carboxylate

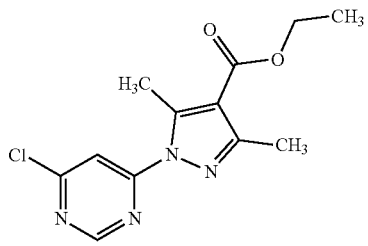 [SMILES: CCOC(=O)c1c(C)nn(-c2cc(Cl)ncn2)c1C]

The desired product was obtained in the same manner as described for 4-chloro-6-(3,5-dimethyl-1H-pyrazol-1-yl)pyrimidine starting from 4,6-dichloropyrimidine (2.00 g, 13.4 mmol) and ethyl 3,5-dimethyl-1H-pyrazole-4-carboxylate (2.26 g, 13.4 mmol) to yield 3.42 g (90% yield) of the desired product.

$^1$H-NMR (400 MHz, DMSO-d$_6$) δ [ppm]: −0.008 (0.47), 0.008 (0.43), 1.298 (4.21), 1.316 (9.05), 1.325 (0.56), 1.334 (4.30), 2.415 (15.87), 2.441 (0.55), 2.947 (16.00), 2.991 (0.53), 4.248 (1.31), 4.266 (4.11), 4.284 (4.07), 4.301 (1.29), 7.994 (3.67), 7.996 (3.62), 9.013 (3.52), 9.015 (3.52).

Intermediate 5

4-chloro-6-[5-(difluoromethyl)-3-methyl-1H-pyrazol-1-yl]pyrimidine

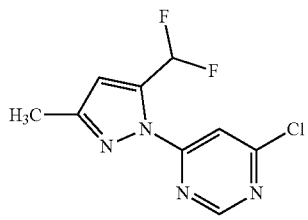 [SMILES: Cc1cc(C(F)F)n(-c2cc(Cl)ncn2)n1]

A solution of 4-chloro-6-hydrazinylpyrimidine (1.00 g, 6.92 mmol, synthesis described e.g. Synlett 2010 (14), 2179-2183) and 1,1-difluoropentane-2,4-dione (941 mg, 6.92 mmol) in ethanol (10 mL) was refluxed overnight. After cooling to room temperature, ethanol was removed under reduced pressure. The resulting crude product was purified by reverse phase HPLC (column: Daicel IC, 250×20 mm, flow 20 mL/min, 95% i-hexane/5% ethanol, room temperature, detection 220 nM) to yield 432 mg (25% yield) of the desired product.

LC-MS (method 11): $R_t$=1.35 min; MS (ESIpos): m/z=245 [M+H]$^+$ $^1$H-NMR (400 MHz, DMSO-d$_6$) δ [ppm]: −0.152 (0.03), 0.144 (0.03), 2.072 (0.10), 2.170 (0.09), 2.332 (16.00), 2.365 (0.07), 2.669 (0.05), 2.709 (0.04), 6.911 (3.24), 7.633 (1.27), 7.768 (2.50), 7.903 (1.23), 7.959 (2.80), 8.961 (2.76).

Intermediate 6

6-chloro-N-[4-ethyl-5-(4-fluorophenyl)-1H-pyrazol-3-yl]pyrimidin-4-amine

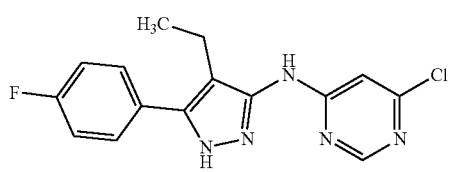 [SMILES: CCc1c(Nc2cc(Cl)ncn2)n[nH]c1-c1ccc(F)cc1]

A solution of 4,6-dichloropyrimidine (2.18 g, 14.6 mmol) and 4-ethyl-5-(4-fluorophenyl)-1H-pyrazol-3-amine (3.00 g, 14.6 mmol) in DMF (33 mL) was treated with sodium iodide (2.63 g, 17.5 mmol) and N,N-diisopropylethylamine (2.8 mL, 16 mmol). The resulting mixture was stirred overnight at 80° C. The amount of DMF was reduced under reduced pressure. The residue was diluted with ethyl acetate. The organic layer was washed with water, brine and dried over sodium sulfate. The solvent was removed under reduced pressure, the remaining residue was triturated with diethyl ether to yield the crude product which was further purified by flash chromatography on silica gel (eluent: cyclohexane/ ethyl acetate) to yield 1.54 g (33% yield) of the desired product.

LC-MS (method 10): $R_t$=1.68 min; MS (ESIpos): m/z=318 [M+H]$^+$ $^1$H-NMR (400 MHz, DMSO-d$_6$) δ [ppm]: 0.977 (6.99), 0.995 (16.00), 1.014 (7.42), 1.912 (2.37), 7.060 (0.88), 7.330 (2.55), 7.352 (5.11), 7.374 (2.89), 7.584 (3.62), 7.598 (4.37), 7.605 (3.97), 7.619 (2.95), 8.418 (6.63), 9.682 (3.10), 12.802 (1.02).

Intermediate 7

N-[4-ethyl-5-(4-fluorophenyl)-1H-pyrazol-3-yl]-6-hydrazinylpyrimidin-4-amine

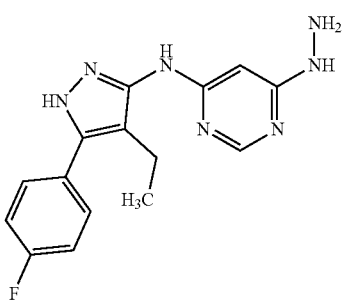 [SMILES: CCc1c(Nc2cc(NN)ncn2)n[nH]c1-c1ccc(F)cc1]

A solution of 6-chloro-N-[4-ethyl-5-(4-fluorophenyl)-1H-pyrazol-3-yl]pyrimidin-4-amine (500 mg, 1.57 mmol) in 1,4-dioxane (10 mL) was treated with hydrazine hydrate (1:1) (230 µl, 4.7 mmol). The resulting mixture was stirred overnight at 70° C. The solvent was removed under reduced pressure and the remaining residue was suspended in acetonitrile. Crystals were collected by filtration, washed with acetonitrile and dried to yield 509 mg (99% yield) of the desired product.

LC-MS (method 10): $R_t$=0.97 min; MS (ESIpos): m/z=314 [M+H]$^+$ $^1$H-NMR (400 MHz, DMSO-d$_6$) δ [ppm]: 0.008 (0.43), 0.982 (7.51), 1.001 (16.00), 1.019 (7.13), 2.075 (0.53), 2.479 (3.24), 4.157 (0.41), 6.255 (0.51), 7.093 (1.10), 7.323 (3.07), 7.596 (3.51), 7.714 (0.89), 7.954 (4.54), 12.623 (0.45).

Intermediate 8

2-[4-ethyl-3-(4-fluorophenyl)-1H-pyrazol-5-yl]-1H-isoindole-1,3(2H)-dione

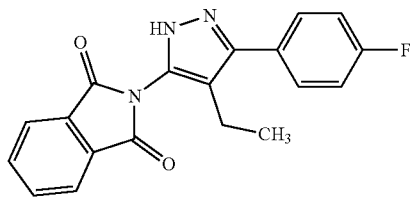 [SMILES: CCc1c(-c2ccc(F)cc2)n[nH]c1N1C(=O)c2ccccc2C1=O]

A solution of 4-ethyl-3-(4-fluorophenyl)-1H-pyrazol-5-amine (1.00 g, 4.87 mmol) and 2-benzofuran-1,3-dione (1.08 g, 7.31 mmol) in acetic acid (10 mL) was refluxed overnight. The mixture was poured into water and extracted with ethyl acetate. The combined organic phases were washed with brine, dried over sodium sulfate and the solvent was removed under reduced pressure. The crude product was triturated with MTBE to afford 1.37 g (84% yield) of the desired product.

LC-MS (method 9): $R_t$=0.97 min; MS (ESIpos): m/z=336 [M+H]$^+$ $^1$H-NMR (400 MHz, DMSO-d$_6$) δ [ppm]: 0.929 (7.10), 0.948 (16.00), 0.967 (7.59), 1.994 (0.59), 2.419 (2.05), 2.437 (6.19), 2.456 (6.07), 2.475 (1.97), 3.340 (3.09), 7.372 (3.70), 7.394 (7.88), 7.417 (4.38), 7.650 (4.81), 7.664 (5.46), 7.672 (4.90), 7.685 (4.17), 7.953 (4.07), 7.961 (4.99), 7.967 (5.39), 7.974 (7.34), 7.985 (1.68), 8.011 (1.41), 8.021 (7.32), 8.029 (5.16), 8.035 (4.95), 8.042 (4.04), 13.386 (5.95).

Intermediate 9

2-[4-ethyl-3-(4-fluorophenyl)-1-methyl-1H-pyrazol-5-yl]-1H-isoindole-1,3 (2H)-dione

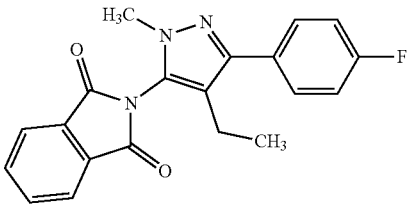 [SMILES: CCc1c(-c2ccc(F)cc2)nn(C)c1N1C(=O)c2ccccc2C1=O]

A solution of 2-[4-ethyl-3-(4-fluorophenyl)-1H-pyrazol-5-yl]-1H-isoindole-1,3(2H)-dione (1.32 g, 3.94 mmol) in DMF (10 mL) was treated with potassium carbonate (1.09 g, 7.88 mmol) and iodomethane (490 µl, 7.9 mmol). The mixture was stirred overnight at room temperature. The mixture was poured into water and extracted with ethyl acetate. The combined organic phases were washed with water, brine, dried over sodium sulfate and the solvent was removed under reduced pressure. The crude product was purified via preparative HPLC (method: column: Reprosil C18; 10 µm; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75-23.00 min=90% B) to yield 977.9 mg of the desired product as regioisomeric mixture. After separation of the regioisomers via SFC using carbon dioxide/methanol as eluents 312 mg of the desired product in a mixture with the ring-opened phthalimide were obtained (13% yield).

LC-MS (method 10): $R_t$=2.03 min; MS (ESIpos): m/z=350 [M+H]$^+$ $^1$H-NMR (400 MHz, DMSO-d$_6$) δ [ppm]: 0.907 (3.03), 0.925 (6.88), 0.944 (3.12), 1.050 (3.20), 1.069 (7.26), 1.088 (3.29), 2.438 (0.89), 2.457 (2.66), 2.476 (2.65), 2.564 (2.73), 2.583 (2.64), 2.601 (0.83), 3.316 (10.74), 3.723 (14.19), 3.821 (16.00), 7.246 (1.92), 7.268 (5.18), 7.291 (5.16), 7.314 (1.92), 7.638 (2.40), 7.652 (2.79), 7.660 (3.40), 7.667 (1.74), 7.674 (2.63), 7.682 (3.15), 7.695 (2.35), 7.703 (2.16), 7.717 (2.08), 7.736 (4.04), 7.739 (3.93), 7.754 (1.36), 7.865 (2.10), 7.884 (1.68), 7.975 (1.95), 7.983 (2.19), 7.989 (2.32), 7.997 (3.16), 8.007 (0.55), 8.044 (0.51), 8.055 (3.24), 8.063 (2.31), 8.069 (2.20), 8.076 (1.92), 10.309 (3.44).

Intermediate 10

2-[4-ethyl-5-(4-fluorophenyl)-1-methyl-1H-pyrazol-3-yl]-1H-isoindole-1,3(2H)-dione

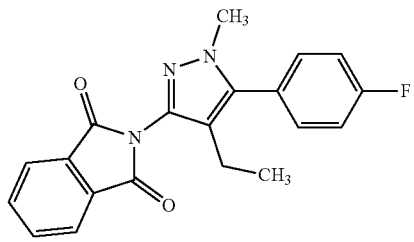 [SMILES: CCc1c(N2C(=O)c3ccccc3C2=O)nn(C)c1-c1ccc(F)cc1]

The desired product was obtained out of the regioisomeric separation described in the experimental procedure of the synthesis of 2-[4-ethyl-3-(4-fluorophenyl)-1H-pyrazol-5-yl]-1H-isoindole-1,3(2H)-dione in 24% yield (383 mg).

LC-MS (method 10): Rt=1.98 min; MS (ESIpos): m/z=350 [M+H]$^+$ $^1$H-NMR (400 MHz, DMSO-d6): δ [ppm]: 0.82 (t, 3H), 2.23 (q, 2H), 3.73 (s, 3H), 7.35-7.44 (m, 2H), 7.56-7.62 (m, 2H), 7.91-7.98 (m, 2H), 7.99-8.06 (m, 2H).

Intermediate 11

4-ethyl-5-(4-fluorophenyl)-1-methyl-1H-pyrazol-3-amine

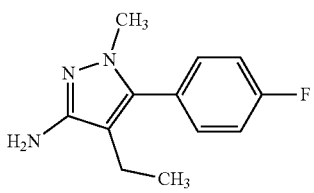

A solution of 2-[4-ethyl-5-(4-fluorophenyl)-1-methyl-1H-pyrazol-3-yl]-1H-isoindole-1,3(2H)-dione (380 mg, 1.09 mmol) in ethanol (7.5 mL) was treated with hydrazine hydrate (1:1) (260 µl, 5.4 mmol).

The mixture was refluxed overnight. After cooling to room temperature a precipitate occurred this was filtered off. The filtrate was concentrated under reduced pressure and the crude product was purified by preparative HPLC (method: column: Reprosil C18; 10 µm; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75-23.00 min=90% B) to obtain 142.6 mg (57% yield) of the desired product.

LC-MS (method 9): R$_t$=0.71 min; MS (ESIpos): m/z=220 [M+H]$^+$ $^1$H-NMR (400 MHz, DMSO-d$_6$) δ [ppm]: 0.905 (7.15), 0.924 (16.00), 0.943 (7.20), 2.165 (2.18), 2.184 (6.66), 2.203 (6.43), 2.221 (1.95), 3.580 (0.87), 7.296 (2.64), 7.301 (1.18), 7.318 (7.81), 7.324 (1.99), 7.335 (1.62), 7.340 (5.83), 7.346 (1.22), 7.354 (1.05), 7.360 (5.70), 7.366 (2.29), 7.374 (6.24), 7.382 (3.70), 7.391 (1.32), 7.396 (2.55), 8.139 (1.15).

Intermediate 12

4-ethyl-3-(4-fluorophenyl)-1-methyl-1H-pyrazol-5-amine

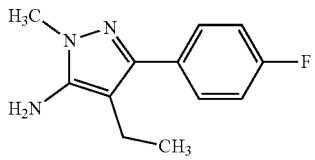

The desired product was prepared in the same manner as described for the synthesis of 4-ethyl-5-(4-fluorophenyl)-1-methyl-1H-pyrazol-3-amine starting from 2-[4-ethyl-3-(4-fluorophenyl)-1-methyl-1H-pyrazol-5-yl]-1H-isoindole-1,3 (2H)-dione (307 mg, 879 µmol) to yield 68.9 mg of the desired product (36% yield).

LC-MS (method 9): R$_t$=0.63 min; MS (ESIpos): m/z=220 [M+H]$^+$ $^1$H-NMR (400 MHz, DMSO-d$_6$) δ [ppm]: 0.976 (7.01), 0.995 (16.00), 1.013 (7.22), 2.398 (2.16), 2.416 (6.63), 2.435 (6.45), 2.454 (2.01), 3.326 (0.79), 3.376 (0.45), 4.995 (1.25), 7.168 (4.18), 7.190 (8.66), 7.212 (4.68), 7.517 (0.63), 7.524 (4.99), 7.530 (2.17), 7.539 (5.62), 7.546 (5.07), 7.555 (1.95), 7.560 (4.38), 8.135 (0.94).

Intermediate 13

6-chloro-N-[4-ethyl-5-(4-fluorophenyl)-1-methyl-1H-pyrazol-3-yl]pyrimidin-4-amine

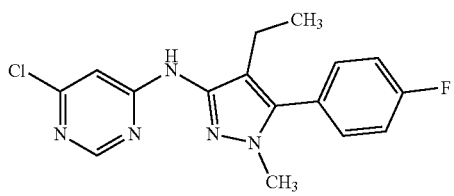 [SMILES: CCc1c(Nc2cc(Cl)ncn2)nn(C)c1-c1ccc(F)cc1]

A solution of 4,6-dichloropyrimidine (1.00 g, 6.71 mmol) and 4-ethyl-5-(4-fluorophenyl)-1-methyl-1H-pyrazol-3-amine (1.47 g, 6.71 mmol) in DMF (10 mL) was treated with N,N-diisopropylethylamine (1.3 ml, 7.4 mmol) and sodium iodide (1.21 g, 8.05 mmol). The resulting mixture was stirred overnight at 80° C. DMF was removed under reduced pressure. The residue was diluted with ethyl acetate and washed with water and brine. The organic phase was dried over sodium sulfate and the solvent was removed under reduced pressure. After trituration of the crude product with diethylether and MTBE the desired pure product was obtained. Preparative HPLC (method: column: Reprosil C18; 10 µm; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75-23.00 min=90% B) of the filtrate yielded additional product. Overall 922 mg of the desired product (41% yield) were obtained.

LC-MS (method 10): R$_t$=1.88 min; MS (ESIpos): m/z=332 [M+H]$^+$ $^1$H-NMR (400 MHz, DMSO-d$_6$) δ [ppm]: 0.855 (3.17), 0.874 (7.29), 0.892 (3.31), 2.281 (0.84), 2.300 (2.49), 2.319

(2.43), 2.337 (0.80), 2.734 (13.43), 2.894 (16.00), 3.320 (10.85), 7.108 (1.02), 7.354 (1.69), 7.376 (3.82), 7.398 (2.27), 7.490 (2.35), 7.496 (1.05), 7.504 (2.67), 7.511 (2.00), 7.521 (0.89), 7.525 (1.67), 7.956 (2.14), 8.416 (2.81), 9.700 (1.21).

Intermediate 14

N-[4-ethyl-5-(4-fluorophenyl)-1-methyl-1H-pyrazol-3-yl]-6-hydrazinylpyrimidin-4-amine

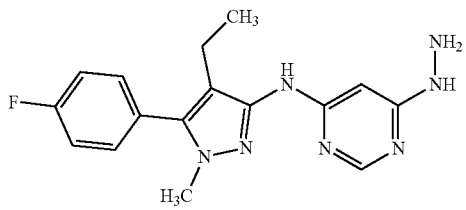 [SMILES: CCc1c(Nc2cc(NN)ncn2)nn(C)c1-c1ccc(F)cc1]

A solution of 6-chloro-N-[4-ethyl-5-(4-fluorophenyl)-1-methyl-1H-pyrazol-3-yl]pyrimidin-4-amine (645 mg, 1.94 mmol) in 1,4-dioxane (13 mL) was treated with hydrazine hydrate (1:1) (280 µl, 5.8 mmol). The resulting mixture was stirred overnight at 70° C. The solvent was removed under reduced pressure. The residue was triturated with acetonitrile to yield 574 mg (90% yield) of the desired product.

LC-MS (method 10): $R_t$=1.07 min; MS (ESIpos): m/z=328 [M+H]$^+$ $^1$H-NMR (400 MHz, DMSO-d$_6$) δ [ppm]: 0.87 (t, 3H), 2.29 (q, 2H), 3.62 (s, 3H), 6.27 (s, 1H), 6.90 (br s, 2H), 7.28-7.42 (m, 2H), 7.46-7.55 (m, 2H), 7.69 (br s, 1H), 7.88-7.97 (m, 1H), 8.38 (s, 1H).

Intermediate 15

2-cyclopropyl-3-(4-fluorophenyl)-3-oxopropanenitrile

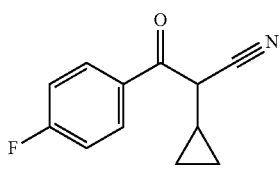 [SMILES: N#CC(C(=O)c1ccc(F)cc1)C1CC1]

Lithium diisopropylamide (34 ml, 2.0 M, 68 mmol in THF) is cooled to −78° C. Then, cyclopropylacetonitrile (5.7 ml, 62 mmol) in 50 mL of THF was slowly added at this temperature. The reaction mixture was stirred at this temperature for 10 min and then, a solution of 4-fluorobenzoyl chloride (4.0 ml, 34 mmol) in 50 mL THF was added dropwise. The reaction mixture was allowed to reach room temperature and stirred for 10 min. A 2 M hydrochloric acid solution was carefully added. Then, ethyl acetate was added. The aqueous layer was extracted 3 times with ethyl acetate. The organic phases were gathered, dried over magnesium sulfate and concentrated under vacuum. The crude product was purified by flash column chromatography on silica gel using cyclohecane/ethyl aceate to afford 4.36 g (75% purity, 47% yield) of the desired product.

LC-MS (method 11): $R_t$=1.17 min; MS (ESIneg): m/z=202 [M−H]$^-$

Intermediate 16

4-cyclopropyl-5-(4-fluorophenyl)-1H-pyrazol-3-amine

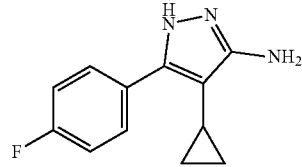 [SMILES: Nc1n[nH]c(-c2ccc(F)cc2)c1C1CC1]

The described example was prepared in the same manner as described in the synthesis of 4-ethyl-5-(4-fluorophenyl)-1H-pyrazol-3-amine starting from 2-cyclopropyl-3-(4-fluorophenyl)-3-oxopropanenitrile (4.36 g, 18.4 mmol) to obtain 4.49 g (78% purity, 88% yield) of the desired product which was used in the next step without any further purification.

LC-MS (method 11): $R_t$=0.90 min; MS (ESIpos): m/z=218 [M+H]$^+$

Intermediate 17

2-[4-cyclopropyl-5-(4-fluorophenyl)-1H-pyrazol-3-yl]-1H-isoindole-1,3 (2H)-dione

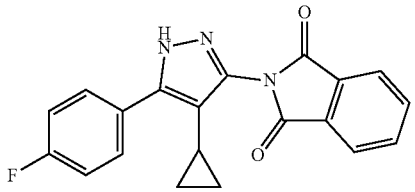 [SMILES: O=C1c2ccccc2C(=O)N1c1n[nH]c(-c2ccc(F)cc2)c1C1CC1]

The described example was prepared in the same manner as described in the synthesis of 2-[4-ethyl-3-(4-fluorophenyl)-1H-pyrazol-5-yl]-1H-isoindole-1,3(2H)-dione starting from 4-cyclopropyl-5-(4-fluorophenyl)-1H-pyrazol-3-amine (4.1 g, 14.7 mmol) to obtain 7.44 g (68% purity, 99% yield) of the desired product which was used in the next step without any further purification.

LC-MS (method 11): Rt=1.28 min; MS (ESIpos): m/z=348 [M+H]$^+$

Intermediate 18

2-[4-cyclopropyl-5-(4-fluorophenyl)-1-methyl-1H-pyrazol-3-yl]-1H-isoindole-1,3 (2H)-dione

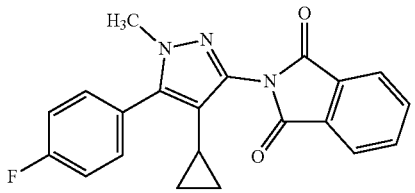 [SMILES: Cn1nc(N2C(=O)c3ccccc3C2=O)c(C2CC2)c1-c1ccc(F)cc1]

A solution of 2-[4-cyclopropyl-5-(4-fluorophenyl)-1H-pyrazol-3-yl]-1H-isoindole-1,3(2H)-dione (7.44 g, 68% purity, 14.6 mmol) in DMF (35 mL) was treated with potassium carbonate (4.03 g, 29.1 mmol) and iodomethane (1.8 ml, 29 mmol). The mixture was stirred at room temperature for 20 hours. Ethyl acetate and water were added. The aqueous layer was extracted with ethyl acetate twice. The organic phases were gathered, dried over magnesium sulfate and concentrated under vacuum. Diethyl ether was added to the brown oily solid and the white precipitate was filtered to afford the described regioisomer. The filtrate was concentrated and purified by flash column chromatography on silica gel using cyclohexane/ethyl acetate to afford both regioisomers. The product was obtained in 31% yield (1.63 g)

LC-MS (method 11): $R_t$=1.37 min; MS (ESIpos): m/z=362 [M+H]$^+$ $^1$H-NMR (400 MHz, DMSO-d$_6$) δ [ppm]: 0.007 (3.24), 0.011 (3.22), 0.020 (3.27), 0.024 (2.82), 0.034 (0.95), 0.448 (0.90), 0.458 (2.50), 0.462 (2.48), 0.468 (1.33), 0.479 (2.62), 0.483 (2.44), 0.494 (0.82), 1.474 (0.76), 1.481 (0.80), 1.486 (0.54), 1.494 (1.39), 1.502 (0.53), 1.507 (0.76), 1.515 (0.69), 3.739 (0.90), 3.753 (16.00), 7.374 (1.91), 7.396 (4.06), 7.418 (2.30), 7.622 (2.40), 7.636 (2.73), 7.643 (2.44), 7.657 (1.99), 7.960 (2.30), 7.968 (2.69), 7.974 (2.88), 7.982 (3.93), 7.992 (0.79), 8.021 (0.85), 8.031 (3.87), 8.039 (2.77), 8.045 (2.57), 8.052 (2.15).

Intermediate 19

2-[4-cyclopropyl-3-(4-fluorophenyl)-1-methyl-1H-pyrazol-5-yl]-1H-isoindole-1,3 (2H)-dione

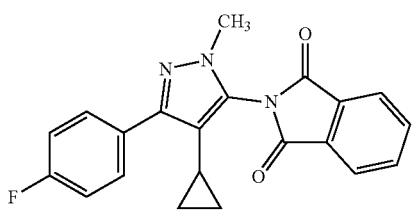 [SMILES: Cn1nc(-c2ccc(F)cc2)c(C2CC2)c1N1C(=O)c2ccccc2C1=O]

The described regioisomer was obtained in 34% yield out of the separation of the regioisomeric mixture in the synthesis of 2-[4-cyclopropyl-5-(4-fluorophenyl)-1-methyl-1H-pyrazol-3-yl]-1H-isoindole-1,3(2H)-dione (1.77 g).

LC-MS (method 11): Rt=1.42 min; MS (ESIpos): m/z=362 [M+H]$^+$ $^1$H-NMR (400 MHz, DMSO-d$_6$) δ [ppm]: −0.009 (2.94), 0.007 (2.77), 0.060 (2.44), 0.069 (2.50), 0.653 (1.99), 0.658 (1.97), 0.673 (2.07), 0.678 (1.95), 1.680 (1.16), 2.327 (0.58), 2.669 (0.60), 3.735 (16.00), 7.265 (2.01), 7.287 (4.10), 7.309 (2.13), 7.889 (2.15), 7.903 (2.34), 7.911 (2.28), 7.925 (2.03), 7.997 (2.44), 8.005 (2.61), 8.011 (2.52), 8.018 (3.77), 8.081 (3.91), 8.088 (2.61), 8.094 (2.67), 8.102 (2.40).

Intermediate 20

4-cyclopropyl-5-(4-fluorophenyl)-1-methyl-1H-pyrazol-3-amine

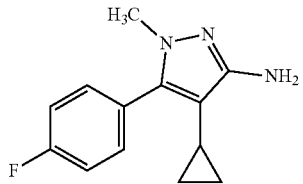 [SMILES: Cn1nc(N)c(C2CC2)c1-c1ccc(F)cc1]

The desired product was obtained in the same manner as described for the synthesis of 4-ethyl-5-(4-fluorophenyl)-1-methyl-1H-pyrazol-3-amine starting from 2-[4-cyclopropyl-5-(4-fluorophenyl)-1-methyl-1H-pyrazol-3-yl]-1H-isoindole-1,3(2H)-dione (1.64 g, 4.53 mmol) to yield 1.02 g (97% yield) of the desired product.

LC-MS (method 11): $R_t$=1.03 min; MS (ESIpos): m/z=232 [M+H]$^+$ $^1$H-NMR (400 MHz, DMSO-d$_6$) δ [ppm]: −0.008 (0.45), 0.008 (0.41), 0.037 (0.74), 0.047 (2.30), 0.052 (2.43), 0.060 (2.62), 0.065 (2.27), 0.074 (0.81), 0.514 (0.80), 0.523 (2.14), 0.528 (2.14), 0.534 (1.03), 0.538 (0.99), 0.544 (2.22), 0.549 (2.14), 0.559 (0.74), 1.396 (0.65), 1.403 (0.67), 1.408 (0.41), 1.416 (1.21), 1.424 (0.40), 1.429 (0.63), 1.436 (0.59), 3.417 (16.00), 3.538 (0.48), 4.351 (3.94), 7.281 (1.70), 7.286 (0.63), 7.298 (0.86), 7.304 (3.89), 7.309 (0.85), 7.320 (0.73), 7.326 (2.32), 7.419 (2.34), 7.425 (0.95), 7.433 (2.58), 7.441 (1.94), 7.450 (0.75), 7.455 (1.66).

Intermediate 21

4-cyclopropyl-3-(4-fluorophenyl)-1-methyl-1H-pyrazol-5-amine

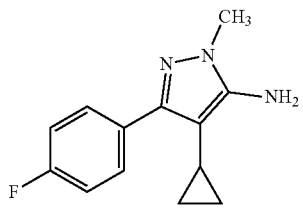 [SMILES: Cn1nc(-c2ccc(F)cc2)c(C2CC2)c1N]

The desired product was obtained in the same manner as described for the synthesis of 4-ethyl-5-(4-fluorophenyl)-1-methyl-1H-pyrazol-3-amine starting from 2-[4-cyclopropyl-3-(4-fluorophenyl)-1-methyl-1H-pyrazol-5-yl]-1H-isoindole-1,3(2H)-dione (1.77 g, 4.90 mmol) to yield 1.09 g (96% yield) of the desired product.

LC-MS (method 11): Rt=0.96 min; MS (ESIpos): m/z=233 [M+H]$^+$ $^1$H-NMR (400 MHz, DMSO-d$_6$) δ [ppm]: 0.149 (2.50), 0.159 (7.93), 0.163 (8.80), 0.172 (8.96), 0.176 (8.13), 0.186 (2.67), 0.751 (2.50), 0.760 (7.11), 0.765 (7.18), 0.770 (3.80), 0.780 (7.55), 0.785 (7.29), 0.795 (2.47), 1.511 (1.10), 1.523 (2.29), 1.530 (2.39), 1.536 (1.63), 1.543 (4.28), 1.550 (1.58), 1.556 (2.28), 1.563 (2.14), 1.576 (0.95), 2.270 (0.44), 3.319 (7.71), 3.364 (0.45), 3.746 (0.55), 4.911 (16.00), 7.141

(0.81), 7.148 (6.92), 7.170 (14.33), 7.193 (7.73), 7.756 (0.92), 7.763 (7.61), 7.768 (3.32), 7.777 (8.56), 7.785 (8.45), 7.794 (3.04), 7.799 (7.27).

Intermediate 22

4-chloro-6-(4-chloro-3,5-dimethyl-1H-pyrazol-1-yl)pyrimidine

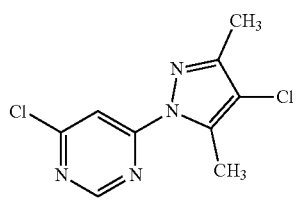

The desired product was prepared in the same manner as described in the synthesis of 4-chloro-6-(3,5-dimethyl-1H-pyrazol-1-yl)pyrimidine starting from 4,6-dichloropyrimidine (2.00 g, 13.4 mmol) and 4-chloro-3,5-dimethyl-1H-pyrazole (1.75 g, 13.4 mmol) to yield 2.16 g (66% yield) of the desired product.

LC-MS (method 9): Rt=1.19 min; MS (ESIpos): m/z=244 [M+H]$^+$ $^1$H-NMR (400 MHz, DMSO-d$_6$) δ [ppm]: 2.060 (0.07), 2.092 (0.09), 2.255 (16.00), 2.277 (0.21), 2.327 (0.12), 2.366 (0.04), 2.414 (0.09), 2.665 (15.71), 2.699 (0.19), 2.730 (0.04), 2.827 (0.09), 2.889 (0.04), 5.290 (0.04), 7.912 (2.83), 8.942 (2.94).

Intermediate 23

2-(2,4-difluorobenzoyl)butanenitrile

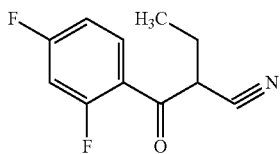

The desired product was prepared in the same manner as described in the synthesis of 2-(4-fluorobenzoyl)butanenitrile starting from methyl 2,4-difluorobenzoate (7.2 ml, 58 mmol) and butanenitrile (1.3 ml, 14 mmol) to obtain 2.73 g (90% yield) of the desired product.

LC-MS (method 10): R$_t$=1.65 min; MS (ESIpos): m/z=210 [M+H]$^+$

Intermediate 24

5-(2,4-difluorophenyl)-4-ethyl-1H-pyrazol-3-amine

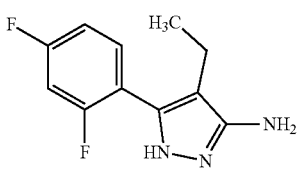

The desired product was prepared in the same manner as described in the synthesis of 4-ethyl-5-(4-fluorophenyl)-1H-pyrazol-3-amine starting from 2-(2,4-difluorobenzoyl)butanenitrile (2.73 g, 13.1 mmol) to obtain 2.13 g (73% yield) of the desired product.

LC-MS (method 10): R$_t$=1.18 min; MS (ESIpos): m/z=224 [M+H]$^+$

Intermediate 25

2-{1-[2-(benzyloxy)ethyl]-4-ethyl-3-(4-fluorophenyl)-1H-pyrazol-5-yl}-1H-isoindole-1,3 (2H)-dione

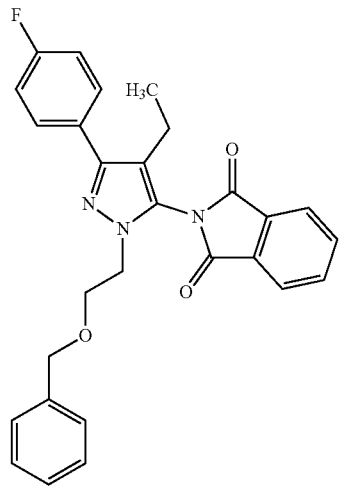 [SMILES: CCc1c(-c2ccc(F)cc2)nn(CCOCc2ccccc2)c1N1C(=O)c2ccccc2C1=O]

A solution of 2-[4-ethyl-3-(4-fluorophenyl)-1H-pyrazol-5-yl]-1H-isoindole-1,3(2H)-dione (1.00 g, 2.98 mmol) in DMF (5.0 mL) was treated with benzyl 2-bromoethyl ether (940 µl, 6.0 mmol) and potassium carbonate (824 mg, 5.96 mmol). The resulting mixture was stirred overnight at room temperature. The mixture was poured into water and extracted with ethyl acetate. The combined organic phases were washed with water, brine, dried over sodium sulfate and the solvent was removed under reduced pressure. The crude product was purified by preparative HPLC (method: column: Reprosil C18; 10 µm; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75-23.00 min=90% B). The obtained regioisomeric mixture was separated using SFC carbon dioxide/ethanol as eluting system to afford 252 mg (18% yield) of the indicated product.

LC-MS (method 10): R$_t$=2.42 min; MS (ESIpos): m/z=470 [M+H]$^+$ $^1$H-NMR (400 MHz, DMSO-d$_6$) δ [ppm]: 0.919 (5.80), 0.938 (12.81), 0.956 (5.98), 2.446 (1.77), 2.465 (5.27), 2.484 (6.64), 3.667 (3.55), 3.681 (7.47), 3.694 (3.83), 4.194 (3.73), 4.207 (6.98), 4.221 (3.33), 4.337 (16.00), 5.754 (3.57), 7.126 (3.40), 7.136 (4.28), 7.144 (4.44), 7.216 (8.33), 7.220 (8.53), 7.229 (4.59), 7.242 (1.07), 7.275 (3.43), 7.297 (6.64), 7.319 (3.59), 7.683 (3.89), 7.697 (4.52), 7.704 (4.26), 7.718 (3.50), 7.947 (3.28), 7.955 (4.02), 7.961 (4.47), 7.968 (6.43), 7.978 (1.49), 7.994 (1.51), 8.004 (6.58), 8.012 (4.28), 8.018 (3.98), 8.026 (3.08).

Intermediate 26

2-{1-[2-(benzyloxy)ethyl]-4-ethyl-5-(4-fluorophenyl)-1H-pyrazol-3-yl}-1H-isoindole-1,3 (2H)-dione

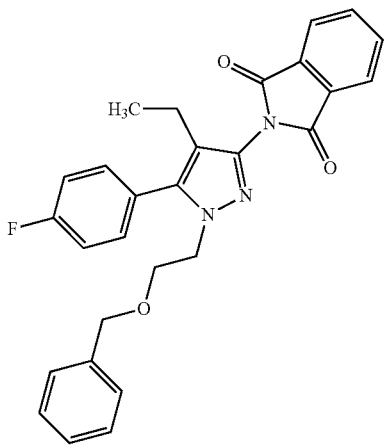 [SMILES: CCc1c(N2C(=O)c3ccccc3C2=O)nn(CCOCc2ccccc2)c1-c1ccc(F)cc1]

The described product was obtained in 9% yield (127 mg) out of the regioisomeric separation in the preparation of 2-{1-[2-(benzyloxy)ethyl]-4-ethyl-3-(4-fluorophenyl)-1H-pyrazol-5-yl}-1H-isoindole-1,3(2H)-dione.

LC-MS (method 10): Rt=2.40 min; MS (ESIpos): m/z=470 [M+H]$^+$ $^1$H-NMR (400 MHz, DMSO-d6) δ [ppm]: 0.81 (t, 3H), 2.22 (q, 2H), 3.74 (t, 2H), 4.16 (t, 2H), 4.36 (s, 2H), 7.18 (d, 2H), 7.23-7.37 (m, 5H), 7.49 (dd, 2H), 7.92-7.99 (m, 2H), 8.00-8.08 (m, 2H).

Intermediate 27

1-[2-(benzyloxy)ethyl]-4-ethyl-3-(4-fluorophenyl)-1H-pyrazol-5-amine

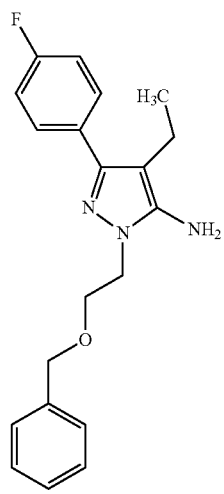 [SMILES: CCc1c(-c2ccc(F)cc2)nn(CCOCc2ccccc2)c1N]

The described product was prepared in the same manner as described for the synthesis of 4-ethyl-5-(4-fluorophenyl)-1-methyl-1H-pyrazol-3-amine starting from 2-{1-[2-(benzyloxy)ethyl]-4-ethyl-3-(4-fluorophenyl)-1H-pyrazol-5-yl}-1H-isoindole-1,3(2H)-dione (230 mg, 490 µmol) to obtain 150 mg (90% yield) of the desired product.

LC-MS (method 10): R$_t$=1.91 min; MS (ESIpos): m/z=340 [M+H]$^+$ $^1$H-NMR (400 MHz, DMSO-d$_6$) δ [ppm]: 0.988 (5.85), 1.006 (13.43), 1.025 (6.05), 1.909 (0.49), 2.414 (1.76), 2.433 (5.46), 2.451 (5.33), 2.470 (1.65), 3.728 (3.49), 3.743 (8.09), 3.757 (3.99), 4.107 (4.00), 4.121 (7.83), 4.136 (3.43), 4.491 (16.00), 4.925 (8.16), 5.754 (3.70), 7.173 (3.36), 7.195 (6.99), 7.217 (3.79), 7.243 (0.58), 7.249 (0.61), 7.260 (2.83), 7.267 (3.62), 7.283 (10.10), 7.295 (7.24), 7.309 (3.09), 7.313 (3.19), 7.330 (1.16), 7.530 (0.57), 7.537 (4.36), 7.543 (1.86), 7.552 (4.94), 7.559 (4.48), 7.569 (1.72), 7.573 (3.86).

Intermediate 28

1-[2-(benzyloxy)ethyl]-4-ethyl-5-(4-fluorophenyl)-1H-pyrazol-3-amine

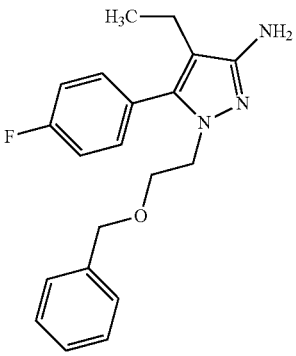 [SMILES: CCc1c(N)nn(CCOCc2ccccc2)c1-c1ccc(F)cc1]

The described product was prepared in the same manner as described for the synthesis of 4-ethyl-5-(4-fluorophenyl)-1-methyl-1H-pyrazol-3-amine starting from 2-{1-[2-(benzyloxy)ethyl]-4-ethyl-5-(4-fluorophenyl)-1H-pyrazol-3-yl}-1H-isoindole-1,3(2H)-dione (125 mg, 266 µmol) to obtain 76.4 mg (85% yield) of the desired product.

LC-MS (method 10): R$_t$=1.91 min; MS (ESIpos): m/z=340 [M+H]$^+$

Intermediate 29

4,4,4-trifluoro-2-(4-fluorobenzoyl)butanenitrile

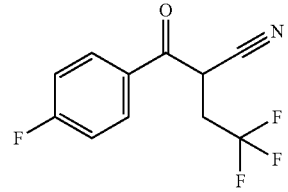 [SMILES: N#CC(CC(F)(F)F)C(=O)c1ccc(F)cc1]

A solution of 4,4,4-trifluorobutanenitrile (4.90 g, 39.8 mmol) in THF (50 mL) was treated at room temperature with lithium bis(trimethylsilyl)amide 1M in THF (50 ml, 1.0 M, 50 mmol). To this solution ethyl 4-fluorobenzoate (3.35 g, 19.9 mmol) was added drop wise. The reaction mixture was stirred for two days. The mixture was poured into water; THF was removed under reduced pressure. The aqueous phase was extracted with MTBE and subsequently acidified by addition of 1 M hydrochloric acid which was extracted again with MTBE. The combined organic phases were washed with brine; the solvent was removed under reduced pressure to obtain 5.65 g (76% yield, 66% purity) of the desired crude product which was used without any further purification.

LC-MS (method 11): Rt=1.19 min; MS (ESIpos): m/z=246 [M+H]$^+$

Intermediate 30

3-(4-fluorophenyl)-4-(2,2,2-trifluoroethyl)-1H-pyrazol-5-amine

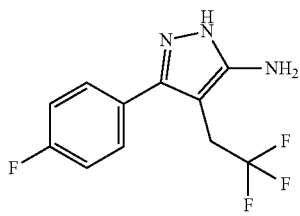 [SMILES: Nc1[nH]nc(-c2ccc(F)cc2)c1CC(F)(F)F]

A solution of 4,4,4-trifluoro-2-(4-fluorobenzoyl)butanenitrile (5.40 g, 66% purity, 14.5 mmol) in ethanol (30 mL) was treated with hydrazine hydrate (1:1) (1.8 ml, 80% purity, 29 mmol). The mixture was stirred for 4 h at 90° C. and overnight at room temperature. The solvent was removed under reduced pressure and the residue was purified by preparative reverse phase HPLC (acetonitrile/water+ 0.1% formic acid) to obtain 884 mg of the desired product (22% yield).

LC-MS (method 11): R$_t$=1.02 min; MS (ESIpos): m/z=260 [M+H]$^+$ $^1$H-NMR (400 MHz, DMSO-d$_6$) δ [ppm]: 2.670 (0.47), 3.420 (5.54), 3.449 (16.00), 3.477 (15.21), 3.504 (4.75), 4.837 (1.25), 7.234 (5.08), 7.255 (9.46), 7.276 (5.57), 7.540 (11.63), 7.554 (13.43), 7.561 (12.57), 7.575 (10.01), 11.814 (1.07).

Intermediate 31

4-methoxybutanenitrile

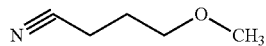

A solution of 4-bromobutanenitrile (670 µl, 6.8 mmol) in methanol (6.8 mL) was treated with sodium methoxide (3.8 ml, 5.4 M, 20 mmol). The mixture was stirred overnight at room temperature. The solvent was removed under reduced pressure; the residue was diluted with water/dichloromethane. After separation of the two layers, the aqueous phase was extracted twice with dichloromethane. The combined organic phases were dried over sodium sulfate and the solvent was removed under reduced pressure to obtain 594 mg (89% yield) of the desired product.

Intermediate 32

2-(4-fluorobenzoyl)-4-methoxybutanenitrile

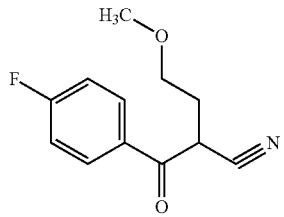 [SMILES: COCCC(C#N)C(=O)c1ccc(F)cc1]

The desired product was prepared in the same manner as described for the synthesis of 2-(4-fluorobenzoyl)butanenitrile starting from 4-methoxybutanenitrile (590 mg, 5.95 mmol) and ethyl 4-fluorobenzoate (3.5 ml, 24 mmol) to obtain 1.22 g (95% yield) of the desired product.

LC-MS (method 10): R$_t$=1.54 min; MS (ESIneg): m/z=220 [M−H]$^-$ $^1$H-NMR (400 MHz, DMSO-d$_6$) δ [ppm]: −0.014 (1.27), −0.008 (4.21), −0.006 (3.87), 0.008 (3.01), 2.052 (0.61), 2.067 (0.81), 2.074 (0.41), 2.087 (0.67), 2.137 (0.69), 2.155 (0.79), 2.168 (0.64), 2.172 (0.45), 3.188 (16.00), 3.275 (7.84), 3.453 (1.22), 3.458 (2.12), 3.467 (2.23), 3.471 (1.76), 3.475 (3.16), 3.482 (1.14), 3.491 (1.24), 5.131 (0.98), 5.144 (1.10), 5.152 (1.05), 5.165 (0.93), 7.295 (0.90), 7.300 (1.40), 7.305 (0.51), 7.317 (2.15), 7.322 (2.62), 7.339 (1.36), 7.344 (1.34), 7.404 (1.58), 7.410 (0.59), 7.427 (3.17), 7.444 (0.60), 7.449 (1.69), 7.579 (0.90), 7.585 (0.41), 7.593 (0.96), 7.601 (0.86), 7.615 (0.78), 7.985 (1.11), 7.990 (0.44), 7.999 (1.18), 8.007 (1.19), 8.016 (0.44), 8.021 (1.09), 8.056 (1.71), 8.061 (0.77), 8.069 (1.83), 8.078 (1.80), 8.086 (0.72), 8.092 (1.63), 10.988 (1.28).

Intermediate 33

5-(4-fluorophenyl)-4-(2-methoxyethyl)-1H-pyrazol-3-amine

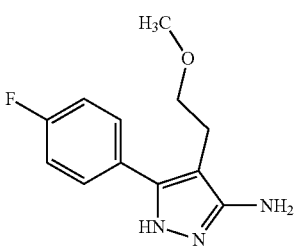 [SMILES: COCCc1c(N)n[nH]c1-c1ccc(F)cc1]

The desired product was prepared in the same manner as described for the synthesis of 4-ethyl-5-(4-fluorophenyl)-1H-pyrazol-3-amine starting from 2-(4-fluorobenzoyl)-4-methoxybutanenitrile (1.22 g, 5.51 mmol) to obtain 953 mg (73% yield) of the desired product.

LC-MS (method 10): R$_t$=1.03 min; MS (ESIpos): m/z=236 [M+H]$^+$ $^1$H-NMR (400 MHz, DMSO-d$_6$) δ [ppm]: 2.598 (1.60), 2.616 (3.31), 2.633 (1.70), 3.222 (16.00), 3.387 (1.53), 7.259 (1.13), 7.525 (1.25), 7.540 (1.63), 7.559 (1.10).

Intermediate 34

1-(6-chloropyrimidin-4-yl)-3-methyl-1H-indazole

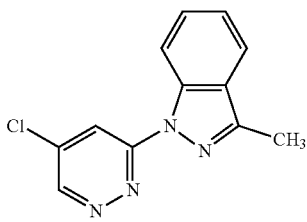 [SMILES: Cc1nn(-c2cc(Cl)cnn2)c2ccccc12]

A solution of 4,6-dichloropyrimidine (1.13 g, 7.57 mmol) and 3-methyl-1H-indazole (1.00 g, 7.57 mmol) in DMF (10 mL) was treated with caesium carbonate (2.47 g, 7.57 mmol) and stirred over the weekend at room temperature. Water was added and the resulting mixture was stirred at room temperature for 30 min. The precipitate was filtered, washed with water and dried under reduced pressure to afford 1.55 g (84% yield) of the desired product which contained minor amounts of the regioisomeric product.

LC-MS (method 11): $R_t$=1.50 min; MS (ESIpos): m/z=245 [M+H]$^+$ $^1$H-NMR (400 MHz, DMSO-d$_6$) δ [ppm]: 2.327 (0.09), 2.365 (0.09), 2.456 (0.11), 2.619 (16.00), 2.670 (0.18), 2.709 (0.09), 2.778 (0.09), 3.035 (0.89), 3.097 (0.09), 7.072 (0.10), 7.093 (0.09), 7.362 (0.10), 7.377 (0.09), 7.408 (1.15), 7.426 (2.35), 7.445 (1.46), 7.593 (0.14), 7.616 (0.13), 7.638 (1.25), 7.658 (2.00), 7.677 (1.15), 7.773 (0.13), 7.794 (0.13), 7.897 (2.29), 7.912 (3.32), 8.280 (0.17), 8.685 (1.81), 8.706 (1.75), 8.960 (2.96), 9.100 (0.18).

Intermediate 35

3-(2,4-difluorophenyl)-1H-pyrazol-5-amine

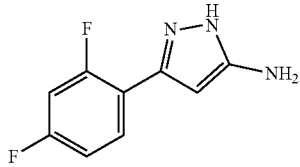 [SMILES: Nc1cc(-c2ccc(F)cc2F)n[nH]1]

A solution of 3-(2,4-difluorophenyl)-3-oxopropanenitrile (9.00 g, 49.7 mmol, synthesis described e.g. in J. Med. Chem. 1079, 22(11), 1385) in ethanol was treated with hydrazine hydrate (1:1) (2.9 ml, 60 mmol). The mixture was refluxed for 3.5 h. After cooling to room temperature saturated sodium hydrogen carbonate solution was added, ethanol was removed under reduced pressure and the residue was extracted with ethyl acetate. The combined organic phases were washed with brine, dried over sodium sulfate and the solvent was removed under reduced pressure to yield 8.36 g (77% yield) of the desired product which was used without any further purification.

LC-MS (method 9): $R_t$=0.53 min; MS (ESIpos): m/z=196 [M+H]$^+$

Intermediate 36

4-chloro-3-(2,4-difluorophenyl)-1H-pyrazol-5-amine

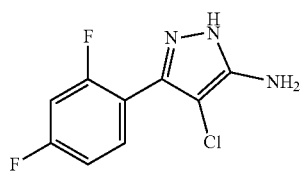 [SMILES: Nc1[nH]nc(-c2ccc(F)cc2F)c1Cl]

A solution of 3-(2,4-difluorophenyl)-1H-pyrazol-5-amine (2.30 g, 11.8 mmol) in acetonitrile (20 mL) was treated with 1-chloropyrrolidine-2,5-dione (1.57 g, 11.8 mmol and stirred at room temperature for 30 min. The mixture was diluted with water and extracted with ethyl acetate. The combined organic phases were washed with water and brine, dried over sodium sulfate and the solvent was removed under reduced pressure to yield 2.53 g (93% yield) of the desired crude product which was used without any further purification.

LC-MS (method 10): $R_t$=1.32 min; MS (ESIpos): m/z=230 [M+H]$^+$

Intermediate 37

2-[4-chloro-3-(2,4-difluorophenyl)-1H-pyrazol-5-yl]-1H-isoindole-1,3 (2H)-dione

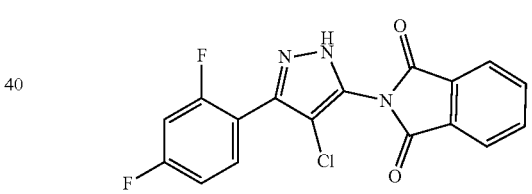

4-chloro-3-(2,4-difluorophenyl)-1H-pyrazol-5-amine (1.97 g, 8.56 mmol) and 2-benzofuran-1,3-dione (1.90 g, 12.8 mmol) in acetic acid (25 mL) were reflux overnight. Acetic acid was removed under reduced pressure. The residue was partitioned between brine and ethyl acetate. The organic phase wash dried over sodium sulfate and the solvent was removed under reduced pressure. The crude product was triturated with MTBE to yield desired product. The filtrate was further purified by preparative HPLC (Sunfire C18 5 m, 75×30 mm, flow 80 mL/min, 40° C., 210 nM, eluent A: water, eluent B: water+1% formic acid, eluent C: acetonitrile, gradient: 0-1 min at 60/5/35 A/B/C, 1-5 min to 47.5/5/47.5, 5.0-5.31 min to 0/5/95, 5.31-6.74 at 0/5/95). In total 2.02 g (63.7% yield) of the desired product were obtained.

LC-MS (method 10): $R_t$=1.84 min; MS (ESIpos): m/z=360 [M+H]$^+$ $^1$H-NMR (400 MHz, DMSO-d$_6$) δ [ppm]: 7.23-7.40 (m, 1H), 7.49-7.63 (m, 1H), 7.76 (td, 1H), 7.92-8.11 (m, 4H), 14.07 (s, 1H).

Intermediate 38

2-[4-chloro-3-(2,4-difluorophenyl)-1-methyl-1H-pyrazol-5-yl]-1H-isoindole-1,3 (2H)-dione

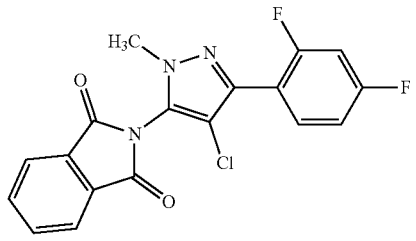 [SMILES: Cn1nc(-c2ccc(F)cc2F)c(Cl)c1N1C(=O)c2ccccc2C1=O]

A solution of 2-[4-chloro-3-(2,4-difluorophenyl)-1H-pyrazol-5-yl]-1H-isoindole-1,3(2H)-dione (1.50 g, 4.17 mmol) in DMF (10 mL) was treated with iodomethane (520 µl, 8.3 mmol) and potassium carbonate (1.15 g, 8.34 mmol). The mixture was stirred for 3 hours at room temperature. The mixture was partitioned between water and ethyl acetate. The organic layer was washed with brine and dried over sodium sulfate. After removal of the solvent under reduced pressure, the regioisomers were separated using preparative HPLC (Daicel Chiralpeak ID 5 µM 20×250 mm, flow: 80 mL/min, detection at 210 nm, 40° C., 0.0-8.0 min at 81% carbon dioxide/9% methanol). To yield 446.4 mg (27% yield) of the desired product.

LC-MS (method 11): $R_t$=1.41 min; MS (ESIpos): m/z=374 [M+H]$^+$

Intermediate 39

2-[4-chloro-5-(2,4-difluorophenyl)-1-methyl-1H-pyrazol-3-yl]-1H-isoindole-1,3 (2H)-dione

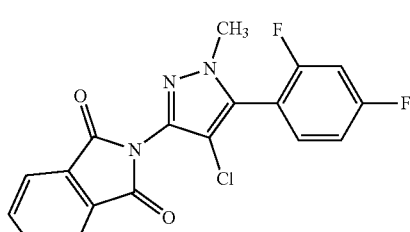

The desired regioisomer was obtained by the regioisomeric separation in the synthesis of 2-[4-chloro-3-(2,4-difluorophenyl)-1-methyl-1H-pyrazol-5-yl]-1H-isoindole-1,3(2H)-dione. 788 mg (50% yield) of the desired product were yielded.

LC-MS (method 11): Rt=1.36 min; MS (ESIpos): m/z=374 [M+H]$^+$

Intermediate 40

4-chloro-3-(2,4-difluorophenyl)-1-methyl-1H-pyrazol-5-amine

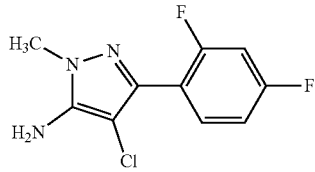 [SMILES: Cn1nc(-c2ccc(F)cc2F)c(Cl)c1N]

A solution of 2-[4-chloro-3-(2,4-difluorophenyl)-1-methyl-1H-pyrazol-5-yl]-1H-isoindole-1,3(2H)-dione (446 mg, 1.19 mmol) in ethanol (15 mL) was treated with hydrazine hydrate (1:1) (290 µl, 6.0 mmol) and stirred for 1 h at 80° C. After cooling to room temperature, the precipitate was removed by filtration. The filtrate was taken to dryness to yield the desired product (281 mg, 97% yield).

LC-MS (method 11): $R_t$=1.06 min; MS (ESIpos): m/z=244 [M+H]$^+$ $^1$H-NMR (400 MHz, DMSO-d$_6$) δ [ppm]: 3.317 (16.00), 5.536 (6.97), 7.119 (0.75), 7.124 (0.81), 7.140 (1.58), 7.146 (1.68), 7.161 (0.88), 7.167 (0.92), 7.288 (0.92), 7.294 (0.87), 7.312 (1.43), 7.318 (1.39), 7.337 (0.95), 7.344 (0.88), 7.469 (1.00), 7.487 (1.29), 7.491 (1.96), 7.508 (1.98), 7.511 (1.12), 7.529 (0.92).

Intermediate 41

4-chloro-5-(2,4-difluorophenyl)-1-methyl-1H-pyrazol-3-amine

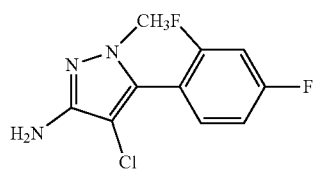

The described product was prepared in a manner analogous to that described in the preparation of 4-chloro-3-(2,4-difluorophenyl)-1-methyl-1H-pyrazol-5-amine starting from 2-[4-chloro-5-(2,4-difluorophenyl)-1-methyl-1H-pyrazol-3-yl]-1H-isoindole-1,3(2H)-dione (788 mg, 2.11 mmol) to yield 384 mg of the desired product (75% yield).

LC-MS (method 11): $R_t$=1.06 min; MS (ESIpos): m/z=244 [M+H]$^+$ $^1$H-NMR (500 MHz, DMSO-d$_6$) δ [ppm]: −0.007 (1.21), 0.006 (0.99), 2.521 (0.42), 3.321 (16.00), 4.913 (12.76), 7.259 (1.43), 7.263 (1.51), 7.276 (3.00), 7.280 (3.06), 7.293 (1.64), 7.297 (1.68), 7.464 (1.99), 7.469 (1.97), 7.483 (2.79), 7.484 (2.83), 7.488 (2.76), 7.503 (2.05), 7.508 (1.99), 7.521 (2.04), 7.534 (2.43), 7.538 (3.83), 7.551 (3.83), 7.555 (2.11), 7.568 (1.79).

Intermediate 42-1

3-(4-fluorophenyl)-1H-pyrazol-5-amine

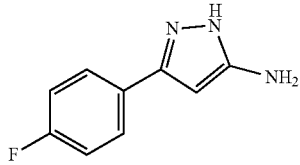

A solution of 3-(4-fluorophenyl)-3-oxopropanenitrile (470 mg, 60% purity, 1.73 mmol, CAS 4640-67-9) in ethanol (3.6 mL) was treated with hydrazine hydrate (1:1) (100 µl, 2.1 mmol). The mixture was refluxed for 3 h and stirred over the weekend at room temperature. The mixture was diluted with started sodium hydrogen carbonate solution, ethanol was removed under reduced pressure. The resulting precipitate was collected by filtration. The filtrate was also taken to dryness and combined with the precipitate to yield 360 mg of a approx. 2:1 mixture of 3-(4-fluorophenyl)-1H-pyrazol-5-amine together with 3-(4-ethoxyphenyl)-1H-pyrazol-5-amine. The mixture was used in the next reaction.

LC-MS (method 10): $R_t$=0.87 min; MS (ESIpos): m/z=178 [M+H]$^+$/$R_t$=0.97 min; MS (ESIpos): m/z=204 [M+H]$^+$ Intermediate 42-2

3-(4-ethoxyphenyl)-1H-pyrazol-5-amine

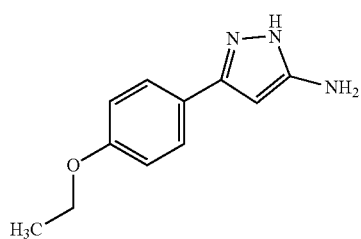

A solution of 3-(4-fluorophenyl)-3-oxopropanenitrile (470 mg, 60% purity, 1.73 mmol, CAS 4640-67-9) in ethanol (3.6 mL) was treated with hydrazine hydrate (1:1) (100 µl, 2.1 mmol). The mixture was refluxed for 3 h and stirred over the weekend at room temperature. The mixture was diluted with started sodium hydrogen carbonate solution, ethanol was removed under reduced pressure. The resulting precipitate was collected by filtration. The filtrate was also taken to dryness and combined with the precipitate to yield 360 mg of a approx. 2:1 mixture of 3-(4-fluorophenyl)-1H-pyrazol-5-amine together with 3-(4-ethoxyphenyl)-1H-pyrazol-5-amine. The mixture was used in the next reaction.

LC-MS (method 10): $R_t$=0.87 min; MS (ESIpos): m/z=178 [M+H]$^+$/$R_t$=0.97 min; MS (ESIpos): m/z=204 [M+H]$^+$ Intermediate 43

4-chloro-3-(4-fluorophenyl)-1H-pyrazol-5-amine

A solution of 3-(4-fluorophenyl)-1H-pyrazol-5-amine (100 mg, 564 µmol, mixture with the ethoxy-by product out of the step before) in acetonitrile (1.1 ml, 20 mmol) was treated with 1-chloropyrrolidine-2,5-dione (75.4 mg, 564 µmol). The mixture was stirred 30 min at room temperature. Water was added and the mixture was three times extracted with ethyl acetate. The combined organic phases were washed with water and brine, dried over sodium sulfate and the solvent was removed under reduced pressure. The crude product was purified by preparative HPLC (method 7) to yield 36 mg (30% yield) of the desired product. The corresponding ethoxy-derivative was also isolated.

LC-MS (method 10): $R_t$=1.31 min; MS (ESIpos): m/z=212 [M+H]$^+$

Intermediate 44

4-chloro-3-(4-ethoxyphenyl)-1H-pyrazol-5-amine

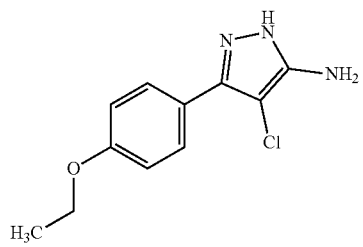 [SMILES: CCOc1ccc(-c2n[nH]c(N)c2Cl)cc1]

The desired product was obtained by the separation of the two components in the synthesis of 4-chloro-3-(4-fluorophenyl)-1H-pyrazol-5-amine in 20% yield (27 mg).

LC-MS (method 10): $R_t$=1.42 min; MS (ESIpos): m/z=238 [M+H]$^+$ $^1$H-NMR (400 MHz, DMSO-d6) δ [ppm]: 1.34 (t, 3H), 4.07 (q, 2H), 4.74 (s, 2H), 7.03 (br d, 2H), 7.63 (br d, 2H), 12.06 (s, 1H).

Intermediate 45

2-methyl-3-oxo-3-phenylpropanenitrile

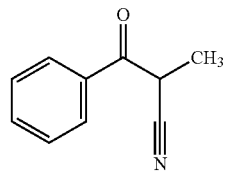

A solution of propanenitrile (3.0 ml, 42 mmol) in THF (130 mL) was treated with lithium bis(trimethylsilyl)amide 1M in THF (120 mL, 1.0 M, 120 mmol). Subsequently ethyl benzoate (24 ml, 170 mmol) was added at room temperature. The mixture was stirred for 4 hours at room temperature. Water was added and the mixture was extracted with dichloromethane. The combined organic phases were discarded. The aqueous phase was acidified with aqueous hydrochloric acid and extracted with dichloromethane. The organic phase was washed with water, brine and dried over sodium sulfate. After removal of the solvent under reduced pressure 7.83 g (98% yield) of the desired product were obtained.

LC-MS (method 10): $R_t$=1.43 min; MS (ESIpos): m/z=160 [M+H]$^+$ $^1$H-NMR (400 MHz, DMSO-d$_6$) δ [ppm]: 1.485 (15.70), 1.503 (16.00), 1.679 (2.50), 1.876 (11.52), 1.878 (13.95), 5.125 (1.69), 5.142 (5.29), 5.160 (5.26), 5.178 (1.64), 7.420 (0.40), 7.429 (0.41), 7.462 (0.76), 7.473 (3.07), 7.477 (3.42), 7.485 (6.48), 7.490 (7.04), 7.496 (1.65), 7.500 (1.30), 7.505 (2.29), 7.525 (1.49), 7.547 (1.82), 7.549 (2.38), 7.552 (2.14), 7.555 (2.00), 7.559 (2.21), 7.565 (1.64), 7.569 (1.70), 7.571 (1.78), 7.574 (1.47), 7.582 (3.45), 7.586 (1.47), 7.600 (7.32), 7.620 (5.31), 7.711 (2.34), 7.714 (1.39), 7.729 (3.48), 7.748 (1.35), 7.751 (0.75), 7.956 (0.68), 7.960 (1.26), 7.964 (1.23), 7.977 (0.93), 7.981 (1.24), 8.031 (6.27), 8.050 (6.00), 10.835 (3.58).

Intermediate 46

4-methyl-3-phenyl-1H-pyrazol-5-amine

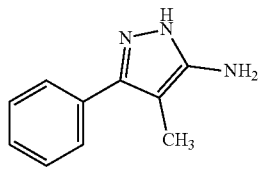

The described product was prepared in a manner analogous to that described in the preparation of 4-ethyl-5-(4-fluorophenyl)-1H-pyrazol-3-amine starting from 2-methyl-3-oxo-3-phenylpropanenitrile (7.83 g, 83% purity, 40.8 mmol) to yield 3.47 g of the desired product 49% yield).

LC-MS (method 10): $R_t$=0.89 min; MS (ESIpos): m/z=174 [M+H]$^+$ $^1$H-NMR (400 MHz, DMSO-d$_6$) δ [ppm]: −0.007 (0.91), 1.983 (16.00), 4.467 (1.03), 7.299 (1.65), 7.313 (1.32), 7.418 (3.61), 7.514 (3.90), 7.531 (3.04), 11.566 (0.82).

Intermediate 47

3-(4-fluorophenyl)-2-methyl-3-oxopropanenitrile

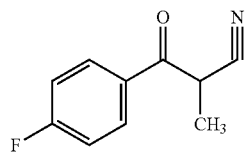

The described product was prepared in a manner analogous to that described in the preparation of 2-methyl-3-oxo-3-phenylpropanenitrile starting from propanenitrile (6.4 ml, 89 mmol) and ethyl 4-fluorobenzoate (4.4 ml, 30 mmol) to yield 4.12 g of the desired product (77% yield).

LC-MS (method 10): $R_t$=1.49 min; MS (ESIpos): m/z=178 [M+H]$^+$ $^1$H-NMR (400 MHz, DMSO-d$_6$) δ [ppm]: 1.493 (15.61), 1.511 (16.00), 1.688 (1.74), 1.881 (12.92), 2.560 (1.31), 5.125 (1.23), 5.143 (3.77), 5.161 (3.74), 5.179 (1.20), 7.296 (1.59), 7.318 (3.35), 7.340 (1.84), 7.412 (3.38), 7.434 (6.92), 7.455 (3.62), 7.617 (1.92), 7.631 (2.22), 7.638 (2.09), 7.652 (1.71), 8.121 (4.30), 8.135 (4.95), 8.143 (4.78), 8.157 (4.13), 10.881 (2.02).

Intermediate 48

3-(4-fluorophenyl)-4-methyl-1H-pyrazol-5-amine

The described product was prepared in a manner analogous to that described in the preparation of 4-methyl-3-phenyl-1H-pyrazol-5-amine starting from 3-(4-fluorophenyl)-2-methyl-3-oxopropanenitrile (4.10 g, 23.1 mmol) to yield 3.86 g of the desired product (86% yield).

LC-MS (method 10): $R_t$=0.98 min; MS (ESIpos): m/z=192 [M+H]$^+$ $^1$H-NMR (400 MHz, DMSO-d$_6$) δ [ppm]: 1.931 (0.42), 1.965 (16.00), 3.336 (1.15), 4.451 (0.49), 7.258 (1.43), 7.554 (1.59), 11.570 (0.45).

Intermediate 49

2-(4-chlorobenzoyl)butanenitrile

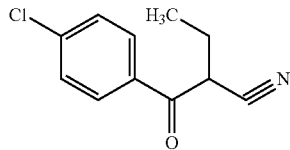

The described product was prepared in a manner analogous to that described in the preparation of 2-methyl-3-oxo-3-phenylpropanenitrile starting from butanenitrile (710 µl, 8.2 mmol) and methyl 4-chlorobenzoate (5.56 g, 32.6 mmol) to yield 1.57 g of the desired product (93% yield).

LC-MS (method 10): $R_t$=1.83 min; MS (ESIpos): m/z=208 [M+H]$^+$ $^1$H-NMR (400 MHz, DMSO-d$_6$) δ [ppm]: 0.989 (7.60), 1.008 (16.00), 1.026 (7.89), 1.057 (2.39), 1.076 (4.91), 1.095 (2.44), 1.763 (0.90), 1.782 (1.44), 1.798 (1.75), 1.817 (2.06), 1.835 (1.34), 1.922 (1.28), 1.935 (1.40), 1.941 (1.51), 1.945 (0.92), 1.953 (1.53), 1.957 (1.42), 1.970 (1.07), 1.975 (1.01), 1.989 (0.79), 2.270 (0.79), 2.289 (2.33), 2.308 (2.25), 2.327 (0.80), 5.136 (2.44), 5.149 (2.73), 5.156 (2.68), 5.169 (2.39), 7.421 (0.62), 7.538 (1.06), 7.544 (1.16), 7.551 (5.96), 7.558 (10.61), 7.563 (3.37), 7.575 (2.31), 7.580 (6.97), 7.654 (1.07), 7.660 (6.98), 7.665 (3.09), 7.677 (2.78), 7.682 (8.02), 7.688 (1.36), 7.924 (0.92), 7.930 (6.97), 7.935 (2.27), 7.947 (2.05), 7.952 (6.41), 8.015 (1.34), 8.022 (8.65), 8.026 (3.25), 8.038 (2.87), 8.043 (7.78), 8.049 (1.16).

Intermediate 50

5-(4-chlorophenyl)-4-ethyl-1H-pyrazol-3-amine

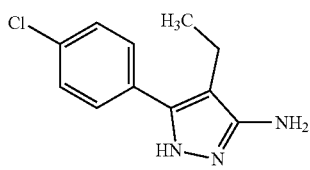

The described product was prepared in a manner analogous to that described in the preparation of 4-methyl-3-phenyl-1H-pyrazol-5-amine starting from 2-(4-chlorobenzoyl)butanenitrile (1.57 g, 7.54 mmol) to yield 1.39 g of the desired product (83% yield).

LC-MS (method 10): $R_t$=1.36 min; MS (ESIpos): m/z=222 [M+H]$^+$ $^1$H-NMR (400 MHz, DMSO-d$_6$) δ [ppm]: −0.008 (1.07), 0.008 (1.06), 0.966 (0.72), 0.981 (0.63), 0.984 (0.66), 1.000 (1.93), 1.011 (7.53), 1.030 (16.00), 1.049 (8.81), 2.367 (0.57), 2.399 (3.87), 2.418 (12.08), 2.437 (11.78), 2.455 (3.63), 3.291 (0.63), 3.509 (2.51), 4.444 (1.13), 7.432 (3.66), 7.435 (1.93), 7.490 (10.19), 11.600 (1.36).

Intermediate 51

(4-fluorobenzoyl)propanedinitrile

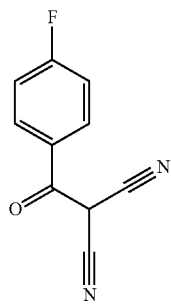 [SMILES: N#CC(C#N)C(=O)c1ccc(F)cc1]

To sodium hydride (2.52 g, 60% purity, 63.1 mmol) in THF (10 mL) at 0 to 5° C. a solution of propanedinitrile (2.08 g, 31.5 mmol) in THF (10 mL) was added dropwise. The mixture was stirred for 15 minutes, subsequently 4-fluorobenzoyl chloride (3.7 ml, 32 mmol) was added. The mixture was allowed to warm up to room temperature and stirred for 1 hour. The mixture was acidified to pH1 and extracted two times with ethyl acetate. The combined organic phases were dried over sodium sulfate, the solvent was removed under reduced pressure. The crude product was triturated from MTBE to yield 4.15 g (67% yield) of the desired product.

LC-MS (method 9): $R_t$=0.49 min; MS (ESIneg): m/z=187 [M−H]$^-$ $^1$H-NMR (400 MHz, DMSO-d$_6$) δ [ppm]: −0.008 (1.19), 0.008 (1.10), 1.175 (0.51), 1.988 (0.99), 3.575 (2.69), 7.145 (0.89), 7.153 (7.89), 7.158 (2.62), 7.169 (3.36), 7.175 (16.00), 7.180 (3.22), 7.192 (2.84), 7.197 (8.67), 7.204 (0.99), 7.605 (0.93), 7.612 (8.57), 7.617 (3.25), 7.626 (9.32), 7.634 (8.54), 7.643 (3.07), 7.648 (7.91), 7.656 (0.84).

Intermediate 52

[(4-fluorophenyl)(methoxy)methylidene]propanedinitrile

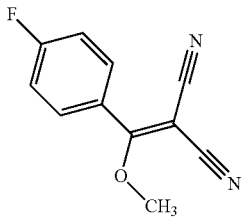

To mixture of sodium hydrogen carbonate (8.45 g, 101 mmol) in water (4.0 mL) and 1,4-dioxane (25 mL) (4-fluorobenzoyl)propanedinitrile (2.37 g, 12.6 mmol) was added. To this mixture dimethyl sulfate (8.9 ml, 93 mmol) was added drop wise and the reaction mixture was refluxed for 2 hours. After cooling to room temperature the mixture was diluted with water and extracted with ethyl acetate. The combined organic phases were washed with brine, dried over sodium sulfate and the solvent was removed under reduced pressure to yield 2 g (79% yield) of the desired product which was used without any further purification in the next step.

Intermediate 53

3-amino-5-(4-fluorophenyl)-1-methyl-1H-pyrazole-4-carbonitrile

A solution of [(4-fluorophenyl)(methoxy)methylidene]propanedinitrile (930 mg, 4.60 mmol) in 2-propanol (9.3 mL) was treated with methylhydrazine (290 μl, 5.5 mmol). The reaction mixture was refluxed for 2 days. Water was added and the mixture was extracted with ethyl acetate. The combined organic phases were washed with brine, dried over sodium sulfate and the solvent was removed under reduced pressure. The crude regioisomeric mixture was separated via preparative HPLC (column: Daicel Chiracel OJ-H-5 5 μM, 250×20 mm, flow 80 mL/min, 92% carbon dioxide/8% methanol, 40° C., detection at 210 nM) to yield 62 mg of the desired product (5% yield).

LC-MS (method 10): $R_t$=1.23 min; MS (ESIpos): m/z=217 [M+H]$^+$ $^1$H-NMR (500 MHz, DMSO-d$_6$) δ [ppm]: 3.168 (1.37), 3.178 (1.37), 3.318 (13.07), 5.640 (16.00), 7.405 (1.04), 7.411 (6.70), 7.415 (2.60), 7.429 (14.37), 7.442 (2.92), 7.446

(7.97), 7.452 (1.03), 7.602 (1.25), 7.608 (7.98), 7.612 (3.73), 7.619 (8.71), 7.625 (7.47), 7.632 (3.17), 7.636 (6.55), 7.642 (0.74).

Intermediate 54

5-amino-3-(4-fluorophenyl)-1-methyl-1H-pyrazole-4-carbonitrile

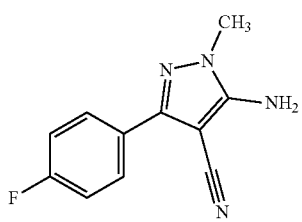 [SMILES: Cn1nc(-c2ccc(F)cc2)c(C#N)c1N]

The desired product was obtained out of the regioisomeric separation from example 3-amino-5-(4-fluorophenyl)-1-methyl-1H-pyrazole-4-carbonitrile in 8% yield (78.5 mg).

LC-MS (method 10): $R_t$=1.35 min; MS (ESIpos): m/z=217 [M+H]$^+$ $^1$H-NMR (500 MHz, DMSO-d$_6$) δ [ppm]: 3.59 (s, 3H), 6.69 (s, 2H), 7.23-7.34 (m, 2H), 7.73-7.85 (m, 2H).

Intermediate 55

2-(cyclohexylcarbonyl)butanenitrile

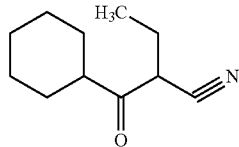

The described product was prepared in a manner analogous to that described in the preparation of 2-methyl-3-oxo-3-phenylpropanenitrile starting from butanenitrile (1.3 ml, 14 mmol) and methyl cyclohexanecarboxylate (8.3 ml, 58 mmol) to yield 2.13 g of the desired product (82% yield).

LC-MS (method 9): $R_t$=0.96 min; MS (ESIneg): m/z=178 [M–H]$^-$

Intermediate 56

5-cyclohexyl-4-ethyl-1H-pyrazol-3-amine

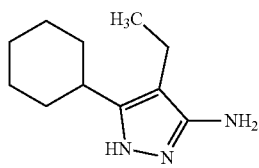

The described product was prepared in a manner analogous to that described in the preparation of 4-methyl-3-phenyl-1H-pyrazol-5-amine starting from 2-(cyclohexylcarbonyl)butanenitrile (2.13 g, 11.9 mmol) to yield 2.16 g of the desired product (94% yield).

LC-MS (method 9): $R_t$=0.62 min; MS (ESIpos): m/z=194 [M+H]$^+$ $^1$H-NMR (400 MHz, DMSO-d$_6$) δ [ppm]: 0.946 (6.97), 0.965 (16.00), 0.984 (7.33), 1.141 (0.68), 1.149 (1.15), 1.172 (0.94), 1.180 (1.53), 1.204 (0.64), 1.211 (0.95), 1.248 (1.11), 1.255 (0.75), 1.279 (2.61), 1.286 (1.68), 1.311 (2.65), 1.342 (1.17), 1.374 (1.17), 1.379 (1.14), 1.405 (2.65), 1.411 (2.61), 1.436 (2.57), 1.442 (2.54), 1.467 (0.92), 1.473 (0.88), 1.658 (4.22), 1.686 (3.41), 1.725 (2.85), 1.757 (2.53), 2.187 (2.22), 2.206 (6.79), 2.225 (6.56), 2.243 (1.99), 2.408 (0.59), 2.416 (1.02), 2.425 (0.65), 2.438 (1.16), 2.446 (1.90), 2.454 (1.09), 2.468 (0.69), 2.476 (1.05), 3.507 (0.47), 4.140 (1.36), 10.860 (0.46).

Intermediate 57

2-(4-methyl-3-phenyl-1H-pyrazol-5-yl)-1H-isoindole-1,3(2H)-dione

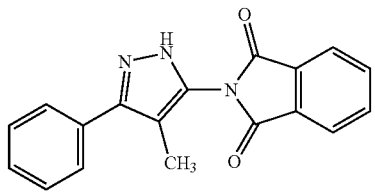 [SMILES: Cc1c(-c2ccccc2)n[nH]c1N1C(=O)c2ccccc2C1=O]

The described product was prepared in a manner analogous to that described in the preparation of 2-[4-ethyl-3-(4-fluorophenyl)-1H-pyrazol-5-yl]-1H-isoindole-1,3(2H)-dione starting from 4-methyl-3-phenyl-1H-pyrazol-5-amine (3.47 g, 20.0 mmol) to obtain 6.66 g (99% yield) of the desired product which was used in the next step without any further purification.

LC-MS (method 10): $R_t$=1.69 min; MS (ESIpos): m/z=304 [M+H]$^+$ $^1$H-NMR (400 MHz, DMSO-d$_6$) δ [ppm]: 1.921 (1.69), 2.029 (16.00), 7.421 (0.74), 7.439 (1.88), 7.457 (1.33), 7.523 (2.34), 7.543 (3.95), 7.562 (2.15), 7.580 (0.94), 7.589 (1.02), 7.595 (1.01), 7.603 (1.32), 7.646 (4.08), 7.665 (3.18), 7.668 (2.35), 7.673 (1.60), 7.681 (0.95), 7.687 (0.92), 7.696 (0.79), 7.935 (0.56), 7.944 (2.50), 7.951 (2.80), 7.957 (2.79), 7.965 (3.92), 7.975 (0.81), 8.000 (0.96), 8.012 (4.19), 8.019 (2.79), 8.026 (2.55), 8.033 (2.13).

Intermediate 58

2-(1,4-dimethyl-3-phenyl-1H-pyrazol-5-yl)-1H-isoindole-1,3(2H)-dione

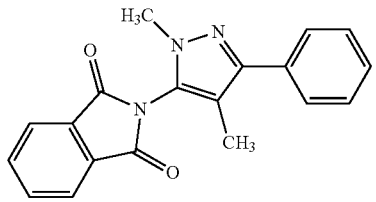 [SMILES: Cc1c(-c2ccccc2)nn(C)c1N1C(=O)c2ccccc2C1=O]

The described product was prepared in a manner analogous to that described in the preparation of 2-[4-ethyl-3-(4-fluorophenyl)-1-methyl-1H-pyrazol-5-yl]-1H-isoindole-1,3

(2H)-dione starting from 2-(4-methyl-3-phenyl-1H-pyrazol-5-yl)-1H-isoindole-1,3(2H)-dione (2.50 g, 8.24 mmol) to obtain 1.08 g (41% yield) of the desired product.

LC-MS (method 10): $R_t$=1.87 min; MS (ESIpos): m/z=318 [M+H]$^+$ $^1$H-NMR (400 MHz, DMSO-d$_6$) δ [ppm]: 1.832 (16.00), 3.320 (10.09), 3.745 (0.43), 7.491 (0.64), 7.510 (3.71), 7.529 (6.44), 7.554 (3.89), 7.571 (3.37), 7.589 (1.10), 7.939 (2.61), 7.947 (3.49), 7.953 (3.69), 7.959 (3.62), 8.004 (4.25), 8.012 (3.42), 8.018 (2.74), 8.025 (1.90).

Intermediate 59

2-(1,4-dimethyl-5-phenyl-1H-pyrazol-3-yl)-1H-isoindole-1,3(2H)-dione

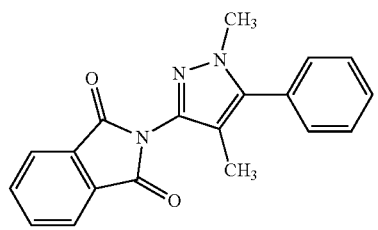 [SMILES: Cc1c(N2C(=O)c3ccccc3C2=O)nn(C)c1-c1ccccc1]

The desired product was obtained in 19% yield (509 mg) out of the regioisomeric separation in the preparation of 2-(1,4-dimethyl-3-phenyl-1H-pyrazol-5-yl)-1H-isoindole-1,3(2H)-dione.

$^1$H-NMR (400 MHz, DMSO-d$_6$) δ [ppm]: 1.830 (0.71), 1.869 (0.09), 2.030 (16.00), 2.188 (0.09), 2.327 (0.05), 2.668 (0.05), 3.315 (13.69), 3.563 (0.08), 3.785 (0.75), 3.915 (0.08), 5.753 (0.13), 7.345 (0.68), 7.363 (1.92), 7.381 (1.39), 7.443 (2.52), 7.462 (4.21), 7.481 (2.06), 7.512 (0.18), 7.530 (0.29), 7.553 (0.19), 7.571 (0.15), 7.682 (4.21), 7.700 (3.54), 7.965 (2.44), 7.973 (2.91), 7.978 (3.15), 7.986 (3.91), 7.996 (0.87), 8.032 (0.78), 8.042 (3.80), 8.050 (2.99), 8.056 (2.74), 8.063 (2.26).

Intermediate 60

1,4-dimethyl-3-phenyl-1H-pyrazol-5-amine

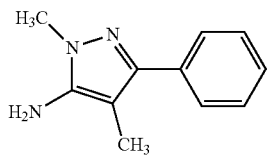

The described product was prepared in a manner analogous to that described in the preparation of 4-ethyl-5-(4-fluorophenyl)-1-methyl-1H-pyrazol-3-amine starting from 2-(1,4-dimethyl-3-phenyl-1H-pyrazol-5-yl)-1H-isoindole-1,3(2H)-dione (1.08 g, 3.40 mmol) to obtain 404 mg (50% yield) of the desired product.

LC-MS (method 16): $R_t$=1.20 min; MS (ESIpos): m/z=188 [M+H]$^+$ $^1$H-NMR (400 MHz, DMSO-d$_6$) δ [ppm]: 0.006 (1.54), 1.771 (16.00), 1.808 (0.74), 1.862 (1.29), 3.320 (2.48), 3.630 (1.33), 3.643 (0.74), 7.329 (2.78), 7.346 (3.33), 7.349 (3.41), 7.388 (0.50), 7.407 (1.89), 7.425 (1.72), 7.470 (2.64), 7.489 (3.52), 7.508 (1.32), 7.532 (0.51), 8.152 (0.40).

Intermediate 61

1,4-dimethyl-5-phenyl-1H-pyrazol-3-amine

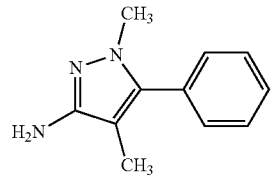

The described product was prepared in a manner analogous to that described in the preparation of 4-ethyl-5-(4-fluorophenyl)-1-methyl-1H-pyrazol-3-amine starting from 2-(1,4-dimethyl-5-phenyl-1H-pyrazol-3-yl)-1H-isoindole-1,3(2H)-dione (500 mg, 1.58 mmol) to obtain 161 mg (54% yield) of the desired product.

LC-MS (method 16): $R_t$=1.16 min; MS (ESIpos): m/z=188 [M+H]$^+$ $^1$H-NMR (400 MHz, DMSO-d$_6$) δ [ppm]: 1.435 (0.90), 1.455 (0.80), 1.768 (0.88), 1.984 (16.00), 2.011 (0.43), 3.329 (1.15), 3.350 (0.99), 3.453 (0.92), 3.644 (0.54), 4.929 (1.26), 7.224 (0.70), 7.243 (1.74), 7.260 (1.28), 7.337 (2.31), 7.355 (3.86), 7.374 (1.84), 7.422 (1.05), 7.437 (0.61), 7.551 (4.46), 7.571 (3.64), 7.903 (0.56), 7.923 (0.54), 8.169 (1.35).

Intermediate 62

1-(4-fluorophenyl)-3,5-dimethyl-4-nitro-1H-pyrazole

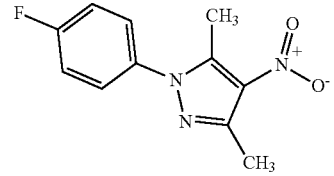

A mixture of 3,5-dimethyl-4-nitro-1H-pyrazole (630 mg, 4.47 mmol), (4-fluorophenyl)boronic acid (625 mg, 4.47 mmol), copper acetate (anhydrous, 1.22 g, 6.80 mmol) and pyridine (3.6 mL) in dichloromethane (6.0 mL) was stirred with 1.0 g of molecular sieves for 2 days at room temperature. The reaction mixture was filtered over Celite and washed with dichloromethane. The organic layer was washed with water. The aqueous layer was extracted twice with dichloromethane. The combined organic phases were dried with sodium sulfate and evaporated under vacuum. The crude product was purified by preparative HPLC (method: column: Reprosil C18; 10 μm; 125×30 mm/flow: 45 ml/min/eluent: A=water (0.1% formic acid), B=acetonitrile/gradient: 0.00-4.25 min=10% B, 4.50 min=20% B, 15.50 min=85% B, 16.00-18.50 min=100% B, 18.75-22.00 min=20% B) to afford 591 mg (56% yield) of the desired product.

LC-MS (method 11): $R_t$=1.25 min; MS (ESIpos): m/z=236 [M+H]$^+$ $^1$H-NMR (400 MHz, DMSO-d$_6$) δ [ppm]: −0.008 (0.46), 2.490 (16.00), 7.416 (1.59), 7.421 (0.56), 7.438 (3.34), 7.454 (0.66), 7.459 (2.02), 7.608 (2.02), 7.614 (0.76), 7.620 (2.11), 7.625 (1.13), 7.631 (1.70), 7.638 (0.67), 7.643 (1.58).

Intermediate 63

1-(4-fluorophenyl)-3,5-dimethyl-1H-pyrazol-4-amine

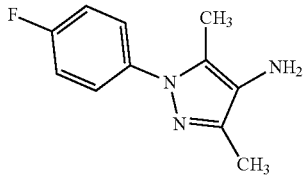

To a solution of 1-(4-fluorophenyl)-3,5-dimethyl-4-nitro-1H-pyrazole (490 mg, 2.08 mmol) in methanol (20 mL) were added iron (582 mg, 10.4 mmol) and concentrated hydrochloric acid (4.9 ml). The reaction mixture was then heated at reflux for 2 h. The reaction mixture was cooled down and neutralized with a saturated solution of sodium hydrogen carbonate and then filtered. The aqueous layer was extracted twice with ethyl acetate. The organic layers were gathered, dried over magnesium sulfate and concentrated under vacuum, to afford 386 mg of the desired product (90% yield).

LC-MS (method 11): $R_t$=0.42 min; MS (ESIpos): m/z=206 [M+H]$^+$ $^1$H-NMR (400 MHz, DMSO-d$_6$) δ [ppm]: 2.104 (15.64), 2.184 (16.00), 3.317 (0.72), 7.259 (2.36), 7.264 (0.86), 7.281 (4.94), 7.297 (0.99), 7.303 (2.98), 7.433 (0.40), 7.441 (2.98), 7.446 (1.20), 7.453 (3.13), 7.458 (1.66), 7.463 (2.49), 7.471 (0.99), 7.476 (2.25).

Intermediate 64

1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic Acid

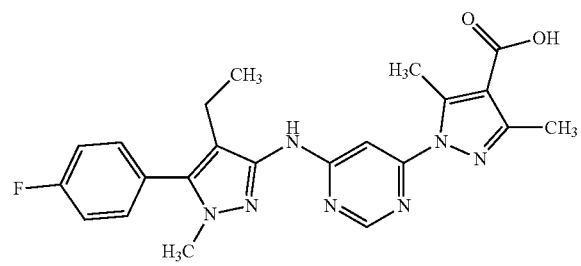 [SMILES: CCc1c(Nc2cc(-n3nc(C)c(C(=O)O)c3C)ncn2)nn(C)c1-c1ccc(F)cc1]

A solution of ethyl 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylate (400 mg, 863 μmol) in THF was treated with aqueous potassium hydroxide solution (2.6 mL, 2.0 M, 5.2 mmol) and aqueous lithium hydroxide solution (4.3 ml, 1.0 M, 4.3 mmol). The mixture was stirred for 4 hours at 90° C. Additional lithium hydroxide solution (4.3 mL, 1.0 M, 4.3 mmol) were added and the mixture was stirred 2 days at 90° C. The mixture was diluted with water and extracted with diethyl ether. The aqueous layer was acidified to pH 3 with hydrochloric acid and extracted with ethyl acetate. The organic layer was washed with brine, dried over sodium sulfate and the solvent was removed under reduced pressure to yield 310 mg (67% yield) of the desired product.

LC-MS (method 10): $R_t$=1.78 min; MS (ESIpos): m/z=436 [M+H]$^+$

Intermediate 65

4-chloro-3-phenyl-1H-pyrazol-5-amine

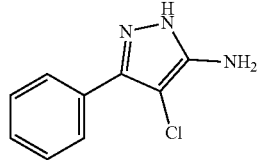 [SMILES: Nc1[nH]nc(-c2ccccc2)c1Cl]

A solution of 3-phenyl-1H-pyrazol-5-amine (4.00 g, 25.1 mmol) in acetonitrile (47 mL) was treated with 1-chloropyrrolidine-2,5-dione (3.36 g, 25.1 mmol) and stirred at room temperature for 30 min. The mixture was diluted with water and extracted with ethyl acetate. The combined organic phases were washed with water, brine, dried over sodium sulfate and the solvent was removed under reduced pressure to yield 5.31 g (quant.) of the desired product which was used without any further purification.

$^1$H-NMR (400 MHz, DMSO-d$_6$) δ [ppm]: 4.63-5.43 (m, 2H), 7.24-7.59 (m, 3H), 7.73 (br s, 2H), 11.72-12.33 (m, 1H).

Intermediate 66

1-(4-fluorophenyl)-3-methyl-4-nitro-1H-pyrazole

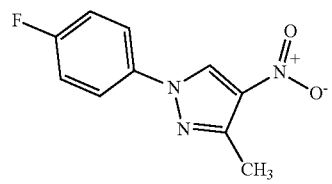

The described product was prepared in a manner analogous to that described in the preparation of 1-(4-fluorophenyl)-3,5-dimethyl-4-nitro-1H-pyrazole starting from 3-methyl-4-nitro-1H-pyrazole (1.00 g, 7.87 mmol) and (4-fluorophenyl)boronic acid (2.20 g, 15.7 mmol) to obtain 1.67 g crude product which was used in the next step without any further purification.

Intermediate 67

1-(4-fluorophenyl)-3-methyl-1H-pyrazol-4-amine

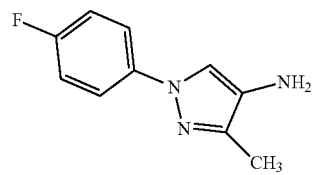

To a solution of 1-(4-fluorophenyl)-3-methyl-4-nitro-1H-pyrazole (1.67 g, 7.55 mmol) in ethanol (50 mL) and ethyl acetate (50 mL) was added palladium on activated carbon (402 mg, 10% purity, 377 μmol) and the suspension was stirred under a hydrogen atmosphere overnight at room temperature. The mixture was filtered over Celite®. The filtrate was evaporated to yield 1.61 g (quant.) of the desired product.

LC-MS (method 12): $R_t$=3.96 min; MS (ESIpos): m/z=192 [M+H]$^+$ $^1$H-NMR (400 MHz, DMSO-d$_6$) δ [ppm]: 1.910 (0.57), 2.116 (16.00), 2.136 (0.61), 2.162 (3.81), 4.038 (0.57), 7.171 (1.37), 7.194 (1.95), 7.216 (3.78), 7.238 (2.01), 7.278 (0.46), 7.300 (0.92), 7.322 (0.52), 7.465 (0.60), 7.477 (0.65), 7.487 (0.50), 7.499 (0.44), 7.590 (5.25), 7.615 (2.42), 7.627 (2.56), 7.638 (2.23), 7.650 (1.99).

Intermediate 68

2-(4-chloro-3-phenyl-1H-pyrazol-5-yl)-1H-isoindole-1,3(2H)-dione

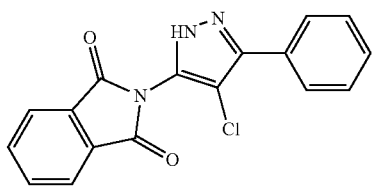 [SMILES: O=C1c2ccccc2C(=O)N1c1[nH]nc(-c2ccccc2)c1Cl]

4-chloro-3-phenyl-1H-pyrazol-5-amine (2.50 g, 12.9 mmol) and 2-benzofuran-1,3-dione (2.87 g, 19.4 mmol) were dissolved in acetic acid (26 mL) and heated under reflux overnight. After rotary evaporation of all volatiles, the crude product (4.18 g, quant.) was used in the next step without further purification.

Intermediate 69

2-(4-chloro-1-methyl-3-phenyl-1H-pyrazol-5-yl)-1H-isoindole-1,3 (2H)-dione

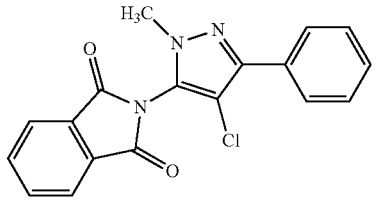 [SMILES: Cn1nc(-c2ccccc2)c(Cl)c1N1C(=O)c2ccccc2C1=O]

2-(4-chloro-3-phenyl-1H-pyrazol-5-yl)-1H-isoindole-1,3 (2H)-dione (4.18 g, 12.9 mmol) and caesium carbonate (60% purity, 14.0 g, 25.8 mmol) were dissolved in dry DMF (32 mL) and treated with iodomethane (1.6 mL, 26 mmol). The reaction mixture was stirred at ambient temperature overnight. It was quenched with water and the mixture stirred for another 15 min. The precipitated solid was collected by filtration, washed with water (3×) and dried to yield the desired product (4.8 g, 1:1 mixture of regioisomers, 70% purity), which was used in the next step without further purification.

Regioisomer1: LC-MS (method 9): Rt=1.03 min; MS (ESIpos): m/z=338 [M+H]$^+$

Regioisomer2: LC-MS (method 9): Rt=1.09 min; MS (ESIpos): m/z=338 [M+H]$^+$

Intermediate 70

4-chloro-1-methyl-3-phenyl-1H-pyrazol-5-amine

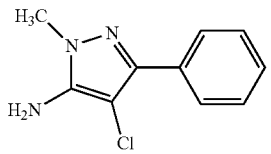

2-(4-chloro-1-methyl-3-phenyl-1H-pyrazol-5-yl)-1H-isoindole-1,3(2H)-dione (4.80 g, 14.2 mmol) was dissolved in ethanol (120 mL) and treated with hydrazine monohydrate (3.5 mL, 71 mmol). The reaction mixture was heated to reflux overnight. After cooling to ambient temperature, the precipitated solid was removed by filtration and washed with ethanol. The combined filtrates were purified by flash column chromatography on silica gel (eluent: dichloromethane/methanol) and preparative HPLC (column: Daicel Chiracel OJ-H 5 μM, 250×20 mm, flow 100 mL/min, 80% carbon dioxide/20% methanol, 40° C., detection at 210 nM) for the separation of the two regioisomers. The desired product was obtained as a white solid (431 mg, 15% yield).

$^1$H-NMR (400 MHz, DMSO-d$_6$) δ [ppm]: 3.309 (16.00), 4.846 (6.68), 7.443 (3.94), 7.464 (6.84), 7.486 (2.33), 7.510 (4.29), 7.529 (4.30), 7.546 (1.30).

Intermediate 71

4-chloro-1-methyl-5-phenyl-1H-pyrazol-3-amine

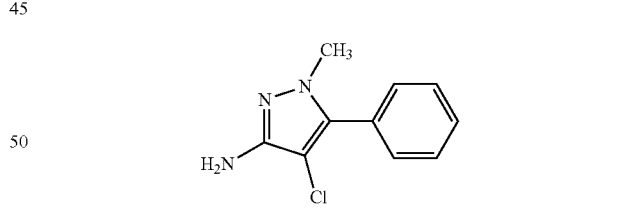

The desired product was obtained from the regioisomer separation described for the synthesis of 4-chloro-1-methyl-3-phenyl-1H-pyrazol-5-amine (576 mg, 20%).

LC-MS (method 10): $R_t$=1.39 min; MS (ESIpos): m/z=208 [M+H]$^+$ $^1$H-NMR (400 MHz, DMSO-d6) δ [ppm]: 0.007 (0.35), 1.038 (0.09), 1.055 (0.20), 1.072 (0.10), 2.327 (0.11), 2.365 (0.08), 2.669 (0.12), 2.709 (0.08), 3.434 (0.09), 3.611 (16.00), 3.783 (0.08), 5.494 (3.59), 7.295 (0.47), 7.314 (1.45), 7.319 (0.47), 7.332 (1.11), 7.382 (1.99), 7.401 (3.20), 7.415 (0.54), 7.420 (1.43), 7.760 (2.67), 7.778 (2.68), 7.781 (1.97).

Intermediate 72

2-[5-(4-fluorophenyl)-4-methyl-1H-pyrazol-3-yl]-1H-isoindole-1,3(2H)-dione

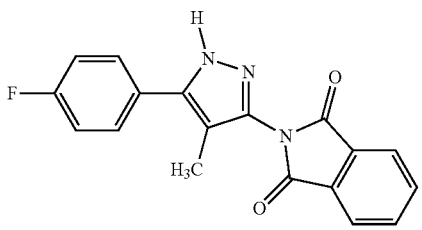 [SMILES: Cc1c(N2C(=O)c3ccccc3C2=O)n[nH]c1-c1ccc(F)cc1]

5-(4-fluorophenyl)-4-methyl-1H-pyrazol-3-amine (1.50 g, 7.84 mmol) and 2-benzofuran-1,3-dione (1.74 g, 11.8 mmol) were suspended in acetic acid (15 mL) and heated under reflux for 1 hour. After cooling to ambient temperature, the solvent was removed under reduced pressure and the residue re-dissolved in methyl t-butyl ether at 50° C. The remaining insoluble solid was collected by filtration and washed further with methyl t-butyl ether. The desired product was obtained, which was used in the next step without further purification (2.2 g, 87% yield).

LC-MS (method 11): Rt=1.22 min; MS (ESIpos): m/z=322 [M+H]$^+$ $^1$H-NMR (400 MHz, DMSO-d$_6$) δ [ppm]: 1.908 (0.50), 1.996 (16.00), 2.327 (0.20), 2.366 (0.15), 2.669 (0.22), 2.709 (0.17), 7.361 (1.84), 7.382 (3.67), 7.404 (2.02), 7.565 (0.21), 7.573 (0.23), 7.579 (0.23), 7.587 (0.30), 7.666 (2.60), 7.680 (3.21), 7.687 (3.04), 7.701 (2.42), 7.940 (3.30), 7.948 (3.94), 7.954 (4.10), 7.962 (6.07), 7.972 (1.27), 7.993 (1.11), 8.003 (5.18), 8.011 (3.63), 8.017 (3.44), 8.025 (2.75), 13.370 (2.34).

Intermediate 73

2-[3-(4-fluorophenyl)-1,4-dimethyl-1H-pyrazol-5-yl]-1H-isoindole-1,3(2H)-dione

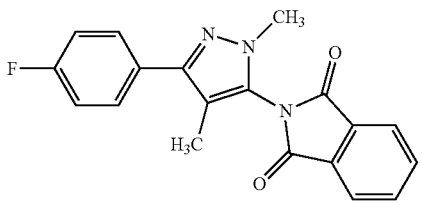 [SMILES: Cc1c(-c2ccc(F)cc2)nn(C)c1N1C(=O)c2ccccc2C1=O]

2-[5-(4-fluorophenyl)-4-methyl-1H-pyrazol-3-yl]-1H-isoindole-1,3(2H)-dione (2.20 g, 6.85 mmol) and potassium carbonate were suspended in DMF (10 mL). Methyl iodide (0.85 mL, 14 mmol) was added and the resulting reaction mixture was stirred at ambient temperature overnight. The reaction was quenched by addition of water and extracted with ethyl acetate (3×). The combined organic phases were dried over sodium sulfate and concentrated. The two produced regioisomers were separated by flash column chromatography on silica gel (eluent: ethyl acetate/cyclohexane 0:100 to 50:50 gradient). The desired product was isolated as a white solid (965 mg, 42% yield) separated from its regioisomer.

$^1$H-NMR (400 MHz, DMSO-d$_6$) δ [ppm]: 1.156 (0.32), 1.174 (0.67), 1.191 (0.33), 1.396 (1.96), 1.987 (1.30), 2.017 (15.46), 3.735 (16.00), 4.019 (0.31), 4.037 (0.29), 7.265 (1.96), 7.287 (4.06), 7.309 (2.15), 7.705 (2.15), 7.711 (0.89), 7.719 (2.38), 7.727 (2.19), 7.736 (0.84), 7.742 (1.96), 7.963 (2.25), 7.971 (2.46), 7.977 (2.43), 7.985 (3.72), 7.995 (0.56), 8.030 (0.54), 8.040 (3.89), 8.047 (2.54), 8.053 (2.57), 8.061 (2.24).

Intermediate 74

2-[5-(4-fluorophenyl)-1,4-dimethyl-1H-pyrazol-3-yl]-1H-isoindole-1,3(2H)-dione

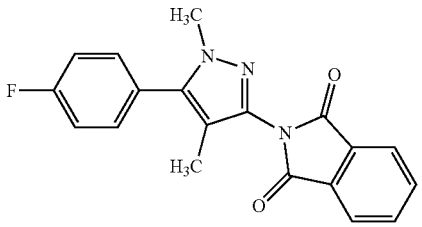 [SMILES: Cc1c(N2C(=O)c3ccccc3C2=O)nn(C)c1-c1ccc(F)cc1]

The desired product was obtained from the regioisomer separation described for 2-[3-(4-fluorophenyl)-1,4-dimethyl-1H-pyrazol-5-yl]-1H-isoindole-1,3 (2H)-dione (904 mg, 39% yield).

$^1$H-NMR (400 MHz, DMSO-d$_6$) δ [ppm]: 1.156 (0.26), 1.173 (0.53), 1.191 (0.27), 1.656 (0.08), 1.817 (15.98), 1.976 (0.10), 1.987 (0.98), 2.017 (0.09), 2.327 (0.08), 2.365 (0.06), 2.669 (0.09), 2.709 (0.06), 3.595 (0.08), 3.735 (0.11), 3.773 (16.00), 3.947 (0.08), 4.001 (0.08), 4.019 (0.24), 4.037 (0.23), 4.054 (0.08), 7.377 (1.84), 7.399 (3.98), 7.421 (2.25), 7.574 (2.33), 7.579 (1.03), 7.587 (2.64), 7.595 (2.15), 7.609 (1.84), 7.934 (2.16), 7.942 (2.49), 7.948 (2.57), 7.955 (3.92), 7.966 (0.73), 7.987 (0.69), 7.998 (3.84), 8.006 (2.45), 8.012 (2.32), 8.020 (1.95).

Intermediate 75

3-(4-fluorophenyl)-1,4-dimethyl-1H-pyrazol-5-amine

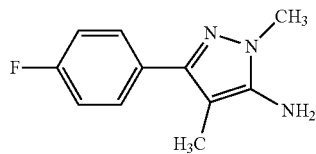

2-[3-(4-fluorophenyl)-1,4-dimethyl-1H-pyrazol-5-yl]-1H-isoindole-1,3(2H)-dione (965 mg, 2.88 mmol) was dissolved in ethanol (24 mL) and hydrazine monohydrate (0.70 mL, 14 mmol) was added at ambient temperature. The reaction mixture was heated under reflux for 2 hours. After cooling to room-temperature, the precipitated white solid was removed by filtration and washed with ethanol. The combined filtrate was concentrated and the residue purified by flash column chromatography on silica gel (eluent: dichlormethane/methanol 92:8) to yield 515 mg of the desired product (85% yield).

LC-MS (method 11): Rt=0.79 min; MS (ESIpos): m/z=206 [M+H]$^+$

¹H-NMR (400 MHz, DMSO-d₆) δ [ppm]: −0.009 (0.15), 0.007 (0.15), 1.234 (0.05), 1.753 (0.07), 1.810 (0.08), 1.970 (15.83), 2.125 (0.08), 2.327 (0.06), 2.366 (0.05), 2.669 (0.07), 2.709 (0.05), 3.377 (0.09), 3.439 (0.07), 3.552 (16.00), 3.724 (0.08), 4.948 (3.84), 7.151 (0.19), 7.158 (1.78), 7.163 (0.60), 7.175 (0.76), 7.181 (3.78), 7.186 (0.75), 7.198 (0.65), 7.203 (2.07), 7.211 (0.24), 7.557 (0.22), 7.564 (2.01), 7.570 (0.80), 7.578 (2.19), 7.586 (2.07), 7.595 (0.76), 7.600 (1.85), 7.608 (0.21).

Intermediate 76

5-(4-fluorophenyl)-1,4-dimethyl-1H-pyrazol-3-amine

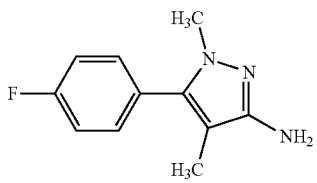

2-[5-(4-fluorophenyl)-1,4-dimethyl-1H-pyrazol-3-yl]-1H-isoindole-1,3(2H)-dione (904 mg, 2.70 mmol) was dissolved in ethanol (22.6 mL) and hydrazine monohydrate (0.65 mL, 13.5 mmol) was added at ambient temperature. The reaction mixture was heated under reflux for 2 hours. After cooling to room-temperature, the precipitated white solid was removed by filtration and washed with ethanol. The combined filtrate was concentrated and the residue purified by flash column chromatography on silica gel (eluent: dichlormethane/methanol 92:8) to yield 451 mg of the desired product as a white solid (82% yield).

LC-MS (method 11): Rt=0.88 min; MS (ESIpos): m/z=206 [M+H]⁺

¹H-NMR (400 MHz, DMSO-d₆) δ [ppm]: 1.753 (15.74), 2.669 (0.14), 3.439 (16.00), 4.442 (3.93), 7.293 (1.45), 7.298 (0.57), 7.309 (0.86), 7.315 (3.99), 7.321 (0.83), 7.332 (0.74), 7.337 (2.71), 7.372 (2.60), 7.378 (0.97), 7.386 (2.85), 7.394 (1.76), 7.402 (0.65), 7.408 (1.41).

Intermediate 77 ethyl 1-(6-chloropyrimidin-4-yl)-5-methyl-1H-pyrazole-3-carboxylate

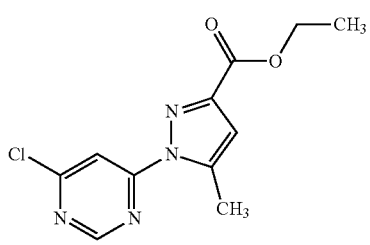 [SMILES: CCOC(=O)c1cc(C)n(-c2cc(Cl)ncn2)n1]

A solution of 4-chloro-6-hydrazinylpyrimidine (2.00 g, 13.8 mmol) and ethyl 2,4-dioxopentanoate (2.19 g, 13.8 mmol) in ethanol (40 ml) was refluxed overnight. After cooling to room temperature a precipitate was formed which was filtered and dried to afford 2.25 g (61% yield) of the desired product. The filtrate was processed further to yield the regioisomeric product.

LC-MS (method 11): Rt=1.33 min; MS (ESIpos): m/z=267 [M+H]⁺

¹H-NMR (600 MHz, DMSO-d₆): δ [ppm]: 1.32 (t, 4H), 4.34 (q, 3H), 6.88 (d, 1H), 8.02 (d, 1H), 9.05 (d, 1H).

Intermediate 78 ethyl 1-(6-chloropyrimidin-4-yl)-3-methyl-1H-pyrazole-5-carboxylate

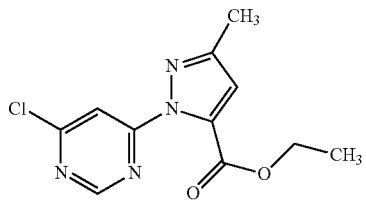 [SMILES: CCOC(=O)c1cc(C)nn1-c1cc(Cl)ncn1]

The filtrate out of the synthesis of ethyl 1-(6-chloropyrimidin-4-yl)-5-methyl-1H-pyrazole-3-carboxylate was concentrated and purified by reparative HPLC (method: column: Reprosil C18; 10 µm; 125×30 mm/flow: 45 ml/min/ eluent: A=water (0.1% formic acid), B=acetonitrile/gradient: 0.00-4.25 min=10% B, 4.50 min=20% B, 15.50 min=85% B, 16.00-18.50 min=100% B, 18.75-22.00 min=20% B) to afford the desired product (544 mg, 15% yield).

LC-MS (method 11): R_t=1.28 min; MS (ESIpos): m/z=267 [M+H]⁺

¹H-NMR (400 MHz, DMSO-d₆) δ [ppm]: 1.214 (4.65), 1.232 (9.58), 1.250 (4.68), 1.304 (0.72), 1.322 (1.49), 1.340 (0.82), 2.289 (0.52), 2.316 (16.00), 2.722 (2.13), 4.280 (1.61), 4.298 (4.62), 4.315 (4.72), 4.333 (2.02), 4.349 (0.72), 6.883 (0.57), 6.914 (4.78), 7.985 (3.83), 8.026 (0.61), 8.933 (3.80), 9.047 (0.60).

Intermediate 79

2-[4-chloro-3-(4-fluorophenyl)-1H-pyrazol-5-yl]-1H-isoindole-1,3 (2H)-dione

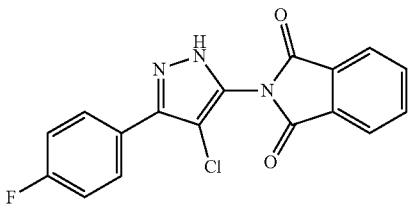 [SMILES: O=C1c2ccccc2C(=O)N1c1[nH]nc(-c2ccc(F)cc2)c1Cl]

The described product was prepared in a manner analogous to that described in the preparation of 2-[4-ethyl-3-(4-fluorophenyl)-1H-pyrazol-5-yl]-1H-isoindole-1,3(2H)-dione starting from 4-chloro-3-(4-fluorophenyl)-1H-pyrazol-5-amine (1.14 g, 5.39 mmol) and 2-benzofuran-1,3-dione (1.20 g, 8.08 mmol) to yield 2.0 g of the desired product [quant.].

LC-MS (method 10): R_t=1.86 min; MS (ESIpos): m/z=342 [M+H]⁺

¹H-NMR (400 MHz, DMSO-d₆) δ [ppm]: −0.149 (0.52), −0.008 (4.13), 0.008 (3.94), 0.146 (0.50), 1.910 (0.92), 2.074 (1.32), 2.329 (0.50), 2.368 (0.52), 2.525 (1.57), 2.667

(0.40), 2.672 (0.54), 2.712 (0.52), 7.427 (6.99), 7.449 (14.26), 7.471 (7.64), 7.571 (1.75), 7.579 (1.92), 7.585 (1.83), 7.593 (2.62), 7.603 (0.41), 7.670 (1.29), 7.678 (1.19), 7.683 (1.19), 7.691 (0.92), 7.848 (8.15), 7.862 (9.33), 7.870 (8.83), 7.883 (7.57), 7.978 (8.99), 7.986 (10.59), 7.992 (11.17), 8.000 (16.00), 8.010 (3.32), 8.021 (1.02), 8.038 (2.68), 8.048 (13.92), 8.056 (10.03), 8.062 (9.64), 8.070 (8.09), 8.081 (1.45), 8.095 (0.54), 8.103 (0.48), 14.071 (8.74).

Intermediate 80

2-[4-chloro-5-(4-fluorophenyl)-1-methyl-1H-pyrazol-3-yl]-1H-isoindole-1,3 (2H)-dione

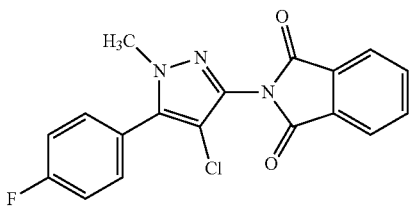 [SMILES: Cn1nc(N2C(=O)c3ccccc3C2=O)c(Cl)c1-c1ccc(F)cc1]

The described product was prepared in a manner analogous to that described in the preparation of 2-[4-ethyl-3-(4-fluorophenyl)-1-methyl-1H-pyrazol-5-yl]-1H-isoindole-1,3 (2H)-dione starting from 2-[4-chloro-3-(4-fluorophenyl)-1H-pyrazol-5-yl]-1H-isoindole-1,3(2H)-dione (2.20 g, 6.44 mmol) and iodomethane (800 µl, 13 mmol) to yield 601 mg of the desired product (23% yield) after separation of the regioisomers (Instrument: THAR SFC-Super Chrom Prep 200, column: Chirapak AD-H (SFC) 5 µm, 250×30 mm, eluent: carbon dioxide/methanol 76:24, pressure: 135 bar, temperature eluent: 38° C., temperature Zyklon: 40° C., pressure Zyklon 24 bar, flow: 108 g/min, UV 210 nm).

LC-MS (method 10): $R_t$=1.99 min; MS (ESIpos): m/z=356 [M+H]$^+$ $^1$H-NMR (400 MHz, DMSO-d$_6$) δ [ppm]: 3.764 (0.61), 3.784 (1.31), 3.873 (16.00), 7.434 (2.11), 7.456 (4.30), 7.478 (2.35), 7.688 (2.38), 7.693 (1.22), 7.701 (2.60), 7.710 (2.33), 7.718 (0.97), 7.723 (1.99), 7.973 (2.24), 7.981 (2.53), 7.987 (2.62), 7.995 (3.88), 8.005 (0.67), 8.035 (0.65), 8.045 (3.91), 8.053 (2.60), 8.059 (2.63), 8.066 (2.23).

Intermediate 81

2-[4-chloro-3-(4-fluorophenyl)-1-methyl-1H-pyrazol-5-yl]-1H-isoindole-1,3 (2H)-dione

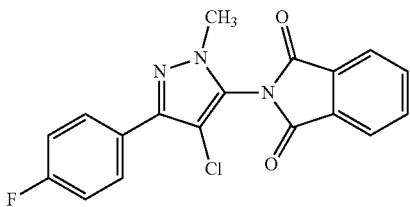 [SMILES: Cn1nc(-c2ccc(F)cc2)c(Cl)c1N1C(=O)c2ccccc2C1=O]

The desired product was obtained out of the separation of the regiosiomers in the preparation of 2-[4-chloro-5-(4-fluorophenyl)-1-methyl-1H-pyrazol-3-yl]-1H-isoindole-1,3 (2H)-dione (789 mg, 34%).

LC-MS (method 10): Rt=2.14 min; MS (ESIpos): m/z=357 [M+H]$^+$ $^1$H-NMR (500 MHz, DMSO-d$_6$): δ [ppm]: 3.87 (s, 3H), 7.28-7.40 (m, 2H), 7.86-7.93 (m, 2H), 7.98-8.04 (m, 2H), 8.07-8.14 (m, 2H).

Intermediate 82

4-chloro-5-(4-fluorophenyl)-1-methyl-1H-pyrazol-3-amine

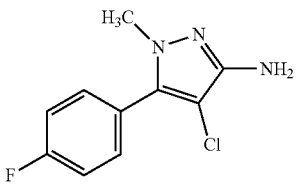

The described product was prepared in a manner analogous to that described in the preparation of 4-ethyl-5-(4-fluorophenyl)-1-methyl-1H-pyrazol-3-amine starting from 2-[4-chloro-5-(4-fluorophenyl)-1-methyl-1H-pyrazol-3-yl]-1H-isoindole-1,3(2H)-dione (600 mg, 1.69 mmol) and hydrazine hydrate (1:1) (410 µl, 8.4 mmol) to yield 370 mg of the desired product (97% yield) after cyrstallisation from acetonitrile.

$^1$H-NMR (400 MHz, DMSO-d$_6$): δ [ppm]: 3.52 (s, 3H), 4.86 (s, 2H), 7.32-7.42 (m, 2H), 7.48-7.56 (m, 2H).

Intermediate 83

4-chloro-3-(4-fluorophenyl)-1-methyl-1H-pyrazol-5-amine

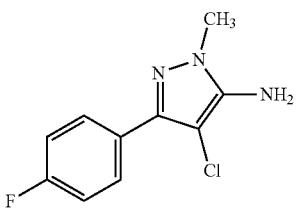

The described product was prepared in a manner analogous to that described in the preparation of 4-ethyl-5-(4-fluorophenyl)-1-methyl-1H-pyrazol-3-amine starting from 2-[4-chloro-3-(4-fluorophenyl)-1-methyl-1H-pyrazol-5-yl]-1H-isoindole-1,3(2H)-dione (790 mg, 2.22 mmol) to yield 490 mg of the desired product (96% yield) after cyrstallisation from acetonitrile.

$^1$H-NMR (400 MHz, DMSO-d6): δ [ppm]: 3.60 (s, 3H), 5.52 (s, 2H), 7.17-7.32 (m, 2H), 7.72-7.91 (m, 2H).

Intermediate 84 ethyl 1-(6-{[4-ethyl-5-(4-fluorophenyl)-1-methyl-1H-pyrazol-3-yl]amino}pyrimidin-4-yl)-3-methyl-1H-pyrazole-5-carboxylate

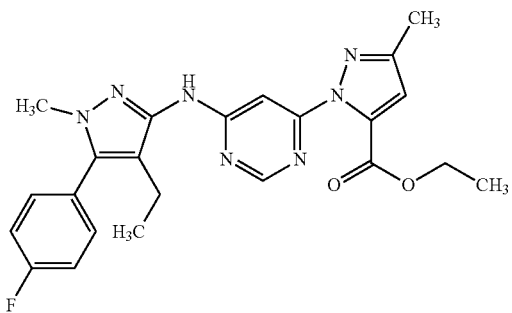 [SMILES: CCOC(=O)c1cc(C)nn1-c1cc(Nc2nn(C)c(-c3ccc(F)cc3)c2CC)ncn1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-ethyl-5-(4-fluorophenyl)-1-methyl-1H-pyrazol-3-amine (100 mg, 456 µmol) and ethyl 1-(6-chloropyrimidin-4-yl)-3-methyl-1H-pyrazole-5-carboxylate (122 mg, 456 µmol) to yield the desired product 106 mg (52% yield).

LC-MS (method 11): Rt=1.43 min; MS (ESIpos): m/z=450 [M+H]$^+$ $^1$H-NMR (400 MHz, DMSO-d6) δ [ppm]: −0.008 (0.67), 0.008 (0.46), 0.877 (3.86), 0.896 (8.85), 0.914 (3.98), 1.074 (0.65), 1.091 (1.28), 1.109 (0.65), 1.196 (5.36), 1.214 (11.31), 1.231 (5.47), 2.272 (16.00), 2.299 (0.98), 2.318 (2.72), 2.336 (2.64), 2.355 (0.85), 3.314 (7.67), 3.375 (0.66), 3.392 (0.63), 4.239 (1.72), 4.257 (5.40), 4.275 (5.33), 4.293 (1.66), 6.750 (5.30), 7.256 (1.59), 7.358 (2.08), 7.363 (0.78), 7.380 (4.69), 7.402 (2.78), 7.506 (2.79), 7.511 (1.21), 7.519 (3.13), 7.527 (2.45), 7.536 (1.02), 7.541 (2.07), 8.413 (3.12), 9.581 (1.76).

Intermediate 85

Sodium (2E)-3-cyano-4-oxopent-2-en-2-olate

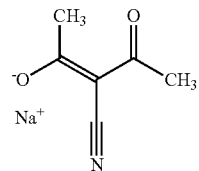

1-(5-methyl-1,2-oxazol-4-yl)ethanone (1000 mg, 7.99 mmol, CAS 6497-21-8) was dissolved in ethanol and the mixture was added to an ethanolic solution of sodium hydroxide (320 mg, 7.99 mmol) which was cooled in dry ice. The white powder that precipitates was filtered and washed with ethanol. The crude product was used as such in the next step 995 mg (84% yield).

Intermediate 86

3,5-dimethyl-1H-pyrazole-4-carbonitrile

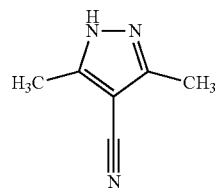

A mixture of sodium (2E)-3-cyano-4-oxopent-2-en-2-olate (995 mg, 6.78 mmol) and hydrazine hydrate (1:1) (390 µl, 8.0 mmol) in water (10 mL) was refluxed overnight. After cooling to room temperature the reaction mixture was concentrated under vacuum to afford 1.03 g (quant.) of the desired product which was used as such in the next step.

LC-MS (method 11): R$_t$=0.58 min; MS (ESIpos): m/z=122 [M+H]$^+$ $^1$H-NMR (400 MHz, DMSO-d$_6$) δ [ppm]: 1.609 (0.43), 2.041 (0.70), 2.084 (16.00), 2.242 (3.61), 3.473 (0.45).

Intermediate 87

1-(6-chloropyrimidin-4-yl)-3,5-dimethyl-1H-pyrazole-4-carbonitrile

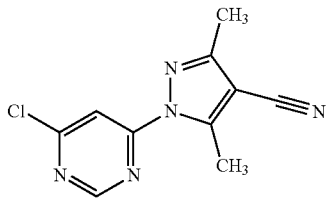 [SMILES: Cc1nn(-c2cc(Cl)ncn2)c(C)c1C#N]

4,6-dichloropyrimidine (1.27 g, 8.50 mmol), 3,5-dimethyl-1H-pyrazole-4-carbonitrile (1.03 g, 8.50 mmol) and caesium carbonate were dissolved in DMF. The reaction mixture was stirred at room temperature overnight. Water was added and the resulting mixture was stirred at room temperature for 30 min. The precipitate was filtered, washed with water and dried under reduced pressure to afford the desired product 1.06 g (53% yield), which was used as such in the next step.

LC-MS (method 11): R$_t$=1.28 min; MS (ESIpos): m/z=234 [M+H]$^+$ $^1$H-NMR (400 MHz, DMSO-d$_6$) δ [ppm]: 2.339 (0.76), 2.378 (15.68), 2.403 (1.58), 2.732 (0.44), 2.781 (0.70), 2.826 (16.00), 2.868 (1.38), 2.891 (0.55), 5.754 (0.68), 8.014 (2.62), 9.038 (2.54).

Intermediate 88

2-[1-(2-{[tert-butyl(dimethyl)silyl]oxy}ethyl)-4-ethyl-3-(4-fluorophenyl)-1H-pyrazol-5-yl]-1H-isoindole-1,3(2H)-dione

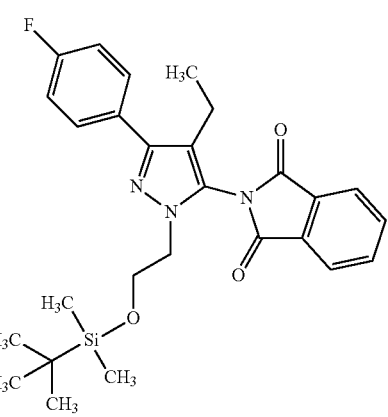

A solution of 2-[4-ethyl-3-(4-fluorophenyl)-1H-pyrazol-5-yl]-1H-isoindole-1,3(2H)-dione (1.27 g, 3.80 mmol) and (2-bromoethoxy)(tert-butyl)dimethylsilane (1.6 ml, 7.6 mmol) in DMF (7.0 ml) was treated with potassium carbonate (1.05 g, 7.60 mmol) and stirred at room temperature of 4 days. The mixture was diluted with water and ethyl acetate. The aqueous layer was extracted twice with ethyl acetate. The organic phases were gathered, dried over sodium sulfate and concentrated under vacuum. The crude product was purified by column chromatography on silica gel using cyclohexane/ethyl acetate to afford two region isomers.

The desired product was obtained in 31% yield (575 mg).

LC-MS (method 11): R$_t$=1.80 min; MS (ESIpos): m/z=494 [M+H]$^+$ $^1$H-NMR (400 MHz, DMSO-d6) δ [ppm]: −0.221 (0.06), −0.071 (11.32), −0.042 (0.17), −0.006 (1.77), 0.041 (0.14), 0.076 (0.05), 0.617 (0.08), 0.774 (16.00), 0.790 (2.87), 0.809 (1.41), 0.848 (0.21), 0.929 (0.08), 1.049 (0.03), 1.151 (0.07), 1.168 (0.14), 1.186 (0.07), 1.982 (0.25), 2.187 (0.38), 2.206 (1.07), 2.225 (1.03), 2.244 (0.32), 2.322 (0.03), 2.362 (0.03), 2.665 (0.03), 3.896 (0.61), 3.909 (1.30), 3.922 (0.74), 4.014 (0.09), 4.045 (0.81), 4.058 (1.25), 4.071 (0.53), 7.365 (0.61), 7.387 (1.29), 7.409 (0.72), 7.566 (0.83), 7.580 (0.95), 7.588 (0.79), 7.602 (0.63), 7.937 (0.80), 7.945 (0.91), 7.951 (0.94), 7.959 (1.26), 7.969 (0.25), 7.997 (0.29), 8.007 (1.31), 8.015 (0.90), 8.020 (0.82), 8.028 (0.68).

Intermediate 89

1-(2-{[tert-butyl(dimethyl)silyl]oxy}ethyl)-4-ethyl-5-(4-fluorophenyl)-1H-pyrazol-3-amine

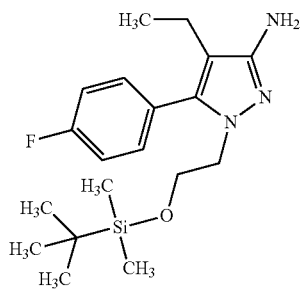 [SMILES: CCc1c(N)nn(CCO[Si](C)(C)C(C)(C)C)c1-c1ccc(F)cc1]

2-[1-(2-{[tert-butyl(dimethyl)silyl]oxy}ethyl)-4-ethyl-5-(4-fluorophenyl)-1H-pyrazol-3-yl]-1H-isoindole-1,3(2H)-dione (875 mg, 1.77 mmol) was dissolved in ethanol and treated with hydrazine hydrate (1:1) (430 µl, 8.9 mmol). The reaction mixture was stirred at 90° C. for 2 hours. The reaction mixture was cooled and filtered. The filtrate was concentrated under vacuum and was used as such in the next step.

LC-MS (method 11): R$_t$=1.58 min; MS (ESIpos): m/z=364 [M+H]$^+$ $^1$H-NMR (400 MHz, DMSO-d$_6$) δ [ppm]: −0.096 (0.56), −0.089 (12.22), −0.081 (0.57), 0.774 (16.00), 0.889 (0.98), 0.907 (2.34), 0.926 (1.05), 2.169 (0.91), 2.188 (0.88), 3.724 (0.93), 3.736 (0.74), 3.771 (0.76), 3.783 (0.97), 4.480 (0.88), 7.280 (0.50), 7.302 (1.24), 7.325 (0.77), 7.386 (0.79), 7.400 (0.88), 7.408 (0.63), 7.422 (0.52).

Intermediate 90

N-[1-(2-{[tert-butyl(dimethyl)silyl]oxy}ethyl)-4-ethyl-5-(4-fluorophenyl)-1H-pyrazol-3-yl]-6-(3,5-dimethyl-1H-pyrazol-1-yl)pyrimidin-4-amine

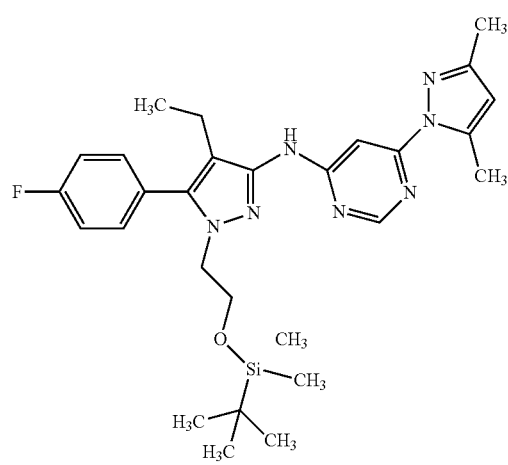

A flame-dried three-necked round-bottom flask equipped with a reflux condenser was charged with 1,4-dimethyl-1H-pyrazol-3-amine (347 mg, 1.5 mmol), 1-(2-{[tert-butyl(dimethyl)silyl]oxy}ethyl)-4-ethyl-5-(4-fluorophenyl)-1H- pyrazol-3-amine (551 mg, 1.5 mmol) and sodium phenoxide (264 mg, 2.3 mmol). The solids were suspended in dry 1,4-dioxane (10 mL) and the mixture was degassed by bubbling Argon through the solution for 3 min. Tris(dibenzylidenacetone)dipalladium (27 mg, 30 µmol) and XantPhos (43 mg, 78 µmol) were added and the mixture again degassed for 1 min. The reaction mixture was heated at 85° C. for 16 hours. After cooling to ambient temperature, the mixture was purified by preparative HPLC (method: column: Reprosil C18; 10 µm; 125×30 mm/flow: 45 ml/min/ eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to afford the desired product (250 mg, 31% yield).

LC-MS (method 10): $R_t$=2.99 min; MS (ESIpos): m/z=536 [M+H]$^+$

Intermediate 91

N-(1,4-dimethyl-1H-pyrazol-3-yl)-6-(3,5-dimethyl-1H-pyrazol-1-yl)pyrimidin-4-amine trifluoroacetate

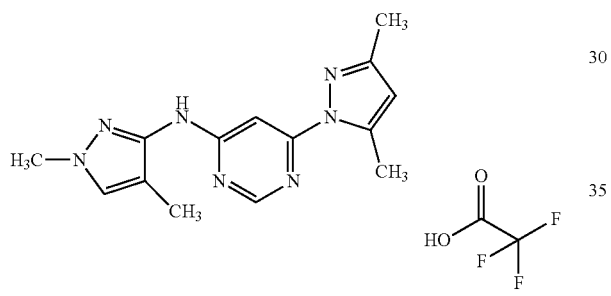

A flame-dried three-necked round-bottom flask equipped with a reflux condenser was charged with 1,4-dimethyl-1H-pyrazol-3-amine (1.00 g, 9.00 mmol), 4-chloro-6-(3,5-dimethyl-1H-pyrazol-1-yl)pyrimidine (2.06 g, 9.90 mmol) and sodium phenoxide (1.57 g, 13.5 mmol). The solids were suspended in dry 1,4-dioxane (18 mL) and the mixture was degassed by bubbling Argon through the solution for 3 min. Tris(dibenzylideneacetone)dipalladium (124 mg, 135 µmol) and XantPhos (156 mg, 270 µmol) were added and the mixture again degassed for 1 min. The reaction mixture was heated at 80° C. for 16 hours. After cooling to ambient temperature, the mixture was diluted with ethyl acetate and filtered through Celite. The combined washings were concentrated and the residue purified by preparative HPLC (column: Chromatorex C18; 250*40 mm, 10 µM, flow 100 mL/min, gradient acetonitrile/water (containing 0.1% trifluoroacetic acid) 90/10 to 5/95) to yield the desired product as its trifluoroacetate salt (1.05 g, 29% yield).

LC-MS (method 11): $R_t$=1.07 min; MS (ESIpos): m/z=284 [M+H]$^+$ $^1$H-NMR (400 MHz, DMSO-d6) δ [ppm]: −0.008 (1.26), 0.008 (0.69), 1.878 (12.45), 2.073 (0.47), 2.169 (14.25), 2.519 (0.73), 2.524 (0.65), 2.609 (12.08), 3.688 (0.42), 3.751 (16.00), 6.117 (3.23), 7.171 (3.60), 7.484 (3.07), 8.415 (3.31), 9.254 (2.53).

Intermediate 92

2-methyl-3-oxo-3-[4-(trifluoromethoxy)phenyl]propanenitrile

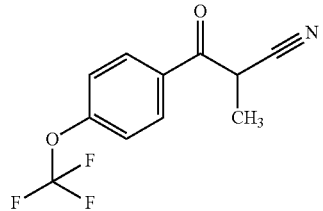 [SMILES: CC(C#N)C(=O)c1ccc(OC(F)(F)F)cc1]

Methyl 4-(trifluoromethoxy)benzoate (5.00 g, 22.7 mmol) and propanenitrile (2.4 mL, 34 mmol) were dissolved in THF and cooled with a water bath to 20° C. Lithium 1,1,1,3,3,3-hexamethyldisilazan-2-ide (1.0 M, 35 mL, 35 mmol) was added slowly and the reaction mixture stirred at ambient temperature for 2 h. The reaction mixture was quenched by the addition of water and extracted with ethyl acetate (3×). The combined organic extracts were dried over magnesium sulfate and concentrated. The residue obtained was used in the next step without further purification (4.00 g, 55% yield, 76% purity).

Intermediate 93

4-methyl-3-[4-(trifluoromethoxy)phenyl]-1H-pyrazol-5-amine

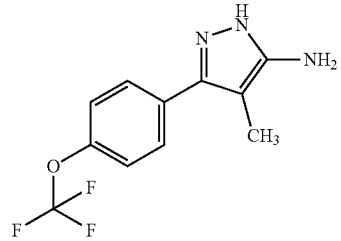 [SMILES: Cc1c(-c2ccc(OC(F)(F)F)cc2)n[nH]c1N]

2-methyl-3-oxo-3-[4-(trifluoromethoxy)phenyl]propanenitrile (4.00 g, 16.4 mmol, 76% purity) was dissolved in ethanol and hydrazine monohydrate (1.6 mL, 33 mmol) was added dropwise via a syringe. The reaction mixture was heated under reflux overnight. All volatiles were removed under reduced pressure and the residue purified by preparative HPLC (column: Chromatorex C18; 250*40 mm, 10 µM, flow 100 mL/min, gradient acetonitrile/water (containing 0.1% trifluoroacetic acid) 90/10 to 5/95) to yield the desired product as a yellow solid (3.0 g, 80% purity, 56% yield).

$^1$H-NMR (400 MHz, DMSO-d$_6$) δ [ppm]: −0.015 (0.51), 1.278 (0.11), 1.297 (0.24), 1.316 (0.12), 1.885 (0.08), 2.047 (16.00), 2.205 (0.08), 2.322 (0.09), 2.361 (0.09), 2.664 (0.10), 2.705 (0.09), 2.798 (0.11), 2.817 (0.11), 7.508 (2.65), 7.530 (3.25), 7.693 (0.66), 7.700 (5.14), 7.705 (1.55), 7.717 (1.49), 7.722 (4.07), 7.729 (0.46), 7.970 (0.37), 7.977 (2.89), 7.982 (0.90), 7.994 (0.92), 7.999 (2.59), 8.141 (0.13), 8.163 (0.13), 11.057 (0.09).

Intermediate 94

2-{4-methyl-3-[4-(trifluoromethoxy)phenyl]-1H-pyrazol-5-yl}-1H-isoindole-1,3(2H)-dione

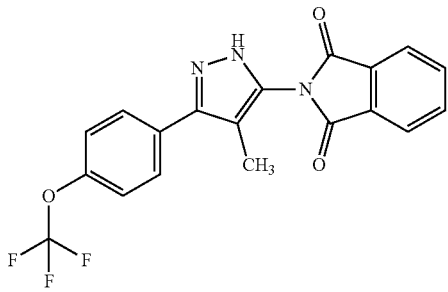 [SMILES: Cc1c(-c2ccc(OC(F)(F)F)cc2)n[nH]c1N1C(=O)c2ccccc2C1=O]

4-methyl-3-[4-(trifluoromethoxy)phenyl]-1H-pyrazol-5-amine (2.00 g, 7.78 mmol) and 2-benzofuran-1,3-dione (1.73 g, 11.7 mmol) were suspended in acetic acid (15 mL) and heated under reflux. After 30 min of heating, all solids were completely dissolved. The reaction mixture was stirred under reflux overnight until full conversion of starting material. After cooling to ambient temperature, the mixture was concentrated under reduced pressure and co-evaporated with methanol (3×). The residue thus obtained was used in the next step without further purification. (3.0 g, 99% yield)

LC-MS (method 10): Rt=2.00 min; MS (ESIpos): m/z=388 [M+H]$^+$

Intermediate 95

2-{1,4-dimethyl-5-[4-(trifluoromethoxy)phenyl]-1H-pyrazol-3-yl}-1H-isoindole-1,3 (2H)-dione

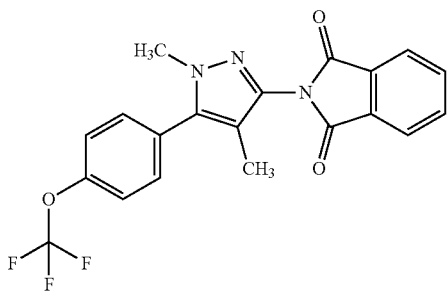 [SMILES: Cc1c(N2C(=O)c3ccccc3C2=O)nn(C)c1-c1ccc(OC(F)(F)F)cc1]

2-{4-methyl-3-[4-(trifluoromethoxy)phenyl]-1H-pyrazol-5-yl}-1H-isoindole-1,3(2H)-dione (3.00 g, 7.75 mmol) and potassium carbonate (2.14 g, 15.5 mmol) were suspended in DMF (11 mL), when iodomethane (960 μL, 15 mmol) was added dropwise. The reaction mixture was stirred at ambient temperature overnight. It was quenched by addition of water and extracted with ethyl acetate (3×). The combined organic extracts were dried over sodium sulfate and concentrated. The residue was purified by flash column chromatography on silica gel (cyclohexane/etyhl acetate gradient) to yield the desired product together with its regioisomer as a mixture (~1:1) as a yellow solid (2.0 g, 64%).

LC-MS (method 10): Rt=2.15 min; MS (ESIpos): m/z=402 [M+H]$^+$

Intermediate 96

1,4-dimethyl-5-[4-(trifluoromethoxy)phenyl]-1H-pyrazol-3-amine

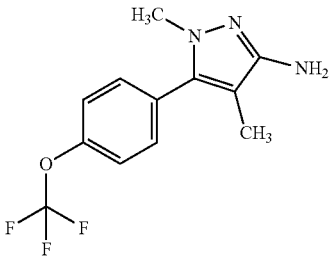 [SMILES: Cc1c(N)nn(C)c1-c1ccc(OC(F)(F)F)cc1]

The mixture of 2-{1,4-dimethyl-5-[4-(trifluoromethoxy)phenyl]-1H-pyrazol-3-yl}-1H-isoindole-1,3(2H)-dione and its regioisomer (2.00 g, 4.98 mmol) was dissolved in ethanol (43 mL) and hydrazine monohydrate was added (1.2 mL, 25 mmol). The reaction mixture was heated under reflux overnight. After cooling to ambient temperature, all volatiles were removed under reduced pressure and the residue was purified by preparative HPLC (column: Daicel Chiralpak IF 250×20 mm, 5 m, Flow: 15 mL/min, T=35° C., eluent: n-heptane/ethanol 75:25) to yield the desired product (329 mg, 24% yield) as a single isomer along with its regioisomer (see Intermediate 106).

LC-MS (method 10): Rt=1.57 min; MS (ESIpos): m/z=272 [M+H]$^+$ $^1$H-NMR (400 MHz, DMSO-d$_6$) δ [ppm]:) 1.77 (s, 3H), 2.86 (s, 3H), 4.48 (s, 2H), 7.46-7.52 (m, 4H).

Intermediate 97

1-(cyclopropylmethyl)-4-ethyl-3-(4-fluorophenyl)-1H-pyrazol-5-amine

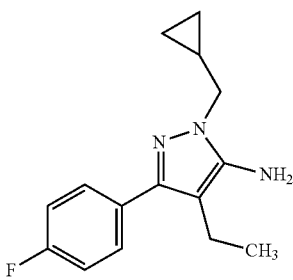 [SMILES: CCc1c(-c2ccc(F)cc2)nn(CC2CC2)c1N]

2-(4-fluorobenzoyl)butanenitrile (300 mg, 1.57 mmol) was dissolved in 2-propanol (10 ml). Then, (cyclopropylmethyl)hydrazine dihydrochloride (299 mg, 1.88 mmol) was added and the reaction mixture was stirred at reflux overnight. After cooling to room temperature a 1 M solution of sodium hydrogencarbonate was added and the reaction mixture was concentrated in vacuum. The crude product was purified by preparative HPLC (method: column: Reprosil C18; 10 μm; 125×30 mm/flow: 45 ml/min/eluent: A=water (0.1% formic acid), B=acetonitrile/gradient: 0.00-4.25 min=10% B, 4.50 min=20% B, 15.50 min=85% B, 16.00-18.50 min=100% B, 18.75-22.00 min=20% B) to afford 154 mg (38% yield).

LC-MS (method 11): R$_t$=1.08 min; MS (ESIpos): m/z=261 [M+H]$^+$ $^1$H-NMR (400 MHz, DMSO-d$_6$) δ [ppm]: 0.31-0.49 (m, 4H), 1.00 (t, 3H), 1.13-1.29 (m, 1H), 2.43 (q, 2H), 3.79 (d, 2H), 4.90 (s, 2H), 7.11-7.26 (m, 2H), 7.47-7.65 (m, 2H).

Intermediate 98

1-cyclopropyl-4-ethyl-3-(4-fluorophenyl)-1H-pyrazol-5-amine

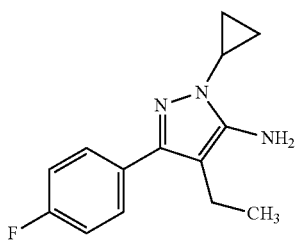 [SMILES: CCc1c(-c2ccc(F)cc2)nn(C2CC2)c1N]

2-(4-fluorobenzoyl)butanenitrile (300 mg, 1.57 mmol) was dissolved in 2-propanol (10 ml). Then, cyclopropylhydrazine dihydrochloride (273 mg, 1.88 mmol) was added and the reaction mixture was stirred at reflux overnight. After cooling to room temperature a 1 M solution of sodium hydrogencarbonate was added and the reaction mixture was concentrated in vacuum. The crude product was purified by preparative HPLC (method: column: Reprosil C18; 10 μm; 125×30 mm/flow: 45 ml/min/eluent: A=water (0.1% formic acid), B=acetonitrile/gradient: 0.00-4.25 min=10% B, 4.50 min=20% B, 15.50 min=85% B, 16.00-18.50 min=100% B, 18.75-22.00 min=20% B) to afford 209 mg (54% yield).

LC-MS (method 11): R$_t$=0.96 min; MS (ESIpos): m/z=247 [M+H]$^+$ $^1$H-NMR (400 MHz, DMSO-d$_6$) δ [ppm]: −0.008 (0.84), 0.008 (0.73), 0.888 (1.03), 0.904 (3.46), 0.909 (3.52), 0.920 (4.25), 0.927 (3.61), 0.935 (3.47), 0.951 (2.66), 0.962 (6.82), 0.972 (9.67), 0.981 (2.34), 0.990 (16.00), 1.009 (6.89), 2.387 (1.94), 2.405 (6.08), 2.424 (5.97), 2.443 (1.86), 3.251 (1.03), 3.261 (1.76), 3.269 (2.27), 3.279 (2.75), 3.283 (1.88), 3.288 (1.88), 3.296 (1.77), 3.306 (1.09), 5.017 (4.79), 7.149 (0.46), 7.157 (3.96), 7.162 (1.43), 7.174 (1.85), 7.179 (8.35), 7.185 (1.84), 7.197 (1.53), 7.202 (4.61), 7.209 (0.55), 7.498 (0.60), 7.506 (4.61), 7.511 (1.88), 7.519 (5.10), 7.527 (4.66), 7.536 (1.79), 7.541 (4.12), 7.549 (0.54), 8.182 (0.93).

Intermediate 99

1-(cyclopropylmethyl)-4-ethyl-3-(4-fluorophenyl)-1H-pyrazol-5-amine

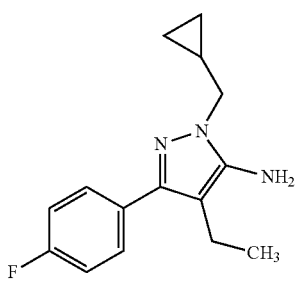 [SMILES: CCc1c(-c2ccc(F)cc2)nn(CC2CC2)c1N]

2-(4-fluorobenzoyl)butanenitrile (300 mg, 1.57 mmol) was dissolved in 2-propanol (10 ml). Then, (cyclopropylmethyl)hydrazine dihydrochloride (299 mg, 1.88 mmol) was added and the reaction mixture was stirred at reflux overnight. A 1 M solution of sodium hydrogencarbonate was added and the reaction mixture was concentrated in vacuum. The crude product was purified by preparative HPLC (method: column: Reprosil C18; 10 μm; 125×30 mm/flow: 45 ml/min/eluent: A=water (0.1% formic acid), B=acetonitrile/gradient: 0.00-4.25 min=10% B, 4.50 min=20% B, 15.50 min=85% B, 16.00-18.50 min=100% B, 18.75-22.00 min=20% B) to afford 154 mg (38% yield) as desired product.

LC-MS (method 11): R$_t$=1.06 min; MS (ESIpos): m/z=261.2 [M+H]$^+$ $^1$H-NMR (400 MHz, DMSO-d$_6$) δ [ppm]: 0.29-0.50 (m, 4H), 1.00 (t, 3H), 1.14-1.28 (m, 1H), 2.43 (q, 2H), 3.79 (d, 2H), 4.90 (s, 2H), 7.13-7.24 (m, 2H), 7.51-7.61 (m, 2H).

Intermediate 100

2-[4-chloro-1-(2,2-difluoroethyl)-3-(4-fluorophenyl)-1H-pyrazol-5-yl]-1H-isoindole-1,3 (2H)-dione

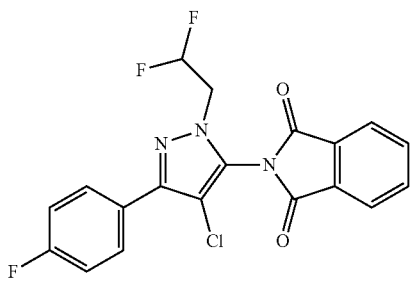 [SMILES: O=C1c2ccccc2C(=O)N1c1c(Cl)c(-c2ccc(F)cc2)nn1CC(F)F]

A solution of 2-[4-chloro-3-(4-fluorophenyl)-1H-pyrazol-5-yl]-1H-isoindole-1,3(2H)-dione (3.00 g, 8.78 mmol) in DMF (30 ml) was treated with 2,2-difluoroethyl trifluoromethanesulfonate (1.3 ml, 9.7 mmol) and (5.72 g, 17.6 mmol). The reaction mixture was stirred at room temperature for 1 h. The reaction mixture was treated with water. Ethyl acetate was added and the water layer was extracted twice. The organic phase was washed with brine, dried over magnesium sulfate and concentrated under vacuum. The crude product was purified by column flash chromatography (cyclohexane/ethyl acetate) to afford two fractions corresponding to the two regioisomers of the desired product. The desired one was obtained in 20% yield (709 mg).

LC-MS (method 11): Rt=1.47 min; MS (ESIpos): m/z=406 [M+H]$^+$

Intermediate 101

2-[4-chloro-1-(2,2-difluoroethyl)-5-(4-fluorophenyl)-1H-pyrazol-3-yl]-1H-isoindole-1,3 (2H)-dione

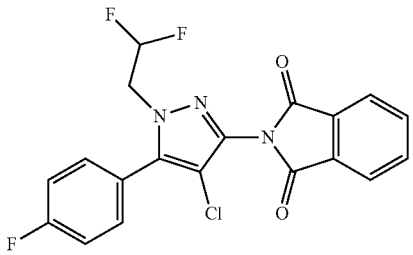 [SMILES: O=C1c2ccccc2C(=O)N1c1nn(CC(F)F)c(-c2ccc(F)cc2)c1Cl]

A solution of 2-[4-chloro-3-(4-fluorophenyl)-1H-pyrazol-5-yl]-1H-isoindole-1,3(2H)-dione (3.00 g, 8.78 mmol) in DMF (30 ml) was treated with 2,2-difluoroethyl trifluoromethanesulfonate (1.3 ml, 9.7 mmol) and (5.72 g, 17.6 mmol). The reaction mixture was stirred at room temperature for 1 h. LC/MS showed no more starting material. The reaction mixture was quenched with water. Ethyl acetate was added and the water layer was extracted twice. The organic phase was washed with brine, dried over magnesium sulfate and concentrated under vacuum. The crude product was purified by column flash chromatography (cyclohexane/ethyl acetate) to afford two fractions corresponding to the two regioisomers of the desired product. The desired regiosimere was obtained in 12% yield (427 mg).

LC-MS (method 11): $R_t$=1.40 min; MS (ESIpos): m/z=406 [m+H]$^+$

Intermediate 102

4-chloro-1-(2,2-difluoroethyl)-3-(4-fluorophenyl)-1H-pyrazol-5-amine

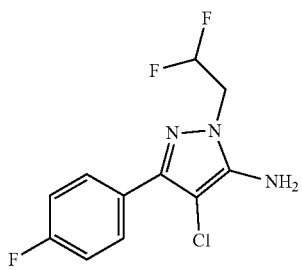 [SMILES: Nc1c(Cl)c(-c2ccc(F)cc2)nn1CC(F)F]

2-[4-chloro-1-(2,2-difluoroethyl)-3-(4-fluorophenyl)-1H-pyrazol-5-yl]-1H-isoindole-1,3(2H)-dione (709 mg, 17.5 mmol) was dissolved in ethanol (5 mL) and treated with hydrazine hydrate (0.42 mL, 8.7 mmol). The reaction mixture was stirred at 80° C. for 1 h. The reaction mixture was cooled and filtered. The filtrate was concentrated under vacuum. The crude product was purified by preparative HPLC (method: column: Reprosil C18; 10 µm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to afford 79.2 mg as desired product (16%).

LC-MS (method 11): $R_t$=1.21 min; MS (ESIneg): m/z=274 [M−H]$^-$

Intermediate 103

4-chloro-1-(2,2-difluoroethyl)-5-(4-fluorophenyl)-1H-pyrazol-3-amine

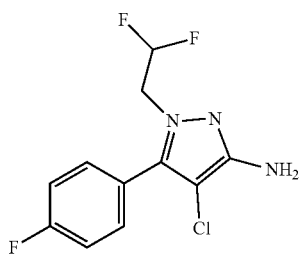

2-[4-chloro-1-(2,2-difluoroethyl)-5-(4-fluorophenyl)-1H-pyrazol-3-yl]-1H-isoindole-1,3(2H)-dione (427 mg, 1.05 mmol) was dissolved in ethanol (5.0 ml) and treated with hydrazine hydrate (1:1) (260 µl, 5.3 mmol). The reaction mixture was stirred at 80° C. for 1 h. The reaction mixture was cooled and filtered. The filtrate was concentrated under vacuum. The crude product was purified by preparative HPLC (method: column: Reprosil C18; 10 µm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to afford 193 mg (67% yield) of the desired product.

LC-MS (method 11): $R_t$=1.16 min; MS (ESIpos): m/z=277 [M+H]$^+$ $^1$H-NMR (400 MHz, DMSO-d$_6$) δ [ppm]: 4.18 (td, 2H), 5.11 (s, 2H), 6.03-6.39 (m, 1H), 7.34-7.42 (m, 2H), 7.43-7.53 (m, 2H).

Intermediate 104

2-(4-fluoro-2-methylbenzoyl)butanenitrile

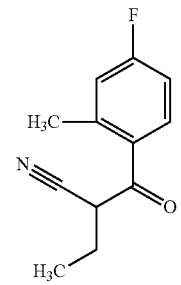

Methyl 4-fluoro-2-methylbenzoate (2.00 g, 11.9 mmol) and butanenitrile (3.1 ml, 36 mmol) are placed in a flask placed under argon and were dissolved in THF (30 ml, 370 mmol). The solution was cooled with a water bath to keep the reaction at room temperature. To this solution lithium 1,1,1,3,3,3-hexamethyldisilazan-2-ide (37 ml, 1.0 M, 37 mmol) was slowly added over 10 minutes. Water and ethyl acetate were added, the mixture was subsequently stirred for 10 minutes and acidified with aqueous hydrochloric acid.

The mixture was three times extracted with ethyl acetate, the combined organic phases were dried over sodium sulfate and concentrated. The crude product (quant.) was used without any further purification in the next step.

LC-MS (method 9): Rt=1.25 min; MS (ESIpos): m/z=206 [M+H]⁺

Intermediate 105

4-ethyl-5-(4-fluoro-2-methylphenyl)-1H-pyrazol-3-amine

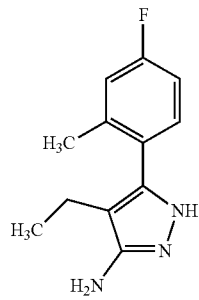

2-(4-fluoro-2-methylbenzoyl)butanenitrile (2.50 g, 12.2 mmol) were dissolved in ethanol (13 ml, 220 mmol), hydrazine (1.5 ml, 64% purity, 30 mmol) was added via syringe. The mixture was heated overnight at 95° C. bath temperature. After cooling to room temperature the reaction mixture was diluted with saturated sodium hydrogencarbonate solution and extracted two times with ethyl acetate. The combined organic phases were dried over magnesium sulfate and concentrated. The crude product was purified b flash chromatography von silica gel (dichloromethane/methanol) to yield the desired product (quant.).

LC-MS (method 9): Rt=0.90 min; MS (ESIpos): m/z=221 [M+H]+

Intermediate 106

1,4-dimethyl-3-[4-(trifluoromethoxy)phenyl]-1H-pyrazol-5-amine

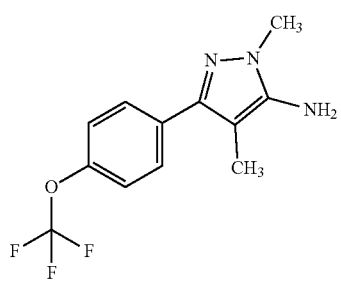 [SMILES: Cc1c(-c2ccc(OC(F)(F)F)cc2)nn(C)c1N]

This compound was obtained during the separation of regioisomers as described above for 1,4-dimethyl-5-[4-(trifluoromethoxy)phenyl]-1H-pyrazol-3-amine by preparative HPLC (column: Daicel Chiralpak IF 250×20 mm, 5 m, Flow: 15 mL/min, T=35° C., eluent: n-heptane/ethanol 75:25) (single isomer, 467 mg, 34% yield).

LC-MS (method 10): R$_t$=1.54 min; MS (ESIpos): m/z=272 [M+H]⁺

¹H-NMR (400 MHz, DMSO-d₆) δ [ppm]: 2.00 (s, 3H), 3.57 (s, 3H), 4.99 (br s, 2H), 7.35 (d, J=8.2 Hz, 2H), 7.66-7.71 (m, 2H).

Intermediate 107

3-methyl-1,5,6,7-tetrahydro-4H-indazol-4-one

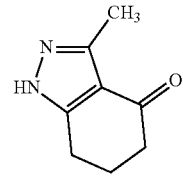

2-Acetylcyclohexane-1,3-dione (1.30 g, 8.43 mmol), hydrazine monohydrate (2.1 ml, 42 mmol) and p-toluenesulfonic acid monohydrate (80.2 mg, 422 µmol) were suspended in ethanol (70 mL) and the reaction mixture was heated to reflux overnight. After cooling to ambient temperature, it was diluted with tetrahydrofuran (65 mL) and aqueous hydrochloric acid (2 M, 75 mL) and vigorously stirred for further 5 h. All organic phase solvents were removed under reduced pressure and the residual aqueous phase was extracted with ethyl acetate. The aqueous phase was basicified with aqueous sodium hydroxide solution and extracted with ethyl acetate. The combined organic phase extracts were dried over sodium sulfate and concentrated to yield the desired product (1.16 g, 89% yield) that was used in the next step without further purification.

LC-MS (method 11): R$_t$=0.42 min; MS (ESIpos): m/z=151 [M+H]⁺

¹H-NMR (400 MHz, dimethylsulfoxide-d6) δ [ppm]: −0.149 (0.55), −0.008 (4.91), 0.008 (4.60), 0.146 (0.56), 1.175 (0.57), 1.908 (1.40), 1.970 (5.21), 1.988 (6.92), 2.006 (5.54), 2.021 (3.61), 2.286 (16.00), 2.315 (9.86), 2.329 (13.89), 2.344 (8.13), 2.367 (1.52), 2.396 (15.12), 2.524 (1.38), 2.669 (3.83), 2.681 (5.70), 2.696 (3.71), 2.764 (3.98), 2.778 (5.96), 2.792 (3.40), 12.741 (1.73), 12.888 (1.29).

Intermediate 108

1-(6-chloropyrimidin-4-yl)-3-methyl-1,5,6,7-tetrahydro-4H-indazol-4-one

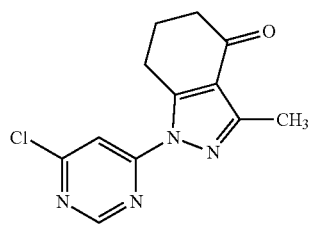 [SMILES: Cc1nn(-c2cc(Cl)ncn2)c2c1C(=O)CCC2]

4,6-Dichloropyrimidine (1.15 g, 7.71 mmol), 3-methyl-1,5,6,7-tetrahydro-4H-indazol-4-one (1.16 g, 7.71 mmol) and cesium carbonate (2.51 g, 7.71 mmol) were dissolved in dimethylformamide (55 mL) and stirred at ambient temperature overnight. Water was then added to cause precipitation of a white solid. After 5 minutes further stirring, the precipitated solid was collected by filtration and dried in an oven at 40° C. overnight to yield the desired product (1.34 g, 58% yield).

LC-MS (method 9): $R_t$=0.90 min; MS (ESIpos): m/z=263 [M+H]$^+$

Intermediate 109

4-(2-cyanopropanoyl)benzonitrile

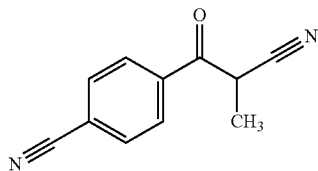

Ethyl 4-cyanobenzoate (10.0 g, 57.1 mmol) and propiononitrile (8.1 ml, 110 mmol) were dissolved in tetrahydrofuran (170 mL) and bis-(trimethylsilyl)lithiumamide (1.0 m in tetrahydrofuran, 120 mL, 120 mmol) was added to this solution dropwise at ambient temperature. The reaction mixture was allowed to stir overnight. The reaction mixture was quenched by addition of water and extracted with dichloromethane. The organic phase was discarded. The product-containing aqueous phase was acidified with aqueous hydrochloric acid solution (6 M) and extracted with dichloromethane (2×). The combined organic phase extracts were washed with water, dried over sodium sulfate and concentrated. The residue was resuspended in diethylether and vigorously stirred. The remaining solid was filtered, washed with diethylether and dried. The product (7.83 g, 75% yield) was used in the next step without further purification.

LC-MS (method 9): $R_t$=0.70 min; MS (ESIneg): m/z=183 [M−H]$^−$ $^1$H-NMR (400 MHz, dimethylsulfoxide-d6) δ [ppm]: 1.473 (3.09), 1.491 (3.18), 1.669 (2.16), 1.892 (16.00), 5.178 (0.78), 5.196 (0.77), 7.616 (0.53), 7.637 (0.59), 7.736 (3.94), 7.757 (4.82), 7.950 (4.87), 7.971 (4.05), 8.047 (0.42), 8.073 (1.09), 8.094 (1.90), 8.155 (2.02), 8.176 (1.19), 11.149 (1.39).

Intermediate 110

4-(3-amino-4-methyl-1H-pyrazol-5-yl)benzonitrile

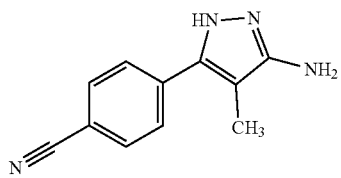

4-(2-cyanopropanoyl)benzonitrile (7.00 g, 38.0 mmol) was dissolved in ethanol (85 mL) and hydrazine monohydrate (2.4 ml, 49 mmol) was added at ambient temperature. The reaction mixture was heated to reflux and stirred for 3 h. After cooling to ambient temperature, the reaction mixture was quenched with aqueous sodium hydrogencarbonate solution (1 M, 50 mL). All volatiles were removed by rotary evaporation causing a yellow solid to precipitate. The solid was filtered, washed with water and dried under vacuum to yield the desired product (6.8 g, 90% yield)

LC-MS (method 10): $R_t$=1.09 min; MS (ESIpos): m/z=199 [M+H]$^+$ $^1$H-NMR (400 MHz, dimethylsulfoxide-d6) δ [ppm]: 2.02 (s, 3H) 4.68 (s, 2H) 7.75 (d, J=8.44 Hz, 2H) 7.87 (d, J=8.44 Hz, 2H) 11.50-12.16 (br s, 1H).

Intermediate 111

4-chloro-6-[4-chloro-5-(difluoromethyl)-3-methyl-1H-pyrazol-1-yl]pyrimidine

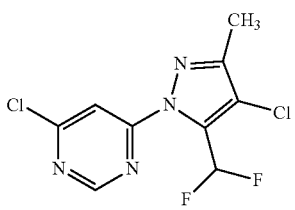 [SMILES: Cc1nn(-c2cc(Cl)ncn2)c(C(F)F)c1Cl]

4-Chloro-6-[5-(difluoromethyl)-3-methyl-1H-pyrazol-1-yl]pyrimidine (1.00 g, 4.09 mmol) was dissolved in acetonitrile (20 mL) and treated with N-chlorosuccinimide (655 mg, 4.91 mmol) at ambient temperature. The reaction mixture was stirred overnight. As LC-MS did not show full conversion, a second aliquot of N-chlorosuccinimide (700 mg, 5.24 mmol) was added and the reaction mixture allowed to stir overnight. Water (75 mL) was added to cause precipitation of a beige solid that was filtered, washed with water and dried under vacuum to yield the desired product (975 mg, 78% yield).

LC-MS (method 10): $R_t$=2.19 min; MS (ESIpos): m/z=279 [M+H]$^+$ $^1$H-NMR (400 MHz, dimethylsulfoxide-d6) δ [ppm]: 2.327 (16.00), 7.817 (1.38), 7.947 (2.75), 8.015 (2.73), 8.078 (1.33), 9.001 (2.65).

Intermediate 112

4-[5-amino-1-(cyclopropylmethyl)-4-methyl-1H-pyrazol-3-yl]benzonitrile

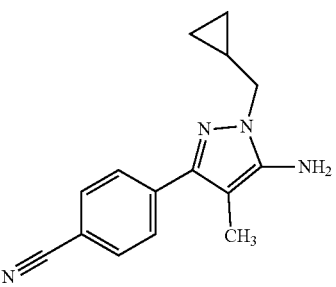 [SMILES: Cc1c(-c2ccc(C#N)cc2)nn(CC2CC2)c1N]

4-(2-cyanopropanoyl)benzonitrile (35.0 g, 190 mmol) was dissolved in 2-propanol (500 mL) and the reaction mixture was heated to 80° C. A solution of (cyclopropylmethyl)hydrazine dihydrochloride (2 M in ethanol, 103 mL, 206 mmol) was added dropwise and the reaction mixture was allowed stir at reflux for 3 days. After cooling to 0° C., the precipitated solid was filtered and discarded, the filtrate was concentrated (but not to dryness). It was diluted with water and basicified with solid sodium hydrogencarbonate to pH 7-8. This mixture was extracted with methyl tert-butylether (3×). The combined organic phase extracts were dried over magnesium sulfate and concentrated. The residue was purified by flash column chromatography (750 g silica gel, gradient cychlohexane/ethyl acetate 80/20 to 50/50) to yield the desired product (29.6 g, 61% yield).

LC-MS (method 10): $R_t$=1.47 min; MS (ESIpos): m/z=253 [M+H]$^+$ $^1$H-NMR (400 MHz, dimethylsulfoxide-d6) δ [ppm]: –0.007 (1.21), 0.354 (3.82), 0.365 (4.26), 0.402 (0.40), 0.431 (3.12), 0.451 (3.41), 1.184 (0.44), 1.199 (0.92), 1.214 (1.17), 1.231 (0.88), 2.033 (15.49), 2.034 (15.43), 3.824 (5.03), 3.841 (4.95), 5.022 (6.26), 7.778 (1.20), 7.798 (16.00), 7.821 (1.09).

Intermediate 113 tert-butyl (2Z)-3-(methylamino)but-2-enoate (10:1 mixture with (2E)-Isomer)

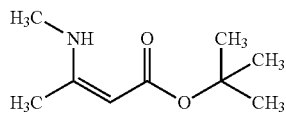

To a suspension of tert-butyl 3-oxobutanoate (17 ml, 100 mmol) and silica gel (1.05 g) was added an aqueous solution of methylamine (40%, 10 mL, 120 mmol). The reaction mixture was stirred overnight at ambient temperature. GC-MS showed full conversion to product. Brine was added and the reaction mixture was extracted with dichloromethane (3×). The combined organic phase extracts were dried over sodium sulfate, concentrated and dried to yield the desired product (16.9 g, 99% yield) as a 10:1 mixture of olefin isomers. The product was used in the next step without further purification.

GC-MS (method 15): $R_t$=3.61 min; MS (EI): m/z=171 [M].

$^1$H-NMR (400 MHz, dimethylsulfoxide-d6) δ [ppm]: 1.371 (16.00), 1.837 (4.88), 2.122 (0.45), 2.819 (2.83), 2.833 (2.81), 4.260 (1.34).

Intermediate 114 tert-butyl (2Z)-2-(difluoroacetyl)-3-(methylamino) but-2-enoate (10:1 mixture with (2E)-Isomer)

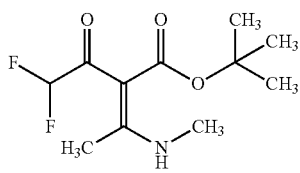 [SMILES: CN/C(C)=C(\C(=O)OC(C)(C)C)C(=O)C(F)F]

Tert-butyl (2Z)-3-(methylamino)but-2-enoate (16.8 g, 98.1 mmol, 10:1 mixture with (2E)-Isomer) and triethylamine (21 ml, 150 mmol) were dissolved in methyl tert-butylether (190 mL) under an argon atmosphere and the resulting solution cooled to 0° C. Difluoroacetic anhydride (15 ml, 120 mmol) was added dropwise and the reaction mixture allowed to warm to ambient temperature and was stirred overnight. The reaction mixture was diluted with methyl tert-butylether and washed with water (3×20 mL). The organic phase was dried over sodium sulfate and concentrated. The residue was titrated with hexanes to yield the desired product as a white solid (20.0 g, 82% yield, 10:1 olefin isomers).

LC-MS (method 10): $R_t$=1.70 min; MS (ESIneg): m/z=248 [M–H]$^-$ $^1$H-NMR (400 MHz, dimethylsulfoxide-d6, only the major isomer is shown) δ [ppm]: 1.46 (s, 9H) 2.22 (s, 3H), 3.06 (d, J=5.14 Hz, 3H), 6.47 (t, J=54.3 Hz, 1H) 11.74 (br s, 1H)

Intermediate 115 tert-butyl 5-(difluoromethyl)-3-methyl-1H-pyrazole-4-carboxylate

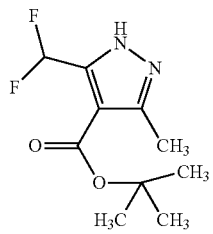

Tert-butyl (2Z)-2-(difluoroacetyl)-3-(methylamino)but-2-enoate (10.0 g, 40.1 mmol, 10:1 mixture with (2E)-Isomer) was dissolved in methanol (94 mL) under an argon atmosphere and the resulting solution was cooled to –20° C. Hydrazine monohydrate (2.9 mL, 60 mmol) was added dropwise and the reaction mixture stirred at –20° C. for 1 h and overnight at ambient temperature. The reaction mixture was concentrated and the residue redissolved in ethyl acetate. The solution was washed with brine (3×) and the organic phase dried over sodium sulfate and concentrated to yield the desired product (6.70 g, 72% yield) that was used without further purification in the next step.

LC-MS (method 9): $R_t$=0.86 min; MS (ESIneg): m/z=231 [M–H]$^-$ $^1$H-NMR (400 MHz, dimethylsulfoxide-d6) δ [ppm]: $^1$H NMR (400 MHz, dimethylsulfoxide-d6) δ ppm 1.50 (s, 9H), 2.42 (s, 3H), 7.11 (t, J=54.2 Hz, 1H), 13.24-13.68 (br s, 1H).

Intermediate 116 tert-butyl 1-(6-chloropyrimidin-4-yl)-5-(difluoromethyl)-3-methyl-1H-pyrazole-4-carboxylate

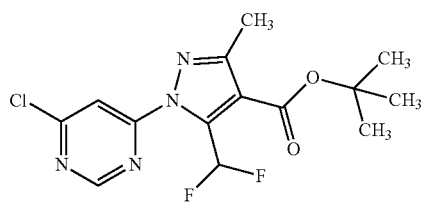 [SMILES: Cc1nn(-c2cc(Cl)ncn2)c(C(F)F)c1C(=O)OC(C)(C)C]

4,6-Dichloropyrimidine (2.57 g, 17.2 mmol) and tert-butyl 5-(difluoromethyl)-3-methyl-1H-pyrazole-4-carboxylate (4.00 g, 17.2 mmol) were suspended in dimethylformamide (10 mL) under an argon atmosphere and cesium carbonate (5.61 g, 17.2 mmol) was added. The reaction mixture was allowed to stir for 72 h at ambient temperature. The reaction mixture was poured into water (200 mL) and stirred for 30 min. The precipitated solid was collected by filtration, washed with water and dried to yield the desired product (4.4 g, 59% yield).

LC-MS (method 9): R$_t$=1.23 min; MS (ESIpos): m/z=345 [M+H]$^+$ $^1$H-NMR (400 MHz, dimethylsulfoxide-d6) δ [ppm]: 1.55 (s, 9H), 2.94 (s, 3H), 7.26 (t, J=53.4 Hz, 1H), 8.04 (s, 1H), 9.09 (s, 1H).

Intermediate 117

1-(6-chloropyrimidin-4-yl)-3-methyl-1H-pyrazolo[3,4-b]pyridine

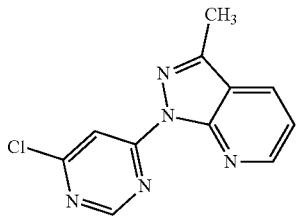 [SMILES: Cc1nn(-c2cc(Cl)ncn2)c2ncccc12]

4,6-Dichloropyrimidine (1.02 g, 6.88 mmol) and 3-methyl-1H-pyrazolo[3,4-b]pyridine (916 mg, 6.88 mmol) were suspended in dimethylformamide (8.4 mL) and cesium carbonate (2.24 g, 6.88 mmol) was added and the reaction mixture was stirred at ambient temperature overnight. Water (80 mL) was added an stirring continued for 30 min. The precipitated solid was collected by filtration, washed with water and dried to yield the desired product (1.21 g, 50% yield) as a 70:30 mixture with its regioisomer 2-(6-chloropyrimidin-4-yl)-3-methyl-pyrazolo[3,4-b]pyridine.

LC-MS (method 10): R$_t$=1.07 min; MS (ESIpos): m/z=246 [M+H]$^+$ $^1$H-NMR (400 MHz, dimethylsulfoxide-d6) δ [ppm]: 2.626 (16.00), 2.674 (0.53), 3.051 (4.99), 3.112 (0.47), 3.129 (0.58), 7.119 (0.51), 7.129 (0.57), 7.141 (0.64), 7.151 (0.63), 7.480 (1.32), 7.492 (1.51), 7.497 (1.67), 7.509 (1.49), 8.325 (1.37), 8.349 (0.75), 8.420 (2.11), 8.439 (2.08), 8.643 (2.73), 8.739 (0.85), 8.754 (2.53), 8.766 (2.51), 8.985 (3.46), 9.128 (1.23).

Intermediate 118

1-(6-chloropyrimidin-4-yl)-3-methyl-1H-pyrazolo[3,4-c]pyridine

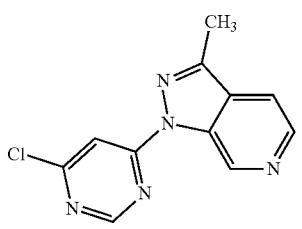 [SMILES: Cc1nn(-c2cc(Cl)ncn2)c2cnccc12]

4,6-dichloropyrimidine (559 mg, 3.76 mmol) and 3-methyl-1H-pyrazolo[3,4-c]pyridine (500 mg, 3.76 mmol) were suspended in dimethylformamide (4.6 mL), cesium carbonate (1.22 g, 3.76 mmol) was added and the reaction mixture stirred at ambient temperature overnight. Water was added and the mixture stirred for another 30 min. The precipitated solid was collected by filtration, washed with water and dried under high vacuum to yield the desired product (670 mg, 62% yield, 85% purity).

LC-MS (method 10): R$_t$=1.67 min; MS (ESIpos): m/z=246 [M+H]$^+$ $^1$H-NMR (400 MHz, dimethylsulfoxide-d6) δ [ppm]: 2.321 (1.43), 2.399 (2.82), 2.448 (1.25), 2.663 (16.00), 2.715 (1.63), 2.732 (0.85), 2.813 (2.92), 2.892 (0.73), 3.044 (0.70), 3.112 (1.11), 7.592 (1.17), 7.761 (0.97), 7.957 (7.17), 7.970 (3.35), 8.559 (2.67), 8.572 (2.82), 8.597 (0.84), 8.611 (1.08), 8.630 (1.13), 8.940 (0.87), 9.042 (4.58), 9.509 (0.67), 10.001 (4.18).

Intermediate 119

4-(4-bromo-3,5-dimethyl-1H-pyrazol-1-yl)-6-chloropyrimidine

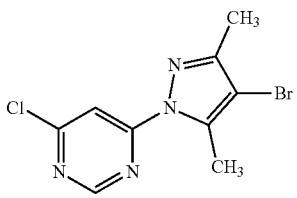

4-chloro-6-(3,5-dimethyl-1H-pyrazol-1-yl)pyrimidine (300 mg, 1.44 mmol) was dissolved in acetonitrile (6.0 mL) and 1-bromopyrrolidine-2,5-dione (307 mg, 1.73 mmol) was added. The reaction mixture was stirred at ambient temperature overnight. Water was added to precipitate and the mixture was stirred for 5 minutes. The precipitated solid was collected by filtration, washed with water, dried overnight in a high-vacuum oven at 40° C. to yield the desired product (373 mg, 90% yield).

LC-MS (method 9): R$_t$=1.19 min; MS (ESIpos): m/z=288 [M+H]$^+$ $^1$H-NMR (400 MHz, dimethylsulfoxide-d6) δ [ppm]: 2.227 (0.61), 2.258 (11.76), 2.262 (15.88), 2.662 (0.76), 2.687 (12.00), 2.690 (16.00), 7.941 (3.30), 8.955 (3.01).

Intermediate 120

2-[1-(cyclopropylmethyl)-4-ethyl-5-(4-fluorophenyl)-1H-pyrazol-3-yl]-1H-isoindole-1,3(2H)-dione

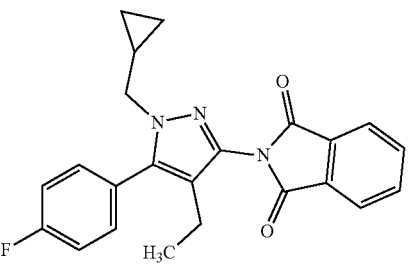 [SMILES: CCc1c(N2C(=O)c3ccccc3C2=O)nn(CC2CC2)c1-c1ccc(F)cc1]

A solution of 2-[4-ethyl-3-(4-fluorophenyl)-1H-pyrazol-5-yl]-1H-isoindole-1,3(2H)-dione (5.00 g, 14.9 mmol) and (9.72 g, 29.8 mmol) in dimethylformamide (51 ml, 660 mmol) was treated with (bromomethyl)cyclopropane (4.3 ml, 45 mmol). The resulting mixture was stirred overnight at ambient temperature. Water was added and the mixture was extracted three times with ethyl acetate. The combined organic phases were washed with brine, dried over sodium sulfate and concentrated under reduced pressure. The crude product was purified by preparative HPLC (column: Daicel Chiralcel OX-H; 250*20 mm, 5 µM, flow 15 mL/min, gradient n-heptane/ethanol 50/50) to yield 1.73 g of the desired product (30%) together with its regioisomer (2.96 g, 48%).

LC-MS (method 10): $R_t$=2.21 min; MS (ESIpos): m/z=390 [M+H]$^+$ $^1$H-NMR (500 MHz, dimethylsulfoxide-d6) δ [ppm]: 0.103 (1.38), 0.112 (4.98), 0.115 (4.07), 0.122 (4.35), 0.124 (4.60), 0.133 (1.43), 0.409 (1.59), 0.417 (4.05), 0.421 (3.97), 0.425 (2.04), 0.430 (2.13), 0.433 (4.07), 0.436 (3.81), 0.446 (1.30), 0.802 (6.97), 0.817 (16.00), 0.832 (6.97), 1.056 (0.51), 1.058 (0.48), 1.066 (0.95), 1.068 (0.89), 1.072 (0.94), 1.075 (0.78), 1.082 (1.52), 1.088 (0.76), 1.091 (0.86), 1.096 (0.83), 1.098 (0.83), 1.105 (0.40), 1.107 (0.40), 2.083 (1.05), 2.196 (1.77), 2.211 (5.34), 2.226 (5.18), 2.242 (1.59), 3.329 (10.70), 3.867 (7.22), 3.881 (7.03), 7.379 (0.52), 7.385 (3.62), 7.389 (1.37), 7.398 (1.88), 7.403 (7.73), 7.407 (1.67), 7.416 (1.47), 7.420 (4.30), 7.426 (0.49), 7.545 (0.69), 7.551 (4.30), 7.555 (1.98), 7.562 (4.76), 7.568 (4.05), 7.575 (1.63), 7.579 (3.48), 7.944 (0.43), 7.947 (0.60), 7.954 (5.16), 7.960 (5.38), 7.965 (4.71), 7.971 (7.64), 7.979 (1.13), 7.981 (0.92), 8.007 (1.05), 8.009 (1.20), 8.017 (8.38), 8.023 (5.07), 8.028 (5.68), 8.034 (4.99).

Intermediate 121

1-(cyclopropylmethyl)-4-ethyl-5-(4-fluorophenyl)-1H-pyrazol-3-amine

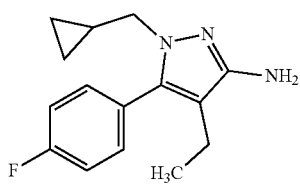 [SMILES: CCc1c(N)nn(CC2CC2)c1-c1ccc(F)cc1]

A solution of 2-[1-(cyclopropylmethyl)-4-ethyl-5-(4-fluorophenyl)-1H-pyrazol-3-yl]-1H-isoindole-1,3(2H)-dione (1.73 g, 4.44 mmol) in ethanol (30 ml, 520 mmol) was treated with hydrazine monohydrate (1.1 ml, 22 mmol). The mixture was refluxed overnight. After cooling to room temperature a white solid occurred with was filtered of. The filtrate was concentrated under reduced pressure. The crude product resolved in acetonitrile, the precipitate was again removed by filtration and the filtrate was taken to dryness to obtain 1.15 g of the desired product (90%).

LC-MS (method 9): $R_t$=0.86 min; MS (ESIpos): m/z=260 [M+H]$^+$ $^1$H-NMR (400 MHz, dimethylsulfoxide-d6) δ [ppm]: −0.015 (1.55), −0.012 (1.57), 0.005 (13.53), 0.021 (1.78), 0.317 (1.59), 0.321 (1.56), 0.331 (6.50), 0.342 (2.99), 0.351 (6.61), 0.362 (1.48), 0.888 (7.30), 0.907 (16.00), 0.925 (7.84), 0.938 (0.89), 0.955 (1.48), 0.962 (1.37), 0.971 (1.99), 0.983 (1.33), 0.987 (1.36), 0.991 (1.35), 1.003 (0.66), 2.141 (2.52), 2.159 (7.42), 2.178 (7.18), 2.197 (2.27), 3.511 (9.88), 3.528 (9.75), 4.459 (11.57), 7.289 (1.71), 7.293 (1.71), 7.311 (7.59), 7.315 (6.56), 7.332 (12.07), 7.343 (8.93), 7.365 (1.47).

Intermediate 122

4-(2-cyanobutanoyl)benzonitrile

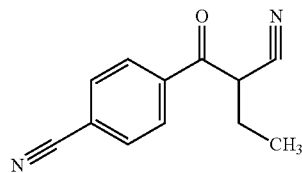

A solution of butanenitrile (10 ml, 110 mmol) in tetrahydrofuran (170 ml, 2.1 mol) was treated with lithium bis(trimethylsilyl)amide (1.0 M in tetrahydrofuran; 120 mL, 1.0 M, 120 mmol) at 30° C. Afterwards ethyl 4-cyanobenzoate (10.0 g, 57.1 mmol) was added dropwise. The resulting mixture was stirred for 4 hours. The reaction was quenched by the addition of water and extracted once with dichloromethane. The aqueous phase was acidified with aqueous hydrochloric acid to pH 2 and subsequently extracted three times with dichloromethane. The combined organic phases were dried over sodium sulphate and the solvent was removed under reduced pressure. The crude product was purified by flash chromatography on silica gel (solvent dichloromethane). Fractions containing the desired product were collected, the solvent was removed and the product was triturated with diethyl ether to yield 8.51 g of the desired product (75%).

LC-MS (method 10): $R_t$=1.50 min; MS (ESIneg): m/z=197 [M−H]$^−$ $^1$H-NMR (400 MHz, dimethylsulfoxide-d6) δ [ppm]: 0.973 (1.48), 0.991 (6.78), 1.008 (11.80), 1.027 (6.35), 1.043 (0.86), 1.068 (7.61), 1.087 (16.00), 1.106 (7.94), 1.753 (0.68), 1.771 (1.14), 1.788 (1.47), 1.807 (1.62), 1.825 (1.05), 1.909 (0.62), 1.928 (1.78), 1.937 (1.24), 1.946 (1.87), 1.955 (1.45), 1.972 (1.02), 1.990 (0.68), 2.296 (2.58), 2.315 (7.53), 2.333 (7.39), 2.352 (2.34), 3.375 (0.44), 3.392 (0.41), 5.194 (1.84), 5.206 (2.09), 5.214 (1.95), 5.226 (1.69), 5.753 (1.44), 7.583 (1.42), 7.603 (1.62), 7.726 (7.45), 7.747 (9.12), 7.948 (9.70), 7.968 (8.16), 8.067 (4.07), 8.088 (6.82), 8.151 (7.11), 8.172 (4.68), 11.133 (1.45).

Intermediate 123

4-[5-amino-1-(cyclopropylmethyl)-4-ethyl-1H-pyrazol-3-yl]benzonitrile

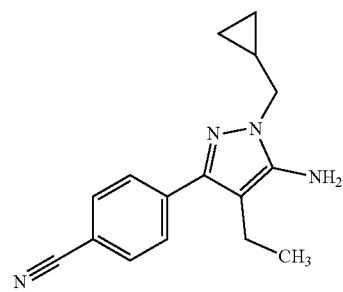 [SMILES: CCc1c(-c2ccc(C#N)cc2)nn(CC2CC2)c1N]

A solution of 4-(2-cyanobutanoyl)benzonitrile (2.00 g, 10.1 mmol) and (cyclopropylmethyl)hydrazine dihydrochloride (2.09 g, 13.1 mmol) in ethanol (20 ml, 340 mmol) was treated with N,N-diisopropylethylamine (4.6 ml, 26 mmol) and refluxed overnight. The conversion was not fully completed, therefore the mixture was left for 2 days, than additional di-isopropyl ethyl amine (2.28 mL, 13.1 mmol) was added and it was refluxed for another night. After cooling to ambient temperature the mixture was concentrated and the remaining material was partitioned between water and ethyl acetate.

The organic phase was washed with saturated sodium carbonate solution, water, and brine and dried over sodium sulphate. The organic phase was concentrated under reduced pressure. The crude material was purified via preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (1.1.9 g, 39%).

LC-MS (method 10): $R_t$=1.60 min; MS (ESIpos): m/z=267 [M+H]$^+$ $^1$H-NMR (400 MHz, dimethylsulfoxide-d6) δ [ppm]: 0.343 (1.68), 0.356 (6.33), 0.368 (7.09), 0.380 (2.23), 0.395 (0.63), 0.404 (0.71), 0.416 (1.20), 0.430 (2.95), 0.439 (5.68), 0.459 (5.80), 0.475 (1.26), 0.558 (0.44), 0.917 (0.65), 0.936 (0.74), 0.955 (1.06), 0.969 (1.05), 0.988 (0.74), 1.007 (7.45), 1.026 (16.00), 1.044 (7.32), 1.106 (0.44), 1.133 (0.50), 1.152 (1.20), 1.170 (1.26), 1.189 (1.04), 1.203 (1.52), 1.210 (1.38), 1.222 (2.06), 1.234 (1.37), 1.239 (1.32), 1.252 (0.66), 1.989 (0.56), 2.441 (0.42), 2.471 (2.48), 3.165 (0.46), 3.178 (0.47), 3.316 (12.97), 3.817 (9.79), 3.834 (9.55), 5.020 (12.64), 7.582 (0.45), 7.603 (0.50), 7.677 (0.59), 7.694 (0.74), 7.746 (7.11), 7.767 (13.35), 7.807 (12.82), 7.827 (6.69), 7.849 (0.58), 7.859 (0.41), 7.953 (0.79), 7.973 (0.73), 7.988 (0.45), 8.009 (0.61), 8.054 (0.56).

Intermediate 124

2-[4-chloro-1-(cyclopropylmethyl)-5-(4-fluorophenyl)-1H-pyrazol-3-yl]-1H-isoindole-1,3(2H)-dione

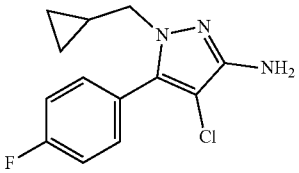

A solution of 2-[4-chloro-3-(4-fluorophenyl)-1H-pyrazol-5-yl]-1H-isoindole-1,3(2H)-dione (1.41 g, 4.13 mmol) in dimethylformamide (10 ml, 130 mmol) was treated with cesium carbonate (2.69 g, 8.25 mmol) and (bromomethyl)cyclopropane (1.2 ml, 12 mmol). The mixture was stirred overnight at ambient temperature. The mixture was portioned between water and ethyl acetate. The organic phase was washed with water and brine, dried over sodium sulfate. The solvent was removed under reduced pressure and the crude product was purified by flash chromatography on silica gel (dichloromethane/ethyl acetate) to yield 328 mg of the desired product (18%) along with its regioisomer (360 mg, 20%).

LC-MS (method 14): $R_t$=1.17 min; MS (ESIpos): m/z=396 [M+H]$^+$ $^1$H-NMR (500 MHz, dimethylsulfoxide-d6) δ [ppm]: −0.007 (0.79), 0.006 (0.57), 0.148 (2.46), 0.157 (9.48), 0.160 (7.73), 0.166 (8.39), 0.169 (8.90), 0.178 (2.64), 0.437 (2.80), 0.445 (7.43), 0.449 (7.31), 0.453 (3.76), 0.461 (7.76), 0.464 (7.28), 0.473 (2.45), 1.086 (0.66), 1.090 (0.97), 1.095 (0.67), 1.099 (1.83), 1.106 (1.77), 1.109 (1.46), 1.115 (2.88), 1.122 (1.44), 1.125 (1.64), 1.129 (1.66), 1.136 (0.60), 1.139 (0.82), 1.145 (0.55), 2.468 (0.62), 2.482 (1.64), 2.496 (1.94), 3.335 (9.81), 4.020 (13.86), 4.034 (13.82), 4.171 (1.59), 4.185 (2.82), 4.199 (1.49), 4.980 (2.68), 5.003 (1.22), 5.013 (1.17), 5.016 (0.86), 5.616 (0.59), 5.635 (0.49), 5.638 (0.45), 5.648 (0.45), 5.652 (0.43), 5.670 (0.49), 5.761 (3.10), 7.433 (0.91), 7.439 (7.17), 7.442 (3.91), 7.447 (1.37), 7.456 (15.46), 7.460 (6.28), 7.470 (2.96), 7.474 (8.54), 7.478 (2.67), 7.638 (1.81), 7.642 (0.89), 7.649 (2.25), 7.652 (2.09), 7.658 (8.27), 7.662 (4.15), 7.669 (8.92), 7.676 (7.61), 7.682 (3.18), 7.686 (6.74), 7.692 (0.77), 7.969 (0.84), 7.972 (1.17), 7.979 (10.94), 7.985 (11.67), 7.990 (11.12), 7.996 (16.00), 8.004 (2.35), 8.006 (1.88), 8.039 (2.08), 8.041 (2.16), 8.049 (15.04), 8.054 (10.57), 8.059 (10.65), 8.066 (9.24), 8.073 (0.85), 8.076 (0.58).

Intermediate 125

4-chloro-1-(cyclopropylmethyl)-5-(4-fluorophenyl)-1H-pyrazol-3-amine

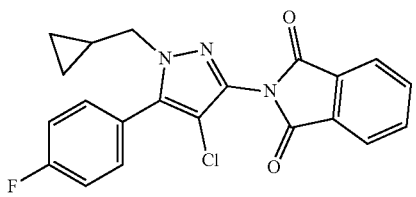 [SMILES: O=C1c2ccccc2C(=O)N1c1nn(CC2CC2)c(-c2ccc(F)cc2)c1Cl]

A solution of 2-[4-chloro-1-(cyclopropylmethyl)-5-(4-fluorophenyl)-1H-pyrazol-3-yl]-1H-isoindole-1,3(2H)-dione (328 mg, 829 µmol) in ethanol (5.7 ml, 97 mmol) was treated with hydrazine monohydrate (200 µl, 4.1 mmol). The mixture was stirred overnight at 90° C. After cooling to ambient temperature the mixture was portioned between water and ethyl acetate. The aqueous was extracted additionally two times with ethyl acetate. The combined organic phases were washed with 1M aqueous sodium hydrogen carbonate solution and brine and dried over sodium sulfate. The solvent was removed under reduced pressure to yield the desired crude product (204 mg, 68%).

LC-MS (method 10): $R_t$=1.77 min; MS (ESIpos): m/z=266 [M+H]$^+$ $^1$H-NMR (500 MHz, dimethylsulfoxide-d6) δ [ppm]: −0.007 (0.73), 0.006 (0.55), 0.021 (2.43), 0.031 (9.25), 0.033 (7.72), 0.040 (8.38), 0.043 (8.72), 0.052 (2.68), 0.347 (2.92), 0.356 (7.67), 0.359 (7.63), 0.363 (3.80), 0.368 (4.03), 0.371 (7.76), 0.375 (7.42), 0.384 (2.59), 0.712 (2.71), 0.727 (6.68), 0.742 (3.24), 0.966 (0.73), 0.971 (0.93), 0.973 (0.85), 0.976 (0.67), 0.980 (1.73), 0.983 (1.65), 0.987 (1.71), 0.990 (1.44), 0.997 (2.77), 1.003 (1.43), 1.006 (1.60), 1.010 (1.59), 1.012 (1.52), 1.017 (0.61), 1.020 (0.78), 1.022 (0.76), 1.026 (0.59), 1.060 (0.48), 1.064 (0.91), 1.079 (1.48), 1.094 (1.47), 1.109 (0.84), 1.533 (0.42), 1.548 (1.12), 1.562 (1.54), 1.577 (1.10), 3.329 (11.01), 3.642 (14.68), 3.656 (14.26), 3.749 (1.55), 3.763 (2.85), 3.777 (1.67), 4.901 (4.50), 4.914 (16.00), 7.346 (0.90), 7.352 (6.62), 7.355 (3.55), 7.359

(1.25), 7.365 (3.66), 7.369 (15.65), 7.372 (6.12), 7.383 (2.99), 7.387 (9.44), 7.390 (3.02), 7.442 (0.40), 7.447 (2.29), 7.451 (1.86), 7.457 (9.35), 7.461 (4.60), 7.468 (9.97), 7.475 (7.44), 7.481 (2.99), 7.485 (6.25), 7.491 (0.70).

Intermediate 126

2-[4-chloro-1-(cyclopropylmethyl)-3-(4-fluorophenyl)-1H-pyrazol-5-yl]-1H-isoindole-1,3(2H)-dione

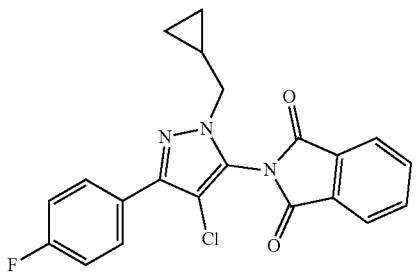 [SMILES: O=C1c2ccccc2C(=O)N1c1c(Cl)c(-c2ccc(F)cc2)nn1CC1CC1]

A solution of 2-[4-chloro-3-(4-fluorophenyl)-1H-pyrazol-5-yl]-1H-isoindole-1,3(2H)-dione (1.41 g, 4.13 mmol) in dimethylformamide (10 ml, 130 mmol) was treated with cesium carbonate (2.69 g, 8.25 mmol) and (bromomethyl)cyclopropane (1.2 ml, 12 mmol). The mixture was stirred overnight at ambient temperature. The mixture was portioned between water and ethyl acetate. The organic phase was washed with water and brine, dried over sodium sulfate. The solvent was removed under reduced pressure and the crude product was purified by flash chromatography on silica gel (dichloromethane/ethyl acetate) to yield 360 mg of the desired product (20%) along with its regioisomer (320 mg, 18%).

LC-MS (method 14): $R_t$=1.24 min; MS (ESIpos): m/z=396 [M+H]$^+$ $^1$H-NMR (500 MHz, dimethylsulfoxide-d6) δ [ppm]: 0.007 (1.08), 0.317 (2.07), 0.326 (8.24), 0.329 (7.16), 0.336 (7.98), 0.338 (7.88), 0.347 (2.69), 0.453 (2.72), 0.461 (6.80), 0.464 (6.64), 0.469 (3.68), 0.477 (7.06), 0.481 (6.41), 0.490 (2.04), 1.237 (0.66), 1.242 (0.98), 1.252 (1.81), 1.258 (1.72), 1.261 (1.44), 1.268 (2.74), 1.274 (1.45), 1.277 (1.62), 1.283 (1.69), 1.292 (0.84), 1.298 (0.55), 2.088 (1.24), 2.520 (0.77), 2.523 (0.92), 2.566 (0.54), 3.327 (16.00), 4.042 (13.04), 4.056 (12.66), 4.223 (1.46), 4.238 (2.31), 4.252 (1.42), 4.980 (0.89), 4.983 (0.88), 5.001 (0.92), 5.004 (0.95), 5.048 (0.90), 5.052 (0.86), 5.082 (1.02), 5.086 (0.93), 5.732 (0.56), 5.752 (0.74), 5.766 (0.75), 5.787 (0.49), 7.339 (2.45), 7.345 (7.14), 7.348 (2.73), 7.357 (5.65), 7.362 (14.66), 7.366 (3.24), 7.376 (3.56), 7.380 (7.52), 7.386 (0.86), 7.899 (1.84), 7.904 (1.11), 7.913 (8.22), 7.917 (4.98), 7.924 (8.87), 7.928 (6.24), 7.931 (7.77), 7.937 (3.23), 7.942 (6.85), 7.948 (0.78), 8.002 (1.16), 8.009 (9.68), 8.015 (10.42), 8.020 (10.52), 8.027 (13.72), 8.034 (2.00), 8.082 (1.54), 8.083 (1.79), 8.092 (13.13), 8.097 (12.13), 8.102 (11.51), 8.109 (10.12), 8.114 (2.48), 8.119 (0.69).

Intermediate 127

4-chloro-1-(cyclopropylmethyl)-3-(4-fluorophenyl)-1H-pyrazol-5-amine

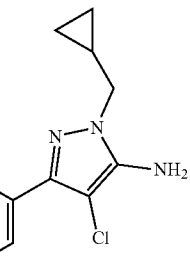

A solution of 2-[4-chloro-1-(cyclopropylmethyl)-3-(4-fluorophenyl)-1H-pyrazol-5-yl]-1H-isoindole-1,3(2H)-dione (360 mg, 909 μmol) in ethanol (8.4 ml, 140 mmol) was treated with hydrazine monohydrate (220 μl, 4.5 mmol). The mixture was stirred overnight at 90° C. After cooling to ambient temperature the mixture was portioned between water and ethyl acetate. The aqueous was extracted additionally two times with ethyl acetate. The combined organic phases were washed with 1M aqueous sodium hydrogen carbonate solution and brine and dried over sodium sulphate. The solvent was removed under reduced pressure to yield the desired crude product (236 mg, 79%).

LC-MS (method 10): $R_t$=1.86 min; MS (ESIpos): m/z=266 [M+H]$^+$ $^1$H-NMR (400 MHz, dimethylsulfoxide-d6) δ [ppm]: 0.348 (1.49), 0.361 (6.51), 0.373 (7.67), 0.385 (2.45), 0.405 (0.61), 0.423 (0.70), 0.440 (2.31), 0.450 (5.63), 0.470 (6.14), 0.485 (1.45), 0.875 (1.59), 0.894 (3.55), 0.912 (1.84), 1.185 (0.82), 1.198 (1.57), 1.205 (1.45), 1.216 (2.28), 1.229 (1.48), 1.234 (1.60), 1.246 (0.87), 1.263 (0.73), 1.281 (1.03), 1.300 (1.00), 1.319 (0.55), 1.653 (0.77), 1.672 (1.07), 1.690 (0.72), 3.843 (11.37), 3.860 (11.20), 3.916 (1.03), 3.934 (1.83), 3.951 (0.98), 5.503 (16.00), 5.541 (0.68), 7.221 (5.38), 7.244 (10.59), 7.266 (5.40), 7.785 (1.92), 7.793 (6.18), 7.798 (3.89), 7.807 (7.89), 7.815 (6.62), 7.824 (3.07), 7.829 (5.44).

Intermediate 128

2-[1-(cyclopropylmethyl)-5-(4-fluorophenyl)-4-methyl-1H-pyrazol-3-yl]-1H-isoindole-1,3(2H)-dione

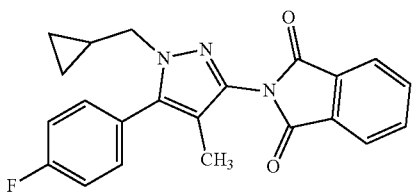 [SMILES: Cc1c(N2C(=O)c3ccccc3C2=O)nn(CC2CC2)c1-c1ccc(F)cc1]

A solution of 2-[5-(4-fluorophenyl)-4-methyl-1H-pyrazol-3-yl]-1H-isoindole-1,3(2H)-dione (1.26 g, 3.93 mmol) in dimethylformamide (10 ml, 130 mmol) was treated with cesium carbonate (2.56 g, 7.87 mmol) and (bromomethyl)cyclopropane (1.1 ml, 12 mmol). The mixture was stirred overnight at ambient temperature. The mixture was portioned between water and ethyl acetate. The organic phase was washed with water and brine, dried over sodium sulfate. The solvent was removed under reduced pressure and the crude product was purified by flash chromatography on silica gel (dichloromethane/ethyl acetate) to yield 513 mg of the desired product (30%) along with its regioisomer (848 mg, 48%).

LC-MS (method 10): $R_t$=2.11 min; MS (ESIpos): m/z=376 [M+H]$^+$ $^1$H-NMR (400 MHz, dimethylsulfoxide-d6) δ [ppm]: −0.008 (0.43), 0.092 (0.67), 0.103 (2.77), 0.106 (2.47), 0.118 (2.86), 0.129 (0.85), 0.387 (0.83), 0.398 (2.20), 0.402 (2.33), 0.407 (1.24), 0.418 (2.33), 0.422 (2.32), 0.433 (0.74), 1.046 (0.51), 1.053 (0.51), 1.065 (0.82), 1.077 (0.49), 1.083 (0.49), 1.794 (16.00), 1.989 (0.69), 2.460 (0.41), 2.524 (0.53), 3.914 (4.13), 3.932 (4.08), 4.056 (0.45), 4.074 (0.63), 7.376 (1.89), 7.398 (4.35), 7.420 (2.60), 7.528 (0.47), 7.544 (2.68), 7.550 (1.54), 7.558 (2.79), 7.566 (2.44), 7.574 (0.91), 7.580 (1.94), 7.936 (2.60), 7.944 (2.98), 7.950 (2.95), 7.958 (4.87), 7.967 (0.90), 7.988 (0.78), 7.998 (4.45), 8.005 (2.70), 8.012 (2.76), 8.019 (2.31).

Intermediate 129

2-[1-(cyclopropylmethyl)-3-(4-fluorophenyl)-4-methyl-1H-pyrazol-5-yl]-1H-isoindole-1,3 (2H)-dione

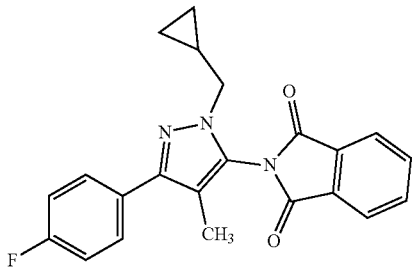 [SMILES: Cc1c(-c2ccc(F)cc2)nn(CC2CC2)c1N1C(=O)c2ccccc2C1=O]

A solution of 2-[3-(4-fluorophenyl)-4-methyl-1H-pyrazol-5-yl]-1H-isoindole-1,3(2H)-dione (1.26 g, 3.93 mmol) in dimethylformamide (10 ml, 130 mmol) was treated with cesium carbonate (2.56 g, 7.87 mmol) and (bromomethyl)cyclopropane (1.1 ml, 12 mmol). The mixture was stirred overnight at ambient temperature. The mixture was portioned between water and ethyl acetate. The organic phase was washed with water and brine, dried over sodium sulfate. The solvent was removed under reduced pressure and the crude product was purified by flash chromatography on silica gel (dichloromethane/ethyl acetate) to yield 848 mg of the desired product (48%) along with its regioisomer (513 mg, 30%).

LC-MS (method 10): $R_t$=2.18 min; MS (ESIpos): m/z=376 [M+H]$^+$

Intermediate 130

1-(cyclopropylmethyl)-3-(4-fluorophenyl)-4-methyl-1H-pyrazol-5-amine

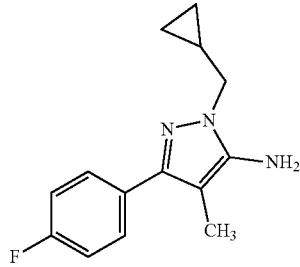 [SMILES: Cc1c(-c2ccc(F)cc2)nn(CC2CC2)c1N]

A solution of 2-[1-(cyclopropylmethyl)-3-(4-fluorophenyl)-4-methyl-1H-pyrazol-5-yl]-1H-isoindole-1,3(2H)-dione (3.70 g, 9.86 mmol) in ethanol (90 ml, 1.5 mol) was treated with hydrazine monohydrate (2.4 ml, 49 mmol). The mixture was stirred overnight at 90° C. After cooling to ambient temperature the mixture was portioned between water and ethyl acetate. The aqueous phase was extracted twice with ethyl acetate. The combined organic phase s were washed with 1.0 M aqueous sodium hydrogen carbonate solution, brine and dried over sodium sulfate. The solution was concentrated to yield the desired product (2.37 g, 96%).

LC-MS (method 9): $R_t$=0.72 min; MS (ESIpos): m/z=246 [M+H]$^+$ $^1$H-NMR (400 MHz, dimethylsulfoxide-d6) δ [ppm]: 0.330 (0.48), 0.342 (1.93), 0.346 (1.95), 0.354 (2.33), 0.357 (2.12), 0.367 (0.93), 0.411 (0.92), 0.420 (1.80), 0.424 (1.53), 0.431 (1.19), 0.440 (2.01), 0.444 (1.53), 0.456 (0.55), 1.180 (0.47), 1.188 (0.45), 1.200 (0.75), 1.212 (0.44), 1.217 (0.44), 1.975 (16.00), 3.787 (4.04), 3.804 (3.98), 4.905 (4.30), 7.164 (2.01), 7.170 (0.70), 7.181 (0.91), 7.187 (4.12), 7.192 (0.88), 7.204 (0.74), 7.209 (2.23), 7.578 (2.22), 7.584 (0.94), 7.593 (2.45), 7.601 (2.27), 7.609 (0.83), 7.615 (2.00).

Intermediate 131

1-(cyclopropylmethyl)-5-(4-fluorophenyl)-4-methyl-1H-pyrazol-3-amine

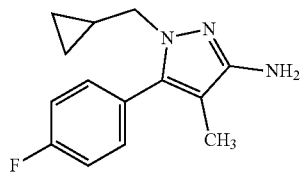 [SMILES: Cc1c(N)nn(CC2CC2)c1-c1ccc(F)cc1]

A solution of 2-[1-(cyclopropylmethyl)-3-(4-fluorophenyl)-4-methyl-1H-pyrazol-5-yl]-1H-isoindole-1,3(2H)-dione (517 mg, 1.38 mmol) in ethanol (11 ml, 180 mmol) was treated with hydrazine monohydrate (330 µl, 6.9 mmol). The mixture was stirred overnight at 90° C. After cooling to ambient temperature the mixture was portioned between water and ethyl acetate. The aqueous phase was extracted twice with ethyl acetate. The combined organic phases were washed with 1.0 M aqueous sodium hydrogen carbonate solution, brine and dried over sodium sulfate. The solution was concentrated to yield the desired product (314 mg, 77%).

LC-MS (method 10): $R_t$=1.51 min; MS (ESIpos): m/z=246 [M+H]$^+$ $^1$H-NMR (400 MHz, dimethylsulfoxide-d6) δ [ppm]: −0.019 (0.73), −0.008 (3.14), 0.018 (0.73), 0.304 (0.80), 0.315 (2.28), 0.318 (2.17), 0.324 (1.08), 0.335 (2.34), 0.350 (0.66), 0.703 (0.57), 0.721 (1.31), 0.739 (0.69), 0.941 (0.56), 0.948 (0.52), 0.961 (0.82), 0.973 (0.48), 0.978 (0.50), 1.530 (0.40), 1.728 (4.37), 1.733 (16.00), 3.317 (5.54), 3.560 (4.30), 3.577 (4.23), 3.681 (0.69), 4.483 (4.40), 7.290 (1.15), 7.312 (4.02), 7.334 (4.22), 7.339 (3.93), 7.353 (3.46), 7.360 (1.75), 7.369 (0.61), 7.375 (0.98).

Intermediate 132

2-[1-(2,2-difluoroethyl)-4-ethyl-3-(4-fluorophenyl)-1H-pyrazol-5-yl]-1H-isoindole-1,3(2H)-dione

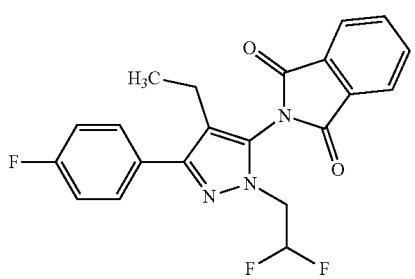 [SMILES: CCc1c(-c2ccc(F)cc2)nn(CC(F)F)c1N1C(=O)c2ccccc2C1=O]

A solution of 2-[4-ethyl-3-(4-fluorophenyl)-1H-pyrazol-5-yl]-1H-isoindole-1,3(2H)-dione (2.50 g, 7.46 mmol) in dimethylformamide (32 ml, 420 mmol) was treated with cesium carbonate (4.86 g, 14.9 mmol) and 2,2-difluoroethyl trifluoromethanesulfonate (2.0 ml, 15 mmol). The mixture was stirred overnight at ambient temperature. One additional equivalent of 2,2-difluoroethyl trifluoromethanesulfonate (0.99 mL, 7.45 mmol) was added and the mixture was again stirred at ambient temperature for 4 hours. The mixture was portioned between water and ethyl acetate. The organic phase was washed with water and brine, dried over sodium sulfate. The solvent was removed under reduced pressure and the crude product was purified by flash chromatography on silica gel (dichloromethane/ethyl acetate 60:1, Biotage SNAP Ultra 50 g) to yield 1.20 g of the desired product (40%) along with its regioisomer (655 mg, 22%).

LC-MS (method 10): $R_t$=2.12 min; MS (ESIpos): m/z=400 [M+H]$^+$ $^1$H-NMR (400 MHz, dimethylsulfoxide-d6) δ [ppm]: 0.897 (7.24), 0.916 (16.00), 0.935 (7.14), 2.074 (2.49), 2.441 (2.14), 2.460 (6.26), 2.478 (6.48), 2.524 (0.73), 4.572 (2.02), 4.581 (2.17), 4.608 (4.05), 4.618 (4.02), 4.645 (2.03), 4.654 (1.80), 6.109 (0.67), 6.119 (1.32), 6.128 (0.57), 6.246 (1.28), 6.256 (2.65), 6.265 (1.20), 6.384 (0.59), 6.393 (1.21), 6.403 (0.59), 7.293 (4.33), 7.316 (8.52), 7.338 (4.46), 7.706 (5.02), 7.712 (2.39), 7.720 (5.50), 7.728 (4.92), 7.737 (2.02), 7.742 (4.22), 7.966 (0.87), 7.975 (5.05), 7.982 (5.52), 7.988 (5.61), 7.996 (7.71), 8.006 (1.29), 8.042 (1.54), 8.052 (8.33), 8.059 (5.73), 8.066 (5.45), 8.073 (4.65), 8.082 (0.42).

Intermediate 133

2-[1-(2,2-difluoroethyl)-4-ethyl-5-(4-fluorophenyl)-1H-pyrazol-3-yl]-1H-isoindole-1,3(2H)-dione

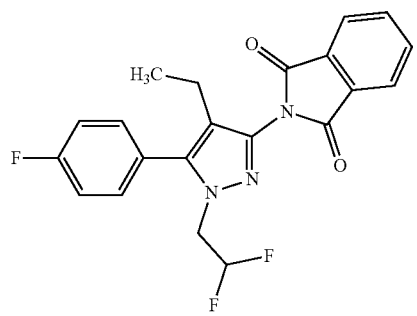 [SMILES: CCc1c(N2C(=O)c3ccccc3C2=O)nn(CC(F)F)c1-c1ccc(F)cc1]

A solution of 2-[4-ethyl-3-(4-fluorophenyl)-1H-pyrazol-5-yl]-1H-isoindole-1,3(2H)-dione (2.50 g, 7.46 mmol) in dimethylformamide (32 ml, 420 mmol) was treated with cesium carbonate (4.86 g, 14.9 mmol) and 2,2-difluoroethyl trifluoromethanesulfonate (2.0 ml, 15 mmol). The mixture was stirred overnight at ambient temperature. One additional equivalent of 2,2-difluoroethyl trifluoromethanesulfonate (0.99 mL, 7.45 mmol) was added and the mixture was again stirred at ambient temperature for 4 hours. The mixture was portioned between water and ethyl acetate. The organic phase was washed with water and brine, dried over sodium sulfate. The solvent was removed under reduced pressure and the crude product was purified by flash chromatography on silica gel (dichloromethane/ethyl acetate 60:1, Biotage SNAP Ultra 50 g) to yield 655 mg of the desired product (22%) along with its regioisomer (1.20 g, 40%).

LC-MS (method 10): $R_t$=2.08 min; MS (ESIpos): m/z=400 [M+H]$^+$

Intermediate 134

1-(2,2-difluoroethyl)-4-ethyl-3-(4-fluorophenyl)-1H-pyrazol-5-amine

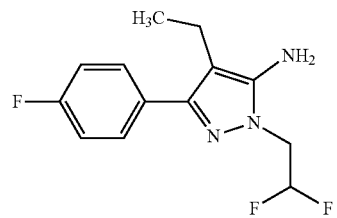 [SMILES: CCc1c(-c2ccc(F)cc2)nn(CC(F)F)c1N]

A solution of 2-[1-(2,2-difluoroethyl)-4-ethyl-3-(4-fluorophenyl)-1H-pyrazol-5-yl]-1H-isoindole-1,3(2H)-dione (1.20 g, 3.00 mmol) in ethanol (20 ml, 340 mmol) was treated with hydrazine monohydrate (730 μl, 15 mmol). The mixture was stirred overnight at 90° C. After cooling to ambient temperature the mixture was portioned between water and ethyl acetate. The aqueous phase was extracted twice with ethyl acetate. The combined organic phases were washed with 1.0 M aqueous sodium hydrogen carbonate solution, brine and dried over sodium sulfate. The solution was concentrated to yield the desired product (800 mg, 98%).

LC-MS (method 10): $R_t$=1.62 min; MS (ESIpos): m/z=270 [M+H]$^+$ $^1$H-NMR (400 MHz, dimethylsulfoxide-d6) δ [ppm]: 0.981 (7.32), 0.999 (16.00), 1.018 (7.26), 2.428 (6.81), 2.446 (6.56), 2.465 (2.20), 4.355 (2.48), 4.366 (2.63), 4.391 (4.85), 4.402 (4.81), 4.427 (2.47), 4.438 (2.23), 5.147 (11.45), 6.147 (0.71), 6.158 (1.40), 6.169 (0.64), 6.286 (1.39), 6.297 (2.80), 6.307 (1.30), 6.425 (0.66), 6.435 (1.32), 6.446 (0.64), 7.190 (4.22), 7.212 (8.47), 7.234 (4.56), 7.549 (5.25), 7.554 (2.68), 7.563 (6.04), 7.571 (5.38), 7.585 (4.46).

Intermediate 135

1-(2,2-difluoroethyl)-4-ethyl-5-(4-fluorophenyl)-1H-pyrazol-3-amine

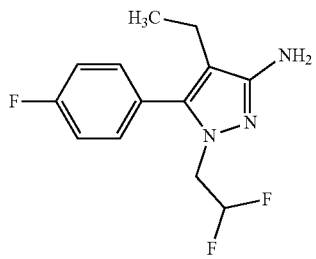 [SMILES: CCc1c(N)nn(CC(F)F)c1-c1ccc(F)cc1]

A solution of 2-[1-(2,2-difluoroethyl)-4-ethyl-5-(4-fluorophenyl)-1H-pyrazol-3-yl]-1H-isoindole-1,3(2H)-dione (655 mg, 1.64 mmol) in ethanol (10 ml, 170 mmol) was treated with hydrazine monohydrate (400 µl, 8.2 mmol). The mixture was stirred overnight at 90° C. After cooling to ambient temperature the mixture was portioned between water and ethyl acetate. The aqueous phase was extracted twice with ethyl acetate. The combined organic phases were washed with 1.0 M aqueous sodium hydrogen carbonate solution, brine and dried over sodium sulfate. The solution was concentrated to yield the desired product (470 mg, quant.).

LC-MS (method 10): $R_t$=1.69 min; MS (ESIpos): m/z=270 [M+H]$^+$ $^1$H-NMR (400 MHz, dimethylsulfoxide-d6) δ [ppm]: −0.008 (0.58), 0.894 (4.65), 0.913 (10.80), 0.932 (4.95), 2.151 (1.41), 2.170 (4.35), 2.189 (4.24), 2.207 (1.30), 3.992 (1.41), 4.002 (1.50), 4.028 (2.87), 4.038 (2.88), 4.063 (1.44), 4.074 (1.33), 4.670 (5.64), 6.021 (0.42), 6.031 (0.89), 6.159 (0.82), 6.170 (1.79), 6.180 (0.82), 6.309 (0.86), 6.319 (0.41), 7.310 (0.44), 7.319 (0.44), 7.334 (9.33), 7.353 (16.00).

Intermediate 136 ethyl 4-chloro-1-(6-chloropyrimidin-4-yl)-3-methyl-1H-pyrazole-5-carboxylate

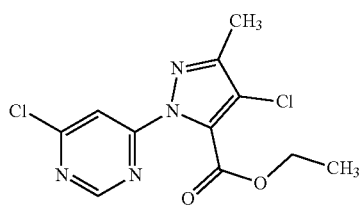 [SMILES: CCOC(=O)c1c(Cl)c(C)nn1-c1cc(Cl)ncn1]

A solution of ethyl 1-(6-chloropyrimidin-4-yl)-3-methyl-1H-pyrazole-5-carboxylate (480 mg, 1.80 mmol) in acetonitrile (8.8 ml, 170 mmol) was treated with 1-chloropyrrolidine-2,5-dione (288 mg, 2.16 mmol). The mixture was stirred 2 days at ambient temperature. Water was added and the mixture was extracted with ethyl acetate (3×). The combined organic phases were washed with water and brine, dried over sodium sulfate and concentrated under reduced pressure. The crude product was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 240 mg of the desired product (63%).

LC-MS (method 10): $R_t$=2.21 min; MS (ESIpos): m/z=301 [M+H]$^+$ $^1$H-NMR (400 MHz, dimethylsulfoxide-d6) δ [ppm]: −0.008 (2.12), 0.008 (1.07), 1.240 (4.60), 1.258 (9.37), 1.276 (4.53), 2.322 (16.00), 2.524 (0.58), 4.359 (1.55), 4.377 (4.54), 4.395 (4.45), 4.413 (1.41), 8.008 (3.31), 8.947 (3.50).

Intermediate 137

2-[1-(cyclobutylmethyl)-4-ethyl-3-(4-fluorophenyl)-1H-pyrazol-5-yl]-1H-isoindole-1,3(2H)-dione

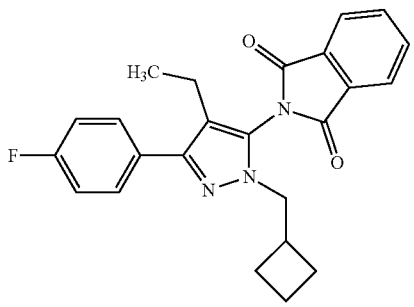 [SMILES: CCc1c(-c2ccc(F)cc2)nn(CC2CCC2)c1N1C(=O)c2ccccc2C1=O]

A solution of 2-[4-ethyl-3-(4-fluorophenyl)-1H-pyrazol-5-yl]-1H-isoindole-1,3(2H)-dione (2.00 g, 5.96 mmol) in dimethylformamide (26 ml, 340 mmol) was treated with cesium carbonate (3.89 g, 11.9 mmol) and (bromomethyl)cyclobutane (1.78 g, 11.9 mmol). The mixture was stirred overnight at ambient temperature. The mixture was diluted with water and extracted with ethyl acetate (3×). The combined organic phase s were washed with water and brine and dried over sodium sulfate. The crude product was purified using flash chromatography on silica gel (method: column: Biotage Snap Ultra 25 g/flow: 75 mL/min./solvent=dichloromethane (100%)) to obtain 904 mg of the desired product together with its regioisomer (320 mg, 13%).

LC-MS (method 10): $R_t$=2.44 min; MS (ESIpos): m/z=404 [M+H]$^+$

¹H-NMR (400 MHz, dimethylsulfoxide-d6) δ [ppm]: −0.008 (1.48), 0.008 (1.25), 0.889 (6.83), 0.908 (16.00), 0.926 (7.12), 1.710 (0.71), 1.716 (0.91), 1.732 (3.35), 1.744 (7.41), 1.752 (6.01), 1.758 (4.72), 1.761 (4.97), 1.774 (1.98), 1.791 (1.33), 1.798 (0.89), 1.817 (0.66), 1.864 (0.41), 1.879 (0.81), 1.892 (1.58), 1.903 (2.64), 1.908 (2.20), 1.918 (2.75), 1.924 (3.44), 1.934 (1.06), 1.938 (0.99), 1.948 (0.42), 2.074 (0.94), 2.406 (1.88), 2.425 (5.83), 2.443 (5.71), 2.462 (1.77), 2.524 (0.45), 2.691 (0.47), 2.710 (1.26), 2.729 (1.39), 2.742 (0.92), 2.747 (1.08), 2.766 (0.55), 4.001 (8.81), 4.019 (8.63), 7.267 (4.04), 7.289 (8.37), 7.306 (1.57), 7.311 (4.50), 7.318 (0.51), 7.672 (0.59), 7.680 (4.66), 7.685 (2.06), 7.694 (5.15), 7.702 (4.86), 7.710 (1.87), 7.716 (4.23), 7.723 (0.49), 7.973 (0.51), 7.982 (4.84), 7.989 (5.33), 7.996 (5.39), 8.003 (7.88), 8.013 (1.20), 8.049 (1.15), 8.059 (8.02), 8.067 (5.27), 8.073 (5.36), 8.081 (4.66), 8.090 (0.40).

Intermediate 138

1-(cyclobutylmethyl)-4-ethyl-3-(4-fluorophenyl)-1H-pyrazol-5-amine

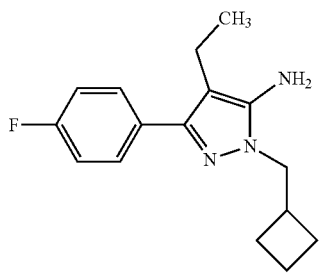 [SMILES: CCc1c(-c2ccc(F)cc2)nn(CC2CCC2)c1N]

A solution of 2-[1-(cyclobutylmethyl)-4-ethyl-3-(4-fluorophenyl)-1H-pyrazol-5-yl]-1H-isoindole-1,3(2H)-dione (900 mg, 2.23 mmol) in ethanol (280 ml, 4.8 mol) was treated with hydrazine monohydrate (540 µl, 11 mmol) and stirred overnight at 90° C. After cooling to ambient temperature the mixture was diluted with water and extracted three times with ethyl acetate. The combined organic phases were washed with 1M aqueous sodium hydrogen carbonate solution and brine, dried over sodium sulfate and concentrated under reduced pressure to yield the desired product (578 mg, 85%).

LC-MS (method 10): $R_t$=1.72 min; MS (ESIpos): m/z=274 [M+H]⁺

¹H-NMR (400 MHz, dimethylsulfoxide-d6) δ [ppm]: 0.976 (7.30), 0.995 (16.00), 1.013 (7.27), 1.049 (0.65), 1.068 (1.28), 1.087 (0.59), 1.772 (1.10), 1.780 (1.99), 1.798 (4.84), 1.816 (8.42), 1.825 (7.95), 1.840 (3.63), 1.851 (1.37), 1.858 (1.67), 1.867 (1.09), 1.888 (0.45), 1.908 (0.72), 1.934 (1.93), 1.945 (3.44), 1.950 (4.10), 1.966 (3.26), 2.002 (0.42), 2.397 (2.32), 2.415 (6.73), 2.434 (6.53), 2.453 (2.17), 2.575 (0.51), 2.689 (0.64), 2.707 (1.45), 2.724 (1.79), 2.745 (1.31), 2.764 (0.71), 3.910 (9.91), 3.928 (9.51), 4.102 (0.80), 4.120 (0.68), 4.892 (11.01), 7.160 (4.17), 7.182 (8.34), 7.204 (4.52), 7.236 (0.40), 7.258 (0.79), 7.280 (0.50), 7.523 (0.96), 7.530 (5.29), 7.536 (2.55), 7.545 (6.07), 7.552 (5.51), 7.561 (2.58), 7.566 (5.07), 7.629 (0.79), 7.636 (0.43), 7.644 (0.66), 7.651 (0.59), 7.666 (0.46), 10.085 (0.49).

Intermediate 139

4-[5-(1,3-dioxo-1,3-dihydro-2H-isoindol-2-yl)-4-methyl-1H-pyrazol-3-yl]benzonitrile

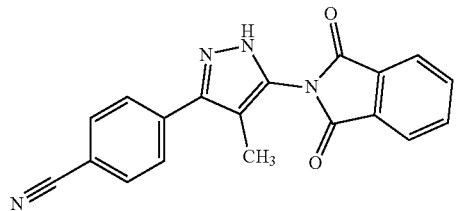 [SMILES: Cc1c(-c2ccc(C#N)cc2)n[nH]c1N1C(=O)c2ccccc2C1=O]

4-(5-amino-4-methyl-1H-pyrazol-3-yl)benzonitrile (6.80 g, 34.3 mmol) and 2-benzofuran-1,3-dione (7.62 g, 51.5 mmol) were suspended in acetic acid (150 mL) and the reaction mixture was heated to 120° C. bath temperature overnight. After cooling to ambient temperature, methyl tert-butylether was added and the precipitated solid collected by filtration, further washed with methyl tert-butylether and dried under high vacuum overnight and further in a drying oven under vacuum at 40° C. to yield the desired product (11.7 g, 104% yield, contained 24% AcOH based on NMR).

LC-MS (method 10): $R_t$=1.60 min; MS (ESIpos): m/z=329 [M+H]⁺

¹H-NMR (400 MHz, dimethylsulfoxide-d6) δ [ppm]: −0.008 (1.62), 0.008 (1.32), 1.909 (12.37), 2.059 (16.00), 2.367 (0.43), 2.524 (1.09), 2.711 (0.42), 7.842 (4.06), 7.863 (5.29), 7.945 (2.96), 7.953 (3.62), 7.959 (3.95), 7.967 (5.31), 7.976 (1.61), 8.002 (6.36), 8.008 (6.35), 8.022 (7.34), 13.648 (3.22).

Intermediate 140

4-[5-(1,3-dioxo-1,3-dihydro-2H-isoindol-2-yl)-1,4-dimethyl-1H-pyrazol-3-yl]benzonitrile as mixture with 4-[3-(1,3-dioxo-1,3-dihydro-2H-isoindol-2-yl)-1,4-dimethyl-1H-pyrazol-5-yl]benzonitrile

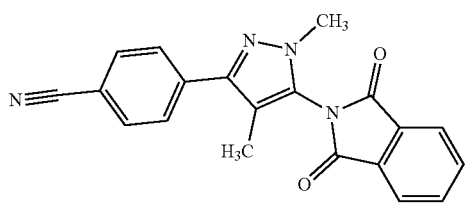

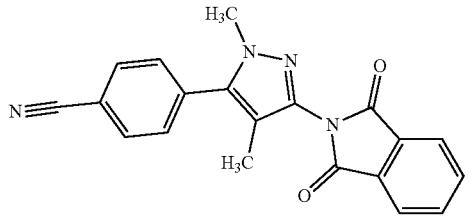

A solution of 4-[3-(1,3-dioxo-1,3-dihydro-2H-isoindol-2-yl)-4-methyl-1H-pyrazol-5-yl]benzonitrile (14.1 g, 42.9 mmol) in dimethylformamide (140 ml, 1.8 mol) was treated with cesium carbonate (27.9 g, 85.8 mmol) and iodomethane (5.3 ml, 86 mmol) at −20° C. The mixture was allowed to warm up to ambient temperature and stirred for 2 hours. The mixture was diluted with water and extracted with ethyl acetate (3×). The combined organic phase s were washed with water (2×), brine and dried over sodium sulfate. Separation of the regioisomers was partially possible by titration with acetonitrile: 1.52 g (8%, 92% pure) of pure 4-[3-(1,3-dioxo-1,3-dihydro-2H-isoindol-2-yl)-1,4-dimethyl-1H-pyrazol-5-yl]benzonitrile 0.19 g (1%) of pure -[5-(1,3-dioxo-1,3-dihydro-2H-isoindol-2-yl)-1,4-dimethyl-1H-pyrazol-3-yl]benzonitrile and 5.75 g (31%) of the regioisomeric mixture were obtained.

LC-MS (method 11, 4-[3-(1,3-dioxo-1,3-dihydro-2H-isoindol-2-yl)-1,4-dimethyl-1H-pyrazol-5-yl]benzonitrile): $R_t$=1.23 min; MS (ESIpos): m/z=343 [M+H]$^+$ LC-MS (method 11, 4-[5-(1,3-dioxo-1,3-dihydro-2H-isoindol-2-yl)-1,4-dimethyl-1H-pyrazol-3-yl]benzonitrile): $R_t$=1.29 min; MS (ESIpos): m/z=343 [M+H]$^+$ Intermediate 141

4-(5-amino-1,4-dimethyl-1H-pyrazol-3-yl)benzonitrile

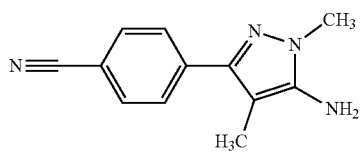 [SMILES: Cc1c(-c2ccc(C#N)cc2)nn(C)c1N]

A solution of 4-[5-(1,3-dioxo-1,3-dihydro-2H-isoindol-2-yl)-1,4-dimethyl-1H-pyrazol-3-yl]benzonitrile/4-[3-(1,3-dioxo-1,3-dihydro-2H-isoindol-2-yl)-1,4-dimethyl-1H-pyrazol-5-yl]benzonitrile approx. 1:1 (5.85 g, 17.1 mmol) in ethanol (150 ml, 2.6 mol) was treated with hydrazine monohydrate (4.2 ml, 85 mmol). The mixture was refluxed for 2.5 hours. After cooling to room temperature the mixture was diluted with water and extracted with ethyl acetate (3×). The combined organic phase s were washed with 1M aqueous sodium hydrogen carbonate solution, brine, dried over sodium sulfate and concentrated under reduced pressure. 3.2 g of the regioisomeric mixture were separated into the regioisomers (column: Chiralpak IG, 5 µM, 250×20 mm, flow: 15 mL/min, n-heptane/ethanol 30/70) to yield 2.30 g of the desired product (63%) together with its regioisomer (680 mg, 19%).

LC-MS (method 11): $R_t$=0.85 min; MS (ESIpos): m/z=213 [M+H]$^+$ $^1$H-NMR (500 MHz, dimethylsulfoxide-d6) δ [ppm]: 2.066 (11.06), 3.422 (0.66), 5.091 (3.28), 7.810 (16.00).

Intermediate 142

4-(3-amino-1,4-dimethyl-1H-pyrazol-5-yl)benzonitrile

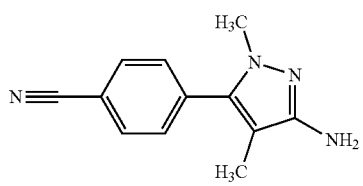 [SMILES: Cc1c(N)nn(C)c1-c1ccc(C#N)cc1]

A solution of 4-[5-(1,3-dioxo-1,3-dihydro-2H-isoindol-2-yl)-1,4-dimethyl-1H-pyrazol-3-yl]benzonitrile/4-[3-(1,3-dioxo-1,3-dihydro-2H-isoindol-2-yl)-1,4-dimethyl-1H-pyrazol-5-yl]benzonitrile approx. 1:1 (5.85 g, 17.1 mmol) in ethanol (150 ml, 2.6 mol) was treated with hydrazine monohydrate (4.2 ml, 85 mmol). The mixture was refluxed for 2.5 hours. After cooling to room temperature the mixture was diluted with water and extracted with ethyl acetate (3×). The combined organic phase s were washed with 1M aqueous sodium hydrogen carbonate solution, brine, dried over sodium sulfate and concentrated under reduced pressure. 3.2 g of the regioisomeric mixture were separated into the regioisomers (column: Chiralpak IG, 5 µM, 250×20 mm, flow: 15 mL/min, n-heptane/ethanol 30/70) to yield 680 mg of the desired product (19%) together with its regioisomer (2.30 g, 63%).

LC-MS (method 11): $R_t$=0.82 min; MS (ESIpos): m/z=213 [M+H]$^+$ $^1$H-NMR (500 MHz, dimethylsulfoxide-d6) δ [ppm]: 1.818 (16.00), 2.091 (0.42), 3.367 (2.38), 4.572 (4.39), 7.571 (4.29), 7.575 (1.55), 7.584 (1.73), 7.588 (4.52), 7.591 (0.88), 7.946 (1.05), 7.949 (4.66), 7.953 (1.57), 7.963 (1.63), 7.966 (4.13), 7.970 (0.75).

Intermediate 143

4-(3,5-dimethyl-4-nitro-1H-pyrazol-1-yl)benzonitrile

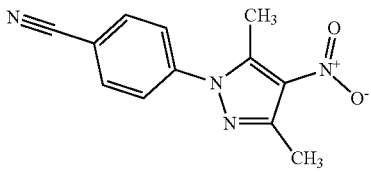 [SMILES: Cc1nn(-c2ccc(C#N)cc2)c(C)c1[N+](=O)[O-]]

A solution of 3,5-dimethyl-4-nitro-1H-pyrazole (5.00 g, 35.4 mmol) and (4-cyanophenyl)boronic acid (5.21 g, 35.4 mmol) in dichloromethane (50 ml, 780 mmol) was treated with anhydrous cupric acetate (9.65 g, 53.1 mmol), pyridine (29 ml, 350 mmol) and molecular sieves (7.93 g). The mixture was stirred under an argon atmosphere at ambient temperature for 2 days. The mixture was filtered over a pad of kieselgur, the remaining filter cake was washed with dichloromethane. The filtrate was washed with water, dried over sodium sulfate and concentrated under reduced pressure. The crude product was purified by flash-chromatography on silica gel (dichloromethane/ethyl acetate 40:1, column: SNAP Ultra 100 g) to yield 2.60 g (30%) of the desired product.

LC-MS (method 9): $R_t$=0.88 min; MS (ESIpos): m/z=243 [M+H]$^+$ $^1$H-NMR (400 MHz, dimethylsulfoxide-d6) δ [ppm]: 2.625 (16.00), 7.797 (0.49), 7.802 (3.48), 7.807 (1.24), 7.819 (1.33), 7.824 (4.13), 7.829 (0.63), 8.076 (0.59), 8.081 (3.97), 8.086 (1.28), 8.098 (1.17), 8.103 (3.35), 8.109 (0.49).

Intermediate 144

4-(4-amino-3,5-dimethyl-1H-pyrazol-1-yl)benzonitrile

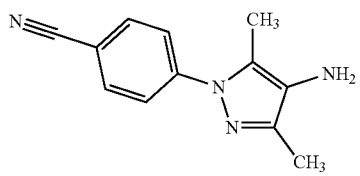 [SMILES: Cc1nn(-c2ccc(C#N)cc2)c(C)c1N]

A solution of 4-(3,5-dimethyl-4-nitro-1H-pyrazol-1-yl)benzonitrile (2.60 g, 10.7 mmol) in methanol (100 ml) was treated with aqueous hydrochloric acid (20 ml, 12 M, 240 mmol) and iron (3.00 g, 53.7 mmol). The mixture was refluxed for 2 hours. The reaction mixture was filtered. The filtrate was neutralized with saturated aqueous sodium hydrogen carbonate solution an extracted with ethyl acetate (3×). The combined organic phases were washed with saturated aqueous sodium hydrogen carbonate solution, brine, dried over sodium sulfate and concentrated under reduced pressure to yield 1.70 g (63%) of the desired product.

LC-MS (method 10): $R_t$=0.73 min; MS (ESIpos): m/z=213 [M+H]$^+$ $^1$H-NMR (400 MHz, dimethylsulfoxide-d6) δ [ppm]: 2.074 (0.73), 2.107 (16.00), 2.283 (14.84), 2.409 (0.41), 3.848 (1.72), 3.858 (2.53), 7.613 (0.43), 7.634 (0.45), 7.663 (3.45), 7.685 (4.10), 7.858 (3.83), 7.879 (3.01), 7.988 (0.63), 8.009 (0.44).

Intermediate 145

4-(3-amino-4-ethyl-1H-pyrazol-5-yl)benzonitrile

A solution of 4-(2-cyanobutanoyl)benzonitrile (3.88 g, 19.5 mmol) in ethanol (50 ml, 860 mmol) was treated with hydrazine hydrate (1:1) (1.1 ml, 23 mmol) and refluxed overnight. After cooling to ambient temperature the mixture was diluted with saturated sodium hydrogen carbonate solution. Ethanol was removed under reduced pressure, the occurring precipitate was collected by filtration, washed with water and dried to yield the desired product (4.06 g, 98%).

LC-MS (method 10): $R_t$=1.09 min; MS (ESIpos): m/z=213 [M+H]$^+$ $^1$H-NMR (400 MHz, dimethylsulfoxide-d6) δ [ppm]: 1.022 (8.30), 1.040 (16.00), 1.058 (7.78), 2.452 (3.40), 2.470 (8.84), 2.489 (9.63), 4.650 (1.64), 7.695 (5.47), 7.713 (6.04), 7.859 (7.60), 7.878 (5.87), 11.790 (2.67).

Intermediate 146

4-[3-(1,3-dioxo-1,3-dihydro-2H-isoindol-2-yl)-4-ethyl-1H-pyrazol-5-yl]benzonitrile

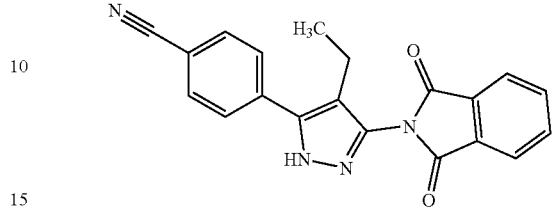

4-(3-amino-4-ethyl-1H-pyrazol-5-yl)benzonitrile (3.00 g, 14.1 mmol) and 2-benzofuran-1,3-dione (3.14 g, 21.2 mmol) were treated with acetic acid (25 ml, 440 mmol) and stirred overnight at 140° C. After cooling to ambient temperature the mixture was diluted with water. The occurring precipitate was collected by filtration, washed with water and dried to yield 4.92 g (98%) of the desired product.

LC-MS (method 10): $R_t$=1.88 min; MS (ESIpos): m/z=343 [M+H]$^+$ $^1$H-NMR (400 MHz, dimethylsulfoxide-d6) δ [ppm]: 0.950 (5.55), 0.968 (11.73), 0.987 (5.71), 1.919 (16.00), 7.833 (3.92), 7.853 (4.73), 7.960 (3.84), 7.968 (5.02), 7.974 (5.60), 7.981 (6.07), 7.992 (2.28), 8.006 (5.09), 8.027 (9.40), 8.048 (3.51), 13.656 (1.36).

Intermediate 147

4-[3-(1,3-dioxo-1,3-dihydro-2H-isoindol-2-yl)-4-ethyl-1-methyl-1H-pyrazol-5-yl]benzonitrile

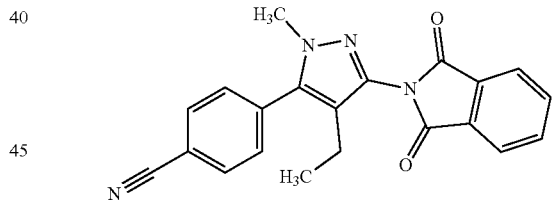

A solution of 4-[5-(1,3-dioxo-1,3-dihydro-2H-isoindol-2-yl)-4-ethyl-1H-pyrazol-3-yl]benzonitrile (2.00 g, 5.84 mmol) in dimethylformamide (10 ml) was treated with cesium carbonate (3.81 g, 11.7 mmol) and iodomethane (1.1 ml, 18 mmol). The mixture was stirred overnight. The mixture was diluted with water and extracted with ethyl acetate (3×). The combined organic phases were washed with water (2×), brine and dried over sodium sulfate. The crude product was purified using flash-chromatography on silica gel (SNAP Ultra 50 g, dichloromethane/ethyl acetate) to obtain 480 mg of the desired product (23%) together with its regioisomer (650.5 mg, 31%).

LC-MS (method 9): $R_t$=0.98 min; MS (ESIpos): m/z=357 [M+H]$^+$ $^1$H-NMR (500 MHz, dimethylsulfoxide-d6) δ [ppm]: 0.811 (7.18), 0.826 (16.00), 0.842 (7.14), 1.178 (0.70), 1.992 (1.39), 2.260 (1.84), 2.275 (5.58), 2.290 (5.42), 2.305 (1.67), 3.331 (9.52), 7.768 (7.97), 7.772 (2.87), 7.782 (3.27), 7.785 (8.91), 7.945 (0.40), 7.948 (0.56), 7.955 (5.16), 7.961 (5.42), 7.966 (5.11), 7.972 (7.75), 7.980 (1.11), 8.012 (1.01), 8.013 (1.13), 8.021 (8.29), 8.027 (5.63), 8.032 (6.59), 8.037 (11.96), 8.046 (1.03), 8.050 (3.10), 8.054 (7.88).

Intermediate 148

4-[5-(1,3-dioxo-1,3-dihydro-2H-isoindol-2-yl)-4-ethyl-1-methyl-1H-pyrazol-3-yl]benzonitrile

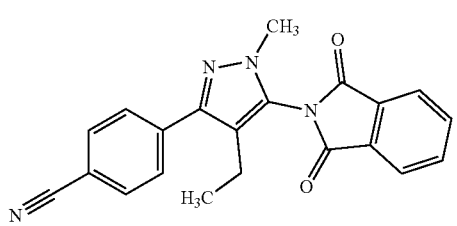 [SMILES: CCc1c(-c2ccc(C#N)cc2)nn(C)c1N1C(=O)c2ccccc2C1=O]

A solution of 4-[5-(1,3-dioxo-1,3-dihydro-2H-isoindol-2-yl)-4-ethyl-1H-pyrazol-3-yl]benzonitrile (2.00 g, 5.84 mmol) in dimethylformamide (10 ml, 130 mmol) was treated with cesium carbonate (3.81 g, 11.7 mmol) and iodomethane (1.1 ml, 18 mmol). The mixture was stirred overnight. The mixture was diluted with water and extracted with ethyl acetate (3×). The combined organic phases were washed with water (2×), brine and dried over sodium sulfate. The crude product was purified using flash-chromatography on silica gel (SNAP Ultra 50 g, dichloromethane/ethyl acetate) to obtain 650.5 mg of the desired product (31%) together with its regioisomer (480 mg, 23%).

LC-MS (method 9): $R_t$=1.03 min; MS (ESIpos): m/z=357 [M+H]$^+$

Intermediate 149

4-(5-amino-4-ethyl-1-methyl-1H-pyrazol-3-yl)benzonitrile

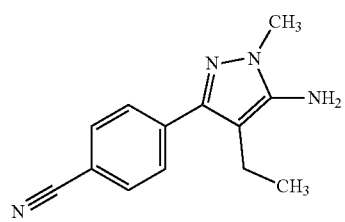 [SMILES: CCc1c(-c2ccc(C#N)cc2)nn(C)c1N]

A solution of 4-[5-(1,3-dioxo-1,3-dihydro-2H-isoindol-2-yl)-4-ethyl-1-methyl-1H-pyrazol-3-yl]benzonitrile (643 mg, 1.80 mmol) in ethanol (6.5 ml, 110 mmol) was treated with hydrazine monohydrate (440 µl, 9.0 mmol) and stirred at 90° C. overnight. After cooling to ambient temperature the mixture was diluted with saturated sodium hydrogen carbonate solution and extracted with ethyl acetate (3×). The combined organic phases were washed with saturated sodium hydrogen carbonate solution and brine, dried over sodium sulfate and concentrated under reduced pressure to yield 379 mg (93%) of the desired product.

LC-MS (method 10): $R_t$=1.29 min; MS (ESIpos): m/z=227 [M+H]$^+$ $^1$H-NMR (400 MHz, dimethylsulfoxide-d6) δ [ppm]: −0.010 (1.29), 0.991 (5.70), 1.010 (12.56), 1.028 (6.32), 2.460 (1.99), 2.478 (5.79), 3.324 (16.00), 5.059 (12.12), 7.726 (5.57), 7.746 (10.37), 7.794 (8.73), 7.814 (5.21).

Intermediate 150

4-(3-amino-4-ethyl-1-methyl-1H-pyrazol-5-yl)benzonitrile

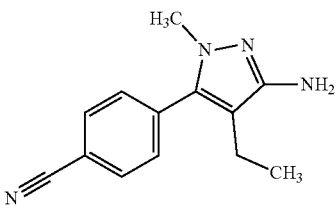 [SMILES: CCc1c(N)nn(C)c1-c1ccc(C#N)cc1]

A solution of 4-[3-(1,3-dioxo-1,3-dihydro-2H-isoindol-2-yl)-4-ethyl-1-methyl-1H-pyrazol-5-yl]benzonitrile (475 mg, 1.33 mmol) in ethanol (5.0 ml, 86 mmol) was treated with hydrazine monohydrate (320 µl, 6.7 mmol) and stirred at 90° C. overnight. After cooling to ambient temperature the mixture was diluted with saturated sodium hydrogen carbonate solution and extracted with ethyl acetate (3×). The combined organic phases were washed with saturated sodium hydrogen carbonate solution and brine, dried over sodium sulfate and concentrated under reduced pressure to yield 255 mg (83%) of the desired product.

LC-MS (method 10): $R_t$=1.24 min; MS (ESIpos): m/z=227 [M+H]$^+$ $^1$H-NMR (400 MHz, dimethylsulfoxide-d6) δ [ppm]: 0.919 (7.41), 0.937 (16.00), 0.956 (7.96), 0.999 (0.66), 2.204 (2.59), 2.222 (7.39), 2.241 (7.20), 2.259 (2.43), 3.330 (14.88), 3.506 (0.62), 3.539 (0.73), 3.556 (0.43), 4.526 (13.13), 7.544 (8.74), 7.564 (9.27), 7.945 (8.78), 7.965 (7.83).

Intermediate 151

4-[cyano(methoxy)acetyl]benzonitrile

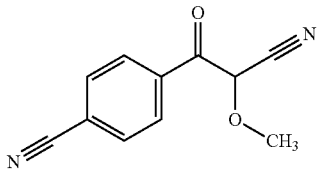

A solution of ethyl 4-cyanobenzoate (10.0 g, 57.1 mmol) and methoxyacetonitrile (8.5 ml, 110 mmol) in tetrahydrofuran (150 ml, 1.8 mol) was treated with bis-(trimethylsilyl)-lithiumamid, 1.0 M solution in tetrahydrofuran (120 ml, 1.0 M, 120 mmol). The mixture was stirred overnight at ambient temperature. The mixture was poured into water and extracted with ethyl acetate. The aqueous phase was acidified with aqueous hydrochloric acid and extracted with dichloromethane (2×). The combined organic phases were washed with water, dried over sodium sulfate and concentrated under reduced pressure to yield 9.20 g of the desired product (52%).

LC-MS (method 9): $R_t$=0.72 min; MS (ESIneg): m/z=199 [M−H]$^-$

¹H-NMR (400 MHz, dimethylsulfoxide-d6) δ [ppm]: −0.008 (1.01), 0.008 (1.08), 1.909 (0.77), 2.524 (0.82), 3.246 (1.44), 3.291 (1.02), 3.320 (10.48), 3.347 (0.79), 3.353 (0.58), 3.378 (0.70), 3.385 (0.60), 3.401 (2.69), 3.451 (0.44), 3.488 (3.57), 3.510 (4.28), 3.565 (12.46), 3.629 (0.45), 3.716 (0.62), 3.727 (1.69), 3.757 (0.90), 3.780 (4.13), 3.935 (9.19), 4.364 (0.70), 5.081 (0.81), 5.217 (1.07), 6.353 (1.33), 7.746 (0.90), 7.762 (3.33), 7.767 (2.22), 7.783 (3.82), 7.810 (11.32), 7.815 (4.74), 7.827 (5.10), 7.832 (16.00), 7.925 (3.07), 7.930 (1.44), 7.940 (15.74), 7.945 (7.05), 7.957 (4.40), 7.962 (11.09), 7.972 (4.40), 7.989 (2.33), 7.994 (6.36), 7.998 (2.80), 8.010 (1.80), 8.020 (1.51), 8.040 (0.74), 8.065 (1.96), 8.073 (5.63), 8.078 (2.16), 8.081 (1.54), 8.087 (3.66), 8.095 (3.83), 8.113 (1.60), 8.135 (0.62), 8.153 (2.44), 8.175 (1.49), 8.653 (1.00), 8.691 (0.86), 8.739 (0.68), 11.168 (4.18), 13.561 (0.42).

Intermediate 152

4-(3-amino-4-methoxy-1H-pyrazol-5-yl)benzonitrile

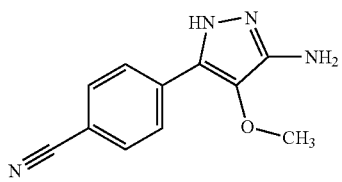 [SMILES: COc1c(N)n[nH]c1-c1ccc(C#N)cc1]

A solution of 4-[cyano(methoxy)acetyl]benzonitrile (9.20 g, 46.0 mmol) in ethanol (340 ml, 5.9 mol) was treated with hydrazine hydrate (1:1) (4.5 ml, 92 mmol) and refluxed for 2 hours. After cooling to ambient temperature the mixture was diluted with saturated sodium hydrogen carbonate solution. Ethanol was removed under reduced pressure, the remaining was diluted with water and extracted with ethyl acetate (2×). The combined organic phases were washed with brine, dried over sodium sulfate and concentrated under reduced pressure to yield 5.88 g (58%) of the desired product.

LC-MS (method 9): $R_t$=0.56 min; MS (ESIpos): m/z=215 [M+H]⁺

¹H-NMR (400 MHz, dimethylsulfoxide-d6) δ [ppm]: 1.175 (0.57), 1.195 (0.49), 1.252 (0.54), 1.989 (0.93), 3.196 (0.63), 3.335 (0.54), 3.633 (1.24), 3.641 (2.48), 3.666 (16.00), 3.762 (1.92), 4.655 (1.34), 4.906 (0.49), 7.414 (0.54), 7.435 (0.57), 7.558 (0.71), 7.580 (0.89), 7.660 (0.50), 7.665 (0.41), 7.682 (0.73), 7.687 (0.51), 7.727 (1.01), 7.749 (1.07), 7.754 (1.20), 7.771 (0.87), 7.776 (0.96), 7.879 (4.77), 7.909 (4.01), 7.928 (3.65), 7.951 (2.99), 7.959 (2.90), 8.008 (0.84), 8.029 (0.44), 9.784 (0.51), 11.899 (1.21).

Intermediate 153

3-{[6-(3,5-dimethyl-1H-pyrazol-1-yl)pyrimidin-4-yl]amino}-5-(4-fluorophenyl)-1-methyl-1H-pyrazole-4-carbaldehyde

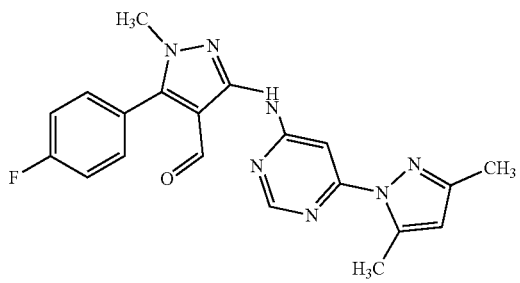 [SMILES: Cc1cc(C)n(-c2cc(Nc3nn(C)c(-c4ccc(F)cc4)c3C=O)ncn2)n1]

A round-bottom flask was charged with 3-amino-5-(4-fluorophenyl)-methyl-1H-pyrazole-4-carbaldehyde (1.00 g, 4.56 mmol) and sodium phenolate (722 mg, 6.22 mmol) and the contents were suspended in 1,4-dioxane (10 mL). The reaction mixture was degassed with Ar for 3 min. Tris(dibenzylideneacetone)dipalladium (49.4 mg, 53.9 μmol), XantPhos (72.0 mg, 124 μmol) and 4-chloro-6-(3,5-dimethylpyrazol-1-yl)pyrimidine (0.865 g, 4.15 mmol) were added and the reaction mixture was degassed again for 1 min. The vial was sealed and heated at 90° C. overnight while vigorously stirring. After cooling to ambient temperature, the reaction mixture was filtered and concentrated. The residue was dissolved in ethyl acetate and washed with brine. The organic phase phase was dried over magnesium sulfate, filtered and concentrated. The residue was purified by preparative SFC (Chiralpak AD SFC 250×20 mm, flow: 80 mL/min, isocratic carbon dioxide/2-propanol 80/20) to yield the desired product (267 mg, 16% yield).

LC-MS (method 10): $R_t$=2.20 min; MS (ESIpos): m/z=392 [M+H]⁺

Intermediate 154

3-oxocyclopent-1-en-1-yl acetate

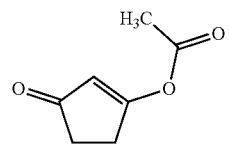

Under an argon atmosphere, cyclopentane-1,3-dione (18.0 g, 183 mmol) was dissolved in dichloromethane and pyridine (15 ml, 180 mmol) was added. Acetyl chloride (14 ml, 200 mmol) was slowly added via syringe and the reaction mixture was stirred overnight at ambient temperature. Ice-cold water was added and the phases were separated. The organic phase was further washed with aqueous hydrochloric acid solution (1 M), saturated aqueous sodium hydrogencarbonate solution and water, dried over sodium sulfate and concentrated. The product thus obtained (23.3 g, 90% yield) was used in the next step without further purification.

LC-MS (method 9): R$_t$=0.35 min; MS (ESIpos): m/z=141 [M+H]$^+$ $^1$H-NMR (400 MHz, dimethylsulfoxide-d6) δ [ppm]: 2.291 (16.00), 2.351 (2.40), 2.356 (1.60), 2.363 (2.48), 2.370 (1.70), 2.375 (2.80), 2.723 (1.53), 2.727 (1.96), 2.735 (1.60), 2.740 (1.65), 2.747 (1.69), 2.752 (1.42), 6.011 (1.04), 6.015 (2.05), 6.019 (1.18).

Intermediate 155

2-acetylcyclopentane-1,3-dione

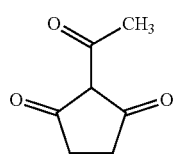

Under an argon atmosphere, 3-oxocyclopent-1-en-1-yl acetate (23.3 g, 166 mmol) was dissolved in acetonitrile (350 mL) and triethylamine (32 mL, 230 mmol) and 2-hydroxy-2-methylpropanenitrile (6.1 mL, 67 mmol) were added subsequently and the reaction mixture stirred overnight at ambient temperature. The reaction mixture was diluted with aqueous hydrochloric acid solution (160 mL, 1 M) and extracted with dichloromethane. For better phase separation, small amounts of Chydrochloric acid$_3$ were added. It was further extracted with dichloromethane and the combined organic phase extracts were washed with water, dried over sodium sulfate and concentrated to yield the product (19.2 g, 82% yield) that was used in the next step without further purification.

LC-MS (method 9): R$_t$=0.23 min; MS (ESIneg): m/z=139 [M–H]$^-$ $^1$H-NMR (400 MHz, CDCl$_3$) δ [ppm]: 2.512 (0.78), 2.527 (16.00), 2.541 (1.08), 2.740 (1.02), 2.755 (1.01), 2.769 (0.70).

Intermediate 156

1-(6-chloropyrimidin-4-yl)-3-methyl-5,6-dihydrocyclopenta[c]pyrazol-4(1H)-one

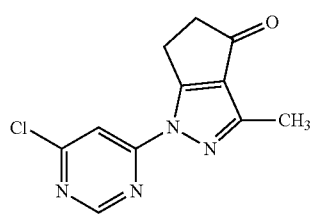 [SMILES: Cc1nn(-c2cc(Cl)ncn2)c2c1C(=O)CC2]

Under an argon atmosphere, 4-chloro-6-hydrazinylpyrimidine (11.3 g, 78.5 mmol) and 2-acetylcyclopentane-1,3-dione (10.0 g, 71.4 mmol) were suspended in ethanol (140 mL) and para-toluenesulfonic acid monohydrate (679 mg, 3.57 mmol) was added. The reaction mixture was stirred overnight at 85° C. bath temperature under slight reflux. After cooling to ambient temperature, it was quenched by addition of saturated aqueous sodium hydrogencarbonate solution and extracted with ethyl acetate (3×). An insoluble solid was filtered off during the extraction and was discarded after further analysis. The combined organic phase extracts were dried over sodium sulfate and concentrated. The residue containing the two regioisomers was dissolved in methanol/acetonitrile (1:1, 800 mL) at 60° C. and purified by preparative SFC (Chiralpak AZ 20 g, 500×400 mm, flow 300 mL/min, isocratic gradient carbon dioxide/ethanol 60/40, stacked injection of 18 mL every 25 min) to yield the desired product (5.36 g, 27% yield) along with its regioisomer 2-(6-chloropyrimidin-4-yl)-3-methyl-5,6-dihydrocyclopenta[c]pyrazol-4(2H)-one (see below).

LC-MS (method 10): R$_t$=1.08 min; MS (ESIpos): m/z=249 [M+H]$^+$ $^1$H-NMR (400 MHz, dimethylsulfoxide-d6) δ [ppm]: –0.008 (0.47), 0.008 (0.45), 2.350 (16.00), 2.394 (1.72), 2.523 (0.48), 2.983 (2.11), 2.989 (1.74), 2.996 (2.34), 3.002 (1.84), 3.008 (2.39), 3.368 (2.27), 3.374 (1.75), 3.381 (2.20), 3.387 (1.65), 3.393 (1.93), 7.929 (3.50), 9.004 (3.30).

Intermediate 157

2-(6-chloropyrimidin-4-yl)-3-methyl-5,6-dihydrocyclopenta[c]pyrazol-4(2H)-one

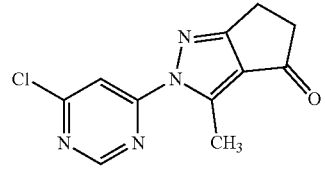 [SMILES: Cc1c2c(nn1-c1cc(Cl)ncn1)CCC2=O]

This intermediate was obtained as a regioisomer during the synthesis of 1-(6-chloropyrimidin-4-yl)-3-methyl-5,6-dihydrocyclopenta[c]pyrazol-4(1H)-one and was purified by preparative SFC (Chiralpak AZ 20μ, 500×400 mm, flow 300 mL/min, isocratic gradient carbon dioxide/ethanol 60/40, stacked injection of 18 mL every 25 min) to yield the desired product (2.56 g, 13% yield).

LC-MS (method 10): R$_t$=1.10 min; MS (ESIpos): m/z=249 [M+H]$^+$ $^1$H-NMR (400 MHz, dimethylsulfoxide-d6) δ [ppm]: 2.845 (16.00), 2.915 (0.88), 2.919 (1.00), 2.928 (2.08), 2.933 (1.53), 2.939 (1.58), 2.948 (2.90), 2.980 (2.87), 2.995 (1.43), 3.000 (1.79), 3.009 (0.95), 3.162 (0.48), 3.175 (0.50), 8.078 (3.79), 9.036 (3.78).

Intermediate 158

4-[1-(2-cyclopropylethyl)-3-(1,3-dioxo-1,3-dihydro-2H-isoindol-2-yl)-4-methyl-1H-pyrazol-5-yl]benzonitrile

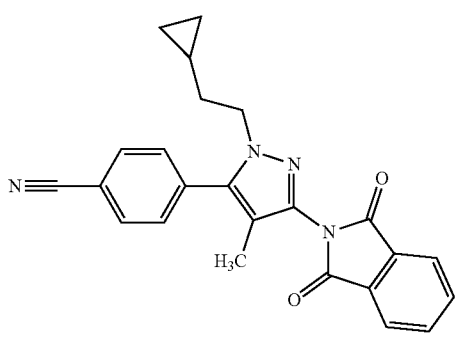 [SMILES: Cc1c(N2C(=O)c3ccccc3C2=O)nn(CCC2CC2)c1-c1ccc(C#N)cc1]

Under an argon atmosphere, 4-[3-(1,3-dioxo-1,3-dihydro-2H-isoindol-2-yl)-4-methyl-1H-pyrazol-5-yl]benzonitrile (2.00 g, 6.09 mmol) and potassium carbonate (1.68 g, 12.2 mmol) were suspended in dimethylformamide (8.9 mL) and (2-bromoethyl)cyclopropane (1.3 ml, 12 mmol) was added. The reaction mixture was stirred overnight at ambient temperature. Water was then added and the cloudy solution filtered. The oily residue was dissolved in ethyl acetate and washed with water. The filtrate and the aqueous phase were combined and extracted with ethyl acetate. The combined organic phase extracts were dried over sodium sulfate and concentrated. The residue was dissolved in methanol/acetonitrile (50 mL) and purified by preparative SFC (Chiralpak AD-H 5 μm, 250×20 mm, flow: 80 mL/min, isocratic carbon dioxide/2-propanol 80/20, injections of 0.8 mL every 20 min) to yield the desired product (270 mg, 63% purity, 7% yield) along with its regioisomer 4-[1-(2-cyclopropylethyl)-5-(1,3-dioxo-1,3-dihydro-2H-isoindol-2-yl)-4-methyl-1H-pyrazol-3-yl]benzonitrile (see below).

LC-MS (method 14): $R_t$=3.49 min; MS (ESIpos): m/z=397 [M+H]$^+$

Intermediate 159

4-[3-amino-1-(2-cyclopropylethyl)-4-methyl-1H-pyrazol-5-yl]benzonitrile

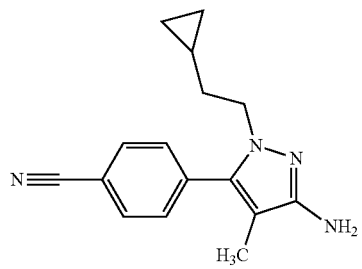 [SMILES: Cc1c(N)nn(CCC2CC2)c1-c1ccc(C#N)cc1]

4-[1-(2-cyclopropylethyl)-3-(1,3-dioxo-1,3-dihydro-2H-isoindol-2-yl)-4-methyl-1H-pyrazol-5-yl]benzonitrile (270 mg, 681 μmol) was dissolved in ethanol (6.4 mL) and hydrazine monohydrate (170 μL, 3.4 mmol) was added. The reaction mixture was heated to reflux for 4 h. After cooling to ambient temperature, it was diluted with water and extracted with ethyl acetate. The organic phase was washed with sat. aqueous sodium hydrogencarbonate and brine and dried over sodium sulfate. The residue was concentrated to yield the desired product (168 mg, 67% purity, 62% yield) and was used without further purification.

LC-MS (method 9): $R_t$=0.79 min; MS (ESIpos): m/z=267 [M+H]$^+$

Intermediate 160

4-[1-(2-cyclopropylethyl)-5-(1,3-dioxo-1,3-dihydro-2H-isoindol-2-yl)-4-methyl-1H-pyrazol-3-yl]benzonitrile

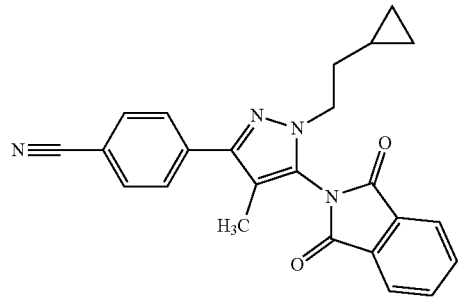 [SMILES: Cc1c(-c2ccc(C#N)cc2)nn(CCC2CC2)c1N1C(=O)c2ccccc2C1=O]

This compound was obtained during the synthesis of its regioisomer 4-[1-(2-cyclopropylethyl)-3-(1,3-dioxo-1,3-dihydro-2H-isoindol-2-yl)-4-methyl-1H-pyrazol-5-yl]benzonitrile. Separation of the regioisomers by preparative SFC (Chiralpak AD-H 5 μm, 250×20 mm, flow: 80 mL/min, isocratic carbon dioxide/2-propanol 80/20, injections of 0.8 mL every 20 min) yielded the title compound (269 mg, 11% yield).

LC-MS (method 9): $R_t$=1.15 min; MS (ESIpos): m/z=397 [M+H]$^+$ $^1$H-NMR (500 MHz, dimethylsulfoxide-d6) δ [ppm]: −0.061 (0.46), −0.052 (1.68), −0.049 (1.57), −0.042 (1.71), −0.031 (0.50), 0.274 (0.51), 0.282 (1.42), 0.286 (1.40), 0.291 (0.70), 0.294 (0.69), 0.298 (1.49), 0.301 (1.37), 0.310 (0.48), 0.611 (0.51), 1.612 (0.61), 1.626 (1.55), 1.640 (1.53), 1.654 (0.59), 2.070 (9.83), 4.071 (1.18), 4.086 (1.87), 4.100 (1.14), 7.918 (16.00), 7.981 (1.70), 7.988 (1.72), 7.992 (1.76), 7.998 (2.45), 8.058 (2.64), 8.065 (1.82), 8.069 (1.80), 8.075 (1.69).

Intermediate 161

4-[5-amino-1-(2-cyclopropylethyl)-4-methyl-1H-pyrazol-3-yl]benzonitrile

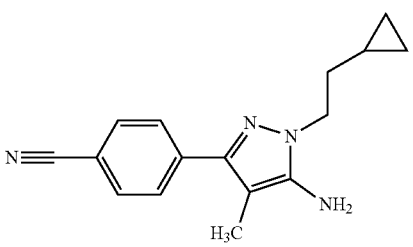 [SMILES: Cc1c(-c2ccc(C#N)cc2)nn(CCC2CC2)c1N]

4-[1-(2-cyclopropylethyl)-5-(1,3-dioxo-1,3-dihydro-2H-isoindol-2-yl)-4-methyl-1H-pyrazol-3-yl]benzonitrile (264 mg, 666 µmol) was dissolved in ethanol (10 mL) and hydrazine monohydrate (160 µL, 3.3 mmol) was added. The reaction mixture was heated to reflux for 4.5 h. After cooling to ambient temperature, the precipitated solid was removed by filtration. The filtrate was concentrated to yield the desired product (209 mg, 57% purity, 67% yield) and was used without further purification.

LC-MS (method 9): $R_t$=0.84 min; MS (ESIpos): m/z=267 [M+H]$^+$

Intermediate 162

1-(6-{[1-(cyclopropylmethyl)-4-ethyl-3-(4-fluorophenyl)-1H-pyrazol-5-yl]amino}pyrimidin-4-yl)-3,5-dimethyl-1H-pyrazole-4-carboxylic acid

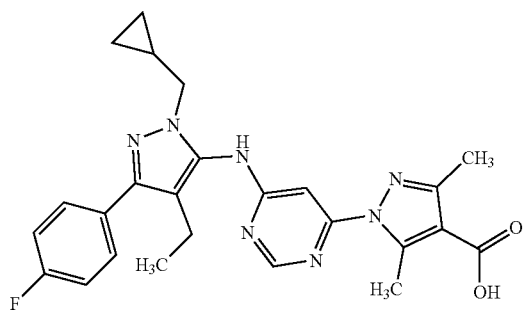 [SMILES: CCc1c(-c2ccc(F)cc2)nn(CC2CC2)c1Nc1cc(-n2nc(C)c(C(=O)O)c2C)ncn1]

A solution of ethyl 1-(6-{[1-(cyclopropylmethyl)-4-ethyl-3-(4-fluorophenyl)-1H-pyrazol-5-yl]amino}pyrimidin-4-yl)-3,5-dimethyl-1H-pyrazole-4-carboxylate (175 mg, 348 µmol) in tetrahydrofuran (2.5 ml, 31 mmol) was treated with aqueous lithium hydroxide solution (1.7 ml, 1.0 M, 1.7 mmol) and stirred overnight at 80° C. and an additional day at 90° C. After cooling to ambient temperature the mixture was diluted with water and extracted once with ethyl acetate. The organic phase was discarded. The aqueous phase was acidified with hydrochloric acid and extracted with ethyl acetate (3×). The combined organic phases were dried over sodium sulfate and concentrated under reduced pressure to yield 71.7 mg (37%) of the desired product.

LC-MS (method 10): $R_t$=1.95 min; MS (ESIpos): m/z=476 [M+H]$^+$ $^1$H-NMR (400 MHz, dimethylsulfoxide-d6) δ [ppm]: −0.149 (0.49), −0.008 (4.42), 0.008 (3.94), 0.146 (0.49), 0.298 (3.16), 0.309 (3.34), 0.437 (3.50), 0.456 (3.66), 0.975 (5.18), 0.993 (11.22), 1.012 (5.36), 1.040 (1.18), 1.057 (2.36), 1.075 (1.20), 1.175 (0.56), 1.188 (1.00), 1.194 (0.99), 1.206 (1.47), 1.218 (0.94), 1.224 (0.99), 1.235 (0.68), 1.910 (1.02), 2.357 (11.03), 2.376 (2.32), 2.443 (1.27), 2.461 (2.79), 2.479 (2.88), 2.811 (8.97), 2.910 (16.00), 2.931 (0.80), 3.433 (0.70), 3.451 (0.68), 3.798 (2.68), 3.814 (2.64), 6.568 (1.44), 7.254 (3.27), 7.276 (6.65), 7.298 (3.68), 7.670 (2.01), 7.685 (2.76), 7.703 (1.89), 8.317 (1.76), 8.522 (0.57), 9.464 (0.45), 12.627 (0.99).

Intermediate 163

N'-acetyl-1-(6-{[1-(cyclopropylmethyl)-4-ethyl-3-(4-fluorophenyl)-1H-pyrazol-5-yl]amino}pyrimidin-4-yl)-3,5-dimethyl-1H-pyrazole-4-carbohydrazide

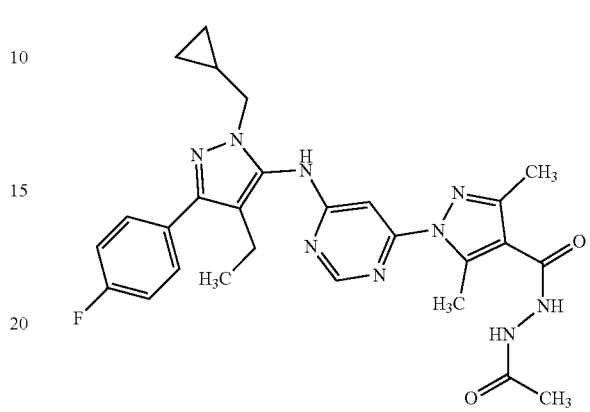

A solution of 1-(6-{[1-(cyclopropylmethyl)-4-ethyl-3-(4-fluorophenyl)-1H-pyrazol-5-yl]amino}pyrimidin-4-yl)-3,5-dimethyl-1H-pyrazole-4-carboxylic acid (68.9 mg, 145 µmol) and acetohydrazide (32.2 mg, 435 µmol) in dimethylformamide (1.0 ml, 13 mmol) was treated with HATU (82.6 mg, 217 µmol) and N,N-diisopropylethylamine (76 µl, 430 µmol). The mixture was stirred overnight at ambient temperature. The mixture was diluted with water and extracted with ethyl acetate (3×). The combined organic phases were dried over Extrelut NT3 and concentrated under reduced pressure to yield 95.4 mg (quant.) of the desired product.

LC-MS (method 10): $R_t$=1.65 min; MS (ESIpos): m/z=532 [M+H]$^+$

Intermediate 164

1-(6-{[4-ethyl-3-(4-fluorophenyl)-1-methyl-1H-pyrazol-5-yl]amino}pyrimidin-4-yl)-3,5-dimethyl-1H-pyrazole-4-carboxylic acid

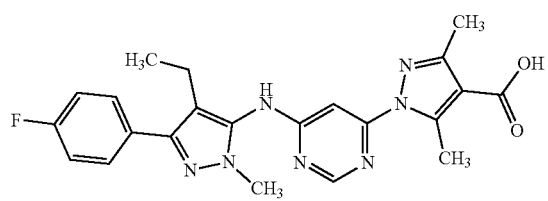 [SMILES: CCc1c(-c2ccc(F)cc2)nn(C)c1Nc1cc(-n2nc(C)c(C(=O)O)c2C)ncn1]

A solution of ethyl 1-(6-{[4-ethyl-3-(4-fluorophenyl)-1-methyl-1H-pyrazol-5-yl]amino}pyrimidin-4-yl)-3,5-dimethyl-1H-pyrazole-4-carboxylate (177 mg, 383 µmol) in tetrahydrofuran (2.5 ml, 31 mmol) was treated with aqueous lithium hydroxide solution (1.9 ml, 1.0 M, 1.9 mmol) and stirred at 85° C. overnight and additionally one day at 90° C. After cooling to ambient temperature the mixture was diluted with water and extracted once with ethyl acetate. The organic phase was discarded. The aqueous phase was acidified with hydrochloric acid and extracted with ethyl acetate (3×). The combined organic phases were dried over sodium sulfate and concentrated under reduced pressure to yield 50.3 mg (30%) of the desired product.

LC-MS (method 10): $R_t$=1.75 min; MS (ESIpos): m/z=436 [M+H]$^+$ $^1$H-NMR (400 MHz, dimethylsulfoxide-d6) δ [ppm]: 0.973 (4.48), 0.991 (9.78), 1.010 (4.67), 1.032 (3.19), 1.047 (3.17), 1.910 (0.49), 2.369 (3.06), 2.448 (1.13), 2.467 (2.85), 2.486 (3.06), 2.913 (16.00), 3.645 (11.42), 7.248 (2.43), 7.270 (5.06), 7.292 (2.88), 7.649 (1.94), 7.664 (2.55), 7.669 (2.49), 7.684 (1.88), 8.536 (0.74), 9.519 (0.96), 12.634 (1.08).

Intermediate 165

N'-acetyl-1-(6-{[4-ethyl-3-(4-fluorophenyl)-1-methyl-1H-pyrazol-5-yl]amino}pyrimidin-4-yl)-3,5-dimethyl-1H-pyrazole-4-carbohydrazide

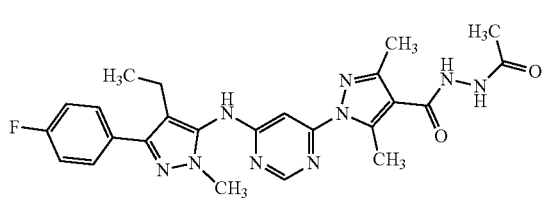 [SMILES: CCc1c(-c2ccc(F)cc2)nn(C)c1Nc1cc(-n2nc(C)c(C(=O)NNC(C)=O)c2C)ncn1]

A solution of 1-(6-{[4-ethyl-3-(4-fluorophenyl)-1-methyl-1H-pyrazol-5-yl]amino}pyrimidin-4-yl)-3,5-dimethyl-1H-pyrazole-4-carboxylic acid (43.8 mg, 101 μmol) and acetohydrazide (22.4 mg, 302 μmol) in dimethylformamide (1.0 ml, 13 mmol) was treated with HATU (57.4 mg, 151 μmol) and N,N-diisopropylethylamine (53 μl, 300 μmol). The mixture was stirred overnight at ambient temperature. The mixture was diluted with water and extracted with ethyl acetate (3×). The combined organic phases were dried over Extrelut NT3 and concentrated under reduced pressure to yield 65.1 mg (quant.) of the desired product LC-MS (method 10): $R_t$=1.45 min; MS (ESIpos): m/z=492 [M+H]$^+$ Intermediate 166

4-[1-(2,2-difluoroethyl)-5-(1,3-dioxo-1,3-dihydro-2H-isoindol-2-yl)-4-methyl-1H-pyrazol-3-yl]benzonitrile

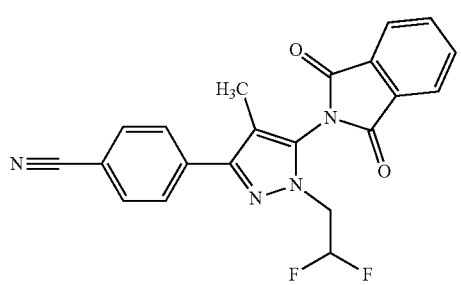 [SMILES: Cc1c(-c2ccc(C#N)cc2)nn(CC(F)F)c1N1C(=O)c2ccccc2C1=O]

A solution of 4-[5-(1,3-dioxo-1,3-dihydro-2H-isoindol-2-yl)-4-methyl-1H-pyrazol-3-yl]benzonitrile (2.50 g, 7.61 mmol) in dimethylformamide (20 ml, 260 mmol) was treated with cesium carbonate (4.96 g, 15.2 mmol) and 2,2-difluoroethyl trifluoromethanesulfonate (2.0 ml, 15 mmol) and was stirred overnight at ambient temperature. The mixture was diluted with water and extracted with ethyl acetate (3×). The combined organic phases were washed with water, brine, dried over sodium sulfate and concentrated under reduced pressure. The crude product was purified by flash-chromatography on silica gel (Biotage SNAP Ultra 50 g, dichloromethane/ethyl acetate 40:1) to yield 1.45 g of the desired product (48%) together with its regioisomer (0.30 g, 10%).

LC-MS (method 10): $R_t$=1.95 min; MS (ESIpos): m/z=393 [M+H]$^+$ $^1$H-NMR (500 MHz, dimethylsulfoxide-d6) δ [ppm]: 2.076 (2.67), 2.083 (16.00), 4.638 (0.84), 4.646 (0.91), 4.668 (1.69), 4.675 (1.73), 4.697 (0.84), 4.704 (0.75), 6.174 (0.57), 6.276 (0.55), 6.283 (1.14), 6.290 (0.54), 6.393 (0.50), 7.921 (1.03), 7.923 (0.81), 7.926 (0.60), 7.939 (10.08), 7.943 (10.02), 7.955 (0.55), 7.959 (0.76), 7.961 (0.97), 7.973 (2.81), 7.979 (2.89), 7.984 (2.73), 7.990 (3.96), 7.998 (0.55), 8.000 (0.44), 8.039 (0.47), 8.041 (0.55), 8.049 (4.29), 8.054 (2.90), 8.059 (3.03), 8.066 (2.75).

Intermediate 167

4-[1-(2,2-difluoroethyl)-3-(1,3-dioxo-1,3-dihydro-2H-isoindol-2-yl)-4-methyl-1H-pyrazol-5-yl]benzonitrile

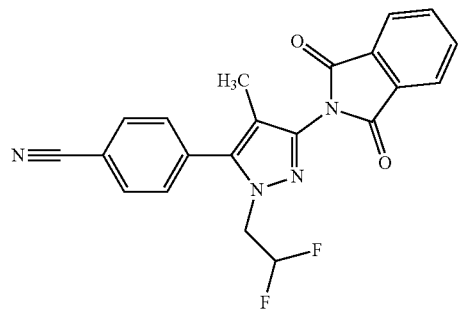 [SMILES: Cc1c(N2C(=O)c3ccccc3C2=O)nn(CC(F)F)c1-c1ccc(C#N)cc1]

A solution of 4-[5-(1,3-dioxo-1,3-dihydro-2H-isoindol-2-yl)-4-methyl-1H-pyrazol-3-yl]benzonitrile (2.50 g, 7.61 mmol) in dimethylformamide (20 ml, 260 mmol) was treated with cesium carbonate (4.96 g, 15.2 mmol) and 2,2-difluoroethyl trifluoromethanesulfonate (2.0 ml, 15 mmol) and was stirred overnight at ambient temperature. The mixture was diluted with water and extracted with ethyl acetate (3×). The combined organic phases were washed with water, brine, dried over sodium sulfate and concentrated under reduced pressure. The crude product was purified by flash-chromatography on silica gel (Biotage SNAP Ultra 50 g, dichloromethane/ethyl acetate 40:1) to yield 300 mg of the desired product (10%) together with its regioisomer (1.45 g, 48%).

LC-MS (method 10): $R_t$=1.91 min; MS (ESIpos): m/z=393 [M+H]$^+$

Intermediate 168

4-[5-amino-1-(2,2-difluoroethyl)-4-methyl-1H-pyrazol-3-yl]benzonitrile

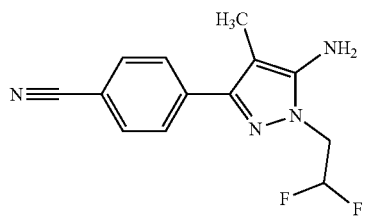 [SMILES: Cc1c(-c2ccc(C#N)cc2)nn(CC(F)F)c1N]

A solution of 4-[1-(2,2-difluoroethyl)-5-(1,3-dioxo-1,3-dihydro-2H-isoindol-2-yl)-4-methyl-1H-pyrazol-3-yl]benzonitrile (1.45 g, 3.70 mmol) in ethanol (25 mL) was treated with hydrazine monohydrate (890 µl, 18.5 mmol) and stirred at 90° C. overnight. After cooling to ambient temperature the mixture was diluted with saturated sodium hydrogen carbonate solution and extracted with ethyl acetate (3×). The combined organic phases were washed with saturated sodium hydrogen carbonate solution and brine, dried over sodium sulfate and concentrated under reduced pressure to yield 950 mg (98%) of the desired product.

LC-MS (method 10): $R_t$=1.43 min; MS (ESIpos): m/z=263 [M+H]$^+$ $^1$H-NMR (600 MHz, dimethylsulfoxide-d6) δ [ppm]: 2.042 (16.00), 3.317 (0.88), 4.433 (1.06), 4.440 (1.16), 4.457 (2.17), 4.464 (2.23), 4.481 (1.11), 4.488 (1.04), 5.238 (5.93), 6.226 (0.61), 6.311 (0.61), 6.318 (1.23), 6.325 (0.63), 6.410 (0.58), 7.796 (2.39), 7.810 (6.51), 7.827 (6.45), 7.841 (2.43).

Intermediate 169

4-[3-amino-1-(2,2-difluoroethyl)-4-methyl-1H-pyrazol-5-yl]benzonitrile

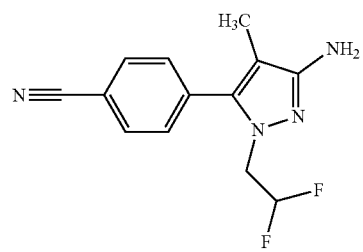 [SMILES: Cc1c(N)nn(CC(F)F)c1-c1ccc(C#N)cc1]

A solution of 4-[1-(2,2-difluoroethyl)-3-(1,3-dioxo-1,3-dihydro-2H-isoindol-2-yl)-4-methyl-1H-pyrazol-5-yl]benzonitrile (300 mg, 765 µmol) in ethanol (5 mL) was treated with hydrazine monohydrate (186 µl, 3.8 mmol) and stirred at 90° C. overnight. After cooling to ambient temperature the mixture was diluted with saturated sodium hydrogen carbonate solution and extracted with ethyl acetate (3×). The combined organic phases were washed with saturated sodium hydrogen carbonate solution and brine, dried over sodium sulfate and concentrated under reduced pressure to yield 180 mg (90%) of the desired product.

LC-MS (method 9): $R_t$=0.71 min; MS (ESIpos): m/z=263 [M+H]$^+$ $^1$H-NMR (400 MHz, dimethylsulfoxide-d6) δ [ppm]: 1.782 (16.00), 4.094 (0.85), 4.105 (0.91), 4.130 (1.75), 4.140 (1.77), 4.166 (0.88), 4.176 (0.81), 4.787 (4.36), 6.021 (0.59), 6.150 (0.52), 6.160 (1.19), 6.170 (0.54), 6.298 (0.55), 7.528 (3.92), 7.533 (1.43), 7.545 (1.49), 7.549 (4.34), 7.961 (4.23), 7.965 (1.44), 7.977 (1.37), 7.982 (3.81).

Intermediate 170

1-(6-chloropyrimidin-4-yl)-3-methyl-1H-pyrazolo[4,3-b]pyridine

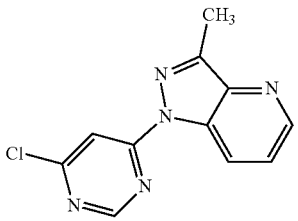 [SMILES: Cc1nn(-c2cc(Cl)ncn2)c2cccnc12]

Under an argon atmosphere 4,6-dichloropyrimidine (1.15 g, 7.72 mmol), 3-methyl-1H-pyrazolo[4,3-b]pyridine (1.03 g, 7.72 mmol) and cesium carbonate (2.52 g, 7.72 mmol) were dissolved in dimethylformamide (9.4 mL) and stirred at ambient temperature overnight. Water was added to the reaction mixture, which was further stirred for 30 min. The precipitated solid was collected by filtration and further washed with water. It was then dried overnight under vacuum in a drying-oven to yield the desired product (1.2 g, 63% yield).

LC-MS (method 9): $R_t$=0.91 min; MS (ESIpos): m/z=246 [M+H]$^+$ $^1$H-NMR (400 MHz, dimethylsulfoxide-d6) δ [ppm]: 2.660 (16.00), 7.658 (1.49), 7.670 (1.55), 7.680 (1.57), 7.691 (1.61), 7.963 (2.08), 8.726 (1.66), 8.729 (1.58), 8.737 (1.67), 8.741 (1.53), 8.961 (1.68), 8.963 (1.36), 8.982 (1.70), 8.985 (1.42), 8.992 (2.46).

Intermediate 171

1-(6-chloropyrimidin-4-yl)-3-methyl-1H-pyrazolo[4,3-c]pyridine

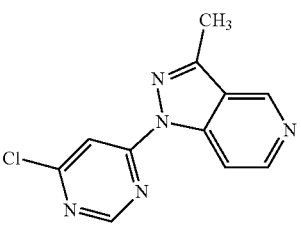 [SMILES: Cc1nn(-c2cc(Cl)ncn2)c2ccncc12]

Under an argon atmosphere, 4,6-dichloropyrimidine (1.12 g, 7.51 mmol), 3-methyl-1H-pyrazolo[4,3-c]pyridine (1.00 g, 7.51 mmol) and cesium carbonate were suspended in dimethylformamide and the reaction mixture was stirred overnight at ambient temperature. Water was added to the reaction mixture, which was further stirred for 30 min. The precipitated solid was collected by filtration and further washed with water. It was then dried overnight under vacuum in a drying-oven to yield the desired product (1.57 g, 85% yield).

LC-MS (method 9): R$_t$=0.63 min; MS (ESIpos): m/z=246 [M+H]$^+$ $^1$H-NMR (400 MHz, dimethylsulfoxide-d6) δ [ppm]: 1.997 (0.97), 2.462 (2.15), 2.561 (0.93), 2.700 (16.00), 2.733 (0.84), 2.785 (1.45), 2.892 (0.71), 3.003 (1.01), 6.892 (0.54), 7.541 (0.53), 7.667 (0.44), 7.963 (2.90), 8.516 (1.87), 8.529 (1.84), 8.590 (0.66), 8.616 (0.63), 8.649 (0.46), 8.667 (2.81), 8.682 (2.43), 8.941 (0.44), 9.001 (0.43), 9.023 (3.18), 9.245 (3.85).

Intermediate 172

4-chloro-6-(3-methyl-1H-pyrazol-1-yl)pyrimidine

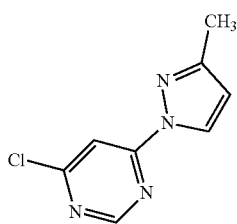

Under an argon atmosphere, 4,6-dichloropyrimidine (1.81 g, 12.2 mmol), 3-methyl-1H-pyrazole (1.00 g, 12.2 mmol) and cesium carbonate (3.97 g, 12.2 mmol) were suspended in dimethylformamide (15 mL) and stirred overnight at ambient temperature. Water was added Water was added to the reaction mixture, which was further stirred for 15 min. The precipitated solid was collected by filtration and further washed with water. It was then dried overnight under vacuum in a drying-oven at 40° C. to yield the desired product (1.58 g, 63% yield).

LC-MS (method 10): R$_t$=1.66 min; MS (ESIpos): m/z=195 [M+H]$^+$ $^1$H-NMR (400 MHz, dimethylsulfoxide-d6) δ [ppm]: 2.316 (16.00), 2.343 (0.21), 2.711 (1.18), 6.445 (0.25), 6.525 (2.49), 6.531 (2.60), 7.817 (0.25), 7.857 (3.22), 7.988 (0.26), 8.569 (2.22), 8.575 (2.46), 8.905 (3.20), 8.957 (0.27).

Intermediate 173

4-chloro-6-(1H-pyrazol-1-yl)pyrimidine

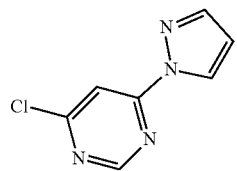 [SMILES: Clc1cc(-n2cccn2)ncn1]

Under an argon atmosphere, 1H-pyrazole (1.00 g, 14.7 mmol), 4,6-dichloropyrimidine (2.19 g, 14.7 mmol) and cesium carbonate (4.79 g, 14.7 mmol) were suspended in dimethylformamide (18 mL) and stirred overnight at ambient temperature. Water was added Water was added to the reaction mixture, which was further stirred for 15 min. The precipitated solid was collected by filtration and further washed with water. It was then dried overnight under vacuum in a drying-oven at 40° C. to yield the desired product (2.02 g, 76% yield).

LC-MS (method 10): R$_t$=1.45 min; MS (ESIpos): m/z=181 [M+H]$^+$ $^1$H-NMR (400 MHz, dimethylsulfoxide-d6) δ [ppm]: 6.705 (9.36), 6.710 (12.76), 6.715 (10.30), 7.978 (16.00), 8.011 (13.25), 8.254 (0.76), 8.705 (12.40), 8.711 (13.01), 8.735 (1.17), 8.742 (1.18), 8.964 (12.88), 8.988 (0.71).

Intermediate 174

4-chloro-6-[4-(trifluoromethyl)-1H-pyrazol-1-yl]pyrimidine

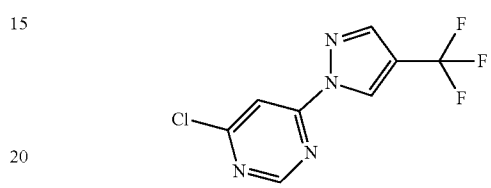

Under an argon atmosphere, 4-(trifluoromethyl)-1H-pyrazole (1.13 g, 8.27 mmol), 4,6-dichloropyrimidine (1.23 g, 8.27 mmol) and cesium carbonate (2.69 g, 8.27 mmol) were suspended in dimethylformamide (10 mL) and stirred overnight at ambient temperature. Water was added to the reaction mixture, which was further stirred for 15 min. Filtration of the cloudy mixture was not possible, therefore the mixture was diluted with brine and extracted with ethyl acetate (3×). The combined organic phase extracts were washed with brine, dried over sodium sulfate and concentrated. The desired product thus obtained (1.6 g, 62% purity, 46% yield) was used in the next step without further purification.

LC-MS (method 11): R$_t$=1.33 min; MS (ESIpos): m/z=249 [M+H]$^+$ $^1$H-NMR (400 MHz, dimethylsulfoxide-d6) δ [ppm]: −0.149 (0.66), −0.008 (4.89), 0.008 (5.43), 0.146 (0.66), 2.329 (0.83), 2.367 (1.03), 2.671 (0.94), 2.711 (1.09), 2.732 (8.86), 2.892 (11.86), 7.953 (1.20), 8.103 (16.00), 8.345 (8.23), 8.482 (14.11), 8.510 (15.23), 8.965 (0.51), 9.060 (12.11), 9.157 (5.91), 9.159 (6.71), 9.362 (12.20), 9.406 (11.77).

Intermediate 175

3-(4-bromophenyl)-2-methyl-3-oxopropanenitrile

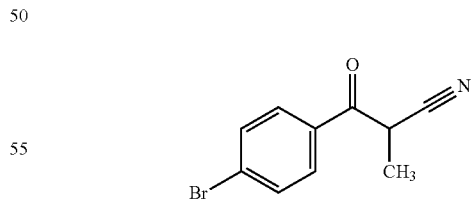

Under an argon atmosphere, ethyl 4-bromobenzoate (7.1 ml, 44 mmol) and propanenitrile (4.4 ml, 61 mmol) were dissolved in tetrahydrofuran (100 mL) and a solution of lithium bis(trimethylsilyl)amide (63 ml, 1.0 M, 63 mmol) was added dropwise at ambient temperature. The reaction mixture was stirred for 2 h, and no further conversion took place. Further aliquots of propanenitrile (1.1 ml, 15 mmol) and lithium bis(trimethylsilyl)amide solution (17 ml, 1.0 M, 17 mmol) were then added and the reaction mixture allowed to stir overnight. The reaction was quenched by addition of water and extracted with dichloromethane. The organic phase was discarded. The aqueous phase was acidified with aqueous hydrochloric acid to pH1-2 and extracted with dichloromethane (3×). The combined organic phase extracts were dried over sodium sulfate and concentrated. The desired product thus obtained (9.17 g, 85% purity, 75% yield) was used in the next step without further purification.

LC-MS (method 10): $R_t$=1.73 min; MS (ESIneg): m/z=236 [M−H]⁻

¹H-NMR (400 MHz, dimethylsulfoxide-d6) δ [ppm]: −0.008 (0.92), 1.458 (10.79), 1.476 (10.91), 1.664 (3.23), 1.854 (16.00), 5.098 (0.89), 5.116 (2.71), 5.134 (2.69), 5.152 (0.89), 7.359 (0.77), 7.380 (0.93), 7.484 (4.07), 7.505 (5.05), 7.674 (5.46), 7.695 (4.62), 7.812 (4.67), 7.833 (6.58), 7.937 (6.71), 7.959 (4.93), 10.936 (1.03).

Intermediate 176

3-(4-bromophenyl)-1,4-dimethyl-1H-pyrazol-5-amine

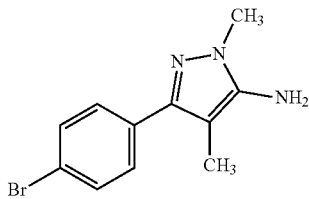

3-(4-bromophenyl)-2-methyl-3-oxopropanenitrile (6.00 g, 25.2 mmol) was dissolved in toluene (100 mL) and methylhydrazine (1.3 ml, 25 mmol) and acetic acid (1.4 ml, 25 mmol) were added subsequently. The reaction mixture was stirred overnight at ambient temperature. The solvent was removed under reduced pressure and the residue redissolved in dichloromethane. It was loaded onto celite and purified by flash column chromatography (SNAP Ultra 100 g, cyclohexane/ethyl acetate gradient 60/40 to 0:100) to yield the desired product (5.56 g, 83% yield) along with its regioisomer (0.53 g, 8%).

LC-MS (method 9): $R_t$=0.70 min; MS (ESIpos): m/z=266 [M+H]⁺

¹H-NMR (400 MHz, dimethylsulfoxide-d6) δ [ppm]: 1.99 (s, 3H), 3.57 (s, 3H), 4.98 (s, 2H), 7.54 (m, 4H).

Intermediate 177

1-[1-(6-chloropyrimidin-4-yl)-3,5-dimethyl-1H-pyrazol-4-yl]ethanone

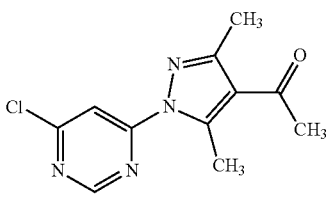 [SMILES: CC(=O)c1c(C)nn(-c2cc(Cl)ncn2)c1C]

A solution of 4,6-dichloropyrimidine (1.08 g, 7.24 mmol) and 1-(3,5-dimethyl-1H-pyrazol-4-yl)ethanone (1.00 g, 7.24 mmol) in dimethylformamide (5.0 ml) was treated with cesium carbonate (2.36 g, 7.24 mmol) and stirred 1.5 hours at ambient temperature. The mixture was diluted with water; the occurring precipitate was collected by filtration, washed with water and dried to yield 1.40 g (74%) of the desired product.

LC-MS (method 10): $R_t$=1.74 min; MS (ESIpos): m/z=251 [M+H]⁺

¹H-NMR (400 MHz, dimethylsulfoxide-d6) δ [ppm]: 2.461 (15.85), 2.922 (16.00), 2.968 (1.34), 7.990 (2.95), 9.014 (3.30).

Intermediate 178

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanone

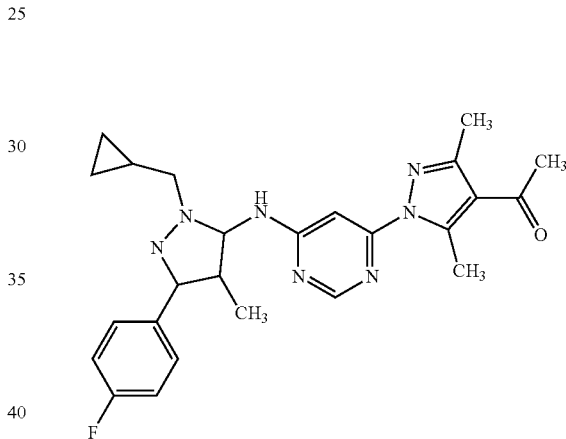

A microwave vial was charged 1-[1-(6-chloropyrimidin-4-yl)-3,5-dimethyl-1H-pyrazol-4-yl]ethanone (530 mg, 2.11 mmol) and 1-(cyclopropylmethyl)-3-(4-fluorophenyl)-4-methyl-1H-pyrazol-5-amine (570 mg, 2.33 mmol) and the contents were suspended in 1,4-dioxane (8.6 ml, 100 mmol). The reaction mixture was degassed with Ar for 3 min. Tris(dibenzylidenaceton)dipalladium (58.1 mg, 63.4 μmol) and Xantphos (73.4 mg, 127 μmol) were added and the reaction mixture was degassed again for 1 min and heated to 85° C. At this temperature and sodium phenolate (270 mg, 2.33 mmol) was added. The vial was sealed and heated at 85° C. for 90 minutes while vigorously stirring. After cooling to ambient temperature, the reaction mixture was diluted with brine and extracted with ethyl acetate (2×). The combined organic phases were dried over sodium sulfate and concentrated under reduced pressure. The crude product was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (305 mg, 26%).

LC-MS (method 11): $R_t$=1.41 min; MS (ESIpos): m/z=460 [M+H]⁺

Intermediate 179

3-(4-fluorophenyl)-2-methoxy-3-oxopropanenitrile

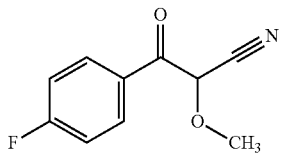

A solution of ethyl 4-fluorobenzoate (4.4 ml, 30 mmol) in tetrahydrofuran (88 ml, 1.1 mol) was treated with lithium bis(trimethylsilyl)amide (62 ml, 1.0 M in tetrahydrofuran, 62 mmol). The mixture was stirred overnight at ambient temperature. The mixture was diluted with water and extracted with dichloromethane. The organic phase was discarded. The aqueous phase was acidified with hydrochloric acid and extracted with dichloromethane (2×). The combined organic phases were washed with water, dried over sodium sulfate and concentrated under reduced pressure to yield 10.0 g (80%) of the desired product.

LC-MS (method 10): $R_t$=1.54 min; MS (ESIneg): m/z=192 [M−H]−

Intermediate 180

3-(4-fluorophenyl)-4-methoxy-1H-pyrazol-5-amine

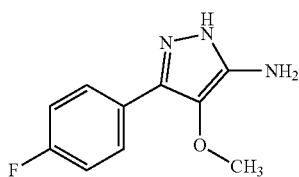

A solution of 3-(4-fluorophenyl)-2-methoxy-3-oxopropanenitrile (4.50 g, 23.3 mmol) in ethanol (40 ml, 690 mmol) was treated with hydrazine hydrate (1:1) (2.3 ml, 47 mmol) and refluxed overnight. After cooling to ambient temperature the mixture was poured into ice water. Saturated sodium hydrogen carbonate solution was added and the mixture was extracted with ethyl acetate. The combined organic phases were washed with brine, dried over sodium sulfate and concentrated under reduced pressure to yield 2.70 g (39%) of the desired product.

LC-MS (method 10): $R_t$=1.07 min; MS (ESIpos): m/z=208 [M+H]+

$^1$H-NMR (400 MHz, dimethylsulfoxide-d6) δ [ppm]: 1.281 (0.58), 1.355 (0.48), 1.719 (0.83), 1.785 (0.65), 1.842 (1.35), 1.857 (0.83), 1.880 (0.56), 1.911 (0.41), 1.931 (4.34), 1.937 (3.87), 1.957 (4.21), 1.972 (4.40), 1.986 (1.87), 2.004 (4.19), 2.019 (0.65), 2.074 (0.68), 2.086 (2.74), 2.168 (0.51), 3.600 (1.14), 3.610 (1.45), 3.631 (16.00), 4.591 (0.85), 7.234 (1.77), 7.256 (3.38), 7.270 (1.65), 7.278 (2.23), 7.303 (0.95), 7.411 (0.64), 7.425 (0.74), 7.432 (0.63), 7.447 (0.50), 7.755 (1.85), 7.769 (2.22), 7.776 (2.12), 7.790 (1.71), 10.430 (1.00).

Intermediate 181

2-[3-(4-fluorophenyl)-4-methoxy-1H-pyrazol-5-yl]-1H-isoindole-1,3 (2H)-dione

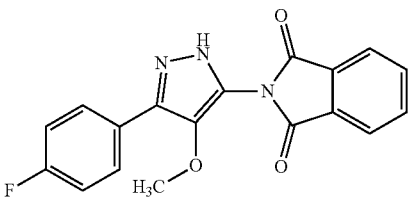 [SMILES: COc1c(-c2ccc(F)cc2)n[nH]c1N1C(=O)c2ccccc2C1=O]

A solution of 3-(4-fluorophenyl)-4-methoxy-1H-pyrazol-5-amine (1.94 g, 90% purity, 8.43 mmol) and 2-benzofuran-1,3-dione (1.87 g, 12.6 mmol) in acetic acid (17 ml) was stirred overnight at 125° C. After cooling to ambient temperature, acetic acid was removed under reduced pressure. The remaining residue was diluted with water and extracted with ethyl acetate. The combined organic phases were washed with water, brine, dried over sodium sulfate and concentrated under reduced pressure. The crude product was purified by flash-chromatography on silica gel (column: Biotage Snap Ultra 50 g, solvent: dichloromethane/ethyl acetate 10:1) to yield 1.60 g of the desired product (56%).

LC-MS (method 10): $R_t$=1.73 min; MS (ESIpos): m/z=338 [M+H]+

$^1$H-NMR (400 MHz, dimethylsulfoxide-d6) δ [ppm]: 0.008 (0.43), 2.074 (3.12), 3.607 (16.00), 7.363 (1.99), 7.385 (3.78), 7.408 (1.95), 7.823 (2.29), 7.837 (2.63), 7.845 (2.34), 7.859 (1.96), 7.965 (2.39), 7.973 (2.85), 7.978 (2.92), 7.986 (3.87), 7.996 (1.03), 8.022 (0.96), 8.032 (3.74), 8.040 (2.70), 8.046 (2.47), 8.054 (2.02), 13.484 (2.62).

Intermediate 182

2-[3-(4-fluorophenyl)-4-methoxy-1-methyl-1H-pyrazol-5-yl]-1H-isoindole-1,3 (2H)-dione

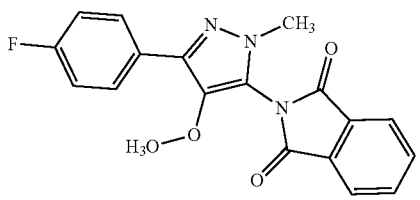 [SMILES: Cn1nc(-c2ccc(F)cc2)c(OO)c1N1C(=O)c2ccccc2C1=O]

A solution of 2-[3-(4-fluorophenyl)-4-methoxy-1H-pyrazol-5-yl]-1H-isoindole-1,3(2H)-dione (1.58 g, 4.68 mmol) in dimethylformamide (15 ml, 200 mmol) was treated with cesium carbonate (3.05 g, 9.37 mmol) and iodomethane (580 μl, 9.4 mmol). The mixture was stirred overnight. The mixture was diluted with water and extracted with ethyl acetate (3×). The combined organic phases were washed with water (2×), brine and dried over sodium sulfate. The crude product was purified using flash-chromatography on silica gel (SNAP Ultra 10 g, dichloromethane/ethyl acetate 40:1) to obtain 84 mg of the desired product (5%) together with its regioisomer (105 mg, 6%).

LC-MS (method 10) $R_t$=1.99 min; MS (ESIpos): m/z=352 [M+H]+

¹H-NMR (400 MHz, dimethylsulfoxide-d6) δ [ppm]: 1.279 (0.43), 3.610 (16.00), 3.711 (13.88), 3.818 (1.03), 3.822 (1.27), 3.945 (0.44), 7.271 (1.59), 7.293 (3.32), 7.315 (1.81), 7.864 (1.87), 7.878 (2.15), 7.886 (2.14), 7.900 (1.81), 7.992 (1.84), 8.000 (2.09), 8.006 (2.24), 8.014 (2.97), 8.025 (0.53), 8.065 (0.50), 8.075 (2.95), 8.083 (2.17), 8.089 (2.09), 8.097 (1.80).

Intermediate 183

2-[5-(4-fluorophenyl)-4-methoxy-1-methyl-1H-pyrazol-3-yl]-1H-isoindole-1,3(2H)-dione

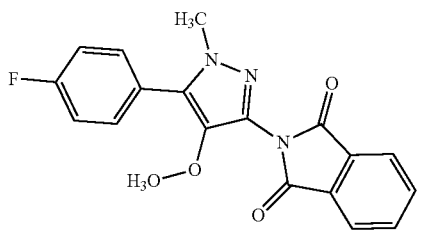 [SMILES: Cn1nc(N2C(=O)c3ccccc3C2=O)c(OO)c1-c1ccc(F)cc1]

A solution of 2-[3-(4-fluorophenyl)-4-methoxy-1H-pyrazol-5-yl]-1H-isoindole-1,3(2H)-dione (1.58 g, 4.68 mmol) in dimethylformamide (15 ml, 200 mmol) was treated with cesium carbonate (3.05 g, 9.37 mmol) and iodomethane (580 μl, 9.4 mmol). The mixture was stirred overnight. The mixture was diluted with water and extracted with ethyl acetate (3×). The combined organic phases were washed with water (2×), brine and dried over sodium sulfate. The crude product was purified using flash-chromatography on silica gel (SNAP Ultra 10 g, dichloromethane/ethyl acetate 40:1) to obtain 105 mg of the desired product (6%) together with its regioisomer (84 mg, 5%).

LC-MS (method 10): $R_t$=1.83 min; MS (ESIpos): m/z=352 [M+H]⁺

¹H-NMR (400 MHz, dimethylsulfoxide-d6) δ [ppm]: 2.073 (0.54), 3.469 (16.00), 3.789 (13.18), 7.386 (1.50), 7.408 (3.04), 7.430 (1.63), 7.643 (1.88), 7.657 (2.27), 7.662 (1.97), 7.678 (1.51), 7.958 (1.62), 7.966 (2.19), 7.971 (2.13), 7.979 (2.75), 8.014 (0.60), 8.025 (2.90), 8.032 (2.17), 8.039 (1.88), 8.046 (1.52).

Intermediate 184

3-(4-fluorophenyl)-4-methoxy-1-methyl-1H-pyrazol-5-amine

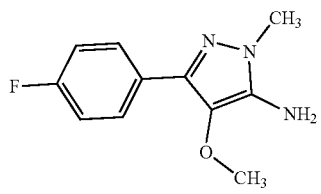 [SMILES: COc1c(-c2ccc(F)cc2)nn(C)c1N]

A solution of 2-[3-(4-fluorophenyl)-4-methoxy-1-methyl-1H-pyrazol-5-yl]-1H-isoindole-1,3(2H)-dione (84.0 mg, 239 μmol) in ethanol (2 mL) was treated with hydrazine monohydrate (58 μl, 1.2 mmol) and stirred at 90° C. overnight. After cooling to ambient temperature the mixture was diluted with water and extracted with ethyl acetate (3×). The combined organic phases were washed with 1M sodium hydrogen carbonate solution and brine, dried over sodium sulfate and concentrated under reduced pressure to yield 51.0 mg (75%) of the desired product.

LC-MS (method 11): $R_t$=0.91 min; MS (ESIpos): m/z=222 [M+H]⁺

¹H-NMR (400 MHz, dimethylsulfoxide-d6) δ [ppm]: −0.008 (0.72), 0.008 (0.69), 1.091 (0.48), 3.537 (14.59), 3.597 (16.00), 5.037 (3.62), 7.165 (1.74), 7.170 (0.65), 7.182 (0.83), 7.188 (3.65), 7.193 (0.83), 7.205 (0.67), 7.210 (1.95), 7.785 (1.81), 7.791 (0.77), 7.799 (2.02), 7.808 (2.01), 7.816 (0.75), 7.822 (1.78).

Intermediate 185

5-(4-fluorophenyl)-4-methoxy-1-methyl-1H-pyrazol-3-amine

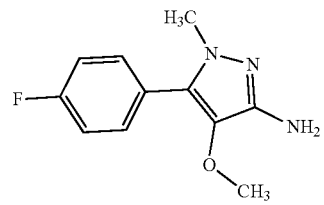 [SMILES: COc1c(N)nn(C)c1-c1ccc(F)cc1]

A solution of 2-[5-(4-fluorophenyl)-4-methoxy-1-methyl-1H-pyrazol-3-yl]-1H-isoindole-1,3(2H)-dione (105 mg, 299 μmol) in ethanol (2.6 mL) was treated with hydrazine monohydrate (73 μl, 1.5 mmol) and stirred at 90° C. overnight. After cooling to ambient temperature the mixture was diluted with water and extracted with ethyl acetate (3×). The combined organic phases were washed with 1M sodium hydrogen carbonate solution and brine, dried over sodium sulfate and concentrated under reduced pressure to yield 67.0 mg (66%) of the desired product.

LC-MS (method 11): $R_t$=0.92 min; MS (ESIpos): m/z=222 [M+H]⁺

¹H-NMR (500 MHz, dimethylsulfoxide-d6) δ [ppm]: 1.714 (0.45), 3.331 (1.36), 3.471 (16.00), 4.539 (1.96), 7.310 (1.83), 7.313 (0.89), 7.327 (3.96), 7.341 (0.96), 7.345 (2.28), 7.476 (2.26), 7.481 (1.24), 7.488 (2.58), 7.494 (2.29), 7.501 (1.07), 7.505 (1.90).

Intermediate 186 ethyl [1-(6-chloropyrimidin-4-yl)-3,5-dimethyl-1H-pyrazol-4-yl]acetate

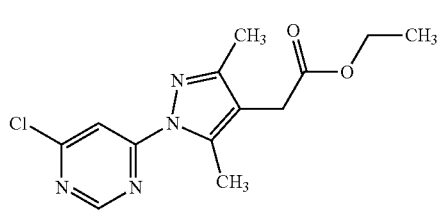 [SMILES: CCOC(=O)Cc1c(C)nn(-c2cc(Cl)ncn2)c1C]

A solution of 4-chloro-6-hydrazinylpyrimidine (5.00 g, 34.6 mmol) in ethanol (70 ml, 1.2 mol) was treated with ethyl 3-acetyl-4-oxopentanoate (6.44 g, 34.6 mmol) and refluxed overnight. After cooling to room temperature the precipitate was collected by filtration, washed with ethanol and dried to yield 5.84 g (57%) of the desired product.

LC-MS (method 10): $R_t$=1.99 min; MS (ESIpos): m/z=295 [M+H]$^+$ $^1$H-NMR (400 MHz, dimethylsulfoxide-d6) δ [ppm]: 1.171 (4.91), 1.188 (10.15), 1.206 (5.04), 2.189 (16.00), 2.611 (14.69), 3.383 (1.43), 3.430 (0.76), 3.449 (0.62), 4.058 (1.62), 4.076 (4.86), 4.094 (4.79), 4.112 (1.56), 7.898 (3.18), 8.897 (3.57).

Intermediate 187 ethyl 1-(6-{[5-(4-fluorophenyl)-1,4-dimethyl-1H-pyrazol-3-yl]amino}pyrimidin-4-yl)-3-methyl-1H-pyrazole-5-carboxylate

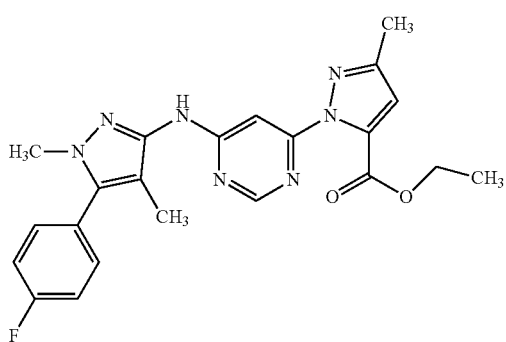 [SMILES: CCOC(=O)c1cc(C)nn1-c1cc(Nc2nn(C)c(-c3ccc(F)cc3)c2C)ncn1]

A microwave vial was charged with 5-(4-fluorophenyl)-1,4-dimethyl-1H-pyrazol-3-amine (84.0 mg, 409 µmol), ethyl 1-(6-chloropyrimidin-4-yl)-3-methyl-1H-pyrazole-5-carboxylate (120 mg, 450 µmol) and sodium phenolate (52.2 mg, 450 µmol) and the contents were suspended in 1,4-dioxane (1.2 mL). The reaction mixture was degassed with Ar for 3 min. Tris(dibenzylideneacetone)dipalladium (4.87 mg, 5.32 µmol) and XantPhos (7.10 mg, 12.3 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (7.8 mg, 4% yield).

LC-MS (method 10): $R_t$=2.00 min; MS (ESIpos): m/z=436 [M+H]$^+$ $^1$H-NMR (400 MHz, dimethylsulfoxide-d6) δ [ppm]: −0.008 (1.08), 0.008 (1.23), 1.196 (4.83), 1.214 (10.43), 1.232 (5.08), 1.866 (11.62), 2.274 (14.25), 2.327 (0.62), 2.670 (0.68), 3.691 (16.00), 4.239 (1.55), 4.257 (4.87), 4.275 (4.83), 4.292 (1.47), 6.751 (4.70), 7.312 (0.91), 7.358 (2.02), 7.380 (4.55), 7.402 (2.66), 7.515 (2.53), 7.521 (1.13), 7.529 (2.83), 7.537 (2.30), 7.546 (0.91), 7.551 (1.94), 8.417 (2.60), 9.630 (1.74).

Intermediate 188 ethyl 1-(6-{[4-ethyl-3-(4-fluorophenyl)-1-methyl-1H-pyrazol-5-yl]amino}pyrimidin-4-yl)-3-methyl-1H-pyrazole-5-carboxylate

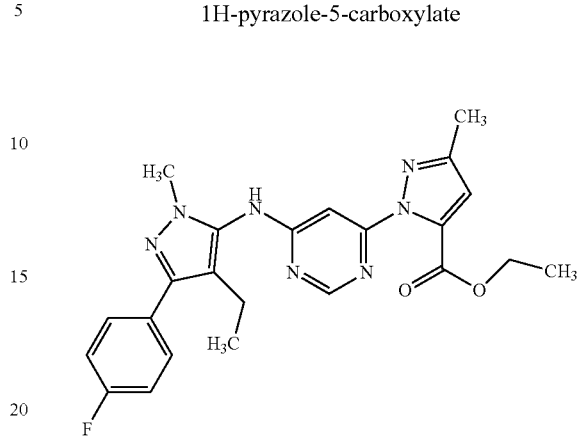

A microwave vial was charged with 4-ethyl-3-(4-fluorophenyl)-1-methyl-1H-pyrazol-5-amine (89.7 mg, 409 µmol), ethyl 1-(6-chloropyrimidin-4-yl)-3-methyl-1H-pyrazole-5-carboxylate (120 mg, 450 µmol) and sodium phenolate (52.2 mg, 450 µmol) and the contents were suspended in 1,4-dioxane (1.2 mL). The reaction mixture was degassed with Ar for 3 min. Tris(dibenzylideneacetone)dipalladium (4.87 mg, 5.32 µmol) and XantPhos (7.10 mg, 12.3 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (42 mg, 80% purity, 18% yield).

LC-MS (method 10): $R_t$=2.04 min; MS (ESIpos): m/z=450 [M+H]$^+$

Intermediate 189

4-chloro-6-(4-fluoro-3,5-dimethyl-1H-pyrazol-1-yl)pyrimidine

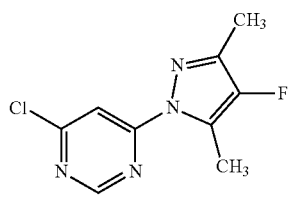

4,6-dichloropyrimidine (1.28 g, 8.59 mmol), 4-fluoro-3,5-dimethyl-1H-pyrazole (980 mg, 8.59 mmol) and cesium carbonate (2.80 g, 8.59 mmol) were suspended in dimethylformamide (5.1 mL) and stirred at ambient temperature overnight. Water was then added and the reaction mixture further stirred for 15 min. The precipitated solid was collected by filtration, washed with water and dried in a drying-oven overnight at 40° C. The desired product thus obtained (1.55 g, 74% yield) was used in the next step without further purification.

LC-MS (method 11): Rt=1.41 min; MS (ESIpos): m/z=227 [M+H]+

¹H-NMR (400 MHz, dimethylsulfoxide-d6) δ [ppm]: −0.008 (0.54), 0.008 (0.45), 2.263 (16.00), 2.282 (0.55), 2.617 (9.61), 2.622 (7.84), 2.646 (0.32), 2.673 (1.24), 7.894 (2.73), 7.923 (0.23), 8.914 (3.27), 8.948 (0.28).

Intermediate 190

2-methyl-3-oxo-3-[4-(trifluoromethoxy)phenyl]propanenitrile

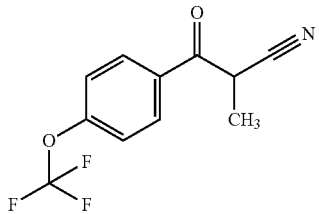 [SMILES: CC(C#N)C(=O)c1ccc(OC(F)(F)F)cc1]

Under an argon atmosphere, ethyl 4-(trifluoromethoxy)benzoate (8.00 g, 34.2 mmol) and propanenitrile (3.7 ml, 51 mmol) were dissolved in tetrahydrofuran (60 mL) and the resulting solution chilled with a water bath. A solution of lithium bis(trimethylsilyl)amide (53 ml, 1.0 M, 53 mmol) was added slowly and the reaction mixture stirred at ambient temperature for 2 h. Water was added and the mixture extracted with ethyl acetate. The organic phase was discarded and the aqueous phase acidified with aqueous hydrochloric acid solution (1.0 M). The acidic aqueous phase was extracted with ethyl acetate (3×) and the combined organic phase extracts were washed with brine, dried over sodium sulfate and concentrated. The desired product thus obtained (6.21 g, 74% yield) was used in the next step without further purification.

LC-MS (method 11): R$_t$=1.27 min; MS (ESIpos): m/z=244 [M+H]+

¹H-NMR (400 MHz, dimethylsulfoxide-d6) δ [ppm]: 0.008 (0.62), 1.474 (8.85), 1.492 (8.96), 1.668 (3.23), 1.837 (1.43), 1.870 (16.00), 1.910 (2.16), 5.129 (0.74), 5.147 (2.20), 5.165 (2.18), 5.183 (0.71), 7.470 (3.36), 7.491 (4.29), 7.553 (1.29), 7.575 (3.87), 7.597 (3.51), 7.672 (4.95), 7.694 (4.07), 8.040 (0.20), 8.055 (0.17), 8.077 (0.19), 8.151 (4.90), 8.173 (4.57), 8.282 (0.38), 8.305 (0.34), 10.971 (0.88).

Intermediate 191

1-(cyclopropylmethyl)-4-methyl-3-[4-(trifluoromethoxy)phenyl]-1H-pyrazol-5-amine

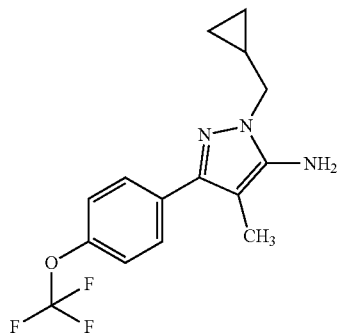 [SMILES: Cc1c(-c2ccc(OC(F)(F)F)cc2)nn(CC2CC2)c1N]

2-methyl-3-oxo-3-[4-(trifluoromethoxy)phenyl]propanenitrile (3.00 g, 12.3 mmol) and (cyclopropylmethyl)hydrazine dihydrochloride (2.45 g, 15.4 mmol) were suspended in 2-propanol (25 mL) and the reaction mixture was stirred under reflux for 3 h. After cooling to ambient temperature, it was concentrated to ⅓ of its original volume and aqueous saturated sodium hydrogencarbonate solution was added carefully. The reaction mixture was extracted with ethyl acetate (3×) and the combined organic phase extracts were washed with brine, dried over sodium sulfate and concentrated. The desired product thus obtained was used in the next step without further purification (3.66 g, 92% yield).

LC-MS (method 10): R$_t$=1.86 min; MS (ESIpos): m/z=312 [M+H]+

¹H-NMR (400 MHz, dimethylsulfoxide-d6) δ [ppm]: 0.008 (0.62), 1.474 (8.85), 1.492 (8.96), 1.668 (3.23), 1.837 (1.43), 1.870 (16.00), 1.910 (2.16), 5.129 (0.74), 5.147 (2.20), 5.165 (2.18), 5.183 (0.71), 7.470 (3.36), 7.491 (4.29), 7.553 (1.29), 7.575 (3.87), 7.597 (3.51), 7.672 (4.95), 7.694 (4.07), 8.040 (0.20), 8.055 (0.17), 8.077 (0.19), 8.151 (4.90), 8.173 (4.57), 8.282 (0.38), 8.305 (0.34), 10.971 (0.88).

Intermediate 192

2-methyl-3-oxo-3-[4-(trifluoromethyl)phenyl]propanenitrile

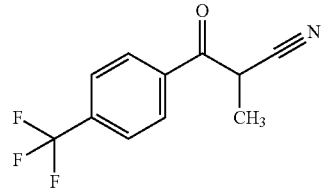 [SMILES: CC(C#N)C(=O)c1ccc(C(F)(F)F)cc1]

Under an argon atmosphere, ethyl 4-(trifluoromethyl)benzoate (3.32 g, 15.2 mmol) and propanenitrile (1.6 ml, 23 mmol) were dissolved in tetrahydrofuran (30 mL) and the resulting solution chilled with a water bath. A solution of lithium bis(trimethylsilyl)amide (24 ml, 1.0 M, 24 mmol) was added slowly and the reaction mixture stirred at ambient temperature for 2 h. Water was added and the mixture extracted with ethyl acetate. The organic phase was discarded and the aqueous phase acidified with aqueous hydrochloric acid solution (1.0 M). The acidic aqueous phase was extracted with ethyl acetate (3×) and the combined organic phase extracts were washed with brine, dried over sodium sulfate and concentrated. The desired product thus obtained (6.21 g, 74% yield) was used in the next step without further purification.

LC-MS (method 11): R$_t$=1.24 min; MS (ESIpos): m/z=228 [M+H]+

H-NMR (400 MHz, dimethylsulfoxide-d6) δ [ppm]: 0.008 (0.30), 1.175 (0.24), 1.482 (2.73), 1.500 (2.76), 1.672 (2.76), 1.849 (0.22), 1.892 (16.00), 1.909 (2.06), 1.989 (0.45), 5.179 (0.24), 5.196 (0.69), 5.214 (0.68), 5.232 (0.24), 7.639 (0.48), 7.659 (0.58), 7.758 (2.82), 7.779 (4.37), 7.846 (4.69), 7.867 (3.09), 7.971 (1.26), 7.991 (1.47), 8.200 (1.45), 8.220 (1.22), 11.103 (0.63).

Intermediate 193

1-(cyclopropylmethyl)-4-methyl-3-[4-(trifluoromethyl)phenyl]-1H-pyrazol-5-amine

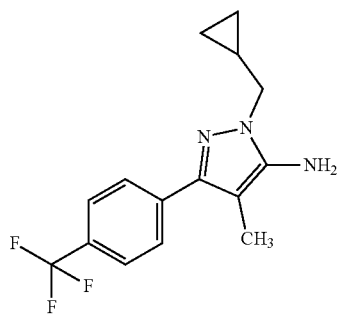 [SMILES: Cc1c(-c2ccc(C(F)(F)F)cc2)nn(CC2CC2)c1N]

2-methyl-3-oxo-3-[4-(trifluoromethyl)phenyl]propanenitrile (1.20 g, 5.28 mmol) and (cyclopropylmethyl)hydrazine dihydrochloride (1.05 g, 6.60 mmol) were suspended in 2-propanol (12 mL) and the reaction mixture was stirred under reflux for 3 h. After cooling to ambient temperature, aqueous saturated sodium hydrogencarbonate solution was added carefully. The reaction mixture was extracted with ethyl acetate (3×) and the combined organic phase extracts were washed with brine, dried over sodium sulfate and concentrated. The desired product thus obtained was used in the next step without further purification (1.52 g, 90% purity, 87% yield).

LC-MS (method 10): $R_t$=1.84 min; MS (ESIpos): m/z=296 [M+H]$^+$ $^1$H-NMR (400 MHz, dimethylsulfoxide-d6) δ [ppm]: 0.347 (0.66), 0.360 (2.54), 0.363 (2.53), 0.372 (2.96), 0.384 (1.01), 0.407 (0.39), 0.427 (1.08), 0.435 (2.29), 0.446 (1.55), 0.455 (2.50), 0.471 (0.56), 1.175 (0.19), 1.194 (0.45), 1.205 (0.67), 1.212 (0.60), 1.224 (0.90), 1.236 (0.63), 1.242 (0.58), 1.254 (0.29), 1.337 (0.22), 1.352 (0.22), 1.693 (0.27), 1.780 (0.18), 1.825 (0.18), 1.990 (0.16), 2.024 (1.18), 2.038 (16.00), 2.135 (0.49), 2.432 (0.46), 3.830 (4.46), 3.847 (4.35), 5.006 (1.95), 7.705 (2.76), 7.726 (3.96), 7.771 (0.98), 7.808 (4.09), 7.828 (2.80), 7.847 (0.28), 7.868 (0.18), 7.892 (0.19), 7.905 (0.19), 8.155 (0.17).

Intermediate 194

4-chloro-6-[5-methyl-3-(propan-2-yl)-1H-pyrazol-1-yl]pyrimidine

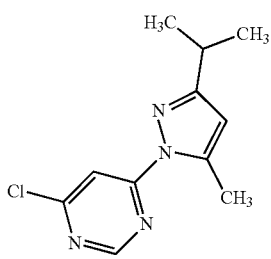 [SMILES: Cc1cc(C(C)C)nn1-c1cc(Cl)ncn1]

4,6-Dichloropyrimidine (1.08 g, 7.25 mmol), 5-methyl-3-(propan-2-yl)-1H-pyrazole (900 mg, 7.25 mmol) and cesium carbonate (2.36 g, 7.25 mmol) were suspended in dimethylformamide (8.8 mL) and the reaction mixture was stirred overnight at ambient temperature. A second batch of 4,6-dichloropyrimidine (1.08 g, 7.25 mmol) was added and the reaction mixture stirred again overnight.

Water was added and the precipitated solid was collected by filtration. The solid was purified by flash column chromatography (SNAP Ultra 25 g, cyclohexane/ethyl acetate gradient, then wash with dichloromethane/methanol 80/20) to yield a mixture of both isomers. The two regioisomers were separated by preparative HPLC (Daicel Chiralpak AS-H 5 μm, 250×20 mm, Flow: 20 mL/min, injections of 30 μL every 7 min, n-heptane/ethanol isocratic 99.5/0.5) to yield the desired product (104 mg, 6% yield).

$^1$H-NMR (400 MHz, dimethylsulfoxide-d6) δ [ppm]: 1.223 (15.72), 1.241 (16.00), 2.671 (9.29), 2.673 (9.86), 2.909 (0.92), 2.927 (1.22), 2.944 (0.89), 6.353 (2.45), 7.897 (2.74), 7.900 (2.95), 8.899 (2.44), 8.901 (2.61).

Intermediate 195 ethyl 4-chloro-1-[6-({1-(cyclopropylmethyl)-4-methyl-3-[4-(trifluoromethoxy)phenyl]-1H-pyrazol-5-yl}amino)pyrimidin-4-yl]-3-methyl-1H-pyrazole-5-carboxylate

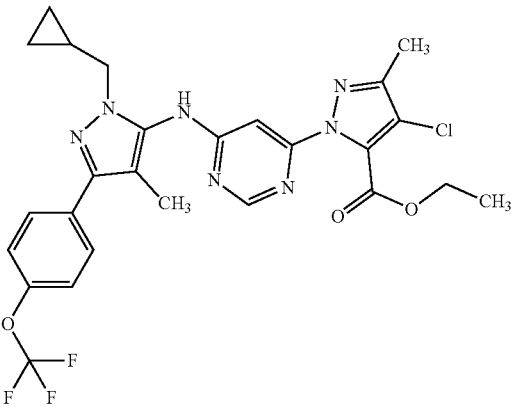 [SMILES: CCOC(=O)c1c(Cl)c(C)nn1-c1cc(Nc2c(C)c(-c3ccc(OC(F)(F)F)cc3)nn2CC2CC2)ncn1]

Under an argon atmosphere, 1-(cyclopropylmethyl)-4-methyl-3-[4-(trifluoromethoxy)phenyl]-1H-pyrazol-5-amine (314 mg, 1.01 mmol) was dissolved in 1,4-dioxane (2.2 mL) and sodium phenolate (117 mg, 1.01 mmol) was added. The reaction mixture was degassed with Ar for 3 min. Tris(dibenzylideneacetone)dipalladium (10.9 mg, 11.9 μmol), XantPhos (15.9 mg, 27.5 μmol) and ethyl 4-chloro-1-(6-chloropyrimidin-4-yl)-3-methyl-1H-pyrazole-5-carboxylate (368 mg, 75% purity, 917 μmol) were added and the reaction mixture was degassed again for 1 min. It was then heated at 90° C. overnight while vigorously stirring. After cooling to ambient temperature, the reaction mixture was loaded on silica gel and purified by flash column chromatography (SNAP Ultra 25 g, cyclohexane/ethyl acetate gradient 95/5 to 20/80) to yield the desired product (176 mg, 80% purity, 27% yield).

LC-MS (method 10) $R_t$=2.59 min; MS (ESIpos): m/z=576 [M+H]$^+$ $^1$H-NMR (400 MHz, dimethylsulfoxide-d6) δ [ppm]: −0.149 (0.26), −0.008 (2.04), 0.008 (2.25), 0.146 (0.30), 0.299 (2.85), 0.346 (0.58), 0.358 (0.60), 0.423 (3.10), 0.442 (3.60), 1.158 (0.60), 1.175 (1.08), 1.190 (1.53), 1.207 (1.45), 1.231 (6.00), 1.249 (11.55), 1.267 (5.92), 1.315 (0.68), 1.363

(0.45), 1.380 (0.27), 1.398 (7.00), 1.428 (0.36), 1.965 (0.21), 1.989 (0.44), 2.000 (2.88), 2.036 (16.00), 2.130 (0.25), 2.147 (0.26), 2.177 (0.26), 2.271 (2.19), 2.328 (0.97), 2.333 (0.84), 2.367 (0.38), 2.375 (0.53), 2.394 (0.23), 2.680 (1.63), 2.711 (0.40), 3.568 (0.48), 3.802 (0.79), 3.819 (0.93), 3.851 (2.49), 3.866 (2.49), 4.329 (2.26), 4.347 (6.84), 4.364 (6.82), 4.382 (2.38), 4.948 (0.84), 7.171 (0.22), 7.342 (0.53), 7.363 (0.60), 7.429 (3.89), 7.450 (4.32), 7.684 (0.79), 7.706 (0.75), 7.827 (2.51), 7.843 (1.99), 8.433 (0.32), 9.625 (0.30).

Intermediate 196 ethyl 1-[6-({1-(cyclopropylmethyl)-4-methyl-3-[4-(trifluoromethoxy)phenyl]-1H-pyrazol-5-yl}amino)pyrimidin-4-yl]-3-methyl-1H-pyrazole-5-carboxylate

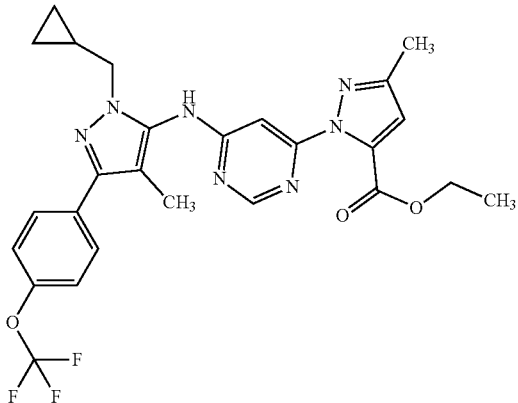 [SMILES: CCOC(=O)c1cc(C)nn1-c1cc(Nc2c(C)c(-c3ccc(OC(F)(F)F)cc3)nn2CC2CC2)ncn1]

Under an argon atmosphere, 1-(cyclopropylmethyl)-4-methyl-3-[4-(trifluoromethoxy)phenyl]-1H-pyrazol-5-amine (314 mg, 1.01 mmol) was dissolved in 1,4-dioxane (2.2 mL) and sodium phenolate (117 mg, 1.01 mmol) was added. The reaction mixture was degassed with Ar for 3 min. Tris(dibenzylideneacetone)dipalladium (10.9 mg, 11.9 µmol), XantPhos (15.9 mg, 27.5 µmol) and ethyl 1-(6-chloropyrimidin-4-yl)-3-methyl-1H-pyrazole-5-carboxylate (272 mg, 90% purity, 917 µmol) were added and the reaction mixture was degassed again for 1 min. It was then heated at 90° C. overnight while vigorously stirring. After cooling to ambient temperature, the reaction mixture was loaded on silica gel and purified by flash column chromatography (SNAP Ultra 25 g, cyclohexane/ethyl acetate gradient 95/5 to 20/80) and further purified by preparative HPLC (column: Chromatorex C18; 125*30 mm, 10 µM, flow 75 mL/min, gradient acetonitrile/water (containing 0.1% trifluoroacetic acid) 5/95 to 95/5) to yield the desired product (114 mg, 23% yield).

LC-MS (method 9): $R_t$=1.25 min; MS (ESIpos): m/z=542 [M+H]$^+$ $^1$H-NMR (400 MHz, dimethylsulfoxide-d6) δ [ppm]: −0.149 (0.20), −0.022 (0.38), 0.008 (1.64), 0.146 (0.20), 0.293 (2.56), 0.303 (2.73), 0.426 (2.85), 0.445 (2.98), 1.164 (0.44), 1.176 (0.82), 1.200 (6.83), 1.218 (13.27), 1.235 (7.16), 2.042 (16.00), 2.261 (2.83), 2.328 (0.42), 2.367 (0.28), 2.670 (0.30), 2.711 (0.24), 3.854 (2.58), 3.870 (2.53), 4.246 (2.10), 4.264 (6.63), 4.282 (6.57), 4.300 (2.06), 6.750 (2.03), 7.429 (3.68), 7.450 (4.07), 7.826 (2.65), 7.847 (2.47), 8.434 (0.44), 9.582 (0.36).

Intermediate 197

N'-acetyl-1-(6-{[4-ethyl-5-(4-fluorophenyl)-1-methyl-1H-pyrazol-3-yl]amino}pyrimidin-4-yl)-3,5-dimethyl-1H-pyrazole-4-carbohydrazide

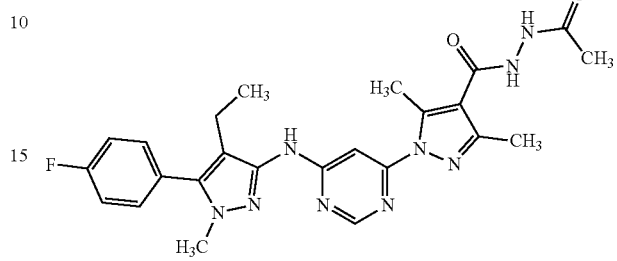

A solution of 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (66.0 mg, 152 µmol) and acetohydrazide (33.7 mg, 455 µmol) in dimethylformamide (1.0 ml, 13 mmol) was treated with HATU (86.4 mg, 227 µmol) and N,N-diisopropylethylamine (79 µl, 450 µmol) and stirred overnight at ambient temperature. The mixture was purified using preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 58.0 mg of the desired product (78%).

LC-MS (method 10): $R_t$=1.46 min; MS (ESIpos): m/z=492 [M+H]$^+$ $^1$H-NMR (400 MHz, dimethylsulfoxide-d6) δ [ppm]: −0.008 (1.43), 0.008 (1.20), 0.873 (3.58), 0.892 (8.13), 0.911 (3.70), 1.141 (0.68), 1.882 (1.12), 1.905 (11.25), 2.299 (11.74), 2.309 (2.88), 2.328 (2.71), 2.346 (0.76), 2.524 (0.59), 2.756 (12.15), 3.652 (16.00), 7.359 (2.13), 7.364 (1.10), 7.376 (2.54), 7.381 (5.24), 7.398 (0.96), 7.403 (2.68), 7.503 (2.56), 7.508 (1.12), 7.516 (2.86), 7.524 (2.25), 7.533 (0.89), 7.538 (1.88), 8.500 (2.43), 9.471 (1.54), 9.701 (2.34), 9.886 (2.71).

Intermediate 198

1-(6-{[4-ethyl-5-(4-fluorophenyl)-1H-methyl-1H-pyrazol-3-yl]amino}pyrimidin-4-yl)-3,5-dimethyl-1H-pyrazole-4-carbaldehyde

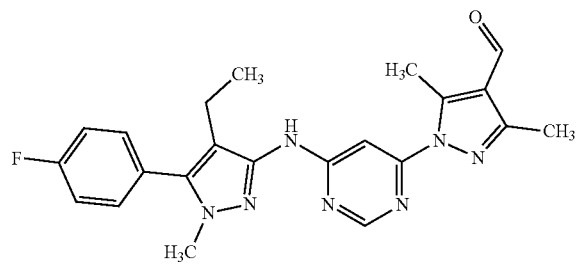 [SMILES: CCc1c(Nc2cc(-n3nc(C)c(C=O)c3C)ncn2)nn(C)c1-c1ccc(F)cc1]

A solution of [1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanol (135 mg, 320 µmol) in dichloromethane (5.0 ml, 78 mmol) was treated with manganese(IV) oxide (139 mg, 1.60 mmol). The mixture was stirred one hour at ambient temperature and left over the weekend. Additional five equivalents of manganese(IV) oxide (139.2 mg, 1.6 mmol) were added at the mixture was again stirred overnight and 4 days at ambient temperature. The mixture was filtered over a pad of kieselgur, which was washed with dichloromethane. The filtrate was concentrated to yield the desired product (108 mg, 74%).

LC-MS (method 10): $R_t$=1.98 min; MS (ESIpos): m/z=420 [M+H]$^+$ $^1$H-NMR (400 MHz, dimethylsulfoxide-d6) δ [ppm]: −0.008 (0.76), 0.008 (0.69), 0.874 (3.39), 0.892 (7.56), 0.911 (3.45), 1.866 (0.48), 2.208 (0.79), 2.293 (0.86), 2.312 (2.31), 2.330 (2.33), 2.349 (0.74), 2.413 (14.46), 2.461 (0.57), 2.613 (0.81), 2.928 (15.57), 2.968 (0.53), 3.610 (0.56), 3.651 (16.00), 5.755 (1.56), 7.359 (1.87), 7.381 (4.33), 7.403 (2.69), 7.428 (1.27), 7.494 (0.44), 7.502 (2.54), 7.507 (1.19), 7.515 (2.82), 7.523 (2.36), 7.532 (0.89), 7.537 (1.94), 8.536 (2.69), 9.570 (1.37), 10.014 (6.17).

Intermediate 199 ethyl 1-[6-({1-(cyclopropylmethyl)-4-methyl-3-[4-(trifluoromethyl)phenyl]-1H-pyrazol-5-yl}amino)pyrimidin-4-yl]-3-methyl-1H-pyrazole-5-carboxylate

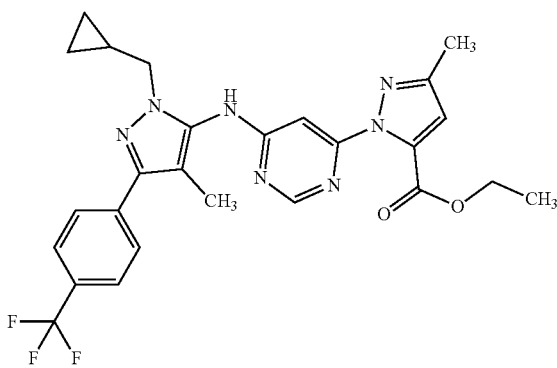 [SMILES: CCOC(=O)c1cc(C)nn1-c1cc(Nc2c(C)c(-c3ccc(C(F)(F)F)cc3)nn2CC2CC2)ncn1]

Under an argon atmosphere, 1-(cyclopropylmethyl)-4-methyl-3-[4-(trifluoromethyl)phenyl]-1H-pyrazol-5-amine (210 mg, 90% purity, 640 μmol) and sodium phenolate (74.3 mg, 640 μmol) and the contents were suspended in 1,4-dioxane (1.4 mL). The reaction mixture was degassed with Ar for 3 min. Tris(dibenzylideneacetone)dipalladium (6.93 mg, 7.56 μmol), XantPhos (10.1 mg, 17.5 μmol) and ethyl 1-(6-chloropyrimidin-4-yl)-3-methyl-1H-pyrazole-5-carboxylate (172 mg, 90% purity, 582 μmol) were added and the reaction mixture was degassed again for 1 min. It was then heated at 90° C. overnight while vigorously stirring. After cooling to ambient temperature, the reaction mixture was loaded onto silica gel and purified by flash column chromatography (SNAP Ultra 25 g, cyclohexane/ethyl acetate gradient 95/5 to 20/80) and further by preparative HPLC (column: Chromatorex C18; 125*30 mm, 10 μM, flow 75 mL/min, gradient acetonitrile/water (containing 0.1% trifluoroacetic acid) 5/95 to 95/5) to yield the desired product (35 mg, 11% yield).

LC-MS (method 9): $R_t$=1.24 min; MS (ESIpos): m/z=526 [M+H]$^+$ $^1$H-NMR (400 MHz, dimethylsulfoxide-d6) δ [ppm]: −0.149 (0.63), −0.023 (1.10), 0.147 (0.61), 0.314 (2.53), 0.433 (2.67), 0.453 (2.77), 0.853 (0.18), 1.200 (6.38), 1.218 (12.78), 1.236 (8.34), 2.073 (16.00), 2.263 (2.55), 2.328 (0.90), 2.367 (0.59), 2.670 (0.88), 2.711 (0.57), 3.875 (2.38), 3.892 (2.32), 4.247 (1.94), 4.264 (6.18), 4.282 (6.11), 4.300 (1.90), 5.754 (9.42), 6.753 (1.98), 7.793 (3.40), 7.813 (4.65), 7.938 (2.77), 7.958 (2.24), 8.431 (0.47), 9.602 (0.35).

Intermediate 200 ethyl 4-chloro-1-[6-({1-(cyclopropylmethyl)-4-methyl-3-[4-(trifluoromethyl)phenyl]-1H-pyrazol-5-yl}amino)pyrimidin-4-yl]-3-methyl-1H-pyrazole-5-carboxylate

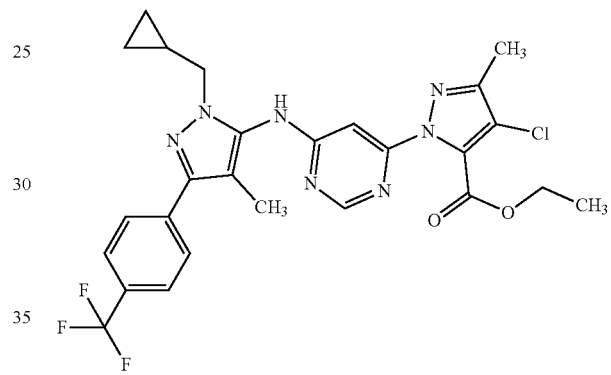

Under an argon atmosphere, 1-(cyclopropylmethyl)-4-methyl-3-[4-(trifluoromethyl)phenyl]-1H-pyrazol-5-amine (210 mg, 90% purity, 640 μmol) and sodium phenolate (74.3 mg, 640 μmol) and the contents were suspended in 1,4-dioxane (1.4 mL). The reaction mixture was degassed with Ar for 3 min. Tris(dibenzylideneacetone)dipalladium (6.93 mg, 7.56 μmol), XantPhos (10.1 mg, 17.5 μmol) and ethyl 4-chloro-1-(6-chloropyrimidin-4-yl)-3-methyl-1H-pyrazole-5-carboxylate (234 mg, 75% purity, 582 μmol) were added and the reaction mixture was degassed again for 1 min. It was then heated at 90° C. overnight while vigorously stirring. After cooling to ambient temperature, the reaction mixture was loaded onto silica gel and purified by flash column chromatography (SNAP Ultra 25 g, cyclohexane/ethyl acetate gradient 95/5 to 20/80) to yield the desired product (45 mg, 82% purity, 11% yield).

LC-MS (method 10): $R_t$=2.56 min; MS (ESIpos): m/z=560 [M+H]$^+$ $^1$H-NMR (400 MHz, dimethylsulfoxide-d6) δ [ppm]: −0.149 (0.56), 0.146 (0.56), 0.310 (2.62), 0.430 (2.76), 0.449 (3.16), 0.851 (0.23), 1.204 (1.52), 1.231 (6.14), 1.249 (11.15), 1.267 (5.62), 1.398 (2.20), 1.614 (0.26), 1.989 (0.23), 2.034 (1.69), 2.067 (16.00), 2.272 (2.16), 2.327 (1.31), 2.367 (0.73), 2.375 (0.45), 2.682 (1.34), 2.710 (0.66), 3.568 (0.52), 3.824 (0.49), 3.841 (0.61), 3.872 (2.30), 4.329 (2.11), 4.347 (6.30), 4.365 (6.23), 4.383 (2.30), 4.995 (0.47), 7.196 (0.21), 7.724 (0.45), 7.793 (3.68), 7.813 (4.87), 7.937 (2.62), 7.956 (1.99), 8.445 (0.40), 9.655 (0.33).

Intermediate 201 ethyl 4-(difluoromethyl)benzoate

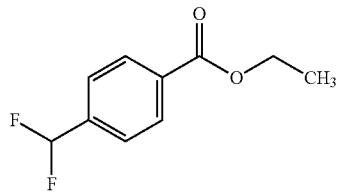

4-(difluoromethyl)benzoic acid (5.00 g, 29.0 mmol) was suspended in thionyl chloride (15 ml, 210 mmol) and refluxed for 30 minutes. After cooling to ambient temperature the mixture was concentrated under reduced pressure. The remaining material was resolved in ethanol (50 ml, 860 mmol) and the mixture was refluxed for 1 hour. After cooling to ambient temperature, the mixture was concentrated under reduced pressure; the remaining residue was resolved in dichloromethane and washed with water (2×). The organic phase was dried over sodium sulfate and concentrated under reduced pressure to yield 5.57 g (96%) of the desired product.

$^1$H-NMR (400 MHz, dimethylsulfoxide-d6) δ [ppm]: −0.014 (1.55), 1.316 (7.29), 1.334 (16.00), 1.345 (9.92), 1.352 (9.81), 1.363 (4.50), 3.334 (3.11), 4.316 (2.45), 4.333 (7.73), 4.345 (5.91), 4.351 (8.54), 4.362 (4.82), 4.369 (3.81), 4.380 (1.50), 6.999 (2.02), 7.009 (1.36), 7.138 (3.87), 7.148 (2.59), 7.277 (1.95), 7.287 (1.33), 7.714 (5.37), 7.732 (7.17), 8.076 (6.10), 8.094 (6.57), 8.106 (4.09).

Intermediate 202

3-[4-(difluoromethyl)phenyl]-2-methyl-3-oxopropanenitrile

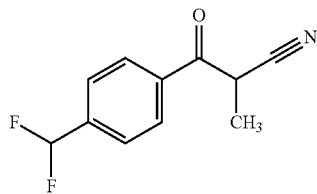

A solution of ethyl 4-(difluoromethyl)benzoate (5.20 g, 26.0 mmol) and propanenitrile (2.8 ml, 39 mmol) in tetrahydrofuran (66 ml, 820 mmol) was treated with a solution of lithium bis(trimethylsilyl)amide (40 ml, 1.0 M in tetrahydrofuran, 40 mmol). The mixture was stirred overnight at ambient temperature. The mixture was diluted with water and extracted once with ethyl acetate. The organic phase was discarded. The aqueous phase was acidified with hydrochloric acid and extracted with dichloromethane (2×). The combined organic phases were washed with water, dried over sodium sulfate and concentrated under reduced pressure to yield 3.52 g (60%) of the desired product.

LC-MS (method 10): R$_t$=1.56 min; MS (ESIneg): m/z=208 [M−H]$^-$ $^1$H-NMR (400 MHz, dimethylsulfoxide-d6) δ [ppm]: 1.489 (6.90), 1.506 (6.88), 1.679 (2.15), 1.889 (16.00), 1.917 (0.73), 5.152 (0.54), 5.169 (1.66), 5.187 (1.64), 5.205 (0.52), 6.961 (1.45), 7.017 (0.99), 7.100 (2.84), 7.156 (1.95), 7.240 (1.34), 7.294 (0.95), 7.578 (0.55), 7.665 (0.75), 7.688 (14.11), 7.712 (0.95), 7.787 (2.51), 7.807 (2.79), 8.147 (3.00), 8.167 (2.67), 10.998 (0.95).

Intermediate 203

1-(cyclopropylmethyl)-3-[4-(difluoromethyl)phenyl]-4-methyl-1H-pyrazol-5-amine

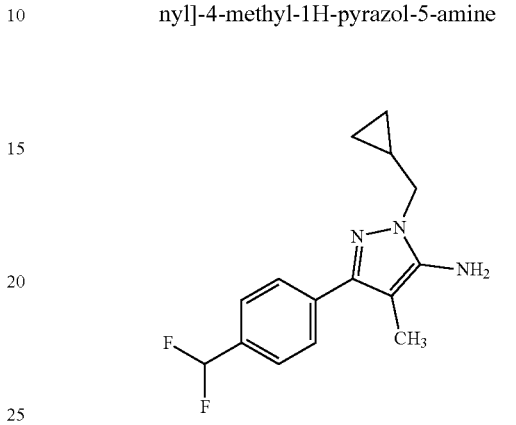

A solution of 3-[4-(difluoromethyl)phenyl]-2-methyl-3-oxopropanenitrile (1.75 g, 8.37 mmol) in 2-propanol (18 ml) was treated with (cyclopropylmethyl)hydrazine dihydrochloride (1.73 g, 10.9 mmol). The mixture was stirred overnight at 95° C. After cooling to ambient temperature and removal of the solvent, the mixture was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 1.38 g (60%) of the desired product.

LC-MS (method 10): R$_t$=1.55 min; MS (ESIpos): m/z=278 [M+H]$^+$ $^1$H-NMR (400 MHz, dimethylsulfoxide-d6) δ [ppm]: 0.343 (0.56), 0.356 (2.14), 0.359 (2.25), 0.368 (2.59), 0.380 (0.97), 0.422 (0.95), 0.431 (1.95), 0.442 (1.31), 0.451 (2.19), 0.468 (0.56), 1.198 (0.53), 1.205 (0.52), 1.217 (0.83), 1.230 (0.51), 1.235 (0.50), 2.019 (16.00), 3.818 (4.07), 3.835 (4.01), 4.986 (0.93), 6.892 (1.14), 7.032 (2.32), 7.172 (1.04), 7.555 (2.53), 7.575 (3.22), 7.717 (3.61), 7.738 (2.83).

Intermediate 204

3-(4-chlorophenyl)-2-methyl-3-oxopropanenitrile

A solution of ethyl 4-chlorobenzoate (4.2 ml, 27 mmol) and propanenitrile (5.8 ml, 81 mmol) in tetrahydrofuran (80 ml, 990 mmol) was treated with a solution of lithium bis(trimethylsilyl)amide (84 ml, 1.0 M in tetrahydrofuran, 84 mmol). The mixture was stirred overnight at ambient temperature. The mixture was diluted with water and extracted once with ethyl acetate. The organic phase was discarded. The aqueous phase was acidified with hydrochloric acid and extracted with dichloromethane (2×). The combined organic phases were washed with water, dried over sodium sulfate and concentrated under reduced pressure to yield 3.52 g (60%) of the desired product.

LC-MS (method 10): $R_t$=1.65 min; MS (ESIpos): m/z=194 [M+H]$^+$

Intermediate 205

3-(4-chlorophenyl)-1-(cyclopropylmethyl)-4-methyl-1H-pyrazol-5-amine

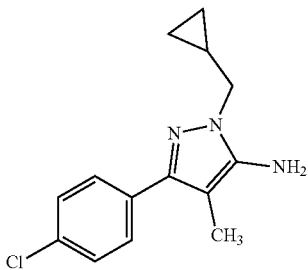 [SMILES: Cc1c(-c2ccc(Cl)cc2)nn(CC2CC2)c1N]

A solution of 3-(4-chlorophenyl)-2-methyl-3-oxopropanenitrile (2.73 g, 14.1 mmol) in 2-propanol (51 ml) was treated with (cyclopropylmethyl)hydrazine dihydrochloride (2.92 g, 18.3 mmol). The mixture was refluxed overnight. After cooling to ambient temperature and the mixture was diluted with water and 1M sodium hydroxide solution was added. The mixture was extracted with ethyl acetate (3×). The combined organic phases were washed with 1M sodium hydrogen carbonate solution, brine, dried over sodium sulfate and concentrated under reduced pressure to yield 3.62 g (96%) of the desired product.

LC-MS (method 10): $R_t$=1.63 min; MS (ESIpos): m/z=262 [M+H]$^+$ $^1$H-NMR (400 MHz, dimethylsulfoxide-d6) δ [ppm]: 0.008 (0.43), 0.331 (0.53), 0.344 (2.14), 0.347 (2.30), 0.356 (2.62), 0.369 (0.99), 0.413 (0.95), 0.423 (2.01), 0.426 (1.83), 0.433 (1.34), 0.442 (2.28), 0.458 (0.58), 1.185 (0.54), 1.191 (0.52), 1.203 (0.83), 1.215 (0.51), 1.223 (0.52), 1.988 (16.00), 3.794 (4.27), 3.811 (4.21), 4.934 (4.93), 7.404 (3.85), 7.421 (1.50), 7.425 (5.00), 7.591 (4.95), 7.607 (1.40), 7.612 (4.05).

Intermediate 206

1-(cyclopropylmethyl)-3-(4-fluorophenyl)-4-methoxy-1H-pyrazol-5-amine

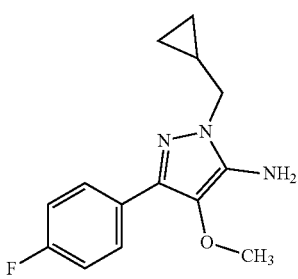 [SMILES: COc1c(-c2ccc(F)cc2)nn(CC2CC2)c1N]

A solution of 3-(4-fluorophenyl)-2-methoxy-3-oxopropanenitrile (2.50 g, 12.9 mmol) in 2-propanol (50 mL) was treated with (cyclopropylmethyl)hydrazine dihydrochloride (2.68 g, 16.8 mmol). The mixture was refluxed overnight. After cooling to ambient temperature the mixture concentrated under reduced pressure. The remaining residue was taken up in acetonitrile, crystalline material was collected by filtration. The solid material was resolved in ethyl acetate and washed with 1M sodium hydroxide solution. The organic phase was dried over sodium sulfate and concentrated under reduced pressure to yield 1.58 g of the desired product (47%).

LC-MS (method 10): $R_t$=1.57 min; MS (ESIpos): m/z=262 [M+H]$^+$ $^1$H-NMR (400 MHz, dimethylsulfoxide-d6) δ [ppm]: −0.008 (0.91), 0.008 (0.78), 0.337 (2.14), 0.349 (7.29), 0.353 (7.32), 0.362 (8.28), 0.365 (7.78), 0.374 (3.16), 0.391 (0.76), 0.398 (0.75), 0.411 (1.24), 0.427 (3.40), 0.436 (6.54), 0.440 (5.92), 0.447 (4.35), 0.456 (7.12), 0.460 (5.63), 0.472 (1.88), 1.171 (0.70), 1.176 (0.97), 1.189 (1.75), 1.191 (1.72), 1.196 (1.75), 1.208 (2.72), 1.216 (1.43), 1.220 (1.64), 1.226 (1.57), 1.228 (1.56), 1.240 (0.77), 1.245 (0.57), 3.317 (16.00), 3.762 (13.65), 3.780 (13.34), 4.989 (15.04), 7.164 (1.07), 7.171 (6.91), 7.176 (2.91), 7.188 (3.41), 7.193 (14.02), 7.211 (2.63), 7.216 (7.35), 7.223 (1.01), 7.792 (1.22), 7.799 (7.39), 7.805 (3.57), 7.814 (8.23), 7.822 (8.20), 7.831 (3.02), 7.836 (6.97), 7.843 (0.92).

Intermediate 207

4-[5-amino-1-(cyclopropylmethyl)-4-methoxy-1H-pyrazol-3-yl]benzonitrile

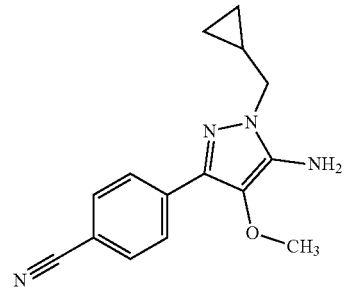 [SMILES: COc1c(-c2ccc(C#N)cc2)nn(CC2CC2)c1N]

A solution of 4-[cyano(methoxy)acetyl]benzonitrile (1.81 g, 9.04 mmol) and (cyclopropylmethyl)hydrazine dihydrochloride (1.87 g, 11.8 mmol) in 2-propanol (36 ml) was refluxed overnight. After cooling to ambient temperature the crude product was purified by flash-chromatography on silica gel (column: Biotage DNAP Ultra 25 g, solvent: 12% dichloromethane/88% ethyl acetate to 100% ethyl acetate) to yield 1.58 g (63%) of the desired product.

LC-MS (method 10): $R_t$=1.53 min; MS (ESIpos): m/z=269 [M+H]$^+$ $^1$H-NMR (400 MHz, dimethylsulfoxide-d6) δ [ppm]: 0.350 (1.94), 0.363 (8.44), 0.365 (8.46), 0.375 (9.90), 0.387 (3.18), 0.406 (0.76), 0.410 (0.74), 0.424 (1.04), 0.441 (3.14), 0.451 (7.31), 0.471 (8.02), 0.486 (1.91), 1.176 (0.51), 1.195 (1.18), 1.207 (1.98), 1.214 (1.94), 1.226 (2.94), 1.238 (1.91), 1.244 (1.91), 1.257 (0.93), 1.321 (0.67), 1.336 (0.67), 3.173 (0.42), 3.323 (3.32), 3.481 (0.66), 3.611 (0.53), 3.804 (14.03), 3.821 (14.13), 4.158 (0.71), 5.120 (13.03), 7.807 (11.20), 7.828 (14.44), 7.944 (0.86), 7.964 (16.00), 7.985 (12.23), 8.012 (0.50).

Intermediate 208

3-(4-chlorophenyl)-1,4-dimethyl-1H-pyrazol-5-amine

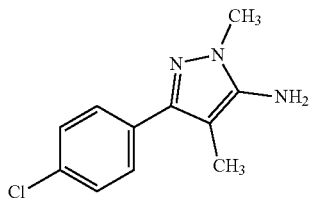

A solution of 3-(4-chlorophenyl)-2-methyl-3-oxopropanenitrile (2.67 g, 13.8 mmol) and methylhydrazine (730 μl, 14 mmol) in toluene was treated with acetic acid (790 μl, 14 mmol) and stirred for 2 days at ambient temperature and 2 additional days at 80° C. The mixture was diluted with water and the volume was reduced under reduced pressure. The mixture was extracted with ethyl acetate (3×). The combined organic phases were washed with water, brine, dried over sodium sulfate and concentrated under reduced pressure. The crude product was purified using preparative HPLC (column: XBridge C18, 5 μM, 75×30 mm, flow 80 mL/min, solvents: A (water), B (acetonitrile/water 80/20+2% formic acid), C (acetonitrile), gradient: 0.00-1.00 min 85% A/10% B/5% C, 1.00-7.20 min to 60% A/10% B/30% C, 7.20-7.40 min to 5% A/10% B/85% C, keep until 8.30 min, 8.30-8.80 min 85% A/10% B/5% C keep until 10.60 min) to yield 1.20 g of the desired product (37%) along with its regioisomer (250 mg, 9.6%).

LC-MS (method 9): $R_t$=0.71 min; MS (ESIpos): m/z=222 [M+H]$^+$ $^1$H-NMR (500 MHz, dimethylsulfoxide-d6) δ [ppm]: 1.987 (16.00), 2.013 (0.56), 3.650 (0.44), 4.987 (3.15), 7.396 (0.66), 7.401 (3.95), 7.405 (1.44), 7.415 (1.69), 7.419 (4.67), 7.424 (0.79), 7.577 (0.85), 7.582 (4.91), 7.586 (1.62), 7.596 (1.56), 7.599 (3.89), 7.604 (0.64).

Intermediate 209

5-(4-chlorophenyl)-1,4-dimethyl-1H-pyrazol-3-amine

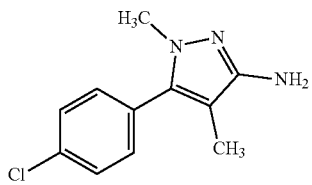

A solution of 3-(4-chlorophenyl)-2-methyl-3-oxopropanenitrile (2.67 g, 13.8 mmol) and methylhydrazine (730 μl, 14 mmol) in toluene was treated with acetic acid (790 μl, 14 mmol) and stirred for 2 days at ambient temperature and 2 additional days at 80° C. The mixture was diluted with water and the volume was reduced under reduced pressure. The mixture was extracted with ethyl acetate (3×). The combined organic phases were washed with water, brine, dried over sodium sulfate and concentrated under reduced pressure. The crude product was purified using preparative HPLC (column: XBridge C18, 5 μM, 75×30 mm, flow 80 mL/min, solvents: A (water), B (acetonitrile/water 80/20+2% formic acid), C (acetonitrile), gradient: 0.00-1.00 min 85% A/10% B/5% C, 1.00-7.20 min to 60% A/10% B/30% C, 7.20-7.40 min to 5% A/10% B/85% C, keep until 8.30 min, 8.30-8.80 min 85% A/10% B/5% C keep until 10.60 min) to yield 250 mg of the desired product (9.6%) along with its regioisomer (1.2 g, 37%).

LC-MS (method 9): $R_t$=0.75 min; MS (ESIpos): m/z=222 [M+H]$^+$ $^1$H-NMR (400 MHz, dimethylsulfoxide-d6) δ [ppm]: 1.381 (0.41), 1.765 (16.00), 1.799 (1.38), 1.984 (2.99), 2.074 (0.69), 3.195 (1.30), 3.314 (10.21), 3.561 (3.09), 4.479 (0.94), 4.977 (1.02), 7.053 (0.47), 7.276 (0.43), 7.362 (3.45), 7.382 (4.55), 7.397 (0.76), 7.418 (0.81), 7.454 (0.41), 7.534 (4.14), 7.555 (3.40), 7.577 (1.00), 7.599 (0.85).

Intermediate 210

2-[1-(2-cyclopropyl-2-oxoethyl)-3-(4-fluorophenyl)-4-methyl-1H-pyrazol-5-yl]-1H-isoindole-1,3(2H)-dione

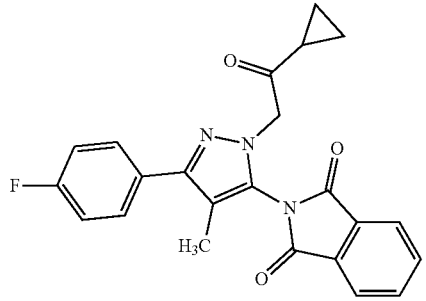 [SMILES: Cc1c(-c2ccc(F)cc2)nn(CC(=O)C2CC2)c1N1C(=O)c2ccccc2C1=O]

2-[5-(4-fluorophenyl)-4-methyl-1H-pyrazol-3-yl]-1H-isoindole-1,3(2H)-dione (5.80 g, 18.0 mmol) and potassium carbonate (4.99 g, 36.1 mmol) were suspended in dimethylformamide (25 mL) and 2-bromo-1-cyclopropylethanone (5.00 g, 30.7 mmol) was slowly added under an argon atmosphere. The reaction mixture was stirred at ambient temperature overnight. Water was added and the mixture stirred for another 5 min. The precipitated solid was collected by filtration and washed with water. It was then dried in a vacuum drying-oven at 40° C. overnight. Further purification by flash column chromatography (SNAP Ultra 100 g, cyclohexane/ethyl acetate gradient 88/12 to 10/90) yielded the desired product (3.78 g, 49% yield).

LC-MS (method 10): $R_t$=2.03 min; MS (ESIpos): m/z=404 [M+H]$^+$ $^1$H-NMR (400 MHz, dimethylsulfoxide-d6) δ [ppm]: −0.008 (1.98), 0.008 (1.97), 0.767 (0.68), 0.778 (1.87), 0.785 (2.92), 0.797 (2.56), 0.804 (1.55), 0.825 (0.66), 0.838 (1.45), 0.844 (2.53), 0.852 (1.60), 0.857 (1.74), 0.864 (2.97), 0.872 (1.54), 0.883 (0.70), 1.157 (1.19), 1.175 (2.38), 1.192 (1.21), 1.891 (0.74), 1.898 (0.81), 1.910 (1.37), 1.921 (0.80), 1.929 (0.68), 1.980 (0.68), 1.988 (4.43), 2.008 (0.44), 2.037 (16.00), 4.020 (1.04), 4.038 (1.05), 5.180 (8.30), 7.277 (2.31), 7.300 (4.83), 7.317 (0.97), 7.322 (2.58), 7.721 (2.60), 7.726 (1.28), 7.735 (2.87), 7.743 (2.72), 7.751 (1.07), 7.757 (2.31), 7.949 (2.74), 7.957 (2.87), 7.963 (2.78), 7.971 (4.37), 7.981 (0.77), 8.010 (0.72), 8.020 (4.33), 8.027 (2.71), 8.034 (2.87), 8.041 (2.45).

Intermediate 211

2-{1-[(±)-2-cyclopropyl-2-hydroxypropyl]-3-(4-fluorophenyl)-4-methyl-1H-pyrazol-5-yl}-1H-isoindole-1,3(2H)-dione (Racemate)

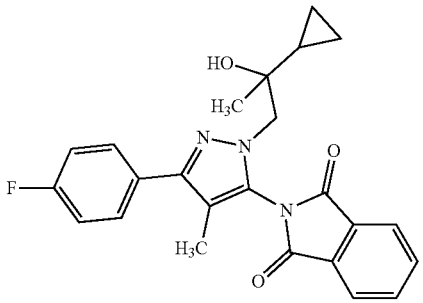 [SMILES: Cc1c(-c2ccc(F)cc2)nn(CC(C)(O)C2CC2)c1N1C(=O)c2ccccc2C1=O]

Under an argon atmosphere, 2-[1-(2-cyclopropyl-2-oxoethyl)-3-(4-fluorophenyl)-4-methyl-1H-pyrazol-5-yl]-1H-isoindole-1,3(2H)-dione (500 mg, 1.24 mmol) was dissolved in tetrahydrofuran (8 mL) and cooled to 0° C. A solution of methylmagnesium bromide in tetrahydrofuran (1.9 mL, 1.0 M, 1.9 mmol). After 2 h, a second aliquot methylmagnesium bromide in tetrahydrofuran (1.5 mL, 1.0 M, 1.5 mmol) was added and the reaction mixture was stirred overnight at ambient temperature. A third aliquot methylmagnesium bromide in tetrahydrofuran (1.5 mL, 1.0 M, 1.5 mmol) was added and the reaction mixture was stirred at ambient temperature for 2 h. It was then carefully quenched by addition of Na$_2$EDTA solution (10%) and extracted with ethyl acetate (2×). The combined organic phase extracts were dried over sodium sulfate, concentrated and to yield a complex mixture that was used in the next step without further purification.

LC-MS (method 11): Rt=1.38 min; MS (ESIpos): m/z=420 [M+H]$^+$

Intermediate 212

(±)-1-[5-amino-3-(4-fluorophenyl)-4-methyl-1H-pyrazol-1-yl]-2-cyclopropylpropan-2-ol (Racemate)

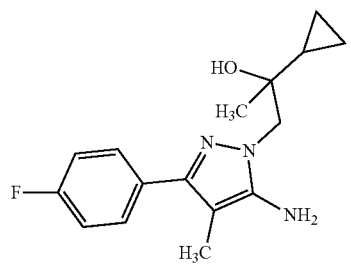 [SMILES: Cc1c(-c2ccc(F)cc2)nn(CC(C)(O)C2CC2)c1N]

The complex mixture containing 2-{1-[(2S)-2-cyclopropyl-2-hydroxypropyl]-3-(4-fluorophenyl)-4-methyl-1H-pyrazol-5-yl}-1H-isoindole-1,3(2H)-dione (510 mg, 1.22 mmol) was dissolved in ethanol (18 mL) and hydrazine monohydrate (300 µL, 6.1 mmol) and acetic acid (210 µL, 3.6 mmol) were added. The reaction mixture was stirred under reflux for 3 h and allowed to cool to ambient temperature and left standing overnight. Water was added to the mixture, which was then extracted with ethyl acetate. The organic phase extract was washed with aqueous saturated sodium hydrogencarbonate solution, dried over sodium sulfate and concentrated. The residue was purified by flash column chromatography (SNAP Ultra 25 g, cyclohexane/ethyl acetate gradient 90/10 to 0/100) to yield the desired product (39 mg, 11% yield).

LC-MS (method 11): R$_t$=1.03 min; MS (ESIpos): m/z=290 [M+H]$^+$, 272 [M-water+H]$^+$

Intermediate 213

2-methyl-3-oxo-3-(pyridin-4-yl)propanenitrile

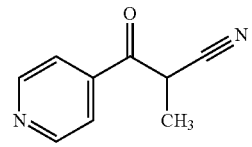

Ethyl pyridine-4-carboxylate (5.0 ml, 33 mmol) and propanenitrile (5.9 ml, 83 mmol) were dissolved in tetrahydrofuran (47 mL) and chilled with a waterbath. A solution of lithium bis(trimethylsilyl)amide (84 mL, 1.0 M, 84 mmol) was slowly added and vigorous stirring. A pale yellow solid starts precipitating immediately. After 30 min, the precipitated solid was collected by filtration, washed with tetrahydrofuran and dried under vacuum. It was then suspended in ethyl acetate and aqueous ammonium chloride solution and adjusted to pH 4-5 with aqueous hydrochloric acid solution (1 M). After phase separation, the aqueous layer was extracted with ethyl acetate (2×). The combined organic phase extracts were dried over sodium sulfate and concentrated to yield the desired product (4.08 g, 75% yield).

LC-MS (method 11): R$_t$=0.53 min; MS (ESIpos): m/z=161 [M+H]$^+$ $^1$H-NMR (400 MHz, dimethylsulfoxide-d6) δ [ppm]: −0.149 (0.18), −0.008 (1.47), 0.008 (1.67), 0.146 (0.17), 1.085 (0.38), 1.104 (0.19), 1.471 (0.66), 1.484 (0.67), 1.564 (0.55), 1.676 (3.26), 1.884 (16.00), 2.328 (0.20), 2.367 (0.17), 2.523 (0.54), 2.670 (0.22), 2.711 (0.18), 5.143 (0.19), 7.412 (0.74), 7.416 (0.55), 7.427 (0.81), 7.523 (4.17), 7.538 (4.45), 7.874 (0.49), 8.694 (4.40), 8.708 (4.64), 8.873 (0.44), 11.166 (0.44).

Intermediate 214

1-(cyclopropylmethyl)-4-methyl-3-(pyridin-4-yl)-1H-pyrazol-5-amine

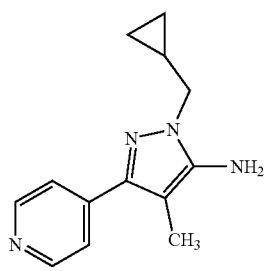 [SMILES: Cc1c(-c2ccncc2)nn(CC2CC2)c1N]

2-methyl-3-oxo-3-(pyridin-4-yl)propanenitrile (2.00 g, 12.5 mmol) and (cyclopropylmethyl)hydrazine dihydrochloride (2.48 g, 15.6 mmol) were suspended in 2-propanol (28 ml) and the reaction mixture heated to reflux for 4.5 h while vigorously stirring. After cooling to ambient temperature, the reaction mixture was carefully quenched by addition of saturated aqueous sodium hydrogencarbonate solution and extracted with ethyl acetate (3×). The combined organic phase extracts were dried over sodium sulfate and concentrated to yield the desired product (2.04 g, 69% yield).

LC-MS (method 9): $R_t$=0.64 min; MS (ESIpos): m/z=229 [M+H]$^+$ $^1$H-NMR (400 MHz, dimethylsulfoxide-d6) δ [ppm]: 0.343 (0.53), 0.358 (2.52), 0.370 (2.88), 0.380 (1.02), 0.424 (0.95), 0.436 (2.10), 0.443 (1.47), 0.453 (2.33), 0.468 (0.56), 1.200 (0.61), 1.205 (0.56), 1.218 (0.89), 1.230 (0.56), 1.237 (0.59), 2.053 (16.00), 3.830 (4.48), 3.847 (4.45), 5.025 (5.06), 7.567 (4.07), 7.571 (3.53), 7.579 (2.63), 7.583 (4.73), 8.516 (3.90), 8.519 (3.54), 8.527 (2.45), 8.531 (4.43).

Intermediate 215

1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylic acid

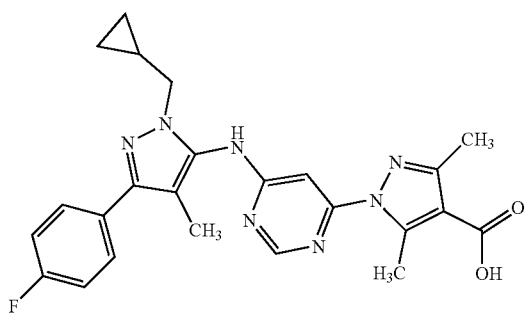 [SMILES: Cc1nn(-c2cc(Nc3c(C)c(-c4ccc(F)cc4)nn3CC3CC3)ncn2)c(C)c1C(=O)O]

A solution of ethyl 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylate (1.38 g, 2.81 mmol) in tetrahydrofuran (19 ml, 230 mmol) was treated with aqueous lithium hydroxide solution (14 ml, 1.0 M, 14 mmol) and stirred for 2 days at ambient temperature followed by reflux overnight. After cooling to room temperature the mixture was diluted with water and acidified with hydrochloric acid. The mixture was extracted with ethyl acetate (3×). The combined organic phases were dried over sodium sulfate and concentrated under reduced pressure to yield 977 mg (75%) of the desired product.

LC-MS (method 10): $R_t$=1.86 min; MS (ESIpos): m/z=462 [M+H]$^+$ $^1$H-NMR (500 MHz, dimethylsulfoxide-d6) δ [ppm]: 0.304 (2.49), 0.313 (2.57), 0.435 (2.69), 0.450 (2.75), 1.183 (0.42), 1.193 (0.77), 1.199 (0.76), 1.209 (1.18), 1.215 (0.62), 1.218 (0.69), 1.223 (0.71), 1.917 (2.17), 2.018 (16.00), 2.367 (1.57), 2.914 (12.32), 3.573 (2.49), 3.842 (1.91), 3.855 (1.85), 7.258 (2.57), 7.262 (1.13), 7.276 (5.09), 7.294 (2.73), 7.722 (1.48), 7.733 (1.99), 7.749 (1.37), 12.614 (0.58).

Intermediate 216

N'-acetyl-1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbohydrazide

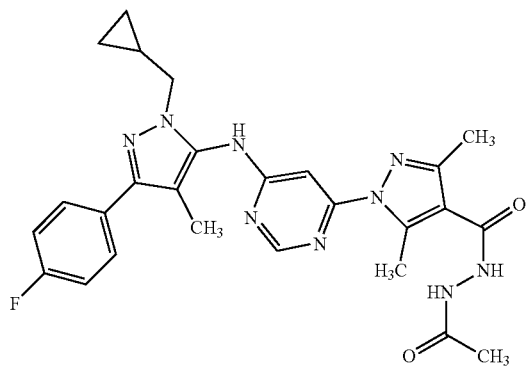 [SMILES: CC(=O)NNC(=O)c1c(C)nn(-c2cc(Nc3c(C)c(-c4ccc(F)cc4)nn3CC3CC3)ncn2)c1C]

A solution of 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylic acid (500 mg, 1.08 mmol) and acetohydrazide (241 mg, 3.25 mmol) in N,N-dimethylformamide (8.3 mL) was treated with HATU (618 mg, 1.63 mmol) and N,N-diisopropylethylamine (570 µl, 3.3 mmol) and stirred one hour at room temperature. The mixture was diluted with water. The occurring precipitate was collected by filtration, washed with water and dried to yield 415 mg (72%) of the desired product.

LC-MS (method 9): $R_t$=0.83 min; MS (ESIpos): m/z=518 [M+H]$^+$ $^1$H-NMR (500 MHz, dimethylsulfoxide-d6) δ [ppm]: 0.006 (0.64), 0.300 (3.00), 0.308 (3.08), 0.430 (3.14), 0.446 (3.20), 1.078 (1.98), 1.092 (3.92), 1.106 (1.99), 1.178 (0.58), 1.188 (1.00), 1.193 (1.00), 1.203 (1.42), 1.212 (0.95), 1.217 (0.96), 1.227 (0.56), 1.882 (1.07), 1.907 (13.23), 2.015 (16.00), 2.293 (1.94), 2.691 (2.06), 2.733 (1.43), 2.774 (13.51), 2.891 (1.58), 3.363 (0.68), 3.376 (1.92), 3.390 (1.89), 3.404 (0.63), 3.838 (2.46), 3.850 (2.40), 7.258 (2.54), 7.276 (4.99), 7.293 (2.74), 7.734 (2.38), 8.519 (0.48), 9.726 (2.68), 9.893 (3.50).

Intermediate 217

1-(6-chloropyrimidin-4-yl)-3,5-dimethyl-1H-pyrazole-4-carbaldehyde

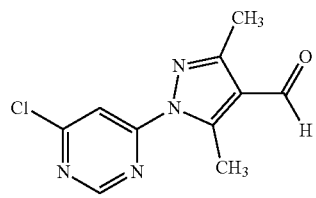 [SMILES: Cc1nn(-c2cc(Cl)ncn2)c(C)c1C=O]

4,6-dichloropyrimidine (6.30 g, 42.3 mmol), 3,5-dimethyl-1H-pyrazole-4-carbaldehyde (5.00 g, 40.3 mmol) and cesium carbonate (13.1 g, 40.3 mmol) were suspended in dimethylformamide and the reaction mixture was stirred overnight at ambient temperature. It was then poured onto water (400 mL) and stirred for another 30 min. The precipitated solid was collected by filtration, washed with water and dried overnight in a dessicator to yield the desired product, which was used in the next step without further purification (7.1 g, 68% purity, 48% yield).

LC-MS (method 11): R$_t$=1.19 min; MS (ESIpos): m/z=236 [M+H]$^+$ $^1$H-NMR (400 MHz, dimethylsulfoxide-d6) δ [ppm]: 0.008 (0.44), 2.284 (0.49), 2.403 (0.64), 2.421 (0.45), 2.432 (0.60), 2.450 (16.00), 2.478 (2.29), 2.732 (0.75), 2.771 (0.56), 2.891 (0.89), 2.947 (0.58), 2.976 (15.72), 3.024 (1.91), 8.020 (2.96), 8.022 (2.99), 9.032 (2.87), 9.035 (2.85), 10.054 (6.02), 10.069 (0.82).

Intermediate 218

4-[1-(cyclopropylmethyl)-5-{[6-(4-formyl-3,5-dimethyl-1H-pyrazol-1-yl)pyrimidin-4-yl]amino}-4-methyl-1H-pyrazol-3-yl]benzonitrile

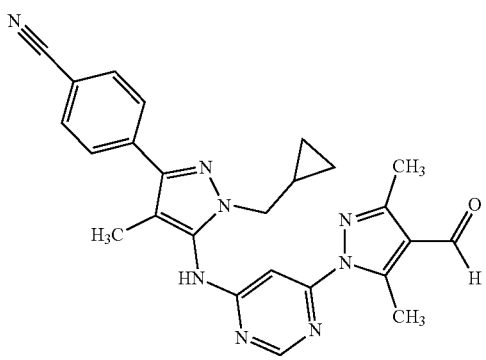 [SMILES: Cc1nn(-c2cc(Nc3c(C)c(-c4ccc(C#N)cc4)nn3CC3CC3)ncn2)c(C)c1C=O]

A microwave vial was charged with 4-[5-amino-1-(cyclopropylmethyl)-4-methyl-1H-pyrazol-3-yl]benzonitrile (96.9 mg, 384 μmol), 1-(6-chloropyrimidin-4-yl)-3,5-dimethyl-1H-pyrazole-4-carbaldehyde (100 mg, 423 μmol) and sodium phenolate (49.1 mg, 423 μmol) and the contents were suspended in 1,4-dioxane (1.4 mL). The reaction mixture was degassed with Ar for 3 min. Tris(dibenzylideneacetone)dipalladium (7.04 mg, 7.68 μmol) and XantPhos (8.89 mg, 15.4 μmol) were added and the reaction mixture was degassed again for 1 min. The vial was sealed and heated at 85° C. overnight while vigorously shaking. After cooling to ambient temperature, the reaction mixture was diluted with water and extracted with ethyl acetate. The organic phase extract was dried over sodium sulfate and concentrated. The residue was purified by flash column chromatography (SNAP Ultra 25 g, cyclohexane/ethyl acetate gradient 90/10 to 0/100) and further by preparative HPLC (column: Chromatorex C18; 250*30 mm, 10 μM, flow 100 mL/min, gradient acetonitrile/water (containing 0.1% trifluoroacetic acid) 10/90 to 90/10) to yield the desired product (24 mg, 14% yield).

LC-MS (method 11): R$_t$=1.36 min; MS (ESIpos): m/z=453 [M+H]$^+$ $^1$H-NMR (400 MHz, dimethylsulfoxide-d6) δ [ppm]: −0.008 (3.29), 0.008 (2.64), 0.308 (2.58), 0.320 (2.81), 0.436 (2.67), 0.456 (2.80), 1.192 (0.71), 1.211 (1.07), 1.230 (0.75), 2.030 (0.43), 2.065 (16.00), 2.328 (0.93), 2.367 (0.73), 2.407 (2.23), 2.670 (0.84), 2.943 (14.84), 3.866 (3.62), 3.884 (3.85), 3.940 (2.51), 7.885 (1.10), 7.908 (13.70), 8.546 (0.51), 9.599 (0.42), 10.016 (3.38).

Intermediate 219

1,4-dimethyl-3-[4-(trifluoromethyl)phenyl]-1H-pyrazol-5-amine

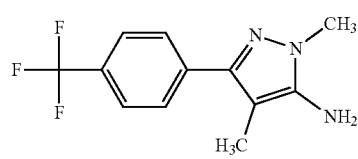 [SMILES: Cc1c(-c2ccc(C(F)(F)F)cc2)nn(C)c1N]

Under an argon atmosphere, 2-methyl-3-oxo-3-[4-(trifluoromethyl)phenyl]propanenitrile (1.00 g, 4.40 mmol) was dissolved in 1,4-dioxane (24 mL) and methylhydrazine (230 μl, 4.4 mmol) and acetic acid (250 μl, 4.4 mmol) were added. The reaction mixture was stirred at ambient temperature. It was then concentrated and the residue redissolved in ethanol (12 mL) and purified by preparative HPLC (Daicel Chiralpak IF 5 μm, 250×20 mm, flow: 15 mL/min, isocratic n-Heptane/ethanol 75/25, 350 μL injections every 15 min) to yield the desired product (469 mg, 38% yield) along with 1,4-dimethyl-5-[4-(trifluoromethyl)phenyl]-1H-pyrazol-3-amine (see below).

LC-MS (method 9): R$_t$=0.83 min; MS (ESIpos): m/z=256 [M+H]$^+$ $^1$H-NMR (400 MHz, dimethylsulfoxide-d6) δ [ppm]: 1.157 (0.45), 1.909 (1.35), 2.033 (16.00), 3.313 (2.26), 5.037 (3.43), 7.698 (2.25), 7.718 (3.47), 7.795 (3.33), 7.816 (2.19).

Intermediate 220

1,4-dimethyl-5-[4-(trifluoromethyl)phenyl]-1H-pyrazol-3-amine

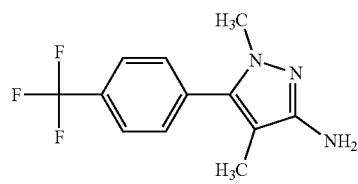 [SMILES: Cc1c(N)nn(C)c1-c1ccc(C(F)(F)F)cc1]

The title compound was observed as a by-product during the synthesis of 1,4-dimethyl-3-[4-(trifluoromethyl)phenyl]-1H-pyrazol-5-amine (see above). It was obtained after purification by preparative HPLC (Daicel Chiralpak IF 5 μm, 250×20 mm, flow: 15 mL/min, isocratic n-Heptane/ethanol 75/25, 350 μL injections every 15 min) as a white solid (120 mg, 11% yield).

$^1$H-NMR (400 MHz, dimethylsulfoxide-d6) δ [ppm]: −0.008 (0.39), 1.798 (16.00), 1.908 (0.59), 3.313 (7.17), 3.678 (0.17), 4.526 (2.20), 7.582 (2.82), 7.603 (3.27), 7.833 (3.37), 7.854 (2.90).

Intermediate 221

3-(2,4-difluorophenyl)-1,4-dimethyl-1H-pyrazol-5-amine

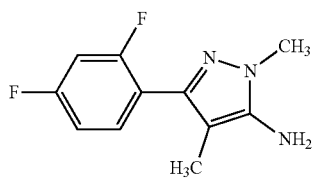 [SMILES: Cc1c(-c2ccc(F)cc2F)nn(C)c1N]

Under an argon atmosphere, 3-(2,4-difluorophenyl)-2-methyl-3-oxopropanenitrile (2.00 g, 10.2 mmol) was dissolved in 1,4-dioxane (57 mL) and methylhydrazine (550 µl, 10 mmol) and acetic acid (590 µl, 10 mmol) were added. The reaction mixture was stirred at ambient temperature. It was then concentrated and the residue redissolved in ethanol (12 mL) and purified by preparative HPLC (Daicel Chiralpak IF 5 µm, 250×20 mm, flow: 15 mL/min, isocratic n-Heptane/ethanol 75/25, 300 µL injections every 15 min) to yield the desired product (1.93 g, 71% yield) along with 5-(2,4-difluorophenyl)-1,4-dimethyl-1H-pyrazol-3-amine (see below).

LC-MS (method 9): $R_t$=0.66 min; MS (ESIpos): m/z=224 [M+H]$^+$ $^1$H-NMR (400 MHz, dimethylsulfoxide-d6) δ [ppm]: 1.762 (15.97), 1.767 (16.00), 1.911 (4.69), 2.075 (1.15), 2.503 (6.48), 2.884 (0.46), 3.322 (3.24), 4.979 (6.91), 7.067 (1.05), 7.073 (1.10), 7.089 (2.21), 7.094 (2.28), 7.110 (1.22), 7.116 (1.24), 7.226 (1.18), 7.233 (1.07), 7.252 (1.99), 7.277 (1.18), 7.282 (1.07), 7.404 (1.33), 7.425 (2.62), 7.443 (2.61), 7.464 (1.17).

Intermediate 222

5-(2,4-difluorophenyl)-1,4-dimethyl-1H-pyrazol-3-amine

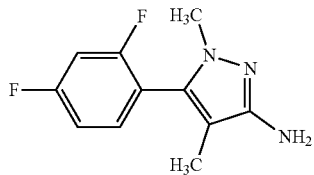

The title compound was observed as a by-product during the synthesis of 3-(2,4-difluorophenyl)-1,4-dimethyl-1H-pyrazol-5-amine (see above). It was obtained after purification by preparative HPLC (Daicel Chiralpak IF 5 µm, 250×20 mm, flow: 15 mL/min, isocratic n-Heptane/ethanol 75/25, 300 µL injections every 15 min) as a white solid (249 mg, 11% yield).

LC-MS (method 9): Rt=0.70 min; MS (ESIpos): m/z=224 [M+H]$^+$ $^1$H-NMR (400 MHz, dimethylsulfoxide-d6) δ [ppm]: −0.008 (1.16), 1.690 (16.00), 1.908 (0.65), 2.327 (0.24), 2.670 (0.29), 3.377 (14.94), 3.397 (0.28), 3.556 (0.26), 3.563 (0.24), 4.479 (3.40), 7.198 (0.60), 7.204 (0.65), 7.219 (1.32), 7.225 (1.41), 7.240 (0.76), 7.246 (0.80), 7.391 (0.74), 7.397 (0.74), 7.407 (0.91), 7.416 (1.33), 7.423 (2.05), 7.428 (1.76), 7.445 (2.13), 7.466 (0.73).

Intermediate 223

1-(cyclopropylmethyl)-3-(2,4-difluorophenyl)-4-methyl-1H-pyrazol-5-amine

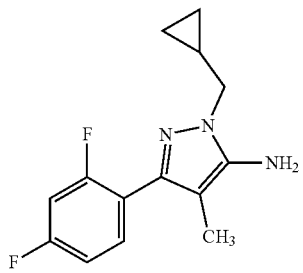 [SMILES: Cc1c(-c2ccc(F)cc2F)nn(CC2CC2)c1N]

3-(2,4-difluorophenyl)-2-methyl-3-oxopropanenitrile (2.19 g, 11.2 mmol) and (cyclopropylmethyl)hydrazine dihydrochloride (2.24 g, 100% purity, 14.1 mmol) were suspended in 2-propanol (23 mL) and the reaction mixture was stirred under reflux for 3 h. It was then concentrated to ⅓ of its original volume, carefully quenched with aqueous saturated sodium hydrogencarbonate solution and extracted with ethyl acetate (3×). The combined organic phase extracts were washed with brine, dried over sodium sulfate and concentrated. The residue was dissolved in dichloromethane, loaded onto silica gel and purified by flash column chromatography (SNAP Ultra 25 g, cyclohexane/ethyl acetate gradient 100/0 to 40/60) to yield the desired product (1.58 g, 52% yield).

LC-MS (method 9): $R_t$=0.77 min; MS (ESIpos): m/z=264 [M+H]$^+$ $^1$H-NMR (400 MHz, dimethylsulfoxide-d6) δ [ppm]: 0.328 (0.97), 0.341 (3.95), 0.344 (3.91), 0.353 (4.63), 0.366 (1.76), 0.402 (0.58), 0.418 (1.74), 0.427 (3.64), 0.431 (3.15), 0.438 (2.26), 0.448 (4.03), 0.451 (3.13), 0.463 (1.09), 1.170 (0.47), 1.175 (0.46), 1.182 (0.92), 1.190 (0.90), 1.194 (0.78), 1.202 (1.46), 1.210 (0.73), 1.214 (0.87), 1.219 (0.85), 1.222 (0.83), 1.234 (0.43), 1.770 (16.00), 1.776 (15.36), 3.651 (0.60), 3.793 (7.85), 3.810 (7.77), 3.934 (0.45), 4.935 (7.16), 4.996 (0.54), 7.072 (1.00), 7.078 (1.07), 7.094 (2.12), 7.100 (2.23), 7.115 (1.17), 7.121 (1.22), 7.228 (1.27), 7.235 (1.20), 7.252 (1.78), 7.255 (1.85), 7.258 (1.80), 7.278 (1.30), 7.285 (1.20), 7.420 (1.31), 7.437 (1.70), 7.441 (2.67), 7.458 (2.61), 7.463 (1.51), 7.480 (1.17).

Intermediate 224

2-{1-[(±)-2-cyclopropyl-2-hydroxyethyl]-3-(4-fluorophenyl)-4-methyl-1H-pyrazol-5-yl}-1H-isoindole-1,3(2H)-dione (Racemate)

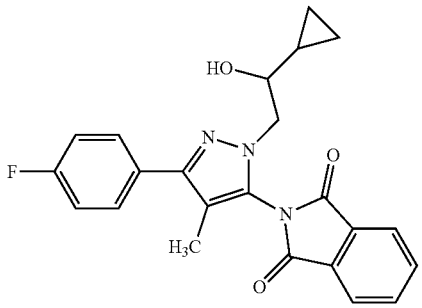 [SMILES: Cc1c(-c2ccc(F)cc2)nn(CC(O)C2CC2)c1N1C(=O)c2ccccc2C1=O]

Under an argon atmosphere, 2-[1-(2-cyclopropyl-2-oxoethyl)-3-(4-fluorophenyl)-4-methyl-1H-pyrazol-5-yl]-1H-isoindole-1,3(2H)-dione (500 mg, 1.24 mmol) was dissolved in toluene (8.0 mL) and cooled to −78° C. A solution of DIBA1-H in toluene (1.1 ml, 1.2 M, 1.4 mmol) was then added dropwise. After complete addition, the reaction mixture was allowed to warm to 0° C. and stirred for further 1.75 h. A second aliquot of DIBA1-H (800 μL, 1.2 m, 0.96 mmol) was added and the reaction mixture further stirred for 1.5 h. It was then quenched by addition of aqueous Rochelle salt solution (20%) and stirred at ambient temperature overnight. The mixture was extracted with ethyl acetate (2×). The combined organic phase extracts were dried over sodium sulfate and concentrated to yield the desired product that was used in the next step without further purification.

LC-MS (method 11): $R_t$=1.37 min; MS (ESIneg): m/z=404 [M−H]$^-$

Intermediate 225

(±)-2-[5-amino-3-(4-fluorophenyl)-4-methyl-1H-pyrazol-1-yl]-1-cyclopropylethanol (Racemate)

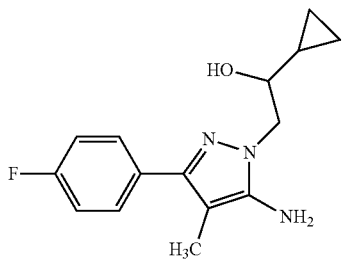 [SMILES: Cc1c(-c2ccc(F)cc2)nn(CC(O)C2CC2)c1N]

2-{1-[(2S)-2-cyclopropyl-2-hydroxyethyl]-3-(4-fluorophenyl)-4-methyl-1H-pyrazol-5-yl}-1H-isoindole-1,3(2H)-dione (456 mg, 1.12 mmol) was dissolved in ethanol (16 mL) and hydrazine monohydrate (270 μL, 5.6 mmol) and acetic acid (320 μL, 5.6 mmol) were added subsequently. The reaction mixture was heated to reflux for 4 h. After cooling to ambient temperature, it was diluted with water and extracted with ethyl acetate. The organic phase extract was washed with aqueous saturated sodium hydrogencarbonate solution, dried over sodium sulfate and concentrated. The residue was purified by flash column chromatography (SNAP Ultra 25 g, cyclohexane/ethyl acetate 80/20 to 0/100) to yield the desired product (186 mg, 77% purity, 46% yield) and was used as such in the next step.

LC-MS (method 11): $R_t$=0.94 min; MS (ESIpos): m/z=276 [M+H]$^+$ $^1$H-NMR (400 MHz, dimethylsulfoxide-d6) δ [ppm]: −0.008 (0.83), 0.008 (0.59), 0.124 (0.43), 0.134 (0.64), 0.146 (1.10), 0.151 (0.85), 0.159 (0.82), 0.163 (0.77), 0.252 (0.65), 0.258 (0.76), 0.265 (0.75), 0.271 (0.89), 0.284 (0.64), 0.293 (0.53), 0.351 (2.20), 0.356 (1.70), 0.371 (2.19), 0.377 (1.70), 0.825 (0.41), 0.832 (0.48), 0.845 (0.86), 0.852 (0.56), 0.857 (0.55), 0.864 (0.80), 0.876 (0.41), 1.983 (16.00), 3.266 (0.60), 3.274 (0.72), 3.285 (1.16), 3.296 (0.98), 3.885 (0.78), 3.904 (0.70), 3.920 (1.66), 3.939 (1.61), 3.971 (1.61), 3.981 (1.60), 4.006 (0.75), 4.016 (0.67), 4.859 (4.87), 5.019 (2.65), 5.031 (2.61), 7.164 (1.98), 7.186 (4.23), 7.203 (0.78), 7.208 (2.36), 7.569 (2.25), 7.575 (0.98), 7.584 (2.52), 7.591 (2.50), 7.600 (0.93), 7.606 (2.16), 7.930 (0.51), 8.366 (0.45).

Intermediate 226

4-chloro-6-[3,5-dimethyl-4-(trifluoromethyl)-1H-pyrazol-1-yl]pyrimidine

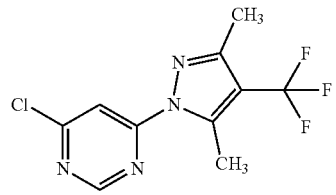 [SMILES: Cc1nn(-c2cc(Cl)ncn2)c(C)c1C(F)(F)F]

4,6-dichloropyrimidine (4.54 g, 30.5 mmol), 3,5-dimethyl-4-(trifluoromethyl)-1H-pyrazole (5.00 g, 30.5 mmol) and cesium carbonate (9.93 g, 30.5 mmol) were suspended in dimethylformamide (18 mL) and stirred at ambient temperature overnight. The crude mixture was poured onto water (400 mL) and further stirred for 30 min. The precipitated solid was collected by filtration and washed with water. It was then dried in a vacuum drying-oven at 40° C. overnight to yield the desired product (6.10 g, 69% yield).

LC-MS (method 10): $R_t$=2.33 min; MS (ESIpos): m/z=277 [M+H]$^+$ $^1$H-NMR (500 MHz, dimethylsulfoxide-d6) δ [ppm]: −0.007 (0.88), 0.006 (0.45), 1.231 (0.20), 1.996 (0.18), 2.003 (0.19), 2.080 (0.19), 2.096 (0.19), 2.192 (1.29), 2.216 (0.38), 2.283 (1.29), 2.348 (16.00), 2.350 (15.23), 2.364 (0.57), 2.374 (1.89), 2.376 (1.79), 2.521 (0.42), 2.525 (0.32), 2.638 (0.19), 2.733 (0.33), 2.793 (15.68), 2.796 (14.90), 2.842 (1.73), 2.844 (1.66), 2.892 (0.36), 8.004 (7.87), 8.006 (7.48), 8.260 (0.44), 9.028 (7.17), 9.029 (6.81), 9.100 (0.44).

Intermediate 227

1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbaldehyde

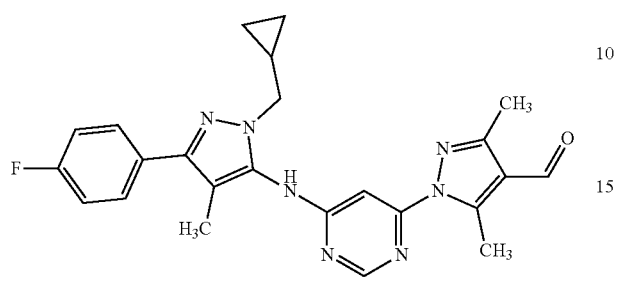

Under an argon atmosphere, 1-(cyclopropylmethyl)-3-(4-fluorophenyl)-4-methyl-1H-pyrazol-5-amine (1.50 g, 6.11 mmol), 1-(6-chloropyrimidin-4-yl)-3,5-dimethyl-1H-pyrazole-4-carbaldehyde (1.59 g, 6.73 mmol) and sodium phenolate (781 mg, 6.73 mmol) were suspended in 1,4-dioxane (25 mL). The reaction mixture was degassed with Ar for 3 min. Tris(dibenzylideneacetone)dipalladium (168 mg, 183 μmol) and XantPhos (212 mg, 367 μmol) were added and the reaction mixture was degassed again for 1 min and heated at 90° C. for 2 h while vigorously stirring. After cooling to ambient temperature, the reaction mixture was loaded onto Celite and purified by flash column chromatography (SNAP Ultra 25 g, cyclohexane/ethyl acetate gradient 90/10 to 0/100) to yield an impure product. This was dissolved in acetonitrile at 60° C. and the solution allowed to cool to ambient temperature overnight. The precipitated sold was collected by filtration and later combined with the other product fraction. The filtrate was concentrated and purified by preparative HPLC (method 3) to yield the product. After combining both product fraction, the desired product was obtained (286 mg, 10% yield).

LC-MS (method 11): $R_t$=1.41 min; MS (ESIpos): m/z=446 [M+H]$^+$

Intermediate 228

2,4-dioxopentan-3-yl acetate

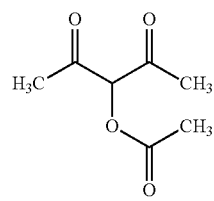

In a 100 ml round-bottom flask was added dimethylsulfoxide and it was degassed with Ar. 3-chloropentane-2,4-dione (8.4 ml, 74 mmol) and sodium acetate (6.10 g, 74.3 mmol) were added under argon and the resulting solution stirred at ambient temperature. After 3 h, the mixture was diluted with water (500 mL) & washed with saturated ammonium chloride (Caution: exothermic!), then extracted with dichloromethane (3×40 ml). The combined organic phase extracts were combined, washed with brine, dried over sodium sulfate and concentrated. The resulting liquid was dried further overnight under high vacuum to remove residual dimethylsulfoxide to yield the desired product as a colorless liquid (12.7 g, 90% purity, 97% yield).

GC-MS (method 15): $R_t$=2.47 min; MS (EI): m/z=158 (5), 116(77), 101 (18), 74 (100).

$^1$H-NMR (500 MHz, dimethylsulfoxide-d6) δ [ppm]: 2.006 (0.83), 2.187 (8.60), 2.222 (16.00), 5.655 (2.46).

Intermediate 229

1-(6-chloropyrimidin-4-yl)-3,5-dimethyl-1H-pyrazol-4-yl acetate

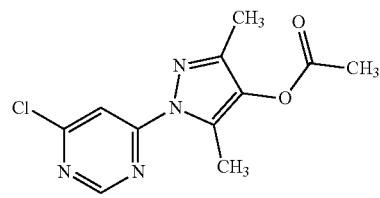 [SMILES: CC(=O)Oc1c(C)nn(-c2cc(Cl)ncn2)c1C]

Under an argon atmosphere, 2,4-dioxopentan-3-yl acetate (7.1 ml, 88% purity, 70 mmol) and 4-chloro-6-hydrazinylpyrimidine (11.2 g, 77.5 mmol) were dissolved in ethanol (100 mL). The reaction mixture was refluxed for 3 h. After cooling to ambient temperature, water was added and the reaction mixture quenched with solid sodium hydrogencarbonate. It was extracted with dichloromethane (3×). The combined organic phase extracts were washed with brine, dried over magnesium sulfate and concentrated. The residue was purified by flash column chromatography (SNAP Ultra 100 g, cyclohexane/ethyl acetate 100/0 to 0/100) and further repurified by flash column chromatography (SNAP Ultra 100 g, cyclohexane/ethyl acetate 100/0 to 60/40) to yield the desired product (7.59 g, 40% yield) along with the saponified by-product 1-(6-chloropyrimidin-4-yl)-3,5-dimethyl-1H-pyrazol-4-ol (4.48 g, 28% yield, see below).

LC-MS (method 11): $R_t$=1.28 min; MS (ESIpos): m/z=267 [M+H]$^+$ $^1$H-NMR (500 MHz, dimethylsulfoxide-d6) δ [ppm]: 2.123 (14.63), 2.344 (16.00), 2.517 (14.59), 7.899 (3.66), 7.901 (3.58), 8.903 (3.35), 8.905 (3.23).

Intermediate 230

1-(6-chloropyrimidin-4-yl)-3,5-dimethyl-1H-pyrazol-4-ol

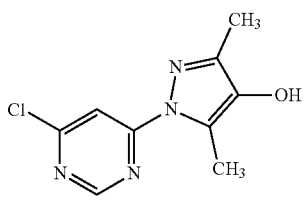

This compound was obtained as a by-product during the synthesis of 1-(6-chloropyrimidin-4-yl)-3,5-dimethyl-1H-pyrazol-4-yl acetate after flash column chromatography (SNAP Ultra 100 g, cyclohexane/ethyl acetate 100/0 to 60/40) to yield the title compound (4.48 g, 28% yield). It can also be prepared by the following procedure:

1-(6-chloropyrimidin-4-yl)-3,5-dimethyl-1H-pyrazol-4-yl acetate (130 mg, 487 µmol) was dissolved in methanol (10 mL) and potassium carbonate (135 mg, 075 µmol) was added at 0° C. The reaction mixture was stirred for 5 min before being quenched by addition of saturated ammonium chloride solution and water. It was extracted with ethyl acetate (3×) and the combined organic phase extracts were dried over sodium sulfate and concentrated. The desired product thus obtained (94 mg, 86% yield) was used in the next step without further purification.

LC-MS (method 11): $R_t$=1.26 min; MS (ESIpos): m/z=267 [M+H]$^+$

Intermediate 231

4-chloro-6-(4-methoxy-3,5-dimethyl-1H-pyrazol-1-yl)pyrimidine

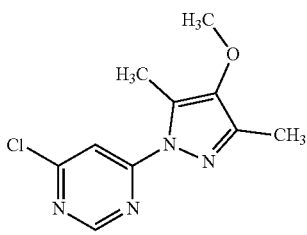 [SMILES: COc1c(C)nn(-c2cc(Cl)ncn2)c1C]

Under an argon atmosphere, 1-(6-chloropyrimidin-4-yl)-3,5-dimethyl-1H-pyrazol-4-ol (1.50 g, 6.68 mmol) was dissolved in dimethylformamide and treated with methyl iodide (0.50 mL, 8.0 mmol) and cesium carbonate (2.61 g, 8.01 mmol). The resulting suspension was allowed to stir overnight at ambient temperature. Water was added and the precipitated solid extracted with ethyl acetate. The organic phase extract was dried over sodium sulfate and concentrated. The residue was purified by flash column chromatography (SNAP Ultra 100 g, cyclohexane/ethyl acetate gradient) to yield the desired product (1.03 g, 64% yield).

LC-MS (method 9): Rt=1.01 min; MS (ESIpos): m/z=239 [M+H]$^+$ $^1$H-NMR (500 MHz, dimethylsulfoxide-d6) δ [ppm]: 2.211 (0.56), 2.239 (12.18), 2.579 (12.12), 3.713 (0.75), 3.736 (16.00), 7.854 (2.75), 7.856 (2.71), 8.870 (2.40), 8.871 (2.36).

Intermediate 232 ethyl 1-(6-{[1-(cyclopropylmethyl)-4-methyl-3-(pyridin-4-yl)-1H-pyrazol-5-yl]amino}pyrimidin-4-yl)-3,5-dimethyl-1H-pyrazole-4-carboxylate

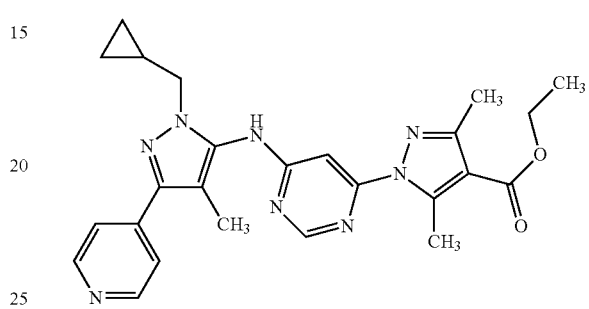

A microwave vial was charged with ethyl 1-(6-chloropyrimidin-4-yl)-3,5-dimethyl-1H-pyrazole-4-carboxylate (318 mg, 95% purity, 1.08 mmol), 1-(cyclopropylmethyl)-4-methyl-3-(pyridin-4-yl)-1H-pyrazol-5-amine (300 mg, 90% purity, 1.18 mmol) and sodium phenolate (137 mg, 1.18 mmol) and the contents were suspended in 1,4-dioxane (3.4 mL). The reaction mixture was degassed with Ar for 3 min. Tris(dibenzylideneacetone)dipalladium (19.7 mg, 21.5 µmol) and XantPhos (24.9 mg, 43.0 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (column: Chromatorex C18; 250*30 mm, 10 µM, flow 100 mL/min, gradient acetonitrile/water (containing 0.1% trifluoroacetic acid) 10/90 to 95/5) to yield the desired product (169 mg, 83% purity, 28% yield).

LC-MS (method 11): $R_t$=1.18 min; MS (ESIpos): m/z=473 [M+H]$^+$ $^1$H-NMR (400 MHz, dimethylsulfoxide-d6) δ [ppm]: −0.149 (0.30), −0.008 (2.29), 0.008 (2.38), 0.146 (0.29), 0.335 (2.44), 0.346 (2.72), 0.423 (0.41), 0.432 (0.54), 0.457 (2.45), 0.476 (2.65), 0.517 (0.37), 1.204 (0.35), 1.216 (0.66), 1.223 (0.65), 1.235 (1.04), 1.246 (0.62), 1.254 (0.66), 1.266 (0.38), 1.291 (3.69), 1.309 (7.51), 1.326 (3.83), 1.339 (1.61), 1.357 (0.72), 2.157 (16.00), 2.261 (2.28), 2.328 (0.67), 2.384 (2.44), 2.485 (3.75), 2.671 (0.52), 2.711 (0.24), 2.918 (12.61), 3.047 (2.40), 3.926 (2.70), 3.944 (2.63), 3.990 (0.83), 4.007 (0.82), 4.233 (1.38), 4.251 (3.54), 4.269 (3.52), 4.286 (1.38), 4.299 (0.94), 4.317 (0.88), 4.334 (0.45), 8.126 (3.23), 8.141 (3.33), 8.411 (0.62), 8.429 (0.66), 8.535 (0.49), 8.692 (0.69), 8.801 (4.43), 8.818 (4.15), 9.401 (0.56), 9.578 (0.69), 9.596 (0.67), 9.675 (0.57).

Intermediate 233

2-[5-(1,3-dioxoisoindolin-2-yl)-4-ethyl-3-(4-fluorophenyl)pyrazol-1-yl]acetonitrile

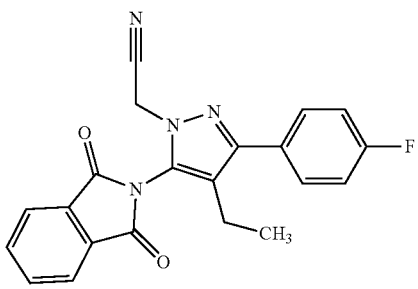 [SMILES: CCc1c(-c2ccc(F)cc2)nn(CC#N)c1N1C(=O)c2ccccc2C1=O]

Under an argon atmosphere, 2-[4-ethyl-3-(4-fluorophenyl)-1H-pyrazol-5-yl]-1H-isoindole-1,3(2H)-dione (1.63 g, 4.86 mmol) was dissolved in acetonitrile (53 mL) and bromoacetonitrile (510 µl, 7.3 mmol) and cesium carbonate (4.75 g, 14.6 mmol) was added. The reaction mixture was stirred for 3.25 h at 60° C. After cooling to ambient temperature, the precipitated salt was removed by filtration and the reaction mixture concentrated to ⅕ of its original volume. Water was added and the precipitated solid collected by filtration and purified by preparative HPLC (column: Chromatorex C18; 250*30 mm, 10 µM, flow 100 mL/min, gradient acetonitrile/water (containing 0.1% trifluoroacetic acid) 10/90 to 90/10). Upon standing, a solid precipitated from the filtrate, which was also purified by preparative HPLC (column: Chromatorex C18; 250*30 mm, 10 µM, flow 100 mL/min, gradient acetonitrile/water (containing 0.1% trifluoroacetic acid) 10/90 to 90/10). Product containing fractions were combined and lyophilized to yield the title compound (490 mg, 27% yield) along with the regioisomeric compound [3-(1,3-dioxo-1,3-dihydro-2H-isoindol-2-yl)-4-ethyl-5-(4-fluorophenyl)-1H-pyrazol-1-yl]acetonitrile (507 mg, 28% yield).

LC-MS (method 10): Rt=2.04 min; MS (ESIpos): m/z=375 [M+H]$^+$

Intermediate 234

2-[4-ethyl-3-(4-fluorophenyl)-1-(2H-tetrazol-5-ylmethyl)-1H-pyrazol-5-yl]-1H-isoindole-1,3 (2H)-dione

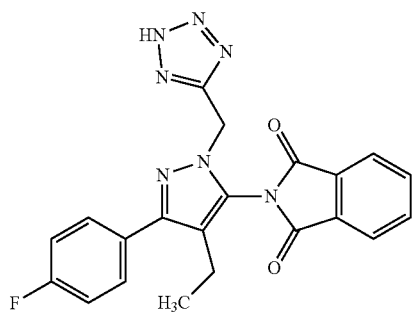 [SMILES: CCc1c(-c2ccc(F)cc2)nn(Cc2nn[nH]n2)c1N1C(=O)c2ccccc2C1=O]

Under an argon atmosphere [5-(1,3-dioxo-1,3-dihydro-2H-isoindol-2-yl)-4-ethyl-3-(4-fluorophenyl)-1H-pyrazol-1-yl]acetonitrile (350 mg, 935 µmol) and azido(trimethyl)silane (250 µl, 1.9 mmol) were dissolved in toluene (6.7 mL) and di-n-butyltinoxide (46.5 mg, 187 µmol) was added. The reaction mixture was heated to 125° C. bath temperature overnight. After cooling to ambient temperature, the reaction mixture was concentrated and the residue purified by flash column chromatography (SNAP Ultra 25 g, dichloromethane/methanol gradient 95/5 to 60/40) to yield the desired product in two fractions: Fraction 1 (213 mg, 74% purity, 40% yield) and fraction 2 (157 mg, 88% purity, 35% yield). The analytical data of fraction 2 is given. For the next step, both fractions were combined and used without further purification.

LC-MS (method 11): R$_t$=1.27 min; MS (ESIpos): m/z=418 [M+H]$^+$ $^1$H-NMR (400 MHz, dimethylsulfoxide-d6) δ [ppm]: −0.149 (0.23), −0.008 (1.91), 0.008 (1.67), 0.146 (0.20), 0.807 (0.68), 0.826 (1.62), 0.845 (0.75), 0.895 (6.76), 0.914 (16.00), 0.932 (7.02), 1.234 (0.31), 2.220 (0.19), 2.239 (0.56), 2.258 (0.54), 2.277 (0.20), 2.327 (0.51), 2.366 (0.17), 2.445 (1.85), 2.464 (5.78), 2.483 (6.41), 2.665 (0.38), 2.670 (0.52), 2.674 (0.39), 2.710 (0.16), 3.168 (3.75), 5.548 (1.49), 5.678 (10.99), 5.754 (1.38), 7.289 (4.19), 7.294 (1.46), 7.311 (8.76), 7.328 (1.56), 7.333 (4.69), 7.401 (0.37), 7.423 (0.79), 7.445 (0.46), 7.636 (0.44), 7.649 (0.49), 7.658 (0.44), 7.671 (0.41), 7.701 (4.54), 7.706 (1.98), 7.714 (5.01), 7.723 (4.69), 7.731 (1.82), 7.737 (4.15), 7.936 (0.49), 7.944 (0.54), 7.950 (0.52), 7.957 (0.89), 7.968 (0.63), 7.977 (4.69), 7.984 (5.26), 7.991 (4.84), 7.998 (9.00), 8.008 (1.70), 8.019 (0.59), 8.029 (1.40), 8.039 (8.48), 8.045 (4.67), 8.052 (5.19), 8.060 (4.42), 8.069 (0.41), 16.622 (0.16).

Intermediate 235

2-{4-ethyl-3-(4-fluorophenyl)-1-[(2-methyl-2H-tetrazol-5-yl)methyl]-1H-pyrazol-5-yl}-1H-isoindole-1,3(2H)-dione 2-[4-ethyl-5-(4-fluorophenyl)-2-[(1-methyltetrazol-5-yl)methyl]pyrazol-3-yl]isoindoline-1,3-dione

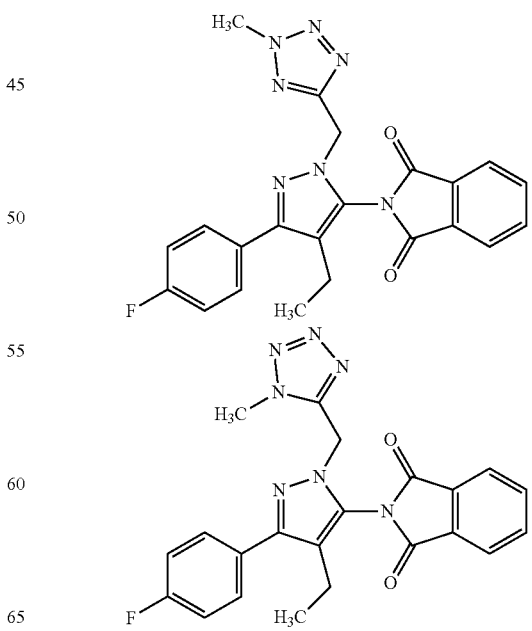

2-[4-ethyl-3-(4-fluorophenyl)-1-(2H-tetrazol-5-ylmethyl)-1H-pyrazol-5-yl]-1H-isoindole-1,3 (2H)-dione (212 mg, 508 μmol) and potassium carbonate (140 mg, 1.02 mmol) were suspended in dimethylformamide (1.0 mL) and methyl iodide was added under argon. The reaction mixture was stirred for 3 h at ambient temperature. Water was added and the reaction mixture was extracted with ethyl acetate (2×). The combined organic phase extracts were washed with brine, dried over sodium sulfate and concentrated. The product mixture thus obtained (211 mg, 87% purity, 84% yield) was a mixture of the two regioisomers and was used without further purification in the next step.

LC-MS (method 11): R$_t$=1.37 min; MS (ESIpos): m/z=432 [M+H]$^+$ $^1$H-NMR (400 MHz, dimethylsulfoxide-d6) δ [ppm]: −0.149 (0.34), 0.008 (2.62), 0.146 (0.33), 0.801 (0.42), 0.819 (0.92), 0.838 (0.50), 0.892 (2.70), 0.897 (2.22), 0.910 (6.21), 0.916 (4.74), 0.929 (2.91), 0.934 (2.14), 1.074 (0.21), 1.094 (0.37), 1.157 (0.83), 1.175 (1.73), 1.192 (0.91), 1.234 (0.68), 1.398 (1.60), 1.988 (3.08), 2.227 (0.26), 2.246 (0.35), 2.265 (0.23), 2.328 (0.51), 2.366 (0.19), 2.440 (0.69), 2.459 (2.51), 2.478 (3.64), 2.670 (0.63), 2.731 (12.62), 2.890 (16.00), 3.038 (1.03), 3.375 (0.37), 3.861 (1.23), 3.926 (1.18), 3.969 (10.10), 4.002 (0.27), 4.020 (0.74), 4.038 (0.76), 4.056 (0.25), 4.138 (0.91), 4.184 (0.37), 4.219 (13.76), 4.332 (1.47), 4.350 (0.36), 5.483 (0.62), 5.560 (6.33), 5.689 (0.54), 5.754 (0.97), 5.775 (4.74), 5.831 (0.43), 7.278 (2.55), 7.300 (5.13), 7.322 (2.76), 7.402 (0.36), 7.418 (0.30), 7.440 (0.20), 7.612 (0.36), 7.634 (0.28), 7.671 (1.52), 7.681 (2.21), 7.685 (2.24), 7.694 (2.83), 7.703 (2.24), 7.706 (1.53), 7.717 (1.61), 7.952 (2.08), 7.984 (2.80), 7.992 (3.25), 7.998 (3.47), 8.006 (5.02), 8.017 (1.05), 8.043 (0.85), 8.053 (5.13), 8.060 (3.15), 8.066 (3.36), 8.074 (2.81).

Intermediate 236

4-ethyl-3-(4-fluorophenyl)-1-[(1-methyl-1H-tetrazol-5-yl)methyl]-1H-pyrazol-5-amine

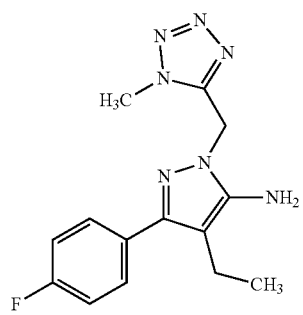 [SMILES: CCc1c(-c2ccc(F)cc2)nn(Cc2nnnn2C)c1N]

The mixture of regioisomers 2-{4-ethyl-3-(4-fluorophenyl)-1-[(2-methyl-2H-tetrazol-5-yl)methyl]-1H-pyrazol-5-yl}-1H-isoindole-1,3(2H)-dione and 2-[4-ethyl-5-(4-fluorophenyl)-2-[(1-methyltetrazol-5-yl)methyl]pyrazol-3-yl]isoindoline-1,3-dione (210 mg, 487 μmol) was suspended in ethanol and hydrazine monohydrate (120 μL, 2.4 mmol) was added. The reaction mixture was refluxed for 3 h and cooled to ambient temperature. The reaction mixture was diluted with water and extracted with ethyl acetate (2×). The combined organic phase extracts were washed with brine, dried over sodium sulfate and concentrated. The residue was dissolved in methanol (14 mL) purified by preparative SFC (Daciel Chiralpak AY-H 5 μm, 250×20 mm, flow: 80 mL/min, 40° C., isocratic carbon dioxide/ethanol 78/22, injections of 0.5 mL every 6 min) to yield the title compound (28.7 mg, 18% yield) as the first eluting isomer (R$_t$=2.84 min) along with the regioisomer (see below).

LC-MS (method 11): R$_t$=1.08 min; MS (ESIpos): m/z=302 [M+H]$^+$ $^1$H-NMR (400 MHz, dimethylsulfoxide-d6) δ [ppm]: 0.008 (0.43), 0.979 (2.48), 0.998 (5.91), 1.016 (2.59), 1.235 (0.24), 2.328 (0.20), 2.366 (0.16), 2.414 (0.76), 2.432 (2.29), 2.451 (2.27), 2.470 (0.77), 2.670 (0.22), 3.038 (0.18), 3.860 (0.18), 4.011 (16.00), 5.237 (3.73), 5.552 (7.90), 5.754 (3.63), 7.174 (1.63), 7.196 (3.43), 7.218 (1.87), 7.506 (1.90), 7.511 (0.77), 7.520 (2.12), 7.528 (1.94), 7.537 (0.70), 7.542 (1.70).

Intermediate 237

4-ethyl-3-(4-fluorophenyl)-1-[(2-methyl-2H-tetrazol-5-yl)methyl]-1H-pyrazol-5-amine

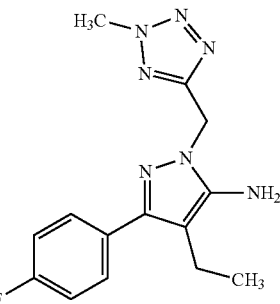

The title compound was obtained during the synthesis of 4-ethyl-3-(4-fluorophenyl)-1-[(1-methyl-1H-tetrazol-5-yl)methyl]-1H-pyrazol-5-amine (see above) after purification by preparative SFC (Daciel Chiralpak AY-H 5 μm, 250×20 mm, flow: 80 mL/min, 40° C., isocratic carbon dioxide/ethanol 78/22, injections of 0.5 mL every 6 min) as the second eluting isomer (R$_t$=4.30 min, 41 mg, 25% yield).

LC-MS (method 11): R$_t$=1.08 min; MS (ESIpos): m/z=302 [M+H]$^+$ $^1$H-NMR (500 MHz, dimethylsulfoxide-d6) δ [ppm]: 0.989 (2.55), 1.004 (5.88), 1.019 (2.58), 2.426 (0.73), 2.440 (2.32), 2.455 (2.24), 2.470 (0.73), 4.335 (16.00), 5.116 (4.01), 5.425 (7.36), 7.168 (1.72), 7.173 (0.60), 7.182 (0.83), 7.186 (3.51), 7.190 (0.73), 7.200 (0.65), 7.204 (1.89), 7.513 (1.89), 7.517 (0.78), 7.524 (2.09), 7.531 (1.89), 7.538 (0.74), 7.542 (1.64).

Intermediate 238 ethyl (2E)-(2-methylhydrazinylidene)ethanoate

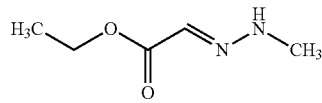

Ethyl oxoacetate (20 ml, 50% purity, 98 mmol) was dissolved in tetrahydrofuran (28 mL) and cooled to 0° C. Methylhydrazine (5.3 ml, 100 mmol) was added dropwise and the reaction mixture stirred for 30 min at 0° C. and overnight at ambient temperature. The reaction mixture was concentrated and the residue redissolved in toluene and concentrated again (3 cycles). The residue was triturated with methyl tert-butylether and stirred 30 min at 0° C. The precipitated solid was collected by filtration, washed with ice-cold methyl tert-butylether and dried to yield the desired product (9.47 g, 74% yield).

LC-MS (method 9): R$_t$=0.42 min; MS (ESIpos): m/z=131 [M+H]$^+$ $^1$H-NMR (400 MHz, dimethylsulfoxide-d6) δ [ppm]: −0.008 (0.72), 0.008 (0.62), 1.186 (7.81), 1.203 (16.00), 1.221 (7.96), 2.788 (11.05), 2.798 (10.89), 3.264 (0.42), 4.076 (2.62), 4.094 (7.93), 4.112 (7.85), 4.130 (2.57), 6.534 (4.89), 8.811 (1.16).

Intermediate 239 ethyl 5-(4-fluorophenyl)-4-hydroxy-1-methyl-1H-pyrazole-3-carboxylate

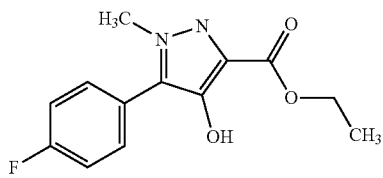

Under an argon atmosphere, ethyl (2E)-(2-methylhydrazinylidene)ethanoate (9.17 g, 70.5 mmol) was dissolved in n-butyl acetate (270 mL) and the solution cooled to 0° C. (4-fluorophenyl)(oxo)acetaldehyde monohydrate (24.0 g, 141 mmol), magnesium sulfate (18.2 g, 150 mmol) and acetic acid (9.1 mL, 160 mmol) were added and the reaction mixture was allowed to warm to ambient temperature and was stirred for 20 min. It was then heated to 110° C. for 1 h. After cooling to ambient temperature, the solids were removed by filtration and washed with ethyl acetate. The filtrate was concentrated and triturated with methyl tert-butylether. The precipitated solid was collected by filtration and washed further with methyl tert-butylether to yield the desired product as a white solid (14.0 g, 75% yield).

LC-MS (method 9): R$_t$=0.85 min; MS (ESIpos): m/z=265 [M+H]$^+$ $^1$H-NMR (400 MHz, dimethylsulfoxide-d6) δ [ppm]: −0.008 (0.51), 0.008 (0.48), 1.279 (4.04), 1.296 (8.61), 1.314 (4.15), 3.791 (16.00), 4.258 (1.32), 4.276 (4.09), 4.293 (4.05), 4.311 (1.27), 7.332 (1.74), 7.337 (0.65), 7.348 (0.86), 7.354 (3.89), 7.371 (0.71), 7.376 (2.23), 7.540 (2.19), 7.546 (0.96), 7.554 (2.40), 7.562 (2.07), 7.571 (0.82), 7.576 (1.82), 8.391 (4.21).

Intermediate 240 ethyl 4-(difluoromethoxy)-5-(4-fluorophenyl)-1-methyl-1H-pyrazole-3-carboxylate

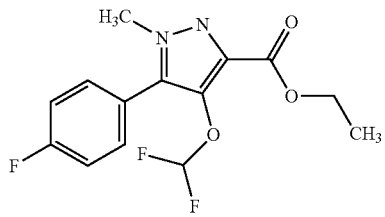

Under an argon atmosphere, potassium hydroxide (26.4 g, 470 mmol) was dissolved in water (120 mL) and the resulting solution treated with acetonitrile (120 mL). When the mixture became homogeneous, was cooled to ca. −30° C. (as low as stirring is still possible). ethyl 5-(4-fluorophenyl)-4-hydroxy-1-methyl-1H-pyrazole-3-carboxylate (6.21 g, 23.5 mmol) was added as a solid, followed by dropwise addition of diethyl [bromo(difluoro)methyl]phosphonate (8.3 ml, 47 mmol) over 5 min. After 15 min, the reaction mixture was neutralized with aqueous hydrochloric acid solution (2 N, 100 mL) and extracted with methyl tert-butylether (3×). The combined organic phase extracts were washed with brine, dried over sodium sulfate and concentrated. The desired product thus obtained (7.87 g, 92% purity, 98% yield) was used in the next step without further purification.

$^1$H NMR (500 MHz, dimethylsulfoxide-d$_6$) δ ppm: 1.30 (t, J=7.1 Hz, 3H), 3.80 (s, 3H), 4.25-4.37 (m, 2H), 6.76-7.15 (m, 1H), 7.35-7.46 (m, 2H), 7.51-7.63 (m, 2H).

Intermediate 241

4-(difluoromethoxy)-5-(4-fluorophenyl)-1-methyl-1H-pyrazole-3-carboxylic acid

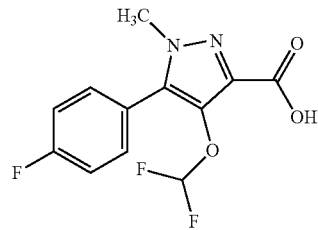 [SMILES: Cn1nc(C(=O)O)c(OC(F)F)c1-c1ccc(F)cc1]

Ethyl 4-(difluoromethoxy)-5-(4-fluorophenyl)-1-methyl-1H-pyrazole-3-carboxylate (7.87 g, 83% purity, 20.8 mmol) was dissolved in tetrahydrofuran/methanol (6:1, 141 mL) and sodium hydroxide solution (100 ml, 1.0 M, 100 mmol) was added. The reaction mixture was stirred for 2 h at ambient temperature. It was then acidified by addition of aqueous hydrochloric acid solution (2 N) and extracted with dichloromethane (3×). The combined organic phase extracts were washed with brine, dried over sodium sulfate and concentrated. The product thus obtained (6.11 g, 98% yield) was used in the next step without further purification.

LC-MS (method 10): Rt=1.47 min; MS (ESIneg): m/z=285 [M−H]$^−$

Intermediate 242 tert-butyl [4-(difluoromethoxy)-5-(4-fluorophenyl)-1-methyl-1H-pyrazol-3-yl]carbamate

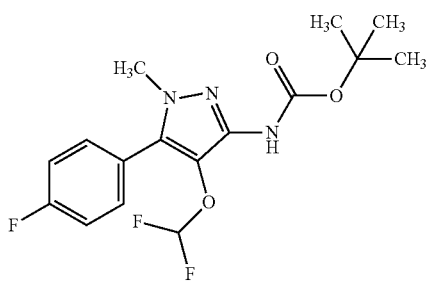 [SMILES: Cn1nc(NC(=O)OC(C)(C)C)c(OC(F)F)c1-c1ccc(F)cc1]

This reaction was carried out behind a safety explosion shield! Under an argon atmosphere (argon flow, open reaction vessel, no bubbler), 4-(difluoromethoxy)-5-(4-fluorophenyl)-1-methyl-1H-pyrazole-3-carboxylic acid (1.33 g, 95% purity, 4.41 mmol) and triethylamine (860 µl, 6.2 mmol) were dissolved in toluene and diphenyl phosphorazidate (1.1 ml, 5.3 mmol) was added. The reaction mixture was stirred for 1 h at ambient temperature, when tert-butanol (20 ml, 210 mmol) was added. The reaction mixture was then heated to 80° C. overnight. After cooling to ambient temperature, water (3 mL) and a solution of trimethylphosphine (7.1 ml, 1.0 M, 7.1 mmol) was added. The reaction mixture was stirred for 1 h at ambient temperature. It was then diluted with saturated aqueous sodium hydrogencarbonate solution and extracted with ethyl acetate (3×). The combined organic phase extracts were washed with saturated aqueous sodium hydrogencarbonate solution and brine, dried over sodium sulfate and concentrated. The desired product thus obtained (1.81 g, 72% purity, 83% yield) was used in the next step without further purification.

LC-MS (method 11): $R_t$=1.32 min; MS (ESIneg): m/z=356 [M−H]⁻

¹H NMR (400 MHz, dimethylsulfoxide-d₆) δ ppm: 1.43 (s, 9H), 3.66 (s, 3H), 6.51-6.93 (t, J=74 Hz, 1H), 7.33-7.44 (m, 2H), 7.49-7.61 (m, 2H), 8.88-8.96 (m, 1H).

Intermediate 243

4-(difluoromethoxy)-5-(4-fluorophenyl)-1-methyl-1H-pyrazol-3-amine

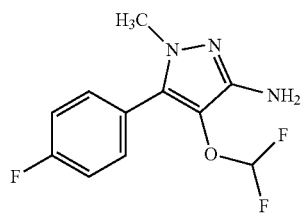 [SMILES: Cn1nc(N)c(OC(F)F)c1-c1ccc(F)cc1]

Tert-butyl [4-(difluoromethoxy)-5-(4-fluorophenyl)-1-methyl-1H-pyrazol-3-yl]carbamate (1.81 g, 5.07 mmol) was dissolved in dichloromethane (10 mL) and trifluoroacetic acid (10 mL) was added. The reaction mixture was stirred at ambient temperature for 1 h. The reaction mixture was concentrated and the residue resuspended in dichloromethane and again concentrated (3 cycles). The residue was dissolved in acetonitrile/water and purified by preparative HPLC (column: Chromatorex C18; 200*40 mm, 10 µM, flow 100 mL/min, gradient acetonitrile/water (containing 0.1% trifluoroacetic acid) 10/90 to 90/10) to yield the desired product (609 mg, 46% yield).

LC-MS (method 11): $R_t$=1.04 min; MS (ESIpos): m/z=

¹H-NMR (500 MHz, dimethylsulfoxide-d6) δ [ppm]: 3.49 (s, 3H), 4.63-4.70 (m, 2H), 6.71 (t, J=75.4 Hz, 1H), 7.31-7.39 (m, 2H), 7.44-7.52 (m, 2H).

Intermediate 244

4-(5-{[6-(4-formyl-3,5-dimethyl-1H-pyrazol-1-yl)pyrimidin-4-yl]amino}-1,4-dimethyl-1H-pyrazol-3-yl)benzonitrile

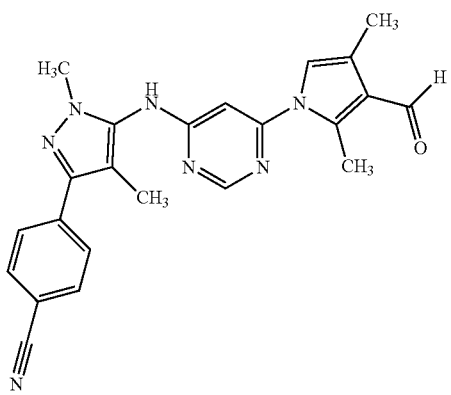 [SMILES: Cc1cn(-c2cc(Nc3c(C)c(-c4ccc(C#N)cc4)nn3C)ncn2)c(C)c1C=O]

A microwave vial was charged 1-(6-chloropyrimidin-4-yl)-3,5-dimethyl-1H-pyrazole-4-carbaldehyde (625 mg, 85% purity, 2.24 mmol) and 4-(5-amino-1,4-dimethyl-1H-pyrazol-3-yl)benzonitrile (524 mg, 2.47 mmol) and the contents were suspended in 1,4-dioxane (6.5 ml, 76 mmol). The reaction mixture was degassed with Ar for 3 min. Tris(dibenzylidenaceton)dipalladium (61.7 mg, 67.3 µmol) and Xantphos (77.9 mg, 135 µmol) were added and the reaction mixture was degassed again for 1 min and heated to 85° C. At this temperature and sodium phenolate (287 mg, 2.47 mmol) was added. The vial was sealed and heated at 85° C. for 90 minutes while vigorously stirring. After cooling to ambient temperature, the reaction mixture was diluted with hydrochloric acid and extracted with ethyl acetate (2×). The combined organic phases were washed with water and brine, dried over sodium sulfate and concentrated under reduced pressure. The crude product was suspended in acetonitrile and left overnight. The occurring precipitate was collected by filtration washed with acetonitrile and dried to yield 300 mg (31%) of the desired product.

LC-MS (method 10): $R_t$=1.74 min; MS (ESIpos): m/z=413 [M+H]⁺

¹H-NMR (400 MHz, dimethylsulfoxide-d6) δ [ppm]: 2.052 (0.44), 2.080 (13.39), 2.471 (1.17), 2.941 (11.95), 2.959 (0.73), 3.014 (0.96), 3.481 (0.74), 3.570 (1.22), 7.340 (0.73), 7.380 (0.75), 7.460 (0.98), 7.464 (1.09), 7.477 (0.83), 7.488 (0.48), 7.780 (0.48), 7.793 (0.50), 7.812 (0.44), 7.820 (0.54), 7.896 (16.00), 8.559 (0.62), 9.685 (1.44), 10.017 (3.25), 10.059 (0.42).

Intermediate 245 ethyl [1-(6-{[1-(4-fluorophenyl)-3,5-dimethyl-1H-pyrazol-4-yl]amino}pyrimidin-4-yl)-3,5-dimethyl-1H-pyrazol-4-yl]acetate

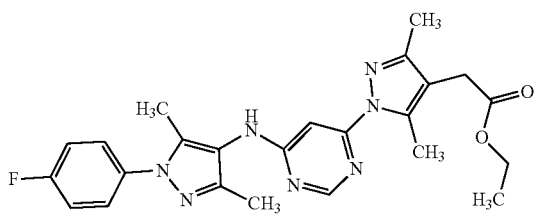 [SMILES: CCOC(=O)Cc1c(C)nn(-c2cc(Nc3c(C)nn(-c4ccc(F)cc4)c3C)ncn2)c1C]

A microwave vial was charged ethyl [1-(6-chloropyrimidin-4-yl)-3,5-dimethyl-1H-pyrazol-4-yl]acetate (255 mg, 866 µmol), 1-(4-fluorophenyl)-3,5-dimethyl-1H-pyrazol-4-amine (230 mg, 85% purity, 953 µmol) and sodium phenolate (111 mg, 953 µmol) and the contents were suspended in 1,4-dioxane (4.2 ml, 49 mmol). The reaction mixture was degassed with Ar for 3 min. Tris(dibenzylidenaceton)dipalladium (10.3 mg, 11.3 µmol) and Xantphos (15.0 mg, 26.0 µmol) were added and the reaction mixture was degassed again for 1 min. The vial was sealed and heated at 85° C. overnight while vigorously stirring. After cooling to ambient temperature, the reaction mixture was filtered and purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (85.0 mg, 19%).

LC-MS (method 10): $R_t$=1.96 min; MS (ESIpos): m/z=464 [M+H]$^+$ $^1$H-NMR (400 MHz, dimethylsulfoxide-d6) δ [ppm]: 1.165 (3.44), 1.183 (7.00), 1.200 (3.53), 1.647 (0.58), 1.999 (1.51), 2.077 (16.00), 2.121 (3.22), 2.177 (11.00), 2.564 (13.98), 3.468 (4.41), 4.047 (1.02), 4.065 (3.01), 4.082 (2.98), 4.100 (1.00), 7.300 (0.41), 7.333 (1.70), 7.355 (3.56), 7.377 (2.18), 7.397 (0.61), 7.592 (1.54), 8.401 (0.62), 8.867 (2.24).

Intermediate 246

3-[4-(difluoromethyl)phenyl]-4-methyl-1H-pyrazol-5-amine

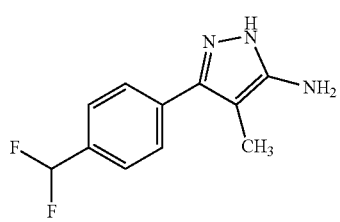 [SMILES: Cc1c(-c2ccc(C(F)F)cc2)n[nH]c1N]

A solution of 3-[4-(difluoromethyl)phenyl]-2-methyl-3-oxopropanenitrile (1.45 g, 6.92 mmol) in ethanol (15 ml) was treated with 8B] and stirred at 95° C. overnight. After cooling to ambient temperature the mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 1.44 g (86.7%) of the desired product.

LC-MS (method 10): $R_t$=1.11 min; MS (ESIpos): m/z=224 [M+H]$^+$ $^1$H-NMR (400 MHz, dimethylsulfoxide-d6) δ [ppm]: 2.004 (16.00), 4.579 (0.44), 6.906 (1.13), 7.046 (2.28), 7.186 (1.05), 7.601 (2.04), 7.621 (3.71), 7.666 (3.98), 7.686 (2.10).

Intermediate 247

2-{3-[4-(difluoromethyl)phenyl]-4-methyl-1H-pyrazol-5-yl}-1H-isoindole-1,3 (2H)-dione

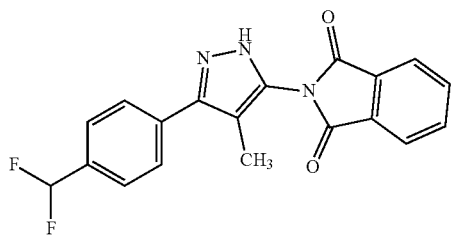 [SMILES: Cc1c(-c2ccc(C(F)F)cc2)n[nH]c1N1C(=O)c2ccccc2C1=O]

A solution of 3-[4-(difluoromethyl)phenyl]-4-methyl-1H-pyrazol-5-amine (765 mg, 3.43 mmol) and 2-benzofuran-1,3-dione (761 mg, 5.14 mmol) in acetic acid (5.0 ml, 87 mmol) was stirred overnight at 140° C. After cooling to ambient temperature the mixture was diluted with water. The occurring precipitate was collected by filtration, washed with water and dried to yield 1.12 g (92%) of the desired product.

$^1$H-NMR (400 MHz, dimethylsulfoxide-d6) δ [ppm]: 1.912 (0.79), 2.046 (16.00), 2.083 (1.98), 3.328 (1.01), 6.972 (2.11), 7.112 (4.41), 7.252 (1.89), 7.724 (2.90), 7.744 (5.10), 7.789 (5.02), 7.809 (2.93), 7.885 (0.45), 7.904 (0.55), 7.946 (3.81), 7.954 (4.61), 7.960 (4.98), 7.968 (7.03), 7.978 (1.55), 8.003 (1.33), 8.012 (5.98), 8.020 (4.71), 8.026 (4.48), 8.034 (3.55), 8.053 (0.85), 8.073 (0.67), 10.072 (1.23), 13.517 (2.37).

Intermediate 248

2-{3-[4-(difluoromethyl)phenyl]-1,4-dimethyl-1H-pyrazol-5-yl}-1H-isoindole-1,3 (2H)-dione

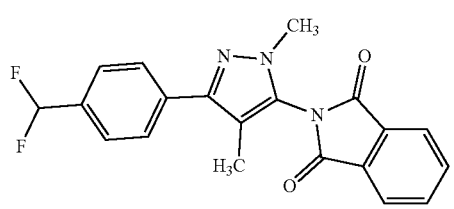 [SMILES: Cc1c(-c2ccc(C(F)F)cc2)nn(C)c1N1C(=O)c2ccccc2C1=O]

A solution of 2-{3-[4-(difluoromethyl)phenyl]-4-methyl-1H-pyrazol-5-yl}-1H-isoindole-1,3(2H)-dione (1.82 g, 5.15 mmol) in dimethylformamide (16 ml, 210 mmol) was treated with cesium carbonate (3.36 g, 10.3 mmol) and iodomethane (640 µl, 10 mmol). The mixture was stirred overnight at ambient temperature. The mixture was poured into saturated ammonium chloride solution. The occurring precipitate was collected by filtration, dried and purified by flash-chromatography (column: SNAP Ultra 50 g/solvent: 99% dichloromethane/1% ethyl acetate to 13% ethyl acetate) to yield 404 mg of the desired product (21%) along with its regioisomer.

LC-MS (method 10): $R_t$=1.88 min; MS (ESIpos): m/z=368 [M+H]$^+$ $^1$H-NMR (400 MHz, dimethylsulfoxide-d6) δ [ppm]: 1.851 (16.00), 1.990 (0.66), 3.317 (10.47), 7.006 (1.16), 7.146 (2.41), 7.285 (1.05), 7.687 (2.38), 7.708 (4.32), 7.754 (4.01), 7.774 (2.22), 7.939 (2.04), 7.947 (2.38), 7.953 (2.57), 7.961 (3.77), 7.971 (0.74), 7.996 (0.67), 8.006 (3.89), 8.014 (2.62), 8.019 (2.50), 8.027 (2.08).

Intermediate 249

2-{5-[4-(difluoromethyl)phenyl]-1,4-dimethyl-1H-pyrazol-3-yl}-1H-isoindole-1,3 (2H)-dione

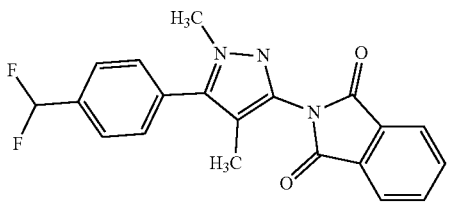

A solution of 2-{3-[4-(difluoromethyl)phenyl]-4-methyl-1H-pyrazol-5-yl}-1H-isoindole-1,3(2H)-dione (1.82 g, 5.15 mmol) in dimethylformamide (16 ml, 210 mmol) was treated with cesium carbonate (3.36 g, 10.3 mmol) and iodomethane (640 µl, 10 mmol). The mixture was stirred overnight at ambient temperature. The mixture was poured into saturated ammonium chloride solution. The occurring precipitate was collected by filtration, dried and purified by flash-chromatography (column: SNAP Ultra 50 g/solvent: 99% dichloromethane/1% ethyl acetate to 13% ethyl acetate) to yield 314 mg of the desired product (17%) along with its regioisomer.

LC-MS (method 10): $R_t$=1.96 min; MS (ESIpos): m/z=368 [M+H]$^+$

Intermediate 250

3-[4-(difluoromethyl)phenyl]-1,4-dimethyl-1H-pyrazol-5-amine

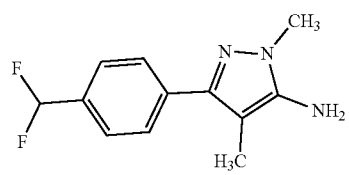 [SMILES: Cc1c(-c2ccc(C(F)F)cc2)nn(C)c1N]

A solution of 2-{3-[4-(difluoromethyl)phenyl]-1,4-dimethyl-1H-pyrazol-5-yl}-1H-isoindole-1,3(2H)-dione (400 mg, 1.09 mmol) in ethanol (10 mL) was treated with hydrazine monohydrate (265 µL, 5.4 mmol) and stirred at 90° C. overnight. After cooling to ambient temperature the mixture was diluted with water and extracted with ethyl acetate (3×). The combined organic phases were washed with saturated sodium hydrogen carbonate solution and brine, dried over sodium sulfate and concentrated under reduced pressure to yield 263 mg (77%) of the desired product.

LC-MS (method 9): $R_t$=0.69 min; MS (ESIpos): m/z=238 [M+H]$^+$ $^1$H-NMR (400 MHz, dimethylsulfoxide-d6) δ [ppm]: 1.790 (16.00), 4.495 (3.95), 6.961 (1.16), 7.100 (2.33), 7.240 (1.11), 7.492 (3.46), 7.512 (4.19), 7.675 (4.01), 7.695 (3.31).

Intermediate 251

5-[4-(difluoromethyl)phenyl]-1,4-dimethyl-1H-pyrazol-3-amine

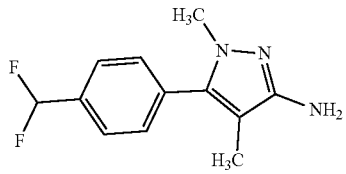 [SMILES: Cc1c(N)nn(C)c1-c1ccc(C(F)F)cc1]

A solution of 2-{5-[4-(difluoromethyl)phenyl]-1,4-dimethyl-1H-pyrazol-3-yl}-1H-isoindole-1,3(2H)-dione (300 mg, 817 µmol) in ethanol (10 mL) was treated with hydrazine monohydrate (199 µL, 4.1 mmol) and stirred at 90° C. overnight. After cooling to ambient temperature the mixture was diluted with saturated sodium hydrogen carbonate solution and extracted with ethyl acetate (3×). The combined organic phases were washed with saturated sodium hydrogen carbonate solution and brine, dried over sodium sulfate and concentrated under reduced pressure to yield 186 mg (90%) of the desired product.

LC-MS (method 9): $R_t$=0.67 min; MS (ESIpos): m/z=238 [M+H]$^+$ $^1$H-NMR (400 MHz, dimethylsulfoxide-d6) δ [ppm]: 2.017 (16.00), 3.320 (3.68), 4.995 (4.91), 6.886 (1.07), 7.026 (2.15), 7.166 (1.00), 7.546 (2.56), 7.566 (3.25), 7.707 (3.65), 7.727 (2.82).

Intermediate 252

4-[3-(1,3-dioxo-1,3-dihydro-2H-isoindol-2-yl)-4-methoxy-1H-pyrazol-5-yl]benzonitrile

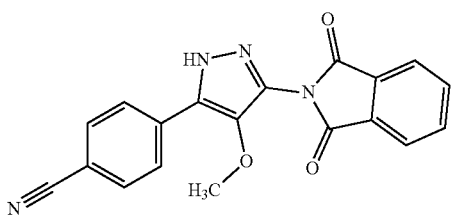 [SMILES: COc1c(N2C(=O)c3ccccc3C2=O)n[nH]c1-c1ccc(C#N)cc1]

A solution of 4-(3-amino-4-methoxy-1H-pyrazol-5-yl)benzonitrile (9.00 g, 42.0 mmol) and 2-benzofuran-1,3-dione (9.33 g, 63.0 mmol) in acetic acid (120 ml) was stirred at 125° C. overnight. After cooling to room temperature the mixture was concentrated under reduced pressure, the remaining residue was diluted with water and extracted with ethyl acetate (3×). The combined organic phases were washed with water and brine, dried over sodium sulfate and concentrated under reduced pressure to yield 17.0 g (quant.) of the desired crude product.

LC-MS (method 9): $R_t$=0.89 min; MS (ESIpos): m/z=345 [M+H]$^+$ $^1$H-NMR (400 MHz, dimethylsulfoxide-d6) δ [ppm]: 1.909 (0.49), 1.988 (0.47), 2.053 (0.43), 2.075 (1.90), 3.170 (0.79), 3.319 (1.33), 3.641 (2.16), 3.663 (13.07), 3.714 (0.78), 7.572 (1.52), 7.580 (1.71), 7.586 (1.86), 7.594 (2.46), 7.604 (0.46), 7.661 (1.86), 7.670 (1.53), 7.675 (1.52), 7.684 (1.19), 7.871 (0.44), 7.892 (0.60), 7.972 (4.39), 7.996 (16.00), 8.019 (3.30), 8.042 (5.43), 8.049 (4.80), 8.062 (3.46), 8.081 (1.80), 8.089 (1.35), 8.094 (1.37), 8.102 (0.98), 13.770 (1.58).

Intermediate 253

4-[5-(1,3-dioxo-1,3-dihydro-2H-isoindol-2-yl)-4-methoxy-1-methyl-1H-pyrazol-3-yl]benzonitrile

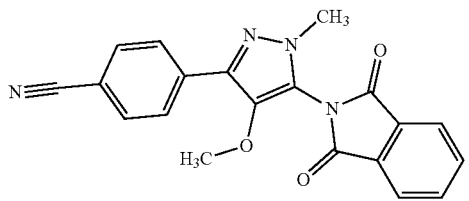 [SMILES: COc1c(-c2ccc(C#N)cc2)nn(C)c1N1C(=O)c2ccccc2C1=O]

A solution of 4-[3-(1,3-dioxo-1,3-dihydro-2H-isoindol-2-yl)-4-methoxy-1H-pyrazol-5-yl]benzonitrile (17.0 g, 49.4 mmol) in dimethylformamide (150 ml, 2.0 mol) was treated with cesium carbonate (32.2 g, 98.7 mmol) and iodomethane (6.1 ml, 99 mmol). The mixture was stirred overnight. The mixture was filtered and poured into saturated ammonium chloride solution. The occurring precipitate was collected by filtration, washed with water and dried. The crude product was purified by flash-chromatography (column; SNAP Ultra 100 g, solvent: dichloromethane/ethyl acetate 40:1) to yield 8.50 g (45%) of the desired product along with its regioiomer.

LC-MS (method 10): $R_t$=1.87 min; MS (ESIpos): m/z=359 [M+H]$^+$ $^1$H-NMR (400 MHz, dimethylsulfoxide-d6) δ [ppm]: 3.313 (14.52), 3.653 (16.00), 7.906 (2.79), 7.928 (3.98), 7.997 (1.95), 8.004 (2.16), 8.010 (2.23), 8.018 (3.16), 8.029 (4.58), 8.051 (2.95), 8.072 (0.44), 8.082 (3.00), 8.089 (2.10), 8.096 (2.08), 8.103 (1.84).

Intermediate 254

4-[3-(1,3-dioxo-1,3-dihydro-2H-isoindol-2-yl)-4-methoxy-1-methyl-1H-pyrazol-5-yl]benzonitrile

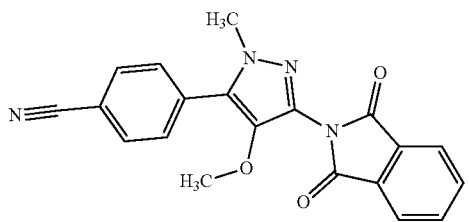 [SMILES: COc1c(N2C(=O)c3ccccc3C2=O)nn(C)c1-c1ccc(C#N)cc1]

A solution of 4-[3-(1,3-dioxo-1,3-dihydro-2H-isoindol-2-yl)-4-methoxy-1H-pyrazol-5-yl]benzonitrile (17.0 g, 49.4 mmol) in dimethylformamide (150 ml, 2.0 mol) was treated with cesium carbonate (32.2 g, 98.7 mmol) and iodomethane (6.1 ml, 99 mmol). The mixture was stirred overnight. The mixture was filtered and poured into saturated ammonium chloride solution. The occurring precipitate was collected by filtration, washed with water and dried. The crude product was purified by flash-chromatography (column; SNAP Ultra 100 g, solvent: dichloromethane/ethyl acetate 40:1) to yield 2.62 g (15%) of the desired product along with its regioiomer.

LC-MS (method 10): $R_t$=1.70 min; MS (ESIpos): m/z=359 [M+H]$^+$ $^1$H-NMR (400 MHz, dimethylsulfoxide-d6) δ [ppm]: 3.315 (8.51), 3.505 (16.00), 7.822 (2.98), 7.843 (3.54), 7.962 (1.65), 7.970 (1.86), 7.975 (1.92), 7.983 (2.88), 7.993 (0.52), 8.031 (4.55), 8.038 (2.29), 8.045 (3.19), 8.049 (3.38).

Intermediate 255

4-(5-amino-4-methoxy-1-methyl-1H-pyrazol-3-yl)benzonitrile

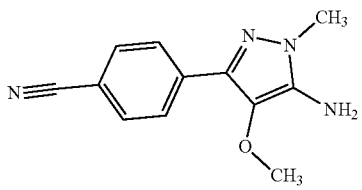 [SMILES: COc1c(-c2ccc(C#N)cc2)nn(C)c1N]

A solution of 4-[5-(1,3-dioxo-1,3-dihydro-2H-isoindol-2-yl)-4-methoxy-1-methyl-1H-pyrazol-3-yl]benzonitrile (8.50 g, 23.7 mmol) in ethanol (260 ml, 4.4 mol) was treated with hydrazine monohydrate (5.8 ml, 120 mmol) and stirred at 90° C. overnight. After cooling to ambient temperature the mixture was diluted with water and extracted with ethyl acetate (3×). The combined organic phases were washed with saturated sodium hydrogen carbonate solution and brine, dried over sodium sulfate and concentrated under reduced pressure to yield 5.85 g (quant.) of the desired product.

LC-MS (method 10): $R_t$=1.15 min; MS (ESIpos): m/z=229 [M+H]$^+$ $^1$H-NMR (400 MHz, dimethylsulfoxide-d6) δ [ppm]: 3.317 (4.36), 3.634 (16.00), 5.163 (3.96), 7.801 (3.08), 7.817 (1.33), 7.822 (4.15), 7.949 (4.22), 7.966 (1.18), 7.970 (3.09).

Intermediate 256

4-(3-amino-4-methoxy-1-methyl-1H-pyrazol-5-yl)benzonitrile

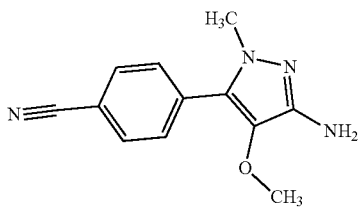 [SMILES: COc1c(N)nn(C)c1-c1ccc(C#N)cc1]

A solution of 4-[3-(1,3-dioxo-1,3-dihydro-2H-isoindol-2-yl)-4-methoxy-1-methyl-1H-pyrazol-5-yl]benzonitrile (2.62 g, 7.31 mmol) in ethanol (100 ml, 1.7 mol) was treated with hydrazine monohydrate (1.8 ml, 37 mmol) and stirred at 90° C. overnight. After cooling to ambient temperature the mixture was diluted with water and extracted with ethyl acetate (3×). The combined organic phases were washed with saturated sodium hydrogen carbonate solution and brine, dried over sodium sulfate and concentrated under reduced pressure to yield 1.62 g (97%) of the desired product.

LC-MS (method 10): $R_t$=1.07 min; MS (ESIpos): m/z=229 [M+H]$^+$ $^1$H-NMR (400 MHz, dimethylsulfoxide-d6) δ [ppm]: 2.075 (0.47), 3.316 (16.00), 4.643 (11.51), 7.654 (9.72), 7.658 (3.74), 7.675 (11.10), 7.941 (11.15), 7.962 (9.25).

Intermediate 257

6-chloro-N-[1-(cyclopropylmethyl)-3-(4-fluorophenyl)-4-methyl-1H-pyrazol-5-yl]pyrimidin-4-amine

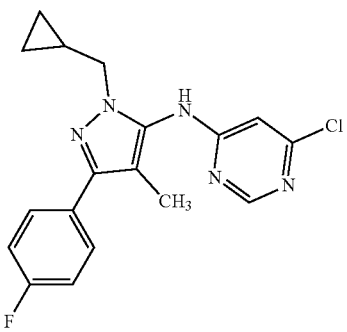 [SMILES: Cc1c(-c2ccc(F)cc2)nn(CC2CC2)c1Nc1cc(Cl)ncn1]

A solution of 4,6-dichloropyrimidine (128 mg, 856 μmol) and 1-(cyclopropylmethyl)-3-(4-fluorophenyl)-4-methyl-1H-pyrazol-5-amine (210 mg, 856 μmol) in dimethylformamide (4.0 ml, 52 mmol) was treated with dimethylformaimde (4 mL) and sodium iodide (154 mg, 1.03 mmol) and stirred two days at 125° C. After cooling to room temperature the mixture was purified by preparative HPLC (method: column: Reprosil C18; 10 μm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 85.0 mg of the desired product (28%).

LC-MS (method 10): $R_t$=1.93 min; MS (ESIpos): m/z=358 [M+H]$^+$ $^1$H-NMR (400 MHz, dimethylsulfoxide-d6) δ [ppm]: 0.272 (0.73), 0.281 (0.77), 0.415 (0.87), 0.435 (0.93), 1.165 (0.41), 1.981 (6.27), 3.568 (16.00), 3.807 (0.87), 3.824 (0.84), 7.244 (0.93), 7.267 (1.95), 7.289 (1.03), 7.703 (0.60), 7.718 (0.75), 7.724 (0.74), 7.739 (0.57).

Intermediate 258

N-[1-(cyclopropylmethyl)-3-(4-fluorophenyl)-4-methyl-1H-pyrazol-5-yl]-6-hydrazinylpyrimidin-4-amine

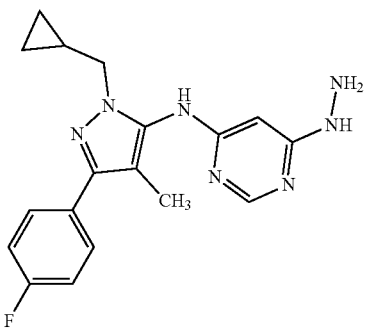 [SMILES: Cc1c(-c2ccc(F)cc2)nn(CC2CC2)c1Nc1cc(NN)ncn1]

A solution of 6-chloro-N-[1-(cyclopropylmethyl)-3-(4-fluorophenyl)-4-methyl-1H-pyrazol-5-yl]pyrimidin-4-amine (83.2 mg, 233 μmol) in 1,4-dioxane (1.5 ml) was treated with hydrazine hydrate (1:1) (34 μl, 700 μmol) and stirred overnight at 70° C. As the conversion was not fully completed additional 3 equivalents of hydrazine monohydrate (34 μL, 697 μmol) were added and it was stirred an additional night at 70° C. After cooling to room temperature a third time 6 equivalents of hydrazine monohydrate (68 μL, 1.39 mmol) were added and stirring was continued at 70° C. for 3 days. The mixture was concentrated under reduced pressure to yield 95.0 mg (81%) of the desired product.

LC-MS (method 11): $R_t$=0.87 min; MS (ESIneg): m/z=352 [M−H]$^-$

Intermediate 259

4-chloro-6-(3,5-dimethyl-4-nitro-1H-pyrazol-1-yl)pyrimidine

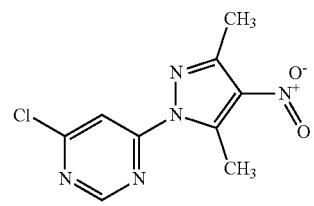

4,6-Dichloropyrimidine (2.22 g, 14.9 mmol), 3,5-dimethyl-4-nitro-1H-pyrazole (2.00 g, 14.2 mmol) and cesium carbonate (4.62 g, 14.2 mmol) were suspended in dimethylformamide (9 mL) and the reaction mixture was stirred for 2.5 h at ambient temperature. It was then poured onto water and stirred for further 5 min. The precipitated solid was collected by filtration, further washed with water and dried in a vacuum drying-oven at 40° C. overnight. The desired product thus obtained (2.98 g, 67% purity, 53% yield) was used in the next step without further purification.

LC-MS (method 11): Rt=1.32 min; MS (ESIpos): m/z=254 [M+H]$^+$ $^1$H-NMR (500 MHz, dimethylsulfoxide-d6) δ [ppm]: 2.525 (15.69), 3.029 (16.00), 3.087 (9.88), 8.077 (3.32), 8.079 (3.24), 8.309 (1.11), 8.311 (1.09), 9.091 (2.92), 9.093 (2.82), 9.220 (1.09), 9.222 (1.05).

Intermediate 260 ethyl 5-fluoropyridine-2-carboxylate hydrochloride

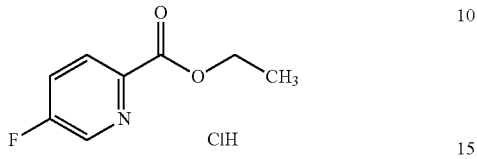

5-fluoropyridine-2-carboxylic acid (5.00 g, 35.4 mmol) was suspended in thionyl chloride (15 ml, 210 mmol) and refluxed for 30 minutes. After cooling to room temperature the mixture was concentrated under reduced pressure. The remaining residue was resolved in ethanol and refluxed for two hours. After cooling to ambient temperature the mixture was concentrated, the residue was suspended in diethyl ether and the occurring crystalline material was collected by filtration, washed with diethyl ether and dried to yield 4.20 g (58%) of the desired product.

LC-MS (method 10): $R_t$=1.10 min; MS (ESIpos): m/z=170 [M+H]$^+$ $^1$H-NMR (500 MHz, dimethylsulfoxide-d6) δ [ppm]: −0.006 (2.46), 1.322 (7.79), 1.336 (16.00), 1.351 (7.74), 4.331 (2.56), 4.345 (7.69), 4.359 (7.52), 4.374 (2.39), 7.900 (1.30), 7.906 (1.35), 7.918 (2.64), 7.924 (2.67), 7.935 (1.48), 7.941 (1.48), 8.143 (2.14), 8.152 (2.15), 8.161 (1.88), 8.170 (1.79), 8.716 (3.64), 8.722 (3.45).

Intermediate 261

3-(5-fluoropyridin-2-yl)-2-methyl-3-oxopropanenitrile

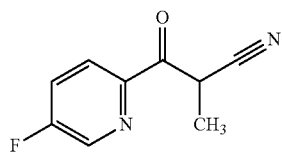

A solution of ethyl 5-fluoropyridine-2-carboxylate hydrochloride (1:1) (6.15 g, 29.9 mmol) and propanenitrile (3.2 ml, 45 mmol) in tetrahydrofuran (76 ml, 940 mmol) was treated with a solution of lithium bis(trimethylsilyl)amide (76 ml, 1.0 M in tetrahydrofuran, 76 mmol). The mixture was stirred overnight at ambient temperature. The mixture was diluted with water and extracted once with ethyl acetate. The organic phase was discarded. The aqueous phase was acidified with hydrochloric acid and extracted with dichloromethane (2×). The combined organic phases were washed with water, dried over sodium sulfate and concentrated under reduced pressure to yield 4.15 g (61%) of the desired product.

LC-MS (method 9): $R_t$=0.71 min; MS (ESIpos): m/z=179 [M+H]$^+$ $^1$H-NMR (400 MHz, dimethylsulfoxide-d6) δ [ppm]: 1.508 (15.88), 1.526 (16.00), 1.785 (1.31), 1.910 (8.45), 5.111 (1.32), 5.129 (3.96), 5.148 (3.92), 5.166 (1.28), 7.861 (1.55), 7.873 (1.88), 7.890 (1.31), 7.974 (1.26), 7.980 (1.31), 7.996 (2.67), 8.002 (2.67), 8.017 (1.61), 8.023 (1.52), 8.119 (0.59), 8.131 (0.59), 8.142 (0.40), 8.160 (2.82), 8.172 (2.93), 8.182 (2.38), 8.193 (2.19), 8.619 (0.41), 8.625 (0.41), 8.693 (2.10), 8.807 (4.74), 8.812 (4.53).

Intermediate 262

1-(cyclopropylmethyl)-3-(5-fluoropyridin-2-yl)-4-methyl-1H-pyrazol-5-amine

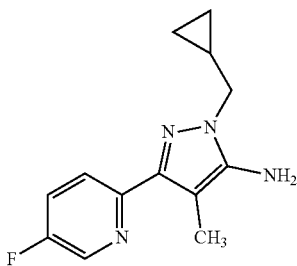 [SMILES: Cc1c(-c2ccc(F)cn2)nn(CC2CC2)c1N]

A solution of 3-(5-fluoropyridin-2-yl)-2-methyl-3-oxopropanenitrile (1.50 g, 8.42 mmol) in ethanol (18 ml) was treated with (cyclopropylmethyl)hydrazine dihydrochloride (2.68 g, 16.8 mmol) and stirred overnight at 95° C. The mixture was purified by preparative HPLC (method: column: Reprosil C18; 10 μm; 125×30 mm/flow: 50 mL/min/ solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 908 mg (44%) of the desired product as mixture with unknown by-products.

LC-MS (method 10): $R_t$=1.25 min; MS (ESIpos): m/z=247 [M+H]$^+$

Intermediate 263

4-(5-{[6-(4-formyl-3,5-dimethyl-1H-pyrazol-1-yl)pyrimidin-4-yl]amino}-4-methoxy-1-methyl-1H-pyrazol-3-yl)benzonitrile

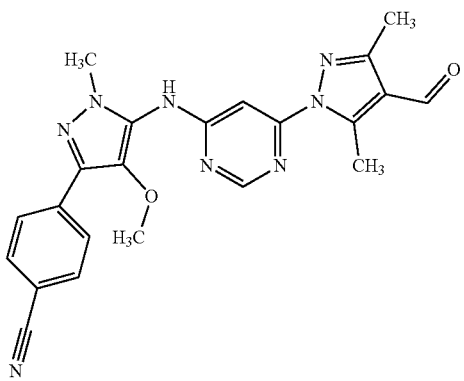 [SMILES: COc1c(-c2ccc(C#N)cc2)nn(C)c1Nc1cc(-n2nc(C)c(C=O)c2C)ncn1]

A microwave vial was charged 1-(6-chloropyrimidin-4-yl)-3,5-dimethyl-1H-pyrazole-4-carbaldehyde (300 mg, 76% purity, 963 μmol) and 4-(5-amino-4-methoxy-1-methyl-1H-pyrazol-3-yl)benzonitrile (242 mg, 1.06 mmol) and the contents were suspended in 1,4-dioxane (3.5 ml, 41 mmol). The reaction mixture was degassed with Ar for 3 min. Tris(dibenzylidenaceton)dipalladium (26.5 mg, 28.9 µmol) and Xantphos (33.4 mg, 57.8 µmol) were added and the reaction mixture was degassed again for 1 min and heated to 85° C. At this temperature and sodium phenolate (123 mg, 1.06 mmol) was added. The vial was sealed and heated at 85° C. for 90 minutes while vigorously stirring. After cooling to ambient temperature, the reaction mixture was left overnight and was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (135 g, 31%).

LC-MS (method 10): $R_t$=1.75 min; MS (ESIpos): m/z=429 [M+H]$^+$ $^1$H-NMR (400 MHz, dimethylsulfoxide-d6) δ [ppm]: 1.647 (0.66), 2.447 (1.99), 2.948 (16.00), 2.971 (1.74), 3.316 (9.14), 3.630 (0.64), 3.662 (14.64), 3.702 (0.64), 5.755 (6.78), 7.366 (0.56), 7.382 (0.63), 7.396 (0.63), 7.870 (4.51), 7.890 (5.78), 8.030 (6.18), 8.051 (4.92), 8.590 (2.28), 9.028 (0.42), 9.709 (1.79), 10.019 (5.08), 10.050 (0.61).

Intermediate 264 ethyl [1-(6-{[3-(4-cyanophenyl)-4-methoxy-1-methyl-1H-pyrazol-5-yl]amino}pyrimidin-4-yl)-3,5-dimethyl-1H-pyrazol-4-yl]acetate

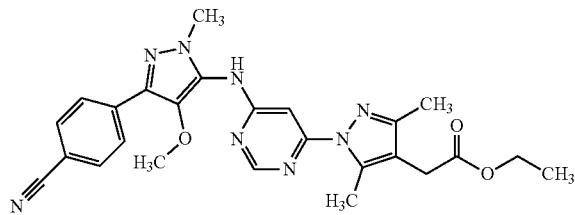 [SMILES: CCOC(=O)Cc1c(C)nn(-c2cc(Nc3c(OC)c(-c4ccc(C#N)cc4)nn3C)ncn2)c1C]

A microwave vial was charged ethyl [1-(6-chloropyrimidin-4-yl)-3,5-dimethyl-1H-pyrazol-4-yl]acetate (117 mg, 398 µmol) and 4-(5-amino-4-methoxy-1-methyl-1H-pyrazol-3-yl)benzonitrile (100 mg, 438 µmol) and the contents were suspended in 1,4-dioxane (6.0 ml, 70 mmol). The reaction mixture was degassed with Ar for 3 min. Tris(dibenzylidenaceton)dipalladium (10.9 mg, 11.9 µmol) and Xantphos (13.8 mg, 23.9 µmol) were added and the reaction mixture was degassed again for 1 min and heated to 85° C. At this temperature and sodium phenolate (50.9 mg, 438 µmol) was added. The vial was sealed and heated at 85° C. for 6 hours while vigorously stirring. After cooling to ambient temperature, the reaction mixture was diluted with hydrochloric acid and extracted with ethyl acetate (2×). The combined organic phases were washed with water and brine, dried over sodium sulfate and concentrated under reduced pressure. The crude product was purified by flash-chromatography (column: SNAP Ultra 10 g, solvent: dichloromethane/ethyl acetate 80:20) to yield the desired product (80.0 mg, 36%).

LC-MS (method 10): $R_t$=1.98 min; MS (ESIpos): m/z=487 [M+H]$^+$ $^1$H-NMR (500 MHz, dimethylsulfoxide-d6) δ [ppm]: 1.171 (3.32), 1.185 (6.90), 1.199 (3.36), 2.143 (2.44), 2.588 (10.58), 3.485 (3.99), 3.581 (2.38), 3.636 (2.81), 3.656 (6.30), 3.730 (16.00), 4.057 (0.95), 4.071 (2.86), 4.086 (2.83), 4.100 (0.91), 5.754 (2.09), 7.802 (0.49), 7.820 (0.64), 7.871 (2.76), 7.874 (1.12), 7.884 (1.27), 7.888 (3.43), 7.952 (0.63), 7.969 (0.50), 8.037 (2.99), 8.054 (2.35), 8.503 (0.95), 9.521 (1.11).

Intermediate 265

4-(cyanoacetyl)benzonitrile

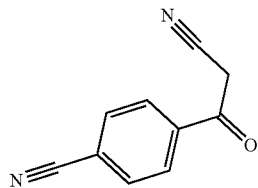 [SMILES: N#CCC(=O)c1ccc(C#N)cc1]

A solution of ethyl 4-cyanobenzoate (5.00 g, 28.5 mmol) in tetrahydrofuran (38 ml, 470 mmol) was treated with potassium tert-butoxide (6.41 g, 57.1 mmol). The mixture was stirred for 5 minutes at ambient temperature and then acetonitrile (1.5 ml, 29 mmol) was added. The reaction mixture was stirred two hours at ambient temperature. The mixture was diluted with hydrochloric acid (2.0 M) under ice bath cooling and extracted with ethyl acetate (2×). The combined organic phases were dried over sodium sulfate and concentrated under reduced pressure. The remaining residue was suspended in diethyl ether; the occurring precipitate was collected by filtration, washed with diethyl ether and dried to yield 4.24 g (87%) of the desired product.

LC-MS (method 10): $R_t$=1.10 min; MS (ESIneg): m/z=169 [M−H]$^+$ $^1$H-NMR (400 MHz, dimethylsulfoxide-d6) δ [ppm]: −0.008 (0.72), 0.008 (0.71), 4.805 (13.54), 5.046 (1.01), 5.419 (1.07), 7.844 (0.86), 7.863 (1.32), 7.904 (0.71), 7.925 (2.18), 7.943 (0.95), 7.971 (1.27), 7.978 (1.21), 7.988 (0.78), 7.993 (1.86), 8.006 (0.61), 8.048 (1.80), 8.070 (14.52), 8.074 (16.00), 8.095 (2.68).

Intermediate 266

4-[5-amino-1-(cyclopropylmethyl)-1H-pyrazol-3-yl]benzonitrile

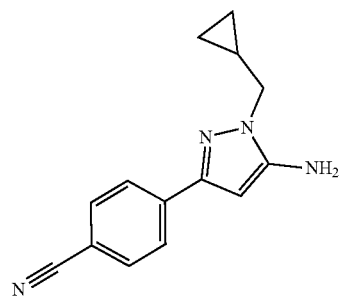 [SMILES: N#Cc1ccc(-c2cc(N)n(CC3CC3)n2)cc1]

A solution of 4-(cyanoacetyl)benzonitrile (4.24 g, 24.9 mmol) and (cyclopropylmethyl)hydrazine dihydrochloride (5.94 g, 37.4 mmol) in 2-propanol (45 ml) was refluxed overnight. After cooling to ambient temperature the volume of the mixture was reduced by half under reduced pressure; then diethyl ether was added and the occurring precipitate was collected filtration, washed with diethyl ether and dried to yield 4.07 g (64%) of the desired product.

LC-MS (method 11): $R_t$=1.04 min; MS (ESIpos): m/z=239 [M+H]$^+$ $^1$H-NMR (400 MHz, dimethylsulfoxide-d6) δ [ppm]: 0.493 (11.98), 0.510 (16.00), 1.303 (0.52), 1.318 (1.19), 1.335 (1.47), 1.350 (1.14), 1.367 (0.53), 2.507 (5.85), 4.071 (3.81), 4.088 (2.39), 6.187 (1.83), 7.214 (0.55), 7.918 (5.85), 7.939 (7.51), 8.032 (0.44), 8.063 (4.28), 8.075 (2.66), 8.082 (2.60).

Intermediate 267

4-[5-amino-4-chloro-1-(cyclopropylmethyl)-1H-pyrazol-3-yl]benzonitrile

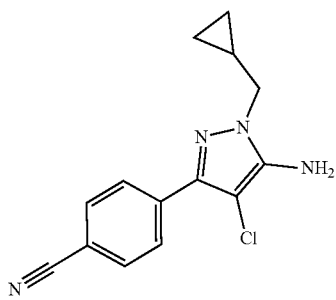 [SMILES: N#Cc1ccc(-c2nn(CC3CC3)c(N)c2Cl)cc1]

A solution of 4-[5-amino-1-(cyclopropylmethyl)-1H-pyrazol-3-yl]benzonitrile (4.07 g, 17.1 mmol) in acetonitrile (50 ml, 950 mmol) was treated with 1-chloropyrrolidine-2,5-dione (2.74 g, 20.5 mmol) and stirred overnight at ambient temperature. The mixture was diluted with water and extracted with ethyl acetate (3×). The combined organic phases were washed with water and brine, dried over sodium sulfate and concentrated under reduced pressure. The remaining residue was suspended in diethyl ether, the occurring precipitate was washed with diethyl ether and dried to yield 1.78 g of the desired product. The filtrate was concentrated under reduced pressure and purified by flash-chromatography on silica gel (solvent: dichloromethane/ethyl acetate 10:1) to yield 1.90 g. In total 3.68 g of the desired product (76%) were obtained.

LC-MS (method 10): $R_t$=1.78 min; MS (ESIpos): m/z=273 [M+H]$^+$ $^1$H-NMR (400 MHz, dimethylsulfoxide-d6) δ [ppm]: 0.371 (0.46), 0.383 (0.51), 0.480 (0.41), 2.073 (4.07), 2.419 (0.60), 2.565 (16.00), 3.169 (12.34), 3.656 (0.48), 3.880 (0.74), 3.897 (0.72), 7.862 (0.62), 7.883 (0.84), 7.987 (0.85), 8.008 (0.61).

Intermediate 268

1-(6-{[1-(cyclopropylmethyl)-3-(4-fluorophenyl)-4-methoxy-1H-pyrazol-5-yl]amino}pyrimidin-4-yl)-3,5-dimethyl-1H-pyrazole-4-carboxylic acid

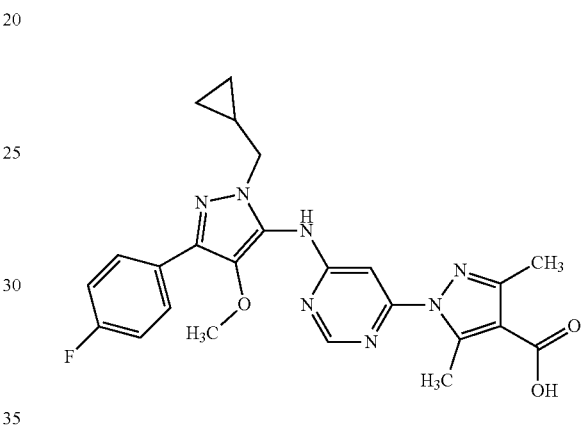

A solution of ethyl 1-(6-{[1-(cyclopropylmethyl)-3-(4-fluorophenyl)-4-methoxy-1H-pyrazol-5-yl]amino}pyrimidin-4-yl)-3,5-dimethyl-1H-pyrazole-4-carboxylate (350 mg, 692 µmol) in tetrahydrofuran (4.6 ml, 57 mmol) was treated with aqueous lithium hydroxide solution (3.5 ml, 1.0 M, 3.5 mmol) and stirred overnight at ambient temperature and an additional night at reflux temperature. After cooling to room temperature the mixture was diluted with water and acidified with hydrochloric acid. The mixture was extracted with ethyl acetate (3×). The combined organic phases were dried over sodium sulfate and concentrated under reduced pressure. The remaining residue was suspended in acetonitrile, the occurring precipitate was collected by filtration, washed with acetonitrile and dried to yield 326 mg (82%) of the desired product.

LC-MS (method 9): $R_t$=1.02 min; MS (ESIpos): m/z=478 [M+H]$^+$ $^1$H-NMR (400 MHz, dimethylsulfoxide-d6) δ [ppm]: 0.296 (0.87), 0.308 (3.43), 0.321 (3.71), 0.333 (1.08), 0.431 (1.08), 0.442 (2.80), 0.444 (2.81), 0.461 (2.97), 0.476 (0.76), 1.180 (0.42), 1.192 (0.75), 1.199 (0.75), 1.211 (1.05), 1.222 (0.72), 1.229 (0.76), 2.325 (0.87), 2.359 (8.59), 2.813 (5.74), 2.911 (16.00), 3.511 (1.55), 3.641 (0.79), 3.777 (2.79), 3.793 (2.71), 6.572 (1.46), 6.758 (0.54), 6.779 (0.56), 7.153 (0.51), 7.245 (2.31), 7.267 (4.55), 7.289 (2.49), 7.882 (2.16), 7.896 (2.73), 7.903 (2.69), 7.918 (2.11), 8.315 (1.57), 8.544 (1.12), 9.841 (1.06).

Intermediate 269

N'-acetyl-1-(6-{[1-(cyclopropylmethyl)-3-(4-fluorophenyl)-4-methoxy-1H-pyrazol-5-yl]amino}pyrimidin-4-yl)-3,5-dimethyl-1H-pyrazole-4-carbohydrazide

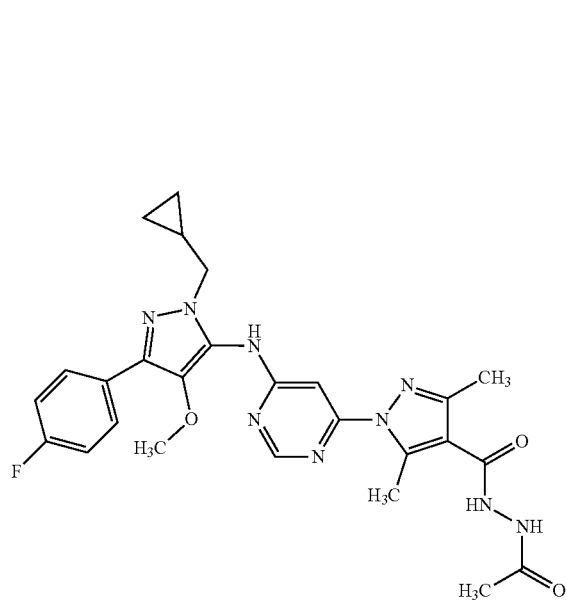 [SMILES: COc1c(-c2ccc(F)cc2)nn(CC2CC2)c1Nc1cc(-n2nc(C)c(C(=O)NNC(C)=O)c2C)ncn1]

A solution of 1-(6-{[1-(cyclopropylmethyl)-3-(4-fluorophenyl)-4-methoxy-1H-pyrazol-5-yl]amino}pyrimidin-4-yl)-3,5-dimethyl-1H-pyrazole-4-carboxylic acid (331 mg, 83% purity, 575 µmol) and acetohydrazide (128 mg, 1.73 mmol) in dimethylformamide (3.0 ml, 39 mmol) was treated with HATU (328 mg, 863 µmol) and N,N-diisopropylethylamine (300 µl, 1.7 mmol) and stirred overnight at ambient temperature. The mixture was diluted with water and extracted with ethyl acetate (3×). The combined organic phases were washed with water and brine, dried over sodium sulfate and concentrated under reduced pressure. The remaining residue was suspended in dichloromethane, the occurring precipitate was collected by filtration, washed with dichloromethane and dried to yield 255 mg (83%) of the desired product.

LC-MS (method 10): $R_t$=1.57 min; MS (ESIpos): m/z=534 [M+H]$^+$ $^1$H-NMR (400 MHz, dimethylsulfoxide-d6) δ [ppm]: −0.008 (0.85), 0.008 (0.92), 0.291 (0.85), 0.302 (3.71), 0.306 (3.30), 0.317 (3.98), 0.328 (1.30), 0.433 (1.13), 0.443 (2.96), 0.447 (2.96), 0.452 (1.70), 0.463 (3.22), 0.467 (2.95), 0.479 (0.93), 1.170 (0.40), 1.183 (0.77), 1.189 (0.76), 1.201 (1.21), 1.213 (0.72), 1.220 (0.76), 1.233 (0.43), 1.879 (1.16), 1.904 (15.07), 2.286 (3.56), 2.690 (1.38), 2.776 (16.00), 2.891 (0.43), 3.316 (8.23), 3.568 (2.81), 3.774 (2.64), 3.791 (2.62), 5.754 (2.51), 7.246 (2.89), 7.268 (5.85), 7.290 (3.07), 7.883 (2.44), 7.898 (2.93), 7.905 (2.86), 7.919 (2.35), 8.542 (1.28), 9.562 (0.55), 9.732 (0.94), 9.895 (1.87).

Intermediate 270

4-(3-{[6-(4-formyl-3,5-dimethyl-1H-pyrazol-1-yl)pyrimidin-4-yl]amino}-4-methoxy-1-methyl-1H-pyrazol-5-yl)benzonitrile

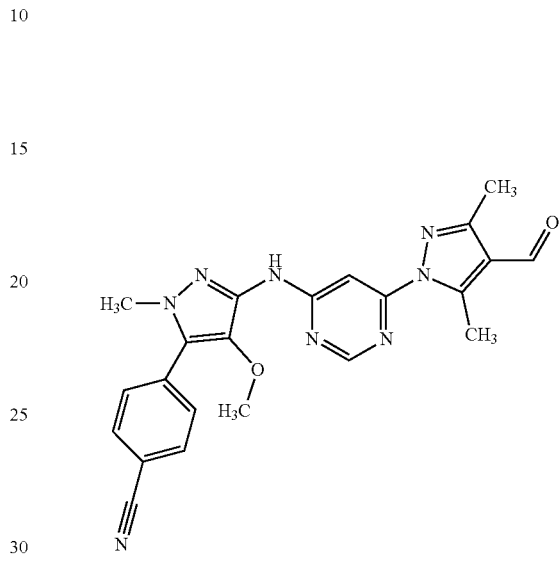

A microwave vial was charged 1-(6-chloropyrimidin-4-yl)-3,5-dimethyl-1H-pyrazole-4-carbaldehyde (291 mg, 76% purity, 936 µmol) and 4-(3-amino-4-methoxy-1-methyl-1H-pyrazol-5-yl)benzonitrile (235 mg, 1.03 mmol) and the contents were suspended in 1,4-dioxane (3.4 ml, 40 mmol). The reaction mixture was degassed with Ar for 3 min. Tris(dibenzylidenaceton)dipalladium (25.7 mg, 28.1 µmol) and Xantphos (32.5 mg, 56.2 µmol) were added and the reaction mixture was degassed again for 1 min and heated to 85° C. At this temperature and sodium phenolate (120 mg, 1.03 mmol) was added. The vial was sealed and heated at 85° C. for 120 minutes while vigorously stirring. The mixture was left at ambient temperature overnight, the reaction mixture was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (73 mg, 18%).

LC-MS (method 10): $R_t$=1.67 min; MS (ESIpos): m/z=429 [M+H]$^+$ $^1$H-NMR (500 MHz, dimethylsulfoxide-d6) δ [ppm]: −0.007 (0.62), 2.074 (0.96), 2.409 (11.88), 2.930 (13.78), 3.540 (0.78), 3.567 (16.00), 3.579 (0.42), 3.769 (0.72), 3.786 (13.57), 7.287 (3.14), 7.776 (3.54), 7.780 (1.48), 7.793 (3.98), 8.007 (4.16), 8.011 (1.51), 8.020 (1.59), 8.024 (3.47), 8.549 (2.48), 9.665 (0.71), 10.014 (5.80).

Intermediate 271

1-[6-({1-(cyclopropylmethyl)-3-[4-(difluoromethyl)phenyl]-4-methyl-1H-pyrazol-5-yl}amino)pyrimidin-4-yl]-3,5-dimethyl-1H-pyrazole-4-carbaldehyde

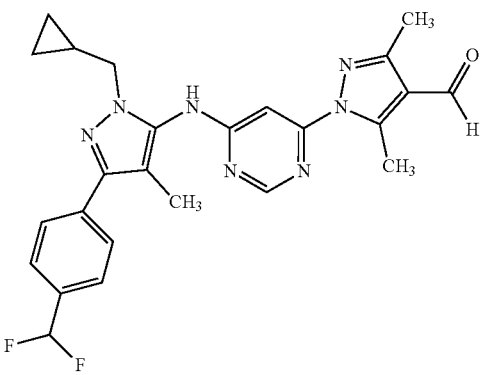 [SMILES: Cc1nn(-c2cc(Nc3c(C)c(-c4ccc(C(F)F)cc4)nn3CC3CC3)ncn2)c(C)c1C=O]

A microwave vial was charged 1-(6-chloropyrimidin-4-yl)-3,5-dimethyl-1H-pyrazole-4-carbaldehyde (408 mg, 76% purity, 1.31 mmol) and 1-(cyclopropylmethyl)-3-[4-(difluoromethyl)phenyl]-4-methyl-1H-pyrazol-5-amine (400 mg, 1.44 mmol) and the contents were suspended in 1,4-dioxane (5.0 ml, 58 mmol). The reaction mixture was degassed with Ar for 3 min. Tris(dibenzylidenaceton)dipalladium (36.0 mg, 39.3 µmol) and Xantphos (45.5 mg, 78.7 µmol) were added and the reaction mixture was degassed again for 1 min and heated to 85° C. At this temperature and sodium phenolate (167 mg, 1.44 mmol) was added. The vial was sealed and heated at 85° C. for 90 minutes while vigorously stirring. The mixture was left overnight at ambient temperature, the reaction mixture was filtered and purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and further flash-chromatography (column: SNAP KP-Sil 10 g, solvent: 92% dichloromethane/8% ethyl acetate to 66% ethyl acetate) to yield the desired product (175 mg, 28%).

LC-MS (method 10): $R_t$=2.08 min; MS (ESIpos): m/z=478 [M+H]$^+$ $^1$H-NMR (400 MHz, dimethylsulfoxide-d6) δ [ppm]: 0.25-0.35 (m, 2H), 0.38-0.54 (m, 2H), 1.13-1.29 (m, 1H), 2.00-2.11 (m, 3H), 2.52-2.57 (m, 3H), 2.86-2.99 (m, 3H), 3.80-3.91 (m, 2H), 6.88-7.48 (m, 2H), 7.53-7.69 (m, 2H), 7.79-7.95 (m, 2H), 8.41-8.72 (m, 1H), 9.40-9.75 (m, 1H), 9.92-10.05 (m, 1H).

Intermediate 272

3-(5-fluoropyridin-2-yl)-4-methyl-1H-pyrazol-5-amine

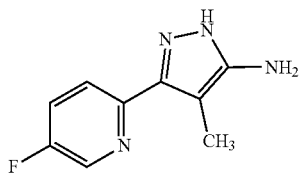

A solution of 3-(5-fluoropyridin-2-yl)-2-methyl-3-oxo-propanenitrile (225 mg, 1.26 mmol) in ethanol (2.7 ml) was treated with hydrazine hydrate (1:1) (120 µl, 2.5 mmol) and stirred overnight at 95° C. After cooling to room temperature the mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 37.8 mg (13%) of the desired product.

LC-MS (method 9): $R_t$=0.45 min; MS (ESIpos): m/z=193 [M+H]$^+$ $^1$H-NMR (400 MHz, dimethylsulfoxide-d6) δ [ppm]: 2.113 (16.00), 7.741 (1.12), 7.747 (1.19), 7.762 (2.21), 7.768 (1.48), 7.776 (1.48), 7.786 (0.49), 8.134 (1.75), 8.557 (1.88), 8.564 (1.91).

Intermediate 273

2-[3-(5-fluoropyridin-2-yl)-4-methyl-1H-pyrazol-5-yl]-1H-isoindole-1,3 (2H)-dione

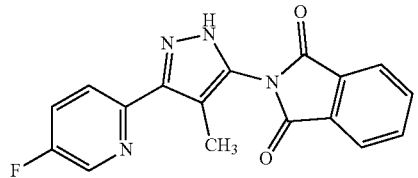 [SMILES: Cc1c(-c2ccc(F)cn2)n[nH]c1N1C(=O)c2ccccc2C1=O]

A solution of 3-(5-fluoropyridin-2-yl)-4-methyl-1H-pyrazol-5-amine (1.75 g, 9.11 mmol) and 2-benzofuran-1,3-dione (2.02 g, 13.7 mmol) in acetic acid (25 ml, 440 mmol) was stirred overnight at 140° C. After cooling to ambient temperature the mixture was diluted with water. The occurring precipitate was collected by filtration, washed with water and dried to yield 3.15 g (96%) of the desired product.

Intermediate 274

2-[5-(5-fluoropyridin-2-yl)-1,4-dimethyl-1H-pyrazol-3-yl]-1H-isoindole-1,3 (2H)-dione

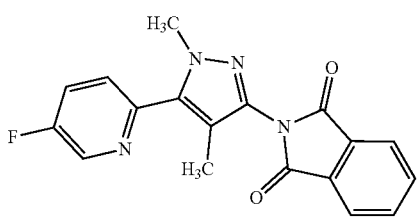 [SMILES: Cc1c(N2C(=O)c3ccccc3C2=O)nn(C)c1-c1ccc(F)cn1]

A solution of 2-[3-(5-fluoropyridin-2-yl)-4-methyl-1H-pyrazol-5-yl]-1H-isoindole-1,3(2H)-dione (3.10 g, 9.62 mmol) in dimethylformamide (30 ml, 390 mmol) was treated with cesium carbonate (6.27 g, 19.2 mmol) and iodomethane (1.2 ml, 19 mmol). The mixture was stirred overnight. The mixture was filtered and purged into saturated ammonium chloride solution. The occurring precipitate was collected by filtration washed with water and dried. The crude product was purified using flash-chromatography (column: SNAP Ultra 50 g, solvent: 96% dichloromethane/

4% ethyl acetate to 34% ethyl acetate) and further preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 580 mg of the desired product (18%) along with its regioisomer.

LC-MS (method 10): R$_t$=1.64 min; MS (ESIpos): m/z=337 [M+H]$^+$ $^1$H-NMR (600 MHz, dimethylsulfoxide-d6) δ [ppm]: 1.940 (15.51), 3.939 (16.00), 7.783 (1.11), 7.790 (1.16), 7.797 (1.38), 7.804 (1.33), 7.923 (0.83), 7.928 (0.89), 7.938 (1.54), 7.943 (1.72), 7.948 (2.58), 7.953 (3.12), 7.957 (3.28), 7.962 (3.69), 7.968 (0.52), 8.005 (0.48), 8.011 (3.78), 8.016 (2.65), 8.020 (2.69), 8.025 (2.43), 8.800 (2.29), 8.805 (2.26).

Intermediate 275

2-[3-(5-fluoropyridin-2-yl)-1,4-dimethyl-1H-pyrazol-5-yl]-1H-isoindole-1,3 (2H)-dione

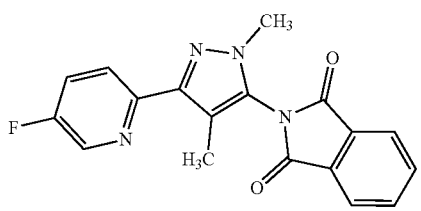 [SMILES: Cc1c(-c2ccc(F)cn2)nn(C)c1N1C(=O)c2ccccc2C1=O]

A solution of 2-[3-(5-fluoropyridin-2-yl)-4-methyl-H-pyrazol-5-yl]-1H-isoindole-1,3(2H)-dione (3.10 g, 9.62 mmol) in N,N-dimethylformamide (30 ml, 390 mmol) was treated with cesium carbonate (6.27 g, 19.2 mmol) and iodomethane (1.2 ml, 19 mmol). The mixture was stirred overnight. The mixture was filtered and purged into saturated ammonium chloride solution. The occurring precipitate was collected by filtration washed with water and dried. The crude product was purified using flash-chromatography (column: SNAP Ultra 50 g, solvent: 96% dichloromethane/ 4% ethyl acetate to 34% ethyl acetate) and further preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 212 mg of the desired product (6%) along with its regioisomer.

LC-MS (method 10): R$_t$=1.82 min; MS (ESIpos): m/z=337 [M+H]$^+$ $^1$H-NMR (600 MHz, dimethylsulfoxide-d6) δ [ppm]: 2.178 (16.00), 3.321 (5.42), 5.753 (0.59), 7.778 (0.61), 7.783 (0.65), 7.793 (1.29), 7.798 (1.35), 7.807 (0.71), 7.812 (0.73), 7.976 (2.33), 7.980 (2.50), 7.984 (2.67), 7.990 (4.16), 7.998 (1.68), 8.006 (1.23), 8.013 (1.18), 8.043 (0.46), 8.049 (3.38), 8.055 (2.65), 8.059 (2.52), 8.064 (2.32), 8.611 (2.36), 8.616 (2.35).

Intermediate 276

5-(5-fluoropyridin-2-yl)-1,4-dimethyl-1H-pyrazol-3-amine

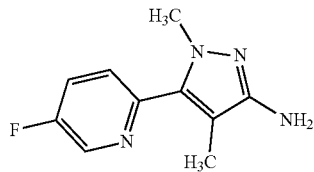

A solution of 2-[5-(5-fluoropyridin-2-yl)-1,4-dimethyl-1H-pyrazol-3-yl]-1H-isoindole-1,3(2H)-dione (206 mg, 612 μmol) in ethanol (7 mL) was treated with hydrazine monohydrate (137 μL, 2.8 mmol) and stirred at 90° C. overnight. After cooling to ambient temperature the mixture was diluted with water and extracted with ethyl acetate (3×). The combined organic phases were washed with saturated sodium hydrogen carbonate solution and brine, dried over sodium sulfate and concentrated under reduced pressure to yield 108 mg (86%) of the desired product.

LC-MS (method 9): R$_t$=0.47 min; MS (ESIpos): m/z=207 [M+H]$^+$ $^1$H-NMR (500 MHz, dimethylsulfoxide-d6) δ [ppm]: 1.870 (16.00), 3.315 (6.20), 3.587 (0.43), 4.494 (3.22), 7.557 (1.20), 7.566 (1.20), 7.574 (1.36), 7.583 (1.29), 7.826 (0.87), 7.832 (0.91), 7.844 (1.62), 7.850 (1.65), 7.861 (0.77), 7.867 (0.78), 8.699 (2.25), 8.705 (2.17).

Intermediate 277

3-(5-fluoropyridin-2-yl)-1,4-dimethyl-1H-pyrazol-5-amine

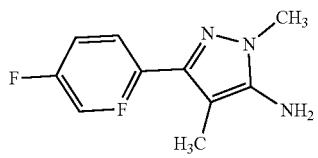

A solution of 2-[3-(5-fluoropyridin-2-yl)-1,4-dimethyl-1H-pyrazol-5-yl]-1H-isoindole-1,3(2H)-dione (747 mg, 2.22 mmol) in ethanol (20 mL) was treated with hydrazine monohydrate (540 μl, 11.1 mmol) and stirred at 90° C. overnight. After cooling to ambient temperature the mixture was diluted with water and extracted with ethyl acetate (3×). The combined organic phases were washed with saturated sodium hydrogen carbonate solution and brine, dried over sodium sulfate and concentrated under reduced pressure to yield 322 mg (67%) of the desired product.

LC-MS (method 9): R$_t$=0.49 min; MS (ESIpos): m/z=207 [M+H]$^+$ $^1$H-NMR (500 MHz, dimethylsulfoxide-d6) δ [ppm]: 1.748 (0.57), 2.139 (15.49), 3.590 (16.00), 4.978 (4.23), 7.634 (0.65), 7.640 (0.67), 7.652 (1.39), 7.658 (1.40), 7.670 (0.78), 7.676 (0.76), 7.840 (1.31), 7.849 (1.32), 7.857 (1.12), 7.867 (1.04), 8.499 (2.25), 8.505 (2.12).

Intermediate 278

4-{5-[(6-chloropyrimidin-4-yl)amino]-1,4-dimethyl-1H-pyrazol-3-yl}benzonitrile

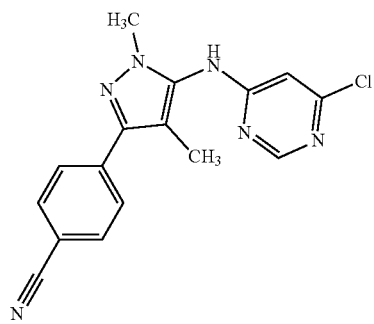 [SMILES: Cc1c(-c2ccc(C#N)cc2)nn(C)c1Nc1cc(Cl)ncn1]

A solution of 4,6-dichloropyrimidine (140 mg, 942 µmol) and 4-(5-amino-1,4-dimethyl-1H-pyrazol-3-yl)benzonitrile (200 mg, 942 µmol) in dimethylformamide (4.4 ml, 57 mmol) was treated with N,N-diisopropylethylamine (180 µl, 1.0 mmol) and sodium iodide (169 mg, 1.13 mmol). The resulting mixture was stirred three days at 125° C. After cooling to ambient temperature the mixture was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 74.0 mg (24%) of the desired product.

LC-MS (method 9): $R_t$=0.83 min; MS (ESIpos): m/z=325 [M+H]$^+$

Intermediate 279

4-{5-[(6-hydrazinylpyrimidin-4-yl)amino]-1,4-dimethyl-1H-pyrazol-3-yl}benzonitrile

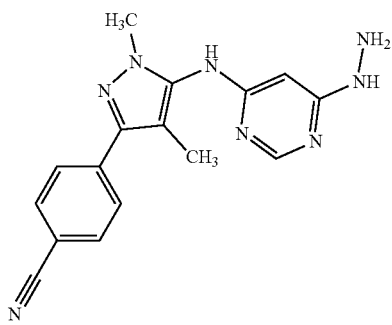 [SMILES: Cc1c(-c2ccc(C#N)cc2)nn(C)c1Nc1cc(NN)ncn1]

A solution of 4-{5-[(6-chloropyrimidin-4-yl)amino]-1,4-dimethyl-1H-pyrazol-3-yl}benzonitrile (73.0 mg, 225 µmol) and hydrazine hydrate (1:1) (33 µl, 670 µmol) in 1,4-dioxane (1.4 ml) was stirred overnight at 70° C. As there was no complete conversion observed, in total further 19 equivalents of hydrazine hydrate (208 µL, 4.27 mmol) was added in portions during one week. Stirring at 80° C. was continued. After cooling to room temperature the mixture was concentrated under reduced pressure to yield 92.0 mg (64%) as the crude product which was used in the next step without further purifications.

LC-MS (method 11): $R_t$=0.71 min; MS (ESIpos): m/z=321 [M+H]$^+$

Intermediate 280

2-methyl-3-(6-methylpyridin-3-yl)-3-oxopropanenitrile

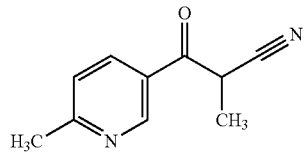

To a solution of methyl 6-methylpyridine-3-carboxylate (3.43 g, 22.7 mmol) and propanenitrile (2.1 ml, 29 mmol) in tetrahydrofuran (48 ml, 590 mmol) cooled in an ice bath was added lithium bistrimethylsilylamide 1M in tetrahydrofuran (29 ml, 1.0 M, 29 mmol) dropwise and the reaction mixture stirred at room temperature overnight. The reaction mixture was cooled in an ice bath and additional propanenitrile (0.81 ml, 11 mmol) was added followed by the dropwise addition of Lithium bistrimethylsilylamide 1M in tetrahydrofuran (11.3 ml, 1.0 M, 11.3 mmol) and the reaction then stirred at room temperature for a further 3 h. The reaction was quenched with ice cold water, and the organic phase solvent then removed in vacuo. The residue was diluted with water (110 ml), acidified to pH 4-5 with 4N hydrochloric acid and extracted three times with methyl tert-butyl ether. The combined organic phase s were dried with sodium sulfate and concentrated in vacuo. The crude product was purified by flash-chromatography on silica gel (dichloromethane:methanol 60:1, column: Biotage SNAP Ultra 50 g) and the residue washed with pentane to yield 3.15 g (100% purity, 80% yield) of the desired product. The target compounds is an approximate 1:1 mixture with its tautomer in solution as determined by NMR.

LC-MS (Method 10): $R_t$=0.94 min; MS (ESIpos): m/z=175 [M+H]$^+$ $^1$H-NMR (400 MHz, dimethylsulfoxide-d6) δ [ppm]: 1.008 (0.41), 1.025 (0.41), 1.106 (2.24), 1.188 (0.42), 1.470 (8.27), 1.488 (8.34), 1.680 (2.51), 1.869 (16.00), 2.520 (15.02), 2.576 (14.43), 3.077 (0.73), 5.108 (0.67), 5.126 (2.07), 5.144 (2.05), 5.162 (0.65), 7.351 (2.11), 7.371 (2.30), 7.477 (2.06), 7.497 (2.17), 7.812 (1.62), 7.817 (1.65), 7.832 (1.49), 7.838 (1.52), 8.232 (1.53), 8.238 (1.55), 8.253 (1.46), 8.259 (1.46), 8.591 (2.43), 8.596 (2.40), 9.048 (2.36), 9.053 (2.32), 10.997 (1.22).

Intermediate 281

1-(cyclopropylmethyl)-4-methyl-3-(6-methylpyridin-3-yl)-1H-pyrazol-5-amine

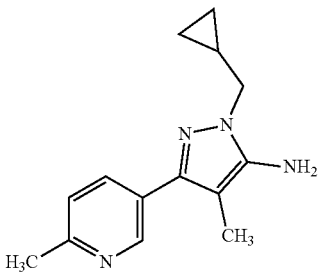 [SMILES: Cc1ccc(-c2nn(CC3CC3)c(N)c2C)cn1]

To rac-2-methyl-3-(6-methylpyridin-3-yl)-3-oxopropanenitrile (500 mg, 2.87 mmol) in 2-propanol (7.5 ml, 97 mmol) at an internal temperature of 80° C. was slowly added (cyclopropylmethyl)hydrazine dihydrochloride (502 mg, 3.16 mmol) and the reaction heated at reflux overnight. The cooled reaction was concentrated in vacuo, the residue dissolved in water and solid sodium hydrogen carbonate added until the solution was pH 7. The aqueous solution was extracted three times with ethyl acetate and the combined organic phase s dried with sodium sulfate and concentrated in vacuo. The crude product was purified by flash-chromatography on silica gel (dichloromethane:methanol 40:1, column: Biotage SNAP Ultra 10 g) to yield 555 mg (100% purity, 80% yield) of the desired product.

LC-MS (Method 10): $R_t$=0.69 min; MS (ESIpos): m/z=243 [M+H]$^+$ $^1$H-NMR (400 MHz, dimethylsulfoxide-d6) δ [ppm]: 0.335 (0.53), 0.348 (2.52), 0.360 (2.95), 0.372 (0.95), 0.414 (0.95), 0.423 (2.21), 0.433 (1.37), 0.443 (2.41), 0.459 (0.51), 1.187 (0.68), 1.206 (0.89), 1.217 (0.59), 1.982 (16.00), 2.466 (12.89), 3.801 (4.40), 3.818 (4.34), 4.951 (5.35), 5.754 (0.46), 7.233 (2.01), 7.253 (2.15), 7.802 (1.68), 7.807 (1.53), 7.822 (1.57), 7.827 (1.43), 8.632 (2.85), 8.636 (2.67).

Intermediate 282

3-(4-fluorophenyl)-1-(2-methoxyethyl)-4-methyl-1H-pyrazol-5-amine

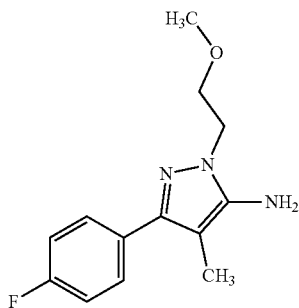 [SMILES: COCCn1nc(-c2ccc(F)cc2)c(C)c1N]

To rac-3-(4-fluorophenyl)-2-methyl-3-oxopropanenitrile (4.38 g, 24.7 mmol) in 2-propanol (64 ml, 840 mmol) at an internal temperature of 80° C. was slowly added (2-methoxyethyl)hydrazine ethanedioate (1:1) (4.90 g, 27.2 mmol) and the reaction heated at reflux for 3.5 h. The cooled reaction mixture was filtered and concentrated in vacuo. The residue was dissolved in ethylacteate, basified with a saturated aqueous solution of sodium bicarbonate to pH 7 and extracted three times with ethyl acetate. The combined organic phase s were dried with sodium sulfate and concentrated in vacuo. The crude product was purified by flash-chromatography on silica gel (gradient 15% to 100% ethylacetate in cyclohexane, column: Biotage SNAP Ultra 100 g) to yield 2.34 g (100% purity, 38% yield) of the desired product.

LC-MS (Method 10): $R_t$=1.26 min; MS (ESIpos): m/z=250 [M+H]$^+$ $^1$H-NMR (500 MHz, dimethylsulfoxide-d6) δ [ppm]: 1.236 (1.58), 1.973 (13.74), 3.252 (16.00), 3.508 (1.01), 3.613 (2.09), 3.625 (4.42), 3.637 (2.24), 4.052 (2.20), 4.064 (4.13), 4.075 (1.95), 4.889 (4.34), 7.172 (1.83), 7.190 (3.67), 7.208 (1.97), 7.581 (2.03), 7.592 (2.42), 7.598 (2.28), 7.609 (1.86).

Intermediate 283 methyl 4-[(tert-butoxycarbonyl)(methyl)amino]benzoate

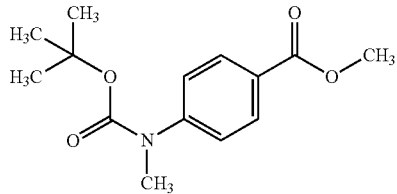 [SMILES: COC(=O)c1ccc(N(C)C(=O)OC(C)(C)C)cc1]

To methyl 4-(methylamino)benzoate (3.99 g, 24.1 mmol) in tetrahydrofuran (48 ml, 590 mmol) was added di-tert-butyl dicarbonate (5.8 ml, 25 mmol) and N,N-dimethylpyridin-4-amine (295 mg, 2.41 mmol) and the reaction stirred overnight at room temperature. The reaction mixture was then diluted with ethylacetate, washed twice with water, once with a saturated aqueous solution of sodium chloride, the organic phase then dried with sodium sulfate and concentrated in vacuo. The crude product was purified by flash-chromatography on silica gel (gradient of ethylacetate in cyclohexane, column: Biotage SNAP Ultra 50 g) to yield 2.79 g (100% purity, 44% yield) of the desired product.

LC-MS (Method 9): $R_t$=1.05 min; MS (ESIpos): m/z=266 [M+H]$^+$ $^1$H-NMR (400 MHz, dimethylsulfoxide-d6) δ [ppm]: 1.420 (16.00), 3.310 (2.45), 3.840 (5.81), 7.440 (1.41), 7.462 (1.53), 7.905 (1.63), 7.909 (0.53), 7.922 (0.51), 7.927 (1.44).

Intermediate 284 rac-tert-butyl [4-(2-cyanopropanoyl)phenyl]methyl-carbamate

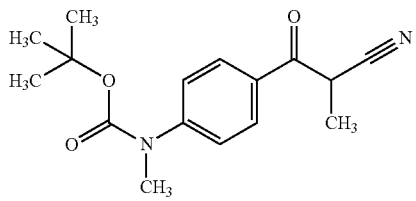 [SMILES: CC(C#N)C(=O)c1ccc(N(C)C(=O)OC(C)(C)C)cc1]

To a solution of methyl 4-[(tert-butoxycarbonyl)(methyl)amino]benzoate (2.68 g, 10.1 mmol) and propanenitrile (1.4 ml, 20 mmol) in tetrahydrofuran (21 ml, 260 mmol) cooled in an ice bath was added lithium bistrimethylsilylamide 1M in tetrahydrofuran (21 ml, 1.0 M, 21 mmol) dropwise and the reaction mixture stirred at room temperature for 1 h. The reaction was quenched with ice cold water, and the organic phase solvent then removed in vacuo. The residue was diluted with water, extracted three times with dichloromethane. The combined organic phase s were dried with sodium sulfate and concentrated in vacuo to yield a portion the target compound (1.015 g, 80% purity). The aqueous phase was subsequently acidified with 4N hydrochloric acid to pH 4 and extracted three times with dichloromethane and once with methyl tert-butylether. The combined organic phase s were dried with sodium sulfate and concentrated in vacuo to yield 2.31 g (100% purity, 79% yield) of the desired product. The target compounds is an approximate 2:1 mixture with its tautomer in solution as determined by NMR.

LC-MS (Method 9): $R_t$=1.00 min; MS (ESIneg): m/z=287 [M−H]$^-$ $^1$H-NMR (400 MHz, dimethylsulfoxide-d6) δ [ppm]: 1.416 (4.56), 1.436 (16.00), 1.464 (2.96), 1.482 (2.95), 1.856 (1.42), 3.217 (1.60), 3.262 (6.12), 5.101 (0.71), 5.119 (0.70), 7.396 (0.49), 7.506 (0.68), 7.513 (1.56), 7.535 (1.62), 7.980 (1.59), 8.001 (1.45).

Intermediate 285

1-(cyclopropylmethyl)-4-methyl-3-[4-(methylamino)phenyl]-1H-pyrazol-5-amine

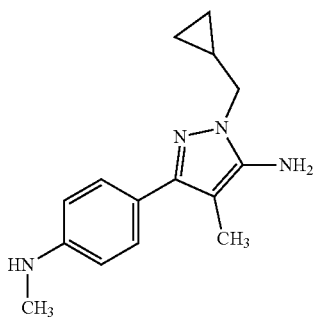 [SMILES: CNc1ccc(-c2nn(CC3CC3)c(N)c2C)cc1]

To tert-butyl [4-(2-cyanopropanoyl)phenyl]methylcarbamate (476 mg, 1.65 mmol) in 2-propanol (4.3 ml, 56 mmol) at an internal temperature of 80° C. was slowly added (cyclopropylmethyl)hydrazine dihydrochloride (289 mg, 1.82 mmol) and the reaction heated at reflux for 3.5 h. The cooled reaction mixture was filtered and concentrated in vacuo. The residue was dissolved in ethylacteate, diluted with water, basified with a saturated aqueous solution of sodium hydrogen carbonate until pH 7 and extracted three times with ethyl acetate. The combined organic phase s were dried with sodium sulfate and concentrated in vacuo. The crude product was purified by flash-chromatography on silica gel (dichloromethane:methanol 60:1, column: Biotage SNAP Ultra 25 g) to yield 259 mg (100% purity, 61% yield) of the desired product.

LC-MS (Method 10): $R_t$=1.00 min; MS (ESIpos): m/z=257 [M+H]$^+$ $^1$H-NMR (500 MHz, dimethylsulfoxide-d6) δ [ppm]: 0.321 (0.65), 0.330 (2.34), 0.333 (2.23), 0.340 (2.56), 0.350 (0.88), 0.400 (0.99), 0.407 (2.10), 0.411 (1.78), 0.416 (1.22), 0.423 (2.20), 0.426 (1.68), 0.436 (0.56), 1.166 (0.54), 1.172 (0.57), 1.174 (0.61), 1.181 (0.82), 1.188 (0.52), 1.191 (0.50), 1.195 (0.48), 1.934 (16.00), 2.674 (6.36), 2.684 (6.17), 3.164 (0.62), 3.175 (0.62), 3.747 (3.97), 3.760 (3.86), 4.746 (4.99), 5.581 (0.98), 5.591 (0.97), 5.751 (1.08), 6.520 (3.97), 6.537 (4.01), 7.303 (4.27), 7.320 (3.87).

Intermediate 286 tert-butyl 2-(6-chloropyrimidin-4-yl)-2,6-dihydropyrrolo[3,4-c]pyrazole-5(4H)-carboxylate

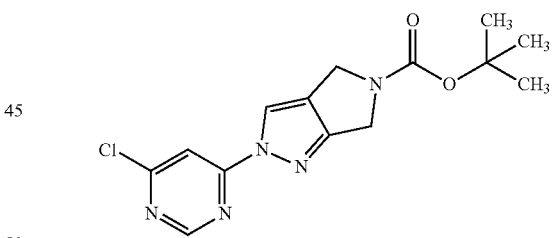

To 4,6-dichloropyrimidine (674 mg, 4.52 mmol) in dimethylformamide (3.4 ml) under an atmosphere of argon was added tert-butyl 2,6-dihydropyrrolo[3,4-c]pyrazole-5(4H)-carboxylate (946 mg, 4.52 mmol) and cesium carbonate (1.47 g, 4.52 mmol) and the reaction stirred overnight at room temperature. The reaction was poured onto water (25 ml) and stirred for 60 minutes. The precipitate was filtered and purified by HPLC (Method 20) to yield 748 mg (100% purity, 51% yield) of the desired product.

LC-MS (Method 10): $R_t$=2.10 min; MS (ESIpos): m/z=322 [M+H]$^+$ $^1$H-NMR (600 MHz, dimethylsulfoxide-d6) δ [ppm]: 1.466 (16.00), 4.400 (1.20), 4.427 (1.38), 4.456 (1.47), 4.477 (1.29), 7.884 (0.67), 7.903 (0.79), 8.467 (0.69), 8.493 (0.62), 8.925 (1.44).

Intermediate 287 ethyl 4-(difluoromethoxy)benzoate

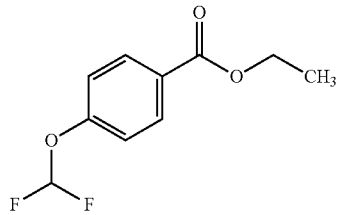

To ethanol (53 ml) at −10° C. was added thionyl chloride (1.03 ml, 14.1 mmol) dropwise, maintaining the temperature under 0° C. at all times. After stirring for 10 minutes at 0° C. 4-(difluoromethoxy)benzoic acid (500 mg, 2.66 mmol) was added and the reaction was stirred overnight at reflux. The cooled reaction mixture was diluted with water and the ethanol removed in vacuo. The aqueous phase was basified with 2N sodium hydroxide to pH 7, extracted three times with dichloromethane and the combined organic phase s then washed with a saturated aqueous solution of sodium chloride, dried with sodium sulfate and concentrated in vacuo to yield 578 mg, (100% purity, 100% yield) of the desired product.

LC-MS (Method 9): $R_t$=0.99 min; Compound does not ionise.

$^1$H-NMR (400 MHz, dimethylsulfoxide-d6) δ [ppm]: 1.302 (7.48), 1.320 (16.00), 1.337 (7.72), 4.287 (2.40), 4.305 (7.40), 4.322 (7.35), 4.340 (2.32), 7.210 (2.52), 7.288 (5.54), 7.310 (5.90), 7.393 (5.04), 7.577 (2.45), 8.000 (0.86), 8.007 (7.30), 8.012 (2.32), 8.024 (2.26), 8.029 (6.84), 8.036 (0.78).

Intermediate 288

3-[4-(difluoromethoxy)phenyl]-2-methyl-3-oxopropanenitrile

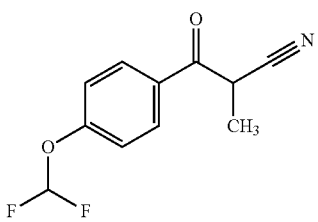 [SMILES: CC(C#N)C(=O)c1ccc(OC(F)F)cc1]

To a solution of ethyl 4-(difluoromethoxy)benzoate (578 mg, 2.67 mmol) and propanenitrile (250 µl, 3.5 mmol) in tetrahydrofuran (5.6 ml, 69 mmol) cooled in an ice bath was added lithium bistrimethylsilylamide 1M in tetrahydrofuran (3.5 ml, 1.0 M, 3.5 mmol) dropwise and the reaction mixture stirred at room temperature overnight. The reaction was quenched with ice cold water, and the organic phase solvent then removed in vacuo. The residue was diluted with water (24 ml), acidified to pH 4 with 4N hydrochloric acid and extracted three times with methyl tert-butyl ether. The combined organic phase s dried with sodium sulfate and concentrated in vacuo to yield 406 mg (88% purity, 59% yield) of the desired product. The target compounds is an approximate 4.5:1 mixture with its tautomer in solution as determined by NMR.

LC-MS (Method 10): $R_t$=1.61 min; MS (ESIpos): m/z=226 [M+H]$^+$ $^1$H-NMR (400 MHz, dimethylsulfoxide-d6) δ [ppm]: 1.106 (1.02), 1.463 (15.91), 1.481 (16.00), 1.673 (2.08), 1.857 (11.95), 2.328 (0.41), 2.366 (0.44), 2.669 (0.44), 2.710 (0.41), 5.103 (1.23), 5.121 (3.95), 5.139 (3.95), 5.157 (1.22), 7.157 (1.08), 7.193 (0.53), 7.257 (3.02), 7.269 (3.41), 7.278 (3.70), 7.341 (2.47), 7.353 (6.79), 7.375 (7.35), 7.452 (5.60), 7.473 (0.62), 7.495 (0.44), 7.525 (1.09), 7.561 (0.53), 7.597 (3.53), 7.619 (3.18), 7.635 (2.83), 7.985 (1.45), 8.007 (1.46), 8.091 (8.30), 8.113 (7.76), 10.863 (1.27).

Intermediate 289

1-(cyclopropylmethyl)-3-[4-(difluoromethoxy)phenyl]-4-methyl-1H-pyrazol-5-amine

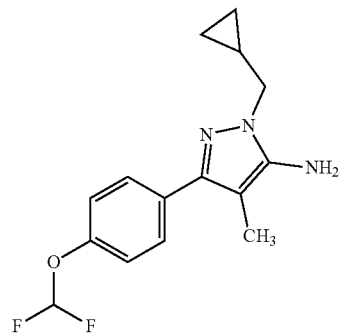 [SMILES: Cc1c(-c2ccc(OC(F)F)cc2)nn(CC2CC2)c1N]

To 3-[4-(difluoromethoxy)phenyl]-2-methyl-3-oxopropanenitrile (406 mg, 1.80 mmol) in 2-propanol (4.7 ml, 61 mmol) at an internal temperature of 80° C. was slowly added (cyclopropylmethyl)hydrazine dihydrochloride (315 mg, 1.98 mmol) and the reaction heated at reflux overnight. The cooled reaction was concentrated in vacuo, the residue dissolved in water (5 ml) and the solution basified to pH 7 with solid sodium hydrogen carbonate. The aqueous solution was extracted three times with ethyl acetate and the combined organic phase s dried with sodium sulfate and concentrated in vacuo. The crude product was purified by flash-chromatography on silica gel (gradient of ethylacetate in cyclohexane, column: Biotage SNAP Ultra 10 g) to yield 403 mg (95% purity, 76% yield) of the desired product.

LC-MS (Method 10): $R_t$=1.52 min; MS (ESIpos): m/z=294 [M+H]$^+$ $^1$H-NMR (400 MHz, dimethylsulfoxide-d6) δ [ppm]: 0.331 (0.53), 0.343 (2.05), 0.347 (2.06), 0.356 (2.44), 0.369 (0.93), 0.412 (0.96), 0.421 (1.89), 0.425 (1.58), 0.432 (1.22), 0.441 (2.08), 0.457 (0.53), 1.182 (0.50), 1.190 (0.48), 1.202 (0.77), 1.214 (0.46), 1.219 (0.44), 1.982 (16.00), 3.791 (3.95), 3.808 (3.88), 4.911 (4.52), 7.042 (1.40), 7.162 (3.43), 7.184 (3.79), 7.228 (2.80), 7.414 (1.36), 7.598 (0.57), 7.605 (4.50), 7.610 (1.48), 7.622 (1.46), 7.627 (4.04), 7.634 (0.47).

Intermediate 290 ethyl 6-oxo-1,6-dihydropyridine-3-carboxylate

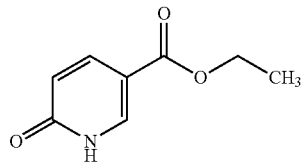

To ethanol (150 ml) at −10° C. was added thionyl chloride (1.9 ml, 26 mmol) dropwise, maintaining the temperature under 0° C. at all times. After stirring for 10 minutes 6-methoxypyridine-3-carboxylic acid (2.00 g, 13.1 mmol) was added and the reaction was stirred overnight at reflux. The cooled reaction mixture was diluted with water and the ethanol removed in vacuo. The aqueous phase was basified with 1N sodium hydroxide to pH 7, extracted three times with dichloromethane and the combined organic phase s then washed with a saturated aqueous solution of sodium chloride, dried with sodium sulfate and concentrated in vacuo to yield 1.87 g, (100% purity, 86% yield) of the desired product.

LC-MS (method 10): $R_t$=0.8 min; Compound does not ionise.

$^1$H-NMR (500 MHz, dimethylsulfoxide-d6) δ [ppm]: 1.255 (7.51), 1.270 (16.00), 1.284 (7.57), 4.206 (2.38), 4.220 (7.44), 4.234 (7.34), 4.249 (2.26), 6.357 (3.35), 6.376 (3.44), 7.777 (2.77), 7.783 (2.82), 7.797 (2.67), 7.802 (2.76), 8.017 (3.23), 8.023 (3.12), 12.112 (0.67).

Intermediate 291 ethyl 6-methoxypyridine-3-carboxylate

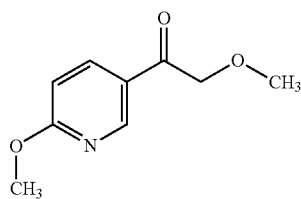

To ethyl 6-oxo-1,6-dihydropyridine-3-carboxylate (1.87 g, 11.2 mmol) in chloroform (25 ml) was added iodomethane (2.5 ml, 40 mmol) and silver carbonate (4.02 g, 14.6 mmol) and the reaction stirred overnight at room temperature. The cooled reaction mixture was filtered, concentrated in vacuo and purified by flash-chromatography on silica gel (gradient 7% to 60% ethylacetate in cyclohexane, column: Biotage SNAP Ultra 50 g) to yield 1.05 g (100% purity, 51% yield) of the desired product.

$^1$H-NMR (500 MHz, dimethylsulfoxide-d6) δ [ppm]: 1.304 (3.72), 1.318 (7.82), 1.333 (3.74), 1.993 (0.47), 3.938 (16.00), 4.290 (1.20), 4.305 (3.68), 4.319 (3.62), 4.333 (1.14), 6.922 (1.68), 6.939 (1.73), 6.941 (1.68), 8.150 (1.43), 8.155 (1.44), 8.168 (1.39), 8.172 (1.39), 8.748 (1.48), 8.752 (1.48).

Intermediate 292 rac-3-(6-methoxypyridin-3-yl)-2-methyl-3-oxopropanenitrile

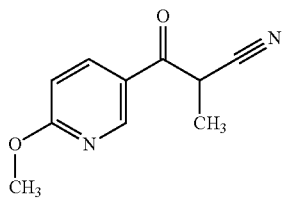

To a solution of ethyl 6-methoxypyridine-3-carboxylate (1.02 g, 5.61 mmol) and propanenitrile (520 µl, 7.3 mmol) in tetrahydrofuran (12 ml, 150 mmol) cooled in an ice bath was added lithium bistrimethylsilylamide 1M in tetrahydrofuran (7.3 ml, 1.0 M, 7.3 mmol) dropwise and the reaction mixture stirred at room temperature for 3 h. The reaction mixture was cooled in an ice bath and additional lithium bistrimethylsilylamide 1M in tetrahydrofuran (2.8 ml, 1.0 M, 2.8 mmol) was added dropwise and the reaction stirred overnight at room temperature. The reaction mixture was cooled in an ice bath and additional lithium bistrimethylsilylamide 1M in tetrahydrofuran (1.12 ml, 1.0 M, 1.2 mmol) was added dropwise and the reaction stirred for 2 h at room temperature. The reaction was quenched with ice cold water, and the organic phase solvent then removed in vacuo. The residue was diluted with water, acidified to pH 4 with 4N hydrochloric acid and extracted three times with dichloromethane. The combined organic phase s dried with sodium sulfate, concentrated in vacuo and purified by flash-chromatography on silica gel (gradient 7% to 65% ethylacetate in cyclohexane, column: Biotage SNAP Ultra 50 g) to yield 729 mg (99% purity, 67% yield) of the desired product. The target compounds is an approximate 2.5:1 mixture with its tautomer in solution, as determined by NMR.

LC-MS (method 9): $R_t$=0.69 min; MS (ESIpos): m/z=191 [M+H]$^+$ $^1$H-NMR (500 MHz, dimethylsulfoxide-d6) δ [ppm]: 1.470 (7.51), 1.484 (7.48), 1.694 (0.88), 1.821 (0.26), 1.854 (3.10), 3.895 (1.69), 3.900 (3.33), 3.925 (0.36), 3.969 (16.00), 5.067 (0.63), 5.082 (1.90), 5.096 (1.88), 5.110 (0.59), 6.905 (0.60), 6.922 (0.63), 6.992 (2.26), 7.009 (2.29), 7.736 (0.09), 7.741 (0.09), 7.753 (0.08), 7.758 (0.09), 7.841 (0.37), 7.854 (0.36), 8.229 (1.52), 8.234 (1.62), 8.246 (1.47), 8.251 (1.45), 8.362 (0.66), 8.897 (2.36), 8.902 (2.30), 10.901 (0.06).

Intermediate 293

1-(cyclopropylmethyl)-3-(6-methoxypyridin-3-yl)-4-methyl-1H-pyrazol-5-amine

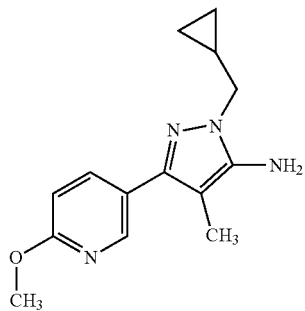 [SMILES: COc1ccc(-c2nn(CC3CC3)c(N)c2C)cn1]

To 3-(6-methoxypyridin-3-yl)-2-methyl-3-oxopropanenitrile (372 mg, 1.95 mmol) in 2-propanol (5.2 ml, 67 mmol) at an internal temperature of 80° C. was slowly added (cyclopropylmethyl)hydrazine dihydrochloride (342 mg, 2.15 mmol) and the reaction heated at reflux overnight. The cooled reaction was concentrated in vacuo, the residue dissolved in ethylacetate, basified with 1 N sodium hydroxide and extracted twice with ethylacetate. The combined organic phase s were dried with sodium sulfate and concentrated in vacuo. The resultant material was then stirred in ethylacetate, filtered and the organic phase concentrated in vacuo. The crude product was purified by flash-chromatography on silica gel (dichloromethane:methanol 50:1, column: Biotage SNAP Ultra 25 g) to yield 111 mg (100% purity, 22% yield) of the desired product.

LC-MS (method 9): $R_t$=0.63 min; MS (ESIpos): m/z=259 [M+H]$^+$ $^1$H-NMR (500 MHz, dimethylsulfoxide-d6) δ [ppm]: 0.336 (0.41), 0.345 (1.43), 0.349 (1.35), 0.355 (1.54), 0.358 (1.38), 0.366 (0.62), 0.416 (0.67), 0.423 (1.32), 0.427 (1.12), 0.432 (0.79), 0.436 (0.72), 0.439 (1.40), 0.443 (1.04), 0.452 (0.41), 1.199 (0.55), 1.968 (12.62), 3.790 (2.76), 3.804 (2.70), 3.865 (16.00), 4.927 (3.02), 6.820 (1.71), 6.821 (1.62), 6.837 (1.73), 6.838 (1.65), 7.868 (1.46), 7.873 (1.45), 7.886 (1.35), 7.890 (1.38), 8.323 (1.61), 8.325 (1.62), 8.328 (1.62), 8.329 (1.45).

Intermediate 294

3-(6-methoxypyridin-3-yl)-1,4-dimethyl-1H-pyrazol-5-amine

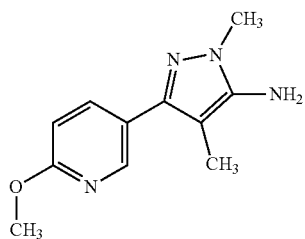 [SMILES: COc1ccc(-c2nn(C)c(N)c2C)cn1]

To 3-(6-methoxypyridin-3-yl)-2-methyl-3-oxopropanenitrile (356 mg, 1.87 mmol) in 2-propanol (5.0 ml, 64 mmol) at an internal temperature of 80° C. was slowly added methylhydrazine (110 µl, 2.1 mmol) and the reaction heated at reflux overnight. The cooled reaction was concentrated in vacuo, the residue dissolved in ethylacetate, basified with 1 N sodium hydroxide and extracted twice with ethylacetate. The combined organic phase s were dried with sodium sulfate, concentrated in vacuo and the crude product was purified by flash-chromatography on silica gel (dichloromethane:methanol 40:1, column: Biotage SNAP Ultra 50 g) to yield 294 mg (91% purity, 65% yield) of the desired product.

LC-MS (method 10): $R_t$=0.90 min; MS (ESIpos): m/z=219 [M+H]$^+$ $^1$H-NMR (500 MHz, dimethylsulfoxide-d6) δ [ppm]: 1.758 (1.51), 1.963 (13.54), 3.446 (1.56), 3.556 (13.94), 3.861 (16.00), 3.903 (1.88), 4.974 (3.14), 6.816 (1.71), 6.817 (1.68), 6.833 (1.75), 6.834 (1.71), 7.853 (1.44), 7.858 (1.44), 7.870 (1.35), 7.875 (1.37), 8.313 (1.61), 8.315 (1.66), 8.318 (1.63), 8.319 (1.51).

Intermediate 295 ethyl 6-(difluoromethyl)pyridine-3-carboxylate

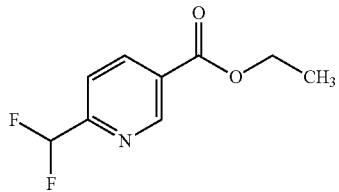

Under an argon atmosphere, 6-(difluoromethyl)pyridine-3-carboxylic acid (1.43 g, 8.24 mmol) was dissolved in thionylchloride (15 mL, 210 mmol) and the reaction mixture was refluxed for 30 minutes. After cooling to ambient temperature, the contents of the flask were concentrated in-vacuo. The residue was dissolved in dry ethanol (50 mL) and the reaction mixture refluxed for 1 h. The mixture was then concentrated and dried to yield the desired product as a dark oil (1.65 g, 98% yield), that was used in the next step without further purification.

LC-MS (method 10): $R_t$=1.52 min; MS (ESIpos): m/z=202 [M+H]$^+$ $^1$H-NMR (500 MHz, dimethylsulfoxide-d6) δ [ppm]: 1.167 (0.55), 1.225 (1.66), 1.240 (3.37), 1.254 (1.67), 1.332 (7.55), 1.346 (16.00), 1.360 (7.50), 1.981 (1.01), 3.993 (0.67), 4.003 (0.71), 4.007 (0.68), 4.018 (0.68), 4.357 (2.38), 4.371 (7.31), 4.385 (7.14), 4.399 (2.23), 6.947 (1.85), 7.056 (3.75), 7.165 (1.71), 7.849 (2.68), 7.865 (2.80), 8.467 (1.85), 8.471 (1.79), 8.484 (1.73), 8.488 (1.66), 9.156 (2.74), 9.159 (2.65).

Intermediate 296

3-[6-(difluoromethyl)pyridin-3-yl]-2-methyl-3-oxo-propanenitrile

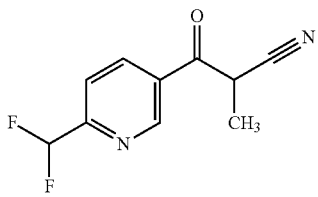

Under an argon atmosphere, ethyl 6-(difluoromethyl)pyridine-3-carboxylate (2.07 g, 10.3 mmol) and propanenitrile (1.1 ml, 15 mmol) were dissolved in dry tetrahydrofuran (16 mL) and chilled with a water bath. A solution of lithium bis(trimethylsilyl)amide in tetrahydrofuran (16 mL, 1.0 M, 16 mmol) was added dropwise. The reaction mixture was then allowed to stir overnight at ambient temperature. It was diluted with water and extracted with ethyl acetate. The organic phase was discarded and the aqueous phase acidified with aqueous hydrochloric acid solution (1 M) to pH 5. It was then extracted with ethyl acetate (3×). The combined organic phase extracts were washed with brine, dried over sodium sulfate and concentrated to yield the desired product (1.8 g, 79% yield), that was used in the next step without further purification LC-MS (method 11): $R_t$=0.90 min; MS (ESIpos): m/z=211 [M+H]$^+$ $^1$H-NMR (500 MHz, dimethylsulfoxide-d6) δ [ppm]: 1.496 (0.74), 1.510 (0.74), 1.689 (2.38), 1.906 (12.19), 1.910 (16.00), 1.989 (0.24), 2.267 (0.17), 5.192 (0.20), 5.207 (0.19), 6.920 (0.97), 6.945 (0.20), 7.030 (1.94), 7.054 (0.40), 7.080 (0.22), 7.139 (0.92), 7.163 (0.18), 7.811 (1.75), 7.828 (1.91), 7.849 (0.30), 7.920 (0.24), 7.935 (0.24), 8.054 (0.20), 8.058 (0.19), 8.070 (0.18), 8.074 (0.17), 8.156 (1.28), 8.160 (1.26), 8.172 (1.16), 8.176 (1.11), 8.451 (0.18), 8.455 (0.18), 8.467 (0.17), 8.471 (0.16), 8.545 (0.22), 8.561 (0.20), 8.735 (0.30), 8.738 (0.29), 8.841 (2.12), 9.148 (0.25), 9.152 (0.24), 9.248 (0.34).

Intermediate 297

3-[6-(difluoromethyl)pyridin-3-yl]-1,4-dimethyl-1H-pyrazol-5-amine

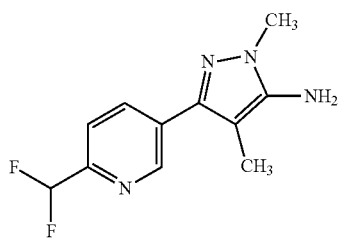 [SMILES: Cc1c(-c2ccc(C(F)F)nc2)nn(C)c1N]

3-[6-(difluoromethyl)pyridin-3-yl]-2-methyl-3-oxopropanenitrile (650 mg, 3.09 mmol) and methylhydrazine (180 μl, 3.4 mmol) were dissolved in 2-propanol (20 mL) and the reaction mixture was refluxed for 4 h. After cooling to ambient temperature, water (20 mL) and saturated aqueous sodium hydrogencarbonate solution was added until pH 8 was obtained. The suspension was then extracted with ethyl acetate (3×), the combined organic phase extracts were washed with brine, dried over sodium sulfate and concentrated. The residue was dissolved in acetonitrile/water and lyophilized to yield the desired product as an off-white powder (591 mg, 76% yield).

LC-MS (method 11): $R_t$=0.80 min; MS (ESIpos): m/z=239 [M+H]$^+$ $^1$H-NMR (500 MHz, dimethylsulfoxide-d6) δ [ppm]: 1.811 (0.63), 2.025 (0.24), 2.038 (15.79), 3.509 (0.65), 3.606 (16.00), 5.098 (3.57), 6.848 (1.06), 6.958 (2.18), 7.068 (0.92), 7.688 (1.56), 7.704 (1.68), 8.120 (1.07), 8.125 (1.05), 8.137 (0.97), 8.141 (0.95), 8.883 (1.57), 8.886 (1.56).

Intermediate 298 tert-butyl [1-(cyclopropylmethyl)-3-(4-fluorophenyl)-4-methyl-1H-pyrazol-5-yl][6-(3,5-dimethyl-4-nitro-1H-pyrazol-1-yl)pyrimidin-4-yl]carbamate

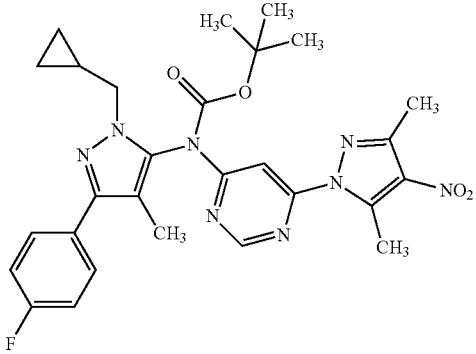 [SMILES: Cc1nn(-c2cc(N(C(=O)OC(C)(C)C)c3c(C)c(-c4ccc(F)cc4)nn3CC3CC3)ncn2)c(C)c1[N+](=O)[O-]]

N-[1-(cyclopropylmethyl)-3-(4-fluorophenyl)-4-methyl-1H-pyrazol-5-yl]-6-(3,5-dimethyl-4-nitro-1H-pyrazol-1-yl)pyrimidin-4-amine (310 mg, 670 μmol) and (293 mg, 1.34 mmol) were dissolved in dichloromethane (13 mL) and 4-dimethylaminopyridine (8.19 mg, 67.0 μmol) was added. The reaction mixture was stirred overnight at ambient temperature. It was quenched by addition of aqueous saturated ammonium chloride solution and extracted with dichloromethane (3×). The combined organic phase extracts were washed with brine, dried over sodium sulfate and concentrated to yield the desired product (300 mg, 76% yield)

LC-MS (method 11): $R_t$=1.76 min; MS (ESIpos): m/z=463 [M-BOC+H]$^+$ $^1$H NMR (500 MHz, dimethylsulfoxide-d$_6$) δ ppm: 0.19-0.32 (m, 2H), 0.38-0.52 (m, 2H), 1.13-1.21 (m, 1H), 1.46 (s, 9H), 1.99 (s, 3H), 2.56 (s, 3H), 3.03 (s, 3H), 3.66-3.75 (m, 1H), 3.75-3.86 (m, 1H), 7.22-7.33 (m, 2H), 7.69-7.80 (m, 2H), 8.59-8.70 (m, 1H), 8.81-8.91 (m, 1H).

Intermediate 299 tert-butyl [6-(4-amino-3,5-dimethyl-1H-pyrazol-1-yl)pyrimidin-4-yl][1-(cyclopropylmethyl)-3-(4-fluorophenyl)-4-methyl-1H-pyrazol-5-yl]carbamate

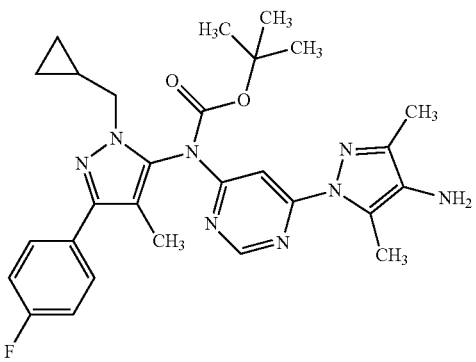

Under an argon atmosphere, tert-butyl [1-(cyclopropylmethyl)-3-(4-fluorophenyl)-4-methyl-1H-pyrazol-5-yl][6-(3,5-dimethyl-4-nitro-1H-pyrazol-1-yl)pyrimidin-4-yl]carbamate (126 mg, 224 µmol) was dissolved in tetrahydrofuran (2 mL) and ethanol (1.5 mL) and palladium (II)hydroxide on charcoal (20%, 45 mg, 64.1 µmol) was added. The argon atmosphere was replaced by a hydrogen atmosphere (1 bar) and the reaction mixture was stirred overnight. After removing the hydrogen atmosphere, the reaction mixture was filtered over celite and the filtrate was concentrated to yield the desired product (118 mg, 69% yield, 71% purity), that was used in the next step without further purification.

LC-MS (method 11): Rt=1.57 min; MS (ESIpos): m/z=433 [M-BOC+H]$^+$

Intermediate 300 ethyl 1-(6-{[4-(difluoromethoxy)-5-(4-fluorophenyl)-1-methyl-H-pyrazol-3-yl]amino}pyrimidin-4-yl)-3,5-dimethyl-1H-pyrazole-4-carboxylate

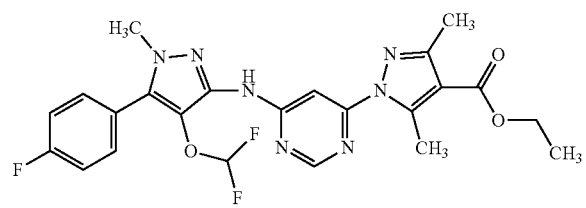 [SMILES: CCOC(=O)c1c(C)nn(-c2cc(Nc3nn(C)c(-c4ccc(F)cc4)c3OC(F)F)ncn2)c1C]

Under an argon atmosphere 4-(difluoromethoxy)-5-(4-fluorophenyl)-1-methyl-1H-pyrazol-3-amine (250 mg, 972 µmol), ethyl 1-(6-chloropyrimidin-4-yl)-3,5-dimethyl-1H-pyrazole-4-carboxylate (300 mg, 1.07 mmol) and sodium phenolate (124 mg, 1.07 mmol) and the contents were suspended in 1,4-dioxane (5.0 mL). The reaction mixture was degassed with Ar for 3 min. Tris(dibenzylideneacetone)dipalladium (26.7 mg, 29.2 µmol) and XantPhos (33.7 mg, 58.3 µmol) were added and the reaction mixture was degassed again for 1 min. The vial was sealed and heated at 85° C. overnight while vigorously shaking. After cooling to ambient temperature, the reaction mixture was diluted with ethyl acetate, filtered over Celite and concentrated. The residue was purified by flash column chromatography (SNAP 25 g, cyclohexane/ethyl acetate gradient 90/10 to 20/80) and further by preparative HPLC (Reprosil C18, 10 µM, 250×50 mm, 150 mL/min, acetonitrile/water (containing 0.1% TFA) gradient 5/95 to 95/5) to yield the desired product (119 mg, 23% yield).

LC-MS (method 10): R$_t$=2.23 min; MS (ESIpos): m/z=502 [M+H]$^+$ $^1$H-NMR (500 MHz, dimethylsulfoxide-d6) δ [ppm]: −0.019 (0.86), 1.230 (2.96), 1.298 (5.05), 1.312 (9.21), 1.326 (4.79), 2.394 (15.45), 2.902 (16.00), 3.734 (15.80), 4.239 (1.76), 4.253 (4.51), 4.267 (4.43), 4.281 (1.65), 6.657 (1.32), 6.805 (2.58), 6.952 (1.25), 7.388 (4.80), 7.406 (5.31), 7.423 (2.98), 7.595 (3.08), 7.606 (3.92), 7.622 (2.66), 8.546 (4.39), 9.707 (3.05).

Intermediate 301 tert-butyl [1-(cyclopropylmethyl)-3-(4-fluorophenyl)-4-methyl-1H-pyrazol-5-yl]{6-[4-(ethylamino)-3,5-dimethyl-1H-pyrazol-1-yl]pyrimidin-4-yl}carbamate

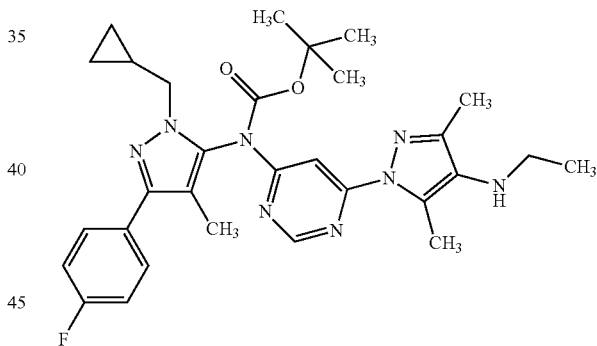

Under an argon atmosphere, tert-butyl [1-(cyclopropylmethyl)-3-(4-fluorophenyl)-4-methyl-1H-pyrazol-5-yl][6-(3,5-dimethyl-4-nitro-1H-pyrazol-1-yl)pyrimidin-4-yl]carbamate (300 mg, 70% purity, 373 µmol) was dissolved in ethanol (6.0 mL) and palladium on charcoal (10%, 37.5 mg) was added. The argon atmosphere was replaced by a hydrogen atmosphere (1 bar) and the reaction mixture was stirred overnight for 30 h. The reaction mixture was then filtered over Celite and the filtrate was concentrated. The residue was purified by flash column chromatography (SNAP Ultra 10 g, cyclohexane/ethyl acetate gradient 95/5 to 35/65) to yield the desired product (25.0 mg, 11% yield) along with tert-butyl [6-(4-amino-3,5-dimethyl-1H-pyrazol-1-yl)pyrimidin-4-yl][1-(cyclopropylmethyl)-3-(4-fluorophenyl)-4-methyl-1H-pyrazol-5-yl]carbamate (see above, 24 mg, 12% yield) as a by-product.

LC-MS (method 11): R$_t$=1.66 min; MS (ESIpos): m/z=460 [M+H]$^+$

¹H-NMR (500 MHz, dimethylsulfoxide-d6) δ [ppm]: −0.007 (0.97), 0.007 (0.66), 0.212 (0.19), 0.220 (0.33), 0.230 (0.41), 0.238 (0.38), 0.248 (0.21), 0.261 (0.22), 0.271 (0.40), 0.279 (0.45), 0.289 (0.34), 0.298 (0.22), 0.401 (0.32), 0.409 (0.33), 0.418 (0.35), 0.425 (0.24), 0.428 (0.24), 0.435 (0.20), 0.447 (0.21), 0.455 (0.23), 0.458 (0.21), 0.465 (0.33), 0.473 (0.31), 0.482 (0.30), 1.034 (1.86), 1.048 (4.06), 1.062 (1.89), 1.137 (0.23), 1.142 (0.23), 1.151 (0.34), 1.161 (0.23), 1.165 (0.22), 1.235 (0.18), 1.398 (0.17), 1.424 (0.79), 1.441 (16.00), 1.553 (0.17), 1.978 (6.16), 2.167 (0.32), 2.212 (6.01), 2.557 (0.19), 2.571 (5.98), 2.858 (0.21), 2.872 (0.77), 2.886 (1.11), 2.900 (0.76), 2.914 (0.21), 3.651 (0.34), 3.665 (0.34), 3.680 (0.52), 3.694 (0.51), 3.725 (0.28), 3.739 (0.52), 3.752 (0.28), 3.764 (0.53), 3.778 (0.51), 3.793 (0.34), 3.806 (0.31), 5.753 (5.53), 7.252 (0.94), 7.257 (0.35), 7.266 (0.51), 7.270 (1.83), 7.274 (0.43), 7.284 (0.40), 7.288 (0.96), 7.717 (0.95), 7.722 (0.46), 7.728 (1.05), 7.735 (0.99), 7.742 (0.41), 7.746 (0.83), 8.468 (1.80), 8.470 (1.81), 8.623 (1.81), 8.625 (1.73).

Intermediate 302

[1-(6-chloropyrimidin-4-yl)-3,5-dimethyl-1H-pyrazol-4-yl]methanol

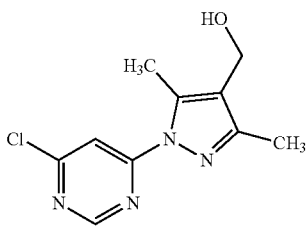 [SMILES: Cc1nn(-c2cc(Cl)ncn2)c(C)c1CO]

Under an argon atmosphere, 1-(6-chloropyrimidin-4-yl)-3,5-dimethyl-1H-pyrazole-4-carbaldehyde (1.00 g, 4.23 mmol) was dissolved in tetrahydrofuran and acetic acid (480 µl, 8.5 mmol) was added. Sodium triacetoxyborohydride (1.41 g, 95% purity, 6.34 mmol) was then added and the reaction mixture was stirred at ambient temperature overnight. Another batch of sodium triacetoxyborohydride (0.94 g, 95% purity, 4.23 mmol) and acetic acid (480 µl, 8.5 mmol) was added and the reaction mixture was stirred for another 6 h. The reaction mixture was then carefully quenched with aqueous saturated ammonium chloride solution and extracted with ethyl acetate (2×). The combined organic phase extracts were dried over sodium sulfate and concentrated. The residue was purified by flash column chromatography (SNAP Ultra 25 g, cyclohexane/ethyl acetate gradient) to yield the desired product (740 mg, 66% yield).

LC-MS (method 11): Rt=0.95 min; MS (ESIpos): m/z=239 [M+H]+

¹H-NMR (500 MHz, dimethylsulfoxide-d6) δ [ppm]: 2.254 (16.00), 2.446 (0.74), 2.650 (15.10), 2.971 (0.72), 4.316 (4.64), 4.326 (4.74), 4.802 (1.52), 4.812 (3.22), 4.823 (1.35), 7.886 (3.92), 7.888 (3.74), 8.891 (3.53), 8.893 (3.36).

Intermediate 303

4-chloro-6-[4-(methoxymethyl)-3,5-dimethyl-1H-pyrazol-1-yl]pyrimidine

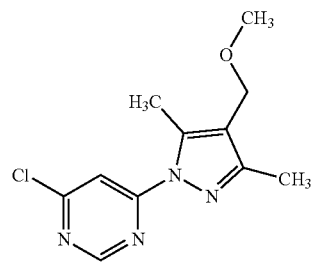 [SMILES: COCc1c(C)nn(-c2cc(Cl)ncn2)c1C]

Under an argon atmosphere, [1-(6-chloropyrimidin-4-yl)-3,5-dimethyl-1H-pyrazol-4-yl]methanol (660 mg, 90% purity, 2.49 mmol) was dissolved in acetonitrile (20 mL) and silver(I) oxide (1.15 g, 4.98 mmol) and methyl iodide (770 µl, 12 mmol) were added. The reaction mixture was stirred at 60° C. overnight. Another batch of silver(I) oxide (0.58 g, 2.49 mmol) and methyl iodide (154 µL, 12 mmol) were added and the reaction mixture stirred overnight at 60° C. Water and saturated aqueous ammonium chloride solution was added and the resulting suspension filtered. The filtrate was extracted with ethyl acetate (2×). The combined organic phase extracts were dried over sodium sulfate and concentrated. The residue was purified by preparative HPLC (column: Reprosil C18; 250*50 mm, 10 µM, flow 150 mL/min, gradient acetonitrile/water (containing 0.1% trifluoroacetic acid) 10/90 to 90/10) to yield the desired product (60 mg, 8% yield)

LC-MS (method 10): Rt=1.84 min; MS (ESIpos): m/z=253 [M+H]+

¹H-NMR (500 MHz, dimethylsulfoxide-d6) δ [ppm]: −0.007 (0.65), 0.007 (0.44), 2.240 (12.46), 2.274 (2.37), 2.664 (11.63), 2.697 (2.24), 3.234 (16.00), 3.692 (3.15), 4.280 (7.19), 5.060 (1.33), 7.907 (2.99), 7.909 (2.89), 7.920 (0.61), 7.921 (0.59), 8.909 (2.66), 8.911 (2.56), 8.930 (0.55), 8.932 (0.53).

Intermediate 304

1-benzyl-3,5-dimethyl-1H-pyrazole

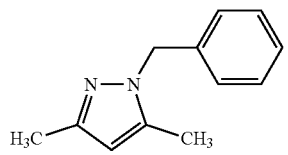

3,5-dimethyl-1H-pyrazole (10.0 g, 104 mmol) was dissolved in acetonitrile (250 mL) and potassium carbonate (17.3 g, 125 mmol) was added. (bromomethyl)benzene (15 ml, 120 mmol) was then added and the reaction mixture stirred overnight at ambient temperature. The precipitated solid was filtered off and the filtrate was concentrated. The residue was purified by flash column chromatography (SNAP Ultra 100 g, cyclohexane/ethyl acetate gradient 88/12 to 0/100) to yield the desired product (13.0 g, 66% yield).

LC-MS (method 11): $R_t$=1.15 min; MS (ESIpos): m/z=187 [M+H]$^+$ $^1$H-NMR (400 MHz, dimethylsulfoxide-d6) δ [ppm]: 2.092 (16.00), 2.143 (14.03), 5.177 (8.08), 5.841 (2.78), 7.070 (2.30), 7.088 (2.73), 7.249 (1.35), 7.267 (1.14), 7.300 (2.40), 7.315 (1.71), 7.319 (3.17), 7.332 (0.49), 7.336 (1.16).

Intermediate 305

1-(1-benzyl-3,5-dimethyl-1H-pyrazol-4-yl)-2,2,2-trifluoroethanone

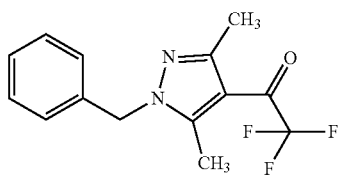 [SMILES: Cc1nn(Cc2ccccc2)c(C)c1C(=O)C(F)(F)F]

Under an argon atmosphere, 1-benzyl-3,5-dimethyl-1H-pyrazole (7.46 g, 40.0 mmol) was dissolved in pyridine (19 mL) and the resulting solution was cooled to 0° C. trifluoroacetic anhydride (6.2 mL, 44 mmol) was added dropwise via syringe and the reaction mixture was allowed to warm to ambient temperature while stirring overnight. Another aliquot of trifluoroacetic anhydride (2.0 mL, 14.2 mmol) was added and the reaction mixture was stirred another 3 h at ambient temperature. Water was added and the mixture was extracted with ethyl acetate (2×). The combined organic phase extracts were dried over sodium sulfate and concentrated. The residue was purified by flash column chromatography (SNAP Ultra 100 g, cyclohexane/ethyl acetate gradient 95/5 to 20/80) to yield the desired product (7.84 g, 65% yield).

LC-MS (method 11): $R_t$=1.40 min; MS (ESIpos): m/z=283 [M+H]$^+$ $^1$H-NMR (500 MHz, dimethylsulfoxide-d6) δ [ppm]: −0.007 (2.06), 0.006 (1.26), 2.338 (10.68), 2.340 (9.98), 2.488 (16.00), 5.382 (9.11), 7.185 (3.00), 7.200 (3.81), 7.203 (2.72), 7.289 (0.65), 7.292 (0.42), 7.299 (0.58), 7.304 (2.03), 7.308 (0.61), 7.316 (1.13), 7.319 (1.70), 7.321 (0.85), 7.348 (3.43), 7.350 (1.47), 7.360 (2.52), 7.363 (4.33), 7.366 (0.95), 7.373 (0.72), 7.377 (1.67), 7.379 (0.91).

Intermediate 306

(±)-1-(1-benzyl-3,5-dimethyl-1H-pyrazol-4-yl)-2,2,2-trifluoroethanol (Racemate)

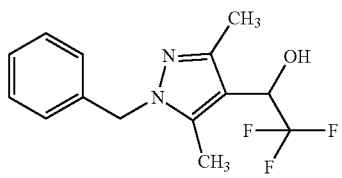 [SMILES: Cc1nn(Cc2ccccc2)c(C)c1C(O)C(F)(F)F]

1-(1-benzyl-3,5-dimethyl-1H-pyrazol-4-yl)-2,2,2-trifluoroethanone (4.37 g, 15.5 mmol) was dissolved in MeOH (31 mL) and sodium borohydride (193 mg, 5.10 mmol) was added at ambient temperature while stirring. The reaction mixture was quenched with saturated aqueous ammonium chloride solution and extracted with ethyl acetate (3×). The combined organic phase extracts were washed with brine, dried over sodium sulfate and concentrated to yield the desired product (4.27 g, 97% yield), which was used in the next step without further purification.

LC-MS (method 11): $R_t$=1.13 min; MS (ESIpos): m/z=285 [M+H]$^+$ $^1$H-NMR (500 MHz, dimethylsulfoxide-d6) δ [ppm]: −0.007 (0.82), 0.006 (0.57), 1.987 (0.54), 2.138 (15.71), 2.193 (16.00), 4.987 (0.89), 4.997 (0.96), 5.003 (0.85), 5.013 (0.82), 5.208 (7.68), 6.442 (4.03), 6.452 (4.00), 6.509 (0.42), 7.093 (2.80), 7.107 (3.29), 7.109 (2.47), 7.245 (0.60), 7.255 (0.50), 7.260 (1.83), 7.264 (0.54), 7.275 (1.36), 7.314 (2.87), 7.316 (1.19), 7.329 (4.05), 7.340 (0.67), 7.343 (1.58).

Intermediate 307

1-benzyl-4-[(±)-1-chloro-2,2,2-trifluoroethyl]-3,5-dimethyl-1H-pyrazole (Racemate)

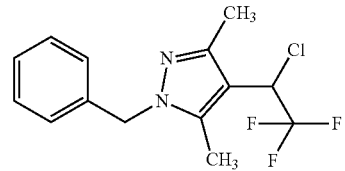 [SMILES: Cc1nn(Cc2ccccc2)c(C)c1C(Cl)C(F)(F)F]

Under an argon atmosphere, a microwave vial was charged with (±)-1-(1-benzyl-3,5-dimethyl-1H-pyrazol-4-yl)-2,2,2-trifluoroethanol (racemate, 500 mg, 1.76 mmol) and 1,2-dichloroethane (4.0 mL) was added. Thionylchloride (320 μl, 4.4 mmol) was then added and the vial was sealed. It was heated to 60° C. overnight while vigorously shaking. After cooling to ambient temperature, the mixture was concentrated and the residue redissolved in dichloromethane and washed with water. The organic phase layer was dried over sodium sulfate and concentrated. The desired product thus obtained (380 mg, 64% yield) was used in the next step without further purification.

LC-MS (method 11): $R_t$=1.41 min; MS (ESIpos): m/z=303 [M+H]$^+$ $^1$H-NMR (500 MHz, dimethylsulfoxide-d6) δ [ppm]: 2.209 (13.27), 2.263 (16.00), 5.243 (7.85), 6.034 (0.64), 6.050 (1.80), 6.066 (1.65), 6.082 (0.49), 7.099 (2.86), 7.113 (3.32), 7.261 (0.59), 7.271 (0.51), 7.275 (1.80), 7.290 (1.36), 7.327 (2.83), 7.342 (3.99), 7.354 (0.69), 7.357 (1.54).

Intermediate 308

(±)-1-(1-benzyl-3,5-dimethyl-1H-pyrazol-4-yl)-2,2,2-trifluoro-N,N-dimethylethanamine (Racemate)

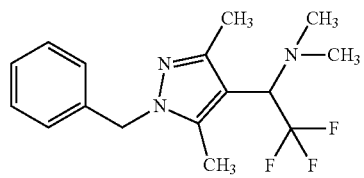 [SMILES: Cc1nn(Cc2ccccc2)c(C)c1C(N(C)C)C(F)(F)F]

1-benzyl-4-[(1R)-1-chloro-2,2,2-trifluoroethyl]-3,5-dimethyl-1H-pyrazole (380 mg, 1.26 mmol) was dissolved in acetonitrile (7 mL) and an aqueous solution of N-methylmethanamine (40%, 320 µL) was added. The reaction mixture was heated overnight at 60° C. After cooling to ambient temperature, a second aliquot of an aqueous solution of N-methylmethanamine (40%, 250 µL) was added. The reaction mixture was heated at 60° C. for another 6.5 h. After cooling to ambient temperature, the reaction mixture was concentrated. The residue was purified by flash column chromatography (SNAP Ultra 10 g, cyclohexane/ethyl acetate gradient 90/10 to 20/80) to yield the desired product (100 mg, 25% yield).

LC-MS (method 11): $R_t$=1.26 min; MS (ESIpos): m/z=312 [M+H]$^+$

Intermediate 309

(±)-1-(3,5-dimethyl-1H-pyrazol-4-yl)-2,2,2-trifluoro-N,N-dimethylethanamine (Racemate)

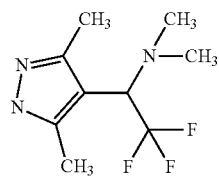

Under an argon atmosphere, (±)-1-(1-benzyl-3,5-dimethyl-1H-pyrazol-4-yl)-2,2,2-trifluoro-N,N-dimethylethanamine (105 mg, 337 µmol) was dissolved in tetrahydrofuran (1.9 mL) and aqueous HCl solution (230 µL). Palladium(II)hydroxide on charcoal (20%, 79.3 mg, 113 µmol) was then added and the argon atmosphere replaced by an hydrogen atmosphere (1 bar). The reaction mixture was stirred overnight at ambient temperature. The reaction mixture was filtered through celite, rinsed with ethyl acetate and the filtrate was diluted with ethyl acetate. It was washed with aqueous sodium hydrogencarbonate solution and the aqueous phase extracted with ethyl acetate. The combined organic phase layers were dried over sodium sulfate and concentrated to yield the desired product (35 mg, 47% yield) that was used in the next step without further purification.

LC-MS (method 11): $R_t$=0.58 min; MS (ESIpos): m/z=222 [M+H]$^+$

Intermediate 310

(±)-1-[1-(6-chloropyrimidin-4-yl)-3,5-dimethyl-1H-pyrazol-4-yl]-2,2,2-trifluoro-N,N-dimethylethanamine (Racemate)

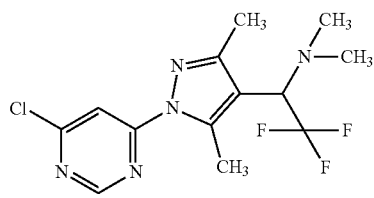 [SMILES: Cc1nn(-c2cc(Cl)ncn2)c(C)c1C(N(C)C)C(F)(F)F]

Under an argon atmosphere, (±)-1-(3,5-dimethyl-1H-pyrazol-4-yl)-2,2,2-trifluoro-N,N-dimethylethanamine (35.0 mg, 158 µmol) was dissolved in N,N-dimethylformamide and 4,6-dichloropyrimidine (25.9 mg, 174 µmol) and potassium carbonate (23.0 mg, 166 µmol) was added. The reaction mixture was stirred at ambient temperature overnight. A second batch of potassium carbonate (16.4 mg, 119 µmol) was added and the reaction mixture was stirred overnight at ambient temperature. The remaining solids were removed by filtration and the filtrate purified by preparative HPLC (column: Chromatorex C18; 125*30 mm, 10 µM, flow 75 mL/min, gradient acetonitrile/water (containing 0.1% trifluoroacetic acid) 10/90 to 90/10) to yield the desired product (8.0 mg, 13% yield).

LC-MS (method 11): $R_t$=1.55 min; MS (ESIpos): m/z=289 [M-NMe$_2$]$^+$ $^1$H-NMR (500 MHz, dimethylsulfoxide-d6) δ [ppm]: 2.294 (16.00), 2.742 (9.77), 4.154 (0.20), 4.172 (0.55), 4.189 (0.51), 4.206 (0.18), 5.752 (0.80), 7.950 (3.31), 7.952 (3.21), 8.943 (2.97), 8.945 (2.87).

Intermediate 311

{[1-(6-chloropyrimidin-4-yl)-3,5-dimethyl-1H-pyrazol-4-yl]oxy}acetonitrile

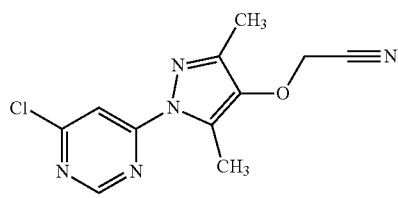 [SMILES: Cc1nn(-c2cc(Cl)ncn2)c(C)c1OCC#N]

Under an argon atmosphere, 1-(6-chloropyrimidin-4-yl)-3,5-dimethyl-1H-pyrazol-4-ol (300 mg, 1.34 mmol) was dissolved in dimethylformamide (6.0 mL) and potassium carbonate (221 mg, 1.60 mmol) and bromoacetonitrile (120 µl, 1.7 mmol) were added. The reaction mixture was stirred at ambient temperature for 3 h. The reaction mixture was then poured onto water (30 mL) and extracted with dichloromethane (2×). The combined organic phase extracts were washed with brine, dried over magnesium sulfate and concentrated to yield the desired product (180 mg, 49% yield) that was used in the next step without further purification.

LC-MS (method 11): Rt=1.23 min; MS (ESIpos): m/z=264 [M+H]$^+$ $^1$H-NMR (500 MHz, DIMETHYLSULFOXIDE-d6) δ [ppm]: 2.126 (0.86), 2.274 (16.00), 2.343 (0.88), 2.521 (0.96), 2.524 (1.17), 2.628 (15.87), 4.993 (12.60), 7.903 (3.92), 7.905 (3.81), 8.911 (3.72), 8.913 (3.55).

Intermediate 312

4-chloro-6-(4-iodo-3,5-dimethyl-1H-pyrazol-1-yl)pyrimidine

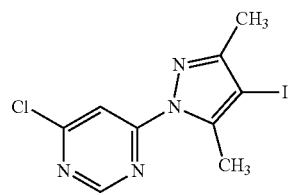

Under an argon atmosphere, 4-chloro-6-(3,5-dimethyl-1H-pyrazol-1-yl)pyrimidine (1.00 g, 4.79 mmol) was dissolved in acetonitrile and the resulting solution heated to 50° C. 1-iodopyrrolidine-2,5-dione (1.29 g, 5.75 mmol) was added in two portions and the reaction mixture stirred at 40° C. overnight. The reaction mixture was stirred another 2.5 h at 55° C. and cooled to ambient temperature. Water was added and the mixture extracted with ethyl acetate (2×). The combined organic extracts were dried over sodium sulfate and concentrated. The residue was purified by flash column chromatography (SNAP Ultra 25 g, cyclohexane/ethyl acetate gradient) to yield the desired product (1.21 g, 71% yield).

LC-MS (method 11): Rt=1.57 min; MS (ESIpos): m/z=335 [M+H]+

$^1$H-NMR (500 MHz, DIMETHYLSULFOXIDE-d6) δ [ppm]: 2.224 (0.80), 2.246 (15.83), 2.657 (0.49), 2.658 (0.47), 2.711 (16.00), 7.917 (3.82), 7.919 (3.69), 8.937 (3.41), 8.938 (3.28).

Intermediate 313 ethyl [1-(6-chloropyrimidin-4-yl)-3,5-dimethyl-1H-pyrazol-4-yl](difluoro)acetate

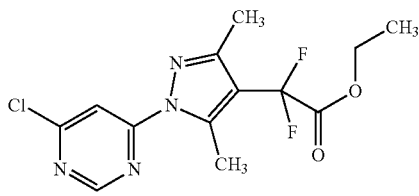 [SMILES: CCOC(=O)C(F)(F)c1c(C)nn(-c2cc(Cl)ncn2)c1C]

Under an argon atmosphere, copper powder (794 mg, 12.5 mmol) was activated by stirring 10 min in each of the following: aqueous hydrogen chloride solution (1 m), water, methanol, acetone and then dried under high vacuum. A solution of ethyl bromo(difluoro)acetate (400 µl, 3.1 mmol) in dimethylsulfoxide (10 mL) was added and the reaction mixture stirred for 1 h at ambient temperature. 4-chloro-6-(4-iodo-3,5-dimethyl-1H-pyrazol-1-yl)pyrimidine (1.10 g, 95% purity, 3.12 mmol) was then added and the reaction mixture stirred overnight at ambient temperature. The reaction mixture was then heated to 50° C. for 3 h, when additional aliquots of activated copper (250 mg, 3.94 mmol) and ethyl bromo(difluoro)acetate (400 µl, 3.1 mmol) were added. The reaction mixture was stirred another 4 h at 50° C. and overnight at ambient temperature. It was then quenched by addition of saturated aqueous ammonium chloride solution and extracted with ethyl acetate (3×). The combined organic extracts were washed with brine, dried over sodium sulfate and concentrated. The residue was purified by flash column chromatography (SNAP Ultra 100 g, cyclohexane/ethyl acetate gradient) to yield an impure product (108 mg, 54% purity, 6% yield) that was used in the next step without further purification.

LC-MS (method 11): Rt=1.51 min; MS (ESIpos): m/z=331 [M+H]+

Intermediate 314 ethyl [1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl](difluoro)acetate

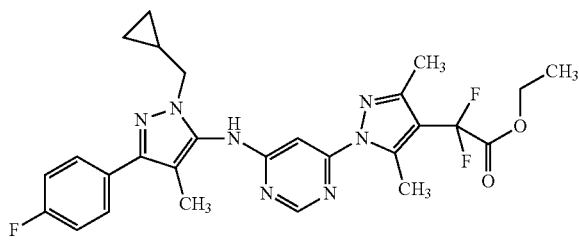 [SMILES: CCOC(=O)C(F)(F)c1c(C)nn(-c2cc(Nc3c(C)c(-c4ccc(F)cc4)nn3CC3CC3)ncn2)c1C]

A microwave vial was charged with 1-(cyclopropylmethyl)-3-(4-fluorophenyl)-4-methyl-1H-pyrazol-5-amine (88.1 mg, 359 µmol) and ethyl [1-(6-chloropyrimidin-4-yl)-3,5-dimethyl-1H-pyrazol-4-yl](difluoro)acetate (108 mg, 327 µmol) and the contents were suspended in dioxane (0.84 mL). The reaction mixture was degassed with Ar for 3 min. Tris(dibenzylideneacetone)dipalladium (8.97 mg, 9.80 mol) and XantPhos (11.3 mg, 19.6 µmol) were added and the reaction mixture was degassed again for 1 min. The vial was heated at 85° C. and sodium phenolate (41.7 mg, 359 µmol) was added, the vial was sealed and heated for 180 min while vigorously shaking. After cooling to ambient temperature, the reaction mixture was quenched by addition of aqueous hydrogen chloride solution and extracted with ethyl acetate (3×). The combined organic extracts were washed with brine, dried over sodium sulfate and concentrated. The residue was purified by preparative HPLC (column: Chromatorex C18; 125*30 mm, 10 µM, flow 75 mL/min, gradient acetonitrile/water (containing 0.1% trifluoroacetic acid) 10/90 to 95/5) to yield the desired product (33 mg, 75% purity, 13% yield).

LC-MS (method 11): Rt=1.61 min; MS (ESIpos): m/z=540 [M+H]+

$^1$H-NMR (600 MHz, DIMETHYLSULFOXIDE-d6) δ [ppm]: 0.005 (0.39), 0.294 (2.46), 0.428 (2.96), 0.441 (2.91), 1.096 (0.19), 1.158 (0.22), 1.172 (0.58), 1.180 (1.03), 1.184 (0.97), 1.192 (1.52), 1.200 (0.96), 1.204 (1.05), 1.212 (0.68), 1.237 (3.55), 1.242 (7.21), 1.249 (6.29), 1.254 (12.76), 1.260 (3.31), 1.265 (6.08), 1.346 (0.45), 1.358 (0.28), 1.913 (0.20), 2.007 (16.00), 2.163 (0.32), 2.202 (0.81), 2.285 (9.48), 2.388 (0.40), 2.477 (0.35), 2.616 (0.38), 2.637 (0.35), 2.706 (10.11), 2.727 (9.33), 2.816 (0.17), 3.835 (1.77), 4.314 (3.02), 4.326 (6.32), 4.338 (5.48), 4.350 (1.78), 4.413 (0.19), 4.425 (0.17), 7.264 (2.48), 7.269 (3.95), 7.279 (5.50), 7.282 (5.61), 7.294 (7.23), 7.328 (1.05), 7.340 (2.16), 7.352 (1.34), 7.493 (2.55), 7.507 (3.46), 7.520 (2.09), 7.729 (1.95), 8.502 (0.26), 8.758 (4.33), 9.512 (0.23).

Intermediate 315

4-chloro-6-[4-(cyclopropylmethoxy)-3,5-dimethyl-1H-pyrazol-1-yl]pyrimidine

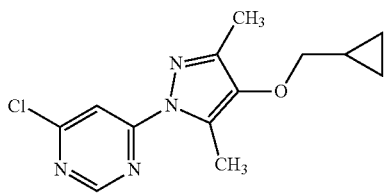 [SMILES: Cc1nn(-c2cc(Cl)ncn2)c(C)c1OCC1CC1]

Under an argon atmosphere, 1-(6-chloropyrimidin-4-yl)-3,5-dimethyl-1H-pyrazol-4-ol (300 mg, 1.34 mmol), potassium carbonate (221 mg, 1.60 mmol) and (bromomethyl)cyclopropane (270 mg, 2.00 mmol) were suspended in N,N-dimethylformamide (5.0 mL). The reaction mixture was stirred at ambient temperature for 24 h. It was poured onto water (30 mL) and extracted with ethyl acetate (3×). The combined organic extracts were washed with brine, dried over magnesium sulfate and concentrated. The residue was suspended in acetonitrile and the remaining solid was filtered off. The filtrate was purified by preparative HPLC (column: Chromatorex C18; 125*30 mm, 10 µM, flow 75 mL/min, gradient acetonitrile/water (containing 0.1% trifluoroacetic acid) 10/90 to 95/5) to yield the desired product (46 mg, 12% yield).

LC-MS (method 11): $R_t$=1.51 min; MS (ESIpos): m/z=279 [M+H]$^+$

Intermediate 316

4-chloro-6-[4-(difluoromethoxy)-3,5-dimethyl-1H-pyrazol-1-yl]pyrimidine

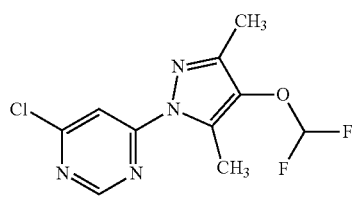 [SMILES: Cc1nn(-c2cc(Cl)ncn2)c(C)c1OC(F)F]

Under an argon atmosphere, potassium hydroxide (1.50 g, 26.7 mmol) was dissolved in water (6.5 mL) and acetonitrile (6.5 mL) was added and the mixture was stirred. When this mixture became homogeneous, it was cooled to −78° C. The dry ice bath was replaced by an ice bath and the mixture allowed to slowly warm to 0° C. As soon as stirring was possible again, 1-(6-chloropyrimidin-4-yl)-3,5-dimethyl-1H-pyrazol-4-ol (300 mg, 1.34 mmol) was added. diethyl [bromo(difluoro)methyl]phosphonate (240 µl, 1.3 mmol) was then added drop-wise over 5 min. After 30 min, a second aliquot of diethyl [bromo(difluoro)methyl]phosphonate (240 µl, 1.3 mmol) and the reaction mixture stirred for another 30 min for a total of 1 h. The reaction mixture was then neutralized by addition of aqueous hydrogen chloride solution (2 N) and extracted with methyl tert-butyl ether (3×). The combined organic extracts were washed with brine, dried over sodium sulfate and concentrated. The desired product thus obtained (485 mg, 75% purity, 99% yield) was used in the next step without further purification.

LC-MS (method 11): $R_t$=1.40 min; MS (ESIpos): m/z=275 [M+H]$^+$

Intermediate 317

1-(cyclopropylmethyl)-3-[6-(difluoromethyl)pyridin-3-yl]-4-methyl-1H-pyrazol-5-amine

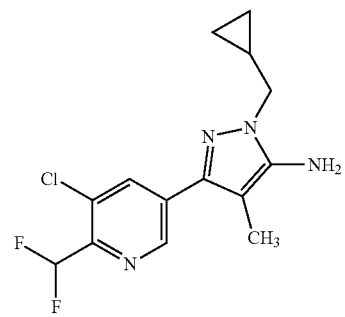 [SMILES: Cc1c(-c2cnc(C(F)F)c(Cl)c2)nn(CC2CC2)c1N]

3-[6-(difluoromethyl)pyridin-3-yl]-2-methyl-3-oxopropanenitrile (650 mg, 3.09 mmol) and (cyclopropylmethyl)hydrazine-hydrogen chloride (1/2) (615 mg, 3.87 mmol) were dissolved in 2-propanol (20 mL) and the reaction mixture was refluxed for 4 h. After cooling to ambient temperature, water and solid sodium hydrogen carbonate were added (gas evolution) until pH 8 was reached. The resulting suspension was then extracted with ethyl acetate (3×), the combined organic extracts were washed with brine, dried over sodium sulfate and concentrated. The residue was redissolved in acetonitrile/water and lyophilized to yield the desired product (691 mg, 80% yield).

LC-MS (method 11): $R_t$=1.01 min; MS (ESIpos): m/z=279 [M+H]$^+$ $^1$H-NMR (500 MHz, DIMETHYLSULFOXIDE-d6) δ [ppm]: 0.355 (0.59), 0.364 (2.02), 0.367 (1.91), 0.374 (2.19), 0.376 (1.95), 0.384 (0.83), 0.432 (0.93), 0.439 (1.86), 0.443 (1.54), 0.448 (1.09), 0.456 (1.94), 0.459 (1.45), 0.468 (0.54), 1.210 (0.48), 1.216 (0.46), 1.226 (0.76), 1.236 (0.46), 1.240 (0.42), 2.039 (16.00), 3.840 (3.77), 3.854 (3.69), 5.055 (4.17), 6.850 (1.15), 6.960 (2.42), 7.070 (1.00), 7.692 (1.82), 7.709 (1.95), 8.131 (1.26), 8.135 (1.23), 8.147 (1.13), 8.151 (1.11), 8.887 (1.97), 8.891 (1.94).

Intermediate 318 methyl 4-carbamoylcubane-1-carboxylate

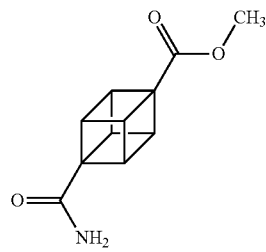

Under an argon atmosphere, 4-(methoxycarbonyl)cubane-1-carboxylic acid (800 mg, 3.88 mmol) was dissolved in tetrahydrofuran (10 mL). The solution was then cooled to −10° C., at which point a solution of triethylamine (590 µl, 4.3 mmol) in tetrahydrofuran (3 mL) followed by ethyl chloroformate (410 µl, 4.3 mmol) were added dropwise. The reaction mixture was stirred at −10° C. for 10 min, when a solution of ammonia (0.5 M in tetrahydrofuran, 78 mL, 39 mmol) was added dropwise. The reaction mixture was then stirred at ambient temperature overnight. It was quenched by addition of water and diluted with ethyl acetate. After phase separation, the organic layer was washed with water (25 ml), aqueous hydrogen chloride solution (2 N), saturated aqueous sodium hydrogencarbonate solution and brine, dried over sodium sulfate and concentrated to yield the desired product (325 mg, 39% yield) that was used in the next step without further purification.

$^1$H-NMR (500 MHz, DIMETHYLSULFOXIDE-d6) δ [ppm]: 1.139 (0.24), 1.357 (1.35), 2.184 (0.18), 3.625 (6.57), 3.628 (1.22), 4.100 (16.00), 4.141 (0.23), 4.147 (0.23), 4.177 (0.32), 6.970 (0.27), 7.278 (0.25).

Intermediate 319 methyl 4-cyanocubane-1-carboxylate

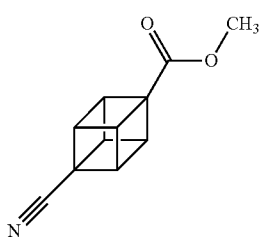

Under an argon atmosphere, methyl 4-carbamoylcubane-1-carboxylate (325 mg, 1.58 mmol) was dissolved in 1,2-dichloroethane (10 mL) and phosphorous oxychloride (740 µl, 7.9 mmol) was added drop-wise. The reaction mixture was then refluxed for 30 min. After cooling to ambient temperature, saturated aqueous sodium hydrogencarbonate solution was slowly added while stirring. The organic phase was separated and washed with water and brine, dried over sodium sulfate and concentrated in-vacuo. The residue was purified by flash column chromatography (SNAP Ultra 50 g, cyclohexane/ethyl acetate 100:0 to 40:60) to afford the desired product as a white solid (181 mg, 61% yield).

$^1$H-NMR (500 MHz, DIMETHYLSULFOXIDE-d6) δ [ppm]: −0.007 (0.87), 1.398 (1.53), 3.309 (16.00), 4.236 (3.64), 4.244 (5.20), 4.246 (5.97), 4.251 (2.82), 4.255 (5.83), 4.261 (0.62), 4.332 (6.03), 4.337 (2.97), 4.341 (5.85), 4.352 (3.44).

Intermediate 320

4-(2-cyanopropanoyl)cubane-1-carbonitrile

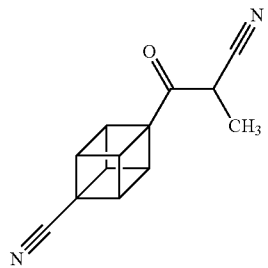 [SMILES: CC(C#N)C(=O)C12C3C4C1C1C2C3C41C#N]

Under an argon atmosphere, methyl 4-cyanocubane-1-carboxylate (175 mg, 935 µmol) and propanenitrile (100 µL, 1.4 mmol) were dissolved in dry tetrahydrofuran (1.5 mL) and the reaction mixture was chilled with a water bath. A solution of LiHMDS (1.4 ml, 1.0 M in tetrahydrofuran, 1.4 mmol) was added dropwise and the reaction mixture was stirred at ambient temperature for 3 h. It was then diluted with water and extracted with ethyl acetate. The organic phase was discarded and the aqueous phase was acidified with aqueous hydrogen chloride solution (1 M) until pH 5 was obtained and extracted with ethyl acetate (3×). The combined organic extracts were washed with brine, dried over sodium sulfate and concentrated to yield the desired product (161 mg, 74% yield) that was used in the next step without further purification.

LC-MS (method 11): $R_t$=0.90 min; MS (ESIneg): m/z=209 [M−H]$^-$ $^1$H-NMR (500 MHz, DIMETHYLSULFOXIDE-d6) δ [ppm]: −0.007 (1.99), 0.006 (1.40), 1.236 (1.19), 1.268 (0.51), 1.346 (4.72), 1.377 (2.08), 1.606 (0.64), 1.687 (4.60), 2.072 (1.59), 3.621 (1.11), 4.197 (1.64), 4.207 (2.13), 4.216 (2.15), 4.246 (0.79), 4.255 (0.70), 4.328 (12.84), 4.386 (16.00).

Intermediate 321

4-[5-amino-1-(cyclopropylmethyl)-4-methyl-1H-pyrazol-3-yl]cubane-1-carbonitrile

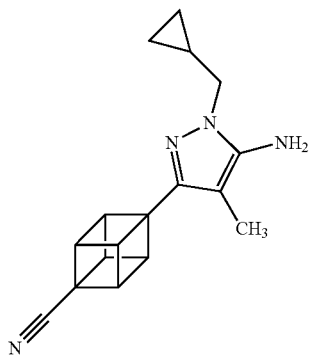 [SMILES: Cc1c(C23C4C5C2C2C3C4C52C#N)nn(CC2CC2)c1N]

4-(2-cyanopropanoyl)cubane-1-carbonitrile (161 mg, 85% purity, 651 µmol) and (cyclopropylmethyl)hydrazine hydrogen chloride (1:2) (129 mg, 814 µmol) were dissolved in 2-propanol (5 mL) and the reaction mixture was heated to reflux while vigorously stirring for 4 h. After cooling to ambient temperature, water (20 mL) and solid sodium hydrogencarbonate was added (gas evolution) until pH 8 was reached. The suspension was then extracted with ethyl acetate (2×). The combined organic extracts were washed with brine, dried over sodium sulfate and concentrated to yield the desired product (109 mg, 59% yield) that was used in the next step without further purification.

LC-MS (method 10): $R_t$=1.05 min; MS (ESIpos): m/z=279 [M+H]$^+$ $^1$H-NMR (500 MHz, DIMETHYLSULFOXIDE-d6) δ [ppm]: −0.120 (0.17), −0.007 (2.01), 0.007 (1.15), 0.117 (0.16), 0.275 (0.61), 0.284 (2.09), 0.287 (1.88), 0.294 (2.10), 0.296 (1.91), 0.304 (0.81), 0.377 (0.88), 0.385 (1.84), 0.389 (1.74), 0.393 (1.03), 0.398 (1.00), 0.401 (1.92), 0.405 (1.62), 0.413 (0.59), 1.095 (0.20), 1.099 (0.25), 1.108 (0.46), 1.115 (0.46), 1.118 (0.38), 1.124 (0.75), 1.131 (0.38), 1.134 (0.43), 1.138 (0.43), 1.148 (0.24), 1.154 (0.22), 1.179 (3.18), 1.192 (3.16), 1.236 (0.25), 1.742 (16.00), 1.784 (0.21), 3.659 (3.60), 3.673 (3.57), 4.081 (0.28), 4.177 (2.71), 4.180 (1.22), 4.186 (3.14), 4.188 (3.43), 4.197 (3.65), 4.202 (0.48), 4.209 (0.49), 4.220 (0.60), 4.229 (0.63), 4.324 (0.60), 4.329 (3.87), 4.331 (2.15), 4.338 (3.81), 4.340 (3.62), 4.349 (2.78), 4.743 (3.71), 4.886 (0.23), 4.898 (0.28), 4.911 (0.21).

Intermediate 322

1-benzyl-3,5-dimethyl-4-[2-(trifluoromethyl)-1,3-dioxolan-2-yl]-1H-pyrazole

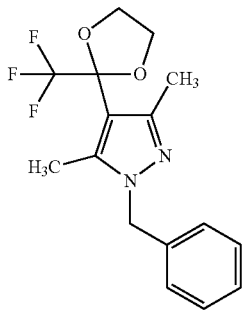 [SMILES: Cc1nn(Cc2ccccc2)c(C)c1C1(C(F)(F)F)OCCO1]

Under an argon atmosphere, 1-(1-benzyl-3,5-dimethyl-1H-pyrazol-4-yl)-2,2,2-trifluoroethan-1-one (10.0 g, 35.4 mmol) and 2-chloroethan-1-ol (12 ml, 180 mmol) were dissolved in N,N-dimethylformamide (35 mL) and tetrahydrofuran (30 mL) and the resulting solution was cooled to −78° C. A solution of potassium 2-methylpropan-2-olate (19.9 g, 177 mmol) in tetrahydrofuran (54 mL) and N,N-dimethylformamide (30 mL) was added dropwise. The cooling bath was removed and the reaction mixture allowed to warm to ambient temperature. After 2 h stirring at ambient temperature, it was quenched with saturated, aqueous ammonium chloride solution and diluted with water. It was extracted with ethyl acetate (3×) and the combined organic extracts were washed with brine (3×), dried over sodium sulfate and concentrated to yield the desired product (11.7 g, 96% yield) that was used in the next step without further purification.

LC-MS (method 10): $R_t$=2.00 min; MS (ESIpos): m/z=327 [M+H]$^+$ $^1$H-NMR (500 MHz, DIMETHYLSULFOXIDE-d6) δ [ppm]: 2.183 (16.00), 2.244 (14.97), 2.732 (3.04), 2.887 (3.73), 3.592 (0.60), 3.601 (0.58), 3.603 (0.61), 4.017 (0.75), 4.032 (2.61), 4.045 (1.04), 4.159 (1.51), 4.166 (1.35), 4.173 (2.82), 4.187 (0.98), 5.225 (7.24), 7.096 (2.60), 7.111 (3.00), 7.251 (0.56), 7.261 (0.46), 7.266 (1.69), 7.270 (0.48), 7.278 (0.81), 7.280 (1.23), 7.320 (2.62), 7.323 (1.07), 7.335 (3.70), 7.346 (0.61), 7.349 (1.43), 7.956 (0.46).

Intermediate 323

3,5-dimethyl-4-[2-(trifluoromethyl)-1,3-dioxolan-2-yl]-1H-pyrazole

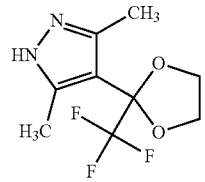 [SMILES: Cc1n[nH]c(C)c1C1(C(F)(F)F)OCCO1]

Under an argon atmosphere, 1-benzyl-3,5-dimethyl-4-[2-(trifluoromethyl)-1,3-dioxolan-2-yl]-1H-pyrazole (11.6 g, 35.5 mmol) was dissolved in tetrahydrofuran/water (9:1, 260 mL) and palladium(II)hydroxide on charcoal (20%, 2.50 g, 3.55 mmol) were added and the reaction mixture chilled with a water bath. The argon atmosphere was replace by an hydrogen atmosphere and the reaction mixture stirred vigorously overnight. A second aliquot of palladium(II)hydroxide on charcoal (20%, 774 mg, 1.10 mmol) was added and the reaction mixture was further hydrogenated under atmospheric pressure overnight. The reaction mixture was filtered over Celite, washed further with tetrahydrofuran and concentrated. The residue was dissolved in dichloromethane and evaporated to dryness (5 cycles) to remove residual water to yield the desired product (7.75 g, 90% yield) that was used in the next step without further purification.

LC-MS (method 11): $R_t$=1.00 min; MS (ESIpos): m/z=237 [M+H]$^+$ $^1$H-NMR (500 MHz, DIMETHYLSULFOXIDE-d6) δ [ppm]: −0.007 (0.49), 1.357 (3.90), 2.174 (9.22), 2.184 (9.44), 2.250 (1.11), 3.982 (0.59), 3.999 (4.28), 4.013 (14.94), 4.026 (5.89), 4.046 (1.15), 4.130 (1.63), 4.149 (8.42), 4.156 (7.67), 4.163 (16.00), 4.177 (5.60), 4.194 (0.68), 12.355 (2.94).

Intermediate 324

4-chloro-6-{3,5-dimethyl-4-[2-(trifluoromethyl)-1,3-dioxolan-2-yl]-1H-pyrazol-1-yl}pyrimidine

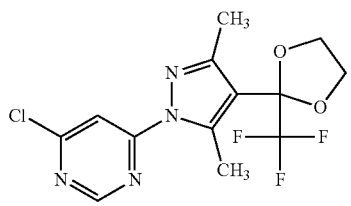 [SMILES: Cc1nn(-c2cc(Cl)ncn2)c(C)c1C1(C(F)(F)F)OCCO1]

Under an argon atmosphere, 3,5-dimethyl-4-[2-(trifluoromethyl)-1,3-dioxolan-2-yl]-1H-pyrazole (5.19 g, 95% purity, 20.9 mmol) was dissolved in N,N-dimethylformamide (47 mL) and 4,6-dichloropyrimidine (4.35 g, 29.2 mmol) and cesium carbonate (9.52 g, 29.2 mmol) was added. The reaction mixture was stirred at ambient temperature overnight. It was then quenched by addition of water and brine and the precipitated solid was collected by filtration, washed with water and dried under high-vacuum to yield the desired product (7.18 g, 90% purity, 89% yield) that was used in the next step without further purification.

LC-MS (method 11): $R_t$=1.54 min; MS (ESIpos): m/z=349 [M+H]$^+$ $^1$H-NMR (400 MHz, DMSO-d6) δ [ppm]: −0.008 (0.83), 0.008 (0.85), 1.356 (0.67), 2.145 (1.05), 2.216 (0.98), 2.309 (16.00), 2.330 (0.93), 2.670 (0.48), 2.772 (13.50), 2.812 (0.58), 4.012 (0.51), 4.089 (0.71), 4.107 (2.69), 4.124 (1.27), 4.147 (0.48), 4.163 (0.58), 4.223 (1.59), 4.231 (1.41), 4.241 (3.06), 4.259 (0.95), 7.949 (4.03), 7.951 (4.03), 8.965 (3.75), 8.967 (3.70).

Intermediate 325

1-(6-chloropyrimidin-4-yl)-3,5-dimethyl-1H-pyrazol-4-yl methyl carbonate

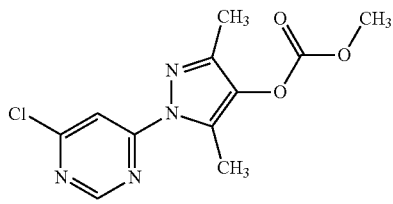 [SMILES: COC(=O)Oc1c(C)nn(-c2cc(Cl)ncn2)c1C]

Under an argon atmosphere, 1-(6-chloropyrimidin-4-yl)-3,5-dimethyl-1H-pyrazol-4-ol (750 mg, 3.34 mmol) was dissolved in N,N-dimethylformamide (10 mL), N,N-diisopropylethylamine (1.7 mL, 10 mmol) was added, followed by addition of methyl carbonochloridate (520 μL, 6.7 mmol). The reaction mixture was stirred at ambient temperature for 5 h. Water was added and the precipitated solid was collected by filtration, washed further with water and dried under high-vacuum to yield the desired product (874 mg, 92% yield).

LC-MS (method 11): $R_t$=1.31 min; MS (ESIpos): m/z=283 [M+H]$^+$ $^1$H NMR (400 MHz, DIMETHYLSULFOXIDE-d$_6$) δ ppm: 2.17 (s, 3H), 2.56 (s, 3H), 3.89 (s, 3H), 7.93 (s, 1H), 8.93 (s, 1H).

Intermediate 326

1-(6-chloropyrimidin-4-yl)-3,5-dimethyl-1H-pyrazol-4-yl methylcarbamate

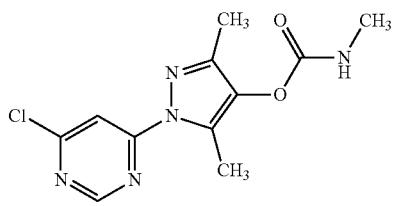 [SMILES: CNC(=O)Oc1c(C)nn(-c2cc(Cl)ncn2)c1C]

Under an argon atmosphere, 1-(6-chloropyrimidin-4-yl)-3,5-dimethyl-1H-pyrazol-4-ol (750 mg, 3.34 mmol) was dissolved in N,N-dimethylformamide (10 mL), N,N-diisopropylethylamine (1.7 ml, 10 mmol) was added, followed by addition of methylcarbamyl chloride (624 mg, 6.68 mmol). The reaction mixture was stirred at ambient temperature for 5 h. Water was added and the precipitated solid was collected by filtration, washed with water and dried under high-vacuum to yield the desired product (844 mg, 89% yield).

LC-MS (method 11): Rt=1.09 min; MS (ESIpos): m/z=282 [M+H]$^+$ $^1$H NMR (400 MHz, DIMETHYLSULFOXIDE-d$_6$) δ ppm: 2.13 (s, 3H), 2.51 (s, 3H), 2.68 (d, J=4.65 Hz, 3H), 7.74-7.83 (m, 1H), 7.90 (s, 1H), 8.90 (s, 1H).

Intermediate 327

1-(6-chloropyrimidin-4-yl)-3,5-dimethyl-1H-pyrazol-4-yl dimethylcarbamate

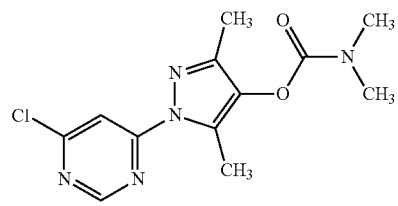 [SMILES: Cc1nn(-c2cc(Cl)ncn2)c(C)c1OC(=O)N(C)C]

Under an argon atmosphere, 1-(6-chloropyrimidin-4-yl)-3,5-dimethyl-1H-pyrazol-4-ol (750 mg, 3.34 mmol) was dissolved in N,N-dimethylformamide (20 mL) and N,N-diisopropylethylamine (1.7 ml, 10 mmol) was added, followed by addition of dimethylcarbamyl chloride (610 μl, 6.7 mmol). The reaction mixture was stirred at ambient temperature for 6 h. As only little conversion was observed by LC-MS, N,N-dimethylaminopyridine (40.8 mg, 334 μmol) was added and the reaction mixture was stirred overnight at ambient temperature. Water was added and the precipitated solid was collected by filtration, washed with water and dried under high-vacuum to yield the desired compound (802 mg, 80% yield).

LC-MS (method 9): $R_t$=0.96 min; MS (ESIpos): m/z=296 [M+H]$^+$ $^1$H-NMR (400 MHz, DIMETHYLSULFOXIDE-d6) δ [ppm]: 2.131 (16.00), 2.521 (15.90), 2.929 (9.90), 3.078 (10.13), 7.907 (3.99), 8.903 (4.05).

Intermediate 328 tert-butyl {4-[5-amino-1-(2-methoxyethyl)-4-methyl-1H-pyrazol-3-yl]phenyl}methylcarbamate

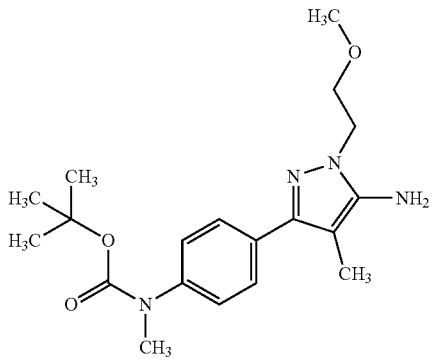 [SMILES: COCCn1nc(-c2ccc(N(C)C(=O)OC(C)(C)C)cc2)c(C)c1N]

To tert-butyl [4-(2-cyanopropanoyl)phenyl]methylcarbamate (1.03 g, 3.58 mmol) in 2-propanol (9.3 ml, 120 mmol) at an internal temperature of 80° C. was slowly added oxalic acid-(2-methoxyethyl)hydrazine (1:1) (710 mg, 3.94 mmol) and the reaction heated at reflux for 4 h. The cooled reaction was filtered and concentrated in vacuo, the residue dissolved in ethylacetate, basified with a saturated aqueous solution of sodium carbonate extracted two times with ethyl acetate. The combined organic phases were washed with a saturated aqueous solution of sodium chloride, dried with sodium sulfate and concentrated in vacuo. The crude product was purified by flash-chromatography on silica gel (gradient 15% ethylacetate in cyclohexane to 100% ethylacetate, column: Biotage SNAP Ultra 50 g). The resultant product was stirred in a mixture of pentane and methyl tert-butyl ether and then filtered to yield 818 mg (100% purity, 63% yield) of the desired product.

LC-MS (Method 9): $R_t$=0.87 min; MS (ESIpos): m/z=361 $[M+H]^+$ $^1$H-NMR (500 MHz, DMSO-d6) δ [ppm]: 1.399 (16.00), 1.987 (7.80), 3.189 (8.33), 3.253 (10.79), 3.614 (0.96), 3.626 (2.18), 3.638 (1.01), 4.055 (0.96), 4.067 (1.89), 4.078 (0.84), 4.872 (2.28), 7.250 (1.72), 7.254 (0.58), 7.264 (0.70), 7.267 (1.87), 7.526 (2.21), 7.530 (0.66), 7.539 (0.69), 7.543 (1.84).

Intermediate 329

1-(2-methoxyethyl)-4-methyl-3-[4-(methylamino)phenyl]-1H-pyrazol-5-amine

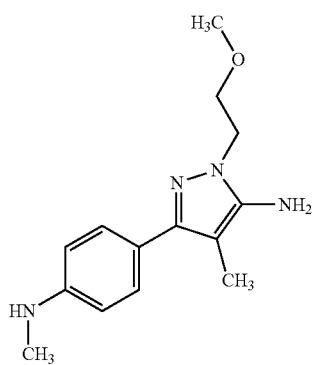 [SMILES: CNc1ccc(-c2nn(CCOC)c(N)c2C)cc1]

To tert-butyl {4-[5-amino-1-(2-methoxyethyl)-4-methyl-1H-pyrazol-3-yl]phenyl}methylcarbamate (816 mg, 2.26 mmol) in 1,4-dioxane (8.3 ml) was added 4N HCl in dioxane (4.2 ml, 4.0 M, 17 mmol) and the reaction stirred for 2 h at room temperature. Additional 4N HCl in dioxane (1.1 ml, 4.0 M, 4.4 mmol) and the reaction stirred for a further 3 h. The reaction mixture was diluted with a saturated aqueous solution of sodium bicarbonate and ethylacetate, the aqueous phase extracted twice with ethylacetate and the combined organic phases dried with sodium sulfate. The organic phase was concentrated in vacuo to yield 650 mg (91% purity, 100% yield) of the desired product.

LC-MS (Method 10): $R_t$=0.84 min; MS (ESIpos): m/z=261 $[M+H]^+$ $^1$H-NMR (500 MHz, DMSO-d6) δ [ppm]: 1.174 (0.67), 1.932 (12.51), 1.988 (1.30), 2.674 (5.86), 2.684 (5.80), 3.250 (16.00), 3.567 (9.19), 3.588 (1.67), 3.600 (3.76), 3.611 (1.79), 4.006 (1.75), 4.018 (3.36), 4.030 (1.53), 4.036 (0.41), 4.737 (3.84), 5.597 (0.87), 5.607 (0.86), 6.518 (3.04), 6.536 (3.14), 7.300 (3.26), 7.317 (3.02).

Intermediate 330

1,4-dimethyl-3-(6-methylpyridin-3-yl)-1H-pyrazol-5-amine

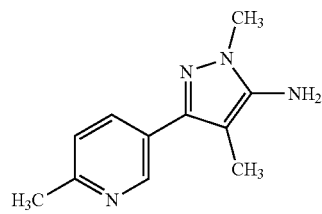

To (2R)-2-methyl-3-(6-methylpyridin-3-yl)-3-oxopropanenitrile (500 mg, 2.87 mmol) in 2-propanol (7.5 ml, 97 mmol) at an internal temperature of 80° C. was slowly added methylhydrazine (170 µl, 3.2 mmol) and the reaction heated at reflux overnight. The cooled reaction was concentrated in vacuo, the residue dissolved in water and solid sodium hydrogen carbonate added until the solution was pH 7. The aqueous solution was extracted three times with ethyl acetate and the combined organic phases dried with sodium sulfate and concentrated in vacuo. The crude product was purified by flash-chromatography on silica gel (dichloromethane:methanol 20:1, column: Biotage SNAP Ultra 50 g) to yield 233 mg (100% purity, 40% yield) of the desired product. The product is unstable when analysed by LCMS.

LC-MS (Method 21): $R_t$=0.94 min; MS (ESIpos): m/z=203 $[M+H]^+$ $^1$H-NMR (500 MHz, DMSO-d6) δ [ppm]: 1.979 (16.00), 2.463 (11.28), 3.317 (12.54), 4.994 (3.33), 7.230 (1.59), 7.246 (1.67), 7.792 (1.36), 7.796 (1.35), 7.808 (1.26), 7.813 (1.25), 8.626 (1.66), 8.629 (1.66).

Intermediate 331

1-(cyclopropylmethyl)-4-methyl-3-[6-(trifluoromethyl)pyridin-3-yl]-1H-pyrazol-5-amine

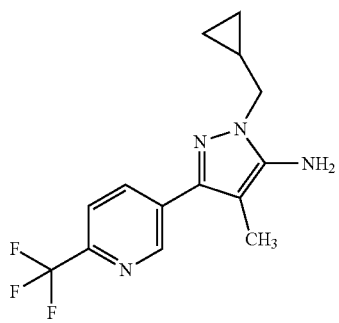 [SMILES: Cc1c(-c2ccc(C(F)(F)F)nc2)nn(CC2CC2)c1N]

A solution of 2-methyl-3-oxo-3-[6-(trifluoromethyl)pyridin-3-yl]propanenitrile (3.16 g, 13.8 mmol) in ethanol (30 ml) was treated with (cyclopropylmethyl)hydrazine-hydrogen chloride (1/2) (4.40 g, 27.7 mmol) and stirred overnight at 95° C. After cooling to ambient temperature the mixture was diluted with saturated sodium bicarbonate solution and the ethanol was removed under reduced pressure. The remaining aqueous was extracted with ethyl acetate (3×). The combined organics were washed with brine, dried over sodium sulfate and concentrated under reduced pressure to yield 3.75 g of the desired product (92%).

LC-MS (Method 10): $R_t$=1.66 min; MS (ESIpos): m/z=297 [M+H]$^+$ $^1$H-NMR (500 MHz, DMSO-d6) δ [ppm]: 0.364 (0.56), 0.374 (1.87), 0.377 (1.75), 0.384 (2.03), 0.386 (1.79), 0.394 (0.82), 0.440 (0.90), 0.448 (1.70), 0.451 (1.40), 0.456 (1.04), 0.461 (0.97), 0.464 (1.79), 0.467 (1.29), 0.477 (0.51), 1.222 (0.45), 1.224 (0.40), 1.228 (0.44), 1.238 (0.71), 1.247 (0.40), 2.064 (16.00), 2.078 (0.52), 3.859 (3.51), 3.873 (3.41), 5.102 (3.86), 7.882 (1.76), 7.883 (1.73), 7.898 (1.93), 8.213 (1.04), 8.216 (0.99), 8.230 (0.90), 8.233 (0.88), 8.985 (1.80), 8.989 (1.72).

Intermediate 332

3-[4-(difluoromethyl)phenyl]-1-(2-methoxyethyl)-4-methyl-1H-pyrazol-5-amine

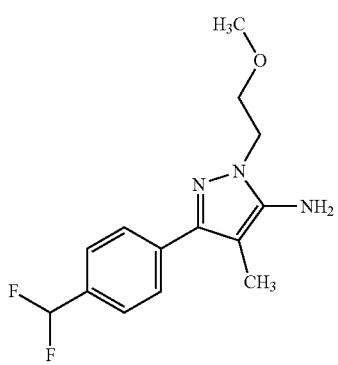 [SMILES: COCCn1nc(-c2ccc(C(F)F)cc2)c(C)c1N]

A solution of 3-[4-(difluoromethyl)phenyl]-2-methyl-3-oxopropanenitrile (3.10 g, 14.8 mmol) in 2-propanol (31 ml) was treated with oxalic acid-(2-methoxyethyl)hydrazine (1/1) (3.47 g, 19.3 mmol) and stirred overnight at 95° C. After cooling to ambient temperature the mixture was concentrated under reduced pressure. The remaining residue was resolved in water and ethyl acetate. The organic phase was washed with water and brine, dried over sodium sulfate and concentrated under reduced pressure. The crude product was purified by flash-chromatography (column: SNAP Ultra 50 g, solvent: dichloromethane/methanol 99:1 to 90/10) and subsequent preparative HPLC (method: column: Reprosil C18; 10 μm; 125×30 mm/flow: 50 ml/min/eluent: A=H2O (0.01% HCOOH), B=acetonitrile/gradient: 0.00-5.00 min=10% B, 6.50 min=20% B, 17.0-19.75 min=100% B, 19.75-23.00 min=90% B) to yield 6.2 g (quant.) of the desired product which was used without any further purification.

Intermediate 333

3-(5-fluoropyridin-2-yl)-1-(2-methoxyethyl)-4-methyl-1H-pyrazol-5-amine

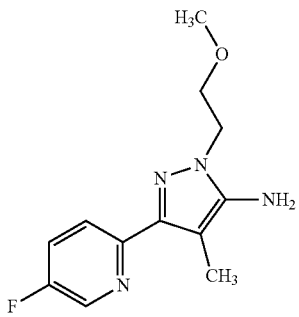 [SMILES: COCCn1nc(-c2ccc(F)cn2)c(C)c1N]

A solution of 3-(5-fluoropyridin-2-yl)-2-methyl-3-oxopropanenitrile (1.50 g, 8.42 mmol) in ethanol (18 ml) was treated with oxalic acid-(2-methoxyethyl)hydrazine (1/1) (3.03 g, 16.8 mmol) and stirred overnight at 95° C. After cooling to ambient temperature the mixture was concentrated under reduced pressure and the remaining residue was suspended in water and extracted with ethyl acetate (3×). The combined organics were washed with water and brine, dried over sodium sulfate and concentrated under reduced pressure. The crude product was purified by flash-chromatograph (column: SNAP Ultra 10 g, solvent: dichloromethane/methanol 100/0 to 96/4) and subsequent preparative HPLC (method: column: Reprosil C18; 10 μm; 125×30 mm/flow: 50 ml/min/eluent: A=H2O (0.01% HCOOH), B=acetonitrile/gradient: 0.00-5.00 min=10% B, 6.50 min=20% B, 17.0-19.75 min=100% B, 19.75-23.00 min=90% B) to yield 509 mg of the desired product (24%).

LC-MS (Method 11): $R_t$=0.84 min; MS (ESIpos): m/z=251 [M+H]$^+$

Intermediate 334

N-[1-(cyclopropylmethyl)-3-(4-fluorophenyl)-4-methyl-1H-pyrazol-5-yl]-6-(5,6-dihydropyrrolo[3,4-c]pyrazol-1 (4H)-yl)pyrimidin-4-amine

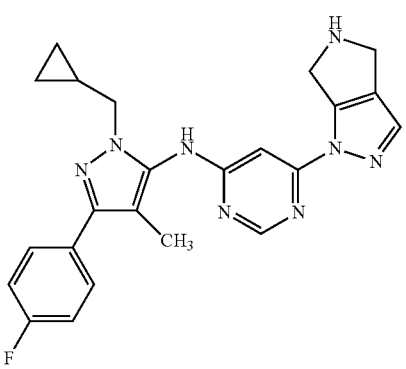 [SMILES: Cc1c(-c2ccc(F)cc2)nn(CC2CC2)c1Nc1cc(-n2ncc3c2CNC3)ncn1]

tert-butyl 1-(6-{[1-(cyclopropylmethyl)-3-(4-fluorophenyl)-4-methyl-1H-pyrazol-5-yl]amino}pyrimidin-4-yl)-4,6-dihydropyrrolo[3,4-c]pyrazole-5(1H)-carboxylate (71.5 mg, 135 μmol) was dissolved in a mixture of trifluoroacetic acid and dichloromethane (2:1, 1.5 ml) and stirred at room temperature for 2 h. The reaction was concentrated in vacuo, and the residue redissolved in ethylacetate. The organic phase was washed with a saturated aqueous solution of sodium bicarbonate. dried with sodium sulfate and concentrated in vacuo. The crude product was purified by flash-chromatography on silica gel (Gradient 20:1 to 15:1 dichloromethane:methanol, column: Biotage SNAP Ultra 10 g) to yield 30.3 mg (100% purity, 52% yield) of the desired product.

LC-MS (Method 9): $R_t$=0.74 min; MS (ESIpos): m/z=431 [M+H]$^+$ $^1$H-NMR (500 MHz, DMSO-d6) δ [ppm]: 0.281 (1.89), 0.411 (2.07), 0.426 (2.05), 1.181 (0.83), 1.230 (0.30), 1.905 (0.47), 2.004 (16.00), 3.835 (1.80), 3.877 (2.74), 4.294 (3.98), 4.771 (0.19), 7.257 (1.94), 7.274 (3.74), 7.292 (1.97), 7.560 (0.35), 7.733 (1.76), 8.466 (0.35), 9.519 (0.30).

Intermediate 335

N-[1-(cyclopropylmethyl)-3-(4-fluorophenyl)-4-methyl-1H-pyrazol-5-yl]-6-(5,6-dihydropyrrolo[3,4-c]pyrazol-2(4H)-yl)pyrimidin-4-amine

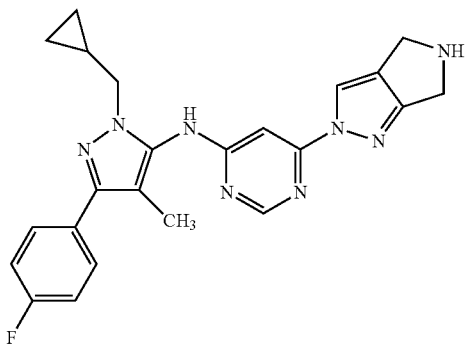 [SMILES: Cc1c(-c2ccc(F)cc2)nn(CC2CC2)c1Nc1cc(-n2cc3c(n2)CNC3)ncn1]

tert-butyl 2-(6-{[1-(cyclopropylmethyl)-3-(4-fluorophenyl)-4-methyl-1H-pyrazol-5-yl]amino}pyrimidin-4-yl)-2,6-dihydropyrrolo[3,4-c]pyrazole-5(4H)-carboxylate (75.0 mg, 141 μmol) was dissolved in a mixture of trifluoroacetic acid and dichloromethane (2:1, 1.5 ml) and stirred at room temperature for 2 h. The reaction was concentrated in vacuo, and the residue redissolved in ethylacetate. The organic phase was washed with a saturated aqueous solution of sodium bicarbonate. dried with sodium sulfate and concentrated in vacuo. The crude product was purified by flash-chromatography on silica gel (15:1 dichloromethane:methanol, column: Biotage SNAP Ultra 10 g) to yield 36.6 mg (100% purity, 60% yield) of the desired product.

LC-MS (Method 9): $R_t$=0.72 min; MS (ESIneg): m/z=429 [M−H]$^-$ $^1$H-NMR (500 MHz, DMSO-d6) δ [ppm]: 0.292 (1.66), 0.412 (1.87), 0.428 (1.86), 1.183 (0.79), 1.233 (0.27), 1.353 (0.14), 1.905 (0.24), 2.014 (16.00), 3.846 (4.77), 4.393 (0.17), 7.260 (1.91), 7.278 (3.89), 7.295 (2.08), 7.745 (1.60), 8.232 (3.61), 8.395 (0.20), 8.464 (0.35), 9.469 (0.28).

Intermediate 336 ethyl 6-(trifluoromethyl)pyridine-3-carboxylate hydrogen chloride

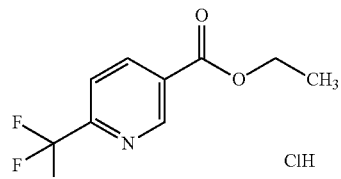

6-(trifluoromethyl)pyridine-3-carboxylic acid (10.0 g, 52.3 mmol) was treated with thionyl chloride (35 ml, 480 mmol) and refluxed for 2 hours. After cooling to ambient temperature the mixture was concentrated under reduced pressure and the remaining residue was resolved in ethanol. The resulting solution was refluxed overnight. After cooling to ambient temperature 11.8 g of the desired product (88%) were obtained which were used without any further purification.

LC-MS (Method 10): $R_t$=1.79 min; MS (ESIpos): m/z=220 [M+H]$^+$

Intermediate 337

2-methyl-3-oxo-3-[6-(trifluoromethyl)pyridin-3-yl]propanenitrile

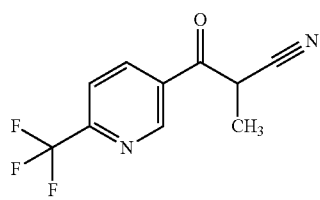 [SMILES: CC(C#N)C(=O)c1ccc(C(F)(F)F)nc1]

A solution of ethyl 6-(trifluoromethyl)pyridine-3-carboxylate-hydrogen chloride (1/1) (11.8 g, 46.2 mmol) and propanenitrile (4.9 ml, 69 mmol) in tertrahydrufuran (120 ml, 1.4 mol) was treated with a solution of lithium bis(trimethylsilyl)amide (120 ml, 1.0 M, 120 mmol). The mixture was stirred overnight at ambient temperature. The mixture was diluted with water and extracted once with ethyl acetate. The organic phase was discarded. The aqueous phase was acidified with 10% citric acid solution and extracted with dichloromethane (2×). The combined organics were washed with water, dried over sodium sulfate and concentrated under reduced pressure to yield 9.25 g (76%) of the desired product.

LC-MS (Method 9): $R_t$=0.78 min; MS (ESIpos): m/z=229 [M+H]$^+$ $^1$H-NMR (500 MHz, DMSO-d6) δ [ppm]: 0.018 (0.46), 1.179 (0.59), 1.507 (0.56), 1.521 (0.55), 1.701 (3.04), 1.916 (2.17), 1.925 (16.00), 1.992 (1.08), 3.350 (0.48), 8.043 (2.57), 8.060 (2.57), 8.268 (1.52), 8.272 (1.47), 8.284 (1.30), 8.288 (1.24), 8.944 (2.52).

Intermediate 338

4-methyl-3-[6-(trifluoromethyl)pyridin-3-yl]-1H-pyrazol-5-amine

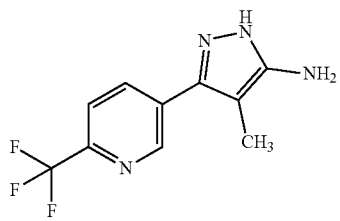 [SMILES: Cc1c(-c2ccc(C(F)(F)F)nc2)n[nH]c1N]

A solution of 2-methyl-3-oxo-3-[6-(trifluoromethyl)pyridin-3-yl]propanenitrile (6.05 g, 26.5 mmol) in ethanol (57 ml) was treated with hydrazine-water (1/1) (2.6 ml, 53 mmol) and stirred at 95° C. overnight. After cooling to ambient temperature the mixture was diluted with saturated sodium carbonate solution and enthanol was removed under reduced pressure. The remaining aqueous was extracted with ethyl acetate (3×). The combined organics were washed with brine, dried over sodium sulfate and the solvent was removed under reduced pressure to yield 6.4 g (100%) of the desired product.

LC-MS (Method 10): $R_t$=1.15 min; MS (ESIpos): m/z=243 [M+H]$^+$

Intermediate 339

2-{4-methyl-3-[6-(trifluoromethyl)pyridin-3-yl]-1H-pyrazol-5-yl}-1H-isoindole-1,3 (2H)-dione

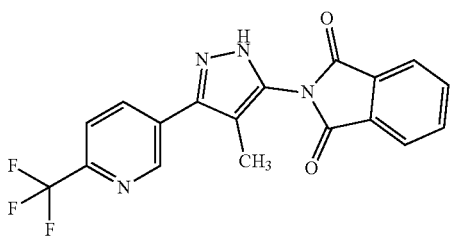 [SMILES: Cc1c(-c2ccc(C(F)(F)F)nc2)n[nH]c1N1C(=O)c2ccccc2C1=O]

A solution of 4-methyl-3-[6-(trifluoromethyl)pyridin-3-yl]-1H-pyrazol-5-amine (6.40 g, 26.4 mmol) and 2-benzofuran-1,3-dione (5.87 g, 39.6 mmol) in acetic acid (75 ml) was stirred for 2 days at 125° C. After cooling to ambient temperature the mixture was evaporated, the residue was resolved in water and ethyl acetate. The organic phase was washed with brine, dried over sodium sulfate and the solvent was removed under reduced pressure to yield 11.6 g of the desired product (72%).

LC-MS (Method 9): $R_t$=0.91 min; MS (ESIpos): m/z=373 [M+H]$^+$ $^1$H-NMR (500 MHz, DMSO-d6) δ [ppm]: −0.007 (0.58), 0.006 (0.46), 1.234 (0.80), 2.076 (1.06), 2.101 (16.00), 7.578 (2.71), 7.584 (2.82), 7.589 (2.61), 7.596 (3.72), 7.603 (0.50), 7.658 (0.50), 7.666 (3.37), 7.673 (2.44), 7.678 (2.49), 7.684 (2.22), 7.957 (5.80), 7.963 (6.59), 7.968 (6.75), 7.974 (8.77), 7.982 (1.72), 8.003 (1.48), 8.009 (1.77), 8.015 (2.63), 8.024 (6.92), 8.030 (5.92), 8.034 (5.42), 8.040 (4.40), 8.068 (2.02), 8.085 (3.58), 8.090 (2.02), 8.096 (1.61), 8.102 (1.33), 8.347 (2.79), 8.363 (2.50), 9.086 (4.01), 13.773 (0.84).

Intermediate 340

2-{1,4-dimethyl-3-[6-(trifluoromethyl)pyridin-3-yl]-1H-pyrazol-5-yl}-1H-isoindole-1,3 (2H)-dione

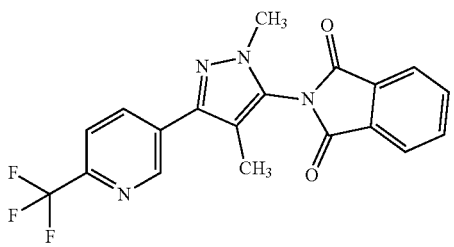 [SMILES: Cc1c(-c2ccc(C(F)(F)F)nc2)nn(C)c1N1C(=O)c2ccccc2C1=O]

A solution of 2-{4-methyl-3-[6-(trifluoromethyl)pyridin-3-yl]-1H-pyrazol-5-yl}-1H-isoindole-1,3(2H)-dione (11.6 g, 31.2 mmol) in dimethylformamide (100 ml, 1.3 mol) was treated with cesium carbonate (20.3 g, 62.3 mmol) and iodomethane (3.9 ml, 62 mmol). The mixture was stirred overnight. The mixture was filtered and poured onto saturated ammonium chloride solution. The mixture was extracted with ethyl acetate (3×). The combined organics were washed with water, brine, dried over sodium sulfate and concentrated under reduced pressure. The crude product was purified by preparative HPLC (column: Kinetex C18 5 μM 100×30 mm, flow: 80 mL/min, solvent: A=water, B=acetonitrile, C=acetonitrile, gradient: 0.00-0.95 min A/B/C 71/4/25; 0.95-5.00 min to A/B/C 46/4/50; 5.00-5.20 min to A/B/C 5/4/91 until 5.70 min; 5.70-5.90 min to A/B/C 71/4/25 until 7.30 min) to yield 5.42 g (45%) of the desired product along with its regioisomer (2.57 g, 21%).

LC-MS (Method 10): $R_t$=1.95 min; MS (ESIpos): m/z=387 [M+H]$^+$ $^1$H-NMR (500 MHz, DMSO-d6) δ [ppm]: 2.075 (0.70), 2.113 (15.68), 3.809 (16.00), 7.976 (2.84), 7.982 (4.73), 7.987 (2.87), 7.993 (3.92), 7.997 (2.56), 8.046 (0.60), 8.054 (3.93), 8.060 (2.83), 8.065 (2.73), 8.071 (2.46), 8.360 (1.27), 8.364 (1.21), 8.376 (1.12), 8.380 (1.06), 9.105 (2.20), 9.109 (2.09).

Intermediate 341

2-{1,4-dimethyl-5-[6-(trifluoromethyl)pyridin-3-yl]-1H-pyrazol-3-yl}-1H-isoindole-1,3 (2H)-dione

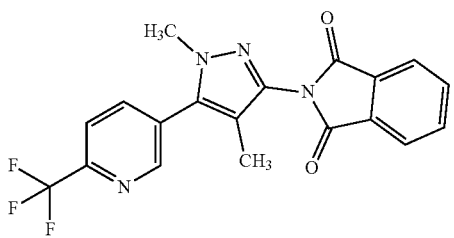 [SMILES: Cc1c(N2C(=O)c3ccccc3C2=O)nn(C)c1-c1ccc(C(F)(F)F)nc1]

A solution of 2-{4-methyl-3-[6-(trifluoromethyl)pyridin-3-yl]-1H-pyrazol-5-yl}-1H-isoindole-1,3(2H)-dione (11.6 g, 31.2 mmol) in dimethylformamide (100 ml, 1.3 mol) was treated with cesium carbonate (20.3 g, 62.3 mmol) and iodomethane (3.9 ml, 62 mmol). The mixture was stirred overnight. The mixture was filtered and poured onto saturated ammonium chloride solution. The mixture was extracted with ethyl acetate (3×). The combined organics were washed with water, brine, dried over sodium sulfate and concentrated under reduced pressure. The crude product was purified by preparative HPLC (column: Kinetex C18 5 µM 100×30 mm, flow: 80 mL/min, solvent: A=water, B=acetonitrile, C=acetonitrile, gradient: 0.00-0.95 min A/B/C 71/4/25; 0.95-5.00 min to A/B/C 46/4/50; 5.00-5.20 min to A/B/C 5/4/91 until 5.70 min; 5.70-5.90 min to A/B/C 71/4/25 until 7.30 min) to yield 2.57 g (21%) of the desired product along with its regioisomer (5.42 g, 45%).

LC-MS (Method 10): $R_t$=1.84 min; MS (ESIpos): m/z=387 [M+H]$^+$

Intermediate 342

1,4-dimethyl-3-[6-(trifluoromethyl)pyridin-3-yl]-1H-pyrazol-5-amine

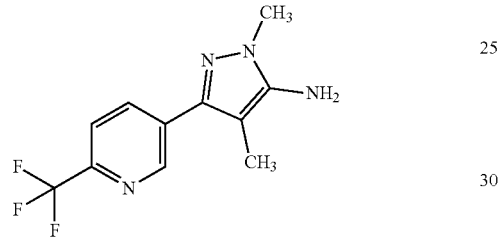

A solution of 2-{1,4-dimethyl-3-[6-(trifluoromethyl)pyridin-3-yl]-1H-pyrazol-5-yl}-1H-isoindole-1,3(2H)-dione (5.42 g, 14.0 mmol) in ethanol (190 ml, 3.3 mol) was treated with hydrazine monohydrate (3.4 ml, 70 mmol) and stirred at 90° C. overnight. After cooling to ambient temperature the mixture was diluted with water and extracted with ethyl acetate (3×). The combined organics were washed with 1M sodium hydrogen carbonate solution and brine, dried over sodium sulfate and concentrated under reduced pressure to yield 3.66 g (99%) of the desired product.

LC-MS (Method 10): $R_t$=1.32 min; MS (ESIpos): m/z=257 [M+H]$^+$ $^1$H-NMR (500 MHz, DMSO-d6) δ [ppm]: 2.058 (16.00), 3.328 (15.45), 5.138 (4.70), 7.878 (2.07), 7.894 (2.26), 8.199 (1.30), 8.202 (1.22), 8.215 (1.15), 8.218 (1.08), 8.975 (2.24), 8.977 (2.13).

Intermediate 343

1,4-dimethyl-5-[6-(trifluoromethyl)pyridin-3-yl]-1H-pyrazol-3-amine

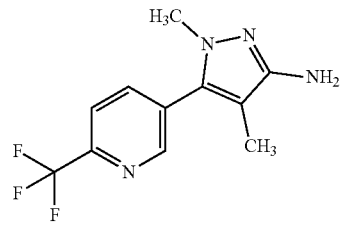 [SMILES: Cc1c(N)nn(C)c1-c1ccc(C(F)(F)F)nc1]

A solution of 2-{1,4-dimethyl-5-[6-(trifluoromethyl)pyridin-3-yl]-1H-pyrazol-3-yl}-1H-isoindole-1,3(2H)-dione (2.57 g, 6.65 mmol) in ethanol (91 ml, 1.6 mol) was treated with hydrazine monohydrate (1.6 ml, 33 mmol) and stirred at 90° C. overnight. After cooling to ambient temperature the mixture was diluted with water and extracted with ethyl acetate (3×). The combined organics were washed with saturated sodium hydrogen carbonate solution and brine, dried over sodium sulfate and concentrated under reduced pressure to yield 1,78 g (98%) of the desired product.

LC-MS (Method 10): $R_t$=1.26 min; MS (ESIpos): m/z=257 [M+H]$^+$ $^1$H-NMR (500 MHz, DMSO-d6) δ [ppm]: 1.830 (16.00), 2.063 (0.44), 2.282 (0.51), 3.065 (0.55), 3.333 (13.10), 3.748 (0.45), 3.861 (0.51), 3.906 (1.09), 4.604 (3.87), 8.014 (1.69), 8.031 (2.30), 8.114 (1.27), 8.118 (1.22), 8.130 (0.90), 8.134 (0.88), 8.800 (1.96), 8.804 (1.88).

Intermediate 344

4-[5-amino-1-(2-methoxyethyl)-4-methyl-1H-pyrazol-3-yl]benzonitrile

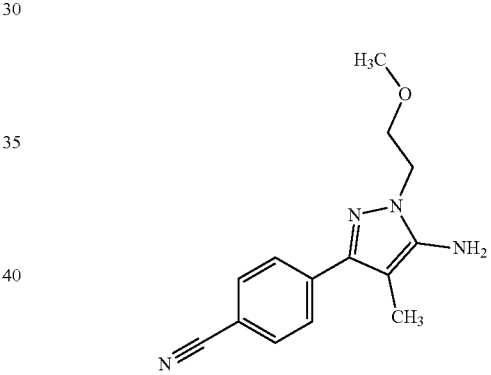

A solution of 4-(2-cyanopropanoyl)benzonitrile (2.73 g, 14.8 mmol) in ethanol (55 ml) was treated with oxalic acid-(2-methoxyethyl)hydrazine (1/1) (5.33 g, 29.6 mmol) and triethylamine (4.5 ml, 33 mmol). The mixture was stirred overnight at 95° C. After cooling to ambient temperature the mixture was diluted with saturated sodium carbonate solution. Ethanol was removed under reduced pressure. The aqueous was extracted with ethyl acetate (3×). The combined organics were washed with brine, dried over sodium sulfate and concentrated under reduced pressure to yield the desired product (3.57 g, 87%).

LC-MS (Method 10): $R_t$=1.33 min; MS (ESIpos): m/z=257 [M+H]$^+$ $^1$H-NMR (400 MHz, DMSO-d6) δ [ppm]: 2.015 (1.40), 2.031 (13.36), 2.523 (0.40), 3.250 (16.00), 3.262 (1.84), 3.628 (1.80), 3.643 (4.13), 3.657 (2.00), 4.080 (0.46), 4.088 (1.91), 4.103 (3.66), 4.117 (1.65), 4.867 (0.46), 5.001 (3.92), 7.588 (0.95), 7.775 (1.17), 7.779 (0.60), 7.796 (6.18), 7.807 (6.11), 7.824 (0.57), 7.829 (1.10).

Intermediate 345

1-(6-{[3-(5-fluoropyridin-2-yl)-1-(2-methoxyethyl)-4-methyl-1H-pyrazol-5-yl]amino}pyrimidin-4-yl)-3,5-dimethyl-1H-pyrazole-4-carboxylic acid

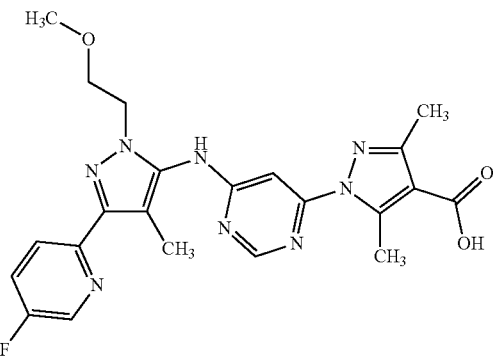 [SMILES: COCCn1nc(-c2ccc(F)cn2)c(C)c1Nc1cc(-n2nc(C)c(C(=O)O)c2C)ncn1]

A solution of ethyl 1-(6-{[3-(5-fluoropyridin-2-yl)-1-(2-methoxyethyl)-4-methyl-1H-pyrazol-5-yl]amino}pyrimidin-4-yl)-3,5-dimethyl-1H-pyrazole-4-carboxylate (68.6 mg, 139 μmol) in tetrahydrofuran (2.0 ml, 25 mmol) was treated with a aqueous solution of lithium hydroxide (690 μl, 1.0 M, 690 μmol) and refluxed for 2 days. After cooling to ambient temperature the mixture was diluted with water and acidified with 10% citric acid solution (pH=6). The aqueous was extracted with ethyl acetate (3×). The combined organics were dried over sodium sulfate and concentrated under reduced pressure. The residue was suspended in acetonitrile, the occurring precipitate was collected by filtration washed with acetonitrile and dried to yield 32.2 mg (50%) of the desired product.

LC-MS (Method 10): R$_t$=1.57 min; MS (ESIpos): m/z=467 [M+H]$^+$ $^1$H-NMR (400 MHz, DMSO-d6) δ [ppm]: 2.144 (16.00), 2.327 (5.77), 2.366 (2.80), 2.523 (12.62), 2.669 (4.78), 2.710 (1.73), 2.900 (13.36), 3.146 (3.71), 3.673 (3.46), 4.142 (1.48), 7.773 (1.57), 7.978 (1.32), 8.593 (2.97), 8.600 (2.89), 9.495 (1.24), 12.632 (2.06).

Intermediate 346

1-[6-({3-[4-(difluoromethyl)phenyl]-1-(2-methoxyethyl)-4-methyl-1H-pyrazol-5-yl}amino)pyrimidin-4-yl]-3,5-dimethyl-1H-pyrazole-4-carboxylic acid

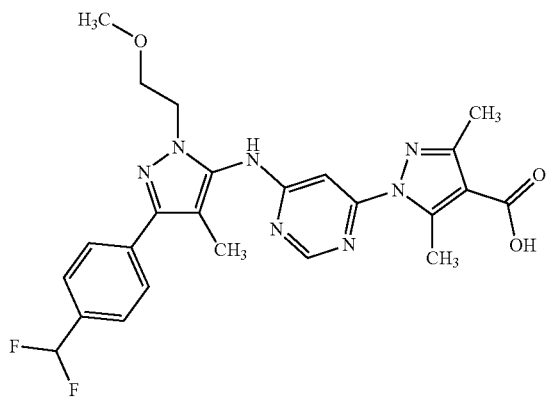 [SMILES: COCCn1nc(-c2ccc(C(F)F)cc2)c(C)c1Nc1cc(-n2nc(C)c(C(=O)O)c2C)ncn1]

A solution of ethyl 1-[6-({3-[4-(difluoromethyl)phenyl]-1-(2-methoxyethyl)-4-methyl-1H-pyrazol-5-yl}amino)pyrimidin-4-yl]-3,5-dimethyl-1H-pyrazole-4-carboxylate (139 mg, 264 μmol) in tetrahydrofuran (3.0 ml, 37 mmol) was treated with a aqueous solution of lithium hydroxide (1.3 ml, 1.0 M, 1.3 mmol) and the mixture was refluxed for 2 days. After cooling to ambient temperature the mixture was diluted with water and acidified with 10% citric acid solution (pH=6). The aqueous was extracted with ethyl acetate (3×). The combined organics were dried over sodium sulfate and concentrated under reduced pressure. The residue was triturated with acetonitrile to yield 92.7 mg (68%) of the desired product.

LC-MS (Method 10): R$_t$=1.75 min; MS (ESIpos): m/z=498 [M+H]$^+$ $^1$H-NMR (400 MHz, DMSO-d6) δ [ppm]: 2.048 (16.00), 2.360 (2.63), 2.907 (13.48), 3.152 (5.46), 3.661 (1.97), 3.675 (4.11), 3.689 (2.22), 4.143 (1.60), 6.938 (1.37), 7.078 (2.95), 7.218 (1.28), 7.637 (2.99), 7.657 (3.81), 7.842 (3.08), 7.861 (2.66), 8.541 (0.83), 9.502 (1.27), 12.639 (0.67).

SPECIFIC EXAMPLES

Example 1

6-(3,5-dimethyl-1H-pyrazol-1-yl)-N-[4-ethyl-5-(4-fluorophenyl)-1-methyl-1H-pyrazol-3-yl]pyrimidin-4-amine

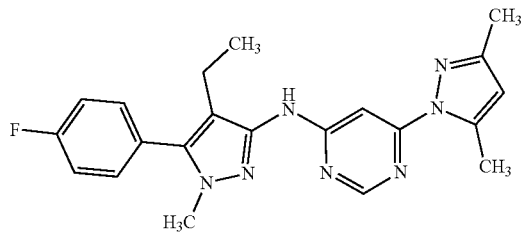 [SMILES: CCc1c(Nc2cc(-n3nc(C)cc3C)ncn2)nn(C)c1-c1ccc(F)cc1]

To a solution of 4-ethyl-5-(4-fluorophenyl)-1-methyl-1H-pyrazol-3-amine (231 mg, 1.05 mmol) in 1,4-dioxane (3.0 mL) sodium phenoxide (167 mg, 1.44 mmol) was added and argon was poured through the mixture. Tris(dibenzylideneacetone)dipalladium(0) (11.4 mg, 12.5 μmol), Xantphos (16.6 mg, 28.8 mmol) and 4-chloro-6-(3,5-dimethyl-1H-pyrazol-1-yl)pyrimidine (200 mg, 959 μmol) were added to the mixture. The reaction vessel was capped and the mixture was stirred at 80° C. overnight. After cooling to room temperature the resulting mixture was separated via preparative HPLC (Column: Reprosil C18; 10 μm; 125×30 mm/Flow: 50 ml/min/Eluent: A=water (0.01% formic acid), B=acetonitrile/Gradient: 0.00-5.00 min=10% B, 6.50 min=20% B, 17.0-19.75 min=100% B, 19.75-23.00 min=90% B) to yield 180 mg of the desired product (48% yield).

LC-MS (method 10): R$_t$=2.16 min; MS (ESIpos): m/z=392 [M+H]$^+$ $^1$H-NMR (400 MHz, DMSO-d$_6$) δ [ppm]: 0.89 (t, 3H), 2.18 (s, 3H), 2.31 (q, 2H), 2.62 (s, 3H), 3.65 (s, 3H), 6.13 (s, 1H), 7.31-7.42 (m, 3H), 7.52 (dd, 2H), 8.44 (s, 1H), 9.33 (s, 1H).

Example 2

6-[5-(difluoromethyl)-3-methyl-1H-pyrazol-1-yl]-N-[4-ethyl-3-(4-fluorophenyl)-1H-pyrazol-5-yl]pyrimidin-4-amine

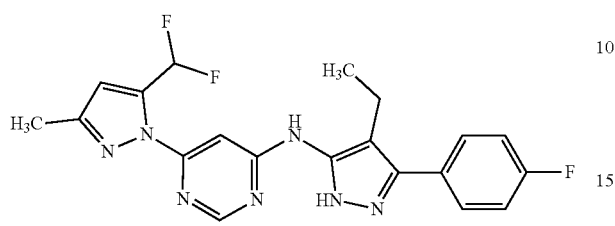

A solution of 4-chloro-6-[5-(difluoromethyl)-3-methyl-1H-pyrazol-1-yl]pyrimidine (128 mg, 523 µmol) and 4-ethyl-3-(4-fluorophenyl)-1H-pyrazol-5-amine (215 mg, 1.05 mmol) in NMP (850 µL) was treated with concentrated aqueous hydrochloric acid (130 µL, 12 M, 1.6 mmol). The resulting mixture was stirred for 1 hour at 200° C. in the microwave. After cooling to room temperature the crude product was purified by preparative HPLC (method: C18, 250×30, flow 50 ml/min, Runtime: 340 min, detection at 210 nm, gradient 40% acetonitrile (6 min)→95% acetonitrile (28 min)→95% acetonitrile (38 min)→34% acetonitrile (39 min), water+0.05% formic acid) to yield 53.5 mg of the desired product (25% yield).

LC-MS (method 10): $R_t$=2.12 min; MS (ESIpos): m/z=414 [M+H]$^+$ $^1$H-NMR (400 MHz, DMSO-d$_6$) δ [ppm]: −0.008 (2.85), 0.008 (2.16), 0.994 (3.88), 1.013 (8.59), 1.032 (4.11), 2.073 (0.64), 2.276 (16.00), 2.328 (0.69), 2.574 (0.96), 2.670 (0.69), 6.762 (4.80), 7.342 (2.38), 7.365 (5.05), 7.387 (2.83), 7.463 (1.14), 7.594 (2.76), 7.607 (3.17), 7.616 (2.81), 7.629 (2.38), 7.696 (1.93), 7.832 (3.66), 7.968 (1.56), 8.483 (3.08), 9.552 (2.16), 12.865 (2.51).

Example 3

N-[4-chloro-3-(2,4-difluorophenyl)-1H-pyrazol-5-yl]-6-(4-chloro-3,5-dimethyl-1H-pyrazol-1-yl)pyrimidin-4-amine

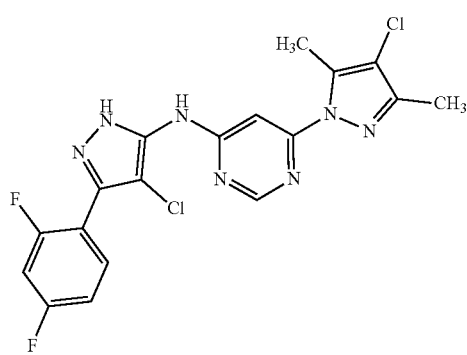 [SMILES: Cc1nn(-c2cc(Nc3[nH]nc(-c4ccc(F)cc4F)c3Cl)ncn2)c(C)c1Cl]

A solution of 4-chloro-6-(4-chloro-3,5-dimethyl-1H-pyrazol-1-yl)pyrimidine (116 mg, 477 µmol) and 4-chloro-3-(2,4-difluorophenyl)-1H-pyrazol-5-amine (121 mg, 525 µmol) in 1-methoxy-2-propanol (2.2 mL) was treated with aqueous hydrochloric acid in 1,4-dioxane (360 µl, 4.0 M, 1.4 mmol). The reaction vessel was capped and the mixture was shaken overnight at 120° C. After cooling to room temperature the resulting mixture was purified by preparative HPLC (method 4) to yield 39.9 mg of the desired compound (17% yield).

LC-MS (method 9): $R_t$=1.24 min; MS (ESIpos): m/z=436 [M+H]$^+$ $^1$H-NMR (400 MHz, DMSO-d$_6$) δ [ppm]: 2.20-2.27 (m, 3H), 2.62-2.69 (m, 3H), 7.15-7.42 (m, 2H), 7.50 (br s, 1H), 7.58-7.78 (m, 1H), 8.50-8.58 (m, 1H), 9.74 (br s, 1H).

Example 4 ethyl 1-(6-{[4-ethyl-5-(4-fluorophenyl)-1H-pyrazol-3-yl]amino}pyrimidin-4-yl)-3,5-dimethyl-1H-pyrazole-4-carboxylate

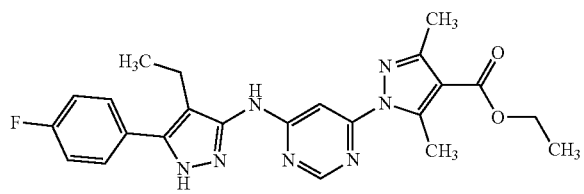 [SMILES: CCOC(=O)c1c(C)nn(-c2cc(Nc3n[nH]c(-c4ccc(F)cc4)c3CC)ncn2)c1C]

A solution of 6-chloro-N-[4-ethyl-5-(4-fluorophenyl)-1H-pyrazol-3-yl]pyrimidin-4-amine (100 mg, 315 mol) and ethyl 3,5-dimethyl-1H-pyrazole-4-carboxylate (106 mg, 629 µmol, CAS 35691-93-1) in DMF (2.0 mL) was treated with caesium carbonate (308 mg, 944 µmol). The reaction mixture was stirred at 160° C. overnight. After cooling to room temperature the mixture was purified by preparative HPLC (method: column: Reprosil C18; 10 µm; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75-23.00 min=90% B) to afford 84.6 mg (60% yield) of the final product.

LC-MS (method 10): $R_t$=2.16 min; MS (ESIpos): m/z=450 [M+H]$^+$ $^1$H-NMR (400 MHz, DMSO-d$_6$) δ [ppm]: 0.008 (0.94), 0.999 (4.17), 1.017 (9.28), 1.031 (3.06), 1.036 (4.41), 1.046 (2.08), 1.287 (5.52), 1.304 (11.52), 1.322 (5.67), 2.366 (15.89), 2.575 (0.97), 2.895 (16.00), 4.226 (1.64), 4.243 (5.08), 4.261 (5.03), 4.279 (1.58), 7.336 (1.15), 7.356 (1.94), 7.376 (1.15), 7.452 (0.67), 7.594 (1.49), 7.608 (1.96), 8.536 (2.40), 9.553 (1.12), 12.835 (1.71).

Example 5

6-(4-chloro-3,5-dimethyl-1H-pyrazol-1-yl)-N-[4-ethyl-5-(4-fluorophenyl)-1H-pyrazol-3-yl]pyrimidin-4-amine

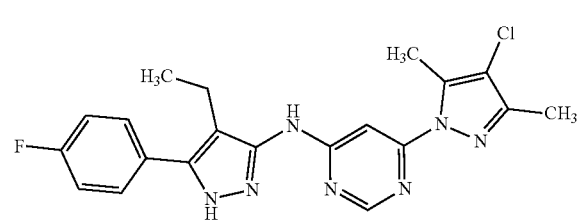 [SMILES: CCc1c(Nc2cc(-n3nc(C)c(Cl)c3C)ncn2)n[nH]c1-c1ccc(F)cc1]

A solution of 6-chloro-N-[4-ethyl-5-(4-fluorophenyl)-1H-pyrazol-3-yl]pyrimidin-4-amine (69.5 mg, 219 mol) and 4-chloro-3,5-dimethyl-1H-pyrazole (143 mg, 1.09 mmol) in NMP (2.5 mL) was treated with DBU (98 μL, 660 μmol). The reaction mixture was stirred 40 minutes at 190° C. under microwave radiation. After cooling to room temperature the crude product was purified by preparative HPLC (method: column: Reprosil C18; 10 μm; 125×30 mm/flow: 50 ml/min/ eluent: A=water (0.01% formic acid), B=acetonitrile/gradient: 0.00-5.00 min=10% B, 6.50 min=20% B, 17.0-19.75 min=100% B, 19.75-23.00 min=90% B) to yield 14.8 mg (16% yield) of the desired product.

LC-MS (method 9): $R_t$=1.21 min; MS (ESIpos): m/z=412 [M+H]$^+$ $^1$H-NMR (400 MHz, DMSO-d$_6$) δ [ppm]: −0.008 (1.44), 0.008 (1.39), 0.993 (3.49), 1.012 (7.57), 1.030 (3.64), 1.234 (0.61), 2.073 (0.57), 2.204 (14.12), 2.524 (2.22), 2.570 (0.99), 2.644 (16.00), 2.670 (0.54), 7.339 (1.81), 7.361 (3.79), 7.383 (2.15), 7.433 (1.23), 7.588 (2.18), 7.602 (2.54), 7.610 (2.31), 7.623 (1.89), 8.487 (2.29), 9.454 (2.31), 12.834 (2.49).

Example 6

N-[4-chloro-5-(2,4-difluorophenyl)-1H-pyrazol-3-yl]-6-(3,5-dimethyl-1H-pyrazol-1-yl)pyrimidin-4-amine

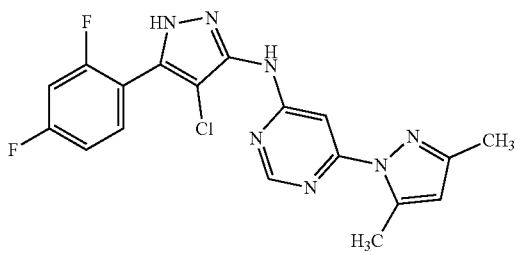 [SMILES: Cc1cc(C)n(-c2cc(Nc3n[nH]c(-c4ccc(F)cc4F)c3Cl)ncn2)n1]

A solution of 4-chloro-6-(3,5-dimethyl-1H-pyrazol-1-yl)pyrimidine (87.6 mg, 420 μmol) and 4-chloro-3-(2,4-difluorophenyl)-1H-pyrazol-5-amine (106 mg, 462 μmol) in 1-methoxy-2-propanol (2.0 mL) was treated with hydrochloric acid in 1,4-dioxane (310 μL, 4.0 M, 1.3 mmol). The reaction mixture was stirred overnight at 120° C. The resulting crude product was purified by preparative HPLC (10-70% acetonitrile/water with 0.1% TFA) to yield 31.5 mg (17% yield) of the final product.

LC-MS (method 10): $R_t$=2.03 min; MS (ESIpos): m/z=402 [M+H]$^+$ $^1$H-NMR (400 MHz, DMSO-d$_6$) δ [ppm]: −0.149 (0.53), −0.008 (4.64), 0.008 (3.90), 0.146 (0.50), 2.187 (13.27), 2.328 (0.80), 2.366 (0.59), 2.523 (2.95), 2.635 (16.00), 2.670 (0.93), 2.710 (0.63), 6.147 (2.76), 7.306 (0.90), 7.362 (1.18), 7.520 (0.63), 7.699 (0.68), 8.490 (1.22), 9.531 (1.09), 13.433 (0.91).

Example 7

N-[4-cyclopropyl-5-(4-fluorophenyl)-1H-pyrazol-3-yl]-6-(3,5-dimethyl-1H-pyrazol-1-yl)pyrimidin-4-amine

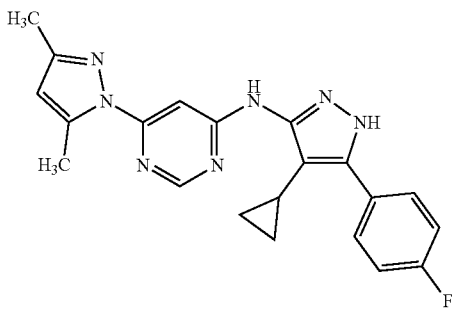 [SMILES: Cc1cc(C)n(-c2cc(Nc3n[nH]c(-c4ccc(F)cc4)c3C3CC3)ncn2)n1]

A solution of 4-chloro-6-(3,5-dimethyl-1H-pyrazol-1-yl)pyrimidine (50.0 mg, 240 μmol) and 4-cyclopropyl-5-(4-fluorophenyl)-1H-pyrazol-3-amine (130 mg, 599 μmol) in DMSO (1.4 mL) was treated with phosphazen-base P(2)-Et (220 μL, 650 μmol) and tBuBrettPhos Pd G3 (20.5 mg, 24.0 μmol). The resulting mixture was stirred for 1 hour at room temperature. Subsequently acetic acid was added and the crude product was purified by preparative HPLC (method: C18, 250×30, flow 50 ml/min, Runtime: 340 min, detection at 210 nm, eluent: A=water (0.05% formic acid), B=acetonitrile, gradient 40% B/60% A (6 min)→95% B/5% A (28 min)→95% B/5% A (38 min)→34% B/76% A (39 min)) to yield 30.4 mg (33% yield) of the desired product.

LC-MS (method 10): $R_t$=2.07 min; MS (ESIpos): m/z=390 [M+H]$^+$ $^1$H-NMR (400 MHz, DMSO-d$_6$) δ [ppm]: −0.008 (1.06), 0.008 (0.86), 0.232 (2.38), 0.241 (2.50), 0.256 (0.75), 0.721 (1.82), 0.738 (2.04), 1.658 (0.77), 1.665 (0.80), 1.678 (1.16), 2.172 (16.00), 2.630 (15.53), 6.125 (3.46), 7.332 (1.78), 7.354 (4.20), 7.359 (2.92), 7.376 (2.06), 7.778 (1.89), 7.792 (2.22), 7.800 (2.11), 7.814 (1.75), 8.454 (2.96), 9.144 (2.66), 12.871 (2.35).

Example 8

6-(4-chloro-3,5-dimethyl-1H-pyrazol-1-yl)-N-[4-cyclopropyl-3-(4-fluorophenyl)-1H-pyrazol-5-yl]pyrimidin-4-amine

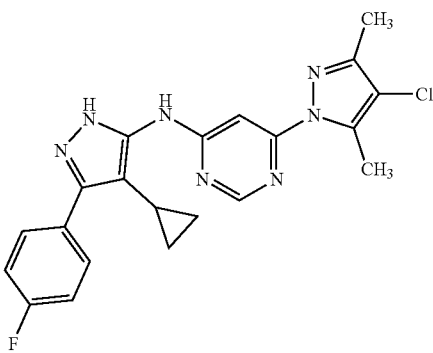 [SMILES: Cc1nn(-c2cc(Nc3[nH]nc(-c4ccc(F)cc4)c3C3CC3)ncn2)c(C)c1Cl]

A solution of 4-cyclopropyl-3-(4-fluorophenyl)-1H-pyrazol-5-amine (220 mg, 1.01 mmol) and 4-chloro-6-(4-chloro-3,5-dimethyl-1H-pyrazol-1-yl)pyrimidine (164 mg, 675 µmol) in DMSO (3.5 mL) was treated with phosphazen-base P(2)-Et (610 µl, 1.8 mmol) and tBuBrettPhos Pd G3 (57.7 mg, 67.5 mol). The resulting mixture was stirred for 1 hour at room temperature. Subsequently acetic acid was added. The solution was directly purified by preparative HPLC (method: column: Reprosil C18; 10 µm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to yield 32.0 mg (7% yield) of the desired product.

LC-MS (method 11): $R_t$=1.58 min; MS (ESIpos): m/z=424 [M+H]$^+$ $^1$H-NMR (600 MHz, DMSO-d$_6$) δ [ppm]: 0.005 (0.54), 0.230 (1.37), 0.727 (1.15), 1.678 (0.75), 2.211 (8.98), 2.518 (0.58), 2.521 (0.58), 2.524 (0.48), 2.649 (16.00), 3.978 (0.43), 5.762 (2.80), 7.358 (1.28), 7.372 (0.95), 7.798 (1.10), 8.497 (1.28), 9.315 (0.78), 12.908 (0.72).

Example 9

N-[5-(2,4-difluorophenyl)-4-ethyl-1H-pyrazol-3-yl]-6-(3,5-dimethyl-1H-pyrazol-1-yl)pyrimidin-4-amine A solution of 4-chloro-6-(3,5-dimethyl-1H-pyrazol-1-yl)pyrimidine (50.0 mg, 240 µmol) and 5-(2,4-difluorophenyl)-4-ethyl-1H-pyrazol-3-amine (107 mg, 479 µmol) in NMP (400 µL) was treated with concentrated aqueous hydrochloric acid (60 µL, 12 M, 710 mmol). The reaction mixture was stirred for 1 hour at 120° C. under microwave radiation. After cooling to room temperature the crude mixture was purified by preparative HPLC (method: C18, 250×30, flow 50 ml/min, Runtime: 340 min, detection at 210 nm, eluent: A=water (0.05% formic acid), B=acetonitrile, gradient 40% B/60% A (6 min)→95% B/5% A (28 min)→95% B/5% A (38 min)→34% B/76% A (39 min)) to afford 10.1 mg (11% yield) of the desired product.

LC-MS (method 10): $R_t$=2.02 min; MS (ESIpos): m/z=396 [M+H]$^+$ $^1$H-NMR (400 MHz, DMSO-d$_6$) δ [ppm]: 0.008 (0.88), 0.909 (3.70), 0.928 (8.31), 0.947 (3.83), 2.073 (2.26), 2.174 (16.00), 2.328 (0.42), 2.365 (0.89), 2.381 (2.31), 2.399 (2.27), 2.417 (0.77), 2.627 (15.33), 2.670 (0.40), 6.128 (4.10), 7.223 (0.56), 7.243 (1.07), 7.261 (0.63), 7.415 (0.65), 7.437 (0.92), 7.462 (0.51), 7.530 (0.78), 7.551 (1.51), 7.568 (1.51), 7.589 (0.68), 8.460 (3.14), 9.379 (0.47).

Example 10

6-(3,5-dimethyl-1H-pyrazol-1-yl)-N-(4-methyl-3-phenyl-1H-pyrazol-5-yl)pyrimidin-4-amine A solution of 4-chloro-6-(3,5-dimethyl-1H-pyrazol-1-yl)pyrimidine (50.0 mg, 240 µmol) and 4-methyl-3-phenyl-1H-pyrazol-5-amine (83.0 mg, 479 µmol) in NMP (390 µL) was treated with concentrated aqueous hydrochloric acid (60 µl, 12 M, 720 µmol). The resulting mixture was stirred for 1 hour at 200° C. under microwave radiation. After cooling to room temperature the crude mixture was purified using preparative (method: C18, 250×30, flow 50 ml/min, Runtime: 340 min, detection at 210 nm, eluent: A=water (0.05% formic acid), B=acetonitrile, gradient 40% B/60% A (6 min)→95% B/5% A (28 min)→95% B/5% A (38 min)→34% B/76% A (39 min)) to yield 36.2 mg (44% yield) of the final product.

LC-MS (method 10): $R_t$=1.86 min; MS (ESIpos): m/z=346 [M+H]$^+$ $^1$H-NMR (400 MHz, DMSO-d$_6$) δ [ppm]: −0.008 (1.55), 0.008 (1.45), 2.076 (14.86), 2.171 (16.00), 2.627 (14.31), 6.124 (3.49), 7.404 (1.66), 7.422 (1.29), 7.458 (1.28), 7.492 (1.94), 7.512 (3.51), 7.530 (1.95), 7.597 (3.70), 7.615 (2.53), 8.458 (2.85), 9.376 (2.99), 12.826 (2.16).

Example 11

6-(4-chloro-3,5-dimethyl-1H-pyrazol-1-yl)-N-(4-methyl-5-phenyl-1H-pyrazol-3-yl)pyrimidin-4-amine A solution of 4-chloro-6-(4-chloro-3,5-dimethyl-1H-pyrazol-1-yl)pyrimidine (128 mg, 525 µmol) and 4-methyl-5-phenyl-1H-pyrazol-3-amine (100 mg, 577 µmol) in NMP (6.0 mL) was treated with hydrochloric acid in 1,4-dioxane (390 µL, 4.0 M, 1.6 mmol). The reaction mixture was stirred for 2 hours at 190° C. under microwave radiation. After cooling to room temperature the resulting mixture was diluted with acetonitrile and water and subsequently purified by preparative HPLC to afford 30.0 mg (15% yield) of the final product.

LC-MS (method 10): $R_t$=2.17 min; MS (ESIpos): m/z=380 [M+H]$^+$ $^1$H-NMR (400 MHz, DMSO-d$_6$) δ [ppm]: −0.008 (1.97), 0.008 (1.60), 2.073 (5.32), 2.079 (9.88), 2.210 (12.85), 2.519 (1.33), 2.524 (1.00), 2.647 (16.00), 2.665 (0.42), 2.670 (0.62), 7.381 (0.59), 7.399 (1.59), 7.418 (1.20), 7.487 (2.02), 7.506 (3.48), 7.525 (1.89), 7.602 (3.17), 7.621 (2.25), 8.499 (3.08), 9.520 (2.08).

Example 12

6-(3,5-dimethyl-1H-pyrazol-1-yl)-N-[4-ethyl-3-(4-fluorophenyl)-1-methyl-1H-pyrazol-5-yl]pyrimidin-4-amine

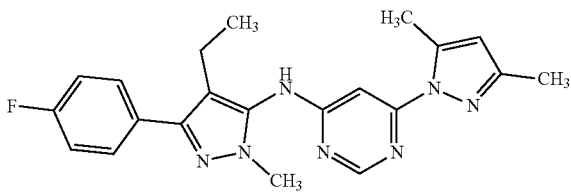 [SMILES: CCc1c(-c2ccc(F)cc2)nn(C)c1Nc1cc(-n2nc(C)cc2C)ncn1]

To a solution of 4-ethyl-3-(4-fluorophenyl)-1-methyl-1H-pyrazol-5-amine (116 mg, 527 μmol) in 1,4-dioxane (2.5 mL) sodium phenoxide (83.5 mg, 719 μmol) was added and argon was poured through the mixture. Tris(dibenzylideneacetone)dipalladium(0) (5.49 mg, 5.99 μmol), Xantphos (8.32 mg, 14.4 μmol) and 4-chloro-6-(3,5-dimethyl-1H-pyrazol-1-yl)pyrimidine (100 mg, 479 μmol) were added to the mixture. The reaction vessel was capped and the mixture was stirred at 80° C. in the microwave for 2 hours. After cooling to room temperature the resulting mixture was separated via preparative HPLC (Column: Reprosil C18; 10 μm; 125×30 mm/Flow: 50 ml/min/Eluent: A=water (0,01% formic acid), B=acetonitrile/Gradient: 0.00-5.00 min=10% B, 6.50 min=20% B, 17.00-19.75 min=100% B, 19.75-23.00 min=90% B) to yield 91 mg of still impure product. Further separation on preparative HPLC (Method 1) yielded 48.8 mg of the desired product (25% yield).

LC-MS (method 10): $R_t$=2.13 min; MS (ESIpos): m/z=392 [M+H]$^+$ $^1$H-NMR (400 MHz, DMSO-d$_6$) δ [ppm]: 0.971 (4.20), 0.989 (9.27), 1.008 (4.34), 1.989 (0.48), 2.175 (4.26), 2.445 (1.04), 2.464 (2.89), 2.483 (3.04), 2.632 (16.00), 3.164 (1.17), 3.177 (1.17), 3.568 (0.57), 3.639 (13.51), 4.076 (0.41), 6.145 (3.06), 7.247 (2.37), 7.269 (4.71), 7.291 (2.53), 7.651 (1.99), 7.665 (2.54), 7.671 (2.38), 7.686 (1.73), 8.469 (1.04), 9.364 (1.79).

Example 13

6-(3,5-dimethyl-1H-pyrazol-1-yl)-N-[4-ethyl-3-(4-fluorophenyl)-1H-pyrazol-5-yl]pyrimidin-4-amine

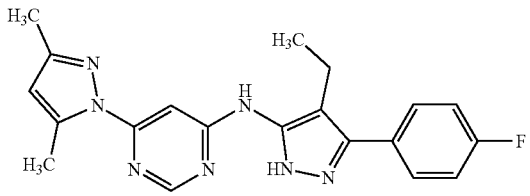 [SMILES: CCc1c(-c2ccc(F)cc2)n[nH]c1Nc1cc(-n2nc(C)cc2C)ncn1]

Tris(dibenzylideneacetone)dipalladium(0) (4.07 mg, 12.0 μmol) and 2,2'-bis(diphenyl-phosphino)-1,1'-binaphthyl (14.9 mg, 24.0 μmol) were suspended in toluene. Argon was poured through the solution for 10 minutes. Subsequently 4-chloro-6-(3,5-dimethyl-1H-pyrazol-1-yl)pyrimidine (50.0 mg, 240 μmol), 4-ethyl-3-(4-fluorophenyl)-1H-pyrazol-5-amine (148 mg, 719 μmol) and potassium tert-butoxylate (93.9 mg, 839 μmol) were added. The reaction mixture was stirred for 15 hours at 90° C. under microwave radiation. The mixture was diluted with saturated ammonium chloride solution and extracted three times with ethyl acetate. The combined organic phases were washed with brine, dried over sodium sulfate and the solvent was removed under reduced pressure. The crude product was purified by preparative HPLC (method: C18, 250×30, flow 50 ml/min, Runtime: 340 min, detection at 210 nm, gradient 40% acetonitrile (6 min)→95% acetonitrile (28 min)→95% acetonitrile (38 min)→34% acetonitrile (39 min), water+ 0.05% formic acid) to afford 7.20 mg (8% yield) of the desired product.

LC-MS (method 10): $R_t$=2.00 min; MS (ESIpos): m/z=378 [M+H]$^+$ $^1$H-NMR (500 MHz, DMSO-d$_6$) δ [ppm]: 1.000 (3.97), 1.015 (8.40), 1.030 (4.01), 2.073 (2.18), 2.166 (15.65), 2.516 (1.85), 2.561 (1.05), 2.626 (16.00), 6.122 (3.25), 7.342 (1.32), 7.360 (2.38), 7.377 (1.47), 7.401 (1.30), 7.595 (1.49), 7.606 (2.00), 7.622 (1.44), 8.451 (2.16), 9.321 (1.73), 12.819 (1.70).

Example 14

N-[4-chloro-3-(4-fluorophenyl)-1H-pyrazol-5-yl]-6-(3,5-dimethyl-1H-pyrazol-1-yl)pyrimidin-4-amine

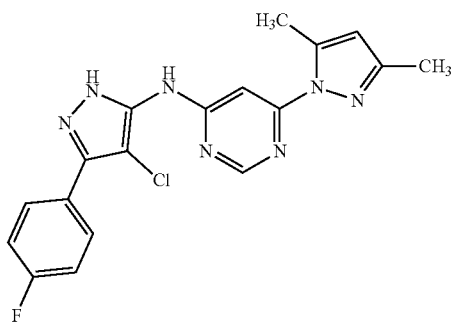 [SMILES: Cc1cc(C)n(-c2cc(Nc3[nH]nc(-c4ccc(F)cc4)c3Cl)ncn2)n1]

A solution of 4-chloro-6-(3,5-dimethyl-1H-pyrazol-1-yl) pyrimidine (44.8 mg, 215 μmol) and 4-chloro-3-(4-fluorophenyl)-1H-pyrazol-5-amine (50.0 mg, 236 μmol) in 1-methoxy-2-propanol (2.5 mL) was treated with hydrochloric acid in 1,4-dioxane (160 μL, 4.0 M, 640 μmol). The reaction mixture was stirred for 3 days at 120° C. The reaction mixture was purified by preparative HPLC (method: column: Reprosil C18; 10 μm; 125×30 mm/flow: 50 ml/min/eluent: A=water (0.1% formic acid), B=acetonitrile/gradient: 0.00-4.25 min=20% B, 4.50 min=30% B, 19.00-22.50 min=100% B, 22.75-25.00 min=20% B) to yield 9.00 mg (11% yield) of the desired product.

LC-MS (method 10): $R_t$=2.06 min; MS (ESIpos): m/z=384 [M+H]$^+$ $^1$H-NMR (500 MHz, DMSO-d$_6$) δ [ppm]: 2.090 (0.86), 2.186 (14.24), 2.225 (0.60), 2.638 (16.00), 2.657 (0.85), 6.140 (3.93), 7.374 (1.47), 7.411 (1.89), 7.868 (2.30), 8.503 (1.80), 9.516 (0.68), 13.483 (1.10).

Example 15 ethyl 1-(6-{[4-cyclopropyl-3-(4-fluorophenyl)-1H-pyrazol-5-yl]amino}pyrimidin-4-yl)-3,5-dimethyl-1H-pyrazole-4-carboxylate

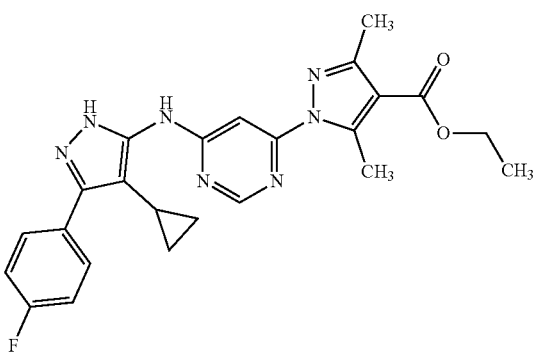 [SMILES: CCOC(=O)c1c(C)nn(-c2cc(Nc3[nH]nc(-c4ccc(F)cc4)c3C3CC3)ncn2)c1C]

4-cyclopropyl-3-(4-fluorophenyl)-1H-pyrazol-5-amine (200 mg, 921 µmol) and ethyl 1-(6-chloropyrimidin-4-yl)-3,5-dimethyl-1H-pyrazole-4-carboxylate (258 mg, 921 µmol) were dissolved in DMSO. Argon was poured through the reaction mixture. Subsequently phosphazen-base P(2)-Et (830 µL, 2.5 mmol) and tBuBrettPhos Pd G3 (78.7 mg, 92.1 µmol) were added. The reaction mixture was stirred at room temperature for 1 hour. Acetic acid was added and the crude mixture was purified by preparative HPLC (method: column: Reprosil C18; 10 µm; 125×30 mm/flow: 45 ml/min/ eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to yield 84.5 mg (18% yield) of the desired product.

LC-MS (method 11): $R_t$=1.50 min; MS (ESIpos): m/z=462 [M+H]$^+$ $^1$H-NMR (400 MHz, DMSO-d$_6$) δ [ppm]: −0.008 (1.95), 0.008 (1.83), 0.240 (1.93), 0.725 (1.94), 0.742 (1.99), 1.091 (0.62), 1.288 (5.41), 1.298 (1.94), 1.306 (11.36), 1.316 (3.17), 1.324 (5.64), 1.334 (1.45), 1.664 (0.70), 1.671 (0.79), 1.684 (1.22), 1.697 (0.74), 1.704 (0.64), 2.372 (14.60), 2.419 (4.59), 2.524 (1.27), 2.900 (16.00), 2.951 (4.60), 4.227 (1.61), 4.245 (5.07), 4.263 (5.12), 4.281 (1.74), 4.285 (1.56), 4.303 (0.41), 7.330 (1.08), 7.350 (1.77), 7.372 (1.29), 7.797 (1.54), 8.001 (0.81), 8.538 (2.26), 9.016 (0.74), 9.386 (1.18), 12.887 (1.40).

Example 16 ethyl 3,5-dimethyl-1-{6-[(4-methyl-5-phenyl-1H-pyrazol-3-yl)amino]pyrimidin-4-yl}-1H-pyrazole-4-carboxylate

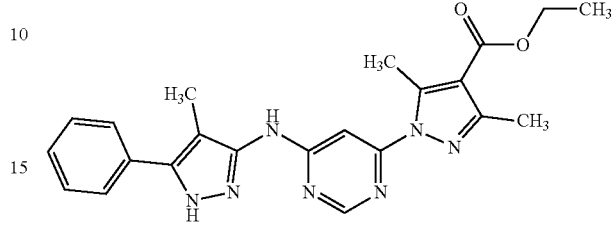

A solution of ethyl 1-(6-chloropyrimidin-4-yl)-3,5-dimethyl-1H-pyrazole-4-carboxylate (147 mg, 525 µmol) and 4-methyl-5-phenyl-1H-pyrazol-3-amine (100 mg, 577 µmol) in NMP (6.0 mL) was treated with hydrochloric acid in 1,4-dioxane (390 µL, 1.6 mmol). The reaction mixture was stirred for 2 hours at 190° C. under microwave radiation. After cooling to room temperature the mixture was diluted with water and acetonitrile and purified by preparative HPLC to afford 42 mg (19% yield) of the final product.

$^1$H-NMR (400 MHz, DMSO-d$_6$) δ [ppm]: −0.009 (2.19), 0.007 (1.74), 1.287 (4.64), 1.305 (10.03), 1.322 (4.74), 2.082 (9.20), 2.327 (0.42), 2.370 (12.85), 2.669 (0.40), 2.895 (16.00), 4.226 (1.45), 4.244 (4.38), 4.262 (4.36), 4.279 (1.46), 4.576 (0.41), 7.381 (0.65), 7.399 (1.79), 7.418 (1.34), 7.486 (2.20), 7.505 (3.78), 7.524 (2.02), 7.601 (3.55), 7.618 (2.60), 8.544 (2.88), 9.617 (2.61).

Example 17

6-(3,5-dimethyl-1H-pyrazol-1-yl)-N-[5-(4-fluorophenyl)-4-methyl-1H-pyrazol-3-yl]pyrimidin-4-amine

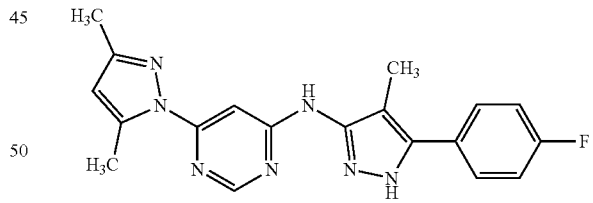

A solution of 4-chloro-6-(3,5-dimethyl-1H-pyrazol-1-yl) pyrimidine (50.0 mg, 240 µmol) and 5-(4-fluorophenyl)-4-methyl-1H-pyrazol-3-amine (137 mg, 719 µmol) in 2-propanol (700 µL) was treated with concentrated aqueous hydrochloric acid (60 µl, 12 M, 720 µmol). The reaction mixture was stirred for 1 hour at 100° C. under microwave radiation and for 10 hours at 130° C. under microwave radiation. After cooling to room temperature the mixture was purified by preparative HPLC (method: C18, 250×30, flow 50 ml/min, Runtime: 340 min, detection at 210 nm, eluent: A=water (0.05% formic acid), B=acetonitrile, gradient 40% B/60% A (6 min)→95% B/5% A (28 min)→95% B/5% A (38 min)→34% B/76% A (39 min)) to afford 15.9 mg (18% yield) of the desired product.

LC-MS (method 10): R$_t$=1.91 min; MS (ESIpos): m/z=364 [M+H]$^+$ $^1$H-NMR (400 MHz, DMSO-d$_6$) δ [ppm]: −0.008 (0.99), 0.008 (0.92), 2.058 (14.37), 2.073 (1.08), 2.172 (16.00), 2.626 (14.22), 2.627 (14.44), 6.127 (3.62), 7.331 (0.87), 7.351 (1.53), 7.372 (0.93), 7.646 (1.49), 8.461 (2.36), 9.388 (0.82).

Example 18

N-[4-ethyl-5-(4-fluorophenyl)-1H-pyrazol-3-yl]-6-(4,5,6,7-tetrahydro-2H-indazol-2-yl)pyrimidin-4-amine

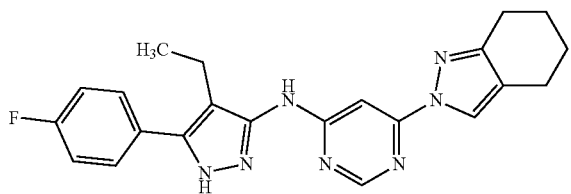 [SMILES: CCc1c(Nc2cc(-n3cc4c(n3)CCCC4)ncn2)n[nH]c1-c1ccc(F)cc1]

The desired product was obtained out of the regioisomeric separation in the synthesis described of N-[4-ethyl-5-(4-fluorophenyl)-1H-pyrazol-3-yl]-6-(4,5,6,7-tetrahydro-1H-indazol-1-yl)pyrimidin-4-amine in 6% yield (7.8 mg).

LC-MS (method 10): Rt=2.12 min; MS (ESIpos): m/z=404 [M+H]$^+$ $^1$H-NMR (400 MHz, DMSO-d$_6$) δ [ppm]: −0.150 (1.61), −0.008 (14.95), 0.008 (14.25), 0.146 (1.54), 0.991 (7.41), 1.009 (16.00), 1.028 (7.76), 1.091 (1.12), 1.233 (1.54), 1.352 (0.91), 1.693 (4.05), 1.753 (3.84), 2.327 (3.49), 2.366 (2.31), 2.614 (4.54), 2.630 (7.55), 2.669 (3.91), 2.709 (2.79), 7.340 (4.05), 7.362 (8.87), 7.384 (6.08), 7.592 (4.61), 7.606 (5.45), 7.614 (4.89), 7.627 (4.12), 8.245 (9.85), 8.424 (6.29), 9.382 (5.73), 12.838 (4.89).

Example 19

N-[4-ethyl-5-(4-fluorophenyl)-1H-pyrazol-3-yl]-6-(3-methyl-1H-indazol-1-yl)pyrimidin-4-amine

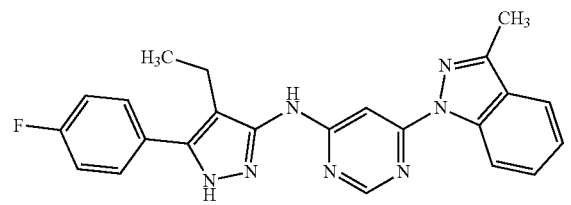 [SMILES: CCc1c(Nc2cc(-n3nc(C)c4ccccc43)ncn2)n[nH]c1-c1ccc(F)cc1]

A solution of 6-chloro-N-[4-ethyl-5-(4-fluorophenyl)-1H-pyrazol-3-yl]pyrimidin-4-amine (100 mg, 315 μmol) and 3-methyl-1H-indazole (83.2 mg, 629 μmol) in DMF (2.0 mL) was treated with caesium carbonate (308 mg, 944 μmol). The reaction mixture was stirred at 160° C. overnight. After cooling to room temperature the mixture was purified by preparative HPLC (method: Column: Reprosil C18; 10 m; 125×30 mm/Flow: 50 ml/min/Eluent: A=water (0.01% formic acid), B=acetonitrile/gradient: 0.00-5.00 min=10% B, 6.50 min=20% B, 17.0-19.75 min=100% B, 19.75-23.00 min=90% B) to afford 43.3 mg (30% yield) of the desired product.

LC-MS (method 10): R$_t$=2.25 min; MS (ESIpos): m/z=414 [M+H]$^+$ $^1$H-NMR (400 MHz, DMSO-d$_6$) δ [ppm]: −0.008 (2.97), 0.006 (1.39), 0.008 (2.01), 1.013 (3.39), 1.032 (7.03), 1.051 (3.45), 1.098 (0.41), 1.234 (0.82), 2.074 (2.92), 2.519 (2.63), 2.524 (2.48), 2.560 (4.03), 2.573 (16.00), 2.596 (1.33), 2.620 (1.51), 2.666 (0.46), 2.670 (0.51), 2.675 (0.43), 2.731 (0.52), 2.891 (0.51), 3.004 (0.91), 5.755 (0.48), 7.287 (0.49), 7.316 (1.37), 7.334 (2.38), 7.351 (2.71), 7.372 (3.65), 7.394 (1.98), 7.522 (1.73), 7.553 (1.39), 7.572 (2.08), 7.592 (1.38), 7.609 (2.28), 7.622 (2.51), 7.630 (2.19), 7.644 (1.76), 7.831 (2.22), 7.851 (2.04), 8.557 (2.44), 8.756 (2.13), 8.777 (1.98), 9.326 (2.74), 12.846 (2.13).

Example 20

6-(5,6-dihydrocyclopenta[c]pyrazol-2(4H)-yl)-N-[4-ethyl-5-(4-fluorophenyl)-1H-pyrazol-3-yl]pyrimidin-4-amine

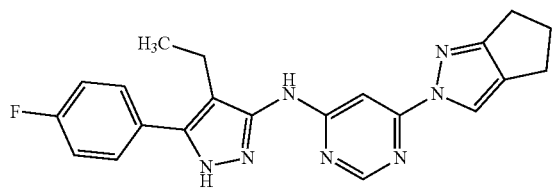 [SMILES: CCc1c(Nc2cc(-n3cc4c(n3)CCC4)ncn2)n[nH]c1-c1ccc(F)cc1]

The desired product was obtained out of the regioisomeric separation in the synthesis of 6-(5,6-dihydrocyclopenta[c]pyrazol-1(4H)-yl)-N-[4-ethyl-5-(4-fluorophenyl)-1H-pyrazol-3-yl]pyrimidin-4-amine in 27% yield (98% purity).

LC-MS (method 10): Rt=2.01 min; MS (ESIpos): m/z=390 [M+H]$^+$ $^1$H-NMR (400 MHz, DMSO-d$_6$) δ [ppm]: 1.00 (t, 3H), 2.31-2.48 (m, 3H), 2.52-2.55 (m, 10H), 2.58-2.71 (m, 4H), 7.26-7.42 (m, 3H), 7.60 (dd, 2H), 8.16 (s, 1H), 8.41 (s, 1H), 9.36 (s, 1H), 12.81 (s, 1H).

Example 21

N-[5-(4-chlorophenyl)-4-ethyl-1H-pyrazol-3-yl]-6-(3,5-dimethyl-1H-pyrazol-1-yl)pyrimidin-4-amine

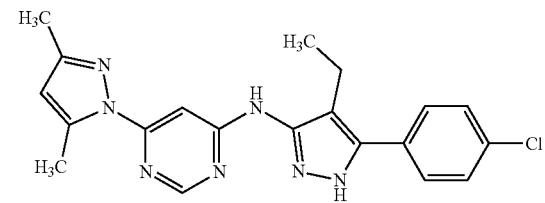 [SMILES: CCc1c(Nc2cc(-n3nc(C)cc3C)ncn2)n[nH]c1-c1ccc(Cl)cc1]

A solution of 4-chloro-6-(3,5-dimethyl-1H-pyrazol-1-yl)pyrimidine (50.0 mg, 240 μmol) and 5-(4-chlorophenyl)-4-ethyl-1H-pyrazol-3-amine (159 mg, 719 μmol) in 2-propanol (700 mL) was treated with concentrated, aqueous hydrochloric acid (60 μL, 12 M, 720 μmol). The reaction mixture was stirred 1 hour at 100° C. under microwave radiation. Subsequently additional 3 eq of concentrated, aqueous hydrochloric acid were added and the mixture was treated again at 130° C. for 1 hour under microwave radiation. After cooling to room temperature the crude mixture was purified by preparative HPLC (method: C18, 250×30, flow 50 ml/min, Runtime: 340 min, detection at 210 nm, eluent: A=water (0.05% formic acid), B=acetonitrile, gradient 40% B/60% A (6 min)→95% B/5% A (28 min)→95% B/5% A (38 min)→34% B/76% A (39 min)) to yield 13.8 mg of the desired product (15% yield).

LC-MS (method 10): $R_t$=2.15 min; MS (ESIpos): m/z=394 [M+H]$^+$ $^1$H-NMR (400 MHz, DMSO-d$_6$) δ [ppm]: −0.008 (0.62), 0.008 (0.62), 0.999 (3.53), 1.017 (7.89), 1.036 (3.92), 2.073 (1.50), 2.165 (14.99), 2.367 (1.01), 2.519 (2.56), 2.524 (2.87), 2.561 (3.53), 2.580 (1.19), 2.625 (15.21), 2.690 (0.62), 2.711 (1.01), 6.122 (3.44), 7.392 (1.94), 7.589 (16.00), 8.450 (2.60), 9.334 (2.78), 12.889 (2.38).

Example 22

N-[4-ethyl-5-(4-fluorophenyl)-1H-pyrazol-3-yl]-6-(4,5,6,7-tetrahydro-1H-indazol-1-yl)pyrimidin-4-amine

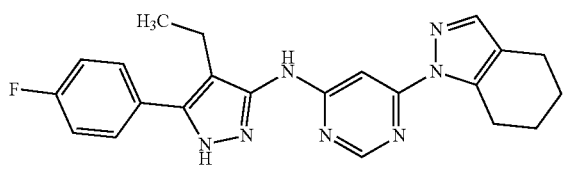 [SMILES: CCc1c(Nc2cc(-n3ncc4c3CCCC4)ncn2)n[nH]c1-c1ccc(F)cc1]

A solution of 6-chloro-N-[4-ethyl-5-(4-fluorophenyl)-1H-pyrazol-3-yl]pyrimidin-4-amine (100 mg, 315 μmol) and 4,5,6,7-tetrahydro-1H-indazole (192 mg, 1.57 mmol) in NMP (2.5 mL) was treated with DBU (140 μL, 940 μmol). The reaction mixture was stirred overnight at 190° C. After cooling to room temperature the crude product was purified by preparative HPLC (method 2) to yield 3.7 mg (3% yield) of the desired product.

LC-MS (method 10): $R_t$=2.21 min; MS (ESIpos): m/z=404 [M+H]$^+$ $^1$H-NMR (400 MHz, DMSO-d$_6$) δ [ppm]: 1.00 (t, 13H), 1.23 (s, 2H), 1.46 (br d, 2H), 1.64-1.71 (m, 9H), 1.71-1.80 (m, 9H), 2.36 (s, 1H), 2.45-2.48 (m, 6H), 2.56-2.72 (m, 5H), 3.13 (t, 6H), 7.34 (br t, 11H), 7.53 (s, 5H), 7.61 (br s, 8H), 8.13 (s, 1H), 8.24 (s, 1H), 8.40-8.49 (m, 4H), 9.34 (br s, 4H), 12.74-12.92 (m, 4H).

Example 23

3-{[6-(3,5-dimethyl-1H-pyrazol-1-yl)pyrimidin-4-yl]amino}-5-(4-fluorophenyl)-1-methyl-1H-pyrazole-4-carbonitrile

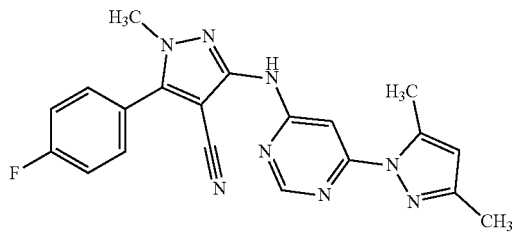 [SMILES: Cc1cc(C)n(-c2cc(Nc3nn(C)c(-c4ccc(F)cc4)c3C#N)ncn2)n1]

4-chloro-6-(3,5-dimethyl-1H-pyrazol-1-yl)pyrimidine (57.9 mg, 277 μmol) and 3-amino-5-(4-fluorophenyl)-1-methyl-1H-pyrazole-4-carbonitrile (60.0 mg, 277 μmol) were solved in DMSO (3.6 mL). Argon was poured through the reaction mixture. Subsequently phosphazen-base P(2)-Et (230 μl, 690 μmol) and tBuBrettPhos Pd G3 (23.7 mg, 27.7 μmol) were added. The reaction mixture was stirred at room temperature overnight. Acetic acid was added and the crude mixture was purified by preparative HPLC (method: column: Reprosil C18; 10 μm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to yield 10.0 mg (9% yield) of the desired product.

LC-MS (method 10): $R_t$=1.94 min; MS (ESIpos): m/z=389 [M+H]$^+$ $^1$H-NMR (500 MHz, DMSO-d$_6$) δ [ppm]: 1.360 (0.43), 2.212 (14.33), 2.644 (11.90), 3.805 (16.00), 3.969 (0.75), 6.162 (3.49), 7.469 (2.51), 7.476 (3.29), 7.482 (1.68), 7.487 (4.56), 7.500 (1.00), 7.505 (2.40), 7.734 (2.34), 7.738 (1.20), 7.745 (2.61), 7.752 (2.37), 7.758 (1.07), 7.762 (2.04), 8.539 (3.82), 8.540 (3.84), 10.212 (3.40).

Example 24

5-{[6-(3,5-dimethyl-1H-pyrazol-1-yl)pyrimidin-4-yl]amino}-3-(4-fluorophenyl)-1-methyl-1H-pyrazole-4-carbonitrile

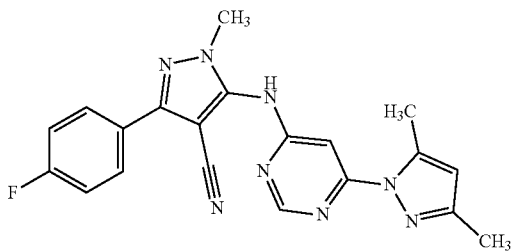 [SMILES: Cc1cc(C)n(-c2cc(Nc3c(C#N)c(-c4ccc(F)cc4)nn3C)ncn2)n1]

4-chloro-6-(3,5-dimethyl-1H-pyrazol-1-yl)pyrimidine (74.3 mg, 356 μmol) and 5-amino-3-(4-fluorophenyl)-1-methyl-1H-pyrazole-4-carbonitrile (77.0 mg, 356 μmol) were solved in DMSO (4.6 mL). Argon was poured through the reaction mixture. Subsequently phosphazen-base P(2)-Et (300 μl, 890 μmol) and tBuBrettPhos Pd G3 (30.4 mg, 35.6 μmol) were added. The reaction mixture was stirred at room temperature for overnight. Acetic acid was added and the crude mixture was purified by preparative HPLC (method: column: Reprosil C18; 10 μm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to yield 90.0 mg (65% yield) of the desired product.

LC-MS (method 10): $R_t$=2.04 min; MS (ESIpos): m/z=389 [M+H]$^+$ $^1$H-NMR (600 MHz, DMSO-d$_6$) δ [ppm]: 2.22 (s, 3H), 2.66 (s, 3H), 3.37 (s, 1H), 3.79 (s, 3H), 6.19 (s, 1H), 7.32 (s, 1H), 7.39 (t, 2H), 7.93 (t, 2H), 8.59 (s, 1H), 10.30 (s, 1H).

Example 25

1-(6-{[4-ethyl-5-(4-fluorophenyl)-1-methyl-1H-pyrazol-3-yl]amino}pyrimidin-4-yl)-3,4-dimethyl-1H-pyrazol-5-ol

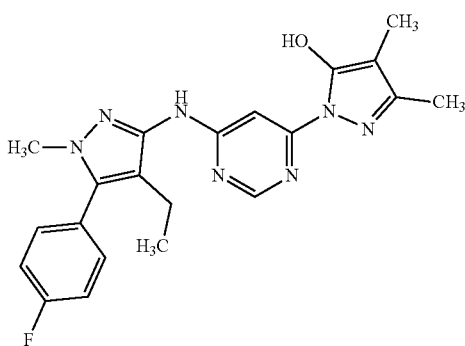 [SMILES: CCc1c(Nc2cc(-n3nc(C)c(C)c3O)ncn2)nn(C)c1-c1ccc(F)cc1]

A solution of N-[4-ethyl-5-(4-fluorophenyl)-1-methyl-1H-pyrazol-3-yl]-6-hydrazinylpyrimidin-4-amine (65.0 mg, 199 µmol) in methanol (2.0 mL) was treated with methyl 2-methyl-3-oxobutanoate (23 µl, 200 µmol) (23 µL, 200 µmol). The reaction mixture was stirred for 3 hours at 80° C. After cooling to room temperature the crude reaction mixture was purified by preparative HPLC (method: column: Reprosil C18; 10 µm; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75.-23.00 min=90% B) to yield 34.8 mg of the desired product (43% yield).

LC-MS (method 9): $R_t$=0.96 min; MS (ESIpos): m/z=408 [M+H]$^+$ $^1$H-NMR (400 MHz, DMSO-d$_6$) δ [ppm]: 0.88 (t, 3H), 1.70 (s, 3H), 2.11 (s, 3H), 2.30 (q, 2H), 3.65 (s, 3H), 7.32-7.42 (m, 2H), 7.44-7.55 (m, 2H), 7.73 (br s, 1H), 8.40 (s, 1H), 9.34 (br s, 1H), 10.61 (s, 1H).

Example 26 tert-butyl 2-(6-{[4-ethyl-5-(4-fluorophenyl)-1H-pyrazol-3-yl]amino}pyrimidin-4-yl)-2,4,5,7-tetrahydro-6H-pyrazolo[3,4-c]pyridine-6-carboxylate

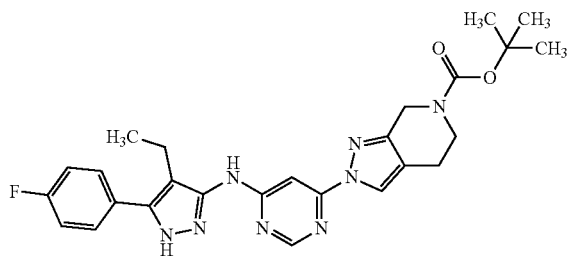 [SMILES: CCc1c(Nc2cc(-n3cc4c(n3)CN(C(=O)OC(C)(C)C)CC4)ncn2)n[nH]c1-c1ccc(F)cc1]

The desired product was obtained out of the regioisomeric separation during the synthesis of tert-butyl 1-(6-{[4-ethyl-5-(4-fluorophenyl)-1H-pyrazol-3-yl]amino}pyrimidin-4-yl)-1,4,6,7-tetrahydro-5H-pyrazolo[4,3-c]pyridine-5-carboxylate in 5% yield (94% purity).

$^1$H-NMR (400 MHz, DMSO-d$_6$) δ [ppm]: –0.008 (1.52), 0.008 (1.57), 0.991 (0.98), 1.010 (2.20), 1.028 (1.04), 1.073 (0.46), 1.091 (0.95), 1.108 (0.49), 1.421 (16.00), 2.558 (0.75), 2.695 (0.46), 2.710 (1.04), 2.725 (0.52), 3.375 (0.48), 3.392 (0.49), 3.619 (0.56), 3.634 (1.00), 3.649 (0.51), 4.464 (1.24), 7.340 (0.57), 7.363 (1.20), 7.385 (0.68), 7.591 (0.66), 7.605 (0.76), 7.613 (0.68), 7.627 (0.56), 8.411 (1.30), 8.455 (0.87), 9.456 (0.66), 12.847 (0.66).

Example 27

6-(5,6-dihydrocyclopenta[c]pyrazol-1 (4H)-yl)-N-[4-ethyl-5-(4-fluorophenyl)-1H-pyrazol-3-yl]pyrimidin-4-amine

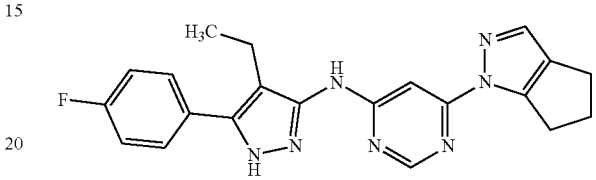

A solution of 6-chloro-N-[4-ethyl-5-(4-fluorophenyl)-1H-pyrazol-3-yl]pyrimidin-4-amine (100 mg, 315 µmol) and 1,4,5,6-tetrahydrocyclopenta[c]pyrazole (170 mg, 1.57 mmol, CAS 2214-03-1) in NMP (2.5 mL) was treated with DBU (140 µl, 940 µmol). The reaction mixture was stirred overnight at 190° C. After cooling to room temperature the crude product was purified by preparative HPLC (method 2) to yield 34.2 mg (28% yield) of the desired product.

LC-MS (method 10): $R_t$=2.09 min; MS (ESIpos): m/z=390 [M+H]$^+$ $^1$H-NMR (400 MHz, DMSO-d$_6$) δ [ppm]: –0.008 (2.23), 0.988 (7.16), 1.006 (16.00), 1.025 (7.68), 1.045 (2.72), 1.073 (3.98), 1.091 (8.06), 1.108 (4.05), 2.328 (0.60), 2.366 (0.43), 2.562 (6.29), 2.670 (0.81), 2.710 (0.46), 3.086 (3.10), 3.104 (5.32), 3.121 (3.11), 3.357 (1.33), 3.375 (3.87), 3.392 (3.87), 3.409 (1.28), 7.272 (0.43), 7.340 (3.26), 7.362 (6.66), 7.384 (3.85), 7.432 (2.71), 7.481 (7.78), 7.588 (3.87), 7.602 (4.51), 7.610 (4.21), 7.623 (3.46), 7.681 (0.42), 8.442 (5.78), 9.392 (5.47), 12.811 (4.67).

Example 28

N-(5-cyclohexyl-4-ethyl-1H-pyrazol-3-yl)-6-(3,5-dimethyl-1H-pyrazol-1-yl)pyrimidin-4-amine

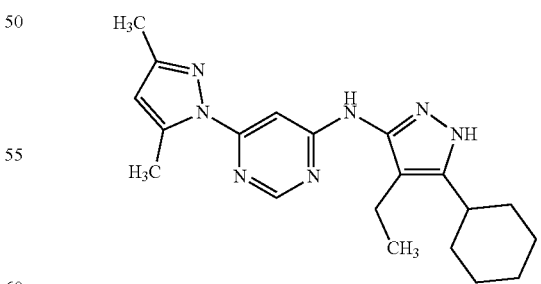

A solution of 4-chloro-6-(3,5-dimethyl-1H-pyrazol-1-yl) pyrimidine (50.0 mg, 240 µmol) and 5-cyclohexyl-4-ethyl-1H-pyrazol-3-amine (92.6 mg, 479 µmol) in NMP (400 µL) was treated with concentrated aqueous hydrochloric acid (60 µL, 12 M, 720 mmol). The resulting mixture was stirred for 1 hour at 200° C. in the microwave. After cooling to room temperature the crude product was purified by preparative HPLC (method: C18, 250×30, flow 50 ml/min, Runtime: 340 min, detection at 210 nm, gradient 40% acetonitrile (6 min)→95% acetonitrile (28 min)→95% acetonitrile (38 min)→34% acetonitrile (39 min), water+0.05% formic acid) to yield 15.2 mg of the desired product (16% yield).

LC-MS (method 10): $R_t$=2.15 min; MS (ESIpos): m/z=366 [M+H]$^+$ $^1$H-NMR (400 MHz, DMSO-d$_6$) δ [ppm]: −0.008 (1.89), 0.008 (1.83), 0.958 (3.10), 0.977 (7.05), 0.995 (3.38), 1.193 (0.63), 1.224 (0.85), 1.256 (0.48), 1.304 (0.52), 1.336 (1.39), 1.368 (1.40), 1.399 (0.59), 1.470 (0.60), 1.494 (1.42), 1.501 (1.50), 1.525 (1.36), 1.532 (1.32), 1.555 (0.52), 1.689 (0.81), 1.720 (0.78), 1.769 (2.55), 1.778 (2.49), 2.161 (16.00), 2.328 (1.20), 2.348 (2.32), 2.367 (2.45), 2.386 (0.75), 2.523 (1.72), 2.592 (0.76), 2.610 (15.20), 2.652 (0.55), 2.660 (0.48), 2.665 (0.51), 2.669 (0.56), 2.674 (0.44), 3.507 (0.46), 6.109 (3.88), 7.432 (1.28), 8.414 (3.22), 9.148 (2.67), 12.131 (2.25).

Example 29

2-(6-{[4-ethyl-5-(4-fluorophenyl)-1-methyl-1H-pyrazol-3-yl]amino}pyrimidin-4-yl)-4,5,6,7-tetrahydro-2H-indazol-3-ol

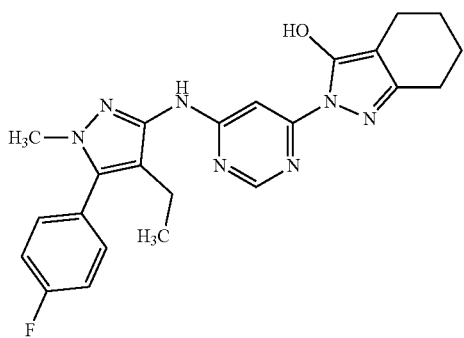 [SMILES: CCc1c(Nc2cc(-n3nc4c(c3O)CCCC4)ncn2)nn(C)c1-c1ccc(F)cc1]

A solution of N-[4-ethyl-5-(4-fluorophenyl)-1-methyl-1H-pyrazol-3-yl]-6-hydrazinylpyrimidin-4-amine (65.0 mg, 199 μmol) in methanol (2.0 mL) was treated with methyl 2-oxocyclohexanecarboxylate (29 μl, 200 μmol). The reaction mixture as stirred for 3 hours at 80° C. After cooling to room temperature the crude mixture was purified using preparative HPLC (method: column: Reprosil C18; 10 μm; 125×30 mm/flow: 50 ml/min/eluent: A=water (0.01% formic acid), B=acetonitrile/gradient: 0.00-5.00 min=10% B, 6.50 min=20% B, 17.00-19.75 min=100% B, 19.75-23.00 min=90% B) to afford 43.6 mg (51% yield) of the desired product.

LC-MS (method 9): $R_t$=1.02 min; MS (ESIpos): m/z=434 [M+H]$^+$ $^1$H-NMR (400 MHz, DMSO-d$_6$) δ [ppm]: 0.88 (t, 3H), 1.53-1.79 (m, 4H), 2.15 (br s, 2H), 2.29 (q, 2H), 2.45 (br s, 1H), 3.64 (s, 3H), 7.30-7.41 (m, 2H), 7.45-7.54 (m, 2H), 7.83 (br s, 1H), 8.39 (s, 1H), 9.29 (br s, 1H), 10.94 (br s, 1H).

Example 30

2-(6-{[4-ethyl-5-(4-fluorophenyl)-1H-pyrazol-3-yl]amino}pyrimidin-4-yl)-4,5,6,7-tetrahydro-2H-indazol-3-ol

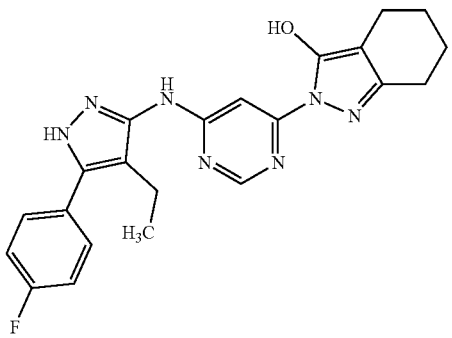 [SMILES: CCc1c(Nc2cc(-n3nc4c(c3O)CCCC4)ncn2)n[nH]c1-c1ccc(F)cc1]

A solution of N-[4-ethyl-5-(4-fluorophenyl)-1H-pyrazol-3-yl]-6-hydrazinylpyrimidin-4-amine (65.0 mg, 207 μmol) in methanol (2.0 mL) was treated with methyl 2-oxocyclohexanecarboxylate (30 μl, 210 μmol). After cooling to room temperature a precipitate occurred with was collected by filtration, washed with methanol and dried to yield 31.0 mg (36% yield) of the final compound.

LC-MS (method 10): $R_t$=1.78 min; MS (ESIpos): m/z=420 [M+H]$^+$ $^1$H-NMR (400 MHz, DMSO-d$_6$) δ [ppm]: 0.008 (1.34), 0.984 (7.35), 1.003 (16.00), 1.022 (7.62), 1.627 (3.51), 1.642 (4.06), 1.668 (2.73), 1.687 (4.05), 1.702 (3.61), 2.116 (3.21), 2.329 (0.49), 2.461 (5.07), 2.476 (4.13), 3.170 (0.84), 7.349 (3.03), 7.607 (3.73), 7.828 (1.21), 8.403 (1.90), 9.209 (0.67), 11.338 (1.44), 12.785 (0.77).

Example 31

N-{1-[2-(benzyloxy)ethyl]-4-ethyl-5-(4-fluorophenyl)-1H-pyrazol-3-yl}-6-(3,5-dimethyl-1H-pyrazol-1-yl)pyrimidin-4-amine

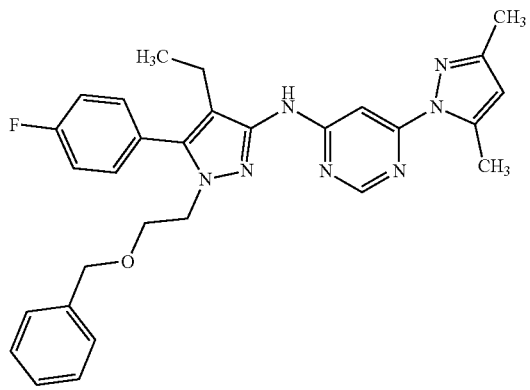 [SMILES: CCc1c(Nc2cc(-n3nc(C)cc3C)ncn2)nn(CCOCc2ccccc2)c1-c1ccc(F)cc1]

A solution of 1-[2-(benzyloxy)ethyl]-4-ethyl-5-(4-fluorophenyl)-1H-pyrazol-3-amine (75.0 mg, 221 μmol) and 4-chloro-6-(3,5-dimethyl-1H-pyrazol-1-yl)pyrimidine (46.1 mg, 221 μmol) in 1-methoxy-2-propanol (1.0 mL) was treated with hydrochloric acid in 1,4-dioxane (170 μl, 4.0 M, 660 µmol). The reaction vessel was capped and the mixture was shaken overnight at 120° C. After cooling to room temperature the resulting mixture was purified by preparative HPLC (method: column: Reprosil C18; 10 m; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75-23.00 min=90% B) to yield 48.3 mg of the desired compound (43% yield).

LC-MS (method 9): $R_t$=1.36 min; MS (ESIpos): m/z=512 $[M+H]^+$ $^1$H-NMR (400 MHz, DMSO-d$_6$) δ [ppm]: 0.870 (4.15), 0.889 (9.45), 0.908 (4.25), 1.238 (2.75), 1.400 (0.80), 2.140 (15.66), 2.282 (1.06), 2.301 (3.16), 2.320 (3.16), 2.338 (1.04), 2.524 (1.07), 2.621 (16.00), 3.466 (0.98), 3.773 (2.01), 3.786 (4.37), 3.799 (2.40), 4.056 (2.44), 4.069 (4.36), 4.083 (2.07), 4.394 (11.10), 6.117 (4.19), 7.144 (3.07), 7.160 (3.87), 7.215 (0.41), 7.233 (1.71), 7.240 (0.57), 7.250 (2.00), 7.264 (3.81), 7.282 (3.68), 7.297 (2.90), 7.318 (5.07), 7.340 (3.04), 7.436 (3.08), 7.441 (1.46), 7.450 (3.50), 7.457 (2.93), 7.471 (2.70), 7.484 (1.60), 8.451 (3.78), 9.411 (3.41).

Example 32

N-{1-[2-(benzyloxy)ethyl]-4-ethyl-3-(4-fluorophenyl)-1H-pyrazol-5-yl}-6-(3,5-dimethyl-1H-pyrazol-1-yl)pyrimidin-4-amine

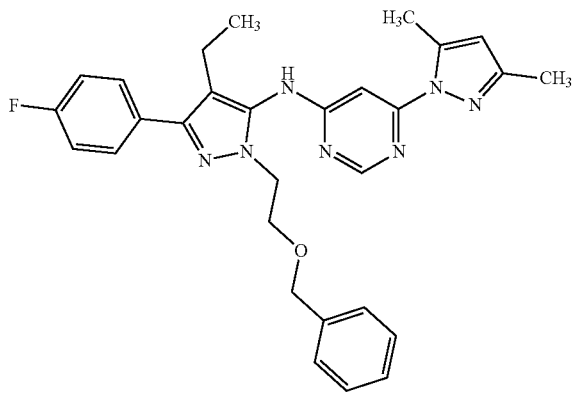 [SMILES: CCc1c(-c2ccc(F)cc2)nn(CCOCc2ccccc2)c1Nc1cc(-n2nc(C)cc2C)ncn1]

To a solution of 1-[2-(benzyloxy)ethyl]-4-ethyl-3-(4-fluorophenyl)-1H-pyrazol-5-amine (145 mg, 427 mol) in 1,4-dioxane (2.0 mL) sodium phenoxide (67.6 mg, 583 µmol) was added and argon was poured through the mixture. Tris(dibenzylideneacetone)dipalladium(0) (4.62 mg, 5.05 µmol), Xantphos (6.74 mg, 11.7 µmol) and 4-chloro-6-(3,5-dimethyl-1H-pyrazol-1-yl)pyrimidine (81.0 mg, 388 µmol) were added to the mixture. The reaction vessel was capped and the mixture was stirred at 80° C. for 3.5 hours.

After cooling to room temperature the resulting mixture was separated via preparative HPLC (Column: Reprosil C18; 10 µm; 125×30 mm/Flow: 50 ml/min/Eluent: A=water (0,01% formic acid), B=acetonitrile/gradient: 0.00-5.00 min=10% B, 6.50 min=20% B, 17.0-19.75 min=100% B, 19.75-23.00 min=90% B) to yield 58.4 mg of the desired product (29% yield).

LC-MS (method 10): $R_t$=2.54 min; MS (ESIpos): m/z=512 $[M+H]^+$ $^1$H-NMR (400 MHz, DMSO-d$_6$) δ [ppm]: –0.150 (0.86), –0.008 (8.38), 0.008 (7.14), 0.146 (0.92), 0.974 (4.59), 0.993 (10.22), 1.012 (4.78), 2.131 (1.70), 2.248 (0.57), 2.327 (1.16), 2.366 (1.14), 2.444 (1.22), 2.463 (3.19), 2.523 (4.51), 2.623 (16.00), 2.669 (1.30), 2.693 (0.46), 2.710 (1.16), 3.162 (8.05), 3.175 (8.32), 3.755 (2.14), 3.769 (4.35), 3.783 (2.32), 4.060 (0.95), 4.073 (2.59), 4.087 (2.59), 4.100 (1.30), 4.130 (2.00), 4.407 (6.22), 6.130 (2.22), 7.170 (2.41), 7.209 (5.32), 7.254 (3.03), 7.277 (5.68), 7.299 (3.03), 7.654 (2.43), 7.669 (3.00), 7.675 (2.76), 7.690 (2.14), 8.432 (0.86), 9.316 (3.05).

Example 33 tert-butyl 1-(6-{[4-ethyl-5-(4-fluorophenyl)-1H-pyrazol-3-yl]amino}pyrimidin-4-yl)-1,4,6,7-tetrahydro-5H-pyrazolo[4,3-c]pyridine-5-carboxylate

A solution of 6-chloro-N-[4-ethyl-5-(4-fluorophenyl)-1H-pyrazol-3-yl]pyrimidin-4-amine (150 mg, 472 mol) and tert-butyl 1,4,6,7-tetrahydro-5H-pyrazolo[4,3-c]pyridine-5-carboxylate (158 mg, 708 µmol, CAS 230301-11-8) in DMF (2.5 mL) was treated with caesium carbonate (461 mg, 1.42 mmol). The reaction mixture was stirred at 120° C. overnight and an additional night at 140° C. The mixture was diluted with water, three times extracted with ethyl acetate. The combined organic phases were washed with water and brine, dried over sodium sulfate and the solvent was removed under reduced pressure. The crude product was purified by preparative reverse phase HPLC (method: column: Reprosil C18; 10 µm; 125×30 mm/flow: 50 ml/min/ eluent: A=water (0,01% formic acid), B=acetonitrile/gradient: 0.00-5.00 min=10% B, 6.50 min=20% B, 17.0-19.75 min=100% B, 19.75-23.00 min=90% B). Subsequently the obtained regioisomeric mixture was separated using (HPLC) method to yield 13.2 mg (6% yield) of the desired product.

LC-MS (method 9): $R_t$=1.18 min; MS (ESIpos): m/z=505 $[M+H]^+$ $^1$H-NMR (400 MHz, DMSO-d6) δ [ppm]: –0.008 (3.40), 0.008 (2.05), 0.988 (1.10), 1.007 (2.36), 1.025 (1.06), 1.073 (0.74), 1.091 (1.48), 1.108 (0.71), 1.424 (16.00), 2.328 (0.41), 2.519 (2.00), 2.524 (1.93), 3.214 (0.83), 3.375 (0.71), 3.392 (0.70), 3.593 (0.62), 3.607 (1.06), 3.621 (0.50), 4.382 (1.39), 7.339 (0.53), 7.361 (1.03), 7.383 (0.62), 7.586 (0.61), 7.600 (0.70), 7.622 (0.53), 7.661 (1.24), 8.459 (0.81), 9.416 (0.72), 12.813 (0.67).

Example 34

1-(6-{[4-ethyl-5-(4-fluorophenyl)-1H-pyrazol-3-yl]amino}pyrimidin-4-yl)-3,4-dimethyl-1H-pyrazol-5-ol

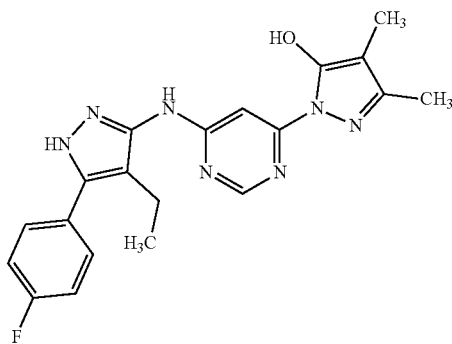 [SMILES: CCc1c(Nc2cc(-n3nc(C)c(C)c3O)ncn2)n[nH]c1-c1ccc(F)cc1]

A suspension of N-[4-ethyl-5-(4-fluorophenyl)-1H-pyrazol-3-yl]-6-hydrazinylpyrimidin-4-amine (65.0 mg, 207 µmol) in methanol (2.0 mL) was treated with methyl 2-methyl-3-oxobutanoate (24 µl, 210 µmol, synthesis described e.g. in Organic Letters 2015, 17(13), 3358-3361). The mixture was stirred 3 h at 90° C. The reaction mixture was purified using preparative reverse phase HPLC (method: column: Reprosil C18; 10 µm; 125×30 mm/flow: 50 ml/min/eluent: A=water (0,01% formic acid), B=acetonitrile/gradient: 0.00-5.00 min=10% B, 6.50 min=20% B, 17.0-19.75 min=100% B, 19.75-23.00 min=90% B) to yield 47.6 mg (58% yield) of the desired product.

LC-MS (method 10): $R_t$=1.72 min; MS (ESIpos): m/z=394 [M+H]$^+$ $^1$H-NMR (400 MHz, DMSO-d$_6$) δ [ppm]: 1.00 (br t, 3H), 1.66 (br s, 3H), 2.11 (br s, 3H), 3.30-3.42 (m, 3H), 7.35 (br s, 2H), 7.53-7.96 (m, 3H), 8.42 (br s, 1H), 9.02-9.83 (m, 1H), 11.38 (br s, 1H), 12.81 (br s, 1H).

Example 35

6-(3,5-dimethyl-1H-pyrazol-1-yl)-N-[3-ethyl-4-(4-fluorophenyl)-1-methyl-1H-pyrazol-5-yl]pyrimidin-4-amine

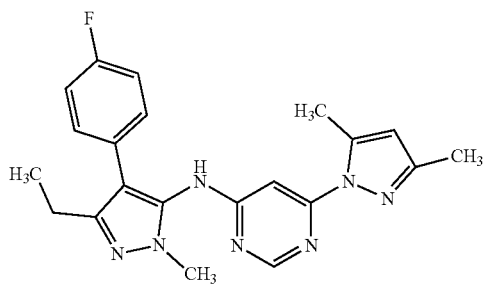 [SMILES: CCc1nn(C)c(Nc2cc(-n3nc(C)cc3C)ncn2)c1-c1ccc(F)cc1]

4-chloro-6-(3,5-dimethyl-1H-pyrazol-1-yl)pyrimidine (100 mg, 479 µmol) and 3-ethyl-4-(4-fluorophenyl)-1-methyl-1H-pyrazol-5-amine (263 mg, 1.20 mmol, commercially available; CAS 956268-27-2) were dissolved in DMSO (3.0 mL). Argon was poured through the reaction mixture. Subsequently phosphazen-base P(2)-Et (430 µl, 1.3 mmol) and tBuBrettPhos Pd G3 (8.0 ml, 58 µmol) were added. The reaction mixture was stirred at room temperature for 1 hour. Acetic acid was added and the crude mixture was purified by preparative HPLC (method 2) to yield 55 mg (28% yield) of the desired product.

LC-MS (method 9): $R_t$=1.06 min; MS (ESIpos): m/z=392 [M+H]$^+$ $^1$H-NMR (400 MHz, DMSO-d$_6$) δ [ppm]: −0.008 (2.01), 0.008 (1.87), 1.119 (6.37), 1.138 (13.92), 1.156 (6.58), 2.172 (13.52), 2.328 (0.57), 2.366 (0.46), 2.523 (1.89), 2.604 (16.00), 2.623 (4.95), 2.642 (4.63), 2.661 (1.68), 2.670 (0.69), 2.710 (0.47), 3.588 (13.46), 3.613 (0.62), 6.131 (3.94), 7.152 (2.68), 7.174 (6.21), 7.196 (3.87), 7.267 (3.00), 7.281 (3.48), 7.288 (2.75), 7.302 (2.09), 8.424 (3.90), 9.401 (2.13).

Example 36

6-(3,5-dimethyl-1H-pyrazol-1-yl)-N-[3-(4-fluorophenyl)-4-(2,2,2-trifluoroethyl)-1H-pyrazol-5-yl]pyrimidin-4-amine

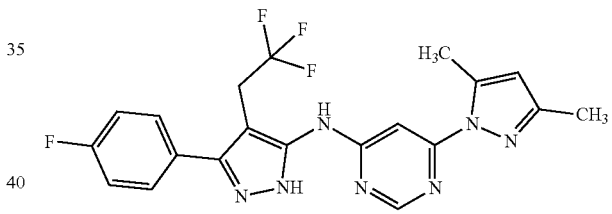

A solution of 4-chloro-6-(3,5-dimethyl-1H-pyrazol-1-yl)pyrimidine (100 mg, 479 µmol) and 3-(4-fluorophenyl)-4-(2,2,2-trifluoroethyl)-1H-pyrazol-5-amine (262 mg, 95% purity, 959 µmol) in NMP (1.0 mL) was treated with concentrated aqueous hydrochloric acid (146 mg, 36% purity, 1.44 mmol). The resulting mixture was stirred for 1 hour at 180° C. in the microwave. After cooling to room temperature the crude product was purified by preparative HPLC (method: C18, 250×30, flow 50 ml/min, Runtime: 340 min, detection at 210 nm, eluent: A=water (0.05% formic acid), B=acetonitrile, gradient 40% B/60% A (6 min)→95% B/5% A (28 min)→95% B/5% A (38 min) →34% B/76% A (39 min)) to yield 60 mg of the desired product (29% yield).

LC-MS (method 11): $R_t$=1.37 min; MS (ESIpos): m/z=432 [M+H]$^+$ $^1$H-NMR (400 MHz, DMSO-d$_6$) δ [ppm]: −0.008 (0.48), 2.194 (16.00), 2.638 (13.48), 3.690 (0.60), 3.718 (1.38), 3.746 (1.30), 3.772 (0.46), 6.142 (2.94), 7.352 (1.26), 7.374 (2.43), 7.396 (1.34), 7.635 (1.72), 7.649 (2.19), 7.656 (2.12), 7.670 (1.66), 7.806 (0.71), 8.497 (2.28), 9.587 (2.14), 13.094 (2.26).

Example 37 tert-butyl 1-(6-{[4-ethyl-5-(4-fluorophenyl)-1H-pyrazol-3-yl]amino}pyrimidin-4-yl)-4,6-dihydropyrrolo[3,4-c]pyrazole-5(1H)-carboxylate

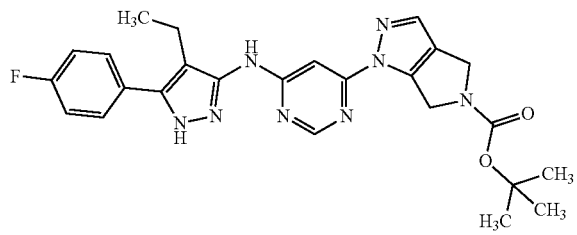 [SMILES: CCc1c(Nc2cc(-n3ncc4c3CN(C(=O)OC(C)(C)C)C4)ncn2)n[nH]c1-c1ccc(F)cc1]

A solution of 6-chloro-N-[4-ethyl-5-(4-fluorophenyl)-1H-pyrazol-3-yl]pyrimidin-4-amine (834 mg, 2.60 mmol) and tert-butyl 4,6-dihydropyrrolo[3,4-c]pyrazole-5(1H)-carboxylate (824 mg, 3.95 mmol, CAS 657428-42-7) in DMF (14.6 mL) was treated with caesium carbonate (2.56 g, 7.89 mmol). The mixture was stirred overnight at 120° C. After cooling to room temperature the crude product was purified by preparative reverse phase HPLC (method: column: Reprosil C18; 10 µm; 125×30 mm/flow: 50 ml/min/eluent: A=water (0.01% formic acid), B=acetonitrile/gradient: 0.00-5.00 min=10% B, 6.50 min=20% B, 17.00-19.75 min=100% B, 19.75-23.00 min=90% B). Subsequently the remaining regioisomeric mixture was separated using (method 4) to yield 145 mg (27% yield) of the desired product.

LC-MS (method 9): Rt=1.15 min; MS (ESIpos): m/z=491 [M+H]+

$^1$H-NMR (400 MHz, DMSO-d$_6$) δ [ppm]: 1.01 (t, 3H), 1.46 (s, 9H), 2.54-2.60 (m, 2H), 4.27-4.54 (m, 4H), 7.22-7.52 (m, 3H), 7.59-7.69 (m, 2H), 8.14 (s, 1H), 8.39 (d, 1H), 8.47 (s, 1H), 9.52 (br s, 1H), 12.80 (br s, 2H).

Example 38

6-(3,5-dimethyl-1H-pyrazol-1-yl)-N-[5-(4-fluorophenyl)-4-(2-methoxyethyl)-1H-pyrazol-3-yl]pyrimidin-4-amine

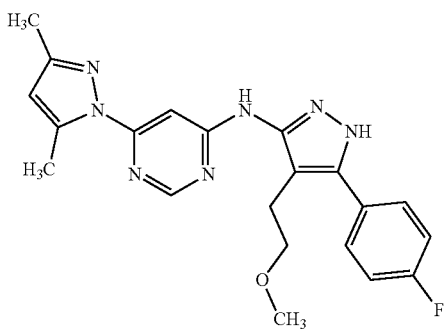 [SMILES: COCCc1c(Nc2cc(-n3nc(C)cc3C)ncn2)n[nH]c1-c1ccc(F)cc1]

4-chloro-6-(3,5-dimethyl-1H-pyrazol-1-yl)pyrimidine (50.0 mg, 240 µmol) and 5-(4-fluorophenyl)-4-(2-methoxyethyl)-1H-pyrazol-3-amine (141 mg, 599 µmol) were dissolved in DMSO (1.4 mL). Argon was poured through the reaction mixture. Subsequently phosphazen-base P(2)-Et (220 µl, 650 µmol) and tBuBrettPhos Pd G3 (20.5 mg, 24.0 µmol were added. The reaction mixture was stirred at room temperature overnight. Acetic acid was added and the crude mixture was purified by preparative HPLC (method: C18, 250×30, flow 50 ml/min, Runtime: 340 min, detection at 210 nm, eluent: A=water (0.05% formic acid), B=acetonitrile, gradient 40% B/60% A (6 min)→95% B/5% A (28 min)→95% B/5% A (38 min)→34% B/76% A (39 min)) to yield 20.6 mg (21% yield) of the desired product.

LC-MS (method 9): R$_t$=1.05 min; MS (ESIpos): m/z=408 [M+H]+

$^1$H-NMR (400 MHz, DMSO-d$_6$) δ [ppm]: 2.177 (16.00), 2.328 (0.65), 2.629 (14.40), 2.670 (0.81), 2.736 (1.82), 2.753 (3.72), 2.770 (1.94), 3.147 (0.88), 3.189 (15.54), 3.412 (2.09), 3.429 (3.92), 3.446 (1.78), 6.129 (4.15), 7.340 (1.98), 7.362 (4.15), 7.384 (2.25), 7.597 (1.31), 7.619 (2.56), 7.633 (2.85), 7.640 (2.53), 7.655 (2.07), 8.466 (3.86), 9.278 (3.78), 12.839 (2.97).

Example 39

N-[4-chloro-3-(4-ethoxyphenyl)-1H-pyrazol-5-yl]-6-(3,5-dimethyl-1H-pyrazol-1-yl)pyrimidin-4-amine

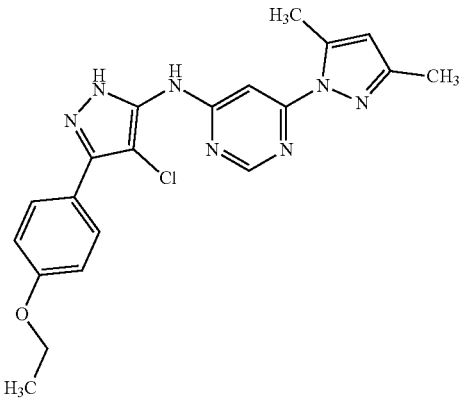 [SMILES: CCOc1ccc(-c2n[nH]c(Nc3cc(-n4nc(C)cc4C)ncn3)c2Cl)cc1]

A solution of 4-chloro-6-(3,5-dimethyl-1H-pyrazol-1-yl)pyrimidine (20.0 mg, 95.6 µmol) and 4-chloro-3-(4-ethoxyphenyl)-1H-pyrazol-5-amine (25.0 mg, 105 µmol) in 1-methoxy-2-propanol (1.1 mL) was treated with hydrochloric acid in 1,4-dioxane (72 µl, 4.0 M, 290 µmol). The reaction vessel was capped and the mixture was shaken at 120° C. for 4 days. After cooling to room temperature the resulting mixture was purified by preparative HPLC (method: column: Reprosil C18; 10 µm; 125×30 mm/flow: 50 ml/min/eluent: A=water (0.1% formic acid), B=acetonitrile/gradient: 0.00-4.25 min=20% B, 4.50 min=30% B, 19.00-22.50 min=100% B, 22.75-25.00 min=20% B) to yield 3.0 mg of the desired compound (7% yield).

LC-MS (method 9): R$_t$=1.14 min; MS (ESIpos): m/z=410 [M+H]+

$^1$H-NMR (500 MHz, DMSO-d$_6$) δ [ppm]: 1.234 (1.09), 1.357 (14.02), 1.370 (8.64), 2.074 (0.64), 2.175 (14.46), 2.291 (0.66), 2.364 (0.92), 2.631 (16.00), 4.093 (5.52), 4.106 (5.41), 6.135 (4.51), 7.029 (0.85), 7.091 (5.27), 7.106 (5.53), 7.340 (3.84), 7.724 (5.04), 7.739 (5.14), 8.028 (0.64), 8.478 (4.16), 9.449 (3.96), 13.310 (3.49).

Example 40 ethyl 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylate

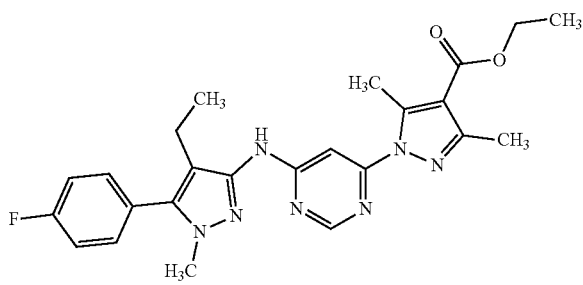 [SMILES: CCOC(=O)c1c(C)nn(-c2cc(Nc3nn(C)c(-c4ccc(F)cc4)c3CC)ncn2)c1C]

A solution of ethyl 1-(6-chloropyrimidin-4-yl)-3,5-dimethyl-1H-pyrazole-4-carboxylate (70.0 mg, 249 mol) (116 mg, 477 μmol) and 4-ethyl-5-(4-fluorophenyl)-1-methyl-1H-pyrazol-3-amine (60.1 mg, 274 mol) in N-methylpyrrolidone (2.8 mL) was treated with hydrochloric acid in 1,4-dioxane (190 μl, 4.0 M, 750 μmol). The reaction was stirred 30 min at 190° C. under microwave radiation. After cooling to room temperature the resulting mixture was purified by preparative HPLC (method: column: Reprosil C18; 10 μm; 125×30 mm/flow: 50 ml/min/eluent: A=water (0.1% formic acid), B=acetonitrile/gradient: 0.00-4.25 min=20% B, 4.50 min=30% B, 19.00-22.50 min=100% B, 22.75-25.00 min=20% B) to yield 15 mg of the desired compound (13% yield).

LC-MS (method 10): $R_t$=2.32 min; MS (ESIpos): m/z=464 [M+H]$^+$ $^1$H-NMR (400 MHz, DMSO-$d_6$) δ [ppm]: 0.872 (3.45), 0.890 (7.62), 0.909 (3.58), 1.290 (4.34), 1.308 (9.11), 1.326 (4.47), 1.356 (0.83), 2.291 (0.88), 2.309 (2.48), 2.328 (2.86), 2.346 (0.88), 2.380 (15.12), 2.670 (0.44), 2.890 (16.00), 3.647 (15.83), 4.230 (1.32), 4.247 (4.15), 4.265 (4.06), 4.283 (1.27), 7.357 (2.01), 7.379 (4.92), 7.401 (2.98), 7.499 (2.57), 7.513 (2.93), 7.521 (2.36), 7.534 (1.92), 8.523 (3.48), 9.544 (1.72).

Example 41

N-[4-cyclopropyl-5-(4-fluorophenyl)-1-methyl-1H-pyrazol-3-yl]-6-(3,5-dimethyl-1H-pyrazol-1-yl)pyrimidin-4-amine

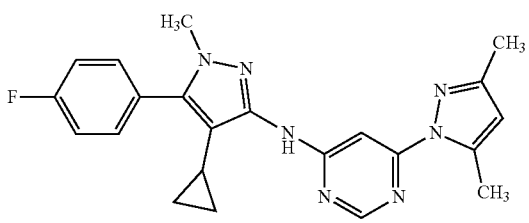 [SMILES: Cc1cc(C)n(-c2cc(Nc3nn(C)c(-c4ccc(F)cc4)c3C3CC3)ncn2)n1]

4-cyclopropyl-5-(4-fluorophenyl)-1-methyl-1H-pyrazol-3-amine (100 mg, 432 μmol) and sodium phenoxide (75.3 mg, 649 μmol) were dissolved in dioxan (2.0 mL). The solution was degassed with argon. 4-chloro-6-(3,5-dimethyl-1H-pyrazol-1-yl)pyrimidine (99.2 mg, 476 μmol), tris(dibenzylideneacetone)dipalladium(0) (5.15 mg, 5.62 μmol) and Xantphos (7.51 mg, 13.0 μmol) were added. The reaction mixture was stirred at 80° C. for 3 days. The crude product was directly purified by preparative HPLC (method: column: Reprosil C18; 10 μm; 125×30 mm/flow: 45 ml/min/eluent: A=water (0.1% formic acid), B=acetonitrile/gradient: 0.00-4.25 min=10% B, 4.50 min=20% B, 15.50 min=85% B, 16.00-18.50 min=100% B, 18.75-22.00 min=20% B) to afford 35.7 mg of the desired product (19% yield).

LC-MS (method 11): $R_t$=1.48 min; MS (ESIpos): m/z=404 [M+H]$^+$ $^1$H-NMR (400 MHz, DMSO-$d_6$) δ [ppm]: 0.008 (0.80), 0.137 (1.09), 0.147 (2.93), 0.152 (2.85), 0.160 (2.95), 0.165 (2.43), 0.175 (0.88), 0.480 (0.98), 0.490 (2.18), 0.495 (2.11), 0.501 (1.29), 0.511 (2.15), 0.516 (1.91), 0.526 (0.62), 1.073 (0.56), 1.091 (1.09), 1.109 (0.54), 1.491 (0.44), 1.504 (0.83), 1.512 (0.85), 1.525 (1.38), 1.533 (0.56), 1.538 (0.73), 1.546 (0.66), 2.186 (15.26), 2.625 (12.50), 2.653 (0.82), 2.678 (0.69), 3.375 (0.55), 3.392 (0.53), 3.662 (16.00), 6.131 (3.70), 7.250 (3.90), 7.350 (2.25), 7.372 (4.51), 7.394 (2.48), 7.548 (2.64), 7.554 (1.36), 7.562 (2.92), 7.570 (2.37), 7.579 (1.04), 7.584 (1.98), 8.441 (3.73), 9.165 (3.54).

Example 42

6-(4-chloro-3,5-dimethyl-1H-pyrazol-1-yl)-N-[4-cyclopropyl-5-(4-fluorophenyl)-1-methyl-1H-pyrazol-3-yl]pyrimidin-4-amine

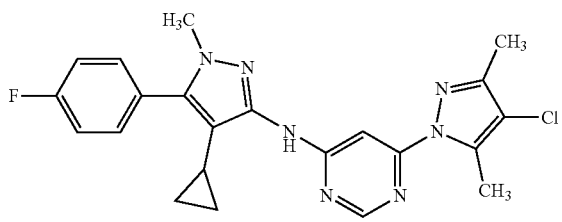 [SMILES: Cc1nn(-c2cc(Nc3nn(C)c(-c4ccc(F)cc4)c3C3CC3)ncn2)c(C)c1Cl]

4-cyclopropyl-5-(4-fluorophenyl)-1-methyl-1H-pyrazol-3-amine (100 mg, 432 μmol) and sodium phenoxide (75.3 mg, 649 μmol) were dissolved in 1,4-dioxane (2.0 mL). The solution was degassed with argon. 4-chloro-6-(4-chloro-3,5-dimethyl-1H-pyrazol-1-yl)pyrimidine (116 mg, 476 μmol), tris(dibenzylideneacetone)dipalladium(0) (5.15 mg, 5.62 μmol) and Xantphos (7.51 mg, 13.0 μmol) were added. The reaction mixture was stirred at 80° C. overnight. The crude product was directly purified by preparative HPLC (method: column: Reprosil C18; 10 μm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to afford 90.9 mg (46% yield) of the desired product.

LC-MS (method 11): $R_t$=1.65 min; MS (ESIpos): m/z=438 [M+H]$^+$

¹H-NMR (400 MHz, DMSO-d₆) δ [ppm]: 0.129 (0.79), 0.139 (2.56), 0.144 (2.81), 0.153 (2.96), 0.157 (2.61), 0.167 (0.92), 0.482 (0.71), 0.492 (1.91), 0.497 (1.95), 0.503 (1.16), 0.513 (2.04), 0.517 (1.92), 0.528 (0.65), 1.507 (0.70), 1.515 (0.74), 1.520 (0.49), 1.528 (1.32), 1.536 (0.49), 1.541 (0.71), 1.549 (0.65), 2.224 (14.96), 2.264 (1.67), 2.644 (16.00), 2.669 (1.17), 2.677 (1.82), 3.663 (15.99), 7.275 (3.47), 7.351 (1.98), 7.373 (4.28), 7.395 (2.46), 7.548 (2.40), 7.553 (1.12), 7.562 (2.71), 7.570 (2.37), 7.579 (0.94), 7.584 (1.99), 8.479 (3.29), 9.297 (3.62).

Example 43

N-[4-cyclopropyl-3-(4-fluorophenyl)-1-methyl-1H-pyrazol-5-yl]-6-(3,5-dimethyl-1H-pyrazol-1-yl)pyrimidin-4-amine

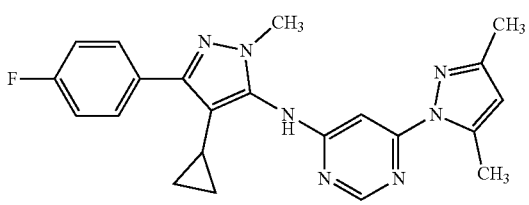 [SMILES: Cc1cc(C)n(-c2cc(Nc3c(C4CC4)c(-c4ccc(F)cc4)nn3C)ncn2)n1]

4-cyclopropyl-3-(4-fluorophenyl)-1-methyl-1H-pyrazol-5-amine (100 mg, 432 μmol) and sodium phenoxide (75.3 mg, 649 μmol) were dissolved in 1,4-dioxan. The solution was degassed with argon. 4-chloro-6-(3,5-dimethyl-1H-pyrazol-1-yl)pyrimidine (99.2 mg, 476 μmol), tris(dibenzylideneacetone)dipalladium(0) (5.15 mg, 5.62 μmol) and Xantphos (7.51 mg, 13.0 μmol) were added. The reaction mixture was stirred at 80° C. for 3 days. The crude product was directly purified by preparative HPLC (method: column: Reprosil C18; 10 μm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to afford 521 mg (27% yield) of the desired product.

LC-MS (method 11): $R_t$=1.44 min; MS (ESIpos): m/z=404 [M+H]⁺

¹H-NMR (500 MHz, DMSO-d₆) δ [ppm]: −0.007 (1.10), 0.006 (0.81), 0.300 (0.73), 0.697 (1.24), 1.077 (0.81), 1.092 (1.61), 1.106 (0.84), 1.634 (0.67), 1.644 (0.92), 2.187 (1.87), 2.228 (3.59), 2.521 (0.49), 2.638 (16.00), 2.662 (2.45), 2.663 (2.42), 3.324 (6.28), 3.376 (0.87), 3.390 (0.85), 6.150 (2.11), 6.269 (0.60), 7.246 (2.08), 7.264 (4.20), 7.282 (2.31), 7.350 (1.41), 7.382 (1.60), 7.457 (0.48), 7.463 (2.10), 7.466 (2.14), 7.478 (1.36), 7.789 (1.31), 7.794 (1.10), 7.798 (1.25), 7.809 (0.98), 7.813 (1.12), 7.820 (1.16), 7.897 (2.23), 7.899 (2.31), 8.469 (0.45), 8.900 (0.69), 8.902 (0.69), 9.373 (0.94).

Example 44

N-[4-cyclopropyl-5-(4-fluorophenyl)-1-methyl-1H-pyrazol-3-yl]-6-(3-methyl-1H-indazol-1-yl)pyrimidin-4-amine

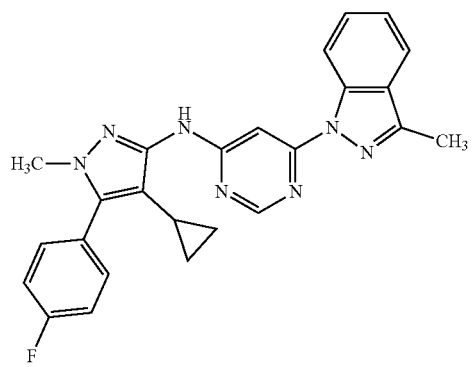 [SMILES: Cc1nn(-c2cc(Nc3nn(C)c(-c4ccc(F)cc4)c3C3CC3)ncn2)c2ccccc12]

To a solution of 4-cyclopropyl-5-(4-fluorophenyl)-1-methyl-1H-pyrazol-3-amine (100 mg, 432 μmol) in 1,4-dioxane (2.0 mL) sodium phenoxide (75.3 mg, 649 μmol) was added and argon was poured through the mixture. Tris(dibenzylideneacetone)dipalladium(0) (5.15 mg, 5.62 μmol), Xantphos (7.51 mg, 13.0 μmol) and 1-(6-chloropyrimidin-4-yl)-3-methyl-1H-indazole (116 mg, 476 μmol) were added to the mixture. The reaction vessel was capped and the mixture was stirred at 80° C. overnight. After cooling to room temperature the resulting mixture was separated via preparative HPLC (Column: Reprosil C18; 10 m; 125×30 mm/Flow: 50 ml/min/Eluent: A=water (0.01% formic acid), B=acetonitrile/Gradient: 0.00-5.00 min=10% B, 6.50 min=20% B, 17.00-19.75 min=100% B, 19.75-23.00 min=90% B) to yield 29.6 mg of the desired product (16% yield).

LC-MS (method 11): $R_t$=1.61 min; MS (ESIpos): m/z=440 [M+H]⁺

¹H-NMR (400 MHz, DMSO-d₆) δ [ppm]: 0.10-0.24 (m, 2H), 0.42-0.60 (m, 2H), 1.55 (tt, 1H), 2.59 (s, 3H), 3.69 (s, 3H), 7.29-7.44 (m, 4H), 7.54-7.62 (m, 3H), 7.85 (d, 1H), 8.55 (s, 1H), 8.76 (d, 1H), 9.16 (s, 1H).

Example 45

6-(4-chloro-3,5-dimethyl-1H-pyrazol-1-yl)-N-[4-cyclopropyl-3-(4-fluorophenyl)-1-methyl-1H-pyrazol-5-yl]pyrimidin-4-amine

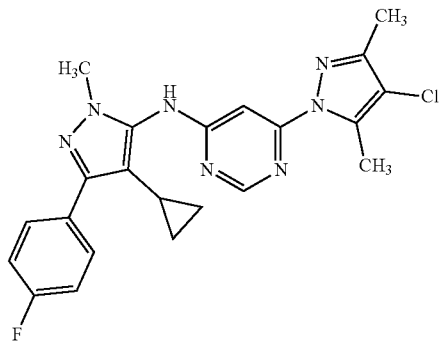 [SMILES: Cc1nn(-c2cc(Nc3c(C4CC4)c(-c4ccc(F)cc4)nn3C)ncn2)c(C)c1Cl]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-cyclopropyl-3-(4-fluorophenyl)-1-methyl-1H-pyrazol-5-amine (100 mg, 432 mol) and 4-chloro-6-(4-chloro-3,5-dimethyl-1H-pyrazol-1-yl)pyrimidine (116 mg, 476 μmol) to yield 35.0 mg of the desired product (17% yield).

LC-MS (method 11): Rt=1.60 min; MS (ESIpos): m/z=438 [M+H]$^+$ $^1$H-NMR (400 MHz, DMSO-d$_6$) δ [ppm]: −0.008 (2.53), 0.008 (1.35), 0.295 (0.74), 0.688 (1.08), 1.640 (0.73), 2.222 (1.83), 2.524 (0.82), 2.656 (16.00), 3.626 (4.35), 7.241 (1.72), 7.263 (3.58), 7.285 (1.98), 7.899 (1.42), 9.466 (0.57).

Example 46

N-[4-ethyl-5-(4-fluorophenyl)-1-methyl-1H-pyrazol-3-yl]-6-(3-methyl-4,5,6,7-tetrahydro-2H-indazol-2-yl)pyrimidin-4-amine

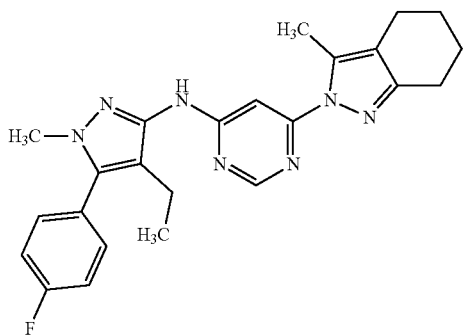 [SMILES: CCc1c(Nc2cc(-n3nc4c(c3C)CCCC4)ncn2)nn(C)c1-c1ccc(F)cc1]

A suspension of N-[4-ethyl-5-(4-fluorophenyl)-1-methyl-1H-pyrazol-3-yl]-6-hydrazinylpyrimidin-4-amine (100 mg, 305 μmol) in methanol (3.0 mL) was treated with 2-acetylcyclohexanone (40 μl, 310 μmol) and stirred overnight at 80° C. After cooling to room temperature a precipitate occurred with was collected by filtration and washed with methanol to give some desired product. The filtrate was taken to dryness, the crude residue was purified by reverse phase HPLC (method: column: Reprosil C18; 10 μm; 125×30 mm/flow: 50 ml/min/eluent: A=water (0,01% formic acid), B=acetonitrile/gradient: 0.00-5.00 min=10% B, 6.50 min=20% B, 17.0-19.75 min=100% B, 19.75.00-23.00 min=90% B). In total 18.1 mg (12% yield) of the desired product were obtained.

LC-MS (method 10): Rt=2.43 min; MS (ESIpos): m/z=432 [M+H]$^+$ $^1$H-NMR (400 MHz, DMSO-d$_6$) δ [ppm]: 0.865 (4.05), 0.884 (8.67), 0.903 (3.99), 1.234 (0.68), 1.716 (2.51), 2.124 (2.39), 2.275 (1.25), 2.294 (3.37), 2.313 (3.36), 2.332 (1.84), 2.367 (1.58), 2.425 (4.39), 2.441 (3.41), 2.524 (5.63), 2.558 (2.66), 2.574 (3.44), 2.588 (1.68), 2.670 (0.78), 2.710 (0.66), 3.103 (0.48), 3.648 (16.00), 7.274 (3.61), 7.355 (2.16), 7.377 (4.72), 7.399 (2.84), 7.500 (3.01), 7.513 (3.32), 7.521 (2.74), 7.535 (2.24), 8.388 (0.66), 8.426 (3.62), 9.246 (0.65), 9.266 (3.06).

Example 47

N-[4-cyclopropyl-3-(4-fluorophenyl)-1-methyl-1H-pyrazol-5-yl]-6-(3-methyl-1H-indazol-1-yl)pyrimidin-4-amine

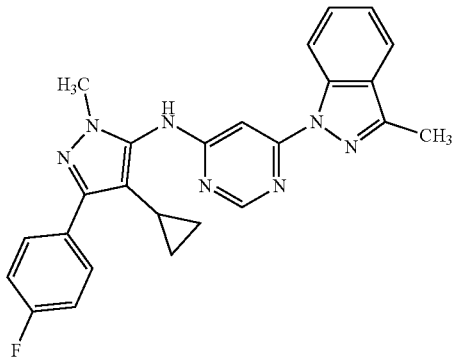 [SMILES: Cc1nn(-c2cc(Nc3c(C4CC4)c(-c4ccc(F)cc4)nn3C)ncn2)c2ccccc12]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-cyclopropyl-3-(4-fluorophenyl)-1-methyl-1H-pyrazol-5-amine (100 mg, 432 μmol) and 1-(6-chloropyrimidin-4-yl)-3-methyl-1H-indazole (116 mg, 476 μmol) to yield 20.0 mg of the desired product (10% yield).

LC-MS (method 11): Rt=1.58 min; MS (ESIpos): m/z=440 [M+H]$^+$ $^1$H-NMR (400 MHz, DMSO-d$_6$) δ [ppm]: −0.149 (0.60), 0.008 (3.86), 0.146 (0.58), 0.335 (2.12), 0.717 (3.44), 1.631 (0.84), 1.652 (1.77), 1.665 (2.79), 1.678 (1.68), 1.699 (0.66), 2.329 (0.89), 2.368 (0.54), 2.631 (1.60), 2.671 (0.98), 2.711 (0.63), 3.654 (16.00), 7.251 (4.64), 7.273 (9.29), 7.296 (5.11), 7.331 (3.27), 7.349 (5.90), 7.368 (3.98), 7.566 (3.34), 7.585 (5.17), 7.605 (3.07), 7.845 (4.00), 7.864 (3.73), 7.920 (4.13), 8.572 (1.76), 8.737 (6.19), 8.759 (5.98), 9.372 (4.32).

Example 48

N-[4-chloro-3-(2,4-difluorophenyl)-1-methyl-1H-pyrazol-5-yl]-6-(4-chloro-3,5-dimethyl-1H-pyrazol-1-yl)pyrimidin-4-amine

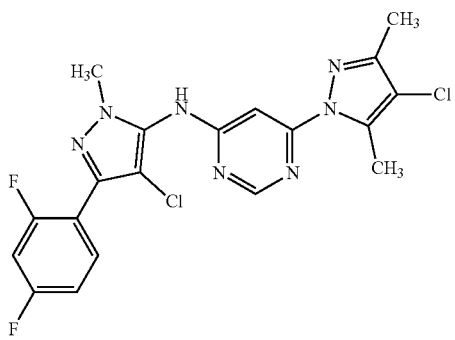 [SMILES: Cc1nn(-c2cc(Nc3c(Cl)c(-c4ccc(F)cc4F)nn3C)ncn2)c(C)c1Cl]

The described product was prepared in a manner analogous to that described in the preparation of N-[4-cyclopropyl-5-(4-fluorophenyl)-1-methyl-1H-pyrazol-3-yl]-6-(3- methyl-1H-indazol-1-yl)pyrimidin-4-amine starting from 4-chloro-3-(2,4-difluorophenyl)-1-methyl-1H-pyrazol-5-amine (100 mg, 410 µmol) and 4-chloro-6-(4-chloro-3,5-dimethyl-1H-pyrazol-1-yl)pyrimidine (110 mg, 451 µmol) to yield 43.4 mg of the desired product (23% yield).

LC-MS (method 11): $R_t$=1.58 min; MS (ESIpos): m/z=450 [M+H]$^+$ $^1$H-NMR (400 MHz, DMSO-d$_6$) δ [ppm]: 0.008 (0.67), 1.074 (0.96), 1.091 (1.94), 1.109 (0.99), 2.236 (11.41), 2.656 (16.00), 3.375 (0.95), 3.392 (0.95), 3.738 (13.08), 7.201 (0.66), 7.207 (0.67), 7.222 (1.24), 7.228 (1.27), 7.243 (0.68), 7.249 (0.71), 7.384 (0.73), 7.390 (0.70), 7.409 (1.10), 7.433 (0.75), 7.440 (0.70), 7.596 (0.70), 7.617 (1.39), 7.634 (1.37), 7.655 (0.65), 8.548 (3.24), 9.797 (2.80).

Example 49

N-[4-chloro-3-(2,4-difluorophenyl)-1-methyl-1H-pyrazol-5-yl]-6-(3-methyl-1H-indazol-1-yl)pyrimidin-4-amine

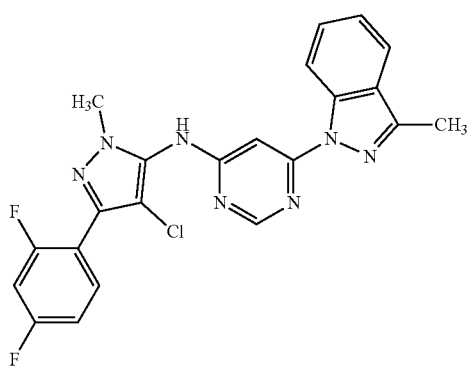 [SMILES: Cc1nn(-c2cc(Nc3c(Cl)c(-c4ccc(F)cc4F)nn3C)ncn2)c2ccccc12]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-3-(2,4-difluorophenyl)-1-methyl-1H-pyrazol-5-amine (100 mg, 410 µmol) and 1-(6-chloropyrimidin-4-yl)-3-methyl-1H-indazole (110 mg, 451 µmol) to yield 94.9 mg of the desired product (51% yield).

LC-MS (method 11): $R_t$=1.55 min; MS (ESIpos): m/z=452 [M+H]$^+$ $^1$H-NMR (400 MHz, DMSO-d$_6$) δ [ppm]: -0.008 (2.39), 0.008 (1.44), 1.074 (1.86), 1.091 (3.77), 1.109 (1.88), 2.525 (1.20), 2.603 (14.21), 3.357 (0.66), 3.375 (1.85), 3.392 (1.80), 3.410 (0.59), 3.763 (16.00), 7.211 (0.94), 7.216 (0.92), 7.232 (1.55), 7.237 (1.54), 7.253 (0.83), 7.259 (0.82), 7.342 (1.38), 7.360 (2.45), 7.379 (1.62), 7.393 (0.95), 7.399 (0.90), 7.419 (1.34), 7.423 (1.29), 7.443 (0.89), 7.449 (0.82), 7.575 (1.34), 7.593 (2.10), 7.614 (1.99), 7.631 (1.15), 7.635 (1.64), 7.652 (1.63), 7.673 (0.73), 7.856 (2.43), 7.876 (2.21), 8.613 (3.92), 8.731 (2.73), 8.752 (2.54), 9.707 (4.17).

Example 50

N-[4-chloro-3-(2,4-difluorophenyl)-1-methyl-1H-pyrazol-5-yl]-6-(3,5-dimethyl-1H-pyrazol-1-yl)pyrimidin-4-amine

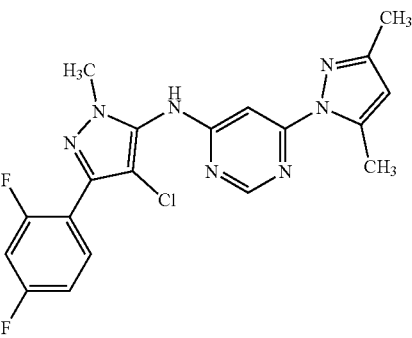 [SMILES: Cc1cc(C)n(-c2cc(Nc3c(Cl)c(-c4ccc(F)cc4F)nn3C)ncn2)n1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-3-(2,4-difluorophenyl)-1-methyl-1H-pyrazol-5-amine (100 mg, 410 µmol) and 4-chloro-6-(3,5-dimethyl-1H-pyrazol-1-yl)pyrimidine (94.2 mg, 451 µmol) to yield 45.2 mg of the desired product (26% yield).

LC-MS (method 10): $R_t$=2.11 min; MS (ESIpos): m/z=416 [M+H]$^+$ $^1$H-NMR (400 MHz, DMSO-d$_6$) δ [ppm]: -0.008 (1.68), 0.008 (1.44), 1.091 (0.78), 2.198 (13.91), 2.524 (0.83), 2.639 (15.19), 3.375 (0.41), 3.736 (16.00), 6.167 (3.99), 7.200 (0.73), 7.207 (0.76), 7.221 (1.42), 7.227 (1.48), 7.242 (0.79), 7.248 (0.82), 7.383 (0.83), 7.390 (0.81), 7.409 (1.25), 7.413 (1.21), 7.433 (0.85), 7.439 (0.82), 7.597 (0.80), 7.614 (1.00), 7.618 (1.60), 7.635 (1.58), 7.639 (0.96), 7.656 (0.74), 8.510 (3.30), 9.694 (2.56).

Example 51 ethyl 1-{6-[(4-chloro-5-phenyl-1H-pyrazol-3-yl)amino]pyrimidin-4-yl}-3,5-dimethyl-1H-pyrazole-4-carboxylate

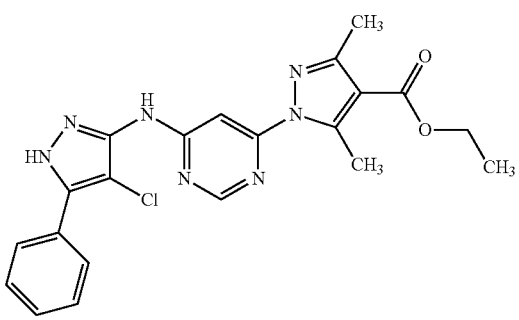 [SMILES: CCOC(=O)c1c(C)nn(-c2cc(Nc3n[nH]c(-c4ccccc4)c3Cl)ncn2)c1C]

In a microwave tube, 4-chloro-5-phenyl-1H-pyrazol-3-amine (75.9 mg, 392 µmol) and sodium phenoxide (62.0 mg, 534 µmol) were suspended in 1,4-dioxane (0.92 mL) and degassed by passing an Argon stream through the suspension. Tris(dibenzylideneaceton)dipalladium (4.24 mg, 4.63

μmol), Xantphos (6.18 mg, 10.7 μmol) and ethyl 1-(6-chloropyrimidin-4-yl)-3,5-dimethyl-1H-pyrazole-4-carboxylate (100 mg, 356 μmol) were added and the reaction vessel was sealed. The reaction mixture was heated at 80° C. overnight. After cooling to ambient temperature, the reaction mixture was filtered and purified by preparative HPLC (method 4) to yield 3.0 mg of the desired compound as an off-white powder (2% yield).

LC-MS (method 10): $R_t$=2.21 min; MS (ESIpos): m/z=438 [M+H]$^+$ $^1$H-NMR (400 MHz, DMSO-d$_6$) δ [ppm]: −0.008 (3.14), 0.008 (2.65), 1.290 (5.10), 1.308 (10.87), 1.316 (0.75), 1.326 (5.25), 2.379 (14.55), 2.419 (0.55), 2.519 (1.62), 2.524 (1.22), 2.670 (0.44), 2.907 (16.00), 2.951 (0.51), 4.231 (1.47), 4.249 (4.72), 4.266 (4.74), 4.284 (1.53), 7.367 (1.06), 7.469 (0.97), 7.487 (0.86), 7.531 (1.31), 7.550 (1.97), 7.568 (1.00), 7.805 (2.05), 7.823 (1.81), 8.574 (1.77), 9.726 (0.41), 13.487 (1.28).

Example 52

N-(4-chloro-1-methyl-5-phenyl-1H-pyrazol-3-yl)-6-(3,5-dimethyl-1H-pyrazol-1-yl)pyrimidin-4-amine

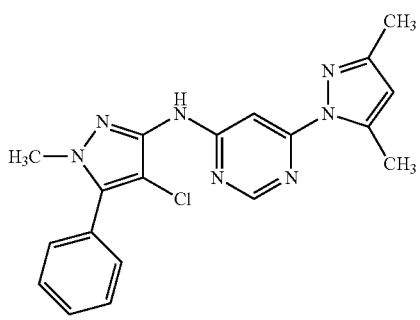 [SMILES: Cc1cc(C)n(-c2cc(Nc3nn(C)c(-c4ccccc4)c3Cl)ncn2)n1]

In a microwave tube, 4-chloro-1-methyl-5-phenyl-1H-pyrazol-3-amine (109 mg, 527 μmol) and sodium phenoxide (83.5 mg, 719 μmol) were suspended in 1,4-dioxane (1.2 mL) and degassed by passing an Argon stream through the suspension. Tris(dibenzylidenaceton)dipalladium (5.71 mg, 6.23 μmol), Xantphos (8.32 mg, 14.4 μmol) and 4-chloro-6-(3,5-dimethyl-1H-pyrazol-1-yl)pyrimidine (100 mg, 479 mol) were added and the reaction vessel was sealed. The reaction mixture was heated at 80° C. overnight. After cooling to ambient temperature, the reaction mixture was filtered and purified by preparative HPLC (method 4) to yield 85.0 mg of the desired compound as an off-white powder (47% yield).

LC-MS (method 10): $R_t$=2.16 min; MS (ESIpos): m/z=380 [M+H]$^+$ $^1$H-NMR (400 MHz, DMSO-d$_6$) δ [ppm]: −0.008 (1.05), 0.008 (0.96), 2.189 (13.99), 2.629 (11.87), 3.784 (16.00), 6.143 (3.13), 7.256 (3.75), 7.257 (3.75), 7.526 (0.45), 7.539 (0.89), 7.545 (0.70), 7.550 (0.92), 7.555 (0.99), 7.561 (1.26), 7.568 (1.03), 7.573 (1.43), 7.580 (13.50), 7.589 (3.38), 7.594 (2.39), 8.471 (2.84), 8.473 (2.84), 9.516 (3.15).

Example 53

6-(4-chloro-3,5-dimethyl-1H-pyrazol-1-yl)-N-(4-chloro-1-methyl-5-phenyl-1H-pyrazol-3-yl)pyrimidin-4-amine

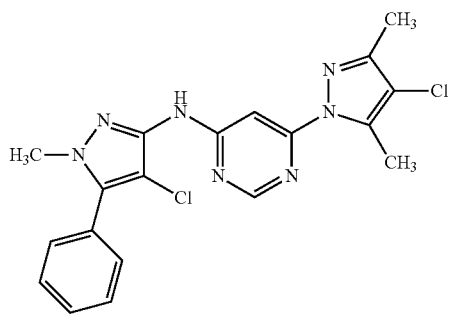 [SMILES: Cc1nn(-c2cc(Nc3nn(C)c(-c4ccccc4)c3Cl)ncn2)c(C)c1Cl]

In a microwave tube, 4-chloro-1-methyl-5-phenyl-1H-pyrazol-3-amine (94.0 mg, 452 μmol) and sodium phenoxide (71.6 mg, 617 μmol) were suspended in 1,4-dioxane (1.1 mL) and degassed by passing an Argon stream through the suspension. Tris(dibenzylidenaceton)dipalladium (4.90 mg, 5.35 μmol), Xantphos (7.14 mg, 12.3 μmol) and 4-chloro-6-(4-chloro-3,5-dimethyl-1H-pyrazol-1-yl)pyrimidine (100 mg, 411 μmol) were added and the reaction vessel was sealed. The reaction mixture was heated at 80° C. overnight. After cooling to ambient temperature, the reaction mixture was filtered and purified by preparative HPLC (method 5) to yield 25.0 mg of the desired compound as an off-white powder (12% yield).

$^1$H-NMR (400 MHz, DMSO-d$_6$) δ [ppm]: −0.151 (0.18), −0.009 (1.54), 0.007 (1.48), 0.145 (0.18), 2.227 (16.00), 2.327 (0.19), 2.365 (0.16), 2.523 (0.63), 2.645 (14.27), 2.669 (4.76), 2.709 (0.17), 3.783 (14.77), 7.236 (0.91), 7.258 (0.78), 7.272 (3.58), 7.315 (0.21), 7.333 (0.50), 7.352 (0.31), 7.482 (0.71), 7.503 (0.87), 7.522 (0.58), 7.539 (0.79), 7.548 (0.70), 7.555 (0.98), 7.560 (1.20), 7.565 (1.07), 7.578 (12.18), 7.586 (2.90), 7.593 (1.90), 7.611 (0.32), 8.508 (2.56), 8.717 (0.75), 9.635 (2.74).

Example 54

6-(4-chloro-3,5-dimethyl-1H-pyrazol-1-yl)-N-(4-chloro-5-phenyl-1H-pyrazol-3-yl)pyrimidin-4-amine

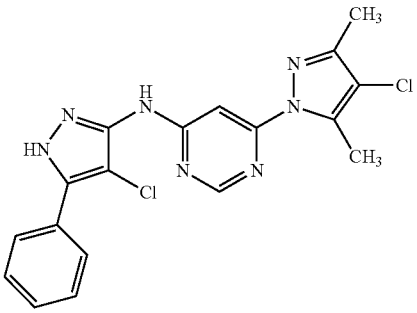 [SMILES: Cc1nn(-c2cc(Nc3n[nH]c(-c4ccccc4)c3Cl)ncn2)c(C)c1Cl]

In a microwave tube, 4-chloro-5-phenyl-1H-pyrazol-3-amine (87.6 mg, 452 μmol) and sodium phenoxide (71.6 mg, 617 μmol) were suspended in 1,4-dioxane (1.1 mL) and degassed by passing an Argon stream through the suspension. Tris(dibenzylidenaceton)dipalladium (4.90 mg, 5.35 µmol), Xantphos (7.14 mg, 12.3 µmol) and 4-chloro-6-(4-chloro-3,5-dimethyl-1H-pyrazol-1-yl)pyrimidine (100 mg, 411 µmol) were added and the reaction vessel was sealed. The reaction mixture was heated at 80° C. overnight. After cooling to ambient temperature, the reaction mixture was filtered and purified by preparative HPLC (method 4) to yield 25.0 mg of the desired compound (4% yield).

LC-MS (method 10): $R_t$=2.35 min; MS (ESIpos): m/z=400 [M+H]$^+$ $^1$H-NMR (400 MHz, DMSO-d$_6$) δ [ppm]: −0.149 (0.58), −0.008 (5.45), 0.008 (4.27), 0.015 (0.55), 0.146 (0.58), 2.073 (0.62), 2.217 (11.13), 2.266 (13.28), 2.328 (0.60), 2.366 (0.57), 2.519 (2.56), 2.524 (1.96), 2.560 (0.54), 2.653 (16.00), 2.670 (1.30), 2.679 (13.87), 2.710 (0.66), 7.364 (1.52), 7.398 (0.46), 7.432 (0.52), 7.447 (0.66), 7.478 (1.30), 7.495 (1.17), 7.540 (1.41), 7.559 (2.01), 7.577 (1.00), 7.797 (2.01), 7.815 (1.87), 7.934 (2.01), 7.937 (1.94), 8.523 (1.45), 8.953 (1.80), 9.623 (1.63), 13.483 (1.90).

Example 55

N-[4-chloro-5-(2,4-difluorophenyl)-1-methyl-1H-pyrazol-3-yl]-6-(3,5-dimethyl-1H-pyrazol-1-yl)pyrimidin-4-amine

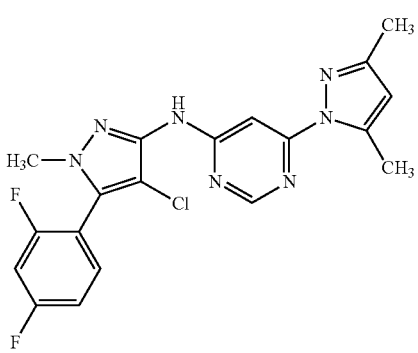 [SMILES: Cc1cc(C)n(-c2cc(Nc3nn(C)c(-c4ccc(F)cc4F)c3Cl)ncn2)n1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-5-(2,4-difluorophenyl)-1-methyl-1H-pyrazol-3-amine (100 mg, 410 µmol) and 4-chloro-6-(3,5-dimethyl-1H-pyrazol-1-yl)pyrimidine (94.2 mg, 451 µmol) to yield 27.0 mg of the desired product (16% yield).

LC-MS (method 11): $R_t$=1.45 min; MS (ESIpos): m/z=416 [M+H]$^+$ $^1$H-NMR (400 MHz, DMSO-d$_6$) δ [ppm]: 2.11-2.26 (m, 3H), 2.63 (s, 3H), 3.71 (s, 3H), 6.14 (s, 1H), 7.26 (s, 1H), 7.34 (td, 1H), 7.55 (td, 1H), 7.69 (td, 1H), 8.47 (s, 1H), 9.55 (s, 1H).

Example 56

N-[4-chloro-5-(2,4-difluorophenyl)-1-methyl-1H-pyrazol-3-yl]-6-(4-chloro-3,5-dimethyl-1H-pyrazol-1-yl)pyrimidin-4-amine

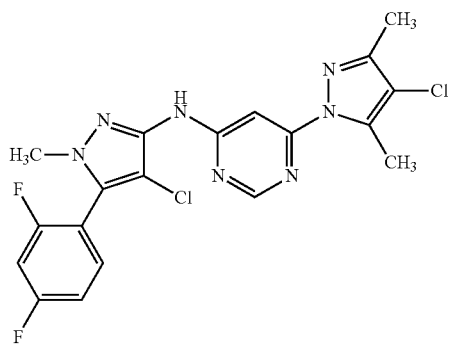 [SMILES: Cc1nn(-c2cc(Nc3nn(C)c(-c4ccc(F)cc4F)c3Cl)ncn2)c(C)c1Cl]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-5-(2,4-difluorophenyl)-1-methyl-1H-pyrazol-3-amine (100 mg, 410 µmol) and 4-chloro-6-(4-chloro-3,5-dimethyl-1H-pyrazol-1-yl)pyrimidine (110 mg, 451 µmol) to yield 42.2 mg of the desired product (23% yield).

LC-MS (method 10): $R_t$=2.46 min; MS (ESIpos): m/z=450 [M+H]$^+$ $^1$H-NMR (400 MHz, DMSO-d$_6$) δ [ppm]: 2.229 (15.92), 2.646 (16.00), 2.671 (1.10), 3.711 (14.26), 7.273 (4.58), 7.314 (0.64), 7.320 (0.66), 7.335 (1.36), 7.341 (1.33), 7.356 (0.74), 7.362 (0.73), 7.529 (0.76), 7.536 (0.73), 7.554 (1.25), 7.559 (1.21), 7.578 (0.74), 7.584 (0.69), 7.664 (0.73), 7.685 (1.42), 7.702 (1.41), 7.723 (0.66), 8.511 (4.29), 9.673 (2.39).

Example 57

N-[4-chloro-5-(2,4-difluorophenyl)-1-methyl-1H-pyrazol-3-yl]-6-(3-methyl-1H-indazol-1-yl)pyrimidin-4-amine

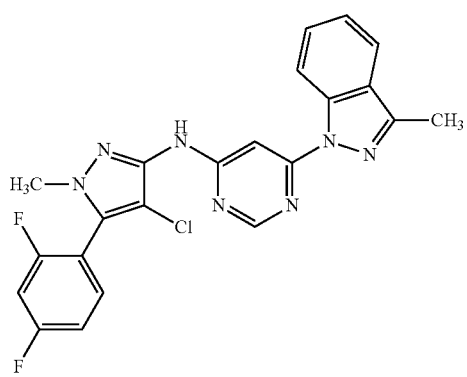 [SMILES: Cc1nn(-c2cc(Nc3nn(C)c(-c4ccc(F)cc4F)c3Cl)ncn2)c2ccccc12]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-5-(2,4-difluorophenyl)-1-methyl-1H-pyrazol-3-amine (100 mg, 410 µmol) and 1-(6-chloropyrimidin-4-yl)-3-methyl-1H-indazole (110 mg, 451 µmol) to yield 44.1 mg of the desired product (24% yield).

LC-MS (method 11): R$_t$=1.60 min; MS (ESIpos): m/z=452 [M+H]$^+$ $^1$H-NMR (400 MHz, DMSO-d$_6$) δ [ppm]: 2.598 (16.00), 3.736 (14.69), 7.327 (1.76), 7.346 (3.70), 7.370 (5.57), 7.539 (0.86), 7.546 (0.82), 7.562 (2.24), 7.580 (2.07), 7.598 (1.30), 7.681 (0.76), 7.702 (1.46), 7.719 (1.51), 7.740 (0.66), 7.844 (2.31), 7.864 (2.12), 8.150 (1.43), 8.579 (4.68), 8.742 (2.49), 8.763 (2.39), 9.558 (3.83).

Example 58

[1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanol

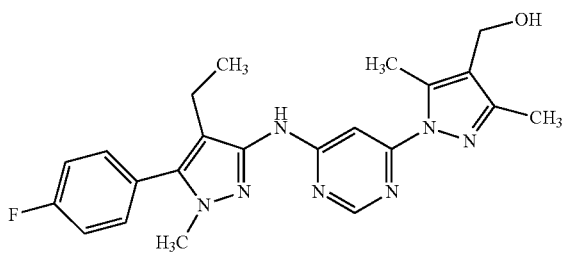 [SMILES: CCc1c(Nc2cc(-n3nc(C)c(CO)c3C)ncn2)nn(C)c1-c1ccc(F)cc1]

A solution of ethyl 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylate (80.0 mg, 173 µmol) in THF (3.0 mL) was treated at 0° C. with diisobutylaluminium hydride (950 µL, 1.0 M in THF, 950 µmol). The mixture was stirred for 1 hour at 0° C. Additional 5.5 eq of diisobutylaluminium hydride were added and it was stirred at room temperature overnight. The mixture was diluted with methanol and aqueous hydrochloric acid (1M) and extracted with ethyl acetate. The combined organic phases were washed with saturated sodium hydrogen carbonate solution, brine, dried over sodium sulfate and the solvent was removed under reduced pressure. The crude mixture was purified by preparative HPLC (method 3) to yield 8.00 mg (11% yield) of the desired product.

LC-MS (method 10): R$_t$=1.72 min; MS (ESIpos): m/z=422 [M+H]$^+$ $^1$H-NMR (500 MHz, DMSO-d$_6$) δ [ppm]: 0.875 (3.62), 0.891 (7.80), 0.905 (3.61), 1.092 (0.78), 1.358 (1.84), 2.210 (14.68), 2.290 (0.92), 2.305 (2.54), 2.320 (2.46), 2.335 (0.90), 2.615 (15.32), 3.377 (0.42), 3.652 (16.00), 4.299 (3.11), 4.307 (3.11), 4.684 (0.72), 4.694 (1.23), 4.704 (0.66), 7.328 (2.33), 7.362 (2.07), 7.366 (0.90), 7.380 (4.35), 7.397 (2.48), 7.504 (2.51), 7.509 (1.24), 7.515 (2.83), 7.522 (2.32), 7.529 (1.02), 7.533 (1.94), 8.446 (3.52), 9.320 (2.36).

Example 59 ethyl 1-(6-{[3-(4-fluorophenyl)-1,4-dimethyl-1H-pyrazol-5-yl]amino}pyrimidin-4-yl)-3,5-dimethyl-1H-pyrazole-4-carboxylate

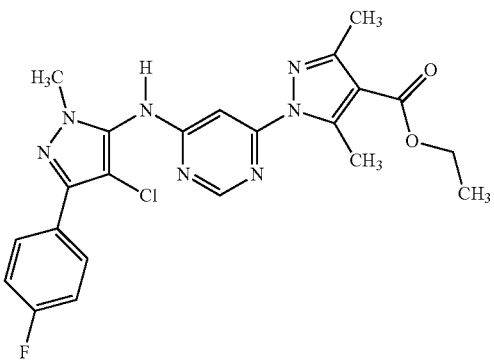 [SMILES: CCOC(=O)c1c(C)nn(-c2cc(Nc3c(Cl)c(-c4ccc(F)cc4)nn3C)ncn2)c1C]

In a microwave tube, ethyl 1-(6-chloropyrimidin-4-yl)-3,5-dimethyl-1H-pyrazole-4-carboxylate (100 mg, 356 µmol), 3-(4-fluorophenyl)-1,4-dimethyl-1H-pyrazol-5-amine (80.4 mg, 392 µmol) and sodium phenoxide (62.0 mg, 534 µmol) were suspended in 1,4-dioxane (1.0 mL) and degassed by passing an Argon stream through the suspension. Tris(dibenzylideneacetone)dipalladium (4.24 mg, 4.63 µmol) and Xantphos (6.18 mg, 10.7 µmol) were added and the reaction vessel was sealed. The reaction mixture was heated at 80° C. overnight. After cooling to ambient temperature, the reaction mixture was filtered and purified by preparative HPLC (method 4) to yield 71 mg of the desired compound (42% yield).

LC-MS (method 10): R$_t$=2.19 min; MS (ESIpos): m/z=450 [M+H]$^+$ $^1$H-NMR (400 MHz, DMSO-d$_6$) δ [ppm]: 1.31 (t, J=7.1 Hz, 3H), 2.02 (s, 3H), 2.91 (s, 3H), 3.66 (s, 3H), 4.26 (q, J=7.2 Hz, 2H), 6.4-7.7 (br s, 1H), 7.22-7.33 (m, 2H), 7.71 (dd, J=8.4, 5.8 Hz, 2H), 8.55 (br s, 1H), 9.60 (br s, 1H).

Example 60 ethyl 1-(6-{[5-(4-fluorophenyl)-4-methyl-1H-pyrazol-3-yl]amino}pyrimidin-4-yl)-3,5-dimethyl-1H-pyrazole-4-carboxylate

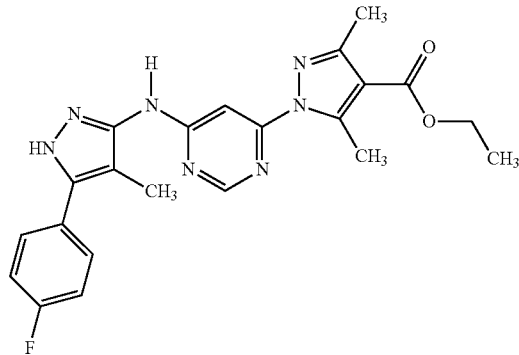 [SMILES: CCOC(=O)c1c(C)nn(-c2cc(Nc3n[nH]c(-c4ccc(F)cc4)c3C)ncn2)c1C]

In a microwave tube, ethyl 1-(6-chloropyrimidin-4-yl)-3,5-dimethyl-1H-pyrazole-4-carboxylate (100 mg, 356 μmol), 5-(4-fluorophenyl)-4-methyl-1H-pyrazol-3-amine (74.9 mg, 392 μmol) and sodium phenoxide (62.0 mg, 534 μmol) were suspended in 1,4-dioxane (1.0 mL) and degassed by passing an Argon stream through the suspension. Tris(dibenzylidenacetone)→dipalladium (4.24 mg, 4.63 μmol) and Xantphos (6.18 mg, 10.7 μmol) were added and the reaction vessel was sealed. The reaction mixture was heated at 80° C. overnight. After cooling to ambient temperature, the reaction mixture was filtered and purified by preparative HPLC (method 4) to yield 18.5 mg of the desired compound as an off-white powder (12% yield).

LC-MS (method 10): $R_t$=2.07 min; MS (ESIpos): m/z=436 [M+H]$^+$ $^1$H-NMR (400 MHz, DMSO-$d_6$) δ [ppm]: 1.31 (t, J=7.1 Hz, 3H), 2.82 (s, 3H), 2.37 (s, 3H), 2.89 (s, 3H), 4.25 (q, J=7.2 Hz, 2H), 7.31-7.41 (m, 2H), 7.51 (br s, 1H), 7.65 (dd, J=8.7, 5.4 Hz, 2H), 8.54 (s, 1H), 9.61 (s, 1H), 12.84 (s, 1H).

Example 61 ethyl 1-(6-{[5-(4-fluorophenyl)-1,4-dimethyl-1H-pyrazol-3-yl]amino}pyrimidin-4-yl)-3,5-dimethyl-1H-pyrazole-4-carboxylate

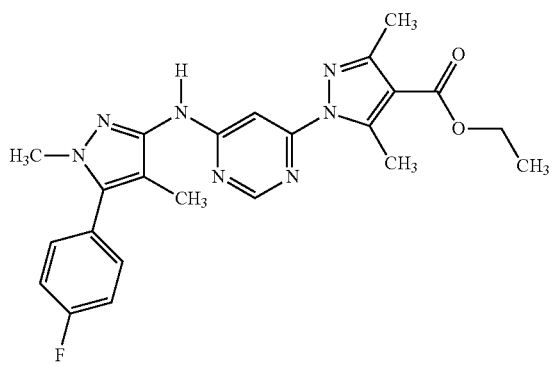 [SMILES: CCOC(=O)c1c(C)nn(-c2cc(Nc3nn(C)c(-c4ccc(F)cc4)c3C)ncn2)c1C]

In a microwave tube, ethyl 1-(6-chloropyrimidin-4-yl)-3,5-dimethyl-1H-pyrazole-4-carboxylate (100 mg, 356 μmol), 5-(4-fluorophenyl)-1,4-dimethyl-1H-pyrazol-3-amine (80.4 mg, 392 μmol) and sodium phenoxide (62.0 mg, 534 μmol) were suspended in 1,4-dioxane (1.0 mL) and degassed by passing an Argon stream through the suspension. Tris(dibenzylidenacetone)-dipalladium (4.24 mg, 4.63 μmol) and Xantphos (6.18 mg, 10.7 μmol) were added and the reaction vessel was sealed. The reaction mixture was heated at 80° C. overnight. After cooling to ambient temperature, the reaction mixture was filtered and purified by preparative HPLC (method 4) to yield 22.0 mg of the desired compound as an off-white powder (14% yield).

LC-MS (method 10): $R_t$=2.23 min; MS (ESIpos): m/z=450 [M+H]$^+$ $^1$H-NMR (400 MHz, DMSO-$d_6$) δ [ppm]: 1.31 (t, J=7.1 Hz, 3H), 1.86 (s, 3H), 2.38 (s, 3H), 2.89 (s, 3H), 3.69 (s, 3H), 4.26 (q, J=7.2 Hz, 2H), 7.34-7.46 (m, 3H), 7.49-7.56 (m, 2H), 8.53 (s, 3H), 9.60 (s, 3H).

Example 62

N-(1,4-dimethyl-5-phenyl-1H-pyrazol-3-yl)-6-(3,5-dimethyl-1H-pyrazol-1-yl)pyrimidin-4-amine

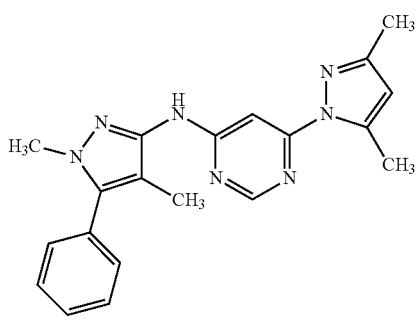 [SMILES: Cc1cc(C)n(-c2cc(Nc3nn(C)c(-c4ccccc4)c3C)ncn2)n1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-6-(3,5-dimethyl-1H-pyrazol-1-yl)pyrimidine (75.0 mg, 359 μmol) and 1,4-dimethyl-5-phenyl-1H-pyrazol-3-amine (74.0 mg, 395 μmol) to yield 43.9 mg of the desired product (32% yield).

LC-MS (method 9): $R_t$=1.06 min; MS (ESIpos): m/z=360 [M+H]$^+$ $^1$H-NMR (400 MHz, DMSO-$d_6$) δ [ppm]: −0.008 (1.43), 0.008 (1.20), 1.073 (0.71), 1.091 (1.46), 1.109 (0.71), 1.647 (0.67), 1.862 (0.41), 2.030 (16.00), 2.172 (3.89), 2.631 (13.69), 3.375 (0.74), 3.392 (0.76), 3.666 (11.36), 3.702 (0.51), 6.144 (3.02), 7.313 (0.68), 7.331 (1.89), 7.350 (1.33), 7.368 (0.62), 7.384 (0.55), 7.397 (0.64), 7.422 (2.38), 7.441 (4.01), 7.460 (2.06), 7.678 (2.97), 7.696 (2.55), 8.474 (1.06), 9.402 (2.18).

Example 63

6-(4-chloro-3,5-dimethyl-1H-pyrazol-1-yl)-N-[1-(4-fluorophenyl)-3,5-dimethyl-1H-pyrazol-4-yl]pyrimidin-4-amine

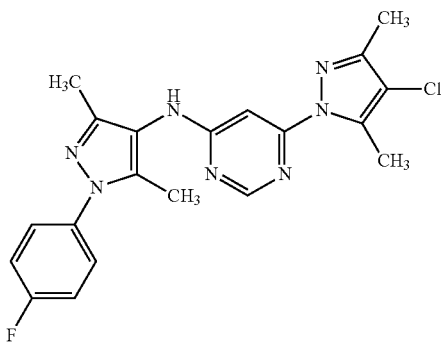 [SMILES: Cc1nn(-c2cc(Nc3c(C)nn(-c4ccc(F)cc4)c3C)ncn2)c(C)c1Cl]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 1-(4-fluorophenyl)-3,5-dimethyl-1H-pyrazol-4-amine (100 mg, 487 µmol) and 4-chloro-6-(4-chloro-3,5-dimethyl-1H-pyrazol-1-yl)pyrimidine (130 mg, 536 µmol) to yield 43.9 mg of the desired product (32% yield).

LC-MS (method 11): $R_t$=1.49 min; MS (ESIpos): m/z=412 [M+H]$^+$ $^1$H-NMR (400 MHz, DMSO-d$_6$) δ [ppm]: 2.075 (16.00), 2.175 (11.07), 2.204 (1.86), 2.632 (13.66), 7.335 (1.44), 7.357 (3.04), 7.379 (1.77), 7.591 (1.48), 8.971 (1.09).

Example 64

6-[5-(difluoromethyl)-3-methyl-1H-pyrazol-1-yl]-N-[4-ethyl-5-(4-fluorophenyl)-1-methyl-1H-pyrazol-3-yl]pyrimidin-4-amine

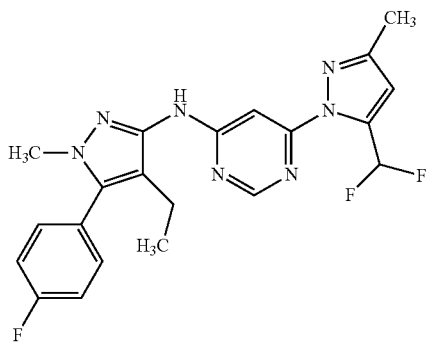 [SMILES: CCc1c(Nc2cc(-n3nc(C)cc3C(F)F)ncn2)nn(C)c1-c1ccc(F)cc1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-ethyl-5-(4-fluorophenyl)-1-methyl-1H-pyrazol-3-amine (81.5 mg, 372 µmol) and 4-chloro-6-[5-(difluoromethyl)-3-methyl-1H-pyrazol-1-yl]pyrimidine (100 mg, 409 µmol) to yield 66.0 mg of the desired product (37% yield).

LC-MS (method 14): $R_t$=3.91 min; MS (ESIpos): m/z=428 [M+H]$^+$ $^1$H-NMR (400 MHz, DMSO-d$_6$) δ [ppm]: −0.008 (1.66), 0.008 (1.57), 0.868 (3.50), 0.887 (8.17), 0.906 (3.62), 2.291 (14.22), 2.301 (4.67), 2.323 (2.52), 2.342 (0.77), 2.523 (0.88), 3.662 (16.00), 6.769 (3.74), 6.853 (0.63), 7.252 (0.70), 7.273 (0.55), 7.292 (0.71), 7.343 (0.44), 7.361 (2.29), 7.383 (5.78), 7.399 (1.08), 7.405 (2.81), 7.490 (0.60), 7.506 (2.90), 7.511 (1.69), 7.519 (2.94), 7.528 (2.48), 7.536 (0.94), 7.541 (1.93), 7.691 (1.21), 7.807 (0.52), 7.827 (2.49), 7.963 (1.07), 8.471 (2.65), 8.720 (0.61), 9.541 (1.63).

Example 65

N-(4-chloro-1-methyl-3-phenyl-1H-pyrazol-5-yl)-6-(3,5-dimethyl-1H-pyrazol-1-yl)pyrimidin-4-amine

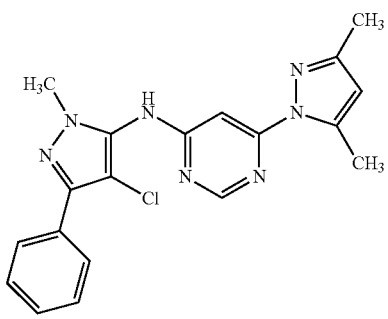 [SMILES: Cc1cc(C)n(-c2cc(Nc3c(Cl)c(-c4ccccc4)nn3C)ncn2)n1]

In a microwave tube, 4-chloro-1-methyl-3-phenyl-1H-pyrazol-5-amine (109 mg, 527 µmol) and sodium phenoxide (83.5 mg, 719 µmol) were suspended in 1,4-dioxane (1.2 mL) and degassed by passing an Argon stream through the suspension. Tris(dibenzylidenaceton)dipalladium (5.71 mg, 6.23 µmol), Xantphos (8.32 mg, 14.4 µmol) and 4-chloro-6-(3,5-dimethyl-1H-pyrazol-1-yl)pyrimidine (100 mg, 479 mol) were added and the reaction vessel was sealed. The reaction mixture was heated at 80° C. overnight. After cooling to ambient temperature, the reaction mixture was filtered and purified by preparative HPLC (method 4) to yield 15.0 mg of the desired compound (8% yield).

LC-MS (method 10): $R_t$=2.14 min; MS (ESIpos): m/z=380 [M+H]$^+$ $^1$H-NMR (400 MHz, DMSO-d$_6$) δ [ppm]: 2.19 (s, 3H), 2.64 (s, 3H), 3.73 (s, 3H), 6.16 (s, 1H), 7.07 (br s, 1H), 7.37-7.43 (m, 1H), 7.46-7.54 (m, 2H), 7.83-7.89 (m, 2H), 8.50 (s, 1H), 9.68 (s, 1H).

Example 66

6-[5-(difluoromethyl)-3-methyl-1H-pyrazol-1-yl]-N-[5-(4-fluorophenyl)-4-methyl-1H-pyrazol-3-yl]pyrimidin-4-amine

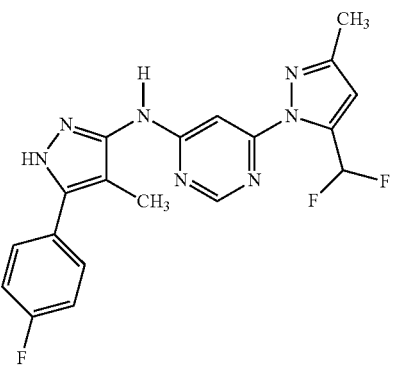 [SMILES: Cc1cc(C(F)F)n(-c2cc(Nc3n[nH]c(-c4ccc(F)cc4)c3C)ncn2)n1]

In a microwave tube, 4-chloro-6-[5-(difluoromethyl)-3-methyl-1H-pyrazol-1-yl]pyrimidine (100 mg, 409 µmol), 5-(4-fluorophenyl)-4-methyl-1H-pyrazol-3-amine (86.0 mg, 450 µmol) and sodium phenoxide (71.2 mg, 613 µmol) were suspended in 1,4-dioxane (1.1 mL) and degassed by passing an Argon stream through the suspension. Tris(dibenzylidenacetone)dipalladium (4.87 mg, 5.31 µmol) and Xantphos (7.10 mg, 12.3 µmol) were added and the reaction vessel was sealed. The reaction mixture was heated at 80° C. overnight. After cooling to ambient temperature, the reaction mixture was filtered and purified by preparative HPLC (method 4) to yield 19.0 mg of the desired compound (9% yield)

LC-MS (method 10): $R_t$=2.03 min; MS (ESIpos): m/z=400 [M+H]$^+$ $^1$H-NMR (400 MHz, DMSO-d$_6$) δ [ppm]: 2.06 (s, 3H), 2.28 (s, 3H), 6.77 (s, 1H), 7.32-7.41 (m, 2H), 7.49-7.56 (br s, 1H), 7.65 (dd, J=8.7, 5.3 Hz, 2H), 7.83 (t, J=55.9 Hz, 1H), 8.49 (s, 1H), 9.61 (s, 1H), 12.88 (s, 1H).

Example 67

6-(4-chloro-3,5-dimethyl-1H-pyrazol-1-yl)-N-[5-(4-fluorophenyl)-1,4-dimethyl-1H-pyrazol-3-yl]pyrimidin-4-amine

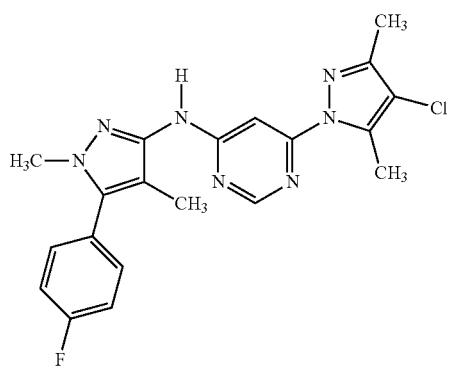 [SMILES: Cc1nn(-c2cc(Nc3nn(C)c(-c4ccc(F)cc4)c3C)ncn2)c(C)c1Cl]

In a microwave tube, 4-chloro-6-(4-chloro-3,5-dimethyl-1H-pyrazol-1-yl)pyrimidine (100 mg, 411 µmol), 5-(4-fluorophenyl)-1,4-dimethyl-1H-pyrazol-3-amine (92.9 mg, 452 µmol) and sodium phenoxide (71.6 mg, 617 µmol) were suspended in 1,4-dioxane (1.1 mL) and degassed by passing an Argon stream through the suspension. Tris(dibenzylidenacetone)dipalladium (4.90 mg, 5.35 µmol) and Xantphos (7.14 mg, 12.3 µmol) were added and the reaction vessel was sealed. The reaction mixture was heated at 80° C. overnight. After cooling to ambient temperature, the reaction mixture was filtered and purified by preparative HPLC (method 4) to yield 59.0 mg of the desired compound (35% yield).

$^1$H-NMR (400 MHz, DMSO-d$_6$) δ [ppm]: −0.150 (0.44), −0.009 (4.38), 0.007 (3.43), 0.145 (0.48), 1.850 (12.78), 2.222 (14.83), 2.327 (0.49), 2.365 (0.50), 2.523 (1.69), 2.640 (15.99), 2.670 (0.72), 2.709 (0.50), 3.687 (16.00), 7.357 (1.96), 7.379 (4.44), 7.401 (3.27), 7.509 (2.56), 7.523 (2.86), 7.531 (2.20), 7.545 (1.91), 8.482 (2.67), 9.503 (2.34).

Example 68

6-(4-chloro-3,5-dimethyl-1H-pyrazol-1-yl)-N-[3-(4-fluorophenyl)-1,4-dimethyl-1H-pyrazol-5-yl]pyrimidin-4-amine

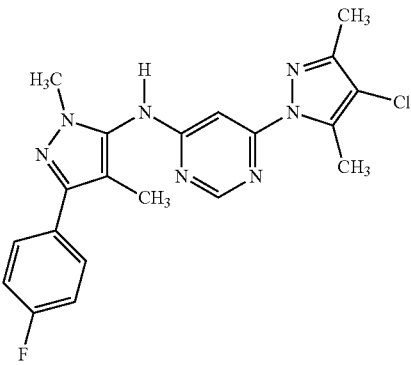 [SMILES: Cc1nn(-c2cc(Nc3c(C)c(-c4ccc(F)cc4)nn3C)ncn2)c(C)c1Cl]

In a microwave tube, 4-chloro-6-(4-chloro-3,5-dimethyl-1H-pyrazol-1-yl)pyrimidine (100 mg, 411 mol), 3-(4-fluorophenyl)-1,4-dimethyl-1H-pyrazol-5-amine (92.9 mg, 452 µmol) and sodium phenoxide (71.6 mg, 617 µmol) were suspended in 1,4-dioxane (1.1 mL) and degassed by passing an Argon stream through the suspension. Tris(dibenzylidenacetone)dipalladium (4.90 mg, 5.35 µmol) and Xantphos (7.14 mg, 12.3 µmol) were added and the reaction vessel was sealed. The reaction mixture was heated at 80° C. overnight. After cooling to ambient temperature, the reaction mixture was filtered and purified by preparative HPLC (method 4) to yield 58.0 mg of the desired compound (35% yield).

$^1$H-NMR (400 MHz, DMSO-d$_6$) δ [ppm]: 2.01 (s, 3H), 2.21 (br s, 3H), 2.65 (s, 3H), 3.66 (s, 3H), 6.84-7.58 (br s, 1H), 7.23-7.31 (m, 2H), 7.67-7.75 (m, 2H), 8.52 (s. 1H), 9.51 (s, 1H).

Example 69

6-[5-(difluoromethyl)-3-methyl-1H-pyrazol-1-yl]-N-[5-(4-fluorophenyl)-1,4-dimethyl-1H-pyrazol-3-yl]pyrimidin-4-amine

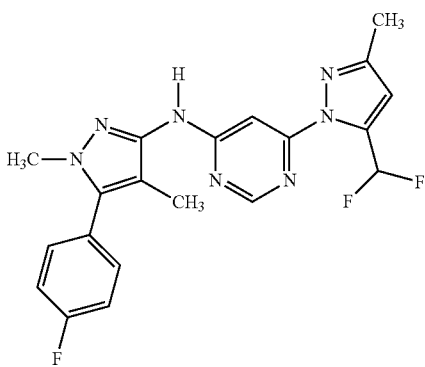 [SMILES: Cc1cc(C(F)F)n(-c2cc(Nc3nn(C)c(-c4ccc(F)cc4)c3C)ncn2)n1]

In a microwave tube, 4-chloro-6-[5-(difluoromethyl)-3-methyl-1H-pyrazol-1-yl]pyrimidine (100 mg, 409 µmol), 5-(4-fluorophenyl)-1,4-dimethyl-1H-pyrazol-3-amine (92.3 mg, 450 µmol) and sodium phenoxide (71.2 mg, 613 µmol)

were suspended in 1,4-dioxane (1.1 mL) and degassed by passing an Argon stream through the suspension. Tris(dibenzylideneacetone)dipalladium (4.87 mg, 5.31 μmol) and Xantphos (7.10 mg, 12.3 μmol) were added and the reaction vessel was sealed. The reaction mixture was heated at 80° C. overnight. After cooling to ambient temperature, the reaction mixture was filtered and purified by preparative HPLC (method 4) to yield 53.4 mg of the desired compound (30% yield).

LC-MS (method 10): R$_t$=2.18 min; MS (ESIpos): m/z=414 [M+H]$^+$ $^1$H-NMR (400 MHz, DMSO-d$_6$) δ [ppm]: 1.854 (11.61), 2.294 (14.14), 3.698 (16.00), 6.770 (4.07), 7.340 (0.50), 7.359 (2.09), 7.381 (5.08), 7.404 (2.78), 7.436 (0.92), 7.459 (0.91), 7.516 (2.60), 7.529 (2.91), 7.537 (2.25), 7.551 (1.92), 7.690 (1.18), 7.779 (0.48), 7.826 (2.57), 7.963 (1.05), 8.476 (3.23), 9.592 (1.96).

Example 70

6-[5-(difluoromethyl)-3-methyl-1H-pyrazol-1-yl]-N-[3-(4-fluorophenyl)-1,4-dimethyl-1H-pyrazol-5-yl]pyrimidin-4-amine

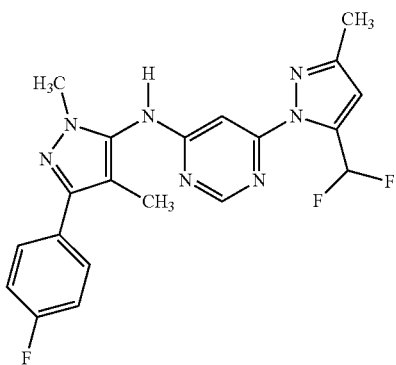 [SMILES: Cc1cc(C(F)F)n(-c2cc(Nc3c(C)c(-c4ccc(F)cc4)nn3C)ncn2)n1]

In a microwave tube, 4-chloro-6-[5-(difluoromethyl)-3-methyl-1H-pyrazol-1-yl]pyrimidine (100 mg, 409 μmol), 5-(4-fluorophenyl)-1,4-dimethyl-1H-pyrazol-3-amine (92.3 mg, 450 μmol) and sodium phenoxide (71.2 mg, 613 μmol) were suspended in 1,4-dioxane (1.1 mL) and degassed by passing an Argon stream through the suspension. Tris(dibenzylideneacetone)dipalladium (4.87 mg, 5.31 μmol) and Xantphos (7.10 mg, 12.3 μmol) were added and the reaction vessel was sealed. The reaction mixture was heated at 80° C. overnight. After cooling to ambient temperature, the reaction mixture was filtered and purified by preparative HPLC (method 4) to yield 53.4 mg of the desired compound (30% yield).

LC-MS (method 10): R$_t$=2.13 min; MS (ESIpos): m/z=414 [M+H]$^+$ $^1$H-NMR (400 MHz, DMSO-d$_6$) δ [ppm]: 2.02 (s, 3H), 2.29 (s, 3H), 3.67 (s, 3H), 6.42-7.48 (br s, 1H), 6.79 (s, 1H), 7.27 (t, J=8.9 Hz, 2H), 7.68-7.76 (m, 2H), 7.82 (t, J=54.3 Hz, 1H), 8.51 (s, 1H), 9.60 (s, 1H).

Example 71

6-(3,5-dimethyl-1H-pyrazol-1-yl)-N-[3-(4-fluorophenyl)-1,4-dimethyl-1H-pyrazol-5-yl]pyrimidin-4-amine

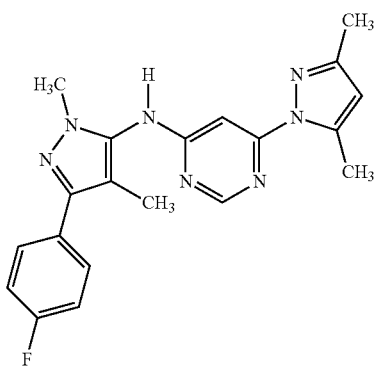 [SMILES: Cc1cc(C)n(-c2cc(Nc3c(C)c(-c4ccc(F)cc4)nn3C)ncn2)n1]

In a microwave tube, 4-chloro-6-(3,5-dimethyl-1H-pyrazol-1-yl)pyrimidine (100 mg, 479 μmol), 3-(4-fluorophenyl)-1,4-dimethyl-1H-pyrazol-5-amine (108 mg, 527 μmol) and sodium phenoxide (83.5 mg, 719 μmol) were suspended in 1,4-dioxane (1.1 mL) and degassed by passing an Argon stream through the suspension. Tris(dibenzylideneacetone)dipalladium (5.71 mg, 6.23 μmol) and Xantphos (8.32 mg, 14.4 μmol) were added and the reaction vessel was sealed. The reaction mixture was heated at 80° C. overnight. After cooling to ambient temperature, the reaction mixture was filtered and purified by preparative HPLC (method 4) to yield 53.2 mg of the desired compound (29% yield).

LC-MS (method 10): R$_t$=2.03 min; MS (ESIpos): m/z=378 [M+H]$^+$ $^1$H-NMR (400 MHz, DMSO-d$_6$) δ [ppm]: 2.02 (s, 3H), 2.17 (br s, 3H), 2.63 (s, 3H), 3.66 (s, 3H), 6.15 (s, 1H), 6.31-7.49 (br s, 1H), 7.27 (t, J=8.9 Hz, 2H), 7.72 (dd, J=8.50, 5.7 Hz, 2H), 8.46 (s, 3H), 9.41 (s, 3H).

Example 72

6-(4-chloro-3,5-dimethyl-1H-pyrazol-1-yl)-N-[5-(4-fluorophenyl)-4-methyl-1H-pyrazol-3-yl]pyrimidin-4-amine

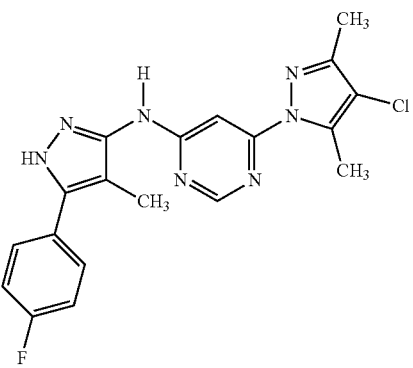 [SMILES: Cc1nn(-c2cc(Nc3n[nH]c(-c4ccc(F)cc4)c3C)ncn2)c(C)c1Cl]

In a microwave tube, 4-chloro-6-(4-chloro-3,5-dimethyl-1H-pyrazol-1-yl)pyrimidine (100 mg, 411 μmol), 5-(4-fluorophenyl)-4-methyl-1H-pyrazol-3-amine (86.5 mg, 452 µmol) and sodium phenoxide (71.6 mg, 617 µmol) were suspended in 1,4-dioxane (1.1 mL) and degassed by passing an Argon stream through the suspension. Tris(dibenzylidenacetone)dipalladium (4.90 mg, 5.35 µmol) and Xantphos (7.14 mg, 12.3 µmol) were added and the reaction vessel was sealed. The reaction mixture was heated at 80° C. overnight. After cooling to ambient temperature, the reaction mixture was filtered and purified by preparative HPLC (method 4) to yield 8.5 mg of the desired compound (5% yield).

LC-MS (method 10): Rt=2.21 min; MS (ESIpos): m/z=398 [M+H]$^+$ $^1$H-NMR (400 MHz, DMSO-d$_6$) δ [ppm]: 2.06 (s, 3H), 2.21 (s, 3H), 2.65 (s, 3H), 7.34-7.40 (m, 2H), 7.45-7.53 (br s, 1H), 7.61-7.67 (m, 2H), 8.48 (s, 1H), 9.51 (s, 1H), 12.87 (s, 1H).

Example 73

6-(3,5-dimethyl-1H-pyrazol-1-yl)-N-[5-(4-fluorophenyl)-1,4-dimethyl-1H-pyrazol-3-yl]pyrimidin-4-amine

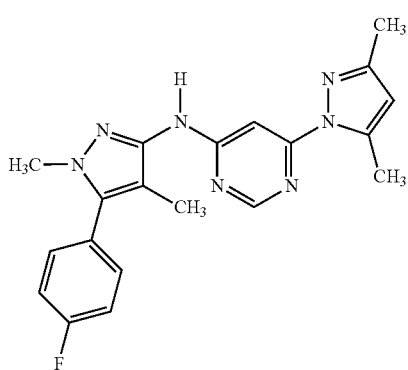 [SMILES: Cc1cc(C)n(-c2cc(Nc3nn(C)c(-c4ccc(F)cc4)c3C)ncn2)n1]

In a microwave tube, 4-chloro-6-(3,5-dimethyl-1H-pyrazol-1-yl)pyrimidine (100 mg, 479 µmol), 5-(4-fluorophenyl)-1,4-dimethyl-1H-pyrazol-3-amine (108 mg, 527 µmol) and sodium phenoxide (83.5 mg, 719 µmol) were suspended in 1,4-dioxane (1.1 mL) and degassed by passing an Argon stream through the suspension. Tris(dibenzylidenacetone)dipalladium (5.71 mg, 6.23 µmol) and Xantphos (8.32 mg, 14.4 µmol) were added and the reaction vessel was sealed. The reaction mixture was heated at 80° C. overnight. After cooling to ambient temperature, the reaction mixture was filtered and purified by preparative HPLC (method 4) to yield 91.0 mg of the desired compound (50% yield).

$^1$H-NMR (400 MHz, DMSO-d$_6$) δ [ppm]: 1.848 (13.69), 2.183 (14.41), 2.327 (0.54), 2.621 (12.35), 2.669 (0.56), 3.687 (16.00), 6.130 (3.47), 7.356 (2.05), 7.378 (5.18), 7.400 (2.73), 7.510 (2.51), 7.524 (2.77), 7.532 (2.21), 7.545 (1.85), 8.445 (3.21), 9.377 (2.85).

Example 74

(±)-[syn-2,6-dimethylmorpholin-4-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone (Racemate)

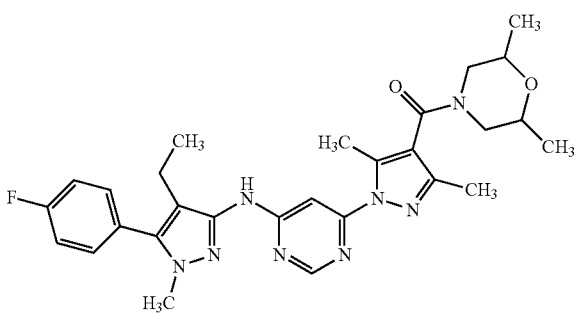 [SMILES: CCc1c(Nc2cc(-n3nc(C)c(C(=O)N4CC(C)OC(C)C4)c3C)ncn2)nn(C)c1-c1ccc(F)cc1]

A mixture of 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (72.6 mg, 167 µmol), cis-2,6-dimethylmorpholine hydrochloride (1:1) (50.6 mg, 333 µmol), (1-[Bis(dimethylamino)methylene]-1H-1,2,3-triazolo[4,5-b]pyridinium 3-oxid hexafluorophosphate) (139 mg, 367 µmol) and N,N-Diisopropylethylamine (120 µl, 700 µmol) was stirred overnight at room temperature. The mixture was directly purified by preparative HPLC (method: column: Reprosil C18; 10 µm; 125×30 mm/flow: 50 ml/min/ eluent: A=water (0.01% formic acid), B=acetonitrile/gradient: 0.00-5.00 min=10% B, 6.50 min=20% B, 17.0-19.75 min=100% B, 19.75-23.00 min=90% B) to yield 49.8 mg (56% yield) of the desired product.

LC-MS (method 10): R$_t$=1.99 min; MS (ESIpos): m/z=533 [M+H]$^+$ $^1$H-NMR (400 MHz, DMSO-d$_6$) δ [ppm]: –0.008 (4.17), 0.008 (2.94), 0.146 (0.41), 0.871 (3.38), 0.890 (7.62), 0.909 (3.51), 1.073 (3.40), 1.091 (5.53), 1.108 (3.43), 2.165 (5.64), 2.286 (0.76), 2.304 (2.17), 2.323 (2.61), 2.366 (0.41), 2.523 (2.02), 2.670 (0.70), 2.710 (0.49), 3.357 (0.82), 3.375 (2.25), 3.392 (2.26), 3.410 (0.95), 3.478 (0.89), 3.651 (16.00), 7.359 (2.06), 7.381 (6.32), 7.403 (2.69), 7.499 (2.50), 7.512 (2.88), 7.520 (2.17), 7.534 (1.85), 8.477 (3.59), 9.433 (2.07).

Example 75

N-(1,4-dimethyl-3-phenyl-1H-pyrazol-5-yl)-6-(3,5-dimethyl-1H-pyrazol-1-yl)pyrimidin-4-amine

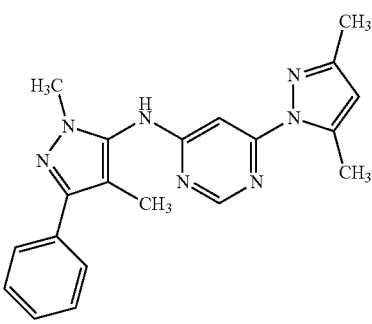 [SMILES: Cc1cc(C)n(-c2cc(Nc3c(C)c(-c4ccccc4)nn3C)ncn2)n1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-6-(3,5-dimethyl-1H-pyrazol-1-yl)pyrimidine (75.0 mg, 359 µmol) and 1,4-dimethyl-3-phenyl-1H-pyrazol-5-amine (74.0 mg, 395 µmol) to yield 54.2 mg of the desired product (42% yield).

LC-MS (method 9): $R_t$=1.07 min; MS (ESIpos): m/z=360 [M+H]$^+$ $^1$H-NMR (400 MHz, DMSO-d$_6$) δ [ppm]: −0.008 (0.76), 0.008 (0.72), 1.073 (0.69), 1.091 (1.39), 1.109 (0.70), 1.862 (14.01), 2.185 (14.42), 2.524 (0.44), 2.624 (12.84), 3.375 (0.71), 3.392 (0.70), 3.702 (16.00), 6.131 (3.36), 7.369 (2.04), 7.457 (2.93), 7.473 (4.28), 7.477 (4.30), 7.495 (1.24), 7.499 (1.38), 7.532 (3.02), 7.551 (3.14), 7.568 (1.11), 8.449 (3.16), 9.374 (2.92).

Example 76

(±)-[1-(6-{[4-ethyl-5-(4-fluorophenyl)-1-methyl-1H-pyrazol-3-yl]amino}pyrimidin-4-yl)-3,5-dimethyl-1H-pyrazol-4-yl](2-methylpyrrolidin-1-yl)methanone

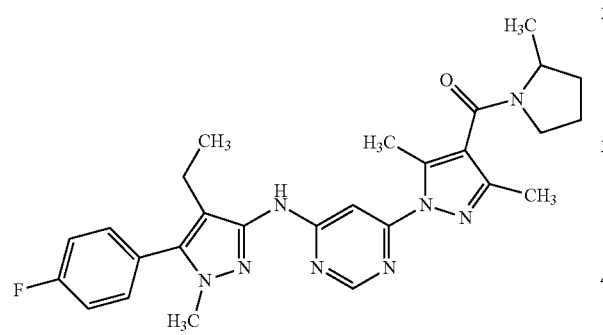

The described product was prepared in a manner analogous to that described in the preparation of (±)-[syn-2,6-dimethylmorpholin-4-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone starting from 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (77.4 mg, 178 µmol) and (±)2-methylpyrrolidine (30.3 mg, 355 µmol) to yield 60.0 mg of the desired product (67% yield).

LC-MS (method 10): $R_t$=2.02 min; MS (ESIpos): m/z=503 [M+H]$^+$ $^1$H-NMR (400 MHz, DMSO-d$_6$) δ [ppm]: −0.008 (2.02), 0.008 (1.48), 0.872 (3.81), 0.891 (8.62), 0.910 (3.94), 1.073 (1.54), 1.091 (3.14), 1.109 (1.60), 1.227 (1.76), 1.241 (1.73), 1.564 (0.44), 1.576 (0.43), 1.873 (0.48), 2.056 (0.43), 2.072 (0.46), 2.168 (6.02), 2.287 (0.81), 2.306 (2.40), 2.324 (2.52), 2.343 (0.75), 2.519 (1.04), 2.524 (0.83), 2.590 (8.35), 3.231 (0.43), 3.357 (0.58), 3.375 (1.59), 3.392 (1.55), 3.410 (0.53), 3.653 (16.00), 7.359 (2.27), 7.364 (1.51), 7.374 (2.12), 7.381 (4.90), 7.398 (0.94), 7.403 (2.73), 7.501 (2.62), 7.507 (1.12), 7.515 (2.91), 7.523 (2.29), 7.531 (0.92), 7.537 (1.95), 8.473 (2.90), 9.418 (2.19).

Example 77

6-(3,5-dimethyl-1H-pyrazol-1-yl)-N-[1-(4-fluorophenyl)-3-methyl-1H-pyrazol-4-yl]pyrimidin-4-amine

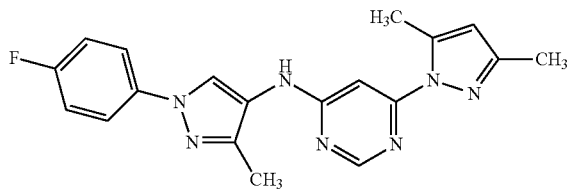 [SMILES: Cc1cc(C)n(-c2cc(Nc3cn(-c4ccc(F)cc4)nc3C)ncn2)n1]

A solution of 4-chloro-6-(3,5-dimethyl-1H-pyrazol-1-yl)pyrimidine (100 mg, 479 µmol) and 1-(4-fluorophenyl)-3-methyl-1H-pyrazol-4-amine (197 mg, 93% purity, 959 µmol) in NMP (1 mL) was treated with concentrated aqueous hydrochloric acid (146 mg, 36%, 1.44 mmol). The resulting mixture was stirred for 1 hour at 180° C. in the microwave. After cooling to room temperature the crude product was poured into water. The precipitate was collected via filtration and purified by preparative HPLC (method 3) to yield 18 mg of the desired product (10% yield).

LC-MS (method 9): $R_t$=1.09 min; MS (ESIpos): m/z=364 [M+H]$^+$ $^1$H-NMR (400 MHz, DMSO-d$_6$) δ [ppm]: 1.232 (0.51), 2.184 (8.68), 2.249 (7.47), 2.634 (16.00), 6.133 (3.86), 7.295 (2.41), 7.317 (4.57), 7.338 (2.57), 7.789 (2.22), 7.800 (2.46), 7.811 (2.32), 7.823 (2.02), 8.511 (2.98), 8.676 (4.19), 9.183 (0.96).

Example 78

6-(3,5-dimethyl-1H-pyrazol-1-yl)-N-[1-(4-fluorophenyl)-3,5-dimethyl-1H-pyrazol-4-yl]pyrimidin-4-amine

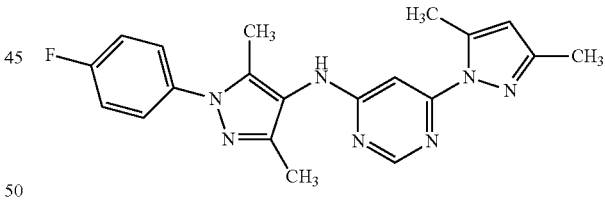

A solution of 4-chloro-6-(3,5-dimethyl-1H-pyrazol-1-yl)pyrimidine (100 mg, 479 µmol) and 1-(4-fluorophenyl)-3,5-dimethyl-1H-pyrazol-4-amine (269 mg, 73% purity, 959 µmol) in NMP (1 mL) was treated with concentrated aqueous hydrochloric acid (146 mg, 1.44 mmol). The resulting mixture was stirred for 1 hour at 180° C. in the microwave. After cooling to room temperature the crude product was poured into water. The precipitate was collected via filtration and purified by preparative HPLC (method 3) to yield 100 mg of the desired product (55% yield).

LC-MS (method 11): $R_t$=1.30 min; MS (ESIpos): m/z=378 [M+H]$^+$ $^1$H-NMR (400 MHz, DMSO-d$_6$) δ [ppm]: 2.077 (16.00), 2.179 (12.02), 2.616 (13.32), 6.117 (2.33), 7.335 (1.57), 7.356 (3.32), 7.378 (1.88), 7.581 (1.27), 7.593 (1.52), 8.397 (0.51), 8.858 (2.50).

Example 79 ethyl 1-{6-[(4-chloro-1-methyl-3-phenyl-1H-pyrazol-5-yl)amino]pyrimidin-4-yl}-3,5-dimethyl-1H-pyrazole-4-carboxylate

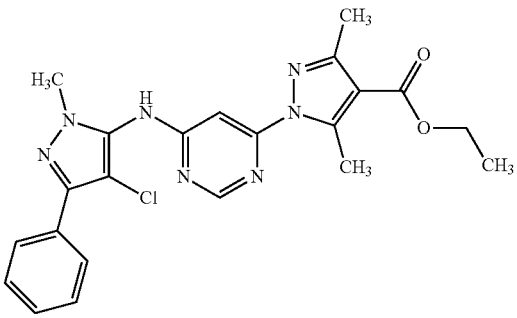 [SMILES: CCOC(=O)c1c(C)nn(-c2cc(Nc3c(Cl)c(-c4ccccc4)nn3C)ncn2)c1C]

In a microwave tube, ethyl 1-(6-chloropyrimidin-4-yl)-3,5-dimethyl-1H-pyrazole-4-carboxylate (100 mg, 356 µmol), 4-chloro-1-methyl-3-phenyl-1H-pyrazol-5-amine (81.4 mg, 392 µmol) and sodium phenoxide (62.0 mg, 534 µmol) were suspended in 1,4-dioxane (1.0 mL) and degassed by passing an Argon stream through the suspension. Tris(dibenzylidenacetone)dipalladium (4.24 mg, 4.63 µmol) and Xantphos (6.18 mg, 10.7 µmol) were added and the reaction vessel was sealed. The reaction mixture was heated at 80° C. overnight. After cooling to ambient temperature, the reaction mixture was filtered and purified by preparative HPLC (method 4) to yield 20.0 mg of the desired compound (12% yield).

LC-MS (method 10): $R_t$=2.28 min; MS (ESIpos): m/z=452 [M+H]$^+$ $^1$H-NMR (400 MHz, DMSO-d$_6$) δ [ppm]: 1.31 (t, J=7.1 Hz, 3H), 2.39 (s, 3H), 2.92 (s, 3H), 3.74 (s, 3H), 4.26 (q, J=7.1 Hz, 2H), 6.89-7.31 (br s, 1H), 7.37-7.43 (m, 1H), 7.45-7.52 (m, 2H), 7.83-7.88 (m, 2H), 8.58 (s, 1H), 9.85 (s, 1H).

Example 80

6-(4-chloro-3,5-dimethyl-1H-pyrazol-1-yl)-N-(4-chloro-1-methyl-3-phenyl-1H-pyrazol-5-yl)pyrimidin-4-amine

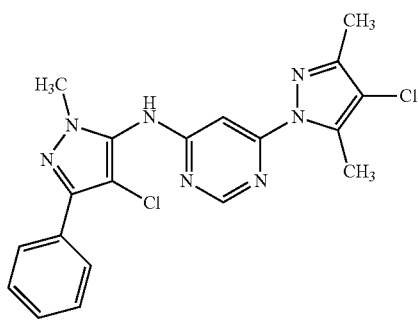 [SMILES: Cc1nn(-c2cc(Nc3c(Cl)c(-c4ccccc4)nn3C)ncn2)c(C)c1Cl]

In a microwave tube, 4-chloro-6-(4-chloro-3,5-dimethyl-1H-pyrazol-1-yl)pyrimidine (100 mg, 411 µmol), 4-chloro-1-methyl-3-phenyl-1H-pyrazol-5-amine (94.0 mg, 452 µmol) and sodium phenoxide (71.6 mg, 617 µmol) were suspended in 1,4-dioxane (1.1 mL) and degassed by passing an Argon stream through the suspension. Tris(dibenzylidenacetone)dipalladium (7.14 mg, 12.3 µmol) and Xantphos (7.14 mg, 12.3 µmol) were added and the reaction vessel was sealed. The reaction mixture was heated at 80° C. overnight. After cooling to ambient temperature, the reaction mixture was filtered and purified by preparative HPLC (method 5) to yield 30.0 mg of the desired compound (18% yield).

LC-MS (method 10): $R_t$=2.45 min; MS (ESIpos): m/z=414 [M+H]$^+$ $^1$H-NMR (400 MHz, DMSO-d$_6$) δ [ppm]: 2.23 (s, 3H), 2.66 (s, 3H), 3.74 (s, 3H), 6.80-7.32 (br s, 1H), 7.37-7.43 (m, 1H), 7.45-7.52 (m, 2H), 7.84-7.89 (m, 2H), 8.54 (s, 1H), 9.78 (s, 1H).

Example 81 ethyl 1-{6-[(4-chloro-1-methyl-5-phenyl-1H-pyrazol-3-yl)amino]pyrimidin-4-yl}-3,5-dimethyl-1H-pyrazole-4-carboxylate

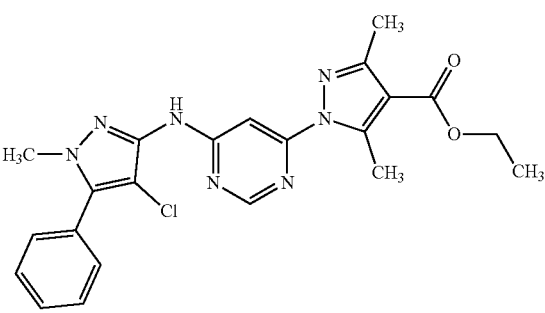 [SMILES: CCOC(=O)c1c(C)nn(-c2cc(Nc3nn(C)c(-c4ccccc4)c3Cl)ncn2)c1C]

In a microwave tube, ethyl 1-(6-chloropyrimidin-4-yl)-3,5-dimethyl-1H-pyrazole-4-carboxylate (100 mg, 356 µmol), 4-chloro-1-methyl-5-phenyl-1H-pyrazol-3-amine (81.4 mg, 392 µmol) and sodium phenoxide (62.0 mg, 534 µmol) were suspended in 1,4-dioxane (1.0 mL) and degassed by passing an Argon stream through the suspension. Tris(dibenzylidenacetone)dipalladium (4.24 mg, 4.63 µmol) and Xantphos (6.18 mg, 10.7 µmol) were added and the reaction vessel was sealed. The reaction mixture was heated at 80° C. overnight. After cooling to ambient temperature, the reaction mixture was filtered and purified by preparative HPLC (method 5) to yield 30.1 mg of the desired compound (19% yield).

LC-MS (method 10): $R_t$=2.35 min; MS (ESIpos): m/z=452 [M+H]$^+$

¹H-NMR (400 MHz, DMSO-d₆) δ [ppm]: −0.008 (1.31), 0.008 (1.07), 1.292 (4.31), 1.309 (9.11), 1.327 (4.41), 2.388 (16.00), 2.524 (0.56), 2.901 (15.36), 2.933 (1.75), 3.783 (15.52), 4.232 (1.24), 4.250 (3.89), 4.258 (0.73), 4.268 (3.85), 4.276 (0.64), 4.285 (1.19), 7.289 (0.49), 7.299 (3.66), 7.312 (0.52), 7.526 (0.59), 7.540 (0.88), 7.551 (0.84), 7.556 (1.10), 7.562 (1.39), 7.566 (1.28), 7.579 (13.15), 7.588 (3.24), 7.594 (2.12), 8.555 (3.38), 8.765 (0.41), 9.724 (2.68).

Example 82

1-[3-{[6-(3,5-dimethyl-1H-pyrazol-1-yl)pyrimidin-4-yl]amino}-5-(4-fluorophenyl)-1-methyl-1H-pyrazol-4-yl]ethanone

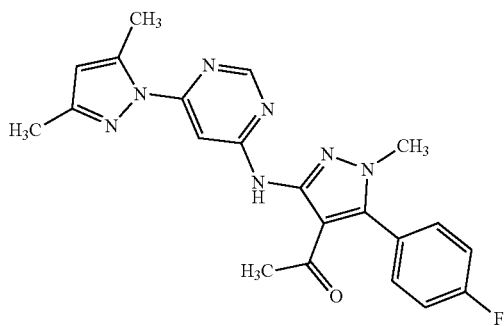 [SMILES: CC(=O)c1c(Nc2cc(-n3nc(C)cc3C)ncn2)nn(C)c1-c1ccc(F)cc1]

A solution of 6-(3,5-dimethyl-1H-pyrazol-1-yl)-N-[4-ethyl-5-(4-fluorophenyl)-1-methyl-1H-pyrazol-3-yl]pyrimidin-4-amine (130 mg, 332 µmol) and iron(III) chloride hexahydrate (89.8 mg, 332 µmol) in pyridine (3.5 ml, 43 mmol) was treated with tert butylhydroperoxide solution (190 µl, 70% purity, 1.3 mmol) and stirred for 2 days at 50° C. Again, 1.0 eq iron(III) chloride hexahydrate (89.8 mg, 332 µmol) and 4.0 eq tert-butylhydroperoxide were added and the mixture was stirred over night at 50° C. After cooling to room temperature saturated EDTA solution was added and the mixture was extracted with dichloromethane and ethyl acetate. The combined organic phases were washed with brine, filtered via a water-repellent filter and concentrated in vacuum. The crude product was purified by preparative HPLC (Waters Autopurificationsystem; column: Waters XBrigde C18 5 100×30 mm; eluent A: water+0.2 Vol-% aq. ammonia solution (32%), eluent B: acetonitrile; gradient: 0.00-0.50 min 40% B (25→70 mL/min), 0.51-5.50 min 40-70% B (70 mL/min), DAD scan: 210-400 nm) to yield the desired product (6.30 mg, 5% yield).

LC-MS (method 13): $R_t$=1.38 min; MS (ESIpos): m/z=406 [M+H]⁺

¹H-NMR (400 MHz, DMSO-d₆): δ [ppm]: 1.85 (s, 3H), 2.23 (s, 3H), 2.61-2.70 (m, 3H), 3.60 (s, 3H), 6.19 (s, 1H), 7.41-7.53 (m, 2H), 7.64-7.75 (m, 2H), 8.45 (d, 1H), 8.61 (d, 1H), 10.05 (s, 1H).

Example 83 ethyl 1-(6-{[4-ethyl-5-(4-fluorophenyl)-1-methyl-1H-pyrazol-3-yl]amino}pyrimidin-4-yl)-5-methyl-1H-pyrazole-3-carboxylate

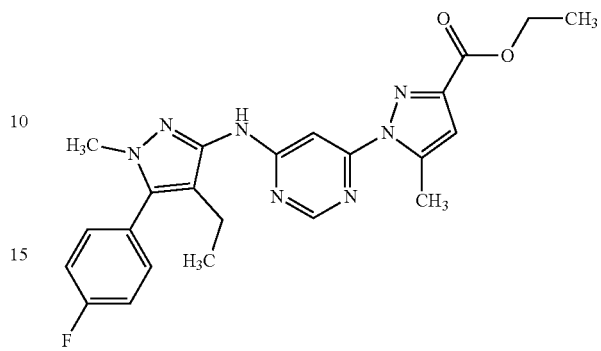

4-Ethyl-5-(4-fluorophenyl)-1-methyl-1H-pyrazol-3-amine (100 mg, 456 µmol) and sodium phenoxyde (79.4 mg, 684 µmol) were dissolved in dioxane. The solution was degassed with argon. Then, ethyl 1-(6-chloropyrimidin-4-yl)-5-methyl-1H-pyrazole-3-carboxylate (122 mg, 456 µmol), tris(dibenzylideneacetone)dipalladium(0) (5.43 mg, 5.93 µmol) and Xantphos (7.92 mg, 13.7 µmol) were added. The reaction mixture was stirred at 80° C. overnight. The reaction mixture was directly purified by preparative HPLC (method: column: Reprosil C18; 10 µm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to afford a brownish powder which was purified again using preparative HPLC (WUPp-LC-basisch) to afford the pure desired product (29.3 mg, 13% yield) and some slightly impure material (51 mg) which was used in the next step.

LC-MS (method 11): $R_t$=1.48 min; MS (ESIpos): m/z=450 [M+H]⁺

¹H-NMR (400 MHz, DMSO-d₆) δ [ppm]: 0.878 (3.73), 0.897 (8.10), 0.916 (3.85), 1.287 (4.30), 1.305 (8.80), 1.323 (4.36), 2.296 (1.00), 2.315 (2.71), 2.333 (2.68), 2.351 (0.89), 2.678 (14.42), 3.653 (16.00), 4.280 (1.39), 4.298 (4.15), 4.315 (4.10), 4.333 (1.33), 6.785 (3.87), 7.343 (0.81), 7.357 (2.12), 7.379 (4.54), 7.400 (2.66), 7.450 (1.87), 7.462 (1.55), 7.478 (0.82), 7.511 (2.64), 7.524 (3.16), 7.531 (2.62), 7.546 (2.02), 7.783 (0.66), 7.795 (0.64), 7.808 (0.53), 7.814 (0.55), 7.822 (0.56), 8.544 (2.94), 9.593 (1.64).

Example 84

6-(4-chloro-3,5-dimethyl-1H-pyrazol-yl)-N-(1,4-dimethyl-5-phenyl-1H-pyrazol-3-yl)pyrimidin-4-amine

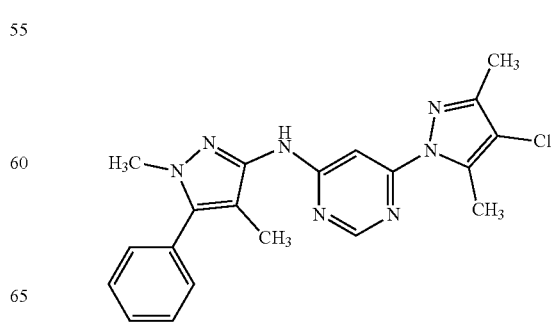

The desired product was obtained in the same manner as described for ethyl 1-(6-{[4-ethyl-5-(4-fluorophenyl)-1-methyl-1H-pyrazol-3-yl]amino}pyrimidin-4-yl)-5-methyl-1H-pyrazole-3-carboxylate starting from 4-chloro-6-(4-chloro-3,5-dimethyl-1H-pyrazol-1-yl)pyrimidine (75.0 mg, 309 μmol) and 1,4-dimethyl-5-phenyl-1H-pyrazol-3-amine (63.5 mg, 339 μmol) to yield 39.3 g (32% yield) of the desired product after purification by preparative HPLC (method: column: Reprosil C18; 10 μm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B).

LC-MS (method 10): $R_t$=2.31 min; MS (ESIpos): m/z=394 [M+H]$^+$ $^1$H-NMR (400 MHz, DMSO-d$_6$) δ [ppm]: 1.262 (0.63), 2.029 (15.61), 2.186 (0.94), 2.212 (3.56), 2.624 (0.45), 2.649 (16.00), 3.668 (10.26), 3.702 (0.53), 7.314 (0.70), 7.332 (1.84), 7.351 (1.31), 7.422 (2.39), 7.442 (4.02), 7.460 (2.08), 7.676 (3.10), 7.695 (2.67), 8.510 (0.75), 9.507 (1.53).

Example 85

[1-(6-{[4-ethyl-5-(4-fluorophenyl)-1-methyl-1H-pyrazol-3-yl]amino}pyrimidin-4-yl)-3,5-dimethyl-1H-pyrazol-4-yl][3-fluoro-3-(trifluoromethyl)azetidin-1-yl]methanone

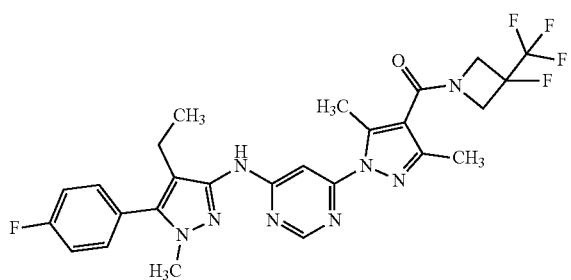 [SMILES: CCc1c(Nc2cc(-n3nc(C)c(C(=O)N4CC(F)(C(F)(F)F)C4)c3C)ncn2)nn(C)c1-c1ccc(F)cc1]

The described product was prepared in a manner analogous to that described in the preparation of (±)-[syn-2,6-dimethylmorpholin-4-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone starting from 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (76.3 mg, 175 μmol) and 3-fluoro-3-(trifluoromethyl)azetidine hydrochloride (1:1) (62.9 mg, 350 μmol, CAS 1803588-53-5) to yield 31 mg of the desired product (32% yield).

LC-MS (method 10): $R_t$=2.14 min; MS (ESIpos): m/z=561 [M+H]$^+$ $^1$H-NMR (400 MHz, DMSO-d$_6$) δ [ppm]: −0.008 (1.97), 0.870 (3.38), 0.889 (7.72), 0.908 (3.53), 2.252 (14.55), 2.287 (0.88), 2.305 (2.35), 2.324 (2.58), 2.343 (0.75), 2.692 (14.95), 3.649 (16.00), 4.464 (3.92), 4.506 (2.80), 7.359 (2.03), 7.381 (6.00), 7.403 (2.72), 7.499 (2.54), 7.512 (2.82), 7.520 (2.25), 7.534 (1.86), 8.501 (3.59), 9.485 (1.74).

Example 86

6-(4-chloro-3,5-dimethyl-1H-pyrazol-1-yl)-N-(1,4-dimethyl-3-phenyl-1H-pyrazol-5-yl)pyrimidin-4-amine

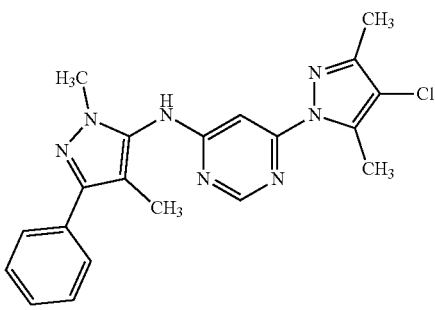 [SMILES: Cc1nn(-c2cc(Nc3c(C)c(-c4ccccc4)nn3C)ncn2)c(C)c1Cl]

The desired product was obtained in the same manner as described for 6-(4-chloro-3,5-dimethyl-1H-pyrazol-1-yl)-N-(1,4-dimethyl-5-phenyl-1H-pyrazol-3-yl)pyrimidin-4-amine starting from 4-chloro-6-(4-chloro-3,5-dimethyl-1H-pyrazol-1-yl)pyrimidine (75.0 mg, 309 μmol) and 1,4-dimethyl-3-phenyl-1H-pyrazol-5-amine (63.5 mg, 339 μmol) to yield 30.1 g (25% yield)

LC-MS (method 10): $R_t$=2.36 min; MS (ESIpos): m/z=394 [M+H]$^+$ $^1$H-NMR (400 MHz, DMSO-d$_6$) δ [ppm]: −0.008 (0.46), 0.008 (0.42), 1.234 (0.47), 1.262 (0.45), 1.865 (12.99), 2.224 (14.72), 2.524 (0.46), 2.642 (15.91), 3.702 (16.00), 5.754 (0.49), 7.404 (1.19), 7.456 (2.84), 7.467 (1.13), 7.473 (4.00), 7.476 (4.28), 7.482 (2.22), 7.497 (1.23), 7.500 (1.40), 7.533 (3.10), 7.551 (3.34), 7.569 (1.14), 8.485 (2.75), 9.500 (2.39).

Example 87 ethyl [1-(6-{[4-ethyl-5-(4-fluorophenyl)-1-methyl-1H-pyrazol-3-yl]amino}pyrimidin-4-yl)-3,5-dimethyl-1H-pyrazol-4-yl]acetate

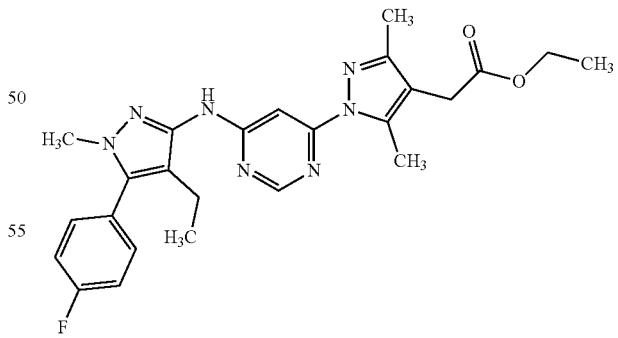

A solution of N-[4-ethyl-5-(4-fluorophenyl)-1-methyl-1H-pyrazol-3-yl]-6-hydrazinylpyrimidin-4-amine (170 mg, 519 μmol) and ethyl 3-acetyl-4-oxopentanoate (91 μl, 520 μmol) in methanol (5.1 ml, 130 mmol) was stirred at 80° C. overnight. After cooling to room temperature the precipitated was filtered, washed with methanol and discarded. The filtrate was concentrated in vacuum and purified by preparative HPLC (method: column: Reprosil C18; 10 µm; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75-23.00 min=90% B) to afford 83 mg of the desired product (33% yield).

LC-MS (method 10): $R_t$=2.18 min; MS (ESIpos): m/z=478 [M+H]$^+$ $^1$H-NMR (600 MHz, DMSO-d$_6$) δ [ppm]: 0.88 (t, 3H), 1.18 (t, 3H), 2.14 (s, 3H), 2.30 (q, 2H), 2.56 (s, 3H), 3.47 (s, 2H), 3.65 (s, 3H), 4.07 (q, 2H), 7.32 (br s, 1H), 7.36-7.42 (m, 2H), 7.46-7.54 (m, 2H), 8.44 (s, 1H), 9.36 (s, 1H).

Example 88

6-(4-chloro-3,5-dimethyl-1H-pyrazol-1-yl)-N-[4-chloro-3-(4-fluorophenyl)-1-methyl-1H-pyrazol-5-yl]pyrimidin-4-amine

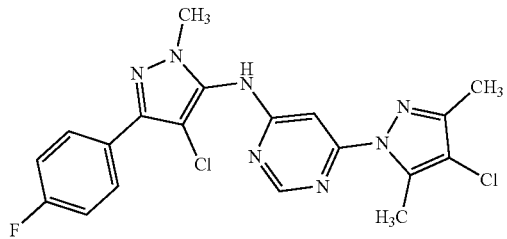 [SMILES: Cc1nn(-c2cc(Nc3c(Cl)c(-c4ccc(F)cc4)nn3C)ncn2)c(C)c1Cl]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 4-chloro-6-(4-chloro-3,5-dimethyl-1H-pyrazol-1-yl)pyrimidine (97.9 mg, 403 µmol) and 4-chloro-3-(4-fluorophenyl)-1-methyl-1H-pyrazol-5-amine (100 mg, 443 µmol) to yield 110 mg of the desired product (61% yield).

LC-MS (method 10): $R_t$=2.50 min; MS (ESIpos): m/z=432 [M+H]$^+$ $^1$H-NMR (400 MHz, DMSO-d$_6$) δ [ppm]: −0.008 (1.02), 0.008 (0.49), 1.074 (0.45), 1.091 (0.89), 1.109 (0.45), 2.228 (9.57), 2.524 (0.71), 2.654 (16.00), 2.669 (1.15), 3.375 (0.46), 3.392 (0.44), 3.729 (12.50), 7.301 (2.29), 7.324 (4.47), 7.341 (0.99), 7.346 (2.32), 7.879 (2.27), 7.884 (1.18), 7.892 (2.53), 7.901 (2.32), 7.909 (1.04), 7.914 (1.96), 8.537 (1.96), 9.790 (3.05).

Example 89

6-(4-chloro-3,5-dimethyl-1H-pyrazol-1-yl)-N-[4-chloro-5-(4-fluorophenyl)-1-methyl-1H-pyrazol-3-yl]pyrimidin-4-amine

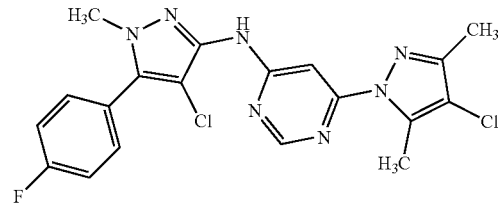 [SMILES: Cc1nn(-c2cc(Nc3nn(C)c(-c4ccc(F)cc4)c3Cl)ncn2)c(C)c1Cl]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 4-chloro-6-(4-chloro-3,5-dimethyl-1H-pyrazol-1-yl)pyrimidine (97.9 mg, 403 µmol) and 4-chloro-5-(4-fluorophenyl)-1-methyl-1H-pyrazol-3-amine (100 mg, 443 µmol) to yield 85.5 mg of the desired product (49% yield).

LC-MS (method 10): $R_t$=2.51 min; MS (ESIneg): m/z=430 [M−H]$^+$ $^1$H-NMR (400 MHz, DMSO-d$_6$) δ [ppm]: −0.008 (0.99), 2.074 (0.83), 2.227 (14.88), 2.646 (15.71), 3.773 (16.00), 7.278 (4.12), 7.409 (1.96), 7.431 (4.35), 7.454 (2.46), 7.628 (2.39), 7.642 (2.63), 7.650 (2.35), 7.659 (0.92), 7.664 (2.00), 8.507 (3.60), 9.645 (2.04).

Example 90

N-[4-chloro-3-(4-fluorophenyl)-1-methyl-1H-pyrazol-5-yl]-6-(3,5-dimethyl-1H-pyrazol-1-yl)pyrimidin-4-amine

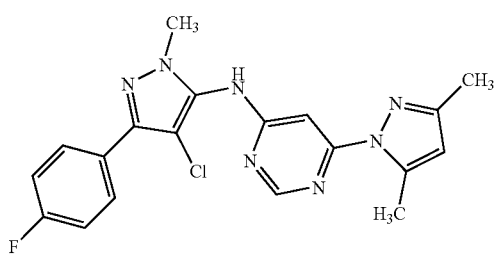 [SMILES: Cc1cc(C)n(-c2cc(Nc3c(Cl)c(-c4ccc(F)cc4)nn3C)ncn2)n1]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 4-chloro-6-(3,5-dimethyl-1H-pyrazol-1-yl)pyrimidine (84.1 mg, 403 µmol) and 4-chloro-3-(4-fluorophenyl)-1-methyl-1H-pyrazol-5-amine (100 mg, 443 µmol) to yield 91.0 mg of the desired product (57% yield).

LC-MS (method 10): $R_t$=2.20 min; MS (ESIpos): m/z=398 [M+H]$^+$ $^1$H-NMR (400 MHz, DMSO-d$_6$) δ [ppm]: 2.190 (11.74), 2.637 (15.92), 3.728 (16.00), 6.162 (4.00), 7.301 (2.37), 7.324 (4.89), 7.346 (2.64), 7.881 (2.51), 7.895 (2.90), 7.902 (2.84), 7.916 (2.36), 8.500 (2.87), 9.688 (4.45).

Example 91

N-[4-chloro-5-(4-fluorophenyl)-1-methyl-1H-pyrazol-3-yl]-6-(3,5-dimethyl-1H-pyrazol-1-yl)pyrimidin-4-amine

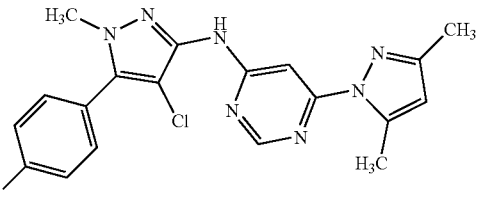

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 4-chloro-6-(3,5-dimethyl-1H-pyrazol-1-yl)pyrimidine (84.1 mg, 403 µmol) and 4-chloro-5-(4-fluorophenyl)-1-methyl-1H-pyrazol-3-amine (100 mg, 443 µmol) to yield 120 mg of the desired product (68% yield).

LC-MS (method 9): $R_t$=1.15 min; MS (ESIpos): m/z=398 [M+H]$^+$ $^1$H-NMR (400 MHz, DMSO-d$_6$) δ [ppm]: 2.189 (14.34), 2.627 (12.67), 3.772 (16.00), 6.143 (3.77), 7.261 (4.40), 7.409 (1.94), 7.431 (4.27), 7.453 (2.44), 7.629 (2.37), 7.643 (2.64), 7.651 (2.31), 7.665 (1.96), 8.470 (4.06), 9.524 (3.45).

Example 92

2-[1-(6-{[4-ethyl-5-(4-fluorophenyl)-1-methyl-1H-pyrazol-3-yl]amino}pyrimidin-4-yl)-3,5-dimethyl-1H-pyrazol-4-yl]ethanol

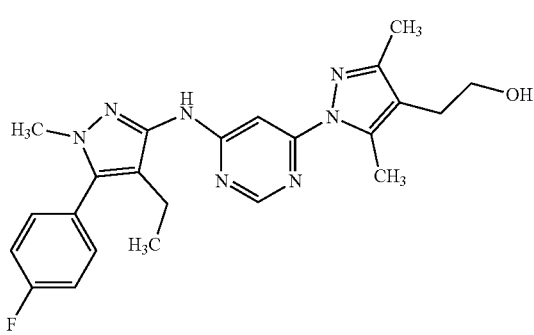 [SMILES: CCc1c(Nc2cc(-n3nc(C)c(CCO)c3C)ncn2)nn(C)c1-c1ccc(F)cc1]

A solution of ethyl [1-(6-{[4-ethyl-5-(4-fluorophenyl)-1-methyl-1H-pyrazol-3-yl]amino}pyrimidin-4-yl)-3,5-dimethyl-1H-pyrazol-4-yl]acetate (70.0 mg, 147 µmol) in dry THF (2.5 mL) was treated with diisobutylaluminium hydride in THF (810 mL, 810 µmol, 1M) at 0° C. The mixture was stirred for 30 min at 0° C. and subsequently diluted with methanol (1 mL) and hydrochloric acid (1M). The resulting mixture was extracted three times with ethyl acetate. The combined organic phases were washed with brine, dried over sodium sulfate and the solvent was removed under reduced pressure. The crude product was purified by preparative HPLC (method 7) to yield the desired product 32.0 mg (50% yield).

LC-MS (method 9): $R_t$=0.94 min; MS (ESIpos): m/z=436 [M+H]$^+$ $^1$H-NMR (500 MHz, DMSO-d$_6$) δ [ppm]: 0.871 (3.45), 0.886 (7.66), 0.901 (3.45), 1.356 (0.49), 2.162 (14.31), 2.285 (0.81), 2.300 (2.31), 2.315 (2.23), 2.330 (0.73), 2.521 (1.83), 2.568 (14.60), 3.411 (1.04), 3.425 (2.30), 3.436 (2.26), 3.450 (0.96), 3.648 (16.00), 4.621 (1.38), 4.631 (3.12), 4.642 (1.31), 7.303 (2.21), 7.360 (1.98), 7.365 (0.76), 7.374 (1.03), 7.378 (4.28), 7.383 (0.95), 7.392 (0.84), 7.396 (2.44), 7.501 (2.41), 7.505 (1.07), 7.512 (2.67), 7.519 (2.15), 7.525 (0.89), 7.530 (1.86), 8.427 (3.24), 9.282 (2.26).

Example 93

6-[5-(difluoromethyl)-3-methyl-1H-pyrazol-1-yl]-N-[1-(4-fluorophenyl)-3,5-dimethyl-1H-pyrazol-4-yl]pyrimidin-4-amine

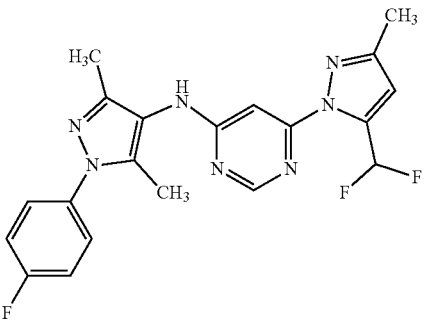 [SMILES: Cc1cc(C(F)F)n(-c2cc(Nc3c(C)nn(-c4ccc(F)cc4)c3C)ncn2)n1]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 1-(4-fluorophenyl)-3,5-dimethyl-1H-pyrazol-4-amine (100 mg, 487 µmol) and 4-chloro-6-[5-(difluoromethyl)-3-methyl-1H-pyrazol-1-yl]pyrimidine (131 mg, 536 µmol) to yield the desired product 85.6 mg (42% yield).

LC-MS (method 11): $R_t$=1.40 min; MS (ESIpos): m/z=414 [M+H]$^+$ $^1$H-NMR (400 MHz, DMSO-d$_6$) δ [ppm]: 2.081 (16.00), 2.182 (7.54), 2.285 (1.25), 6.760 (1.87), 7.340 (1.26), 7.361 (2.56), 7.383 (1.46), 7.601 (1.27), 7.687 (1.23), 7.823 (2.44), 7.959 (1.11), 9.057 (0.72).

Example 94

[1-(6-{[4-ethyl-5-(4-fluorophenyl)-1-methyl-1H-pyrazol-3-yl]amino}pyrimidin-4-yl)-5-methyl-1H-pyrazol-3-yl]methanol

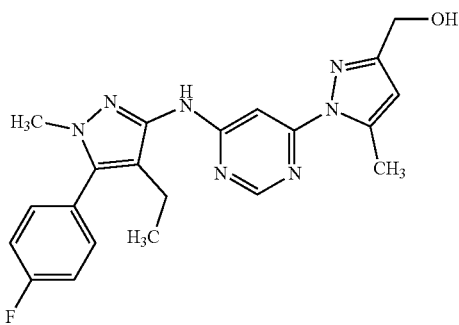 [SMILES: CCc1c(Nc2cc(-n3nc(CO)cc3C)ncn2)nn(C)c1-c1ccc(F)cc1]

The described product was prepared in a manner analogous to that described in the preparation of 2-[1-(6-{[4-ethyl-5-(4-fluorophenyl)-1-methyl-1H-pyrazol-3-yl]amino}pyrimidin-4-yl)-3,5-dimethyl-1H-pyrazol-4-yl]ethanol starting from ethyl 1-(6-{[4-ethyl-5-(4-fluorophenyl)-1-methyl-1H-pyrazol-3-yl]amino}pyrimidin-4-yl)-5-methyl-1H-pyrazole-3-carboxylate (51.0 mg, 113 µmol) to yield the desired product (8.00 mg, 17% yield) after purification by preparative HPLC (method: column: Reprosil C18; m; 125×30 mm/flow: 45 ml/min/eluent: A=water (0.1% formic acid), B=acetonitrile/gradient: 0.00-4.25 min=10% B, 4.50 min=20% B, 15.50 min=85% B, 16.00-18.50 min=100% B, 18.75-22.00 min=20% B).

LC-MS (method 11): $R_t$=1.20 min; MS (ESIpos): m/z=408 [M+H]$^+$ $^1$H-NMR (400 MHz, DMSO-d$_6$) δ [ppm]: 0.869 (3.56), 0.888 (8.08), 0.907 (3.66), 1.091 (0.40), 2.282 (0.91), 2.300 (2.68), 2.319 (2.64), 2.338 (0.88), 2.524 (0.45), 2.652 (13.24), 2.685 (0.69), 3.650 (16.00), 4.407 (5.27), 4.422 (5.44), 5.143 (1.52), 5.158 (3.03), 5.172 (1.40), 6.282 (3.59), 7.341 (2.59), 7.357 (2.04), 7.379 (4.37), 7.401 (2.65), 7.500 (2.67), 7.506 (1.21), 7.514 (2.89), 7.522 (2.43), 7.530 (0.95), 7.535 (1.96), 8.461 (2.99), 9.365 (2.83).

Example 95

N-[4-cyclopropyl-5-(4-fluorophenyl)-1-methyl-1H-pyrazol-3-yl]-6-[5-(difluoromethyl)-3-methyl-1H-pyrazol-1-yl]pyrimidin-4-amine

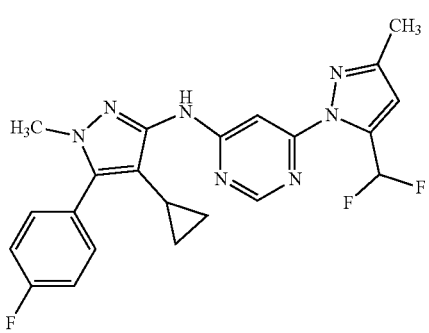 [SMILES: Cc1cc(C(F)F)n(-c2cc(Nc3nn(C)c(-c4ccc(F)cc4)c3C3CC3)ncn2)n1]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 4-cyclopropyl-5-(4-fluorophenyl)-1-methyl-1H-pyrazol-3-amine (100 mg, 432 µmol) and 4-chloro-6-[5-(difluoromethyl)-3-methyl-1H-pyrazol-1-yl]pyrimidine (116 mg, 476 µmol) to yield the desired product 76.2 mg (40% yield).

LC-MS (method 11): $R_t$=1.53 min; MS (ESIpos): m/z=440 [M+H]$^+$ $^1$H-NMR (400 MHz, DMSO-d$_6$) δ [ppm]: 0.133 (0.94), 0.144 (3.14), 0.148 (3.27), 0.157 (3.54), 0.161 (3.00), 0.171 (1.06), 0.486 (0.81), 0.496 (2.17), 0.499 (2.17), 0.516 (2.30), 0.531 (0.72), 1.497 (0.41), 1.510 (0.83), 1.518 (0.90), 1.531 (1.53), 1.539 (0.62), 1.544 (0.84), 1.552 (0.77), 2.298 (16.00), 3.318 (5.41), 6.772 (4.86), 7.294 (4.15), 7.354 (2.25), 7.376 (4.85), 7.398 (2.73), 7.556 (2.79), 7.570 (3.24), 7.578 (2.71), 7.592 (2.27), 7.699 (1.39), 7.835 (2.89), 7.971 (1.25), 8.475 (4.38), 9.397 (4.11).

Example 96

N-[4-cyclopropyl-3-(4-fluorophenyl)-1-methyl-1H-pyrazol-5-yl]-6-[5-(difluoromethyl)-3-methyl-1H-pyrazol-1-yl]pyrimidin-4-amine

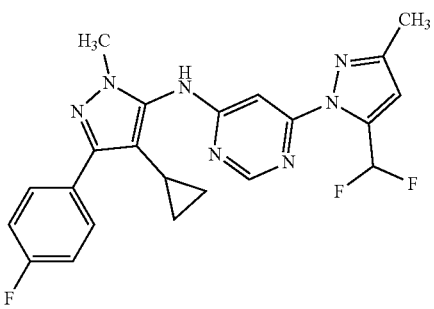 [SMILES: Cc1cc(C(F)F)n(-c2cc(Nc3c(C4CC4)c(-c4ccc(F)cc4)nn3C)ncn2)n1]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 4-cyclopropyl-3-(4-fluorophenyl)-1-methyl-1H-pyrazol-5-amine (100 mg, 432 µmol) and 4-chloro-6-[5-(difluoromethyl)-3-methyl-1H-pyrazol-1-yl]pyrimidine (116 mg, 476 µmol) to yield the desired product 57.0 mg (30% yield).

LC-MS (method 11): $R_t$=1.49 min; MS (ESIpos): m/z=440 [M+H]$^+$ $^1$H-NMR (400 MHz, DMSO-d$_6$) δ [ppm]: 0.293 (4.14), 0.703 (6.11), 1.074 (0.51), 1.091 (1.01), 1.109 (0.52), 1.645 (3.58), 2.298 (7.65), 3.164 (0.66), 3.176 (0.64), 3.375 (0.58), 3.392 (0.52), 3.632 (16.00), 6.790 (7.75), 7.243 (6.27), 7.264 (11.96), 7.286 (6.81), 7.692 (4.44), 7.828 (9.04), 7.902 (6.39), 7.964 (4.49), 8.494 (1.50), 9.549 (2.34).

Example 97

6-(4-chloro-3,5-dimethyl-1H-pyrazol-1-yl)-N-[4-ethyl-3-(4-fluorophenyl)-1-methyl-1H-pyrazol-5-yl]pyrimidin-4-amine

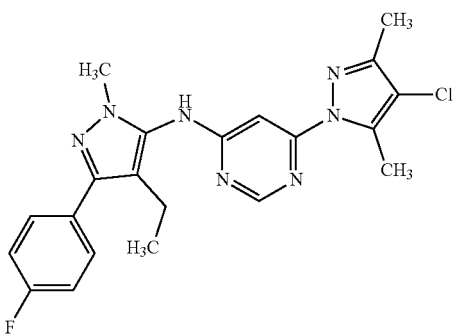 [SMILES: CCc1c(-c2ccc(F)cc2)nn(C)c1Nc1cc(-n2nc(C)c(Cl)c2C)ncn1]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 4-ethyl-3-(4-fluorophenyl)-1-methyl-1H-pyrazol-5-amine (100 mg, 456 µmol) and 4-chloro-6-(4-chloro-3,5-dimethyl-1H-pyrazol-1-yl)pyrimidine (122 mg, 502 µmol) to yield the desired product 79.7 mg (41% yield).

LC-MS (method 11): R$_t$=1.59 min; MS (ESIpos): m/z=426 [M+H]$^+$ $^1$H-NMR (400 MHz, DMSO-d$_6$) δ [ppm]: 0.969 (3.64), 0.988 (7.84), 1.006 (3.75), 2.214 (3.11), 2.445 (0.92), 2.463 (2.44), 2.482 (2.57), 2.649 (13.05), 3.316 (16.00), 7.248 (1.88), 7.269 (3.78), 7.291 (2.08), 7.651 (1.69), 7.666 (2.26), 7.685 (1.53), 8.504 (0.73), 9.467 (1.07).

Example 98

6-(3,5-dimethyl-1H-pyrazol-1-yl)-N-{1,4-dimethyl-5-[4-(trifluoromethoxy)phenyl]-1H-pyrazol-3-yl}pyrimidin-4-amine

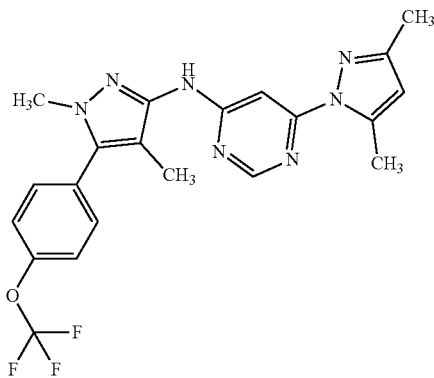 [SMILES: Cc1cc(C)n(-c2cc(Nc3nn(C)c(-c4ccc(OC(F)(F)F)cc4)c3C)ncn2)n1]

4-chloro-6-(3,5-dimethyl-1H-pyrazol-1-yl)pyrimidine (35.0 mg, 168 μmol) and 1,4-dimethyl-5-[4-(trifluoromethoxy)phenyl]-1H-pyrazol-3-amine (50.0 mg, 184 μmol) were dissolved in N-methylpyrrolidone (1.7 mL) and hydrochloric acid in 1,4-dioxane (210 μl, 4.0 M, 840 μmol) was added. The reaction vessel was sealed and the reaction mixture was heated to 190° C. under microwave irradiation for 20 h. The crude mixture was purified by preparative HPLC (method 3) to yield the desired product as a white powder (4.5 mg, 6% yield).

$^1$H-NMR (400 MHz, DMSO-d$_6$) δ [ppm]: 1.865 (13.92), 2.023 (0.20), 2.184 (14.55), 2.327 (0.20), 2.366 (0.17), 2.622 (13.33), 2.669 (0.19), 2.709 (0.15), 2.754 (0.43), 3.710 (16.00), 6.131 (3.58), 7.377 (2.01), 7.524 (2.44), 7.545 (3.66), 7.616 (5.53), 7.638 (3.45), 8.004 (0.15), 8.025 (0.14), 8.449 (3.43), 9.397 (3.15).

Example 99

6-(4-chloro-3,5-dimethyl-1H-pyrazol-1-yl)-N-[4-ethyl-5-(4-fluorophenyl)-1-methyl-1H-pyrazol-3-yl]pyrimidin-4-amine

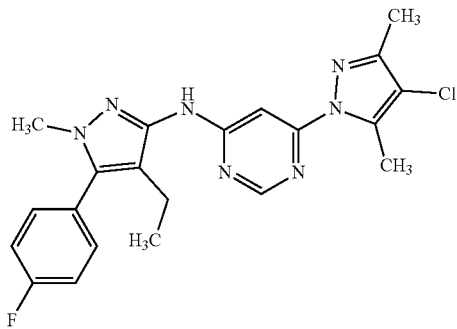 [SMILES: CCc1c(Nc2cc(-n3nc(C)c(Cl)c3C)ncn2)nn(C)c1-c1ccc(F)cc1]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 4-ethyl-5-(4-fluorophenyl)-1-methyl-1H-pyrazol-3-amine (100 mg, 456 μmol) and 4-chloro-6-(4-chloro-3,5-dimethyl-1H-pyrazol-1-yl)pyrimidine (122 mg, 502 μmol) to yield the desired product 86.1 mg (41% yield) after purification by preparative HPLC (method: column: Reprosil C18; m; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B followed by KINTEX-S-E).

LC-MS (method 11): R$_t$=1.61 min; MS (ESIpos): m/z=426 [M+H]$^+$ $^1$H-NMR (400 MHz, DMSO-d$_6$) δ [ppm]: 0.869 (3.80), 0.888 (8.48), 0.906 (3.96), 2.219 (14.98), 2.286 (1.04), 2.305 (2.98), 2.323 (2.94), 2.342 (0.97), 2.641 (16.00), 3.315 (11.15), 7.358 (2.48), 7.367 (2.62), 7.380 (4.79), 7.402 (2.70), 7.500 (2.67), 7.514 (3.06), 7.521 (2.60), 7.535 (2.03), 8.478 (3.41), 9.453 (2.59).

Example 100

N-[4-chloro-3-(4-fluorophenyl)-1-methyl-1H-pyrazol-5-yl]-6-(3-methyl-1H-indazol-1-yl)pyrimidin-4-amine

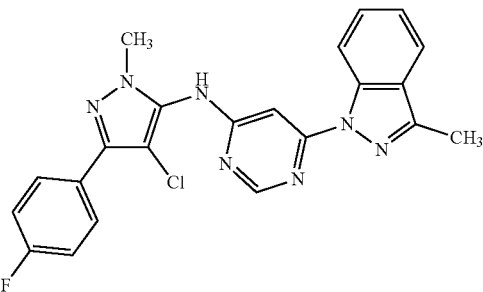 [SMILES: Cc1nn(-c2cc(Nc3c(Cl)c(-c4ccc(F)cc4)nn3C)ncn2)c2ccccc12]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 1-(6-chloropyrimidin-4-yl)-3-methyl-1H-indazole (78.9 mg, 322 μmol) and 4-chloro-3-(4-fluorophenyl)-1-methyl-1H-pyrazol-5-amine (80.0 mg, 355 μmol) to yield the desired product 75.0 mg (52% yield).

LC-MS (method 9): R$_t$=1.26 min; MS (ESIpos): m/z=434 [M+H]$^+$ $^1$H-NMR (400 MHz, DMSO-d$_6$) δ [ppm]: 2.594 (11.62), 3.753 (16.00), 7.311 (2.39), 7.333 (4.95), 7.356 (4.48), 7.376 (1.68), 7.571 (1.43), 7.592 (2.14), 7.610 (1.30), 7.852 (2.32), 7.872 (2.18), 7.897 (2.46), 7.911 (2.84), 7.919 (2.70), 7.933 (2.27), 8.602 (3.06), 8.730 (2.64), 8.752 (2.54), 9.697 (4.13).

Example 101

6-(3,5-dimethyl-1H-pyrazol-1-yl)-N-{1,4-dimethyl-5-[4-(trifluoromethyl)phenyl]-1H-pyrazol-3-yl}pyrimidin-4-amine

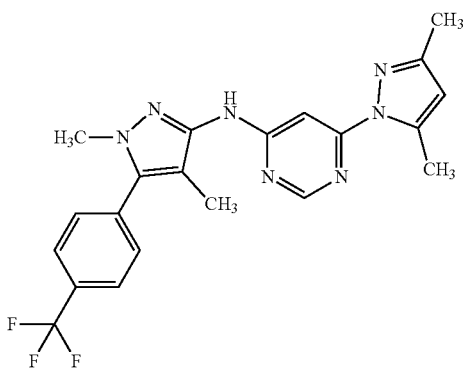 [SMILES: Cc1cc(C)n(-c2cc(Nc3nn(C)c(-c4ccc(C(F)(F)F)cc4)c3C)ncn2)n1]

A microwave tube was charged with N-(1,4-dimethyl-1H-pyrazol-3-yl)-6-(3,5-dimethyl-1H-pyrazol-1-yl)pyrimidin-4-amine trifluoroacetate (47.8 mg, 120 µmol), 1-bromo-4-(trifluoromethyl)benzene (34 µl, 240 µmol) and potassium acetate (24.8 mg, 253 µmol). The solids were suspended in N,N-dimethylacetamide (500 µL) and the mixture was degassed by passing an argon flow through the suspension for 3 min. 1,4-Bis(diphenylphosphino)butane-palladium(II) chloride (3.63 mg, 6.01 µmol) was added and the reaction mixture was further degassed for 1 min. The vessel was sealed and heated at 150° C. for 16 h. After cooling to ambient temperature, the reaction mixture was filtered and the filtrate purified by preparative HPLC (method 3) to yield the desired product (4.2 mg, 8% yield).

LC-MS (method 11): $R_t$=1.49 min; MS (ESIpos): m/z=428 [M+H]$^+$ $^1$H-NMR (600 MHz, DMSO-d$_6$) δ [ppm]: 1.89 (s, 3H), 2.19 (s, 3H), 2.63 (s, 3H), 3.74 (s, 3H), 6.14 (s, 1H), 7.39 (br s, 1H), 7.73 (d, 2H), 7.90 (d, 2H), 7.915 (3.63), 8.46 (s, 1H), 9.45 (s, 1H).

Example 102

N-[1-(4-fluorophenyl)-3,5-dimethyl-1H-pyrazol-4-yl]-6-(3-methyl-1H-indazol-1-yl)pyrimidin-4-amine

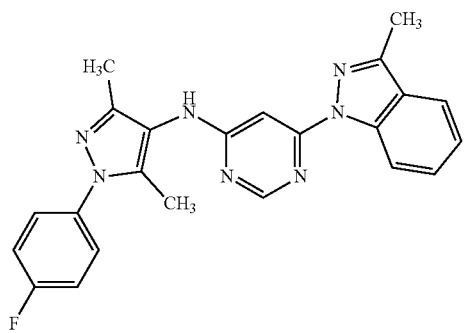 [SMILES: Cc1nn(-c2ccc(F)cc2)c(C)c1Nc1cc(-n2nc(C)c3ccccc32)ncn1]

The described product was prepared in a manner analogous to that described in the preparation of 6-(4-chloro-3,5-dimethyl-1H-pyrazol-1-yl)-N-(1,4-dimethyl-5-phenyl-1H-pyrazol-3-yl)pyrimidin-4-amine starting from 1-(4-fluorophenyl)-3,5-dimethyl-1H-pyrazol-4-amine (100 mg, 487 µmol) and 1-(6-chloropyrimidin-4-yl)-3-methyl-1H-indazole (131 mg, 536 µmol) to yield the desired product 25.2 mg (12% yield) after purification by preparative HPLC (method: column: Reprosil C18; 10 µm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B followed by method 3).

LC-MS (method 11): $R_t$=1.47 min; MS (ESIpos): m/z=414 [M+H]$^+$ $^1$H-NMR (400 MHz, DMSO-d$_6$) δ [ppm]: 2.106 (16.00), 2.208 (10.65), 7.309 (1.19), 7.328 (2.38), 7.347 (3.01), 7.369 (3.27), 7.391 (1.87), 7.544 (1.39), 7.564 (2.16), 7.583 (1.47), 7.617 (1.80), 7.824 (1.75), 7.844 (1.48), 8.506 (0.67), 8.735 (2.04), 8.756 (1.97), 8.866 (4.21).

Example 103

N-[1-(4-fluorophenyl)-3,5-dimethyl-1H-pyrazol-4-yl]-6-(3-methyl-2H-indazol-2-yl)pyrimidin-4-amine

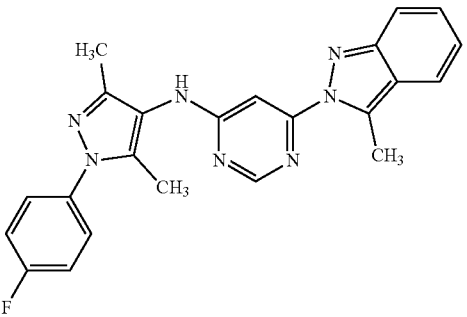 [SMILES: Cc1nn(-c2ccc(F)cc2)c(C)c1Nc1cc(-n2nc3ccccc3c2C)ncn1]

The described regioisomer was obtained by the regioisomeric separation of the reaction mixture in the preparation of N-[1-(4-fluorophenyl)-3,5-dimethyl-1H-pyrazol-4-yl]-6-(3-methyl-H-indazol-1-yl)pyrimidin-4-amine. The starting material thereof contained some of the regioisomeric product. 9.30 mg of the depicted product were obtained.

LC-MS (method 11): Rt=1.38 min; MS (ESIpos): m/z=414 [M+H]$^+$ $^1$H-NMR (500 MHz, DMSO-d$_6$) δ [ppm]: −0.007 (0.47), 1.229 (0.54), 2.079 (0.54), 2.084 (0.65), 2.114 (16.00), 2.161 (0.43), 2.209 (8.30), 2.996 (10.54), 7.038 (0.68), 7.280 (0.49), 7.308 (0.64), 7.348 (1.78), 7.366 (3.24), 7.383 (1.88), 7.613 (1.20), 7.748 (0.72), 7.764 (0.73), 9.133 (0.85).

Example 104

[1-(6-{[4-ethyl-5-(4-fluorophenyl)-1-methyl-1H-pyrazol-3-yl]amino}pyrimidin-4-yl)-3-methyl-1H-pyrazol-5-yl]methanol

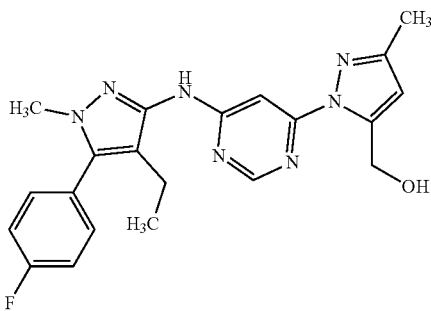 [SMILES: CCc1c(Nc2cc(-n3nc(C)cc3CO)ncn2)nn(C)c1-c1ccc(F)cc1]

A solution of ethyl 1-(6-{[4-ethyl-5-(4-fluorophenyl)-1-methyl-1H-pyrazol-3-yl]amino}pyrimidin-4-yl)-3-methyl-1H-pyrazole-5-carboxylate (90.0 mg, 200 µmol) in THF (4.0 ml) was treated with diisobutylaluminium hydride in THF (1.0 ml, 1.0 M, 1.0 mmol) at 0° C. The reaction mixture was stirred at 0° C. for 30 min. Methanol (1 mL) and aqueous hydrochloric acid (0.5 M, 1 mL) were added and the mixture was extracted with ethyl acetate. The combined organic phases were washed with saturated sodium hydrogen carbonate solution, dried over sodium sulfate and the solvent was removed under vacuum. The crude product was purified by preparative HPLC (method 7) to yield 11.5 mg (14% yield).

LC-MS (method 11): $R_t$=1.28 min; MS (ESIpos): m/z=408 [M+H]$^+$ $^1$H-NMR (400 MHz, DMSO-$d_6$) δ [ppm]: 0.869 (3.72), 0.888 (8.29), 0.906 (3.90), 1.091 (0.50), 2.218 (14.77), 2.282 (1.03), 2.301 (2.95), 2.320 (2.90), 2.338 (0.99), 3.659 (16.00), 4.844 (4.16), 4.859 (4.32), 5.448 (1.14), 5.464 (2.32), 5.479 (1.05), 6.315 (4.43), 7.333 (2.86), 7.359 (1.92), 7.381 (4.37), 7.403 (2.66), 7.504 (2.54), 7.518 (2.93), 7.525 (2.67), 7.539 (2.04), 8.444 (3.66), 9.402 (2.99).

Example 105

[1-(6-{[4-ethyl-5-(4-fluorophenyl)-1-methyl-1H-pyrazol-3-yl]amino}pyrimidin-4-yl)-3,5-dimethyl-1H-pyrazol-4-yl](piperidin-1-yl)methanone

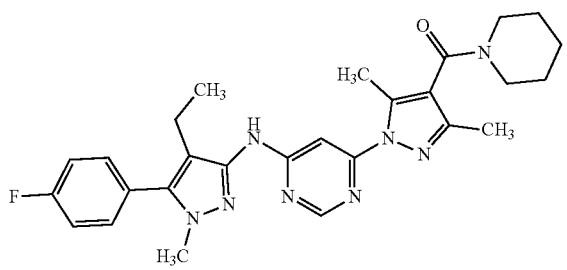 [SMILES: CCc1c(Nc2cc(-n3nc(C)c(C(=O)N4CCCCC4)c3C)ncn2)nn(C)c1-c1ccc(F)cc1]

The described product was prepared in a manner analogous to that described in the preparation of (±)-[syn-2,6-dimethylmorpholin-4-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone (racemate) starting from 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (76.8 mg, 176 µmol) and piperidine (35 µl, 350 µmol) to yield the desired product 58.6 mg (66% yield).

LC-MS (method 10): $R_t$=2.08 min; MS (ESIpos): m/z=503 [M+H]$^+$ $^1$H-NMR (400 MHz, DMSO-$d_6$) δ [ppm]: −0.008 (3.08), 0.008 (1.38), 0.872 (3.59), 0.891 (7.71), 0.909 (3.47), 1.074 (1.35), 1.091 (2.71), 1.109 (1.35), 1.474 (1.22), 1.600 (1.68), 2.159 (14.51), 2.287 (0.95), 2.305 (2.45), 2.324 (2.49), 2.343 (0.72), 2.579 (15.31), 3.357 (0.85), 3.375 (1.63), 3.392 (1.54), 3.410 (0.62), 3.572 (0.65), 3.652 (16.00), 7.359 (2.58), 7.371 (2.67), 7.381 (4.82), 7.403 (2.65), 7.500 (2.76), 7.506 (1.35), 7.514 (3.01), 7.522 (2.27), 7.536 (1.87), 8.473 (3.59), 9.427 (2.19).

Example 106

[1-ent-(6-{[4-ethyl-5-(4-fluorophenyl)-1-methyl-1H-pyrazol-3-yl]amino}pyrimidin-4-yl)-3,5-dimethyl-1H-pyrazol-4-yl](2-methylpyrrolidin-1-yl)methanone

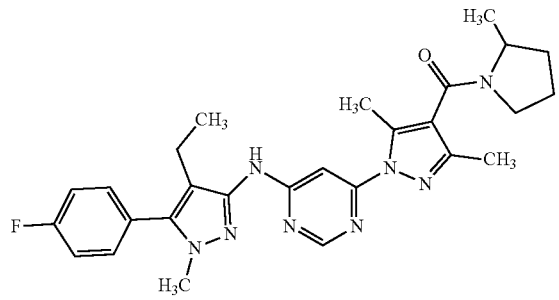 [SMILES: CCc1c(Nc2cc(-n3nc(C)c(C(=O)N4CCCC4C)c3C)ncn2)nn(C)c1-c1ccc(F)cc1]

A sample of racemic [1-(6-{[4-ethyl-5-(4-fluorophenyl)-1-methyl-1H-pyrazol-3-yl]amino}pyrimidin-4-yl)-3,5-dimethyl-1H-pyrazol-4-yl](2-methylpyrrolidin-1-yl)methanone (30 mg, 59.7 µmol) was separated using chiral HPLC (column: Daicel Chiralpak IG; 250*20 mm, 5 µM, flow 15 mL/min, 40° C., eluent 50% n-heptan/50% ethanol+0.2% diethylamine) to give 14.5 mg of the first eluting enantiomer of [1-(6-{[4-ethyl-5-(4-fluorophenyl)-1-methyl-1H-pyrazol-3-yl]amino}pyrimidin-4-yl)-3,5-dimethyl-1H-pyrazol-4-yl](2-methylpyrrolidin-1-yl)methanone (48% yield from racemate).

LC-MS (method 10): $R_t$=2.03 min; MS (ESIpos): m/z=503 [M+H]$^+$

Chiral HPLC (Daicel Chiralcel 5 µM 100×4.6 mm, Solvent: 50% n-heptan/50% ethanol 0.2% diethylamine; 40° C., 1 mL/min) $R_t$=10.1 min, >99% enantiomeric excess.

$^1$H-NMR (400 MHz, DMSO-$d_6$) δ [ppm]: −0.008 (1.91), 0.008 (1.56), 0.872 (4.07), 0.891 (8.78), 0.910 (4.05), 1.227 (1.94), 1.241 (1.97), 1.564 (0.46), 1.874 (0.51), 2.071 (0.50), 2.168 (6.28), 2.287 (0.86), 2.306 (2.49), 2.324 (2.64), 2.343 (0.80), 2.524 (0.85), 2.590 (8.69), 3.230 (0.46), 3.653 (16.00), 7.359 (2.29), 7.374 (2.18), 7.381 (4.92), 7.403 (2.74), 7.502 (2.63), 7.507 (1.12), 7.515 (2.93), 7.523 (2.31), 7.532 (0.92), 7.537 (1.96), 8.473 (2.99), 9.418 (2.25).

Optical rotation: [α]=+46.10 (c=1.00, methanol, 589 nm).

Example 107

[1-ent-(6-{[4-ethyl-5-(4-fluorophenyl)-1-methyl-1H-pyrazol-3-yl]amino}pyrimidin-4-yl)-3,5-dimethyl-1H-pyrazol-4-yl](2-methylpyrrolidin-1-yl)methanone

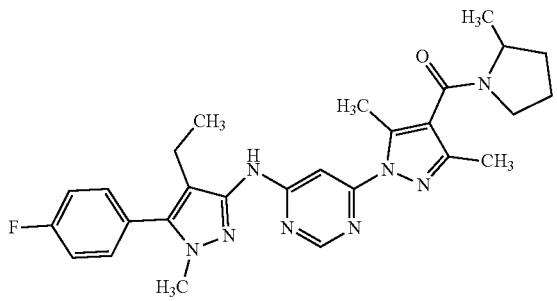 [SMILES: CCc1c(Nc2cc(-n3nc(C)c(C(=O)N4CCCC4C)c3C)ncn2)nn(C)c1-c1ccc(F)cc1]

A sample of racemic [1-(6-{[4-ethyl-5-(4-fluorophenyl)-1-methyl-1H-pyrazol-3-yl]amino}pyrimidin-4-yl)-3,5-dimethyl-1H-pyrazol-4-yl](2-methylpyrrolidin-1-yl)methanone (30 mg, 59.7 μmol) was separated using chiral HPLC (column: Daicel Chiralpak IG; 250*20 mm, 5 μM, flow 15 mL/min, 40° C., eluent 50% n-heptan/50% ethanol+0.2% diethylamine) to give 15.1 mg of the second eluting enantiomer of [1-(6-{[4-ethyl-5-(4-fluorophenyl)-1-methyl-1H-pyrazol-3-yl]amino}pyrimidin-4-yl)-3,5-dimethyl-1H-pyrazol-4-yl](2-methylpyrrolidin-1-yl)methanone (50% yield from racemat).

LC-MS (method 10): Rt=2.03 min; MS (ESIpos): m/z=503 [M+H]+

Chiral HPLC (Daicel Chiralcel 5 μM 100×4.6 mm, Solvent: 50% n-heptan/50% ethanol 0.2% diethylamine; 40° C., 1 mL/min) $R_t$=12.8 min, >99% enantiomeric excess.

$^1$H-NMR (400 MHz, DMSO-d$_6$) δ [ppm]: 0.871 (4.20), 0.890 (8.64), 0.908 (4.03), 1.239 (2.17), 1.563 (0.51), 1.711 (0.39), 1.873 (0.56), 2.071 (0.54), 2.167 (6.71), 2.286 (0.93), 2.305 (2.56), 2.323 (2.75), 2.589 (8.94), 3.652 (16.00), 4.149 (0.43), 7.358 (2.44), 7.380 (4.97), 7.402 (2.70), 7.500 (2.67), 7.514 (2.99), 7.522 (2.33), 7.535 (1.87), 8.472 (3.61), 9.417 (2.33).

Optical rotation: [α]=−47.1° (c=1.00, methanol, 589 nm).

Example 108

1-(6-{[4-ethyl-5-(4-fluorophenyl)-1H-pyrazol-3-yl]amino}pyrimidin-4-yl)-3,5-dimethyl-1H-pyrazole-4-carbonitrile

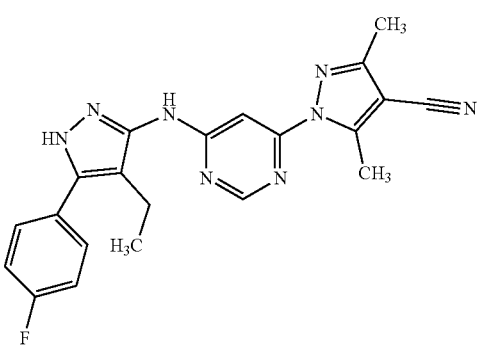 [SMILES: CCc1c(Nc2cc(-n3nc(C)c(C#N)c3C)ncn2)n[nH]c1-c1ccc(F)cc1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-ethyl-5-(4-fluorophenyl)-1H-pyrazol-3-amine (100 mg, 487 μmol) and 1-(6-chloropyrimidin-4-yl)-3,5-dimethyl-1H-pyrazole-4-carbonitrile (125 mg, 536 μmol) to yield the desired product 39.2 mg (19% yield).

LC-MS (method 11): $R_t$=1.37 min; MS (ESIpos): m/z=403 [M+H]+

$^1$H-NMR (400 MHz, DMSO-d$_6$) δ [ppm]: 0.996 (3.59), 1.014 (7.84), 1.033 (3.78), 2.323 (12.75), 2.377 (0.66), 2.573 (0.97), 2.792 (16.00), 2.825 (0.61), 7.333 (1.37), 7.355 (2.54), 7.376 (1.60), 7.487 (0.49), 7.597 (1.72), 7.611 (2.23), 7.631 (1.61), 8.546 (2.12), 9.631 (1.36), 12.862 (0.55).

Example 109

2-[1-(6-{[5-(4-fluorophenyl)-1,4-dimethyl-1H-pyrazol-3-yl]amino}pyrimidin-4-yl)-3 5-dimethyl-1H-pyrazol-4-yl]propan-2-ol

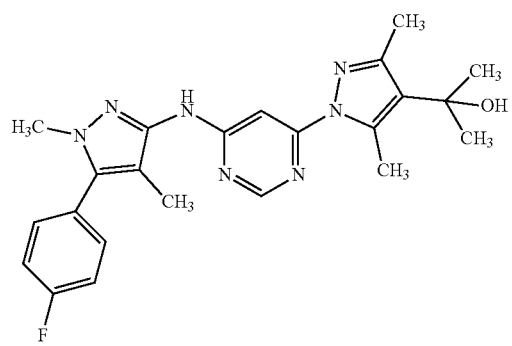 [SMILES: Cc1nn(-c2cc(Nc3nn(C)c(-c4ccc(F)cc4)c3C)ncn2)c(C)c1C(C)(C)O]

Ethyl 1-(6-{[5-(4-fluorophenyl)-1,4-dimethyl-1H-pyrazol-3-yl]amino}pyrimidin-4-yl)-3,5-dimethyl-1H-pyrazole-4-carboxylate (24.0 mg, 53.4 μmol) was dissolved in THF and the resulting solution cooled to 0° C. Methyl magnesiumbromide (1.0 M in THF, 210 μL, 210 μmol) was added and the reaction mixture was allowed to warm to ambient temperature while stirring. After 90 min, excess Grignard reagent was quenched with aq. saturated ammonium chloride solution and extracted with ethyl acetate (3×). The combined organic extracts were washed with brine, dried over sodium sulfate and concentrated. The residue was purified by preparative HPLC (column: Chromatorex C18; 125*30 mm, 10 μM, flow 75 mL/min, gradient acetonitrile/water (containing 0.1% trifluoroacetic acid) 90/10 to 5/95) to yield the desired product (11.8 mg, 51% yield).

LC-MS (method 11): $R_t$=1.25 min; MS (ESIpos): m/z=436 [M+H]+

$^1$H-NMR (400 MHz, DMSO-d$_6$) δ [ppm]: −0.149 (0.49), 0.008 (4.64), 0.146 (0.47), 1.471 (16.00), 1.853 (7.70), 2.276 (7.89), 2.328 (0.47), 2.670 (0.47), 2.715 (8.25), 7.329 (1.02), 7.355 (1.08), 7.377 (2.40), 7.399 (1.40), 7.506 (1.35), 7.519 (1.52), 7.527 (1.28), 7.541 (1.03), 8.456 (2.19), 9.411 (1.58).

Example 110

N-[4-chloro-5-(4-fluorophenyl)-1-methyl-1H-pyrazol-3-yl]-6-(3-methyl-1H-indazol-1-yl)pyrimidin-4-amine

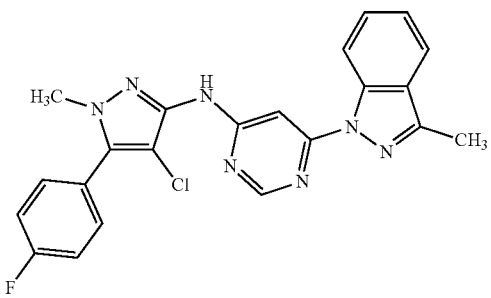 [SMILES: Cc1nn(-c2cc(Nc3nn(C)c(-c4ccc(F)cc4)c3Cl)ncn2)c2ccccc12]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 1-(6-chloropyrimidin-4-yl)-3-methyl-1H-indazole (78.9 mg, 322 µmol) and 4-chloro-5-(4-fluorophenyl)-1-methyl-1H-pyrazol-3-amine (80.0 mg, 355 µmol) to yield the desired product (20 mg, 14%) after preparative HPLC (method: column: Reprosil C18; 10 µm; 125×30 mm/flow: 50 ml/min/eluent: A=water (0.1% formic acid), B=acetonitrile/gradient: 0.00-4.25 min=20% B, 4.50 min=30% B, 19.00-22.50 min=100% B, 22.75-25.00 min=20% B followed by method 8).

$^1$H-NMR (500 MHz, DMSO-d$_6$): δ [ppm]: 2.60 (s, 3H), 3.80 (s, 3H), 7.31-7.40 (m, 2H), 7.44 (t, 2H), 7.58 (t, 1H), 7.64-7.70 (m, 2H), 7.85 (d, 1H), 8.58 (s, 1H), 8.71-8.79 (m, 1H), 9.53 (s, 1H).

Example 111

2-[3-{[6-(3,5-dimethyl-1H-pyrazol-1-yl)pyrimidin-4-yl]amino}-4-ethyl-5-(4-fluorophenyl)-1H-pyrazol-1-yl]ethanol

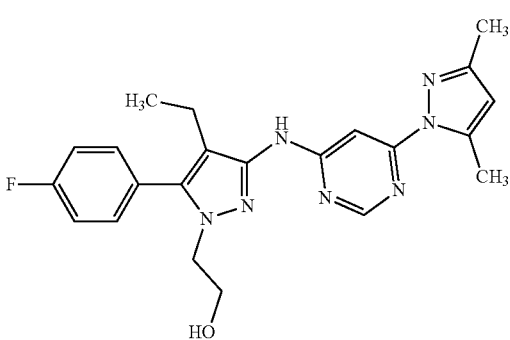 [SMILES: CCc1c(Nc2cc(-n3nc(C)cc3C)ncn2)nn(CCO)c1-c1ccc(F)cc1]

N-[1-(2-{[tert-butyl(dimethyl)silyl]oxy}ethyl)-4-ethyl-5-(4-fluorophenyl)-1H-pyrazol-3-yl]-6-(3,5-dimethyl-1H-pyrazol-1-yl)pyrimidin-4-amine (50.0 mg, 93.3 µmol) was stirred in hydrochlorid acid in dioxane (4M, 1.5 ml) for 1 hour at room temperature. The mixture was diluted with dichloromethane and the solvent was removed under reduced pressure. This was done twice to yield the desired product 41.9 mg (quant.).

LC-MS (method 11): R$_t$=1.32 min; MS (ESIpos): m/z=422 [M+H]$^+$ $^1$H-NMR (400 MHz, DMSO-d$_6$) δ [ppm]: 0.876 (4.03), 0.895 (9.08), 0.913 (4.21), 1.234 (0.52), 2.195 (16.00), 2.295 (1.12), 2.313 (3.33), 2.332 (3.30), 2.351 (1.10), 2.632 (14.50), 3.569 (2.31), 3.716 (2.06), 3.731 (4.89), 3.746 (2.67), 3.911 (2.62), 3.926 (4.59), 3.941 (1.96), 4.868 (0.75), 5.756 (0.71), 6.163 (4.20), 7.354 (2.05), 7.376 (4.51), 7.398 (2.64), 7.522 (2.83), 7.536 (3.86), 7.543 (4.38), 7.557 (2.69), 8.519 (3.20), 9.742 (0.42).

Example 112

1-(6-{[4-ethyl-5-(4-fluorophenyl)-1-methyl-1H-pyrazol-3-yl]amino}pyrimidin-4-yl)-3,5-dimethyl-1H-pyrazole-4-carbonitrile

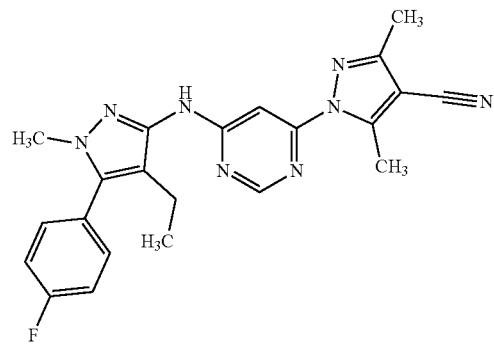 [SMILES: CCc1c(Nc2cc(-n3nc(C)c(C#N)c3C)ncn2)nn(C)c1-c1ccc(F)cc1]

The described product was prepared in an analogous manner to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-ethyl-5-(4-fluorophenyl)-1-methyl-1H-pyrazol-3-amine (100 mg, 456 µmol) and 1-(6-chloropyrimidin-4-yl)-3,5-dimethyl-1H-pyrazole-4-carbonitrile (147 mg, 80% purity, 502 µmol) to yield 38.1 mg (20% yield) of the desired product after purification by preparative HPLC (method: column: Reprosil C18; 10 µm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00.-27.00 min=20% B followed by method 3).

LC-MS (method 11): R$_t$=1.45 min; MS (ESIneg): m/z=415 [M−H]$^−$ $^1$H-NMR (400 MHz, DMSO-d$_6$) δ [ppm]: 0.868 (3.76), 0.887 (7.82), 0.906 (3.61), 2.289 (1.22), 2.307 (2.93), 2.336 (14.26), 2.787 (14.61), 3.651 (16.00), 7.342 (0.56), 7.359 (2.04), 7.381 (4.53), 7.402 (2.74), 7.421 (1.45), 7.462 (0.89), 7.477 (0.64), 7.499 (2.73), 7.513 (3.06), 7.520 (2.44), 7.534 (1.85), 7.781 (0.45), 7.794 (0.41), 8.147 (0.42), 8.530 (3.30), 9.611 (1.43).

Example 113

1-[1-(6-{[5-(4-fluorophenyl)-1,4-dimethyl-1H-pyrazol-3-yl]amino}pyrimidin-4-yl)-3,5-dimethyl-1H-pyrazol-4-yl]ethanone

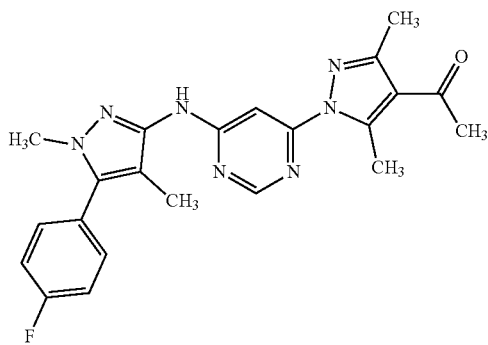 [SMILES: CC(=O)c1c(C)nn(-c2cc(Nc3nn(C)c(-c4ccc(F)cc4)c3C)ncn2)c1C]

Ethyl 1-(6-{[5-(4-fluorophenyl)-1,4-dimethyl-1H-pyrazol-3-yl]amino}pyrimidin-4-yl)-3,5-dimethyl-1H-pyrazole-4-carboxylate (24.0 mg, 53.4 µmol) was dissolved in THF and the resulting solution was cooled to 0° C. Methyl magnesiumbromide (1.0 M in THF, 210 µL, 210 µmol) was added and the reaction mixture allowed to warm to ambient temperature while stirring. After 90 min, excess Grignard reagent was quenched with saturated aqueous ammonium chloride solution and extracted with ethyl acetate (3×). The combined organic extracts were washed with brine, dried over sodium sulfate and concentrated. The residue was purified by preparative HPLC (column: Chromatorex C18; 125*30 mm, 10 µM, flow 75 mL/min, gradient acetonitrile/water (containing 0.1% trifluoroacetic acid) 90/10 to 5/95) to yield desired ketone in 8% yield (1.7 mg).

LC-MS (method 11): $R_t$=1.29 min; MS (ESIpos): m/z=420 [M+H]$^+$ $^1$H-NMR (500 MHz, DMSO-$d_6$) δ [ppm]: 1.86 (s, 3H), 2.45 (br d, 6H), 2.86 (s, 3H), 3.68 (s, 3H), 7.25-7.45 (m, 3H), 7.48-7.58 (m, 2H), 8.54 (s, 1H), 9.62 (br s, 1H).

Example 114

6-(3,5-dimethyl-1H-pyrazol-1-yl)-N-[4-ethyl-5-(4-fluorophenyl)-1-(methylsulfonyl)-1H-pyrazol-3-yl]pyrimidin-4-amine

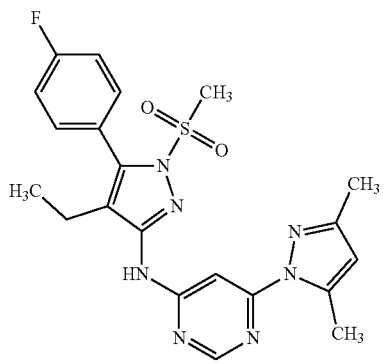 [SMILES: CCc1c(Nc2cc(-n3nc(C)cc3C)ncn2)nn(S(C)(=O)=O)c1-c1ccc(F)cc1]

A solution of 6-(3,5-dimethyl-1H-pyrazol-1-yl)-N-[4-ethyl-3-(4-fluorophenyl)-1H-pyrazol-5-yl]pyrimidin-4-amine (30.0 mg, 79.5 µmol) and triethylamine (22 µl, 160 µmol) in dichloromethane (320 µl, 4.9 mmol) was treated with methanesulfonyl chloride (7.4 µl, 95 µmol) and stirred overnight at room temperature. 4-Dimethylaminopyridine (1.94 mg, 15.9 µmol) was added and it was stirred for 1 hour at room temperature. Further methanesulfonyl chloride (7.4 µl, 95 µmol) in acetonitrile (600 µl) was added. After 1.5 h at room temperature pyridine (300 µl) was added and it was stirred over night at 40° C. Again, 0.6 mL acetonitrile and 0.6 mL pyridine were added and it was stirred overnight at 40° C.

After that, further 0.3 mL DMF and 5 eq of trimethylamine were added and it was stirred for 7 hours at 40° C. and over the weekend at room temperature. Potassium carbonate (33.0 mg, 238 µmol) was added and the reaction mixture was stirred 6.5 h at 40° C., over night at 70° C. and 5 h at 100° C. The solvent was removed under reduced pressure. The residue was suspended in acetonitrile/water, the precipitate was removed by filtration. The filtrate was taken to dryness and purified by preparative HPLC (method: C18, 250×30, flow 50 ml/min, Runtime: 340 min, detection at 210 nm, eluent: A=water (0.05% formic acid), B=acetonitrile, gradient 40% B/60% A (6 min)→95% B/5% A (28 min)→95% B/5% A (38 min)→34% B/76% A (39 min)) to yield the desired product (2.30 mg, 6% yield).

LC-MS (method 9): $R_t$=1.13 min; MS (ESIpos): m/z=456 [M+H]$^+$ $^1$H-NMR (600 MHz, DMSO-$d_6$) δ [ppm]: 0.897 (3.54), 0.909 (7.44), 0.922 (3.62), 1.296 (0.57), 2.189 (15.25), 2.335 (0.96), 2.348 (2.87), 2.360 (2.79), 2.373 (0.89), 2.639 (0.52), 2.655 (13.87), 3.477 (16.00), 3.508 (0.80), 3.910 (1.07), 6.173 (4.07), 7.303 (1.93), 7.318 (4.01), 7.332 (2.27), 7.511 (2.18), 7.519 (2.59), 7.525 (2.48), 7.534 (2.03), 8.087 (1.51), 8.597 (4.39), 10.065 (1.32).

Example 115

6-(4-chloro-3,5-dimethyl-1H-pyrazol-1-yl)-N-[1-(cyclopropylmethyl)-4-ethyl-3-(4-fluorophenyl)-1H-pyrazol-5-yl]pyrimidin-4-amine

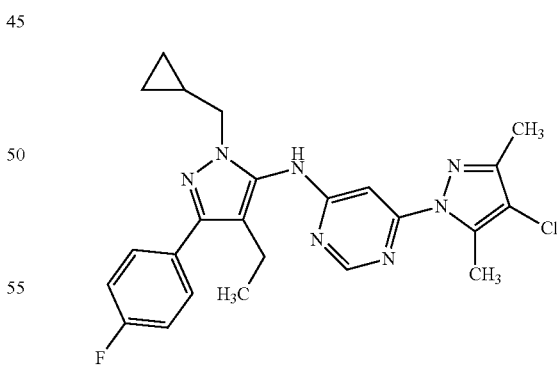

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 1-(cyclopropylmethyl)-4-ethyl-3-(4-fluorophenyl)-1H-pyrazol-5-amine (105 mg, 405 µmol) and 4-chloro-6-(4-chloro-3,5-dimethyl-1H-pyrazol-1-yl)pyrimidine (108 mg, 445 µmol) to yield the desired product 88.5 mg (96% purity, 45% yield) after preparative HPLC (method: column: Reprosil C18; 10 μm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B followed by method 3).

LC-MS (method 11): $R_t$=1.70 min; MS (ESIpos): m/z=466 [M+H]$^+$ $^1$H-NMR (400 MHz, DMSO-d$_6$) δ [ppm]: 0.17-0.54 (m, 4H), 0.99 (t, 3H), 1.14-1.28 (m, 1H), 2.20 (br s, 3H), 2.40-2.49 (m, 2H), 2.64 (s, 3H), 3.80 (br d, 2H), 6.51 (br s, 1H), 7.27 (t, 2H), 7.69 (br t, 2H), 8.49 (br s, 1H), 9.42 (br s, 1H).

Example 116

6-(3,5-dimethyl-1H-pyrazol-1-yl)-N-{1,4-dimethyl-3-[4-(trifluoromethoxy)phenyl]-1H-pyrazol-5-yl}pyrimidin-4-amine

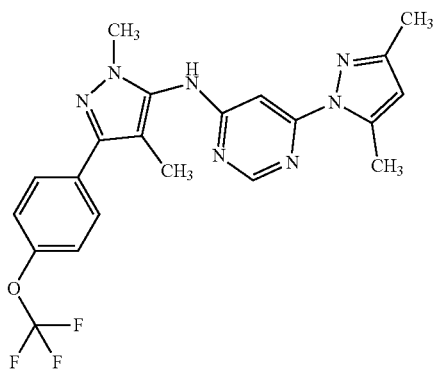 [SMILES: Cc1cc(C)n(-c2cc(Nc3c(C)c(-c4ccc(OC(F)(F)F)cc4)nn3C)ncn2)n1]

A microwave vial was charged with 4-chloro-6-(3,5-dimethyl-1H-pyrazol-1-yl)pyrimidine (69.9 mg, 335 μmol) and 1,4-dimethyl-3-[4-(trifluoromethoxy)phenyl]-1H-pyrazol-5-amine (100 mg, 369 μmol), which were dissolved in N-methyl-2-pyrrolidone (2.6 mL) and treated with a solution of hydrochloric acid in dioxane (4 M, 0.4 mL). The microwave vial was sealed and heated to 190° C. for 20 h in a laboratory microwave. After cooling to ambient temperature and removal of the volatiles under vacuum, the residue was purified by preparative HPLC (method 3) to yield the desired product (7.6 mg, 5% yield).

LC-MS (method 10): $R_t$=2.28 min; MS (ESIpos): m/z=444 [M+H]$^+$ $^1$H-NMR (400 MHz, DMSO-d$_6$) δ [ppm]: −0.008 (3.48), 0.008 (3.36), 0.146 (0.42), 2.041 (16.00), 2.072 (0.98), 2.174 (4.28), 2.198 (0.92), 2.210 (0.68), 2.328 (0.45), 2.366 (0.41), 2.631 (14.18), 2.670 (0.51), 2.710 (0.43), 3.674 (11.50), 3.704 (1.33), 6.147 (2.94), 7.420 (3.09), 7.441 (3.32), 7.804 (3.37), 7.825 (2.99), 8.473 (0.96), 9.424 (2.47).

Example 117

6-(4-chloro-3,5-dimethyl-1H-pyrazol-1-yl)-N-{1,4-dimethyl-5-[4-(trifluoromethoxy)phenyl]-1H-pyrazol-3-yl}pyrimidin-4-amine

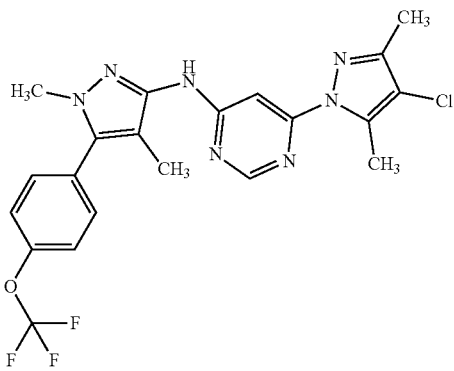 [SMILES: Cc1nn(-c2cc(Nc3nn(C)c(-c4ccc(OC(F)(F)F)cc4)c3C)ncn2)c(C)c1Cl]

A microwave vial was charged with 4-chloro-6-(4-chloro-3,5-dimethyl-1H-pyrazol-1-yl)pyrimidine (61.1 mg, 251 μmol) and 1,4-dimethyl-5-[4-(trifluoromethoxy)phenyl]-1H-pyrazol-3-amine (75.0 mg, 277 μmol), which were dissolved in NMP (2.6 mL) and treated with a solution of hydrochloric acid in dioxane (4 M, 0.3 mL). The microwave vial was sealed and heated to 190° C. for 20 h in a laboratory microwave. After cooling to ambient temperature and removal of the volatiles under vacuum, the residue was purified was purified by preparative HPLC (method 4) to yield the desired product as a white powder (18.7 mg, 15% yield).

LC-MS (method 10): $R_t$=2.55 min; MS (ESIpos): m/z=478 [M+H]$^+$ $^1$H-NMR (400 MHz, DMSO-d$_6$) δ [ppm]: 1.87 (s, 3H), 2.22 (s, 3H), 2.64 (s, 3H), 3.71 (s, 3H), 7.39-7.45 (m, 1H), 7.51-7.56 (m, 2H), 7.60-7.65 (m, 2H), 8.49 (s, 1H), 9.52 (s, 1H).

Example 118

4-(3-{[6-(3,5-dimethyl-1H-pyrazol-1-yl)pyrimidin-4-yl]amino}-1,4-dimethyl-1H-pyrazol-5-yl)benzonitrile

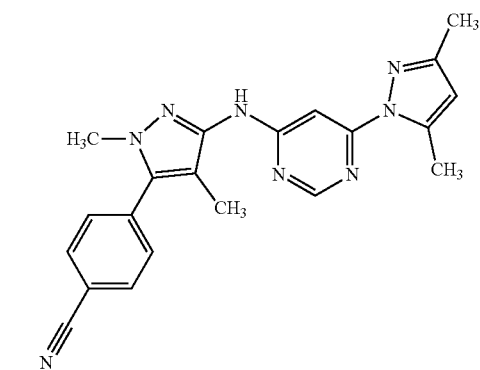 [SMILES: Cc1cc(C)n(-c2cc(Nc3nn(C)c(-c4ccc(C#N)cc4)c3C)ncn2)n1]

A microwave tube was charged with N-(1,4-dimethyl-1H-pyrazol-3-yl)-6-(3,5-dimethyl-1H-pyrazol-1-yl)pyrimidin- 4-amine (100 mg, 353 μmol), 4-bromobenzonitrile (106 mg, 582 μmol) and potassium acetate (72.7 mg, 741 μmol). The solids were suspended in N,N-dimethylacetamide (1.2 mL) and the reaction mixture was degassed by passing an argon flow through the suspension for 3 min. 1,4-Bis(diphenylphosphino)butane-palladium(II) chloride (10.7 mg, 17.6 μmol) was added and the reaction mixture further degassed for 1 min. The vessel was sealed and heated at 150° C. for 16 h. After cooling to ambient temperature, the reaction mixture was filtered and the filtrate purified by preparative HPLC (column: Chromatorex C18; 125*30 mm, 10 μM, flow 75 mL/min, gradient acetonitrile/water (containing 0.1% trifluoroacetic acid) 90/10 to 5/95) to yield the desired product (13.6 mg, 10% yield).

LC-MS (method 11): $R_t$=1.30 min; MS (ESIneg): m/z=383 [M−H]⁻

$^1$H-NMR (400 MHz, DMSO-d$_6$) δ [ppm]: 0.008 (1.80), 1.885 (13.27), 2.185 (13.76), 2.328 (0.59), 2.366 (0.64), 2.523 (1.83), 2.623 (12.59), 2.670 (0.60), 2.710 (0.58), 3.737 (16.00), 3.759 (1.19), 6.135 (3.52), 7.381 (2.04), 7.699 (4.01), 7.720 (4.64), 7.818 (0.85), 8.004 (4.47), 8.024 (3.96), 8.453 (3.84), 9.435 (2.84).

Example 119

N-[1-cyclopropyl-4-ethyl-3-(4-fluorophenyl)-1H-pyrazol-5-yl]-6-(3,5-dimethyl-1H-pyrazol-1-yl)pyrimidin-4-amine

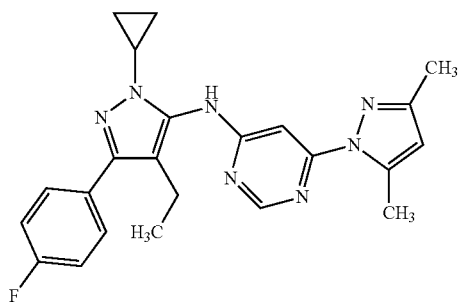 [SMILES: CCc1c(-c2ccc(F)cc2)nn(C2CC2)c1Nc1cc(-n2nc(C)cc2C)ncn1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 1-cyclopropyl-4-ethyl-3-(4-fluorophenyl)-1H-pyrazol-5-amine (100 mg, 408 μmol) and 4-chloro-6-(3,5-dimethyl-1H-pyrazol-1-yl)pyrimidine (93.6 mg, 448 μmol) to yield 77.5 mg of the desired product (96% purity, 44% yield) after purification by preparative HPLC (method: column: Reprosil C18; 10 μm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00.00-27.00 min=20% B and subsequently method 3).

LC-MS (method 11): $R_t$=1.53 min; MS (ESIneg): m/z=416 [M−H]⁻

$^1$H-NMR (400 MHz, DMSO-d$_6$) δ [ppm]: −0.008 (0.54), 0.008 (0.40), 0.867 (2.27), 0.880 (2.21), 0.885 (2.17), 0.973 (4.23), 0.992 (9.50), 1.010 (4.60), 1.040 (2.21), 1.074 (0.51), 1.091 (0.67), 2.175 (3.30), 2.436 (0.96), 2.454 (2.71), 2.473 (2.73), 2.635 (16.00), 3.358 (0.44), 3.368 (0.63), 3.375 (1.09), 3.386 (1.12), 3.393 (1.04), 3.403 (0.61), 6.144 (2.91), 7.241 (2.52), 7.263 (5.20), 7.285 (2.86), 7.639 (1.70), 7.654 (2.23), 7.660 (2.15), 7.674 (1.61), 8.471 (0.88), 9.393 (1.01).

Example 120

6-(4-chloro-3,5-dimethyl-1H-pyrazol-1-yl)-N-[1-cyclopropyl-4-ethyl-3-(4-fluorophenyl)-1H-pyrazol-5-yl]pyrimidin-4-amine

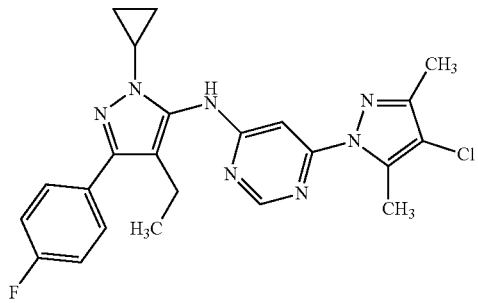 [SMILES: CCc1c(-c2ccc(F)cc2)nn(C2CC2)c1Nc1cc(-n2nc(C)c(Cl)c2C)ncn1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 1-cyclopropyl-4-ethyl-3-(4-fluorophenyl)-1H-pyrazol-5-amine (110 mg, 448 μmol) and 4-chloro-6-(4-chloro-3,5-dimethyl-1H-pyrazol-1-yl)pyrimidine (120 mg, 493 μmol) to yield 9.40 mg (100% purity, 5% yield) of the desired product.

LC-MS (method 11): $R_t$=1.68 min; MS (ESIpos): m/z=452 [M+H]⁺

$^1$H-NMR (400 MHz, DMSO-d$_6$) δ [ppm]: 0.78-0.93 (m, 2H), 0.93-1.06 (m, 5H), 2.09-2.27 (m, 3H), 2.37-2.48 (m, 2H), 2.65 (s, 3H), 3.33-3.46 (m, 1H), 7.26 (t, 2H), 7.56-7.72 (m, 2H), 8.50 (br s, 1H), 9.49 (br s, 1H).

Example 121

N-[1-(cyclopropylmethyl)-4-ethyl-3-(4-fluorophenyl)-1H-pyrazol-5-yl]-6-(3,5-dimethyl-1H-pyrazol-1-yl)pyrimidin-4-amine

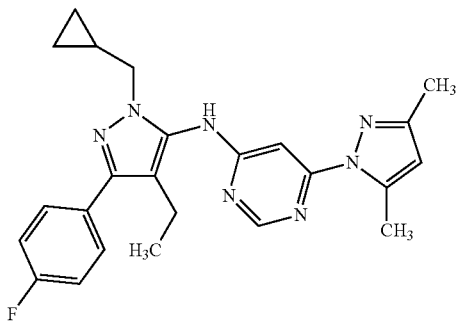 [SMILES: CCc1c(-c2ccc(F)cc2)nn(CC2CC2)c1Nc1cc(-n2nc(C)cc2C)ncn1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 1-(cyclopropylmethyl)-4-ethyl-3-(4-fluorophenyl)-1H-pyrazol-5-amine (100 mg, 386 μmol) and 4-chloro-6-(3,5- dimethyl-1H-pyrazol-1-yl)pyrimidine (88.5 mg, 424 µmol) to yield 95.5 mg (98% purity, 56% yield) of the desired product.

LC-MS (method 11): $R_t$=1.56 min; MS (ESIneg): m/z=430 [M−H]⁻

¹H-NMR (400 MHz, DMSO-d₆) δ [ppm]: 0.298 (2.53), 0.309 (2.69), 0.435 (2.73), 0.454 (2.86), 0.977 (3.81), 0.995 (8.34), 1.014 (3.99), 1.176 (0.41), 1.188 (0.76), 1.195 (0.73), 1.207 (1.11), 1.219 (0.70), 1.225 (0.74), 2.171 (2.98), 2.444 (0.82), 2.463 (2.16), 2.481 (2.13), 2.630 (16.00), 2.654 (0.43), 2.684 (0.45), 3.797 (2.30), 3.813 (2.29), 6.139 (2.67), 7.255 (2.44), 7.277 (4.94), 7.299 (2.70), 7.676 (1.57), 7.690 (2.26), 7.710 (1.54), 8.459 (0.74), 9.337 (0.64).

Example 122 methyl 4-(3-{[6-(3,5-dimethyl-1H-pyrazol-1-yl)pyrimidin-4-yl]amino}-1,4-dimethyl-1H-pyrazol-5-yl)benzoate

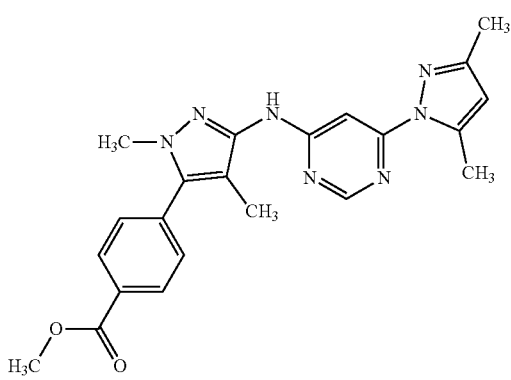 [SMILES: COC(=O)c1ccc(-c2c(C)c(Nc3cc(-n4nc(C)cc4C)ncn3)nn2C)cc1]

A microwave tube was charged with N-(1,4-dimethyl-1H-pyrazol-3-yl)-6-(3,5-dimethyl-1H-pyrazol-1-yl)pyrimidin-4-amine (100 mg, 353 µmol), methyl 4-bromobenzoate (125 mg, 582 µmol) and potassium acetate (72.7 mg, 741 µmol). The solids were suspended in N,N-dimethylacetamide (1.2 mL) and the reaction mixture was degassed by passing an argon flow through the suspension for 3 min. 1,4-Bis(diphenylphosphino)butane-palladium(II) chloride (10.7 mg, 17.6 µmol) was added and the reaction mixture further degassed for 1 min. The vessel was sealed and heated at 150° C. for 16 h. After cooling to ambient temperature, the reaction mixture was filtered and the filtrate purified by preparative HPLC (method 7) to yield the desired product (13.6 mg, 10% yield).

LC-MS (method 11): $R_t$=1.37 min; MS (ESIneg): m/z=416 [M−H]⁻

¹H-NMR (400 MHz, DMSO-d₆) δ [ppm]: 1.89 (s, 3H), 2.19 (s, 3H), 2.62 (s, 3H), 3.74 (s, 3H), 3.90 (s, 3H), 6.13 (s, 1H), 7.37 (s, 1H), 7.65 (m, 2H), 8.10 (m, 2H), 8.45 (s, 1H), 9.41 (s, 1H).

Example 123 azetidin-1-yl[1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone

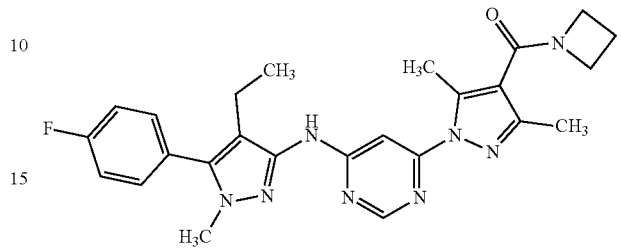

The described product was prepared in a manner analogous to that described in the preparation of (±)-[syn-2,6-dimethylmorpholin-4-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone (racemate) starting from 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (50.0 mg, 115 µmol) and azetidine (31 µl, 460 µmol) to yield 44.1 mg (100% purity, 81% yield) of the desired product.

LC-MS (method 11): $R_t$=1.77 min; MS (ESIpos): m/z=475 [M+H]⁺

¹H-NMR (400 MHz, DMSO-d₆) δ [ppm]: −0.008 (1.23), 0.008 (1.04), 0.869 (3.43), 0.888 (7.95), 0.907 (3.53), 1.073 (1.03), 1.091 (2.13), 1.109 (1.07), 2.202 (0.53), 2.227 (15.10), 2.241 (2.09), 2.260 (1.39), 2.284 (0.92), 2.303 (2.30), 2.322 (2.31), 2.340 (0.74), 2.524 (0.58), 2.656 (15.60), 3.375 (1.07), 3.392 (1.04), 3.650 (16.00), 3.988 (2.05), 7.358 (2.61), 7.363 (2.43), 7.374 (1.28), 7.380 (4.57), 7.397 (0.86), 7.402 (2.68), 7.499 (2.55), 7.505 (1.07), 7.513 (2.83), 7.521 (2.23), 7.529 (0.87), 7.535 (1.91), 8.482 (2.83), 9.443 (1.86).

Example 124

(3,3-difluoroazetidin-1-yl) [1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone

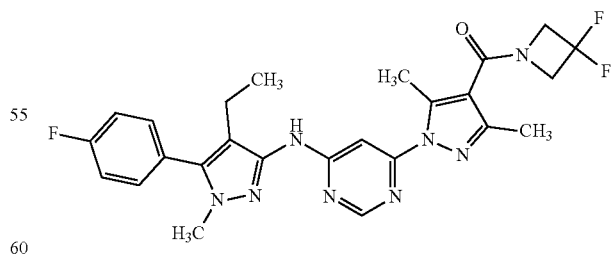

The described product was prepared in a manner analogous to that described in the preparation of (±)-[syn-2,6-dimethylmorpholin-4-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone (racemate) starting from 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (50.0 mg, 115 μmol) and 3,3-difluoroazetidine hydrochloride (1:1) (29.7 mg, 230 μmol) to yield 44.8 mg (100% purity, 76% yield) of the desired product.

LC-MS (method 11): $R_t$=1.94 min; MS (ESIpos): m/z=511 [M+H]$^+$ $^1$H-NMR (400 MHz, DMSO-d$_6$) δ [ppm]: −0.008 (1.02), 0.008 (0.78), 0.871 (3.50), 0.890 (7.96), 0.908 (3.57), 1.073 (0.63), 1.091 (1.27), 1.109 (0.65), 2.261 (14.32), 2.288 (0.87), 2.306 (2.35), 2.325 (2.35), 2.344 (0.75), 2.524 (0.50), 2.697 (15.46), 3.375 (0.63), 3.392 (0.63), 3.650 (16.00), 4.430 (3.42), 4.462 (7.04), 4.493 (3.12), 7.359 (2.03), 7.364 (0.90), 7.381 (5.93), 7.398 (1.06), 7.403 (2.73), 7.500 (2.58), 7.506 (1.15), 7.513 (2.89), 7.522 (2.25), 7.530 (0.91), 7.535 (1.90), 8.499 (2.69), 9.480 (1.75).

Example 125

2-[1-(6-{[4-ethyl-5-(4-fluorophenyl)-1-methyl-1H-pyrazol-3-yl]amino}pyrimidin-4-yl)-3-methyl-1H-pyrazol-5-yl]propan-2-ol

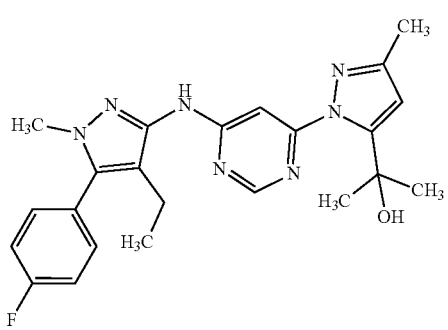 [SMILES: CCc1c(Nc2cc(-n3nc(C)cc3C(C)(C)O)ncn2)nn(C)c1-c1ccc(F)cc1]

ethyl 1-(6-{[4-ethyl-5-(4-fluorophenyl)-1-methyl-1H-pyrazol-3-yl]amino}pyrimidin-4-yl)-3-methyl-1H-pyrazole-5-carboxylate (100 mg, 222 μmol) was dissolved in THF, under argon. At 0° C. bromo(methyl)magnesium (780 μl, 1.0 M, 780 μmol) was added dropwise. The reaction mixture was stirred at 0° C. for 2 h. Additional 3.5 eq of methylmagnesium bromide were added and the reaction mixture was stirred for 2 h. Then ammonium chloride solution was used to dilute the reaction. Then, ethyl acetate was added. The aqueous layer was extracted twice with ethyl acetate. The organic layers were combined, dried over magnesium sulfate and concentrated under vacuum. The crude product was purified by preparative HPLC (method: column: Reprosil C18; 10 μm; 125×30 mm/flow: 45 ml/min/eluent: A=water (0.1% formic acid), B=acetonitrile/gradient: 0.00-4.25 min=20% B, 4.50 min=70% B, 15.50 min=85% B, 16.00-23.00 min=100% B, 23.00-27.00 min=20% B) to afford 65.9 mg (100% purity, 68% yield) of the desired product.

LC-MS (method 11): $R_t$=1.40 min; MS (ESIneg): m/z=434 [M−H]$^−$ $^1$H-NMR (400 MHz, DMSO-d$_6$) δ [ppm]: 0.878 (2.40), 0.897 (5.40), 0.916 (2.50), 1.091 (0.49), 1.478 (16.00), 2.204 (9.48), 2.297 (0.54), 2.315 (1.51), 2.334 (1.51), 2.352 (0.50), 3.656 (10.93), 6.281 (3.81), 7.361 (1.31), 7.383 (2.92), 7.405 (1.75), 7.441 (0.72), 7.506 (1.76), 7.520 (1.99), 7.527 (1.59), 7.541 (1.29), 7.753 (3.67), 8.538 (2.05), 9.662 (0.77).

Example 126

[1-(6-{[4-ethyl-5-(4-fluorophenyl)-1-methyl-1H-pyrazol-3-yl]amino}pyrimidin-4-yl)-3,5-dimethyl-1H-pyrazol-4-yl](3-fluoroazetidin-1-yl)methanone

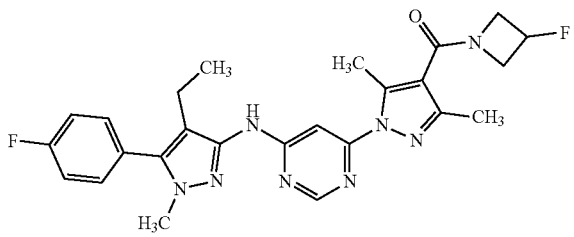 [SMILES: CCc1c(Nc2cc(-n3nc(C)c(C(=O)N4CC(F)C4)c3C)ncn2)nn(C)c1-c1ccc(F)cc1]

The described product was prepared in a manner analogous to that described in the preparation of (±)-[syn-2,6-dimethylmorpholin-4-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone (racemate) starting from 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (50.0 mg, 115 μmol) and 3-fluoroazetidine hydrochloride (1:1) (25.6 mg, 230 μmol) to yield 40.9 mg (100% purity, 72% yield) of the desired product.

LC-MS (method 10): $R_t$=1.79 min; MS (ESIpos): m/z=493 [M+H]$^+$ $^1$H-NMR (400 MHz, DMSO-d$_6$) δ [ppm]: 0.89 (t, 3H), 2.24 (s, 3H), 2.28-2.39 (m, 2H), 2.67 (s, 3H), 3.65 (s, 3H), 3.90-4.17 (m, 2H), 4.33 (br s, 2H), 5.29-5.58 (m, 1H), 7.24-7.42 (m, 3H), 7.46-7.60 (m, 2H), 8.49 (s, 1H), 9.46 (s, 1H).

Example 127

1-(6-{[4-ethyl-5-(4-fluorophenyl)-1-methyl-1H-pyrazol-3-yl]amino}pyrimidin-4-yl)-N,N,3,5-tetramethyl-1H-pyrazole-4-carboxamide

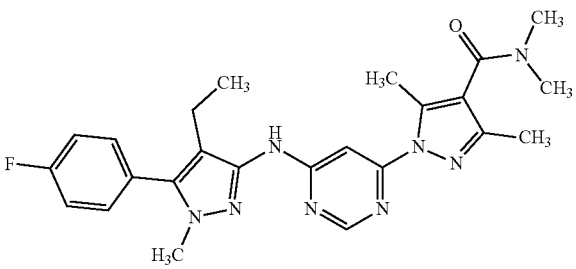 [SMILES: CCc1c(Nc2cc(-n3nc(C)c(C(=O)N(C)C)c3C)ncn2)nn(C)c1-c1ccc(F)cc1]

The described product was prepared in a manner analogous to that described in the preparation of (±)-[syn-2,6-dimethylmorpholin-4-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone (racemate) starting from 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (50.0 mg, 115 μmol) and N-methylmethanamine (230 μl, 2.0 M, 460 μmol) to yield 40.3 mg (100% purity, 76% yield) of the desired product.

LC-MS (method 10): $R_t$=1.75 min; MS (ESIpos): m/z=463 [M+H]⁺

¹H-NMR (400 MHz, DMSO-d₆) δ [ppm]: 0.89 (t, 3H), 2.16 (s, 3H), 2.31 (q, 2H), 2.58 (s, 3H), 2.78-3.07 (m, 6H), 3.65 (s, 3H), 7.30-7.43 (m, 3H), 7.47-7.55 (m, 2H), 8.47 (s, 1H), 9.43 (s, 1H).

Example 128

[3-(difluoromethyl)pyrrolidin-1-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone

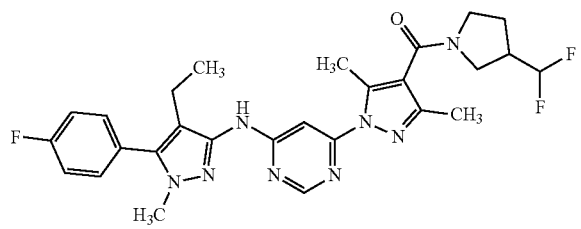 [SMILES: CCc1c(Nc2cc(-n3nc(C)c(C(=O)N4CCC(C(F)F)C4)c3C)ncn2)nn(C)c1-c1ccc(F)cc1]

The described product was prepared in a manner analogous to that described in the preparation of (±)-[syn-2,6-dimethylmorpholin-4-yl][1-(6-{[4-ethyl-5-(4-fluorophenyl)-1-methyl-1H-pyrazol-3-yl]amino}pyrimidin-4-yl)-3,5-dimethyl-1H-pyrazol-4-yl]methanone (racemate) starting from 1-(6-{[4-ethyl-5-(4-fluorophenyl)-1-methyl-1H-pyrazol-3-yl]amino}pyrimidin-4-yl)-3,5-dimethyl-1H-pyrazole-4-carboxylic acid (50.0 mg, 115 µmol) and 3-(difluoromethyl)pyrrolidine hydrochloride (1:1) (36.2 mg, 230 µmol) to yield 50.3 mg (100% purity, 81% yield) of the desired product.

LC-MS (method 10): $R_t$=1.89 min; MS (ESIpos): m/z=539 [M+H]⁺

¹H-NMR (400 MHz, DMSO-d₆) δ [ppm]: 0.89 (t, 3H), 1.78-2.11 (m, 2H), 2.18 (s, 3H), 2.26-2.39 (m, 2H), 2.60 (s, 3H), 2.64-2.89 (m, 1H), 3.33-3.70 (m, 7H), 5.88-6.38 (m, 1H), 7.31-7.43 (m, 3H), 7.47-7.58 (m, 2H), 8.48 (s, 1H), 9.43 (s, 1H).

Example 129

N-[4-chloro-1-(2,2-difluoroethyl)-3-(4-fluorophenyl)-1H-pyrazol-5-yl]-6-(3,5-dimethyl-1H-pyrazol-1-yl)pyrimidin-4-amine

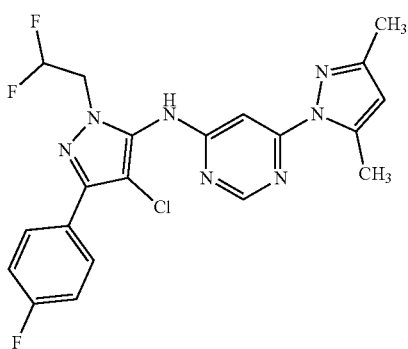 [SMILES: Cc1cc(C)n(-c2cc(Nc3c(Cl)c(-c4ccc(F)cc4)nn3CC(F)F)ncn2)n1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-1-(2,2-difluoroethyl)-3-(4-fluorophenyl)-1H-pyrazol-5-amine (90.0 mg, 326 µmol) and 4-chloro-6-(3,5-dimethyl-1H-pyrazol-1-yl)pyrimidine (74.9 mg, 359 µmol) to yield 61.8 mg (96% purity, 41% yield) of the desired product after preparative HPLC (method: column: Reprosil C18; 10 µm; 125×30 mm/flow: 45 ml/min/eluent: A=water (0.1% formic acid), B=acetonitril/gradient: 0.00-4.25 min=20% B, 4.50 min=70% B, 15.50 min=85% B, 16.00-23.00 min=100% B, 23.00-27.00 min=20% B and subsequently method 4).

LC-MS (method 11): $R_t$=1.52 min; MS (ESIneg): m/z=446 [M−H]⁻

¹H-NMR (600 MHz, DMSO-d₆) δ [ppm]: 2.19 (s, 3H), 2.60-2.66 (m, 3H), 4.48-4.69 (m, 2H), 6.16 (s, 1H), 6.27-6.54 (m, 1H), 7.03-7.24 (m, 1H), 7.30-7.39 (m, 2H), 7.85-7.97 (m, 2H), 8.50 (s, 1H), 9.73 (s, 1H).

Example 130

N-[4-chloro-1-(2,2-difluoroethyl)-5-(4-fluorophenyl)-1H-pyrazol-3-yl]-6-(4-chloro-3,5-dimethyl-1H-pyrazol-1-yl)pyrimidin-4-amine

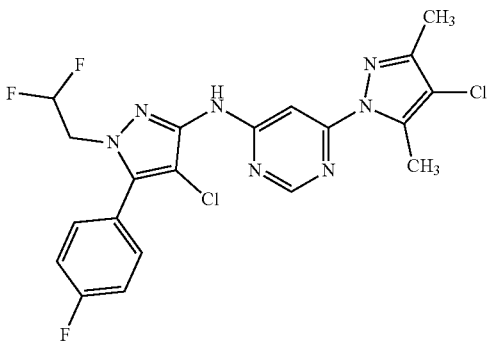 [SMILES: Cc1nn(-c2cc(Nc3nn(CC(F)F)c(-c4ccc(F)cc4)c3Cl)ncn2)c(C)c1Cl]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-1-(2,2-difluoroethyl)-5-(4-fluorophenyl)-1H-pyrazol-3-amine (95.0 mg, 345 µmol) and 4-chloro-6-(4-chloro-3,5-dimethyl-1H-pyrazol-1-yl)pyrimidine (92.2 mg, 379 µmol) to yield 78.2 mg (98% purity, 46% yield) of the desired product.

LC-MS (method 11): $R_t$=1.66 min; MS (ESIpos): m/z=482 [M+H]⁺

¹H-NMR (400 MHz, DMSO-d₆) δ [ppm]: 2.22 (s, 3H), 2.60-2.71 (m, 3H), 4.49 (td, 2H), 6.12-6.53 (m, 1H), 7.33-7.49 (m, 3H), 7.53-7.63 (m, 2H), 8.53 (s, 1H), 9.80 (s, 1H).

Example 131

6-(3,5-dimethyl-1H-pyrazol-1-yl)-N-[4-ethyl-5-(4-fluoro-2-methylphenyl)-1H-pyrazol-3-yl]pyrimidin-4-amine

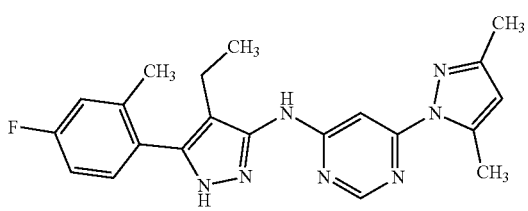 [SMILES: CCc1c(Nc2cc(-n3nc(C)cc3C)ncn2)n[nH]c1-c1ccc(F)cc1C]

4-chloro-6-(3,5-dimethyl-1H-pyrazol-1-yl)pyrimidine (70.0 mg, 335 µmol) and 4-ethyl-5-(4-fluoro-2-methylphenyl)-1H-pyrazol-3-amine (147 mg, 671 µmol) are charged in a flask with NMP (700 µl). At room temperature, aqueous hydrochloric acid (84 µl, 12 M, 1.0 mmol) is added, and the reaction mixture is heated in a microwave for 1 h to 200° C. The reaction mixture was directly purified by preparative HPLC (Chromatorex C18 10µ 125×40 mm gradient A=water+0.5% formic acid, B=acetonitrle, 0 min=5% B, 3 min 25% B wash, then injection, 3 min 25% B, 20 min=75% B, 20.1 min=95% B, 25 min=95% B, 25.1 min=end, flow 75 mL/min, detection at 210 nm) to obtain 29.0 mg (100% purity, 22% yield) as desired product.

LC-MS (method 11): $R_t$=1.42 min; MS (ESIneg): m/z=390 [M−H]−

$^1$H-NMR (400 MHz, DMSO-d$_6$) δ [ppm]: −0.008 (2.23), 0.007 (2.04), 0.845 (3.98), 0.864 (8.90), 0.882 (4.12), 2.172 (16.00), 2.212 (15.63), 2.254 (0.97), 2.273 (2.74), 2.292 (2.69), 2.311 (0.89), 2.329 (0.40), 2.627 (15.30), 5.754 (0.76), 6.125 (4.08), 7.113 (0.54), 7.133 (1.12), 7.155 (0.66), 7.222 (0.99), 7.245 (1.03), 7.295 (1.10), 7.311 (1.31), 7.332 (0.92), 7.459 (0.61), 8.461 (3.10), 9.360 (1.06), 12.511 (0.57).

Example 132

N-[4-chloro-1-(2,2-difluoroethyl)-5-(4-fluorophenyl)-1H-pyrazol-3-yl]-6-(3,5-dimethyl-1H-pyrazol-1-yl)pyrimidin-4-amine

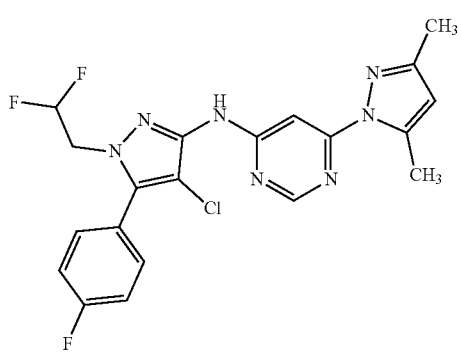 [SMILES: Cc1cc(C)n(-c2cc(Nc3nn(CC(F)F)c(-c4ccc(F)cc4)c3Cl)ncn2)n1]

The described product was prepared in a manner analogous to that described in the preparation of N-[4-cyclopropyl-5-(4-fluorophenyl)-1-methyl-1H-pyrazol-3-yl]-6-(3-methyl-1H-indazol-1-yl)pyrimidin-4-amine starting from 4-chloro-1-(2,2-difluoroethyl)-5-(4-fluorophenyl)-1H-pyrazol-3-amine (95.0 mg, 345 µmol) and 4-chloro-6-(3,5-dimethyl-1H-pyrazol-1-yl)pyrimidine (79.1 mg, 379 µmol) to yield 74.3 mg (100% purity, 48% yield) of the desired product after purification by preparative HPLC (method: column: Reprosil C18; 10 µm; 125×30 mm/flow: 45 ml/min/eluent: A=water (0.1% formic acid), B=acetonitril/gradient: 0.00-4.25 min=20% B, 4.50 min=70% B, 15.50 min=85% B, 16.00-23.00 min=100% B, 23.00-27.00 min=20% B and subsequently method 4)

LC-MS (method 11): $R_t$=1.51 min; MS (ESIpos): m/z=448 [M+H]+

$^1$H-NMR (600 MHz, DMSO-d$_6$) δ [ppm]: 2.19 (s, 3H), 2.63 (s, 3H), 4.49 (td, 2H), 6.14 (s, 1H), 6.23-6.53 (m, 1H), 7.38 (s, 1H), 7.44 (t, 2H), 7.59 (dd, 2H), 8.49 (s, 1H), 9.71 (s, 1H).

Example 133

1-(6-{[4-ethyl-5-(4-fluorophenyl)-1-methyl-1H-pyrazol-3-yl]amino}pyrimidin-4-yl)-3-methyl-1,5,6,7-tetrahydro-4H-indazol-4-one

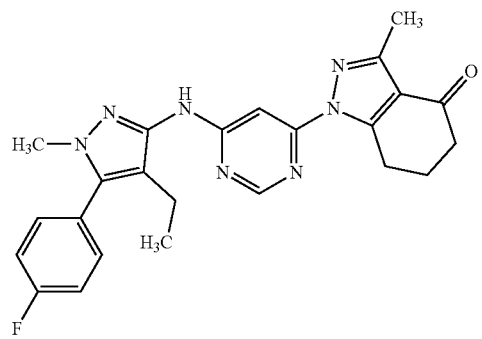 [SMILES: CCc1c(Nc2cc(-n3nc(C)c4c3CCCC4=O)ncn2)nn(C)c1-c1ccc(F)cc1]

1-(6-chloropyrimidin-4-yl)-3-methyl-1,5,6,7-tetrahydro-4H-indazol-4-one (300 mg, 1.14 mmol) was dissolved in 1,4-dioxane (3.0 mL) in a round-bottom flask under an argon atmosphere and sodium phenolate (181 mg, 1.56 mmol) was added. The reaction mixture was degassed with Ar for 3 min. Tris(dibenzylideneacetone)dipalladium (14.3 mg, 15.6 µmol), XantPhos (18.0 mg, 31.1 µmol) and 4-ethyl-5-(4-fluorophenyl)-1-methyl-1H-pyrazol-3-amine (228 mg, 1.04 mmol) were added. The reaction mixture was heated to 90° C. and stirred vigorously overnight. After cooling to ambient temperature, the reaction mixture was filtered and concentrated. The residue was purified by preparative HPLC (column: Chromatorex C18; 250*30 mm, 10 µM, flow 100 mL/min, gradient acetonitrile/water (containing 0.1% trifluoroacetic acid) 10/90 to 95/5) to yield the desired product (148 mg, 32% yield).

LC-MS (method 10): $R_t$=2.06 min; MS (ESIpos): m/z=446 [M+H]+

$^1$H-NMR (400 MHz, dimethylsulfoxide-d6) δ [ppm]: 0.89 (t, 3H) 2.04-2.12 (m, 2H) 2.27-2.35 (m, 2H) 2.38-2.46 (m, 5H) 3.39-3.47 (m, 2H) 3.66 (s, 3H) 7.34-7.42 (m, 2H) 7.43 (s, 1H), 7.46-7.58 (m, 2H) 8.47-8.56 (m, 1H) 9.48-9.59 (m, 1H)

Example 134

(±)-1-(6-{[4-ethyl-5-(4-fluorophenyl)-1-methyl-1H-pyrazol-3-yl]amino}pyrimidin-4-yl)-3,4-dimethyl-4,5,6,7-tetrahydro-1H-indazol-4-ol (Racemate)

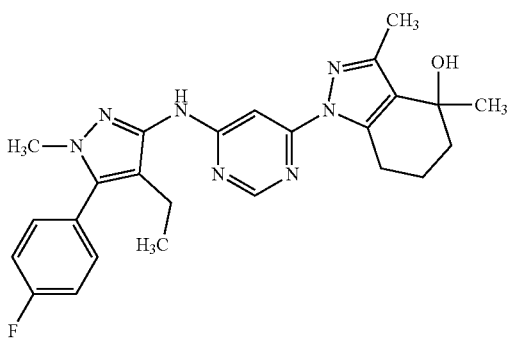 [SMILES: CCc1c(Nc2cc(-n3nc(C)c4c3CCCC4(C)O)ncn2)nn(C)c1-c1ccc(F)cc1]

1-(6-{[4-ethyl-5-(4-fluorophenyl)-1-methyl-1H-pyrazol-3-yl]amino}pyrimidin-4-yl)-3-methyl-1-1,5,6,7-tetrahydro-4H-indazol-4-one (34.5 mg, 77.4 µmol) was dissolved in tetrahydrofuran (0.73 mL), cooled to 0° C. and MeMgBr in tetrahydrofuran (1.0 m, 310 µL, 310 µmol) was added dropwise. The reaction mixture was allowed to stir at ambient temperature for 20 minutes. It was then recooled to 0° C., and further 150 µL MeMgBr (1.0 m, 150 µL, 150 µmol) were added. The ice bath was removed and the reaction mixture allowed to stir at ambient temperature for 20 minutes. It was then quenched by addition of saturated aqueous ammonium chloride solution and extracted with ethyl acetate (3×). The combined organic phase layers were dried over sodium sulfate, concentrated and the residue purified by flash column chromatography (KP-Sil 10 g, cyclohexane/ethyl acetate gradient (12-100%, 10 CV) and ethyl acetate (100%, 7 CV) to yield the desired product (19 mg, 53% yield).

LC-MS (method 9): $R_t$=1.03 min; MS (ESIpos): m/z=462 [M+H]$^+$ $^1$H-NMR (400 MHz, dimethylsulfoxide-d6) δ [ppm]: −0.149 (1.20), −0.008 (10.10), 0.008 (8.65), 0.146 (1.12), 0.862 (3.46), 0.881 (7.96), 0.900 (3.56), 1.157 (3.69), 1.175 (7.58), 1.193 (3.82), 1.398 (2.77), 1.408 (11.45), 1.701 (3.76), 1.919 (0.61), 1.988 (13.89), 2.274 (0.86), 2.292 (2.59), 2.313 (15.92), 2.328 (1.58), 2.366 (0.48), 2.524 (2.03), 2.670 (0.76), 2.710 (0.48), 3.061 (2.34), 3.075 (1.25), 3.650 (16.00), 4.003 (1.07), 4.021 (3.28), 4.039 (3.26), 4.056 (1.04), 4.686 (5.42), 5.754 (1.04), 7.293 (2.70), 7.358 (1.98), 7.380 (4.50), 7.402 (2.72), 7.498 (2.57), 7.512 (2.85), 7.520 (2.31), 7.534 (1.96), 8.398 (3.46), 9.279 (2.70).

Example 135

4-(3-{[6-(3,5-dimethyl-1H-pyrazol-1-yl)pyrimidin-4-yl]amino}-4-methyl-1H-pyrazol-5-yl)benzonitrile

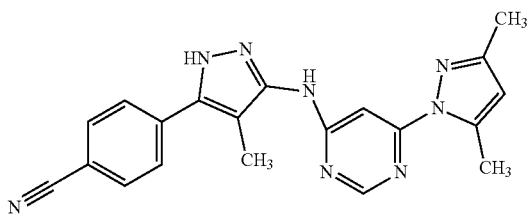 [SMILES: Cc1cc(C)n(-c2cc(Nc3n[nH]c(-c4ccc(C#N)cc4)c3C)ncn2)n1]

A microwave vial was charged with 4-(3-amino-4-methyl-1H-pyrazol-5-yl)benzonitrile (100 mg, 504 µmol), 4-chloro-6-(3,5-dimethyl-1H-pyrazol-1-yl)pyrimidine (95.7 mg, 459 µmol) and sodium phenolate (79.9 mg, 688 µmol) and the contents were suspended in 1,4-dioxane (1.1 mL). The reaction mixture was degassed with Ar for 3 min. Tris(dibenzylideneacetone)dipalladium (5.46 mg, 5.96 µmol) and XantPhos (7.96 mg, 13.8 µmol) were added and the reaction mixture degassed again for 1 min. The vial was sealed and heated at 85° C. overnight while vigorously shaking. After cooling to ambient temperature, the reaction mixture was filtered, diluted with dimethylsulfoxide and purified by preparative HPLC (method 7) to yield the desired product (26 mg, 13% yield) along with its regioisomeric coupling product (6.3 mg, 3% yield)

LC-MS (method 11): $R_t$=1.27 min; MS (ESIneg): m/z=369 [M−H]$^-$ $^1$H-NMR (400 MHz, dimethylsulfoxide-d6) δ [ppm]: −0.008 (1.66), 0.008 (1.32), 2.115 (14.73), 2.173 (15.69), 2.228 (0.83), 2.243 (0.69), 2.524 (0.77), 2.628 (16.00), 2.664 (0.73), 2.678 (0.94), 6.131 (2.87), 7.455 (0.77), 7.803 (1.42), 7.822 (1.81), 7.899 (0.69), 7.972 (1.91), 7.991 (1.52), 8.467 (1.59), 9.445 (1.27), 13.107 (1.30).

Example 136 ethyl 1-(6-{[5-(4-cyanophenyl)-4-methyl-1H-pyrazol-3-yl]amino}pyrimidin-4-yl)-3,5-dimethyl-1H-pyrazole-4-carboxylate

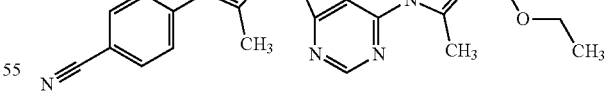

A microwave vial was charged with (100 mg, 504 µmol), ethyl 1-(6-chloropyrimidin-4-yl)-3,5-dimethyl-1H-pyrazole-4-carboxylate (156 mg, 555 µmol) and sodium phenolate (87.8 mg, 757 µmol) and the contents were suspended in 1,4-dioxane (1.2 mL). The reaction mixture was degassed with argon for 3 min. Tris(dibenzylideneacetone)dipalladium (6.01 mg, 6.56 µmol) and XantPhos (8.76 mg, 15.1 µmol) were added and the reaction mixture degassed again for 1 min. The vial was sealed and heated at 85° C. overnight while vigorously shaking. After cooling to ambient temperature, the reaction mixture was filtered, diluted with dimethylsulfoxide and purified by preparative HPLC (method 7) to yield the desired product (30.3 mg, 13% yield) along with the regioisomeric coupling product (6.2 mg, 3% yield).

LC-MS (Method 10): R$_t$=1.96 min; MS (ESIpos): m/z=443 [M+H]$^+$ $^1$H-NMR (400 MHz, dimethylsulfoxide-d6) δ [ppm]: −0.149 (0.47), −0.008 (4.24), 0.008 (3.91), 0.146 (0.47), 1.288 (6.31), 1.306 (13.40), 1.324 (6.60), 1.647 (1.03), 2.119 (13.50), 2.372 (16.00), 2.898 (15.22), 4.228 (1.81), 4.245 (5.69), 4.263 (5.66), 4.281 (1.80), 7.368 (0.79), 7.385 (0.81), 7.398 (0.99), 7.488 (0.58), 7.821 (1.73), 7.856 (0.68), 7.872 (0.47), 7.969 (1.96), 8.550 (2.08), 9.666 (0.94), 13.129 (0.98).

Example 137

4-(3-{[6-(4-chloro-3,5-dimethyl-1H-pyrazol-1-yl)pyrimidin-4-yl]amino}-4-methyl-1H-pyrazol-5-yl)benzonitrile

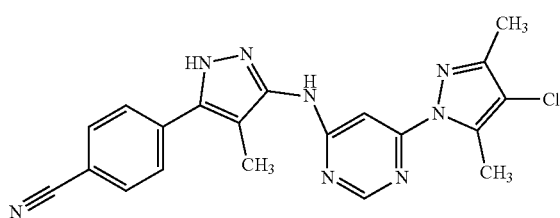 [SMILES: Cc1nn(-c2cc(Nc3n[nH]c(-c4ccc(C#N)cc4)c3C)ncn2)c(C)c1Cl]

A microwave vial was charged with 4-(3-amino-4-methyl-1H-pyrazol-5-yl)benzonitrile (100 mg, 504 μmol), 4-chloro-6-(4-chloro-3,5-dimethyl-1H-pyrazol-1-yl)pyrimidine (135 mg, 555 μmol) and sodium phenolate (87.8 mg, 757 μmol) and the contents were suspended in 1,4-dioxane (1.2 mL). The reaction mixture was degassed with Ar for 3 min. Tris(dibenzylideneacetone)dipalladium (6.01 mg, 6.56 μmol) and XantPhos (8.76 mg, 15.1 μmol) were added and the reaction mixture was degassed again for 1 min. The vial was sealed and heated at 85° C. overnight while vigorously shaking. After cooling to ambient temperature, the reaction mixture was filtered, diluted with dimethylsulfoxide and purified by preparative HPLC (method 7) to yield the desired product (26.8 mg, 13% yield) along with its regioisomeric coupling product (5.8 mg, 3% yield).

LC-MS (method 10): R$_t$=2.10 min; MS (ESIpos): m/z=405 [M+H]$^+$ $^1$H-NMR (400 MHz, dimethylsulfoxide-d6) δ [ppm]: −0.150 (0.73), −0.008 (6.39), 0.008 (5.90), 0.146 (0.70), 2.115 (13.04), 2.211 (13.77), 2.328 (0.51), 2.366 (0.48), 2.646 (16.00), 2.710 (0.46), 7.341 (0.53), 7.381 (0.64), 7.465 (1.13), 7.478 (1.16), 7.780 (0.67), 7.798 (2.87), 7.819 (3.60), 7.905 (1.13), 7.973 (3.35), 7.993 (2.66), 8.501 (2.25), 9.572 (2.12), 13.122 (1.99).

Example 138

1-[1-(6-{[5-(4-fluorophenyl)-1,4-dimethyl-1H-pyrazol-3-yl]amino}pyrimidin-4-yl)-3,5-dimethyl-1H-pyrazol-4-yl]cyclopropanol

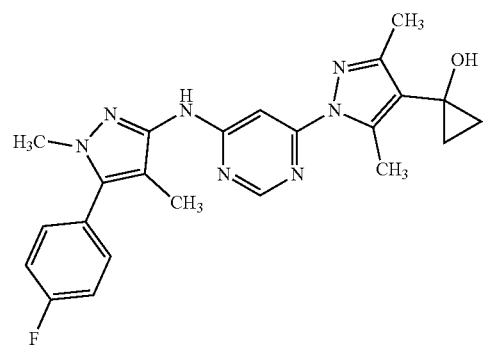 [SMILES: Cc1nn(-c2cc(Nc3nn(C)c(-c4ccc(F)cc4)c3C)ncn2)c(C)c1C1(O)CC1]

In a flame-dried schlenk tube, ethyl 1-(6-{[5-(4-fluorophenyl)-1,4-dimethyl-1H-pyrazol-3-yl]amino}pyrimidin-4-yl)-3,5-dimethyl-1H-pyrazole-4-carboxylate (30.0 mg, 66.7 μmol) was dissolved in tetrahydrofuran (630 μL, 7.7 mmol) and the resulting solution cooled to 0° C. Titanium tetraisopropoxide (22 μl, 73 μmol) was added slowly via syringe. After 5 min, a solution of ethylmagnesium bromide (1.0 M in tetrahydrofuran, 230 μl, 230 μmol) was added dropwise and the reaction mixture stirred for 3 h at 0° C. The ice-bath was then removed and the reaction mixture allowed to stir overnight at ambient temperature. It was quenched by addition of saturated aqueous ammonium chloride solution and extracted with ethyl acetate (3×). The combined organic phase extracts washed with brine, dried over sodium sulfate and concentrated. The residue was purified by preparative HPLC (column: Chromatorex C18; 125*40 mm, 10 μM, flow 100 mL/min, gradient acetonitrile/water (containing 0.1% trifluoroacetic acid) 10/90 to 95/5) to yield the desired product (4.4 mg, 15% yield) after lyophilisation.

LC-MS (method 10): R$_t$=1.77 min; MS (ESIpos): m/z=434 [M+H]$^+$ $^1$H-NMR (500 MHz, dimethylsulfoxide-d6) δ [ppm]: 0.006 (2.48), 0.645 (1.48), 0.654 (4.27), 0.658 (3.94), 0.667 (1.54), 0.932 (1.65), 0.940 (4.25), 0.944 (3.82), 0.954 (1.33), 1.848 (14.25), 2.276 (15.49), 2.362 (0.78), 2.635 (0.51), 2.702 (16.00), 3.928 (1.77), 7.361 (3.65), 7.379 (5.00), 7.397 (2.75), 7.512 (2.82), 7.523 (3.14), 7.529 (2.55), 7.540 (2.09), 8.452 (4.04), 9.396 (2.97).

Example 139

6-[4-chloro-5-(difluoromethyl)-3-methyl-1H-pyrazol-1-yl]-N-[3-(4-fluorophenyl)-1,4-dimethyl-1H-pyrazol-5-yl]pyrimidin-4-amine

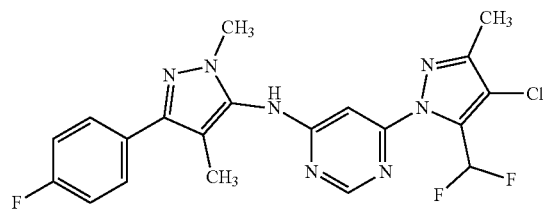 [SMILES: Cc1nn(-c2cc(Nc3c(C)c(-c4ccc(F)cc4)nn3C)ncn2)c(C(F)F)c1Cl]

A microwave vial was charged with 3-(4-fluorophenyl)-1,4-dimethyl-1H-pyrazol-5-amine (80.0 mg, 390 µmol), 4-chloro-6-[4-chloro-5-(difluoromethyl)-3-methyl-1H-pyrazol-1-yl]pyrimidine (120 mg, 429 µmol) and sodium phenolate (67.9 mg, 585 µmol) and the contents were suspended in 1,4-dioxane (1.0 mL). The reaction mixture was degassed with Ar for 3 min. Tris(dibenzylideneacetone)dipalladium (4.64 mg, 5.07 µmol) and XantPhos (6.77 mg, 11.7 µmol) were added and the reaction mixture was degassed again for 1 min. The vial was sealed and heated at 85° C. overnight while vigorously shaking. After cooling to ambient temperature, the reaction mixture was filtered, diluted with dimethylsulfoxide and purified by preparative HPLC (method 4) to yield the desired product (57 mg, 32% yield) as a white powder.

LC-MS (method 10): $R_t$=2.31 min; MS (ESIpos): m/z=448 [M+H]$^+$ $^1$H-NMR (400 MHz, dimethylsulfoxide-d6) δ [ppm]: 2.017 (16.00), 2.073 (1.20), 2.280 (2.24), 2.328 (0.43), 2.680 (1.03), 3.664 (7.81), 7.247 (1.79), 7.269 (3.60), 7.291 (2.03), 7.698 (1.37), 7.713 (1.96), 7.730 (1.32), 7.901 (1.10), 8.032 (2.19), 8.163 (1.02), 8.528 (0.43), 9.677 (0.67).

Example 140

6-[4-chloro-5-(difluoromethyl)-3-methyl-1H-pyrazol-1-yl]-N-[5-(4-fluorophenyl)-4-methyl-1H-pyrazol-3-yl]pyrimidin-4-amine

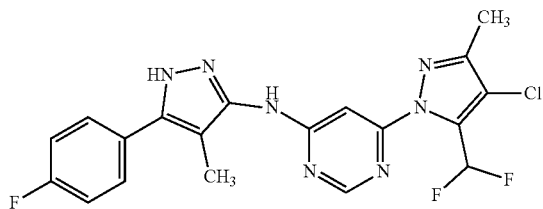 [SMILES: Cc1nn(-c2cc(Nc3n[nH]c(-c4ccc(F)cc4)c3C)ncn2)c(C(F)F)c1Cl]

A microwave vial was charged with 5-(4-fluorophenyl)-4-methyl-1H-pyrazol-3-amine (100 mg, 523 µmol), 4-chloro-6-[4-chloro-5-(difluoromethyl)-3-methyl-1H-pyrazol-1-yl]pyrimidine (161 mg, 575 µmol) and sodium phenolate (91.1 mg, 784 µmol) and the contents were suspended in 1,4-dioxane (1.0 mL). The reaction mixture was degassed with Ar for 3 min. Tris(dibenzylideneacetone)dipalladium (6.23 mg, 6.80 µmol) and XantPhos (9.08 mg, 15.7 µmol) were added and the reaction mixture was degassed again for 1 min. The vial was sealed and heated at 85° C. overnight while vigorously shaking. After cooling to ambient temperature, the reaction mixture was filtered, diluted with dimethylsulfoxide and purified by preparative HPLC (method 5) to yield the desired product (11.8 mg, 4% yield) as a white powder along with the regioisomeric coupling product (26.0 mg, 11% yield).

LC-MS (method 10): $R_t$=2.21 min; MS (ESIpos): m/z=434 [M+H]$^+$ $^1$H-NMR (400 MHz, dimethylsulfoxide-d6) δ [ppm]: 2.08 (s, 3H), 2.27 (s, 3H), 7.32-7.39 (m, 2H), 7.44-7.61 (m, 1H), 7.60-7.66 (m, 2H), 8.04 (t, J=51.4 Hz, 1H), 8.52 (s, 1H), 9.72 (br s, 1H), 12.88 (br s, 1H).

Example 141

4-[1-(cyclopropylmethyl)-5-{[6-(3,5-dimethyl-1H-pyrazol-1-yl)pyrimidin-4-yl]amino}-4-methyl-1H-pyrazol-3-yl]benzonitrile

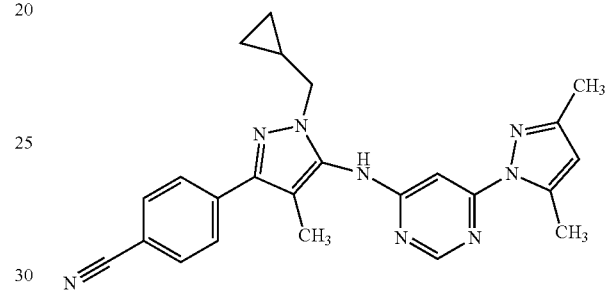

A solution of 4-chloro-6-(3,5-dimethyl-1H-pyrazol-1-yl)pyrimidine (1.50 g, 7.21 mmol) in 1,4-dioxane (34 ml) was degassed with argon and heated to an internal temperature of 85° C. To the heated solution was added 4-[5-amino-1-(cyclopropylmethyl)-4-methyl-1H-pyrazol-3-yl]benzonitrile (2.00 g, 7.93 mmol), tris(dibenzylidenaceton)dipalladium (198 mg, 216 µmol), Xantphos (229 mg, 432 µmol) and finally sodium phenolate (920 mg, 7.93 mmol) before heating at 85° C. for an additional 30 minutes. The reaction mixture was added to a saturated solution of sodium hydrogen carbonate (11 mL), and the solution extracted three times with ethyl acetate. The combined organic phases were washed with a saturated solution of sodium carbonate, dried with sodium sulfate and concentrated in vacuo. The crude product was purified by flash-chromatography on silica gel (gradient 10% to 80% ethylacetate in cyclohexane, column: Biotage SNAP Ultra 100 g) and the residue washed with pentane to yield 2.04 g (100% purity, 67% yield) of the desired product.

LC-MS (Method 9): $R_t$=1.14 min; MS (ESIpos): m/z=425 [M+H]$^+$ $^1$H-NMR (400 MHz, dimethylsulfoxide-d6) δ [ppm]: 0.306 (2.74), 0.318 (3.02), 0.433 (2.68), 0.453 (2.86), 1.177 (0.42), 1.191 (0.78), 1.198 (0.71), 1.209 (1.08), 1.222 (0.68), 1.229 (0.72), 2.063 (16.00), 2.171 (3.52), 2.629 (15.52), 3.861 (2.69), 3.878 (2.64), 5.754 (0.46), 6.145 (3.06), 7.886 (1.12), 7.907 (11.00), 7.934 (1.02), 8.461 (0.80), 9.420 (0.95).

Example 142

4-[1-(cyclopropylmethyl)-5-{(6-[5-(difluoromethyl)-3-methyl-1H-pyrazol-1-yl]pyrimidin-4-yl}amino)-4-methyl-1H-pyrazol-3-yl]benzonitrile

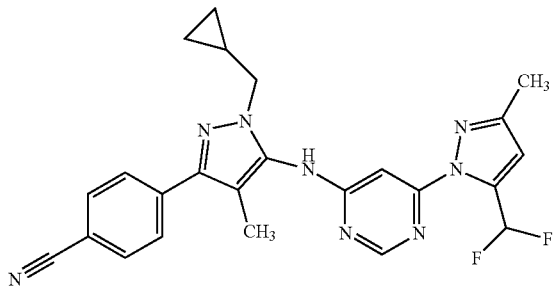 [SMILES: Cc1cc(C(F)F)n(-c2cc(Nc3c(C)c(-c4ccc(C#N)cc4)nn3CC3CC3)ncn2)n1]

A microwave vial was charged with 4-[5-amino-1-(cyclopropylmethyl)-4-methyl-1H-pyrazol-3-yl]benzonitrile (100 mg, 396 µmol), 4-chloro-6-[5-(difluoromethyl)-3-methyl-1H-pyrazol-1-yl]pyrimidine (107 mg, 436 µmol) and sodium phenolate (69.0 mg, 594 µmol) and the contents were suspended in 1,4-dioxane (1.0 mL). The reaction mixture was degassed with Ar for 3 min. Tris(dibenzylideneacetone)dipalladium (4.72 mg, 5.15 µmol) and XantPhos (6.88 mg, 11.9 µmol) were added and the reaction mixture was degassed again for 1 min. The vial was sealed and heated at 85° C. overnight while vigorously shaking. After cooling to ambient temperature, the reaction mixture was filtered, diluted with dimethylsulfoxide and purified by preparative HPLC (method 4) to yield the desired product (31 mg, 15% yield).

LC-MS (method 9): $R_t$=1.18 min; MS (ESIpos): m/z=461 [M+H]$^+$ $^1$H-NMR (400 MHz, dimethylsulfoxide-d6) δ [ppm]: 0.26-0.35 (m, 2H), 0.40-0.49 (m, 2H), 1.14-1.27 (m, 1H), 2.03-2.10 (m, 3H), 2.19-2.38 (m, 3H), 3.80-3.94 (m, 2H), 6.79 (s, 1H), 7.64-7.99 (m, 5H), 8.27-8.71 (m, 1H), 9.37-9.90 (m, 1H).

Example 143

N-[1-(cyclopropylmethyl)-4-ethyl-5-(4-fluorophenyl)-1H-pyrazol-3-yl]-6-(3,5-dimethyl-1H-pyrazol-1-yl)pyrimidin-4-amine

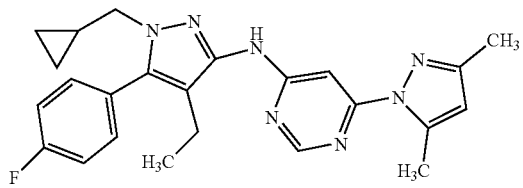 [SMILES: CCc1c(Nc2cc(-n3nc(C)cc3C)ncn2)nn(CC2CC2)c1-c1ccc(F)cc1]

A microwave vial was charged 4-chloro-6-(3,5-dimethyl-1H-pyrazol-1-yl)pyrimidine (79.0 mg, 379 µmol), 1-(cyclopropylmethyl)-4-ethyl-5-(4-fluorophenyl)-1H-pyrazol-3-amine (120 mg, 90% purity, 416 µmol) and sodium phenolate (65.9 mg, 568 µmol) and the contents were suspended in 1,4-dioxane (2.7 ml, 32 mmol). The reaction mixture was degassed with Ar for 3 min. Tris(dibenzylideneaceton)dipalladium (4.51 mg, 4.92 µmol) and Xantphos (6.57 mg, 11.4 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 4) to yield the desired product (84.0 mg, 51%).

LC-MS (method 10): $R_t$=2.44 min; MS (ESIpos): m/z=432 [M+H]$^+$ $^1$H-NMR (400 MHz, dimethylsulfoxide-d6) δ [ppm]: −0.008 (0.90), 0.008 (0.76), 0.184 (0.66), 0.196 (2.68), 0.210 (2.82), 0.222 (0.79), 0.420 (0.93), 0.431 (2.52), 0.435 (2.59), 0.440 (1.38), 0.451 (2.68), 0.454 (2.54), 0.466 (0.78), 0.869 (3.83), 0.888 (8.83), 0.907 (3.96), 1.033 (0.63), 1.040 (0.63), 1.052 (0.99), 1.064 (0.59), 1.070 (0.60), 2.168 (16.00), 2.285 (0.93), 2.303 (2.74), 2.322 (2.75), 2.341 (0.87), 2.524 (0.40), 2.628 (14.84), 3.759 (4.68), 3.776 (4.61), 6.125 (3.96), 7.354 (2.04), 7.377 (4.90), 7.399 (3.06), 7.469 (2.92), 7.475 (1.31), 7.483 (3.30), 7.491 (2.54), 7.500 (0.99), 7.505 (2.08), 7.595 (0.68), 8.456 (3.32), 9.399 (3.28).

Example 144

6-(4-chloro-3,5-dimethyl-1H-pyrazol-1-yl)-N-[1-(cyclopropylmethyl)-4-ethyl-5-(4-fluorophenyl)-1H-pyrazol-3-yl]pyrimidin-4-amine

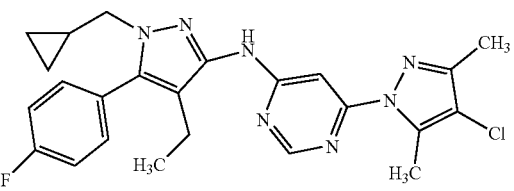 [SMILES: CCc1c(Nc2cc(-n3nc(C)c(Cl)c3C)ncn2)nn(CC2CC2)c1-c1ccc(F)cc1]

A microwave vial was charged 4-chloro-6-(4-chloro-3,5-dimethyl-1H-pyrazol-1-yl)pyrimidine (92.0 mg, 379 µmol), 1-(cyclopropylmethyl)-4-ethyl-5-(4-fluorophenyl)-1H-pyrazol-3-amine (120 mg, 90% purity, 416 µmol) and sodium phenolate (65.9 mg, 568 µmol) and the contents were suspended in 1,4-dioxane (2.7 ml, 32 mmol). The reaction mixture was degassed with Ar for 3 min. Tris (dibenzylidenaceton)dipalladium (4.51 mg, 4.92 µmol) and Xantphos (6.57 mg, 11.4 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 5) to yield the desired product (72.0 mg, 41%).

LC-MS (method 10): $R_t$=2.72 min; MS (ESIpos): m/z=466 [M+H]$^+$

¹H-NMR (400 MHz, dimethylsulfoxide-d6) δ [ppm]: −0.008 (1.02), 0.008 (0.94), 0.204 (2.11), 0.215 (2.23), 0.423 (0.76), 0.433 (2.11), 0.437 (2.18), 0.453 (2.25), 0.468 (0.65), 0.868 (3.19), 0.887 (7.26), 0.905 (3.27), 1.030 (0.57), 1.037 (0.56), 1.049 (0.85), 1.061 (0.52), 1.067 (0.52), 2.206 (14.04), 2.289 (0.76), 2.307 (2.14), 2.326 (2.20), 2.345 (0.69), 2.649 (16.00), 3.758 (3.91), 3.776 (3.85), 7.355 (1.78), 7.377 (4.33), 7.399 (2.75), 7.469 (2.53), 7.475 (1.19), 7.483 (2.87), 7.491 (2.22), 7.505 (1.78), 8.493 (3.22), 9.531 (2.05).

Example 145 ethyl 1-(6-{[1-(cyclopropylmethyl)-4-ethyl-5-(4-fluorophenyl)-1H-pyrazol-3-yl]amino}pyrimidin-4-yl)-3,5-dimethyl-1H-pyrazole-4-carboxylate

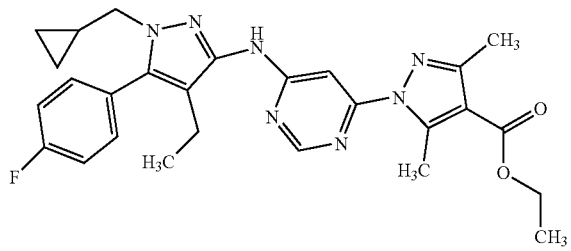 [SMILES: CCOC(=O)c1c(C)nn(-c2cc(Nc3nn(CC4CC4)c(-c4ccc(F)cc4)c3CC)ncn2)c1C]

A microwave vial was charged ethyl 1-(6-chloropyrimidin-4-yl)-3,5-dimethyl-1H-pyrazole-4-carboxylate (106 mg, 379 μmol), 1-(cyclopropylmethyl)-4-ethyl-5-(4-fluorophenyl)-1H-pyrazol-3-amine (120 mg, 90% purity, 416 μmol) and sodium phenolate (65.9 mg, 568 μmol) and the contents were suspended in 1,4-dioxane (2.7 ml, 32 mmol). The reaction mixture was degassed with Ar for 3 min. Tris (dibenzylidenaceton)dipalladium (4.51 mg, 4.92 μmol) and Xantphos (6.57 mg, 11.4 μmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 5) to yield the desired product (82.0 mg, 43%).

LC-MS (method 10): $R_t$=2.58 min; MS (ESIpos): m/z=504 [M+H]⁺

¹H-NMR (400 MHz, dimethylsulfoxide-d6) δ [ppm]: 0.008 (0.50), 0.192 (2.20), 0.204 (2.31), 0.412 (0.79), 0.423 (2.28), 0.426 (2.27), 0.443 (2.39), 0.458 (0.65), 0.873 (3.22), 0.892 (7.18), 0.910 (3.31), 1.028 (0.60), 1.035 (0.59), 1.047 (0.92), 1.058 (0.54), 1.065 (0.57), 1.289 (4.41), 1.307 (9.29), 1.324 (4.50), 2.296 (0.76), 2.314 (2.05), 2.333 (2.10), 2.367 (13.94), 2.905 (16.00), 3.756 (3.98), 3.773 (3.91), 4.228 (1.32), 4.246 (4.14), 4.264 (4.09), 4.281 (1.28), 7.355 (1.79), 7.377 (4.26), 7.399 (2.67), 7.469 (2.57), 7.483 (2.94), 7.491 (2.20), 7.505 (1.77), 8.539 (3.05), 9.625 (1.56).

Example 146

(rac)-1-(6-{[4-ethyl-5-(4-fluorophenyl)-1-methyl-1H-pyrazol-3-yl]amino}pyrimidin-4-yl)-3,4-dimethyl-1,4,5,6-tetrahydrocyclopenta[c]pyrazol-4-ol

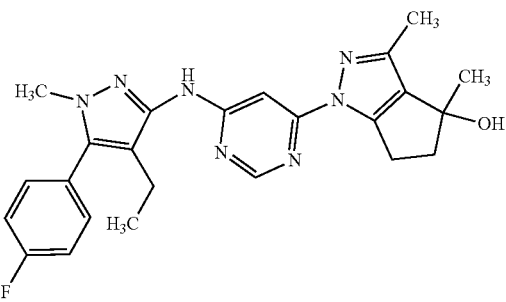 [SMILES: CCc1c(Nc2cc(-n3nc(C)c4c3CCC4(C)O)ncn2)nn(C)c1-c1ccc(F)cc1]

1-(6-{[4-ethyl-5-(4-fluorophenyl)-1-methyl-1H-pyrazol-3-yl]amino}pyrimidin-4-yl)-3-methyl-5,6-dihydrocyclopenta[c]pyrazol-4(1H)-one (46.0 mg, 107 μmol) was dissolved in tetrahydrofuran and cooled with a waterbath of 20° C. A solution of methylmagnesium bromide (1.0 M in tetrahydrofuran, 430 μl, 430 μmol) was added dropwise. After 30 minutes stirring at 20° C., a second aliquot of methylmagnesium bromide (1.0 M in tetrahydrofuran, 250 μL, 250 μmol) was added. The reaction mixture was stirred for 20 minutes at ambient temperature before being quenched by addition of saturated aqueous ammonium chloride solution. It was extracted with ethyl acetate (3×), the combined organic phase extracts were washed with brine, dried over sodium sulfate and concentrated. The residue was purified by flash column chromatography (KP Sil 10 g, cyclohexane/ethyl acetate gradient 70/30 to 0/100 10CV, 0/100 5 CV, flow: 36 mL/min). The product-containing fractions were combined, concentrated and dried under vacuum to yield the desired product (34 mg, 66% yield).

LC-MS (method 11): $R_t$=1.29 min; MS (ESIneg): m/z=446 [M−H]⁻

¹H-NMR (400 MHz, dimethylsulfoxide-d6) δ [ppm]: 2.21 (s, 3H), 2.24-2.38 (m, 2H), 2.40-2.48 (m, 1H), 2.90-3.22 (m, 2H), 3.66 (s, 3H), 4.95 (s, 1H), 7.22 (s, 1H), 7.31-7.60 (m, 4H), 8.39 (s, 1H), 9.31 (s, 1H).

Example 147 ethyl 1-(6-{[1-(cyclopropylmethyl)-4-ethyl-3-(4-fluorophenyl)-1H-pyrazol-5-yl]amino}pyrimidin-4-yl)-3,5-dimethyl-1H-pyrazole-4-carboxylate

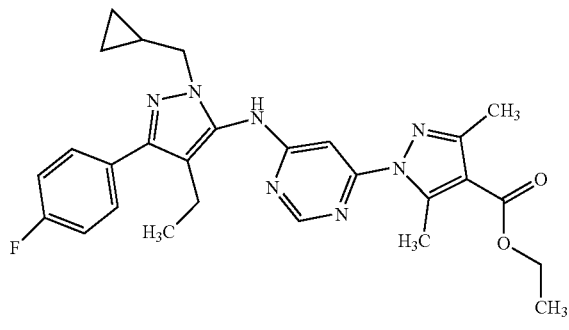 [SMILES: CCOC(=O)c1c(C)nn(-c2cc(Nc3c(CC)c(-c4ccc(F)cc4)nn3CC3CC3)ncn2)c1C]

A microwave vial was charged ethyl 1-(6-chloropyrimidin-4-yl)-3,5-dimethyl-1H-pyrazole-4-carboxylate (88.6 mg, 315 µmol), 1-(cyclopropylmethyl)-4-ethyl-3-(4-fluorophenyl)-1H-pyrazol-5-amine (120 mg, 75% purity, 347 µmol) and sodium phenolate (54.9 mg, 473 µmol) and the contents were suspended in 1,4-dioxane (2.2 ml, 26 mmol). The reaction mixture was degassed with Ar for 3 min. Tris(dibenzylidenaceton)dipalladium (3.76 mg, 4.10 µmol) and Xantphos (5.48 mg, 9.46 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 4) to yield the desired product (75.0 mg, 47%).

LC-MS (method 10): R$_t$=2.55 min; MS (ESIpos): m/z=504 [M+H]$^+$ $^1$H-NMR (400 MHz, dimethylsulfoxide-d6) δ [ppm]: 0.297 (3.93), 0.307 (3.97), 0.436 (4.33), 0.456 (4.33), 0.974 (5.80), 0.993 (11.75), 1.012 (5.63), 1.091 (0.53), 1.174 (0.73), 1.187 (1.25), 1.194 (1.23), 1.205 (1.69), 1.217 (1.14), 1.223 (1.14), 1.235 (0.67), 1.287 (4.85), 1.304 (8.86), 1.322 (4.54), 2.369 (2.80), 2.461 (3.89), 2.479 (4.21), 2.912 (16.00), 3.798 (3.41), 3.813 (3.27), 4.227 (1.72), 4.245 (4.29), 4.262 (4.15), 4.280 (1.49), 7.254 (3.49), 7.276 (6.81), 7.298 (3.80), 7.671 (2.52), 7.686 (3.35), 7.703 (2.22), 8.523 (0.59), 9.483 (0.54).

Example 148

6-[4-chloro-5-(difluoromethyl)-3-methyl-1H-pyrazol-1-yl]-N-[1-(cyclopropylmethyl)-4-ethyl-3-(4-fluorophenyl)-1H-pyrazol-5-yl]pyrimidin-4-amine

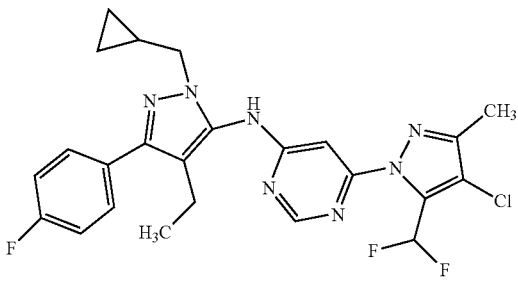 [SMILES: CCc1c(-c2ccc(F)cc2)nn(CC2CC2)c1Nc1cc(-n2nc(C)c(Cl)c2C(F)F)ncn1]

A microwave vial was charged 4-chloro-6-[4-chloro-5-(difluoromethyl)-3-methyl-1H-pyrazol-1-yl]pyrimidine (88.0 mg, 315 µmol), 1-(cyclopropylmethyl)-4-ethyl-3-(4-fluorophenyl)-1H-pyrazol-5-amine (120 mg, 75% purity, 347 µmol) and sodium phenolate (54.9 mg, 473 µmol) and the contents were suspended in 1,4-dioxane (2.2 ml, 26 mmol). The reaction mixture was degassed with Ar for 3 min. Tris(dibenzylidenaceton)dipalladium (3.76 mg, 4.10 µmol) and Xantphos (5.48 mg, 9.46 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 5) to yield the desired product (62.0 mg, 39%).

LC-MS (method 10): R$_t$=2.60 min; MS (ESIpos): m/z=502 [M+H]$^+$ $^1$H-NMR (400 MHz, dimethylsulfoxide-d6) δ [ppm]: 0.300 (4.54), 0.434 (5.29), 0.453 (5.45), 0.969 (7.46), 0.988 (16.00), 1.007 (7.69), 1.091 (0.40), 1.195 (2.11), 2.288 (2.75), 2.367 (0.84), 2.456 (3.77), 2.476 (4.00), 2.670 (0.66), 2.711 (0.54), 3.806 (3.68), 7.256 (4.08), 7.278 (8.28), 7.300 (4.79), 7.688 (3.57), 7.904 (2.41), 8.036 (4.82), 8.167 (2.16), 8.494 (0.70), 9.547 (0.63).

Example 149 ethyl 1-(6-{[3-(4-cyanophenyl)-1-(cyclopropylmethyl)-4-methyl-1H-pyrazol-5-yl]amino}pyrimidin-4-yl)-3,5-dimethyl-1H-pyrazole-4-carboxylate

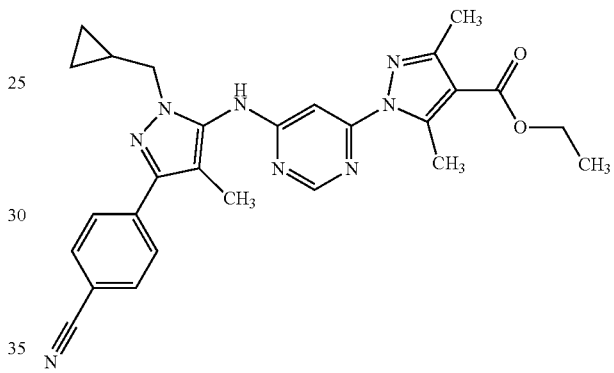

A round-bottom flask was charged with 4-[5-amino-1-(cyclopropylmethyl)-4-methyl-1H-pyrazol-3-yl]benzonitrile (1.00 g, 3.96 mmol), ethyl 1-(6-chloropyrimidin-4-yl)-3,5-dimethyl-1H-pyrazole-4-carboxylate (1.22 g, 4.36 mmol) and sodium phenolate (506 mg, 4.36 mmol) and the contents were suspended in 1,4-dioxane (1.0 mL). The reaction mixture was degassed with Ar for 3 min. Tris (dibenzylideneacetone)dipalladium (47.2 mg, 51.5 µmol) and XantPhos (68.8 mg, 119 µmol) were added and the reaction mixture was degassed again for 1 min. The reaction mixture was heated at 85° C. overnight while vigorously stirring. After cooling to ambient temperature, the reaction mixture was diluted with water and extracted with ethyl acetate. The organic phase extract was dried over sodium sulfate and concentrated. The residue was purified by flash column chromatography (SNAP Ultra 50 g, gradient cyclohexane/ethyl acetate 88/12 to 0/100) to yield the desired product (917 mg, 47% yield).

LC-MS (method 11): R$_t$=1.54 min; MS (ESIpos): m/z=497 [M+H]$^+$ $^1$H-NMR (400 MHz, dimethylsulfoxide-d6) δ [ppm]: −0.149 (0.42), −0.008 (3.61), 0.008 (3.11), 0.146 (0.42), 0.307 (2.56), 0.320 (2.84), 0.436 (2.57), 0.456 (2.76), 1.157 (0.91), 1.175 (1.98), 1.193 (1.58), 1.199 (0.74), 1.211 (1.11), 1.231 (0.71), 1.288 (3.61), 1.306 (7.36), 1.323 (3.69), 1.398 (2.60), 1.988 (3.20), 2.064 (16.00), 2.328 (0.77), 2.376 (2.12), 2.670 (0.52), 2.911 (12.61), 3.568 (2.16), 3.865 (2.23), 3.882 (2.21), 4.021 (0.75), 4.039 (0.77), 4.229 (1.08), 4.247 (3.23), 4.265 (3.23), 4.282 (1.07), 7.885 (0.77), 7.907 (13.79), 7.931 (0.82), 8.534 (0.44), 9.582 (0.41).

Example 150

4-[5-{[6-(4-chloro-3,5-dimethyl-1H-pyrazol-1-yl)pyrimidin-4-yl]amino}-1-(cyclopropylmethyl)-4-methyl-1H-pyrazol-3-yl]benzonitrile

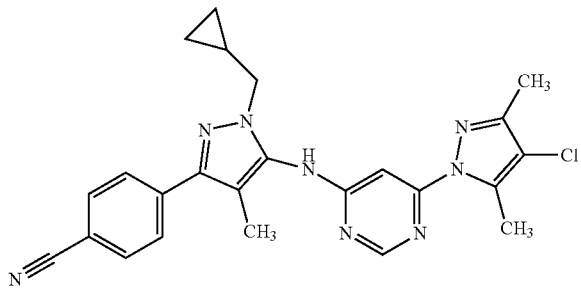 [SMILES: Cc1nn(-c2cc(Nc3c(C)c(-c4ccc(C#N)cc4)nn3CC3CC3)ncn2)c(C)c1Cl]

A microwave vial was charged with 4-[5-amino-1-(cyclopropylmethyl)-4-methyl-1H-pyrazol-3-yl]benzonitrile (100 mg, 396 µmol), 4-chloro-6-(4-chloro-3,5-dimethyl-1H-pyrazol-1-yl)pyrimidine (106 mg, 436 µmol) and sodium phenolate (69.0 mg, 594 µmol) and the contents were suspended in 1,4-dioxane (1.1 mL). The reaction mixture was degassed with Ar for 3 min. Tris(dibenzylideneacetone)dipalladium (4.72 mg, 5.15 µmol) and XantPhos (6.88 mg, 11.9 µmol) were added and the reaction mixture was degassed again for 1 min. The vial was sealed and heated at 85° C. overnight while vigorously shaking. After cooling to ambient temperature, the reaction mixture was filtered, diluted with dimethylsulfoxide and purified by preparative HPLC (method 4) to yield an impure product fraction (102 mg). Upon attempted dissolution in dimethylsulfoxide, a white solid remains and was filtered off. The filtrate was further purified by preparative HPLC (method 8) to yield the desired product (51 mg, 27% yield).

LC-MS (method 10): $R_t$=2.54 min; MS (ESIpos): m/z=459 [M+H]$^+$ $^1$H-NMR (400 MHz, dimethylsulfoxide-d6) δ [ppm]: −0.008 (2.32), 0.008 (2.05), 0.303 (2.08), 0.315 (2.29), 0.431 (2.13), 0.451 (2.29), 1.187 (0.59), 1.194 (0.56), 1.206 (0.89), 1.218 (0.53), 1.224 (0.55), 2.061 (14.73), 2.211 (2.16), 2.523 (0.98), 2.648 (16.00), 2.670 (0.55), 3.860 (1.98), 3.878 (1.93), 7.887 (0.74), 7.907 (10.23), 7.932 (0.67), 8.495 (0.46), 9.518 (0.44).

Example 151 ethyl 1-(6-{[1-(cyclopropylmethyl)-5-(4-fluorophenyl)-4-methyl-1H-pyrazol-3-yl]amino}pyrimidin-4-yl)-3,5-dimethyl-1H-pyrazole-4-carboxylate

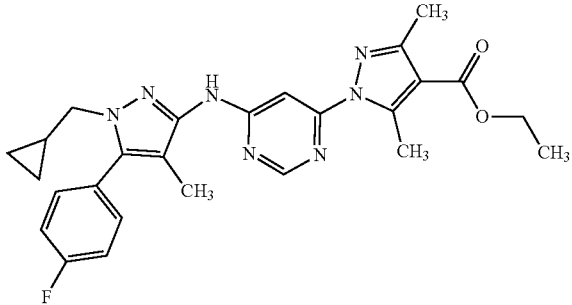 [SMILES: CCOC(=O)c1c(C)nn(-c2cc(Nc3nn(CC4CC4)c(-c4ccc(F)cc4)c3C)ncn2)c1C]

A microwave vial was charged ethyl 1-(6-chloropyrimidin-4-yl)-3,5-dimethyl-1H-pyrazole-4-carboxylate (143 mg, 511 µmol), 1-(cyclopropylmethyl)-5-(4-fluorophenyl)-4-methyl-1H-pyrazol-3-amine (138 mg, 562 µmol) and sodium phenolate (88.9 mg, 766 µmol) and the contents were suspended in 1,4-dioxane (2.3 ml, 27 mmol). The reaction mixture was degassed with Ar for 3 min. Tris(dibenzylidenaceton)dipalladium (6.08 mg, 6.64 µmol) and Xantphos (8.86 mg, 15.3 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method: column: Reprosil C18; 10 µm; 125×30 mm/flow: 50 mL/min/solvent: A=water (0.1% formic acid), B=acetonitrile/gradient: 0.00-4.25 min=20% B, 4.50 min=30% B, 19.00-22.50 min=100% B, 22.75-25.00 min=20%) to yield the desired product (34.7 mg, 14%).

LC-MS (method 10): $R_t$=2.61 min; MS (ESIpos): m/z=490 [M+H]$^+$ $^1$H-NMR (400 MHz, dimethylsulfoxide-d6) δ [ppm]: −0.008 (3.04), 0.008 (1.96), 0.201 (1.87), 0.213 (1.91), 0.407 (0.87), 0.418 (2.07), 0.422 (2.16), 0.438 (2.12), 0.453 (0.59), 1.029 (0.54), 1.049 (0.82), 1.289 (4.51), 1.307 (9.63), 1.325 (4.58), 1.504 (0.77), 1.860 (8.28), 2.002 (0.48), 2.328 (0.55), 2.370 (13.74), 2.523 (1.50), 2.670 (0.54), 2.905 (16.00), 3.802 (3.69), 3.819 (3.71), 4.229 (1.29), 4.246 (4.18), 4.264 (4.11), 4.282 (1.29), 7.355 (1.79), 7.377 (4.20), 7.400 (2.64), 7.477 (2.61), 7.483 (1.24), 7.491 (2.83), 7.499 (2.26), 7.513 (1.84), 8.544 (2.66), 9.669 (1.89).

Example 152 ethyl 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylate

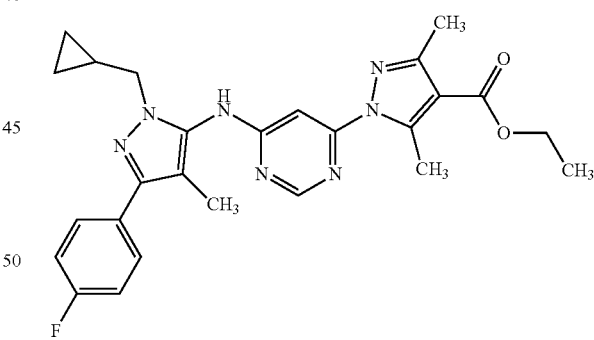

A microwave vial was charged ethyl 1-(6-chloropyrimidin-4-yl)-3,5-dimethyl-1H-pyrazole-4-carboxylate (112 mg, 399 µmol), 1-(cyclopropylmethyl)-3-(4-fluorophenyl)-4-methyl-1H-pyrazol-5-amine (108 mg, 439 µmol) and sodium phenolate (69.4 mg, 598 µmol) and the contents were suspended in 1,4-dioxane (1.8 ml, 21 mmol). The reaction mixture was degassed with Ar for 3 min. Tris(dibenzylidenaceton)dipalladium (4.75 mg, 5.18 µmol) and Xantphos (6.92 mg, 12.0 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method: column: Reprosil C18; 10 μm; 125×30 mm/flow: 50 mL/min/solvent: A=water (0.1% formic acid), B=acetonitrile/gradient: 0.00-4.25 min=20% B, 4.50 min=30% B, 19.00-22.50 min=100% B, 22.75-25.00 min=20%) to yield the desired product (133 mg, 68%).

LC-MS (method 11): R$_t$=1.59 min; MS (ESIpos): m/z=490 [M+H]$^+$ $^1$H-NMR (400 MHz, dimethylsulfoxide-d6) δ [ppm]: 0.294 (2.81), 0.306 (3.08), 0.426 (2.83), 0.446 (3.02), 1.073 (0.47), 1.091 (0.94), 1.109 (0.47), 1.167 (0.43), 1.180 (0.79), 1.186 (0.75), 1.198 (1.16), 1.216 (0.75), 1.230 (0.43), 1.287 (3.77), 1.304 (7.56), 1.322 (3.86), 2.009 (16.00), 2.368 (2.59), 2.388 (2.94), 2.910 (13.62), 2.933 (1.71), 3.375 (0.51), 3.392 (0.49), 3.830 (2.49), 3.847 (2.46), 4.228 (1.20), 4.245 (3.43), 4.263 (3.47), 4.280 (1.24), 7.252 (2.49), 7.274 (5.14), 7.296 (2.81), 7.312 (0.56), 7.711 (1.73), 7.726 (2.31), 7.746 (1.59), 8.533 (0.51), 10.193 (0.66).

Example 153 ethyl 1-(6-{[4-chloro-1-(cyclopropylmethyl)-5-(4-fluorophenyl)-1H-pyrazol-3-yl]amino}pyrimidin-4-yl)-3,5-dimethyl-1H-pyrazole-4-carboxylate

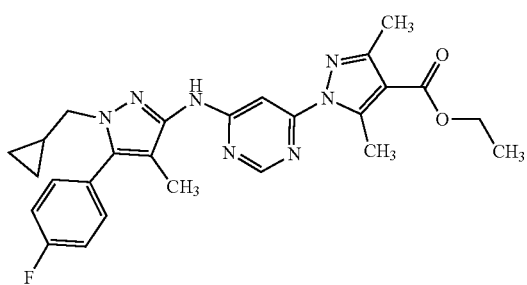 [SMILES: CCOC(=O)c1c(C)nn(-c2cc(Nc3nn(CC4CC4)c(-c4ccc(F)cc4)c3C)ncn2)c1C]

A microwave vial was charged ethyl 1-(6-chloropyrimidin-4-yl)-3,5-dimethyl-1H-pyrazole-4-carboxylate (121 mg, 429 μmol), 4-chloro-1-(cyclopropylmethyl)-5-(4-fluorophenyl)-1H-pyrazol-3-amine (126 mg, 472 μmol) and sodium phenolate (74.8 mg, 644 μmol) and the contents were suspended in 1,4-dioxane (1.9 ml, 22 mmol). The reaction mixture was degassed with Ar for 3 min. Tris(dibenzylidenaceton)dipalladium (5.11 mg, 5.58 μmol) and Xantphos (7.45 mg, 12.9 μmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method: column: Reprosil C18; 10 μm; 125×30 mm/flow: 50 mL/min/solvent: A=water (0.1% formic acid), B=acetonitrile/gradient: 0.00-4.25 min=20% B, 4.50 min=30% B, 19.00-22.50 min=100% B, 22.75-25.00 min=20%) to yield the desired product (105 mg, 44%).

LC-MS (method 11): R$_t$=1.71 min; MS (ESIpos): m/z=510 [M+H]$^+$ $^1$H-NMR (400 MHz, dimethylsulfoxide-d6) δ [ppm]: 0.197 (1.02), 0.209 (3.23), 0.221 (3.24), 0.233 (0.90), 0.436 (1.20), 0.447 (2.91), 0.450 (2.97), 0.467 (2.96), 0.482 (0.86), 1.054 (0.48), 1.066 (0.80), 1.073 (0.83), 1.085 (1.11), 1.092 (0.77), 1.103 (0.70), 1.290 (4.80), 1.308 (9.29), 1.326 (4.52), 2.377 (14.64), 2.911 (16.00), 3.893 (4.78), 3.911 (4.59), 4.230 (1.56), 4.248 (4.26), 4.266 (4.09), 4.284 (1.30), 7.407 (2.23), 7.429 (4.61), 7.451 (2.68), 7.518 (1.20), 7.586 (2.88), 7.600 (3.19), 7.608 (2.69), 7.622 (2.14), 8.573 (3.31), 9.806 (3.24).

Example 154

4-[5-({6-[4-chloro-5-(difluoromethyl)-3-methyl-1H-pyrazol-1-yl]pyrimidin-4-yl}amino)-1-(cyclopropylmethyl)-4-methyl-1H-pyrazol-3-yl]benzonitrile

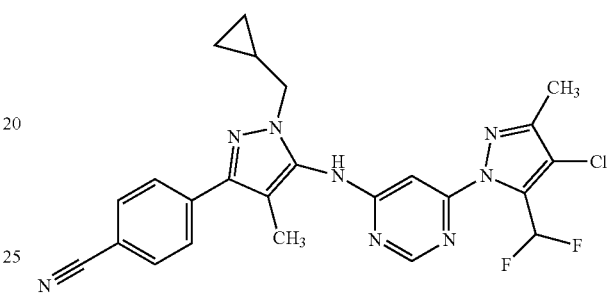

A microwave vial was charged with 4-[5-amino-1-(cyclopropylmethyl)-4-methyl-1H-pyrazol-3-yl]benzonitrile (200 mg, 793 μmol), 4-chloro-6-[4-chloro-5-(difluoromethyl)-3-methyl-1H-pyrazol-1-yl]pyrimidine (243 mg, 872 μmol) and sodium phenolate (101 mg, 872 μmol) and the contents were suspended in 1,4-dioxane (2.2 mL). The reaction mixture was degassed with Ar for 3 min. Tris(dibenzylideneacetone)dipalladium (9.44 mg, 10.3 μmol) and XantPhos (13.8 mg, 23.8 μmol) were added and the reaction mixture was degassed again for 1 min. The vial was sealed and heated at 85° C. overnight while vigorously shaking. After cooling to ambient temperature, the reaction mixture was concentrated and purified by flash column chromatography (KPSil 25 g, gradient cyclohexane/ethyl acetate 90/10 to 40:60) to yield the desired product (110 mg, 26% yield) that was dried overnight under high-vacuum.

LC-MS (method 10): R$_t$=2.40 min; MS (ESIpos): m/z=495 [M+H]$^+$ $^1$H-NMR (400 MHz, dimethylsulfoxide-d6) δ [ppm]: 0.26-0.38 (m, 2H), 0.41-0.50 (m, 2H), 1.12-1.30 (m, 1H), 2.06 (s, 3H), 2.18-2.38 (br s, 3H), 3.79-3.95 (m, 2H), 7.91 (s, 4H), 7.87-8.20 (m, 1H), 8.34-8.84 (m, 1H), 9.40-10.06 (m, 1H).

Example 155 ethyl 1-(6-{[4-ethyl-3-(4-fluorophenyl)-1-methyl-1H-pyrazol-5-yl]amino}pyrimidin-4-yl)-3,5-dimethyl-1H-pyrazole-4-carboxylate

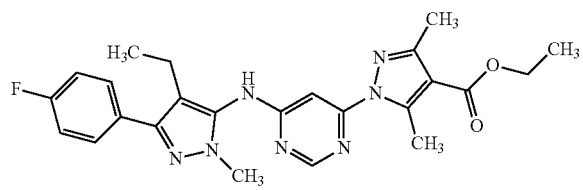 [SMILES: CCOC(=O)c1c(C)nn(-c2cc(Nc3c(CC)c(-c4ccc(F)cc4)nn3C)ncn2)c1C]

A microwave vial was charged ethyl 1-(6-chloropyrimidin-4-yl)-3,5-dimethyl-1H-pyrazole-4-carboxylate (200 mg, 712 µmol), 4-ethyl-3-(4-fluorophenyl)-1-methyl-1H-pyrazol-5-amine (172 mg, 784 µmol) and sodium phenolate (91.0 mg, 784 µmol) and the contents were suspended in 1,4-dioxane (3.3 ml, 39 mmol). The reaction mixture was degassed with Ar for 3 min. Tris(dibenzylidenaceton)dipalladium (8.48 mg, 9.26 µmol) and Xantphos (12.4 mg, 21.4 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method: column: Reprosil C18; 10 µm; 125×30 mm/flow: 50 mL/min/ solvent: A=water (0.1% formic acid), B=acetonitrile/gradient: 0.00-4.25 min=20% B, 4.50 min=30% B, 19.00-22.50 min=100% B, 22.75-25.00 min=20%)) to yield the desired product (194 mg, 54%).

LC-MS (method 10): $R_t$=2.30 min; MS (ESIpos): m/z=464 [M+H]$^+$ $^1$H-NMR (400 MHz, dimethylsulfoxide-d6) δ [ppm]: 0.972 (4.73), 0.991 (10.20), 1.009 (4.99), 1.289 (4.19), 1.307 (8.39), 1.324 (4.25), 2.378 (3.04), 2.448 (1.27), 2.466 (3.16), 2.632 (0.44), 2.915 (16.00), 3.644 (12.19), 3.675 (0.53), 4.230 (1.29), 4.247 (3.79), 4.265 (3.77), 4.283 (1.31), 7.247 (2.63), 7.269 (5.31), 7.291 (2.96), 7.342 (1.37), 7.382 (1.53), 7.465 (2.40), 7.478 (1.55), 7.489 (0.48), 7.649 (2.07), 7.663 (2.75), 7.669 (2.67), 7.684 (1.97), 7.782 (1.44), 7.794 (1.37), 7.807 (1.10), 7.813 (1.20), 7.821 (1.27), 8.544 (0.78), 9.540 (0.99).

Example 156 ethyl 1-(6-{[3-(4-cyanophenyl)-1-(cyclopropylmethyl)-4-ethyl-1H-pyrazol-5-yl]amino}pyrimidin-4-yl)-3,5-dimethyl-1H-pyrazole-4-carboxylate

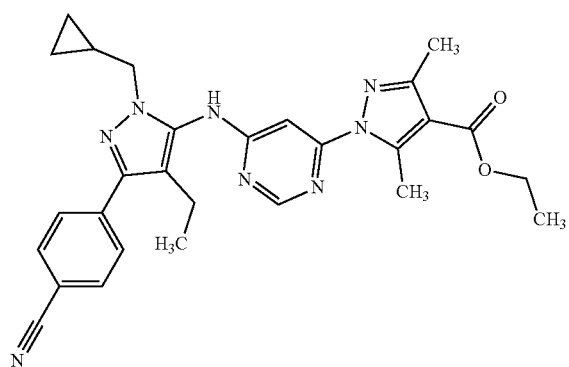 [SMILES: CCOC(=O)c1c(C)nn(-c2cc(Nc3c(CC)c(-c4ccc(C#N)cc4)nn3CC3CC3)ncn2)c1C]

A microwave vial was charged ethyl 1-(6-chloropyrimidin-4-yl)-3,5-dimethyl-1H-pyrazole-4-carboxylate (125 mg, 445 µmol), 4-[5-amino-1-(cyclopropylmethyl)-4-ethyl-1H-pyrazol-3-yl]benzonitrile (130 mg, 490 µmol) and sodium phenolate (77.5 mg, 668 µmol) and the contents were suspended in 1,4-dioxane (2.5 ml, 29 mmol). The reaction mixture was degassed with Ar for 3 min. Tris(dibenzylidenaceton)dipalladium (5.30 mg, 5.79 µmol) and Xantphos (7.73 mg, 13.4 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were dried over Extrelute NT3 and concentrated under reduced pressure. The crude product was purified by preparative HPLC (method 5) to yield the desired product (117 mg, 49%).

LC-MS (method 10): $R_t$=2.37 min; MS (ESIpos): m/z=511 [M+H]$^+$ $^1$H-NMR (400 MHz, dimethylsulfoxide-d6) δ [ppm]: 0.312 (3.56), 0.322 (3.61), 0.447 (3.88), 0.467 (3.96), 0.982 (0.94), 0.994 (5.34), 1.013 (11.32), 1.032 (5.43), 1.158 (0.48), 1.176 (0.96), 1.187 (0.70), 1.199 (1.17), 1.206 (1.11), 1.218 (1.65), 1.233 (1.29), 1.249 (0.71), 1.289 (4.70), 1.306 (9.22), 1.324 (4.73), 1.990 (1.33), 2.360 (2.77), 2.369 (2.45), 2.405 (1.78), 2.915 (16.00), 2.953 (1.28), 3.833 (3.02), 3.848 (2.93), 4.229 (1.41), 4.247 (4.01), 4.264 (4.04), 4.282 (1.50), 7.827 (0.41), 7.865 (1.87), 7.887 (7.59), 7.898 (12.40), 7.919 (2.82), 7.941 (0.83), 8.525 (0.65), 9.539 (0.55).

Example 157

4-[5-{[6-(4-chloro-3,5-dimethyl-1H-pyrazol-1-yl)pyrimidin-4-yl]amino}-1-(cyclopropylmethyl)-4-ethyl-1H-pyrazol-3-yl]benzonitrile

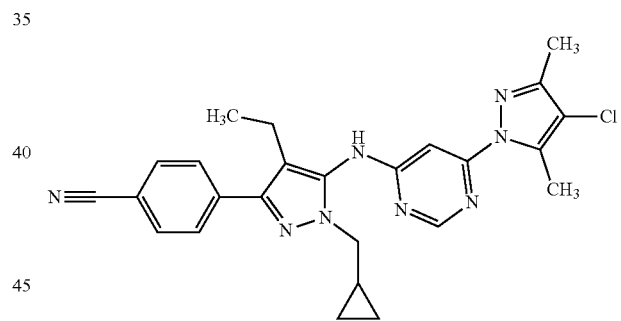

A microwave vial was charged 4-chloro-6-(4-chloro-3,5-dimethyl-1H-pyrazol-1-yl)pyrimidine (125 mg, 514 µmol), 4-[5-amino-1-(cyclopropylmethyl)-4-ethyl-1H-pyrazol-3-yl]benzonitrile (151 mg, 566 µmol) and sodium phenolate (89.5 mg, 771 µmol) and the contents were suspended in 1,4-dioxane (2.5 ml, 29 mmol). The reaction mixture was degassed with Ar for 3 min. Tris(dibenzylidenaceton)dipalladium (6.12 mg, 6.68 µmol) and Xantphos (8.93 mg, 15.4 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were dried over Extrelut NT3 and concentrated under reduced pressure. The crude product was purified by flash chromatography on silica gel (dichloromethane/ethyl acetate) to yield the desired product (154 mg, 60%).

LC-MS (method 11): $R_t$=1.66 min; MS (ESIpos): m/z=473 [M+H]$^+$

¹H-NMR (400 MHz, dimethylsulfoxide-d6) δ [ppm]: 0.310 (3.07), 0.319 (3.06), 0.446 (3.43), 0.465 (3.34), 0.993 (4.36), 1.012 (8.85), 1.030 (4.44), 1.092 (0.60), 1.185 (0.61), 1.197 (0.99), 1.205 (0.98), 1.216 (1.31), 1.227 (0.95), 1.234 (0.95), 2.213 (2.52), 2.647 (16.00), 3.832 (2.79), 3.847 (2.61), 5.756 (2.06), 7.869 (1.77), 7.890 (6.58), 7.899 (9.32), 7.919 (1.99), 8.489 (0.65), 9.480 (0.56).

Example 158 ethyl 1-(6-{[4-chloro-1-(cyclopropylmethyl)-3-(4-fluorophenyl)-1H-pyrazol-5-yl]amino}pyrimidin-4-yl)-3,5-dimethyl-1H-pyrazole-4-carboxylate

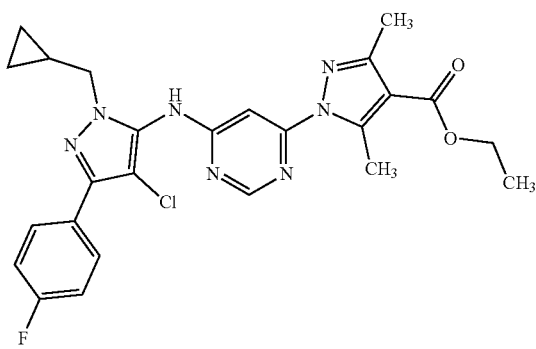 [SMILES: CCOC(=O)c1c(C)nn(-c2cc(Nc3c(Cl)c(-c4ccc(F)cc4)nn3CC3CC3)ncn2)c1C]

A microwave vial was charged ethyl 1-(6-chloropyrimidin-4-yl)-3,5-dimethyl-1H-pyrazole-4-carboxylate (81.4 mg, 290 µmol), 4-chloro-1-(cyclopropylmethyl)-3-(4-fluorophenyl)-1H-pyrazol-5-amine (84.8 mg, 319 µmol) and sodium phenolate (50.5 mg, 435 µmol) and the contents were suspended in 1,4-dioxane (1.3 ml, 15 mmol). The reaction mixture was degassed with Ar for 3 min. Tris(dibenzylideneaceton)dipalladium (3.45 mg, 3.77 µmol) and Xantphos (5.04 mg, 8.70 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×30 mm/flow: 50 mL/min/solvent: A=water (0.1% formic acid), B=acetonitrile/gradient: 0.00-4.25 min=20% B, 4.50 min=30% B, 19.00-22.50 min=100% B, 22.75-25.00 min=20%) to yield the desired product (67.0 mg, 45%).

LC-MS (method 10): $R_t$=2.50 min; MS (ESIpos): m/z=510 [M+H]⁺

¹H-NMR (400 MHz, dimethylsulfoxide-d6) δ [ppm]: 0.318 (0.67), 0.330 (2.81), 0.343 (3.10), 0.355 (0.96), 0.453 (0.84), 0.463 (2.49), 0.466 (2.41), 0.483 (2.66), 0.498 (0.59), 1.158 (1.45), 1.176 (2.94), 1.194 (1.59), 1.203 (0.40), 1.216 (0.69), 1.223 (0.68), 1.234 (1.09), 1.246 (0.66), 1.254 (0.68), 1.292 (4.37), 1.309 (9.05), 1.327 (4.48), 1.989 (5.37), 2.385 (6.60), 2.920 (16.00), 2.959 (0.50), 3.900 (3.00), 3.918 (2.99), 4.004 (0.45), 4.021 (1.31), 4.039 (1.31), 4.057 (0.45), 4.234 (1.31), 4.251 (3.99), 4.269 (3.96), 4.287 (1.26), 7.309 (2.28), 7.331 (4.62), 7.353 (2.49), 7.896 (2.15), 7.910 (2.49), 7.918 (2.40), 7.932 (2.04), 8.570 (1.50), 9.807 (1.22).

Example 159

2-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]propan-2-ol

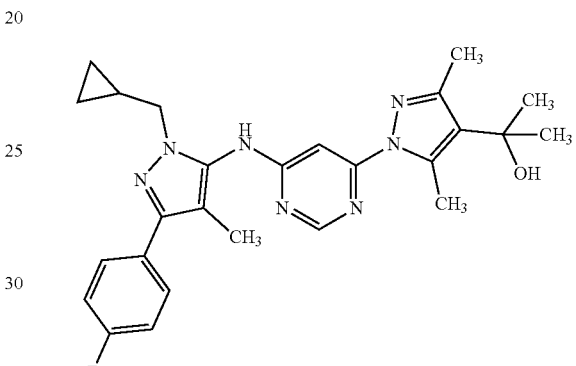

Ethyl 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylate (5.00 g, 95% purity, 9.70 mmol) was dissolved in tetrahydrofuran (200 mL) under an argon atmosphere and the resulting solution was cooled to 0° C. A solution of bromo(methyl)magnesium (3.0 M, 16 ml, 49 mmol) was added dropwise and the reaction mixture was allowed to slowly reach ambient temperature and was stirred overnight. The reaction was quenched with aqueous Na₂EDTA solution (10%, 50 mL) and stirring was continued for 30 min. After further dilution with water (200 mL), it was extracted with ethyl acetate (200 mL). The organic phase extract was dried over sodium sulfate and concentrated. The residue was purified by flash column chromatography (340 g silica gel, cyclohexane/ethyl acetate 1:1) to yield the desired product as a white solid (2.95 g, 64% yield).

LC-MS (method 11): $R_t$=1.38 min; MS (ESIneg): m/z=474 [M–H]⁻

¹H-NMR (400 MHz, dimethylsulfoxide-d6) δ [ppm]: –0.008 (0.67), 0.008 (0.83), 0.280 (0.45), 0.293 (1.95), 0.305 (2.17), 0.316 (0.65), 0.424 (1.88), 0.443 (2.02), 1.158 (2.16), 1.175 (4.48), 1.186 (0.60), 1.193 (2.57), 1.209 (0.50), 1.217 (0.50), 1.465 (16.00), 1.989 (7.83), 2.005 (11.66), 2.265 (2.42), 2.743 (11.95), 3.826 (1.94), 3.844 (1.91), 4.003 (0.64), 4.021 (1.85), 4.039 (1.84), 4.057 (0.61), 4.855 (3.26), 7.249 (1.70), 7.271 (3.50), 7.293 (1.90), 7.709 (1.39), 7.723 (1.71), 7.730 (1.67), 7.744 (1.30), 8.461 (0.53), 9.361 (0.65).

Example 160

2-[1-(6-{[4-chloro-1-(cyclopropylmethyl)-5-(4-fluorophenyl)-1H-pyrazol-3-yl]amino}pyrimidin-4-yl)-3,5-dimethyl-1H-pyrazol-4-yl]propan-2-ol

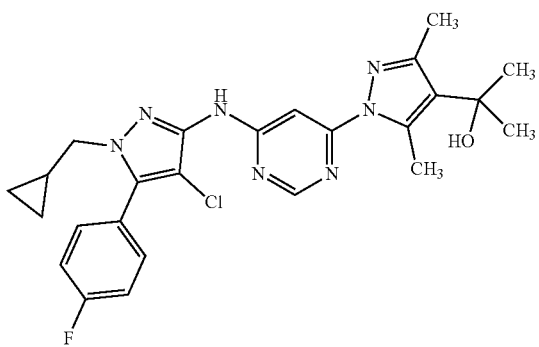 [SMILES: Cc1nn(-c2cc(Nc3nn(CC4CC4)c(-c4ccc(F)cc4)c3Cl)ncn2)c(C)c1C(C)(C)O]

A solution of ethyl 1-(6-{[4-chloro-1-(cyclopropylmethyl)-5-(4-fluorophenyl)-1H-pyrazol-3-yl]amino}pyrimidin-4-yl)-3,5-dimethyl-1H-pyrazole-4-carboxylate (93.0 mg, 182 µmol) in tetrahydrofuran (3.0 ml, 37 mmol) was treated with bromo(methyl)magnesium (210 µl, 3.0 M, 640 µmol) at 0° C. The mixture was stirred at ambient temperature overnight. The mixture was diluted with water and purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 44.4 mg (49%) of the desired product.

LC-MS (method 11): $R_t$=1.49 min; MS (ESIpos): m/z=496 [M+H]$^+$ $^1$H-NMR (400 MHz, dimethylsulfoxide-d6) δ [ppm]: 0.202 (1.55), 0.215 (1.68), 0.227 (0.48), 0.431 (0.44), 0.445 (1.36), 0.462 (1.40), 0.477 (0.41), 1.080 (0.51), 1.091 (0.47), 1.472 (16.00), 2.274 (8.04), 2.742 (8.49), 3.886 (2.30), 3.904 (2.27), 4.851 (3.25), 7.404 (1.12), 7.426 (3.19), 7.448 (1.43), 7.580 (1.34), 7.594 (1.52), 7.602 (1.33), 7.615 (1.07), 8.492 (2.10), 9.586 (2.06).

Example 161

4-[1-(cyclopropylmethyl)-5-{[6-(3,5-dimethyl-1H-pyrazol-1-yl)pyrimidin-4-yl]amino}-4-ethyl-1H-pyrazol-3-yl]benzonitrile

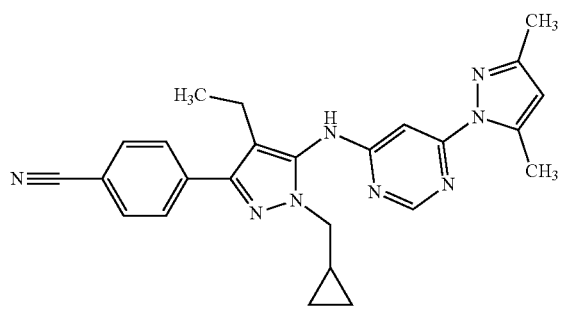 [SMILES: CCc1c(-c2ccc(C#N)cc2)nn(CC2CC2)c1Nc1cc(-n2nc(C)cc2C)ncn1]

A microwave vial was charged 4-chloro-6-(3,5-dimethyl-1H-pyrazol-1-yl)pyrimidine (125 mg, 599 µmol), 4-[5-amino-1-(cyclopropylmethyl)-4-ethyl-1H-pyrazol-3-yl]benzonitrile (176 mg, 659 µmol) and sodium phenolate (104 mg, 899 µmol) and the contents were suspended in 1,4-dioxane (2.5 ml, 29 mmol). The reaction mixture was degassed with Ar for 3 min. Tris(dibenzylidenaceton)dipalladium (7.13 mg, 7.79 µmol) and Xantphos (10.4 mg, 18.0 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and additionally by flash chromatography on silica gel (dichloromethane/ethyl acetate) to yield the desired product (139 mg, 53%).

LC-MS (method 10): $R_t$=2.25 min; MS (ESIpos): m/z=439 [M+H]$^+$ $^1$H-NMR (400 MHz, dimethylsulfoxide-d6) δ [ppm]: −0.008 (1.01), 0.008 (1.04), 0.309 (2.41), 0.321 (2.64), 0.443 (2.59), 0.463 (2.78), 0.994 (3.93), 1.012 (8.83), 1.031 (4.12), 1.157 (0.73), 1.175 (1.53), 1.186 (0.43), 1.193 (1.03), 1.205 (0.70), 1.216 (1.11), 1.228 (0.69), 1.235 (0.73), 1.989 (2.71), 2.172 (2.35), 2.630 (16.00), 3.828 (2.17), 3.845 (2.14), 4.021 (0.63), 4.039 (0.64), 6.144 (2.60), 7.868 (1.18), 7.889 (5.74), 7.898 (9.64), 7.919 (1.68), 8.456 (0.67), 9.384 (0.69).

Example 162

N-[1-(2,2-difluoroethyl)-4-ethyl-3-(4-fluorophenyl)-1H-pyrazol-5-yl]-6-(3,5-dimethyl-1H-pyrazol-1-yl)pyrimidin-4-amine

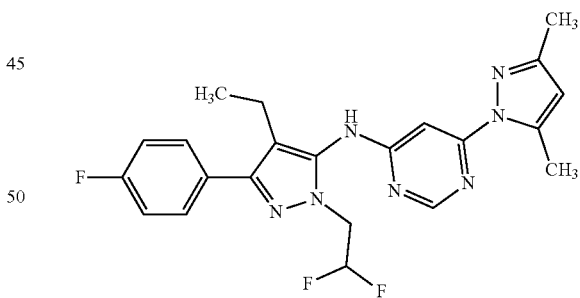

A microwave vial was charged 4-chloro-6-(3,5-dimethyl-1H-pyrazol-1-yl)pyrimidine (70.4 mg, 338 mol), 1-(2,2-difluoroethyl)-4-ethyl-3-(4-fluorophenyl)-1H-pyrazol-5-amine (100 mg, 371 µmol) and potassium phosphate (107 mg, 506 µmol) and the contents were suspended in 1,4-dioxane (3.8 ml, 45 mmol). The reaction mixture was degassed with Ar for 3 min. Tris(dibenzylidenaceton)dipalladium (4.02 mg, 4.39 µmol) and Xantphos (5.86 mg, 10.1 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×40 mm/flow: 75 mL/min/solvent: A=water (0.1% formic acid), B=acetonitril/gradient: 0.00-5.50 min=10% B, 17.65-19.48 min=95% B, 19.66 min=10% B) to yield the desired product (37.0 mg, 22%).

LC-MS (method 10): $R_t$=2.23 min; MS (ESIpos): m/z=442 [M+H]$^+$ $^1$H-NMR (400 MHz, dimethylsulfoxide-d6) δ [ppm]: −0.008 (0.70), 0.961 (4.01), 0.979 (9.11), 0.998 (4.23), 1.356 (0.73), 2.181 (5.22), 2.450 (0.95), 2.468 (2.96), 2.634 (16.00), 4.396 (0.76), 4.431 (1.33), 4.465 (0.74), 6.151 (3.53), 6.206 (0.41), 6.216 (0.79), 6.344 (0.73), 6.353 (1.56), 6.363 (0.75), 6.491 (0.73), 7.272 (2.55), 7.294 (5.18), 7.316 (2.81), 7.342 (0.83), 7.382 (0.83), 7.461 (1.13), 7.465 (1.20), 7.478 (0.73), 7.674 (2.03), 7.688 (2.48), 7.695 (2.32), 7.709 (1.82), 7.781 (0.71), 7.790 (0.56), 7.794 (0.64), 7.807 (0.48), 7.814 (0.55), 7.821 (0.59), 8.465 (1.62), 9.394 (2.57).

Example 163

6-(4-chloro-3,5-dimethyl-1H-pyrazol-1-yl)-N-[1-(2,2-difluoroethyl)-4-ethyl-3-(4-fluorophenyl)-1H-pyrazol-5-yl]pyrimidin-4-amine

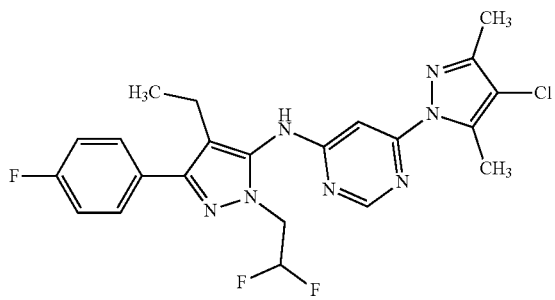 [SMILES: CCc1c(-c2ccc(F)cc2)nn(CC(F)F)c1Nc1cc(-n2nc(C)c(Cl)c2C)ncn1]

A microwave vial was charged 4-chloro-6-(4-chloro-3,5-dimethyl-1H-pyrazol-1-yl)pyrimidine (82.1 mg, 338 µmol), 1-(2,2-difluoroethyl)-4-ethyl-3-(4-fluorophenyl)-1H-pyrazol-5-amine (100 mg, 371 µmol) and potassium phosphate (107 mg, 506 µmol) and the contents were suspended in 1,4-dioxane (2.4 ml, 28 mmol). The reaction mixture was degassed with Ar for 3 min. Tris(dibenzylidenaceton)dipalladium (4.02 mg, 4.39 µmol) and Xantphos (5.86 mg, 10.1 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×40 mm/flow: 75 mL/min/solvent: A=water (0.1% formic acid), B=acetonitril/gradient: 0.00-5.50 min=10% B, 17.65-19.48 min=95% B, 19.66 min=10% B) to yield the desired product (33.0 mg, 21%).

LC-MS (method 10): $R_t$=2.49 min; MS (ESIpos): m/z=476 [M+H]$^+$ $^1$H-NMR (400 MHz, dimethylsulfoxide-d6) δ [ppm]: 0.957 (3.55), 0.976 (7.83), 0.995 (3.65), 1.141 (0.50), 1.234 (0.73), 2.220 (3.64), 2.447 (0.86), 2.465 (2.45), 2.485 (3.08), 2.652 (16.00), 4.399 (0.63), 4.434 (1.14), 4.469 (0.64), 6.214 (0.65), 6.342 (0.62), 6.352 (1.31), 6.361 (0.65), 6.489 (0.62), 7.272 (2.06), 7.294 (4.19), 7.316 (2.31), 7.673 (1.60), 7.687 (2.04), 7.694 (1.96), 7.708 (1.50), 8.501 (0.91), 9.493 (1.33).

Example 164

4-[5-({6-[4-chloro-5-(difluoromethyl)-3-methyl-1H-pyrazol-1-yl]pyrimidin-4-yl}amino)-1-(cyclopropylmethyl)-4-ethyl-1H-pyrazol-3-yl]benzonitrile

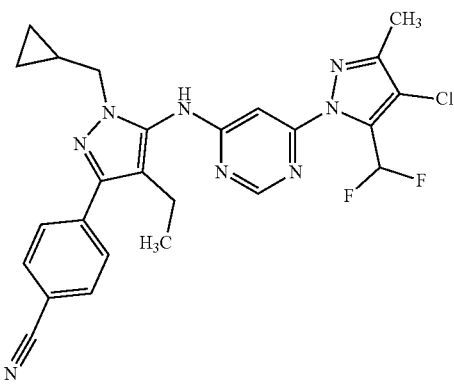 [SMILES: CCc1c(-c2ccc(C#N)cc2)nn(CC2CC2)c1Nc1cc(-n2nc(C)c(Cl)c2C(F)F)ncn1]

A microwave vial was charged 4-chloro-6-[4-chloro-5-(difluoromethyl)-3-methyl-1H-pyrazol-1-yl]pyrimidine (125 mg, 448 µmol), 4-[5-amino-1-(cyclopropylmethyl)-4-ethyl-1H-pyrazol-3-yl]benzonitrile (131 mg, 493 µmol) and sodium phenolate (78.0 mg, 672 µmol) and the contents were suspended in 1,4-dioxane (2.5 ml, 29 mmol). The reaction mixture was degassed with Ar for 3 min. Tris(dibenzylidenaceton)dipalladium (5.33 mg, 5.82 µmol) and Xantphos (7.77 mg, 13.4 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were dried over Extrelut NT3 and concentrated under reduced pressure. The crude product was purified by flash chromatography (dichloromethane/ethyl acetate, Biotage SNAP KP-Sil 10 g) and subsequent preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (37.5 mg, 30%).

LC-MS (method 10): $R_t$=2.43 min; MS (ESIpos): m/z=509 [M+H]$^+$ $^1$H-NMR (400 MHz, dimethylsulfoxide-d6) δ [ppm]: 0.319 (4.87), 0.449 (5.54), 0.468 (5.75), 0.994 (7.41), 1.013 (15.85), 1.032 (7.82), 1.075 (1.90), 1.093 (3.76), 1.110 (1.93), 1.184 (0.86), 1.196 (1.56), 1.203 (1.56), 1.215 (2.19), 1.232 (1.68), 1.245 (0.84), 2.295 (3.02), 2.372 (0.50), 2.684 (0.44), 3.358 (0.69), 3.376 (1.85), 3.393 (1.82), 3.411 (0.62), 3.836 (3.89), 3.848 (3.96), 7.318 (0.55), 7.901 (16.00), 7.921 (3.86), 8.039 (4.59), 8.170 (2.13), 8.500 (0.79), 9.608 (0.70).

Example 165

4-[1-(cyclopropylmethyl)-5-({6-[4-(2-hydroxypropan-2-yl)-3,5-dimethyl-1H-pyrazol-1-yl]pyrimidin-4-yl}amino)-4-methyl-1H-pyrazol-3-yl]benzonitrile

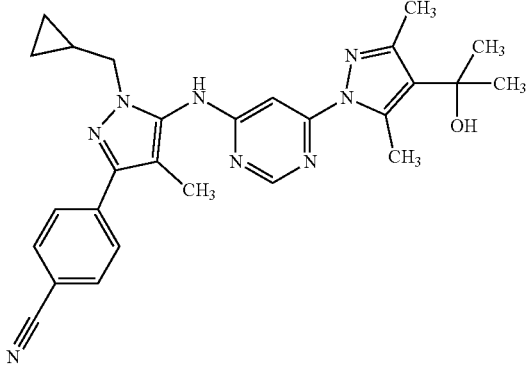 [SMILES: Cc1nn(-c2cc(Nc3c(C)c(-c4ccc(C#N)cc4)nn3CC3CC3)ncn2)c(C)c1C(C)(C)O]

Ethyl 1-(6-{[3-(4-cyanophenyl)-1-(cyclopropylmethyl)-4-methyl-1H-pyrazol-5-yl]amino}pyrimi-din-4-yl)-3,5-dimethyl-1H-pyrazole-4-carboxylate (610 mg, 1.23 mmol) was dissolved in tetrahydrofuran under an argon atmosphere and the resulting solution cooled to 0° C. A solution of methylmagnesium bromide (4.9 ml, 1.0 M, 4.9 mmol) was added dropwise and the reaction mixture allowed to warm to ambient temperature. After 1.5 h, another aliquot of methylmagnesium bromide (4.9 ml, 1.0 M, 4.9 mmol) was added and the reaction mixture stirred for another hour. It was then quenched with cold saturated aqueous ammonium chloride solution and extracted with ethyl acetate (2×). The combined organic phase extracts were dried over sodium sulfate and concentrated. The residue was purified by flash column chromatography (50 g Snap Ultra, methanol/dichloromethane gradient 1/99 to 5/95) to yield the desired product (278 mg, 47% yield) after concentration of all product-containing fractions.

LC-MS (method 11): $R_t$=1.32 min; MS (ESIpos): m/z=483 [M+H]$^+$ $^1$H-NMR (400 MHz, dimethylsulfoxide-d6) δ [ppm]: −0.008 (1.14), 0.008 (1.29), 0.306 (1.89), 0.317 (2.10), 0.433 (1.86), 0.453 (1.97), 1.190 (0.49), 1.196 (0.48), 1.209 (0.77), 1.220 (0.46), 1.228 (0.47), 1.465 (16.00), 2.059 (12.66), 2.073 (0.53), 2.267 (2.33), 2.742 (12.26), 3.859 (1.86), 3.876 (1.83), 4.856 (3.35), 7.881 (0.56), 7.904 (10.49), 7.928 (0.56), 8.459 (0.57), 9.410 (0.67).

Example 166 tert-butyl 5-(difluoromethyl)-1-(6-{[4-ethyl-5-(4-fluorophenyl)-1-methyl-1H-pyrazol-3-yl]amino}pyrimidin-4-yl)-3-methyl-1H-pyrazole-4-carboxylate

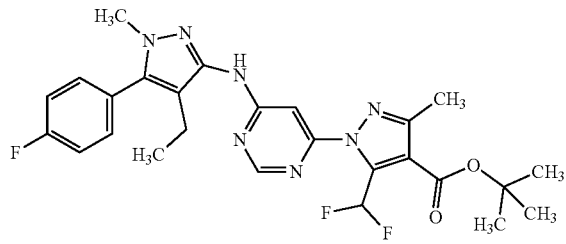 [SMILES: CCc1c(Nc2cc(-n3nc(C)c(C(=O)OC(C)(C)C)c3C(F)F)ncn2)nn(C)c1-c1ccc(F)cc1]

A round-bottom flask was charged with 4-ethyl-5-(4-fluorophenyl)-1-methyl-1H-pyrazol-3-amine (1.19 g, 5.42 mmol) and sodium phenolate (859 mg, 7.40 mmol) and the contents were suspended in 1,4-dioxane (12 mL). The reaction mixture was degassed with Ar for 3 min. Tris(dibenzylideneacetone)dipalladium (58.7 mg, 64.1 µmol), XantPhos (85.6 mg, 148 µmol) and tert-butyl 1-(6-chloropyrimidin-4-yl)-5-(difluoromethyl)-3-methyl-1H-pyrazole-4-carboxylate (1.70 g, 4.93 mmol) were added and the reaction mixture was degassed again for 1 min. The vial was sealed and heated at 90° C. overnight while vigorously stirring. After cooling to ambient temperature, the reaction mixture was filtered, concentrated and purified by flash column chromatography (Snap Ultra 50 g, gradient cyclohexane/ethyl acetate 95/5 to 50:50) to yield the desired product (490 mg, 19% yield).

LC-MS (method 10): $R_t$=2.52 min; MS (ESIpos): m/z=528 [M+H]$^+$ $^1$H-NMR (400 MHz, dimethylsulfoxide-d6) δ [ppm]: −0.008 (0.31), 0.008 (0.31), 0.875 (1.16), 0.894 (2.65), 0.913 (1.21), 1.398 (0.46), 1.503 (0.18), 1.539 (16.00), 1.560 (0.45), 2.298 (0.25), 2.316 (0.69), 2.334 (0.70), 2.353 (0.23), 2.524 (0.26), 2.874 (5.17), 3.639 (5.51), 7.099 (0.39), 7.233 (0.83), 7.355 (0.71), 7.360 (0.35), 7.367 (0.47), 7.377 (1.56), 7.399 (0.98), 7.421 (0.24), 7.501 (0.89), 7.506 (0.42), 7.514 (1.00), 7.522 (0.81), 7.531 (0.33), 7.536 (0.67), 8.579 (0.73), 9.701 (0.24).

Example 167

N-[4-ethyl-5-(4-fluorophenyl)-1-methyl-1H-pyrazol-3-yl]-6-(3-methyl-2H-pyrazolo[3,4-b]pyridin-2-yl)pyrimidin-4-amine

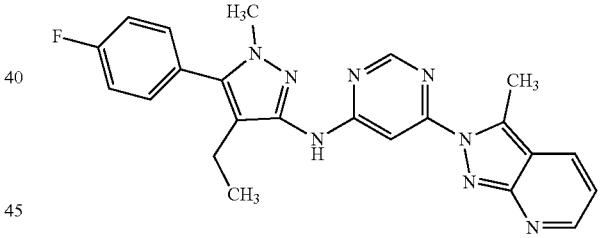

A microwave vial was charged with the mixture of 1-(6-chloropyrimidin-4-yl)-3-methyl-1H-pyrazolo[3,4-b]pyridine and 2-(6-chloropyrimidin-4-yl)-3-methyl-pyrazolo[3,4-b]pyridine (70:30, 185 mg, 753 µmol) and sodium phenolate (119 mg, 1.03 mmol) and the contents were suspended in 1,4-dioxane (2.0 mL). The reaction mixture was degassed with Ar for 3 min. Tris(dibenzylideneacetone)dipalladium (9.40 mg, 10.3 µmol), XantPhos (11.9 mg, 20.5 µmol) and 4-ethyl-5-(4-fluorophenyl)-1-methyl-1H-pyrazol-3-amine (150 mg, 684 µmol) were added and the reaction mixture was degassed again for 1 min. The vial was sealed and heated at 90° C. overnight while vigorously shaking. After cooling to ambient temperature, the reaction mixture was filtered, diluted with dimethylsulfoxide and purified by preparative HPLC (column: Chromatorex C18; 125*30 mm, 10 µM, flow 75 mL/min, gradient acetonitrile/water (containing 0.1% trifluoroacetic acid) 10/90 to 90/10) and further repurified by preparative HPLC (method 1) to yield the desired product (20 mg, 6% yield) along with the regioisomer (56 mg, 18% yield).

LC-MS (method 10): $R_t$=2.05 min; MS (ESIpos): m/z=429 [M+H]$^+$ $^1$H-NMR (400 MHz, dimethylsulfoxide-d6) δ [ppm]: −0.008 (0.77), 0.008 (0.66), 0.896 (3.29), 0.906 (1.22), 0.914 (7.58), 0.933 (3.37), 2.320 (0.86), 2.338 (2.37), 2.357 (2.25), 2.375 (0.73), 2.524 (0.61), 2.608 (1.35), 3.019 (15.78), 3.675 (16.00), 7.088 (1.56), 7.099 (1.53), 7.110 (1.57), 7.120 (1.65), 7.360 (1.91), 7.366 (0.76), 7.383 (4.27), 7.394 (0.73), 7.399 (0.93), 7.405 (2.64), 7.413 (0.48), 7.524 (0.57), 7.531 (2.48), 7.536 (1.13), 7.544 (2.70), 7.553 (2.18), 7.561 (0.89), 7.566 (1.86), 7.623 (2.10), 8.306 (1.76), 8.311 (1.83), 8.328 (1.73), 8.332 (1.72), 8.635 (2.32), 8.679 (1.81), 8.684 (1.76), 8.689 (1.85), 8.694 (1.62), 9.693 (1.71).

Example 168

N-[4-ethyl-5-(4-fluorophenyl)-1-methyl-1H-pyrazol-3-yl]-6-(3-methyl-1H-pyrazolo[3,4-c]pyridin-1-yl)pyrimidin-4-amine

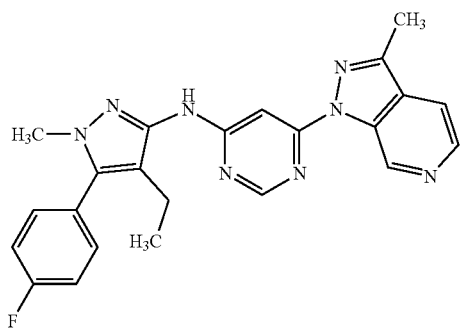 [SMILES: CCc1c(Nc2cc(-n3nc(C)c4ccncc43)ncn2)nn(C)c1-c1ccc(F)cc1]

A round bottom flask was charged with 1-(6-chloropyrimidin-4-yl)-3-methyl-1H-pyrazolo[3,4-c]pyridine (123 mg, 502 µmol) and sodium phenolate (79.4 mg, 684 µmol) and the contents were suspended in 1,4-dioxane (1.3 mL). The reaction mixture was degassed with Ar for 3 min. Tris(dibenzylideneacetone)dipalladium (6.26 mg, 6.84 µmol), XantPhos (7.92 mg, 13.7 µmol) and 4-ethyl-5-(4-fluorophenyl)-1-methyl-1H-pyrazol-3-amine (100 mg, 456 µmol) was added and the reaction mixture was degassed again for 1 min. The vial was sealed and heated at 90° C. overnight while vigorously stirring. After cooling to ambient temperature, the reaction mixture was filtered, diluted with dimethylsulfoxide and purified by preparative HPLC (method 7) to yield the desired product (38 mg, 17% yield).

LC-MS (method 10): $R_t$=2.09 min; MS (ESIpos): m/z=429 [M+H]$^+$ $^1$H-NMR (500 MHz, dimethylsulfoxide-d6) δ [ppm]: 0.91 (t, J=7.4 Hz, 3H), 2.35 (q, J=7.4 Hz, 2H), 2.63 (s, 3H), 3.69 (s, 3H), 7.34-7.46 (m, 2H), 7.46-7.60 (m, 3H), 7.90 (dd, J=5.36, 1.26 Hz, 1H), 8.47 (d, J=5.36 Hz, 1H), 8.61 (s, 1H), 9.48 (s, 1H), 10.08 (s, 1H).

Example 169

N-[1-(cyclopropylmethyl)-5-(4-fluorophenyl)-4-methyl-1H-pyrazol-3-yl]-6-(3,5-dimethyl-1H-pyrazol-1-yl)pyrimidin-4-amine

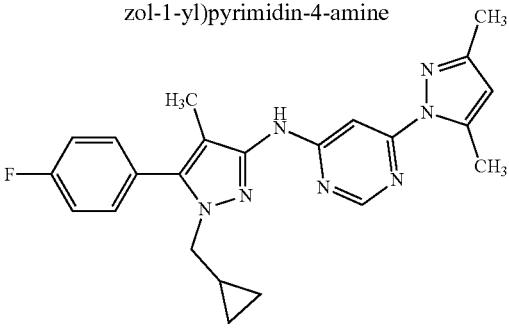

A microwave vial was charged 4-chloro-6-(3,5-dimethyl-1H-pyrazol-1-yl)pyrimidine (75.9 mg, 364 µmol), 1-(cyclopropylmethyl)-5-(4-fluorophenyl)-4-methyl-1H-pyrazol-3-amine (98.1 mg, 400 µmol) and sodium phenolate (63.3 mg, 545 µmol) and the contents were suspended in 1,4-dioxane (2.0 ml, 23 mmol). The reaction mixture was degassed with Ar for 3 min. Tris(dibenzylidenaceton)dipalladium (4.33 mg, 4.73 µmol) and Xantphos (6.31 mg, 10.9 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over Extrelut NT3 and concentrated under reduced pressure. The crude product was purified by preparative HPLC (method 8) to yield the desired product (551. mg, 36%).

LC-MS (method 10): $R_t$=2.58 min; MS (ESIpos): m/z=418 [M+H]$^+$ $^1$H-NMR (400 MHz, dimethylsulfoxide-d6) δ [ppm]: 0.213 (3.62), 0.224 (3.79), 0.432 (3.59), 0.452 (3.63), 0.464 (0.83), 1.028 (0.45), 1.046 (0.87), 1.058 (1.19), 1.070 (0.82), 1.076 (0.82), 1.856 (14.80), 2.173 (15.76), 2.631 (16.00), 3.166 (0.41), 3.179 (0.42), 3.807 (5.14), 3.824 (5.07), 6.127 (4.26), 7.356 (1.96), 7.378 (4.75), 7.400 (3.07), 7.480 (2.87), 7.497 (3.45), 7.514 (2.21), 7.665 (0.71), 8.464 (4.15), 9.453 (4.70).

Example 170

6-(4-chloro-3,5-dimethyl-1H-pyrazol-1-yl)-N-[1-(cyclopropylmethyl)-5-(4-fluorophenyl)-4-methyl-1H-pyrazol-3-yl]pyrimidin-4-amine

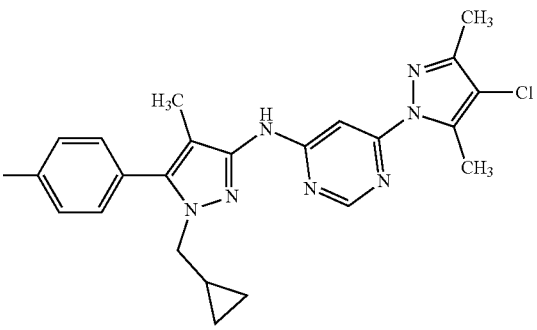

A microwave vial was charged 4-chloro-6-(4-chloro-3,5-dimethyl-1H-pyrazol-1-yl)pyrimidine (88.4 mg, 364 µmol), 1-(cyclopropylmethyl)-5-(4-fluorophenyl)-4-methyl-1H-pyrazol-3-amine (98.1 mg, 400 µmol) and sodium phenolate (63.3 mg, 545 µmol) and the contents were suspended in 1,4-dioxane (2.0 ml, 23 mmol). The reaction mixture was degassed with Ar for 3 min. Tris(dibenzylidenaceton)dipalladium (4.33 mg, 4.73 µmol) and Xantphos (6.31 mg, 10.9 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over Extrelut NT3 and concentrated under reduced pressure. The crude product was purified by preparative HPLC (method 8) to yield the desired product (44.7 mg, 27%).

LC-MS (method 9): $R_t$=1.38 min; MS (ESIpos): m/z=452 [M+H]$^+$ $^1$H-NMR (400 MHz, dimethylsulfoxide-d6) δ [ppm]: 0.216 (2.25), 0.228 (2.38), 0.420 (0.82), 0.434 (2.41), 0.450 (2.43), 0.466 (0.69), 1.036 (0.62), 1.042 (0.59), 1.054 (0.92), 1.074 (1.51), 1.091 (2.14), 1.109 (1.00), 1.856 (10.75), 2.210 (14.48), 2.229 (0.53), 2.650 (16.00), 2.671 (0.69), 3.375 (1.02), 3.392 (0.97), 3.805 (4.22), 3.822 (4.18), 7.356 (1.91), 7.378 (4.46), 7.400 (2.89), 7.478 (2.78), 7.492 (3.03), 7.500 (2.54), 7.513 (1.96), 8.499 (3.75), 9.580 (2.82).

Example 171

N-[1-(cyclopropylmethyl)-3-(4-fluorophenyl)-4-methyl-1H-pyrazol-5-yl]-6-(3,5-dimethyl-1H-pyrazol-1-yl)pyrimidin-4-amine

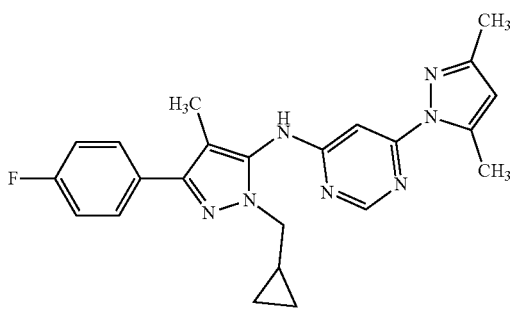 [SMILES: Cc1cc(C)n(-c2cc(Nc3c(C)c(-c4ccc(F)cc4)nn3CC3CC3)ncn2)n1]

A microwave vial was charged 4-chloro-6-(3,5-dimethyl-1H-pyrazol-1-yl)pyrimidine (75.0 mg, 359 µmol), 1-(cyclopropylmethyl)-3-(4-fluorophenyl)-4-methyl-1H-pyrazol-5-amine (97.0 mg, 395 µmol) and sodium phenolate (62.6 mg, 539 µmol) and the contents were suspended in 1,4-dioxane (1.5 ml, 18 mmol). The reaction mixture was degassed with Ar for 3 min. Tris(dibenzylidenaceton)dipalladium (4.28 mg, 4.67 µmol) and Xantphos (6.24 mg, 10.8 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over Extrelut NT3 and concentrated under reduced pressure. The crude product was purified by preparative HPLC (method 8) to yield the desired product (33.0 mg, 20%).

LC-MS (method 10): $R_t$=2.26 min; MS (ESIpos): m/z=418 [M+H]$^+$ $^1$H-NMR (400 MHz, dimethylsulfoxide-d6) δ [ppm]: −0.008 (1.41), 0.008 (1.27), 0.293 (2.60), 0.305 (2.86), 0.422 (2.63), 0.442 (2.79), 1.178 (0.71), 1.185 (0.70), 1.197 (1.08), 1.209 (0.66), 1.216 (0.67), 2.009 (16.00), 2.168 (3.50), 2.188 (2.00), 2.629 (15.78), 2.654 (1.04), 3.826 (2.61), 3.844 (2.58), 6.141 (3.06), 7.252 (2.74), 7.274 (5.22), 7.297 (2.76), 7.383 (0.45), 7.716 (1.62), 7.731 (2.15), 7.736 (2.10), 7.751 (1.58), 8.462 (0.78), 9.371 (0.79).

Example 172

6-[4-chloro-5-(difluoromethyl)-3-methyl-1H-pyrazol-1-yl]-N-[1-(2,2-difluoroethyl)-4-ethyl-5-(4-fluorophenyl)-1H-pyrazol-3-yl]pyrimidin-4-amine

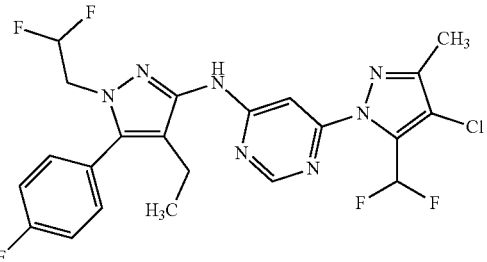

A microwave vial was charged 4-chloro-6-[4-chloro-5-(difluoromethyl)-3-methyl-1H-pyrazol-1-yl]pyrimidine (94.2 mg, 338 µmol), 1-(2,2-difluoroethyl)-4-ethyl-5-(4-fluorophenyl)-1H-pyrazol-3-amine (100 mg, 371 µmol) and sodium phenolate (58.8 mg, 506 µmol) and the contents were suspended in 1,4-dioxane (2.4 ml, 28 mmol). The reaction mixture was degassed with Ar for 3 min. Tris(dibenzylidenaceton)dipalladium (4.02 mg, 4.39 µmol) and Xantphos (5.86 mg, 10.1 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 5) to yield the desired product (82.0 mg, 43%).

LC-MS (method 9): $R_t$=1.30 min; MS (ESIpos): m/z=512 [M+H]$^+$ $^1$H-NMR (400 MHz, dimethylsulfoxide-d6) δ [ppm]: −0.008 (1.66), 0.008 (1.10), 0.864 (4.01), 0.883 (8.88), 0.902 (3.94), 2.277 (16.00), 2.308 (2.57), 2.327 (2.66), 2.345 (0.88), 2.367 (0.41), 2.519 (1.71), 2.524 (1.63), 4.306 (1.11), 4.316 (1.20), 4.343 (2.25), 4.352 (2.20), 4.379 (1.11), 4.389 (0.99), 6.150 (0.75), 6.278 (0.74), 6.287 (1.57), 6.296 (0.71), 6.424 (0.69), 7.375 (2.15), 7.380 (0.95), 7.397 (5.20), 7.414 (1.15), 7.419 (3.34), 7.466 (3.28), 7.472 (1.53), 7.480 (3.63), 7.488 (2.50), 7.496 (1.08), 7.502 (2.02), 7.548 (0.54), 7.907 (1.41), 8.038 (3.12), 8.170 (1.26), 8.525 (2.96), 9.803 (1.70).

Example 173

N-[1-(2,2-difluoroethyl)-4-ethyl-5-(4-fluorophenyl)-1H-pyrazol-3-yl]-6-(3,5-dimethyl-1H-pyrazol-1-yl)pyrimidin-4-amine

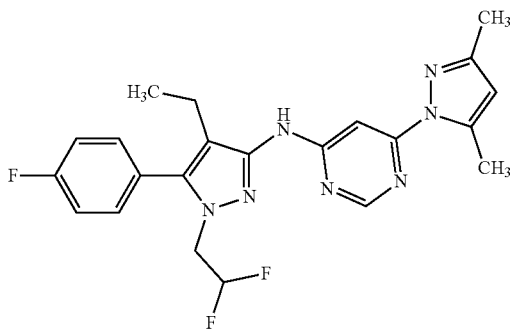 [SMILES: CCc1c(Nc2cc(-n3nc(C)cc3C)ncn2)nn(CC(F)F)c1-c1ccc(F)cc1]

A microwave vial was charged 4-chloro-6-(3,5-dimethyl-1H-pyrazol-1-yl)pyrimidine (70.4 mg, 338 µmol), 1-(2,2-difluoroethyl)-4-ethyl-5-(4-fluorophenyl)-1H-pyrazol-3-amine (100 mg, 371 µmol) and sodium phenolate (58.8 mg, 506 µmol) and the contents were suspended in 1,4-dioxane (3.8 ml, 45 mmol). The reaction mixture was degassed with Ar for 3 min. Tris(dibenzylidenaceton)dipalladium (4.02 mg, 4.39 µmol) and Xantphos (5.86 mg, 10.1 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 4) to yield the desired product (40.0 mg, 27%).

LC-MS (method 9): $R_t$=1.18 min; MS (ESIpos): m/z=442 [M+H]$^+$ $^1$H-NMR (400 MHz, dimethylsulfoxide-d6) δ [ppm]: 0.865 (4.13), 0.884 (8.87), 0.902 (4.25), 2.178 (15.81), 2.283 (1.23), 2.301 (3.58), 2.320 (3.55), 2.338 (1.22), 2.625 (16.00), 4.296 (1.30), 4.305 (1.38), 4.333 (2.65), 4.342 (2.63), 4.369 (1.37), 4.378 (1.25), 6.132 (4.28), 6.147 (0.48), 6.157 (0.82), 6.285 (0.80), 6.294 (1.60), 6.303 (0.79), 6.432 (0.76), 7.373 (1.81), 7.395 (4.43), 7.417 (2.85), 7.462 (3.30), 7.477 (5.09), 7.482 (5.10), 7.496 (2.28), 8.463 (4.38), 9.484 (4.34).

Example 174

6-(4-chloro-3,5-dimethyl-1H-pyrazol-1-yl)-N-[1-(2,2-difluoroethyl)-4-ethyl-5-(4-fluorophenyl)-1H-pyrazol-3-yl]pyrimidin-4-amine

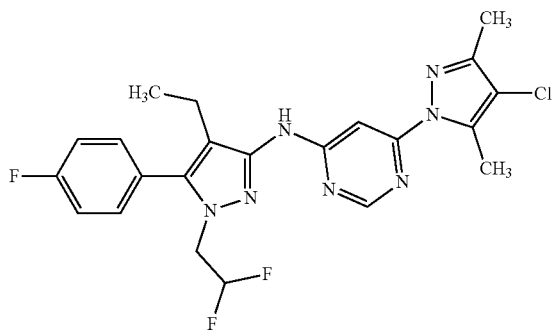 [SMILES: CCc1c(Nc2cc(-n3nc(C)c(Cl)c3C)ncn2)nn(CC(F)F)c1-c1ccc(F)cc1]

A microwave vial was charged 4-chloro-6-(4-chloro-3,5-dimethyl-1H-pyrazol-1-yl)pyrimidine (82.1 mg, 338 µmol), 1-(2,2-difluoroethyl)-4-ethyl-5-(4-fluorophenyl)-1H-pyrazol-3-amine (100 mg, 371 µmol) and sodium phenolate (58.8 mg, 506 µmol) and the contents were suspended in 1,4-dioxane (2.4 ml, 28 mmol). The reaction mixture was degassed with Ar for 3 min. Tris(dibenzylidenaceton)dipalladium (4.02 mg, 4.39 µmol) and Xantphos (5.86 mg, 10.1 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 5) to yield the desired product (57.0 mg, 32%).

LC-MS (method 9): $R_t$=1.32 min; MS (ESIpos): m/z=476 [M+H]$^+$ $^1$H-NMR (400 MHz, dimethylsulfoxide-d6) δ [ppm]: 0.865 (3.58), 0.884 (8.04), 0.902 (3.74), 2.074 (0.91), 2.215 (15.14), 2.229 (1.33), 2.288 (0.97), 2.306 (2.78), 2.325 (2.80), 2.343 (0.89), 2.644 (16.00), 2.670 (1.17), 4.299 (1.06), 4.308 (1.14), 4.336 (2.16), 4.345 (2.19), 4.372 (1.10), 4.381 (1.01), 6.153 (0.70), 6.281 (0.67), 6.290 (1.41), 6.299 (0.68), 6.428 (0.66), 7.374 (1.75), 7.396 (4.45), 7.418 (2.89), 7.463 (2.91), 7.477 (3.37), 7.484 (2.68), 7.499 (2.20), 7.513 (1.28), 8.502 (4.11), 9.609 (2.90).

Example 175

6-(4-chloro-3,5-dimethyl-1H-pyrazol-1-yl)-N-[1-(cyclopropylmethyl)-3-(4-fluorophenyl)-4-methyl-1H-pyrazol-5-yl]pyrimidin-4-amine

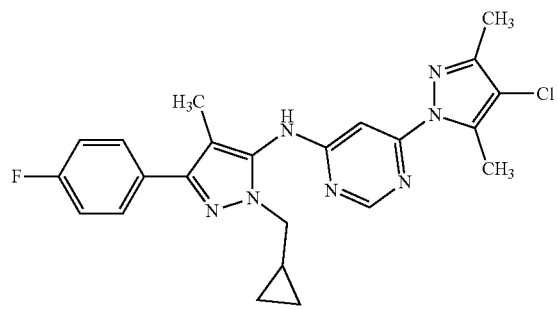 [SMILES: Cc1nn(-c2cc(Nc3c(C)c(-c4ccc(F)cc4)nn3CC3CC3)ncn2)c(C)c1Cl]

A microwave vial was charged 4-chloro-6-(4-chloro-3,5-dimethyl-1H-pyrazol-1-yl)pyrimidine (100 mg, 411 µmol), 1-(cyclopropylmethyl)-3-(4-fluorophenyl)-4-methyl-1H-pyrazol-5-amine (111 mg, 452 µmol) and sodium phenolate (71.6 mg, 617 µmol) and the contents were suspended in 1,4-dioxane (2.0 ml, 23 mmol). The reaction mixture was degassed with Ar for 3 min. Tris(dibenzylidenaceton)dipalladium (4.90 mg, 5.35 µmol) and Xantphos (7.14 mg, 12.3 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 8) and subsequently by flash chromatography on silica gel (dichloromethane/ethyl acetate, Biotage, SNAP KP-Sil 10 g) to yield the desired product (66.3 mg, 35%).

LC-MS (method 10): R$_t$=2.76 min; MS (ESIpos): m/z=452 [M+H]$^+$ $^1$H-NMR (400 MHz, dimethylsulfoxide-d6) δ [ppm]: 0.291 (2.59), 0.302 (2.80), 0.422 (2.64), 0.442 (2.80), 1.175 (0.72), 1.182 (0.68), 1.194 (1.05), 1.205 (0.65), 1.212 (0.68), 2.007 (15.14), 2.207 (2.73), 2.646 (16.00), 3.164 (5.16), 3.177 (5.32), 3.827 (2.48), 3.844 (2.43), 4.064 (0.60), 4.077 (1.73), 4.090 (1.69), 4.104 (0.56), 7.252 (2.09), 7.274 (4.21), 7.296 (2.29), 7.715 (1.54), 7.729 (2.07), 7.749 (1.43), 8.498 (0.53), 9.470 (0.46).

Example 176

6-[4-chloro-5-(difluoromethyl)-3-methyl-1H-pyrazol-1-yl]-N-[1-(cyclopropylmethyl)-3-(4-fluorophenyl)-4-methyl-1H-pyrazol-5-yl]pyrimidin-4-amine

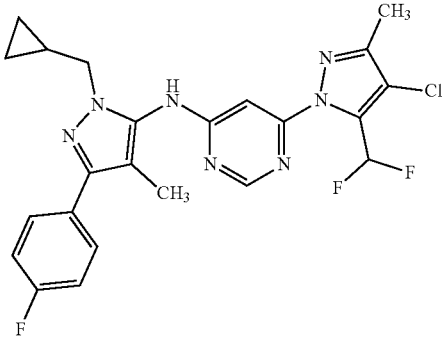 [SMILES: Cc1nn(-c2cc(Nc3c(C)c(-c4ccc(F)cc4)nn3CC3CC3)ncn2)c(C(F)F)c1Cl]

A microwave vial was charged 4-chloro-6-[4-chloro-5-(difluoromethyl)-3-methyl-1H-pyrazol-1-yl]pyrimidine (100 mg, 358 µmol), 1-(cyclopropylmethyl)-3-(4-fluorophenyl)-4-methyl-1H-pyrazol-5-amine (96.7 mg, 394 µmol) and sodium phenolate (62.4 mg, 537 µmol) and the contents were suspended in 1,4-dioxane (2.0 ml, 23 mmol). The reaction mixture was degassed with Ar for 3 min. Tris (dibenzylidenaceton)dipalladium (4.27 mg, 4.66 µmol) and Xantphos (6.22 mg, 10.7 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over Extrelut NT3 and concentrated under reduced pressure. The crude product was purified by preparative HPLC (method 8) to yield the desired product (20.0 mg, 10%).

LC-MS (method 10): R$_t$=2.46 min; MS (ESIpos): m/z=488 [M+H]$^+$ $^1$H-NMR (400 MHz, dimethylsulfoxide-d6) δ [ppm]: 0.290 (2.86), 0.301 (3.02), 0.425 (3.09), 0.445 (3.21), 1.161 (0.46), 1.173 (0.86), 1.180 (0.83), 1.192 (1.23), 1.204 (0.77), 1.211 (0.81), 1.223 (0.43), 2.010 (16.00), 2.296 (5.48), 3.832 (2.23), 3.847 (2.21), 7.255 (2.20), 7.277 (4.56), 7.298 (3.73), 7.327 (0.43), 7.346 (0.70), 7.366 (0.53), 7.493 (0.79), 7.512 (1.14), 7.532 (0.55), 7.733 (2.11), 7.863 (0.40), 7.904 (1.38), 7.994 (0.76), 8.036 (2.76), 8.167 (1.27), 8.749 (1.16).

Example 177 ethyl 1-(6-{[1-(2,2-difluoroethyl)-4-ethyl-5-(4-fluorophenyl)-1H-pyrazol-3-yl]amino}pyrimidin-4-yl)-3,5-dimethyl-1H-pyrazole-4-carboxylate

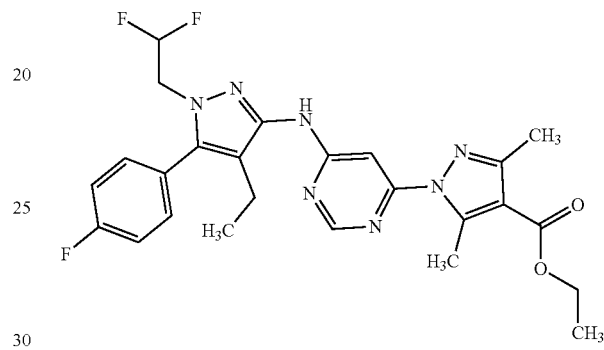

A microwave vial was charged ethyl 1-(6-chloropyrimidin-4-yl)-3,5-dimethyl-1H-pyrazole-4-carboxylate (94.8 mg, 338 µmol), 1-(2,2-difluoroethyl)-4-ethyl-5-(4-fluorophenyl)-1H-pyrazol-3-amine (100 mg, 371 µmol) and sodium phenolate (58.8 mg, 506 µmol) and the contents were suspended in 1,4-dioxane (2.4 ml, 28 mmol). The reaction mixture was degassed with Ar for 3 min. Tris (dibenzylidenaceton)dipalladium (4.02 mg, 4.39 µmol) and Xantphos (5.86 mg, 10.1 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 8) and subsequent flash chromatography on silica gel (cyclohexane/ethyl acetate 3:1) to yield the desired product (25.0 mg, 14%).

LC-MS (method 10): R$_t$=2.43 min; MS (ESIpos): m/z=514 [M+H]$^+$ $^1$H-NMR (400 MHz, dimethylsulfoxide-d6) δ [ppm]: 0.870 (3.77), 0.888 (8.24), 0.907 (3.93), 1.074 (0.69), 1.091 (1.39), 1.109 (0.71), 1.290 (4.26), 1.308 (8.80), 1.326 (4.37), 2.295 (1.01), 2.313 (2.86), 2.332 (2.92), 2.351 (1.02), 2.376 (15.00), 2.899 (16.00), 3.375 (0.70), 3.392 (0.70), 4.230 (1.33), 4.248 (4.06), 4.266 (4.03), 4.284 (1.37), 4.297 (1.18), 4.307 (1.24), 4.334 (2.32), 4.343 (2.34), 4.370 (1.19), 4.379 (1.09), 6.150 (0.73), 6.279 (0.71), 6.288 (1.48), 6.297 (0.73), 6.425 (0.69), 7.374 (1.74), 7.396 (4.42), 7.418 (2.89), 7.464 (2.93), 7.477 (3.40), 7.484 (2.58), 7.499 (1.91), 7.543 (0.96), 8.550 (3.71), 9.701 (2.49).

Example 178 ethyl 4-chloro-1-(6-{[4-ethyl-5-(4-fluorophenyl)-1-methyl-1H-pyrazol-3-yl]amino}pyrimidin-4-yl)-3-methyl-1H-pyrazole-5-carboxylate

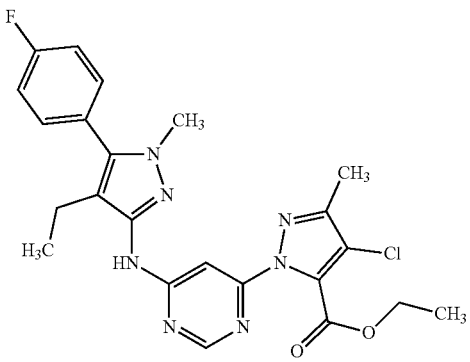 [SMILES: CCOC(=O)c1c(Cl)c(C)nn1-c1cc(Nc2nn(C)c(-c3ccc(F)cc3)c2CC)ncn1]

A microwave vial was charged ethyl 4-chloro-1-(6-chloropyrimidin-4-yl)-3-methyl-1H-pyrazole-5-carboxylate (340 mg, 1.13 mmol), 4-ethyl-5-(4-fluorophenyl)-1-methyl-1H-pyrazol-3-amine (272 mg, 1.24 mmol) and sodium phenolate (197 mg, 1.69 mmol) and the contents were suspended in 1,4-dioxane (10 ml, 120 mmol). The reaction mixture was degassed with Ar for 3 min. Tris(dibenzylidenaceton)dipalladium (13.4 mg, 14.7 µmol) and Xantphos (19.6 mg, 33.9 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method 4) and subsequently by flash chromatography on silica gel (cyclohexane/ethyl acetate 2:1) to yield the desired product (90.0 mg, 16%).

LC-MS (method 10): $R_t$=2.39 min; MS (ESIpos): m/z=484 [M+H]$^+$ $^1$H-NMR (400 MHz, dimethylsulfoxide-d6) δ [ppm]: 0.870 (3.65), 0.888 (7.93), 0.907 (3.60), 1.227 (4.94), 1.245 (10.13), 1.263 (4.88), 2.258 (0.69), 2.278 (15.19), 2.294 (1.12), 2.312 (2.42), 2.331 (2.48), 2.350 (0.76), 2.524 (1.25), 3.658 (16.00), 4.322 (1.60), 4.339 (4.83), 4.357 (4.76), 4.375 (1.47), 7.313 (1.11), 7.359 (2.08), 7.381 (4.59), 7.403 (2.72), 7.505 (2.74), 7.519 (3.04), 7.526 (2.51), 7.540 (2.01), 8.420 (2.91), 9.670 (1.25).

Example 179

6-[4-chloro-5-(difluoromethyl)-3-methyl-1H-pyrazol-1-yl]-N-[1-(2,2-difluoroethyl)-4-ethyl-3-(4-fluorophenyl)-1H-pyrazol-5-yl]pyrimidin-4-amine

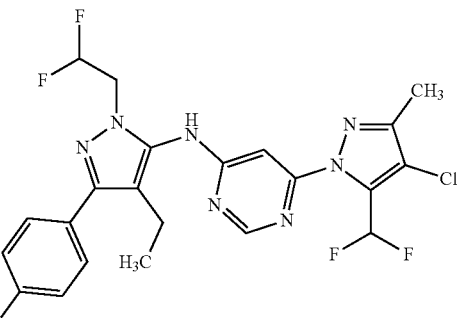

A microwave vial was charged 4-chloro-6-[4-chloro-5-(difluoromethyl)-3-methyl-1H-pyrazol-1-yl]pyrimidine (94.2 mg, 338 µmol), 1-(2,2-difluoroethyl)-4-ethyl-3-(4-fluorophenyl)-1H-pyrazol-5-amine (100 mg, 371 µmol) and sodium phenolate (58.8 mg, 506 µmol) and the contents were suspended in 1,4-dioxane (2.4 ml, 28 mmol). The reaction mixture was degassed with Ar for 3 min. Tris (dibenzylidenaceton)dipalladium (4.02 mg, 4.39 µmol) and Xantphos (5.86 mg, 10.1 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (35.0 mg, 20%).

LC-MS (method 10): $R_t$=2.44 min; MS (ESIpos): m/z=512 [M+H]$^+$ $^1$H-NMR (400 MHz, dimethylsulfoxide-d6) δ [ppm]: −0.008 (5.69), 0.008 (3.54), 0.146 (0.42), 0.956 (7.47), 0.975 (16.00), 0.994 (7.34), 1.073 (1.02), 1.091 (1.97), 1.108 (1.02), 1.234 (0.64), 1.356 (1.66), 2.284 (4.46), 2.327 (1.17), 2.366 (0.87), 2.448 (2.06), 2.466 (7.00), 2.524 (4.29), 2.670 (0.76), 2.686 (0.42), 2.710 (0.76), 3.357 (0.53), 3.375 (1.08), 3.392 (1.04), 4.437 (1.89), 6.205 (0.64), 6.215 (1.21), 6.343 (1.25), 6.353 (2.44), 6.362 (1.17), 6.490 (1.17), 6.499 (0.64), 7.274 (4.01), 7.296 (7.81), 7.318 (4.24), 7.675 (2.72), 7.689 (3.54), 7.709 (2.31), 7.910 (2.53), 8.041 (4.99), 8.173 (2.23), 8.521 (1.08), 9.654 (1.15).

Example 180 ethyl 1-(6-{[1-(2,2-difluoroethyl)-4-ethyl-3-(4-fluorophenyl)-1H-pyrazol-5-yl]amino}pyrimidin-4-yl)-3,5-dimethyl-1H-pyrazole-4-carboxylate

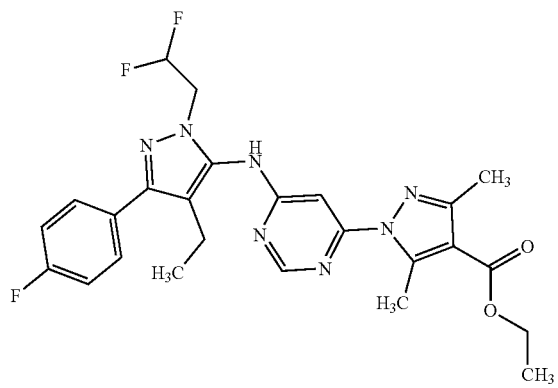 [SMILES: CCOC(=O)c1c(C)nn(-c2cc(Nc3c(CC)c(-c4ccc(F)cc4)nn3CC(F)F)ncn2)c1C]

A microwave vial was charged ethyl 1-(6-chloropyrimidin-4-yl)-3,5-dimethyl-1H-pyrazole-4-carboxylate (94.8 mg, 338 µmol), 1-(2,2-difluoroethyl)-4-ethyl-3-(4-fluorophenyl)-1H-pyrazol-5-amine (100 mg, 371 µmol) and sodium phenolate (58.8 mg, 506 µmol) and the contents were suspended in 1,4-dioxane (2.4 ml, 28 mmol). The reaction mixture was degassed with Ar for 3 min. Tris(dibenzylidenaceton)dipalladium (4.02 mg, 4.39 µmol) and Xantphos (5.86 mg, 10.1 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The crude product was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (85.0 mg, 49%).

LC-MS (method 10): $R_t$=2.38 min; MS (ESIpos): m/z=514 [M+H]$^+$ $^1$H-NMR (400 MHz, dimethylsulfoxide-d6) δ [ppm]: −0.008 (3.10), 0.008 (2.60), 0.961 (4.24), 0.979 (9.40), 0.998 (4.37), 1.291 (4.40), 1.308 (9.07), 1.326 (4.46), 2.073 (1.71), 2.328 (0.71), 2.382 (3.51), 2.450 (1.11), 2.469 (3.01), 2.524 (1.73), 2.670 (0.55), 2.710 (0.46), 2.917 (16.00), 4.232 (1.28), 4.250 (4.00), 4.268 (3.96), 4.285 (1.30), 4.404 (0.70), 4.437 (1.31), 4.471 (0.71), 6.215 (0.79), 6.343 (0.73), 6.353 (1.57), 6.362 (0.74), 6.490 (0.74), 7.271 (2.56), 7.293 (5.29), 7.316 (2.93), 7.672 (1.91), 7.686 (2.39), 7.693 (2.31), 7.707 (1.79), 8.539 (0.93), 9.562 (1.16).

Example 181

2-[1-(6-{[4-ethyl-5-(4-fluorophenyl)-1H-pyrazol-3-yl]amino}pyrimidin-4-yl)-3,5-dimethyl-1H-pyrazol-4-yl]propan-2-ol

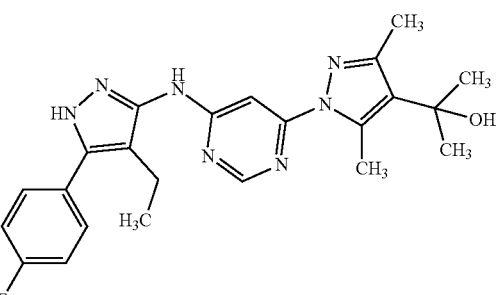

A solution of ethyl 1-(6-{[4-ethyl-5-(4-fluorophenyl)-1H-pyrazol-3-yl]amino}pyrimidin-4-yl)-3,5-dimethyl-1H-pyrazole-4-carboxylate (187 mg, 416 µmol) in tetrahydrofuran (5.6 ml) was treated with bromo(methyl)magnesium (1.9 ml, 1.0 M in tetrahydrofurane, 1.9 mmol) at 0° C. The mixture was stirred for 2 h at 0° C. No conversion was observed. The mixture was allowed to warm to ambient temperature and additional 4.5 eq of bromo(methyl)magnesium (1.87 mL, 1.87 mmol, 1.0 M in tetrahydrofuran) were added. The mixture was stirred 2 days at ambient temperature. Additional 4.5 eq bromo(methyl)magnesium (0.62 mL, 1.87 mmol, 3 M in diethyl ether) were added and stirring was extended for 4 days. The mixture was diluted with saturated ammonium chloride solution and extracted with ethyl acetate. The combined organic phases were dried over magnesium sulfate and the solvent was removed under reduced pressure. The crude product was purified by preparative HPLC (method: column: Reprosil C18; 10 µm; 125×30 mm/flow: 20 mL/min/solvent: A=water (0.1% formic acid), B=acetonitrile) to obtain 26.7 mg of the desired product (14%).

LC-MS (method 10): $R_t$=1.76 min; MS (ESIpos): m/z=436 [M+H]$^+$ $^1$H-NMR (400 MHz, dimethylsulfoxide-d6) δ [ppm]: −0.008 (1.36), 0.008 (1.23), 0.995 (1.54), 1.013 (3.40), 1.032 (1.59), 1.466 (16.00), 2.073 (1.62), 2.259 (5.60), 2.562 (0.55), 2.722 (4.32), 4.837 (1.85), 7.334 (0.66), 7.356 (0.91), 7.378 (0.52), 7.604 (0.78), 8.454 (0.76), 9.325 (0.62), 12.792 (0.76).

Example 182

N-[1-(cyclobutylmethyl)-4-ethyl-3-(4-fluorophenyl)-1H-pyrazol-5-yl]-6-(3,5-dimethyl-1H-pyrazol-1-yl)pyrimidin-4-amine

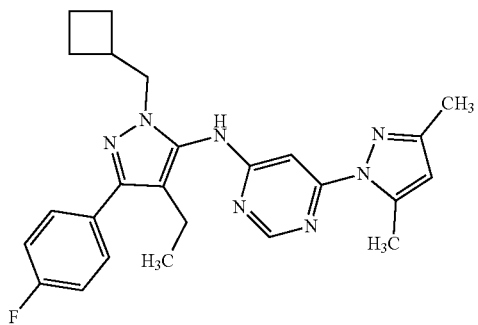 [SMILES: CCc1c(-c2ccc(F)cc2)nn(CC2CCC2)c1Nc1cc(-n2nc(C)cc2C)ncn1]

A microwave vial was charged 4-chloro-6-(3,5-dimethyl-1H-pyrazol-1-yl)pyrimidine (31.2 mg, 150 mol), 1-(cyclobutylmethyl)-4-ethyl-3-(4-fluorophenyl)-1H-pyrazol-5-amine (50.0 mg, 90% purity, 165 mol) and sodium phenolate (26.1 mg, 224 µmol) and the contents were suspended in 1,4-dioxane (1.5 ml, 18 mmol). The reaction mixture was degassed with Ar for 3 min. Tris(dibenzylidenaceton)dipalladium (1.78 mg, 1.95 µmol) and Xantphos (2.60 mg, 4.49 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were filtered over an Extrelut column, the solution was concentrated under reduced pressure and the crude product was purified by flash chromatography (method: column: Biotage KP-Sil 10 g; solvent A: dichloromethane (91%) solvent B: ethyl acetate (9%)) to yield the desired product (19.7 mg, 28%).

LC-MS (method 11): $R_t$=1.63 min; MS (ESIpos): m/z=446 [M+H]$^+$ $^1$H-NMR (400 MHz, dimethylsulfoxide-d6) δ [ppm]: −0.149 (1.58), −0.008 (13.80), 0.008 (11.10), 0.146 (1.52), 0.859 (0.45), 0.958 (4.11), 0.977 (8.90), 0.995 (4.23), 1.766 (4.23), 1.791 (1.63), 1.953 (1.80), 2.167 (2.59), 2.210 (2.03), 2.327 (1.52), 2.332 (1.13), 2.366 (2.08), 2.446 (2.14), 2.465 (2.37), 2.519 (6.31), 2.524 (5.35), 2.559 (1.35), 2.561 (1.13), 2.567 (1.01), 2.575 (0.73), 2.632 (16.00), 2.665 (1.35), 2.670 (1.63), 2.674 (1.41), 2.695 (1.92), 2.710 (2.31), 2.724 (0.96), 2.743 (1.13), 2.761 (0.90), 3.939 (1.92), 3.955 (1.86), 6.144 (2.48), 7.245 (2.42), 7.267 (5.01), 7.289 (2.70), 7.670 (2.03), 7.758 (0.56), 8.458 (0.73), 8.881 (0.45), 9.330 (0.62).

Example 183

N-[4-chloro-1-(cyclopropylmethyl)-5-(4-fluorophenyl)-1H-pyrazol-3-yl]-6-(4-chloro-3,5-dimethyl-1H-pyrazol-1-yl)pyrimidin-4-amine

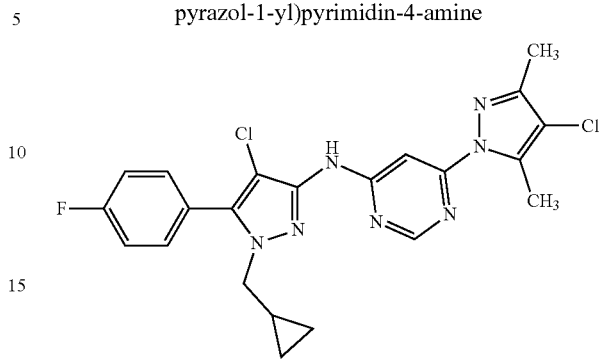

A microwave vial was charged 4-chloro-6-(4-chloro-3,5-dimethyl-1H-pyrazol-1-yl)pyrimidine (62.4 mg, 257 µmol), 4-chloro-1-(cyclopropylmethyl)-5-(4-fluorophenyl)-1H-pyrazol-3-amine (75.0 mg, 282 µmol) and sodium phenolate (44.7 mg, 385 µmol) and the contents were suspended in 1,4-dioxane (1.5 ml, 18 mmol). The reaction mixture was degassed with Ar for 3 min. Tris(dibenzylidenaceton)dipalladium (3.05 mg, 3.34 µmol) and Xantphos (4.45 mg, 7.70 µmol) were added and the reaction mixture was degassed again for 1 min. The vial was sealed and heated at 85° C. overnight while vigorously stirring. After cooling to ambient temperature, the reaction mixture purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (31.1 mg, 26%).

LC-MS (method 10): Rt=2.83 min; MS (ESIpos): m/z=472 [M+H]$^+$ $^1$H-NMR (400 MHz, dimethylsulfoxide-d6) δ [ppm]: 0.205 (0.70), 0.218 (3.02), 0.230 (3.29), 0.242 (0.92), 0.444 (0.88), 0.458 (2.81), 0.477 (2.87), 0.490 (0.81), 1.067 (0.71), 1.073 (0.67), 1.086 (1.04), 1.097 (0.66), 1.105 (0.69), 2.217 (15.17), 2.652 (16.00), 3.163 (0.58), 3.176 (0.60), 3.893 (4.82), 3.911 (4.78), 7.407 (2.10), 7.429 (4.68), 7.451 (2.75), 7.504 (1.47), 7.586 (2.68), 7.599 (3.00), 7.607 (2.75), 7.621 (2.22), 8.527 (4.17), 9.719 (3.86).

Example 184

N-[4-chloro-1-(cyclopropylmethyl)-5-(4-fluorophenyl)-1H-pyrazol-3-yl]-6-[4-chloro-5-(difluoromethyl)-3-methyl-1H-pyrazol-1-yl]pyrimidin-4-amine

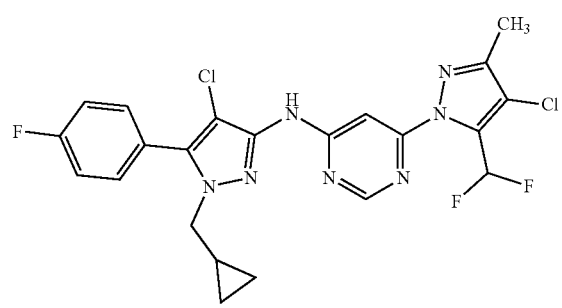 [SMILES: Cc1nn(-c2cc(Nc3nn(CC4CC4)c(-c4ccc(F)cc4)c3Cl)ncn2)c(C(F)F)c1Cl]

A microwave vial was charged 4-chloro-6-[4-chloro-5-(difluoromethyl)-3-methyl-1H-pyrazol-1-yl]pyrimidine (101 mg, 364 µmol), 4-chloro-1-(cyclopropylmethyl)-5-(4-fluorophenyl)-1H-pyrazol-3-amine (106 mg, 400 µmol) and sodium phenolate (63.3 mg, 545 µmol) and the contents were suspended in 1,4-dioxane (2.0 ml, 23 mmol). The reaction mixture was degassed with Ar for 3 min. Tris(dibenzylideneaceton)dipalladium (4.33 mg, 4.73 µmol) and Xantphos (6.31 mg, 10.9 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2x). The combined organic phases were dried over Extrelut NT3 and concentrated under reduced pressure. The crude product was purified by preparative HPLC (method 8) to yield the desired product (22.2 mg, 12%).

LC-MS (method 10): $R_t$=2.74 min; MS (ESIpos): m/z=508 [M+H]$^+$ $^1$H-NMR (400 MHz, dimethylsulfoxide-d6) δ [ppm]: −0.149 (0.88), −0.008 (11.34), 0.008 (6.94), 0.146 (0.85), 0.220 (2.48), 0.231 (2.54), 0.449 (0.95), 0.459 (2.48), 0.463 (2.48), 0.479 (2.51), 0.495 (0.72), 1.087 (1.11), 1.646 (0.42), 2.280 (16.00), 2.327 (1.24), 2.366 (1.14), 2.523 (5.83), 2.670 (1.40), 2.710 (1.24), 3.898 (4.76), 3.916 (4.56), 7.409 (2.54), 7.431 (5.38), 7.453 (3.10), 7.525 (0.72), 7.589 (3.00), 7.603 (3.29), 7.611 (2.77), 7.625 (2.38), 7.911 (1.40), 8.043 (3.13), 8.174 (1.27), 8.552 (3.19), 9.924 (2.12).

Example 185

N-[4-chloro-1-(cyclopropylmethyl)-3-(4-fluorophenyl)-1H-pyrazol-5-yl]-6-(4-chloro-3,5-dimethyl-1H-pyrazol-1-yl)pyrimidin-4-amine

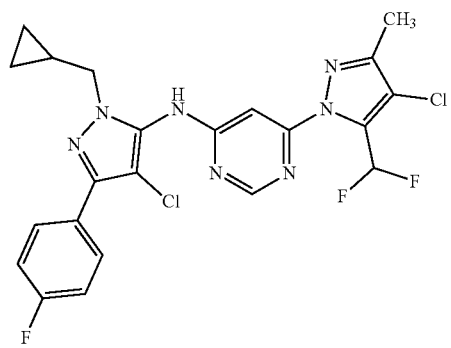

A microwave vial was charged 4-chloro-6-(4-chloro-3,5-dimethyl-1H-pyrazol-1-yl)pyrimidine (62.4 mg, 257 µmol), 4-chloro-1-(cyclopropylmethyl)-3-(4-fluorophenyl)-1H-pyrazol-5-amine (75.0 mg, 282 µmol) and sodium phenolate (44.7 mg, 385 µmol) and the contents were suspended in 1,4-dioxane (1.5 ml, 18 mmol). The reaction mixture was degassed with Ar for 3 min. Tris(dibenzylideneaceton)dipalladium (3.05 mg, 3.34 µmol) and Xantphos (4.45 mg, 7.70 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2x). The combined organic phases were dried over Extrelut NT3 and concentrated under reduced pressure. The crude product was purified by preparative HPLC (method 8) to yield the desired product (25.8 mg, 21%).

LC-MS (method 10): $R_t$=2.71 min; MS (ESIpos): m/z=472 [M+H]$^+$ $^1$H-NMR (400 MHz, dimethylsulfoxide-d6) δ [ppm]: −0.149 (0.59), −0.008 (5.23), 0.008 (4.70), 0.146 (0.53), 0.310 (0.59), 0.322 (2.49), 0.335 (2.68), 0.347 (0.81), 0.455 (2.19), 0.475 (2.34), 1.225 (0.91), 2.091 (1.17), 2.222 (7.10), 2.328 (0.85), 2.366 (0.89), 2.523 (2.63), 2.651 (16.00), 2.670 (1.10), 2.710 (0.93), 3.891 (2.89), 3.908 (2.80), 7.307 (2.12), 7.329 (4.40), 7.351 (2.36), 7.896 (1.91), 7.909 (2.19), 7.918 (2.21), 7.931 (1.89), 8.513 (1.44).

Example 186

N-[4-chloro-1-(cyclopropylmethyl)-3-(4-fluorophenyl)-1H-pyrazol-5-yl]-6-[4-chloro-5-(difluoromethyl)-3-methyl-1H-pyrazol-1-yl]pyrimidin-4-amine

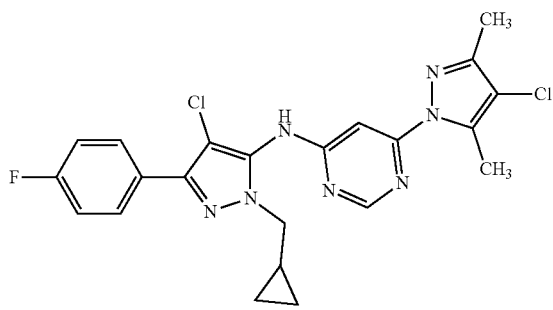 [SMILES: Cc1nn(-c2cc(Nc3c(Cl)c(-c4ccc(F)cc4)nn3CC3CC3)ncn2)c(C)c1Cl]

A microwave vial was charged 4-chloro-6-[4-chloro-5-(difluoromethyl)-3-methyl-1H-pyrazol-1-yl]pyrimidine (71.6 mg, 257 µmol), 4-chloro-1-(cyclopropylmethyl)-3-(4-fluorophenyl)-1H-pyrazol-5-amine (75.0 mg, 282 µmol) and sodium phenolate (44.7 mg, 385 µmol) and the contents were suspended in 1,4-dioxane (1.5 ml, 18 mmol). The reaction mixture was degassed with Ar for 3 min. Tris(dibenzylideneaceton)dipalladium (3.05 mg, 3.34 µmol) and Xantphos (4.45 mg, 7.70 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2x). The combined organic phases were dried over Extrelut NT3 and concentrated under reduced pressure. The crude product was purified by preparative HPLC (method 8) to yield the desired product (10.7 mg, 7%).

LC-MS (method 9): $R_t$=1.38 min; MS (ESIpos): m/z=508 [M+H]$^+$ $^1$H-NMR (400 MHz, dimethylsulfoxide-d6) δ [ppm]: −0.150 (0.81), −0.008 (7.88), 0.008 (6.26), 0.146 (0.87), 0.310 (1.99), 0.323 (8.19), 0.335 (9.40), 0.347 (3.21), 0.460 (7.78), 0.480 (8.25), 1.194 (1.12), 1.207 (2.09), 1.214 (1.99), 1.226 (3.18), 1.237 (2.43), 1.244 (2.15), 1.647 (2.52), 2.184 (0.50), 2.288 (16.00), 2.295 (15.84), 2.327 (1.68), 2.366 (1.49), 2.636 (0.50), 2.670 (1.21), 2.688 (0.65), 2.710 (1.28), 2.994 (0.47), 3.900 (7.60), 3.917 (7.50), 3.938 (1.34), 3.955 (1.00), 5.754 (0.65), 6.833 (1.43), 7.193 (1.12), 7.219 (1.40), 7.241 (1.87), 7.267 (2.65), 7.286 (2.99), 7.296 (3.18), 7.311 (7.25), 7.333 (14.13), 7.355 (8.00), 7.365 (3.49), 7.384 (2.86), 7.396 (2.96), 7.437 (1.28), 7.492 (2.27), 7.511 (2.43), 7.531 (1.49), 7.823 (0.62), 7.861 (1.31), 7.898 (9.31), 7.911 (7.04), 7.919 (6.69), 7.933 (5.45), 7.993 (1.74), 8.030 (7.88), 8.044 (0.81), 8.124 (0.81), 8.161 (3.55), 8.553 (3.30), 8.591 (0.96), 8.749 (1.93), 9.827 (0.65), 9.902 (1.96).

Example 187

N-[4-chloro-1-(cyclopropylmethyl)-3-(4-fluorophenyl)-1H-pyrazol-5-yl]-6-(3,5-dimethyl-1H-pyrazol-1-yl)pyrimidin-4-amine

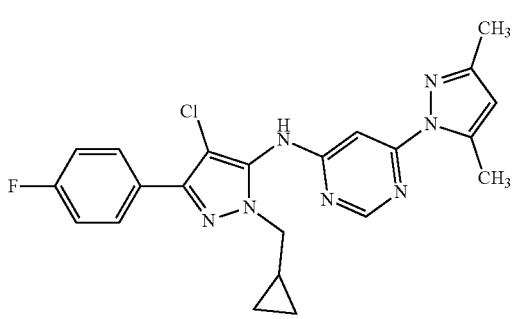 [SMILES: Cc1cc(C)n(-c2cc(Nc3c(Cl)c(-c4ccc(F)cc4)nn3CC3CC3)ncn2)n1]

A microwave vial was charged 4-chloro-6-(3,5-dimethyl-1H-pyrazol-1-yl)pyrimidine (58.0 mg, 278 µmol), 4-chloro-1-(cyclopropylmethyl)-3-(4-fluorophenyl)-1H-pyrazol-5-amine (81.2 mg, 306 µmol) and sodium phenolate (48.4 mg, 417 µmol) and the contents were suspended in 1,4-dioxane (1.2 ml, 14 mmol). The reaction mixture was degassed with Ar for 3 min. Tris(dibenzylidenaceton)dipalladium (3.31 mg, 3.61 µmol) and Xantphos (4.82 mg, 8.34 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over Extrelut NT3 and concentrated under reduced pressure. The crude product was purified by preparative HPLC (method 8) to yield the desired product (12.5 mg, 10%).

LC-MS (method 10): $R_t$=2.46 min; MS (ESIpos): m/z=438 [M+H]$^+$ $^1$H-NMR (400 MHz, dimethylsulfoxide-d6) δ [ppm]: −0.149 (0.68), −0.008 (6.01), 0.146 (0.66), 0.324 (2.94), 0.339 (3.35), 0.350 (1.01), 0.447 (0.91), 0.457 (2.59), 0.477 (2.81), 1.030 (0.58), 1.045 (0.51), 1.229 (1.22), 1.647 (0.58), 2.081 (1.06), 2.183 (9.69), 2.327 (0.91), 2.366 (0.91), 2.634 (16.00), 2.670 (1.09), 2.710 (1.01), 3.892 (3.58), 3.910 (3.63), 6.157 (4.21), 7.307 (2.71), 7.330 (5.55), 7.352 (2.92), 7.398 (0.58), 7.898 (2.48), 7.912 (2.87), 7.920 (2.79), 7.934 (2.38), 8.483 (2.54).

Example 188

2-[1-(6-{[1-(cyclopropylmethyl)-4-ethyl-5-(4-fluorophenyl)-1H-pyrazol-3-yl]amino}pyrimidin-4-yl)-3,5-dimethyl-1H-pyrazol-4-yl]propan-2-ol

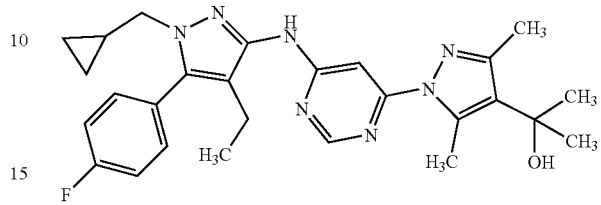

A solution of ethyl 1-(6-{[1-(cyclopropylmethyl)-4-ethyl-5-(4-fluorophenyl)-1H-pyrazol-3-yl]amino}pyrimidin-4-yl)-3,5-dimethyl-1H-pyrazole-4-carboxylate (69.0 mg, 137 µmol) in tetrahydrofuran (2.8 ml, 35 mmol) was treated with methyllithium (300 µl, 1.6 M in diethyl ether, 480 mol) at 0° C. The mixture was stirred for 30 minutes at 0° C. The mixture was diluted with aqueous saturated ammonium chloride solution and extracted with ethyl acetate (3×). The combined organic phases were dried over magnesium sulfate and concentrated under reduced pressure. The crude product was purified using preparative HPLC (method 3) to yield 20.0 mg (28%) of the desired product.

LC-MS (method 10): $R_t$=2.19 min; MS (ESIpos): m/z=490 [M+H]$^+$ $^1$H-NMR (400 MHz, dimethylsulfoxide-d6) δ [ppm]: −0.008 (1.11), 0.008 (0.71), 0.181 (1.34), 0.195 (1.41), 0.207 (0.47), 0.406 (0.52), 0.417 (1.25), 0.420 (1.29), 0.426 (0.73), 0.437 (1.37), 0.440 (1.23), 0.452 (0.50), 0.870 (2.05), 0.888 (4.44), 0.907 (1.98), 1.044 (0.55), 1.470 (16.00), 1.982 (0.57), 2.167 (0.74), 2.263 (7.01), 2.287 (0.58), 2.305 (1.36), 2.324 (1.39), 2.343 (0.43), 2.524 (0.62), 2.592 (0.78), 2.732 (7.92), 3.094 (0.73), 3.751 (2.13), 3.768 (2.07), 7.352 (1.07), 7.374 (2.51), 7.396 (1.55), 7.463 (1.50), 7.469 (0.86), 7.477 (1.70), 7.484 (1.36), 7.493 (0.58), 7.499 (1.08), 8.461 (1.95), 9.405 (1.33).

Example 189

3-(3-{[6-(3,5-dimethyl-1H-pyrazol-1-yl)pyrimidin-4-yl]amino}-1,4-dimethyl-1H-pyrazol-5-yl)benzonitrile

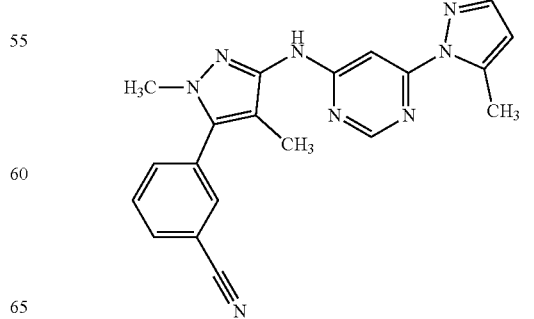

N-(1,4-dimethyl-1H-pyrazol-3-yl)-6-(3,5-dimethyl-H-pyrazol-1-yl)pyrimidin-4-amine (100 mg, 353 µmol), 3-bromobenzonitrile (106 mg, 582 µmol) and potassium acetate (72.7 mg, 741 µmol) were suspended in DMA and degassed with argon for 3 min. 1,4-bis(diphenylphosphino)butane-η3-allyl-palladium(II) chloride was then added and the reaction mixture was degassed again for 1 min. The vial was sealed and heated at 150° C. overnight while vigorously shaking. The mixture was diluted with dimethylsulfoxide, filtered and purified by preparative HPLC (method 7) to yield an impure product fraction that was further purified by preparative HPLC (Luna 5µ C18 100×21.2 mm, flow: 25 mL/min, water (containing 0.1% formic acid)/acetonitrile gradient 0-1 min 98/2; 1-10 min 98/2 to 40/60; 10-12 min 40/60 to 5/95; 12-18 min 5/95) to yield the desired product (1.6 mg, 1% yield).

LC-MS (method 10): $R_t$=1.95 min; MS (ESIpos): m/z=385 [M+H]$^+$ $^1$H-NMR (500 MHz, dimethylsulfoxide-d6) δ [ppm]: 1.875 (13.21), 2.187 (15.08), 2.521 (0.40), 2.525 (0.40), 2.624 (13.74), 2.995 (2.11), 3.724 (16.00), 6.134 (3.95), 7.387 (1.56), 7.738 (1.13), 7.753 (2.77), 7.769 (1.87), 7.823 (1.98), 7.839 (1.33), 7.947 (1.86), 7.963 (1.61), 8.016 (3.12), 8.452 (3.77), 9.419 (2.80).

Example 190

2-[5-(difluoromethyl)-1-(6-{[4-ethyl-5-(4-fluorophenyl)-1-methyl-1H-pyrazol-3-yl]amino}pyrimidin-4-yl)-3-methyl-1H-pyrazol-4-yl]propan-2-ol

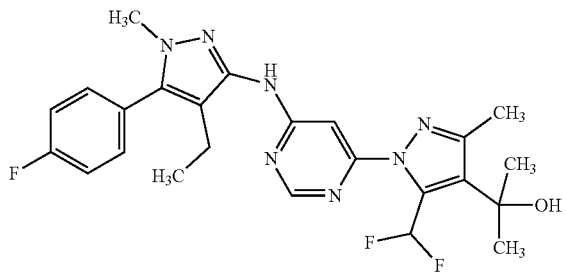 [SMILES: CCc1c(Nc2cc(-n3nc(C)c(C(C)(C)O)c3C(F)F)ncn2)nn(C)c1-c1ccc(F)cc1]

Tert-butyl 5-(difluoromethyl)-1-(6-{[4-ethyl-5-(4-fluorophenyl)-1-methyl-1H-pyrazol-3-yl]amino}pyrimidin-4-yl)-3-methyl-1H-pyrazole-4-carboxylate (200 mg, 379 µmol) was dissolved in diethylether (4.6 mL) and the resulting solution cooled to 0° C. A solution of methyllithium (1.6 M in diethylether, 950 µl, 1.5 mmol) added dropwise and the reaction mixture stirred at 0° C. for 3 h and overnight at ambient temperature. The reaction mixture was quenched by addition of water and extracted with ethyl acetate (3×). The combined organic phase extracts were dried over magnesium sulfate and concentrated. The residue was purified by preparative HPLC (column: Chromatorex C18; 250*30 mm, 10 µM, flow 100 mL/min, gradient acetonitrile/water (containing 0.1% trifluoroacetic acid) 10/90 to 95/5) to yield an impure product fraction that was repurified on preparative HPLC (method 3) to yield the desired product (5 mg, 2% yield).

LC-MS (method 9): $R_t$=1.07 min; MS (ESIpos): m/z=486 [M+H]$^+$ $^1$H-NMR (400 MHz, dimethylsulfoxide-d6) δ [ppm]: −0.008 (2.07), 0.008 (1.75), 0.876 (2.69), 0.895 (5.58), 0.914 (2.57), 1.430 (0.86), 1.497 (1.75), 1.509 (16.00), 1.545 (0.68), 1.555 (1.03), 2.295 (0.64), 2.314 (1.62), 2.332 (1.86), 2.388 (0.40), 2.524 (1.10), 2.601 (2.81), 2.665 (8.83), 2.822 (0.69), 3.633 (10.31), 3.642 (3.50), 3.649 (1.33), 3.661 (0.98), 5.081 (0.46), 5.096 (0.47), 5.268 (2.90), 7.178 (0.58), 7.262 (0.42), 7.314 (1.38), 7.353 (1.77), 7.358 (1.34), 7.375 (3.20), 7.380 (2.03), 7.397 (2.16), 7.451 (0.67), 7.499 (1.87), 7.512 (2.16), 7.520 (1.90), 7.534 (1.56), 8.534 (1.69), 9.577 (0.65).

Example 191

6-(4-bromo-3,5-dimethyl-1H-pyrazol-1-yl)-N-[4-ethyl-5-(4-fluorophenyl)-1-methyl-1H-pyrazol-3-yl]pyrimidin-4-amine

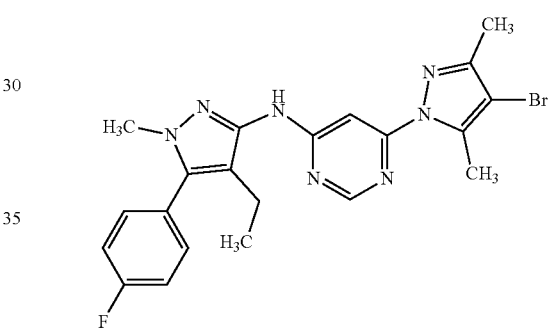

A microwave vial was charged with 4-ethyl-5-(4-fluorophenyl)-1-methyl-1H-pyrazol-3-amine (178 mg, 814 µmol), 4-(4-bromo-3,5-dimethyl-1H-pyrazol-1-yl)-6-chloropyrimidine (213 mg, 740 µmol) and sodium phenolate (112 mg, 962 µmol) the contents were suspended in 1,4-dioxane (2.1 mL). The reaction mixture was degassed with Ar for 3 min. Tris(dibenzylideneacetone)dipalladium (8.81 mg, 9.62 µmol) and XantPhos (12.8 mg, 22.2 µmol) were added and the reaction mixture was degassed again for 1 min. The vial was sealed and heated at 85° C. overnight while vigorously shaking. After cooling to ambient temperature, the reaction mixture was diluted with water and extracted with ethyl acetate. The organic phase extract was dried over sodium sulfate and concentrated. The residue was purified by flash column chromatography (SNAP Ultra 10 g, cyclohexane/ethyl acetate gradient 88/12 to 0/100) to yield the desired product (193 mg, 50% yield).

LC-MS (method 10): $R_t$=2.50 min; MS (ESIpos): m/z=470 [M+H]$^+$ $^1$H-NMR (400 MHz, dimethylsulfoxide-d6) δ [ppm]: 0.90 (s, 3H), 1.51 (s, 3H), 2.28-2.38 (m, 2H), 2.67 (s, 3H), 3.63 (s, 3H), 7.26-7.45 (m, 3H), 7.45-7.60 (m, 2H), 8.53 (s, 1H), 9.47-9.66 (br s, 1H).

Example 192 tert-butyl 1-(6-{[3-(4-cyanophenyl)-1-(cyclopropylmethyl)-4-methyl-1H-pyrazol-5-yl]amino}pyrimidin-4-yl)-5-(difluoromethyl)-3-methyl-1H-pyrazole-4-carboxylate

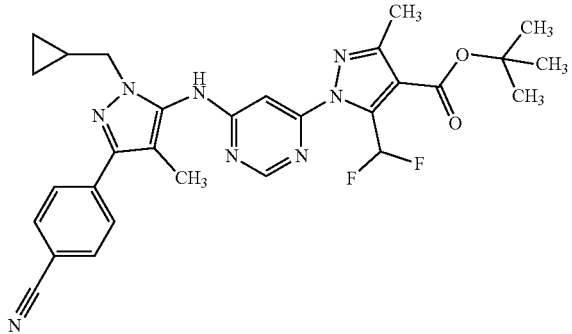 [SMILES: Cc1nn(-c2cc(Nc3c(C)c(-c4ccc(C#N)cc4)nn3CC3CC3)ncn2)c(C(F)F)c1C(=O)OC(C)(C)C]

A microwave vial was charged with 4-[5-amino-1-(cyclopropylmethyl)-4-methyl-1H-pyrazol-3-yl]benzonitrile (200 mg, 793 µmol) and sodium phenolate (125 mg, 1.08 mmol) and the contents were suspended in 1,4-dioxane (2.0 mL). The reaction mixture was degassed with Ar for 3 min. Tris(dibenzylideneacetone)dipalladium (8.58 mg, 9.37 µmol), XantPhos (12.5 mg, 21.6 µmol) and tert-butyl 1-(6-chloropyrimidin-4-yl)-5-(difluoromethyl)-3-methyl-1H-pyrazole-4-carboxylate (248 mg, 721 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 5) to yield the desired product (34 mg, 70% purity, 6% yield).

LC-MS (method 10): $R_t$=2.54 min; MS (ESIpos): m/z=561 [M+H]$^+$ $^1$H-NMR (400 MHz, dimethylsulfoxide-d6) δ [ppm]: −0.008 (0.72), 0.008 (0.73), 1.543 (16.00), 2.065 (2.17), 2.911 (5.09), 7.237 (0.81), 7.281 (0.90), 7.300 (1.07), 7.303 (0.93), 7.343 (0.63), 7.362 (0.45), 7.371 (1.46), 7.491 (0.78), 7.511 (1.04), 7.530 (0.53), 7.903 (2.87), 8.827 (0.94).

Example 193 tert-butyl 1-(6-{[1-(cyclopropylmethyl)-4-ethyl-3-(4-fluorophenyl)-1H-pyrazol-5-yl]amino}pyrimidin-4-yl)-5-(difluoromethyl)-3-methyl-1H-pyrazole-4-carboxylate

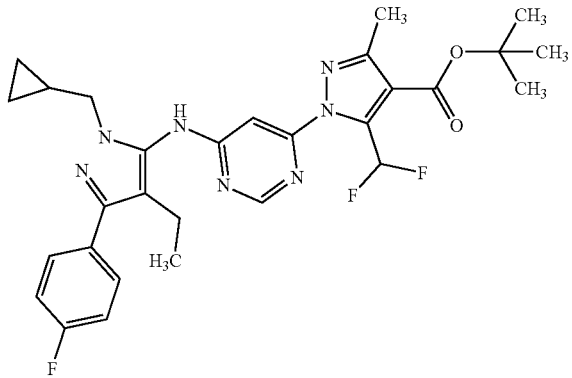 [SMILES: CC/C(C(=N)c1ccc(F)cc1)=C(/NCC1CC1)Nc1cc(-n2nc(C)c(C(=O)OC(C)(C)C)c2C(F)F)ncn1]

A microwave vial was charged with 1-(cyclopropylmethyl)-4-ethyl-3-(4-fluorophenyl)-1H-pyrazol-5-amine (200 mg, 771 µmol) and sodium phenolate (122 mg, 1.05 mmol) and the contents were suspended in 1,4-dioxane (2.0 mL). The reaction mixture was degassed with Ar for 3 min. Tris(dibenzylideneacetone)dipalladium (8.35 mg, 9.11 µmol), XantPhos (12.2 mg, 21.0 µmol) and tert-butyl 1-(6-chloropyrimidin-4-yl)-5-(difluoromethyl)-3-methyl-1H-pyrazole-4-carboxylate (242 mg, 701 µmol) were added and the reaction mixture was degassed again for 1 min. The vial was sealed and heated at 90° C. overnight while vigorously shaking. After cooling to ambient temperature, the reaction mixture was filtered and concentrated. The residue was redissolved in dimethylsulfoxide and purified by preparative HPLC (method 5) to yield the desired product (40 mg, 10% yield).

LC-MS (method 9): $R_t$=1.38 min; MS (ESIpos): m/z=567 [M+H]$^+$ $^1$H-NMR (400 MHz, dimethylsulfoxide-d6) δ [ppm]: −0.149 (0.25), −0.008 (2.00), 0.008 (1.74), 0.146 (0.24), 0.299 (1.57), 0.310 (1.71), 0.439 (1.71), 0.458 (1.82), 0.972 (3.02), 0.991 (6.75), 1.009 (3.15), 1.061 (0.18), 1.209 (0.74), 1.538 (16.00), 2.328 (0.32), 2.367 (0.41), 2.440 (0.66), 2.459 (1.72), 2.477 (1.85), 2.524 (0.85), 2.670 (0.33), 2.710 (0.37), 2.905 (2.64), 3.799 (1.27), 3.814 (1.26), 7.251 (2.05), 7.274 (4.04), 7.296 (2.25), 7.371 (0.27), 7.662 (1.25), 7.676 (1.55), 7.697 (1.09), 8.548 (0.28), 9.569 (0.25).

Example 194

6-(3,5-dimethyl-1H-pyrazol-1-yl)-N-[5-(4-fluorophenyl)-1-methyl-4-(pyrrolidin-1-ylmethyl)-1H-pyrazol-3-yl]pyrimidin-4-amine

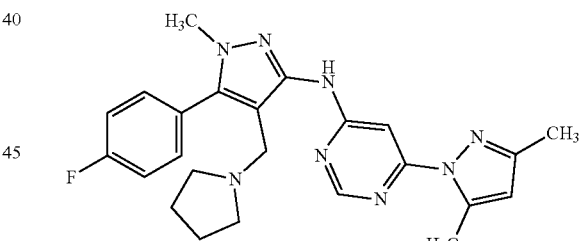

3-{[6-(3,5-dimethyl-1H-pyrazol-1-yl)pyrimidin-4-yl]amino}-5-(4-fluorophenyl)-1-methyl-1H-pyrazole-4-carbaldehyde (50.0 mg, 128 µmol) and pyrrolidine (13 µl, 150 µmol) were dissolved in tetrahydrofuran (2.0 mL) and acetic acid (22 µl, 380 µmol) and sodium triacetoxyborohydride (32.5 mg, 153 µmol) were added. The reaction mixture was allowed to stirred overnight at ambient temperature. It was then quenched with water and extracted with ethyl acetate (3×). The combined organic phase extracts were dried over sodium sulfate and concentrated. The residue was purified by preparative HPLC ( ) to yield the desired product (5 mg, 8% yield) after lyophilisation of product-containing fractions.

LC-MS (method 10): $R_t$=1.27 min; MS (ESIpos): m/z=447 [M+H]$^+$

¹H-NMR (400 MHz, dimethylsulfoxide-d6) δ [ppm]: −0.008 (2.41), 0.008 (2.16), 1.753 (3.85), 1.891 (0.75), 2.192 (1.25), 2.208 (16.00), 2.252 (1.23), 2.260 (1.13), 2.328 (0.40), 2.367 (0.51), 2.460 (0.93), 2.643 (13.78), 2.670 (1.43), 2.710 (0.59), 3.271 (1.16), 3.283 (1.15), 3.735 (1.00), 4.204 (3.06), 4.216 (3.02), 4.464 (0.62), 4.727 (0.82), 4.783 (0.56), 4.794 (0.55), 6.168 (3.90), 7.422 (2.04), 7.444 (4.33), 7.466 (2.44), 7.617 (2.40), 7.631 (2.74), 7.639 (2.41), 7.652 (2.02), 7.890 (1.15), 8.550 (4.35), 9.675 (0.46), 9.886 (3.36).

Example 195

2-[4-chloro-1-(6-{[4-ethyl-5-(4-fluorophenyl)-1-methyl-1H-pyrazol-3-yl]amino}pyrimidin-4-yl)-3-methyl-1H-pyrazol-5-yl]propan-2-ol

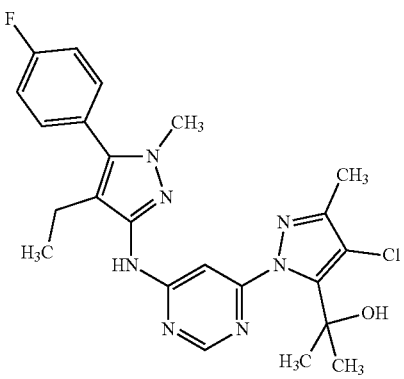 [SMILES: CCc1c(Nc2cc(-n3nc(C)c(Cl)c3C(C)(C)O)ncn2)nn(C)c1-c1ccc(F)cc1]

A solution of ethyl 4-chloro-1-(6-{[4-ethyl-5-(4-fluorophenyl)-1-methyl-1H-pyrazol-3-yl]amino}pyrimidin-4-yl)-3-methyl-1H-pyrazole-5-carboxylate (77.0 mg, 159 µmol) in tetrahydrofuran (3.0 ml, 37 mmol) was treated with bromo(methyl)magnesium (560 µl, 1.0 M in tetrahydrofuran, 560 µmol) at 0° C. The mixture was stirred 30 minutes at 0° C. and one hour at ambient temperature. Another 2 equivalents of bromo(methyl)magnesium (0.32 mL, 0.32 mmol, 1.0 M in tetrahydrofuran) were added at 0° C. and it was stirred for 30 minutes at 0° C. The mixture was diluted with saturated ammonia chloride solution and extracted with ethyl acetate (3×). The combined organic phases were dried over magnesium sulfate and concentrated under reduced pressure. The crude product was purified using flash chromatography (cyclohexane/ethyl acetate) yielding 24.7 mg (30%) of the desired product.

LC-MS (method 9): $R_t$=1.21 min; MS (ESIpos): m/z=470 [M+H]⁺

¹H-NMR (400 MHz, dimethylsulfoxide-d6) δ [ppm]: −0.008 (1.16), 0.008 (1.02), 0.875 (2.13), 0.894 (4.95), 0.912 (2.18), 1.356 (1.29), 1.596 (16.00), 2.185 (9.41), 2.300 (0.43), 2.318 (1.32), 2.337 (1.29), 2.356 (0.41), 2.519 (0.82), 2.524 (0.62), 3.637 (10.54), 6.810 (0.43), 7.275 (0.41), 7.355 (1.23), 7.360 (0.48), 7.377 (2.84), 7.394 (0.55), 7.399 (1.71), 7.494 (1.63), 7.499 (0.70), 7.507 (1.83), 7.515 (1.45), 7.524 (0.59), 7.529 (1.24), 8.535 (1.63), 9.717 (0.55).

Example 196

4-(3-{[6-(4-chloro-3,5-dimethyl-1H-pyrazol-1-yl)pyrimidin-4-yl]amino}-1,4-dimethyl-1H-pyrazol-5-yl)benzonitrile

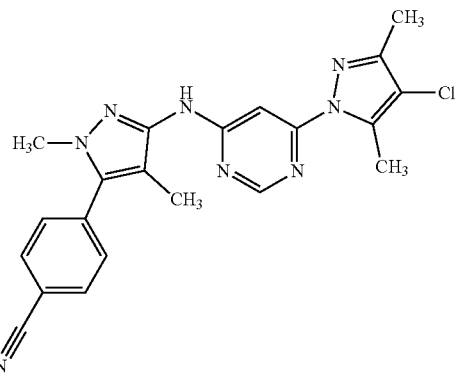

A microwave vial was charged with 4-(3-amino-1,4-dimethyl-1H-pyrazol-5-yl)benzonitrile (60.0 mg, 283 µmol), 4-chloro-6-(4-chloro-3,5-dimethyl-1H-pyrazol-1-yl)pyrimidine (75.6 mg, 311 µmol) and sodium phenolate (36.1 mg, 311 µmol) and the contents were suspended in 1,4-dioxane (0.9 mL). The reaction mixture was degassed with Ar for 3 min. Tris(dibenzylideneacetone)dipalladium (3.88 mg, 4.24 mol) and XantPhos (4.91 mg, 8.48 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 6) to yield the desired product (31 mg, 26% yield).

LC-MS (method 10): $R_t$=2.23 min; MS (ESIpos): m/z=419 [M+H]⁺

¹H-NMR (400 MHz, dimethylsulfoxide-d6) δ [ppm]: −0.008 (2.52), 1.647 (0.86), 1.887 (13.10), 2.224 (14.65), 2.641 (15.76), 2.679 (0.41), 3.736 (16.00), 7.368 (0.65), 7.384 (0.76), 7.398 (1.04), 7.412 (1.31), 7.698 (4.17), 7.719 (4.86), 8.004 (4.63), 8.025 (4.11), 8.488 (2.85), 9.550 (2.26).

Example 197

4-(5-{[6-(3,5-dimethyl-1H-pyrazol-1-yl)pyrimidin-4-yl]amino}-1,4-dimethyl-1H-pyrazol-3-yl)benzonitrile

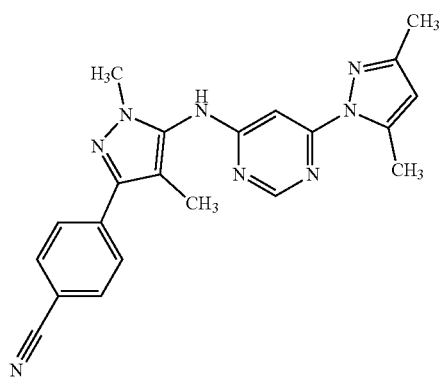 [SMILES: Cc1cc(C)n(-c2cc(Nc3c(C)c(-c4ccc(C#N)cc4)nn3C)ncn2)n1]

A microwave vial was charged with 4-(5-amino-1,4-dimethyl-1H-pyrazol-3-yl)benzonitrile (80.0 mg, 377 µmol), 4-chloro-6-(3,5-dimethyl-1H-pyrazol-1-yl)pyrimidine (86.5 mg, 415 µmol) and sodium phenolate (48.1 mg, 415 µmol) and the contents were suspended in 1,4-dioxane (1.2 mL). The reaction mixture was degassed with Ar for 3 min. Tris(dibenzylideneacetone)dipalladium (5.18 mg, 5.65 µmol) and XantPhos (6.54 mg, 11.3 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 1) to yield the desired product (32 mg, 21% yield).

LC-MS (method 11): $R_t$=1.33 min; MS (ESIneg): m/z=383 [M−H]⁻

¹H-NMR (400 MHz, dimethylsulfoxide-d6) δ [ppm]: −0.008 (2.46), 0.008 (2.56), 2.073 (14.45), 2.177 (3.63), 2.228 (0.43), 2.523 (0.74), 2.631 (11.90), 2.665 (0.48), 3.695 (9.97), 6.150 (2.50), 7.897 (16.00), 8.471 (0.77), 9.457 (1.59).

Example 198

4-[1-(2-cyclopropylethyl)-5-{[6-(3,5-dimethyl-1H-pyrazol-1-yl)pyrimidin-4-yl]amino}-4-methyl-1H-pyrazol-3-yl]benzonitrile

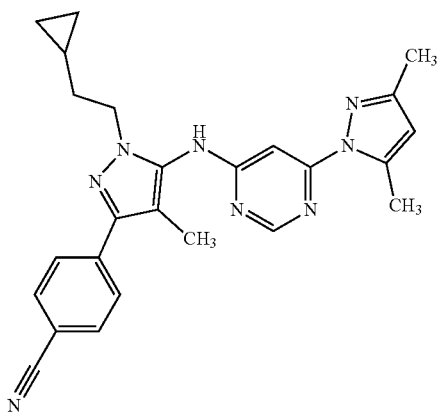 [SMILES: Cc1cc(C)n(-c2cc(Nc3c(C)c(-c4ccc(C#N)cc4)nn3CCC3CC3)ncn2)n1]

A microwave vial was charged with 4-[5-amino-1-(2-cyclopropylethyl)-4-methyl-1H-pyrazol-3-yl]benzonitrile (51.5 mg, 193 µmol), 4-chloro-6-(3,5-dimethyl-1H-pyrazol-1-yl)pyrimidine (44.4 mg, 213 µmol) and sodium phenolate (24.7 mg, 213 µmol) and the contents were suspended in 1,4-dioxane (0.6 mL). The reaction mixture was degassed with Ar for 3 min. Tris(dibenzylideneacetone)dipalladium (2.66 mg, 2.90 µmol) and XantPhos (3.36 mg, 5.80 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 6) to yield the desired product (5.9 mg, 7% yield).

¹H-NMR (400 MHz, dimethylsulfoxide-d6) δ [ppm]: −0.063 (2.98), −0.054 (3.01), −0.051 (2.85), −0.008 (2.13), 0.008 (2.08), 0.309 (1.97), 0.327 (2.14), 0.608 (0.62), 0.626 (0.88), 0.645 (0.56), 1.633 (0.94), 1.651 (2.67), 1.668 (2.68), 1.686 (0.96), 2.062 (16.00), 2.168 (2.74), 2.524 (0.73), 2.630 (14.20), 2.675 (0.41), 4.021 (1.18), 4.038 (2.06), 4.055 (1.15), 6.146 (2.73), 7.875 (0.89), 7.897 (11.21), 7.923 (0.83), 8.465 (0.75), 9.413 (0.84).

Example 199

4-(4-{[6-(3,5-dimethyl-1H-pyrazol-1-yl)pyrimidin-4-yl]amino}-3,5-dimethyl-1H-pyrazol-1-yl)benzonitrile

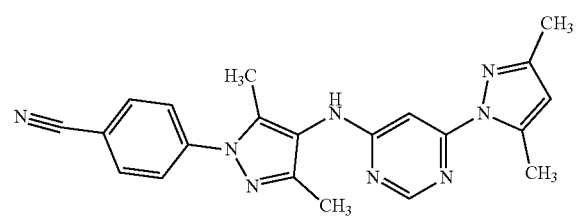 [SMILES: Cc1cc(C)n(-c2cc(Nc3c(C)nn(-c4ccc(C#N)cc4)c3C)ncn2)n1]

A microwave vial was charged 4-chloro-6-(3,5-dimethyl-1H-pyrazol-1-yl)pyrimidine (89.4 mg, 428 µmol), 4-(4-amino-3,5-dimethyl-1H-pyrazol-1-yl)benzonitrile (100 mg, 471 µmol) and sodium phenolate (74.6 mg, 642 µmol) and the contents were suspended in 1,4-dioxane (3.1 ml, 36 mmol). The reaction mixture was degassed with Ar for 3 min. Tris(dibenzylidenaceton)dipalladium (5.10 mg, 5.57 µmol) and Xantphos (7.43 mg, 12.8 µmol) were added and the reaction mixture was degassed again for 1 min. The vial was sealed and heated at 85° C. overnight while vigorously shaking. After cooling to ambient temperature, the reaction mixture was purified by preparative HPLC (method: column: Reprosil C18; 10 µm; 125×40 mm/flow: 75 mL/min/ solvent: A=water (0.1% formic acid), B=acetonitrile/gradient: 0.00-5.50 min=10% B, 17.65-19.48 min=95% B, 19.66 min=10% B) to yield the desired product (47.0 mg, 28%).

LC-MS (method 10): $R_t$=1.86 min; MS (ESIpos): m/z=385 [M+H]⁺

¹H-NMR (400 MHz, dimethylsulfoxide-d6) δ [ppm]: 2.073 (2.04), 2.104 (16.00), 2.168 (2.41), 2.294 (11.75), 2.328 (0.44), 2.367 (0.41), 2.616 (13.94), 2.670 (0.42), 6.122 (2.44), 7.811 (2.06), 7.832 (2.58), 7.979 (4.02), 8.000 (3.21), 8.403 (0.55), 8.931 (3.32).

Example 200

4-[4-({6-[4-chloro-5-(difluoromethyl)-3-methyl-1H-pyrazol-1-yl]pyrimidin-4-yl}amino)-3,5-dimethyl-1H-pyrazol-1-yl]benzonitrile

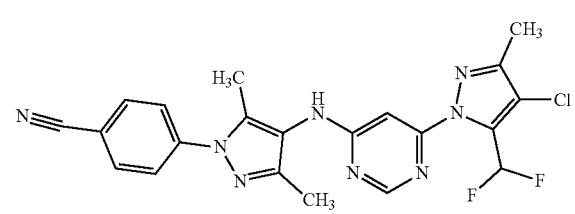 [SMILES: Cc1nn(-c2cc(Nc3c(C)nn(-c4ccc(C#N)cc4)c3C)ncn2)c(C(F)F)c1Cl]

A microwave vial was charged 4-chloro-6-[4-chloro-5-(difluoromethyl)-3-methyl-1H-pyrazol-1-yl]pyrimidine (120 mg, 428 µmol), 4-(4-amino-3,5-dimethyl-1H-pyrazol-1-yl)benzonitrile (100 mg, 471 µmol) and sodium phenolate (54.7 mg, 471 µmol) and the contents were suspended in 1,4-dioxane (3.1 ml, 36 mmol). The reaction mixture was degassed with Ar for 3 min. Tris(dibenzylidenaceton)dipalladium (5.10 mg, 5.57 µmol) and Xantphos (7.43 mg, 12.8 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (90.0 mg, 44%).

LC-MS (method 10): $R_t$=2.17 min; MS (ESIpos): m/z=455 [M+H]$^+$ $^1$H-NMR (400 MHz, dimethylsulfoxide-d6) δ [ppm]: −0.008 (3.25), 0.008 (2.00), 2.073 (13.13), 2.086 (0.74), 2.106 (16.00), 2.292 (10.62), 2.327 (1.09), 2.367 (0.45), 2.524 (1.66), 2.670 (0.44), 7.827 (1.54), 7.901 (0.73), 7.983 (2.69), 8.004 (2.19), 8.033 (1.49), 8.165 (0.66), 9.208 (0.60).

Example 201

4-(5-{[6-(4-chloro-3,5-dimethyl-1H-pyrazol-1-yl)pyrimidin-4-yl]amino}-1,4-dimethyl-1H-pyrazol-3-yl)benzonitrile

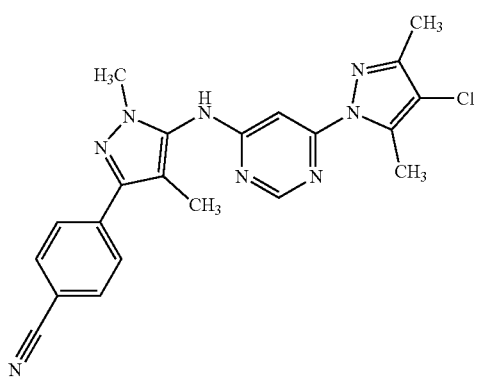 [SMILES: Cc1nn(-c2cc(Nc3c(C)c(-c4ccc(C#N)cc4)nn3C)ncn2)c(C)c1Cl]

A microwave vial was charged with 4-(5-amino-1,4-dimethyl-1H-pyrazol-3-yl)benzonitrile (80.0 mg, 377 µmol), 4-chloro-6-(4-chloro-3,5-dimethyl-1H-pyrazol-1-yl)pyrimidine (101 mg, 415 µmol) and sodium phenolate (48.1 mg, 415 µmol) and the contents were suspended in 1,4-dioxane (1.2 mL). The reaction mixture was degassed with Ar for 3 min. Tris(dibenzylideneacetone)dipalladium (5.18 mg, 5.65 µmol) and XantPhos (6.54 mg, 11.3 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 6) to yield the desired product (52.8 mg, 33% yield).

LC-MS (method 10): $R_t$=2.27 min; MS (ESIpos): m/z=419 [M+H]$^+$ $^1$H-NMR (400 MHz, dimethylsulfoxide-d6) δ [ppm]: −0.008 (3.02), 0.008 (1.55), 2.071 (14.95), 2.216 (3.05), 2.266 (0.57), 2.649 (14.46), 2.679 (0.58), 3.696 (8.98), 7.896 (16.00), 8.505 (0.65), 9.555 (0.69).

Example 202

4-[5-{[6-(4-acetyl-3,5-dimethyl-1H-pyrazol-1-yl)pyrimidin-4-yl]amino}-1-(cyclopropylmethyl)-4-ethyl-1H-pyrazol-3-yl]benzonitrile

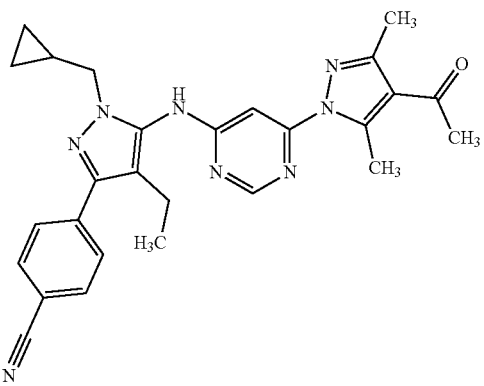 [SMILES: CCc1c(-c2ccc(C#N)cc2)nn(CC2CC2)c1Nc1cc(-n2nc(C)c(C(C)=O)c2C)ncn1]

A solution of ethyl 1-(6-{[3-(4-cyanophenyl)-1-(cyclopropylmethyl)-4-ethyl-1H-pyrazol-5-yl]amino}pyrimidin-4-yl)-3,5-dimethyl-1H-pyrazole-4-carboxylate (108 mg, 212 µmol) in tetrahydrofuran (2.5 ml, 31 mmol) was treated at 0° C. with bromo(methyl)magnesium (250 µl, 3.0 M in diethyl ether, 740 µmol). The mixture was stirred overnight at ambient temperature. Two further equivalents of bromo(methyl)magnesium (141 µL, 0.42 mmol, 3.0 M in diethyl ether) were added and it was stirred overnight. The mixture was diluted with water and purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 12.4 mg (12%) of the desired product.

LC-MS (method 11): $R_t$=1.41 min; MS (ESIpos): m/z=481 [M+H]$^+$ $^1$H-NMR (400 MHz, dimethylsulfoxide-d6) δ [ppm]: −0.149 (0.93), −0.008 (7.98), 0.008 (7.34), 0.146 (0.88), 0.308 (4.99), 0.446 (5.28), 0.465 (5.09), 0.960 (2.69), 0.979 (6.07), 0.993 (7.34), 1.012 (14.73), 1.030 (7.73), 1.199 (1.76), 1.217 (2.06), 1.234 (1.86), 2.328 (1.81), 2.366 (2.30), 2.466 (13.60), 2.670 (2.06), 2.710 (2.20), 2.893 (16.00), 3.793 (2.01), 3.811 (2.25), 3.833 (3.72), 3.850 (3.67), 7.178 (1.22), 7.197 (1.42), 7.267 (1.37), 7.286 (0.93), 7.428 (1.17), 7.448 (1.81), 7.467 (0.93), 7.830 (2.06), 7.851 (4.94), 7.864 (2.45), 7.885 (12.92), 7.898 (15.12), 7.919 (3.47), 8.151 (0.93), 8.245 (1.17), 8.535 (0.73), 9.266 (0.54), 9.550 (0.69).

Example 203

4-[1-(cyclopropylmethyl)-4-ethyl-5-{[6-(3-methyl-1H-pyrazolo[3,4-c]pyridin-1-yl)pyrimidin-4-yl]amino}-1H-pyrazol-3-yl]benzonitrile

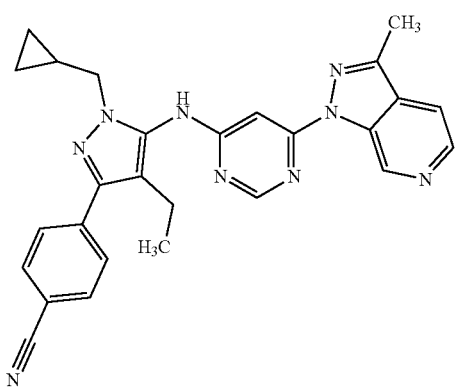 [SMILES: CCc1c(-c2ccc(C#N)cc2)nn(CC2CC2)c1Nc1cc(-n2nc(C)c3ccncc32)ncn1]

A microwave vial was charged 1-(6-chloropyrimidin-4-yl)-3-methyl-1H-pyrazolo[3,4-c]pyridine (100 mg, 407 µmol), 4-[5-amino-1-(cyclopropylmethyl)-4-ethyl-1H-pyrazol-3-yl]benzonitrile (119 mg, 448 µmol) and sodium phenolate (61.4 mg, 529 µmol) and the contents were suspended in 1,4-dioxane (2.5 ml, 29 mmol). The reaction mixture was degassed with Ar for 3 min. Tris(dibenzylidenaceton)dipalladium (4.85 mg, 5.29 µmol) and Xantphos (7.07 mg, 12.2 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography on silica gel (column: SNAP KP-Sil 10 g, dichloromethane/ethyl acetate) to yield the desired product (30.2 mg, 16%).

LC-MS (method 10): $R_t$=2.03 min; MS (ESIpos): m/z=476 [M+H]$^+$ $^1$H-NMR (400 MHz, dimethylsulfoxide-d6) δ [ppm]: −0.008 (2.92), 0.008 (2.70), 0.324 (3.25), 0.334 (3.42), 0.451 (3.52), 0.471 (3.66), 1.016 (5.28), 1.035 (11.35), 1.053 (5.44), 1.158 (1.12), 1.176 (2.26), 1.194 (1.24), 1.208 (0.59), 1.220 (1.08), 1.238 (1.68), 1.257 (1.03), 1.990 (4.08), 2.568 (3.24), 2.587 (2.08), 2.618 (2.89), 2.712 (0.48), 3.863 (2.82), 3.878 (2.82), 4.022 (0.99), 4.039 (0.96), 7.911 (16.00), 8.475 (4.31), 8.488 (4.14), 8.625 (0.67), 9.509 (0.59), 10.037 (5.68).

Example 204

N-[1-(cyclopropylmethyl)-3-(4-fluorophenyl)-4-methyl-1H-pyrazol-5-yl]-6-(3-methyl-1H-pyrazolo[3,4-c]pyridin-1-yl)pyrimidin-4-amine A microwave vial was charged 1-(6-chloropyrimidin-4-yl)-3-methyl-1H-pyrazolo[3,4-c]pyridine (100 mg, 407 µmol), 1-(cyclopropylmethyl)-3-(4-fluorophenyl)-4-methyl-1H-pyrazol-5-amine (110 mg, 448 µmol) and sodium phenolate (61.4 mg, 529 µmol) and the contents were suspended in 1,4-dioxane (2.5 ml, 29 mmol). The reaction mixture was degassed with Ar for 3 min. Tris(dibenzylidenaceton)dipalladium (4.85 mg, 5.29 µmol) and Xantphos (7.07 mg, 12.2 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography on silica gel (column: SNAP KP-Sil 10 g, SCM/ethyl acetate) to yield the desired product (31.3 mg, 17%).

LC-MS (method 10): $R_t$=2.05 min; MS (ESIpos): m/z=455 [M+H]$^+$ $^1$H-NMR (400 MHz, dimethylsulfoxide-d6) δ [ppm]: 0.307 (2.86), 0.319 (3.14), 0.430 (2.85), 0.450 (3.06), 0.822 (0.50), 1.176 (0.62), 1.188 (0.47), 1.194 (0.59), 1.200 (0.83), 1.207 (0.80), 1.219 (1.27), 1.231 (1.12), 1.237 (1.00), 1.249 (0.59), 1.286 (0.49), 1.301 (0.45), 1.990 (1.01), 2.042 (16.00), 2.565 (0.48), 2.615 (3.22), 2.672 (0.47), 3.860 (2.66), 3.877 (2.62), 5.756 (0.97), 7.265 (2.23), 7.288 (4.50), 7.310 (2.53), 7.755 (2.10), 7.892 (1.82), 7.905 (2.06), 8.473 (3.37), 8.486 (3.29), 8.633 (0.57), 9.499 (0.59), 10.042 (4.09).

Example 205

N-[1-(cyclopropylmethyl)-4-ethyl-3-(4-fluorophenyl)-1H-pyrazol-5-yl]-6-(3-methyl-1H-pyrazolo[3,4-c]pyridin-1-yl)pyrimidin-4-amine

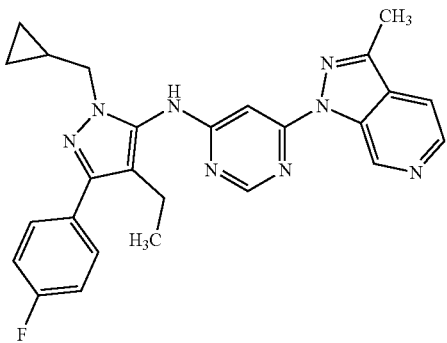 [SMILES: CCc1c(-c2ccc(F)cc2)nn(CC2CC2)c1Nc1cc(-n2nc(C)c3ccncc32)ncn1]

A microwave vial was charged 1-(6-chloropyrimidin-4-yl)-3-methyl-1H-pyrazolo[3,4-c]pyridine (100 mg, 407 µmol), 1-(cyclopropylmethyl)-4-ethyl-3-(4-fluorophenyl)-1H-pyrazol-5-amine (116 mg, 448 µmol) and sodium phenolate (61.4 mg, 529 µmol) and the contents were suspended in 1,4-dioxane (2.5 ml, 29 mmol). The reaction mixture was degassed with Ar for 3 min. Tris(dibenzylidenaceton)dipalladium (4.85 mg, 5.29 µmol) and Xantphos (7.07 mg, 12.2 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were dried over Extrelut NT3 and concentrated under reduced pressure. The crude product was purified by preparative HPLC (method 6) to yield the desired product (91.0 mg, 48%).

LC-MS (method 10): $R_t$=2.14 min; MS (ESIpos): m/z=469 [M+H]$^+$ $^1$H-NMR (400 MHz, dimethylsulfoxide-d6) δ [ppm]: −0.008 (1.63), 0.309 (4.77), 0.320 (6.56), 0.331 (3.82), 0.345 (1.21), 0.441 (4.83), 0.460 (5.07), 0.531 (0.65), 0.542 (1.57), 0.546 (1.70), 0.551 (0.81), 0.562 (1.69), 0.566 (1.63), 0.577 (0.52), 0.997 (7.29), 1.016 (16.00), 1.035 (7.63), 1.147 (0.46), 1.154 (0.42), 1.166 (0.68), 1.177 (0.57), 1.186 (0.67), 1.196 (0.93), 1.207 (1.45), 1.214 (1.42), 1.226 (2.15), 1.238 (1.39), 1.244 (1.39), 1.257 (0.71), 1.647 (2.30), 1.757 (1.24), 2.613 (3.77), 2.672 (0.81), 2.713 (0.45), 3.829 (3.94), 3.845 (3.87), 4.068 (4.03), 4.086 (3.97), 6.550 (0.41), 6.582 (0.43), 6.924 (0.40), 7.267 (3.93), 7.289 (7.79), 7.311 (4.34), 7.342 (2.13), 7.358 (0.68), 7.370 (1.98), 7.383 (3.15), 7.399 (2.25), 7.417 (0.64), 7.422 (0.59), 7.462 (2.88), 7.466 (3.09), 7.479 (2.05), 7.490 (0.84), 7.501 (0.44), 7.630 (0.52), 7.667 (1.06), 7.676 (1.44), 7.682 (1.66), 7.690 (3.16), 7.700 (2.94), 7.713 (3.42), 7.728 (3.76), 7.736 (2.27), 7.742 (1.67), 7.751 (1.08), 7.782 (1.81), 7.791 (1.46), 7.795 (1.64), 7.808 (1.23), 7.815 (1.39), 7.822 (1.48), 7.854 (0.43), 7.890 (2.68), 7.902 (2.77), 8.472 (6.57), 8.485 (6.26), 8.624 (0.74), 9.459 (0.68), 10.038 (7.04), 10.196 (5.04).

Example 206

N-[4-ethyl-3-(4-fluorophenyl)-1-methyl-1H-pyrazol-5-yl]-6-(3-methyl-1H-pyrazolo[3,4-c]pyridin-1-yl)pyrimidin-4-amine

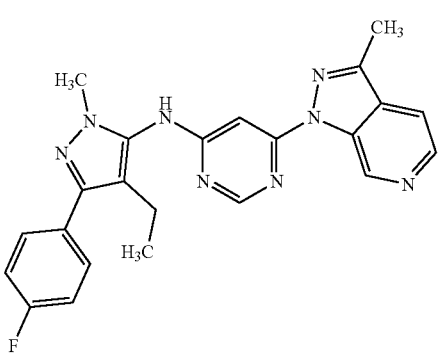 [SMILES: CCc1c(-c2ccc(F)cc2)nn(C)c1Nc1cc(-n2nc(C)c3ccncc32)ncn1]

A microwave vial was charged 1-(6-chloropyrimidin-4-yl)-3-methyl-1H-pyrazolo[3,4-c]pyridine (100 mg, 407 µmol), 4-ethyl-3-(4-fluorophenyl)-1-methyl-1H-pyrazol-5-amine (98.2 mg, 448 µmol) and sodium phenolate (61.4 mg, 529 µmol) and the contents were suspended in 1,4-dioxane (2.5 ml, 29 mmol). The reaction mixture was degassed with Ar for 3 min. Tris(dibenzylidenaceton)dipalladium (4.85 mg, 5.29 µmol) and Xantphos (7.07 mg, 12.2 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were dried Extrelut NT3 and concentrated under reduced pressure. The crude product was purified by preparative HPLC (method 1) to yield the desired product (85.4 mg, 49%).

LC-MS (method 10): $R_t$=1.91 min; MS (ESIpos): m/z=429 [M+H]$^+$ $^1$H-NMR (400 MHz, dimethylsulfoxide-d6) δ [ppm]: −0.008 (1.09), 0.008 (0.89), 0.993 (6.14), 1.012 (13.66), 1.031 (6.52), 1.047 (0.45), 1.676 (1.18), 1.758 (3.87), 2.064 (4.78), 2.476 (1.42), 2.620 (4.42), 2.631 (5.03), 2.673 (0.51), 2.712 (2.33), 3.674 (16.00), 5.756 (2.22), 7.260 (3.46), 7.282 (6.54), 7.304 (3.70), 7.315 (1.05), 7.355 (0.46), 7.506 (0.47), 7.526 (0.57), 7.673 (2.11), 7.688 (2.92), 7.707 (2.04), 7.893 (2.54), 7.906 (2.74), 8.474 (5.37), 8.487 (5.19), 8.521 (0.47), 8.535 (0.46), 8.554 (0.42), 8.567 (0.42), 8.633 (0.97), 8.832 (0.49), 9.407 (0.41), 10.039 (5.58), 10.106 (0.43).

Example 207

N-[4-chloro-1-(cyclopropylmethyl)-5-(4-fluorophenyl)-1H-pyrazol-3-yl]-6-(3-methyl-1H-pyrazolo[3,4-c]pyridin-1-yl)pyrimidin-4-amine

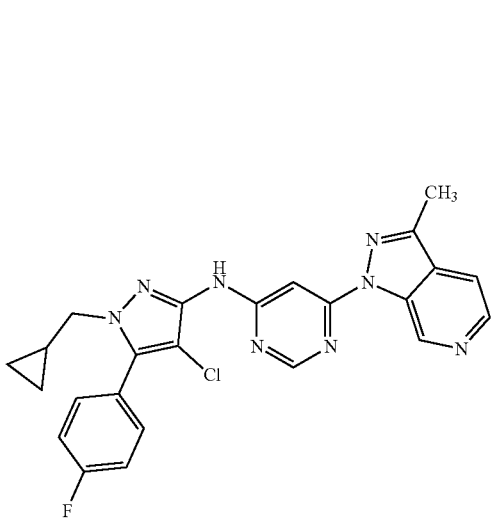 [SMILES: Cc1nn(-c2cc(Nc3nn(CC4CC4)c(-c4ccc(F)cc4)c3Cl)ncn2)c2cnccc12]

A microwave vial was charged 1-(6-chloropyrimidin-4-yl)-3-methyl-1H-pyrazolo[3,4-c]pyridine (75.0 mg, 305 µmol), 4-chloro-1-(cyclopropylmethyl)-5-(4-fluorophenyl)-1H-pyrazol-3-amine (89.2 mg, 336 µmol) and sodium phenolate (46.1 mg, 397 µmol) and the contents were suspended in 1,4-dioxane (1.9 ml, 22 mmol). The reaction mixture was degassed with Ar for 3 min. Tris(dibenzylidenaceton)dipalladium (3.63 mg, 3.97 µmol) and Xantphos (5.30 mg, 9.16 µmol) were added and the reaction mixture was degassed again for 1 min. The vial was sealed and heated at 85° C. overnight while vigorously stirring. After cooling to ambient temperature, the reaction mixture was diluted water and extracted with ethyl acetate (2×). The combined organic phases were dried over Extrelut NT3 and concentrated under reduced pressure. The crude product was purified by preparative HPLC (method 8) to yield the desired product (14.2 mg, 9%).

LC-MS (method 9): $R_t$=1.17 min; MS (ESIpos): m/z=475 [M+H]$^+$ $^1$H-NMR (400 MHz, dimethylsulfoxide-d6) δ [ppm]: 0.008 (1.98), 0.265 (2.59), 0.278 (2.73), 0.490 (0.85), 0.501 (2.34), 0.504 (2.40), 0.520 (2.50), 0.536 (0.70), 0.814 (0.43), 1.105 (0.63), 1.112 (0.62), 1.124 (0.96), 1.136 (0.59), 1.143 (0.59), 1.234 (0.41), 1.648 (1.05), 2.328 (0.42), 2.627 (16.00), 2.670 (0.52), 2.710 (0.44), 3.924 (4.52), 3.942 (4.45), 5.754 (0.87), 7.366 (0.68), 7.382 (0.86), 7.394 (0.82), 7.419 (2.26), 7.441 (4.94), 7.463 (2.97), 7.607 (3.03), 7.613 (1.86), 7.621 (4.07), 7.629 (3.50), 7.637 (1.43), 7.643 (2.44), 7.897 (2.26), 7.911 (2.41), 8.472 (3.30), 8.486 (3.19), 8.656 (3.51), 9.737 (3.72), 10.060 (3.55).

Example 208

4-(4-{[6-(4-chloro-3,5-dimethyl-1H-pyrazol-1-yl)pyrimidin-4-yl]amino}-3,5-dimethyl-1H-pyrazol-1-yl)benzonitrile

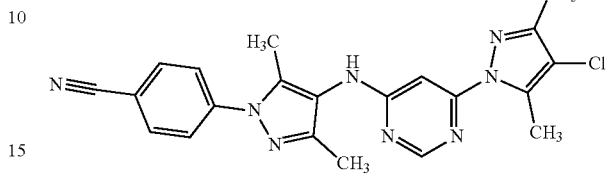

A microwave vial was charged 4-chloro-6-(4-chloro-3,5-dimethyl-1H-pyrazol-1-yl)pyrimidine (104 mg, 428 µmol), 4-(4-amino-3,5-dimethyl-1H-pyrazol-1-yl)benzonitrile (100 mg, 471 µmol) and sodium phenolate (54.7 mg, 471 µmol) and the contents were suspended in 1,4-dioxane (3.1 ml, 36 mmol). The reaction mixture was degassed with Ar for 3 min. Tris(dibenzylidenaceton)dipalladium (5.10 mg, 5.57 µmol) and Xantphos (7.43 mg, 12.8 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (102 mg, 54%).

LC-MS (method 9): $R_t$=1.12 min; MS (ESIpos): m/z=419 [M+H]$^+$ $^1$H-NMR (500 MHz, dimethylsulfoxide-d6) δ [ppm]: −0.006 (1.09), 0.006 (0.58), 2.074 (1.33), 2.104 (16.00), 2.211 (1.03), 2.292 (8.87), 2.633 (13.19), 7.462 (0.41), 7.811 (1.50), 7.827 (1.47), 7.981 (2.77), 7.998 (2.28), 9.039 (1.09).

Example 209

4-(5-{[6-(3,5-dimethyl-1H-pyrazol-1-yl)pyrimidin-4-yl]amino}-4-ethyl-1-methyl-1H-pyrazol-3-yl)benzonitrile

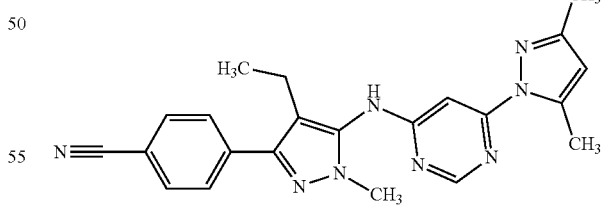

A microwave vial was charged 4-chloro-6-(3,5-dimethyl-1H-pyrazol-1-yl)pyrimidine (125 mg, 599 mol), 4-(5-amino-4-ethyl-1-methyl-1H-pyrazol-3-yl)benzonitrile (190 mg, 839 µmol) and sodium phenolate (104 mg, 899 µmol) and the contents were suspended in 1,4-dioxane (2.5 ml, 29 mmol). The reaction mixture was degassed with Ar for 3 min. Tris(dibenzylidenaceton)dipalladium (7.13 mg, 7.79 mol) and Xantphos (10.4 mg, 18.0 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were dried over Extrelut NT3 and concentrated under reduced pressure. The crude product was purified by preparative HPLC (method 1) to yield the desired product (88.8 mg, 37%).

LC-MS (method 9): $R_t$=1.06 min; MS (ESIpos): m/z=399 [M+H]$^+$ $^1$H-NMR (400 MHz, dimethylsulfoxide-d6) δ [ppm]: −0.008 (0.71), 0.991 (3.93), 1.010 (8.75), 1.028 (4.11), 2.178 (3.93), 2.524 (2.90), 2.561 (0.97), 2.633 (16.00), 3.675 (13.09), 5.755 (0.70), 6.150 (3.36), 7.848 (2.00), 7.869 (5.81), 7.890 (7.92), 7.911 (2.56), 8.469 (1.15), 9.415 (1.88).

Example 210

4-(3-{[6-(3,5-dimethyl-1H-pyrazol-1-yl)pyrimidin-4-yl]amino}-4-ethyl-1-methyl-1H-pyrazol-5-yl)benzonitrile

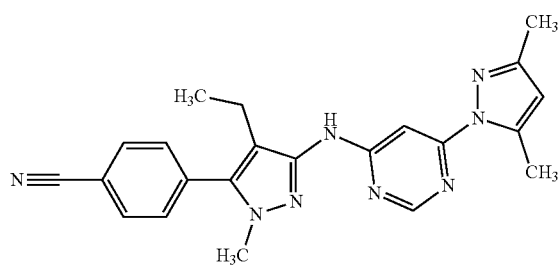 [SMILES: CCc1c(Nc2cc(-n3nc(C)cc3C)ncn2)nn(C)c1-c1ccc(C#N)cc1]

A microwave vial was charged 4-chloro-6-(3,5-dimethyl-1H-pyrazol-1-yl)pyrimidine (95.0 mg, 455 mol), 4-(3-amino-4-ethyl-1-methyl-1H-pyrazol-5-yl)benzonitrile (124 mg, 546 μmol) and sodium phenolate (79.3 mg, 683 μmol) and the contents were suspended in 1,4-dioxane (1.9 ml, 22 mmol). The reaction mixture was degassed with Ar for 3 min. Tris(dibenzylidenaceton)dipalladium (5.42 mg, 5.92 mol) and Xantphos (7.90 mg, 13.7 μmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×).

The combined organic phases were dried over Extrelut NT3 and concentrated under reduced pressure.

The crude product was purified by preparative HPLC (method 6) to yield the desired product (30.1 mg, 15%).

LC-MS (method 9): $R_t$=1.03 min; MS (ESIpos): m/z=399 [M+H]$^+$ $^1$H-NMR (400 MHz, dimethylsulfoxide-d6) δ [ppm]: −0.008 (0.96), 0.008 (0.82), 0.874 (3.47), 0.893 (7.92), 0.911 (3.58), 2.181 (14.36), 2.319 (0.93), 2.337 (2.73), 2.356 (2.56), 2.367 (0.54), 2.375 (0.84), 2.524 (0.45), 2.623 (12.99), 3.697 (16.00), 6.132 (3.44), 7.338 (2.77), 7.689 (4.16), 7.710 (4.86), 8.007 (4.61), 8.027 (4.13), 8.445 (2.99), 9.371 (2.84).

Example 211

4-(1,4-dimethyl-5-{[6-(3-methyl-4-oxo-5,6-dihydro-cyclopenta[c]pyrazol-1(4H)-yl)pyrimidin-4-yl]amino}-1H-pyrazol-3-yl)benzonitrile

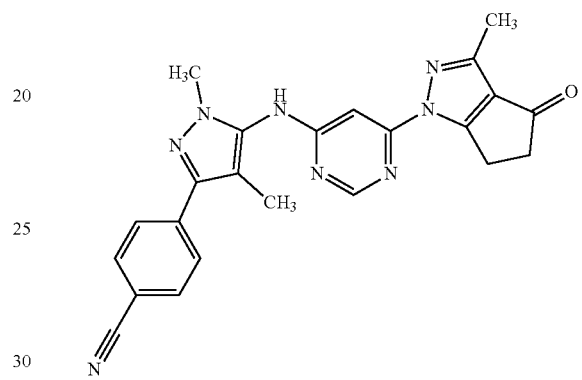

A microwave vial was charged with 4-(5-amino-1,4-dimethyl-1H-pyrazol-3-yl)benzonitrile (93.9 mg, 442 μmol), 1-(6-chloropyrimidin-4-yl)-3-methyl-5,6-dihydrocyclopenta[c]pyrazol-4(1H)-one (100 mg, 402 μmol) and sodium phenolate (51.4 mg, 442 μmol) and the contents were suspended in 1,4-dioxane (1.2 mL). The reaction mixture was degassed with Ar for 3 min. Tris(dibenzylideneacetone)dipalladium (5.52 mg, 6.03 μmol) and XantPhos (6.98 mg, 12.1 μmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (X-Bridge C18 5 m 100×30 mm, solvent A: water, solvent B: acetonitrile, flow: 65 mL/min plus 5 mL/min 2% NH3 in water, gradient: 0-2 min 10% solvent B, 2-2.2 min to 30% solvent B, 2.2-7 min to 70% solvent B, 7-7.5 min to 92% solvent B, 7.5-9 min at 92% B) to yield the desired product (17.5 mg, 9% yield).

LC-MS (method 10): $R_t$=1.71 min; MS (ESIpos): m/z=425 [M+H]$^+$ $^1$H-NMR (400 MHz, dimethylsulfoxide-d6) δ [ppm]: −0.008 (2.37), 0.008 (2.19), 2.079 (16.00), 2.308 (1.90), 2.365 (1.30), 2.670 (0.43), 2.861 (0.45), 2.941 (1.71), 2.947 (1.71), 2.953 (1.96), 2.960 (1.79), 2.966 (1.84), 3.340 (2.11), 3.347 (1.93), 3.353 (2.06), 3.358 (1.85), 3.365 (1.79), 3.704 (6.45), 7.902 (11.30), 8.531 (0.42).

Example 212

4-[1-(2-cyclopropylethyl)-3-{[6-(3,5-dimethyl-1H-pyrazol-1-yl)pyrimidin-4-yl]amino}-4-methyl-1H-pyrazol-5-yl]benzonitrile

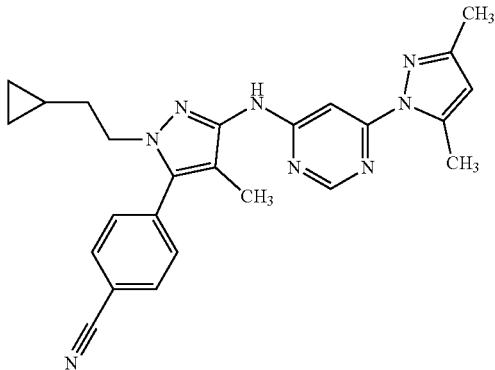 [SMILES: Cc1cc(C)n(-c2cc(Nc3nn(CCC4CC4)c(-c4ccc(C#N)cc4)c3C)ncn2)n1]

A microwave vial was charged with 4-[3-amino-1-(2-cyclopropylethyl)-4-methyl-1H-pyrazol-5-yl]benzonitrile (50.0 mg, 188 µmol), 4-chloro-6-(3,5-dimethyl-1H-pyrazol-1-yl)pyrimidine (43.1 mg, 206 µmol) and sodium phenolate (24.0 mg, 206 µmol) and the contents were suspended in 1,4-dioxane (0.6 mL). The reaction mixture was degassed with Ar for 3 min. Tris(dibenzylideneacetone)dipalladium (3.26 mg, 5.63 µmol) and XantPhos (2.58 mg, 2.82 µmol) were added and the reaction mixture was degassed again for 1 min. The vial was sealed and heated at 85° C. overnight while vigorously stirring. After cooling to ambient temperature, the reaction mixture was filtered and concentrated. The residue was redissolved in dimethylsulfoxide and purified by preparative HPLC (method 6) to yield the desired product (17.5 mg, 21% yield).

$^1$H-NMR (400 MHz, dimethylsulfoxide-d6) δ [ppm]: −0.149 (0.60), −0.135 (0.83), −0.124 (3.18), −0.112 (3.34), −0.098 (0.89), −0.008 (5.08), 0.008 (3.84), 0.146 (0.50), 0.275 (0.85), 0.289 (2.57), 0.295 (1.41), 0.305 (2.86), 0.309 (2.72), 0.319 (0.89), 0.472 (0.68), 0.491 (0.89), 1.564 (1.06), 1.581 (3.05), 1.598 (3.03), 1.615 (1.06), 1.878 (14.15), 2.168 (16.00), 2.328 (0.73), 2.366 (0.75), 2.624 (14.71), 2.670 (0.77), 2.710 (0.79), 4.023 (2.03), 4.039 (4.09), 4.057 (1.97), 6.126 (4.13), 7.562 (0.83), 7.662 (4.88), 7.684 (5.52), 8.003 (5.42), 8.024 (4.75), 8.461 (3.74), 9.475 (3.44).

Example 213 ethyl 1-(6-{[3-(4-cyanophenyl)-1,4-dimethyl-1H-pyrazol-5-yl]amino}pyrimidin-4-yl)-3,5-dimethyl-1H-pyrazole-4-carboxylate

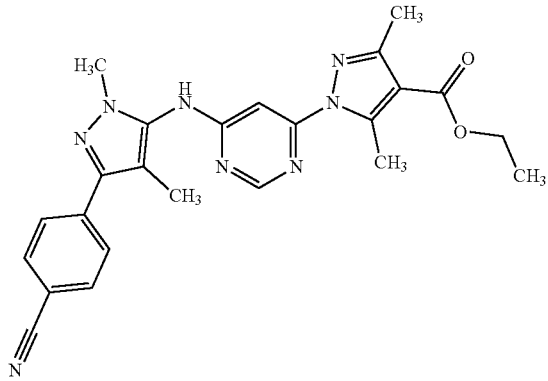 [SMILES: CCOC(=O)c1c(C)nn(-c2cc(Nc3c(C)c(-c4ccc(C#N)cc4)nn3C)ncn2)c1C]

A microwave vial was charged ethyl 1-(6-chloropyrimidin-4-yl)-3,5-dimethyl-1H-pyrazole-4-carboxylate (250 mg, 891 µmol), 4-(5-amino-1,4-dimethyl-1H-pyrazol-3-yl)benzonitrile (208 mg, 980 mol) and sodium phenolate (155 mg, 1.34 mmol) and the contents were suspended in 1,4-dioxane (4.0 ml, 46 mmol). The reaction mixture was degassed with Ar for 3 min. Tris(dibenzylidenaceton)dipalladium (10.6 mg, 11.6 µmol) and Xantphos (15.5 mg, 26.7 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were washed with brine, dried over sodium sulfate and concentrated under reduced pressure. The crude product was triturated with diethyl ether, the precipitate was collected by filtration, dried and purified by preparative HPLC (method: column: Reprosil C18; 10 µm; 125×30 mm/flow: 50 mL/min/solvent: A=water (0.1% formic acid), B=acetonitrile/gradient: 0.00-4.25 min=20% B, 4.50 min=30% B, 19.00-22.50 min=100% B, 22.75-25.00 min=20%) to yield the desired product (141 mg, 35%).

LC-MS (method 10): $R_t$=2.07 min; MS (ESIpos): m/z=457 [M+H]$^+$ $^1$H-NMR (400 MHz, dimethylsulfoxide-d6) δ [ppm]: 1.290 (3.11), 1.307 (6.43), 1.325 (3.17), 2.076 (14.85), 2.379 (2.45), 2.911 (11.63), 3.702 (8.12), 4.230 (0.92), 4.248 (2.80), 4.266 (2.77), 4.284 (0.90), 7.896 (16.00), 8.546 (0.48), 9.635 (0.96).

Example 214

4-(4-methoxy-3-{[6-(3-methyl-1H-pyrazolo[3,4-c]pyridin-1-yl)pyrimidin-4-yl]amino}-1H-pyrazol-5-yl)benzonitrile

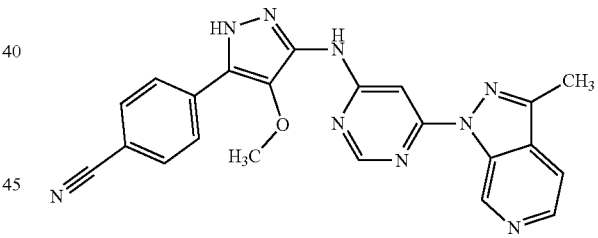

A microwave vial was charged 1-(6-chloropyrimidin-4-yl)-3-methyl-1H-pyrazolo[3,4-c]pyridine (104 mg, 424 µmol), 4-(3-amino-4-methoxy-1H-pyrazol-5-yl)benzonitrile (100 mg, 467 µmol) and sodium phenolate (54.2 mg, 467 µmol) and the contents were suspended in 1,4-dioxane (3.0 ml, 35 mmol). The reaction mixture was degassed with Ar for 3 min. Tris(dibenzylidenaceton)dipalladium (5.05 mg, 5.52 mol) and Xantphos (7.37 mg, 12.7 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) and subsequently by flash-chromatography (column: Biotage KP-Sil 10 g; solvent A: dichloromethane 98%, solvent B: methanol 2%) to yield the desired product (3.7 mg, 2%).

LC-MS (method 10): R$_t$=2.16 min; MS (ESIpos): m/z=424 [M+H]$^+$ $^1$H-NMR (400 MHz, dimethylsulfoxide-d6) δ [ppm]: −0.149 (1.05), −0.008 (14.55), 0.008 (9.18), 0.146 (1.05), 1.235 (0.41), 1.780 (1.05), 2.031 (0.86), 2.214 (1.95), 2.227 (0.95), 2.328 (1.00), 2.366 (1.00), 2.524 (4.36), 2.670 (1.27), 2.686 (2.23), 2.711 (15.05), 3.162 (0.64), 3.175 (0.59), 3.729 (16.00), 6.975 (3.91), 7.673 (0.59), 7.971 (5.55), 7.983 (2.64), 7.986 (2.73), 7.993 (4.73), 8.158 (4.73), 8.179 (3.55), 8.268 (3.73), 8.552 (2.86), 8.565 (2.64), 8.837 (0.55), 9.063 (3.82), 9.065 (3.45), 10.095 (3.00).

Example 215

1-[1-(6-{[4-ethyl-5-(4-fluorophenyl)-1-methyl-1H-pyrazol-3-yl]amino}pyrimidin-4-yl)-3,5-dimethyl-1H-pyrazol-4-yl]cyclobutanol

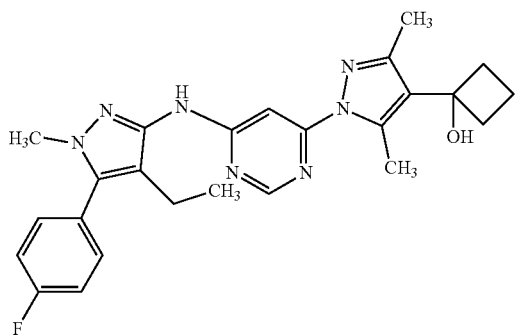 [SMILES: CCc1c(Nc2cc(-n3nc(C)c(C4(O)CCC4)c3C)ncn2)nn(C)c1-c1ccc(F)cc1]

Under an argon atmosphere, 6-(4-bromo-3,5-dimethyl-1H-pyrazol-1-yl)-N-[4-ethyl-5-(4-fluorophenyl)-1-methyl-1H-pyrazol-3-yl]pyrimidin-4-amine (24.2 mg, 51.5 μmol) was dissolved in tetrahydrofuran (0.5 mL) and cooled to −15° C. A solution of i-PrMgCl*LiCl (99 μl, 1.3 M, 130 μmol) was added slowly and stirred for 20 min at −15° C. and 50 min at 0° C. cyclobutanone (7.7 μl, 100 μmol) was then added at 0° C. and the reaction mixture was stirred for 15 min. A second aliquot of cyclobutanone (7.7 μl, 100 μmol) was added and the reaction mixture stirred for further 40 min. It was then quenched by careful addition of sat. aqueous ammonium chloride solution, diluted with water and extracted with ethyl acetate. The organic phase extract was washed with brine, dried over sodium sulfate and concentrated. The residue was purified by flash column chromatography (KP Sil 10 g, cyclohexane/ethyl acetate gradient 88/12 to 0/100) to yield the desired product (4.0 mg, 17% yield).

LC-MS (method 10): R$_t$=2.01 min; MS (ESIpos): m/z=462 [M+H]$^+$ $^1$H-NMR (500 MHz, dimethylsulfoxide-d6) δ [ppm]: −0.007 (1.37), 0.006 (0.92), 0.872 (3.36), 0.887 (7.33), 0.902 (3.32), 1.161 (2.11), 1.175 (4.27), 1.189 (2.15), 1.734 (0.54), 1.744 (0.45), 1.754 (0.67), 1.988 (8.05), 2.118 (0.79), 2.163 (0.87), 2.181 (13.77), 2.201 (0.53), 2.215 (0.53), 2.228 (1.09), 2.234 (0.79), 2.245 (1.34), 2.252 (1.12), 2.261 (1.01), 2.286 (0.78), 2.301 (2.22), 2.316 (2.13), 2.327 (1.08), 2.519 (1.70), 2.523 (1.48), 2.579 (14.13), 2.613 (0.53), 2.706 (0.79), 3.643 (16.00), 4.008 (0.62), 4.023 (1.85), 4.037 (1.84), 4.051 (0.60), 5.149 (5.43), 5.754 (1.53), 7.304 (1.66), 7.360 (2.06), 7.364 (0.79), 7.378 (4.43), 7.391 (0.87), 7.395 (2.53), 7.499 (2.49), 7.504 (1.14), 7.510 (2.76), 7.517 (2.26), 7.523 (0.92), 7.528 (1.93), 8.440 (2.94), 9.324 (1.76).

Example 216

4-[5-({6-[5-(difluoromethyl)-3-methyl-1H-pyrazol-1-yl]pyrimidin-4-yl}amino)-4-ethyl-1-methyl-1H-pyrazol-3-yl]benzonitrile

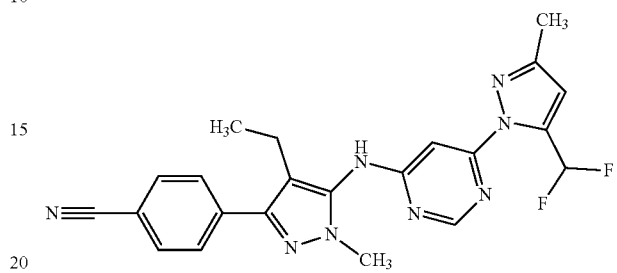

A microwave vial was charged 4-chloro-6-[5-(difluoromethyl)-3-methyl-H-pyrazol-1-yl]pyrimidine (125 mg, 511 μmol), 4-(5-amino-4-ethyl-1-methyl-1H-pyrazol-3-yl)benzonitrile (162 mg, 715 μmol) and sodium phenolate (89.0 mg, 766 μmol) and the contents were suspended in 1,4-dioxane (2.1 ml, 25 mmol). The reaction mixture was degassed with Ar for 3 min. Tris(dibenzylidenaceton)dipalladium (6.08 mg, 6.64 μmol) and Xantphos (8.87 mg, 15.3 μmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were dried over Extrelut NT3 and concentrated under reduced pressure. The crude product was purified by preparative HPLC (method 6) to yield the desired product (89.0 mg, 38%).

LC-MS (method 10): R$_t$=2.13 min; MS (ESIpos): m/z=435 [M+H]$^+$ $^1$H-NMR (400 MHz, dimethylsulfoxide-d6) δ [ppm]: 0.990 (6.46), 1.009 (13.80), 1.027 (6.69), 1.567 (0.92), 2.087 (0.41), 2.292 (4.45), 2.368 (0.40), 2.563 (1.57), 2.705 (0.61), 3.682 (16.00), 6.791 (4.58), 7.684 (2.18), 7.820 (4.47), 7.851 (3.15), 7.871 (7.37), 7.892 (10.37), 7.912 (3.55), 7.956 (1.94), 8.499 (1.17), 9.597 (1.60).

Example 217

4-[3-({6-[5-(difluoromethyl)-3-methyl-1H-pyrazol-1-yl]pyrimidin-4-yl}amino)-4-ethyl-1-methyl-1H-pyrazol-5-yl]benzonitrile

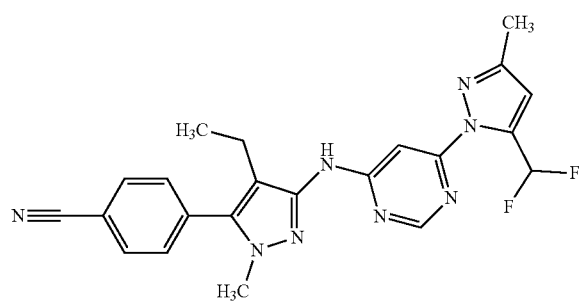 [SMILES: CCc1c(Nc2cc(-n3nc(C)cc3C(F)F)ncn2)nn(C)c1-c1ccc(C#N)cc1]

A microwave vial was charged 4-chloro-6-[5-(difluoromethyl)-3-methyl-H-pyrazol-1-yl]pyrimidine (110 mg, 450 µmol), 4-(3-amino-4-ethyl-1-methyl-1H-pyrazol-5-yl)benzonitrile (122 mg, 540 µmol) and sodium phenolate (78.3 mg, 674 µmol) and the contents were suspended in 1,4-dioxane (1.9 ml, 22 mmol). The reaction mixture was degassed with Ar for 3 min. Tris(dibenzylidenaceton)dipalladium (5.35 mg, 5.85 µmol) and Xantphos (7.81 mg, 13.5 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were dried over Extrelut NT3 and concentrated under reduced pressure. The crude product was purified by preparative HPLC (method 6) and subsequently by flash-chromatography (column: Biotage KP-Sil 10 g; dichloromethane/ethyl acetate) to yield the desired product (58.4 mg, 28%).

LC-MS (method 10): $R_t$=2.13 min; MS (ESIpos): m/z=435 [M+H]$^+$ $^1$H-NMR (400 MHz, dimethylsulfoxide-d6) δ [ppm]: −0.008 (2.53), 0.008 (2.42), 0.874 (3.44), 0.893 (7.91), 0.911 (3.56), 1.566 (0.79), 2.293 (13.66), 2.324 (0.92), 2.342 (2.31), 2.361 (2.24), 2.380 (0.76), 3.695 (0.80), 3.708 (16.00), 6.772 (4.01), 7.392 (1.61), 7.695 (4.64), 7.716 (4.99), 7.827 (2.48), 7.963 (1.06), 8.010 (4.98), 8.031 (4.32), 8.477 (3.05), 9.585 (1.73).

Example 218

N-[4-chloro-1-(cyclopropylmethyl)-3-(4-fluorophenyl)-1H-pyrazol-5-yl]-6-(3-methyl-1H-pyrazolo[3,4-c]pyridin-1-yl)pyrimidin-4-amine

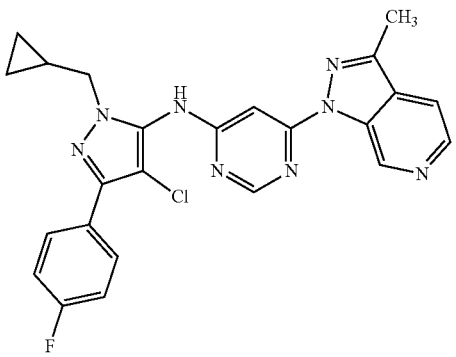 [SMILES: Cc1nn(-c2cc(Nc3c(Cl)c(-c4ccc(F)cc4)nn3CC3CC3)ncn2)c2cnccc12]

A microwave vial was charged 1-(6-chloropyrimidin-4-yl)-3-methyl-1H-pyrazolo[3,4-c]pyridine (75.0 mg, 305 µmol), 4-chloro-1-(cyclopropylmethyl)-3-(4-fluorophenyl)-1H-pyrazol-5-amine (89.2 mg, 336 µmol) and sodium phenolate (46.1 mg, 397 µmol) and the contents were suspended in 1,4-dioxane (1.9 ml, 22 mmol). The reaction mixture was degassed with Ar for 3 min. Tris(dibenzylidenaceton)dipalladium (3.63 mg, 3.97 µmol) and Xantphos (5.30 mg, 9.16 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were dried over Extrelut NT3 and concentrated under reduced pressure. The crude product was purified by preparative HPLC (method 6) and subsequently by flash-chromatography on silica gel (SNAP KP-Sil 10 g, dichloromethane/ethyl acetate) to yield the desired product (22.3 mg, 15%).

LC-MS (method 10): $R_t$=2.19 min; MS (ESIpos): m/z=475 [M+H]$^+$ $^1$H-NMR (400 MHz, dimethylsulfoxide-d6) δ [ppm]: 0.008 (1.34), 0.328 (1.73), 0.339 (6.54), 0.352 (6.92), 0.364 (1.93), 0.456 (2.04), 0.467 (5.77), 0.486 (5.91), 0.501 (1.21), 1.232 (2.13), 1.240 (1.75), 1.252 (2.31), 1.263 (1.45), 1.270 (1.48), 1.282 (0.89), 1.300 (0.44), 2.629 (16.00), 2.671 (0.59), 3.927 (6.78), 3.944 (6.46), 7.320 (4.71), 7.342 (8.97), 7.365 (4.54), 7.902 (4.79), 7.919 (7.54), 7.933 (5.29), 7.940 (4.72), 7.954 (3.69), 8.483 (6.13), 8.497 (5.72), 8.654 (3.33), 9.762 (3.04), 10.037 (7.37).

Example 219 ethyl 1-(6-{[1-(4-cyanophenyl)-3,5-dimethyl-1H-pyrazol-4-yl]amino}pyrimidin-4-yl)-3,5-dimethyl-1H-pyrazole-4-carboxylate

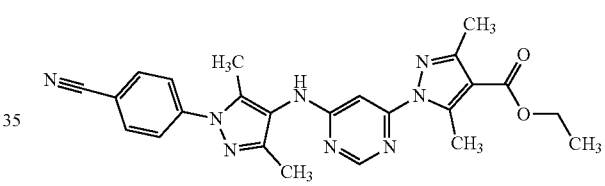

A microwave vial was charged ethyl 1-(6-chloropyrimidin-4-yl)-3,5-dimethyl-1H-pyrazole-4-carboxylate (120 mg, 428 µmol), 4-(4-amino-3,5-dimethyl-1H-pyrazol-1-yl)benzonitrile (100 mg, 471 µmol) and sodium phenolate (54.7 mg, 471 µmol) and the contents were suspended in 1,4-dioxane (3.1 ml, 36 mmol). The reaction mixture was degassed with Ar for 3 min. Tris(dibenzylidenaceton)dipalladium (5.10 mg, 5.57 µmol) and Xantphos (7.43 mg, 12.8 µmol) were added and the reaction mixture was degassed again for 1 min. The vial was sealed and heated at 85° C. overnight while vigorously stirring. After cooling to ambient temperature, the reaction mixture was diluted with saturated sodium bicarbonate solution and extracted with ethyl acetate (2×). The combined organic phases were dried over sodium sulfate and concentrated under reduced pressure. The remaining residue was taken up in dichloromethane, an precipitate occurred which was collected by filtration and dried to yield the desired product (80.0 mg, 39%).

LC-MS (method 10): $R_t$=2.02 min; MS (ESIpos): m/z=457 [M+H]$^+$ $^1$H-NMR (400 MHz, dimethylsulfoxide-d6) δ [ppm]: −0.008 (1.16), 1.287 (2.63), 1.304 (5.18), 1.322 (2.69), 2.075 (0.68), 2.111 (16.00), 2.284 (2.58), 2.293 (13.09), 2.369 (1.46), 2.387 (1.54), 2.888 (7.26), 4.226 (0.83), 4.243 (2.30), 4.261 (2.32), 4.278 (0.86), 7.686 (0.44), 7.807 (1.92), 7.828 (2.42), 7.858 (0.53), 7.979 (3.80), 8.001 (3.12), 9.120 (0.95).

Example 220

3-[1-(6-{[4-ethyl-5-(4-fluorophenyl)-1-methyl-1H-pyrazol-3-yl]amino}pyrimidin-4-yl)-3,5-dimethyl-1H-pyrazol-4-yl]oxetan-3-ol

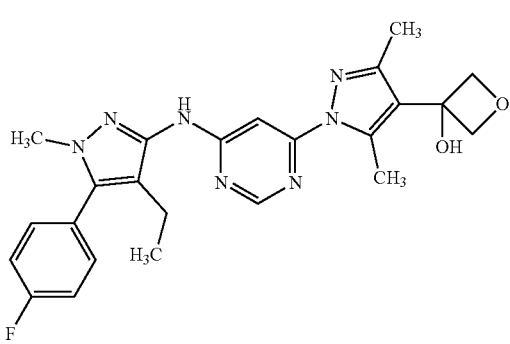 [SMILES: CCc1c(Nc2cc(-n3nc(C)c(C4(O)COC4)c3C)ncn2)nn(C)c1-c1ccc(F)cc1]

Under an argon atmosphere, 6-(4-bromo-3,5-dimethyl-1H-pyrazol-1-yl)-N-[4-ethyl-5-(4-fluorophenyl)-1-methyl-1H-pyrazol-3-yl]pyrimidin-4-amine (45.0 mg, 95.7 µmol) was dissolved in tetrahydrofuran (0.95 mL) and cooled to −15° C. A solution of i-PrMgCl*LiCl (180 µl, 1.3 M, 240 µmol) was added slowly and stirred for 50 min at −15° C., when a second aliquot of i-PrMgCl*LiCl (180 µl, 1.3 M, 240 µmol) was added. After 50 min stirring at −15° C., (180 µl, 1.3 M, 240 µmol) was added at ambient temperature. The reaction mixture was stirred for 50 min. It was then quenched by careful addition of sat. aqueous ammonium chloride solution, diluted with water and extracted with ethyl acetate. The organic phase extract was washed with brine, dried over sodium sulfate and concentrated. The residue was purified by flash column chromatography (KP Sil 25 g, dichloromethane/methanol 98/2 to 90/10) to yield the desired product (5.0 mg, 10% yield).

LC-MS (method 10): $R_t$=1.67 min; MS (ESIpos): m/z=464 [M+H]$^+$ $^1$H-NMR (600 MHz, dimethylsulfoxide-d6) δ [ppm]: 0.692 (0.69), 0.703 (0.67), 0.729 (0.72), 0.740 (0.75), 0.811 (0.81), 0.822 (1.32), 0.832 (0.88), 0.842 (0.47), 0.854 (0.55), 0.876 (2.99), 0.888 (6.00), 0.901 (2.90), 1.237 (1.92), 1.424 (2.88), 1.543 (2.02), 2.065 (0.72), 2.108 (10.81), 2.161 (1.05), 2.292 (0.85), 2.305 (2.20), 2.317 (2.12), 2.330 (0.76), 2.485 (12.62), 2.612 (0.42), 2.910 (0.57), 3.568 (0.53), 3.643 (11.86), 4.411 (0.47), 4.421 (0.42), 4.542 (0.57), 4.658 (3.47), 4.669 (3.69), 5.012 (3.52), 5.023 (3.30), 5.396 (0.44), 5.747 (16.00), 5.953 (0.50), 5.995 (4.14), 7.329 (1.60), 7.361 (1.53), 7.375 (3.29), 7.390 (1.91), 7.499 (1.88), 7.508 (2.38), 7.522 (1.66), 7.901 (0.43), 8.455 (2.80), 9.350 (1.74).

Example 221

4-[5-{[6-(4-chloro-3,5-dimethyl-1H-pyrazol-1-yl)pyrimidin-4-yl]amino}-1-(2-cyclopropylethyl)-4-methyl-1H-pyrazol-3-yl]benzonitrile

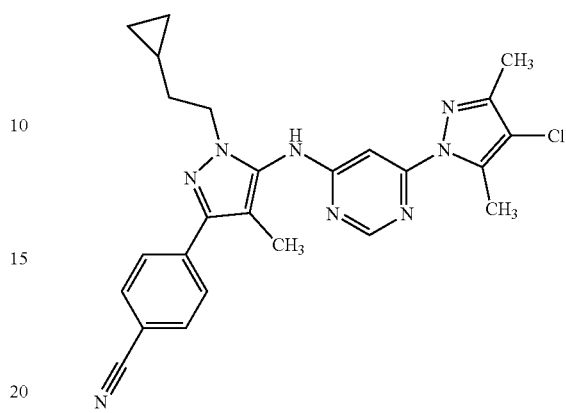

A microwave vial was charged with 4-[5-amino-1-(2-cyclopropylethyl)-4-methyl-1H-pyrazol-3-yl]benzonitrile (50.0 mg, 188 µmol), 4-chloro-6-(4-chloro-3,5-dimethyl-1H-pyrazol-1-yl)pyrimidine (50.2 mg, 206 µmol) and sodium phenolate (24.0 mg, 206 µmol) and the contents were suspended in 1,4-dioxane (0.58 mL). The reaction mixture was degassed with Ar for 3 min. Tris(dibenzylideneacetone)dipalladium (2.58 mg, 2.82 µmol) and XantPhos (3.26 mg, 5.63 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 8) to yield the desired product (32 mg, 36% yield).

$^1$H-NMR (400 MHz, dimethylsulfoxide-d6) δ [ppm]: −0.149 (0.82), −0.063 (3.04), −0.054 (3.08), −0.008 (7.01), 0.008 (6.29), 0.146 (0.80), 0.306 (1.94), 0.323 (2.08), 0.622 (0.78), 1.356 (0.72), 1.629 (0.96), 1.647 (2.70), 1.665 (2.64), 1.682 (0.94), 2.058 (15.72), 2.073 (1.14), 2.208 (2.14), 2.328 (0.66), 2.366 (0.64), 2.648 (16.00), 2.670 (0.82), 2.710 (0.62), 4.036 (1.94), 7.897 (12.34), 7.921 (0.66), 8.498 (0.50), 9.515 (0.50).

Example 222

4-[3-{[6-(4-chloro-3,5-dimethyl-1H-pyrazol-1-yl)pyrimidin-4-yl]amino}-1-(2-cyclopropylethyl)-4-methyl-1H-pyrazol-5-yl]benzonitrile

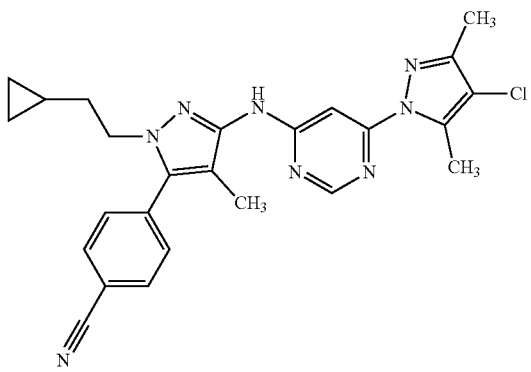 [SMILES: Cc1nn(-c2cc(Nc3nn(CCC4CC4)c(-c4ccc(C#N)cc4)c3C)ncn2)c(C)c1Cl]

A microwave vial was charged with 4-[3-amino-1-(2-cyclopropylethyl)-4-methyl-1H-pyrazol-5-yl]benzonitrile (44.0 mg, 165 μmol), 4-chloro-6-(4-chloro-3,5-dimethyl-1H-pyrazol-1-yl)pyrimidine (44.2 mg, 182 μmol) and sodium phenolate (21.1 mg, 182 μmol) and the contents were suspended in 1,4-dioxane (0.5 mL). The reaction mixture was degassed with Ar for 3 min. Tris(dibenzylideneacetone)dipalladium (2.27 mg, 2.48 μmol) and XantPhos (2.87 mg, 4.96 μmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 8) to yield the desired product (25 mg, 33% yield).

LC-MS (method 11): $R_t$=1.67 min; MS (ESIpos): m/z=473 [M+H]$^+$ $^1$H-NMR (400 MHz, dimethylsulfoxide-d6) δ [ppm]: −0.149 (0.47), −0.137 (0.67), −0.126 (2.56), −0.114 (2.70), −0.101 (0.78), −0.054 (0.41), −0.008 (3.63), 0.008 (3.13), 0.146 (0.41), 0.274 (0.73), 0.284 (1.96), 0.288 (2.12), 0.294 (1.24), 0.304 (2.55), 0.308 (2.37), 0.318 (0.93), 0.470 (0.54), 0.489 (0.75), 1.356 (0.89), 1.562 (0.83), 1.579 (2.43), 1.596 (2.42), 1.613 (0.84), 1.881 (10.37), 2.059 (1.74), 2.073 (0.95), 2.205 (13.73), 2.367 (0.46), 2.524 (0.97), 2.644 (16.00), 2.670 (0.52), 2.711 (0.47), 4.023 (1.73), 4.040 (3.51), 4.057 (1.72), 7.662 (4.00), 7.683 (4.65), 7.897 (1.35), 8.004 (4.50), 8.025 (4.09), 8.498 (2.89), 9.603 (2.32).

Example 223

N-[4-ethyl-5-(4-fluorophenyl)-1-methyl-1H-pyrazol-3-yl]-6-(3-methyl-1H-pyrazolo[4,3-b]pyridin-1-yl)pyrimidin-4-amine

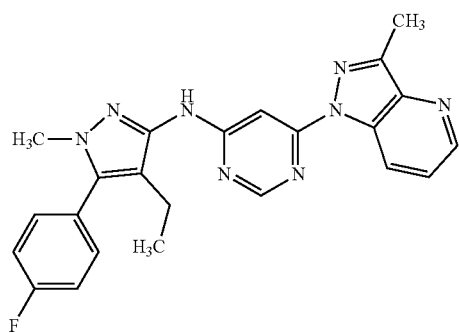 [SMILES: CCc1c(Nc2cc(-n3nc(C)c4ncccc43)ncn2)nn(C)c1-c1ccc(F)cc1]

A microwave vial was charged with 4-ethyl-5-(4-fluorophenyl)-1-methyl-1H-pyrazol-3-amine (100 mg, 456 μmol), 1-(6-chloropyrimidin-4-yl)-3-methyl-1H-pyrazolo[4,3-b]pyridine (123 mg, 502 μmol) and sodium phenolate (63.5 mg, 547 μmol) and the contents were suspended in 1,4-dioxane (1.3 mL). The reaction mixture was degassed with Ar for 3 min. Tris(dibenzylideneacetone)dipalladium (6.26 mg, 6.84 μmol) and XantPhos (7.92 mg, 13.7 μmol) were added and the reaction mixture was degassed again for 1 min. The vial was sealed and heated at 90° C. overnight while vigorously shaking. After cooling to ambient temperature, the reaction mixture was filtered and concentrated. The residue was redissolved in dimethylsulfoxide and purified by preparative HPLC (method 3) to yield the desired product (105 mg, 51% yield).

LC-MS (method 9): Rt=1.12 min; MS (ESIpos): m/z=429 [M+H]$^+$ $^1$H-NMR (500 MHz, dimethylsulfoxide-d6) δ [ppm]: −0.007 (1.19), 0.007 (0.79), 0.892 (3.29), 0.908 (7.42), 0.922 (3.26), 2.321 (0.71), 2.336 (2.01), 2.351 (1.95), 2.366 (0.72), 2.633 (16.00), 3.688 (13.85), 7.374 (2.05), 7.378 (1.07), 7.388 (1.01), 7.392 (4.22), 7.397 (0.90), 7.406 (0.81), 7.410 (2.41), 7.463 (0.53), 7.466 (0.53), 7.478 (0.41), 7.496 (1.05), 7.524 (2.46), 7.529 (1.03), 7.535 (2.55), 7.542 (2.08), 7.549 (0.83), 7.553 (1.79), 7.579 (1.86), 7.588 (1.79), 7.596 (1.75), 7.605 (1.79), 8.560 (2.81), 8.657 (2.04), 8.660 (2.06), 8.666 (1.99), 8.669 (1.85), 9.015 (1.97), 9.018 (1.97), 9.033 (1.89), 9.035 (1.73), 9.435 (1.86).

Example 224

N-[4-ethyl-5-(4-fluorophenyl)-1-methyl-1H-pyrazol-3-yl]-6-(3-methyl-1H-pyrazolo[4,3-c]pyridin-1-yl)pyrimidin-4-amine

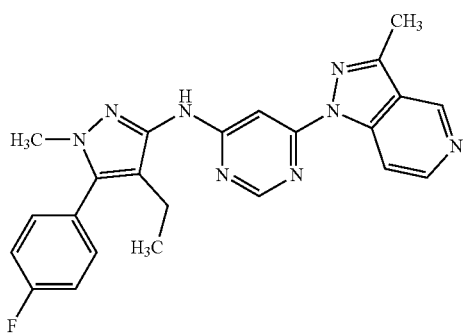 [SMILES: CCc1c(Nc2cc(-n3nc(C)c4cnccc43)ncn2)nn(C)c1-c1ccc(F)cc1]

A microwave vial was charged with 1-(6-chloropyrimidin-4-yl)-3-methyl-1H-pyrazolo[4,3-c]pyridine (123 mg, 502 μmol) and sodium phenolate (63.5 mg, 547 μmol) and the contents were suspended in 1,4-dioxane (1.3 mL). The reaction mixture was degassed with Ar for 3 min. Tris(dibenzylideneacetone)dipalladium (7.92 mg, 13.7 μmol), XantPhos (6.26 mg, 6.84 μmol) and 4-ethyl-5-(4-fluorophenyl)-1-methyl-1H-pyrazol-3-amine (100 mg, 456 μmol) were added and the reaction mixture was degassed again for 1 min. The reaction mixture was stirred at 90° C. bath temperature overnight. After cooling to ambient temperature, the reaction mixture was filtered and concentrated. The residue was redissolved in dimethylsulfoxide and purified by preparative HPLC (method 7) to yield the desired product (5 mg, 2% yield).

LC-MS (method 10): $R_t$=1.63 min; MS (ESIpos): m/z=429 [M+H]$^+$ $^1$H-NMR (500 MHz, dimethylsulfoxide-d6) δ [ppm]: −0.120 (0.44), −0.007 (4.92), 0.006 (3.32), 0.117 (0.44), 0.887 (3.48), 0.902 (7.95), 0.917 (3.58), 0.995 (0.65), 2.316 (0.74), 2.331 (2.09), 2.346 (2.06), 2.362 (1.36), 2.519 (1.32), 2.523 (0.94), 2.636 (0.86), 2.670 (16.00), 2.675 (3.47), 2.711 (0.68), 3.401 (1.00), 3.682 (14.85), 7.285 (0.67), 7.293 (0.47), 7.308 (0.47), 7.372 (2.29), 7.390 (4.58), 7.408 (2.58), 7.494 (1.06), 7.505 (0.79), 7.520 (2.85), 7.531 (2.85), 7.538 (2.36), 7.544 (0.98), 7.549 (1.98), 8.556 (1.06), 8.568 (4.18), 8.570 (4.27), 8.574 (6.62), 8.578 (3.12), 8.586 (1.47), 8.636 (0.48), 8.648 (0.48), 8.814 (0.58), 9.191 (4.15), 9.193 (4.05), 9.231 (0.53), 9.469 (1.64).

Example 225

N-[1-(cyclopropylmethyl)-4-ethyl-3-(4-fluorophenyl)-1H-pyrazol-5-yl]-6-[3,5-dimethyl-4-(5-methyl-1,3,4-oxadiazol-2-yl)-1H-pyrazol-1-yl]pyrimidin-4-amine

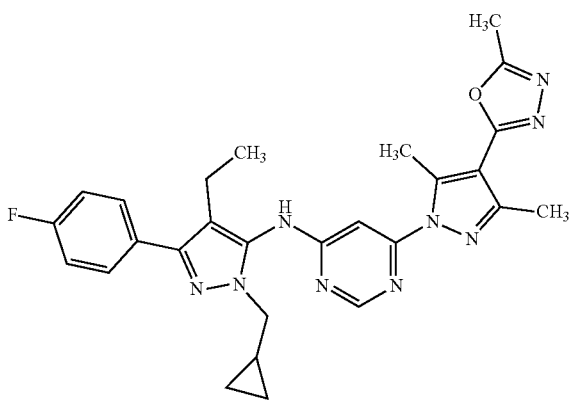 [SMILES: CCc1c(-c2ccc(F)cc2)nn(CC2CC2)c1Nc1cc(-n2nc(C)c(-c3nnc(C)o3)c2C)ncn1]

A solution of N'-acetyl-1-(6-{[1-(cyclopropylmethyl)-4-ethyl-3-(4-fluorophenyl)-1H-pyrazol-5-yl]amino}pyrimidin-4-yl)-3,5-dimethyl-1H-pyrazole-4-carbohydrazide (95.4 mg, 179 µmol) in tetrahydrofuran (2.5 ml, 31 mmol) was treated with Burgess reagent (59.9 mg, 251 µmol) and stirred overnight at ambient temperature. The mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (49.1 mg, 53%).

LC-MS (method 10): $R_t$=2.15 min; MS (ESIpos): m/z=514 [M+H]$^+$ $^1$H-NMR (400 MHz, dimethylsulfoxide-d6) δ [ppm]: 0.304 (3.03), 0.314 (3.14), 0.442 (3.39), 0.462 (3.52), 0.983 (4.25), 1.002 (8.98), 1.020 (4.39), 1.181 (0.53), 1.193 (0.96), 1.200 (0.95), 1.212 (1.37), 1.231 (1.03), 1.426 (1.76), 2.369 (0.43), 2.469 (4.21), 2.571 (16.00), 2.973 (15.38), 3.808 (2.47), 3.822 (2.48), 3.991 (0.85), 7.258 (2.62), 7.280 (5.38), 7.302 (3.05), 7.692 (2.55), 8.543 (0.55), 9.489 (0.41).

Example 226

6-[3,5-dimethyl-4-(5-methyl-1,3,4-oxadiazol-2-yl)-1H-pyrazol-1-yl]-N-[4-ethyl-3-(4-fluorophenyl)-1-methyl-1H-pyrazol-5-yl]pyrimidin-4-amine

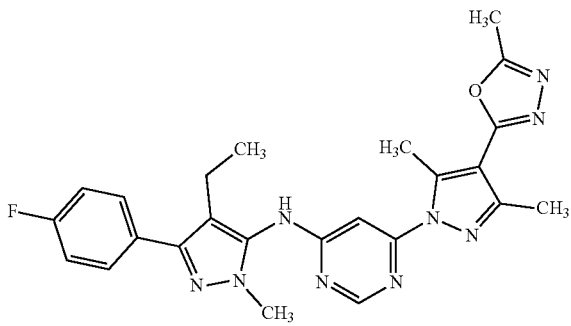 [SMILES: CCc1c(-c2ccc(F)cc2)nn(C)c1Nc1cc(-n2nc(C)c(-c3nnc(C)o3)c2C)ncn1]

A solution of N'-acetyl-1-(6-{[4-ethyl-3-(4-fluorophenyl)-1-methyl-1H-pyrazol-5-yl]amino}pyrimidin-4-yl)-3,5-dimethyl-1H-pyrazole-4-carbohydrazide (65.1 mg, 132 µmol) in tetrahydrofuran (2.5 ml, 31 mmol) was treated with Burgess reagent (44.2 mg, 185 µmol) and stirred overnight at ambient temperature. The mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (20.0 mg, 29%).

LC-MS (method 10): $R_t$=1.94 min; MS (ESIpos): m/z=474 [M+H]$^+$ $^1$H-NMR (400 MHz, dimethylsulfoxide-d6) δ [ppm]: −0.149 (0.52), 0.146 (0.42), 0.978 (4.01), 0.997 (8.45), 1.015 (4.11), 1.234 (0.60), 1.760 (0.46), 1.904 (0.83), 2.328 (0.98), 2.366 (0.81), 2.473 (5.09), 2.573 (16.00), 2.670 (1.02), 2.710 (0.79), 2.773 (1.00), 2.976 (15.46), 3.602 (0.50), 3.652 (10.06), 7.251 (2.32), 7.273 (4.78), 7.295 (2.73), 7.654 (1.81), 7.668 (2.50), 7.687 (1.79), 8.560 (0.75), 9.544 (0.94).

Example 227

4-[5-({6-[(±)-4-hydroxy-3,4-dimethyl-5,6-dihydrocyclopenta[c]pyrazol-1(4H)-yl]pyrimidin-4-yl}amino)-1,4-dimethyl-1H-pyrazol-3-yl]benzonitrile (Racemate)

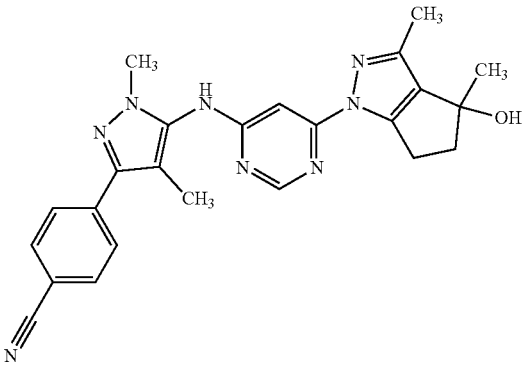 [SMILES: Cc1nn(-c2cc(Nc3c(C)c(-c4ccc(C#N)cc4)nn3C)ncn2)c2c1C(C)(O)CC2]

4-(1,4-dimethyl-5-{[6-(3-methyl-4-oxo-5,6-dihydrocyclopenta[c]pyrazol-1 (4H)-yl)pyrimidin-4-yl]amino}-1H-pyrazol-3-yl)benzonitrile (15.5 mg, 36.5 µmol) was dissolved in tetrahydrofuran (0.5 mL) and chilled with a water bath. A solution of methylmagnesium bromide (150 µl, 1.0 M, 150 µmol) was added. After 30 min stirring, a second aliquot of methylmagnesium bromide (80 µL, 1.0 M, 80 µmol) was added and the reaction mixture stirred for another 20 min. It was then quenched by careful addition of sat. aqueous ammonium chloride solution and extracted with ethyl acetate (3×). The combined organic phase extracts were dried over sodium sulfate and concentrated. The residue was purified by flash column chromatography (SNAP Ultra 10 g, dichloromethane/methanol gradient 98/2 to 96/4) to yield the desired product (4.8 mg, 27% yield).

LC-MS (method 10): $R_t$=1.66 min; MS (ESIpos): m/z=441 [M+H]$^+$ $^1$H-NMR (500 MHz, dimethylsulfoxide-d6) δ [ppm]: −0.120 (0.45), −0.007 (5.87), 0.007 (2.99), 1.235 (1.85), 1.451 (7.02), 1.478 (1.26), 2.067 (16.00), 2.079 (1.69), 2.201 (2.52), 2.362 (0.72), 2.438 (1.22), 2.448 (1.26), 2.456

(1.41), 2.465 (2.24), 2.606 (0.82), 2.635 (0.73), 2.976 (0.56), 2.997 (1.78), 3.010 (0.72), 3.020 (0.52), 3.103 (0.68), 3.120 (0.80), 3.129 (0.82), 3.147 (0.65), 3.568 (0.42), 3.690 (8.44), 4.966 (3.34), 5.754 (2.18), 7.899 (12.87), 8.432 (0.72), 9.453 (1.03).

Example 228

4-(1,4-dimethyl-3-{[6-(3-methyl-1H-pyrazolo[3,4-c]pyridin-1-yl)pyrimidin-4-yl]amino}-1H-pyrazol-5-yl)benzonitrile

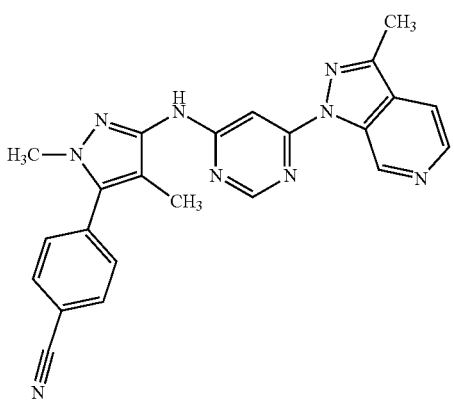 [SMILES: Cc1c(Nc2cc(-n3nc(C)c4ccncc43)ncn2)nn(C)c1-c1ccc(C#N)cc1]

Under an argon atmosphere, 1-(6-chloropyrimidin-4-yl)-3-methyl-1H-pyrazolo[3,4-c]pyridine (82.8 mg, 337 µmol) and sodium phenolate (53.3 mg, 459 µmol) were suspended in 1,4-dioxane (0.88 mL). The reaction mixture was degassed with Ar for 3 min. Tris(dibenzylideneacetone)dipalladium (4.21 mg, 4.59 µmol), XantPhos (5.32 mg, 9.19 µmol) and 4-(3-amino-1,4-dimethyl-1H-pyrazol-5-yl)benzonitrile (65.0 mg, 306 µmol) were added and the reaction mixture was degassed again for 1 min. The vial was sealed and heated at 90° C. overnight while vigorously shaking. After cooling to ambient temperature, the reaction mixture was diluted with dichloromethane and concentrated. It was redissolved in dimethylsulfoxide, filtered and purified by preparative HPLC (method 7) to yield the desired product (41 mg, 32% yield).

LC-MS (method 10): $R_t$=1.67 min; MS (ESIpos): m/z=422 [M+H]$^+$ $^1$H-NMR (400 MHz, dimethylsulfoxide-d6) δ [ppm]: −0.008 (1.10), 0.008 (1.07), 1.920 (13.57), 2.636 (15.68), 3.771 (16.00), 5.755 (2.88), 7.551 (1.05), 7.719 (4.31), 7.740 (4.98), 7.892 (1.98), 7.895 (2.07), 7.905 (2.08), 7.908 (2.15), 8.016 (5.06), 8.037 (4.34), 8.465 (3.26), 8.479 (3.09), 8.618 (3.47), 9.567 (2.80), 10.063 (3.51).

Example 229

N-[4-ethyl-3-(4-fluorophenyl)-1-methyl-1H-pyrazol-5-yl]-6-(3-methyl-1H-pyrazolo[4,3-b]pyridin-1-yl)pyrimidin-4-amine

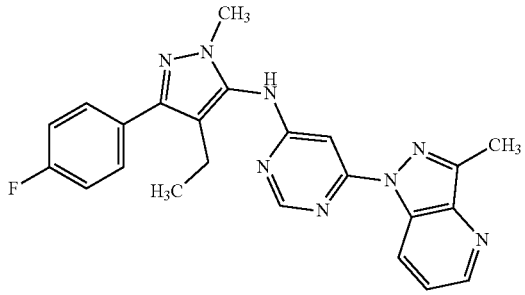 [SMILES: CCc1c(-c2ccc(F)cc2)nn(C)c1Nc1cc(-n2nc(C)c3ncccc32)ncn1]

Under an argon atmosphere, 1-(6-chloropyrimidin-4-yl)-3-methyl-1H-pyrazolo[4,3-b]pyridine (123 mg, 502 µmol) and sodium phenolate (79.4 mg, 684 µmol) were suspended in 1,4-dioxane (1.3 mL). The reaction mixture was degassed with Ar for 3 min. Tris(dibenzylideneacetone)dipalladium (6.26 mg, 6.84 µmol), XantPhos (7.92 mg, 13.7 µmol) and 4-ethyl-3-(4-fluorophenyl)-1-methyl-1H-pyrazol-5-amine (100 mg, 456 µmol) were added and the reaction mixture was degassed again for 1 min. The vial was sealed and heated at 90° C. overnight while vigorously shaking. After cooling to ambient temperature, the reaction mixture was diluted with dichloromethane and concentrated. It was redissolved in dimethylsulfoxide, filtered and purified by preparative HPLC (method 3) to yield the desired product (141 mg, 72% yield).

LC-MS (method 10): $R_t$=2.08 min; MS (ESIpos): m/z=429 [M+H]$^+$ $^1$H-NMR (400 MHz, dimethylsulfoxide-d6) δ [ppm]: −0.008 (1.39), 0.008 (1.05), 0.993 (6.42), 1.012 (13.68), 1.031 (6.35), 1.567 (0.61), 2.476 (2.56), 2.622 (5.06), 2.631 (6.29), 2.673 (0.52), 3.672 (16.00), 5.756 (5.27), 7.260 (3.52), 7.269 (1.80), 7.271 (1.81), 7.282 (6.78), 7.295 (1.54), 7.304 (3.73), 7.313 (1.26), 7.342 (0.45), 7.354 (0.54), 7.370 (0.54), 7.383 (0.54), 7.400 (0.41), 7.462 (0.52), 7.466 (0.53), 7.506 (0.60), 7.526 (0.69), 7.545 (0.48), 7.584 (4.03), 7.595 (4.06), 7.605 (3.96), 7.616 (4.06), 7.628 (0.54), 7.639 (0.56), 7.649 (0.69), 7.660 (1.14), 7.673 (2.43), 7.688 (3.13), 8.587 (1.18), 8.664 (3.82), 8.667 (3.89), 8.675 (3.72), 8.678 (3.46), 8.785 (0.56), 8.787 (0.54), 8.993 (4.20), 8.997 (4.12), 9.014 (4.07), 9.018 (3.70), 9.467 (2.33).

Example 230

N-[4-ethyl-3-(4-fluorophenyl)-1-methyl-1H-pyrazol-5-yl]-6-(3-methyl-1H-pyrazolo[4,3-c]pyridin-1-yl)pyrimidin-4-amine

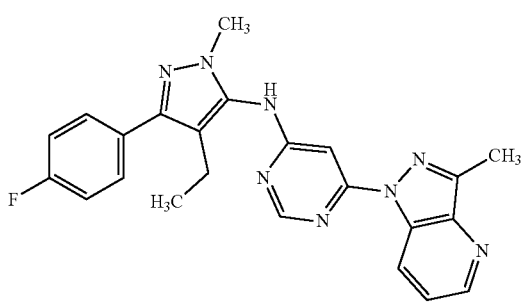 [SMILES: CCc1c(-c2ccc(F)cc2)nn(C)c1Nc1cc(-n2nc(C)c3ncccc32)ncn1]

Under an argon atmosphere, 1-(6-chloropyrimidin-4-yl)-3-methyl-1H-pyrazolo[4,3-c]pyridine (123 mg, 502 μmol) and sodium phenolate (79.4 mg, 684 μmol) were suspended in 1,4-dioxane (1.3 mL). The reaction mixture was degassed with Ar for 3 min. Tris(dibenzylideneacetone)dipalladium (6.26 mg, 6.84 μmol), XantPhos (7.92 mg, 13.7 μmol) and 4-ethyl-3-(4-fluorophenyl)-1-methyl-1H-pyrazol-5-amine (100 mg, 456 μmol) were added and the reaction mixture was degassed again for 1 min. The vial was sealed and heated at 90° C. overnight while vigorously shaking. After cooling to ambient temperature, the reaction mixture was diluted with dichloromethane and concentrated. It was redissolved in dimethylsulfoxide, filtered and purified by preparative HPLC (method 7) to yield the desired product (31 mg, 16% yield).

LC-MS (method 10): $R_t$=1.61 min; MS (ESIpos): m/z=429 [M+H]$^+$ $^1$H-NMR (400 MHz, dimethylsulfoxide-d6) δ [ppm]: −0.149 (1.19), −0.008 (9.97), 0.008 (10.01), 0.146 (1.15), 0.986 (6.24), 1.004 (13.91), 1.023 (6.52), 2.328 (1.85), 2.366 (1.48), 2.664 (6.56), 2.675 (9.07), 2.710 (1.93), 3.664 (16.00), 5.754 (6.93), 7.257 (3.41), 7.280 (6.77), 7.302 (3.86), 7.351 (0.70), 7.502 (0.86), 7.522 (1.15), 7.541 (0.62), 7.683 (3.20), 8.542 (2.87), 8.557 (6.03), 8.583 (9.48), 8.598 (5.33), 8.636 (1.39), 8.650 (1.03), 8.815 (1.07), 9.198 (4.72), 9.231 (1.15), 9.493 (1.72).

Example 231

4-[1-(cyclopropylmethyl)-4-methyl-5-{[6-(3-methyl-1H-pyrazolo[3,4-c]pyridin-1-yl)pyrimidin-4-yl]amino}-1H-pyrazol-3-yl]benzonitrile

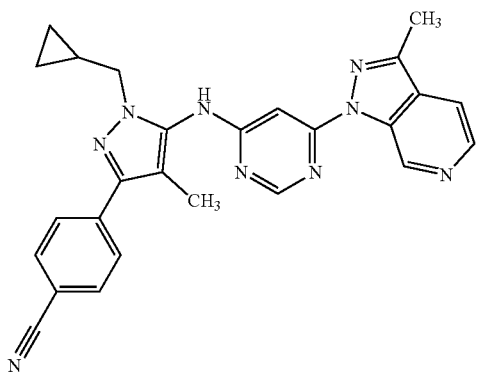 [SMILES: Cc1c(-c2ccc(C#N)cc2)nn(CC2CC2)c1Nc1cc(-n2nc(C)c3ccncc32)ncn1]

Under an argon atmosphere, 1-(6-chloropyrimidin-4-yl)-3-methyl-1H-pyrazolo[3,4-c]pyridine (161 mg, 654 μmol) and sodium phenolate (104 mg, 892 μmol) were suspended in 1,4-dioxane (1.7 mL). The reaction mixture was degassed with Ar for 3 min. Tris(dibenzylideneacetone)dipalladium (8.17 mg, 8.92 μmol), XantPhos (10.3 mg, 17.8 μmol) and 4-[5-amino-1-(cyclopropylmethyl)-4-methyl-1H-pyrazol-3-yl]benzonitrile (150 mg, 594 μmol) were added and the reaction mixture was degassed again for 1 min. The vial was sealed and heated at 90° C. overnight while vigorously shaking. After cooling to ambient temperature, the reaction mixture was diluted with dichloromethane and concentrated. It was redissolved in dimethylsulfoxide, filtered and purified by preparative HPLC (method 7) to yield the desired product (90 mg, 33% yield).

LC-MS (method 10): $R_t$=1.94 min; MS (ESIpos): m/z=462 [M+H]$^+$ $^1$H-NMR (400 MHz, dimethylsulfoxide-d6) δ [ppm]: 0.320 (2.95), 0.331 (3.20), 0.440 (2.96), 0.460 (3.12), 1.201 (0.45), 1.212 (0.83), 1.220 (0.80), 1.231 (1.29), 1.243 (0.77), 1.250 (0.78), 2.096 (16.00), 2.616 (2.95), 2.632 (2.05), 2.671 (0.50), 3.894 (2.66), 3.911 (2.60), 5.755 (6.76), 7.898 (2.93), 7.906 (2.85), 7.920 (8.28), 7.932 (4.98), 7.953 (1.47), 8.474 (3.37), 8.487 (3.27), 8.627 (0.52), 9.543 (0.66), 10.038 (4.00).

Example 232

4-[1-(cyclopropylmethyl)-4-methyl-5-{[6-(3-methyl-1H-pyrazolo[4,3-b]pyridin-1-yl)pyrimidin-4-yl]amino}-1H-pyrazol-3-yl]benzonitrile

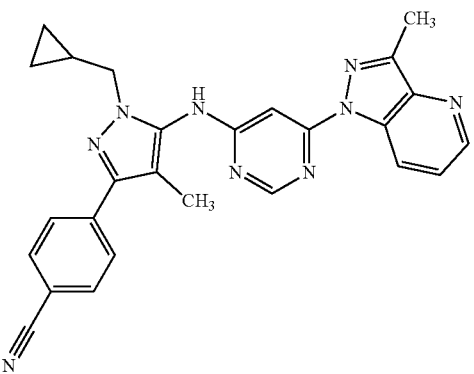 [SMILES: Cc1c(-c2ccc(C#N)cc2)nn(CC2CC2)c1Nc1cc(-n2nc(C)c3ncccc32)ncn1]

Under an argon atmosphere, 1-(6-chloropyrimidin-4-yl)-3-methyl-1H-pyrazolo[4,3-b]pyridine (161 mg, 654 μmol) and sodium phenolate (104 mg, 892 μmol) were suspended in 1,4-dioxane (1.7 mL). The reaction mixture was degassed with Ar for 3 min. Tris(dibenzylideneacetone)dipalladium (8.17 mg, 8.92 mol), XantPhos (10.3 mg, 17.8 μmol) and 4-[5-amino-1-(cyclopropylmethyl)-4-methyl-1H-pyrazol-3-yl]benzonitrile (150 mg, 594 μmol) were added and the reaction mixture was degassed again for 1 min. The vial was sealed and heated at 90° C. overnight while vigorously shaking. After cooling to ambient temperature, the reaction mixture was diluted with dichloromethane and concentrated. It was redissolved in dimethylsulfoxide, filtered and purified by preparative HPLC (method 3) to yield the desired product (196 mg, 71% yield).

LC-MS (method 10): $R_t$=2.11 min; MS (ESIpos): m/z=462 [M+H]$^+$ $^1$H-NMR (400 MHz, dimethylsulfoxide-d6) δ [ppm]: 0.318 (3.64), 0.329 (3.92), 0.439 (3.57), 0.459 (3.74), 1.199 (0.52), 1.212 (0.97), 1.219 (0.97), 1.230 (1.41), 1.248 (0.94), 2.094 (16.00), 2.617 (3.89), 2.671 (0.62), 3.890 (3.19), 3.907 (3.18), 5.755 (7.17), 7.341 (0.45), 7.382 (0.55), 7.462 (0.83), 7.475 (0.51), 7.580 (1.11), 7.585 (1.64), 7.591 (1.33), 7.596 (1.75), 7.606 (1.73), 7.612 (1.40), 7.617 (1.66), 7.790 (0.43), 7.898 (1.99), 7.919 (8.20), 7.929 (5.66), 7.950 (1.74), 8.581 (0.79), 8.664 (2.61), 8.667 (2.48), 8.674 (2.62), 8.994 (2.19), 9.015 (2.18), 9.521 (1.07).

Example 233

4-[1-(cyclopropylmethyl)-4-methyl-5-{[6-(3-methyl-1H-pyrazolo[4,3-c]pyridin-1-yl)pyrimidin-4-yl]amino}-1H-pyrazol-3-yl]benzonitrile

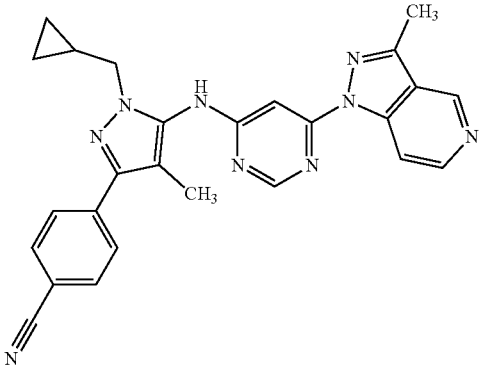 [SMILES: Cc1c(-c2ccc(C#N)cc2)nn(CC2CC2)c1Nc1cc(-n2nc(C)c3cnccc32)ncn1]

Under an argon atmosphere, 1-(6-chloropyrimidin-4-yl)-3-methyl-1H-pyrazolo[4,3-c]pyridine (161 mg, 654 µmol) and sodium phenolate (104 mg, 892 µmol) were suspended in 1,4-dioxane (1.7 mL). The reaction mixture was degassed with Ar for 3 min. Tris(dibenzylideneacetone)dipalladium (8.17 mg, 8.92 mol), XantPhos (10.3 mg, 17.8 µmol) and 4-[5-amino-1-(cyclopropylmethyl)-4-methyl-1H-pyrazol-3-yl]benzonitrile (150 mg, 594 µmol) were added and the reaction mixture was degassed again for 1 min. The vial was sealed and heated at 90° C. overnight while vigorously shaking. After cooling to ambient temperature, the reaction mixture was diluted with dichloromethane and concentrated. It was redissolved in dimethylsulfoxide, filtered and purified by preparative HPLC (method 7) to yield the desired product (31 mg, 11% yield).

LC-MS (method 10): $R_t$=1.66 min; MS (ESIpos): m/z=462 [M+H]$^+$ $^1$H-NMR (400 MHz, dimethylsulfoxide-d6) δ [ppm]: -0.008 (2.97), 0.008 (1.60), 0.315 (3.09), 0.327 (3.22), -0.008 (2.97), 0.437 (3.16), 0.456 (3.20), 1.195 (0.52), 1.208 (0.92), 1.214 (0.89), 1.226 (1.36), 1.245 (0.83), 1.257 (0.41), 1.435 (0.46), 2.035 (0.56), 2.089 (16.00), 2.525 (1.53), 2.657 (3.01), 2.711 (0.70), 3.888 (2.65), 3.904 (2.50), 5.755 (7.43), 7.382 (0.43), 7.461 (0.43), 7.466 (0.44), 7.805 (0.41), 7.898 (1.88), 7.919 (8.69), 7.927 (5.13), 7.949 (1.39), 8.539 (1.92), 8.541 (1.89), 8.554 (3.79), 8.556 (3.79), 8.583 (6.09), 8.597 (3.45), 9.196 (2.73), 9.548 (0.65).

Example 234

4-[1-(2,2-difluoroethyl)-5-({6-[5-(difluoromethyl)-3-methyl-1H-pyrazol-1-yl]pyrimidin-4-yl}amino)-4-methyl-1H-pyrazol-3-yl]benzonitrile

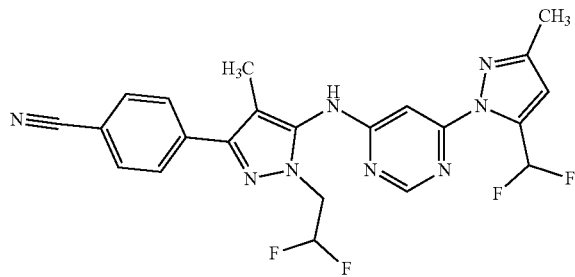 [SMILES: Cc1cc(C(F)F)n(-c2cc(Nc3c(C)c(-c4ccc(C#N)cc4)nn3CC(F)F)ncn2)n1]

A microwave vial was charged 4-chloro-6-[5-(difluoromethyl)-3-methyl-H-pyrazol-1-yl]pyrimidine (84.8 mg, 347 µmol), 4-[5-amino-1-(2,2-difluoroethyl)-4-methyl-1H-pyrazol-3-yl]benzonitrile (100 mg, 381 µmol) and sodium phenolate (44.3 mg, 381 µmol) and the contents were suspended in 1,4-dioxane (2.5 ml, 29 mmol). The reaction mixture was degassed with Ar for 3 min. Tris(dibenzylidenaceton)dipalladium (4.13 mg, 4.51 µmol) and Xantphos (6.02 mg, 10.4 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (73.0 mg, 43%).

LC-MS (method 9): $R_t$=1.11 min; MS (ESIpos): m/z=471 [M+H]$^+$ $^1$H-NMR (500 MHz, dimethylsulfoxide-d6) δ [ppm]: -0.007 (1.00), 0.006 (0.74), 1.078 (1.39), 1.092 (2.81), 1.106 (1.40), 1.989 (0.59), 2.069 (16.00), 2.294 (2.37), 3.363 (0.48), 3.377 (1.39), 3.391 (1.37), 3.405 (0.46), 4.523 (0.82), 6.258 (0.53), 6.360 (0.54), 6.368 (1.07), 6.375 (0.56), 6.477 (0.51), 6.794 (2.54), 7.713 (1.09), 7.822 (2.22), 7.924 (13.28), 8.503 (0.57), 9.657 (0.74).

Example 235

4-[3-({6-[4-chloro-5-(difluoromethyl)-3-methyl-1H-pyrazol-1-yl]pyrimidin-4-yl}amino)-1,4-dimethyl-1H-pyrazol-5-yl]benzonitrile

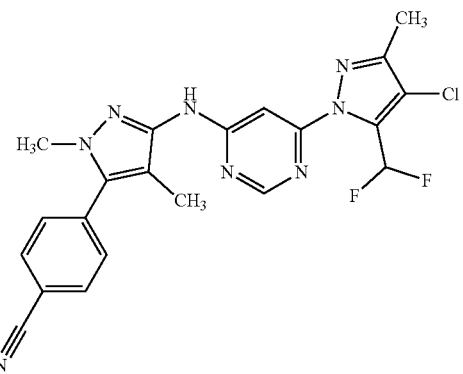

A microwave vial was charged with 4-(3-amino-1,4-dimethyl-1H-pyrazol-5-yl)benzonitrile (55.0 mg, 259 µmol), 4-chloro-6-[4-chloro-5-(difluoromethyl)-3-methyl-1H-pyrazol-1-yl]pyrimidine (79.5 mg, 285 µmol) and sodium phenolate (33.1 mg, 285 µmol) and the contents were suspended in 1,4-dioxane (0.8 mL). The reaction mixture was degassed with Ar for 3 min. Tris(dibenzylideneacetone)dipalladium (3.56 mg, 3.89 µmol) and XantPhos (4.50 mg, 7.77 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 6) to yield the desired product (21.7 mg, 18% yield).

¹H-NMR (400 MHz, dimethylsulfoxide-d6) δ [ppm]: −0.008 (0.75), 0.008 (0.72), 1.892 (10.29), 2.288 (14.30), 2.328 (0.55), 2.523 (0.67), 3.743 (16.00), 7.461 (0.56), 7.702 (4.28), 7.723 (4.91), 7.901 (1.22), 8.007 (4.86), 8.028 (4.62), 8.033 (3.42), 8.164 (1.08), 8.510 (2.45), 9.745 (1.38).

Example 236

4-[3-({6-[5-(difluoromethyl)-3-methyl-1H-pyrazol-1-yl]pyrimidin-4-yl}amino)-1,4-dimethyl-1H-pyrazol-5-yl]benzonitrile

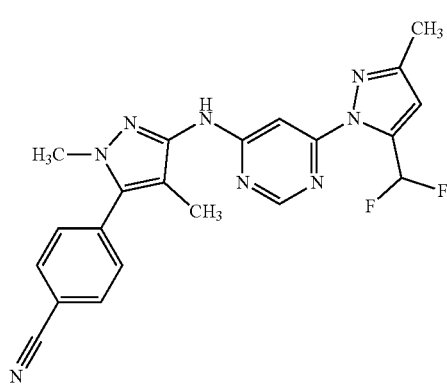 [SMILES: Cc1cc(C(F)F)n(-c2cc(Nc3nn(C)c(-c4ccc(C#N)cc4)c3C)ncn2)n1]

A microwave vial was charged with 4-(3-amino-1,4-dimethyl-1H-pyrazol-5-yl)benzonitrile (55.0 mg, 259 µmol), 4-chloro-6-[5-(difluoromethyl)-3-methyl-1H-pyrazol-1-yl]pyrimidine (69.7 mg, 285 µmol) and sodium phenolate (33.1 mg, 285 µmol) and the contents were suspended in 1,4-dioxane (0.8 mL). The reaction mixture was degassed with Ar for 3 min. Tris(dibenzylideneacetone)dipalladium (3.56 mg, 3.89 µmol) and XantPhos (4.50 mg, 7.77 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 1) to yield the desired product (29.8 mg, 27% yield).

¹H-NMR (400 MHz, dimethylsulfoxide-d6) δ [ppm]: −0.008 (0.52), 0.008 (0.60), 1.890 (11.52), 2.296 (13.68), 3.747 (16.00), 6.774 (3.85), 7.439 (0.91), 7.691 (1.24), 7.704 (4.25), 7.725 (4.89), 7.827 (2.44), 7.963 (1.06), 8.007 (4.89), 8.028 (4.25), 8.483 (2.84), 9.637 (1.96).

Example 237

4-[5-({6-[4-chloro-5-(difluoromethyl)-3-methyl-1H-pyrazol-1-yl]pyrimidin-4-yl}amino)-1-(2-cyclopropylethyl)-4-methyl-1H-pyrazol-3-yl]benzonitrile

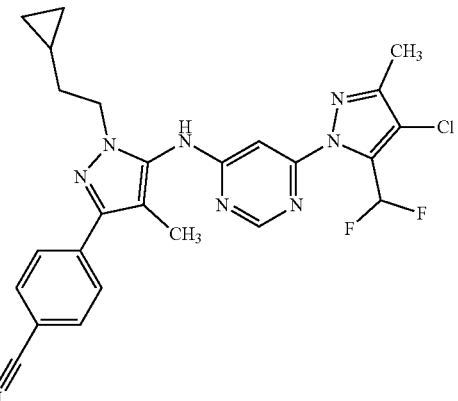

A microwave vial was charged with 4-[5-amino-1-(2-cyclopropylethyl)-4-methyl-1H-pyrazol-3-yl]benzonitrile (50.0 mg, 188 µmol), 4-chloro-6-[4-chloro-5-(difluoromethyl)-3-methyl-1H-pyrazol-1-yl]pyrimidine (57.6 mg, 206 µmol) and sodium phenolate (24.0 mg, 206 µmol) and the contents were suspended in 1,4-dioxane (0.6 mL). The reaction mixture was degassed with Ar for 3 min. Tris(dibenzylideneacetone)dipalladium (2.58 mg, 2.82 µmol) and XantPhos (3.26 mg, 5.63 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 8) to yield the desired product (7.5 mg, 8% yield).

LC-MS (method 11): R$_t$=1.62 min; MS (ESIpos): m/z=509 [M+H]⁺

¹H-NMR (400 MHz, dimethylsulfoxide-d6) δ [ppm]: −0.058 (3.54), −0.049 (3.54), −0.008 (1.29), 0.146 (0.17), 0.306 (2.16), 0.326 (2.29), 0.620 (0.86), 1.630 (1.06), 1.647 (2.95), 1.665 (2.85), 1.682 (1.04), 2.061 (16.00), 2.280 (1.55), 2.323 (0.95), 2.328 (0.91), 2.346 (0.41), 2.367 (0.50), 2.670 (0.48), 2.711 (0.39), 4.040 (1.88), 7.298 (0.19), 7.900 (13.30), 8.032 (2.16), 8.164 (0.99), 8.519 (0.35), 9.652 (0.32).

Example 238

1-[1-(6-{[4-ethyl-5-(4-fluorophenyl)-1-methyl-1H-pyrazol-3-yl]amino}pyrimidin-4-yl)-3,5-dimethyl-1H-pyrazol-4-yl]-2-methylpropan-2-ol

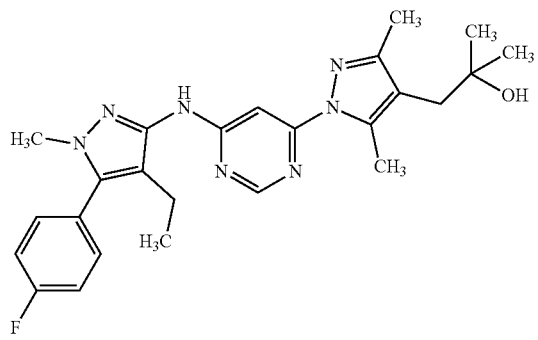 [SMILES: CCc1c(Nc2cc(-n3nc(C)c(CC(C)(C)O)c3C)ncn2)nn(C)c1-c1ccc(F)cc1]

A solution of ethyl [1-(6-{[4-ethyl-5-(4-fluorophenyl)-1-methyl-1H-pyrazol-3-yl]amino}pyrimidin-4-yl)-3,5-dimethyl-1H-pyrazol-4-yl]acetate (257 mg, 538 µmol) in tetrahydrofuran (10 ml, 130 mmol) was treated at 0° C. with bromo(methyl)magnesium (1.9 ml, 1.0 M in tetrahydrofuran, 1.9 mmol). The mixture was stirred 30 min at 0° C. and then allowed to warm up to room temperature. It was left overnight. Additionally 3.5 equivalents of bromo(methyl)magnesium (0.63 mL, 1.88 mmol, 3.0 M in diethyl ether) were added and it was stirred one hour at ambient temperature. The mixture was diluted with saturated aqueous ammonium chloride solution and extracted with ethyl acetate (3×). The combined organic phases were dried over sodium sulfate, concentrated under reduced pressure and the crude product was purified by flash-chromatography on silica gel (dichloromethane/methanol 20:1, column: Biotage SNAP Ultra 10 g) to yield the desired product (75.0 mg, 30%).

LC-MS (method 10): $R_t$=2.01 min; MS (ESIpos): m/z=464 [M+H]$^+$ $^1$H-NMR (400 MHz, dimethylsulfoxide-d6) δ [ppm]: 0.870 (2.60), 0.889 (5.71), 0.908 (2.64), 1.073 (1.43), 1.091 (16.00), 1.108 (1.45), 2.171 (9.63), 2.282 (0.71), 2.300 (1.97), 2.319 (1.95), 2.338 (0.69), 2.433 (4.17), 2.567 (9.32), 3.357 (0.69), 3.375 (1.49), 3.392 (1.66), 3.409 (1.28), 3.649 (11.66), 7.328 (1.84), 7.356 (1.28), 7.378 (2.83), 7.400 (1.70), 7.498 (1.68), 7.512 (1.95), 7.519 (1.64), 7.533 (1.26), 8.434 (2.44), 9.301 (0.78).

Example 239

4-[3-({6-[4-chloro-5-(difluoromethyl)-3-methyl-1H-pyrazol-1-yl]pyrimidin-4-yl}amino)-1-(2-cyclopropylethyl)-4-methyl-1H-pyrazol-5-yl]benzonitrile

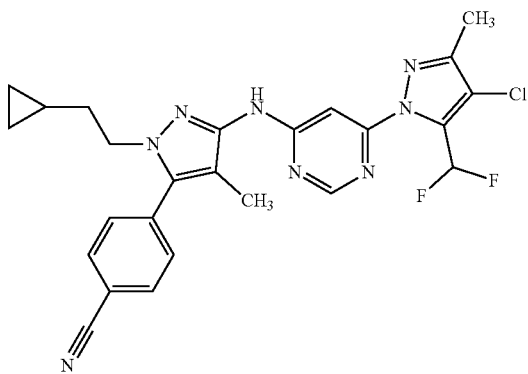 [SMILES: Cc1nn(-c2cc(Nc3nn(CCC4CC4)c(-c4ccc(C#N)cc4)c3C)ncn2)c(C(F)F)c1Cl]

A microwave vial was charged with 4-[3-amino-1-(2-cyclopropylethyl)-4-methyl-1H-pyrazol-5-yl]benzonitrile (44.0 mg, 165 µmol), 4-chloro-6-[4-chloro-5-(difluoromethyl)-3-methyl-1H-pyrazol-1-yl]pyrimidine (50.7 mg, 182 µmol) and sodium phenolate (21.1 mg, 182 µmol) and the contents were suspended in 1,4-dioxane (0.5 mL). The reaction mixture was degassed with Ar for 3 min. Tris (dibenzylideneacetone)dipalladium (2.27 mg, 2.48 µmol) and XantPhos (2.87 mg, 4.96 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 8) to yield the desired product (8 mg, 10% yield).

LC-MS (method 11): $R_t$=1.65 min; MS (ESIpos): m/z=509 [M+H]$^+$ $^1$H-NMR (400 MHz, dimethylsulfoxide-d6) δ [ppm]: −0.134 (0.86), −0.123 (3.42), −0.120 (3.41), −0.111 (3.65), −0.098 (1.03), −0.008 (2.00), 0.008 (2.23), 0.278 (0.91), 0.288 (2.56), 0.291 (2.78), 0.298 (1.55), 0.308 (3.12), 0.312 (2.98), 0.322 (1.03), 0.474 (0.70), 0.492 (0.97), 0.511 (0.60), 1.563 (1.07), 1.581 (3.15), 1.598 (3.15), 1.614 (1.10), 1.886 (10.00), 2.268 (16.00), 2.328 (0.42), 2.523 (0.97), 2.670 (0.43), 4.031 (2.14), 4.047 (4.44), 4.064 (2.13), 7.667 (5.53), 7.688 (6.25), 7.910 (1.54), 8.007 (6.07), 8.028 (5.44), 8.041 (3.54), 8.173 (1.37), 8.521 (3.16), 9.805 (1.84).

Example 240

4-[5-({6-[5-(difluoromethyl)-3-methyl-1H-pyrazol-1-yl]pyrimidin-4-yl}amino)-1,4-dimethyl-1H-pyrazol-3-yl]benzonitrile

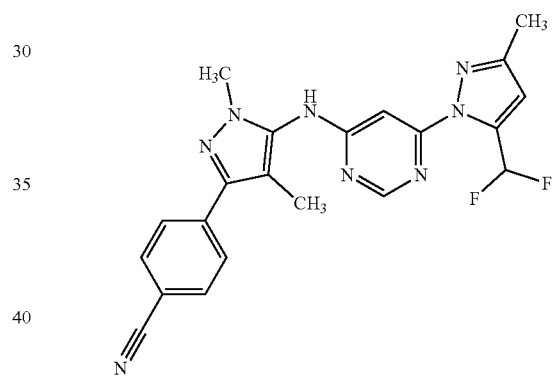

A microwave vial was charged with 4-(5-amino-1,4-dimethyl-1H-pyrazol-3-yl)benzonitrile (65.0 mg, 306 µmol), 4-chloro-6-[5-(difluoromethyl)-3-methyl-1H-pyrazol-1-yl]pyrimidine (74.9 mg, 306 µmol) and sodium phenolate (39.1 mg, 337 µmol) and the contents were suspended in 1,4-dioxane (0.95 mL). The reaction mixture was degassed with Ar for 3 min. Tris(dibenzylideneacetone)dipalladium (4.21 mg, 4.59 µmol) and XantPhos (5.32 mg, 9.19 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 1) to yield the desired product (20.4 mg, 16% yield).

LC-MS (method 10): $R_t$=2.03 min; MS (ESIpos): m/z=421 [M+H]$^+$ $^1$H-NMR (400 MHz, dimethylsulfoxide-d6) δ [ppm]: −0.008 (2.97), 0.008 (2.94), 2.076 (16.00), 2.289 (2.27), 2.327 (0.73), 2.367 (0.53), 2.670 (0.53), 2.710 (0.54), 3.701 (7.40), 6.792 (2.54), 7.682 (1.13), 7.818 (2.36), 7.900 (12.74), 7.954 (1.10), 8.503 (0.53), 9.639 (0.72).

Example 241

4-[5-({6-[4-chloro-5-(difluoromethyl)-3-methyl-1H-pyrazol-1-yl]pyrimidin-4-yl}amino)-1,4-dimethyl-1H-pyrazol-3-yl]benzonitrile

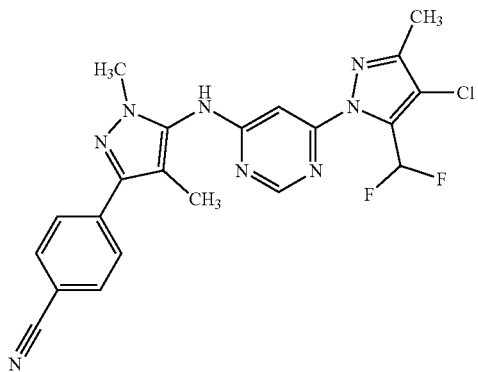 [SMILES: Cc1nn(-c2cc(Nc3c(C)c(-c4ccc(C#N)cc4)nn3C)ncn2)c(C(F)F)c1Cl]

A microwave vial was charged with 4-(5-amino-1,4-dimethyl-1H-pyrazol-3-yl)benzonitrile (65.0 mg, 306 μmol), 4-chloro-6-[4-chloro-5-(difluoromethyl)-3-methyl-1H-pyrazol-1-yl]pyrimidine (85.5 mg, 306 μmol) and sodium phenolate (39.1 mg, 337 μmol) and the contents were suspended in 1,4-dioxane (0.95 mL). The reaction mixture was degassed with Ar for 3 min. Tris(dibenzylideneacetone)dipalladium (4.21 mg, 4.59 μmol) and XantPhos (5.32 mg, 9.19 μmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 6) to yield the desired product (17 mg, 11% yield).

LC-MS (method 10): $R_t$=2.19 min; MS (ESIpos): m/z=455 [M+H]$^+$ $^1$H-NMR (400 MHz, dimethylsulfoxide-d6) δ [ppm]: −0.008 (2.24), 0.008 (2.35), 2.073 (16.00), 2.284 (1.89), 2.327 (4.16), 3.700 (6.58), 7.817 (0.41), 7.898 (14.12), 7.948 (0.72), 8.014 (0.70), 8.016 (0.78), 8.030 (2.17), 8.162 (0.96), 8.527 (0.40), 9.002 (0.68), 9.719 (0.56).

Example 242

N-[4-ethyl-5-(4-fluorophenyl)-1-methyl-1H-pyrazol-3-yl]-6-(3-methyl-1H-pyrazol-1-yl)pyrimidin-4-amine

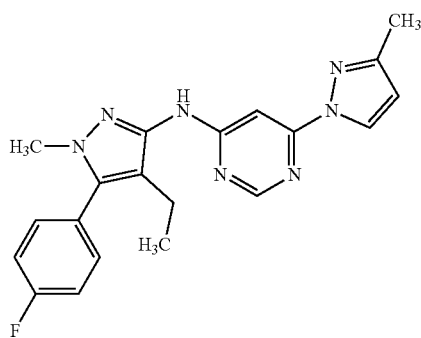 [SMILES: CCc1c(Nc2cc(-n3ccc(C)n3)ncn2)nn(C)c1-c1ccc(F)cc1]

A microwave vial was charged with 4-chloro-6-(3-methyl-1H-pyrazol-1-yl)pyrimidine (97.6 mg, 502 μmol) and sodium phenolate (63.5 mg, 547 μmol) and the contents were suspended in 1,4-dioxane (1.3 mL). The reaction mixture was degassed with Ar for 3 min. Tris(dibenzylideneacetone)dipalladium (6.26 mg, 6.84 μmol), XantPhos (7.92 mg, 13.7 μmol) and 4-ethyl-5-(4-fluorophenyl)-1-methyl-1H-pyrazol-3-amine (100 mg, 456 μmol) were added and the reaction mixture was degassed again for 1 min. The vial was sealed and heated at 85° C. overnight while vigorously shaking. After cooling to ambient temperature, the reaction mixture was diluted with dimethylsulfoxide, filtered and purified by preparative HPLC (method 3) to yield the desired product (65 mg, 37% yield).

LC-MS (method 10): $R_t$=2.03 min; MS (ESIpos): m/z=378 [M+H]$^+$ $^1$H-NMR (400 MHz, dimethylsulfoxide-d6) δ [ppm]: −0.008 (0.44), 0.008 (0.44), 0.871 (3.56), 0.889 (8.34), 0.908 (3.72), 1.647 (0.36), 2.075 (0.21), 2.274 (13.93), 2.281 (3.25), 2.289 (1.19), 2.308 (2.66), 2.326 (2.62), 2.345 (0.86), 2.670 (0.26), 3.652 (0.42), 3.669 (16.00), 6.386 (2.94), 6.392 (2.98), 6.466 (0.35), 6.472 (0.36), 7.149 (0.46), 7.151 (0.51), 7.270 (0.41), 7.289 (0.58), 7.292 (0.52), 7.308 (2.25), 7.340 (0.32), 7.362 (2.12), 7.367 (0.93), 7.379 (1.20), 7.384 (4.76), 7.401 (1.17), 7.406 (2.79), 7.413 (0.37), 7.488 (0.45), 7.493 (0.23), 7.510 (2.96), 7.515 (1.23), 7.524 (2.98), 7.532 (2.36), 7.540 (0.93), 7.545 (1.96), 8.140 (1.47), 8.437 (2.65), 8.459 (2.70), 8.466 (2.70), 8.540 (0.32), 8.546 (0.32), 8.674 (0.33), 8.676 (0.35), 9.432 (2.27).

Example 243

4-[1-(cyclopropylmethyl)-4-methyl-5-{[6-(3-methyl-1H-pyrazol-1-yl)pyrimidin-4-yl]amino}-1H-pyrazol-3-yl]benzonitrile

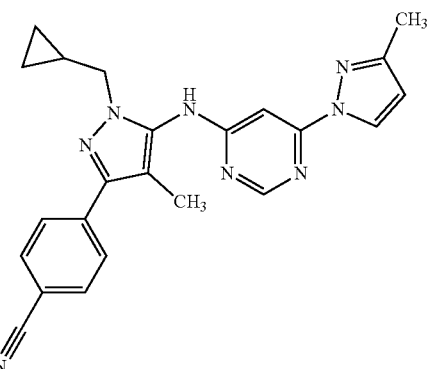

A microwave vial was charged with 4-chloro-6-(3-methyl-1H-pyrazol-1-yl)pyrimidine (84.8 mg, 436 μmol) and sodium phenolate (55.2 mg, 476 μmol) and the contents were suspended in 1,4-dioxane (1.1 mL). The reaction mixture was degassed with Ar for 3 min. Tris(dibenzylideneacetone)dipalladium (6.88 mg, 11.9 μmol), XantPhos (5.44 mg, 5.94 μmol) and 4-[5-amino-1-(cyclopropylmethyl)-4-methyl-1H-pyrazol-3-yl]benzonitrile (100 mg, 396 μmol), were added and the reaction mixture was degassed again for 1 min. The vial was sealed and heated at 85° C. overnight while vigorously shaking. After cooling to ambient temperature, the reaction mixture was filtered, diluted with dimethylsulfoxide and purified by preparative HPLC (method 2) to yield the desired product (40 mg, 24% yield).

LC-MS (method 10): $R_t$=2.04 min; MS (ESIpos): m/z=411 [M+H]$^+$ $^1$H-NMR (400 MHz, dimethylsulfoxide-d6) δ [ppm]: 0.008 (1.05), 0.305 (2.67), 0.315 (2.89), 0.429 (2.77), 0.449 (2.99), 1.176 (0.40), 1.189 (0.77), 1.195 (0.77), 1.207 (1.13), 1.219 (0.78), 1.226 (0.77), 1.238 (0.43), 1.647 (0.52), 2.072 (16.00), 2.260 (2.76), 2.281 (1.57), 3.870 (2.38), 3.886 (2.43), 6.405 (2.22), 7.368 (0.43), 7.385 (0.45), 7.398 (0.52), 7.893 (1.50), 7.913 (8.38), 7.921 (5.38), 7.943 (1.56), 8.467 (4.06), 8.473 (4.03), 9.523 (0.54).

Example 244

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]cyclopropanol

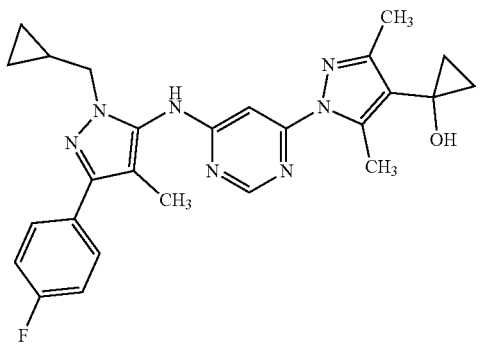 [SMILES: Cc1nn(-c2cc(Nc3c(C)c(-c4ccc(F)cc4)nn3CC3CC3)ncn2)c(C)c1C1(O)CC1]

Under an argon atmosphere a Schlenk tube was charged with titanium isopropoxide (300 μl, 1.0 mmol) in tetrahydrofuran (2.0 ml, 25 mmol). At −18° C. ethylmagensium bromide 1.0 M solution in tetrahydrofuran (3.1 ml, 1.0 M, 3.1 mmol) was added. The mixture was stirred 30 minutes at −18° C., subsequently a solution of ethyl 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylate (250 mg, 100% purity, 511 μmol) in 1.5 mL tetrahydrofuran was added and the resulting mixture was stirred at ambient temperature overnight. The mixture was diluted with saturated aqueous ammonium chloride solution and water and extracted with ethyl acetate (3×). The combined organic phases were washed with water, brine, dried over sodium sulfate and concentrated under reduced pressure. The crude product was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequent flash-chromatography on silica gel to yield 44.2 mg (18%) of the desired product along with (±)-1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]propan-1-ol (racemic) (41.5 mg, 16%).

LC-MS (method 9): $R_t$=1.03 min; MS (ESIpos): m/z=474 [M+H]$^+$ $^1$H-NMR (400 MHz, dimethylsulfoxide-d6) δ [ppm]: 0.289 (2.61), 0.300 (2.83), 0.420 (2.56), 0.439 (2.71), 0.648 (3.43), 0.930 (1.45), 0.941 (3.86), 0.957 (1.27), 1.158 (1.74), 1.176 (3.65), 1.193 (2.48), 1.211 (0.69), 1.989 (5.99), 2.004 (14.99), 2.262 (3.44), 2.714 (16.00), 3.826 (2.54), 3.843 (2.51), 4.003 (0.47), 4.021 (1.36), 4.039 (1.35), 4.057 (0.45), 5.479 (4.01), 7.252 (2.08), 7.274 (4.26), 7.296 (2.32), 7.714 (1.64), 7.728 (2.16), 7.733 (2.12), 7.748 (1.54), 8.467 (0.77), 9.361 (0.72).

Example 245

N-[4-ethyl-5-(4-fluorophenyl)-1-methyl-1H-pyrazol-3-yl]-6-(1H-pyrazol-1-yl)pyrimidin-4-amine

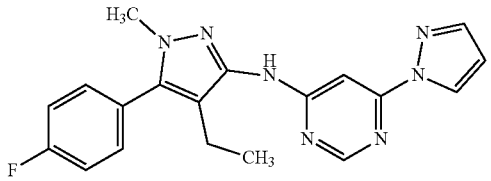 [SMILES: CCc1c(Nc2cc(-n3cccn3)ncn2)nn(C)c1-c1ccc(F)cc1]

A microwave vial was charged with 4-ethyl-5-(4-fluorophenyl)-1-methyl-1H-pyrazol-3-amine (80.0 mg, 365 μmol), 4-chloro-6-(1H-pyrazol-1-yl)pyrimidine (72.5 mg, 401 μmol) and sodium phenolate (46.6 mg, 401 μmol) and the contents were suspended in 1,4-dioxane (1.0 mL). The reaction mixture was degassed with Ar for 3 min. Tris(dibenzylideneacetone)dipalladium (4.34 mg, 4.74 μmol) and XantPhos (6.33 mg, 10.9 μmol) were added and the reaction mixture was degassed again for 1 min. The vial was sealed and heated at 85° C. overnight while vigorously shaking. After cooling to ambient temperature, the reaction mixture was concentrated and purified by flash column chromatography (SNAP Ultra 25 g, cyclohexane/ethyl acetate gradient 90/10 to 40/60) to yield the desired product (57 mg, 42% yield).

LC-MS (method 10): $R_t$=1.95 min; MS (ESIpos): m/z=364 [M+H]$^+$ $^1$H-NMR (400 MHz, dimethylsulfoxide-d6) δ [ppm]: −0.149 (0.53), −0.008 (8.13), 0.008 (4.15), 0.014 (0.56), 0.146 (0.52), 0.869 (3.68), 0.888 (8.25), 0.906 (3.57), 2.296 (1.03), 2.314 (2.75), 2.333 (2.92), 2.351 (0.81), 2.367 (0.52), 2.524 (2.54), 2.670 (0.61), 2.710 (0.50), 3.665 (16.00), 6.578 (2.31), 6.582 (2.49), 6.585 (2.51), 6.589 (2.17), 7.360 (2.14), 7.366 (1.03), 7.382 (4.65), 7.405 (2.87), 7.425 (1.79), 7.509 (2.69), 7.514 (1.29), 7.522 (2.98), 7.531 (2.32), 7.539 (1.06), 7.545 (1.94), 7.856 (2.75), 7.859 (2.66), 8.482 (2.39), 8.587 (2.60), 8.592 (2.45), 8.594 (2.37), 9.524 (2.63).

Example 246

4-[1-(cyclopropylmethyl)-4-methyl-5-{[6-(1H-pyrazol-1-yl)pyrimidin-4-yl]amino}-1H-pyrazol-3-yl]benzonitrile

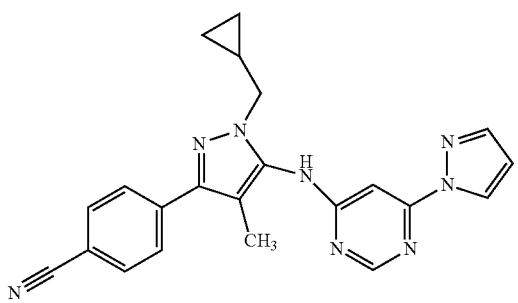 [SMILES: Cc1c(-c2ccc(C#N)cc2)nn(CC2CC2)c1Nc1cc(-n2cccn2)ncn1]

A microwave vial was charged with 4-[5-amino-1-(cyclopropylmethyl)-4-methyl-1H-pyrazol-3-yl]benzonitrile (80.0 mg, 317 μmol), 4-chloro-6-(1H-pyrazol-1-yl)pyrimidine (63.0 mg, 349 μmol) and sodium phenolate (40.5 mg, 349 μmol) and the contents were suspended in 1,4-dioxane (0.9 mL). The reaction mixture was degassed with Ar for 3 min. Tris(dibenzylideneacetone)dipalladium (3.77 mg, 4.12 mol) and XantPhos (5.50 mg, 9.51 μmol) were added and the reaction mixture was degassed again for 1 min. The vial was sealed and heated at 85° C. overnight while vigorously shaking. After cooling to ambient temperature, the reaction mixture was concentrated and purified by flash column chromatography (SNAP Ultra 25 g, cyclohexane/ethyl acetate gradient 90/10 to 40/60) to yield the desired product (27 mg, 21% yield).

LC-MS (method 10): $R_t$=1.95 min; MS (ESIpos): m/z=397 [M+H]$^+$ $^1$H-NMR (400 MHz, dimethylsulfoxide-d6) δ [ppm]: −0.149 (0.28), −0.008 (3.77), 0.008 (2.72), 0.146 (0.29), 0.300 (2.23), 0.311 (2.29), 0.422 (2.26), 0.442 (2.28), 1.157 (0.26), 1.175 (0.61), 1.193 (0.76), 1.202 (0.87), 1.234 (0.44), 1.989 (0.47), 2.036 (0.43), 2.069 (16.00), 2.328 (0.29), 2.367 (0.25), 2.524 (1.23), 2.670 (0.31), 2.710 (0.26), 3.875 (2.12), 3.892 (2.01), 5.754 (2.21), 6.595 (1.92), 7.855 (0.59), 7.890 (1.56), 7.912 (8.79), 7.918 (6.26), 7.940 (1.05), 8.508 (0.38), 8.593 (2.77), 8.599 (2.72), 9.616 (0.65).

Example 247

4-[1-(cyclopropylmethyl)-4-methyl-5-({6-[4-(trifluoromethyl)-1H-pyrazol-1-yl]pyrimidin-4-yl}amino)-1H-pyrazol-3-yl]benzonitrile

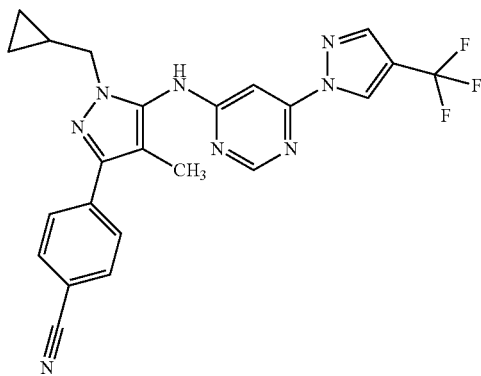 [SMILES: Cc1c(-c2ccc(C#N)cc2)nn(CC2CC2)c1Nc1cc(-n2cc(C(F)(F)F)cn2)ncn1]

A microwave vial was charged with 4-[5-amino-1-(cyclopropylmethyl)-4-methyl-1H-pyrazol-3-yl]benzonitrile (80.0 mg, 317 μmol), 4-chloro-6-[4-(trifluoromethyl)-1H-pyrazol-1-yl]pyrimidine (140 mg, 62% purity, 349 μmol) and sodium phenolate (40.5 mg, 349 μmol) and the contents were suspended in 1,4-dioxane (0.9 mL). The reaction mixture was degassed with Ar for 3 min. Tris(dibenzylideneacetone)dipalladium (3.77 mg, 4.12 μmol) and XantPhos (5.50 mg, 9.51 μmol) were added and the reaction mixture was degassed again for 1 min. The vial was sealed and heated at 85° C. overnight while vigorously shaking. After cooling to ambient temperature, the reaction mixture was concentrated and the residue purified by flash column chromatography (KP Sil 25 g, cyclohexane/ethyl acetate gradient 90/10 to 40/60) to yield the desired product (37 mg, 24% yield).

LC-MS (method 10): $R_t$=2.26 min; MS (ESIpos): m/z=465 [M+H]$^+$ $^1$H-NMR (400 MHz, dimethylsulfoxide-d6) δ [ppm]: −0.149 (1.09), −0.008 (9.41), 0.008 (9.55), 0.146 (1.07), 0.310 (1.92), 0.424 (1.87), 0.445 (1.89), 1.193 (0.75), 1.434 (0.32), 1.988 (0.69), 2.069 (16.00), 2.327 (1.17), 2.366 (0.83), 2.669 (1.23), 2.710 (0.93), 3.879 (1.57), 5.754 (3.55), 7.912 (9.25), 8.343 (0.29), 8.552 (0.29), 9.185 (3.33), 9.768 (0.32).

Example 248

4-[1-(2,2-difluoroethyl)-5-{[6-(3,5-dimethyl-1H-pyrazol-1-yl)pyrimidin-4-yl]amino}-4-methyl-1H-pyrazol-3-yl]benzonitrile

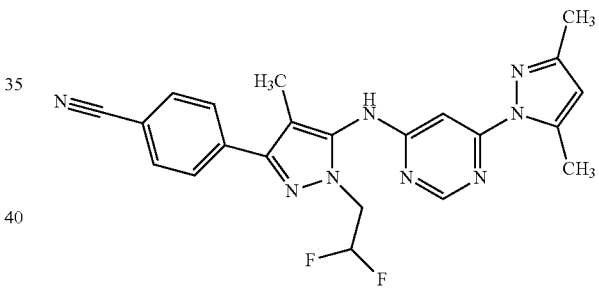

A microwave vial was charged 4-chloro-6-(3,5-dimethyl-1H-pyrazol-1-yl)pyrimidine (72.3 mg, 347 μmol), 4-[5-amino-1-(2,2-difluoroethyl)-4-methyl-1H-pyrazol-3-yl]benzonitrile (100 mg, 381 μmol) and sodium phenolate (44.3 mg, 381 μmol) and the contents were suspended in 1,4-dioxane (2.5 ml, 29 mmol). The reaction mixture was degassed with Ar for 3 min. Tris(dibenzylidenaceton)dipalladium (4.13 mg, 4.51 μmol) and Xantphos (6.02 mg, 10.4 μmol) were added and the reaction mixture was degassed again for 1 min. The vial was sealed and heated at 85° C. overnight while vigorously stirring. After cooling to ambient temperature, the reaction mixture was filtered and purified by preparative HPLC (method 3) to yield the desired product (64.0 mg, 38%).

LC-MS (method 10): $R_t$=2.05 min; MS (ESIpos): m/z=435 [M+H]$^+$ $^1$H-NMR (400 MHz, dimethylsulfoxide-d6) δ [ppm]: −0.008 (1.20), 0.008 (1.44), 2.065 (11.96), 2.183 (4.62), 2.633 (10.27), 2.654 (1.02), 4.477 (0.51), 4.513 (0.94), 4.545 (0.51), 6.154 (2.42), 6.228 (0.50), 6.356 (0.47), 6.365 (0.99), 6.374 (0.50), 6.502 (0.46), 7.921 (16.00), 8.469 (1.04), 9.481 (1.76).

Example 249

(±)-1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanol (Racemic)

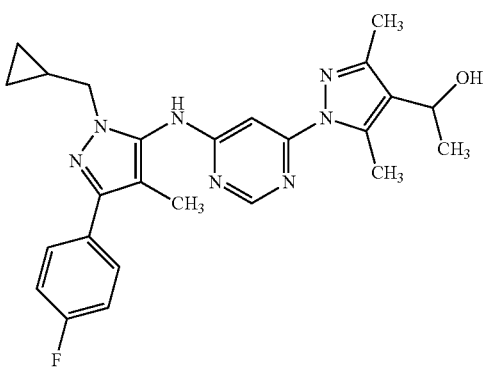 [SMILES: Cc1nn(-c2cc(Nc3c(C)c(-c4ccc(F)cc4)nn3CC3CC3)ncn2)c(C)c1C(C)O]

A solution of 1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanone (51.9 mg, 113 µmol) in methanol (2.0 ml, 49 mmol) was treated with sodium borohydride (2.14 mg, 56.5 µmol). The mixture was stirred 30 minutes at ambient temperature. The mixture was diluted with 1 mL water and purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography on silica gel (column: SNAP KP-Sil 10 g, dichloromethane/ethyl acetate) to yield 17.1 mg (33%) of the desired product.

LC-MS (method 11): $R_t$=1.32 min; MS (ESIpos): m/z=462 [M+H]$^+$ $^1$H-NMR (400 MHz, dimethylsulfoxide-d6) δ [ppm]: −0.008 (0.63), 0.008 (0.77), 0.291 (2.36), 0.302 (2.61), 0.420 (2.30), 0.440 (2.46), 1.175 (0.85), 1.182 (0.66), 1.194 (1.04), 1.206 (0.63), 1.212 (0.64), 1.232 (0.52), 1.320 (4.71), 1.336 (4.82), 2.003 (14.03), 2.234 (2.91), 2.631 (16.00), 3.824 (2.35), 3.841 (2.31), 4.765 (0.79), 4.773 (0.87), 4.782 (0.83), 4.789 (0.85), 4.909 (2.09), 4.916 (1.97), 5.754 (0.71), 7.251 (2.08), 7.273 (4.26), 7.295 (2.30), 7.712 (1.53), 7.726 (1.98), 7.732 (1.91), 7.746 (1.43), 8.453 (0.70), 9.345 (0.74).

Example 250

N-[4-ethyl-5-(4-fluorophenyl)-1-methyl-1H-pyrazol-3-yl]-6-[4-(trifluoromethyl)-1H-pyrazol-1-yl]pyrimidin-4-amine

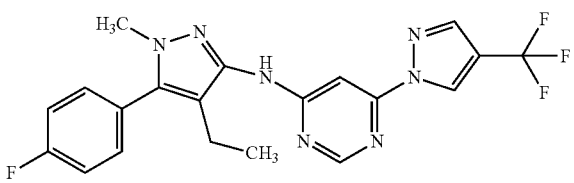 [SMILES: CCc1c(Nc2cc(-n3cc(C(F)(F)F)cn3)ncn2)nn(C)c1-c1ccc(F)cc1]

A microwave vial was charged with 4-ethyl-5-(4-fluorophenyl)-1-methyl-1H-pyrazol-3-amine (160 mg, 730 µmol), 4-chloro-6-[4-(trifluoromethyl)-1H-pyrazol-1-yl]pyrimidine (322 mg, 62% purity, 803 µmol) and sodium phenolate (93.2 mg, 803 µmol) and the contents were suspended in 1,4-dioxane (2.1 mL). The reaction mixture was degassed with Ar for 3 min. Tris(dibenzylideneacetone)dipalladium (8.69 mg, 9.49 µmol) and XantPhos (12.7 mg, 21.9 µmol) were added and the reaction mixture was degassed again for 1 min. The vial was sealed and heated at 85° C. overnight while vigorously shaking. After cooling to ambient temperature, the reaction mixture was concentrated and the residue purified by flash column chromatography (SNAP Ultra 25 g, cyclohexane/ethyl acetate gradient 90/10 to 40/60) to yield the desired product (144 mg, 43% yield).

LC-MS (method 10): $R_t$=2.31 min; MS (ESIpos): m/z=432 [M+H]$^+$ $^1$H-NMR (400 MHz, dimethylsulfoxide-d6) δ [ppm]: −0.008 (1.37), 0.008 (1.45), 0.774 (0.35), 0.844 (0.32), 0.852 (0.20), 0.870 (3.53), 0.889 (8.09), 0.907 (3.54), 1.235 (0.26), 1.398 (1.58), 2.303 (0.77), 2.322 (2.24), 2.340 (2.13), 2.359 (0.70), 2.671 (0.20), 2.711 (0.16), 3.642 (0.45), 3.666 (16.00), 3.752 (0.58), 3.784 (0.65), 5.755 (0.82), 7.330 (0.17), 7.354 (0.28), 7.361 (2.00), 7.366 (0.81), 7.383 (4.57), 7.400 (1.00), 7.406 (2.80), 7.421 (0.40), 7.443 (0.23), 7.511 (3.21), 7.516 (1.93), 7.524 (3.44), 7.533 (2.65), 7.541 (1.13), 7.546 (2.17), 7.584 (0.25), 7.598 (0.19), 7.815 (0.36), 7.818 (0.37), 8.332 (3.69), 8.405 (0.35), 8.414 (0.21), 8.549 (2.43), 8.951 (0.32), 8.953 (0.33), 9.162 (2.92), 9.307 (0.27), 9.730 (1.36).

Example 251

4-[1-(2,2-difluoroethyl)-3-({6-[5-(difluoromethyl)-3-methyl-1H-pyrazol-1-yl]pyrimidin-4-yl}amino)-4-methyl-1H-pyrazol-5-yl]benzonitrile

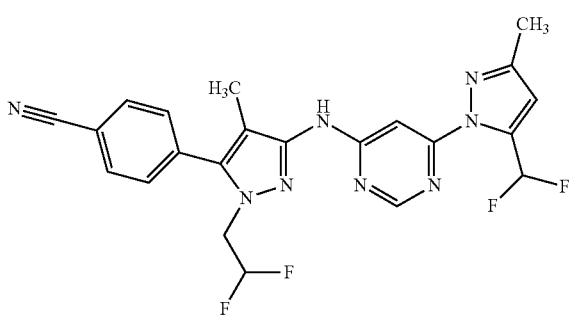 [SMILES: Cc1cc(C(F)F)n(-c2cc(Nc3nn(CC(F)F)c(-c4ccc(C#N)cc4)c3C)ncn2)n1]

A microwave vial was charged 4-chloro-6-[5-(difluoromethyl)-3-methyl-H-pyrazol-1-yl]pyrimidine (73.8 mg, 302 µmol), 4-[3-amino-1-(2,2-difluoroethyl)-4-methyl-1H-pyrazol-5-yl]benzonitrile (87.0 mg, 332 µmol) and sodium phenolate (38.5 mg, 332 µmol) and the contents were suspended in 1,4-dioxane (2.2 ml, 25 mmol). The reaction mixture was degassed with Ar for 3 min. Tris(dibenzylidenaceton)dipalladium (3.59 mg, 3.92 µmol) and Xantphos (5.23 mg, 9.05 µmol) were added and the reaction mixture was degassed again for 1 min. The vial was sealed and heated at 85° C. overnight while vigorously stirring. After cooling to ambient temperature, the reaction mixture was diluted with water and filtered over a column with Extrelut and silica gel (solvent: dichloromethane/ethyl acetate 20:1). The filtrate was concentrated under reduced pressure and the crude product was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 36.0 mg (25%) of the desired product.

LC-MS (method 10): $R_t$=2.12 min; MS (ESIpos): m/z=471 [M+H]$^+$ $^1$H-NMR (400 MHz, dimethylsulfoxide-d6) δ [ppm]: −0.008 (0.90), 0.008 (0.90), 1.073 (0.47), 1.091 (0.95), 1.109 (0.47), 1.883 (13.58), 2.292 (16.00), 3.375 (0.51), 3.392 (0.50), 4.414 (1.05), 4.423 (1.16), 4.450 (2.18), 4.459 (2.22), 4.487 (1.12), 4.496 (1.02), 6.158 (0.75), 6.285 (0.73), 6.295 (1.53), 6.304 (0.73), 6.432 (0.69), 6.777 (4.65), 7.573 (0.70), 7.663 (5.08), 7.684 (5.92), 7.691 (1.91), 7.828 (2.91), 7.964 (1.24), 8.022 (5.69), 8.043 (5.13), 8.508 (3.79), 9.787 (3.25).

Example 252

4-[1-(2,2-difluoroethyl)-3-{[6-(3,5-dimethyl-1H-pyrazol-1-yl)pyrimidin-4-yl]amino}-4-methyl-1H-pyrazol-5-yl]benzonitrile

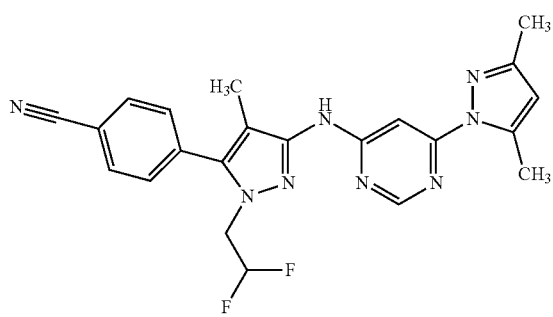 [SMILES: Cc1cc(C)n(-c2cc(Nc3nn(CC(F)F)c(-c4ccc(C#N)cc4)c3C)ncn2)n1]

A microwave vial was charged 4-chloro-6-(3,5-dimethyl-1H-pyrazol-1-yl)pyrimidine (62.9 mg, 302 µmol), 4-[3-amino-1-(2,2-difluoroethyl)-4-methyl-1H-pyrazol-5-yl]benzonitrile (87.0 mg, 332 µmol) and sodium phenolate (38.5 mg, 332 µmol) and the contents were suspended in 1,4-dioxane (2.2 ml, 25 mmol). The reaction mixture was degassed with Ar for 3 min. Tris(dibenzylidenaceton)dipalladium (3.59 mg, 3.92 µmol) and Xantphos (5.23 mg, 9.05 µmol) were added and the reaction mixture was degassed again for 1 min. The vial was sealed and heated at 85° C. overnight while vigorously stirring. After cooling to ambient temperature, the reaction mixture was filtered and purified by preparative HPLC (method 3) to yield the desired product (56.0 mg, 38%).

LC-MS (method 10): $R_t$=2.01 min; MS (ESIpos): m/z=435 [M+H]$^+$ $^1$H-NMR (400 MHz, dimethylsulfoxide-d6) δ [ppm]: 1.647 (0.48), 1.879 (15.67), 2.074 (3.82), 2.182 (15.31), 2.502 (16.00), 2.625 (14.92), 4.401 (1.18), 4.410 (1.27), 4.437 (2.41), 4.446 (2.43), 4.474 (1.24), 4.482 (1.13), 6.136 (4.01), 6.156 (0.79), 6.284 (0.76), 6.293 (1.52), 6.302 (0.75), 6.430 (0.71), 7.383 (0.41), 7.531 (1.64), 7.657 (4.75), 7.678 (5.11), 8.019 (4.94), 8.039 (4.21), 8.475 (3.99), 9.580 (4.53).

Example 253

6-(3,5-dimethyl-1H-pyrazol-1-yl)-N-[5-(4-fluorophenyl)-4-methoxy-1-methyl-1H-pyrazol-3-yl]pyrimidin-4-amine

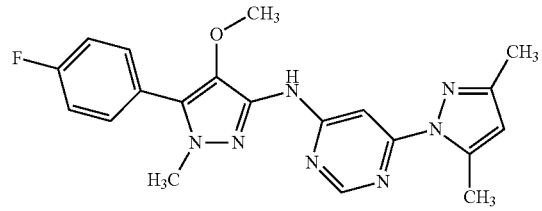 [SMILES: COc1c(Nc2cc(-n3nc(C)cc3C)ncn2)nn(C)c1-c1ccc(F)cc1]

A microwave vial was charged 4-chloro-6-(3,5-dimethyl-1H-pyrazol-1-yl)pyrimidine (49.7 mg, 238 µmol), 5-(4-fluorophenyl)-4-methoxy-1-methyl-1H-pyrazol-3-amine (58.0 mg, 262 µmol) and sodium phenolate (30.4 mg, 262 µmol) and the contents were suspended in 1,4-dioxane (1.7 ml, 20 mmol). The reaction mixture was degassed with Ar for 3 min. Tris(dibenzylidenaceton)dipalladium (2.84 mg, 3.10 µmol) and Xantphos (4.14 mg, 7.15 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (35.5 mg, 36%).

LC-MS (method 10): $R_t$=1.98 min; MS (ESIpos): m/z=394 [M+H]$^+$ $^1$H-NMR (400 MHz, dimethylsulfoxide-d6) δ [ppm]: 2.074 (1.05), 2.176 (11.46), 2.227 (0.49), 2.623 (10.61), 2.663 (0.45), 3.531 (16.00), 3.718 (13.08), 6.130 (3.01), 7.205 (3.65), 7.207 (3.61), 7.364 (1.63), 7.386 (3.53), 7.408 (1.97), 7.592 (2.00), 7.597 (0.96), 7.606 (2.26), 7.614 (1.95), 7.623 (0.83), 7.628 (1.65), 8.448 (2.88), 9.368 (2.12).

Example 254

6-(3,5-dimethyl-1H-pyrazol-1-yl)-N-[3-(4-fluorophenyl)-4-methoxy-1-methyl-1H-pyrazol-5-yl]pyrimidin-4-amine

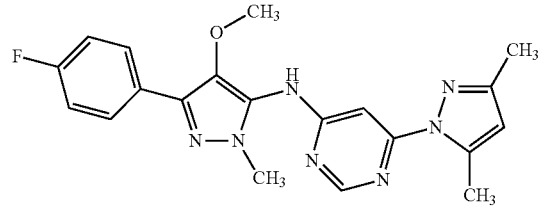 [SMILES: COc1c(-c2ccc(F)cc2)nn(C)c1Nc1cc(-n2nc(C)cc2C)ncn1]

A microwave vial was charged 4-chloro-6-(3,5-dimethyl-1H-pyrazol-1-yl)pyrimidine (39.4 mg, 189 mol), 3-(4-fluorophenyl)-4-methoxy-1-methyl-1H-pyrazol-5-amine (46.0 mg, 208 µmol) and sodium phenolate (24.1 mg, 208 µmol) and the contents were suspended in 1,4-dioxane (1.3 ml, 16 mmol). The reaction mixture was degassed with Ar for 3 min. Tris(dibenzylidenaceton)dipalladium (2.25 mg, 2.46 mol) and Xantphos (3.28 mg, 5.67 µmol) were added and the reaction mixture was degassed again for 1 min. The vial was sealed and heated at 85° C. overnight while vigorously stirring. After cooling to ambient temperature, the reaction mixture was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (32.5 mg, 43%).

LC-MS (method 10): $R_t$=2.04 min; MS (ESIpos): m/z=394 [M+H]$^+$ $^1$H-NMR (400 MHz, dimethylsulfoxide-d6) δ [ppm]: −0.008 (0.84), 0.008 (0.92), 1.091 (0.45), 2.174 (4.04), 2.635 (10.22), 3.615 (8.71), 3.683 (16.00), 6.151 (2.30), 7.236 (1.68), 7.258 (3.44), 7.281 (1.81), 7.868 (1.52), 7.882 (1.74), 7.890 (1.70), 7.904 (1.46), 8.494 (1.20), 9.464 (1.41).

Example 255

4-(3-{[6-(4-bromo-3,5-dimethyl-1H-pyrazol-1-yl) pyrimidin-4-yl]amino}-1,4-dimethyl-1H-pyrazol-5-yl)benzonitrile

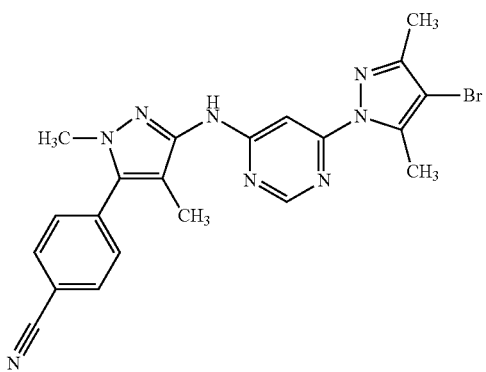 [SMILES: Cc1nn(-c2cc(Nc3nn(C)c(-c4ccc(C#N)cc4)c3C)ncn2)c(C)c1Br]

4-(3-{[6-(3,5-dimethyl-1H-pyrazol-1-yl)pyrimidin-4-yl] amino}-1,4-dimethyl-1H-pyrazol-5-yl)benzonitrile (84.0 mg, 218 µmol) was dissolved in acetonitrile, 1-bromopyrrolidine-2,5-dione (46.7 mg, 262 µmol) was added at ambient temperature and the reaction mixture stirred overnight. Water was added and the mixture stirred for further 5 min. The precipitated solid was collected by filtration, washed with water and dried overnight in a vacuum drying-oven at 40° C. The filtrate was extracted with ethyl acetate, the organic phase extract was dried over sodium sulfate and concentrated. Both solids were combined and lyophilized from acetonitrile/water. It was further purified by preparative HPLC (method 2) to yield the desired product (12 mg, 12% yield).

LC-MS (method 10): $R_t$=2.25 min; MS (ESIpos): m/z=463 [M+H]$^+$ $^1$H-NMR (400 MHz, dimethylsulfoxide-d6) δ [ppm]: 1.887 (12.71), 2.221 (14.72), 2.653 (16.00), 2.670 (0.45), 3.736 (15.81), 7.415 (1.20), 7.698 (4.27), 7.719 (4.76), 8.004 (4.72), 8.025 (3.98), 8.491 (2.64), 9.553 (2.35).

Example 256

1-{[1-(6-{[4-ethyl-5-(4-fluorophenyl)-1-methyl-1H-pyrazol-3-yl]amino}pyrimidin-4-yl)-3,5-dimethyl-1H-pyrazol-4-yl]methyl}cyclopropanol

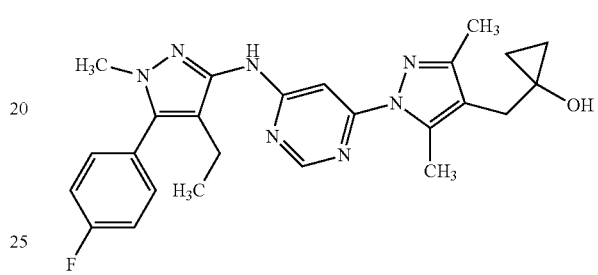

Under an argon atmosphere a Schlenk tube was charged with a ethyl [1-(6-{[4-ethyl-5-(4-fluorophenyl)-1-methyl-1H-pyrazol-3-yl]amino}pyrimidin-4-yl)-3,5-dimethyl-1H-pyrazol-4-yl]acetate (235 mg, 90% purity, 443 µmol) in tetrahydrofuran (2.0 ml, 25 mmol). Titanium isopropoxylate (140 µl, 490 µmol) and ethylmagnesium bromide (1.6 ml, 1.0 M in tetrahydrofuran, 1.6 mmol) were added at 0° C. The mixture was stirred 2 hours at 0° C. and overnight at ambient temperature. The mixture was diluted with saturated ammonium chloride solution. The occurring precipitate was filtered off. The filtrate was extracted with ethyl acetate (3×). The combined organic phases were washed with brine, dried over sodium sulfate and concentrated under reduced pressure. The crude product was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 5.5 mg (3%) of the desired product along with propan-2-yl [1-(6-{[4-ethyl-5-(4-fluorophenyl)-1-methyl-1H-pyrazol-3-yl] amino}pyrimidin-4-yl)-3,5-dimethyl-1H-pyrazol-4-yl]acetate as by-product.

LC-MS (method 10): $R_t$=1.96 min; MS (ESIpos): m/z=462 [M+H]$^+$ $^1$H-NMR (500 MHz, dimethylsulfoxide-d6) δ [ppm]: 0.343 (1.14), 0.353 (3.37), 0.357 (3.13), 0.365 (1.40), 0.509 (1.25), 0.517 (3.14), 0.521 (2.85), 0.531 (0.93), 0.876 (3.50), 0.891 (7.88), 0.906 (3.46), 2.172 (0.44), 2.186 (13.76), 2.290 (0.75), 2.305 (2.13), 2.320 (2.05), 2.334 (0.65), 2.583 (14.04), 2.657 (5.30), 3.651 (16.00), 5.221 (5.06), 7.319 (1.96), 7.361 (2.11), 7.366 (0.78), 7.375 (1.02), 7.379 (4.46), 7.384 (0.91), 7.393 (0.85), 7.397 (2.53), 7.503 (2.47), 7.507 (1.04), 7.514 (2.70), 7.520 (2.17), 7.527 (0.84), 7.531 (1.87), 8.432 (2.96), 8.434 (2.87), 9.285 (2.09).

Example 257 ethyl [1-(6-{[1-(4-cyanophenyl)-3,5-dimethyl-1H-pyrazol-4-yl]amino}pyrimidin-4-yl)-3,5-dimethyl-1H-pyrazol-4-yl]acetate

Example 258 ethyl 1-(6-{[3-(4-cyanophenyl)-1-(cyclopropylmethyl)-4-methyl-1H-pyrazol-5-yl]amino}pyrimidin-4-yl)-3-methyl-1H-pyrazole-5-carboxylate

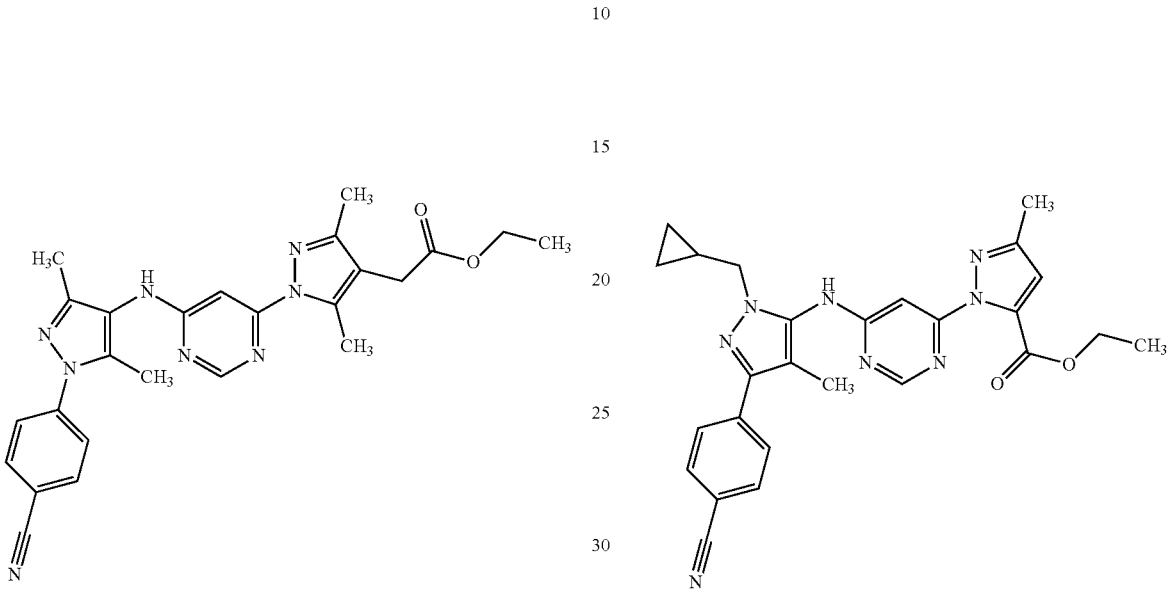

A microwave vial was charged 4-(4-amino-3,5-dimethyl-1H-pyrazol-1-yl)benzonitrile (250 mg, 1.18 mmol), ethyl [1-(6-chloropyrimidin-4-yl)-3,5-dimethyl-1H-pyrazol-4-yl]acetate (382 mg, 1.30 mmol) and sodium phenolate (150 mg, 1.30 mmol) and the contents were suspended in 1,4-dioxane (5.0 ml, 58 mmol). The reaction mixture was degassed with Ar for 3 min. Tris(dibenzylidenaceton)dipalladium (32.4 mg, 35.3 µmol) and Xantphos (40.9 mg, 70.7 µmol) were added and the reaction mixture was degassed again for 1 min. The vial was sealed and heated at 85° C. overnight while vigorously stirring. After cooling to ambient temperature, the reaction mixture was diluted with 1.0 M hydrochloric acid and extracted with ethyl acetate (2×). The combined organic phases were dried over Extrelut NT3 and concentrated under reduced pressure. The crude product was recrystallized from acetonitrile to yield the desired product (82.0 mg, 43%).

LC-MS (method 10): $R_t$=1.90 min; MS (ESIpos): m/z=471 [M+H]$^+$ $^1$H-NMR (400 MHz, dimethylsulfoxide-d6) δ [ppm]: 1.166 (3.51), 1.183 (7.23), 1.201 (3.62), 1.647 (0.80), 2.086 (0.67), 2.107 (16.00), 2.131 (2.04), 2.294 (10.13), 2.566 (13.92), 3.470 (4.27), 3.887 (1.43), 4.048 (1.03), 4.066 (3.02), 4.083 (2.99), 4.101 (1.00), 7.367 (0.59), 7.384 (0.60), 7.397 (0.72), 7.811 (1.64), 7.831 (2.02), 7.978 (3.67), 7.999 (2.86), 8.078 (0.41), 8.406 (0.52), 8.940 (2.67).

A microwave vial was charged with 4-[5-amino-1-(cyclopropylmethyl)-4-methyl-1H-pyrazol-3-yl]benzonitrile (103 mg, 409 µmol), ethyl 1-(6-chloropyrimidin-4-yl)-3-methyl-1H-pyrazole-5-carboxylate (120 mg, 450 µmol) and sodium phenolate (52.2 mg, 450 µmol) and the contents were suspended in 1,4-dioxane (1.2 mL). The reaction mixture was degassed with Ar for 3 min. Tris(dibenzylideneacetone)dipalladium (4.87 mg, 5.32 µmol) and XantPhos (7.10 mg, 12.3 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (23 mg, 11% yield).

LC-MS (method 10): $R_t$=2.07 min; MS (ESIpos): m/z=483 [M+H]$^+$ $^1$H-NMR (400 MHz, dimethylsulfoxide-d6) δ [ppm]: −0.008 (0.44), 0.008 (0.48), 0.302 (2.29), 0.313 (2.48), 0.432 (2.56), 0.452 (2.70), 1.186 (0.77), 1.199 (6.89), 1.217 (14.07), 1.235 (6.88), 1.288 (0.54), 1.306 (1.10), 1.323 (0.56), 2.073 (16.00), 2.263 (2.56), 2.328 (0.43), 2.708 (1.37), 3.873 (2.31), 3.890 (2.29), 4.246 (2.12), 4.264 (6.78), 4.282 (6.75), 4.299 (2.14), 4.308 (0.60), 4.326 (0.51), 6.753 (2.19), 6.846 (0.41), 7.281 (0.41), 7.300 (0.48), 7.345 (0.60), 7.887 (1.41), 7.909 (9.94), 7.916 (6.20), 7.938 (1.10), 8.428 (0.43), 8.794 (0.41).

Example 259 ethyl 4-chloro-1-(6-{[5-(4-fluorophenyl)-1,4-dimethyl-1H-pyrazol-3-yl]amino}pyrimidin-4-yl)-3-methyl-1H-pyrazole-5-carboxylate

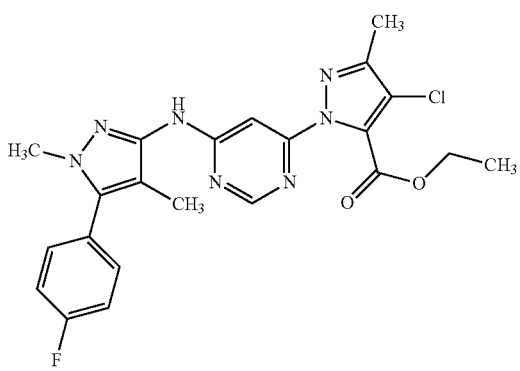 [SMILES: CCOC(=O)c1c(Cl)c(C)nn1-c1cc(Nc2nn(C)c(-c3ccc(F)cc3)c2C)ncn1]

A microwave vial was charged with 5-(4-fluorophenyl)-1,4-dimethyl-1H-pyrazol-3-amine (74.4 mg, 362 μmol), ethyl 4-chloro-1-(6-chloropyrimidin-4-yl)-3-methyl-1H-pyrazole-5-carboxylate (120 mg, 398 μmol) and sodium phenolate (46.3 mg, 398 μmol) and the contents were suspended in 1,4-dioxane (1.0 mL). The reaction mixture was degassed with Ar for 3 min. Tris(dibenzylideneacetone)dipalladium (4.31 mg, 4.71 μmol) and XantPhos (6.29 mg, 10.9 μmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (10.5 mg, 6% yield).

LC-MS (method 10): $R_t$=2.29 min; MS (ESIpos): m/z=470 [M+H]$^+$ $^1$H-NMR (400 MHz, dimethylsulfoxide-d6) δ [ppm]: −0.008 (1.19), 0.008 (1.15), 1.228 (4.97), 1.246 (10.73), 1.264 (5.10), 1.304 (0.71), 1.322 (1.55), 1.340 (0.77), 1.863 (11.32), 2.281 (15.27), 2.323 (0.51), 2.328 (0.62), 2.366 (0.27), 2.668 (2.83), 2.692 (0.38), 2.710 (0.27), 3.688 (2.96), 3.696 (16.00), 4.322 (1.68), 4.340 (5.36), 4.358 (5.30), 4.375 (1.63), 7.359 (2.49), 7.364 (1.32), 7.381 (5.27), 7.403 (3.00), 7.515 (3.04), 7.521 (1.35), 7.529 (3.29), 7.537 (2.69), 7.546 (1.04), 7.551 (2.29), 8.424 (2.32), 8.573 (0.29), 9.720 (1.33).

Example 260

N-[3-(4-bromophenyl)-1,4-dimethyl-1H-pyrazol-5-yl]-6-(3,5-dimethyl-1H-pyrazol-1-yl)pyrimidin-4-amine

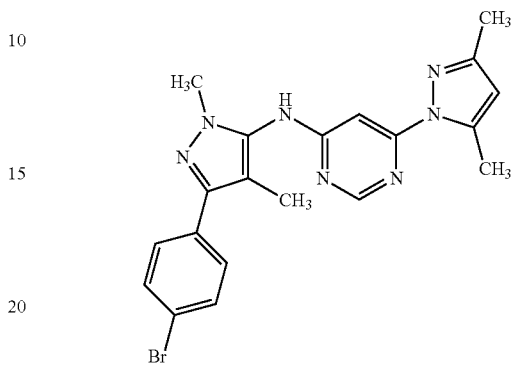

In a microwave vial, 4-chloro-6-(3,5-dimethyl-1H-pyrazol-1-yl)pyrimidine (400 mg, 1.92 mmol) and 3-(4-bromophenyl)-1,4-dimethyl-1H-pyrazol-5-amine (561 mg, 2.11 mmol) were dissolved in N-methylpyrrolidone (2.5 mL) and a solution of hydrochloric acid in 1,4-dioxane (1.9 ml, 4.0 M, 7.7 mmol) was added. The vial was sealed and irradiated in a microwave at 190° C. for 2 h while stirring. The mixture was diluted with acetonitrile and water and purified by preparative HPLC (column: Chromatorex C18; 250*40 mm, 10 μM, flow 100 mL/min, gradient acetonitrile/water (containing 0.1% trifluoroacetic acid) 10/90 to 95/5) to yield the desired product (312 mg, 36% yield).

LC-MS (method 9): $R_t$=1.17 min; MS (ESIpos): m/z=438 [M+H]$^+$ $^1$H-NMR (400 MHz, dimethylsulfoxide-d6) δ [ppm]: 2.025 (16.00), 2.073 (0.53), 2.174 (4.49), 2.630 (14.25), 2.670 (0.52), 3.665 (11.59), 6.146 (3.12), 7.614 (1.35), 7.635 (8.18), 7.644 (6.80), 7.666 (1.19), 8.469 (1.04), 9.420 (2.40).

Example 261

2-[4-chloro-1-(6-{[5-(4-fluorophenyl)-1,4-dimethyl-1H-pyrazol-3-yl]amino}pyrimidin-4-yl)-3-methyl-1H-pyrazol-5-yl]propan-2-ol

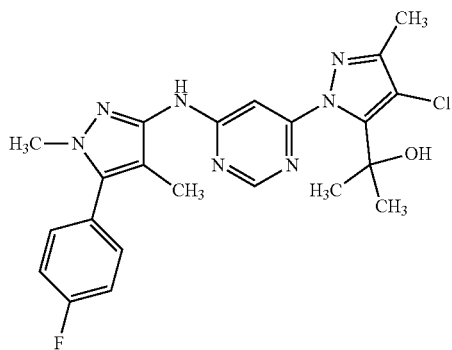 [SMILES: Cc1nn(-c2cc(Nc3nn(C)c(-c4ccc(F)cc4)c3C)ncn2)c(C(C)(C)O)c1Cl]

Under an argon atmosphere, ethyl 4-chloro-1-(6-{[5-(4-fluorophenyl)-1,4-dimethyl-1H-pyrazol-3-yl]amino}pyrimidin-4-yl)-3-methyl-1H-pyrazole-5-carboxylate (9.00 mg, 19.2 µmol) was dissolved in tetrahydrofuran and the solution cooled to 0° C. A solution of bromo(methyl)magnesium (96 µl, 1.0 M, 96 µmol) was added dropwise and the reaction mixture was stirred for 4 h at ambient temperature. A second aliquot of bromo(methyl)magnesium (96 µl, 1.0 M in tetrahydrofuran, 96 µmol) was added and the reaction mixture was stirred at ambient temperature overnight. The reaction mixture was carefully quenched by addition of water and extracted with dichloromethane (3×). The combined organic phase extracts were dried over magnesium sulfate and concentrated. The residue was purified by flash column chromatography (SNAP Ultra 10 g, cyclohexane/ethyl acetate gradient 95/5 to 5/95) to yield the desired product (2.0 mg, 21% yield).

LC-MS (method 10): $R_t$=2.21 min; MS (ESIpos): m/z=456 [M+H]$^+$

Example 262

2-[1-(6-{[5-(4-fluorophenyl)-1,4-dimethyl-1H-pyrazol-3-yl]amino}pyrimidin-4-yl)-3-methyl-1H-pyrazol-5-yl]propan-2-ol

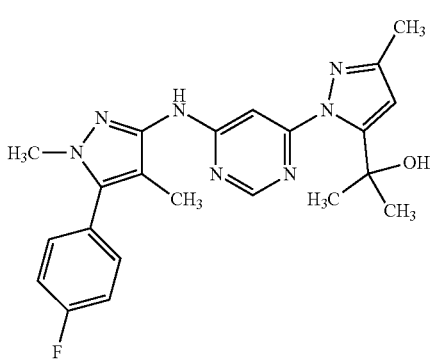 [SMILES: Cc1cc(C(C)(C)O)n(-c2cc(Nc3nn(C)c(-c4ccc(F)cc4)c3C)ncn2)n1]

Under an argon atmosphere, ethyl 1-(6-{[5-(4-fluorophenyl)-1,4-dimethyl-1H-pyrazol-3-yl]amino}pyrimidin-4-yl)-3-methyl-1H-pyrazole-5-carboxylate (7.80 mg, 17.9 µmol) was dissolved in tetrahydrofuran (0.7 mL) and the solution cooled to 0° C. A solution of bromo(methyl)magnesium (90 µl, 1.0 M, 90 µmol) was added dropwise and the reaction mixture was stirred for 4 h at ambient temperature. A second aliquot of bromo(methyl)magnesium (90 µl, 1.0 M, 90 µmol) was added and the reaction mixture was stirred at ambient temperature overnight. The reaction mixture was carefully quenched by addition of water and extracted with dichloromethane (3×). The combined organic phase extracts were dried over magnesium sulfate and concentrated. The residue was purified by flash column chromatography (SNAP Ultra 10 g, cyclohexane/ethyl acetate gradient 95/5 to 5/95) to yield the desired product (2.5 mg, 32% yield).

LC-MS (method 10): $R_t$=1.96 min; MS (ESIpos): m/z=422 [M+H]$^+$

Example 263

4-[1-(cyclopropylmethyl)-5-({6-[5-(2-hydroxypropan-2-yl)-3-methyl-1H-pyrazol-1-yl]pyrimidin-4-yl}amino)-4-methyl-1H-pyrazol-3-yl]benzonitrile

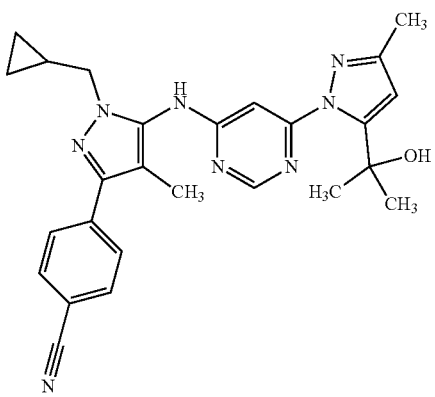 [SMILES: Cc1cc(C(C)(C)O)n(-c2cc(Nc3c(C)c(-c4ccc(C#N)cc4)nn3CC3CC3)ncn2)n1]

Under an argon atmosphere, ethyl 1-(6-{[3-(4-cyanophenyl)-1-(cyclopropylmethyl)-4-methyl-1H-pyrazol-5-yl]amino}pyrimidin-4-yl)-3-methyl-1H-pyrazole-5-carboxylate (21.0 mg, 43.5 µmol) was dissolved in tetrahydrofuran and the solution cooled to 0° C. A solution of bromo(methyl)magnesium (220 µl, 1.0 M in tetrahydrofuran, 220 µmol) was added dropwise and the reaction mixture was stirred for 4 h at ambient temperature. A second aliquot of bromo(methyl)magnesium (220 µl, 1.0 M in tetrahydrofuran, 220 µmol) was added and the reaction mixture was stirred at ambient temperature overnight. The reaction mixture was carefully quenched by addition of water and extracted with dichloromethane (3×). The combined organic phase extracts were dried over magnesium sulfate and concentrated. The residue was purified by flash column chromatography (SNAP Ultra 10 g, cyclohexane/ethyl acetate gradient 95/5 to 5/95) to yield the desired product (5.0 mg, 23% yield).

LC-MS (method 10): $R_t$=2.01 min; MS (ESIpos): m/z=469 [M+H]$^+$

Example 264

2-[1-(6-{[4-ethyl-3-(4-fluorophenyl)-1-methyl-1H-pyrazol-5-yl]amino}pyrimidin-4-yl)-3-methyl-1H-pyrazol-5-yl]propan-2-ol

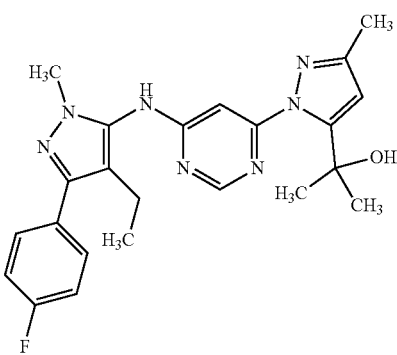 [SMILES: CCc1c(-c2ccc(F)cc2)nn(C)c1Nc1cc(-n2nc(C)cc2C(C)(C)O)ncn1]

Under an argon atmosphere, ethyl 1-(6-{[4-ethyl-3-(4-fluorophenyl)-1-methyl-1H-pyrazol-5-yl]amino}pyrimidin-4-yl)-3-methyl-1H-pyrazole-5-carboxylate (44.0 mg, 97.9 µmol) was dissolved in tetrahydrofuran (2.0 mL) and the solution cooled to 0° C. A solution of bromo(methyl)magnesium (490 µl, 1.0 M in tetrahydrofuran, 490 µmol) was added dropwise and the reaction mixture was stirred for 4 h at ambient temperature. A second aliquot of bromo(methyl)magnesium (490 µl, 1.0 M in tetrahydrofuran, 490 µmol) was added and the reaction mixture was stirred at ambient temperature overnight. The reaction mixture was carefully quenched by addition of water and extracted with dichloromethane (3×). The combined organic phase extracts were dried over magnesium sulfate and concentrated. The residue was purified by flash column chromatography (SNAP Ultra 10 g, cyclohexane/ethyl acetate gradient 95/5 to 5/95) to yield the desired product (19 mg, 45% yield).

LC-MS (method 10): $R_t$=1.98 min; MS (ESIpos): m/z=436 [M+H]$^+$

Example 265

6-(4-bromo-3,5-dimethyl-1H-pyrazol-1-yl)-N-[4-ethyl-3-(4-fluorophenyl)-1-methyl-1H-pyrazol-5-yl]pyrimidin-4-amine

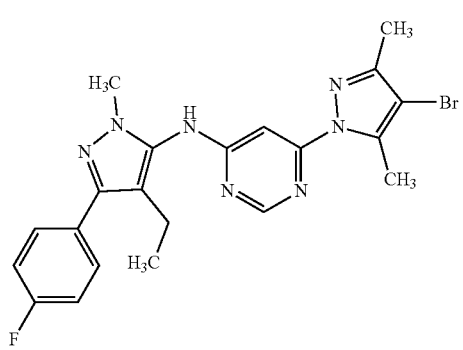 [SMILES: CCc1c(-c2ccc(F)cc2)nn(C)c1Nc1cc(-n2nc(C)c(Br)c2C)ncn1]

Under an argon atmosphere, a round-bottom flask was charged with 4-ethyl-3-(4-fluorophenyl)-1-methyl-1H-pyrazol-5-amine (1.00 g, 4.56 mmol), 4-(4-bromo-3,5-dimethyl-1H-pyrazol-1-yl)-6-chloropyrimidine (1.19 g, 4.15 mmol) and sodium phenolate (529 mg, 4.56 mmol) and the contents were suspended in 1,4-dioxane (12 mL). The reaction mixture was degassed with Ar for 3 min. Tris(dibenzylideneacetone)dipalladium (49.4 mg, 53.9 µmol) and XantPhos (72.0 mg, 124 µmol) were added and the reaction mixture was degassed again for 1 min. The reaction mixture was heated at 85° C. overnight while vigorously stirring. After cooling to ambient temperature, the reaction mixture was diluted with water and extracted with ethyl acetate. The organic phase extract was dried over sodium sulfate and concentrated. The residue purified by flash column chromatography (SNAP Ultra 50 g, cyclohexane/ethyl acetate gradient 98/12 to 0/100). to yield the desired product (969 mg, 45% yield).

LC-MS (method 10): $R_t$=2.47 min; MS (ESIpos): m/z=470 [M+H]$^+$ $^1$H-NMR (400 MHz, dimethylsulfoxide-d6) δ [ppm]: −0.149 (0.26), −0.008 (2.20), 0.008 (1.95), 0.146 (0.25), 0.966 (3.51), 0.985 (7.95), 1.004 (3.66), 1.157 (0.47), 1.175 (1.00), 1.193 (0.49), 1.398 (0.56), 1.988 (1.79), 2.211 (2.46), 2.328 (0.39), 2.366 (0.22), 2.442 (0.68), 2.461 (1.99), 2.480 (2.13), 2.663 (16.00), 2.710 (0.24), 3.568 (0.18), 3.638 (9.64), 4.021 (0.42), 4.038 (0.43), 7.247 (1.94), 7.269 (4.02), 7.291 (2.25), 7.648 (1.36), 7.662 (1.79), 7.683 (1.34), 8.508 (0.65), 9.467 (0.78).

Example 266

4-(5-{[6-(4-fluoro-3,5-dimethyl-1H-pyrazol-1-yl)pyrimidin-4-yl]amino}-4-methyl-1H-pyrazol-3-yl)benzonitrile

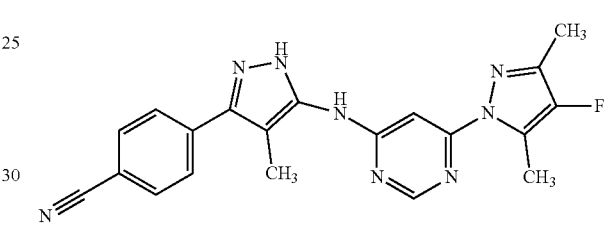

A microwave vial was charged with 4-(3-amino-4-methyl-1H-pyrazol-5-yl)benzonitrile (63.6 mg, 321 µmol), 4-chloro-6-(4-fluoro-3,5-dimethyl-1H-pyrazol-1-yl)pyrimidine (80.0 mg, 353 µmol) and sodium phenolate (41.0 mg, 353 µmol) and the contents were suspended in 1,4-dioxane (0.9 mL). The reaction mixture was degassed with Ar for 3 min. Tris(dibenzylideneacetone)dipalladium (3.82 mg, 4.17 µmol) and XantPhos (5.57 mg, 9.63 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (XBridge C18 5 µm 100×30 mm, solvent A: water, solvent B: acetonitrile, flow: 65 mL/min plus 5 mL 2% formic acid in water, gradient 0-2 min: 20% B, 2-7 min: to 92% B, 7-9 min: 92% B) to yield the desired product (3.8 mg, 3% yield).

LC-MS (method 10): $R_t$=1.97 min; MS (ESIpos): m/z=389 [M+H]$^+$ $^1$H-NMR (400 MHz, dimethylsulfoxide-d6) δ [ppm]: −0.149 (1.01), −0.008 (7.45), 0.008 (6.99), 0.146 (1.01), 1.646 (0.64), 2.112 (13.79), 2.208 (16.00), 2.327 (3.13), 2.366 (1.20), 2.592 (11.03), 2.596 (12.69), 2.670 (3.59), 2.710 (1.20), 7.385 (0.64), 7.468 (1.20), 7.797 (4.32), 7.818 (5.70), 7.908 (2.30), 7.973 (5.70), 7.994 (4.51), 8.474 (3.13), 8.509 (0.83), 9.522 (3.31), 9.658 (0.46), 13.115 (2.85).

Example 267

6-(4-fluoro-3,5-dimethyl-1H-pyrazol-1-yl)-N-[5-(4-fluorophenyl)-1,4-dimethyl-1H-pyrazol-3-yl]pyrimidin-4-amine

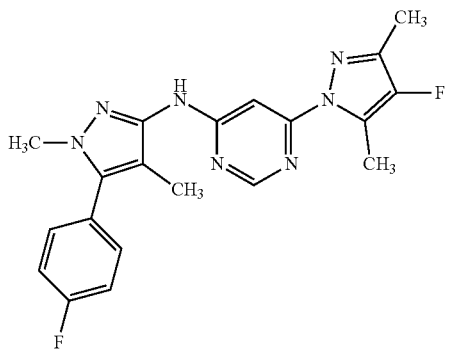 [SMILES: Cc1nn(-c2cc(Nc3nn(C)c(-c4ccc(F)cc4)c3C)ncn2)c(C)c1F]

A microwave vial was charged with 5-(4-fluorophenyl)-1,4-dimethyl-1H-pyrazol-3-amine (85.0 mg, 414 μmol), 4-chloro-6-(4-fluoro-3,5-dimethyl-1H-pyrazol-1-yl)pyrimidine (103 mg, 456 μmol) and sodium phenolate (52.9 mg, 456 μmol) and the contents were suspended in 1,4-dioxane (1.2 mL). The reaction mixture was degassed with Ar for 3 min. Tris(dibenzylideneacetone)dipalladium (4.93 mg, 5.38 μmol) and XantPhos (7.19 mg, 12.4 μmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 4) to yield the desired product (2.0 mg, 1% yield).

LC-MS (method 10): Rt=2.21 min; MS (ESIpos): m/z=396 [M+H]$^+$ $^1$H-NMR (400 MHz, dimethylsulfoxide-d6) δ [ppm]: −0.008 (0.94), 0.008 (1.33), 1.848 (13.09), 2.221 (13.78), 2.327 (0.49), 2.670 (0.64), 3.688 (16.00), 7.357 (2.02), 7.379 (4.89), 7.385 (1.96), 7.396 (1.47), 7.402 (2.85), 7.509 (2.54), 7.514 (1.09), 7.523 (2.78), 7.531 (2.23), 7.539 (0.87), 7.545 (1.91), 8.456 (2.78), 9.455 (2.52).

Example 268

4-[1-(cyclopropylmethyl)-5-{[6-(4-fluoro-3,5-dimethyl-1H-pyrazol-1-yl)pyrimidin-4-yl]amino}-4-methyl-1H-pyrazol-3-yl]benzonitrile

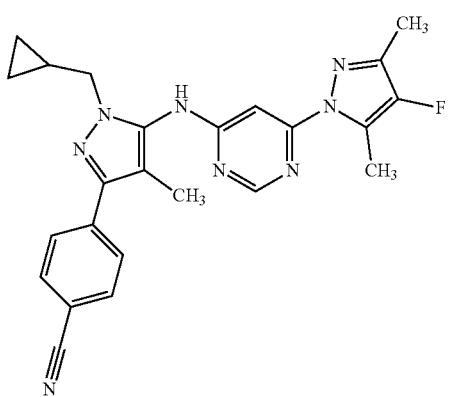 [SMILES: Cc1nn(-c2cc(Nc3c(C)c(-c4ccc(C#N)cc4)nn3CC3CC3)ncn2)c(C)c1F]

A microwave vial was charged with 4-[5-amino-1-(cyclopropylmethyl)-4-methyl-1H-pyrazol-3-yl]benzonitrile (300 mg, 1.19 mmol), 4-chloro-6-(4-fluoro-3,5-dimethyl-1H-pyrazol-1-yl)pyrimidine (296 mg, 1.31 mmol) and sodium phenolate (152 mg, 1.31 mmol) and the contents were suspended in 1,4-dioxane (3.4 mL). The reaction mixture was degassed with Ar for 3 min. Tris(dibenzylideneacetone)dipalladium (14.2 mg, 15.5 μmol) and XantPhos (20.6 mg, 35.7 μmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 4) to yield the desired product (54 mg, 10% yield).

LC-MS (method 11): R$_t$=1.54 min; MS (ESIpos): m/z=443 [M+H]$^+$ $^1$H-NMR (400 MHz, dimethylsulfoxide-d6) δ [ppm]: −0.008 (0.70), 0.008 (0.69), 0.302 (2.50), 0.314 (2.76), 0.431 (2.58), 0.451 (2.76), 1.174 (0.36), 1.186 (0.69), 1.193 (0.66), 1.205 (1.03), 1.217 (0.63), 1.223 (0.66), 1.236 (0.34), 2.060 (16.00), 2.209 (2.74), 2.329 (0.19), 2.671 (0.21), 3.859 (2.43), 3.876 (2.39), 7.885 (0.90), 7.907 (10.87), 7.933 (0.90), 8.473 (0.52), 9.478 (0.62).

Example 269

N-[4-ethyl-5-(4-fluorophenyl)-1-methyl-1H-pyrazol-3-yl]-6-(4-fluoro-3,5-dimethyl-1H-pyrazol-1-yl)pyrimidin-4-amine

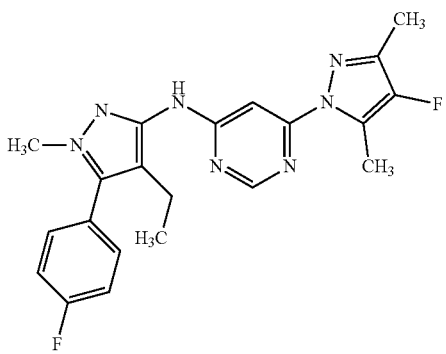

A microwave vial was charged with 4-ethyl-5-(4-fluorophenyl)-1-methyl-1H-pyrazol-3-amine (79.2 mg, 361 μmol), 4-chloro-6-(4-fluoro-3,5-dimethyl-1H-pyrazol-1-yl)pyrimidine (90.0 mg, 397 μmol) and sodium phenolate (46.1 mg, 397 μmol) and the contents were suspended in 1,4-dioxane (1.0 mL). The reaction mixture was degassed with Ar for 3 min. Tris(dibenzylideneacetone)dipalladium (4.30 mg, 4.69 μmol) and XantPhos (6.27 mg, 10.8 μmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (XBridge C18 5 μm 100×30 mm, solvent A: water, solvent B: acetonitrile, flow: 65 mL/min plus 5 mL 2% formic acid in water, gradient 0-2 min: 50% B, 2-2.2 min: to 70% B, 2.2-7 min: 70 to 92% B, 7-9 min: 92% B) to yield the desired product (4 mg, 3% yield).

LC-MS (method 10): R$_t$=2.33 min; MS (ESIpos): m/z=410 [M+H]$^+$

Example 270

6-[4-chloro-5-(difluoromethyl)-3-methyl-1H-pyrazol-1-yl]-N-[4-ethyl-5-(4-fluorophenyl)-1-methyl-1H-pyrazol-3-yl]pyrimidin-4-amine

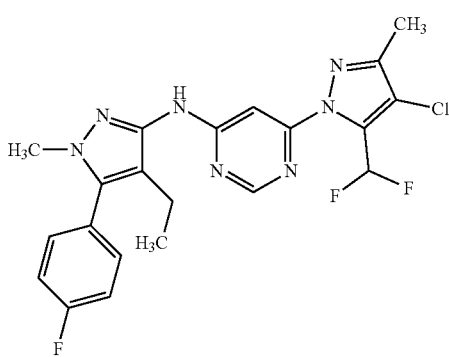 [SMILES: CCc1c(Nc2cc(-n3nc(C)c(Cl)c3C(F)F)ncn2)nn(C)c1-c1ccc(F)cc1]

A solution of 4-chloro-6-[4-chloro-5-(difluoromethyl)-3-methyl-1H-pyrazol-1-yl]pyrimidine (170 mg, 609 µmol) and 4-ethyl-5-(4-fluorophenyl)-1-methyl-1H-pyrazol-3-amine (147 mg, 670 µmol) in 1-methoxy-2-propanol (3.4 ml, 35 mmol) was treated with concentrated hydrochloric acid (150 µl, 12 M, 1.8 mmol) and stirred overnight at 120° C. The mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 90.2 mg of the desired product (32%).

LC-MS (method 11): R$_t$=1.59 min; MS (ESIpos): m/z=462 [M+H]$^+$ $^1$H-NMR (400 MHz, dimethylsulfoxide-d6) δ [ppm]: 0.869 (3.71), 0.888 (7.95), 0.907 (3.64), 1.074 (0.65), 1.091 (1.29), 1.109 (0.64), 2.283 (14.46), 2.310 (2.49), 2.329 (2.42), 2.347 (0.78), 3.375 (0.65), 3.393 (0.62), 3.659 (16.00), 7.360 (2.09), 7.382 (4.58), 7.405 (3.18), 7.504 (2.72), 7.518 (3.05), 7.525 (2.43), 7.539 (1.91), 7.905 (1.24), 8.037 (2.61), 8.168 (1.13), 8.501 (3.10), 9.654 (1.27).

Example 271

6-[3,5-dimethyl-4-(5-methyl-1,3,4-oxadiazol-2-yl)-1H-pyrazol-1-yl]-N-[4-ethyl-5-(4-fluorophenyl)-1-methyl-1H-pyrazol-3-yl]pyrimidin-4-amine

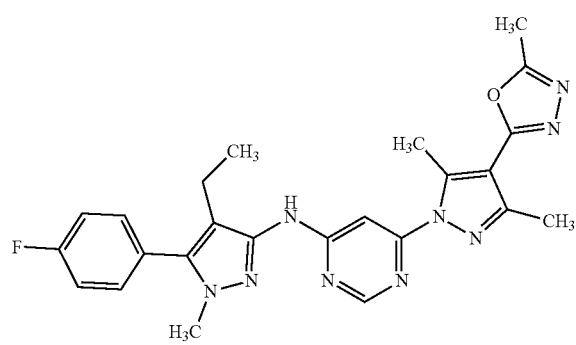 [SMILES: CCc1c(Nc2cc(-n3nc(C)c(-c4nnc(C)o4)c3C)ncn2)nn(C)c1-c1ccc(F)cc1]

A solution of N'-acetyl-1-(6-{[4-ethyl-5-(4-fluorophenyl)-1-methyl-1H-pyrazol-3-yl]amino}pyrimidin-4-yl)-3,5-dimethyl-1H-pyrazole-4-carbohydrazide (56.8 mg, 116 µmol) in tetrahydrofuran (2.5 ml, 31 mmol) was treated with Burgess Reagent (38.6 mg, 162 µmol) and stirred overnight at ambient temperature. The mixture was purified using preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B). To remove remaining trimethylamine the product after preparative HPLC was resolved in dichloromethane, extracted with water, washed with saturated ammonium chloride solution, water, dried over Extrelut NT3 and concentrated to yield 30.4 mg (56%) of the desired product.

LC-MS (method 10): R$_t$=1.96 min; MS (ESIpos): m/z=474 [M+H]$^+$ $^1$H-NMR (400 MHz, dimethylsulfoxide-d6) δ [ppm]: 0.879 (3.68), 0.898 (7.78), 0.916 (3.67), 1.091 (0.72), 1.974 (1.96), 2.299 (1.24), 2.317 (2.74), 2.336 (2.65), 2.355 (0.93), 2.366 (0.47), 2.460 (15.47), 2.573 (16.00), 2.957 (15.09), 3.375 (0.41), 3.656 (15.14), 3.786 (0.58), 3.803 (0.56), 4.905 (0.66), 7.186 (0.52), 7.361 (2.02), 7.383 (4.36), 7.405 (2.66), 7.440 (1.54), 7.505 (2.68), 7.519 (3.07), 7.526 (2.50), 7.540 (1.94), 8.537 (2.85), 9.548 (1.83).

Example 272

[1-(6-{[4-ethyl-5-(4-fluorophenyl)-1-methyl-1H-pyrazol-3-yl]amino}pyrimidin-4-yl)-3,5-dimethyl-1H-pyrazol-4-yl][3-(trifluoromethyl)pyrrolidin-1-yl]methanone

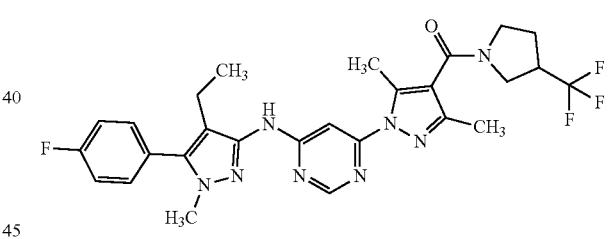

A solution of [A9 and 3-(trifluoromethyl)pyrrolidine (31.9 mg, 230 µmol) in N,N-diisopropylethylamine (60 µl, 340 µmol) was treated with HATU (65.5 mg, 172 µmol) and dimethylformamide (1.0 ml, 13 mmol) and stirred overnight at ambient temperature. The mixture was purified by preparative HPLC ((method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 54.1 (85%) of the desired product.

LC-MS (method 10): R$_t$=2.01 min; MS (ESIpos): m/z=557 [M+H]$^+$ $^1$H-NMR (400 MHz, dimethylsulfoxide-d6) δ [ppm]: −0.008 (0.75), 0.008 (0.47), 0.874 (3.50), 0.893 (7.71), 0.911 (3.47), 1.074 (1.72), 1.092 (3.48), 1.109 (1.73), 2.017 (0.44), 2.179 (13.70), 2.289 (0.89), 2.308 (2.35), 2.327 (2.29), 2.345 (0.73), 2.604 (12.81), 3.358 (1.11), 3.376 (2.42), 3.393 (2.45), 3.410 (1.05), 3.654 (16.00), 7.359 (2.21), 7.365 (1.09), 7.381 (6.03), 7.399 (1.06), 7.404 (2.68), 7.502 (2.64), 7.507 (1.22), 7.515 (2.93), 7.523 (2.22), 7.532 (0.93), 7.537 (1.85), 8.481 (3.24), 9.441 (2.10).

Example 273

1-(6-{[4-ethyl-5-(4-fluorophenyl)-1-methyl-1H-pyrazol-3-yl]amino}pyrimidin-4-yl)-3-methyl-5,6-dihydrocyclopenta[c]pyrazol-4(1H)-one

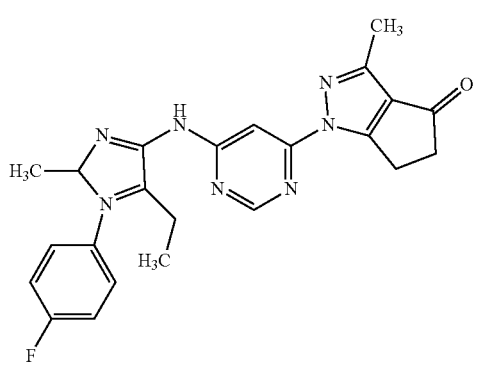

Under an argon atmosphere, a round-bottom flask was charged with 4-ethyl-5-(4-fluorophenyl)-1-methyl-1H-pyrazol-3-amine (228 mg, 1.04 mmol), 1-(6-chloropyrimidin-4-yl)-3-methyl-5,6-dihydrocyclopenta[c]pyrazol-4(1H)-one (284 mg, 1.14 mmol) and sodium phenolate (181 mg, 1.56 mmol) and the contents were suspended in 1,4-dioxane (3.0 mL). The reaction mixture was degassed with Ar for 3 min. Tris(dibenzylideneacetone)dipalladium (18.0 mg, 31.1 µmol) and XantPhos (14.3 mg, 15.6 µmol) were added and the reaction mixture was degassed again for 1 min. The reaction mixture was heated at 85° C. overnight while vigorously stirring. After cooling to ambient temperature, the reaction mixture was filtered and concentrated. The residue was redissolved in dimethylsulfoxide and purified by preparative HPLC (column: Chromatorex C18; 250*30 mm, 10 µM, flow 10 to 50 mL/min, isocratic acetonitrile/water (containing 0.1% trifluoroacetic acid) 20/80 as some component precipitated on the column; then flow 75 mL/min gradient acetonitrile/water (containing 0.1% trifluoroacetic acid) 25/75 to 95/5) to yield the desired product (61 mg, 13% yield) along with the regioisomer 2-(6-{[4-ethyl-5-(4-fluorophenyl)-1-methyl-1H-pyrazol-3-yl]amino}pyrimidin-4-yl)-3-methyl-5,6-dihydrocyclopenta[c]pyrazol-4(2H)-one (see below).

LC-MS (method 9): $R_t$=1.02 min; MS (ESIpos): m/z=432 [M+H]$^+$ $^1$H-NMR (400 MHz, dimethylsulfoxide-d6) δ [ppm]: −0.149 (0.50), −0.008 (4.33), 0.008 (4.09), 0.146 (0.51), 0.869 (3.60), 0.888 (8.15), 0.907 (3.72), 2.289 (0.95), 2.312 (16.00), 2.326 (3.03), 2.345 (0.83), 2.367 (0.51), 2.523 (1.71), 2.670 (0.59), 2.711 (0.46), 2.804 (0.87), 2.934 (2.08), 2.940 (2.04), 2.947 (2.35), 2.953 (2.20), 2.959 (2.23), 3.347 (2.89), 3.353 (2.98), 3.360 (3.46), 3.365 (3.55), 3.372 (4.03), 3.666 (15.57), 7.362 (2.92), 7.384 (4.99), 7.406 (2.89), 7.507 (2.71), 7.512 (1.26), 7.521 (3.05), 7.529 (2.50), 7.543 (2.07), 8.503 (2.79), 9.560 (1.63).

Example 274

2-(6-{[4-ethyl-5-(4-fluorophenyl)-1-methyl-1H-pyrazol-3-yl]amino}pyrimidin-4-yl)-3-methyl-5,6-dihydrocyclopenta[c]pyrazol-4(2H)-one

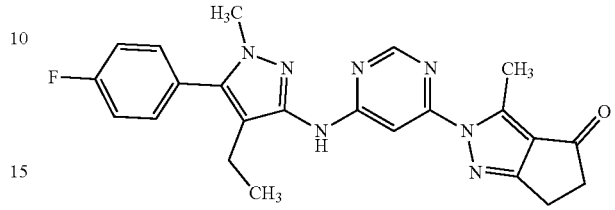

This compound was obtained as a by-product during the synthesis of the regioisomer 1-(6-{[4-ethyl-5-(4-fluorophenyl)-1-methyl-1H-pyrazol-3-yl]amino}pyrimidin-4-yl)-3-methyl-5,6-dihydrocyclopenta[c]pyrazol-4(1H)-one (see above). Preparative HPLC purification yielded the title compound (6.0 mg, 81% purity, 1% yield).

LC-MS (method 9): $R_t$=1.00 min; MS (ESIpos): m/z=432 [M+H]$^+$ $^1$H-NMR (400 MHz, dimethylsulfoxide-d6) δ [ppm]: −0.150 (1.70), 0.146 (1.74), 0.874 (3.91), 0.893 (8.37), 0.911 (4.15), 1.236 (0.48), 1.848 (5.75), 2.313 (4.60), 2.332 (4.63), 2.366 (2.25), 2.383 (2.76), 2.669 (2.49), 2.710 (1.77), 2.804 (15.52), 2.902 (3.54), 2.934 (3.68), 3.657 (16.00), 3.743 (0.71), 7.163 (1.12), 7.243 (3.91), 7.359 (5.04), 7.382 (7.69), 7.404 (6.09), 7.433 (4.73), 7.506 (3.30), 7.520 (3.78), 7.542 (2.59), 7.980 (1.67), 8.000 (1.53), 8.539 (3.47), 9.593 (2.21).

Example 275

6-(3,5-dimethyl-1H-pyrazol-1-yl)-N-[5-(4-fluorophenyl)-1-methyl-4-{[3-(trifluoromethyl)azetidin-1-yl]methyl}-1H-pyrazol-3-yl]pyrimidin-4-amine

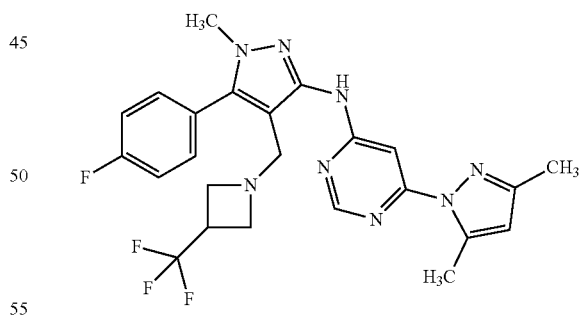

Under an argon atmosphere, 3-{[6-(3,5-dimethyl-1H-pyrazol-1-yl)pyrimidin-4-yl]amino}-5-(4-fluorophenyl)-1-methyl-1H-pyrazole-4-carbaldehyde (50.0 mg, 128 µmol) and 3-(trifluoromethyl)azetidine (19.2 mg, 153 µmol) were dissolved in tetrahydrofuran (2.0 mL) and acetic acid (22 µl, 380 µmol) and sodium triacetoxyborohydride (32.5 mg, 153 µmol) were added. The reaction mixture was stirred overnight at ambient temperature. Water was carefully added to quench the reaction, which was then extracted with ethyl acetate (3×). The combined organic phase extracts were dried over sodium sulfate and concentrated. The residue was purified by preparative HPLC (XBridge C18 5 μm 100×30 mm, solvent A: water, solvent B: acetonitrile, flow: 65 mL/min plus 5 mL 2% formic acid in water, gradient 0-2 min: 10% B, 2-2.2 min: to 30% B, 2.2-7 min: 30 to 70% B, 7-7.5 min: to 92% B, 7.5-9 min: 92% B) to yield the desired product (3.0 mg, 5% yield)

LC-MS (method 9): $R_t$=0.78 min; MS (ESIpos): m/z=501 [M+H]$^+$ $^1$H-NMR (400 MHz, dimethylsulfoxide-d6) δ [ppm]: −0.008 (1.83), 0.008 (1.83), 2.199 (15.19), 2.632 (13.00), 3.044 (2.43), 3.256 (3.04), 3.266 (2.59), 3.392 (5.94), 3.683 (16.00), 6.147 (3.68), 7.370 (2.01), 7.392 (4.40), 7.414 (2.52), 7.566 (2.42), 7.580 (2.74), 7.588 (2.37), 7.596 (0.95), 7.602 (2.00), 7.773 (1.19), 8.486 (3.60), 9.320 (3.64).

Example 276

2-[1-(6-{[4-chloro-5-(4-fluorophenyl)-1-methyl-1H-pyrazol-3-yl]amino}pyrimidin-4-yl)-3,5-dimethyl-1H-pyrazol-4-yl]propan-2-ol

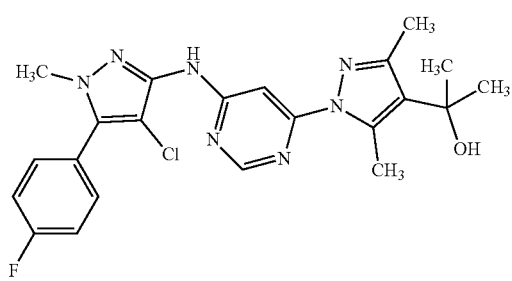 [SMILES: Cc1nn(-c2cc(Nc3nn(C)c(-c4ccc(F)cc4)c3Cl)ncn2)c(C)c1C(C)(C)O]

Under an argon atmosphere, ethyl 1-(6-{[4-chloro-5-(4-fluorophenyl)-1-methyl-1H-pyrazol-3-yl]amino}pyrimidin-4-yl)-3,5-dimethyl-1H-pyrazole-4-carboxylate (95.0 mg, 202 μmol) was dissolved in tetrahydrofuran (4.0 mL) and the solution cooled to 0° C. A solution of bromo(methyl)magnesium (1.0 ml, 1.0 M, 1.0 mmol) was added dropwise and the reaction mixture was stirred overnight at ambient temperature. The reaction mixture was carefully quenched by addition of aqueous Na$_2$EDTA solution (10%) and ethyl acetate was added. After standing overnight, the organic phase was decanted and concentrated. The residue was purified by flash column chromatography (SNAP Ultra 25 g, cyclohexane/ethyl acetate gradient 95/5 to 5/95) to yield the desired product (22 mg, 24% yield).

LC-MS (method 10): $R_t$=1.87 min; MS (ESIpos): m/z=456 [M+H]$^+$ $^1$H-NMR (400 MHz, dimethylsulfoxide-d6) δ [ppm]: −0.008 (0.68), 0.008 (0.81), 1.157 (0.35), 1.175 (0.73), 1.193 (0.38), 1.237 (0.17), 1.472 (16.00), 1.988 (1.30), 2.282 (8.01), 2.328 (0.21), 2.670 (0.22), 2.727 (8.28), 2.751 (0.63), 3.724 (0.51), 3.763 (8.50), 4.021 (0.32), 4.038 (0.32), 4.851 (3.08), 4.872 (0.23), 5.754 (0.56), 7.211 (2.18), 7.321 (0.16), 7.407 (1.05), 7.429 (2.33), 7.451 (1.33), 7.623 (1.28), 7.629 (0.60), 7.637 (1.38), 7.645 (1.26), 7.654 (0.50), 7.659 (1.07), 8.474 (1.86), 9.529 (1.77).

Example 277

2-[1-(6-{[4-chloro-3-(4-fluorophenyl)-1-methyl-1H-pyrazol-5-yl]amino}pyrimidin-4-yl)-3,5-dimethyl-1H-pyrazol-4-yl]propan-2-ol

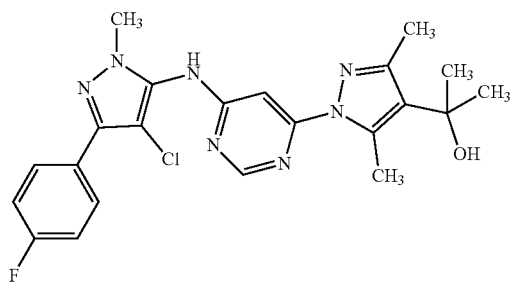 [SMILES: Cc1nn(-c2cc(Nc3c(Cl)c(-c4ccc(F)cc4)nn3C)ncn2)c(C)c1C(C)(C)O]

Under an argon atmosphere, ethyl 1-(6-{[4-chloro-3-(4-fluorophenyl)-1-methyl-1H-pyrazol-5-yl]amino}pyrimidin-4-yl)-3,5-dimethyl-1H-pyrazole-4-carboxylate (180 mg, 383 μmol) was dissolved in tetrahydrofuran (7.6 mL) and the solution cooled to 0° C. A solution of bromo(methyl)magnesium (1.9 mL, 1.0 M, 1.9 mmol) was added dropwise and the reaction mixture was stirred overnight at ambient temperature. The reaction mixture was carefully quenched by addition of aqueous Na$_2$EDTA solution (10%) and ethyl acetate was added. After standing overnight, the organic phase was decanted and concentrated. The residue was purified by flash column chromatography (SNAP Ultra 25 g, cyclohexane/ethyl acetate gradient 95/5 to 5/95) to yield the desired product (100 mg, 57% yield).

LC-MS (method 10): $R_t$=1.88 min; MS (ESIpos): m/z=456 [M+H]$^+$ $^1$H-NMR (400 MHz, dimethylsulfoxide-d6) δ [ppm]: 1.48 (s, 6H), 2.29 (s, 3H), 2.75 (s, 3H), 3.73 (s, 3H), 4.87 (s, 1H), 6.92-7.22 (br s, 1H), 7.26-7.36 (m, 2H), 7.81-7.96 (m, 2H), 8.50 (s, 1H), 9.69 (s, 1H).

Example 278

2-[4-chloro-1-(6-{[4-chloro-3-(4-fluorophenyl)-1-methyl-1H-pyrazol-5-yl]amino}pyrimidin-4-yl)-3-methyl-1H-pyrazol-5-yl]propan-2-ol

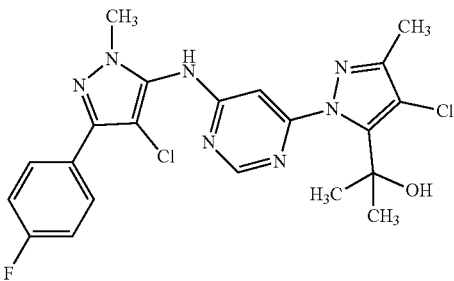 [SMILES: Cc1nn(-c2cc(Nc3c(Cl)c(-c4ccc(F)cc4)nn3C)ncn2)c(C(C)(C)O)c1Cl]

Under an argon atmosphere, ethyl 4-chloro-1-(6-{[4-chloro-3-(4-fluorophenyl)-1-methyl-1H-pyrazol-5-yl]amino}pyrimidin-4-yl)-3-methyl-1H-pyrazole-5-carboxylate (154 mg, 314 μmol) was dissolved in tetrahydrofuran (6.2 mL) and the solution cooled to 0° C. A solution of bromo(methyl)magnesium (1.6 mL, 1.0 M, 1.6 mmol) was added dropwise and the reaction mixture was stirred overnight at ambient temperature. The reaction mixture was carefully quenched by addition of aqueous Na₂EDTA solution (10%) and ethyl acetate was added. After standing overnight, the organic phase was decanted and concentrated. The residue was purified by flash column chromatography (SNAP Ultra 25 g, cyclohexane/ethyl acetate gradient 95/5 to 5/95) to yield the desired product (110 mg, 70% yield).

LC-MS (method 10): $R_t$=2.24 min; MS (ESIpos): m/z=476 [M+H]⁺

¹H-NMR (400 MHz, dimethylsulfoxide-d6) δ [ppm]: -0.008 (0.40), 0.008 (0.50), 1.157 (1.76), 1.175 (3.58), 1.184 (0.46), 1.193 (1.83), 1.398 (0.34), 1.541 (1.85), 1.601 (1.36), 1.614 (16.00), 1.989 (6.48), 2.196 (5.94), 2.650 (1.61), 2.674 (0.19), 3.725 (1.58), 3.737 (9.23), 3.763 (0.68), 4.003 (0.51), 4.021 (1.55), 4.039 (1.53), 4.057 (0.52), 5.139 (0.42), 6.612 (1.56), 7.300 (1.73), 7.305 (0.67), 7.322 (3.57), 7.340 (0.68), 7.345 (1.90), 7.429 (0.19), 7.862 (0.28), 7.867 (0.30), 7.874 (1.77), 7.879 (0.90), 7.888 (1.88), 7.896 (1.91), 7.904 (0.74), 7.910 (1.57), 8.531 (0.27), 8.564 (0.17), 8.586 (1.34), 9.843 (0.27), 9.979 (1.29).

Example 279

2-[1-(6-{[4-chloro-5-(4-fluorophenyl)-1-methyl-1H-pyrazol-3-yl]amino}pyrimidin-4-yl)-3-methyl-1H-pyrazol-5-yl]propan-2-ol

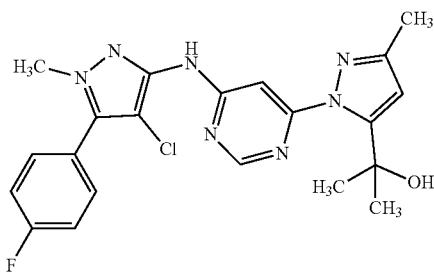

Under an argon atmosphere, ethyl 1-(6-{[4-chloro-5-(4-fluorophenyl)-1-methyl-1H-pyrazol-3-yl]amino}pyrimidin-4-yl)-3-methyl-1H-pyrazole-5-carboxylate (124 mg, 272 μmol) was dissolved in tetrahydrofuran (5.4 mL) and the solution cooled to 0° C. A solution of bromo(methyl)magnesium (1.4 mL, 1.0 M, 1.4 mmol) was added dropwise and the reaction mixture was stirred overnight at ambient temperature. The reaction mixture was carefully quenched by addition of aqueous Na₂EDTA solution (10%) and ethyl acetate was added. After standing overnight, the organic phase was decanted and concentrated. The residue was purified by flash column chromatography (SNAP Ultra 25 g, cyclohexane/ethyl acetate gradient 95/5 to 5/95) to yield the desired product (80 mg, 63% yield).

LC-MS (method 10): $R_t$=2.01 min; MS (ESIpos): m/z=442 [M+H]⁺

¹H-NMR (400 MHz, dimethylsulfoxide-d6) δ [ppm]: -0.008 (0.74), 0.008 (0.75), 1.450 (2.00), 1.483 (16.00), 2.213 (10.55), 2.647 (0.80), 2.670 (0.18), 3.744 (0.22), 3.756 (1.07), 3.778 (11.86), 5.022 (0.34), 5.754 (0.73), 6.297 (4.03), 6.311 (0.29), 7.357 (2.77), 7.411 (1.70), 7.434 (3.33), 7.451 (0.81), 7.456 (1.85), 7.614 (0.17), 7.633 (1.90), 7.647 (2.07), 7.656 (2.18), 7.661 (3.94), 7.669 (1.69), 8.476 (0.22), 8.568 (2.66), 9.569 (0.20), 9.844 (1.73).

Example 280

(±)-1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]propan-1-ol (Racemic)

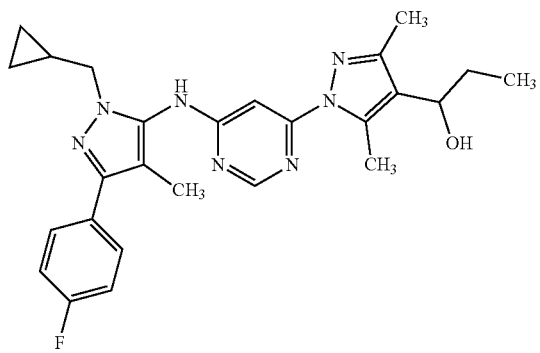 [SMILES: CCC(O)c1c(C)nn(-c2cc(Nc3c(C)c(-c4ccc(F)cc4)nn3CC3CC3)ncn2)c1C]

Under an argon atmosphere a Schlenk tube was charged with titanium isopropoxide (300 μl, 1.0 mmol) in tetrahydrofuran (2.0 ml, 25 mmol). At -18° C. ethylmagensium bromide 1.0 M solution in tetrahydrofuran (3.1 ml, 1.0 M, 3.1 mmol) was added. The mixture was stirred 30 minutes at -18° C., subsequently a solution of ethyl 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylate (250 mg, 100% purity, 511 μmol) in 1.5 mL tetrahydrofuran was added and the resulting mixture was stirred at ambient temperature overnight. The mixture was diluted with saturated aqueous ammonium chloride solution and water and extracted with ethyl acetate (3×). The combined organic phases were washed with water, brine, dried over sodium sulfate and concentrated under reduced pressure. The crude product was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequent flash-chromatography on silica gel to yield 41.5 mg (16%) of the described product along with 1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]cyclopropanol (41.5 mg, 18%).

LC-MS (method 10): $R_t$=20.40 min; MS (ESIpos): m/z=476 [M+H]⁺

¹H-NMR (600 MHz, dimethylsulfoxide-d6) δ [ppm]: 0.005 (0.75), 0.297 (2.47), 0.304 (2.53), 0.428 (2.54), 0.441 (2.59), 0.793 (2.69), 0.806 (5.60), 0.818 (2.82), 1.181 (0.43), 1.189 (0.77), 1.195 (0.76), 1.201 (1.04), 1.209 (0.67), 1.213 (0.70), 1.222 (0.43), 1.227 (0.42), 1.234 (0.56), 1.359 (1.53), 1.571 (0.54), 1.582 (0.64), 1.594 (0.64), 1.725 (0.43), 1.737 (0.70), 1.748 (0.70), 1.759 (0.59), 2.009 (14.10), 2.185 (0.48), 2.216 (2.02), 2.627 (16.00), 2.717 (0.79), 3.832 (2.06), 3.843 (2.07), 4.475 (0.95), 4.480 (0.96), 4.917 (1.75), 4.921 (1.75), 7.255 (2.00), 7.270 (4.10), 7.285 (2.22), 7.720 (1.39), 7.730 (1.92), 7.743 (1.41), 8.454 (0.54), 9.331 (0.54).

Example 281 ethyl [1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]acetate

Example 282

[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]methanol

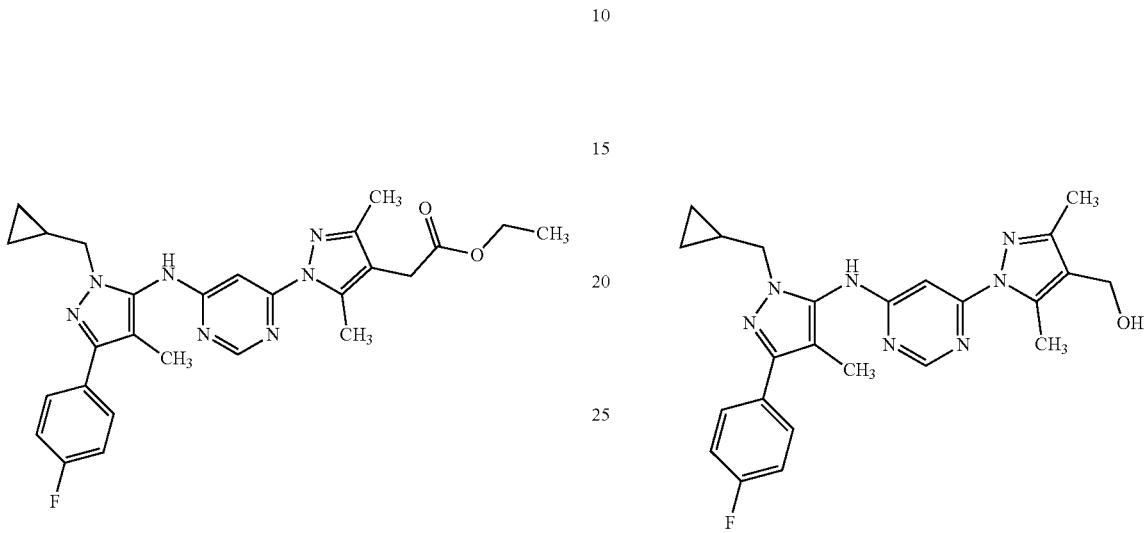

A microwave vial was charged ethyl [1-(6-chloropyrimidin-4-yl)-3,5-dimethyl-1H-pyrazol-4-yl]acetate (1.09 g, 3.71 mmol) and 1-(cyclopropylmethyl)-3-(4-fluorophenyl)-4-methyl-1H-pyrazol-5-amine (1.20 g, 83% purity, 4.08 mmol) and the contents were suspended in 1,4-dioxane (15 ml, 180 mmol). The reaction mixture was degassed with Ar for 3 min. Tris(dibenzylidenaceton)dipalladium (102 mg, 111 µmol) and Xantphos (129 mg, 222 µmol) were added and the reaction mixture was degassed again for 1 min and heated to 85° C. At this temperature and sodium phenolate (473 mg, 4.08 mmol) was added. The vial was sealed and heated at 85° C. for 90 minutes while vigorously stirring. After cooling to ambient temperature, the reaction mixture was diluted with brine and extracted with ethyl acetate (2×). The combined organic phases were dried over sodium sulfate and concentrated under reduced pressure. The crude product was purified by flash-chromatography on silic gel (column: Biotage SNAP Ultra 25 g, solvent: 92% dichloromethane/8% ethyl acetate to 66% ethyl acetate) to yield the desired product (1.13 g, 61%).

LC-MS (method 10): $R_t$=2.29 min; MS (ESIpos): m/z=504 [M+H]$^+$ $^1$H-NMR (400 MHz, dimethylsulfoxide-d6) δ [ppm]: 0.295 (2.56), 0.307 (2.83), 0.424 (2.65), 0.444 (2.84), 1.166 (4.39), 1.183 (9.03), 1.201 (5.12), 1.218 (0.78), 1.230 (0.40), 1.980 (0.74), 2.012 (14.68), 2.134 (3.16), 2.582 (16.00), 3.321 (14.65), 3.832 (2.44), 3.849 (2.39), 4.049 (1.29), 4.067 (3.84), 4.085 (3.80), 4.102 (1.25), 7.252 (2.15), 7.274 (4.33), 7.296 (2.38), 7.719 (1.60), 7.733 (2.08), 7.739 (2.01), 7.754 (1.46), 8.470 (0.65), 9.379 (0.74).

Under an argon atmosphere a solution of ethyl 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylate (160 mg, 327 µmol) in (3.0 ml, 37 mmol) was treated with lithium aluminium hydride (330 µl, 1.0 M in tetrahydrofuran, 330 µmol) at −78° C. The resulting mixture was stirred for 30 minutes at this temperature and subsequently 30 minutes at ambient temperature. The mixture was diluted with methanol and purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 41.0 mg (25%) of the desired product.

LC-MS (method 10): $R_t$=1.78 min; MS (ESIpos): m/z=448 [M+H]$^+$ $^1$H-NMR (400 MHz, dimethylsulfoxide-d6) δ [ppm]: −0.008 (1.66), 0.008 (1.38), 0.292 (2.17), 0.303 (2.34), 0.420 (2.22), 0.440 (2.29), 0.868 (0.52), 0.887 (1.26), 0.906 (0.54), 1.157 (0.46), 1.175 (0.73), 1.183 (0.64), 1.195 (0.96), 1.207 (0.60), 1.213 (0.56), 1.986 (0.50), 2.006 (13.72), 2.132 (0.55), 2.196 (2.89), 2.207 (3.77), 2.318 (0.52), 2.328 (0.82), 2.612 (3.29), 2.620 (16.00), 2.661 (0.59), 2.670 (0.47), 3.650 (2.55), 3.826 (2.22), 3.843 (2.17), 4.288 (2.85), 4.301 (3.07), 4.693 (0.98), 4.706 (1.87), 4.720 (0.85), 7.251 (2.01), 7.274 (4.19), 7.296 (2.29), 7.323 (0.47), 7.379 (0.74), 7.401 (0.46), 7.500 (0.42), 7.514 (0.46), 7.714 (1.39), 7.728 (1.82), 7.749 (1.31), 8.444 (0.69), 8.465 (0.64), 9.317 (0.45), 9.361 (0.66).

Example 283

(±)-1-(6-{[1-(cyclopropylmethyl)-3-(4-fluorophenyl)-4-methyl-1H-pyrazol-5-yl]amino}pyrimidin-4-yl)-3,4-dimethyl-1,4,5,6-tetrahydrocyclopenta[c]pyrazol-4-ol (Racemate)

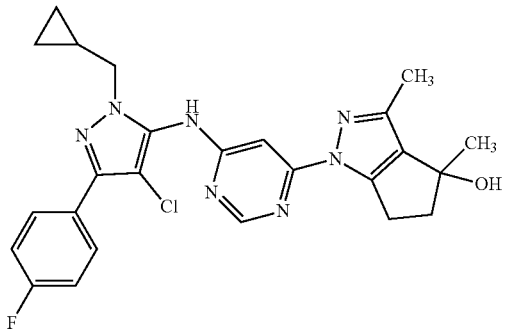 [SMILES: Cc1nn(-c2cc(Nc3c(Cl)c(-c4ccc(F)cc4)nn3CC3CC3)ncn2)c2c1C(C)(O)CC2]

Under an argon atmosphere, 1-(6-{[1-(cyclopropylmethyl)-3-(4-fluorophenyl)-4-methyl-1H-pyrazol-5-yl]amino}pyrimidin-4-yl)-3-methyl-5,6-dihydrocyclopenta[c]pyrazol-4(1H)-one (298 mg, 56% purity, 365 µmol) was dissolved in tetrahydrofuran (3.4 mL) and the solution chilled with a water bath. A solution of bromo(methyl)magnesium (2.6 mL, 1.0 M, 2.6 mmol) was added dropwise and the reaction mixture was stirred for 30 min at ambient temperature. A second aliquot of bromo(methyl)magnesium (1.0 mL, 1.0 M, 1.0 mmol) was added and the reaction mixture was stirred at ambient temperature overnight. A third aliquot of bromo(methyl)magnesium (1.0 mL, 1.0 M, 1.0 mmol) was added and the reaction mixture was stirred at ambient temperature for 1 h. The reaction mixture was carefully quenched by addition of aqueous $Na_2EDTA$ (10%) and extracted with ethyl acetate (2×). The combined organic phase extracts were dried over magnesium sulfate and concentrated. The residue was purified by flash column chromatography (SNAP Ultra 10 g, cyclohexane/ethyl acetate gradient 88/12 to 0/100) to yield an impure product fraction. The residue was resuspended in acetonitrile/water and the insoluble solids were removed by filtration. The filtrate was purified by preparative HPLC (column: Chromatorex C18; 250*30 mm, 10 µM, flow 75 mL/min, gradient acetonitrile/water 5/95 to 95/5) to yield the desired product (12.0 mg, 7% yield).

LC-MS (method 10): $R_t$=1.97 min; MS (ESIpos): m/z=474 [M+H]$^+$ $^1$H-NMR (400 MHz, dimethylsulfoxide-d6) δ [ppm]: −0.149 (0.48), −0.022 (0.48), −0.008 (4.07), 0.008 (3.85), 0.146 (0.49), 0.281 (2.50), 0.292 (2.69), 0.414 (2.66), 0.433 (2.83), 1.171 (0.77), 1.183 (1.12), 1.201 (0.73), 1.213 (0.42), 1.234 (0.79), 1.446 (8.03), 1.470 (1.87), 2.003 (16.00), 2.192 (2.51), 2.304 (0.42), 2.327 (0.64), 2.366 (0.35), 2.431 (0.94), 2.444 (0.90), 2.453 (1.31), 2.469 (1.27), 2.475 (1.12), 2.654 (3.28), 2.665 (0.60), 2.670 (0.67), 2.674 (0.53), 2.710 (0.45), 2.950 (0.41), 2.962 (0.44), 2.970 (0.54), 2.982 (0.48), 2.992 (0.84), 3.005 (0.82), 3.013 (0.81), 3.025 (0.58), 3.092 (0.62), 3.107 (0.84), 3.112 (0.82), 3.126 (0.72), 3.135 (0.51), 3.149 (0.55), 3.169 (0.32), 3.825 (2.41), 3.842 (2.38), 4.957 (2.74), 5.028 (0.53), 7.254 (1.91), 7.276 (3.95), 7.298 (2.18), 7.721 (1.43), 7.735 (1.98), 7.754 (1.40), 8.424 (0.48), 9.375 (0.54).

Example 284 ethyl 1-[6-({1-(cyclopropylmethyl)-4-methyl-3-[4-(trifluoromethoxy)phenyl]-1H-pyrazol-5-yl}amino)pyrimidin-4-yl]-3,5-dimethyl-1H-pyrazole-4-carboxylate

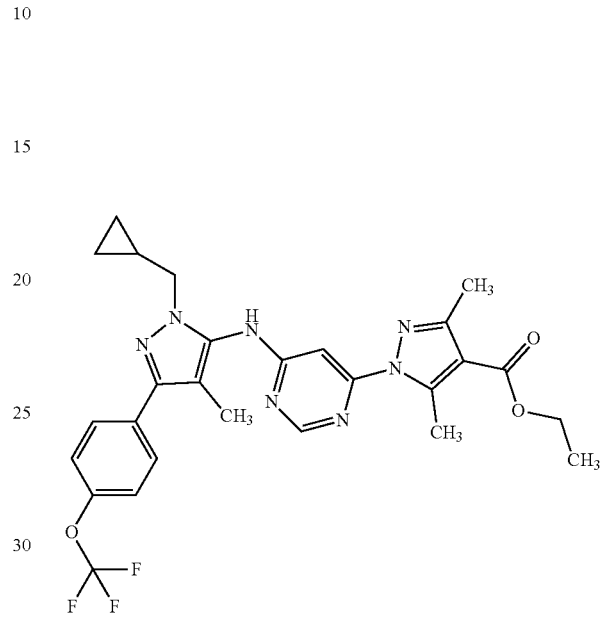

A microwave vial was charged with ethyl 1-(6-chloropyrimidin-4-yl)-3,5-dimethyl-1H-pyrazole-4-carboxylate (258 mg, 917 µmol), 1-(cyclopropylmethyl)-4-methyl-3-[4-(trifluoromethoxy)phenyl]-1H-pyrazol-5-amine (314 mg, 1.01 mmol) and sodium phenolate (117 mg, 1.01 mmol) and the contents were suspended in 1,4-dioxane (2.2 mL). The reaction mixture was degassed with Ar for 3 min. Tris(dibenzylideneacetone)dipalladium (109 mg, 119 µmol) and XantPhos (159 mg, 275 µmol) were added and the reaction mixture was degassed again for 1 min. The vial was sealed and heated at 90° C. overnight while vigorously shaking. After cooling to ambient temperature, the reaction mixture was loaded on silica gel and purified by flash column chromatography (SNAP Ultra 25 g, cyclohexane/ethyl acetate gradient 95/5 to 20/80) to yield the desired product (210 mg, 40% yield).

LC-MS (method 10): $R_t$=2.58 min; MS (ESIpos): m/z=556 [M+H]$^+$ $^1$H-NMR (400 MHz, dimethylsulfoxide-d6) δ [ppm]: 0.300 (2.94), 0.312 (3.24), 0.346 (0.36), 0.359 (0.36), 0.430 (3.09), 0.450 (3.28), 1.172 (0.47), 1.184 (0.85), 1.191 (0.83), 1.203 (1.23), 1.214 (0.82), 1.222 (0.86), 1.234 (0.65), 1.287 (3.77), 1.305 (7.56), 1.323 (3.91), 1.398 (1.27), 1.428 (0.16), 2.000 (1.51), 2.034 (16.00), 2.130 (0.31), 2.372 (2.43), 2.473 (0.27), 2.671 (0.25), 2.712 (0.16), 2.912 (13.35), 2.952 (0.19), 3.802 (0.44), 3.820 (0.54), 3.846 (2.54), 3.863 (2.49), 4.228 (1.18), 4.246 (3.44), 4.264 (3.44), 4.282 (1.20), 4.949 (0.44), 7.342 (0.34), 7.363 (0.34), 7.428 (3.51), 7.449 (3.89), 7.685 (0.41), 7.707 (0.37), 7.816 (3.06), 7.837 (2.77), 8.539 (0.44), 9.555 (0.41).

Example 285 ethyl 1-[6-({1-(cyclopropylmethyl)-4-methyl-3-[4-(trifluoromethyl)phenyl]-1H-pyrazol-5-yl}amino)pyrimidin-4-yl]-3,5-dimethyl-1H-pyrazole-4-carboxylate

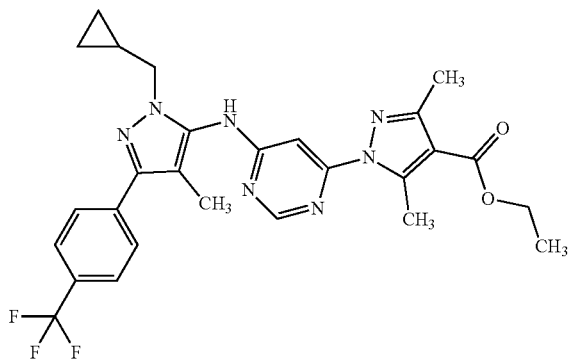 [SMILES: CCOC(=O)c1c(C)nn(-c2cc(Nc3c(C)c(-c4ccc(C(F)(F)F)cc4)nn3CC3CC3)ncn2)c1C]

A microwave vial was charged with ethyl 1-(6-chloropyrimidin-4-yl)-3,5-dimethyl-1H-pyrazole-4-carboxylate (163 mg, 582 µmol), 1-(cyclopropylmethyl)-4-methyl-3-[4-(trifluoromethyl)phenyl]-1H-pyrazol-5-amine (210 mg, 90% purity, 640 µmol) and sodium phenolate (74.3 mg, 640 µmol) and the contents were suspended in 1,4-dioxane (1.4 mL). The reaction mixture was degassed with Ar for 3 min. Tris(dibenzylideneacetone)dipalladium (69.3 mg, 75.6 µmol) and XantPhos (101 mg, 175 µmol) were added and the reaction mixture was degassed again for 1 min. The vial was sealed and heated at 90° C. overnight while vigorously shaking. After cooling to ambient temperature, the reaction mixture was loaded on silica gel and purified by flash column chromatography (SNAP Ultra 25 g, cyclohexane/ethyl acetate gradient 95/5 to 20/80) to yield the desired product (70 mg, 21% yield).

LC-MS (method 10): $R_t$=2.56 min; MS (ESIpos): m/z=540 [M+H]$^+$ $^1$H-NMR (400 MHz, dimethylsulfoxide-d6) δ [ppm]: 0.311 (2.85), 0.322 (3.14), 0.356 (0.42), 0.372 (0.42), 0.438 (3.05), 0.458 (3.22), 1.186 (0.57), 1.216 (1.32), 1.236 (1.25), 1.289 (3.81), 1.306 (7.52), 1.324 (3.86), 1.398 (8.76), 2.035 (2.12), 2.066 (16.00), 2.329 (0.72), 2.376 (2.44), 2.914 (13.27), 3.568 (0.41), 3.825 (0.59), 3.842 (0.68), 3.868 (2.46), 3.885 (2.44), 4.230 (1.19), 4.248 (3.44), 4.265 (3.42), 4.283 (1.19), 4.997 (0.64), 7.725 (0.54), 7.792 (3.62), 7.812 (4.92), 7.930 (3.43), 7.950 (2.61), 8.544 (0.52), 9.577 (0.42).

Example 286

4-[1-(cyclopropylmethyl)-4-methyl-5-({6-[5-methyl-3-(propan-2-yl)-1H-pyrazol-1-yl]pyrimidin-4-yl}amino)-1H-pyrazol-3-yl]benzonitrile

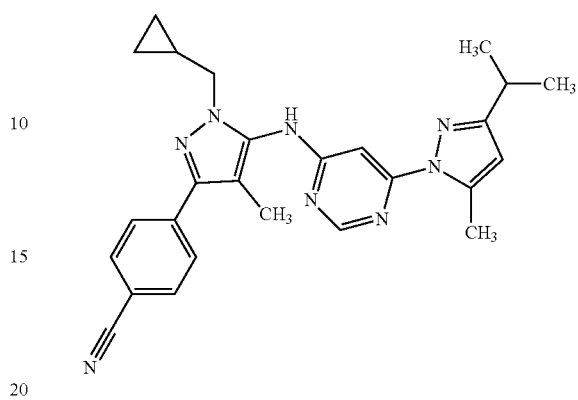

A microwave vial was charged with 4-chloro-6-[5-methyl-3-(propan-2-yl)-1H-pyrazol-1-yl]pyrimidine (105 mg, 90% purity, 399 µmol), 4-[5-amino-1-(cyclopropylmethyl)-4-methyl-1H-pyrazol-3-yl]benzonitrile (130 mg, 85% purity, 439 µmol) and sodium phenolate (51.0 mg, 439 µmol) and the contents were suspended in 1,4-dioxane (0.96 mL). The reaction mixture was degassed with Ar for 3 min. Tris(dibenzylideneacetone)dipalladium (4.75 mg, 5.19 µmol) and XantPhos (6.93 mg, 12.0 µmol) were added and the reaction mixture was degassed again for 1 min. The vial was sealed and heated at 90° C. overnight while vigorously shaking. After cooling to ambient temperature, the reaction mixture was loaded on silica gel and purified by flash column chromatography (SNAP Ultra 25 g, cyclohexane/ethyl acetate gradient 95/5 to 20/80) to yield the desired product (52 mg, 28% yield).

LC-MS (method 10): $R_t$=2.44 min; MS (ESIpos): m/z=453 [M+H]$^+$ $^1$H-NMR (400 MHz, dimethylsulfoxide-d6) δ [ppm]: 0.310 (2.39), 0.322 (2.68), 0.436 (2.18), 0.455 (2.32), 1.200 (4.79), 1.214 (4.91), 1.398 (5.34), 1.436 (0.25), 1.868 (0.18), 2.060 (11.40), 2.257 (0.18), 2.329 (0.21), 2.350 (0.21), 2.640 (11.66), 2.671 (0.31), 2.888 (0.50), 3.569 (0.42), 3.861 (2.16), 3.878 (2.14), 6.225 (3.00), 7.903 (16.00), 8.450 (0.81), 9.430 (1.00).

Example 287

1-{[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]methyl}cyclopropanol

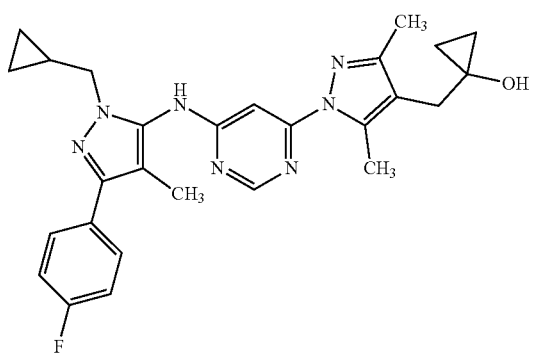 [SMILES: Cc1nn(-c2cc(Nc3c(C)c(-c4ccc(F)cc4)nn3CC3CC3)ncn2)c(C)c1CC1(O)CC1]

Under an argon atmosphere a Schlenk tube was charged with titanium isopropoxide (290 μl, 990 μmol) in tetrahydrofuran (1.9 ml, 24 mmol) at −18° C. At this temperature ethylmagnesium bromide (3.0 ml, 1.0 M in tetrahydrofuran, 3.0 mmol) was added at the mixture was stirred 30 minutes at −18° C. Subsequently a solution of ethyl [1-(6-{[1-(cyclopropylmethyl)-3-(4-fluorophenyl)-4-methyl-1H-pyrazol-5-yl]amino}pyrimidin-4-yl)-3,5-dimethyl-H-pyrazol-4-yl]acetate (250 mg, 496 μmol) in 1.5 mL tetrahydrofuran was added and it was stirred 20 minutes at −18° C. and overnight at ambient temperature. The mixture was diluted with potassium sodium tartrate solution and water. The mixture was extracted with ethyl acetate (3×). The combined organic phases were washed with water, brine, dried over sodium sulfate and concentrated under reduced pressure. The crude product was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 25.-9 mg (11%) of the desired product.

LC-MS (method 10): $R_t$=2.02 min; MS (ESIpos): m/z=488 [M+H]$^+$ $^1$H-NMR (400 MHz, dimethylsulfoxide-d6) δ [ppm]: 0.008 (2.18), 0.290 (2.81), 0.302 (3.04), 0.329 (1.30), 0.345 (3.97), 0.357 (1.56), 0.421 (2.73), 0.441 (2.90), 0.498 (1.48), 0.510 (3.88), 0.525 (1.08), 1.073 (0.49), 1.091 (0.95), 1.108 (0.47), 1.163 (0.42), 1.175 (0.75), 1.181 (0.74), 1.194 (1.09), 1.206 (0.69), 1.212 (0.73), 1.968 (0.55), 2.006 (15.61), 2.170 (3.39), 2.571 (1.00), 2.589 (16.00), 2.649 (4.73), 3.375 (0.56), 3.392 (0.55), 3.825 (2.60), 3.842 (2.58), 5.213 (4.27), 7.251 (2.28), 7.273 (4.82), 7.296 (2.71), 7.714 (1.73), 7.729 (2.30), 7.749 (1.71), 8.451 (0.86), 9.331 (0.94).

Example 288

1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbonitrile

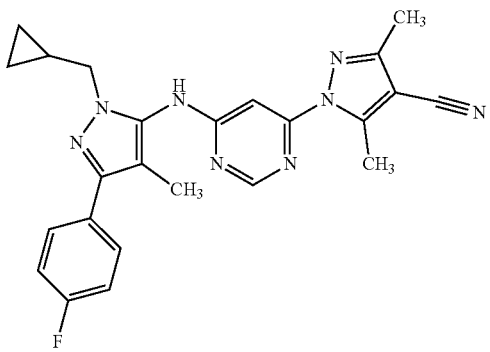 [SMILES: Cc1nn(-c2cc(Nc3c(C)c(-c4ccc(F)cc4)nn3CC3CC3)ncn2)c(C)c1C#N]

A microwave vial was charged 1-(6-chloropyrimidin-4-yl)-3,5-dimethyl-1H-pyrazole-4-carbonitrile (1.00 g, 77% purity, 3.30 mmol) and 1-(cyclopropylmethyl)-3-(4-fluorophenyl)-4-methyl-1H-pyrazol-5-amine (889 mg, 3.62 mmol) and the contents were suspended in 1,4-dioxane (15 ml, 180 mmol). The reaction mixture was degassed with Ar for 3 min. Tris(dibenzylidenaceton)dipalladium (90.5 mg, 98.9 μmol) and Xantphos (114 mg, 198 μmol) were added and the reaction mixture was degassed again for 1 min and heated to 85° C. At this temperature and sodium phenolate (421 mg, 3.62 mmol) was added. The vial was sealed and heated at 85° C. for 90 minutes while vigorously stirring. After cooling to ambient temperature, the reaction mixture was diluted with saturated sodium hydrogen carbonate solution and extracted with ethyl acetate (2×). The combined organic phases were washed with brine dried over sodium sulfate and concentrated under reduced pressure. The crude product was purified by flash-chromatography on silica gel (column; Biotage Snap Ultra 50 g, solvent: dichloromethane/ethyl acetate 20:1) to yield the desired product (870 mg, 57%).

LC-MS (method 10): $R_t$=2.24 min; MS (ESIpos): m/z=443 [M+H]$^+$ $^1$H-NMR (400 MHz, dimethylsulfoxide-d6) δ [ppm]: 0.288 (2.39), 0.299 (2.56), 0.422 (2.66), 0.442 (2.80), 1.171 (0.70), 1.189 (1.03), 1.201 (0.71), 1.208 (0.69), 1.975 (1.41), 2.005 (14.57), 2.329 (2.06), 2.796 (16.00), 3.787 (0.44), 3.804 (0.58), 3.828 (2.01), 3.844 (1.99), 4.906 (0.40), 7.252 (2.06), 7.275 (4.16), 7.297 (2.32), 7.713 (1.40), 7.729 (1.91), 7.745 (1.31).

Example 289

2-{1-[6-({1-(cyclopropylmethyl)-4-methyl-3-[4-(trifluoromethoxy)phenyl]-1H-pyrazol-5-yl}amino)pyrimidin-4-yl]-3,5-dimethyl-1H-pyrazol-4-yl}propan-2-ol

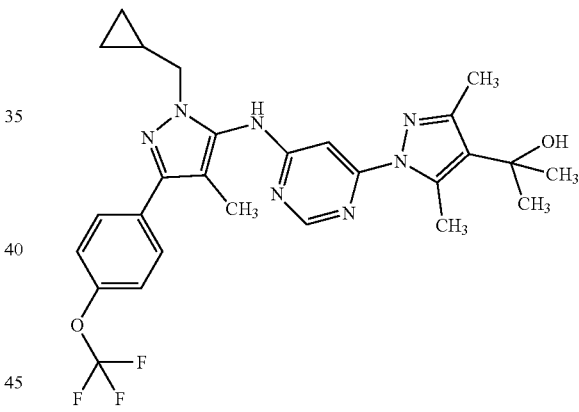

Under an argon atmosphere, ethyl 1-[6-({1-(cyclopropylmethyl)-4-methyl-3-[4-(trifluoromethoxy)phenyl]-1H-pyrazol-5-yl}amino)pyrimidin-4-yl]-3,5-dimethyl-1H-pyrazole-4-carboxylate (150 mg, 270 μmol) was dissolved in tetrahydrofuran (5.3 mL) and the solution cooled to 0° C. A solution of bromo(methyl)magnesium (1.3 ml, 1.0 M, 1.3 mmol) was added dropwise and the reaction mixture was stirred overnight at ambient temperature. The reaction mixture was carefully quenched by addition of aqueous Na$_2$EDTA solution (10%) and extracted with ethyl acetate. The organic phase extract was concentrated and the residue was purified by flash column chromatography (SNAP Ultra 25 g, cyclohexane/ethyl acetate gradient 95/5 to 5/95) to yield the desired product (28 mg, 19% yield).

LC-MS (method 10): $R_t$=2.22 min; MS (ESIpos): m/z=542 [M+H]$^+$ $^1$H-NMR (400 MHz, dimethylsulfoxide-d6) δ [ppm]: −0.149 (0.50), 0.146 (0.48), 0.296 (2.01), 0.308 (2.20), 0.426 (1.92), 0.446 (2.05), 1.199 (0.82), 1.398 (0.45), 1.464 (16.00), 1.988 (0.67), 2.027 (11.59), 2.264 (2.49), 2.327

(0.58), 2.367 (0.35), 2.670 (0.56), 2.711 (0.39), 2.742 (11.85), 3.840 (1.95), 3.857 (1.90), 4.854 (3.35), 7.425 (2.49), 7.446 (2.70), 7.812 (2.72), 7.834 (2.49), 8.464 (0.65), 9.379 (0.71).

Example 290

2-{4-chloro-1-[6-({1-(cyclopropylmethyl)-4-methyl-3-[4-(trifluoromethoxy)phenyl]-1H-pyrazol-5-yl}amino)pyrimidin-4-yl]-3-methyl-1H-pyrazol-5-yl}propan-2-ol

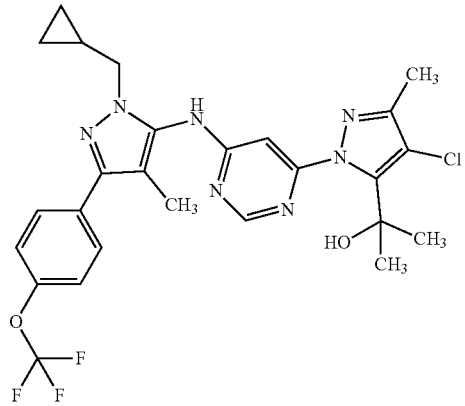 [SMILES: Cc1nn(-c2cc(Nc3c(C)c(-c4ccc(OC(F)(F)F)cc4)nn3CC3CC3)ncn2)c(C(C)(C)O)c1Cl]

Under an argon atmosphere, ethyl 4-chloro-1-[6-({1-(cyclopropylmethyl)-4-methyl-3-[4-(trifluoromethoxy)phenyl]-1H-pyrazol-5-yl}amino)pyrimidin-4-yl]-3-methyl-1H-pyrazole-5-carboxylate (176 mg, 306 μmol) was dissolved in tetrahydrofuran (6.0 mL) and the solution cooled to 0° C. A solution of bromo(methyl)magnesium (1.5 ml, 1.0 M, 1.5 mmol) was added dropwise and the reaction mixture was stirred overnight at ambient temperature. The reaction mixture was carefully quenched by addition of aqueous Na$_2$EDTA solution (10%) and extracted with ethyl acetate. The organic phase extract was concentrated and the residue was purified by flash column chromatography (SNAP Ultra 25 g, cyclohexane/ethyl acetate gradient 95/5 to 5/95) to yield the desired product (42 mg, 23% yield).

LC-MS (method 10): R$_t$=2.58 min; MS (ESIpos): m/z=562 [M+H]$^+$ $^1$H-NMR (400 MHz, dimethylsulfoxide-d6) δ [ppm]: −0.008 (1.12), 0.008 (1.16), 0.296 (2.44), 0.308 (2.69), 0.431 (2.56), 0.450 (2.72), 1.142 (0.16), 1.158 (1.08), 1.176 (2.34), 1.184 (0.79), 1.194 (1.71), 1.207 (0.77), 1.215 (0.79), 1.227 (0.49), 1.233 (0.47), 1.398 (11.86), 1.527 (0.66), 1.601 (13.94), 1.989 (3.13), 2.001 (0.30), 2.023 (2.04), 2.036 (16.00), 2.181 (2.07), 2.329 (0.22), 2.524 (0.72), 2.642 (1.54), 2.667 (0.23), 2.711 (0.33), 3.853 (2.61), 3.870 (2.51), 4.004 (0.25), 4.021 (0.78), 4.039 (0.77), 4.057 (0.25), 7.425 (3.75), 7.446 (4.06), 7.792 (0.76), 7.810 (4.44), 7.832 (3.78), 8.552 (0.41), 9.682 (0.27).

Example 291

2-{1-[6-({1-(cyclopropylmethyl)-4-methyl-3-[4-(trifluoromethoxy)phenyl]-1H-pyrazol-5-yl}amino)pyrimidin-4-yl]-3-methyl-1H-pyrazol-5-yl}propan-2-ol

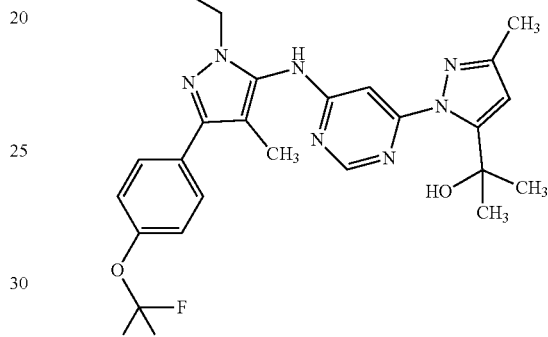

Under an argon atmosphere, ethyl 1-[6-({1-(cyclopropylmethyl)-4-methyl-3-[4-(trifluoromethoxy)phenyl]-1H-pyrazol-5-yl}amino)pyrimidin-4-yl]-3-methyl-1H-pyrazole-5-carboxylate (114 mg, 211 μmol) was dissolved in tetrahydrofuran (4.2 mL) and the solution cooled to 0° C. A solution of bromo(methyl)magnesium (1.1 ml, 1.0 M in tetrahydrofuran, 1.1 mmol) was added dropwise and the reaction mixture was stirred overnight at ambient temperature. The reaction mixture was carefully quenched by addition of aqueous Na$_2$EDTA solution (10%) and extracted with ethyl acetate. The organic phase extract was concentrated and the residue was purified by flash column chromatography (SNAP Ultra 25 g, cyclohexane/ethyl acetate gradient 95/5 to 5/95) to yield the desired product (75 mg, 66% yield).

LC-MS (method 10): R$_t$=2.37 min; MS (ESIpos): m/z=528 [M+H]$^+$ $^1$H-NMR (400 MHz, dimethylsulfoxide-d6) δ [ppm]: −0.149 (0.31), 0.146 (0.32), 0.300 (2.12), 0.311 (2.30), 0.428 (2.09), 0.448 (2.18), 1.157 (0.97), 1.175 (2.10), 1.193 (1.49), 1.205 (0.88), 1.236 (0.41), 1.398 (0.97), 1.489 (16.00), 1.988 (3.37), 2.043 (10.27), 2.202 (1.28), 2.328 (0.41), 2.367 (0.34), 2.670 (0.40), 2.711 (0.35), 3.855 (1.73), 3.871 (1.68), 4.003 (0.29), 4.021 (0.85), 4.039 (0.82), 4.056 (0.27), 6.300 (1.52), 7.430 (2.63), 7.451 (2.85), 7.620 (2.69), 7.819 (1.77), 7.840 (1.66), 8.545 (0.31), 9.644 (0.26).

Example 292

2-{1-[6-({1-(cyclopropylmethyl)-4-methyl-3-[4-(trifluoromethyl)phenyl]-1H-pyrazol-5-yl}amino)pyrimidin-4-yl]-3,5-dimethyl-1H-pyrazol-4-yl}propan-2-ol

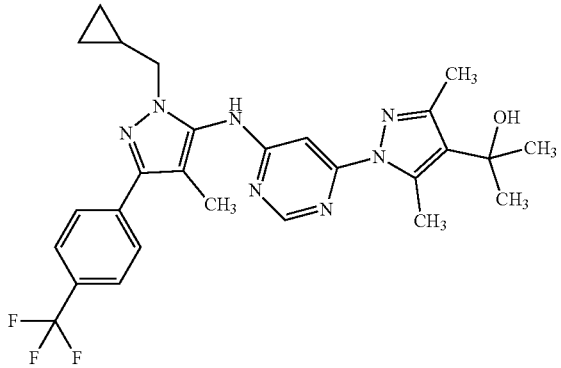 [SMILES: Cc1nn(-c2cc(Nc3c(C)c(-c4ccc(C(F)(F)F)cc4)nn3CC3CC3)ncn2)c(C)c1C(C)(C)O]

Under an argon atmosphere, ethyl 1-[6-({1-(cyclopropylmethyl)-4-methyl-3-[4-(trifluoromethyl)phenyl]-1H-pyrazol-5-yl}amino)pyrimidin-4-yl]-3,5-dimethyl-1H-pyrazole-4-carboxylate (70.0 mg, 130 µmol) was dissolved in tetrahydrofuran (2.6 mL) and the solution cooled to 0° C. A solution of bromo(methyl)magnesium (650 µl, 1.0 M in tetrahydrofuran, 650 µmol) was added dropwise and the reaction mixture was stirred overnight at ambient temperature. The reaction mixture was carefully quenched by addition of aqueous Na$_2$EDTA solution (10%) and ethyl acetate was added. After standing overnight, the organic phase was decanted and concentrated. The residue was purified by flash column chromatography (SNAP Ultra 25 g, cyclohexane/ethyl acetate gradient 95/5 to 5/95) to yield the desired product (10 mg, 15% yield).

LC-MS (method 10): R$_t$=2.20 min; MS (ESIpos): m/z=526 [M+H]$^+$ $^1$H-NMR (400 MHz, dimethylsulfoxide-d6) δ [ppm]: −0.149 (0.41), −0.008 (3.49), 0.008 (3.14), 0.146 (0.38), 0.307 (2.04), 0.319 (2.23), 0.436 (1.92), 0.454 (2.05), 1.157 (0.50), 1.175 (1.12), 1.193 (0.95), 1.213 (0.83), 1.232 (0.67), 1.398 (2.02), 1.466 (16.00), 1.988 (1.73), 2.060 (11.72), 2.267 (2.43), 2.327 (0.50), 2.367 (0.33), 2.670 (0.45), 2.710 (0.33), 2.745 (11.75), 3.862 (1.95), 3.879 (1.93), 4.021 (0.45), 4.038 (0.43), 4.857 (3.33), 5.754 (0.41), 7.789 (2.50), 7.810 (3.42), 7.927 (2.74), 7.947 (2.11), 8.465 (0.64), 9.405 (0.71).

Example 293

2-{1-[6-({1-(cyclopropylmethyl)-4-methyl-3-[4-(trifluoromethyl)phenyl]-1H-pyrazol-5-yl}amino)pyrimidin-4-yl]-3-methyl-1H-pyrazol-5-yl}propan-2-ol

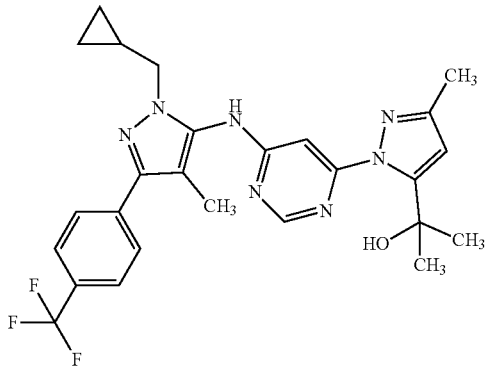 [SMILES: Cc1cc(C(C)(C)O)n(-c2cc(Nc3c(C)c(-c4ccc(C(F)(F)F)cc4)nn3CC3CC3)ncn2)n1]

Under an argon atmosphere, ethyl 1-[6-({1-(cyclopropylmethyl)-4-methyl-3-[4-(trifluoromethyl)phenyl]-1H-pyrazol-5-yl}amino)pyrimidin-4-yl]-3-methyl-1H-pyrazole-5-carboxylate (35.0 mg, 66.6 µmol) was dissolved in tetrahydrofuran (1.3 mL) and the solution cooled to 0° C. A solution of bromo(methyl)magnesium (330 µl, 1.0 M in tetrahydrofuran, 330 µmol) was added dropwise and the reaction mixture was stirred overnight at ambient temperature. The reaction mixture was carefully quenched by addition of aqueous Na$_2$EDTA solution (10%) and ethyl acetate was added. After standing overnight, the organic phase was decanted and concentrated. The residue was purified by flash column chromatography (SNAP Ultra 25 g, cyclohexane/ethyl acetate gradient 95/5 to 5/95) to yield the desired product (17 mg, 49% yield).

LC-MS (method 10): R$_t$=2.34 min; MS (ESIpos): m/z=512 [M+H]$^+$ $^1$H-NMR (400 MHz, dimethylsulfoxide-d6) δ [ppm]: 0.146 (0.17), 0.311 (2.14), 0.322 (2.26), 0.437 (2.08), 0.457 (2.17), 1.158 (0.18), 1.175 (0.37), 1.192 (0.43), 1.201 (0.65), 1.208 (0.65), 1.219 (0.97), 1.238 (0.86), 1.398 (10.74), 1.492 (16.00), 1.989 (0.51), 2.076 (10.95), 2.209 (1.32), 2.328 (0.25), 2.367 (0.18), 2.671 (0.26), 2.712 (0.18), 3.879 (1.71), 3.894 (1.69), 6.303 (1.55), 7.616 (2.71), 7.794 (2.60), 7.815 (3.44), 7.933 (2.07), 7.953 (1.65), 8.552 (0.32), 9.667 (0.28).

Example 294

2-{4-chloro-1-[6-({1-(cyclopropylmethyl)-4-methyl-3-[4-(trifluoromethyl)phenyl]-1H-pyrazol-5-yl}amino)pyrimidin-4-yl]-3-methyl-1H-pyrazol-5-yl}propan-2-ol

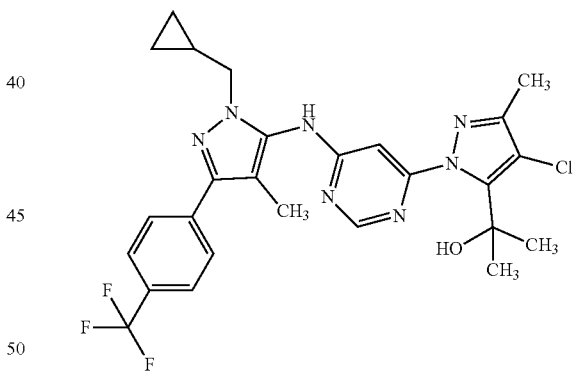

Under an argon atmosphere, ethyl 4-chloro-1-[6-({1-(cyclopropylmethyl)-4-methyl-3-[4-(trifluoromethyl)phenyl]-1H-pyrazol-5-yl}amino)pyrimidin-4-yl]-3-methyl-1H-pyrazole-5-carboxylate (45.0 mg, 80.4 µmol) was dissolved in tetrahydrofuran (1.6 mL) and the solution cooled to 0° C. A solution of bromo(methyl)magnesium (400 µl, 1.0 M in tetrahydrofuran, 400 µmol) was added dropwise and the reaction mixture was stirred overnight at ambient temperature. The reaction mixture was carefully quenched by addition of aqueous Na$_2$EDTA solution (10%) and ethyl acetate was added. After standing overnight, the organic phase was decanted and concentrated. The residue was purified by flash column chromatography (SNAP Ultra 25 g, cyclohexane/ethyl acetate gradient 95/5 to 5/95) to yield the desired product (22 mg, 44% yield).

LC-MS (method 10): $R_t$=2.56 min; MS (ESIpos): m/z=546 [M+H]$^+$ $^1$H-NMR (400 MHz, dimethylsulfoxide-d6) δ [ppm]: −0.149 (0.41), 0.146 (0.44), 0.306 (2.81), 0.317 (3.03), 0.439 (2.87), 0.458 (2.98), 0.854 (0.21), 1.141 (0.41), 1.157 (1.57), 1.175 (3.01), 1.193 (2.09), 1.208 (1.32), 1.236 (1.25), 1.398 (6.01), 1.529 (0.84), 1.602 (16.00), 1.758 (0.22), 1.905 (0.21), 1.988 (4.60), 2.055 (2.36), 2.067 (15.98), 2.183 (2.64), 2.257 (0.53), 2.327 (0.51), 2.367 (0.46), 2.643 (1.56), 2.670 (0.56), 2.711 (0.51), 3.875 (2.94), 3.892 (2.79), 4.003 (0.39), 4.021 (1.13), 4.039 (1.16), 4.056 (0.43), 4.383 (0.17), 4.394 (0.17), 6.825 (0.21), 7.790 (3.88), 7.811 (5.29), 7.924 (4.40), 7.944 (3.11), 8.556 (0.48), 9.697 (0.34).

Example 295

2-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-1,1,1,3,3,3-hexafluoropropan-2-ol

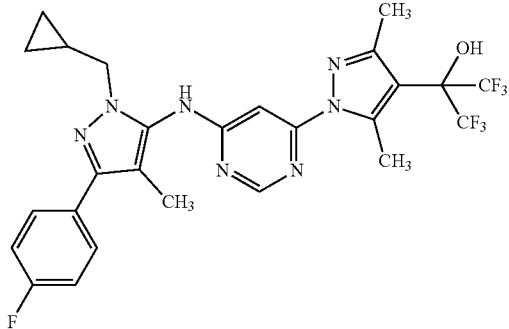 [SMILES: Cc1nn(-c2cc(Nc3c(C)c(-c4ccc(F)cc4)nn3CC3CC3)ncn2)c(C)c1C(O)(C(F)(F)F)C(F)(F)F]

Molecular Sieves (4 Å) were placed in a round-bottom flask and dried in a vacuum drying-oven overnight at 120° C. After cooling to ambient temperature, tetrabutylammonium fluoride trihydrate (197 mg, 705 μmol) was added and toluene (1.5 mL) was added and the suspension stirred for 30 min. A solution of ethyl 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylate (115 mg, 235 μmol) in toluene (4.5 mL) was then added, the mixture was stirred for 5 min and cooled to 0° C. trimethyl(trifluoromethyl)silane (170 μl, 1.2 mmol) was then added and stirred at ambient temperature for 3 h. Further aliquots of tetrabutylammonium fluoride trihydrate (98 mg, 353 μmol) and trimethyl(trifluoromethyl)silane (85 μl, 0.6 mmol) dissolved in dry toluene (800 μL, dried over 4 Å molecular sieves) were added and the reaction mixture was stirred at ambient temperature overnight. The reaction mixture was filtered through Celite and the filtrate was concentrated. The residue was purified by flash column chromatography (SNAP Ultra 25 g, cyclohexane/ethyl acetate gradient 90/10 to 0/100) to yield the desired product (8 mg, 6% yield) along with impure fractions. Impure fractions were concentrated and repurified by flash column chromatography and preparative HPLC (method 6) to yield the desired product (18 mg, 13% yield).

LC-MS (method 11): Rt=1.54 min; MS (ESIpos): m/z=584 [M+H]$^+$ $^1$H-NMR (400 MHz, dimethylsulfoxide-d6) δ [ppm]: −0.149 (0.34), −0.008 (2.74), 0.008 (3.12), 0.146 (0.32), 0.295 (2.70), 0.306 (3.00), 0.427 (2.74), 0.446 (2.92), 1.168 (0.38), 1.180 (0.73), 1.187 (0.73), 1.199 (1.12), 1.211 (0.69), 1.217 (0.72), 1.229 (0.37), 2.011 (16.00), 2.266 (2.20), 2.323 (0.53), 2.328 (0.62), 2.367 (0.39), 2.670 (0.56), 2.711 (0.63), 2.733 (9.33), 3.831 (2.38), 3.847 (2.35), 7.249 (2.57), 7.271 (5.34), 7.294 (2.90), 7.709 (1.80), 7.724 (2.31), 7.731 (2.27), 7.745 (1.72), 8.516 (3.86), 9.531 (0.39).

Example 296

N-[4-ethyl-5-(4-fluorophenyl)-1-methyl-1H-pyrazol-3-yl]-6-{4-[(3-fluoroazetidin-1-yl)methyl]-3,5-dimethyl-1H-pyrazol-1-yl}pyrimidin-4-amine A solution of 1-(6-{[4-ethyl-5-(4-fluorophenyl)-1-methyl-1H-pyrazol-3-yl]amino}pyrimidin-4-yl)-3,5-dimethyl-1H-pyrazole-4-carbaldehyde (50.0 mg, 119 μmol) and 3-fluoroazetidine hydrochloride (1:1) (17.3 mg, 155 μmol) in tetrahydrofuran (2.0 ml, 25 mmol) was treated with acetic acid (14 μl, 240 mol). The mixture was stirred one hour at ambient temperature, subsequently sodium triacetoxyborhydride (40.4 mg, 191 μmol) was added and the mixture was again stirred overnight at ambient temperature. Additional 1.6 equivalents sodium triacetoxyborhydride (40.4 mg, 0.19 mmol) were added and it was stirred an additional hour. The mixture was diluted with water and purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 37.8 mg of the desired product (66%).

LC-MS (method 10): $R_t$=1.31 min; MS (ESIneg): m/z=477 [M−H]$^−$ $^1$H-NMR (400 MHz, dimethylsulfoxide-d6) δ [ppm]: 0.869 (3.77), 0.888 (8.55), 0.906 (3.92), 1.856 (0.47), 2.194 (15.66), 2.249 (0.55), 2.281 (0.95), 2.300 (2.81), 2.319 (2.74), 2.337 (0.95), 2.628 (16.00), 2.666 (0.62), 3.022 (0.92), 3.033 (1.10), 3.039 (1.13), 3.045 (1.21), 3.057 (1.17), 3.081 (1.04), 3.093 (1.17), 3.099 (1.16), 3.104 (1.23), 3.116 (1.13), 3.316 (0.42), 3.450 (8.54), 3.465 (1.84), 3.469 (1.71), 3.473 (1.76), 3.488 (2.16), 3.502 (1.52), 3.507 (1.44), 3.511 (1.40), 3.525 (1.12), 3.604 (0.67), 5.032 (0.58), 5.045 (0.84), 5.058 (0.54), 5.177 (0.56), 5.190 (0.83), 5.202 (0.55), 5.755 (3.32), 7.326 (3.03), 7.357 (2.08), 7.379 (4.64), 7.401 (2.74), 7.498 (2.76), 7.503 (1.28), 7.512 (3.11), 7.519 (2.43), 7.533 (2.01), 8.142 (5.42), 8.442 (4.14), 9.327 (2.89).

Example 297

6-{3,5-dimethyl-4-[(4-methylpiperazin-1-yl)methyl]-1H-pyrazol-1-yl}-N-[4-ethyl-5-(4-fluorophenyl)-1-methyl-1H-pyrazol-3-yl]pyrimidin-4-amine

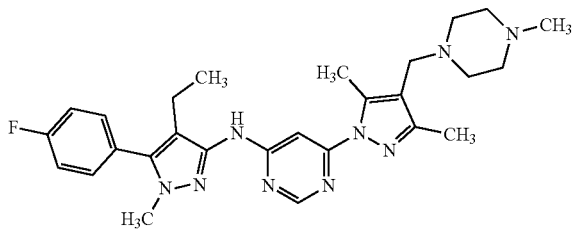 [SMILES: CCc1c(Nc2cc(-n3nc(C)c(CN4CCN(C)CC4)c3C)ncn2)nn(C)c1-c1ccc(F)cc1]

A solution of 1-(6-{[4-ethyl-5-(4-fluorophenyl)-1-methyl-1H-pyrazol-3-yl]amino}pyrimidin-4-yl)-3,5-dimethyl-1H-pyrazole-4-carbaldehyde (50.0 mg, 119 µmol) and 1-methylpiperazine (17 µl, 150 µmol) in tetrahydrofuran (2.0 ml, 25 mmol) was treated with acetic acid (14 µl, 240 µmol) and stirred for one hour at room temperature. Subsequently sodium triacetoxyborhydride (40.4 mg, 191 µmol) was added and it was stirred again overnight at ambient temperature. The mixture was diluted with water and purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 43.6 mg (73%) of the desired product.

LC-MS (method 10): $R_t$=1.32 min; MS (ESIneg): m/z=502 [M-H]$^-$ $^1$H-NMR (400 MHz, dimethylsulfoxide-d6) δ [ppm]: 0.869 (3.77), 0.888 (8.64), 0.906 (3.95), 1.074 (0.71), 1.091 (1.47), 1.109 (0.74), 1.855 (0.44), 2.147 (13.58), 2.177 (15.99), 2.233 (0.96), 2.281 (2.12), 2.299 (4.20), 2.318 (4.37), 2.337 (2.75), 2.592 (16.00), 2.630 (0.52), 3.256 (7.54), 3.283 (0.78), 3.357 (1.00), 3.375 (1.50), 3.392 (1.48), 3.410 (0.97), 3.603 (0.68), 7.324 (3.04), 7.357 (2.10), 7.379 (4.74), 7.401 (2.80), 7.498 (2.80), 7.503 (1.24), 7.511 (3.09), 7.519 (2.42), 7.528 (0.96), 7.533 (2.02), 8.177 (1.89), 8.438 (4.02), 9.317 (2.98).

Example 298

4-[5-({6-[4-(2-hydroxypropan-2-yl)-3,5-dimethyl-1H-pyrazol-1-yl]pyrimidin-4-yl}amino)-1,4-dimethyl-1H-pyrazol-3-yl]benzonitrile

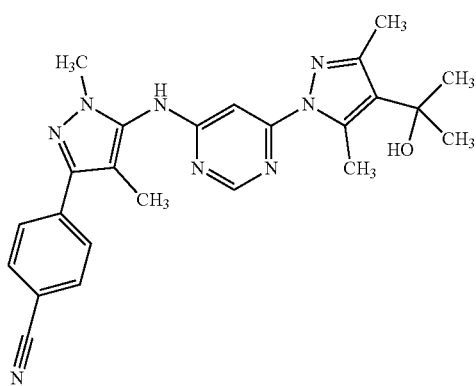 [SMILES: Cc1nn(-c2cc(Nc3c(C)c(-c4ccc(C#N)cc4)nn3C)ncn2)c(C)c1C(C)(C)O]

A solution of ethyl 1-(6-{[3-(4-cyanophenyl)-1,4-dimethyl-1H-pyrazol-5-yl]amino}pyrimidin-4-yl)-3,5-dimethyl-1H-pyrazole-4-carboxylate (59.0 mg, 129 µmol) in tetrahydrofuran (2.0 ml, 25 mmol) was treated at 0° C. with methylmagnesium bromide (150 µl, 3.0 M in diethyl ether, 450 µmol) and stirred overnight at room temperature. The mixture was cooled down to 0° C. and additional 3.5 equivalents of methylmagnesium bromide (150 µL, 3.0 M in diethyl ether, 459 µmol) were added. The mixture was stirred 3 hours at ambient temperature. As no conversion could be observed, a solution of methyl lithium (160 µl, 1.6 M in diethyl ether, 260 µmol) was added at –18° C. and it was stirred overnight at ambient temperature. Again no conversion was observed. The mixture was left over the weekend and then a solution of methylmagnesium chloride (86 µl, 3.0 M in tetrahydrofuran, 260 µmol) was added and again the mixture was stirred overnight at room temperature. The mixture was diluted with methanol and potassium sodium tartrate solution. The mixture was extracted with ethyl acetate (3×). The combined organic phases were dried over Extrelut NT3, concentrated under reduced pressure and the crude product was purified by preparative HPLC (method 7) to yield 14.2 mg (24%) of the desired product.

LC-MS (method 10): $R_t$=1.64 min; MS (ESIpos): m/z=443 [M+H]$^+$ $^1$H-NMR (400 MHz, dimethylsulfoxide-d6) δ [ppm]: –0.008 (1.66), 0.008 (1.67), 1.469 (16.00), 2.069 (10.83), 2.274 (2.96), 2.744 (11.16), 3.694 (8.30), 4.861 (3.57), 7.893 (15.74), 8.469 (0.81), 9.457 (1.64).

Example 299 ethyl 1-(6-{[5-(4-cyanophenyl)-1,4-dimethyl-1H-pyrazol-3-yl]amino}pyrimidin-4-yl)-3,5-dimethyl-1H-pyrazole-4-carboxylate

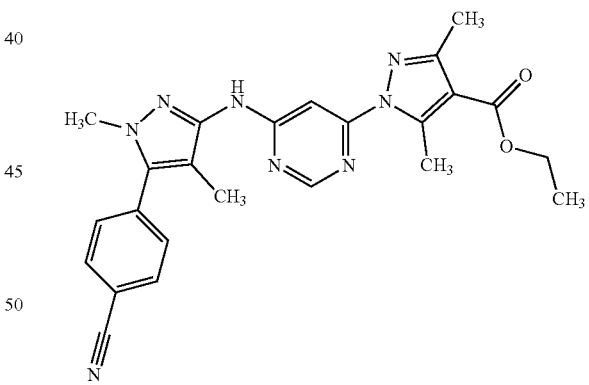

A microwave vial was charged ethyl 1-(6-chloropyrimidin-4-yl)-3,5-dimethyl-1H-pyrazole-4-carboxylate (250 mg, 891 µmol), 4-(3-amino-1,4-dimethyl-1H-pyrazol-5-yl)benzonitrile (208 mg, 980 µmol) and sodium phenolate (155 mg, 1.34 mmol) and the contents were suspended in 1,4-dioxane (4.0 ml, 46 mmol). The reaction mixture was degassed with Ar for 3 min. Tris(dibenzylidenaceton)dipalladium (10.6 mg, 11.6 µmol) and Xantphos (15.5 mg, 26.7 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were washed with water and brine, dried over sodium sulfate and concentrated under reduced pressure. The crude product was purified by preparative HPLC (method: column: Reprosil C18; 10 μm; 125×30 mm/flow: 50 mL/min/ solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (47.6 mg, 12%).

LC-MS (method 9): $R_t$=1.08 min; MS (ESIpos): m/z=457 [M+H]$^+$ $^1$H-NMR (400 MHz, dimethylsulfoxide-d6) δ [ppm]: 1.291 (4.38), 1.309 (8.89), 1.326 (4.48), 1.796 (0.46), 1.894 (13.15), 1.909 (1.58), 2.384 (14.88), 2.891 (15.59), 3.163 (0.41), 3.177 (0.43), 3.489 (0.45), 3.734 (16.00), 4.230 (1.40), 4.248 (4.13), 4.266 (4.07), 4.284 (1.35), 7.432 (1.35), 7.699 (4.49), 7.719 (5.04), 8.004 (4.95), 8.025 (4.31), 8.534 (3.31), 9.641 (2.47).

Example 300

4-[3-({6-[4-(2-hydroxypropan-2-yl)-3,5-dimethyl-1H-pyrazol-1-yl]pyrimidin-4-yl}amino)-1,4-dimethyl-1H-pyrazol-5-yl]benzonitrile

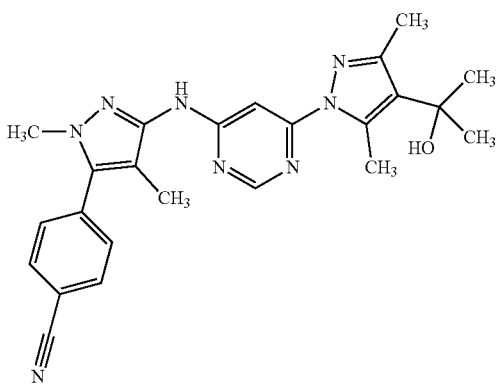 [SMILES: Cc1nn(-c2cc(Nc3nn(C)c(-c4ccc(C#N)cc4)c3C)ncn2)c(C)c1C(C)(C)O]

A solution of ethyl 1-(6-{[5-(4-cyanophenyl)-1,4-dimethyl-1H-pyrazol-3-yl]amino}pyrimidin-4-yl)-3,5-dimethyl-1H-pyrazole-4-carboxylate (38.0 mg, 83.2 μmol) in tetrahydrofuran (2.0 ml, 25 mmol) was treated at 0° C. with a solution of methylmagnesium bromide (97 μl, 3.0 M in diethyl ether, 290 μmol) and stirred overnight at ambient temperature. No conversion was observed. Additional 3.5 equivalents of methylmagnesium bromide (97 μl, 3.0 M in diethyl ether, 290 μmol) were added at 0° C. and it was stirred for 3 hours at room temperature. No conversion was observed. The mixture was cooled to −18° C. and a solution of methyl lithium (104 μL, 0.17 mmol, 1.6 M in diethyl ether) was added. The mixture was stirred overnight at ambient temperature. No conversion was observed. The mixture was left over the weekend, then a solution of methylmagnesium chloride (55 μl, 3.0 M in tetrahydrofuran, 170 μmol) was added and the mixture was stirred overnight. The mixture was diluted with methanol and potassium sodium tartrate solution, and extracted with ethyl acetate (3×). The combined organic phases were dried over Extrelut NT3, concentrated under reduced pressure and the crude product was purified by preparative HPLC (method 7) to yield 4.40 mg (12%) of the desired product.

LC-MS (method 10): $R_t$=1.62 min; MS (ESIpos): m/z=443 [M+H]$^+$ $^1$H-NMR (400 MHz, dimethylsulfoxide-d6) δ [ppm]: −0.008 (1.63), 0.008 (1.59), 1.472 (16.00), 1.887 (7.33), 2.277 (7.95), 2.717 (8.35), 3.726 (8.40), 4.842 (3.17), 7.331 (0.89), 7.694 (2.18), 7.715 (2.54), 8.002 (2.45), 8.022 (2.15), 8.458 (1.55), 9.440 (1.45).

Example 301

4-[4-({6-[4-(2-hydroxy-2-methylpropyl)-3,5-dimethyl-1H-pyrazol-1-yl]pyrimidin-4-yl}amino)-3,5-dimethyl-1H-pyrazol-1-yl]benzonitrile

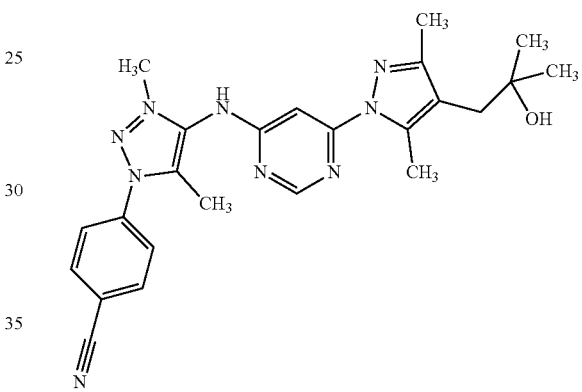

A solution of ethyl [1-(6-{[1-(4-cyanophenyl)-3,5-dimethyl-1H-pyrazol-4-yl]amino}pyrimidin-4-yl)-3,5-dimethyl-1H-pyrazol-4-yl]acetate (162 mg, 344 μmol) in tetrahydrofuran (3.5 ml, 43 mmol) was treated with a solution of chloro(methyl)magnesium (400 μl, 3.0 M in tetrahydrofuran, 1.2 mmol) at 0° C. and stirred 2 hours at ambient temperature. The mixture was diluted with water and extracted with ethyl acetate. The combined organic phases were dried over Extrelut NT3 and concentrated under reduced pressure. The crude product was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography on silica gel (column: Biotage SNAP KP-Sil 19 g, solvent: 100% dichloromethane to 96% dichloromethane/4% methanol) to yield 43.4 mg (28%) of the desired product.

LC-MS (method 10): $R_t$=1.65 min; MS (ESIpos): m/z=457 [M+H]$^+$ $^1$H-NMR (400 MHz, dimethylsulfoxide-d6) δ [ppm]: −0.008 (0.66), 0.008 (0.66), 1.074 (3.98), 1.085 (16.00), 1.091 (9.62), 1.108 (2.57), 2.104 (15.72), 2.158 (2.13), 2.294 (11.41), 2.425 (3.97), 2.563 (14.99), 3.357 (0.73), 3.375 (2.10), 3.392 (2.08), 3.410 (0.68), 4.232 (3.48), 7.810 (1.95), 7.831 (2.44), 7.978 (3.94), 7.999 (3.11), 8.387 (0.55), 8.881 (3.50).

Example 302

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-2-methylpropan-2-ol

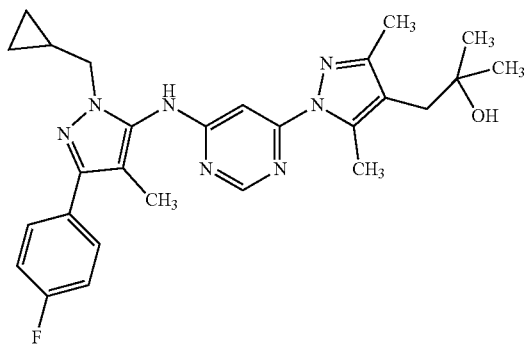 [SMILES: Cc1nn(-c2cc(Nc3c(C)c(-c4ccc(F)cc4)nn3CC3CC3)ncn2)c(C)c1CC(C)(C)O]

A solution ethyl [1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]acetate (570 mg, 1.13 mmol) in tetrahydrofuran (12 ml, 140 mmol) was treated with chloro(methyl)magnesium (1.3 ml, 3.0 M, 4.0 mmol) at 0° C. and stirred for 2 hours at ambient temperature. The mixture was diluted with potassium sodium tartrate and water, and extracted with ethyl acetate (3×). The combined organic phases were washed with water, dried over sodium sulfate and concentrated under reduced pressure. The crude product was purified by flash-chromatography on silica gel (column: Biotage SNAP Ultra 25 g, solvent: dichloromethane/methanol 20:1) and subsequently by preparative HPLC (column: 250×20 mm YMC Chiralart Cellulose SC, 5 µM, flow: 15 mL/min, solvent: n-heptane 30%/ethanol 70%) to yield 193 mg (35%) of the desired product along with its by-product 1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]propan-2-one.

LC-MS (method 10): $R_t$=2.10 min; MS (ESIpos): m/z=490 [M+H]$^+$ $^1$H-NMR (500 MHz, dimethylsulfoxide-d6) δ [ppm]: −0.006 (0.78), 0.007 (0.58), 0.295 (2.10), 0.305 (2.23), 0.425 (2.19), 0.441 (2.27), 1.086 (16.00), 1.183 (0.63), 1.188 (0.62), 1.198 (0.96), 1.207 (0.62), 1.212 (0.62), 2.009 (13.17), 2.160 (2.07), 2.429 (3.79), 2.577 (14.87), 3.308 (1.52), 3.324 (2.11), 3.329 (0.91), 3.829 (1.78), 3.842 (1.73), 4.237 (3.72), 7.255 (1.97), 7.273 (3.97), 7.291 (2.13), 7.719 (1.26), 7.730 (1.70), 7.746 (1.21), 8.449 (0.55), 9.319 (0.56).

Example 303 ethyl 4-chloro-1-(6-{[4-chloro-5-(4-fluorophenyl)-1-methyl-1H-pyrazol-3-yl]amino}pyrimidin-4-yl)-3-methyl-1H-pyrazole-5-carboxylate

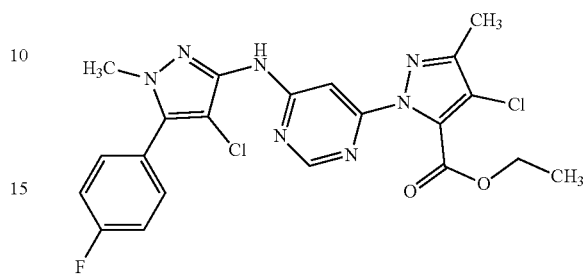

4-chloro-5-(4-fluorophenyl)-1-methyl-1H-pyrazol-3-amine (200 mg, 886 µmol) and sodium phenolate (103 mg, 886 µmol) were suspended in 1,4-dioxane (1.9 mL). The reaction mixture was degassed with Ar for 3 min. Tris(dibenzylideneacetone)dipalladium (9.59 mg, 10.5 µmol) and XantPhos (14.0 mg, 24.2 µmol) and ethyl 4-chloro-1-(6-chloropyrimidin-4-yl)-3-methyl-1H-pyrazole-5-carboxylate (324 mg, 75% purity, 806 µmol) were added and the reaction mixture was degassed again for 1 min. The reaction mixture was heated at 90° C. overnight while vigorously stirring. After cooling to ambient temperature, the reaction mixture was loaded onto silica gel and purified by flash column chromatography (SNAP Ultra 25 g, cyclohexane/ethyl acetate gradient 95/5 to 20/80) to yield the desired product (188 mg, 43% yield).

LC-MS (method 10): $R_t$=2.37 min; MS (ESIpos): m/z=490 [M+H]$^+$ $^1$H-NMR (400 MHz, dimethylsulfoxide-d6) δ [ppm]: −0.008 (1.89), 0.008 (1.79), 1.157 (0.41), 1.175 (0.85), 1.193 (0.44), 1.227 (4.68), 1.245 (10.15), 1.254 (0.99), 1.263 (5.09), 1.309 (0.78), 1.326 (1.42), 1.345 (0.69), 1.398 (1.94), 1.989 (1.47), 2.284 (14.88), 2.328 (0.44), 2.675 (2.50), 3.737 (0.66), 3.778 (16.00), 4.324 (1.51), 4.342 (4.75), 4.360 (4.71), 4.378 (1.49), 7.202 (3.33), 7.384 (0.45), 7.411 (2.14), 7.433 (4.72), 7.455 (2.64), 7.633 (2.51), 7.639 (1.15), 7.647 (2.82), 7.655 (2.43), 7.669 (2.15), 8.451 (3.07), 8.597 (0.41), 9.860 (2.15).

Example 304

2-[4-chloro-1-(6-{[4-chloro-5-(4-fluorophenyl)-1-methyl-1H-pyrazol-3-yl]amino}pyrimidin-4-yl)-3-methyl-1H-pyrazol-5-yl]propan-2-ol

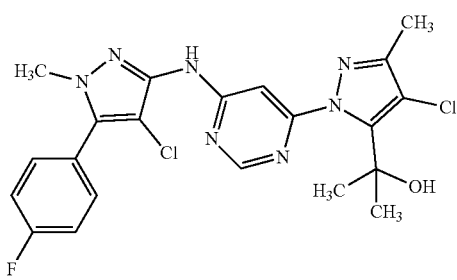 [SMILES: Cc1nn(-c2cc(Nc3nn(C)c(-c4ccc(F)cc4)c3Cl)ncn2)c(C(C)(C)O)c1Cl]

Under an argon atmosphere, ethyl 4-chloro-1-(6-{[4-chloro-5-(4-fluorophenyl)-1-methyl-1H-pyrazol-3-yl]amino}pyrimidin-4-yl)-3-methyl-1H-pyrazole-5-carboxylate (188 mg, 383 μmol) was dissolved in tetrahydrofuran (7.6 mL) and the solution cooled to 0° C. A solution of bromo(methyl)magnesium (1.9 ml, 1.0 M, 1.9 mmol) was added dropwise and the reaction mixture was stirred overnight at ambient temperature. The reaction mixture was carefully quenched by addition of aqueous Na₂EDTA solution (10%) and ethyl acetate was added. After standing overnight, the organic phase was decanted and concentrated. The residue was purified by flash column chromatography (SNAP Ultra 25 g, cyclohexane/ethyl acetate gradient 95/5 to 5/95) and further by preparative HPLC (method 6) to yield the desired product (22 mg, 24% yield).

LC-MS (method 10): $R_t$=2.26 min; MS (ESIpos): m/z=476 [M+H]⁺

¹H-NMR (400 MHz, dimethylsulfoxide-d6) δ [ppm]: −0.008 (0.71), 1.600 (16.00), 2.190 (9.16), 3.762 (9.96), 6.691 (1.14), 7.154 (2.09), 7.407 (1.21), 7.429 (2.69), 7.451 (1.52), 7.623 (1.48), 7.636 (1.66), 7.645 (1.50), 7.658 (1.26), 8.562 (2.19), 9.884 (0.89).

Example 305

N-{1-(cyclopropylmethyl)-3-[4-(difluoromethyl)phenyl]-4-methyl-1H-pyrazol-5-yl}-6-(3,5-dimethyl-1H-pyrazol-1-yl)pyrimidin-4-amine

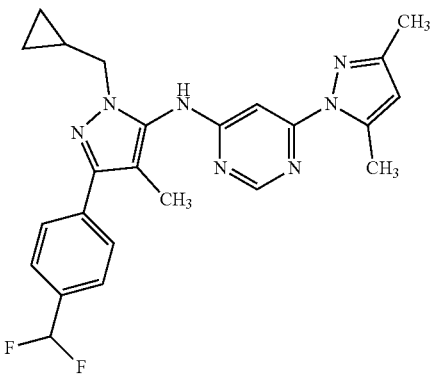 [SMILES: Cc1cc(C)n(-c2cc(Nc3c(C)c(-c4ccc(C(F)F)cc4)nn3CC3CC3)ncn2)n1]

A microwave vial was charged 4-chloro-6-(3,5-dimethyl-1H-pyrazol-1-yl)pyrimidine (56.1 mg, 269 mol) and 1-(cyclopropylmethyl)-3-[4-(difluoromethyl)phenyl]-4-methyl-1H-pyrazol-5-amine (82.0 mg, 296 μmol) and the contents were suspended in 1,4-dioxane (1.1 ml, 13 mmol). The reaction mixture was degassed with Ar for 3 min. Tris(dibenzylidenaceton)dipalladium (7.38 mg, 8.06 μmol) and Xantphos (9.33 mg, 16.1 μmol) were added and the reaction mixture was degassed again for 1 min and heated to 85° C. At this temperature and sodium phenolate (34.3 mg, 296 μmol) was added. The vial was sealed and heated at 85° C. for 90 minutes while vigorously stirring. After cooling to ambient temperature, the reaction mixture was purified by preparative HPLC (method: column: Reprosil C18; 10 m; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography in silica gel (column; Biotage SNAP KP-Sil 10 g, solvent: 92% dichloromethane/8% ethyl acetate to 66% ethyl acetate) to yield the desired product (44.3 mg, 37%).

LC-MS (method 10): $R_t$=2.29 min; MS (ESIpos): m/z=450 [M+H]⁺

¹H-NMR (400 MHz, dimethylsulfoxide-d6) δ [ppm]: −0.008 (0.49), 0.008 (0.41), 0.305 (2.63), 0.316 (2.87), 0.431 (2.63), 0.451 (2.81), 1.074 (0.69), 1.091 (1.44), 1.109 (0.73), 1.193 (0.71), 1.200 (0.70), 1.211 (1.09), 1.223 (0.67), 1.231 (0.71), 2.050 (16.00), 2.170 (3.20), 2.631 (15.46), 3.375 (0.72), 3.392 (0.72), 3.853 (2.58), 3.870 (2.52), 6.143 (2.92), 6.938 (1.56), 7.078 (3.22), 7.218 (1.41), 7.637 (3.22), 7.657 (3.95), 7.848 (3.13), 7.867 (2.63), 8.468 (0.78), 9.395 (0.84).

Example 306

N-{1-(cyclopropylmethyl)-4-methyl-3-[4-(trifluoromethyl)phenyl]-1H-pyrazol-5-yl}-6-(3,5-dimethyl-1H-pyrazol-1-yl)pyrimidin-4-amine

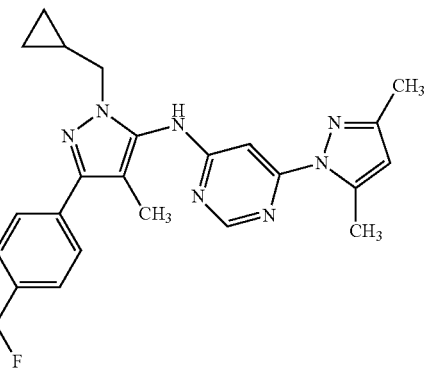

A microwave vial was charged with 1-(cyclopropylmethyl)-4-methyl-3-[4-(trifluoromethyl)phenyl]-1H-pyrazol-5-amine (131 mg, 90% purity, 401 μmol) and sodium phenolate (46.5 mg, 401 μmol) and the contents were suspended in 1,4-dioxane (0.9 mL). The reaction mixture was degassed with Ar for 3 min. Tris(dibenzylideneacetone)dipalladium (6.67 mg, 7.28 μmol), XantPhos (8.43 mg, 14.6 μmol) and 4-chloro-6-(3,5-dimethyl-1H-pyrazol-1-yl)pyrimidine (80.0 mg, 95% purity, 364 μmol), were added and the reaction mixture was degassed again for 1 min. The vial was sealed and heated at 90° C. overnight while vigorously shaking. After cooling to ambient temperature, the reaction mixture was filtered and concentrated. The residue was redissolved in dimethylsulfoxide and purified by preparative HPLC (method 3) to yield the desired product (40 mg, 23% yield).

LC-MS (method 10): $R_t$=2.49 min; MS (ESIpos): m/z=468 [M+H]⁺

¹H-NMR (400 MHz, dimethylsulfoxide-d6) δ [ppm]: −0.149 (0.36), −0.008 (2.73), 0.008 (2.58), 0.146 (0.33), 0.306 (2.65), 0.317 (2.86), 0.434 (2.83), 0.453 (2.99), 0.951 (0.19), 1.181 (0.41), 1.194 (0.78), 1.200 (0.78), 1.212 (1.19), 1.223 (0.74), 1.231 (0.75), 2.068 (16.00), 2.284 (1.93), 2.324 (0.79), 2.328 (0.81), 2.367 (0.36), 2.670 (0.45), 2.704 (0.30), 2.711 (0.30), 3.871 (2.16), 3.887 (2.16), 6.788 (2.44), 7.684 (1.56), 7.795 (3.28), 7.819 (5.96), 7.938 (2.39), 7.956 (3.42), 8.500 (0.44), 9.579 (0.36).

Example 307

N-{1-(cyclopropylmethyl)-4-methyl-3-[4-(trifluoromethyl)phenyl]-1H-pyrazol-5-yl}-6-[5-(difluoromethyl)-3-methyl-1H-pyrazol-1-yl]pyrimidin-4-amine

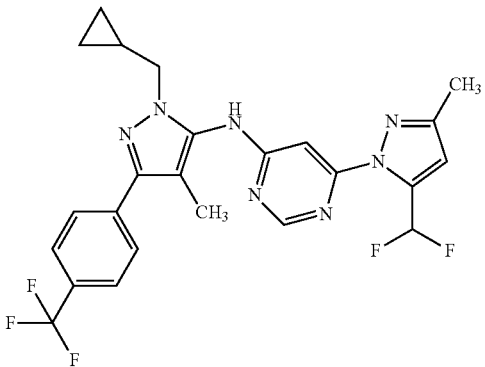 [SMILES: Cc1cc(C(F)F)n(-c2cc(Nc3c(C)c(-c4ccc(C(F)(F)F)cc4)nn3CC3CC3)ncn2)n1]

1-(cyclopropylmethyl)-4-methyl-3-[4-(trifluoromethyl)phenyl]-1H-pyrazol-5-amine (126 mg, 90% purity, 384 µmol) and sodium phenolate (44.6 mg, 384 µmol) were suspended in 1,4-dioxane (0.84 mL).
The reaction mixture was degassed with Ar for 3 min. Tris(dibenzylideneacetone)dipalladium (6.40 mg, 6.99 µmol), XantPhos (8.09 mg, 14.0 µmol) and 4-chloro-6-[5-(difluoromethyl)-3-methyl-1H-pyrazol-1-yl]pyrimidine (90.0 mg, 95% purity, 350 µmol) were added and the reaction mixture was degassed again for 1 min. The vial was sealed and heated at 90° C. overnight while vigorously shaking. After cooling to ambient temperature, the reaction mixture was filtered and concentrated. The residue was redissolved in dimethylsulfoxide and purified by preparative HPLC (method 4) to yield the desired product (37 mg, 21% yield).

LC-MS (method 10): $R_t$=2.51 min; MS (ESIpos): m/z=504 [M+H]$^+$ $^1$H-NMR (400 MHz, dimethylsulfoxide-d6) δ [ppm]: −0.008 (2.86), 0.008 (2.70), 0.307 (2.43), 0.319 (2.69), 0.434 (2.44), 0.453 (2.62), 1.196 (0.65), 1.202 (0.63), 1.214 (1.01), 1.226 (0.63), 1.232 (0.63), 2.064 (16.00), 2.172 (3.06), 2.328 (0.43), 2.631 (14.66), 2.670 (0.47), 3.863 (2.42), 3.881 (2.38), 6.145 (2.64), 7.792 (3.04), 7.812 (4.11), 7.933 (2.94), 7.953 (2.30), 8.469 (0.69), 9.412 (0.78).

Example 308

N-{1-(cyclopropylmethyl)-4-methyl-3-[4-(trifluoromethoxy)phenyl]-1H-pyrazol-5-yl}-6-(3,5-dimethyl-1H-pyrazol-1-yl)pyrimidin-4-amine

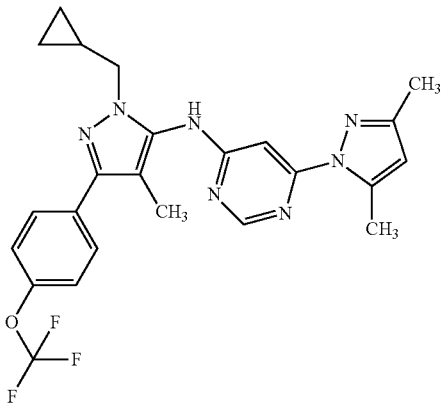 [SMILES: Cc1cc(C)n(-c2cc(Nc3c(C)c(-c4ccc(OC(F)(F)F)cc4)nn3CC3CC3)ncn2)n1]

1-(cyclopropylmethyl)-4-methyl-3-[4-(trifluoromethoxy)phenyl]-1H-pyrazol-5-amine (139 mg, 90% purity, 401 µmol) and sodium phenolate (46.5 mg, 401 µmol) were suspended in 1,4-dioxane (0.88 mL). The reaction mixture was degassed with Ar for 3 min. Tris(dibenzylideneacetone)dipalladium (6.67 mg, 7.28 µmol), XantPhos (8.43 mg, 14.6 µmol) and 4-chloro-6-(3,5-dimethyl-1H-pyrazol-1-yl)pyrimidine (80.0 mg, 95% purity, 364 µmol) were added and the reaction mixture was degassed again for 1 min. The vial was sealed and heated at 90° C. overnight while vigorously shaking. After cooling to ambient temperature, the reaction mixture was filtered and concentrated. The residue was redissolved in dimethylsulfoxide and purified by preparative HPLC (method 3) to yield the desired product (42 mg, 23% yield).

LC-MS (method 10): $R_t$=2.51 min; MS (ESIpos): m/z=484 [M+H]$^+$ $^1$H-NMR (400 MHz, dimethylsulfoxide-d6) δ [ppm]: −0.149 (0.45), −0.008 (3.69), 0.008 (3.48), 0.298 (2.61), 0.310 (2.88), 0.425 (2.68), 0.445 (2.84), 1.181 (0.72), 1.200 (1.09), 1.219 (0.66), 2.032 (16.00), 2.168 (3.42), 2.328 (0.55), 2.367 (0.46), 2.630 (15.80), 2.670 (0.61), 2.710 (0.52), 3.841 (2.56), 3.858 (2.55), 6.143 (3.03), 7.428 (3.32), 7.449 (3.74), 7.820 (3.05), 7.842 (2.84), 8.464 (0.80), 9.390 (0.84).

Example 309

N-{1-(cyclopropylmethyl)-4-methyl-3-[4-(trifluoromethoxy)phenyl]-1H-pyrazol-5-yl}-6-[5-(difluoromethyl)-3-methyl-1H-pyrazol-1-yl]pyrimidin-4-amine

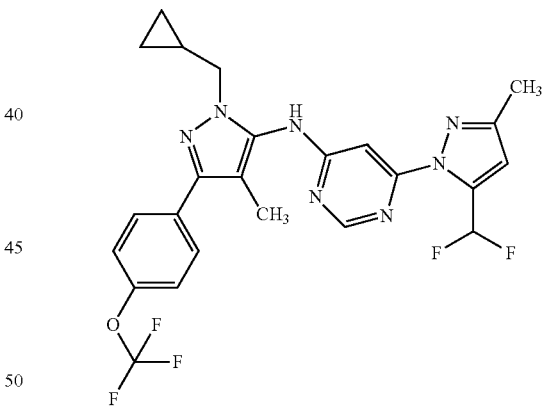

1-(cyclopropylmethyl)-4-methyl-3-[4-(trifluoromethoxy)phenyl]-1H-pyrazol-5-amine (133 mg, 90% purity, 384 µmol) and sodium phenolate (44.6 mg, 384 µmol) were suspended in 1,4-dioxane (0.84 mL). The reaction mixture was degassed with Ar for 3 min. Tris(dibenzylideneacetone)dipalladium (6.40 mg, 6.99 µmol), XantPhos (8.09 mg, 14.0 µmol) and 4-chloro-6-[5-(difluoromethyl)-3-methyl-1H-pyrazol-1-yl]pyrimidine (90.0 mg, 95% purity, 350 µmol) were added and the reaction mixture was degassed again for 1 min. The vial was sealed and heated at 90° C. overnight while vigorously shaking. After cooling to ambient temperature, the reaction mixture was filtered and concentrated. The residue was redissolved in dimethylsulfoxide and purified by preparative HPLC (method 3) to yield the desired product (49 mg, 26% yield).

LC-MS (method 10): R$_f$=2.50 min; MS (ESIpos): m/z=520 [M+H]$^+$ $^1$H-NMR (400 MHz, dimethylsulfoxide-d6) δ [ppm]: −0.149 (0.42), −0.008 (3.56), 0.008 (3.09), 0.146 (0.40), 0.295 (2.95), 0.306 (3.15), 0.425 (3.13), 0.445 (3.27), 1.165 (0.46), 1.178 (0.87), 1.185 (0.84), 1.197 (1.28), 1.216 (0.82), 2.035 (16.00), 2.280 (2.18), 2.327 (0.90), 2.366 (0.57), 2.670 (0.50), 2.702 (0.28), 2.710 (0.47), 3.847 (2.39), 3.864 (2.36), 6.784 (2.56), 7.431 (3.50), 7.451 (3.88), 7.682 (1.68), 7.818 (5.14), 7.843 (2.14), 7.954 (1.53), 8.496 (0.44), 9.569 (0.37).

Example 310

6-(4-chloro-3,5-dimethyl-1H-pyrazol-1-yl)-N-{1-(cyclopropylmethyl)-4-methyl-3-[4-(trifluoromethoxy)phenyl]-1H-pyrazol-5-yl}pyrimidin-4-amine

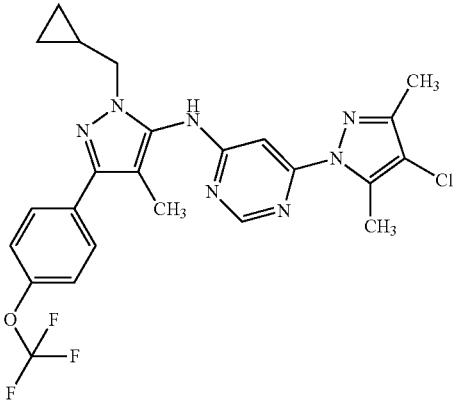 [SMILES: Cc1nn(-c2cc(Nc3c(C)c(-c4ccc(OC(F)(F)F)cc4)nn3CC3CC3)ncn2)c(C)c1Cl]

A microwave vial was charged with 4-chloro-6-(4-chloro-3,5-dimethyl-1H-pyrazol-1-yl)pyrimidine (80.0 mg, 95% purity, 313 µmol), 1-(cyclopropylmethyl)-4-methyl-3-[4-(trifluoromethoxy)phenyl]-1H-pyrazol-5-amine (119 mg, 90% purity, 344 µmol) and sodium phenolate (39.9 mg, 344 µmol) and the contents were suspended in 1,4-dioxane (1.0 mL). The reaction mixture was degassed with Ar for 3 min. Tris(dibenzylideneacetone)dipalladium (5.73 mg, 6.25 µmol) and XantPhos (7.24 mg, 12.5 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (47 mg, 29% yield).

LC-MS (method 10): R$_f$=2.74 min; MS (ESIpos): m/z=518 [M+H]$^+$ $^1$H-NMR (400 MHz, dimethylsulfoxide-d6) δ [ppm]: −0.149 (0.27), −0.008 (2.20), 0.008 (2.08), 0.146 (0.24), 0.295 (2.17), 0.306 (2.37), 0.424 (2.20), 0.444 (2.33), 1.179 (0.60), 1.197 (0.92), 2.030 (14.01), 2.208 (2.29), 2.328 (0.34), 2.367 (0.28), 2.648 (16.00), 2.670 (0.54), 2.711 (0.32), 3.841 (2.05), 3.859 (1.99), 7.429 (2.78), 7.450 (3.05), 7.819 (2.28), 7.840 (2.14), 8.500 (0.51), 9.489 (0.42).

Example 311

6-(4-chloro-3,5-dimethyl-1H-pyrazol-1-yl)-N-{1-(cyclopropylmethyl)-4-methyl-3-[4-(trifluoromethyl)phenyl]-1H-pyrazol-5-yl}pyrimidin-4-amine

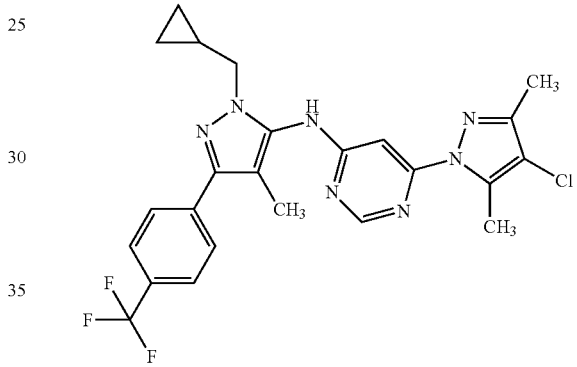

A microwave vial was charged with 4-chloro-6-(4-chloro-3,5-dimethyl-1H-pyrazol-1-yl)pyrimidine (80.0 mg, 95% purity, 313 µmol), 1-(cyclopropylmethyl)-4-methyl-3-[4-(trifluoromethyl)phenyl]-1H-pyrazol-5-amine (113 mg, 90% purity, 344 µmol) and sodium phenolate (39.9 mg, 344 µmol) and the contents were suspended in 1,4-dioxane (0.75 mL). The reaction mixture was degassed with Ar for 3 min. Tris(dibenzylideneacetone)dipalladium (5.73 mg, 6.25 µmol) and XantPhos (7.24 mg, 12.5 µmol) were added and the reaction mixture was degassed again for 1 min. The vial was sealed and heated at 85° C. overnight while vigorously stirring. After cooling to ambient temperature, the reaction mixture was filtered and concentrated. The residue was redissolved in dimethylsulfoxide and purified by preparative HPLC (method 3) to yield the desired product (30 mg, 19% yield).

LC-MS (method 10): R$_f$=2.72 min; MS (ESIpos): m/z=502 [M+H]$^+$ $^1$H-NMR (400 MHz, dimethylsulfoxide-d6) δ [ppm]: −0.149 (0.61), −0.008 (7.03), 0.008 (4.63), 0.146 (0.57), 0.306 (2.13), 0.317 (2.23), 0.432 (2.21), 0.452 (2.23), 1.192 (0.63), 1.210 (0.89), 1.893 (0.16), 2.062 (13.54), 2.212 (2.36), 2.328 (0.69), 2.366 (0.41), 2.524 (2.25), 2.650 (16.00), 2.670 (0.89), 2.710 (0.45), 3.593 (0.18), 3.863 (2.05), 3.881 (1.89), 7.792 (2.76), 7.813 (3.55), 7.931 (2.50), 7.951 (1.89), 8.502 (0.49), 9.511 (0.45).

Example 312

N-[3-(4-chlorophenyl)-1-(cyclopropylmethyl)-4-methyl-1H-pyrazol-5-yl]-6-(3,5-dimethyl-1H-pyrazol-1-yl)pyrimidin-4-amine

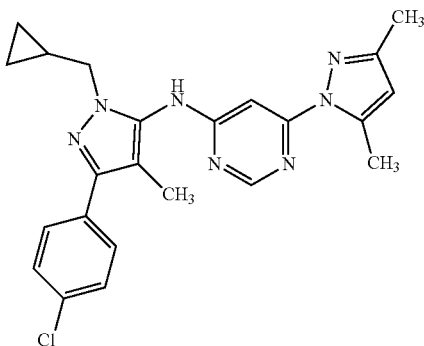 [SMILES: Cc1cc(C)n(-c2cc(Nc3c(C)c(-c4ccc(Cl)cc4)nn3CC3CC3)ncn2)n1]

A microwave vial was charged 4-chloro-6-(3,5-dimethyl-1H-pyrazol-1-yl)pyrimidine (109 mg, 521 μmol), 3-(4-chlorophenyl)-1-(cyclopropylmethyl)-4-methyl-1H-pyrazol-5-amine (150 mg, 573 μmol) and sodium phenolate (66.5 mg, 573 μmol) and the contents were suspended in 1,4-dioxane (3.0 ml, 35 mmol). The reaction mixture was degassed with Ar for 3 min. Tris(dibenzylidenaceton)dipalladium (6.20 mg, 6.77 μmol) and Xantphos (9.04 mg, 15.6 μmol) were added and the reaction mixture was degassed again for 1 min. The vial was sealed and heated at 85° C. overnight while vigorously stirring. After cooling to ambient temperature, the reaction mixture was filtered and purified by preparative HPLC (method 4) to yield the desired product (123 mg, 54%).

LC-MS (method 10): $R_t$=2.45 min; MS (ESIpos): m/z=434 [M+H]$^+$ $^1$H-NMR (400 MHz, dimethylsulfoxide-d6) δ [ppm]: −0.008 (0.67), 0.008 (0.63), 0.295 (2.51), 0.306 (2.77), 0.318 (0.82), 0.424 (2.53), 0.444 (2.70), 1.180 (0.67), 1.187 (0.66), 1.199 (1.05), 1.211 (0.63), 1.218 (0.64), 2.019 (16.00), 2.074 (0.55), 2.169 (3.20), 2.629 (15.37), 3.833 (2.50), 3.850 (2.47), 6.141 (2.82), 7.491 (4.49), 7.512 (5.61), 7.720 (3.36), 7.742 (2.89), 8.461 (0.66), 9.381 (0.77).

Example 313

N-[3-(4-chlorophenyl)-1-(cyclopropylmethyl)-4-methyl-1H-pyrazol-5-yl]-6-[5-(difluoromethyl)-3-methyl-1H-pyrazol-1-yl]pyrimidin-4-amine

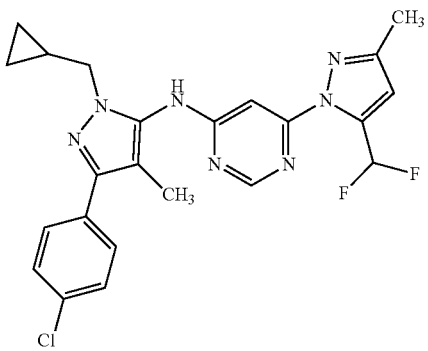 [SMILES: Cc1cc(C(F)F)n(-c2cc(Nc3c(C)c(-c4ccc(Cl)cc4)nn3CC3CC3)ncn2)n1]

A microwave vial was charged 4-chloro-6-[5-(difluoromethyl)-3-methyl-H-pyrazol-1-yl]pyrimidine (127 mg, 521 μmol), 3-(4-chlorophenyl)-1-(cyclopropylmethyl)-4-methyl-1H-pyrazol-5-amine (150 mg, 573 μmol) and sodium phenolate (66.5 mg, 573 μmol) and the contents were suspended in 1,4-dioxane (3.0 ml, 35 mmol). The reaction mixture was degassed with Ar for 3 min. Tris(dibenzylidenaceton)dipalladium (6.20 mg, 6.77 μmol) and Xantphos (9.04 mg, 15.6 μmol) were added and the reaction mixture was degassed again for 1 min. The vial was sealed and heated at 85° C. overnight while vigorously stirring. After cooling to ambient temperature, the reaction mixture was filtered and purified by preparative HPLC (method 4) to yield the desired product (102 mg, 40%).

LC-MS (method 10): $R_t$=2.48 min; MS (ESIpos): m/z=470 [M+H]$^+$ $^1$H-NMR (400 MHz, dimethylsulfoxide-d6) δ [ppm]: −0.008 (1.56), 0.008 (1.54), 0.292 (2.69), 0.304 (2.90), 0.424 (2.87), 0.444 (3.05), 1.074 (0.50), 1.091 (1.06), 1.109 (0.53), 1.165 (0.43), 1.177 (0.80), 1.184 (0.79), 1.196 (1.22), 1.208 (0.75), 1.215 (0.77), 2.022 (16.00), 2.086 (2.34), 2.283 (2.03), 2.328 (0.62), 2.701 (0.42), 3.375 (0.53), 3.392 (0.53), 3.840 (2.22), 3.856 (2.18), 6.784 (2.50), 7.494 (4.28), 7.515 (5.14), 7.682 (1.70), 7.724 (2.43), 7.744 (2.11), 7.818 (3.43), 7.953 (1.46), 8.491 (0.42).

Example 314 ethyl 1-(6-{[3-(4-chlorophenyl)-1-(cyclopropylmethyl)-4-methyl-1H-pyrazol-5-yl]amino}pyrimidin-4-yl)-3,5-dimethyl-1H-pyrazole-4-carboxylate

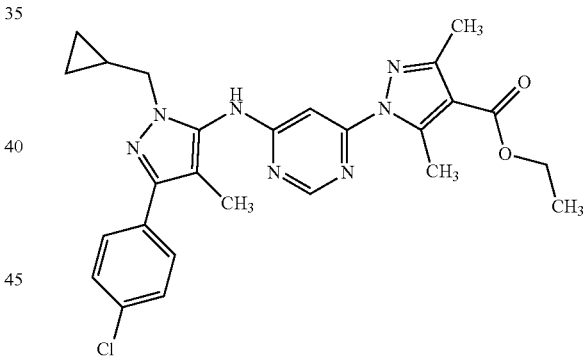

A microwave vial was charged ethyl 1-(6-chloropyrimidin-4-yl)-3,5-dimethyl-1H-pyrazole-4-carboxylate (244 mg, 868 μmol), 3-(4-chlorophenyl)-1-(cyclopropylmethyl)-4-methyl-1H-pyrazol-5-amine (250 mg, 955 μmol) and sodium phenolate (111 mg, 955 μmol) and the contents were suspended in 1,4-dioxane (5.0 ml, 58 mmol). The reaction mixture was degassed with Ar for 3 min. Tris(dibenzylidenaceton)dipalladium (10.3 mg, 11.3 μmol) and Xantphos (15.1 mg, 26.0 μmol) were added and the reaction mixture was degassed again for 1 min. The vial was sealed and heated at 85° C. overnight while vigorously stirring. After cooling to ambient temperature, the reaction mixture was filtered and purified by preparative HPLC (method 4) to yield the desired product (147 mg, 33%).

LC-MS (method 10): $R_t$=2.57 min; MS (ESIpos): m/z=506 [M+H]$^+$ $^1$H-NMR (400 MHz, dimethylsulfoxide-d6) δ [ppm]: −0.008 (1.07), 0.008 (0.79), 0.296 (2.60), 0.308 (2.81), 0.427 (2.69), 0.447 (2.84), 1.182 (0.73), 1.189 (0.71), 1.201 (1.10), 1.212 (0.67), 1.220 (0.69), 1.287 (3.57), 1.305 (7.21), 1.323 (3.62), 2.020 (16.00), 2.329 (0.54), 2.369 (2.17), 2.524 (0.46), 2.910 (12.58), 3.837 (2.27), 3.854 (2.24), 4.228 (1.08), 4.246 (3.23), 4.263 (3.21), 4.281 (1.10), 7.491 (4.46), 7.512 (5.52), 7.716 (3.22), 7.737 (2.79).

Example 315

N-[1-(cyclopropylmethyl)-3-(4-fluorophenyl)-4-methoxy-1H-pyrazol-5-yl]-6-(3,5-dimethyl-1H-pyrazol-1-yl)pyrimidin-4-amine

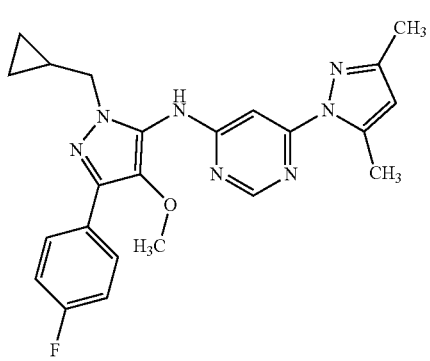 [SMILES: COc1c(-c2ccc(F)cc2)nn(CC2CC2)c1Nc1cc(-n2nc(C)cc2C)ncn1]

A microwave vial was charged 4-chloro-6-(3,5-dimethyl-1H-pyrazol-1-yl)pyrimidine (100 mg, 479 μmol) and 1-(cyclopropylmethyl)-3-(4-fluorophenyl)-4-methoxy-1H-pyrazol-5-amine (138 mg, 527 μmol) and the contents were suspended in 1,4-dioxane (2.0 ml, 23 mmol). The reaction mixture was degassed with Ar for 3 min. Tris(dibenzylidenaceton)dipalladium (13.2 mg, 14.4 μmol) and Xantphos (16.6 mg, 28.8 μmol) were added and the reaction mixture was degassed again for 1 min and heated to 85° C. At this temperature and sodium phenolate (61.2 mg, 527 μmol) was added. The vial was sealed and heated at 85° C. for 90 minutes while vigorously stirring. After cooling to ambient temperature, the reaction mixture was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography on silica gel (column: Biotage SNAP KP-Sil 10 g, solvent: 92% dichloromethane/8% ethyl acetate to 66% ethyl acetate) to yield the desired product (82.4 mg, 40%).

LC-MS (method 10): $R_f$=2.29 min; MS (ESIpos): m/z=434 [M+H]$^+$ $^1$H-NMR (400 MHz, dimethylsulfoxide-d6) δ [ppm]: −0.008 (1.32), 0.008 (1.28), 0.287 (0.50), 0.299 (2.08), 0.302 (1.83), 0.313 (2.18), 0.324 (0.74), 0.429 (0.68), 0.439 (1.71), 0.443 (1.72), 0.449 (1.02), 0.459 (1.85), 0.463 (1.68), 0.475 (0.56), 1.177 (0.45), 1.185 (0.44), 1.197 (0.69), 1.209 (0.41), 1.216 (0.43), 2.167 (3.15), 2.633 (10.14), 3.641 (0.50), 3.684 (16.00), 3.765 (1.81), 3.783 (1.78), 6.146 (2.30), 7.243 (1.71), 7.266 (3.48), 7.288 (1.84), 7.883 (1.47), 7.897 (1.70), 7.905 (1.67), 7.919 (1.40), 8.484 (1.05), 9.435 (0.76).

Example 316

4-[1-(cyclopropylmethyl)-5-{[6-(3,5-dimethyl-1H-pyrazol-1-yl)pyrimidin-4-yl]amino}-4-methoxy-1H-pyrazol-3-yl]benzonitrile

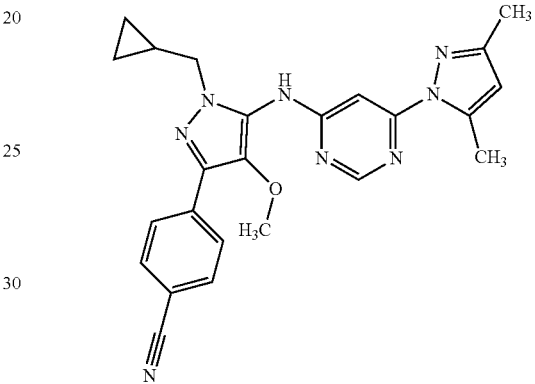

A microwave vial was charged 4-chloro-6-(3,5-dimethyl-1H-pyrazol-1-yl)pyrimidine (100 mg, 479 mol) and 4-[5-amino-(cyclopropylmethyl)-4-methoxy-1H-pyrazol-3-yl]benzonitrile (141 mg, 527 mol) and the contents were suspended in 1,4-dioxane (2.0 ml, 23 mmol). The reaction mixture was degassed with Ar for 3 min. Tris(dibenzylidenaceton)dipalladium (13.2 mg, 14.4 μmol) and Xantphos (16.6 mg, 28.8 μmol) were added and the reaction mixture was degassed again for 1 min and heated to 85° C. At this temperature and sodium phenolate (61.2 mg, 527 μmol) was added. The vial was sealed and heated at 85° C. for 90 minutes while vigorously stirring. After cooling to ambient temperature, the reaction mixture was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography on silica gel (column: Biotage SNAP KP-Sil 10 g, solvent: 92% dichloromethane/8% ethyl acetate to 66% ethyl acetate) to yield the desired product (107 mg, 51%).

LC-MS (method 10): $R_f$=2.21 min; MS (ESIpos): m/z=441 [M+H]$^+$ $^1$H-NMR (400 MHz, dimethylsulfoxide-d6) δ [ppm]: 0.302 (0.76), 0.314 (3.29), 0.328 (3.59), 0.340 (1.10), 0.442 (1.02), 0.452 (2.67), 0.456 (2.68), 0.472 (2.89), 0.476 (2.69), 0.488 (0.80), 1.194 (0.80), 1.201 (0.70), 1.212 (1.08), 1.224 (0.67), 1.231 (0.73), 2.172 (5.11), 2.634 (16.00), 3.314 (13.53), 3.800 (2.97), 3.818 (2.94), 6.151 (3.61), 7.878 (4.40), 7.899 (5.68), 8.049 (5.34), 8.070 (4.23), 8.488 (1.70), 9.487 (1.33).

Example 317

1-[1-(6-{[1-(cyclopropylmethyl)-3-(4-fluorophenyl)-4-methoxy-1H-pyrazol-5-yl]amino}pyrimidin-4-yl)-3,5-dimethyl-1H-pyrazol-4-yl]ethanone

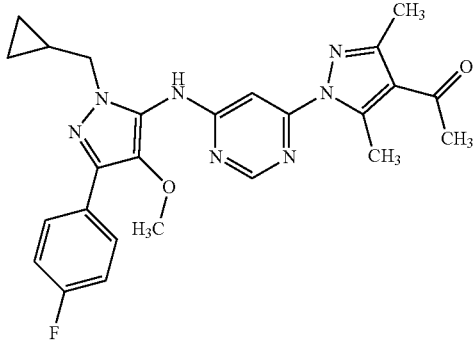 [SMILES: COc1c(-c2ccc(F)cc2)nn(CC2CC2)c1Nc1cc(-n2nc(C)c(C(C)=O)c2C)ncn1]

A microwave vial was charged 1-[1-(6-chloropyrimidin-4-yl)-3,5-dimethyl-1H-pyrazol-4-yl]ethanone (200 mg, 798 µmol) and 1-(cyclopropylmethyl)-3-(4-fluorophenyl)-4-methoxy-1H-pyrazol-5-amine (229 mg, 878 µmol) and the contents were suspended in 1,4-dioxane (3.3 ml, 39 mmol). The reaction mixture was degassed with Ar for 3 min. Tris(dibenzylidenaceton)dipalladium (21.9 mg, 23.9 µmol) and Xantphos (27.7 mg, 47.9 µmol) were added and the reaction mixture was degassed again for 1 min and heated to 85° C. At this temperature and sodium phenolate (102 mg, 878 µmol) was added. The vial was sealed and heated at 85° C. for 90 minutes while vigorously stirring. After cooling to ambient temperature, the reaction mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (168 mg, 44%).

LC-MS (method 10): $R_t$=2.10 min; MS (ESIpos): m/z=476 [M+H]$^+$ $^1$H-NMR (400 MHz, dimethylsulfoxide-d6) δ [ppm]: 0.292 (0.92), 0.305 (4.59), 0.317 (5.04), 0.328 (1.30), 0.435 (1.20), 0.446 (3.86), 0.466 (4.07), 0.480 (0.90), 1.091 (0.63), 1.173 (0.64), 1.184 (0.98), 1.191 (1.04), 1.203 (1.38), 1.213 (0.93), 1.221 (0.95), 1.233 (0.52), 2.464 (1.89), 2.895 (16.00), 3.314 (12.54), 3.775 (3.52), 3.792 (3.48), 7.245 (2.65), 7.267 (5.07), 7.289 (2.62), 7.879 (2.78), 7.894 (3.55), 7.899 (3.47), 7.914 (2.62), 8.568 (1.52), 9.614 (0.87).

Example 318

4-[5-{[6-(4-acetyl-3,5-dimethyl-1H-pyrazol-1-yl)pyrimidin-4-yl]amino}-1-(cyclopropylmethyl)-4-methoxy-1H-pyrazol-3-yl]benzonitrile

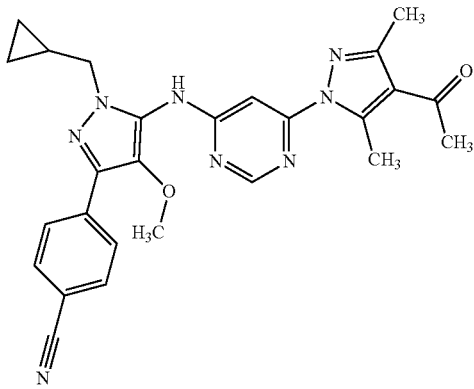 [SMILES: COc1c(-c2ccc(C#N)cc2)nn(CC2CC2)c1Nc1cc(-n2nc(C)c(C(C)=O)c2C)ncn1]

A microwave vial was charged 1-[1-(6-chloropyrimidin-4-yl)-3,5-dimethyl-1H-pyrazol-4-yl]ethanone (200 mg, 798 µmol) and 4-[5-amino-1-(cyclopropylmethyl)-4-methoxy-1H-pyrazol-3-yl]benzonitrile (235 mg, 878 µmol) and the contents were suspended in 1,4-dioxane (3.3 ml, 39 mmol). The reaction mixture was degassed with Ar for 3 min. Tris(dibenzylidenaceton)dipalladium (21.9 mg, 23.9 µmol) and Xantphos (27.7 mg, 47.9 µmol) were added and the reaction mixture was degassed again for 1 min and heated to 85° C. At this temperature and sodium phenolate (102 mg, 878 µmol) was added. The vial was sealed and heated at 85° C. for 90 minutes while vigorously stirring. After cooling to ambient temperature, the reaction mixture was purified by preparative HPLC (method: column: Reprosil C18; m; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography on silica gel (column: Biotage SNAP KP-Sil 10 g, solvent: 92% dichloromethane/8% ethyl acetate to 66% ethyl acetate) to yield the desired product (177 mg, 46%).

LC-MS (method 10): $R_t$=2.02 min; MS (ESIpos): m/z=483 [M+H]$^+$ $^1$H-NMR (400 MHz, dimethylsulfoxide-d6) δ [ppm]: 0.309 (0.87), 0.321 (3.83), 0.335 (4.06), 0.347 (1.23), 0.449 (1.17), 0.460 (3.11), 0.463 (2.97), 0.469 (1.73), 0.479 (3.33), 0.495 (0.89), 1.159 (1.38), 1.177 (2.84), 1.195 (1.73), 1.201 (0.88), 1.209 (0.81), 1.220 (1.26), 1.232 (0.81), 1.239 (0.83), 1.251 (0.43), 1.990 (5.32), 2.467 (13.80), 2.898 (16.00), 3.320 (8.34), 3.811 (2.90), 3.829 (2.86), 4.005 (0.46), 4.022 (1.31), 4.040 (1.29), 4.058 (0.43), 7.878 (4.90), 7.899 (6.04), 8.047 (6.24), 8.067 (4.79), 8.572 (1.33), 9.664 (0.75).

Example 319 ethyl 1-(6-{[1-(cyclopropylmethyl)-3-(4-fluorophenyl)-4-methoxy-1H-pyrazol-5-yl]amino}pyrimidin-4-yl)-3,5-dimethyl-1H-pyrazole-4-carboxylate

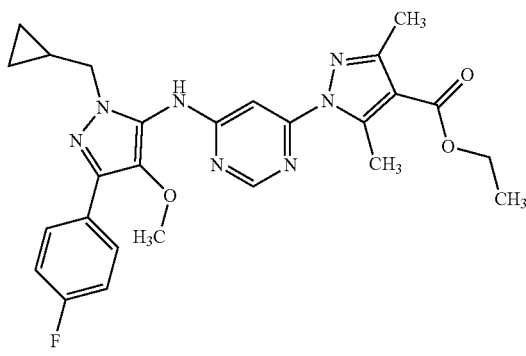 [SMILES: CCOC(=O)c1c(C)nn(-c2cc(Nc3c(OC)c(-c4ccc(F)cc4)nn3CC3CC3)ncn2)c1C]

A microwave vial was charged ethyl 1-(6-chloropyrimidin-4-yl)-3,5-dimethyl-1H-pyrazole-4-carboxylate (200 mg, 712 µmol) and 1-(cyclopropylmethyl)-3-(4-fluorophenyl)-4-methoxy-1H-pyrazol-5-amine (205 mg, 784 µmol) and the contents were suspended in 1,4-dioxane (3.0 ml, 35 mmol). The reaction mixture was degassed with Ar for 3 min. Tris(dibenzylidenaceton)dipalladium (19.6 mg, 21.4 µmol) and Xantphos (24.7 mg, 42.7 µmol) were added and the reaction mixture was degassed again for 1 min and heated to 85° C. At this temperature and sodium phenolate (91.0 mg, 784 µmol) was added. The vial was sealed and heated at 85°

C. for 90 minutes while vigorously stirring. After cooling to ambient temperature, the reaction mixture was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (204 mg, 57%).

LC-MS (method 10): R$_t$=2.41 min; MS (ESIpos): m/z=506 [M+H]$^+$ $^1$H-NMR (400 MHz, dimethylsulfoxide-d6) δ [ppm]: 0.295 (0.90), 0.309 (4.61), 0.321 (5.13), 0.332 (1.36), 0.438 (1.18), 0.450 (3.89), 0.470 (4.06), 0.483 (0.95), 1.075 (0.44), 1.093 (0.90), 1.110 (0.46), 1.178 (0.91), 1.190 (1.01), 1.196 (1.15), 1.208 (1.41), 1.219 (0.97), 1.227 (1.01), 1.238 (0.53), 1.287 (4.19), 1.304 (8.40), 1.322 (4.32), 1.992 (0.74), 2.368 (4.80), 2.917 (16.00), 3.323 (5.52), 3.375 (0.44), 3.393 (0.44), 3.778 (3.46), 3.795 (3.44), 4.226 (1.34), 4.244 (3.89), 4.261 (3.87), 4.279 (1.34), 7.245 (2.52), 7.267 (5.05), 7.288 (2.80), 7.886 (2.73), 7.901 (3.47), 7.907 (3.47), 7.922 (2.69), 8.564 (1.41), 9.610 (0.89).

Example 320 ethyl 1-(6-{[3-(4-cyanophenyl)-1-(cyclopropylmethyl)-4-methoxy-1H-pyrazol-5-yl]amino}pyrimidin-4-yl)-3,5-dimethyl-1H-pyrazole-4-carboxylate

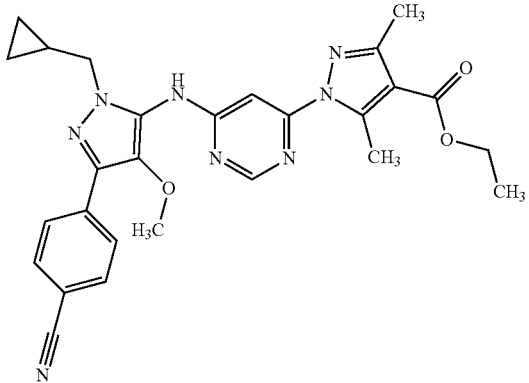 [SMILES: CCOC(=O)c1c(C)nn(-c2cc(Nc3c(OC)c(-c4ccc(C#N)cc4)nn3CC3CC3)ncn2)c1C]

A microwave vial was charged ethyl 1-(6-chloropyrimidin-4-yl)-3,5-dimethyl-1H-pyrazole-4-carboxylate (200 mg, 712 μmol) and 4-[5-amino-1-(cyclopropylmethyl)-4-methoxy-1H-pyrazol-3-yl]benzonitrile (210 mg, 784 μmol) and the contents were suspended in 1,4-dioxane (3.0 ml, 35 mmol).

The reaction mixture was degassed with Ar for 3 min. Tris(dibenzylidenaceton)dipalladium (19.6 mg, 21.4 μmol) and Xantphos (24.7 mg, 42.7 μmol) were added and the reaction mixture was degassed again for 1 min and heated to 85° C. At this temperature and sodium phenolate (91.0 mg, 784 μmol) was added. The vial was sealed and heated at 85° C. for 90 minutes while vigorously stirring. After cooling to ambient temperature, the reaction mixture was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (205 mg, 56%).

LC-MS (method 10): R$_t$=2.33 min; MS (ESIpos): m/z=513 [M+H]$^+$ $^1$H-NMR (400 MHz, dimethylsulfoxide-d6) δ [ppm]: 0.307 (0.88), 0.319 (3.88), 0.332 (4.15), 0.344 (1.22), 0.447 (1.17), 0.458 (3.16), 0.461 (3.06), 0.478 (3.39), 0.493 (0.87), 1.075 (1.02), 1.092 (2.08), 1.110 (1.06), 1.187 (0.46), 1.198 (0.86), 1.205 (0.83), 1.217 (1.27), 1.229 (0.97), 1.236 (0.86), 1.248 (0.45), 1.289 (4.28), 1.306 (8.69), 1.324 (4.37), 2.372 (4.05), 2.919 (16.00), 3.317 (9.20), 3.375 (1.01), 3.393 (0.99), 3.807 (2.91), 3.824 (2.87), 4.229 (1.30), 4.246 (3.85), 4.264 (3.82), 4.282 (1.28), 7.878 (4.67), 7.899 (5.89), 8.047 (5.94), 8.067 (4.63), 8.566 (1.29), 9.654 (0.79).

Example 321

4-[5-{[6-(4-acetyl-3,5-dimethyl-1H-pyrazol-1-yl)pyrimidin-4-yl]amino}-1-(cyclopropylmethyl)-4-methyl-1H-pyrazol-3-yl]benzonitrile

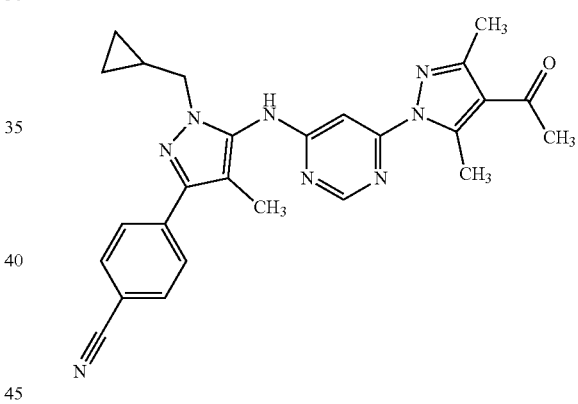

This product was obtained as a by-product during the synthesis of 4-[1-(cyclopropylmethyl)-5-({6-[4-(2-hydroxypropan-2-yl)-3,5-dimethyl-1H-pyrazol-1-yl]pyrimidin-4-yl}amino)-4-methyl-1H-pyrazol-3-yl]benzonitrile (see example 167) after purification by flash column chromatography (SNAP Ultra 10 g, dichloromethane/methanol gradient 99/1 to 95/5). The title compound was obtained as an off-white solid after lyophilisation (55 mg, 10% yield).

LC-MS (method 10): R$_t$=1.97 min; MS (ESIpos): m/z=467 [M+H]$^+$ $^1$H-NMR (400 MHz, dimethylsulfoxide-d6) δ [ppm]: −0.149 (0.25), −0.008 (2.06), 0.008 (2.10), 0.146 (0.23), 0.311 (2.49), 0.321 (2.74), 0.438 (2.51), 0.457 (2.67), 1.181 (0.39), 1.194 (0.71), 1.201 (0.71), 1.213 (1.08), 1.225 (0.74), 1.233 (0.94), 1.306 (0.25), 2.065 (16.00), 2.328 (0.41), 2.467 (8.99), 2.608 (0.79), 2.670 (0.38), 2.890 (10.02), 2.914 (0.58), 3.868 (2.26), 3.885 (2.23), 7.886 (0.72), 7.907 (13.49), 7.931 (0.72), 8.026 (0.21), 8.540 (0.43), 9.588 (0.39).

Example 322

(±)-4-{1-(cyclopropylmethyl)-5-[(6-{3,5-dimethyl-4-[(2S)-1,1,1-trifluoro-2-hydroxypropan-2-yl]-1H-pyrazol-1-yl}pyrimidin-4-yl)amino]-4-methyl-1H-pyrazol-3-yl}benzonitrile (Racemate)

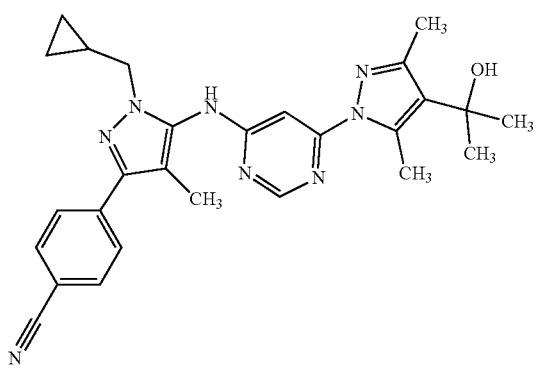 [SMILES: Cc1nn(-c2cc(Nc3c(C)c(-c4ccc(C#N)cc4)nn3CC3CC3)ncn2)c(C)c1C(C)(C)O]

Molecular Sieves (4 Å) were placed in a round-bottom flask and dried in a vacuum drying-oven overnight at 120° C. After cooling to ambient temperature, tetrabutylammonium fluoride trihydrate (132 mg, 472 µmol) and toluene (1.0 mL) were added and the suspension stirred for 30 min. A solution of 4-[5-{[6-(4-acetyl-3,5-dimethyl-1H-pyrazol-1-yl)pyrimidin-4-yl]amino}-1-(cyclopropylmethyl)-4-methyl-1H-pyrazol-3-yl]benzonitrile (55.0 mg, 118 µmol) in toluene (4.5 mL) was then added, the mixture was stirred for 5 min and cooled to 0° C. Trimethyl(trifluoromethyl)silane (100 µl, 710 µmol) was then added and stirred at ambient temperature for 3.5 h. A second aliquot of trimethyl(trifluoromethyl)silane (60 µl, 0.4 mmol) was added and the reaction mixture was stirred at ambient temperature overnight. The reaction mixture was diluted with ethyl acetate and water, the molecular sieves removed by filtration and washed further with ethyl acetate. After separation of the layers, the aqueous phase was extracted again with ethyl acetate and the combined organic phase were dried over sodium sulfate and concentrated. The residue was purified by preparative HPLC (column: Chromatorex C18; 125*30 mm, 10 µM, flow 75 mL/min, gradient acetonitrile/water 5/95 to 90/10) to yield the desired product (8 mg, 13% yield) along with a by-product ((±)-2-{1-[6-({3-[4-(2-amino-1,1,1,3,3,3-hexafluoropropan-2-yl)phenyl]-1-(cyclopropylmethyl)-4-methyl-1H-pyrazol-5-yl}amino)pyrimidin-4-yl]-3,5-dimethyl-1H-pyrazol-4-yl}-1,1,1-trifluoropropan-2-ol (racemate)).

LC-MS (method 11): $R_t$=1.41 min; MS (ESIpos): m/z=537 [M+H]$^+$ $^1$H-NMR (400 MHz, dimethylsulfoxide-d6) δ [ppm]: −0.149 (0.48), −0.023 (0.76), −0.008 (4.03), 0.146 (0.44), 0.306 (2.56), 0.317 (2.82), 0.433 (2.50), 0.453 (2.68), 0.853 (0.30), 0.918 (0.30), 0.936 (0.82), 0.954 (0.38), 1.209 (1.14), 1.234 (2.54), 1.764 (6.89), 2.061 (16.00), 2.272 (2.50), 2.327 (0.98), 2.366 (0.42), 2.670 (1.00), 2.710 (0.54), 2.747 (12.36), 3.860 (2.34), 3.878 (2.30), 5.754 (1.80), 6.437 (2.98), 7.881 (0.88), 7.903 (13.26), 8.487 (0.64), 9.493 (0.62).

Example 323 tert-butyl 3-[4-(5-{[6-(3,5-dimethyl-1H-pyrazol-1-yl)pyrimidin-4-yl]amino}-1,4-dimethyl-1H-pyrazol-3-yl)phenyl]azetidine-1-carboxylate

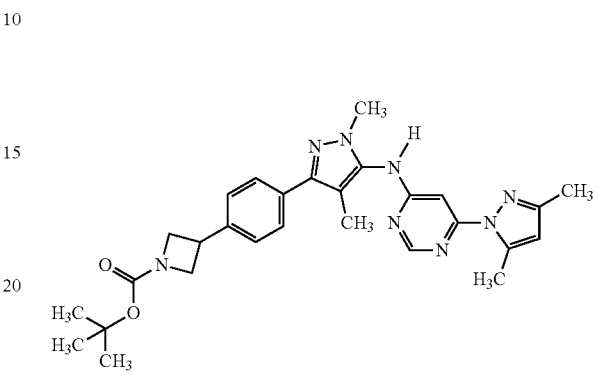

In a microwave vial, (30.7 mg, 27.4 µmol), N-[3-(4-bromophenyl)-1,4-dimethyl-1H-pyrazol-5-yl]-6-(3,5-dimethyl-1H-pyrazol-1-yl)pyrimidin-4-amine (120 mg, 274 µmol), and lithium hydroxide (19.7 mg, 821 µmol) were loaded. DME (5.5 mL) was then added.

The nickel pre-catalyst was then prepared in a second microwave vial. To this vial, nickel (II) chloride dimethoxyethane adduct (32.9 mg, 0.15 mmol) and 4,4'-di-tert-butyl-2,2'-bipyridine (48.3 mg, 0.18 mmol) were loaded and dissolved in DME (12 mL), placed under argon, sealed and sonicated for 5 minutes.

An aliquot of the nickel pre-catalyst solution just prepared (1.1 mL) was syringed into the vial containing the reactants. The solution was degassed a second time by sparging with argon while stirring for 10 minutes. Under a constant flow of argon, tert-butyl 3-bromoazetidine-1-carboxylate (220 µl, 1.4 mmol) and 1,1,1,3,3,3-hexamethyl-2-(trimethylsilyl)trisilane (250 µl, 820 µmol) were then added to the reaction mixture using a Hamilton syringe. The microwave vial was then sealed with Parafilm, stirred and irradiated with two 34 W blue LED lamps (3 cm away) for 15 h. The reaction mixture was concentrated and the residue dissolved in acetonitrile/water and purified by preparative HPLC (column: Chromatorex C18; 125*30 mm, 10 µM, flow 75 mL/min, gradient acetonitrile/water (containing 0.1% trifluoroacetic acid) 30/70 to 95/5) to yield the desired product (60 mg, 86% purity, 37% yield).

LC-MS (method 10): $R_t$=2.29 min; MS (ESIpos): m/z=515 [M+H]$^+$ $^1$H-NMR (400 MHz, dimethylsulfoxide-d6) δ [ppm]: −0.149 (0.20), −0.008 (1.57), 0.008 (1.69), 0.082 (0.66), 0.146 (0.28), 1.169 (0.21), 1.366 (0.34), 1.413 (16.00), 2.025 (4.55), 2.171 (1.11), 2.327 (0.34), 2.366 (0.30), 2.523 (0.88), 2.630 (4.10), 2.669 (0.38), 2.710 (0.31), 3.662 (3.05), 3.850 (0.73), 4.272 (0.49), 6.144 (0.81), 7.394 (0.98), 7.414 (1.14), 7.635 (0.23), 7.643 (0.20), 7.667 (0.89), 7.687 (0.71), 8.472 (0.26), 9.397 (0.59).

Example 324

N-[3-(4-cyclopropylphenyl)-1,4-dimethyl-1H-pyrazol-5-yl]-6-(3,5-dimethyl-1H-pyrazol-1-yl)pyrimidin-4-amine

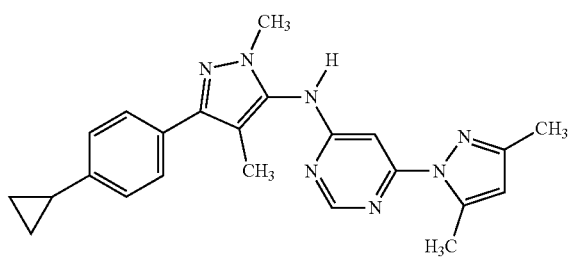 [SMILES: Cc1cc(C)n(-c2cc(Nc3c(C)c(-c4ccc(C5CC5)cc4)nn3C)ncn2)n1]

In a microwave vial, (30.7 mg, 27.4 µmol), N-[3-(4-bromophenyl)-1,4-dimethyl-1H-pyrazol-5-yl]-6-(3,5-dimethyl-1H-pyrazol-1-yl)pyrimidin-4-amine (120 mg, 274 µmol), and lithium hydroxide (19.7 mg, 821 µmol) were loaded. DME (5.5 mL) was then added.

The nickel pre-catalyst was then prepared in a second microwave vial. To this vial, nickel (II) chloride dimethoxyethane adduct (32.98 mg, 0.15 mmol, 0.25 equiv.) and 4,4'-di-tert-butyl-2,2'-bipyridine (48.30 mg, 0.18 mmol, 0.3 equiv.) were loaded and dissolved in DME (12 mL), placed under argon, sealed and sonicated for 5 minutes.

An aliquot of the nickel pre-catalyst solution just prepared (1.1 mL) was syringed into the vial containing the reactants. The solution was degassed a second time by sparging with argon while stirring for 10 minutes. Under a constant flow of argon, bromocyclopropane (110 µl, 1.4 mmol) and 1,1,1,3,3,3-hexamethyl-2-(trimethylsilyl)trisilane (204 mg, 821 µmol) were then added to the reaction mixture using a Hamilton syringe. The microwave vial was then sealed with Parafilm, stirred and irradiated with two 34 W blue LED lamps (3 cm away) for 15 hours. The reaction mixture was concentrated, the residue was dissolved in acetonitrile/water and purified by preparative HPLC (column: Chromatorex C18; 125*30 mm, 10 µM, flow 75 mL/min, gradient acetonitrile/water (containing 0.1% trifluoroacetic acid) 30/70 to 95/5) to yield the desired product (3.7 mg, 3% yield).

LC-MS (method 11): $R_t$=1.51 min; MS (ESIpos): m/z=400 [M+H]$^+$ $^1$H-NMR (400 MHz, dimethylsulfoxide-d6) δ [ppm]: −0.150 (1.49), −0.008 (11.36), 0.008 (13.32), 0.083 (6.78), 0.103 (5.12), 0.146 (2.80), 0.696 (2.80), 0.708 (2.86), 0.889 (1.55), 0.960 (2.50), 0.975 (2.62), 1.117 (1.72), 1.169 (2.86), 1.233 (1.55), 1.943 (1.25), 2.002 (14.45), 2.018 (2.20), 2.168 (4.58), 2.327 (2.91), 2.366 (2.26), 2.628 (16.00), 2.669 (2.86), 2.710 (2.20), 3.646 (9.99), 6.141 (3.27), 7.125 (3.81), 7.146 (3.93), 7.547 (2.97), 7.567 (2.74), 8.469 (1.25), 9.379 (2.02).

Example 325

(±)-2-cyclopropyl-1-[5-{[6-(3,5-dimethyl-1H-pyrazol-1-yl)pyrimidin-4-yl]amino}-3-(4-fluorophenyl)-4-methyl-1H-pyrazol-1-yl]propan-2-ol (Racemate)

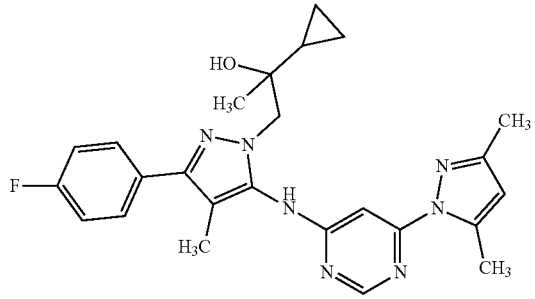 [SMILES: Cc1cc(C)n(-c2cc(Nc3c(C)c(-c4ccc(F)cc4)nn3CC(C)(O)C3CC3)ncn2)n1]

A microwave vial was charged with (2S)-1-[5-amino-3-(4-fluorophenyl)-4-methyl-1H-pyrazol-1-yl]-2-cyclopropylpropan-2-ol (39.0 mg, 135 µmol), 4-chloro-6-(3,5-dimethyl-1H-pyrazol-1-yl)pyrimidine (30.9 mg, 148 µmol) and sodium phenolate (17.2 mg, 148 µmol) and the contents were suspended in 1,4-dioxane (0.5 mL). The reaction mixture was degassed with Ar for 3 min. Tris(dibenzylideneacetone)dipalladium (2.47 mg, 2.70 µmol) and XantPhos (3.12 mg, 5.39 µmol) were added and the reaction mixture was degassed again for 1 min. The vial was sealed and heated at 85° C. overnight while vigorously shaking. After cooling to ambient temperature, the reaction mixture was filtered and concentrated. The residue was purified by flash column chromatography (SNAP Ultra 10 g, cyclohexane/ethyl acetate gradient 95/5 to 0/100) to yield the desired product (16 mg, 25% yield).

LC-MS (method 11): $R_t$=1.56 min; MS (ESIpos): m/z=462 [M+H]$^+$ $^1$H-NMR (400 MHz, dimethylsulfoxide-d6) δ [ppm]: 0.126 (1.01), 0.147 (0.97), 0.160 (0.85), 0.187 (1.20), 0.221 (2.77), 0.232 (2.90), 0.805 (0.80), 0.812 (0.85), 0.826 (1.37), 0.839 (0.75), 0.846 (0.71), 1.085 (14.07), 1.236 (0.43), 1.977 (0.41), 2.009 (16.00), 2.171 (5.84), 2.328 (0.84), 2.629 (15.59), 2.670 (1.07), 2.710 (0.47), 3.984 (2.86), 4.511 (0.91), 6.143 (3.57), 7.256 (2.30), 7.278 (4.83), 7.300 (2.77), 7.707 (2.05), 7.721 (2.61), 7.728 (2.61), 7.742 (2.16), 8.462 (1.29), 9.199 (2.98).

Example 326

(±)-N-[1-(cyclopropylmethyl)-3-(4-fluorophenyl)-4-methyl-1H-pyrazol-5-yl]-6-{4-[1-methoxyethyl]-3,5-dimethyl-1H-pyrazol-1-yl}pyrimidin-4-amine (Racemic)

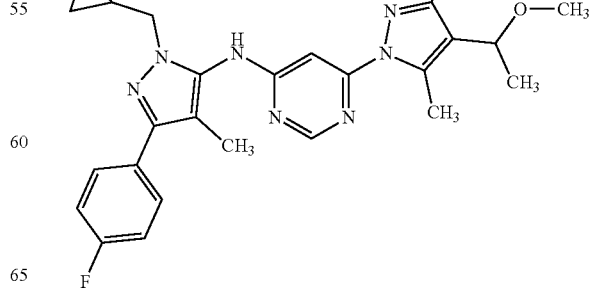

A solution of 1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanone (304 mg, 662 µmol) in methanol (12 ml, 290 mmol) was treated with sodium borohydride (12.5 mg, 331 µmol). The mixture was stirred 2 hours at ambient temperature. The mixture was treated with some drops of concentrated hydrochloric acid and stirred overnight at ambient temperature. The mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography on silica gel (column: SNAP KP-Sil 10 g, dichloromethane/ethyl acetate) to yield 102 mg (33%) of the desired product along with traces of the corresponding.

LC-MS (method 9): $R_t$=1.18 min; MS (ESIpos): m/z=476 [M+H]$^+$ $^1$H-NMR (400 MHz, dimethylsulfoxide-d6) δ [ppm]: 0.294 (2.78), 0.305 (2.99), 0.425 (2.71), 0.444 (2.83), 1.177 (0.87), 1.185 (0.72), 1.197 (1.10), 1.209 (0.70), 1.216 (0.70), 1.228 (0.40), 1.352 (5.16), 1.368 (5.19), 1.990 (0.73), 2.009 (14.58), 2.202 (3.29), 2.502 (10.92), 2.636 (16.00), 3.094 (12.53), 3.828 (2.51), 3.845 (2.52), 4.369 (0.47), 4.385 (1.46), 4.401 (1.47), 4.418 (0.51), 7.252 (1.94), 7.274 (4.09), 7.296 (2.29), 7.715 (1.58), 7.730 (2.18), 7.735 (2.22), 7.750 (1.69), 8.468 (0.70), 9.377 (0.83).

Example 327

N-[1-(cyclopropylmethyl)-3-(4-fluorophenyl)-4-methyl-1H-pyrazol-5-yl]-6-{4-[1-methoxyethyl]-3,5-dimethyl-1H-pyrazol-1-yl}pyrimidin-4-amine

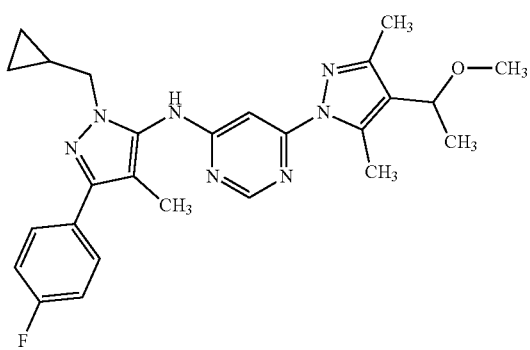 [SMILES: COC(C)c1c(C)nn(-c2cc(Nc3c(C)c(-c4ccc(F)cc4)nn3CC3CC3)ncn2)c1C]

A sample of racemic N-[1-(cyclopropylmethyl)-3-(4-fluorophenyl)-4-methyl-1H-pyrazol-5-yl]-6-{4-[1-methoxyethyl]-3,5-dimethyl-1H-pyrazol-1-yl}pyrimidin-4-amine (101.5 mg, 0.21 mmol) was separated using SFC chromatography (column: AD-H; 250*20 mm, 5 µM, flow 80 mL/min, 40° C., solvent 84% carbon dioxide/16% 2-propanol) to give 25.6 mg of the first eluting enantiomer of N-[1-(cyclopropylmethyl)-3-(4-fluorophenyl)-4-methyl-1H-pyrazol-5-yl]-6-{4-[1-methoxyethyl]-3,5-dimethyl-1H-pyrazol-1-yl}pyrimidin-4-amine (25% yield from racemate).

LC-MS (method 10): $R_t$=2.29 min; MS (ESIpos): m/z=476 [M+H]$^+$

Chiral HPLC (SFC, Daicel AD, Solvent: 80% carbon dioxide/20% 2-propanol) Rt=1.43 min, >99.5% enantiomeric excess.

$^1$H-NMR (400 MHz, dimethylsulfoxide-d6) δ [ppm]: −0.008 (1.06), 0.008 (1.10), 0.292 (2.17), 0.304 (2.40), 0.423 (2.20), 0.443 (2.34), 1.177 (0.59), 1.184 (0.58), 1.196 (0.92), 1.208 (0.56), 1.215 (0.57), 1.352 (4.33), 1.368 (4.39), 2.008 (13.51), 2.201 (2.58), 2.635 (16.00), 3.093 (11.64), 3.827 (2.21), 3.844 (1.99), 4.369 (0.41), 4.385 (1.29), 4.402 (1.28), 4.418 (0.41), 7.252 (2.01), 7.274 (4.12), 7.296 (2.24), 7.713 (1.43), 7.728 (1.81), 7.734 (1.78), 7.749 (1.32), 8.466 (0.59), 9.375 (0.64).

Example 328

N-[1-(cyclopropylmethyl)-3-(4-fluorophenyl)-4-methyl-1H-pyrazol-5-yl]-6-{4-[1-methoxyethyl]-3,5-dimethyl-1H-pyrazol-1-yl}pyrimidin-4-amine

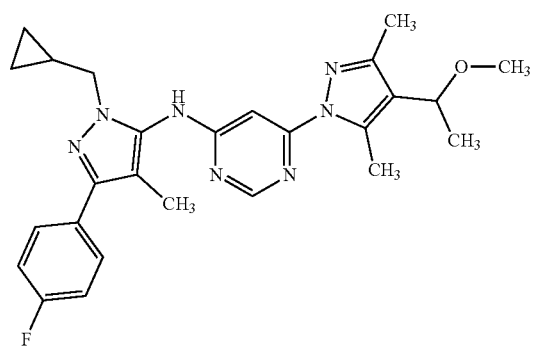 [SMILES: COC(C)c1c(C)nn(-c2cc(Nc3c(C)c(-c4ccc(F)cc4)nn3CC3CC3)ncn2)c1C]

A sample of racemic N-[1-(cyclopropylmethyl)-3-(4-fluorophenyl)-4-methyl-1H-pyrazol-5-yl]-6-{4-[1-methoxyethyl]-3,5-dimethyl-1H-pyrazol-1-yl}pyrimidin-4-amine (101.5 mg, 0.21 mmol) was separated using SFC chromatography (column: AD-H; 250*20 mm, 5 µM, flow 80 mL/min, 40° C., solvent 84% carbon dioxide/16% 2-propanol) to give 25.0 mg of the second eluting enantiomer of N-[1-(cyclopropylmethyl)-3-(4-fluorophenyl)-4-methyl-1H-pyrazol-5-yl]-6-{4-[1-methoxyethyl]-3,5-dimethyl-1H-pyrazol-1-yl}pyrimidin-4-amine (25% yield from racemate).

LC-MS (method 10): $R_t$=2.29 min; MS (ESIpos): m/z=476 [M+H]$^+$

Chiral HPLC (SFC, Daicel AD, Solvent: 80% carbon dioxide/20% 2-propanol) Rt=1.43 min, >98.1% enantiomeric excess.

$^1$H-NMR (400 MHz, dimethylsulfoxide-d6) δ [ppm]: −0.008 (0.91), 0.008 (1.00), 0.292 (2.27), 0.304 (2.49), 0.424 (2.26), 0.443 (2.42), 1.178 (0.60), 1.185 (0.61), 1.196 (0.96), 1.209 (0.60), 1.215 (0.59), 1.352 (4.42), 1.368 (4.47), 2.008 (13.57), 2.201 (2.74), 2.635 (16.00), 3.093 (11.77), 3.827 (2.10), 3.844 (2.09), 4.369 (0.42), 4.385 (1.31), 4.401 (1.31), 4.418 (0.43), 7.252 (2.02), 7.274 (4.19), 7.296 (2.27), 7.714 (1.45), 7.728 (1.90), 7.735 (1.87), 7.749 (1.41), 8.465 (0.67), 9.376 (0.68).

Example 329

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanol

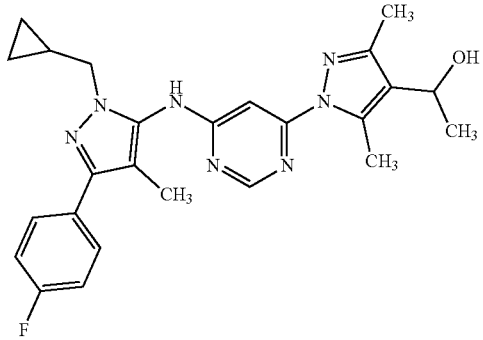 [SMILES: Cc1nn(-c2cc(Nc3c(C)c(-c4ccc(F)cc4)nn3CC3CC3)ncn2)c(C)c1C(C)O]

A sample of racemic 1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanol (100.4 mg, 0.18 mmol) was separated using SFC chromatography (column: AD-H; 250*20 mm, 5 µM, flow 80 mL/min, 40° C., solvent 84% carbon dioxide/16% 2-propanol) to give 8.5 mg of the first eluting enantiomer of 1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanol (9% yield from racemate) along with the methoxy derivative.

LC-MS (method 10): R$_t$=1.89 min; MS (ESIpos): m/z=462 [M+H]$^+$

Chiral HPLC (SFC, Daicel AD, Solvent: 80% carbon dioxide/20% 2-propanol) Rt=1.43 min, >99.5% enantiomeric excess.

$^1$H-NMR (400 MHz, dimethylsulfoxide-d6) δ [ppm]: −0.008 (1.66), 0.008 (1.47), 0.068 (0.69), 0.291 (2.28), 0.302 (2.49), 0.420 (2.24), 0.440 (2.37), 1.030 (1.08), 1.045 (1.07), 1.176 (0.63), 1.182 (0.61), 1.194 (0.94), 1.206 (0.59), 1.212 (0.59), 1.320 (4.52), 1.336 (4.57), 2.003 (13.84), 2.234 (2.83), 2.631 (16.00), 3.824 (2.24), 3.841 (2.22), 4.765 (0.76), 4.773 (0.84), 4.782 (0.79), 4.789 (0.82), 4.908 (2.01), 4.916 (1.89), 7.251 (1.99), 7.273 (4.25), 7.295 (2.34), 7.712 (1.44), 7.726 (1.89), 7.732 (1.90), 7.747 (1.47), 8.453 (0.71), 9.349 (0.68).

Example 330

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanol

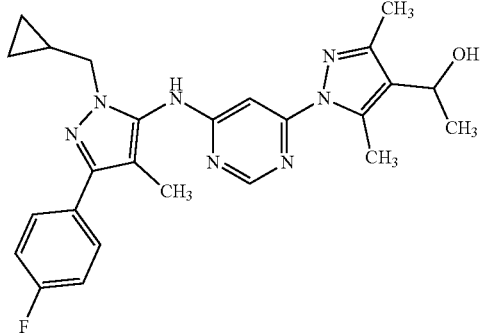 [SMILES: Cc1nn(-c2cc(Nc3c(C)c(-c4ccc(F)cc4)nn3CC3CC3)ncn2)c(C)c1C(C)O]

A sample of racemic 1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanol (100.4 mg, 0.18 mmol) was separated using SFC chromatography (column: AD-H; 250*20 mm, 5 µM, flow 80 mL/min, 40° C., solvent 84% carbon dioxide/16% 2-propanol) to give 9.4 mg of the second eluting enantiomer of 1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanol (9% yield from racemate) along with the methoxy derivative.

LC-MS (method 10): R$_t$=1.89 min; MS (ESIpos): m/z=462 [M+H]$^+$

Chiral HPLC (SFC, Daicel AD, Solvent: 80% carbon dioxide/20% 2-propanol) Rt=1.43 min, >99.5% enantiomeric excess.

$^1$H-NMR (400 MHz, dimethylsulfoxide-d6) δ [ppm]: −0.008 (0.98), 0.008 (0.90), 0.290 (2.30), 0.302 (2.53), 0.420 (2.28), 0.440 (2.42), 1.030 (0.67), 1.045 (0.68), 1.175 (0.64), 1.182 (0.61), 1.194 (0.94), 1.206 (0.58), 1.213 (0.59), 1.320 (4.69), 1.336 (4.74), 2.004 (14.03), 2.234 (2.87), 2.632 (16.00), 3.824 (2.29), 3.841 (2.24), 4.765 (0.78), 4.773 (0.87), 4.782 (0.82), 4.789 (0.83), 4.909 (2.05), 4.916 (1.91), 7.251 (2.06), 7.273 (4.22), 7.295 (2.29), 7.712 (1.48), 7.726 (1.90), 7.732 (1.84), 7.747 (1.40), 8.453 (0.69), 9.347 (0.71).

Example 331

(±)-4-{1-(cyclopropylmethyl)-5-[(6-{4-[(1S)-1-hydroxyethyl]-3,5-dimethyl-1H-pyrazol-1-yl}pyrimidin-4-yl)amino]-4-methoxy-1H-pyrazol-3-yl}benzonitrile (Racemic)

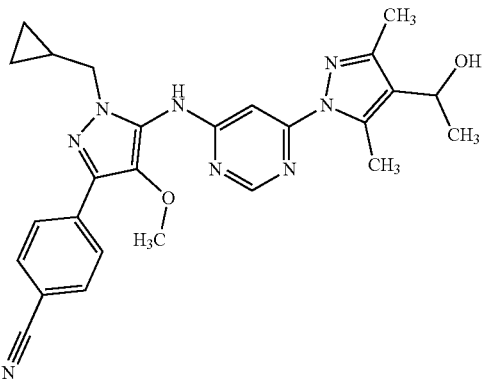 [SMILES: COc1c(-c2ccc(C#N)cc2)nn(CC2CC2)c1Nc1cc(-n2nc(C)c(C(C)O)c2C)ncn1]

A solution of 4-[5-{[6-(4-acetyl-3,5-dimethyl-1H-pyrazol-1-yl)pyrimidin-4-yl]amino}-1-(cyclopropylmethyl)-4-methoxy-1H-pyrazol-3-yl]benzonitrile (144 mg, 298 µmol) in methanol (5.3 ml, 130 mmol) was treated with sodium borohydride (11.3 mg, 298 µmol). The mixture was stirred at ambient temperature overnight. The mixture was diluted with water, dichloromethane and filtered over Extrelut NT3. The filtrate was concentrated under reduced pressure to yield 136 mg (93%) of the desired product.

LC-MS (method 10): R$_t$=1.87 min; MS (ESIpos): m/z=485 [M+H]$^+$ $^1$H-NMR (400 MHz, dimethylsulfoxide-d6) δ [ppm]: 0.300 (0.50), 0.312 (2.08), 0.315 (1.88), 0.326 (2.20), 0.338 (0.73), 0.441 (0.69), 0.451 (1.70), 0.455 (1.73), 0.461 (1.03), 0.471 (1.86), 0.475 (1.69), 0.486 (0.53), 1.074 (1.60), 1.091

(3.26), 1.109 (1.65), 1.191 (0.45), 1.199 (0.45), 1.211 (0.70), 1.223 (0.43), 1.230 (0.47), 1.322 (4.24), 1.338 (4.28), 2.238 (3.05), 2.637 (12.13), 3.357 (0.58), 3.375 (1.64), 3.392 (1.61), 3.410 (0.53), 3.725 (16.00), 3.798 (1.84), 3.815 (1.82), 4.770 (0.66), 4.777 (0.72), 4.786 (0.68), 4.794 (0.70), 4.917 (1.73), 4.924 (1.61), 7.876 (2.99), 7.898 (3.86), 8.046 (3.51), 8.067 (2.71), 8.478 (1.02), 9.464 (0.53).

Example 332

4-{1-(cyclopropylmethyl)-5-[(6-{4-[1-hydroxyethyl]-3,5-dimethyl-1H-pyrazol-1-yl}pyrimidin-4-yl)amino]-4-methoxy-1H-pyrazol-3-yl}benzonitrile

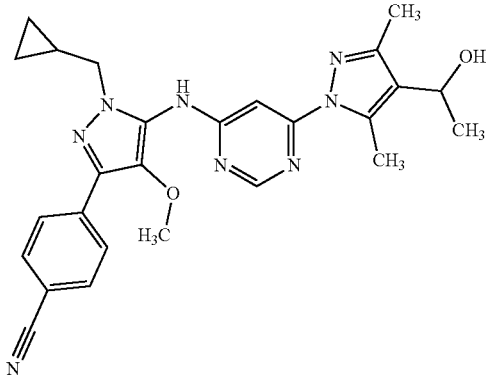 [SMILES: COc1c(-c2ccc(C#N)cc2)nn(CC2CC2)c1Nc1cc(-n2nc(C)c(C(C)O)c2C)ncn1]

A sample of racemic 4-{1-(cyclopropylmethyl)-5-[(6-{4-[1-hydroxyethyl]-3,5-dimethyl-1H-pyrazol-1-yl}pyrimidin-4-yl)amino]-4-methoxy-1H-pyrazol-3-yl}benzonitrile (102 mg, 0.21 mmol) was separated using SFC chromatography (column: AD-H; 250*20 mm, 5 µM, flow 80 mL/min, 40° C., solvent 78% carbon dioxide/22% 2-propanol) to give 27.6 mg of the second eluting enantiomer of 4-{1-(cyclopropylmethyl)-5-[(6-{4-[1-hydroxyethyl]-3,5-dimethyl-1H-pyrazol-1-yl}pyrimidin-4-yl)amino]-4-methoxy-1H-pyrazol-3-yl}benzonitrile (27% yield from racemate) along with the first eluting enantiomer (34.2 mg).

LC-MS (method 9): $R_t$=0.95 min; MS (ESIpos): m/z=485 [M+H]$^+$

Chiral HPLC (SFC, Daicel AD-3, Solvent: 80% carbon dioxide/20% 2-propanol) Rt=1.43 min, >99.5% enantiomeric excess.

$^1$H-NMR (400 MHz, dimethylsulfoxide-d6) δ [ppm]: −0.008 (1.16), 0.008 (1.19), 0.299 (0.51), 0.311 (2.12), 0.314 (1.90), 0.325 (2.25), 0.337 (0.72), 0.440 (0.69), 0.450 (1.73), 0.454 (1.75), 0.460 (1.01), 0.470 (1.88), 0.474 (1.70), 0.486 (0.53), 1.190 (0.45), 1.197 (0.43), 1.209 (0.70), 1.221 (0.41), 1.228 (0.44), 1.321 (4.32), 1.337 (4.36), 2.237 (3.05), 2.524 (0.54), 2.636 (12.36), 3.723 (16.00), 3.796 (1.88), 3.814 (1.86), 4.769 (0.68), 4.776 (0.74), 4.785 (0.69), 4.793 (0.72), 4.915 (1.80), 4.923 (1.66), 7.877 (2.87), 7.898 (3.88), 8.044 (3.48), 8.066 (2.75), 8.477 (0.97), 9.460 (0.81).

Example 333

(±)-4-{1-(cyclopropylmethyl)-4-methoxy-5-[(6-{4-[1-methoxyethyl]-3,5-dimethyl-1H-pyrazol-1-yl}pyrimidin-4-yl)amino]-1H-pyrazol-3-yl}benzonitrile (Racemic)

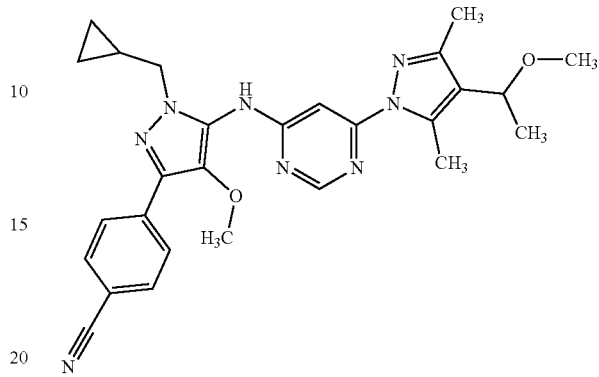

A solution of 4-{1-(cyclopropylmethyl)-5-[(6-{4-[1-hydroxyethyl]-3,5-dimethyl-1H-pyrazol-1-yl}pyrimidin-4-yl)amino]-4-methoxy-1H-pyrazol-3-yl}benzonitrile (113 mg, 233 µmol) in methanol (5.0 ml, 120 mmol) and trifluoroacetic acid (500 µl, 6.5 mmol) was stirred at ambient temperature overnight. The mixture was concentrated and purified by flash-chromatography on silica gel (column: SNAP KP-Sil 10 g, solvent: 92% dichloromethane/8% ethyl acetate to 66% ethyl acetate) to yield 78.1 mg (67%) of the desired product.

LC-MS (method 10): $R_t$=2.22 min; MS (ESIpos): m/z=499 [M+H]$^+$ $^1$H-NMR (400 MHz, dimethylsulfoxide-d6) δ [ppm]: 0.301 (0.69), 0.313 (2.85), 0.327 (3.08), 0.338 (0.95), 0.442 (0.92), 0.453 (2.37), 0.457 (2.38), 0.462 (1.39), 0.473 (2.57), 0.476 (2.34), 0.488 (0.70), 1.192 (0.66), 1.199 (0.63), 1.211 (0.98), 1.223 (0.60), 1.230 (0.66), 1.353 (5.51), 1.370 (5.55), 2.204 (3.92), 2.640 (16.00), 3.095 (15.00), 3.683 (0.53), 3.799 (2.60), 3.816 (2.53), 4.373 (0.48), 4.389 (1.58), 4.406 (1.56), 4.422 (0.47), 7.877 (4.12), 7.898 (5.25), 8.046 (4.87), 8.067 (3.76), 8.491 (1.44), 9.492 (1.05).

Example 334

4-{1-(cyclopropylmethyl)-4-methoxy-5-[(6-{4-[1-methoxyethyl]-3,5-dimethyl-1H-pyrazol-1-yl}pyrimidin-4-yl)amino]-1H-pyrazol-3-yl}benzonitrile

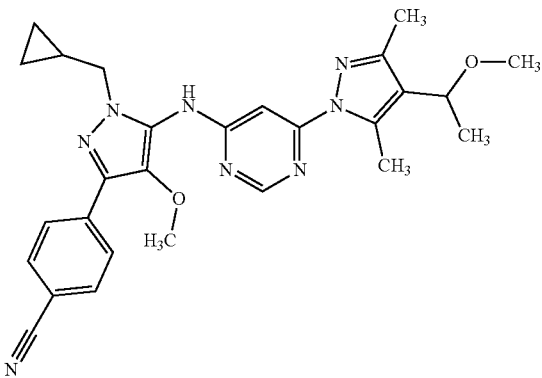 [SMILES: COc1c(-c2ccc(C#N)cc2)nn(CC2CC2)c1Nc1cc(-n2nc(C)c(C(C)OC)c2C)ncn1]

A sample of racemic 4-{1-(cyclopropylmethyl)-4-methoxy-5-[(6-{4-[1-methoxyethyl]-3,5-dimethyl-1H-pyrazol-1-yl}pyrimidin-4-yl)amino]-1H-pyrazol-3-yl}benzonitrile (62 mg, 0.16 mmol) was separated using preparative HPLC (column: 250*20 mm Daicel Chiralcel OJ-H, 5 μM, flow 15 mL/min, 40° C., solvent 85% n-Heptan/15% ethanol) to give 27.0 mg of the first eluting enantiomer of 4-{1-(cyclopropylmethyl)-4-methoxy-5-[(6-{4-[1-methoxyethyl]-3,5-dimethyl-1H-pyrazol-1-yl}pyrimidin-4-yl)amino]-1H-pyrazol-3-yl}benzonitrile (44% yield from racemate).

LC-MS (method 10): $R_t$=2.21 min; MS (ESIpos): m/z=499 [M+H]$^+$

Chiral HPLC (Daicel Chiralcel OJ-H, 5 μM, flow 1 mL/min, solvent: 85% 2-propanol/15% ethanol) Rt=4.8 min, >98% enantiomeric excess.

$^1$H-NMR (400 MHz, dimethylsulfoxide-d6) δ [ppm]: −0.008 (0.48), 0.301 (0.66), 0.313 (2.38), 0.327 (2.44), 0.338 (0.76), 0.442 (0.86), 0.453 (1.98), 0.457 (1.97), 0.462 (1.18), 0.473 (2.07), 0.477 (1.86), 0.488 (0.57), 1.003 (0.97), 1.021 (1.94), 1.039 (0.98), 1.192 (0.56), 1.199 (0.54), 1.211 (0.81), 1.223 (0.50), 1.230 (0.56), 1.353 (4.69), 1.370 (4.61), 1.892 (2.54), 2.204 (3.21), 2.524 (0.75), 2.581 (0.84), 2.599 (0.87), 2.617 (0.53), 2.640 (12.95), 3.095 (12.17), 3.728 (16.00), 3.799 (2.03), 3.816 (1.92), 4.373 (0.44), 4.389 (1.35), 4.406 (1.31), 7.877 (3.12), 7.898 (3.97), 8.046 (3.72), 8.067 (2.85), 8.491 (0.96).

Example 335

4-{1-(cyclopropylmethyl)-4-methoxy-5-[(6-{4-[(1S)-1-methoxyethyl]-3,5-dimethyl-1H-pyrazol-1-yl}pyrimidin-4-yl)amino]-1H-pyrazol-3-yl}benzonitrile

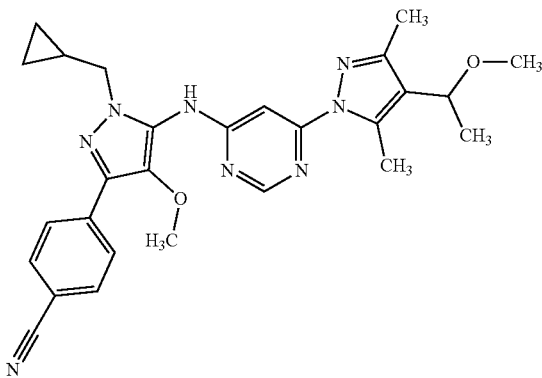 [SMILES: COc1c(-c2ccc(C#N)cc2)nn(CC2CC2)c1Nc1cc(-n2nc(C)c(C(C)OC)c2C)ncn1]

A sample of racemic 4-{1-(cyclopropylmethyl)-4-methoxy-5-[(6-{4-[1-methoxyethyl]-3,5-dimethyl-1H-pyrazol-1-yl}pyrimidin-4-yl)amino]-1H-pyrazol-3-yl}benzonitrile (62 mg, 0.16 mmol) was separated using preparative HPLC (column: 250*20 mm Daicel Chiralcel OJ-H, 5 μM, flow 15 mL/min, 40° C., solvent 85% n-Heptan/15% ethanol) to give 24.0 mg of the second eluting enantiomer of 4-{1-(cyclopropylmethyl)-4-methoxy-5-[(6-{4-[1-methoxyethyl]-3,5-dimethyl-1H-pyrazol-1-yl}pyrimidin-4-yl)amino]-1H-pyrazol-3-yl}benzonitrile (39% yield from racemate).

LC-MS (method 10): $R_t$=2.21 min; MS (ESIpos): m/z=499 [M+H]$^+$

Chiral HPLC (Daicel Chiralcel OJ-H, 5 μM, flow 1 mL/min, solvent: 85% 2-propanol/15% ethanol) Rt=5.3 min, >98% enantiomeric excess.

$^1$H-NMR (400 MHz, dimethylsulfoxide-d6) δ [ppm]: 0.300 (0.46), 0.312 (1.97), 0.327 (2.13), 0.338 (0.69), 0.442 (0.65), 0.453 (1.63), 0.457 (1.63), 0.462 (0.92), 0.473 (1.78), 0.477 (1.63), 0.489 (0.52), 1.192 (0.46), 1.199 (0.43), 1.211 (0.69), 1.223 (0.43), 1.231 (0.45), 1.353 (4.04), 1.370 (4.12), 2.204 (2.79), 2.640 (12.17), 3.095 (11.56), 3.728 (16.00), 3.799 (1.66), 3.816 (1.64), 4.389 (1.19), 4.406 (1.17), 7.877 (3.05), 7.898 (3.96), 8.046 (3.58), 8.067 (2.76), 8.491 (1.08), 9.489 (0.62).

Example 336

(±)-1-[1-(6-{[1-(cyclopropylmethyl)-3-(4-fluorophenyl)-4-methoxy-1H-pyrazol-5-yl]amino}pyrimidin-4-yl)-3,5-dimethyl-1H-pyrazol-4-yl]ethanol (Racemate)

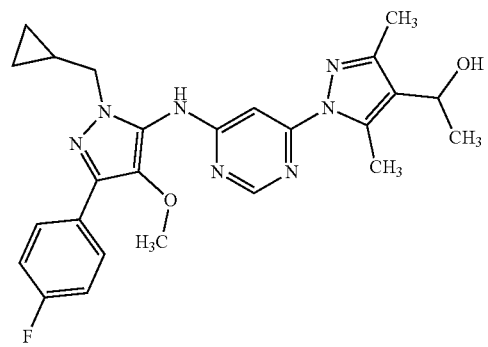 [SMILES: COc1c(-c2ccc(F)cc2)nn(CC2CC2)c1Nc1cc(-n2nc(C)c(C(C)O)c2C)ncn1]

A solution of 1-[1-(6-{[1-(cyclopropylmethyl)-3-(4-fluorophenyl)-4-methoxy-1H-pyrazol-5-yl]amino}pyrimidin-4-yl)-3,5-dimethyl-1H-pyrazol-4-yl]ethanone (139 mg, 292 μmol) in methanol (5.0 ml, 120 mmol) was treated with sodium borohydride (11.0 mg, 292 μmol) and stirred 30 minutes at room temperature. The mixture was diluted with water, dichloromethane and filtered over Extrelut NT3. The filtrate was concentrated to yield 133 mg (93%) of the desired product.

LC-MS (method 10): $R_t$=1.95 min; MS (ESIpos): m/z=478 [M+H]$^+$ $^1$H-NMR (400 MHz, dimethylsulfoxide-d6) δ [ppm]: 0.286 (0.55), 0.298 (2.45), 0.311 (2.64), 0.324 (0.79), 0.429 (0.73), 0.439 (2.01), 0.443 (1.93), 0.448 (1.10), 0.459 (2.15), 0.475 (0.56), 1.074 (1.09), 1.091 (2.21), 1.109 (1.12), 1.178 (0.55), 1.186 (0.51), 1.197 (0.78), 1.209 (0.48), 1.216 (0.51), 1.321 (4.78), 1.337 (4.82), 2.234 (3.66), 2.637 (13.01), 3.375 (1.08), 3.392 (1.06), 3.680 (16.00), 3.764 (2.22), 3.781 (2.18), 4.768 (0.75), 4.776 (0.82), 4.784 (0.77), 4.792 (0.78), 4.913 (1.93), 4.920 (1.76), 7.243 (1.64), 7.265 (3.29), 7.287 (1.72), 7.881 (1.65), 7.896 (1.96), 7.903 (1.86), 7.917 (1.53), 8.475 (1.13), 9.414 (0.74).

Example 337

4-(5-{[6-(4-acetyl-3,5-dimethyl-1H-pyrazol-1-yl)pyrimidin-4-yl]amino}-1,4-dimethyl-1H-pyrazol-3-yl)benzonitrile

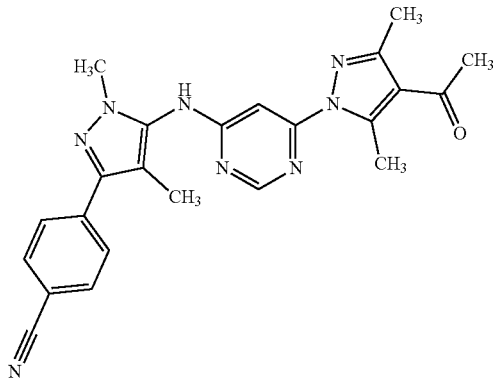 [SMILES: CC(=O)c1c(C)nn(-c2cc(Nc3c(C)c(-c4ccc(C#N)cc4)nn3C)ncn2)c1C]

A microwave vial was charged 1-[1-(6-chloropyrimidin-4-yl)-3,5-dimethyl-1H-pyrazol-4-yl]ethanone (250 mg, 997 μmol) and 4-(5-amino-1,4-dimethyl-1H-pyrazol-3-yl)benzonitrile (233 mg, 1.10 mmol) and the contents were suspended in 1,4-dioxane (4.0 ml, 47 mmol). The reaction mixture was degassed with Ar for 3 min. Tris(dibenzylidenaceton)dipalladium (27.4 mg, 29.9 μmol) and Xantphos (34.6 mg, 59.8 μmol) were added and the reaction mixture was degassed again for 1 min and heated to 85° C. At this temperature and sodium phenolate (127 mg, 1.10 mmol) was added. The vial was sealed and heated at 85° C. for 90 minutes while vigorously stirring. After cooling to ambient temperature, the reaction mixture was diluted with 1.0 M hydrochloric acid and ethyl acetate. The aqueous phase was extracted with ethyl acetate. The combined organic phases were washed with water, brine and dried over sodium sulfate and concentrated under reduced pressure. The crude product was suspended in acetonitrile, the crystalline material was collect by filtration and dried to yield 280 mg (62%) of the desired product.

LC-MS (method 10): $R_t$=1.73 min; MS (ESIpos): m/z=427 [M+H]$^+$ $^1$H-NMR (400 MHz, dimethylsulfoxide-d6) δ [ppm]: 2.082 (14.13), 2.469 (10.11), 2.891 (11.15), 2.907 (0.98), 3.377 (1.43), 3.571 (1.01), 7.895 (16.00), 8.553 (0.72), 9.653 (1.19).

Example 338

(±)-4-{5-[(6-{4-[1-methoxyethyl]-3,5-dimethyl-1H-pyrazol-1-yl}pyrimidin-4-yl)amino]-1,4-dimethyl-1H-pyrazol-3-yl}benzonitrile

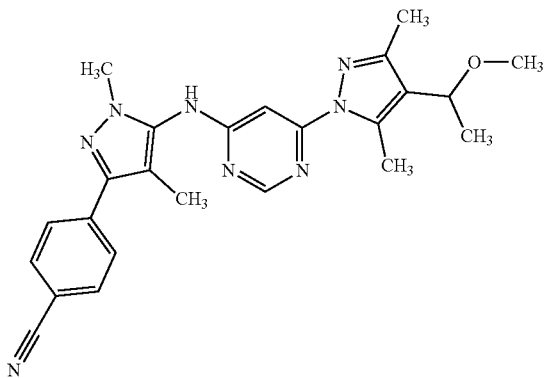 [SMILES: COC(C)c1c(C)nn(-c2cc(Nc3c(C)c(-c4ccc(C#N)cc4)nn3C)ncn2)c1C]

A solution of 4-(5-{[6-(4-acetyl-3,5-dimethyl-H-pyrazol-1-yl)pyrimidin-4-yl]amino}-1,4-dimethyl-1H-pyrazol-3-yl)benzonitrile (200 mg, 469 μmol) in methanol (8.3 ml, 210 mmol) was treated with sodium borohydride (8.87 mg, 234 μmol) and stirred 2 hours at room temperature. Conversion to the alcohol was observed. Some drops hydrochloric acid were added and the mixture was stirred overnight. The mixture was purified by preparative HPLC (method: column: Reprosil C18; 10 μm; 125×30 mm/flow: 50 mL/min/ solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 71.1 mg (34%) of the desired product.

LC-MS (method 9): $R_t$=1.06 min; MS (ESIpos): m/z=443 [M+H]$^+$ $^1$H-NMR (400 MHz, dimethylsulfoxide-d6) δ [ppm]: −0.008 (1.19), 0.008 (1.18), 1.356 (4.54), 1.373 (4.59), 2.072 (13.08), 2.210 (3.28), 2.636 (13.65), 3.096 (11.84), 3.694 (9.23), 4.389 (1.37), 4.406 (1.34), 4.422 (0.40), 7.896 (16.00), 8.474 (0.79), 9.464 (2.05).

Example 339

4-{5-[(6-{4-[1-methoxyethyl]-3,5-dimethyl-1H-pyrazol-1-yl}pyrimidin-4-yl)amino]-1,4-dimethyl-1H-pyrazol-3-yl}benzonitrile

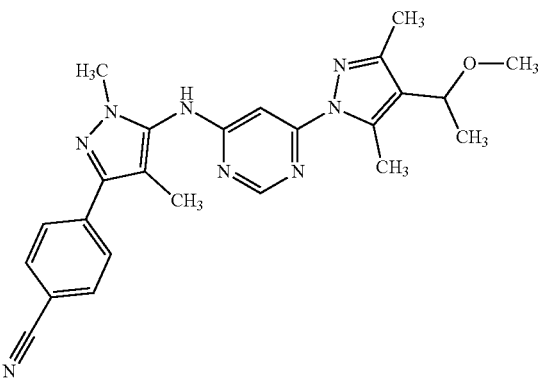 [SMILES: COC(C)c1c(C)nn(-c2cc(Nc3c(C)c(-c4ccc(C#N)cc4)nn3C)ncn2)c1C]

A sample of racemic 4-{5-[(6-{4-[1-methoxyethyl]-3,5-dimethyl-1H-pyrazol-1-yl}pyrimidin-4-yl)amino]-1,4-dimethyl-1H-pyrazol-3-yl}benzonitrile (58 mg, 0.13 mmol) was separated using preparative SFC (column: 250*20 mm AD-H, 5 μM, flow 80 mL/min, 40° C., solvent 85% carbon dioxide/15% methanol) to give 17.1 mg of the first eluting enantiomer of 4-{5-[(6-{4-[1-methoxyethyl]-3,5-dimethyl-1H-pyrazol-1-yl}pyrimidin-4-yl)amino]-1,4-dimethyl-1H-pyrazol-3-yl}benzonitrile (29% yield from racemate).

LC-MS (method 9): $R_t$=1.06 min; MS (ESIpos): m/z=443 [M+H]$^+$

Chiral HPLC (SFC, Daicel A, 5 μM, flow 3 mL/min, solvent: 85% carbon dioxide/15% iso-propanol) Rt=3.0 min, >99.5% enantiomeric excess.

$^1$H-NMR (400 MHz, dimethylsulfoxide-d6) δ [ppm]: 1.357 (4.31), 1.373 (4.36), 2.073 (12.69), 2.211 (3.21), 2.636 (13.48), 3.097 (11.65), 3.695 (9.08), 4.390 (1.30), 4.407 (1.29), 7.897 (16.00), 8.476 (0.90), 9.465 (1.99).

Example 340

4-{5-[(6-{4-[1-methoxyethyl]-3,5-dimethyl-1H-pyrazol-1-yl}pyrimidin-4-yl)amino]-1,4-dimethyl-1H-pyrazol-3-yl}benzonitrile

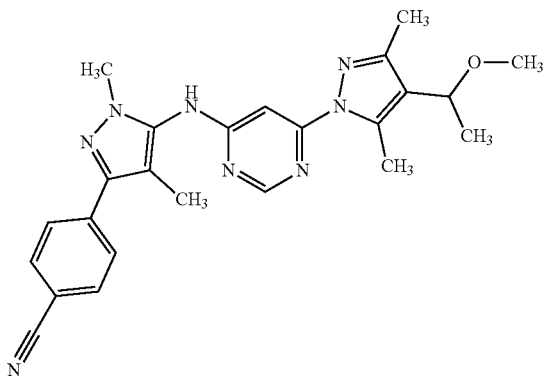 [SMILES: COC(C)c1c(C)nn(-c2cc(Nc3c(C)c(-c4ccc(C#N)cc4)nn3C)ncn2)c1C]

A sample of racemic 4-{5-[(6-{4-[1-methoxyethyl]-3,5-dimethyl-1H-pyrazol-1-yl}pyrimidin-4-yl)amino]-1,4-dimethyl-1H-pyrazol-3-yl}benzonitrile (58 mg, 0.13 mmol) was separated using preparative SFC (column: 250*20 mm AD-H, 5 µM, flow 80 mL/min, 40° C., solvent 85% carbon dioxide/15% methanol) to give 16.7 mg of the second eluting enantiomer of 4-{5-[(6-{4-[1-methoxyethyl]-3,5-dimethyl-1H-pyrazol-1-yl}pyrimidin-4-yl)amino]-1,4-dimethyl-1H-pyrazol-3-yl}benzonitrile (29% yield from racemate).

LC-MS (method 9): $R_t$=1.06 min; MS (ESIpos): m/z=443 [M+H]$^+$

Chiral HPLC (SFC, Daicel AD, 5 µM, flow 3 mL/min, solvent: 85% carbon dioxide/15% iso-propanol) Rt=3.6 min, >99.5% enantiomeric excess.

$^1$H-NMR (400 MHz, dimethylsulfoxide-d6) δ [ppm]: 1.357 (4.32), 1.373 (4.35), 2.073 (12.85), 2.210 (3.08), 2.636 (13.65), 3.097 (11.71), 3.696 (9.03), 4.390 (1.31), 4.406 (1.29), 7.897 (16.00), 8.475 (0.83), 9.465 (1.94).

Example 341

(±)-4-{1-(cyclopropylmethyl)-5-[(6-{4-[1-hydroxyethyl]-3,5-dimethyl-1H-pyrazol-1-yl}pyrimidin-4-yl)amino]-4-methyl-1H-pyrazol-3-yl}benzonitrile (Racemate)

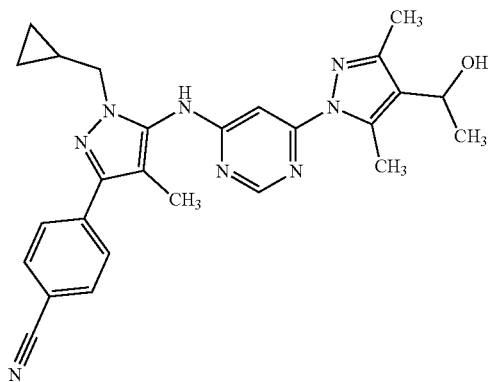 [SMILES: Cc1nn(-c2cc(Nc3c(C)c(-c4ccc(C#N)cc4)nn3CC3CC3)ncn2)c(C)c1C(C)O]

A solution of 4-[5-{[6-(4-acetyl-3,5-dimethyl-1H-pyrazol-1-yl)pyrimidin-4-yl]amino}-1-(cyclopropylmethyl)-4-methyl-1H-pyrazol-3-yl]benzonitrile (293 mg, 628 µmol) in methanol was treated with sodium borohydride (11.9 mg, 314 µmol) and stirred 39 minutes at ambient temperature. Complete conversion to the alcohol was observed. Some drops of hydrochloric acid were added and the mixture was left overnight. The mixture was diluted with water and extracted with ethyl acetate. The organic phases were dried over Extrelut NT3. The crude product was purified by flash-chromatography (column: Biotage SNAP KP-Sil 10 g, solvent: 90% dichloromethane/10% ethyl acetate to 88% dichloromethane/12% ethylacetate to 100% ethyl acetate) to yield 81.6 mg (28%) of the desired product.

LC-MS (method 10): $R_t$=1.81 min; MS (ESIpos): m/z=469 [M+H]$^+$ $^1$H-NMR (400 MHz, dimethylsulfoxide-d6) δ [ppm]: 0.305 (2.36), 0.316 (2.61), 0.431 (2.29), 0.451 (2.41), 1.073 (1.11), 1.091 (2.29), 1.109 (1.14), 1.177 (0.39), 1.189 (0.65), 1.207 (0.97), 1.226 (0.64), 1.322 (4.85), 1.338 (4.90), 1.365 (0.53), 2.059 (14.27), 2.238 (2.98), 2.314 (1.02), 2.367 (0.19), 2.632 (16.00), 2.670 (0.24), 2.696 (0.99), 2.710 (0.20), 3.357 (0.47), 3.375 (1.15), 3.392 (1.14), 3.409 (0.38), 3.859 (2.31), 3.877 (2.26), 4.771 (1.04), 4.787 (1.07), 4.914 (0.99), 7.885 (0.79), 7.906 (11.26), 7.931 (0.84), 8.451 (0.83), 9.395 (0.87).

Example 342

(±)-4-{1-(cyclopropylmethyl)-5-[(6-{4-[1-ethoxyethyl]-3,5-dimethyl-1H-pyrazol-1-yl}pyrimidin-4-yl)amino]-4-methyl-1H-pyrazol-3-yl}benzonitrile

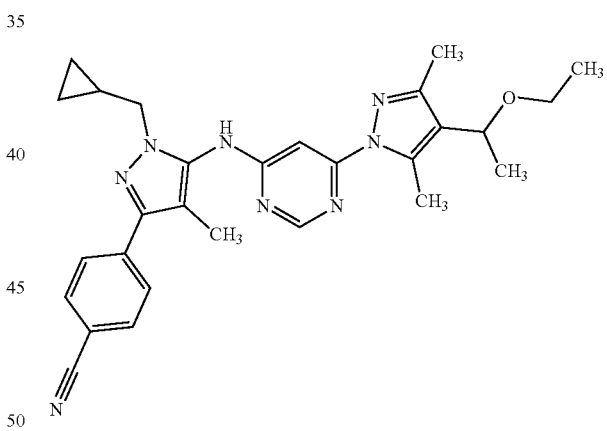

A sample of racemic 4-{1-(cyclopropylmethyl)-5-[(6-{4-[1-hydroxyethyl]-3,5-dimethyl-1H-pyrazol-1-yl}pyrimidin-4-yl)amino]-4-methyl-1H-pyrazol-3-yl}benzonitrile (62 mg, 132 µmol) were submitted for chiral separation (column: 250*20 mm Daicel Chiralcel OJ-H-, 5 µM, flow 15 mL/min, 70° C., solvent 85% n-heptane/15% ethanol). Instead of the desired enantiomers 24.0 mg of the described product were obtained.

LC-MS (method 9): $R_t$=1.23 min; MS (ESIpos): m/z=497 [M+H]$^+$ $^1$H-NMR (400 MHz, dimethylsulfoxide-d6) δ [ppm]: 0.306 (2.70), 0.317 (2.92), 0.434 (2.62), 0.453 (2.78), 1.062 (3.39), 1.079 (6.92), 1.097 (3.51), 1.178 (0.46), 1.190 (0.75), 1.196 (0.73), 1.208 (1.09), 1.220 (0.71), 1.227 (0.73), 1.346 (5.06), 1.363 (5.09), 2.062 (14.99), 2.211 (3.16), 2.632 (16.00), 3.206 (0.59), 3.227 (1.16), 3.245 (1.37), 3.263

(1.48), 3.280 (1.31), 3.861 (2.43), 3.878 (2.37), 4.472 (0.48), 4.488 (1.42), 4.505 (1.41), 4.521 (0.46), 7.886 (1.00), 7.907 (11.28), 7.933 (0.88), 8.461 (0.85), 9.422 (0.93).

Example 343

(±)-N-[5-(4-fluorophenyl)-1,4-dimethyl-1H-pyrazol-3-yl]-6-{4-[1-methoxyethyl]-3,5-dimethyl-1H-pyrazol-1-yl}pyrimidin-4-amine (Racemate)

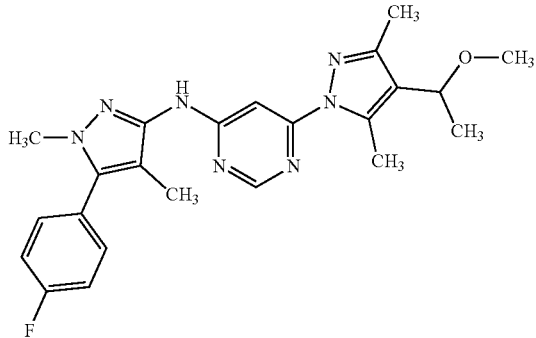 [SMILES: COC(C)c1c(C)nn(-c2cc(Nc3nn(C)c(-c4ccc(F)cc4)c3C)ncn2)c1C]

A solution of 1-[1-(6-{[5-(4-fluorophenyl)-1,4-dimethyl-1H-pyrazol-3-yl]amino}pyrimidin-4-yl)-3,5-dimethyl-1H-pyrazol-4-yl]ethanone (130 mg, 310 μmol) in methanol (5.5 ml, 140 mmol) was treated with sodium borohydride (5.86 mg, 155 μmol) and stirred 2 hours at room temperature. Complete conversion to the alcohol was observed. Some drops hydrochloric acid were added and the mixture was left overnight. The mixture was purified using preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 60.1 mg (45%) of the desired product.

LC-MS (method 9): $R_t$=1.11 min; MS (ESIpos): m/z=436 [M+H]$^+$ $^1$H-NMR (400 MHz, dimethylsulfoxide-d6) δ [ppm]: 1.361 (6.20), 1.378 (6.26), 1.852 (11.72), 2.216 (12.59), 2.622 (13.08), 2.635 (0.57), 3.101 (16.00), 3.686 (13.52), 4.371 (0.47), 4.388 (1.70), 4.404 (1.69), 4.421 (0.47), 7.357 (1.74), 7.379 (4.49), 7.402 (2.19), 7.510 (2.10), 7.523 (2.35), 7.531 (1.96), 7.545 (1.61), 8.454 (3.28), 9.399 (2.54).

Example 344

N-[5-(4-fluorophenyl)-1,4-dimethyl-1H-pyrazol-3-yl]-6-{4-[1-methoxyethyl]-3,5-dimethyl-1H-pyrazol-1-yl}pyrimidin-4-amine

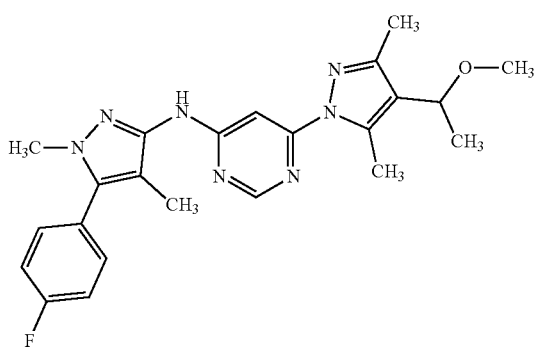 [SMILES: COC(C)c1c(C)nn(-c2cc(Nc3nn(C)c(-c4ccc(F)cc4)c3C)ncn2)c1C]

A sample of racemic N-[5-(4-fluorophenyl)-1,4-dimethyl-1H-pyrazol-3-yl]-6-{4-[1-methoxyethyl]-3,5-dimethyl-1H-pyrazol-1-yl}pyrimidin-4-amine (42 mg, 0.10 mmol) was separated using preparative SFC (column: 250*20 mm AD-H, 5 μM, flow 80 mL/min, 40° C., solvent 72% carbon dioxide/28% methanol) to give 13.4 mg of the first eluting enantiomer of N-[5-(4-fluorophenyl)-1,4-dimethyl-1H-pyrazol-3-yl]-6-{4-[1-methoxyethyl]-3,5-dimethyl-1H-pyrazol-1-yl}pyrimidin-4-amine (32% yield from racemate).

LC-MS (method 9): $R_t$=1.11 min; MS (ESIpos): m/z=436 [M+H]$^+$

Chiral HPLC (SFC, Daicel AD, 5 μM, flow 3 mL/min, solvent: 70% carbon dioxide/30% iso-propanol) Rt=1.79 min, >99.5% enantiomeric excess.

$^1$H-NMR (400 MHz, dimethylsulfoxide-d6) δ [ppm]: 1.361 (5.75), 1.378 (5.80), 1.852 (10.71), 2.216 (11.87), 2.622 (12.42), 3.101 (16.00), 3.686 (12.80), 4.371 (0.44), 4.388 (1.64), 4.404 (1.60), 4.421 (0.43), 7.357 (1.67), 7.363 (0.81), 7.374 (2.13), 7.379 (4.21), 7.396 (0.71), 7.402 (2.10), 7.509 (2.01), 7.515 (0.85), 7.523 (2.22), 7.531 (1.76), 7.540 (0.68), 7.545 (1.51), 8.454 (2.74), 9.397 (2.23).

Example 345

N-[5-(4-fluorophenyl)-1,4-dimethyl-1H-pyrazol-3-yl]-6-{4-[1-methoxyethyl]-3,5-dimethyl-1H-pyrazol-1-yl}pyrimidin-4-amine

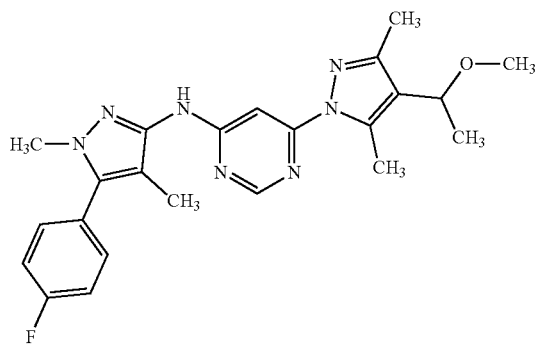 [SMILES: COC(C)c1c(C)nn(-c2cc(Nc3nn(C)c(-c4ccc(F)cc4)c3C)ncn2)c1C]

A sample of racemic N-[5-(4-fluorophenyl)-1,4-dimethyl-1H-pyrazol-3-yl]-6-{4-[1-methoxyethyl]-3,5-dimethyl-1H-pyrazol-1-yl}pyrimidin-4-amine (42 mg, 0.10 mmol) was separated using preparative SFC (column: 250*20 mm AD-H, 5 μM, flow 80 mL/min, 40° C., solvent 72% carbon dioxide/28% methanol) to give 15.8 mg of the second eluting enantiomer of N-[5-(4-fluorophenyl)-1,4-dimethyl-1H-pyrazol-3-yl]-6-{4-[1-methoxyethyl]-3,5-dimethyl-1H-pyrazol-1-yl}pyrimidin-4-amine (38% yield from racemate).

LC-MS (method 9): $R_t$=1.11 min; MS (ESIpos): m/z=436 [M+H]$^+$

Chiral HPLC (SFC, Daicel AD, 5 μM, flow 3 mL/min, solvent: 70% carbon dioxide/30% iso-propanol) Rt=2.63 min, >99.5% enantiomeric excess $^1$H-NMR (400 MHz, dimethylsulfoxide-d6) δ [ppm]: 1.245 (0.69), 1.361 (5.72), 1.378 (5.74), 1.852 (10.82), 2.216 (11.78), 2.623 (12.26), 3.102 (16.00), 3.686 (12.95), 3.836 (1.29), 4.371 (0.43), 4.388 (1.60), 4.404 (1.57), 4.421 (0.43), 4.943 (0.76), 7.357 (1.65), 7.363 (0.80), 7.374 (2.15), 7.379 (4.26), 7.396 (0.73), 7.402 (2.10), 7.510 (2.00), 7.515 (0.85), 7.523 (2.22), 7.531 (1.78), 7.540 (0.68), 7.545 (1.52), 8.454 (2.95), 9.397 (2.21).

Example 346

N-[4-chloro-5-(4-fluorophenyl)-1-methyl-1H-pyrazol-3-yl]-6-[5-(difluoromethyl)-3-methyl-1H-pyrazol-1-yl]pyrimidin-4-amine

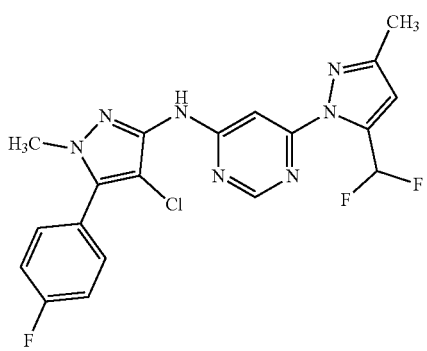 [SMILES: Cc1cc(C(F)F)n(-c2cc(Nc3nn(C)c(-c4ccc(F)cc4)c3Cl)ncn2)n1]

A microwave vial was charged 4-chloro-6-[5-(difluoromethyl)-3-methyl-H-pyrazol-1-yl]pyrimidine (100 mg, 409 µmol) and 4-chloro-5-(4-fluorophenyl)-1-methyl-1H-pyrazol-3-amine (101 mg, 450 µmol) and the contents were suspended in 1,4-dioxane (2.0 ml). The reaction mixture was degassed with Ar for 3 min. Tris(dibenzylidenaceton)dipalladium (11.2 mg, 12.3 µmol) and Xantphos (14.2 mg, 24.5 µmol) were added and the reaction mixture was degassed again for 1 min and heated to 85° C. At this temperature and sodium phenolate (52.2 mg, 450 µmol) was added. The vial was sealed and heated at 85° C. for 90 minutes while vigorously stirring. After cooling to ambient temperature, the reaction mixture was diluted with hydrochloric acid and extracted with ethyl acetate (2×). The combined organic phases were dried over Extrelut NT3 and concentrated under reduced pressure. The crude product was recrystallized from acetonitrile to yield 106.8 mg (59.5%) of the desired product.

LC-MS (method 10): $R_t$=2.27 min; MS (ESIpos): m/z=434 [M+H]$^+$ $^1$H-NMR (400 MHz, dimethylsulfoxide-d6) δ [ppm]: 2.300 (13.49), 3.317 (16.00), 3.569 (0.57), 6.783 (3.96), 7.299 (4.34), 7.413 (1.82), 7.435 (4.02), 7.457 (2.30), 7.636 (2.28), 7.650 (2.59), 7.657 (2.40), 7.671 (1.96), 7.688 (1.21), 7.824 (2.39), 7.960 (1.05), 8.505 (3.71), 9.742 (3.05).

Example 347

2-[1-(6-{[3-(4-chlorophenyl)-1-(cyclopropylmethyl)-4-methyl-1H-pyrazol-5-yl]amino}pyrimidin-4-yl)-3,5-dimethyl-1H-pyrazol-4-yl]propan-2-ol

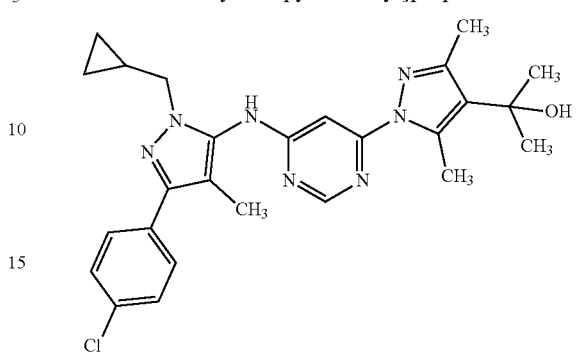

A solution of ethyl 1-(6-{[3-(4-chlorophenyl)-1-(cyclopropylmethyl)-4-methyl-1H-pyrazol-5-yl]amino}pyrimidin-4-yl)-3,5-dimethyl-1H-pyrazole-4-carboxylate (136 mg, 269 µmol) in tetrahydrofuran (2.7 ml, 34 mmol) was treated at 0° C. with chloro(methyl)magnesium (310 µl, 3.0 M, 940 µmol). The mixture was stirred overnight at ambient temperature. The mixture was diluted with potassium sodium tartrate solution and water, and extracted with ethyl acetate (3×). The combined organic phases were dried over Extrelut NT3 and concentrated under reduced pressure. The crude product was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 20 mg (15%) of the desired product.

LC-MS (method 10): $R_t$=2.14 min; MS (ESIpos): m/z=492 [M+H]$^+$ $^1$H-NMR (400 MHz, dimethylsulfoxide-d6) δ [ppm]: 0.294 (2.08), 0.305 (2.24), 0.424 (1.98), 0.444 (2.08), 1.091 (0.81), 1.108 (0.40), 1.180 (0.60), 1.186 (0.57), 1.198 (0.82), 1.216 (0.52), 1.356 (0.43), 1.464 (16.00), 2.014 (11.59), 2.265 (2.55), 2.742 (11.76), 3.375 (0.43), 3.392 (0.40), 3.831 (1.97), 3.848 (1.95), 4.854 (3.36), 7.488 (3.28), 7.509 (4.15), 7.713 (3.07), 7.734 (2.66), 8.458 (0.62), 9.373 (0.70).

Example 348

1-(6-{[5-(4-fluorophenyl)-1,4-dimethyl-1H-pyrazol-3-yl]amino}pyrimidin-4-yl)-3,5-dimethyl-1H-pyrazole-4-carbonitrile

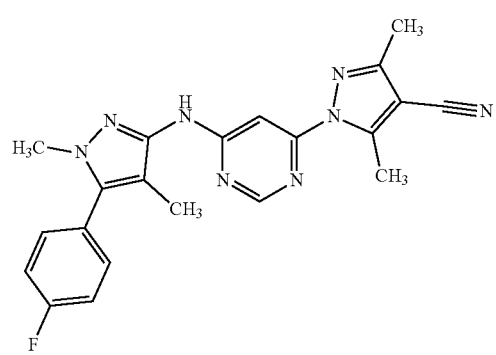 [SMILES: Cc1nn(-c2cc(Nc3nn(C)c(-c4ccc(F)cc4)c3C)ncn2)c(C)c1C#N]

A microwave vial was charged 1-(6-chloropyrimidin-4-yl)-3,5-dimethyl-1H-pyrazole-4-carbonitrile (175 mg, 77% purity, 576 µmol), 5-(4-fluorophenyl)-1,4-dimethyl-1H-pyrazol-3-amine (130 mg, 633 µmol) and sodium phenolate (73.5 mg, 633 µmol) and the contents were suspended in 1,4-dioxane (3.3 ml, 39 mmol). The reaction mixture was degassed with Ar for 3 min. Tris(dibenzylidenaceton)dipalladium (6.85 mg, 7.49 µmol) and Xantphos (10.0 mg, 17.3 µmol) were added and the reaction mixture was degassed again for 1 min. The vial was sealed and heated at 85° C. overnight while vigorously stirring. After cooling to ambient temperature, the reaction mixture was filtered and purified by preparative HPLC (method 3) to yield the desired product (70.0 mg, 30%).

LC-MS (method 10): $R_t$=2.04 min; MS (ESIpos): m/z=403 [M+H]$^+$ $^1$H-NMR (400 MHz, dimethylsulfoxide-d6) δ [ppm]: 1.855 (11.25), 2.339 (14.01), 2.786 (15.03), 3.688 (16.00), 7.358 (1.83), 7.380 (4.10), 7.402 (2.45), 7.464 (0.71), 7.510 (2.51), 7.524 (2.82), 7.531 (2.32), 7.545 (1.90), 8.536 (2.86), 9.662 (1.56).

Example 349

1-(6-{[1-(cyclopropylmethyl)-4-ethyl-3-(4-fluorophenyl)-1H-pyrazol-5-yl]amino}pyrimidin-4-yl)-3,5-dimethyl-1H-pyrazole-4-carbonitrile

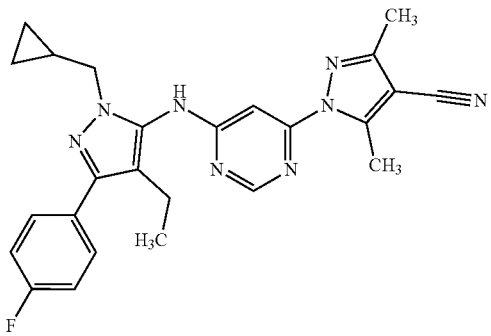 [SMILES: CCc1c(-c2ccc(F)cc2)nn(CC2CC2)c1Nc1cc(-n2nc(C)c(C#N)c2C)ncn1]

A microwave vial was charged 1-(6-chloropyrimidin-4-yl)-3,5-dimethyl-1H-pyrazole-4-carbonitrile (138 mg, 77% purity, 456 µmol), 1-(cyclopropylmethyl)-4-ethyl-3-(4-fluorophenyl)-1H-pyrazol-5-amine (130 mg, 501 µmol) and sodium phenolate (58.2 mg, 501 µmol) and the contents were suspended in 1,4-dioxane (2.6 ml, 31 mmol). The reaction mixture was degassed with Ar for 3 min. Tris(dibenzylidenaceton)dipalladium (5.43 mg, 5.92 µmol) and Xantphos (7.91 mg, 13.7 µmol) were added and the reaction mixture was degassed again for 1 min. The vial was sealed and heated at 85° C. overnight while vigorously stirring. After cooling to ambient temperature, the reaction mixture was filtered and purified by preparative HPLC (method 4) to yield the desired product (56.0 mg, 26%).

LC-MS (method 10): $R_t$=2.29 min; MS (ESIpos): m/z=457 [M+H]$^+$ $^1$H-NMR (500 MHz, dimethylsulfoxide-d6) δ [ppm]: −0.006 (1.45), 0.006 (0.82), 0.295 (2.10), 0.435 (2.59), 0.450 (2.60), 0.972 (4.15), 0.987 (8.51), 1.002 (4.12), 1.078 (1.10), 1.092 (2.20), 1.106 (1.11), 1.195 (1.10), 2.347 (1.30), 2.359 (1.21), 2.363 (1.21), 2.404 (1.87), 2.456 (1.83), 2.471 (1.95), 2.796 (16.00), 2.870 (1.65), 3.391 (1.75), 3.405 (0.62), 3.799 (1.77), 7.259 (2.13), 7.276 (4.29), 7.294 (2.43), 7.686 (1.82).

Example 350

N-[1-(cyclopropylmethyl)-4-methyl-3-(pyridin-4-yl)-1H-pyrazol-5-yl]-6-(3,5-dimethyl-1H-pyrazol-1-yl)pyrimidin-4-amine

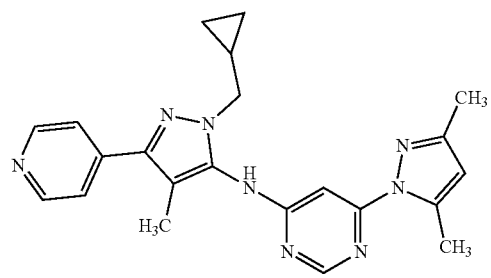 [SMILES: Cc1cc(C)n(-c2cc(Nc3c(C)c(-c4ccncc4)nn3CC3CC3)ncn2)n1]

A microwave vial was charged with 1-(cyclopropylmethyl)-4-methyl-3-(pyridin-4-yl)-1H-pyrazol-5-amine (79.0 mg, 346 µmol), 4-chloro-6-(3,5-dimethyl-1H-pyrazol-1-yl)pyrimidine (79.4 mg, 381 µmol) and sodium phenolate (44.2 mg, 381 µmol) and the contents were suspended in 1,4-dioxane (1.3 mL).

The reaction mixture was degassed with Ar for 3 min. Tris(dibenzylideneacetone)dipalladium (6.34 mg, 6.92 µmol) and XantPhos (8.01 mg, 13.8 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (Instrument: Waters Prep LC/MS System, Column: XBridge C18 5 µm 100×30 mm; Solvent A: water, solvent B: acetonitrile, flow: 65 mL/min plus 5 ml 2% aqueous ammonia solution, room temperature, wavelength 200-400 nm, At-column injection; gradient: 0-2 min 10% solvent B, 2-2.2 min to 30% solvent B, 2.2-7 min to 70% solvent B, 7-7.5 min to 92% solvent B, 7.5-9 min at 92% B) to yield the desired product (32.8 mg, 23% yield).

LC-MS (method 11): $R_t$=1.02 min; MS (ESIneg): m/z=399 [M−H]$^-$ $^1$H-NMR (400 MHz, dimethylsulfoxide-d6) δ [ppm]: −0.149 (0.30), −0.008 (2.63), 0.008 (2.41), 0.146 (0.27), 0.308 (2.49), 0.319 (2.76), 0.433 (2.53), 0.453 (2.68), 1.179 (0.35), 1.191 (0.65), 1.198 (0.65), 1.211 (1.02), 1.222 (0.63), 1.230 (0.64), 2.081 (16.00), 2.172 (3.25), 2.228 (2.24), 2.328 (0.52), 2.367 (0.29), 2.523 (1.36), 2.630 (14.92), 2.665 (2.01), 2.710 (0.32), 3.866 (2.50), 3.884 (2.48), 6.146 (2.69), 6.271 (0.32), 7.694 (3.29), 7.709 (3.54), 7.900 (0.35), 8.464 (0.66), 8.608 (4.65), 8.612 (3.20), 8.620 (3.06), 8.623 (4.69), 8.903 (0.28), 9.419 (0.90).

Example 351

6-(4-chloro-3,5-dimethyl-1H-pyrazol-1-yl)-N-[1-(cyclopropylmethyl)-4-methyl-3-(pyridin-4-yl)-1H-pyrazol-5-yl]pyrimidin-4-amine

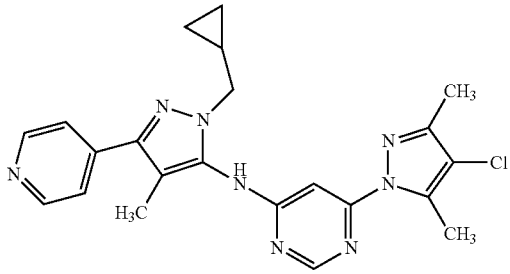 [SMILES: Cc1nn(-c2cc(Nc3c(C)c(-c4ccncc4)nn3CC3CC3)ncn2)c(C)c1Cl]

A microwave vial was charged with 1-(cyclopropylmethyl)-4-methyl-3-(pyridin-4-yl)-1H-pyrazol-5-amine (200 mg, 876 µmol), 4-chloro-6-(4-chloro-3,5-dimethyl-1H-pyrazol-1-yl)pyrimidine (234 mg, 964 µmol) and sodium phenolate (112 mg, 964 µmol) and the contents were suspended in 1,4-dioxane (2.5 mL). The reaction mixture was degassed with Ar for 3 min. Tris(dibenzylideneacetone)dipalladium (16.0 mg, 17.5 µmol) and XantPhos (20.3 mg, 35.0 µmol) were added and the reaction mixture was degassed again for 1 min. The vial was sealed and heated at 85° C. overnight while vigorously shaking. After cooling to ambient temperature, the reaction mixture was quenched with aqueous sodium hydrogencarbonate solution and extracted with ethyl acetate. The organic phase extract was washed with brine, dried over sodium sulfate and concentrated. The residue was purified by flash column chromatography (SNAP Ultra 25 g, cyclohexane/ethyl acetate gradient 88/12 to 0/100) to yield the desired product (112 mg, 29% yield).

LC-MS (method 11): $R_t$=1.30 min; MS (ESIpos): m/z=435 [M+H]$^+$ $^1$H-NMR (400 MHz, dimethylsulfoxide-d6) δ [ppm]: −0.008 (1.18), 0.008 (1.37), 0.306 (2.17), 0.317 (2.41), 0.433 (2.23), 0.453 (2.39), 1.188 (0.60), 1.195 (0.58), 1.207 (0.91), 1.219 (0.55), 1.226 (0.59), 2.079 (13.98), 2.212 (2.33), 2.649 (16.00), 2.670 (0.45), 3.867 (2.11), 3.884 (2.07), 7.693 (2.77), 7.707 (2.91), 8.500 (0.44), 8.609 (3.88), 8.624 (3.87), 9.518 (0.47).

Example 352

1-(6-{[3-(4-cyanophenyl)-1-(cyclopropylmethyl)-4-methyl-1H-pyrazol-5-yl]amino}pyrimidin-4-yl)-3,5-dimethyl-1H-pyrazole-4-carbonitrile

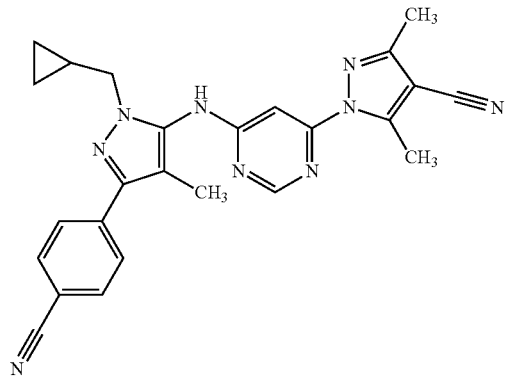 [SMILES: Cc1nn(-c2cc(Nc3c(C)c(-c4ccc(C#N)cc4)nn3CC3CC3)ncn2)c(C)c1C#N]

A microwave vial was charged 1-(6-chloropyrimidin-4-yl)-3,5-dimethyl-1H-pyrazole-4-carbonitrile (142 mg, 77% purity, 468 µmol), 4-[5-amino-1-(cyclopropylmethyl)-4-methyl-1H-pyrazol-3-yl]benzonitrile (130 mg, 515 µmol) and sodium phenolate (59.8 mg, 515 µmol) and the contents were suspended in 1,4-dioxane (2.7 ml, 32 mmol). The reaction mixture was degassed with Ar for 3 min. Tris(dibenzylidenaceton)dipalladium (5.58 mg, 6.09 µmol) and Xantphos (8.13 mg, 14.1 µmol) were added and the reaction mixture was degassed again for 1 min. The vial was sealed and heated at 85° C. overnight while vigorously stirring. After cooling to ambient temperature, the reaction mixture was filtered and purified by preparative HPLC (method 4) and an additional preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (37.0 mg, 17%).

LC-MS (method 10): $R_t$=2.14 min; MS (ESIpos): m/z=450 [M+H]$^+$ $^1$H-NMR (400 MHz, dimethylsulfoxide-d6) δ [ppm]: −0.008 (1.35), 0.008 (1.27), 0.302 (2.33), 0.313 (2.53), 0.432 (2.45), 0.452 (2.61), 1.074 (1.29), 1.091 (2.62), 1.109 (1.32), 1.184 (0.68), 1.191 (0.67), 1.203 (1.01), 1.215 (0.62), 1.221 (0.65), 2.060 (15.39), 2.329 (2.02), 2.796 (16.00), 3.357 (0.78), 3.375 (1.43), 3.393 (1.35), 3.410 (0.47), 3.862 (1.96), 3.879 (1.96), 7.908 (12.65).

Example 353 ethyl 1-(6-{[5-(4-chlorophenyl)-1,4-dimethyl-1H-pyrazol-3-yl]amino}pyrimidin-4-yl)-3,5-dimethyl-1H-pyrazole-4-carboxylate

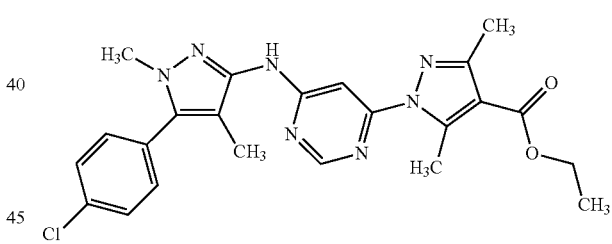

A microwave vial was charged ethyl 1-(6-chloropyrimidin-4-yl)-3,5-dimethyl-1H-pyrazole-4-carboxylate (161 mg, 574 µmol), 5-(4-chlorophenyl)-1,4-dimethyl-1H-pyrazol-3-amine (140 mg, 632 µmol) and sodium phenolate (73.3 mg, 632 µmol) and the contents were suspended in 1,4-dioxane (3.3 ml, 39 mmol). The reaction mixture was degassed with Ar for 3 min. Tris(dibenzylidenaceton)dipalladium (6.83 mg, 7.46 µmol) and Xantphos (9.97 mg, 17.2 µmol) were added and the reaction mixture was degassed again for 1 min. The vial was sealed and heated at 85° C. overnight while vigorously stirring. After cooling to ambient temperature, the reaction mixture was filtered and purified by preparative HPLC (method 4) to yield the desired product (138 mg, 49%).

LC-MS (method 10): $R_t$=2.41 min; MS (ESIpos): m/z=466 [M+H]$^+$ $^1$H-NMR (400 MHz, dimethylsulfoxide-d6) δ [ppm]: 1.290 (4.44), 1.308 (9.24), 1.326 (4.65), 1.868 (12.80), 2.030 (0.78), 2.382 (14.96), 2.889 (15.62), 2.910 (0.79), 2.933 (0.62), 3.672 (0.53), 3.699 (16.00), 4.230 (1.37), 4.248 (4.25), 4.265 (4.23), 4.283 (1.38), 7.426 (1.09), 7.495 (3.74), 7.516 (5.58), 7.596 (5.28), 7.617 (3.59), 8.529 (3.17), 9.607 (2.25).

Example 354

N-[3-(4-chlorophenyl)-1,4-dimethyl-1H-pyrazol-5-yl]-6-(3,5-dimethyl-1H-pyrazol-1-yl)pyrimidin-4-amine

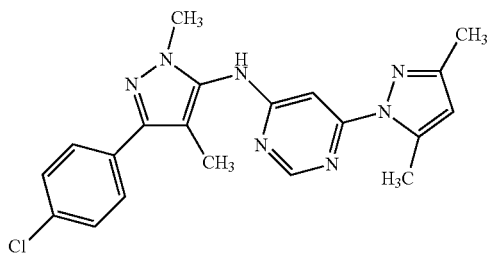 [SMILES: Cc1cc(C)n(-c2cc(Nc3c(C)c(-c4ccc(Cl)cc4)nn3C)ncn2)n1]

A microwave vial was charged 4-chloro-6-(3,5-dimethyl-1H-pyrazol-1-yl)pyrimidine (128 mg, 615 μmol), 3-(4-chlorophenyl)-1,4-dimethyl-1H-pyrazol-5-amine (150 mg, 677 μmol) and sodium phenolate (78.5 mg, 677 μmol) and the contents were suspended in 1,4-dioxane (3.5 ml, 41 mmol). The reaction mixture was degassed with Ar for 3 min. Tris(dibenzylidenaceton)dipalladium (7.32 mg, 8.00 μmol) and Xantphos (10.7 mg, 18.5 μmol) were added and the reaction mixture was degassed again for 1 min. The vial was sealed and heated at 85° C. overnight while vigorously stirring. After cooling to ambient temperature, the reaction mixture was filtered and purified by preparative HPLC (method 4) to yield the desired product (117 mg, 46%).

LC-MS (method 10): R$_t$=2.19 min; MS (ESIpos): m/z=394 [M+H]$^+$ $^1$H-NMR (400 MHz, dimethylsulfoxide-d6) δ [ppm]: −0.008 (0.90), 0.008 (0.98), 2.027 (16.00), 2.074 (0.47), 2.174 (4.26), 2.630 (14.11), 3.666 (11.41), 6.145 (2.95), 7.483 (3.96), 7.504 (4.80), 7.703 (3.75), 7.724 (3.09), 8.470 (0.91), 9.419 (2.37).

Example 355

N-[5-(4-chlorophenyl)-1,4-dimethyl-1H-pyrazol-3-yl]-6-(3,5-dimethyl-1H-pyrazol-1-yl)pyrimidin-4-amine

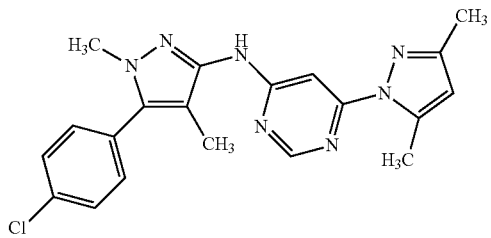 [SMILES: Cc1cc(C)n(-c2cc(Nc3nn(C)c(-c4ccc(Cl)cc4)c3C)ncn2)n1]

A microwave vial was charged 4-chloro-6-(3,5-dimethyl-1H-pyrazol-1-yl)pyrimidine (89.8 mg, 431 μmol), 5-(4-chlorophenyl)-1,4-dimethyl-1H-pyrazol-3-amine (105 mg, 474 μmol) and sodium phenolate (55.0 mg, 474 μmol) and the contents were suspended in 1,4-dioxane (2.5 ml, 29 mmol). The reaction mixture was degassed with Ar for 3 min. Tris(dibenzylidenaceton)dipalladium (5.13 mg, 5.60 μmol) and Xantphos (7.47 mg, 12.9 μmol) were added and the reaction mixture was degassed again for 1 min. The vial was sealed and heated at 85° C. overnight while vigorously stirring. After cooling to ambient temperature, the reaction mixture was diluted with hydrochlorid acid and extracted with ethyl acetate (2×). The combined organic phases were dried over Extrelut NT3 and concentrated under reduced pressure. The crude product was purified by preparative HPLC (method 4) to yield the desired product (20.0 mg, 11%).

LC-MS (method 10): R$_t$=2.19 min; MS (ESIpos): m/z=394 [M+H]$^+$ $^1$H-NMR (400 MHz, dimethylsulfoxide-d6) δ [ppm]: −0.008 (1.48), 0.008 (1.58), 1.566 (0.75), 1.646 (0.76), 1.859 (13.87), 2.027 (1.99), 2.073 (0.52), 2.184 (14.80), 2.328 (0.47), 2.622 (13.05), 2.653 (0.53), 2.670 (0.55), 3.666 (1.39), 3.702 (16.00), 6.131 (3.70), 6.147 (0.44), 7.341 (0.51), 7.370 (2.53), 7.382 (1.21), 7.398 (0.82), 7.461 (0.78), 7.465 (0.89), 7.484 (0.85), 7.496 (3.87), 7.517 (5.68), 7.596 (5.67), 7.617 (3.71), 7.702 (0.51), 7.724 (0.48), 7.781 (0.46), 7.794 (0.44), 7.821 (0.40), 8.447 (3.63), 9.389 (2.95).

Example 356 ethyl 1-(6-{[4-chloro-5-(4-fluorophenyl)-1-methyl-1H-pyrazol-3-yl]amino}pyrimidin-4-yl)-3,5-dimethyl-1H-pyrazole-4-carboxylate

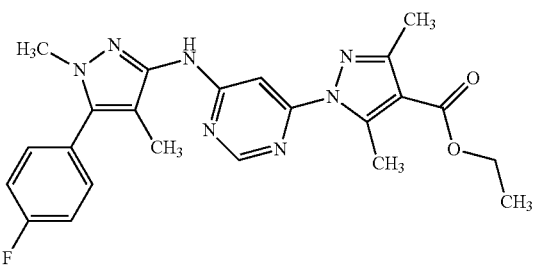 [SMILES: CCOC(=O)c1c(C)nn(-c2cc(Nc3nn(C)c(-c4ccc(F)cc4)c3C)ncn2)c1C]

4-chloro-5-(4-fluorophenyl)-1-methyl-1H-pyrazol-3-amine (200 mg, 886 μmol) and sodium phenolate (103 mg, 886 μmol) and were suspended in 1,4-dioxane (1.9 mL). The reaction mixture was degassed with Ar for 3 min. Tris (dibenzylideneacetone)dipalladium (9.59 mg, 10.5 μmol), XantPhos (14.0 mg, 24.2 μmol) and ethyl 1-(6-chloropyrimidin-4-yl)-3,5-dimethyl-1H-pyrazole-4-carboxylate (226 mg, 806 μmol) were added and the reaction mixture was degassed again for 1 min. the reaction mixture was heated at 90° C. overnight while vigorously stirring. After cooling to ambient temperature, the reaction mixture was filtered and concentrated. The residue was purified by flash column chromatography (SNAP Ultra 25 g, cyclohexane/ethyl acetate gradient 95/5 to 20/80) to yield the desired product (95 mg, 24% yield).

LC-MS (method 10): R$_t$=2.35 min; MS (ESIpos): m/z=470 [M+H]$^+$ $^1$H-NMR (400 MHz, dimethylsulfoxide-d6) δ [ppm]: −0.008 (1.30), 0.008 (1.32), 1.157 (0.16), 1.175 (0.30), 1.274 (0.17), 1.291 (4.76), 1.309 (10.08), 1.327 (4.84), 1.398 (1.96), 1.988 (0.46), 2.328 (0.25), 2.387 (15.76), 2.670 (0.26), 2.899 (16.00), 2.919 (1.51), 2.946 (1.14), 3.733 (1.04), 3.770 (15.97), 3.882 (0.53), 4.232 (1.31), 4.250 (4.21), 4.267 (4.18), 4.278 (0.49), 4.285 (1.30), 7.301

(3.62), 7.324 (0.43), 7.346 (0.23), 7.409 (2.00), 7.414 (0.74), 7.425 (0.92), 7.431 (4.41), 7.448 (0.83), 7.453 (2.49), 7.466 (0.24), 7.628 (2.37), 7.633 (1.05), 7.642 (2.60), 7.650 (2.28), 7.658 (0.88), 7.664 (2.00), 7.733 (0.37), 7.877 (0.22), 7.890 (0.24), 7.899 (0.22), 7.912 (0.20), 8.553 (3.06), 8.580 (0.18), 8.932 (0.29), 9.732 (2.56), 9.863 (0.21).

Example 357

1-[1-(6-{[4-chloro-5-(4-fluorophenyl)-1-methyl-1H-pyrazol-3-yl]amino}pyrimidin-4-yl)-3,5-dimethyl-1H-pyrazol-4-yl]cyclopropanol

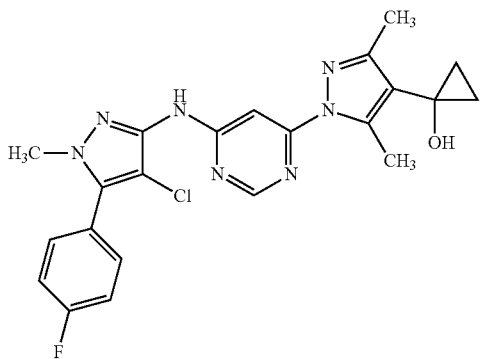 [SMILES: Cc1nn(-c2cc(Nc3nn(C)c(-c4ccc(F)cc4)c3Cl)ncn2)c(C)c1C1(O)CC1]

Under an argon atmosphere a Schlenk tube was charged with titanium isopropoxide (310 µl, 1.0 mmol) in tetrahydrofuran (2.0 ml, 25 mmol) and a solution of ethylmagnesium bromide (3.1 ml, 1.0 M in tetrahydrofuran, 3.1 mmol) was added at −18° C. The mixture was stirred at this temperature for 30 minutes, than a solution of ethyl 1-(6-{[4-chloro-5-(4-fluorophenyl)-1-methyl-1H-pyrazol-3-yl]amino}pyrimidin-4-yl)-3,5-dimethyl-1H-pyrazole-4-carboxylate (245 mg, 521 µmol) in 1.5 mL tetrahydrofuran was added. The mixture was stirred overnight at room temperature. No complete conversion was observed, therefor additional 2 equivalents of ethylmagnesium bromide (1.1 ml, 1.0 M in tetrahydrofuran, 1.1 mmol) were added. The mixture was again left overnight. The mixture was diluted with water and extracted with ethyl acetate (3×). The combined organic phases were washed with water, brine, dried over sodium sulfate and concentrated under reduced pressure. The crude product was purified by preparative HPLC (method 17) to yield 34.3 mg (14%) of the desired product.

LC-MS (method 9): $R_t$=0.95 min; MS (ESIpos): m/z=454 [M+H]$^+$ $^1$H-NMR (400 MHz, dimethylsulfoxide-d6) δ [ppm]: −0.008 (0.89), 0.008 (0.91), 0.644 (1.13), 0.656 (3.45), 0.661 (3.41), 0.673 (1.37), 0.930 (1.35), 0.941 (3.57), 0.947 (3.38), 0.959 (1.23), 2.281 (14.40), 2.524 (0.62), 2.709 (15.11), 3.768 (16.00), 5.471 (5.44), 5.754 (3.58), 7.241 (3.94), 7.243 (4.15), 7.408 (2.02), 7.413 (0.78), 7.430 (4.45), 7.447 (0.88), 7.452 (2.54), 7.626 (2.46), 7.632 (1.13), 7.640 (2.68), 7.648 (2.35), 7.657 (0.92), 7.662 (2.04), 8.472 (3.36), 9.520 (3.30).

Example 358

4-{1-(cyclopropylmethyl)-5-[(6-{3,5-dimethyl-4-[(±)-2,2,2-trifluoro-1-hydroxyethyl]-1H-pyrazol-1-yl}pyrimidin-4-yl)amino]-4-methyl-1H-pyrazol-3-yl}benzonitrile (Racemate)

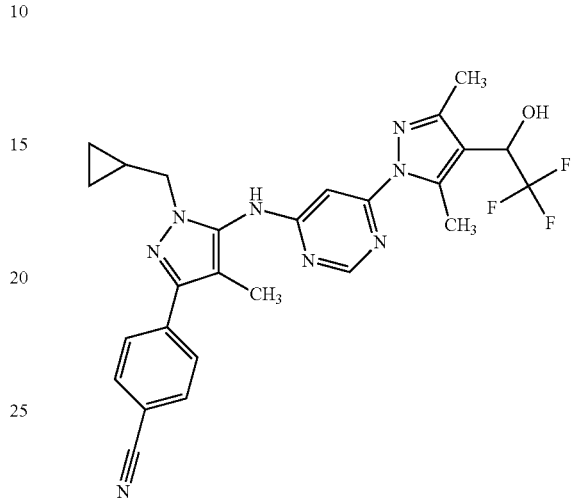

Molecular Sieves (4 Å) were placed in a round-bottom flask and dried in a vacuum drying-oven overnight at 120° C. After cooling to ambient temperature, tetrabutylammonium fluoride trihydrate (42.6 mg, 152 µmol) and toluene (1.0 mL) were added and the suspension stirred for 30 min. A solution of 4-[1-(cyclopropylmethyl)-5-{[6-(4-formyl-3,5-dimethyl-1H-pyrazol-1-yl)pyrimidin-4-yl]amino}-4-methyl-1H-pyrazol-3-yl]benzonitrile (23.0 mg, 50.8 µmol) in toluene (0.5 mL) was then added, the mixture was stirred for 5 min and cooled to 0° C. Trimethyl(trifluoromethyl)silane (38 µL, 250 µmol) was then added and stirred at ambient temperature for 1 h. The reaction mixture was diluted with ethyl acetate and water, the molecular sieves removed by filtration and washed further with ethyl acetate. After separation of the layers, the aqueous phase was extracted again with ethyl acetate and the combined organic phase extracts were dried over sodium sulfate and concentrated. The residue was purified by preparative HPLC (column: Chromatorex C18; 125*30 mm, 10 µM, flow 75 mL/min, gradient acetonitrile/water 5/95 to 90/10) to yield the desired product (8 mg, 85% purity, 26% yield).

LC-MS (method 11): $R_t$=1.39 min; MS (ESIneg): m/z=521 [M−H]$^-$ $^1$H-NMR (400 MHz, dimethylsulfoxide-d6) δ [ppm]: −0.149 (0.65), −0.008 (5.04), 0.008 (5.06), 0.146 (0.61), 0.306 (2.70), 0.317 (2.95), 0.433 (2.64), 0.453 (2.78), 1.148 (0.16), 1.178 (0.40), 1.190 (0.71), 1.196 (0.71), 1.209 (1.10), 1.228 (0.77), 2.025 (0.27), 2.062 (16.00), 2.242 (2.57), 2.328 (0.87), 2.367 (0.49), 2.407 (0.25), 2.674 (14.99), 2.710 (0.51), 2.943 (1.34), 3.861 (2.35), 3.878 (2.34), 5.157 (0.69), 6.699 (1.56), 6.709 (1.57), 7.885 (1.08), 7.906 (12.20), 7.931 (0.88), 8.487 (0.53), 9.478 (0.55), 10.017 (0.31).

Example 359

4-{1-(cyclopropylmethyl)-5-[(6-{3,5-dimethyl-4-[2,2,2-trifluoro-1-hydroxyethyl]-1H-pyrazol-1-yl}pyrimidin-4-yl)amino]-4-methyl-1H-pyrazol-3-yl}benzonitrile

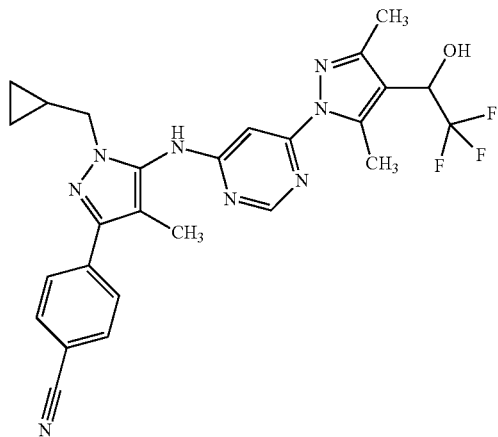 [SMILES: Cc1nn(-c2cc(Nc3c(C)c(-c4ccc(C#N)cc4)nn3CC3CC3)ncn2)c(C)c1C(O)C(F)(F)F]

Obtained from separation of the enantiomers of a racemic sample of 4-{1-(cyclopropylmethyl)-5-[(6-{3,5-dimethyl-4-[(±)-2,2,2-trifluoro-1-hydroxyethyl]-1H-pyrazol-1-yl}pyrimidin-4-yl)amino]-4-methyl-1H-pyrazol-3-yl}benzonitrile (racemate 12.0 mg dissolved in ethanol, 1.5 mL) by preparative HPLC (Chiralpak AD-H 5 m, 250×30 mm, flow: 40 mL/min, isocratic: 2-propanol/n-heptane 15/85) to yield the title compound as the first eluting enantiomer (3.4 mg, 28% from racemate).

LC-MS (method 11): $R_t$=1.38 min; MS (ESIpos): m/z=523 [M+H]$^+$

Chiral HPLC (Daicel IC-3 3 μm, 50×4.6 mm, isocratic i-hexane/2-propanol 90/10): Rt=5.82 min, 90% ee

Example 360

4-{1-(cyclopropylmethyl)-5-[(6-{3,5-dimethyl-4-[(1S)-2,2,2-trifluoro-1-hydroxyethyl]-1H-pyrazol-1-yl}pyrimidin-4-yl)amino]-4-methyl-1H-pyrazol-3-yl}benzonitrile

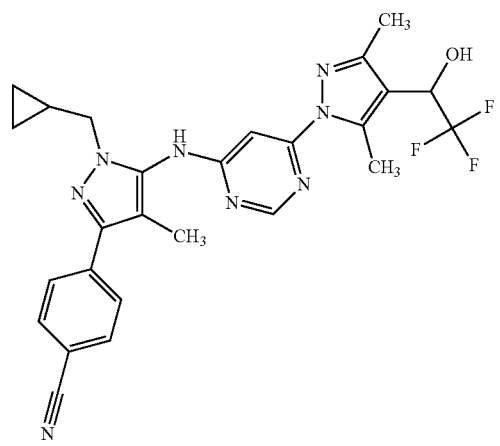 [SMILES: Cc1nn(-c2cc(Nc3c(C)c(-c4ccc(C#N)cc4)nn3CC3CC3)ncn2)c(C)c1C(O)C(F)(F)F]

Obtained from separation of the enantiomers of a racemic sample of 4-{1-(cyclopropylmethyl)-5-[(6-{3,5-dimethyl-4-[(±)-2,2,2-trifluoro-1-hydroxyethyl]-1H-pyrazol-1-yl}pyrimidin-4-yl)amino]-4-methyl-1H-pyrazol-3-yl}benzonitrile (racemate 12.0 mg dissolved in ethanol, 1.5 mL) by preparative HPLC (Chiralpak AD-H 5 m, 250×30 mm, flow: 40 mL/min, isocratic: 2-propanol/n-heptane 15/85) to yield the title compound as the second eluting enantiomer (2.2 mg, 18% from racemate).

LC-MS (method 11): $R_t$=1.38 min; MS (ESIpos): m/z=523 [M+H]$^+$

Chiral HPLC (Daicel IC-3 3 μm, 50×4.6 mm, isocratic i-hexane/2-propanol 90/10): Rt=8.11 min, 99% ee

Example 361 ethyl 1-[6-({1,4-dimethyl-3-[4-(trifluoromethoxy)phenyl]-1H-pyrazol-5-yl}amino)pyrimidin-4-yl]-3,5-dimethyl-1H-pyrazole-4-carboxylate

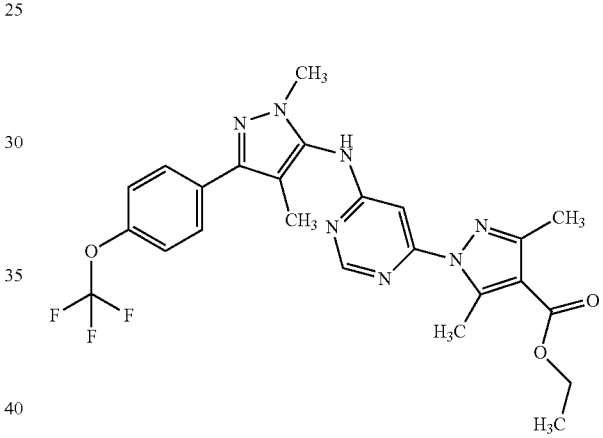

1,4-dimethyl-3-[4-(trifluoromethoxy)phenyl]-1H-pyrazol-5-amine (300 mg, 1.11 mmol) and sodium phenolate (128 mg, 1.11 mmol) and the contents were suspended in 1,4-dioxane (4.0 mL). The reaction mixture was degassed with Ar for 3 min. Tris(dibenzylideneacetone)dipalladium (12.0 mg, 13.1 μmol), XantPhos (17.5 mg, 30.2 μmol) and ethyl 1-(6-chloropyrimidin-4-yl)-3,5-dimethyl-1H-pyrazole-4-carboxylate (282 mg, 1.01 mmol) were added and the reaction mixture was degassed again for 1 min. The vial was sealed and heated at 90° C. overnight while vigorously shaking. After cooling to ambient temperature, the reaction mixture loaded onto silica gel and purified by flash column chromatography (SNAP Ultra 25 g, cyclohexane/ethyl acetate gradient 95/5 to 35/65) to yield the desired product (119 mg, 23% yield).

LC-MS (method 9): $R_t$=1.30 min; MS (ESIpos): m/z=516 [M+H]$^+$ $^1$H-NMR (400 MHz, dimethylsulfoxide-d6) δ [ppm]: −0.008 (1.69), 0.008 (1.71), 1.289 (3.67), 1.307 (7.55), 1.324 (3.76), 1.398 (1.52), 1.988 (0.50), 2.043 (16.00), 2.328 (0.48), 2.378 (2.87), 2.912 (14.29), 3.680 (9.39), 4.230 (1.08), 4.248 (3.32), 4.266 (3.29), 4.283 (1.09), 7.420 (2.87), 7.440 (3.15), 7.800 (3.15), 7.821 (2.86), 8.550 (0.62), 9.603 (1.04).

Example 362 ethyl 1-[6-({1,4-dimethyl-3-[4-(trifluoromethyl)phenyl]-1H-pyrazol-5-yl}amino)pyrimidin-4-yl]-3,5-dimethyl-1H-pyrazole-4-carboxylate

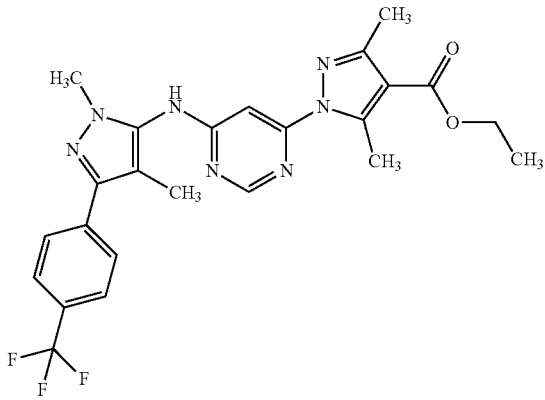 [SMILES: CCOC(=O)c1c(C)nn(-c2cc(Nc3c(C)c(-c4ccc(C(F)(F)F)cc4)nn3C)ncn2)c1C]

1,4-dimethyl-3-[4-(trifluoromethyl)phenyl]-1H-pyrazol-5-amine (223 mg, 874 µmol) and sodium phenolate (101 mg, 874 µmol) were suspended in 1,4-dioxane (3.2 mL). The reaction mixture was degassed with Ar for 3 min. Tris(dibenzylideneacetone)dipalladium (9.46 mg, 10.3 µmol), XantPhos (13.8 mg, 23.8 µmol) and ethyl 1-(6-chloropyrimidin-4-yl)-3,5-dimethyl-1H-pyrazole-4-carboxylate (223 mg, 794 µmol) were added and the reaction mixture was degassed again for 1 min. The reaction mixture was heated at 90° C. overnight while vigorously stirring. After cooling to ambient temperature, the reaction mixture was loaded onto silica gel and purified by flash column chromatography (SNAP Ultra 25 g, cyclohexane/ethyl acetate gradient 95/5 to 35/65) to yield the desired product (175 mg, 44% yield).

LC-MS (method 9): $R_t$=1.28 min; MS (ESIpos): m/z=500 [M+H]$^+$ $^1$H-NMR (400 MHz, dimethylsulfoxide-d6) δ [ppm]: 0.008 (0.83), 1.158 (0.45), 1.176 (0.87), 1.194 (0.45), 1.290 (3.70), 1.308 (7.55), 1.326 (3.77), 1.398 (2.19), 1.989 (1.52), 2.078 (16.00), 2.380 (2.99), 2.914 (14.30), 3.704 (9.62), 4.231 (1.12), 4.249 (3.37), 4.267 (3.35), 4.285 (1.15), 7.784 (2.97), 7.805 (4.05), 7.916 (3.30), 7.937 (2.46), 8.552 (0.64), 9.629 (1.13).

Example 363 ethyl 1-(6-{[3-(2,4-difluorophenyl)-1,4-dimethyl-1H-pyrazol-5-yl]amino}pyrimidin-4-yl)-3,5-dimethyl-1H-pyrazole-4-carboxylate

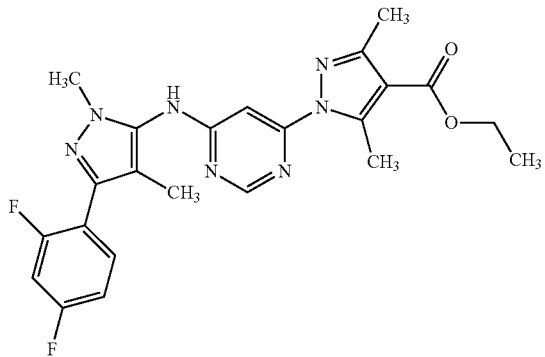 [SMILES: CCOC(=O)c1c(C)nn(-c2cc(Nc3c(C)c(-c4ccc(F)cc4F)nn3C)ncn2)c1C]

3-(2,4-difluorophenyl)-1,4-dimethyl-1H-pyrazol-5-amine (300 mg, 1.34 mmol) and sodium phenolate (156 mg, 1.34 mmol) were suspended in 1,4-dioxane (4.9 mL). The reaction mixture was degassed with Ar for 3 min. Tris(dibenzylideneacetone)dipalladium (14.5 mg, 15.9 µmol), XantPhos (21.2 mg, 36.7 mol) and ethyl 1-(6-chloropyrimidin-4-yl)-3,5-dimethyl-1H-pyrazole-4-carboxylate (343 mg, 1.22 mmol) were added and the reaction mixture was degassed again for 1 min. The reaction mixture was heated at 90° C. overnight while vigorously stirring. After cooling to ambient temperature, the reaction mixture was loaded onto silica gel and purified by flash column chromatography (SNAP Ultra 25 g, cyclohexane/ethyl acetate gradient 95/5 to 35/65) to yield the desired product (263 mg, 46% yield).

LC-MS (method 9): $R_t$=1.18 min; MS (ESIpos): m/z=468 [M+H]$^+$ $^1$H-NMR (400 MHz, dimethylsulfoxide-d6) δ [ppm]: −0.149 (0.18), −0.008 (1.60), 0.008 (1.47), 0.146 (0.17), 1.157 (0.80), 1.175 (1.58), 1.193 (0.80), 1.291 (4.33), 1.309 (9.02), 1.327 (4.42), 1.824 (8.11), 1.828 (8.35), 1.909 (0.29), 1.989 (2.84), 2.328 (0.34), 2.384 (5.22), 2.671 (0.29), 2.915 (16.00), 3.679 (9.94), 4.003 (0.22), 4.021 (0.68), 4.039 (0.69), 4.057 (0.22), 4.233 (1.28), 4.251 (3.95), 4.268 (3.94), 4.286 (1.28), 7.153 (0.66), 7.160 (0.72), 7.175 (1.21), 7.180 (1.28), 7.194 (0.76), 7.200 (0.82), 7.326 (0.72), 7.332 (0.73), 7.352 (1.24), 7.357 (1.24), 7.376 (0.75), 7.382 (0.74), 7.540 (0.64), 7.561 (1.35), 7.579 (1.32), 7.600 (0.61), 8.558 (1.09), 9.597 (0.91).

Example 364 ethyl 1-(6-{[1-(cyclopropylmethyl)-3-(2,4-difluorophenyl)-4-methyl-1H-pyrazol-5-yl]amino}pyrimidin-4-yl)-3,5-dimethyl-1H-pyrazole-4-carboxylate

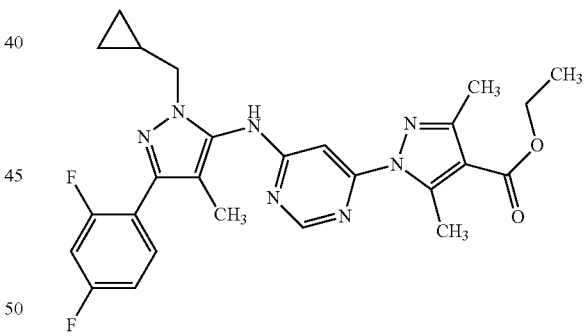

A microwave vial was charged with ethyl 1-(6-chloropyrimidin-4-yl)-3,5-dimethyl-1H-pyrazole-4-carboxylate (275 mg, 95% purity, 932 µmol), 1-(cyclopropylmethyl)-3-(2,4-difluorophenyl)-4-methyl-1H-pyrazol-5-amine (300 mg, 90% purity, 1.03 mmol) and sodium phenolate (119 mg, 1.03 mmol) and the contents were suspended in 1,4-dioxane (3.0 mL). The reaction mixture was degassed with Ar for 3 min. Tris(dibenzylideneacetone)dipalladium (17.1 mg, 18.6 µmol) and XantPhos (21.6 mg, 37.3 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (column: Chromatorex C18; 250*40 mm, 10 µM, flow 100 mL/min, gradient acetonitrile/water (containing 0.1% trifluoroacetic acid) 10/90 to 95/5) and further purified by flash column chromatography (SNAP Ultra 25 g, cyclohexane/ethyl acetate gradient) to yield the desired product (117 mg, 23% yield).

LC-MS (method 11): $R_t$=1.58 min; MS (ESIpos): m/z=508 [M+H]$^+$ $^1$H-NMR (400 MHz, dimethylsulfoxide-d6) δ [ppm]: −0.149 (0.33), −0.008 (2.67), 0.008 (2.03), 0.146 (0.29), 0.279 (0.69), 0.291 (2.86), 0.304 (3.12), 0.316 (0.87), 0.429 (2.63), 0.449 (2.79), 1.149 (0.23), 1.168 (0.40), 1.180 (0.72), 1.187 (0.69), 1.199 (1.07), 1.211 (0.67), 1.218 (0.68), 1.231 (0.49), 1.290 (4.66), 1.308 (9.61), 1.326 (4.74), 1.398 (11.27), 1.819 (9.11), 1.824 (9.09), 2.328 (0.48), 2.333 (0.42), 2.379 (4.01), 2.419 (0.42), 2.671 (0.40), 2.711 (0.22), 2.915 (16.00), 2.951 (0.27), 3.575 (0.18), 3.592 (0.39), 3.608 (0.18), 3.847 (2.43), 3.864 (2.42), 4.231 (1.35), 4.249 (4.22), 4.267 (4.23), 4.284 (1.41), 7.160 (0.69), 7.167 (0.76), 7.181 (1.39), 7.187 (1.50), 7.202 (0.86), 7.208 (0.92), 7.329 (0.74), 7.335 (0.76), 7.359 (1.27), 7.379 (0.79), 7.385 (0.79), 7.558 (0.60), 7.580 (1.33), 7.597 (1.29), 7.618 (0.61), 8.548 (0.73), 9.545 (0.36).

Example 365

4-[1-(cyclopropylmethyl)-4-methyl-5-{[6-(3-methyl-4-oxo-5,6-dihydrocyclopenta[c]pyrazol-1(4H)-yl)pyrimidin-4-yl]amino}-1H-pyrazol-3-yl]benzonitrile

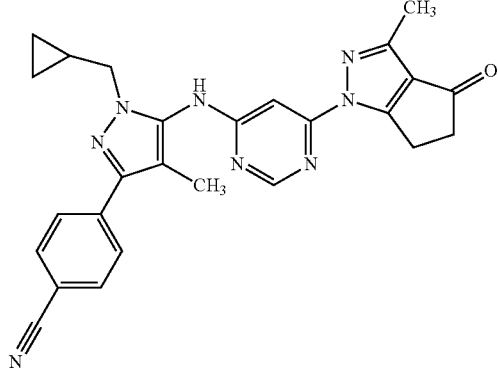 [SMILES: Cc1nn(-c2cc(Nc3c(C)c(-c4ccc(C#N)cc4)nn3CC3CC3)ncn2)c2c1C(=O)CC2]

1-(6-chloropyrimidin-4-yl)-3-methyl-5,6-dihydrocyclopenta[c]pyrazol-4(1H)-one (500 mg, 2.01 mmol) and sodium phenolate (257 mg, 2.21 mmol) were suspended in 1,4-dioxane (X mL). The reaction mixture was degassed with Ar for 3 min. Tris(dibenzylideneacetone)dipalladium (34.9 mg, 60.3 μmol), XantPhos (27.6 mg, 30.2 μmol) and 4-[5-amino-1-(cyclopropylmethyl)-4-methyl-1H-pyrazol-3-yl]benzonitrile (558 mg, 2.21 mmol) were added and the reaction mixture was degassed again for 1 min. The reaction mixture was heated at 90° C. overnight while vigorously stirring. After cooling to ambient temperature, the reaction mixture was diluted with water and extracted with ethyl acetate (3×).

The combined organic phase extracts were dried over sodium sulfate and concentrated. The residue was dissolved in dimethylsulfoxide (20 mL) purified by preparative HPLC (Kinetex C18 5 μm, 150×30 mm; water/acetonitrile gradient 65/35 to 5/95; flow: 75 mL/min, 500 μL injections every 10 min) to yield the desired product (230 mg, 22% yield).

LC-MS (method 9): $R_t$=1.03 min; MS (ESIpos): m/z=465 [M+H]$^+$ $^1$H-NMR (500 MHz, dimethylsulfoxide-d6) δ [ppm]: −0.120 (0.23), −0.007 (2.52), 0.007 (1.77), 0.117 (0.23), 0.305 (2.41), 0.313 (2.45), 0.435 (2.81), 0.451 (2.83), 1.182 (0.47), 1.191 (0.85), 1.197 (0.84), 1.206 (1.25), 1.216 (0.78), 1.221 (0.78), 1.231 (0.40), 2.070 (16.00), 2.074 (7.68), 2.306 (1.28), 2.359 (0.59), 2.363 (0.65), 2.366 (0.49), 2.520 (0.72), 2.523 (0.54), 2.633 (0.29), 2.636 (0.40), 2.640 (0.29), 2.813 (1.23), 2.939 (2.27), 2.948 (2.66), 2.954 (2.40), 2.958 (2.32), 3.165 (0.23), 3.175 (0.25), 3.339 (3.05), 3.344 (2.76), 3.350 (2.98), 3.354 (2.63), 3.359 (2.58), 3.874 (1.76), 7.910 (7.53), 8.518 (0.28), 9.608 (0.27).

Example 366

4-[4-({6-[4-(2-hydroxypropan-2-yl)-3,5-dimethyl-1H-pyrazol-1-yl]pyrimidin-4-yl}amino)-3,5-dimethyl-1H-pyrazol-1-yl]benzonitrile

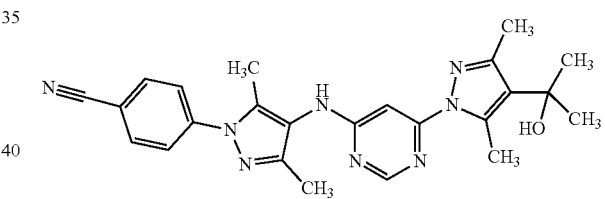

A solution of ethyl 1-(6-{[1-(4-cyanophenyl)-3,5-dimethyl-1H-pyrazol-4-yl]amino}pyrimidin-4-yl)-3,5-dimethyl-1H-pyrazole-4-carboxylate (193 mg, 423 μmol) in tetrahydrofuran (8.3 ml, 100 mmol) was treated at 0° C. with chloro(methyl)magnesium (490 μl, 3.0 M, 1.5 mmol) and stirred overnight at ambient temperature. The mixture was diluted with potassium sodium tartrate solution and water and extracted with ethyl acetate (3×). The combined organic phases were dried over Extrelut NT3 and concentrated under reduced pressure. The crude product was purified by preparative HPLC (method: column: Reprosil C18; 10 μm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) and (method 1) to yield 7.00 mg (4%) of the desired product.

LC-MS (method 10): $R_t$=1.54 min; MS (ESIpos): m/z=443 [M+H]$^+$ $^1$H-NMR (400 MHz, dimethylsulfoxide-d6) δ [ppm]: 1.464 (16.00), 2.105 (15.42), 2.263 (2.37), 2.289 (14.61), 2.328 (0.49), 2.720 (12.21), 4.838 (2.69), 7.804 (2.54), 7.825 (3.16), 7.975 (4.37), 7.997 (3.46), 8.399 (0.59), 8.933 (2.72).

Example 367 ethyl 1-(6-{[3-(4-chlorophenyl)-1,4-dimethyl-1H-pyrazol-5-yl]amino}pyrimidin-4-yl)-3,5-dimethyl-1H-pyrazole-4-carboxylate

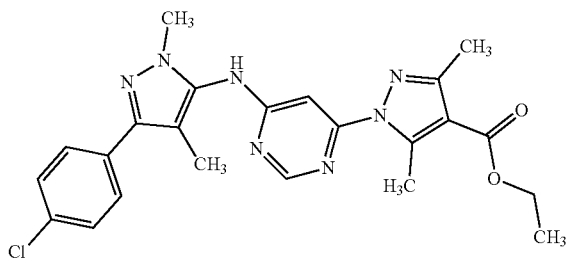 [SMILES: CCOC(=O)c1c(C)nn(-c2cc(Nc3c(C)c(-c4ccc(Cl)cc4)nn3C)ncn2)c1C]

A microwave vial was charged ethyl 1-(6-chloropyrimidin-4-yl)-3,5-dimethyl-1H-pyrazole-4-carboxylate (288 mg, 1.03 mmol), 3-(4-chlorophenyl)-1,4-dimethyl-1H-pyrazol-5-amine (250 mg, 1.13 mmol) and sodium phenolate (131 mg, 1.13 mmol) and the contents were suspended in 1,4-dioxane (5.0 ml, 58 mmol). The reaction mixture was degassed with Ar for 3 min. Tris(dibenzylidenaceton)dipalladium (12.2 mg, 13.3 µmol) and Xantphos (17.8 mg, 30.8 µmol) were added and the reaction mixture was degassed again for 1 min. The vial was sealed and heated at 85° C. overnight while vigorously stirring. After cooling to ambient temperature, the reaction mixture was filtered and purified by preparative HPLC (method 4) and (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (190 mg, 40%).

LC-MS (method 9): $R_t$=1.26 min; MS (ESIpos): m/z=466 [M+H]$^+$ $^1$H-NMR (400 MHz, dimethylsulfoxide-d6) δ [ppm]: −0.008 (0.40), 1.074 (0.64), 1.091 (1.32), 1.109 (0.66), 1.289 (0.69), 1.306 (7.46), 1.324 (3.69), 2.030 (16.00), 2.377 (2.71), 2.524 (0.40), 2.910 (13.93), 3.375 (0.69), 3.392 (0.66), 3.672 (8.98), 4.230 (1.08), 4.248 (3.28), 4.265 (3.24), 4.283 (1.04), 7.483 (3.85), 7.504 (4.80), 7.699 (3.48), 7.720 (2.89), 8.545 (0.50), 9.597 (0.96).

Example 368

2-[1-(6-{[1-(cyclopropylmethyl)-3-(2,4-difluorophenyl)-4-methyl-1H-pyrazol-5-yl]amino}pyrimidin-4-yl)-3,5-dimethyl-1H-pyrazol-4-yl]propan-2-ol

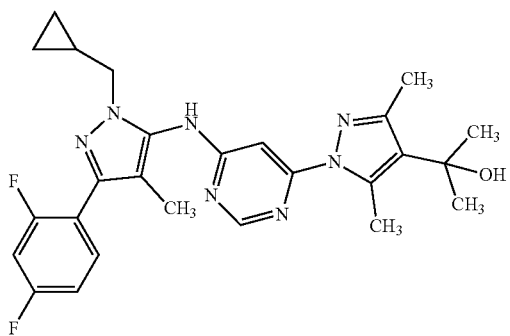 [SMILES: Cc1nn(-c2cc(Nc3c(C)c(-c4ccc(F)cc4F)nn3CC3CC3)ncn2)c(C)c1C(C)(C)O]

Under an argon atmosphere, ethyl 1-(6-{[1-(cyclopropylmethyl)-3-(2,4-difluorophenyl)-4-methyl-1H-pyrazol-5-yl]amino}pyrimidin-4-yl)-3,5-dimethyl-1H-pyrazole-4-carboxylate (80.0 mg, 158 µmol) was dissolved in tetrahydrofuran and the solution cooled to 0° C. A solution of bromo(methyl)magnesium (790 µl, 1.0 M, 790 µmol) was added dropwise and the reaction mixture was stirred overnight at ambient temperature. The reaction mixture was carefully quenched by addition of aqueous Na$_2$EDTA solution (10%) and extracted with ethyl acetate. The organic phase extract was dried over sodium sulfate and concentrated. The residue was purified by flash column chromatography (SNAP Ultra 10 g, cyclohexane/ethyl acetate gradient 95/5 to 5/95) to yield the desired product (6 mg, 7% yield).

LC-MS (method 11): $R_t$=1.38 min; MS (ESIneg): m/z=492 [M−H]$^−$ $^1$H-NMR (400 MHz, dimethylsulfoxide-d6) δ [ppm]: 0.275 (0.39), 0.288 (1.76), 0.300 (1.96), 0.426 (1.56), 0.446 (1.69), 1.157 (0.32), 1.164 (0.25), 1.175 (0.77), 1.183 (0.45), 1.194 (0.71), 1.213 (0.45), 1.233 (0.36), 1.398 (2.08), 1.468 (16.00), 1.812 (5.38), 1.818 (5.49), 1.988 (0.65), 2.273 (3.61), 2.328 (0.26), 2.469 (0.29), 2.670 (0.21), 2.746 (9.82), 2.894 (0.19), 3.589 (0.16), 3.841 (1.73), 3.859 (1.71), 4.020 (0.20), 4.038 (0.17), 4.857 (3.27), 7.157 (0.46), 7.163 (0.49), 7.178 (0.88), 7.184 (0.95), 7.199 (0.50), 7.205 (0.53), 7.327 (0.46), 7.333 (0.46), 7.354 (0.81), 7.377 (0.46), 7.382 (0.45), 7.555 (0.42), 7.576 (0.87), 7.593 (0.84), 7.615 (0.38), 8.469 (0.90), 9.369 (0.51).

Example 369

(±)-1-cyclopropyl-2-[5-{[6-(3,5-dimethyl-1H-pyrazol-1-yl)pyrimidin-4-yl]amino}-3-(4-fluorophenyl)-4-methyl-1H-pyrazol-1-yl]ethanol (Racemate)

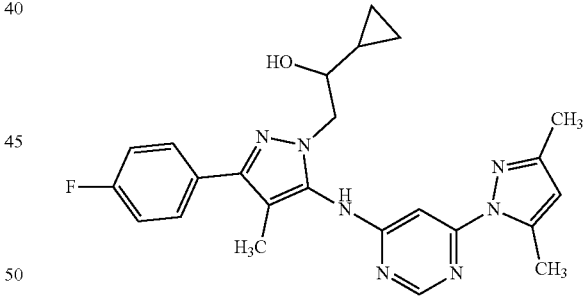

A microwave vial was charged with (±)-2-[5-amino-3-(4-fluorophenyl)-4-methyl-1H-pyrazol-1-yl]-1-cyclopropylethanol (racemate, 185 mg, 672 µmol), 4-chloro-6-(3,5-dimethyl-1H-pyrazol-1-yl)pyrimidine (154 mg, 739 µmol) and sodium phenolate (85.8 mg, 739 µmol) and the contents were suspended in 1,4-dioxane (2.3 mL). The reaction mixture was degassed with Ar for 3 min. Tris(dibenzylideneacetone)dipalladium (12.3 mg, 13.4 µmol) and XantPhos (15.6 mg, 26.9 µmol) were added and the reaction mixture was degassed again for 1 min. The vial was sealed and heated at 85° C. overnight while vigorously shaking. After cooling to ambient temperature, the reaction mixture was diluted with dimethylsulfoxide, filtered and purified by preparative HPLC (method 6) to yield the desired product (70 mg, 23% yield).

LC-MS (method 11): R$_t$=1.42 min; MS (ESIneg): m/z=446 [M−H]⁻

¹H-NMR (400 MHz, dimethylsulfoxide-d6) δ [ppm]: −0.149 (0.42), −0.008 (3.82), 0.008 (3.44), 0.031 (0.64), 0.146 (0.40), 0.179 (0.75), 0.187 (0.92), 0.200 (0.86), 0.253 (0.22), 0.274 (0.72), 0.289 (1.62), 0.308 (1.66), 0.744 (0.47), 0.756 (0.80), 0.775 (0.76), 2.003 (16.00), 2.166 (3.63), 2.328 (0.53), 2.332 (0.40), 2.367 (0.26), 2.523 (1.21), 2.628 (13.81), 2.665 (0.46), 2.670 (0.56), 2.674 (0.42), 2.710 (0.29), 3.988 (1.63), 4.890 (0.85), 6.140 (2.78), 7.245 (2.10), 7.267 (4.36), 7.289 (2.40), 7.700 (1.68), 7.714 (2.11), 7.721 (2.05), 7.735 (1.64), 8.461 (0.83), 9.270 (1.04).

Example 370

1-cyclopropyl-2-[5-{[6-(3,5-dimethyl-1H-pyrazol-1-yl)pyrimidin-4-yl]amino}-3-(4-fluorophenyl)-4-methyl-1H-pyrazol-1-yl]ethanol

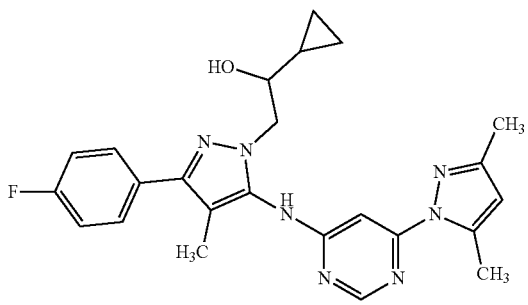 [SMILES: Cc1cc(C)n(-c2cc(Nc3c(C)c(-c4ccc(F)cc4)nn3CC(O)C3CC3)ncn2)n1]

Obtained from separation of the enantiomers of a racemic sample of (±)-1-cyclopropyl-2-[5-{[6-(3,5-dimethyl-1H-pyrazol-1-yl)pyrimidin-4-yl]amino}-3-(4-fluorophenyl)-4-methyl-1H-pyrazol-1-yl]ethanol (racemate, 40.6 mg dissolved in 2-propanol/dichloromethane 1:1, 4 mL) by preparative HPLC (Daicel Chiralpak IC 5 µm, 250×20 mm, flow: 15 mL/min, isocratic: 2-propanol/n-heptane 20/80) to yield the title compound as the first eluting enantiomer (10.8 mg, 27% from racemate).

LC-MS (method 11): Rt=1.43 min; MS (ESIneg): m/z=446 [M−H]⁻

Chiral HPLC (Daicel IC-3 3 µm, 50×4.6 mm, isocratic i-hexane/2-propanol 80/20): Rt=1.17 min, >99% ee ¹H-NMR (400 MHz, dimethylsulfoxide-d6) δ [ppm]: 0.029 (0.94), 0.180 (0.82), 0.189 (1.01), 0.201 (0.97), 0.289 (1.97), 0.309 (1.99), 0.756 (0.89), 1.238 (0.17), 1.996 (16.00), 2.165 (4.58), 2.328 (0.44), 2.366 (0.45), 2.624 (15.02), 2.670 (0.53), 2.710 (0.46), 3.336 (1.89), 3.352 (0.74), 3.989 (2.11), 4.004 (1.89), 6.132 (3.31), 7.241 (2.22), 7.263 (4.70), 7.286 (2.55), 7.696 (1.89), 7.710 (2.34), 7.717 (2.34), 7.731 (1.82), 8.440 (0.97).

Example 371

1-cyclopropyl-2-[5-{[6-(3,5-dimethyl-1H-pyrazol-1-yl)pyrimidin-4-yl]amino}-3-(4-fluorophenyl)-4-methyl-1H-pyrazol-1-yl]ethanol

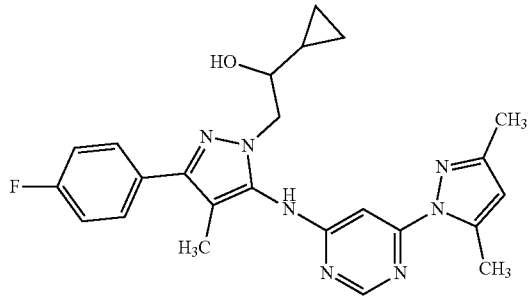 [SMILES: Cc1cc(C)n(-c2cc(Nc3c(C)c(-c4ccc(F)cc4)nn3CC(O)C3CC3)ncn2)n1]

Obtained from separation of the enantiomers of a racemic sample of (±)-1-cyclopropyl-2-[5-{[6-(3,5-dimethyl-1H-pyrazol-1-yl)pyrimidin-4-yl]amino}-3-(4-fluorophenyl)-4-methyl-1H-pyrazol-1-yl]ethanol (racemate, 40.6 mg dissolved in 2-propanol/dichloromethane 1:1, 4 mL) by preparative HPLC (Daicel Chiralpak IC 5 µm, 250×20 mm, flow: 15 mL/min, isocratic: 2-propanol/n-heptane 20/80) to yield the title compound as the second eluting enantiomer (11.2 mg, 28% from racemate).

LC-MS (method 11): Rt=1.43 min; MS (ESIneg): m/z=446 [M−H]⁻

Chiral HPLC (Daicel IC-3 3 µm, 50×4.6 mm, isocratic i-hexane/2-propanol 80/20): Rt=2.27 min, 98.7% ee ¹H-NMR (400 MHz, dimethylsulfoxide-d6) δ [ppm]: 0.178 (0.81), 0.188 (0.97), 0.201 (0.93), 0.288 (1.70), 0.308 (1.73), 0.756 (0.81), 0.775 (0.83), 1.105 (1.17), 1.120 (1.11), 1.136 (0.25), 1.154 (0.54), 1.172 (0.30), 1.234 (0.25), 2.003 (16.00), 2.166 (3.99), 2.328 (0.33), 2.367 (0.29), 2.628 (14.50), 2.669 (0.46), 2.710 (0.39), 2.911 (0.22), 2.929 (0.22), 3.344 (1.05), 3.988 (1.71), 4.885 (1.23), 4.898 (1.22), 6.140 (3.21), 7.245 (2.20), 7.267 (4.56), 7.289 (2.48), 7.700 (1.77), 7.714 (2.26), 7.721 (2.20), 7.735 (1.82), 8.463 (1.10), 9.270 (1.48).

Example 372

N-[1-(cyclopropylmethyl)-3-(4-fluorophenyl)-4-methyl-1H-pyrazol-5-yl]-6-[3,5-dimethyl-4-(5-methyl-1,3,4-oxadiazol-2-yl)-1H-pyrazol-1-yl]pyrimidin-4-amine

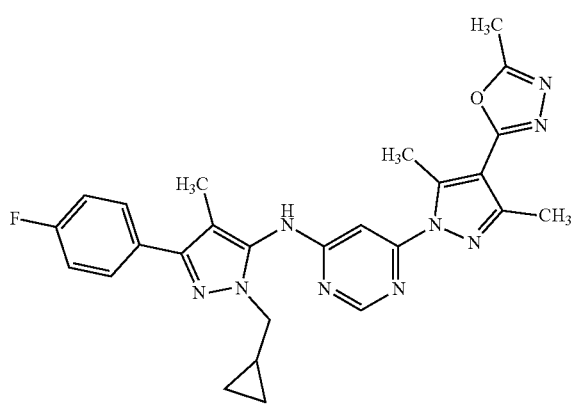 [SMILES: Cc1nnc(-c2c(C)nn(-c3cc(Nc4c(C)c(-c5ccc(F)cc5)nn4CC4CC4)ncn3)c2C)o1]

A solution of N'-acetyl-1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbohydrazide (410 mg, 792 μmol) in tetrahydrofuran (40 ml, 490 mmol) was treated with Burges reagent (264 mg, 1.11 mmol) and stirred one hour at room temperature. Additional 1.4 equivalents of Burgess reagent (264 mg, 1.11 mmol) were added and it was stirred again for one hour. The mixture was diluted with water and extracted with dichloromethane (3×). The combined organic phases were dried over magnesium sulfate and concentrated under reduced pressure. The crude product was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 259 mg (65%) of the desired product.

LC-MS (method 10): $R_t$=2.05 min; MS (ESIpos): m/z=500 [M+H]$^+$ $^1$H-NMR (500 MHz, dimethylsulfoxide-d6) δ [ppm]: 0.304 (2.87), 0.314 (2.91), 0.435 (3.11), 0.451 (3.15), 1.183 (0.50), 1.193 (0.89), 1.199 (0.88), 1.208 (1.35), 1.218 (0.81), 1.223 (0.81), 1.232 (0.48), 2.021 (15.22), 2.571 (16.00), 2.970 (15.84), 3.845 (2.10), 3.857 (2.03), 5.755 (0.99), 7.260 (2.54), 7.277 (5.04), 7.295 (2.73), 7.736 (2.13).

Example 373

4-[1-(cyclopropylmethyl)-5-({6-[3,5-dimethyl-4-(trifluoromethyl)-1H-pyrazol-1-yl]pyrimidin-4-yl}amino)-4-methyl-1H-pyrazol-3-yl]benzonitrile

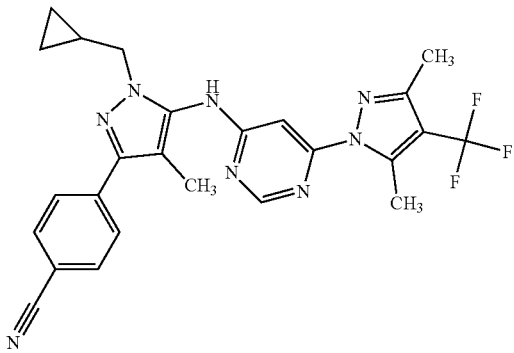 [SMILES: Cc1nn(-c2cc(Nc3c(C)c(-c4ccc(C#N)cc4)nn3CC3CC3)ncn2)c(C)c1C(F)(F)F]

4-chloro-6-[3,5-dimethyl-4-(trifluoromethyl)-1H-pyrazol-1-yl]pyrimidine (500 mg, 95% purity, 1.72 mmol) and sodium phenolate (219 mg, 1.89 mmol) were suspended in 1,4-dioxane (5.5 mL). The reaction mixture was degassed with Ar for 3 min. Tris(dibenzylideneacetone)dipalladium (47.2 mg, 51.5 μmol), XantPhos (59.6 mg, 103 μmol) and 4-[5-amino-1-(cyclopropylmethyl)-4-methyl-1H-pyrazol-3-yl]benzonitrile (530 mg, 90% purity, 1.89 mmol) were added and the reaction mixture was degassed again for 1 min. The reaction mixture was heated at 90° C. for 3 h while vigorously stirring. After cooling to ambient temperature, the reaction mixture was diluted with water and aqueous hydrochloric acid (1 N) and extracted with ethyl acetate. The organic phase extract was dried over sodium sulfate and concentrated. The residue was purified by flash column chromatography (SNAP Ultra 25 g, cyclohexane/ethyl acetate gradient) to yield the desired product (427 mg, 49% yield).

LC-MS (method 9): $R_t$=1.28 min; MS (ESIpos): m/z=493 [M+H]$^+$ $^1$H-NMR (600 MHz, dimethylsulfoxide-d6) δ [ppm]: 0.310 (2.03), 0.318 (2.12), 0.443 (2.27), 0.456 (2.34), 1.187 (0.23), 1.191 (0.33), 1.200 (0.64), 1.204 (0.62), 1.212 (0.99), 1.220 (0.58), 1.225 (0.62), 1.233 (0.34), 1.237 (0.24), 1.346 (0.26), 2.067 (16.00), 2.165 (0.35), 2.305 (1.17), 2.337 (0.54), 2.386 (0.18), 2.760 (6.87), 3.873 (1.58), 3.883 (1.56), 7.888 (1.47), 7.902 (7.16), 7.910 (4.24), 7.924 (1.10), 7.947 (0.16), 7.961 (0.18), 8.026 (0.30), 8.040 (0.21), 8.540 (0.25), 9.595 (0.20).

Example 374

(±)-1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-2,2,2-trifluoroethanol (Racemate)

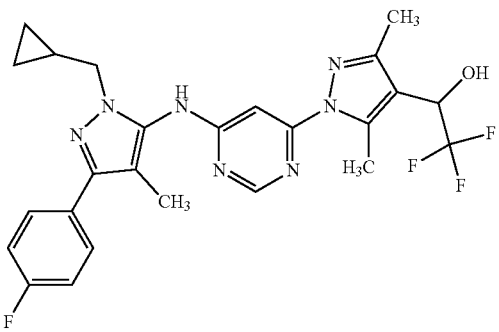 [SMILES: Cc1nn(-c2cc(Nc3c(C)c(-c4ccc(F)cc4)nn3CC3CC3)ncn2)c(C)c1C(O)C(F)(F)F]

Molecular Sieves (4 Å) were placed in a round-bottom flask and dried in a vacuum drying-oven overnight at 120° C. After cooling to ambient temperature, tetrabutylammonium fluoride trihydrate (179 mg, 640 μmol) and toluene (5.0 mL) were added and the suspension stirred for 30 min. A solution of 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbaldehyde (95.0 mg, 213 μmol) in dichloromethane (1.0 mL) was then added, the mixture was stirred for 5 min and cooled to 0° C. Trimethyl(trifluoromethyl)silane (160 μL, 1.1 mmol) was then added and stirred at ambient temperature for 1.5 h. Furthermore, trimethyl(trifluoromethyl)silane (80 μL, 0.55 mmol), tetrabutylammonium fluoride trihydrate (70 mg, 250 μmol) and dichloromethane (1 mL) were added and the reaction mixture stirred for another 1 h. The reaction mixture was diluted with ethyl acetate and water, the molecular sieves removed by filtration and washed further with ethyl acetate. After separation of the layers in the filtrate, the aqueous phase was extracted again with ethyl acetate and the combined organic phase extracts were dried over sodium sulfate and concentrated. The residue was purified by flash column chromatography (SNAP Ultra 25 g, cyclohexane/ethyl acetate gradient 88/12 to 30/70) to yield the desired product (43 mg, 39% yield).

LC-MS (method 11): $R_t$=1.43 min; MS (ESIpos): m/z=516 [M+H]$^+$ $^1$H-NMR (500 MHz, dimethylsulfoxide-d6) δ [ppm]: −0.007 (0.65), 0.006 (0.41), 0.294 (2.49), 0.303 (2.51), 0.425 (2.66), 0.441 (2.68), 1.161 (2.53), 1.176 (5.23), 1.181 (0.88), 1.190 (3.06), 1.197 (1.18), 1.206 (0.69), 1.213 (0.69), 1.221 (0.36), 1.227 (0.27), 1.236 (0.19), 1.398 (6.28), 1.967

(1.79), 1.989 (9.25), 2.008 (15.94), 2.238 (1.76), 2.363 (0.20), 2.367 (0.16), 2.637 (0.20), 2.675 (16.00), 2.943 (0.66), 3.801 (0.36), 3.830 (1.94), 3.843 (1.89), 4.009 (0.69), 4.023 (2.06), 4.038 (2.03), 4.052 (0.67), 5.161 (0.67), 5.754 (11.43), 6.721 (1.03), 7.177 (0.19), 7.193 (0.21), 7.244 (0.38), 7.255 (2.46), 7.262 (1.15), 7.273 (4.88), 7.291 (2.62), 7.446 (0.24), 7.673 (0.26), 7.684 (0.31), 7.690 (0.31), 7.702 (0.38), 7.718 (1.39), 7.729 (1.90), 7.744 (1.34), 8.486 (0.44), 9.431 (0.35).

Example 375

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-2,2,2-trifluoroethanol

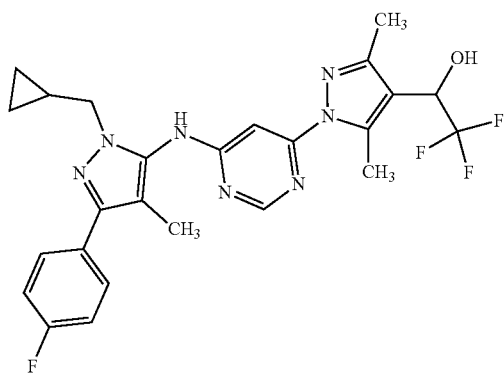 [SMILES: Cc1nn(-c2cc(Nc3c(C)c(-c4ccc(F)cc4)nn3CC3CC3)ncn2)c(C)c1C(O)C(F)(F)F]

Obtained from separation of the enantiomers of a racemic sample of (±)-1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-2,2,2-trifluoroethanol (racemate, 118.0 mg dissolved in 2-propanol/dichloromethane/n-Heptane 3:2:1, 6 mL) by preparative HPLC (Daicel Chiralpak IA 5 µm, 250×20 mm, flow: 15 mL/min, 40° C. isocratic: 2-propanol/n-heptane 10/90, 350 µL per injection) to yield the title compound as the first eluting enantiomer (42.5 mg, 36% from racemate).

LC-MS (method 10): $R_t$=2.09 min; MS (ESIpos): m/z=516 [M+H]$^+$

Chiral HPLC (Daicel IC-3 5 µm, 250×4.6 mm, flow: 1.0 mL/min isocratic i-hexane/2-propanol 90/10): Rt=9.198 min, 97% ee $^1$H-NMR (600 MHz, dimethylsulfoxide-d6) δ [ppm]: 0.005 (0.56), 0.293 (2.25), 0.301 (2.35), 0.426 (2.45), 0.440 (2.50), 1.184 (0.66), 1.188 (0.66), 1.196 (1.07), 1.208 (0.61), 2.007 (15.49), 2.237 (1.64), 2.384 (0.41), 2.673 (16.00), 3.830 (1.79), 3.841 (1.79), 5.155 (0.72), 6.679 (1.64), 6.687 (1.64), 7.254 (2.15), 7.269 (4.40), 7.284 (2.35), 7.718 (1.23), 7.728 (1.74), 7.740 (1.23).

Example 376

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-2,2,2-trifluoroethanol

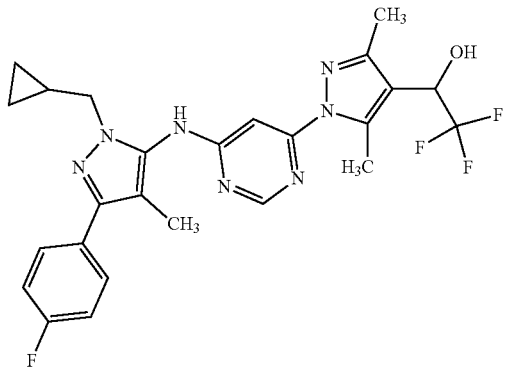 [SMILES: Cc1nn(-c2cc(Nc3c(C)c(-c4ccc(F)cc4)nn3CC3CC3)ncn2)c(C)c1C(O)C(F)(F)F]

Obtained from separation of the enantiomers of a racemic sample of (±)-1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-2,2,2-trifluoroethanol (racemate, 118.0 mg dissolved in 2-propanol/dichloromethane/n-Heptane 3:2:1, 6 mL) by preparative (Daicel Chiralpak IA 5 µm, 250×20 mm, flow: 15 mL/min, 40° C. isocratic: 2-propanol/n-heptane 10/90, 350 µL per injection) to yield the title compound as the second eluting enantiomer (45.6 mg, 39% from racemate).

LC-MS (method 10): $R_t$=2.09 min; MS (ESIpos): m/z=516 [M+H]$^+$

Chiral HPLC (Daicel IC-3 5 µm, 250×4.6 mm, flow: 1.0 mL/min, isocratic i-hexane/2-propanol 90/10): Rt=11.10 min, 99% ee $^1$H-NMR (600 MHz, dimethylsulfoxide-d6) δ [ppm]: 0.005 (0.57), 0.284 (1.13), 0.293 (2.51), 0.301 (2.55), 0.426 (2.79), 0.440 (2.75), 1.176 (0.48), 1.184 (0.77), 1.188 (0.77), 1.196 (1.17), 1.209 (0.69), 1.966 (4.08), 2.007 (15.52), 2.237 (1.66), 2.384 (0.40), 2.673 (16.00), 2.941 (0.93), 3.801 (0.69), 3.813 (0.77), 3.830 (1.94), 3.841 (1.90), 5.157 (0.73), 6.678 (1.74), 6.687 (1.78), 7.186 (0.40), 7.243 (0.61), 7.254 (2.51), 7.258 (2.22), 7.269 (4.77), 7.284 (2.42), 7.443 (0.57), 7.673 (0.57), 7.682 (0.65), 7.687 (0.65), 7.697 (0.57), 7.717 (1.33), 7.727 (1.86), 7.740 (1.33).

Example 377

2-{1-[6-({1,4-dimethyl-3-[4-(trifluoromethoxy)phenyl]-1H-pyrazol-5-yl}amino)pyrimidin-4-yl]-3,5-dimethyl-1H-pyrazol-4-yl}propan-2-ol

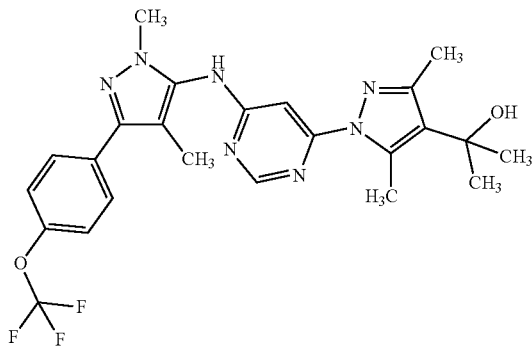 [SMILES: Cc1nn(-c2cc(Nc3c(C)c(-c4ccc(OC(F)(F)F)cc4)nn3C)ncn2)c(C)c1C(C)(C)O]

Under an argon atmosphere, ethyl 1-[6-({1,4-dimethyl-3-[4-(trifluoromethoxy)phenyl]-1H-pyrazol-5-yl}amino)pyrimidin-4-yl]-3,5-dimethyl-1H-pyrazole-4-carboxylate (115 mg, 223 µmol) was dissolved in tetrahydrofuran (4.4 mL) and the solution was cooled to 0° C. A solution of bromo(methyl)magnesium (1.1 ml, 1.0 M, 1.1 mmol) was added dropwise and the reaction mixture was stirred overnight at ambient temperature. The reaction mixture was carefully quenched by addition of aqueous Na$_2$EDTA solution (10%) and ethyl acetate was added. The organic phase extract was dried over sodium sulfate and concentrated. The residue was purified by flash column chromatography (SNAP Ultra 25 g, cyclohexane/ethyl acetate gradient 95/5 to 5/95) to yield the desired product (20 mg, 18% yield).

LC-MS (method 10): R$_t$=2.06 min; MS (ESIpos): m/z=502 [M+H]$^+$ $^1$H-NMR (400 MHz, dimethylsulfoxide-d6) δ [ppm]: −0.008 (0.91), 0.008 (0.77), 1.157 (0.42), 1.175 (0.80), 1.193 (0.41), 1.235 (0.29), 1.398 (2.92), 1.468 (16.00), 1.909 (0.54), 1.988 (1.24), 2.037 (10.99), 2.272 (2.94), 2.328 (0.24), 2.524 (0.48), 2.670 (0.21), 2.744 (11.24), 3.673 (8.09), 4.021 (0.29), 4.039 (0.30), 4.859 (3.46), 7.417 (1.95), 7.438 (2.18), 7.796 (2.73), 7.818 (2.45), 8.472 (0.74), 9.424 (1.56).

Example 378

2-[1-(6-{[3-(2,4-difluorophenyl)-1,4-dimethyl-1H-pyrazol-5-yl]amino}pyrimidin-4-yl)-3,5-dimethyl-1H-pyrazol-4-yl]propan-2-ol

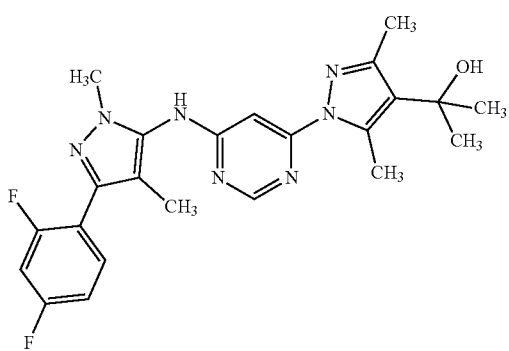 [SMILES: Cc1nn(-c2cc(Nc3c(C)c(-c4ccc(F)cc4F)nn3C)ncn2)c(C)c1C(C)(C)O]

Under an argon atmosphere, ethyl 1-(6-{[3-(2,4-difluorophenyl)-1,4-dimethyl-1H-pyrazol-5-yl]amino}pyrimidin-4-yl)-3,5-dimethyl-1H-pyrazole-4-carboxylate (259 mg, 554 µmol) was dissolved in tetrahydrofuran (11 mL) and the solution was cooled to 0° C. A solution of bromo(methyl)magnesium (2.8 ml, 1.0 M, 2.8 mmol) was added dropwise and the reaction mixture was stirred overnight at ambient temperature. The reaction mixture was carefully quenched by addition of aqueous Na$_2$EDTA solution (10%) and ethyl acetate was added. The organic phase was dried over sodium sulfate and concentrated.

The residue was purified by flash column chromatography (SNAP Ultra 25 g, cyclohexane/ethyl acetate gradient 95/5 to 5/95) to yield the desired product (17 mg, 7% yield).

LC-MS (method 10): R$_t$=1.81 min; MS (ESIpos): m/z=454 [M+H]$^+$ $^1$H-NMR (400 MHz, dimethylsulfoxide-d6) δ [ppm]: −0.008 (1.64), 0.008 (1.85), 1.157 (0.99), 1.175 (2.00), 1.193 (1.03), 1.471 (16.00), 1.816 (4.76), 1.821 (5.54), 1.988 (3.56), 2.279 (4.09), 2.328 (0.41), 2.434 (1.33), 2.471 (3.74), 2.670 (0.43), 2.747 (9.93), 2.895 (4.06), 3.671 (7.28), 3.681 (3.06), 4.021 (0.85), 4.038 (0.84), 4.861 (3.32), 7.157 (0.54), 7.176 (0.97), 7.197 (0.58), 7.330 (0.53), 7.355 (0.96), 7.374 (0.52), 7.380 (0.54), 7.536 (0.46), 7.558 (1.04), 7.576 (0.94), 7.596 (0.42), 8.479 (1.05), 9.420 (1.06).

Example 379

2-{1-[6-({1,4-dimethyl-3-[4-(trifluoromethyl)phenyl]-1H-pyrazol-5-yl}amino)pyrimidin-4-yl]-3,5-dimethyl-1H-pyrazol-4-yl}propan-2-ol

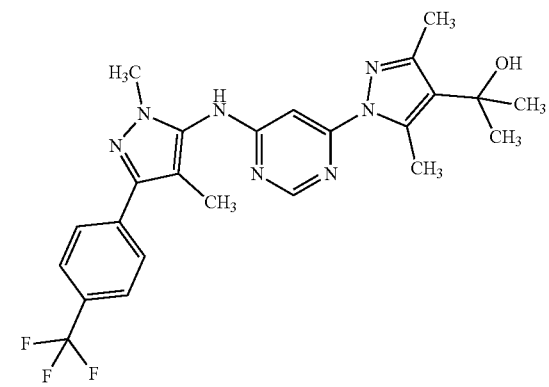 [SMILES: Cc1nn(-c2cc(Nc3c(C)c(-c4ccc(C(F)(F)F)cc4)nn3C)ncn2)c(C)c1C(C)(C)O]

Under an argon atmosphere, ethyl 1-[6-({1,4-dimethyl-3-[4-(trifluoromethyl)phenyl]-1H-pyrazol-5-yl}amino)pyrimidin-4-yl]-3,5-dimethyl-1H-pyrazole-4-carboxylate (170 mg, 340 µmol) was dissolved in tetrahydrofuran and the solution cooled to 0° C. A solution of bromo(methyl)magnesium (1.7 ml, 1.0 M, 1.7 mmol) was added dropwise and the reaction mixture was stirred overnight at ambient temperature. The reaction mixture was carefully quenched by addition of aqueous Na$_2$EDTA solution (10%) and ethyl acetate was added. The organic phase was separated, dried over sodium sulfate and concentrated. The residue was purified by flash column chromatography (SNAP Ultra 25 g, cyclohexane/ethyl acetate gradient 95/5 to 5/95) to yield the desired product (90 mg, 54% yield).

LC-MS (method 10): R$_t$=2.03 min; MS (ESIpos): m/z=486 [M+H]$^+$ $^1$H-NMR (400 MHz, dimethylsulfoxide-d6) δ [ppm]: −0.008 (0.80), 0.008 (0.88), 1.157 (0.98), 1.175 (1.98), 1.193 (1.01), 1.235 (0.17), 1.398 (0.80), 1.470 (16.00), 1.989 (3.49), 2.071 (10.90), 2.274 (2.96), 2.328 (0.27), 2.671 (0.24), 2.746 (11.21), 2.893 (0.17), 3.695 (8.24), 4.003 (0.28), 4.021 (0.84), 4.039 (0.85), 4.056 (0.29), 4.861 (3.64), 7.781 (2.05), 7.802 (2.82), 7.913 (2.48), 7.934 (1.83), 8.475 (0.88), 9.451 (1.60).

Example 380

2-[1-(6-{[1-(cyclopropylmethyl)-4-methyl-3-(pyridin-4-yl)-1H-pyrazol-5-yl]amino}pyrimidin-4-yl)-3,5-dimethyl-1H-pyrazol-4-yl]propan-2-ol

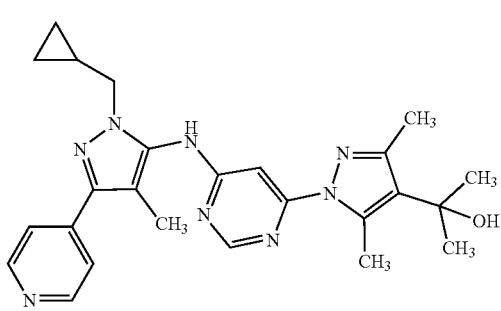 [SMILES: Cc1nn(-c2cc(Nc3c(C)c(-c4ccncc4)nn3CC3CC3)ncn2)c(C)c1C(C)(C)O]

Under an argon atmosphere, ethyl 1-(6-{[1-(cyclopropylmethyl)-4-methyl-3-(pyridin-4-yl)-1H-pyrazol-5-yl]amino}pyrimidin-4-yl)-3,5-dimethyl-1H-pyrazole-4-carboxylate (120 mg, 254 µmol) was dissolved in tetrahydrofuran and the solution cooled to 0° C. A solution of bromo(methyl)magnesium (2.5 ml, 1.0 M, 2.5 mmol) was added dropwise and the reaction mixture was stirred overnight at ambient temperature. As low conversion was observed, a second aliquot of bromo(methyl)magnesium (2.5 ml, 1.0 M, 2.5 mmol) was added. After 3 h, conversion was still low and a solution of chloro(methyl)magnesium (420 µl, 3.0 M, 1.3 mmol) was added. The reaction mixture was allowed to stir overnight. The reaction mixture was carefully quenched by addition of aqueous Na$_2$EDTA solution (10%) and ethyl acetate was added. The organic phase was separated, dried over sodium sulfate and concentrated. The residue was purified by flash column chromatography (SNAP Ultra 25 g, cyclohexane/ethyl acetate gradient 95/5 to 5/95, followed by dichloromethane/methanol 4:1 isocratic) to yield the desired product (20 mg, 16% yield).

LC-MS (method 11): R$_t$=0.92 min; MS (ESIpos): m/z=459 [M+H]$^+$ $^1$H-NMR (400 MHz, dimethylsulfoxide-d6) δ [ppm]: −0.008 (2.50), 0.008 (2.12), 0.308 (2.34), 0.318 (2.61), 0.436 (2.21), 0.454 (2.36), 1.175 (0.50), 1.210 (1.00), 1.234 (0.93), 1.465 (16.00), 1.908 (1.36), 1.988 (0.47), 2.076 (12.83), 2.168 (1.23), 2.270 (2.65), 2.297 (1.40), 2.328 (0.78), 2.367 (0.44), 2.632 (0.45), 2.670 (0.78), 2.691 (0.48), 2.711 (0.56), 2.743 (12.49), 3.865 (2.16), 3.883 (2.24), 4.857 (3.34), 7.403 (0.45), 7.425 (0.45), 7.687 (3.33), 7.702 (3.57), 8.462 (0.67), 8.606 (3.98), 8.621 (4.24), 9.411 (0.79).

Example 381

N-[1-(cyclopropylmethyl)-3-(4-fluorophenyl)-4-methyl-1H-pyrazol-5-yl]-6-[3,5-dimethyl-4-(trifluoromethyl)-1H-pyrazol-1-yl]pyrimidin-4-amine

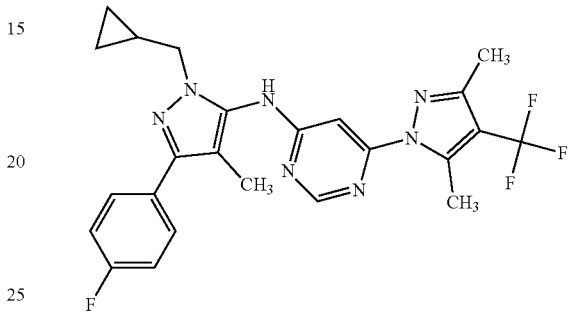

A microwave vial was charged with 4-chloro-6-[3,5-dimethyl-4-(trifluoromethyl)-1H-pyrazol-1-yl]pyrimidine (97.1 mg, 95% purity, 334 µmol) and 1-(cyclopropylmethyl)-3-(4-fluorophenyl)-4-methyl-1H-pyrazol-5-amine (100 mg, 90% purity, 367 µmol) and the contents were suspended in 1,4-dioxane (1.1 mL). The reaction mixture was degassed with Ar for 3 min. Tris(dibenzylideneacetone)dipalladium (6.11 mg, 6.67 µmol) and XantPhos (7.72 mg, 13.3 µmol) were added and the reaction mixture was degassed again for 1 min. Finally, sodium phenolate (42.6 mg, 367 µmol) was added to the reaction mixture. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 8) and further by flash column chromatography (SNAP Ultra 10 g, cyclohexane/ethyl acetate 1:2) to yield the desired product (41 mg, 24% yield).

LC-MS (method 10): R$_t$=2.54 min; MS (ESIpos): m/z=486 [M+H]$^+$ $^1$H-NMR (400 MHz, dimethylsulfoxide-d6) δ [ppm]: −0.008 (1.04), 0.008 (0.89), 0.293 (2.35), 0.305 (2.59), 0.426 (2.45), 0.446 (2.62), 1.165 (0.34), 1.177 (0.65), 1.184 (0.63), 1.196 (0.98), 1.208 (0.60), 1.215 (0.61), 1.227 (0.31), 2.010 (16.00), 2.031 (0.29), 2.300 (1.84), 2.319 (4.35), 2.322 (4.21), 2.367 (0.23), 2.524 (0.57), 2.671 (0.28), 2.675 (0.21), 2.759 (7.87), 2.779 (3.45), 2.782 (3.37), 3.832 (2.04), 3.849 (2.02), 7.252 (2.23), 7.274 (5.03), 7.289 (2.16), 7.292 (2.23), 7.296 (2.72), 7.319 (1.70), 7.321 (1.76), 7.340 (0.86), 7.359 (0.55), 7.488 (1.14), 7.509 (1.37), 7.523 (0.33), 7.528 (0.74), 7.712 (1.44), 7.726 (1.89), 7.746 (1.31), 8.541 (0.34), 8.776 (1.22), 8.778 (1.20), 9.574 (0.31).

Example 382

6-[3,5-dimethyl-4-(trifluoromethyl)-1H-pyrazol-1-yl]-N-[3-(4-fluorophenyl)-1,4-dimethyl-1H-pyrazol-5-yl]pyrimidin-4-amine

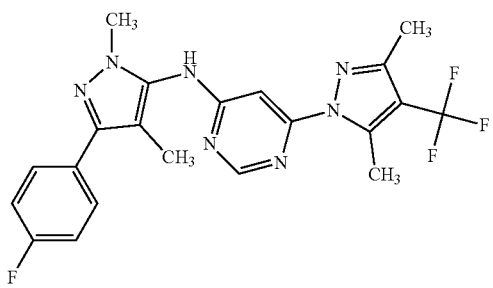 [SMILES: Cc1nn(-c2cc(Nc3c(C)c(-c4ccc(F)cc4)nn3C)ncn2)c(C)c1C(F)(F)F]

A microwave vial was charged with 4-chloro-6-[3,5-dimethyl-4-(trifluoromethyl)-1H-pyrazol-1-yl]pyrimidine (116 mg, 95% purity, 399 µmol) and 3-(4-fluorophenyl)-1,4-dimethyl-1H-pyrazol-5-amine (100 mg, 90% purity, 439 µmol) and the contents were suspended in 1,4-dioxane (1.3 mL). The reaction mixture was degassed with Ar for 3 min. Tris(dibenzylideneacetone)dipalladium (7.30 mg, 7.97 mol) and XantPhos (9.23 mg, 15.9 µmol) were added and the reaction mixture was degassed again for 1 min. Finally, sodium phenolate (50.9 mg, 439 µmol) was added to the reaction mixture. The vial was sealed and heated at 85° C. overnight while vigorously shaking. After cooling to ambient temperature, the reaction mixture was diluted with dimethylsulfoxide, filtered and purified by preparative HPLC (method 8) and further by flash column chromatography (SNAP Ultra 10 g, cyclohexane/ethyl acetate gradient 88/12 to 0:100) to yield the desired product (41 mg, 24% yield).

LC-MS (method 10): $R_t$=2.34 min; MS (ESIpos): m/z=446 [M+H]$^+$ $^1$H-NMR (400 MHz, dimethylsulfoxide-d6) δ [ppm]: 1.157 (0.64), 1.175 (1.38), 1.193 (0.68), 1.399 (0.16), 1.989 (2.63), 2.018 (16.00), 2.074 (0.20), 2.306 (2.43), 2.367 (0.30), 2.670 (0.54), 2.710 (0.28), 2.760 (7.37), 3.666 (8.40), 4.021 (0.61), 4.038 (0.61), 4.057 (0.21), 7.245 (1.92), 7.267 (3.94), 7.289 (2.17), 7.694 (1.54), 7.708 (1.91), 7.729 (1.43), 8.552 (0.62), 9.622 (0.67).

Example 383

6-[3,5-dimethyl-4-(trifluoromethyl)-1H-pyrazol-1-yl]-N-[5-(4-fluorophenyl)-1,4-dimethyl-1H-pyrazol-3-yl]pyrimidin-4-amine

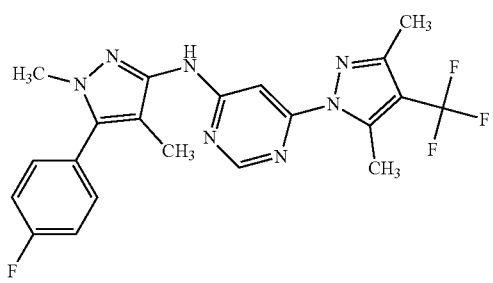 [SMILES: Cc1nn(-c2cc(Nc3nn(C)c(-c4ccc(F)cc4)c3C)ncn2)c(C)c1C(F)(F)F]

A microwave vial was charged with 4-chloro-6-[3,5-dimethyl-4-(trifluoromethyl)-1H-pyrazol-1-yl]pyrimidine (116 mg, 95% purity, 399 µmol) and 5-(4-fluorophenyl)-1,4-dimethyl-1H-pyrazol-3-amine (100 mg, 90% purity, 439 µmol) and the contents were suspended in 1,4-dioxane (1.3 mL). The reaction mixture was degassed with Ar for 3 min. Tris(dibenzylideneacetone)dipalladium (7.30 mg, 7.97 µmol) and XantPhos (9.23 mg, 15.9 µmol) were added and the reaction mixture was degassed again for 1 min. Finally, sodium phenolate (50.9 mg, 439 µmol) was added, the vial was sealed and heated at 85° C. overnight while vigorously shaking. After cooling to ambient temperature, the reaction mixture was filtered and concentrated. The residue was redissolved in dimethylsulfoxide and purified by preparative HPLC (method X) to yield the desired product (20 mg, 11% yield).

LC-MS (method 9): $R_t$=1.27 min; MS (ESIpos): m/z=446 [M+H]$^+$ $^1$H-NMR (400 MHz, dimethylsulfoxide-d6) δ [ppm]: −0.008 (1.70), 0.008 (1.84), 1.861 (10.88), 2.019 (0.77), 2.311 (7.12), 2.313 (7.35), 2.739 (7.22), 2.742 (7.44), 3.666 (0.47), 3.686 (16.00), 7.358 (1.96), 7.363 (0.81), 7.380 (4.55), 7.397 (0.91), 7.403 (2.74), 7.438 (0.75), 7.461 (0.54), 7.511 (2.48), 7.516 (1.09), 7.524 (2.72), 7.532 (2.26), 7.541 (0.90), 7.546 (1.94), 8.538 (2.92), 9.644 (1.38).

Example 384

N-[1-(cyclopropylmethyl)-4-methyl-3-(pyridin-4-yl)-1H-pyrazol-5-yl]-6-[3,5-dimethyl-4-(trifluoromethyl)-1H-pyrazol-1-yl]pyrimidin-4-amine

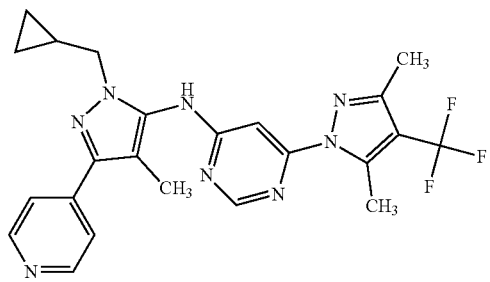 [SMILES: Cc1nn(-c2cc(Nc3c(C)c(-c4ccncc4)nn3CC3CC3)ncn2)c(C)c1C(F)(F)F]

A microwave vial was charged with 4-chloro-6-[3,5-dimethyl-4-(trifluoromethyl)-1H-pyrazol-1-yl]pyrimidine (104 mg, 95% purity, 358 µmol) and 1-(cyclopropylmethyl)-4-methyl-3-(pyridin-4-yl)-1H-pyrazol-5-amine (100 mg, 90% purity, 394 µmol) and the contents were suspended in 1,4-dioxane (1.1 mL). The reaction mixture was degassed with Ar for 3 min. Tris(dibenzylideneacetone)dipalladium (6.56 mg, 7.17 µmol) and XantPhos (8.29 mg, 14.3 µmol) were added and the reaction mixture was degassed again for 1 min. Finally, sodium phenolate (45.8 mg, 394 µmol) was added and the vial was sealed and heated at 85° C. overnight while vigorously shaking. After cooling to ambient temperature, the reaction mixture was filtered, diluted with dimethylsulfoxide and purified by preparative HPLC (method 6) to yield the desired product (26 mg, 15% yield).

LC-MS (method 9): $R_t$=0.92 min; MS (ESIpos): m/z=469 [M+H]$^+$

¹H-NMR (400 MHz, dimethylsulfoxide-d6) δ [ppm]: −0.149 (0.17), −0.008 (1.64), 0.008 (1.07), 0.309 (2.42), 0.321 (2.62), 0.438 (2.52), 0.458 (2.67), 1.179 (0.35), 1.192 (0.67), 1.199 (0.65), 1.211 (1.01), 1.223 (0.63), 1.229 (0.63), 1.241 (0.32), 2.083 (16.00), 2.241 (0.26), 2.304 (1.94), 2.367 (0.27), 2.761 (8.09), 3.873 (2.14), 3.890 (2.10), 7.691 (3.19), 7.706 (3.37), 8.546 (0.35), 8.610 (4.36), 8.625 (4.29), 9.617 (0.35).

Example 385

N-[1-(cyclopropylmethyl)-3-(4-fluorophenyl)-4-methyl-1H-pyrazol-5-yl]-6-(4-methoxy-3,5-dimethyl-1H-pyrazol-1-yl)pyrimidin-4-amine

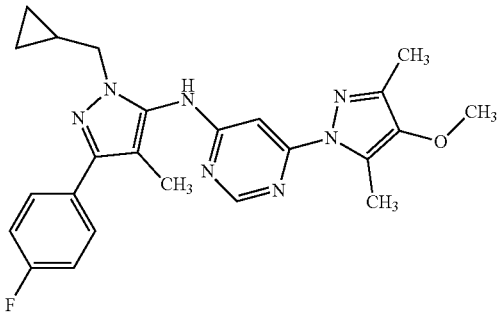 [SMILES: COc1c(C)nn(-c2cc(Nc3c(C)c(-c4ccc(F)cc4)nn3CC3CC3)ncn2)c1C]

Under an argon atmosphere 4-chloro-6-(4-methoxy-3,5-dimethyl-1H-pyrazol-1-yl)pyrimidine (150 mg, 100% purity, 628 µmol) was dissolved in 1,4-dioxane (2.0 mL) and the resulting solution heated to 85° C. 1-(cyclopropylmethyl)-3-(4-fluorophenyl)-4-methyl-1H-pyrazol-5-amine (188 mg, 90% purity, 691 µmol), tris(dibenzylideneacetone)dipalladium (17.3 mg, 18.9 µmol) and XantPhos (21.8 mg, 37.7 µmol) were added and the reaction mixture was degassed with Ar for 3 min. Finally, sodium phenolate (80.3 mg, 691 µmol) was added and the reaction mixture was degassed again for 1 min. It was then heated at 85° C. for 4 h while vigorously stirring. After cooling to ambient temperature, the reaction mixture was quenched by addition of aqueous hydrochloric acid (1 M). It was extracted with ethyl acetate (2×) and the combined organic phase extracts were dried over sodium sulfate and concentrated. The residue was purified by flash column chromatography (SNAP Ultra 25 g, cyclohexane/ethyl acetate gradient) to yield the desired product (202 mg, 70% yield).

LC-MS (method 10): $R_t$=2.25 min; MS (ESIpos): m/z=448 [M+H]$^+$

¹H-NMR (500 MHz, dimethylsulfoxide-d6) δ [ppm]: −0.007 (0.43), 0.292 (2.30), 0.301 (2.42), 0.423 (2.48), 0.439 (2.60), 1.162 (1.60), 1.168 (0.43), 1.176 (3.36), 1.184 (0.74), 1.190 (2.02), 1.193 (1.14), 1.203 (0.66), 1.208 (0.67), 1.397 (0.94), 1.989 (5.46), 2.006 (16.00), 2.179 (2.21), 2.226 (0.46), 3.697 (9.47), 3.726 (0.61), 3.827 (2.02), 3.840 (2.02), 4.010 (0.40), 4.024 (1.20), 4.038 (1.19), 7.256 (2.25), 7.274 (4.52), 7.292 (2.41), 7.720 (1.37), 7.732 (1.86), 7.747 (1.32), 8.447 (0.54), 9.357 (0.52).

Example 386

(±)-1-(6-{[1-(cyclopropylmethyl)-3-(4-fluorophenyl)-4-methyl-1H-pyrazol-5-yl]amino}pyrimidin-4-yl)-3-methyl-4-(trifluoromethyl)-1,4,5,6-tetrahydrocyclopenta[c]pyrazol-4-ol (Racemate)

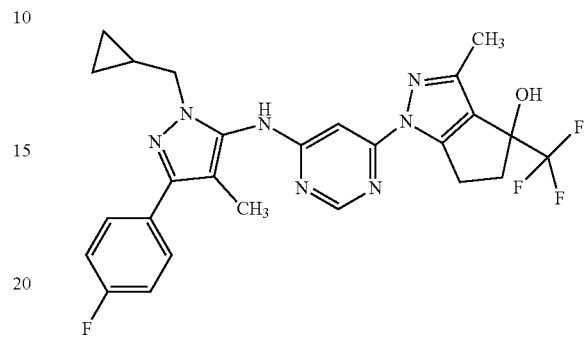

Molecular Sieves (powder, 4 Å) were placed in a round-bottom flask and dried in a vacuum drying-oven overnight at 120° C. After cooling to ambient temperature, tetrabutylammonium fluoride trihydrate (214 mg, 765 µmol) and toluene (5.0 mL) were added and the suspension stirred for 30 min. A solution of 1-(6-{[1-(cyclopropylmethyl)-3-(4-fluorophenyl)-4-methyl-1H-pyrazol-5-yl]amino}pyrimidin-4-yl)-3-methyl-5,6-dihydrocyclopenta[c]pyrazol-4(1H)-one (70.0 mg, 153 µmol) in dichloromethane (1.0 mL) was then added, the mixture was stirred for 5 min and cooled to 0° C. Trimethyl(trifluoromethyl)silane (180 µL, 1.2 mmol) was then added and the reaction mixture was stirred at ambient temperature for 3.5 h. After 2.5 h, dichloromethane (1 mL) was added to solubilize the reaction components. The reaction mixture was diluted with ethyl acetate and water, the molecular sieves removed by filtration and washed further with ethyl acetate. After separation of the layers in the filtrate, the aqueous phase was extracted again with ethyl acetate and the combined organic phase extracts were dried over sodium sulfate and concentrated. The residue was purified by preparative HPLC (column: Chromatorex C18; 125*30 mm, 10 µM, flow 75 mL/min, gradient acetonitrile/water (containing 0.1% trifluoroacetic acid) 5/95 to 95/5) to yield the desired product (43 mg, 39% yield).

LC-MS (method 11): $R_t$=1.47 min; MS (ESIpos): m/z=528 [M+H]$^+$

¹H-NMR (400 MHz, dimethylsulfoxide-d6) δ [ppm]: −0.150 (0.35), −0.022 (0.51), −0.008 (3.03), 0.008 (2.18), 0.146 (0.32), 0.284 (2.61), 0.295 (2.76), 0.416 (2.90), 0.436 (3.06), 0.918 (0.85), 0.936 (1.75), 0.955 (0.82), 1.154 (0.46), 1.167 (0.81), 1.174 (0.78), 1.186 (1.19), 1.204 (0.76), 1.234 (0.81), 1.283 (0.25), 1.302 (0.46), 1.320 (0.42), 1.337 (0.21), 1.569 (0.28), 2.006 (16.00), 2.086 (0.38), 2.196 (2.37), 2.328 (0.69), 2.366 (0.47), 2.523 (1.88), 2.670 (0.61), 2.710 (0.36), 2.877 (0.56), 2.888 (0.71), 2.899 (0.86), 2.911 (1.22), 2.924 (0.69), 2.934 (0.65), 2.944 (0.62), 3.069 (0.54), 3.082 (0.58), 3.091 (0.55), 3.103 (0.55), 3.112 (1.02), 3.125 (1.07), 3.134 (0.94), 3.147 (0.81), 3.183 (0.33), 3.217 (0.80), 3.228 (0.91), 3.239 (0.99), 3.249 (0.93), 3.260 (0.69), 3.271 (0.73), 3.283 (0.83), 3.829 (2.11), 3.844 (2.08), 6.595 (3.35), 7.255 (2.11), 7.277 (4.25), 7.299 (2.34), 7.736 (1.95), 8.460 (0.44), 9.472 (0.36).

Example 387

(±)-4-{5-[(6-{3,5-dimethyl-4-[2,2,2-trifluoro-1-hydroxyethyl]-1H-pyrazol-1-yl}pyrimidin-4-yl)amino]-1,4-dimethyl-1H-pyrazol-3-yl}benzonitrile (Racemic)

Example 388

6-(3,5-dimethyl-1H-pyrazol-1-yl)-N-{4-ethyl-3-(4-fluorophenyl)-1-[(2-methyl-2H-tetrazol-5-yl)methyl]-1H-pyrazol-5-yl}pyrimidin-4-amine

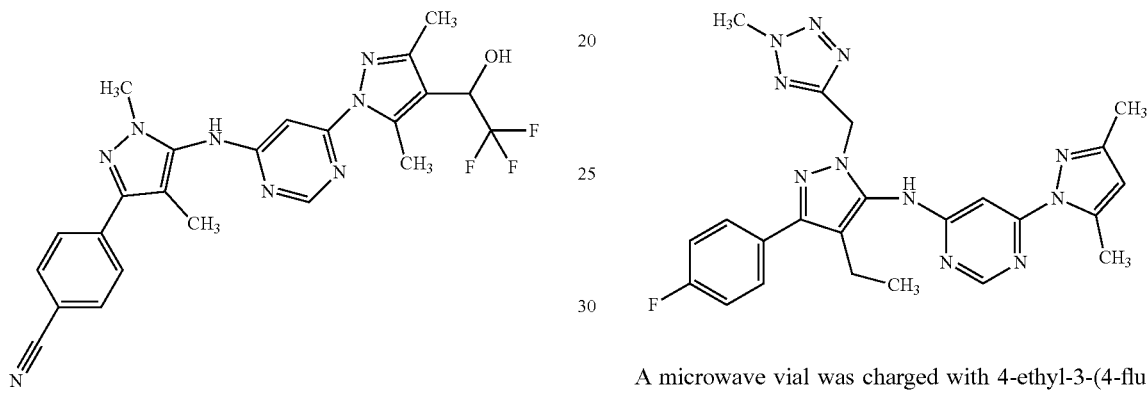

Molecular sieves was suspended in toluene (8.0 ml, 75 mmol) and tetrabutylammonium fluoride hydrate (305 mg, 1.09 mmol) was added under an argon atmosphere. A solution of 4-(5-{[6-(4-formyl-3,5-dimethyl-1H-pyrazol-1-yl)pyrimidin-4-yl]amino}-1,4-dimethyl-1H-pyrazol-3-yl)benzonitrile (150 mg, 364 µmol) in toluene (2 mL) and tetrahydrofuran (3 mL) was added and the resulting mixture was stirred 5 minutes at ambient temperature. At 0° C. trimethyl(trifluoromethyl)silane (270 µl, 1.8 mmol) was added and it was stirred for an addition hour at ambient temperature. The mixture was diluted with water and extracted with ethyl acetate (2×). The combined organic phases were dried over sodium sulfate and concentrated under reduced pressure. The crude product was purified by preparative HPLC (method 2) to yield 13.9 mg (8%) of the desired product along with (±)-1-{1-[6-({3-[4-(2-amino-1,1,1,3,3,3-hexafluoropropan-2-yl)phenyl]-1,4-dimethyl-1H-pyrazol-5-yl}amino)pyrimidin-4-yl]-3,5-dimethyl-1H-pyrazol-4-yl}-2,2,2-trifluoroethanol as by-product.

LC-MS (method 10): $R_t$=1.83 min; MS (ESIpos): m/z=483 [M+H]$^+$ $^1$H-NMR (400 MHz, dimethylsulfoxide-d6) δ [ppm]: −0.008 (1.07), 0.008 (1.00), 2.073 (13.30), 2.247 (2.95), 2.676 (11.93), 3.697 (8.79), 5.152 (0.57), 5.165 (0.68), 5.171 (0.64), 5.184 (0.57), 5.755 (2.32), 6.701 (2.14), 6.714 (2.16), 7.896 (16.00), 8.497 (0.65), 9.521 (1.62).

A microwave vial was charged with 4-ethyl-3-(4-fluorophenyl)-1-[(2-methyl-2H-tetrazol-5-yl)methyl]-1H-pyrazol-5-amine (36.0 mg, 119 µmol), 4-chloro-6-(3,5-dimethyl-1H-pyrazol-1-yl)pyrimidine (27.4 mg, 131 µmol) and sodium phenolate (15.3 mg, 131 µmol) and the contents were suspended in 1,4-dioxane (0.41 mL). The reaction mixture was degassed with Ar for 3 min. Tris(dibenzylideneacetone)dipalladium (2.19 mg, 2.39 µmol) and XantPhos (2.77 mg, 4.78 µmol) were added and the reaction mixture was degassed again for 1 min. The vial was sealed and heated at 85° C. overnight while vigorously shaking. After cooling to ambient temperature, the reaction mixture was concentrated. The residue was redissolved in dimethylsulfoxide, filtered and purified by preparative HPLC (method 3) to yield the desired product (14.8 mg, 24% yield).

LC-MS (method 11): $R_t$=1.42 min; MS (ESIpos): m/z=474 [M+H]$^+$ $^1$H-NMR (400 MHz, dimethylsulfoxide-d6) δ [ppm]: −0.149 (0.22), −0.008 (1.66), 0.008 (1.73), 0.146 (0.19), 0.957 (4.36), 0.976 (9.81), 0.995 (4.55), 1.566 (0.18), 1.647 (1.23), 2.179 (5.69), 2.187 (5.39), 2.327 (0.41), 2.366 (0.42), 2.442 (0.95), 2.460 (2.59), 2.479 (2.83), 2.629 (16.00), 2.654 (2.48), 2.670 (0.51), 2.710 (0.45), 4.217 (2.20), 5.468 (3.31), 6.148 (3.52), 6.209 (0.55), 7.151 (0.16), 7.173 (0.22), 7.207 (0.67), 7.254 (2.98), 7.276 (5.73), 7.299 (2.87), 7.330 (0.41), 7.348 (0.32), 7.368 (0.92), 7.384 (0.96), 7.397 (1.11), 7.466 (0.29), 7.480 (0.68), 7.500 (0.73), 7.520 (0.38), 7.656 (1.68), 7.671 (2.21), 7.690 (1.56), 7.854 (0.19), 7.870 (0.20), 8.413 (0.94), 8.678 (0.53), 9.350 (3.45).

Example 389

2-[1-(6-{[1-(cyclopropylmethyl)-4-methyl-3-(4-methylphenyl)-1H-pyrazol-5-yl]amino}pyrimidin-4-yl)-3,5-dimethyl-1H-pyrazol-4-yl]propan-2-ol

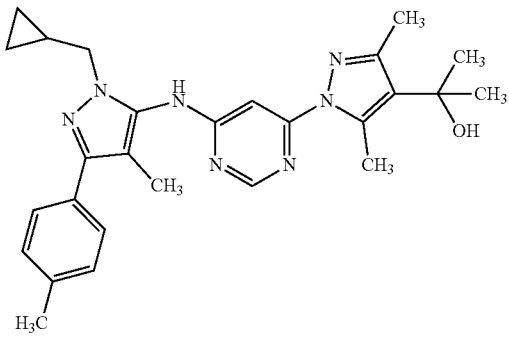 [SMILES: Cc1ccc(-c2nn(CC3CC3)c(Nc3cc(-n4nc(C)c(C(C)(C)O)c4C)ncn3)c2C)cc1]

Under an argon atmosphere a solution of ethyl 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylate (45.4 g, 95% purity, 88.1 mmol) in tetrahydrofuran (1.8 l) was treated with bromo(methyl)magnesium (150 ml, 3.0 M, 440 mmol) at 0° C. The resulting mixture was allowed to warm up to ambient temperature and was stirred overnight. The mixture was diluted with aqueous sodium ethylendiaminetetraacetic acid solution (450 mL, 10%) and stirred for 30 minutes. 2000 mL water and ethyl acetate were added and the organic phase was separated and washed over sodium sulfate. The organic phase was concentrated under reduced pressure and the crude product was purified by flash-chromatography (cyclohexane/ethyl acetate 1:1) and MPLC-column (dichloromethane/acetone 8:2) to yield 930 mg (2.1%) of the described product as a byproduct along with para-flour derivative.

LC-MS (method 9): $R_t$=1.04 min; MS (ESIpos): m/z=472 [M+H]$^+$ $^1$H-NMR (500 MHz, dimethylsulfoxide-d6) δ [ppm]: 0.296 (2.31), 0.305 (2.43), 0.425 (2.35), 0.441 (2.43), 1.187 (0.68), 1.193 (0.69), 1.196 (0.57), 1.203 (1.06), 1.209 (0.58), 1.212 (0.64), 1.217 (0.63), 1.469 (15.43), 1.766 (3.47), 2.006 (15.68), 2.076 (0.84), 2.226 (0.44), 2.245 (0.80), 2.269 (1.86), 2.342 (13.08), 2.750 (16.00), 3.335 (14.61), 3.828 (1.93), 3.842 (1.90), 4.859 (3.44), 7.243 (3.61), 7.258 (3.94), 7.272 (0.42), 7.582 (3.12), 7.598 (2.75), 8.466 (0.57), 9.348 (0.50).

Example 390

N-[1-(cyclopropylmethyl)-3-(4-fluorophenyl)-4-methyl-1H-pyrazol-5-yl]-6-{4-[(3,3-difluoroazetidin-1-yl)methyl]-3,5-dimethyl-1H-pyrazol-1-yl}pyrimidin-4-amine

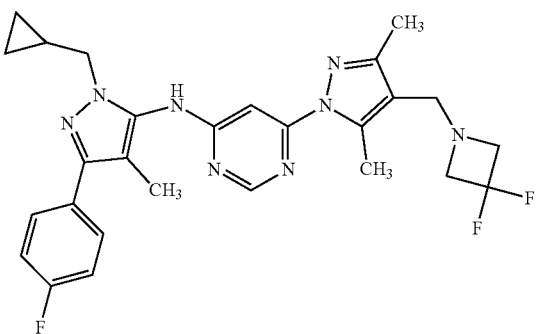 [SMILES: Cc1nn(-c2cc(Nc3c(C)c(-c4ccc(F)cc4)nn3CC3CC3)ncn2)c(C)c1CN1CC(F)(F)C1]

A solution of 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbaldehyde (190 mg, 426 µmol) and 3,3-difluoroazetidine hydrochloride (1:1) (71.8 mg, 554 µmol) in tetrahydrofuran (3.5 ml, 43 mmol) was treated with acetic acid (49 µl, 850 µmol) and stirred one hour at ambient temperature. Subsequently sodium triacetoxyborohydride (145 mg, 682 µmol) was added and the mixture was stirred overnight at ambient temperature. The mixture was diluted with 3 mL water and purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) and subsequent by method 7 to yield 31.9 mg of the desired product (13%).

LC-MS (method 10): $R_t$=2.01 min; MS (ESIneg): m/z=521 [M−H]$^-$ $^1$H-NMR (400 MHz, dimethylsulfoxide-d6) δ [ppm]: 0.289 (2.97), 0.301 (3.10), 0.419 (2.94), 0.439 (3.04), 1.181 (0.92), 1.193 (1.20), 2.003 (16.00), 2.196 (3.35), 2.216 (3.04), 2.327 (1.04), 2.366 (0.76), 2.619 (0.89), 2.650 (14.07), 2.709 (0.73), 3.487 (1.96), 3.518 (3.83), 3.545 (4.55), 3.655 (0.63), 3.823 (2.81), 3.839 (2.75), 4.315 (0.47), 7.208 (0.54), 7.251 (2.53), 7.273 (5.38), 7.295 (2.78), 7.498 (0.47), 7.712 (1.80), 7.731 (2.47), 7.746 (1.80), 7.997 (0.54), 8.132 (2.06), 8.463 (0.82), 8.675 (0.47), 9.379 (0.85).

Example 391

6-(3,5-dimethyl-1H-pyrazol-1-yl)-N-{4-ethyl-3-(4-fluorophenyl)-1-[(1-methyl-1H-tetrazol-5-yl)methyl]-1H-pyrazol-5-yl}pyrimidin-4-amine

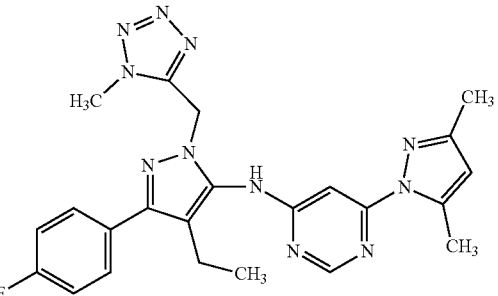

A microwave vial was charged with 4-ethyl-3-(4-fluorophenyl)-1-[(1-methyl-1H-tetrazol-5-yl)methyl]-1H-pyrazol-5-amine (27.0 mg, 89.6 µmol), 4-chloro-6-(3,5-dimethyl-1H-pyrazol-1-yl)pyrimidine (20.6 mg, 98.6 µmol) and sodium phenolate (13.5 mg, 116 µmol) and the contents were suspended in 1,4-dioxane (0.31 mL). The reaction mixture was degassed with Ar for 3 min. Tris(dibenzylideneacetone)dipalladium (2.46 mg, 2.69 µmol) and XantPhos (3.11 mg, 5.38 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (15.6 mg, 33% yield).

LC-MS (method 11): $R_t$=1.42 min; MS (ESIneg): m/z=472 [M−H]$^-$

¹H-NMR (400 MHz, dimethylsulfoxide-d6) δ [ppm]: 0.960 (4.09), 0.978 (8.71), 0.997 (3.96), 1.646 (1.06), 2.191 (5.88), 2.327 (1.55), 2.366 (0.98), 2.463 (8.96), 2.631 (15.04), 2.670 (1.53), 2.710 (0.84), 4.014 (16.00), 5.616 (6.13), 6.157 (3.54), 7.256 (2.44), 7.279 (4.95), 7.301 (2.71), 7.368 (0.96), 7.385 (1.01), 7.397 (1.08), 7.639 (2.04), 7.654 (2.41), 7.675 (1.72), 8.398 (0.98), 9.435 (2.93).

Example 392

(±)-1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-2,2-difluoroethanol (Racemate)

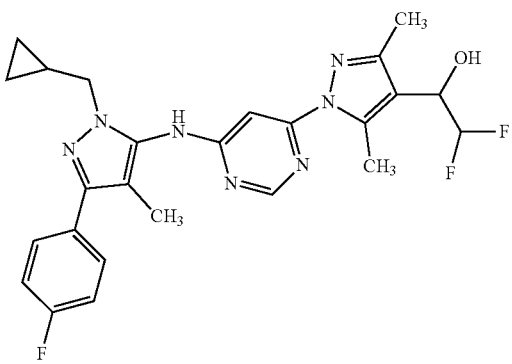 [SMILES: Cc1nn(-c2cc(Nc3c(C)c(-c4ccc(F)cc4)nn3CC3CC3)ncn2)c(C)c1C(O)C(F)F]

Molecular sieves (powder, 4 Å) and tetrabutylammonium fluoride trihydrate (82.8 mg, 296 μmol) were flame-dried under vacuum. After cooling to ambient temperature, the mixture was suspended in toluene (1.5 mL) and stirred for 30 min. A solution of 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbaldehyde (44.0 mg, 98.8 μmol) in toluene (1 mL) was added and the reaction mixture stirred for 20 min. It was then cooled to −20° C. an (difluoromethyl)(trimethyl)silane (67 μl, 490 μmol) was added dropwise. The reaction mixture was allowed to warm to ambient temperature and stirred for 1 h. It was then quenched by addition of water and diluted with ethyl acetate. The molecular sieves was removed by filtration and further was with ethyl acetate. After separation of the layers in the filtrate, the aqueous phase was further extracted with ethyl acetate and the combined organic phase extracts dried over sodium sulfate and concentrated. The residue was purified by preparative HPLC to yield the desired product (11.3 mg, 23% yield).

LC-MS (method 11): R$_t$=1.37 min; MS (ESIpos): m/z=498 [M+H]⁺

¹H-NMR (400 MHz, dimethylsulfoxide-d6) δ [ppm]: −0.150 (0.16), −0.008 (1.14), 0.008 (1.00), 0.290 (2.42), 0.302 (2.65), 0.421 (2.41), 0.441 (2.56), 1.176 (0.65), 1.194 (1.06), 2.005 (16.00), 2.221 (2.66), 2.328 (0.67), 2.366 (0.40), 2.524 (1.61), 2.646 (15.97), 2.670 (0.74), 2.710 (0.43), 3.825 (2.27), 3.843 (2.25), 4.765 (0.70), 5.944 (0.41), 6.040 (1.80), 6.073 (0.83), 6.083 (0.83), 6.223 (0.40), 7.250 (2.25), 7.272 (4.69), 7.295 (2.54), 7.712 (1.54), 7.726 (2.01), 7.747 (1.44), 8.475 (0.67), 9.401 (0.55).

Example 393

1-[1-(6-{[1-(4-fluorophenyl)-3,5-dimethyl-1H-pyrazol-4-yl]amino}pyrimidin-4-yl)-3,5-dimethyl-1H-pyrazol-4-yl]-2-methylpropan-2-ol

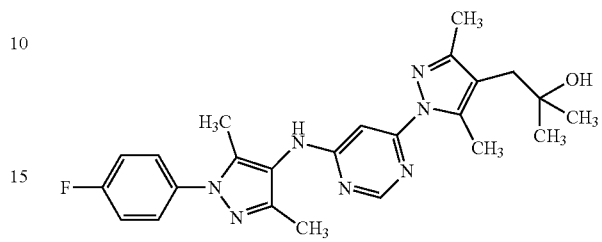

A solution of ethyl [1-(6-{[1-(4-fluorophenyl)-3,5-dimethyl-1H-pyrazol-4-yl]amino}pyrimidin-4-yl)-3,5-dimethyl-1H-pyrazol-4-yl]acetate (80.0 mg, 173 μmol) in tetrahydrofuran (1.8 ml, 22 mmol) was treated with bromo(methyl)magnesium (200 μl, 3.0 M in diethyl ether, 600 μmol) t 0° C. The mixture was stirred 30 min at ambient temperature and additional 3.5 equivalents of bromo(methyl)magnesium solution (200 μl, 3.0 M in diethyl ether, 600 μmol) were added. The mixture was stirred overnight at ambient temperature and diluted with water. The mixture was extracted with ethyl acetate (3×). The combined organic phases were dried over sodium sulfate and concentrated under reduced pressure. The crude product was purified by preparative HPLC (method: column: Reprosil C18; 10 μm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 7 mg (9%) of the desired product).

LC-MS (method 10): R$_t$=1.72 min; MS (ESIpos): m/z=450 [M+H]⁺

¹H-NMR (500 MHz, dimethylsulfoxide-d6) δ [ppm]: 1.087 (14.16), 1.106 (1.38), 1.358 (0.99), 2.081 (16.00), 2.181 (10.82), 2.565 (13.78), 3.363 (0.78), 3.377 (1.24), 3.391 (1.17), 3.405 (0.61), 7.339 (1.80), 7.357 (3.53), 7.374 (1.96), 7.594 (1.73), 8.387 (0.62), 8.816 (3.32).

Example 394

1-(6-{[1-(cyclopropylmethyl)-3-(4-fluorophenyl)-4-methyl-1H-pyrazol-5-yl]amino}pyrimidin-4-yl)-3-methyl-5,6-dihydrocyclopenta[c]pyrazol-4(1H)-one

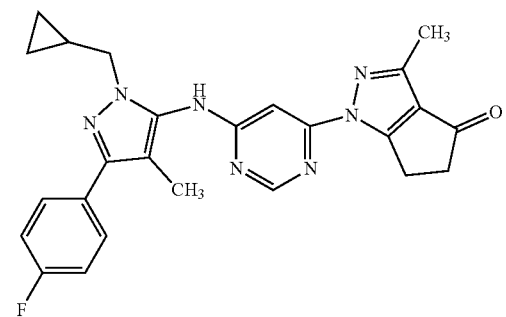 [SMILES: Cc1nn(-c2cc(Nc3c(C)c(-c4ccc(F)cc4)nn3CC3CC3)ncn2)c2c1C(=O)CC2]

Under an argon atmosphere, 1-(6-chloropyrimidin-4-yl)-3-methyl-5,6-dihydrocyclopenta[c]pyrazol-4(1H)-one (500 mg, 2.01 mmol) and sodium phenolate (257 mg, 2.21 mmol) and the contents were suspended in 1,4-dioxane (5.8 mL). The reaction mixture was degassed with Ar for 3 min. Tris(dibenzylideneacetone)dipalladium (34.9 mg, 60.3 µmol), XantPhos (27.6 mg, 30.2 µmol) and 1-(cyclopropylmethyl)-3-(4-fluorophenyl)-4-methyl-1H-pyrazol-5-amine (543 mg, 2.21 mmol) were added and the reaction mixture was degassed again for 1 min. The reaction mixture was heated at 85° C. overnight while vigorously stirring. After cooling to ambient temperature, the reaction mixture was quenched with brine and extracted with ethyl acetate (2×). The combined organic phase extracts were dried over sodium sulfate and concentrated. The residue was purified by flash column chromatography (SNAP Ultra 50 g, dichloromethane/methanol gradient 99/1 to 90/10) and further purified by preparative HPLC (Kinetex C18 5 µm, 150×30 mm, flow: 75 mL/min, 40° C., acetonitrile/water gradient 35/65 to 95/5) to yield the desired product (195 mg, 19% yield).

LC-MS (method 9): $R_t$=1.08 min; MS (ESIpos): m/z=458 [M+H]$^+$ $^1$H-NMR (500 MHz, dimethylsulfoxide-d6) δ [ppm]: 0.006 (0.88), 0.293 (2.40), 0.300 (2.44), 0.425 (2.70), 0.441 (2.74), 1.168 (0.44), 1.178 (0.81), 1.184 (0.78), 1.193 (1.13), 1.203 (0.74), 1.208 (0.74), 1.217 (0.38), 2.015 (12.55), 2.305 (1.14), 2.360 (0.44), 2.364 (0.46), 2.520 (0.50), 2.524 (0.34), 2.634 (0.17), 2.637 (0.23), 2.641 (0.16), 2.812 (0.57), 2.937 (2.21), 2.946 (2.63), 3.322 (16.00), 3.338 (3.21), 3.343 (2.86), 3.348 (3.06), 3.352 (2.67), 3.358 (2.62), 7.262 (1.82), 7.279 (3.43), 7.297 (1.92), 7.739 (1.49), 8.503 (0.25), 9.587 (0.29).

Example 395

2-(6-{[1-(cyclopropylmethyl)-3-(4-fluorophenyl)-4-methyl-1H-pyrazol-5-yl]amino}pyrimidin-4-yl)-3-methyl-5,6-dihydrocyclopenta[c]pyrazol-4(2H)-one

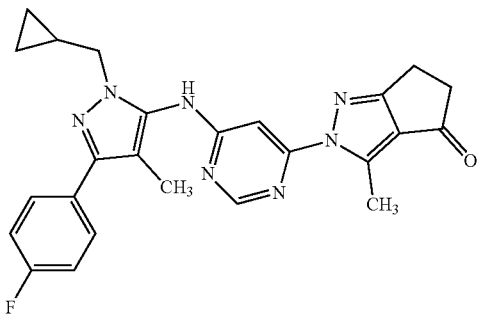 [SMILES: Cc1c(-c2ccc(F)cc2)nn(CC2CC2)c1Nc1cc(-n2nc3c(c2C)C(=O)CC3)ncn1]

Under an argon atmosphere, 2-(6-chloropyrimidin-4-yl)-3-methyl-5,6-dihydrocyclopenta[c]pyrazol-4(2H)-one (1.70 g, 95% purity, 6.49 mmol) was dissolved in 1,4-dioxane (21 mL) and the resulting solution was heated to 85° C. and degassed with argon for 3 min. 1-(cyclopropylmethyl)-3-(4-fluorophenyl)-4-methyl-1H-pyrazol-5-amine (1.95 g, 90% purity, 7.14 mmol), tris(dibenzylideneaceton)dipalladium (178 mg, 195 µmol) and XantPhos (225 mg, 390 µmol) were added and the mixture again degassed with argon for 1 min. Sodium phenolate (829 mg, 7.14 mmol) was then added and the reaction mixture stirred at 85° C. for 3.5 h. After cooling to ambient temperature, the reaction mixture was quenched with aqueous hydrochloric acid solution (1 N) and extracted with ethyl acetate (3×). The organic phases were filtered, the filtrate was dried over sodium sulfate and concentrated. The residue was purified by flash column chromatography (SNAP Ultra 50 g, cyclohexane/ethyl acetate gradient) and further purified by preparative HPLC (column: Reprosil C18; 250*50 mm, 10 µM, flow 150 mL/min, gradient acetonitrile/water (containing 0.1% trifluoroacetic acid) 10/90 to 90/10) to yield the desired product (714 mg, 23% yield).

LC-MS (method 11): Rt=1.36 min; MS (ESIpos): m/z=458 [M+H]$^+$ $^1$H-NMR (500 MHz, dimethylsulfoxide-d6) δ [ppm]: −0.007 (0.25), 0.296 (1.48), 0.303 (1.49), 0.427 (1.71), 0.442 (1.71), 1.170 (0.28), 1.179 (0.52), 1.185 (0.52), 1.194 (0.71), 1.204 (0.48), 1.209 (0.47), 1.219 (0.24), 2.021 (11.58), 2.813 (16.00), 2.836 (1.17), 2.885 (1.23), 2.905 (0.96), 2.919 (0.96), 2.952 (0.57), 3.332 (0.21), 3.844 (1.36), 3.855 (1.32), 7.260 (1.65), 7.278 (3.39), 7.296 (1.97), 7.348 (0.19), 7.356 (0.32), 7.357 (0.32), 7.499 (0.16), 7.514 (0.18), 7.743 (1.26), 8.568 (0.21), 8.785 (0.23), 8.787 (0.23), 9.608 (0.18).

Example 396

2-{1-[6-({1-(cyclopropylmethyl)-3-[4-(difluoromethyl)phenyl]-4-methyl-11H-pyrazol-5-yl}amino)pyrimidin-4-yl]-3,5-dimethyl-1H-pyrazol-4-yl}propan-2-ol

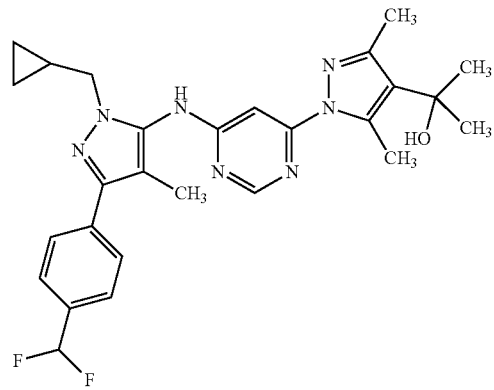 [SMILES: Cc1nn(-c2cc(Nc3c(C)c(-c4ccc(C(F)F)cc4)nn3CC3CC3)ncn2)c(C)c1C(C)(C)O]

A solution of ethyl 1-[6-({1-(cyclopropylmethyl)-3-[4-(difluoromethyl)phenyl]-4-methyl-1H-pyrazol-5-yl}amino)pyrimidin-4-yl]-3,5-dimethyl-1H-pyrazole-4-carboxylate (177 mg, 339 µmol) in tetrahydrofuran (3.5 ml, 44 mmol) was treated with chloro(methyl)magnesium (400 µl, 3.0 M in tetrahydrofuran, 1.2 mmol) at 0° C. The mixture was stirred overnight at ambient temperature. As the conversion was not fully completed, the mixture was again cooled down to 0° C. and additional 3.5 eq of chloro(methyl)magnesium solution (400 µl, 3.0 M in tetrahydrofuran, 1.2 mmol) were added. The mixture was stirred 3 hours at ambient temperature. The mixture was diluted with potassium sodium tartrate solution and extracted with ethyl acetate (2×). The combined organic phases were dried over Extrelut NT3 and concentrated under reduced pressure. The crude product was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 112 mg (65%) of the desired product.

LC-MS (method 10): $R_t$=2.01 min; MS (ESIpos): m/z=508 [M+H]$^+$ $^1$H-NMR (500 MHz, dimethylsulfoxide-d6) δ [ppm]: 0.307 (2.29), 0.317 (2.40), 0.326 (0.68), 0.435 (2.38), 0.451 (2.55), 1.188 (0.44), 1.198 (0.74), 1.204 (0.68), 1.214 (1.07), 1.220 (0.55), 1.223 (0.63), 1.228 (0.66), 1.239 (0.69), 1.253 (0.86), 1.267 (0.52), 1.468 (15.78), 2.048 (15.95), 2.087 (1.97), 2.149 (0.64), 2.272 (2.01), 2.748 (16.00), 3.856 (1.94), 3.870 (1.88), 4.858 (3.61), 5.754 (1.75), 6.964 (1.46), 7.076 (3.21), 7.188 (1.30), 7.638 (2.98), 7.654 (3.51), 7.845 (2.89), 7.861 (2.45), 8.468 (0.57), 9.389 (0.56).

Example 397

6-(4-chloro-3,5-dimethyl-1H-pyrazol-1-yl)-N-[1-(cyclopropylmethyl)-4-methyl-3-(6-methylpyridin-3-yl)-1H-pyrazol-5-yl]pyrimidin-4-amine

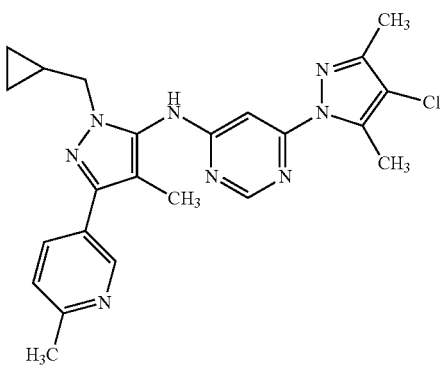 [SMILES: Cc1ccc(-c2nn(CC3CC3)c(Nc3cc(-n4nc(C)c(Cl)c4C)ncn3)c2C)cn1]

A solution of 1-(cyclopropylmethyl)-4-methyl-3-(6-methylpyridin-3-yl)-1H-pyrazol-5-amine (100 mg, 413 μmol) in 1,4-dioxane (2.0 ml) was degassed with argon and heated to an internal temperature of 85° C. To the heated solution was added 4-chloro-6-(4-chloro-3,5-dimethyl-1H-pyrazol-1-yl)pyrimidine (110 mg, 454 μmol), tris(dibenzylidenaceton)dipalladium (11.3 mg, 12.4 μmol), Xantphos (13.1 mg, 24.8 μmol) and finally sodium phenolate (52.7 mg, 454 μmol) before heating at 85° C. for an additional 30 minutes. The reaction mixture was added to a saturated aqueous solution of sodium hydrogen carbonate (11 mL), and the solution extracted three times with ethyl acetate. The combined organic phase s were washed with a saturated aqueous solution of sodium chloride, dried with sodium sulfate and concentrated in vacuo. The crude product was purified by flash-chromatography on silica gel (Gradient 10% to 100% ethylacetate in cyclohexane, column: Biotage SNAP Ultra 10 g) to yield 122 mg (100% purity, 66% yield) of the desired product.

LC-MS (Method 10): $R_t$=1.82 min; MS (ESIpos): m/z=449 [M+H]$^+$ $^1$H-NMR (400 MHz, dimethylsulfoxide-d6) δ [ppm]: 0.293 (0.85), 0.305 (0.95), 0.423 (0.86), 0.442 (0.93), 1.167 (0.12), 1.186 (0.23), 1.199 (0.36), 1.217 (0.23), 1.236 (0.10), 2.014 (5.42), 2.210 (1.02), 2.539 (16.00), 2.647 (6.50), 3.840 (0.84), 3.857 (0.81), 7.318 (0.85), 7.339 (0.89), 7.944 (0.42), 7.959 (0.39), 8.497 (0.21), 8.757 (0.75), 9.480 (0.16).

Example 398

6-(4-chloro-3,5-dimethyl-1H-pyrazol-1-yl)-N-{1-(cyclopropylmethyl)-3-[4-(difluoromethoxy)phenyl]-4-methyl-1H-pyrazol-5-yl}pyrimidin-4-amine

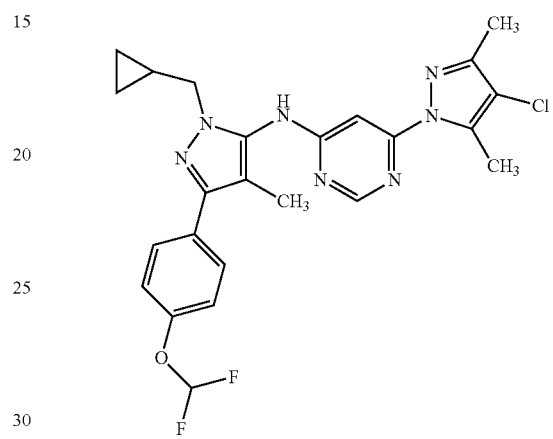

A solution of 1-(cyclopropylmethyl)-3-[4-(difluoromethoxy)phenyl]-4-methyl-1H-pyrazol-5-amine (100 mg, 341 μmol) in 1,4-dioxane (1.6 ml) was degassed with argon and heated to an internal temperature of 85° C. To the heated solution was added 4-chloro-6-(4-chloro-3,5-dimethyl-1H-pyrazol-1-yl)pyrimidine (91.2 mg, 375 μmol), tris(dibenzylidenaceton)dipalladium (9.37 mg, 10.2 μmol), Xantphos (10.8 mg, 20.5 μmol) and finally sodium phenolate (43.5 mg, 375 μmol) before heating at 85° C. for an additional 30 minutes. To the reaction mixture at 85° C. was added additional portions of 4-chloro-6-(4-chloro-3,5-dimethyl-1H-pyrazol-1-yl)pyrimidine (45.6 mg, 188 μmol), tris(dibenzylidenaceton)dipalladium (4.7 mg, 5.1 μmol), Xantphos (5.4 mg, 10.3 μmol) and sodium phenolate (22 mg, 188 μmol) before heating at 85° C. for a further 30 minutes. The reaction mixture was added to a saturated solution of sodium hydrogen carbonate (9 mL), and the solution extracted three times with ethyl acetate. The combined organic phase s were washed with a saturated solution of sodium chloride, dried with sodium sulfate and concentrated in vacuo. The crude product was by flash-chromatography on silica gel (gradient 2% to 20% ethylacetate in cyclohexane, column: Biotage SNAP Ultra 10 g) to yield 54.0 mg (100% purity, 32% yield) of the desired product.

LC-MS (Method 10): $R_t$=2.52 min; MS (ESIpos): m/z=500 [M+H]$^+$ $^1$H-NMR (400 MHz, dimethylsulfoxide-d6) δ [ppm]: 0.301 (1.45), 0.420 (1.35), 0.440 (1.43), 1.136 (0.18), 1.192 (0.55), 1.242 (0.20), 1.397 (16.00), 2.011 (8.72), 2.207 (1.45), 2.647 (10.93), 3.828 (1.20), 7.093 (1.20), 7.234 (2.42), 7.264 (2.58), 7.278 (2.56), 7.463 (1.17), 7.735 (1.50), 7.756 (1.39), 8.486 (0.23), 9.462 (0.22).

Example 399

N-[1-(cyclopropylmethyl)-3-(4-fluorophenyl)-4-methyl-1H-pyrazol-5-yl]-6-[3,5-dimethyl-4-(methylsulfanyl)-1H-pyrazol-1-yl]pyrimidin-4-amine

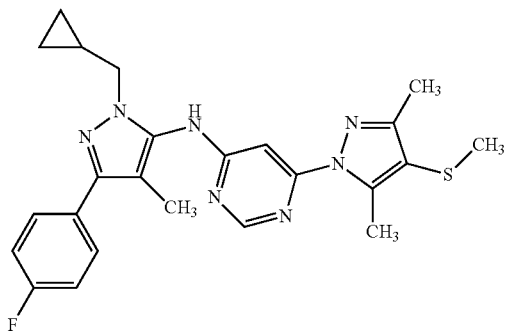 [SMILES: CSc1c(C)nn(-c2cc(Nc3c(C)c(-c4ccc(F)cc4)nn3CC3CC3)ncn2)c1C]

Under an argon atmosphere, 6-(4-bromo-3,5-dimethyl-1H-pyrazol-1-yl)-N-[1-(cyclopropylmethyl)-3-(4-fluorophenyl)-4-methyl-1H-pyrazol-5-yl]pyrimidin-4-amine (50.0 mg, 101 µmol) was dissolved in tetrahydrofuran (1.0 mL) and sodium hydride (4.43 mg, 60% purity, 111 µmol) was added. The reaction mixture was stirred for 10 min and was then cooled to −70° C. A solution of n-butyllithium in hexanes (178 µL, 2.5 M, 440 µmol) was added. After 10 min, (S)-methyl methanethiosulfonate (19 µl, 200 µmol) was added and the reaction mixture allowed to warm to ambient temperature. After reaching ambient temperature, the reaction mixture was quenched with saturated ammonium chloride solution and diluted with water. It was extracted with ethyl acetate (3×). The combined organic phase extracts were washed with brine, dried over sodium sulfate and concentrated. The residue was purified by preparative HPLC (column: Chromatorex C18; 125*30 mm, 10 µM, flow 100 mL/min, gradient acetonitrile/water (containing 0.1% trifluoroacetic acid) 10/90 to 90/10) to yield the desired product (22 mg, 41% yield) along with a by-product (N-{1-(cyclopropylmethyl)-3-[4-fluoro-3-(methylsulfanyl)phenyl]-4-methyl-1H-pyrazol-5-yl}-6-(3,5-dimethyl-1H-pyrazol-1-yl)pyrimidin-4-amine, see below).

LC-MS (method 11): $R_t$=1.65 min; MS (ESIpos): m/z=464 [M+H]$^+$ $^1$H-NMR (500 MHz, dimethylsulfoxide-d6) δ [ppm]: −0.019 (0.82), −0.007 (0.27), 0.006 (0.20), 0.297 (2.37), 0.306 (2.50), 0.427 (2.64), 0.444 (2.73), 0.852 (0.20), 1.170 (0.26), 1.176 (0.38), 1.185 (0.71), 1.191 (0.78), 1.200 (1.11), 1.207 (0.74), 1.209 (0.74), 1.216 (0.77), 1.229 (1.86), 1.340 (0.26), 1.988 (0.23), 2.013 (14.67), 2.029 (2.37), 2.135 (5.48), 2.171 (7.92), 2.196 (0.86), 2.215 (0.33), 2.224 (0.42), 2.266 (1.83), 2.309 (0.35), 2.421 (0.34), 2.432 (0.34), 2.582 (0.19), 2.632 (1.87), 2.713 (0.17), 2.733 (16.00), 3.837 (1.91), 3.849 (2.00), 6.140 (0.34), 7.257 (2.08), 7.261 (1.20), 7.275 (4.28), 7.293 (2.39), 7.298 (0.82), 7.522 (0.19), 7.592 (0.22), 7.605 (0.22), 7.723 (1.25), 7.735 (1.74), 7.750 (1.29), 8.499 (0.47), 9.454 (0.36).

Example 400

N-[4-(difluoromethoxy)-5-(4-fluorophenyl)-1-methyl-1H-pyrazol-3-yl]-6-(3,5-dimethyl-1H-pyrazol-1-yl)pyrimidin-4-amine

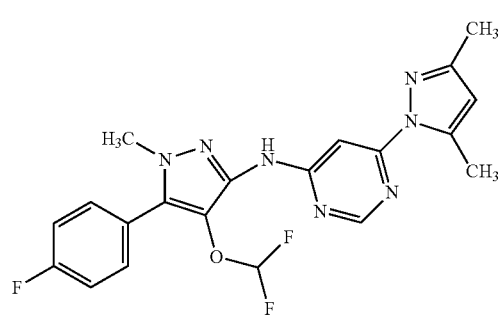 [SMILES: Cc1cc(C)n(-c2cc(Nc3nn(C)c(-c4ccc(F)cc4)c3OC(F)F)ncn2)n1]

A microwave vial was charged with 4-(difluoromethoxy)-5-(4-fluorophenyl)-1-methyl-1H-pyrazol-3-amine (300 mg, 1.17 mmol) and 4-chloro-6-(3,5-dimethyl-1H-pyrazol-1-yl)pyrimidine (268 mg, 1.28 mmol), and the contents were suspended in 1,4-dioxane (4.0 mL). The reaction mixture was degassed with Ar for 5 min. Tris(dibenzylideneacetone)dipalladium (320 mg, 350 µmol), XantPhos (405 mg, 700 µmol) and sodium phenolate (149 mg, 1.28 mmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (146 mg, 29% yield).

LC-MS (method 11): $R_t$=1.39 min; MS (ESIpos): m/z=430 [M+H]$^+$ $^1$H-NMR (500 MHz, dimethylsulfoxide-d6) δ [ppm]: 2.196 (16.00), 2.629 (12.16), 3.316 (13.56), 6.144 (3.48), 6.651 (1.49), 6.799 (2.88), 6.946 (1.25), 7.342 (2.36), 7.386 (2.37), 7.391 (0.85), 7.400 (1.08), 7.404 (4.95), 7.409 (0.95), 7.418 (0.89), 7.422 (2.68), 7.591 (2.65), 7.596 (1.12), 7.602 (2.89), 7.609 (2.47), 7.616 (0.96), 7.620 (2.19), 8.461 (3.81), 8.463 (3.66), 9.486 (3.10).

Example 401

N-[1-(cyclopropylmethyl)-3-(4-fluorophenyl)-4-methyl-1H-pyrazol-5-yl]-6-[3,5-dimethyl-4-(methylsulfinyl)-1H-pyrazol-1-yl]pyrimidin-4-amine

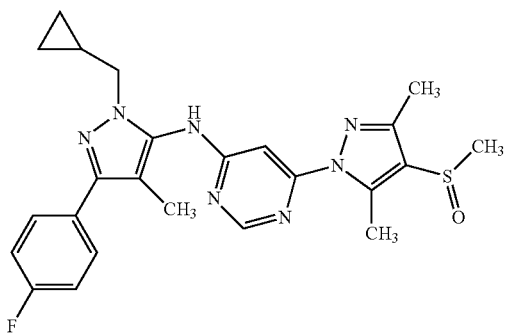 [SMILES: Cc1nn(-c2cc(Nc3c(C)c(-c4ccc(F)cc4)nn3CC3CC3)ncn2)c(C)c1S(C)=O]

N-[1-(cyclopropylmethyl)-3-(4-fluorophenyl)-4-methyl-1H-pyrazol-5-yl]-6-[3,5-dimethyl-4-(methylsulfanyl)-1H-pyrazol-1-yl]pyrimidin-4-amine (40.0 mg, 95% purity, 82.0 µmol) was dissolved in dichloromethane (2.0 mL) and the solution cooled to 0° C. Meta-chloroperbenzoicacid (18.4 mg, 77% purity, 82.0 µmol) was slowly added and the reaction mixture stirred for 15 min at 0° C. It was then quenched by addition of aqueous saturated sodium hydrogencarbonate solution, and extracted with dichloromethane (3×). The combined organic phase extracts were washed with brine, dried over sodium sulfate and concentrated. The residue was purified by preparative HPLC (column: Chromatorex C18; 120*30 mm, 10 µM, flow 75 mL/min, gradient acetonitrile/water (containing 0.1% trifluoroacetic acid) 10/90 to 90/10) to yield the desired product (16 mg, 35% yield).

LC-MS (method 11): $R_t$=1.23 min; MS (ESIpos): m/z=480 [M+H]$^+$ $^1$H-NMR (400 MHz, dimethylsulfoxide-d6) δ [ppm]: −0.008 (1.08), 0.008 (0.73), 0.290 (2.39), 0.302 (2.52), 0.424 (2.45), 0.443 (2.55), 0.917 (0.20), 1.161 (1.00), 1.180 (1.90), 1.193 (1.10), 1.198 (1.21), 1.212 (0.66), 1.231 (0.61), 1.246 (1.72), 1.262 (2.87), 1.279 (1.42), 1.408 (2.79), 1.564 (0.16), 1.646 (0.27), 2.007 (14.00), 2.073 (0.28), 2.131 (1.21), 2.162 (0.96), 2.328 (0.36), 2.367 (0.73), 2.410 (1.99), 2.560 (0.54), 2.670 (0.25), 2.710 (0.28), 2.767 (16.00), 2.909 (8.18), 2.972 (0.60), 3.011 (0.30), 3.080 (0.37), 3.092 (0.34), 3.098 (0.32), 3.110 (0.35), 3.125 (0.22), 3.136 (0.20), 3.144 (0.18), 3.155 (0.19), 3.614 (0.28), 3.624 (0.29), 3.640 (0.26), 3.831 (2.41), 3.848 (2.38), 6.970 (0.37), 7.097 (0.42), 7.225 (0.44), 7.253 (1.92), 7.275 (3.99), 7.297 (2.22), 7.713 (1.31), 7.728 (1.81), 7.747 (1.29), 8.524 (0.38), 9.536 (0.34).

Example 402

1-(6-{[1-(cyclopropylmethyl)-3-(4-fluorophenyl)-4-methyl-1H-pyrazol-5-yl]amino}pyrimidin-4-yl)-N,N,3,5-tetramethyl-1H-pyrazole-4-carboxamide

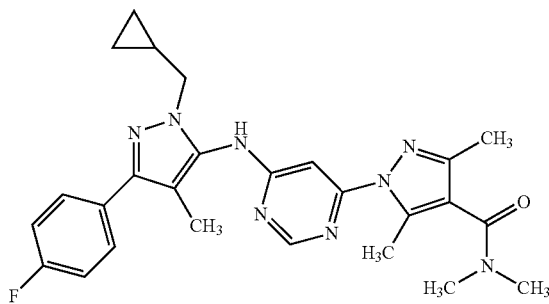 [SMILES: Cc1nn(-c2cc(Nc3c(C)c(-c4ccc(F)cc4)nn3CC3CC3)ncn2)c(C)c1C(=O)N(C)C]

A solution of 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylic acid (360 mg, 780 µmol) and N-methylmethanamine (430 µl, 2.0 M in tetrahydrofuran, 860 µmol) in dimethylformamide (6.7 ml, 88 mmol) was treated with N,N-diisopropylethylamine (410 µl, 2.3 mmol) and HATU (386 mg, 1.01 mmol). The mixture was stirred overnight at ambient temperature. The mixture was diluted with saturated sodium hydrogen carbonate solution and extracted with ethyl acetate (3×). The combined organic phases were washed with brine, dried over sodium sulfate and concentrated under reduced pressure. The crude product was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 340 mg (89%) of the desired product.

LC-MS (method 10): $R_t$=1.84 min; MS (ESIpos): m/z=489 [M+H]$^+$ $^1$H-NMR (400 MHz, dimethylsulfoxide-d6) δ [ppm]: 0.295 (2.18), 0.306 (2.35), 0.426 (2.28), 0.446 (2.39), 1.074 (0.41), 1.091 (0.82), 1.109 (0.41), 1.179 (0.62), 1.187 (0.60), 1.198 (0.94), 1.210 (0.57), 1.217 (0.57), 2.012 (13.19), 2.150 (2.19), 2.586 (16.00), 2.906 (3.01), 2.978 (3.29), 3.375 (0.42), 3.392 (0.41), 3.832 (1.91), 3.848 (1.91), 7.253 (1.97), 7.275 (4.18), 7.298 (2.32), 7.717 (1.23), 7.731 (1.72), 7.751 (1.30), 8.500 (0.50), 9.452 (0.41).

Example 403

(±)-2-(6-{[1-(cyclopropylmethyl)-3-(4-fluorophenyl)-4-methyl-1H-pyrazol-5-yl]amino}pyrimidin-4-yl)-3-methyl-4-(trifluoromethyl)-2,4,5,6-tetrahydrocyclopenta[c]pyrazol-4-ol (Racemate)

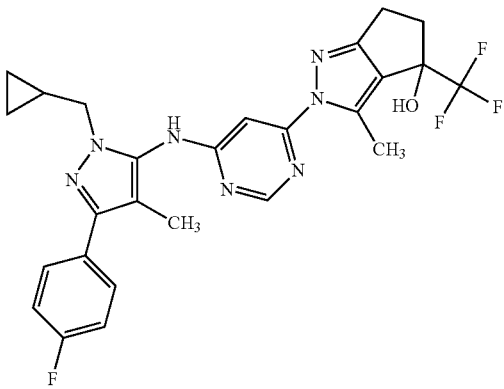 [SMILES: Cc1c(-c2ccc(F)cc2)nn(CC2CC2)c1Nc1cc(-n2nc3c(c2C)C(O)(C(F)(F)F)CC3)ncn1]

Molecular Sieves (4 Å) and tetrabutylammonium fluoride trihydrate (110 mg, 393 µmol) were placed in a round-bottom flask and flame-dried. After cooling to ambient temperature, tetrabutylammonium under an argon atmosphere, it was suspended in toluene (2 mL) and the suspension was stirred at ambient temperature for 30 min. 2-(6-{[1-(cyclopropylmethyl)-3-(4-fluorophenyl)-4-methyl-1H-pyrazol-5-yl]amino}pyrimidin-4-yl)-3-methyl-5,6-dihydrocyclopenta[c]pyrazol-4(2H)-one (75.0 mg, 80% purity, 131 µmol) was added and the reaction mixture stirred for 5 min before being cooled to 0° C. trimethyl(trifluoromethyl)silane (97 µl, 660 µmol) was added dropwise and the reaction mixture was allowed to stir overnight at ambient temperature. Further batches of dry molecular sieves (4 Å), tetrabutylammonium fluoride (110 mg, 393 µmol) and trimethyl(trifluoromethyl)silane (97 µl, 660 mol) were added and the reaction mixture was stirred for another 3 h. Further batches of dry molecular sieves (4 Å), tetrabutylammonium fluoride (110 mg, 393 µmol) and trimethyl(trifluoromethyl)silane (97 µl, 660 µmol) were added and the reaction mixture was stirred for another 1 h. Further batches of dry molecular sieves (4 Å), tetrabutylammonium fluoride (110 mg, 393 µmol) and trimethyl(trifluoromethyl)silane (97 µl, 660 µmol) were added and the reaction mixture was stirred for another 1 h. The reaction mixture was then quenched by addition of water and diluted with ethyl acetate. The solids were removed by filtration and the layers in the filtrate separated.

The aqueous phase was extracted with ethyl acetate. The combined organic phase extracts were washed with brine, dried over sodium sulfate and concentrated. The residue was purified by preparative HPLC (column: Chromatorex C18; 125*30 mm, 10 μM, flow 75 mL/min, gradient acetonitrile/water (containing 0.1% trifluoroacetic acid) 10/90 to 90/10) to yield the desired product (34 mg, 47% yield).

LC-MS (method 11): $R_t$=1.43 min; MS (ESIpos): m/z=528 [M+H]$^+$ $^1$H-NMR (500 MHz, dimethylsulfoxide-d6) δ [ppm]: −0.021 (0.18), −0.006 (1.01), 0.006 (0.56), 0.288 (1.96), 0.296 (2.01), 0.419 (2.20), 0.435 (2.24), 1.161 (0.37), 1.171 (0.67), 1.176 (0.67), 1.186 (0.94), 1.200 (0.62), 1.210 (0.33), 1.233 (0.18), 2.013 (16.00), 2.074 (0.19), 2.422 (0.71), 2.435 (0.55), 2.672 (15.24), 2.697 (0.68), 2.800 (0.89), 2.943 (0.42), 2.965 (0.26), 3.834 (2.03), 3.847 (1.98), 4.329 (0.22), 6.651 (0.17), 7.257 (2.34), 7.275 (4.78), 7.293 (2.57), 7.335 (0.16), 7.728 (1.39), 7.740 (1.89), 7.754 (1.34), 8.514 (0.45), 9.471 (0.44).

Example 404

(±)-2-(6-{[1-(cyclopropylmethyl)-3-(4-fluorophenyl)-4-methyl-1H-pyrazol-5-yl]amino}pyrimidin-4-yl)-3,4-dimethyl-2,4,5,6-tetrahydrocyclopenta[c]pyrazol-4-ol (Racemate)

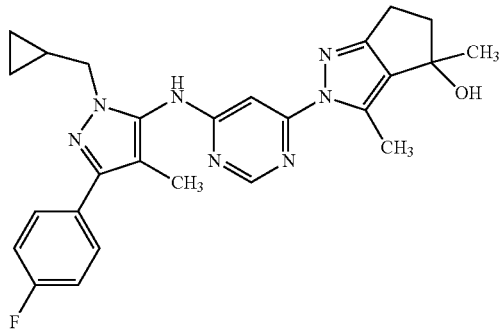 [SMILES: Cc1c(-c2ccc(F)cc2)nn(CC2CC2)c1Nc1cc(-n2nc3c(c2C)C(C)(O)CC3)ncn1]

Under an argon atmosphere, 2-(6-{[1-(cyclopropylmethyl)-3-(4-fluorophenyl)-4-methyl-1H-pyrazol-5-yl]amino}pyrimidin-4-yl)-3-methyl-5,6-dihydrocyclopenta[c]pyrazol-4(2H)-one (80.0 mg, 80% purity, 140 μmol) was dissolved in tetrahydrofuran and the solution cooled to 0° C. A solution of bromo(methyl)magnesium (700 μl, 1.0 M in tetrahydrofuran, 700 μmol) was added dropwise and the reaction mixture was allowed to slowly warm to ambient temperature and stirred for 2 h. The reaction mixture was carefully quenched by addition of aqueous Na$_2$EDTA solution (10%) and extracted with ethyl acetate (3×). The combined organic phase extracts were washed with brine, dried over sodium sulfate and concentrated. The residue was purified by flash column chromatography (SNAP Ultra 10 g, cyclohexane/ethyl acetate gradient) and further purified by preparative HPLC (column: Chromatorex C18; 125*30 mm, 10 μM, flow 75 mL/min, gradient acetonitrile/water 10/90 to 90/10) to yield the desired product (30 mg, 45% yield).

LC-MS (method 10): $R_t$=1.92 min; MS (ESIpos): m/z=474 [M+H]$^+$ $^1$H-NMR (400 MHz, dimethylsulfoxide-d6) δ [ppm]: 0.284 (1.88), 0.294 (2.04), 0.413 (1.97), 0.433 (2.10), 1.181 (0.81), 1.470 (7.75), 2.007 (14.48), 2.289 (0.91), 2.304 (1.80), 2.323 (1.25), 2.655 (16.00), 2.710 (0.57), 3.827 (2.15), 3.844 (2.08), 5.030 (3.48), 7.252 (2.07), 7.274 (4.27), 7.296 (2.27), 7.721 (1.44), 7.735 (1.82), 7.742 (1.77), 7.756 (1.36), 8.469 (0.78), 9.363 (0.87).

Example 405

(±)-cyclopropyl[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]methanol (Racemate)

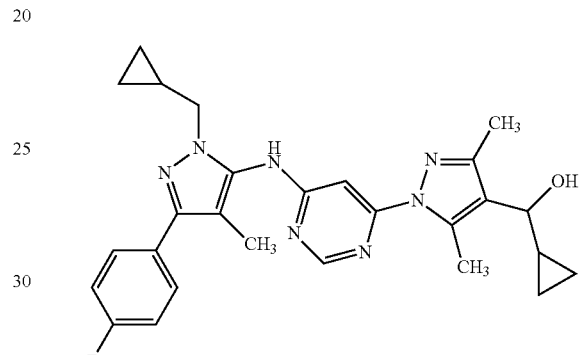

Under an argon atmosphere, 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbaldehyde (80.0 mg, 180 μmol) was dissolved in tetrahydrofuran and the solution cooled to 0° C. A solution of bromo(cyclopropyl)magnesium (1.8 ml, 0.50 M in tetrahydrofuran, 900 μmol) was added dropwise and the reaction mixture was stirred for 1 h at ambient temperature. The reaction mixture was carefully quenched by addition of aqueous Na$_2$EDTA solution (10%) and extracted with ethyl acetate (2×). The combined organic phase extracts were dried over sodium sulfate and concentrated. The residue was purified by flash column chromatography (SNAP Ultra 25 g, cyclohexane/ethyl acetate gradient 95/5 to 20/80) to yield the desired product (49 mg, 56% yield).

LC-MS (method 11): $R_t$=1.38 min; MS (ESIpos): m/z=488 [M+H]$^+$ $^1$H-NMR (400 MHz, dimethylsulfoxide-d6) δ [ppm]: 0.008 (0.53), 0.120 (0.83), 0.132 (1.01), 0.141 (0.71), 0.292 (2.44), 0.304 (2.85), 0.316 (1.17), 0.328 (0.88), 0.348 (1.76), 0.365 (1.83), 0.380 (1.02), 0.391 (0.72), 0.422 (2.44), 0.442 (2.60), 0.481 (0.65), 0.499 (0.86), 0.514 (0.85), 0.526 (0.39), 1.157 (1.03), 1.175 (2.30), 1.183 (1.37), 1.193 (1.92), 1.214 (1.04), 1.233 (0.46), 1.398 (0.88), 1.988 (2.69), 2.007 (14.02), 2.199 (0.29), 2.250 (2.92), 2.328 (0.35), 2.366 (0.20), 2.626 (16.00), 2.670 (0.45), 2.710 (0.27), 3.827 (2.28), 3.844 (2.30), 3.949 (0.90), 3.957 (0.99), 3.968 (0.99), 3.976 (0.97), 4.002 (0.28), 4.021 (0.66), 4.038 (0.65), 4.056 (0.24), 4.958 (2.09), 4.966 (2.15), 5.754 (2.47), 7.251 (1.94), 7.274 (4.14), 7.296 (2.31), 7.713 (1.42), 7.728 (1.92), 7.734 (1.93), 7.748 (1.51), 8.457 (0.62), 9.352 (0.73).

Example 406

6-(4-bromo-3,5-dimethyl-1H-pyrazol-1-yl)-N-[1-(cyclopropylmethyl)-3-(4-fluorophenyl)-4-methyl-1H-pyrazol-5-yl]pyrimidin-4-amine

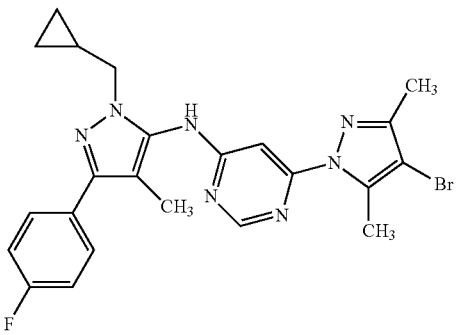 [SMILES: Cc1nn(-c2cc(Nc3c(C)c(-c4ccc(F)cc4)nn3CC3CC3)ncn2)c(C)c1Br]

Under an argon atmosphere, 4-(4-bromo-3,5-dimethyl-1H-pyrazol-1-yl)-6-chloropyrimidine (1.00 g, 95% purity, 3.30 mmol) was suspended in 1,4-dioxane (11 mL). The reaction mixture was degassed with Ar for 3 min and heated to 85° C. 1-(cyclopropylmethyl)-3-(4-fluorophenyl)-4-methyl-1H-pyrazol-5-amine (991 mg, 90% purity, 3.63 mmol), tris(dibenzylideneacetone)dipalladium (90.8 mg, 99.1 µmol) and XantPhos (115 mg, 198 µmol) were added and was degassed again for 1 min. Finally, sodium phenolate (422 mg, 3.63 mmol) were added and the reaction mixture was heated at 85° C. for 3 h while vigorously stirring. After cooling to ambient temperature, the reaction mixture was quenched with aqueous hydrochloric acid solution (1 N) and extracted with ethyl acetate. The organic phase extracts were filtered and dried over sodium sulfate. The residue was purified by flash column chromatography (SNAP Ultra 50 g, cyclohexane/ethyl acetate gradient to yield the desired product (1.04 g, 60% yield).

LC-MS (method 10): $R_t$=2.56 min; MS (ESIpos): m/z=496 [M+H]$^+$ $^1$H-NMR (400 MHz, dimethylsulfoxide-d6) δ [ppm]: 0.289 (1.68), 0.301 (1.81), 0.421 (1.72), 0.441 (1.82), 1.174 (0.49), 1.193 (0.71), 1.398 (16.00), 2.005 (10.52), 2.205 (1.84), 2.328 (0.16), 2.367 (0.24), 2.660 (12.10), 2.710 (0.18), 3.826 (1.59), 3.843 (1.57), 7.252 (1.51), 7.274 (3.02), 7.296 (1.63), 7.713 (1.02), 7.727 (1.39), 7.747 (0.93), 8.502 (0.39), 9.469 (0.28).

Example 407

N-{3-[4-(difluoromethyl)phenyl]-1,4-dimethyl-1H-pyrazol-5-yl}-6-(3,5-dimethyl-1H-pyrazol-1-yl)pyrimidin-4-amine

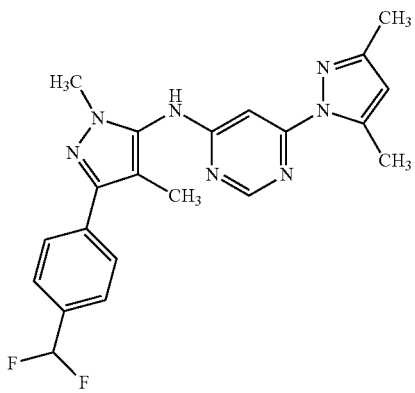 [SMILES: Cc1cc(C)n(-c2cc(Nc3c(C)c(-c4ccc(C(F)F)cc4)nn3C)ncn2)n1]

A microwave vial was charged 4-chloro-6-(3,5-dimethyl-1H-pyrazol-1-yl)pyrimidine (99.9 mg, 479 µmol) and 3-[4-(difluoromethyl)phenyl]-1,4-dimethyl-1H-pyrazol-5-amine (125 mg, 527 µmol) and the contents were suspended in 1,4-dioxane (1.8 ml, 21 mmol). The reaction mixture was degassed with Ar for 3 min. Tris(dibenzylidenaceton)dipalladium (13.2 mg, 14.4 µmol) and Xantphos (16.6 mg, 28.7 µmol) were added and the reaction mixture was degassed again for 1 min and heated to 85° C. At this temperature and sodium phenolate (61.2 mg, 527 µmol) was added. The vial was sealed and heated at 85° C. for 90 minutes while vigorously stirring. After cooling to ambient temperature, the reaction mixture was filtered and purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (100 mg, 48%).

LC-MS (method 10): $R_t$=2.05 min; MS (ESIpos): m/z=410 [M+H]$^+$ $^1$H-NMR (500 MHz, dimethylsulfoxide-d6) δ [ppm]: 1.904 (16.00), 1.981 (0.91), 2.199 (15.29), 2.243 (0.55), 2.632 (13.78), 2.718 (0.46), 3.569 (1.69), 3.707 (1.00), 5.166 (0.65), 6.164 (3.99), 7.031 (1.31), 7.143 (2.77), 7.254 (1.20), 7.457 (3.04), 7.633 (3.57), 7.649 (4.25), 7.742 (4.05), 7.758 (3.09), 8.519 (4.59), 9.805 (0.54).

Example 408

6-[5-(difluoromethyl)-3-methyl-1H-pyrazol-1-yl]-N-{3-[4-(difluoromethyl)phenyl]-1,4-dimethyl-1H-pyrazol-5-yl}pyrimidin-4-amine

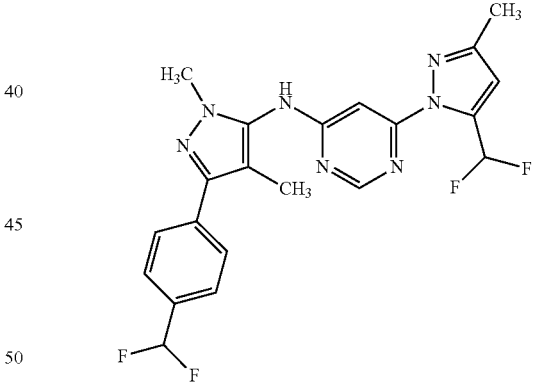

A microwave vial was charged 4-chloro-6-[5-(difluoromethyl)-3-methyl-H-pyrazol-1-yl]pyrimidine (117 mg, 479 µmol) and 3-[4-(difluoromethyl)phenyl]-1,4-dimethyl-1H-pyrazol-5-amine (125 mg, 527 mol) and the contents were suspended in 1,4-dioxane (1.8 ml, 21 mmol). The reaction mixture was degassed with Ar for 3 min. Tris(dibenzylidenaceton)dipalladium (13.2 mg, 14.4 µmol) and Xantphos (16.6 mg, 28.7 µmol) were added and the reaction mixture was degassed again for 1 min and heated to 85° C. At this temperature and sodium phenolate (61.2 mg, 527 µmol) was added. The vial was sealed and heated at 85° C. for 90 minutes while vigorously stirring. After cooling to ambient temperature, the reaction mixture was diluted with water and extracted with dichloromethane (2×). The combined organic phases were dried over sodium sulfate and concentrated under reduced pressure. The crude product was purified by preparative HPLC (method 4) to yield the desired product (39.0 mg, 17%).

LC-MS (method 10): R$_t$=2.17 min; MS (ESIpos): m/z=446 [M+H]$^+$ $^1$H-NMR (500 MHz, dimethylsulfoxide-d6) δ [ppm]: 1.886 (9.21), 2.299 (13.47), 3.736 (16.00), 6.774 (3.77), 7.024 (1.16), 7.136 (2.47), 7.248 (1.01), 7.442 (0.55), 7.633 (2.66), 7.650 (3.41), 7.723 (1.11), 7.738 (3.20), 7.754 (2.32), 7.832 (2.23), 7.941 (0.90), 8.485 (2.70), 9.621 (1.32).

Example 409

N-{5-[4-(difluoromethyl)phenyl]-1,4-dimethyl-1H-pyrazol-3-yl}-6-(3,5-dimethyl-1H-pyrazol-1-yl)pyrimidin-4-amine

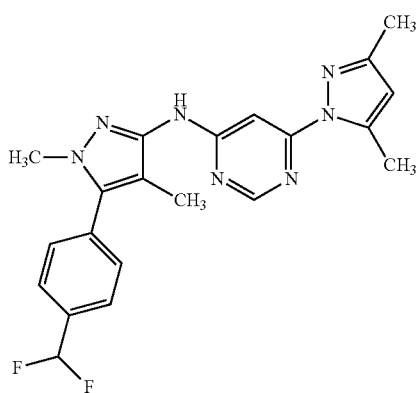 [SMILES: Cc1cc(C)n(-c2cc(Nc3nn(C)c(-c4ccc(C(F)F)cc4)c3C)ncn2)n1]

A microwave vial was charged 4-chloro-6-(3,5-dimethyl-1H-pyrazol-1-yl)pyrimidine (72.0 mg, 345 µmol), 5-[4-(difluoromethyl)phenyl]-1,4-dimethyl-1H-pyrazol-3-amine (90.0 mg, 379 µmol) and sodium phenolate (44.0 mg, 379 µmol) and the contents were suspended in 1,4-dioxane (1.3 ml, 15 mmol). The reaction mixture was degassed with Ar for 3 min. Tris(dibenzylidenaceton)dipalladium (9.47 mg, 10.3 µmol) and Xantphos (12.0 mg, 20.7 µmol) were added and the reaction mixture was degassed again for 1 min. The vial was sealed and heated at 85° C. overnight while vigorously stirring. After cooling to ambient temperature, the reaction mixture was diluted with water and extracted with dichloromethane (2×). The combined organic phases were dried over sodium sulfate and concentrated under reduced pressure. The crude product was purified by preparative HPLC (method 3) to yield the desired product (50.7 mg, 36%).

LC-MS (method 10): R$_t$=2.06 min; MS (ESIpos): m/z=410 [M+H]$^+$ $^1$H-NMR (500 MHz, dimethylsulfoxide-d6) δ [ppm]: 2.063 (16.00), 2.177 (2.14), 2.634 (11.00), 3.323 (14.41), 6.145 (2.13), 6.962 (1.13), 7.074 (2.38), 7.186 (1.00), 7.633 (2.24), 7.649 (2.57), 7.837 (2.17), 7.853 (1.83), 8.479 (0.60), 9.439 (1.53).

Example 410

4-[3-({6-[5-(difluoromethyl)-3-methyl-1H-pyrazol-1-yl]pyrimidin-4-yl}amino)-4-methoxy-1-methyl-1H-pyrazol-5-yl]benzonitrile

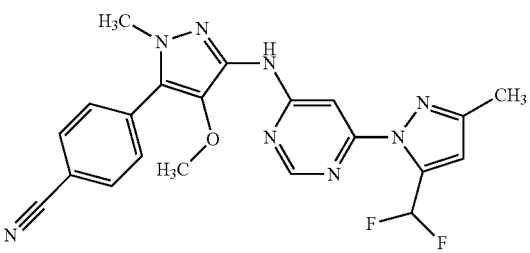 [SMILES: COc1c(Nc2cc(-n3nc(C)cc3C(F)F)ncn2)nn(C)c1-c1ccc(C#N)cc1]

A microwave vial was charged 4-chloro-6-[5-(difluoromethyl)-3-methyl-H-pyrazol-1-yl]pyrimidine (487 mg, 1.99 mmol) and 4-(3-amino-4-methoxy-1-methyl-1H-pyrazol-5-yl)benzonitrile (500 mg, 2.19 mmol) and the contents were suspended in 1,4-dioxane (12 ml, 140 mmol). The reaction mixture was degassed with Ar for 3 min. Tris(dibenzylidenaceton)dipalladium (54.7 mg, 59.7 µmol) and Xantphos (69.1 mg, 119 µmol) were added and the reaction mixture was degassed again for 1 min and heated to 85° C. At this temperature and sodium phenolate (254 mg, 2.19 mmol) was added. The vial was sealed and heated at 85° C. for 90 minutes while vigorously stirring. After cooling to ambient temperature, the reaction mixture was filtered and purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (373 mg, 43%).

LC-MS (method 9): R$_t$=1.04 min; MS (ESIpos): m/z=437 [M+H]$^+$ $^1$H-NMR (500 MHz, dimethylsulfoxide-d6) δ [ppm]: 2.288 (9.06), 3.564 (16.00), 3.784 (0.53), 3.794 (11.99), 6.774 (2.71), 7.246 (3.11), 7.248 (3.02), 7.716 (0.75), 7.780 (3.19), 7.784 (1.13), 7.794 (1.32), 7.798 (3.52), 7.824 (1.62), 7.933 (0.65), 8.005 (0.86), 8.008 (3.80), 8.012 (1.19), 8.022 (1.27), 8.026 (3.12), 8.487 (2.09), 9.644 (0.63).

Example 411

4-[5-({6-[5-(difluoromethyl)-3-methyl-1H-pyrazol-1-yl]pyrimidin-4-yl}amino)-4-methoxy-1-methyl-1H-pyrazol-3-yl]benzonitrile

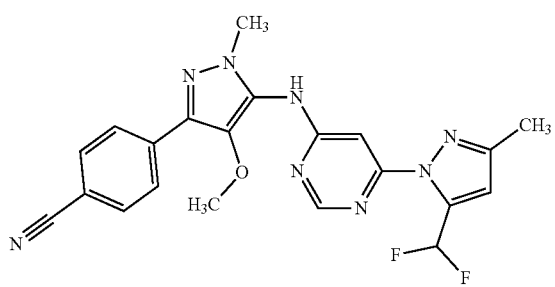 [SMILES: COc1c(-c2ccc(C#N)cc2)nn(C)c1Nc1cc(-n2nc(C)cc2C(F)F)ncn1]

A microwave vial was charged 4-chloro-6-[5-(difluoromethyl)-3-methyl-H-pyrazol-1-yl]pyrimidine (97.4 mg, 398 µmol) and 4-(5-amino-4-methoxy-1-methyl-1H-pyrazol-3-yl)benzonitrile (100 mg, 438 mol) and the contents were suspended in 1,4-dioxane (3.2 ml, 37 mmol). The reaction mixture was degassed with Ar for 3 min. Tris(dibenzylidenaceton)dipalladium (10.9 mg, 11.9 µmol) and Xantphos (13.8 mg, 23.9 µmol) were added and the reaction mixture was degassed again for 1 min and heated to 85° C. At this temperature and sodium phenolate (50.9 mg, 438 µmol) was added. The vial was sealed and heated at 85° C. for 120 minutes while vigorously stirring. After cooling to ambient temperature, the reaction mixture was diluted with hydrochlorid acid and extracted with ethyl acetate (2×). The combined organic phases were washer with water and brine, dried over sodium sulfate and concentrated under reduced pressure. The crude product was purified by flash-chromatography (column: SNAP Ultra 10 g, solvent. dichloromethane/ethyl acetate 4:1) to yield the desired product (136 mg, 78%).

LC-MS (method 10): $R_t$=2.04 min; MS (ESIpos): m/z=437 [M+H]$^+$ $^1$H-NMR (400 MHz, dimethylsulfoxide-d6) δ [ppm]: 1.615 (0.48), 2.289 (2.65), 3.633 (0.43), 3.659 (6.23), 3.728 (16.00), 6.798 (2.27), 7.685 (0.94), 7.821 (2.01), 7.873 (2.72), 7.894 (3.53), 7.957 (0.84), 8.034 (3.12), 8.055 (2.39), 8.534 (0.85), 9.703 (0.83).

Example 412

N-[4-(difluoromethoxy)-5-(4-fluorophenyl)-1-methyl-1H-pyrazol-3-yl]-6-[5-(difluoromethyl)-3-methyl-1H-pyrazol-1-yl]pyrimidin-4-amine

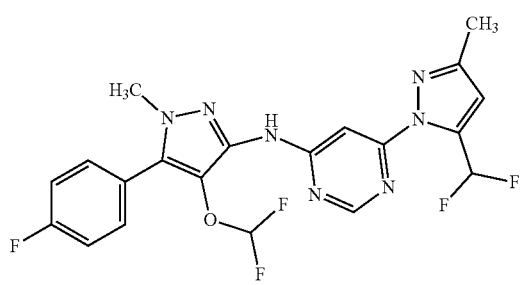 [SMILES: Cc1cc(C(F)F)n(-c2cc(Nc3nn(C)c(-c4ccc(F)cc4)c3OC(F)F)ncn2)n1]

A microwave vial was charged with 4-(difluoromethoxy)-5-(4-fluorophenyl)-1-methyl-1H-pyrazol-3-amine (120 mg, 467 µmol) and 4-chloro-6-[5-(difluoromethyl)-3-methyl-1H-pyrazol-1-yl]pyrimidine (126 mg, 513 µmol), and the contents were suspended in 1,4-dioxane (1.6 mL). The reaction mixture was degassed with Ar for 3 min. Tris (dibenzylideneacetone)dipalladium (128 mg, 140 µmol) and XantPhos (162 mg, 280 µmol) were added and the reaction mixture was degassed again for 1 min. Finally, sodium phenolate (59.6 mg, 513 µmol) was added and the vial was sealed and heated at 85° C. overnight while vigorously shaking. After cooling to ambient temperature, the reaction mixture was filtered and concentrated. The residue was redissolved in dimethylsulfoxide and purified by preparative HPLC (method 6) and repurified by flash column chromatography (SNAP Ultra 10 g, cyclohexane/ethyl acetate gradient 100/0 to 50/50) to yield the desired product (71 mg, 32% yield).

LC-MS (method 11): $R_t$=1.45 min; MS (ESIpos): m/z=466 [M+H]$^+$ $^1$H-NMR (600 MHz, dimethylsulfoxide-d6) δ [ppm]: 2.308 (14.67), 3.741 (16.00), 5.748 (2.58), 6.673 (1.30), 6.780 (3.84), 6.796 (2.53), 6.919 (1.12), 7.380 (1.29), 7.390 (2.29), 7.393 (0.86), 7.401 (0.98), 7.404 (4.42), 7.408 (0.96), 7.416 (0.79), 7.419 (2.46), 7.597 (2.28), 7.601 (1.02), 7.606 (2.52), 7.612 (2.31), 7.617 (0.89), 7.620 (2.08), 7.738 (0.98), 7.829 (2.18), 7.920 (0.86), 8.494 (3.20), 9.684 (1.97).

Example 413

6-(4-chloro-3,5-dimethyl-1H-pyrazol-1-yl)-N-[4-(difluoromethoxy)-5-(4-fluorophenyl)-1-methyl-1H-pyrazol-3-yl]pyrimidin-4-amine

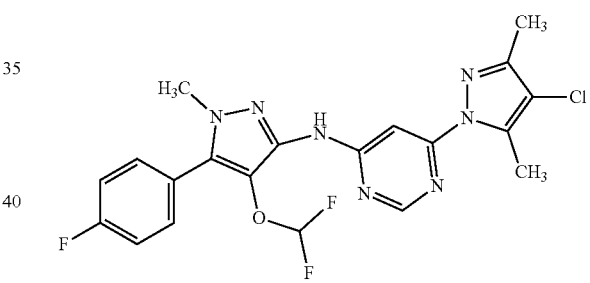

A microwave vial was charged with 4-(difluoromethoxy)-5-(4-fluorophenyl)-1-methyl-1H-pyrazol-3-amine (100 mg, 389 µmol), 4-chloro-6-(4-chloro-3,5-dimethyl-1H-pyrazol-1-yl)pyrimidine (104 mg, 428 µmol) and the contents were suspended in 1,4-dioxane (1.4 mL). The resulting reaction mixture was degassed with Ar for 3 min. Tris(dibenzylideneacetone)dipalladium (107 mg, 117 µmol) and XantPhos (135 mg, 233 µmol) were added and the reaction mixture was degassed again for 1 min. Finally, sodium phenolate (49.6 mg, 428 µmol) was added and the vial was sealed and heated at 85° C. overnight while vigorously shaking. After cooling to ambient temperature, the reaction mixture was filtered and concentrated. The residue was redissolved in dimethylsulfoxide and purified by preparative HPLC (method 6) to yield the desired product (59 mg, 33% yield).

LC-MS (method 11): $R_t$=1.55 min; MS (ESIpos): m/z=464 [M+H]$^+$ $^1$H NMR (500 MHz, dimethylsulfoxide-d$_6$) δ ppm: 2.23 (s, 3H), 2.65 (s, 3H), 3.73 (s, 3H), 6.80 (t, J=74 Hz, 1H), 7.33-7.46 (m, 3H), 7.55-7.66 (m, 2H), 8.50 (s, 1H), 9.61 (s, 1H).

Example 414

6-(4-chloro-3,5-dimethyl-1H-pyrazol-1-yl)-N-[3-(4-fluorophenyl)-1-(2-methoxyethyl)-4-methyl-1H-pyrazol-5-yl]pyrimidin-4-amine

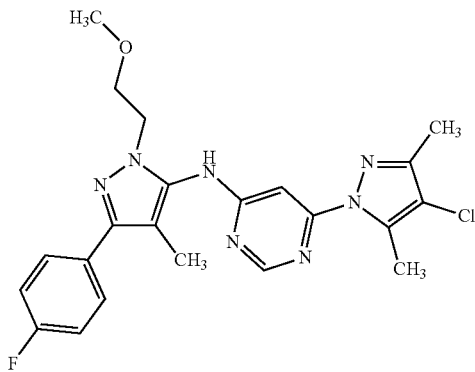 [SMILES: COCCn1nc(-c2ccc(F)cc2)c(C)c1Nc1cc(-n2nc(C)c(Cl)c2C)ncn1]

A solution of 1-(cyclopropylmethyl)-4-methyl-3-(6-methylpyridin-3-yl)-1H-pyrazol-5-amine (100 mg, 413 µmol) in 1,4-dioxane (1.5 ml) was degassed with argon and heated to an internal temperature of 85° C. To the heated solution was added 3-(4-fluorophenyl)-1-(2-methoxyethyl)-4-methyl-1H-pyrazol-5-amine (88.0 mg, 353 µmol), tris(dibenzylideneaceton)dipalladium (8.82 mg, 9.63 µmol), Xantphos (10.2 mg, 19.3 µmol) and finally sodium phenolate (41.0 mg, 353 µmol) before heating at 85° C. for an additional 30 minutes. The reaction mixture was added to a saturated aqueous solution of sodium hydrogen carbonate (180 mL), and the solution extracted three times with ethyl acetate. The combined organic phase s were washed with a saturated solution of sodium chloride, dried with sodium sulfate and concentrated in vacuo. The crude product was purified by flash-chromatography on silica gel (Gradient 18% to 100% ethylacetate in cyclohexane, column: Biotage SNAP Ultra 10 g) to yield 91.0 mg (100% purity, 62% yield) of the desired product.

LC-MS (Method 9): $R_t$=1.27 min; MS (ESIpos): m/z=456 [M+H]$^+$ $^1$H-NMR (500 MHz, dimethylsulfoxide-d6) δ [ppm]: 2.002 (13.79), 2.205 (1.68), 2.646 (16.00), 3.142 (2.96), 3.647 (1.55), 3.658 (3.06), 3.669 (1.57), 4.112 (0.94), 7.257 (1.72), 7.261 (0.72), 7.275 (3.49), 7.293 (1.88), 7.716 (0.96), 7.727 (1.31), 7.743 (0.96), 8.503 (0.45), 9.419 (0.92).

Example 415

N-[1-(cyclopropylmethyl)-4-methyl-3-(6-methylpyridin-3-yl)-1H-pyrazol-5-yl]-6-[5-(difluoromethyl)-3-methyl-1H-pyrazol-1-yl]pyrimidin-4-amine

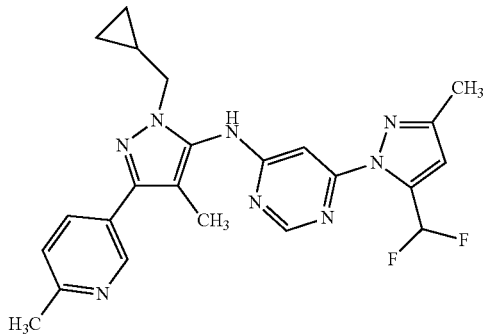 [SMILES: Cc1ccc(-c2nn(CC3CC3)c(Nc3cc(-n4nc(C)cc4C(F)F)ncn3)c2C)cn1]

In a sealed microwave tube under argon, 1-(cyclopropylmethyl)-4-methyl-3-(6-methylpyridin-3-yl)-1H-pyrazol-5-amine (60.0 mg, 248 µmol), 4-chloro-6-[5-(difluoromethyl)-3-methyl-1H-pyrazol-1-yl]pyrimidine (66.6 mg, 272 µmol), (31.6 mg, 272 µmol), (6.80 mg, 7.43 µmol), (7.85 mg, 14.9 µmol) were dissolved in 1,4-dioxane (1.2 ml). The reaction mixture was heated at 90° C. for 30 minutes. The cooled reaction mixture was diluted with ethylacetate, washed with a saturated aqueous solution of sodium hydrogen carbonate and the aqueous phase then extracted twice with ethylacetate. The combined organic phase s were dried with sodium sulfate and concentrated in vacuo. The crude product was purified by flash-chromatography on silica gel (Gradient 18% to 100% ethylacetate in cyclohexane, column: Biotage SNAP Ultra 10 g) to yield the desired product 57.4 mg (100% purity, 51% yield).

LC-MS (Method 10): $R_t$=1.60 min; MS (ESIpos): m/z=451 [M+H]$^+$ $^1$H-NMR (500 MHz, CHLOROFORM-d) δ [ppm]: 0.335 (0.68), 0.345 (2.84), 0.356 (2.88), 0.366 (0.73), 0.556 (0.75), 0.566 (2.36), 0.568 (2.36), 0.582 (2.44), 0.594 (0.58), 1.269 (0.61), 1.275 (0.59), 1.285 (0.93), 1.295 (0.55), 1.301 (0.59), 1.316 (0.28), 2.122 (16.00), 2.248 (0.16), 2.302 (12.32), 2.615 (15.34), 3.952 (3.20), 3.966 (3.14), 6.594 (3.59), 6.728 (0.55), 6.848 (0.56), 7.236 (2.14), 7.252 (2.24), 7.644 (1.18), 7.753 (2.36), 7.863 (1.09), 7.969 (1.67), 7.974 (1.64), 7.986 (1.59), 7.990 (1.54), 8.529 (3.96), 8.530 (4.07), 8.871 (2.34), 8.875 (2.21).

Example 416

2-(6-{[1-(cyclopropylmethyl)-3-(4-fluorophenyl)-4-methyl-1H-pyrazol-5-yl]amino}pyrimidin-4-yl)-1,2,4,5,6,7-hexahydro-3H-indazol-3-one

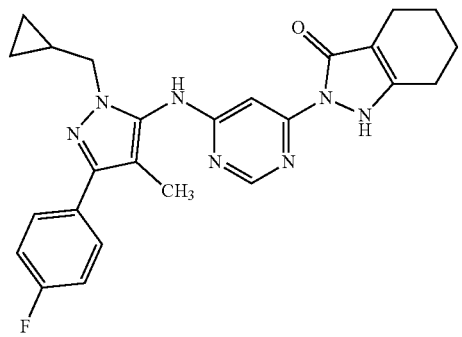 [SMILES: Cc1c(-c2ccc(F)cc2)nn(CC2CC2)c1Nc1cc(-n2[nH]c3c(c2=O)CCCC3)ncn1]

A solution of N-[1-(cyclopropylmethyl)-3-(4-fluorophenyl)-4-methyl-1H-pyrazol-5-yl]-6-hydrazinylpyrimidin-4-amine (95.0 mg, 70% purity, 188 µmol) in methanol (2.0 ml, 49 mmol) was treated with methyl 2-oxocyclohexanecarboxylate (28 µl, 190 µmol) and stirred for 4 hours at 80° C. The mixture was concentrated under reduced pressure and purified by preparative HPLC ((method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) and subsequent by using (method 18) to yield 12.0 mg (14%) of the desired product.

LC-MS (method 10): $R_t$=2.01 min; MS (ESIpos): m/z=460 [M+H]$^+$ $^1$H-NMR (500 MHz, dimethylsulfoxide-d6) δ [ppm]: 0.277 (2.99), 0.286 (3.13), 0.407 (2.84), 0.423 (2.97), 1.071 (0.66), 1.085 (1.32), 1.099 (0.67), 1.156 (0.49), 1.166 (0.85), 1.170 (0.86), 1.180 (1.19), 1.190 (0.80), 1.195 (0.78), 1.204 (0.42), 1.353 (0.44), 1.624 (1.88), 1.632 (1.96), 1.682 (1.97), 1.692 (1.88), 1.993 (16.00), 2.118 (1.83), 2.446 (1.81), 2.458 (2.98), 3.355 (0.59), 3.369 (0.79), 3.383 (0.72), 3.827 (2.49), 3.840 (2.40), 7.251 (2.51), 7.268 (4.90), 7.286 (2.60), 7.697 (2.51), 7.709 (3.04), 7.715 (2.89), 7.726 (2.31), 8.424 (0.98), 9.393 (3.80), 11.409 (2.35).

Example 417

6-(4-chloro-3,5-dimethyl-1H-pyrazol-1-yl)-N-{1-(cyclopropylmethyl)-4-methyl-3-[4-(methylamino)phenyl]-1H-pyrazol-5-yl}pyrimidin-4-amine

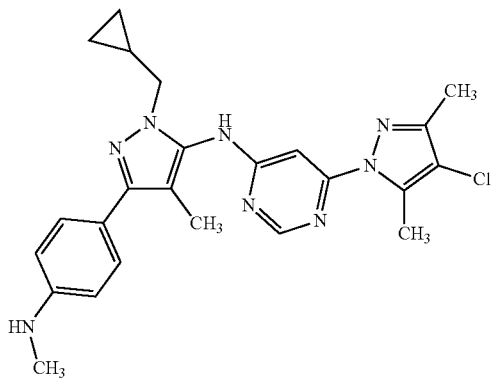 [SMILES: CNc1ccc(-c2nn(CC3CC3)c(Nc3cc(-n4nc(C)c(Cl)c4C)ncn3)c2C)cc1]

In a sealed microwave tube under argon, 1-(cyclopropylmethyl)-4-methyl-3-[4-(methylamino)phenyl]-1H-pyrazol-5-amine (60.0 mg, 234 μmol), 4-chloro-6-(4-chloro-3,5-dimethyl-1H-pyrazol-1-yl)pyrimidine (62.6 mg, 257 μmol), (29.9 mg, 257 μmol), (6.43 mg, 7.02 μmol), (7.42 mg, 14.0 μmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 8% to 60% ethylacetate in cyclohexane, column: Biotage SNAP Ultra 10 g) to yield the desired product 75.3 mg (100% purity, 69% yield).

LC-MS (Method 10): $R_t$=2.33 min; MS (ESIpos): m/z=463 [M+H]$^+$ $^1$H-NMR (600 MHz, dimethylsulfoxide-d6) δ [ppm]: 0.279 (1.55), 0.408 (1.78), 0.421 (1.82), 1.173 (0.82), 1.184 (0.53), 1.960 (11.87), 2.198 (1.12), 2.644 (16.00), 2.703 (9.03), 2.712 (9.13), 3.784 (1.35), 3.794 (1.35), 5.708 (0.69), 5.746 (0.20), 6.589 (3.72), 6.604 (3.82), 7.429 (1.45), 7.442 (1.41), 8.486 (0.22), 9.389 (0.18).

Example 418 ethyl 1-(6-{[1-(cyclopropylmethyl)-4-methyl-3-(6-methylpyridin-3-yl)-1H-pyrazol-5-yl]amino}pyrimidin-4-yl)-3,5-dimethyl-1H-pyrazole-4-carboxylate

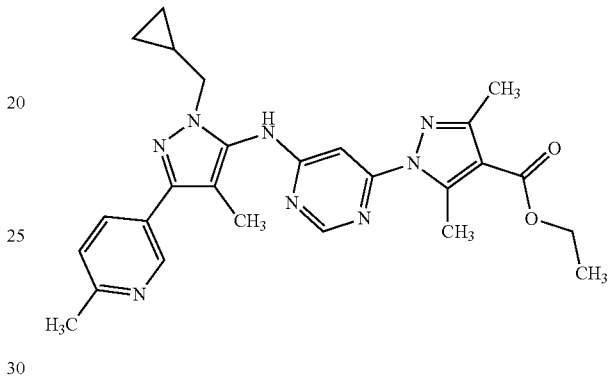

In a sealed microwave tube under argon, 1-(cyclopropylmethyl)-4-methyl-3-(6-methylpyridin-3-yl)-1H-pyrazol-5-amine (150 mg, 619 μmol), ethyl 1-(6-chloropyrimidin-4-yl)-3,5-dimethyl-1H-pyrazole-4-carboxylate (191 mg, 681 μmol), tris(dibenzylidenaceton)dipalladium (17.0 mg, 18.6 μmol), Xantphos (19.6 mg, 37.1 μmol) were dissolved in 1,4-dioxane (3.0 ml). The reaction mixture was heated to 90° C. and after 2 minutes was added sodium phenolate (79.0 mg, 681 μmol), and the reaction continued stirring for an additional 30 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 20% to 100% ethylacetate in cyclohexane, column: Biotage SNAP Ultra 10 g) to yield 181 mg (100% purity, 60% yield) of the desired product.

LC-MS (Method 10): $R_t$=1.69 min; MS (ESIpos): m/z=487 [M+H]$^+$ $^1$H-NMR (500 MHz, CHLOROFORM-d) δ [ppm]: 0.008 (12.21), 0.014 (0.36), 0.338 (0.54), 0.348 (2.19), 0.359 (2.17), 0.369 (0.61), 0.558 (0.63), 0.568 (1.80), 0.570 (1.78), 0.574 (0.85), 0.584 (1.88), 0.586 (1.71), 0.596 (0.50), 1.250 (0.14), 1.264 (0.30), 1.274 (0.45), 1.280 (0.45), 1.290 (0.74), 1.300 (0.43), 1.304 (0.41), 1.316 (0.27), 1.364 (4.47), 1.378 (9.65), 1.393 (4.54), 2.119 (13.19), 2.423 (10.66), 2.610 (12.82), 2.988 (16.00), 3.952 (2.56), 3.966 (2.52), 4.304 (1.33), 4.318 (4.23), 4.332 (4.16), 4.347 (1.28), 6.678 (0.44), 6.876 (0.37), 7.229 (1.72), 7.245 (1.79), 7.958 (1.48), 7.962 (1.48), 7.974 (1.39), 7.978 (1.39), 8.587 (3.75), 8.589 (3.70), 8.858 (1.82), 8.861 (1.80).

Example 419 cyclopropyl[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]methanol

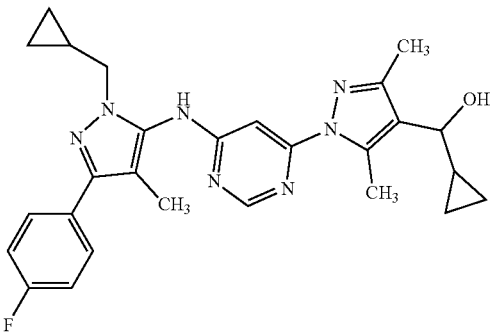 [SMILES: Cc1nn(-c2cc(Nc3c(C)c(-c4ccc(F)cc4)nn3CC3CC3)ncn2)c(C)c1C(O)C1CC1]

Obtained from separation of the enantiomers of a racemic sample of (±)-1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbaldehyde (racemate 49 mg dissolved in ethanol/n-heptane 1:2, 3 mL) by preparative HPLC (Daicel Chiralpak IG 5 m, 250×20 mm, 35° C., flow: 15 mL/min, isocratic ethanol/n-heptane 90/10, injections of 0.4 mL every 17 min) to yield the title compound as the first eluting enantiomer (18 mg, 37% from racemate).

LC-MS (method 11): R$_t$=1.37 min; MS (ESIpos): m/z=488 [M+H]$^+$

Chiral HPLC (Daicel Chiralpak IG 5 μm, 250×4.6 mm, isocratic i-hexane/ethanol 90/10+0.2% diethylamine): Rt=11.7 min, 99% ee $^1$H-NMR (500 MHz, dimethylsulfoxide-d6) δ [ppm]: −0.007 (1.38), 0.007 (0.83), 0.293 (0.95), 0.303 (0.99), 0.349 (0.48), 0.363 (0.55), 0.369 (0.46), 0.424 (1.00), 0.440 (1.02), 1.186 (0.54), 1.196 (0.68), 1.210 (0.42), 1.378 (16.00), 1.387 (14.69), 1.818 (0.52), 1.828 (0.67), 1.839 (0.74), 2.007 (6.37), 2.250 (0.85), 2.626 (8.04), 2.941 (0.49), 3.424 (0.72), 3.446 (0.58), 3.452 (0.59), 3.468 (0.46), 3.484 (1.26), 3.491 (0.78), 3.504 (0.51), 3.543 (0.46), 3.551 (0.50), 3.634 (0.63), 3.655 (0.48), 3.696 (0.61), 3.718 (0.53), 3.828 (0.79), 3.841 (0.77), 4.958 (0.76), 4.964 (0.77), 7.255 (0.96), 7.273 (1.94), 7.291 (1.04), 7.717 (0.55), 7.728 (0.73), 7.745 (0.54).

Example 420 cyclopropyl[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]methanol

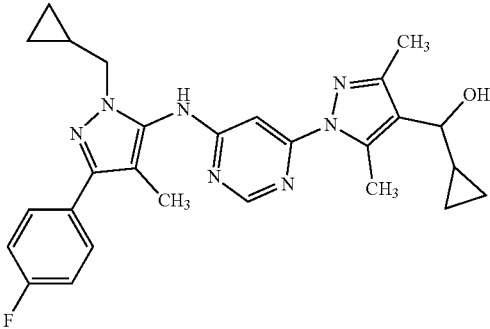 [SMILES: Cc1nn(-c2cc(Nc3c(C)c(-c4ccc(F)cc4)nn3CC3CC3)ncn2)c(C)c1C(O)C1CC1]

Obtained from separation of the enantiomers of a racemic sample of (±)-1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbaldehyde (racemate 49 mg dissolved in ethanol/n-heptane 1:2, 3 mL) by preparative HPLC (Daicel Chiralpak IG 5 m, 250×20 mm, 35° C., flow: 15 mL/min, isocratic ethanol/n-heptane 90/10, injections of 0.4 mL every 17 min) to yield the title compound as the second eluting enantiomer (18 mg, 37% from racemate).

LC-MS (method 11): R$_t$=1.37 min; MS (ESIpos): m/z=488 [M+H]$^+$

Chiral HPLC (Daicel Chiralpak IG 5 μm, 250×4.6 mm, isocratic i-hexane/ethanol 90/10+0.2% diethylamine): Rt=13.2 min, 99% ee $^1$H-NMR (500 MHz, dimethylsulfoxide-d6) δ [ppm]: −0.120 (0.17), −0.007 (1.99), 0.007 (1.11), 0.116 (0.66), 0.122 (0.71), 0.132 (0.81), 0.293 (2.12), 0.303 (2.19), 0.331 (0.71), 0.349 (1.04), 0.363 (1.24), 0.379 (0.81), 0.388 (0.58), 0.424 (2.19), 0.440 (2.25), 0.495 (0.78), 0.501 (0.75), 0.511 (0.63), 1.141 (0.27), 1.156 (0.66), 1.170 (0.88), 1.186 (1.19), 1.196 (1.46), 1.210 (0.93), 1.388 (0.17), 2.007 (13.07), 2.251 (1.89), 2.362 (0.30), 2.626 (16.00), 3.828 (1.77), 3.841 (1.71), 3.958 (0.81), 3.967 (0.80), 4.958 (1.76), 4.964 (1.69), 7.255 (1.99), 7.273 (3.93), 7.291 (2.05), 7.717 (1.23), 7.729 (1.66), 7.744 (1.16), 8.455 (0.50), 9.347 (0.46).

Example 421

N-[1-(cyclopropylmethyl)-3-(5-fluoropyridin-2-yl)-4-methyl-1H-pyrazol-5-yl]-6-(3,5-dimethyl-1H-pyrazol-1-yl)pyrimidin-4-amine

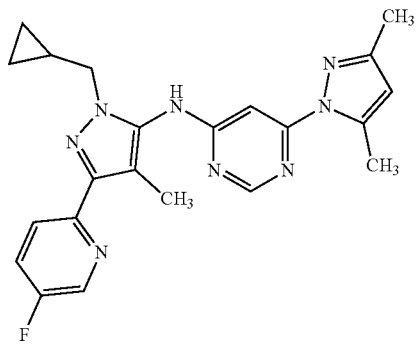 [SMILES: Cc1cc(C)n(-c2cc(Nc3c(C)c(-c4ccc(F)cn4)nn3CC3CC3)ncn2)n1]

A microwave vial was charged 4-chloro-6-(3,5-dimethyl-1H-pyrazol-1-yl)pyrimidine (86.6 mg, 415 mol) and 1-(cyclopropylmethyl)-3-(5-fluoropyridin-2-yl)-4-methyl-1H-pyrazol-5-amine (225 mg, 50% purity, 457 μmol) and the contents were suspended in 1,4-dioxane (1.6 ml, 19 mmol). The reaction mixture was degassed with Ar for 3 min. Tris(dibenzylidenaceton)dipalladium (11.4 mg, 12.5 μmol) and Xantphos (14.4 mg, 24.9 μmol) were added and the reaction mixture was degassed again for 1 min and heated to 85° C. At this temperature and sodium phenolate (53.0 mg, 457 μmol) was added. The vial was sealed and heated at 85° C. for 90 minutes while vigorously stirring. After cooling to ambient temperature, the reaction mixture was left overnight and purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography (column: SNAP KP-Sil 10 g, solvent: 96% dichloromethane/4% ethyl acetate to 66% dichloromethane/34% ethyl acetate to 54% dichloromethane/46% ethyl acetate) to yield the desired product (45.3 mg, 25%).

LC-MS (method 10): R$_t$=2.19 min; MS (ESIpos): m/z=419 [M+H]$^+$ $^1$H-NMR (500 MHz, dimethylsulfoxide-d6) δ [ppm]: 0.311 (1.79), 0.320 (1.84), 0.404 (0.41), 0.416 (0.41), 0.437 (1.99), 0.453 (2.00), 1.198 (0.58), 1.204 (0.57), 1.213 (0.88), 1.220 (0.48), 1.223 (0.55), 1.229 (0.58), 1.519 (1.31), 2.154 (16.00), 2.171 (1.55), 2.629 (12.81), 3.864 (1.43), 3.877 (1.38), 6.136 (1.70), 7.755 (0.55), 7.761 (0.61), 7.773 (1.16), 7.779 (1.24), 7.790 (0.67), 7.796 (0.68), 7.996 (0.69), 8.005 (0.76), 8.013 (0.69), 8.022 (0.61), 8.462 (0.42), 8.595 (2.28), 8.601 (2.26), 9.395 (0.44), 9.664 (0.49).

Example 422

N-[1-(cyclopropylmethyl)-3-(5-fluoropyridin-2-yl)-4-methyl-1H-pyrazol-5-yl]-6-[5-(difluoromethyl)-3-methyl-1H-pyrazol-1-yl]pyrimidin-4-amine

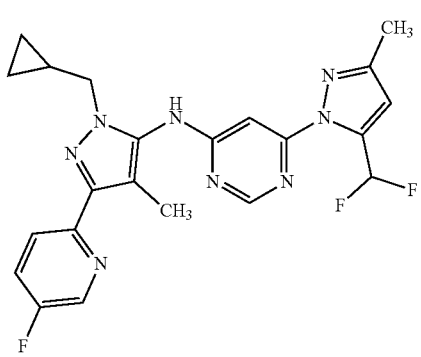 [SMILES: Cc1cc(C(F)F)n(-c2cc(Nc3c(C)c(-c4ccc(F)cn4)nn3CC3CC3)ncn2)n1]

A microwave vial was charged 4-chloro-6-[5-(difluoromethyl)-3-methyl-H-pyrazol-1-yl]pyrimidine (102 mg, 415 μmol) and 1-(cyclopropylmethyl)-3-(5-fluoropyridin-2-yl)-4-methyl-1H-pyrazol-5-amine (225 mg, 50% purity, 457 μmol) and the contents were suspended in 1,4-dioxane (1.6 ml, 19 mmol). The reaction mixture was degassed with Ar for 3 min. Tris(dibenzylidenaceton)dipalladium (11.4 mg, 12.5 μmol) and Xantphos (14.4 mg, 24.9 μmol) were added and the reaction mixture was degassed again for 1 min and heated to 85° C. At this temperature and sodium phenolate (53.0 mg, 457 μmol) was added. The vial was sealed and heated at 85° C. for 90 minutes while vigorously stirring. After cooling to ambient temperature, the reaction mixture was left overnight and purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and subsequently by flash-chromatography (column: SNAP KP-Sil 10 g, solvent: 96% dichloromethane/4% ethyl acetate to 34% ethyl acetate) to yield the desired product (36.4 mg, 18%).

LC-MS (method 10): R$_t$=2.23 min; MS (ESIpos): m/z=455 [M+H]$^+$ $^1$H-NMR (500 MHz, dimethylsulfoxide-d6) δ [ppm]: 1.847 (0.68), 2.193 (0.55), 2.197 (0.75), 2.201 (0.53), 3.026 (16.00).

Example 423

N-[1-(cyclopropylmethyl)-3-(4-fluorophenyl)-4-methyl-1H-pyrazol-5-yl]-6-[3,5-dimethyl-4-(methylsulfonyl)-1H-pyrazol-1-yl]pyrimidin-4-amine

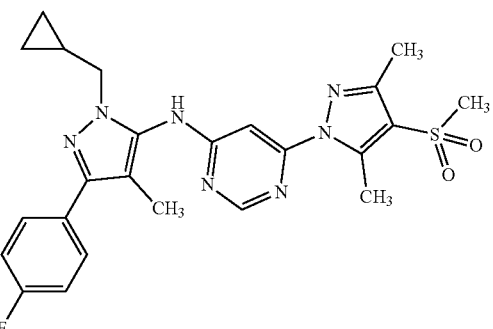

N-[1-(cyclopropylmethyl)-3-(4-fluorophenyl)-4-methyl-1H-pyrazol-5-yl]-6-[3,5-dimethyl-4-(methylsulfanyl)-1H-pyrazol-1-yl]pyrimidin-4-amine (20.0 mg, 95% purity, 41.0 μmol) was dissolved in dichloromethane (1.0 mL) and cooled to 0° C. Meta-chloroperbenzoic acid (18.4 mg, 77% purity, 82.0 μmol) was added slowly and the reaction mixture stirred for 30 min at 0° C. The reaction was quenched by careful addition of aqueous saturated sodium hydrogencarbonate solution and extracted with dichloromethane (3×). The combined organic phase extracts were washed with brine, dried over sodium sulfate and concentrated. The residue was purified by preparative HPLC (column: Chromatorex C18; 125*30 mm, 10 μM, flow 75 mL/min, gradient acetonitrile/water (containing 0.1% trifluoroacetic acid) 10/90 to 90/10) to yield the desired product (6 mg, 28% yield).

LC-MS (method 11): R$_t$=1.34 min; MS (ESIneg): m/z=494 [M−H]$^-$ $^1$H-NMR (500 MHz, dimethylsulfoxide-d6) δ [ppm]: −0.007 (1.65), 0.007 (0.90), 0.293 (2.45), 0.302 (2.51), 0.428 (2.73), 0.444 (2.76), 1.169 (0.45), 1.179 (0.78), 1.185 (0.74), 1.194 (1.13), 1.204 (0.71), 1.209 (0.74), 1.234 (0.30), 2.009 (16.00), 2.045 (0.38), 2.168 (0.22), 2.233 (0.26), 2.390 (1.39), 2.620 (0.18), 2.631 (0.54), 2.876 (10.29), 3.384 (0.26), 3.836 (1.84), 3.847 (1.81), 4.354 (0.20), 7.256 (2.30), 7.274 (4.56), 7.292 (2.47), 7.727 (2.01), 8.549 (0.31), 9.576 (0.21).

Example 424

N-[5-(4-fluorophenyl)-1,4-dimethyl-1H-pyrazol-3-yl]-6-[4-(trifluoromethyl)-1H-pyrazol-1-yl]pyrimidin-4-amine

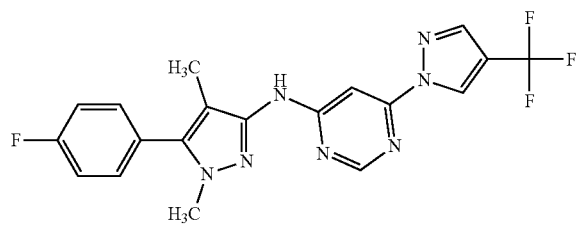 [SMILES: Cc1c(Nc2cc(-n3cc(C(F)(F)F)cn3)ncn2)nn(C)c1-c1ccc(F)cc1]

A microwave vial was charged 4-chloro-6-[4-(trifluoromethyl)-1H-pyrazol-1-yl]pyrimidine (100 mg, 402 µmol) and 5-(4-fluorophenyl)-1,4-dimethyl-1H-pyrazol-3-amine (90.8 mg, 442 µmol) and the contents were suspended in 1,4-dioxane (1.7 ml, 20 mmol). The reaction mixture was degassed with Ar for 3 min. Tris(dibenzylidenaceton)dipalladium (4.79 mg, 5.23 µmol) and Xantphos (6.98 mg, 12.1 mol) were added and the reaction mixture was degassed again for 1 min and heated to 85° C. At this temperature and sodium phenolate (70.0 mg, 603 µmol) was added. The vial was sealed and heated at 85° C. for 90 minutes while vigorously stirring. After cooling to ambient temperature, the reaction mixture was left overnight, diluted with water and extracted with dichloromethane (2×). The combined organic phases were dried over sodium sulfate and concentrated under reduced pressure. The crude product was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (90.2 mg, 54%).

LC-MS (method 11): $R_t$=1.46 min; MS (ESIneg): m/z=416 [M−H]⁻

¹H-NMR (500 MHz, dimethylsulfoxide-d6) δ [ppm]: −0.007 (0.44), 2.026 (16.00), 3.677 (5.60), 7.254 (1.75), 7.272 (3.47), 7.290 (1.87), 7.707 (1.19), 7.719 (1.62), 7.734 (1.11), 9.187 (3.39), 9.760 (0.51).

Example 425

(±)-4-{5-[(6-{3,5-dimethyl-4-[2,2,2-trifluoro-1-hydroxyethyl]-1H-pyrazol-1-yl}pyrimidin-4-yl)amino]-4-methoxy-1-methyl-1H-pyrazol-3-yl}benzonitrile (Racemic)

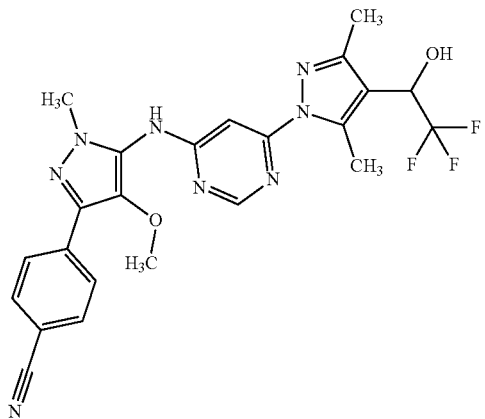 [SMILES: COc1c(-c2ccc(C#N)cc2)nn(C)c1Nc1cc(-n2nc(C)c(C(O)C(F)(F)F)c2C)ncn1]

Under an argon atmosphere a Schlenk tube was charged with molecular sieves in toluene (6 mL). To this mixture tetrabutylammonium fluoride hydrate (256 mg, 917 µmol) was added and the mixture was stirred at ambient temperature for 30 minutes. Subsequently a solution of 4-(5-{[6-(4-formyl-3,5-dimethyl-1H-pyrazol-1-yl)pyrimidin-4-yl]amino}-4-methoxy-1-methyl-1H-pyrazol-3-yl)benzonitrile (131 mg, 306 µmol) in toluene (3 mL) was added and it was stirred for 5 minutes. Then, trimethyl(trifluoromethyl)silane (230 µl, 1.5 mmol) at −18° C. was added and the reaction mixture was stirred 10 minutes at −18° C. and one hour at ambient temperature. The mixture was diluted with water, filtered and extracted with ethyl acetate (2×). The combined organic phases were dried over sodium sulfate, concentrated under reduced pressure and the crude product was purified using preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and by (method 7) to yield the desired product (30.2 mg, 20%).

LC-MS (method 10): $R_t$=1.82 min; MS (ESIpos): m/z=499 [M+H]⁺

¹H-NMR (500 MHz, dimethylsulfoxide-d6) δ [ppm]: 1.078 (1.50), 1.092 (3.10), 1.106 (1.51), 2.250 (1.77), 2.684 (8.33), 3.363 (0.50), 3.377 (1.48), 3.391 (1.45), 3.405 (0.47), 3.656 (5.09), 3.729 (16.00), 5.170 (0.41), 6.709 (1.45), 6.719 (1.46), 7.872 (2.58), 7.875 (0.99), 7.885 (1.13), 7.889 (3.12), 8.035 (2.78), 8.038 (0.99), 8.048 (0.97), 8.052 (2.13), 8.525 (0.73), 9.574 (0.71).

Example 426

N-[1-(cyclopropylmethyl)-3-(4-fluorophenyl)-4-methyl-1H-pyrazol-5-yl]-6-[4-(trifluoromethyl)-1H-pyrazol-1-yl]pyrimidin-4-amine

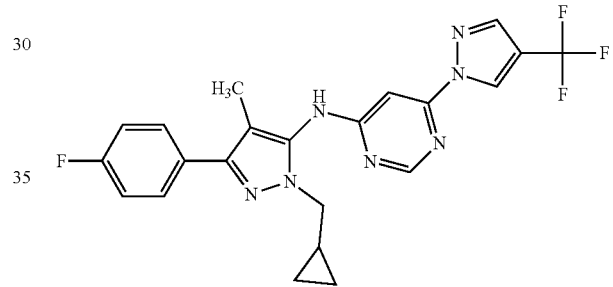

A microwave vial was charged 4-chloro-6-[4-(trifluoromethyl)-1H-pyrazol-1-yl]pyrimidine (100 mg, 402 µmol) and 1-(cyclopropylmethyl)-3-(4-fluorophenyl)-4-methyl-1H-pyrazol-5-amine (109 mg, 442 µmol) and the contents were suspended in 1,4-dioxane (1.7 ml, 20 mmol). The reaction mixture was degassed with Ar for 3 min. Tris(dibenzylidenaceton)dipalladium (4.79 mg, 5.23 µmol) and Xantphos (6.98 mg, 12.1 µmol) were added and the reaction mixture was degassed again for 1 min and heated to 85° C. At this temperature and sodium phenolate (70.0 mg, 603 µmol) was added. The vial was sealed and heated at 85° C. for 90 minutes while vigorously stirring. The mixture was left overnight at ambient temperature, diluted with water and dichloromethane (2×). The combined organic phases were dried over sodium sulfate and concentrated under reduced pressure. The crude product was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and by flash-chromatography (column: SNAP KP-Sil 10 g, solvent: 96% dichloromethane/4% ethyl acetate to 34% ethyl acetate) to yield the desired product (87.8 mg, 48%).

LC-MS (method 10): $R_t$=2.32 min; MS (ESIpos): m/z=458 [M+H]⁺

¹H-NMR (500 MHz, dimethylsulfoxide-d6) δ [ppm]: 0.296 (1.34), 0.418 (1.35), 0.433 (1.35), 1.190 (0.56), 2.017 (16.00), 3.850 (1.09), 7.262 (1.40), 7.280 (2.79), 7.298 (1.50), 7.739 (1.22), 9.181 (3.15).

Example 427

N-[3-(4-fluorophenyl)-1,4-dimethyl-1H-pyrazol-5-yl]-6-[4-(trifluoromethyl)-1H-pyrazol-1-yl]pyrimidin-4-amine

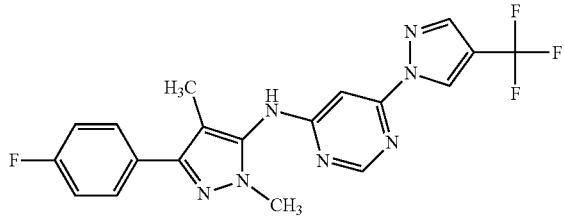 [SMILES: Cc1c(-c2ccc(F)cc2)nn(C)c1Nc1cc(-n2cc(C(F)(F)F)cn2)ncn1]

A microwave vial was charged 4-chloro-6-[4-(trifluoromethyl)-1H-pyrazol-1-yl]pyrimidine (100 mg, 402 μmol) and 3-(4-fluorophenyl)-1,4-dimethyl-1H-pyrazol-5-amine (90.8 mg, 442 μmol) and the contents were suspended in 1,4-dioxane (1.7 ml, 20 mmol). The reaction mixture was degassed with Ar for 3 min. Tris(dibenzylidenaceton)dipalladium (4.79 mg, 5.23 μmol) and Xantphos (6.98 mg, 12.1 μmol) were added and the reaction mixture was degassed again for 1 min and heated to 85° C. At this temperature and sodium phenolate (70.0 mg, 603 μmol) was added. The vial was sealed and heated at 85° C. for 90 minutes while vigorously stirring. The mixture was left overnight at ambient temperature, diluted with water and dichloromethane (2×). The combined organic phases were dried over sodium sulfate and concentrated under reduced pressure. The crude product was purified by preparative HPLC (method: column: Reprosil C18; 10 μm; 125×30 mm/flow: 50 mL/min/ solvent: A=water (0.01% formic acid), B=acetonitrile/gradient: 0.00-5.00 min=10% B, 6.50 min=20% B, 17.0-19.75 min=100% B, 19.75-23.00 min=90% B) and by flash-chromatography (column: SNAP KP-Sil 10 g, solvent: 96% dichloromethane/4% ethyl acetate to 45% ethyl acetate) to yield the desired product (66.9 mg, 40%).

LC-MS (method 10): $R_t$=2.19 min; MS (ESIpos): m/z=418 [M+H]⁺

¹H-NMR (500 MHz, dimethylsulfoxide-d6) δ [ppm]: 1.880 (9.59), 3.328 (16.00), 7.368 (2.31), 7.372 (0.91), 7.382 (1.26), 7.386 (4.93), 7.390 (1.12), 7.399 (1.00), 7.404 (2.77), 7.522 (0.49), 7.528 (2.77), 7.532 (1.31), 7.539 (3.10), 7.545 (2.57), 7.552 (1.15), 7.556 (2.24), 8.337 (4.37), 8.560 (2.52), 9.166 (3.34), 9.789 (1.45).

Example 428

4-[5-({6-[4-(2-hydroxy-2-methylpropyl)-3,5-dimethyl-1H-pyrazol-1-yl]pyrimidin-4-yl}amino)-4-methoxy-1-methyl-1H-pyrazol-3-yl]benzonitrile

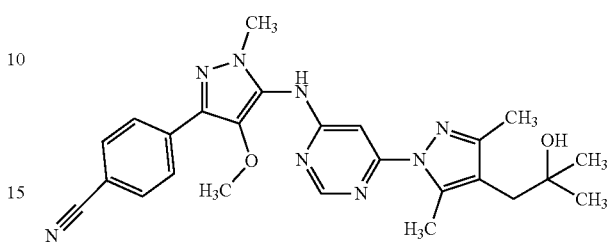

Under an argon atmosphere a solution of ethyl [1-(6-{[3-(4-cyanophenyl)-4-methoxy-1-methyl-1H-pyrazol-5-yl]amino}pyrimidin-4-yl)-3,5-dimethyl-1H-pyrazol-4-yl]acetate (80.0 mg, 164 μmol) in tetrahydrofuran (3.2 ml, 39 mmol) was treated with chloro(methyl)magnesium (190 μl, 3.0 M in tetrahydrofuran, 580 μmol) at 0° C. The mixture was stirred overnight at ambient temperature. The mixture was diluted with potassium sodium tartrate solution and water and extracted with ethyl acetate. The organic phase was dried over magnesium sulfate and concentrated under reduced pressure. The crude product was purified by flash-chromatography for two times (column: SNAP Ultra 10 g, solvent: 100% dichloromethane to 6% methanol/dichloromethane and column: KP-Sil 10 g, solvent: ethyl acetate/ cyclo-hexane 1:1 to ethyl acetate) to yield 9.20 mg (10%) of the desired product.

LC-MS (method 10): Rt=1.80 min; MS (ESIpos): m/z=473 [M+H]⁺

¹H-NMR (500 MHz, dimethylsulfoxide-d6) δ [ppm]: −0.007 (0.63), 0.007 (0.42), 1.090 (11.74), 1.161 (1.34), 1.175 (2.65), 1.190 (1.32), 1.989 (4.62), 2.146 (0.78), 2.169 (2.30), 2.436 (3.07), 2.584 (9.75), 3.578 (0.46), 3.633 (0.72), 3.636 (0.63), 3.652 (6.64), 3.729 (16.00), 3.750 (0.49), 4.023 (1.04), 4.037 (1.04), 4.241 (3.29), 7.870 (2.95), 7.874 (1.19), 7.884 (1.35), 7.888 (3.53), 8.035 (3.19), 8.039 (1.16), 8.052 (2.44), 8.482 (0.98), 9.463 (1.25).

Example 429

1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-ol

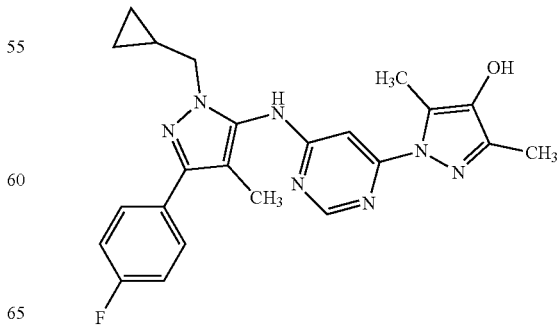

A microwave vial was charged with 1-(6-chloropyrimidin-4-yl)-3,5-dimethyl-1H-pyrazol-4-ol (75.0 mg, 334 µmol) and 1-(cyclopropylmethyl)-3-(4-fluorophenyl)-4-methyl-1H-pyrazol-5-amine (100 mg, 90% purity, 367 µmol) and the contents were suspended in 1,4-dioxane (1.1 mL). The reaction mixture was degassed with Ar for 3 min. Tris(dibenzylideneacetone)dipalladium (6.11 mg, 6.68 µmol) and XantPhos (7.73 mg, 13.4 µmol) were added and the reaction mixture was degassed again for 1 min. Finally, sodium phenolate (42.6 mg, 367 µmol) was added and the vial was sealed and heated at 85° C. overnight while vigorously shaking. After cooling to ambient temperature, the reaction mixture was diluted with ethyl acetate and filtered. The filtrate was washed with brine, dried over sodium sulfate and concentrated. The residue was purified by flash column chromatography (SNAP Ultra 25 g, cyclohexane/ethyl acetate gradient) and further by preparative HPLC (column: Chromatorex C18; 125*30 mm, 10 µM, flow 75 mL/min, gradient acetonitrile/water (containing 0.1% trifluoroacetic acid) 10/90 to 95/5) to yield the desired product (5.5 mg, 4% yield).

LC-MS (method 10): $R_t$=1.87 min; MS (ESIpos): m/z=434 [M+H]$^+$ $^1$H-NMR (500 MHz, dimethylsulfoxide-d6) δ [ppm]: 0.291 (2.45), 0.300 (2.53), 0.420 (2.42), 0.436 (2.50), 1.183 (0.79), 1.193 (1.06), 1.233 (0.35), 1.412 (0.29), 1.649 (0.64), 1.983 (0.58), 2.002 (12.79), 2.073 (0.64), 2.106 (2.92), 2.515 (16.00), 3.820 (2.47), 3.833 (2.38), 7.110 (0.18), 7.255 (1.95), 7.273 (3.96), 7.290 (2.20), 7.717 (1.43), 7.730 (2.01), 7.745 (1.43), 8.403 (0.76), 9.270 (0.96).

Example 430

N-{1-(cyclopropylmethyl)-3-[4-fluoro-3-(methylsulfanyl)phenyl]-4-methyl-1H-pyrazol-5-yl}-6-(3,5-dimethyl-1H-pyrazol-1-yl)pyrimidin-4-amine

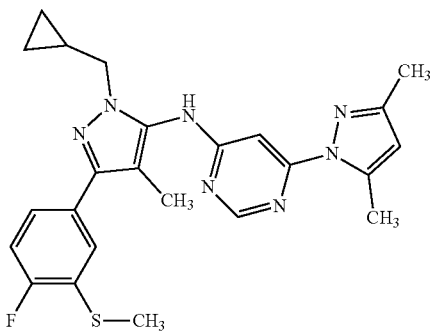 [SMILES: CSc1cc(-c2nn(CC3CC3)c(Nc3cc(-n4nc(C)cc4C)ncn3)c2C)ccc1F]

This compound was obtained as a by-product during the synthesis of N-[1-(cyclopropylmethyl)-3-(4-fluorophenyl)-4-methyl-1H-pyrazol-5-yl]-6-[3,5-dimethyl-4-(methylsulfanyl)-1H-pyrazol-1-yl]pyrimidin-4-amine. It was purified by preparative HPLC (column: Chromatorex C18; 125*30 mm, 10 µM, flow 100 mL/min, gradient acetonitrile/water (containing 0.1% trifluoroacetic acid) 10/90 to 90/10) to yield the title compound (10 mg, 5% yield).

LC-MS (method 11): $R_t$=1.58 min; MS (ESIpos): m/z=464 [M+H]$^+$ $^1$H-NMR (600 MHz, dimethylsulfoxide-d6) δ [ppm]: 0.319 (2.53), 0.326 (2.55), 0.449 (2.57), 0.462 (2.60), 1.205 (0.41), 1.213 (0.73), 1.218 (0.73), 1.225 (1.01), 1.233 (0.72), 1.238 (0.74), 1.249 (0.77), 2.033 (0.72), 2.046 (11.47), 2.154 (7.62), 2.191 (2.64), 2.241 (0.60), 2.249 (0.92), 2.272 (0.69), 2.558 (16.00), 2.650 (12.22), 3.863 (2.24), 3.874 (2.26), 4.133 (0.87), 6.155 (2.27), 7.279 (1.07), 7.295 (1.75), 7.310 (1.28), 7.541 (0.92), 7.614 (1.12), 7.625 (1.20), 8.485 (0.63), 9.398 (0.59).

Example 431 tert-butyl 1-(6-{[1-(cyclopropylmethyl)-3-(4-fluorophenyl)-4-methyl-1H-pyrazol-5-yl]amino}pyrimidin-4-yl)-4,6-dihydropyrrolo[3,4-c]pyrazole-5(1H)-carboxylate

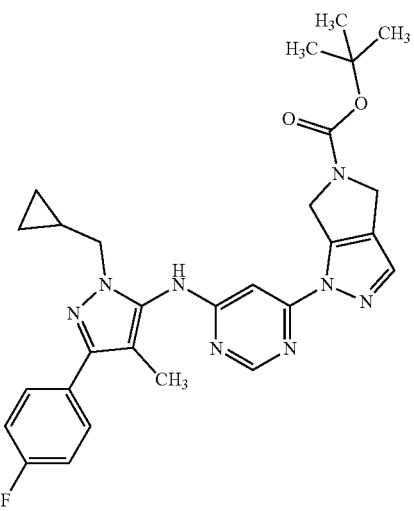 [SMILES: Cc1c(-c2ccc(F)cc2)nn(CC2CC2)c1Nc1cc(-n2ncc3c2CN(C(=O)OC(C)(C)C)C3)ncn1]

In a sealed microwave tube under argon, 1-(cyclopropylmethyl)-3-(4-fluorophenyl)-4-methyl-1H-pyrazol-5-amine (60.0 mg, 245 µmol), tert-butyl 1-(6-chloropyrimidin-4-yl)-4,6-dihydropyrrolo[3,4-c]pyrazole-5(1H)-carboxylate (86.6 mg, 269 µmol), sodium phenolate (31.2 mg, 269 µmol), tris(dibenzylidenaceton)dipalladium (6.72 mg, 7.34 µmol), Xantphos (7.76 mg, 14.7 µmol) were dissolved in 1,4-dioxane (1.2 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 20% to 100% ethylacetate in cyclohexane, column: Biotage SNAP Ultra 10 g) and then by preparative HPLC (method 19) to yield 78.2 mg (100% purity, 60% yield) of the desired product.

LC-MS (Method 9): $R_t$=1.26 min; MS (ESIpos): m/z=531 [M+H]$^+$ $^1$H-NMR (500 MHz, dimethylsulfoxide-d6) δ [ppm]: 0.292 (1.18), 0.413 (1.29), 0.429 (1.30), 1.183 (0.53), 1.230 (0.41), 1.453 (12.33), 1.468 (16.00), 2.007 (10.49), 3.837 (0.96), 4.326 (0.94), 4.352 (0.78), 4.738 (1.20), 4.766 (1.41), 7.257 (1.19), 7.275 (2.30), 7.292 (1.22), 7.634 (0.11), 7.735 (1.10), 8.513 (0.18), 9.557 (0.19).

Example 432

6-[5-(difluoromethyl)-3-methyl-1H-pyrazol-1-yl]-N-{5-[4-(difluoromethyl)phenyl]-1,4-dimethyl-1H-pyrazol-3-yl}pyrimidin-4-amine

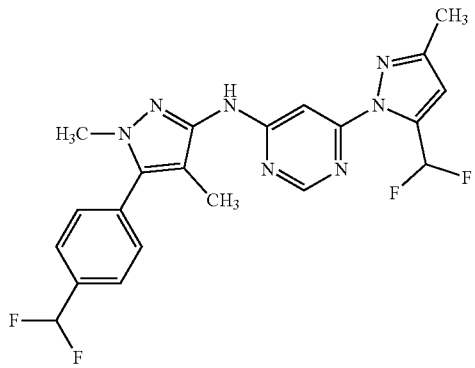 [SMILES: Cc1cc(C(F)F)n(-c2cc(Nc3nn(C)c(-c4ccc(C(F)F)cc4)c3C)ncn2)n1]

A microwave vial was charged 4-chloro-6-[5-(difluoromethyl)-3-methyl-H-pyrazol-1-yl]pyrimidine (84.4 mg, 345 µmol), 5-[4-(difluoromethyl)phenyl]-1,4-dimethyl-1H-pyrazol-3-amine (90.0 mg, 379 µmol) and sodium phenolate (44.0 mg, 379 µmol) and the contents were suspended in 1,4-dioxane (1.3 ml, 15 mmol). The reaction mixture was degassed with Ar for 3 min. Tris(dibenzylidenaceton)dipalladium (9.47 mg, 10.3 µmol) and Xantphos (12.0 mg, 20.7 µmol) were added and the reaction mixture was degassed again for 1 min. The vial was sealed and heated at 85° C. overnight while vigorously stirring. After cooling to ambient temperature, the reaction mixture was diluted with water and extracted with dichloromethane (2×). The combined organic phases were dried over sodium sulfate and concentrated under reduced pressure. The crude product was purified by preparative HPLC (method 4) and further flash-chromatography on silica gel to yield the desired product (65.0 mg, 40%).

LC-MS (method 10): $R_t$=2.15 min; MS (ESIpos): m/z=446 [M+H]$^+$ $^1$H-NMR (500 MHz, dimethylsulfoxide-d6) δ [ppm]: 1.162 (0.55), 1.176 (1.11), 1.190 (0.58), 1.989 (2.08), 2.064 (16.00), 2.290 (1.51), 2.340 (0.43), 3.694 (5.68), 4.024 (0.47), 4.038 (0.47), 6.789 (2.05), 6.963 (1.22), 7.075 (2.56), 7.187 (1.09), 7.634 (2.52), 7.650 (2.84), 7.714 (1.13), 7.822 (2.59), 7.838 (1.86), 7.853 (1.55), 7.931 (1.01), 9.639 (1.13).

Example 433 tert-butyl 2-(6-{[1-(cyclopropylmethyl)-3-(4-fluorophenyl)-4-methyl-1H-pyrazol-5-yl]amino}pyrimidin-4-yl)-2,6-dihydropyrrolo[3,4-c]pyrazole-5(4H)-carboxylate

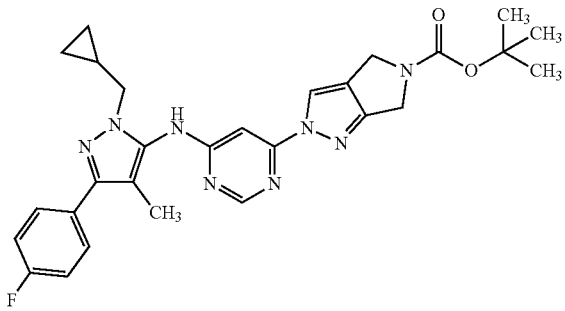 [SMILES: Cc1c(-c2ccc(F)cc2)nn(CC2CC2)c1Nc1cc(-n2cc3c(n2)CN(C(=O)OC(C)(C)C)C3)ncn1]

In a sealed microwave tube under argon, 1-(cyclopropylmethyl)-3-(4-fluorophenyl)-4-methyl-1H-pyrazol-5-amine (60.0 mg, 245 µmol), tert-butyl 2-(6-chloropyrimidin-4-yl)-2,6-dihydropyrrolo[3,4-c]pyrazole-5(4H)-carboxylate (86.6 mg, 269 µmol), sodium phenolate (31.2 mg, 269 µmol), tris(dibenzylidenaceton)dipalladium (6.72 mg, 7.34 µmol), Xantphos (7.76 mg, 14.7 µmol) were dissolved in 1,4-dioxane (1.2 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 20% to 100% ethylacetate in cyclohexane, column: Biotage SNAP Ultra 10 g) and then by preparative HPLC (method 19) to yield 80.2 mg (100% purity, 62% yield) of the desired product.

LC-MS (Method 9): $R_t$=1.24 min; MS (ESIpos): m/z=531 [M+H]$^+$ $^1$H-NMR (500 MHz, dimethylsulfoxide-d6) δ [ppm]: −0.009 (0.72), 0.290 (1.47), 0.411 (1.63), 0.426 (1.65), 1.159 (0.52), 1.173 (0.99), 1.181 (0.73), 1.187 (0.75), 1.230 (0.69), 1.448 (16.00), 1.514 (0.53), 1.987 (0.91), 2.011 (6.91), 2.015 (6.96), 3.835 (1.42), 4.370 (1.42), 4.393 (1.70), 7.259 (1.44), 7.276 (2.81), 7.294 (1.50), 7.740 (1.27), 8.377 (1.64), 8.396 (1.30), 8.501 (0.22), 9.546 (0.24).

Example 434

N-[5-(4-fluorophenyl)-1,4-dimethyl-1H-pyrazol-3-yl]-6-(4-methoxy-3,5-dimethyl-1H-pyrazol-1-yl)pyrimidin-4-amine

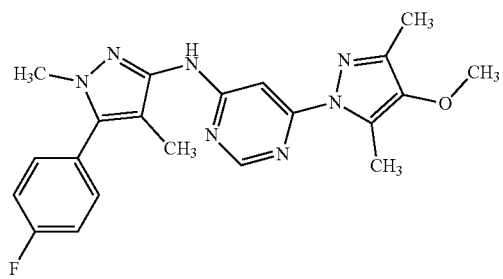 [SMILES: COc1c(C)nn(-c2cc(Nc3nn(C)c(-c4ccc(F)cc4)c3C)ncn2)c1C]

A microwave vial was charged with 4-chloro-6-(4-methoxy-3,5-dimethyl-1H-pyrazol-1-yl)pyrimidine (100 mg, 100% purity, 419 µmol) and 5-(4-fluorophenyl)-1,4-dimethyl-1H-pyrazol-3-amine (94.6 mg, 461 µmol) and the contents were suspended in 1,4-dioxane (1.3 mL). The reaction mixture was degassed with Ar for 3 min. Tris (dibenzylideneacetone)dipalladium (11.5 mg, 12.6 µmol) and XantPhos (14.5 mg, 25.1 µmol) were added and the reaction mixture was degassed again for 1 min. Finally, sodium phenolate (53.5 mg, 461 µmol) was added and the vial was sealed and heated at 85° C. overnight while vigorously shaking. After cooling to ambient temperature, the reaction mixture was diluted with dimethylsulfoxide, filtered and purified by preparative HPLC (method 3) to yield the desired product (92 mg, 53% yield).

LC-MS (method 9): $R_t$=1.10 min; MS (ESIpos): m/z=408 [M+H]$^+$ $^1$H-NMR (500 MHz, dimethylsulfoxide-d6) δ [ppm]: 1.847 (8.63), 2.194 (10.48), 3.687 (11.28), 3.703 (16.00), 7.355 (1.03), 7.361 (1.77), 7.365 (0.71), 7.374 (0.92), 7.379

(3.13), 7.383 (0.83), 7.392 (0.75), 7.397 (1.85), 7.512 (1.70), 7.516 (0.72), 7.523 (1.87), 7.529 (1.49), 7.536 (0.61), 7.540 (1.30), 8.429 (2.21), 9.366 (1.70).

Example 435

4-(3-{[6-(4-methoxy-3,5-dimethyl-1H-pyrazol-1-yl)pyrimidin-4-yl]amino}-1,4-dimethyl-1H-pyrazol-5-yl)benzonitrile

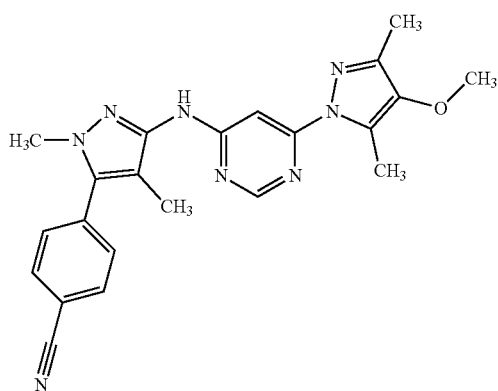 [SMILES: COc1c(C)nn(-c2cc(Nc3nn(C)c(-c4ccc(C#N)cc4)c3C)ncn2)c1C]

A microwave vial was charged with 4-chloro-6-(4-methoxy-3,5-dimethyl-1H-pyrazol-1-yl)pyrimidine (100 mg, 100% purity, 419 μmol) and 4-(3-amino-1,4-dimethyl-1H-pyrazol-5-yl)benzonitrile (97.8 mg, 461 μmol), and the contents were suspended in 1,4-dioxane (1.3 mL). The reaction mixture was degassed with Ar for 3 min. Tris(dibenzylideneacetone)dipalladium (11.5 mg, 12.6 μmol) and XantPhos (14.5 mg, 25.1 μmol) were added and the reaction mixture was degassed again for 1 min. Finally, sodium phenolate (53.5 mg, 461 μmol) was added, the vial was sealed and heated at 85° C. overnight while vigorously shaking. After cooling to ambient temperature, the reaction mixture was diluted with dimethylsulfoxide, filtered and purified by preparative HPLC (method 3) to yield the desired product (108 mg, 55% yield).

LC-MS (method 9): $R_t$=1.02 min; MS (ESIpos): m/z=415 [M+H]$^+$ $^1$H-NMR (500 MHz, dimethylsulfoxide-d6) δ [ppm]: −0.007 (0.41), 1.647 (0.60), 1.882 (7.84), 2.195 (9.66), 2.212 (0.48), 2.558 (0.54), 3.703 (16.00), 3.713 (0.75), 3.735 (10.38), 7.359 (0.80), 7.370 (0.53), 7.384 (0.48), 7.394 (0.48), 7.698 (2.65), 7.702 (0.94), 7.711 (1.03), 7.715 (2.90), 8.004 (3.01), 8.008 (0.97), 8.018 (0.97), 8.021 (2.67), 8.433 (1.91), 8.434 (1.90), 9.412 (1.50).

Example 436

4-(5-{[6-(4-methoxy-3,5-dimethyl-1H-pyrazol-1-yl)pyrimidin-4-yl]amino}-1,4-dimethyl-1H-pyrazol-3-yl)benzonitrile

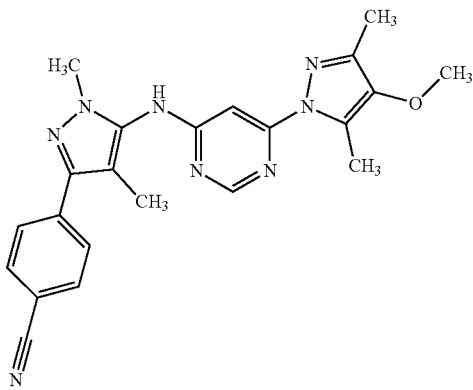 [SMILES: COc1c(C)nn(-c2cc(Nc3c(C)c(-c4ccc(C#N)cc4)nn3C)ncn2)c1C]

A microwave vial was charged with 4-chloro-6-(4-methoxy-3,5-dimethyl-1H-pyrazol-1-yl)pyrimidine (100 mg, 100% purity, 419 μmol) and 4-(5-amino-1,4-dimethyl-1H-pyrazol-3-yl)benzonitrile (97.8 mg, 461 μmol), and the contents were suspended in 1,4-dioxane (1.3 mL). The reaction mixture was degassed with Ar for 3 min. Tris(dibenzylideneacetone)dipalladium (11.5 mg, 12.6 μmol) and XantPhos (14.5 mg, 25.1 μmol) were added and the reaction mixture was degassed again for 1 min. Finally, sodium phenolate (53.5 mg, 461 μmol) was added and the vial was sealed and heated at 85° C. overnight while vigorously shaking. After cooling to ambient temperature, the reaction mixture was diluted with dimethylsulfoxide, filtered and purified by preparative HPLC (method 3) to yield the desired product (78 mg, 43% yield).

LC-MS (method 9): $R_t$=1.05 min; MS (ESIpos): m/z=415 [M+H]$^+$ $^1$H-NMR (500 MHz, dimethylsulfoxide-d6) δ [ppm]: −0.007 (0.40), 0.006 (0.28), 1.526 (0.23), 1.647 (0.59), 2.068 (16.00), 2.187 (2.54), 3.691 (9.61), 3.702 (10.96), 7.371 (0.39), 7.385 (0.42), 7.395 (0.45), 7.896 (14.92), 7.914 (0.37), 8.454 (0.70), 9.444 (1.66).

Example 437

N-[3-(4-fluorophenyl)-1,4-dimethyl-1H-pyrazol-5-yl]-6-(4-methoxy-3,5-dimethyl-1H-pyrazol-1-yl)pyrimidin-4-amine

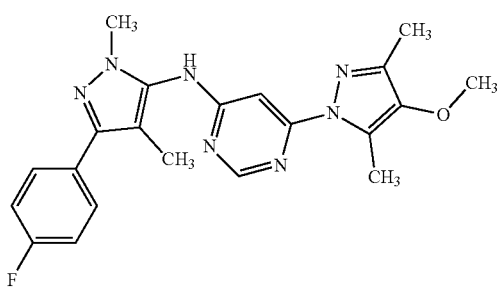 [SMILES: COc1c(C)nn(-c2cc(Nc3c(C)c(-c4ccc(F)cc4)nn3C)ncn2)c1C]

A microwave vial was charged with 4-chloro-6-(4-methoxy-3,5-dimethyl-1H-pyrazol-1-yl)pyrimidine (100 mg, 100% purity, 419 µmol) and 3-(4-fluorophenyl)-1,4-dimethyl-1H-pyrazol-5-amine (94.6 mg, 461 µmol), and the contents were suspended in 1,4-dioxane (1.3 mL). The reaction mixture was degassed with Ar for 3 min. Tris(dibenzylideneacetone)dipalladium (11.5 mg, 12.6 µmol) and XantPhos (14.5 mg, 25.1 µmol) were added and the reaction mixture was degassed again for 1 min. Finally, sodium phenolate (53.5 mg, 461 µmol) was added and the vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (67 mg, 38% yield).

LC-MS (method 9): $R_t$=1.09 min; MS (ESIpos): m/z=408 [M+H]$^+$ $^1$H-NMR (500 MHz, dimethylsulfoxide-d6) δ [ppm]: −0.007 (0.42), 2.012 (16.00), 2.183 (2.57), 3.655 (9.20), 3.700 (10.51), 7.249 (1.97), 7.253 (0.76), 7.267 (3.93), 7.284 (2.05), 7.700 (1.36), 7.711 (1.66), 7.717 (1.59), 7.728 (1.20), 8.454 (0.68), 9.393 (1.60).

Example 438 ethyl 1-(6-{[1-(cyclopropylmethyl)-3-(5-fluoropyridin-2-yl)-4-methyl-1H-pyrazol-5-yl]amino}pyrimidin-4-yl)-3,5-dimethyl-1H-pyrazole-4-carboxylate

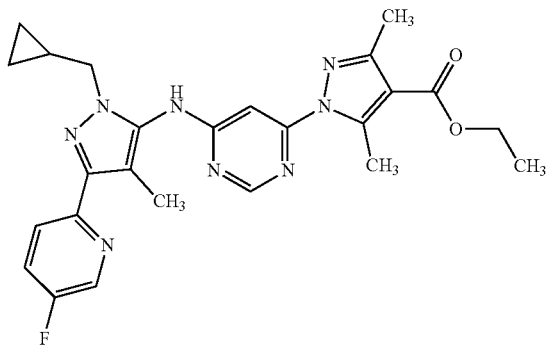 [SMILES: CCOC(=O)c1c(C)nn(-c2cc(Nc3c(C)c(-c4ccc(F)cn4)nn3CC3CC3)ncn2)c1C]

A microwave vial was charged ethyl 1-(6-chloropyrimidin-4-yl)-3,5-dimethyl-1H-pyrazole-4-carboxylate (117 mg, 415 µmol) and 1-(cyclopropylmethyl)-3-(5-fluoropyridin-2-yl)-4-methyl-1H-pyrazol-5-amine (225 mg, 50% purity, 457 µmol) and the contents were suspended in 1,4-dioxane (1.6 ml, 19 mmol). The reaction mixture was degassed with Ar for 3 min. Tris(dibenzylidenaceton)dipalladium (11.4 mg, 12.5 µmol) and Xantphos (14.4 mg, 24.9 µmol) were added and the reaction mixture was degassed again for 1 min and heated to 85° C. At this temperature and sodium phenolate (53.0 mg, 457 µmol) was added. The vial was sealed and heated at 85° C. for 90 minutes while vigorously stirred. After cooling to ambient temperature, the reaction mixture was filtered and preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and further by flash-chromatography (column: SNAP KP-Sil 10 g, solvent: 96% dichloromethane/4% ethyl acetate to 66% dichloromethane/34% ethyl acetate to 50% dichloromethane/50% ethyl acetate) to yield the desired product (62.7 mg, 31%).

LC-MS (method 10): $R_t$=2.34 min; MS (ESIpos): m/z=491 [M+H]$^+$ $^1$H-NMR (500 MHz, dimethylsulfoxide-d6) δ [ppm]: −0.007 (0.53), 0.314 (2.05), 0.323 (2.09), 0.442 (2.26), 0.458 (2.30), 1.177 (0.42), 1.191 (0.52), 1.201 (0.69), 1.207 (0.67), 1.217 (1.04), 1.226 (0.75), 1.231 (0.74), 1.242 (0.49), 1.289 (2.49), 1.303 (4.64), 1.317 (2.39), 1.991 (0.54), 2.156 (16.00), 2.368 (1.64), 2.909 (10.82), 3.867 (1.47), 3.878 (1.44), 4.230 (0.81), 4.244 (2.14), 4.258 (2.12), 4.272 (0.78), 7.754 (0.60), 7.760 (0.67), 7.772 (1.27), 7.778 (1.37), 7.789 (0.75), 7.795 (0.77), 7.991 (0.73), 8.000 (0.83), 8.008 (0.76), 8.017 (0.66), 8.592 (2.63), 8.598 (2.64).

Example 439

6-(4-chloro-3,5-dimethyl-1H-pyrazol-1-yl)-N-[1-(cyclopropylmethyl)-3-(5-fluoropyridin-2-yl)-4-methyl-1H-pyrazol-5-yl]pyrimidin-4-amine

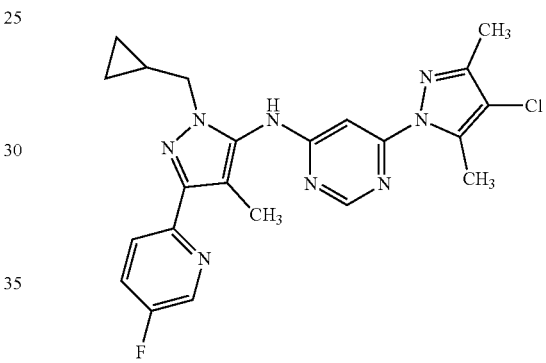

A microwave vial was charged 4-chloro-6-(4-chloro-3,5-dimethyl-1H-pyrazol-1-yl)pyrimidine (101 mg, 415 µmol) and 1-(cyclopropylmethyl)-3-(5-fluoropyridin-2-yl)-4-methyl-1H-pyrazol-5-amine (225 mg, 50% purity, 457 µmol) and the contents were suspended in 1,4-dioxane (1.6 ml, 19 mmol). The reaction mixture was degassed with Ar for 3 min. Tris(dibenzylidenaceton)dipalladium (11.4 mg, 12.5 µmol) and Xantphos (14.4 mg, 24.9 µmol) were added and the reaction mixture was degassed again for 1 min and heated to 85° C. At this temperature and sodium phenolate (53.0 mg, 457 µmol) was added. The vial was sealed and heated at 85° C. for 90 minutes while vigorously stirred. After cooling to ambient temperature, the reaction mixture was filtered and purified by preparative HPLC (method: column: Reprosil C18; 10 m; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and further by flash-chromatography (column: SNAP KP-Sil 10 g, solvent: 96% dichloromethane/4% ethyl acetate to 66% dichloromethane/34% ethyl acetate to 55% dichloromethane/45% ethyl acetate) to yield the desired product (50.6 mg, 27%).

LC-MS (method 10): $R_t$=2.50 min; MS (ESIpos): m/z=453 [M+H]$^+$ $^1$H-NMR (500 MHz, dimethylsulfoxide-d6) δ [ppm]: 0.310 (1.78), 0.319 (1.78), 0.438 (1.97), 0.454 (1.95), 1.079 (0.58), 1.093 (1.17), 1.107 (0.59), 1.163 (1.91), 1.178 (3.84), 1.192 (2.15), 1.196 (0.64), 1.202 (0.59), 1.212 (0.83), 1.221

(0.54), 1.226 (0.55), 1.991 (7.07), 2.153 (14.26), 2.199 (1.13), 2.645 (16.00), 3.378 (0.58), 3.391 (0.57), 3.571 (1.75), 3.866 (1.40), 3.877 (1.35), 4.011 (0.58), 4.026 (1.66), 4.040 (1.64), 4.054 (0.55), 7.755 (0.52), 7.761 (0.57), 7.773 (1.06), 7.779 (1.10), 7.790 (0.61), 7.796 (0.60), 7.995 (0.67), 8.003 (0.75), 8.011 (0.68), 8.020 (0.57), 8.593 (2.14), 8.599 (2.08).

Example 440 propan-2-yl [1-(6-{[4-ethyl-5-(4-fluorophenyl)-1-methyl-1H-pyrazol-3-yl]amino}pyrimidin-4-yl)-3,5-dimethyl-1H-pyrazol-4-yl]acetate

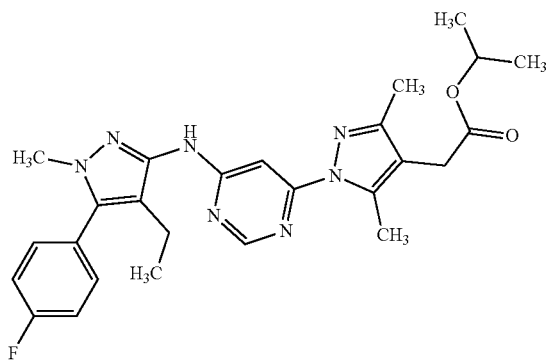 [SMILES: CCc1c(Nc2cc(-n3nc(C)c(CC(=O)OC(C)C)c3C)ncn2)nn(C)c1-c1ccc(F)cc1]

Under an argon atmosphere a Schlenk tube was charged with a ethyl [1-(6-{[4-ethyl-5-(4-fluorophenyl)-1-methyl-1H-pyrazol-3-yl]amino}pyrimidin-4-yl)-3,5-dimethyl-1H-pyrazol-4-yl]acetate (235 mg, 90% purity, 443 µmol) in tetrahydrofuran (2.0 ml, 25 mmol). Titanium isopropoxylate (140 µl, 490 µmol) and ethylmagnesium bromide (1.6 ml, 1.0 M in tetrahydrofuran, 1.6 mmol) were added at 0° C. The mixture was stirred 2 hours at 0° C. and overnight at ambient temperature. The mixture was diluted with saturated ammonium chloride solution. The occurring precipitate was filtered off. The filtrate was extracted with ethyl acetate (3×). The combined organic phases were washed with brine, dried over sodium sulfate and concentrated under reduced pressure. The crude product was purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 85.0 mg (39%) of the described by-product along with the desired product 1-{[1-(6-{[4-ethyl-5-(4-fluorophenyl)-1-methyl-1H-pyrazol-3-yl]amino}pyrimidin-4-yl)-3,5-dimethyl-1H-pyrazol-4-yl]methyl}cyclopropanol.

LC-MS (method 10): $R_t$=2.31 min; MS (ESIpos): m/z=492 [M+H]$^+$ $^1$H-NMR (500 MHz, dimethylsulfoxide-d6) δ [ppm]: 0.006 (0.48), 0.874 (2.95), 0.889 (6.35), 0.904 (2.94), 1.091 (0.55), 1.180 (16.00), 1.192 (15.88), 2.145 (11.95), 2.289 (0.74), 2.304 (2.08), 2.319 (2.01), 2.334 (0.65), 2.571 (12.11), 3.312 (14.32), 3.435 (6.49), 4.862 (0.45), 4.875 (1.13), 4.887 (1.51), 4.900 (1.11), 4.912 (0.43), 7.329 (1.88), 7.361 (1.66), 7.379 (3.55), 7.396 (2.02), 7.503 (2.05), 7.507 (1.04), 7.514 (2.33), 7.520 (1.92), 7.531 (1.57), 8.446 (2.96), 9.335 (1.91).

Example 441

4-[4-chloro-1-(cyclopropylmethyl)-5-{[6-(3,5-dimethyl-1H-pyrazol-1-yl)pyrimidin-4-yl]amino}-1H-pyrazol-3-yl]benzonitrile

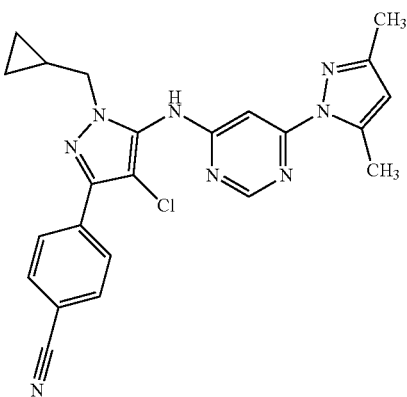 [SMILES: Cc1cc(C)n(-c2cc(Nc3c(Cl)c(-c4ccc(C#N)cc4)nn3CC3CC3)ncn2)n1]

A microwave vial was charged 4-chloro-6-(3,5-dimethyl-1H-pyrazol-1-yl)pyrimidine (100 mg, 479 µmol), 4-[5-amino-4-chloro-1-(cyclopropylmethyl)-1H-pyrazol-3-yl]benzonitrile (144 mg, 527 µmol) and sodium phenolate (61.2 mg, 527 µmol) and the contents were suspended in 1,4-dioxane (2.2 ml, 26 mmol). The reaction mixture was degassed with Ar for 3 min. Tris(dibenzylidenaceton)dipalladium (5.71 mg, 6.23 µmol) and Xantphos (8.32 mg, 14.4 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were washed with water and brine, dried over sodium sulfate and concentrated under reduced pressure. The crude product was purified by preparative HPLC (method: column: Reprosil C18; 10 µm; 125×30 mm/flow: 50 mL/min/ solvent: A=water (0.1% formic acid), B=acetonitrile/gradient: 0.00-4.25 min=20% B, 4.50 min=30% B, 19.00-22.50 min=100% B, 22.75-25.00 min=20% B) to yield the desired product (33.1 mg, 16%).

LC-MS (method 10): $R_t$=2.32 min; MS (ESIpos): m/z=445 [M+H]$^+$ $^1$H-NMR (400 MHz, dimethylsulfoxide-d6) δ [ppm]: −0.008 (2.40), 0.008 (2.44), 0.326 (0.76), 0.338 (3.16), 0.352 (3.42), 0.363 (1.12), 0.458 (0.95), 0.468 (2.73), 0.472 (2.70), 0.488 (2.93), 0.504 (0.66), 1.210 (0.43), 1.223 (0.72), 1.242 (1.15), 1.261 (0.69), 2.187 (9.98), 2.328 (0.82), 2.636 (16.00), 2.670 (0.92), 3.930 (3.79), 3.948 (3.79), 6.163 (4.02), 7.952 (4.51), 7.973 (6.68), 8.086 (5.99), 8.107 (4.48), 8.489 (2.27), 9.693 (2.24).

Example 442 ethyl 1-(6-{[4-chloro-3-(4-cyanophenyl)-1-(cyclo-propylmethyl)-1H-pyrazol-5-yl]amino}pyrimidin-4-yl)-3,5-dimethyl-1H-pyrazole-4-carboxylate

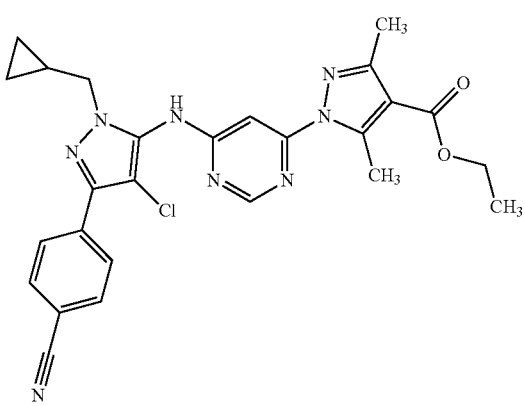 [SMILES: CCOC(=O)c1c(C)nn(-c2cc(Nc3c(Cl)c(-c4ccc(C#N)cc4)nn3CC3CC3)ncn2)c1C]

A microwave vial was charged ethyl 1-(6-chloropyrimidin-4-yl)-3,5-dimethyl-1H-pyrazole-4-carboxylate (250 mg, 891 μmol), 4-[5-amino-4-chloro-1-(cyclopropylmethyl)-1H-pyrazol-3-yl]benzonitrile (267 mg, 980 μmol) and sodium phenolate (114 mg, 980 μmol) and the contents were suspended in 1,4-dioxane (4.2 ml, 49 mmol). The reaction mixture was degassed with Ar for 3 min. Tris(dibenzylidenaceton)dipalladium (10.6 mg, 11.6 μmol) and Xantphos (15.5 mg, 26.7 μmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were washed with water and brine, dried over sodium sulfate and concentrated under reduced pressure. The crude product was purified by preparative HPLC (method: column: Reprosil C18; 10 μm; 125×30 mm/flow: 50 mL/min/solvent: A=water (0.1% formic acid), B=acetonitrile/gradient: 0.00-4.25 min=20% B, 4.50 min=30% B, 19.00-22.50 min=100% B, 22.75-25.00 min=20% B) to yield the desired product (62.5 mg, 13%).

LC-MS (method 10): $R_t$=2.42 min; MS (ESIpos): m/z=517 [M+H]$^+$ $^1$H-NMR (400 MHz, dimethylsulfoxide-d6) δ [ppm]: −0.008 (1.71), 0.008 (1.01), 0.330 (0.78), 0.341 (2.73), 0.355 (2.76), 0.367 (0.86), 0.461 (0.95), 0.472 (2.39), 0.475 (2.21), 0.492 (2.47), 0.507 (0.53), 1.091 (0.44), 1.227 (0.72), 1.234 (0.87), 1.246 (1.04), 1.258 (0.68), 1.265 (0.74), 1.292 (4.88), 1.298 (1.49), 1.310 (9.90), 1.316 (2.18), 1.327 (4.72), 1.334 (0.98), 1.356 (0.53), 2.388 (7.78), 2.418 (2.38), 2.920 (16.00), 2.933 (1.59), 2.950 (2.27), 3.936 (2.92), 3.953 (2.79), 4.234 (1.40), 4.252 (4.20), 4.270 (4.20), 4.287 (1.41), 7.951 (3.92), 7.956 (1.68), 7.968 (2.14), 7.973 (5.53), 7.999 (0.43), 8.002 (0.42), 8.083 (5.13), 8.087 (1.90), 8.104 (3.66), 8.570 (1.54), 9.858 (1.29).

Example 443

4-(3-{[6-(3,5-dimethyl-1H-pyrazol-1-yl)pyrimidin-4-yl]amino}-4-methoxy-1-methyl-1H-pyrazol-5-yl)benzonitrile

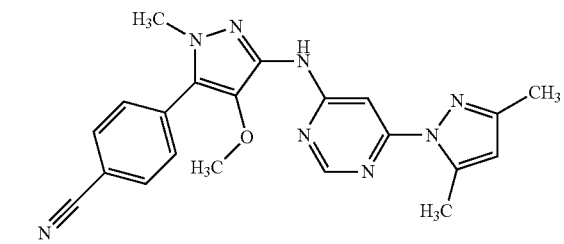 [SMILES: COc1c(Nc2cc(-n3nc(C)cc3C)ncn2)nn(C)c1-c1ccc(C#N)cc1]

A microwave vial was charged 4-chloro-6-(3,5-dimethyl-1H-pyrazol-1-yl)pyrimidine (499 mg, 2.39 mmol) and 4-(3-amino-4-methoxy-1-methyl-1H-pyrazol-5-yl)benzonitrile (600 mg, 2.63 mmol) and the contents were suspended in 1,4-dioxane (19 ml, 220 mmol). The reaction mixture was degassed with Ar for 3 min. Tris(dibenzylidenaceton)dipalladium (65.6 mg, 71.7 μmol) and Xantphos (83.0 mg, 143 μmol) were added and the reaction mixture was degassed again for 1 min and heated to 85° C. At this temperature and sodium phenolate (305 mg, 2.63 mmol) was added. The vial was sealed and heated at 85° C. for 90 minutes while vigorously stirring. After cooling to ambient temperature, the reaction mixture was diluted with hydrochloric acid and extracted with ethyl acetate (2×). The combined organic phases were washed with water and brine, dried over sodium sulfate and concentrated under reduced pressure. The crude product was purified by flash-chromatography (column: SNAP Ultra 25 g, solvent: dichloromethane/ethyl acetate 1:1) to yield the desired product (630 mg, 65%).

LC-MS (method 10): $R_t$=1.82 min; MS (ESIpos): m/z=401 [M+H]$^+$ $^1$H-NMR (400 MHz, dimethylsulfoxide-d6) δ [ppm]: −0.016 (1.05), 2.159 (4.70), 2.522 (16.00), 3.292 (2.94), 3.525 (4.97), 3.548 (5.33), 3.766 (5.36), 6.115 (1.41), 7.183 (1.50), 7.752 (2.91), 7.983 (3.21), 8.435 (1.57), 9.403 (1.42).

Example 444

4-(5-{[6-(3,5-dimethyl-1H-pyrazol-1-yl)pyrimidin-4-yl]amino}-4-methoxy-1-methyl-1H-pyrazol-3-yl)benzonitrile

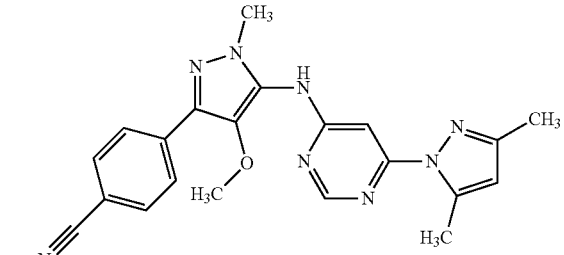

A microwave vial was charged 4-chloro-6-(3,5-dimethyl-1H-pyrazol-1-yl)pyrimidine (83.1 mg, 398 μmol) and 4-(5-amino-4-methoxy-1-methyl-1H-pyrazol-3-yl)benzonitrile (100 mg, 438 µmol) and the contents were suspended in 1,4-dioxane (2.8 ml, 33 mmol). The reaction mixture was degassed with Ar for 3 min. Tris(dibenzylidenaceton)dipalladium (4.74 mg, 5.18 µmol) and Xantphos (6.91 mg, 11.9 µmol) were added and the reaction mixture was degassed again for 1 min and heated to 85° C. At this temperature and sodium phenolate (50.9 mg, 438 µmol) was added. The vial was sealed and heated at 85° C. for 90 minutes while vigorously stirring. After cooling to ambient temperature, the reaction mixture was filtered and purified by preparative HPLC (method 7) to yield the desired product (43.0 mg, 27%).

LC-MS (method 9): $R_t$=1.01 min; MS (ESIpos): m/z=401 [M+H]$^+$ $^1$H-NMR (400 MHz, dimethylsulfoxide-d6) δ [ppm]: −0.008 (0.62), 0.008 (0.68), 2.178 (3.94), 2.637 (9.70), 3.652 (8.39), 3.729 (16.00), 6.157 (2.40), 7.870 (2.84), 7.891 (3.85), 8.033 (3.50), 8.055 (2.73), 8.498 (1.40), 9.516 (1.65).

Example 445

4-[4-chloro-1-(cyclopropylmethyl)-5-({6-[5-(difluoromethyl)-3-methyl-1H-pyrazol-1-yl]pyrimidin-4-yl}amino)-1H-pyrazol-3-yl]benzonitrile

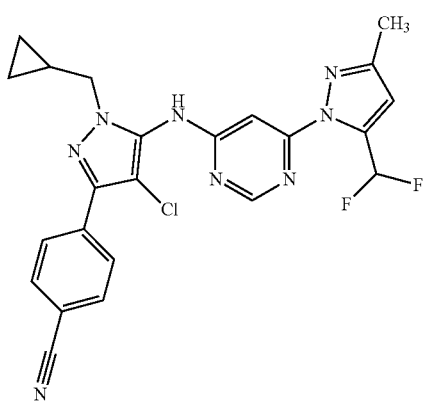 [SMILES: Cc1cc(C(F)F)n(-c2cc(Nc3c(Cl)c(-c4ccc(C#N)cc4)nn3CC3CC3)ncn2)n1]

A microwave vial was charged 4-chloro-6-[5-(difluoromethyl)-3-methyl-1H-pyrazol-1-yl]pyrimidine (100 mg, 409 µmol), 4-[5-amino-4-chloro-1-(cyclopropylmethyl)-1H-pyrazol-3-yl]benzonitrile (123 mg, 450 µmol) and sodium phenolate (52.2 mg, 450 µmol) and the contents were suspended in 1,4-dioxane (1.9 ml, 22 mmol). The reaction mixture was degassed with Ar for 3 min. Tris(dibenzylidenaceton)dipalladium (4.87 mg, 5.31 µmol) and Xantphos (7.10 mg, 12.3 µmol) were added and the reaction mixture was degassed again for 1 min. The vial was sealed and heated at 85° C. overnight while vigorously stirring. After cooling to ambient temperature, the reaction mixture was diluted with water and extracted with ethyl acetate (2×). The combined organic phases were washed with water and brine, dried over sodium sulfate and concentrated under reduced pressure. The crude product was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (34.7 mg, 18%).

LC-MS (method 11): $R_t$=1.55 min; MS (ESIpos): m/z=481 [M+H]$^+$ $^1$H-NMR (400 MHz, dimethylsulfoxide-d6) δ [ppm]: −0.149 (0.95), −0.007 (9.69), 0.146 (0.97), 0.325 (1.72), 0.337 (7.15), 0.350 (7.92), 0.362 (2.38), 0.458 (2.10), 0.468 (6.41), 0.471 (6.23), 0.488 (6.92), 0.503 (1.46), 1.210 (0.90), 1.222 (1.74), 1.230 (1.74), 1.241 (2.64), 1.253 (1.59), 1.260 (1.62), 2.073 (0.95), 2.298 (16.00), 2.328 (1.36), 2.670 (1.00), 2.708 (1.10), 3.939 (7.33), 3.957 (7.23), 5.754 (1.97), 6.804 (9.15), 7.679 (3.23), 7.815 (6.62), 7.954 (10.97), 7.976 (14.00), 8.087 (11.85), 8.108 (8.77), 8.528 (3.46), 9.875 (2.79).

Example 446 ethyl 1-(6-{[3-(4-cyanophenyl)-4-methoxy-1-methyl-1H-pyrazol-5-yl]amino}pyrimidin-4-yl)-3,5-dimethyl-1H-pyrazole-4-carboxylate

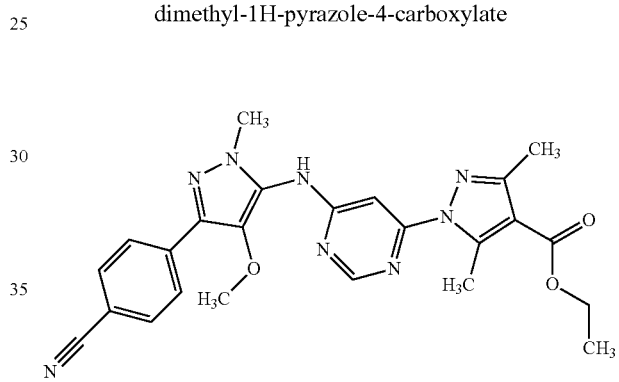

A microwave vial was charged ethyl 1-(6-chloropyrimidin-4-yl)-3,5-dimethyl-1H-pyrazole-4-carboxylate (215 mg, 766 µmol) and 4-(5-amino-4-methoxy-1-methyl-1H-pyrazol-3-yl)benzonitrile (192 mg, 842 µmol) and the contents were suspended in 1,4-dioxane (6.8 ml, 80 mmol). The reaction mixture was degassed with Ar for 3 min. Tris (dibenzylidenaceton)dipalladium (9.12 mg, 9.96 µmol) and Xantphos (13.3 mg, 23.0 µmol) were added and the reaction mixture was degassed again for 1 min and heated to 85° C. At this temperature and sodium phenolate (97.8 mg, 842 µmol) was added. The vial was sealed and heated at 85° C. for 90 minutes while vigorously stirring. After cooling to ambient temperature, the reaction mixture was diluted with hydrochloric acid and extracted with ethyl acetate (2×). The combined organic phases were dried over Extrelut NT3 and concentrated under reduced pressure. The crude product was recrystallized from acetonitrile to yield the desired product (167 mg, 46%).

LC-MS (method 10): $R_t$=2.11 min; MS (ESIpos): m/z=473 [M+H]$^+$ $^1$H-NMR (400 MHz, dimethylsulfoxide-d6) δ [ppm]: 1.290 (3.15), 1.308 (6.39), 1.325 (3.21), 2.378 (3.97), 2.919 (11.28), 3.633 (0.43), 3.657 (8.77), 3.728 (16.00), 4.231 (0.99), 4.249 (2.89), 4.267 (2.86), 4.284 (0.96), 7.870 (3.05), 7.891 (3.80), 8.029 (3.92), 8.050 (3.00), 8.575 (1.21), 9.684 (1.29).

Example 447 ethyl 1-(6-{[4-chloro-5-(4-fluorophenyl)-1-methyl-1H-pyrazol-3-yl]amino}pyrimidin-4-yl)-3-methyl-1H-pyrazole-5-carboxylate

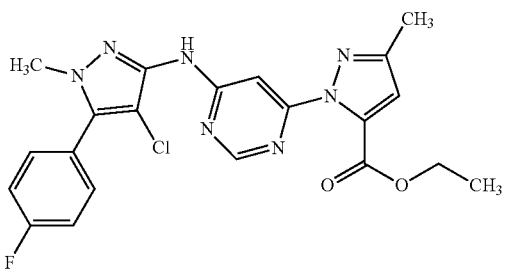 [SMILES: CCOC(=O)c1cc(C)nn1-c1cc(Nc2nn(C)c(-c3ccc(F)cc3)c2Cl)ncn1]

A microwave vial was charged with 4-chloro-5-(4-fluorophenyl)-1-methyl-1H-pyrazol-3-amine (200 mg, 886 µmol) and sodium phenolate (103 mg, 886 µmol) and the contents were suspended in 1,4-dioxane (1.9 mL). The reaction mixture was degassed with Ar for 3 min. ethyl 1-(6-chloropyrimidin-4-yl)-3-methyl-1H-pyrazole-5-carboxylate (239 mg, 90% purity, 806 µmol), Tris(dibenzylideneacetone)dipalladium (9.59 mg, 10.5 µmol) and XantPhos (14.0 mg, 24.2 µmol) were added and the reaction mixture was degassed again for 1 min. The vial was sealed and heated at 90° C. overnight while vigorously shaking. After cooling to ambient temperature, the reaction mixture was loaded onto silica gel and purified by flash column chromatography (SNAP Ultra 25 g, cyclohexane/ethyl acetate gradient 95/5 to 20/80) to yield the desired product (124 mg, 30% yield).

LC-MS (method 10): $R_t$=2.10 min; MS (ESIpos): m/z=456 [M+H]$^+$ $^1$H-NMR (400 MHz, dimethylsulfoxide-d6) δ [ppm]: −0.008 (0.90), 0.008 (1.07), 1.157 (0.44), 1.175 (0.90), 1.198 (4.38), 1.215 (9.45), 1.226 (0.72), 1.233 (4.65), 1.292 (0.45), 1.310 (0.94), 1.328 (0.45), 1.398 (4.08), 1.989 (1.59), 2.278 (12.99), 2.685 (1.10), 3.740 (0.45), 3.776 (16.00), 4.243 (1.35), 4.260 (4.35), 4.278 (4.33), 4.296 (1.37), 4.305 (0.49), 4.322 (0.42), 6.761 (4.57), 7.155 (3.16), 7.157 (3.26), 7.410 (1.98), 7.415 (0.74), 7.432 (4.32), 7.449 (0.81), 7.454 (2.41), 7.634 (2.41), 7.639 (1.07), 7.647 (2.64), 7.656 (2.31), 7.664 (0.88), 7.669 (2.01), 8.443 (2.84), 9.769 (2.35).

Example 448 ethyl 4-chloro-1-(6-{[4-chloro-3-(4-fluorophenyl)-1-methyl-1H-pyrazol-5-yl]amino}pyrimidin-4-yl)-3-methyl-1H-pyrazole-5-carboxylate

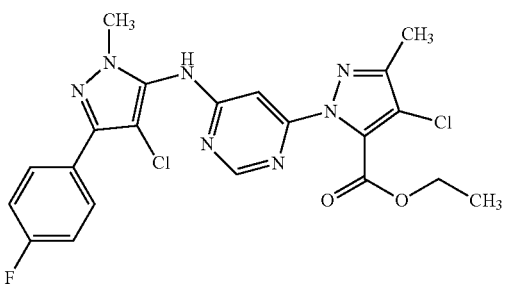 [SMILES: CCOC(=O)c1c(Cl)c(C)nn1-c1cc(Nc2c(Cl)c(-c3ccc(F)cc3)nn2C)ncn1]

A microwave vial was charged with 4-chloro-3-(4-fluorophenyl)-1-methyl-1H-pyrazol-5-amine (200 mg, 886 µmol) and sodium phenolate (103 mg, 886 µmol) and the contents were suspended in 1,4-dioxane (1.9 mL). The reaction mixture was degassed with Ar for 3 min. ethyl 4-chloro-1-(6-chloropyrimidin-4-yl)-3-methyl-1H-pyrazole-5-carboxylate (324 mg, 75% purity, 806 µmol), tris(dibenzylideneacetone)dipalladium (9.59 mg, 10.5 µmol) and XantPhos (14.0 mg, 24.2 µmol) were added and the reaction mixture was degassed again for 1 min. The vial was sealed and heated at 85° C. overnight while vigorously shaking. After cooling to ambient temperature, the reaction mixture was loaded onto silica gel and purified by flash column chromatography (SNAP Ultra 25 g, cyclohexane/ethyl acetate 95/5 to 20/80) to yield the desired product (154 mg, 33% yield).

LC-MS (method 10): $R_t$=2.35 min; MS (ESIpos): m/z=490 [M+H]$^+$ $^1$H-NMR (400 MHz, dimethylsulfoxide-d6) δ [ppm]: −0.008 (1.29), 0.008 (1.55), 1.157 (1.51), 1.175 (3.02), 1.193 (1.53), 1.237 (7.34), 1.245 (1.40), 1.255 (15.51), 1.272 (7.41), 1.304 (0.50), 1.321 (0.86), 1.338 (0.51), 1.398 (13.21), 1.989 (5.51), 2.287 (10.21), 2.329 (0.43), 2.671 (0.41), 2.675 (0.44), 2.687 (3.42), 3.738 (16.00), 3.779 (1.22), 4.003 (0.43), 4.021 (1.30), 4.039 (1.29), 4.056 (0.43), 4.336 (2.40), 4.342 (0.73), 4.354 (7.54), 4.371 (7.47), 4.389 (2.37), 7.303 (3.64), 7.325 (7.42), 7.347 (3.94), 7.433 (0.41), 7.873 (0.93), 7.881 (3.00), 7.886 (2.11), 7.895 (3.79), 7.903 (3.38), 7.912 (1.48), 7.917 (2.74), 8.479 (2.28), 9.965 (2.57).

Example 449 ethyl 1-(6-{[4-chloro-3-(4-fluorophenyl)-1-methyl-1H-pyrazol-5-yl]amino}pyrimidin-4-yl)-3,5-dimethyl-1H-pyrazole-4-carboxylate

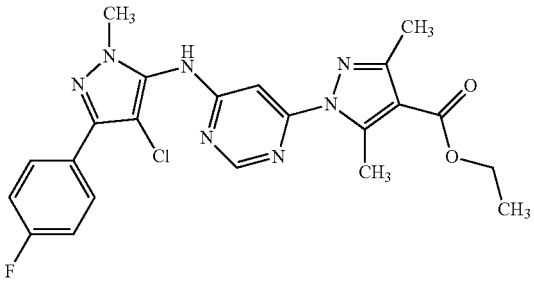 [SMILES: CCOC(=O)c1c(C)nn(-c2cc(Nc3c(Cl)c(-c4ccc(F)cc4)nn3C)ncn2)c1C]

A microwave vial was charged with 4-chloro-3-(4-fluorophenyl)-1-methyl-1H-pyrazol-5-amine (200 mg, 886 µmol) and sodium phenolate (103 mg, 886 µmol) and the contents were suspended in 1,4-dioxane (1.9 mL). The reaction mixture was degassed with Ar for 3 min. ethyl 1-(6-chloropyrimidin-4-yl)-3,5-dimethyl-1H-pyrazole-4-carboxylate (226 mg, 806 µmol), tris(dibenzylideneacetone)dipalladium (9.59 mg, 10.5 µmol) and XantPhos (14.0 mg, 24.2 µmol) were added and the reaction mixture was degassed again for 1 min. The vial was sealed and heated at 85° C. overnight while vigorously shaking. After cooling to ambient temperature, the reaction mixture was loaded onto silica gel and purified by flash column chromatography (cyclohexane/ethyl acetate 95/5 to 20/80) to yield the desired product (185 mg, 49% yield).

LC-MS (method 10): $R_t$=2.33 min; MS (ESIpos): m/z=470 [M+H]$^+$

¹H-NMR (400 MHz, dimethylsulfoxide-d6) δ [ppm]:
-0.008 (0.80), 0.008 (0.53), 1.158 (0.62), 1.175 (1.23),
1.193 (0.63), 1.293 (4.71), 1.311 (9.76), 1.328 (4.65), 1.398
(0.91), 1.989 (2.04), 2.390 (7.85), 2.471 (0.70), 2.899 (1.16),
2.919 (16.00), 3.734 (11.85), 3.772 (0.86), 4.021 (0.48),
4.039 (0.47), 4.235 (1.40), 4.253 (4.11), 4.271 (4.01), 4.288
(1.24), 7.302 (2.49), 7.307 (1.00), 7.319 (1.23), 7.324 (4.66),
7.341 (0.93), 7.346 (2.47), 7.878 (2.22), 7.883 (1.13), 7.891
(2.46), 7.900 (2.36), 7.908 (0.98), 7.914 (2.00), 8.580 (1.65),
9.863 (2.55).

Example 450

N-[1-(cyclopropylmethyl)-3-(4-fluorophenyl)-4-methoxy-1H-pyrazol-5-yl]-6-[3,5-dimethyl-4-(5-methyl-1,3,4-oxadiazol-2-yl)-1H-pyrazol-1-yl]pyrimidin-4-amine

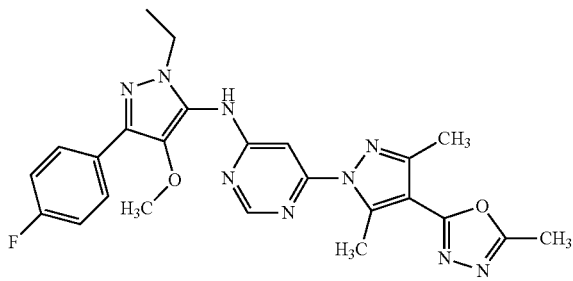 [SMILES: CCn1nc(-c2ccc(F)cc2)c(OC)c1Nc1cc(-n2nc(C)c(-c3nnc(C)o3)c2C)ncn1]

A solution of N'-acetyl-1-(6-{[1-(cyclopropylmethyl)-3-(4-fluorophenyl)-4-methoxy-1H-pyrazol-5-yl]amino}pyrimidin-4-yl)-3,5-dimethyl-1H-pyrazole-4-carbohydrazide (250 mg, 469 µmol) in tetrahydrofuran (10 ml, 120 mmol) was treated with Burgess reagent (223 mg, 937 µmol) and stirred over the weekend at ambient temperature. The mixture was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 168 mg (69%) of the desired product.

LC-MS (method 10): $R_t$=2.03 min; MS (ESIpos): m/z=516 [M+H]⁺

¹H-NMR (400 MHz, dimethylsulfoxide-d6) δ [ppm]:
0.296 (0.62), 0.309 (2.92), 0.322 (3.24), 0.334 (0.94), 0.439
(0.85), 0.450 (2.39), 0.453 (2.37), 0.470 (2.58), 0.485 (0.68),
1.189 (0.62), 1.196 (0.60), 1.208 (0.91), 1.220 (0.58), 1.227
(0.61), 2.571 (13.24), 2.976 (13.06), 3.693 (16.00), 3.782
(2.06), 3.799 (2.05), 7.248 (1.93), 7.270 (3.86), 7.292 (2.07),
7.886 (1.75), 7.900 (2.16), 7.907 (2.11), 7.921 (1.68), 8.578
(0.83), 9.614 (0.55).

Example 451

4-(4-{[6-(4-acetyl-3,5-dimethyl-1H-pyrazol-1-yl)pyrimidin-4-yl]amino}-3,5-dimethyl-1H-pyrazol-1-yl)benzonitrile

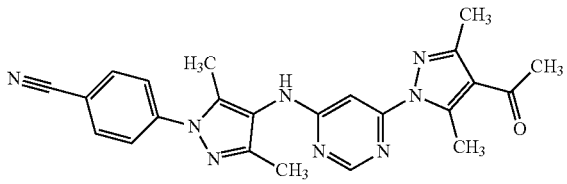 [SMILES: CC(=O)c1c(C)nn(-c2cc(Nc3c(C)nn(-c4ccc(C#N)cc4)c3C)ncn2)c1C]

A microwave vial was charged 1-[1-(6-chloropyrimidin-4-yl)-3,5-dimethyl-1H-pyrazol-4-yl]ethanone (250 mg, 997 µmol) and 4-(4-amino-3,5-dimethyl-1H-pyrazol-1-yl)benzonitrile (274 mg, 85% purity, 1.10 mmol) and the contents were suspended in 1,4-dioxane (4.0 ml, 47 mmol). The reaction mixture was degassed with Ar for 3 min. Tris(dibenzylideneaceton)dipalladium (27.4 mg, 29.9 µmol) and Xantphos (34.6 mg, 59.8 µmol) were added and the reaction mixture was degassed again for 1 min and heated to 85° C. At this temperature and sodium phenolate (127 mg, 1.10 mmol) was added. The vial was sealed and heated at 85° C. for 90 minutes while vigorously stirring. After cooling to ambient temperature, the reaction mixture was diluted with hydrochloric acid and extracted with ethyl acetate (2×). The combined organic phases were washed with water and brine, dried over sodium sulfate and concentrated under reduced pressure. The remaining residue was suspended in acetonitrile, the occurring precipitate was collected by filtration, washed and dried to yield 200 mg of the desired product. The filtrate was concentrated and purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield further 50 mg of the desired product (total yield: 250 mg, 60%).

LC-MS (method 10): $R_t$=1.62 min; MS (ESIpos): m/z=427 [M+H]⁺

¹H-NMR (400 MHz, dimethylsulfoxide-d6) δ [ppm]:
0.007 (1.11), 2.114 (16.00), 2.293 (14.46), 2.307 (1.33),
2.328 (0.43), 2.367 (0.61), 2.462 (7.23), 2.866 (5.87), 7.806
(2.10), 7.827 (2.68), 7.979 (3.88), 8.001 (3.14), 9.133 (0.93).

Example 452

N-[1-(cyclopropylmethyl)-3-(4-fluorophenyl)-4-methyl-1H-pyrazol-5-yl]-6-{4-[(3-fluoroazetidin-1-yl)methyl]-3,5-dimethyl-1H-pyrazol-1-yl}pyrimidin-4-amine

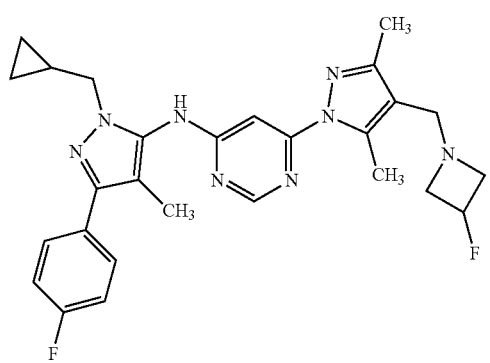 [SMILES: Cc1nn(-c2cc(Nc3c(C)c(-c4ccc(F)cc4)nn3CC3CC3)ncn2)c(C)c1CN1CC(F)C1]

A solution of 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carbaldehyde (180 mg, 404 µmol) and 3-fluoroazetidine hydrochloride (1:1) (58.6 mg, 525 µmol) in tetrahydrofuran (3.5 ml, 43 mmol) was treated with acetic acid (46 µl, 810 µmol) and stirred for one hour at ambient temperature. Subsequently, sodium triacetoxyborohydride (137 mg, 646 µmol) was added and the mixture was stirred overnight at ambient temperature. The mixture was diluted with water (3 mL) and purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield 80.0 mg (37%) of the desired product.

LC-MS (method 10): $R_t$=1.44 min; MS (ESIneg): m/z=503 [M−H]$^-$ $^1$H-NMR (400 MHz, dimethylsulfoxide-d6) δ [ppm]: 0.008 (0.65), 0.290 (2.81), 0.302 (2.79), 0.420 (2.86), 0.440 (2.79), 1.164 (0.50), 1.175 (0.81), 1.183 (0.86), 1.195 (1.15), 1.212 (0.67), 1.975 (1.02), 2.005 (14.84), 2.180 (3.15), 2.524 (1.08), 2.637 (16.00), 3.005 (0.82), 3.028 (1.01), 3.040 (0.88), 3.065 (0.87), 3.082 (1.01), 3.437 (5.46), 3.470 (1.74), 3.485 (1.29), 3.507 (0.80), 3.823 (2.60), 3.840 (2.39), 5.026 (0.55), 5.039 (0.74), 5.052 (0.50), 5.170 (0.54), 5.183 (0.74), 5.196 (0.49), 7.251 (2.54), 7.273 (4.83), 7.296 (2.50), 7.713 (1.85), 7.727 (2.30), 7.748 (1.49), 8.138 (1.60), 8.457 (0.73), 9.363 (0.77).

Example 453 ethyl 1-(6-{[1-(4-fluorophenyl)-3,5-dimethyl-1H-pyrazol-4-yl]amino}pyrimidin-4-yl)-3,5-dimethyl-1H-pyrazole-4-carboxylate

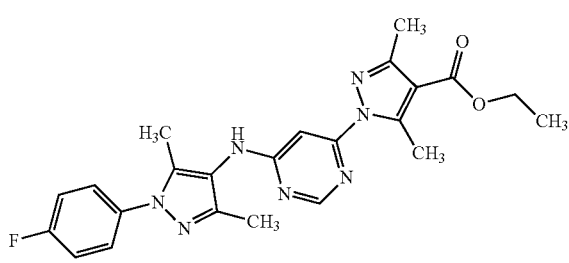 [SMILES: CCOC(=O)c1c(C)nn(-c2cc(Nc3c(C)nn(-c4ccc(F)cc4)c3C)ncn2)c1C]

A microwave vial was charged ethyl 1-(6-chloropyrimidin-4-yl)-3,5-dimethyl-1H-pyrazole-4-carboxylate (301 mg, 1.07 mmol), 1-(4-fluorophenyl)-3,5-dimethyl-1H-pyrazol-4-amine (285 mg, 85% purity, 1.18 mmol) and sodium phenolate (137 mg, 1.18 mmol) and the contents were suspended in 1,4-dioxane (5.2 ml, 61 mmol). The reaction mixture was degassed with Ar for 3 min. Tris(dibenzylidenaceton)dipalladium (12.8 mg, 13.9 µmol) and Xantphos (18.6 mg, 32.2 µmol) were added and the reaction mixture was degassed again for 1 min. The vial was sealed and heated at 85° C. overnight while vigorously stirring. After cooling to ambient temperature, the reaction mixture was filtered and purified by preparative HPLC (method: column: Reprosil C18; 10 µm; 125×40 mm/flow: 75 mL/min/solvent: A=water (0.1% formic acid), B=acetonitrile/gradient: 0.00-5.50 min=10% B, 17.65-19.48 min=95% B, 19.66 min=10% B) to yield the desired product (150 mg, 31%).

LC-MS (method 10): $R_t$=2.09 min; MS (ESIpos): m/z=450 [M+H]$^+$ $^1$H-NMR (400 MHz, dimethylsulfoxide-d6) δ [ppm]: 1.091 (0.61), 1.285 (2.43), 1.303 (4.80), 1.320 (2.48), 2.082 (16.00), 2.175 (11.93), 2.368 (1.46), 2.885 (7.23), 4.224 (0.76), 4.242 (2.13), 4.259 (2.10), 4.277 (0.78), 7.333 (1.46), 7.355 (3.23), 7.377 (1.87), 7.590 (1.59), 9.054 (0.58).

Example 454 ethyl 1-[6-({1-(cyclopropylmethyl)-3-[4-(difluoromethyl)phenyl]-4-methyl-1H-pyrazol-5-yl}amino)pyrimidin-4-yl]-3,5-dimethyl-1H-pyrazole-4-carboxylate

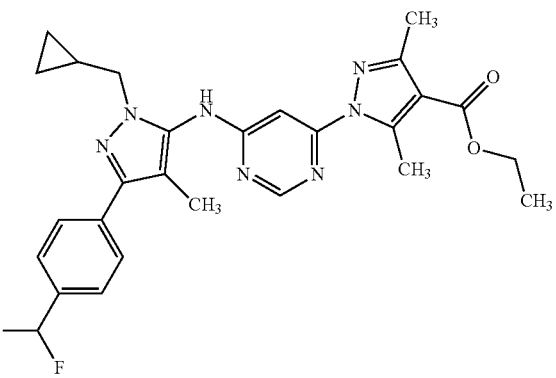

A microwave vial was charged ethyl 1-(6-chloropyrimidin-4-yl)-3,5-dimethyl-1H-pyrazole-4-carboxylate (368 mg, 1.31 mmol) and 1-(cyclopropylmethyl)-3-[4-(difluoromethyl)phenyl]-4-methyl-1H-pyrazol-5-amine (400 mg, 1.44 mmol) and the contents were suspended in 1,4-dioxane (5.0 ml, 58 mmol). The reaction mixture was degassed with Ar for 3 min. Tris(dibenzylidenaceton)dipalladium (36.0 mg, 39.3 µmol) and Xantphos (45.5 mg, 78.7 µmol) were added and the reaction mixture was degassed again for 1 min and heated to 85° C. At this temperature and sodium phenolate (167 mg, 1.44 mmol) was added. The vial was sealed and heated at 85° C. for 90 minutes while vigorously stirring. The mixture was left overnight at ambient temperature, the reaction mixture was filtered and purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) and further by flash-chromatography (column: SNAP KP-Sil 10 g, solvent: 92% dichloromethane/8% ethyl acetate to 34% dichloromethane/66% ethyl acetate) to yield the desired product (364 mg, 53%).

LC-MS (method 10): $R_t$=2.37 min; MS (ESIpos): m/z=522 [M+H]$^+$ $^1$H-NMR (400 MHz, dimethylsulfoxide-d6) δ [ppm]: 0.308 (2.61), 0.319 (2.85), 0.435 (2.67), 0.455 (2.84), 1.176 (0.83), 1.183 (0.41), 1.194 (0.95), 1.203 (0.73), 1.215 (1.13), 1.227 (0.70), 1.233 (0.73), 1.288 (3.54), 1.305 (7.16), 1.323 (3.62), 1.990 (1.12), 2.052 (16.00), 2.373 (2.15), 2.913 (13.30), 3.315 (12.00), 3.859 (2.27), 3.876 (2.23), 4.228 (1.09), 4.246 (3.21), 4.264 (3.19), 4.281 (1.10), 6.938 (1.62), 7.078 (3.47), 7.218 (1.46), 7.637 (3.29), 7.657 (4.07), 7.844 (3.04), 7.864 (2.59), 8.540 (0.50).

Example 455

N-[1-(cyclopropylmethyl)-4-methyl-3-(6-methylpyridin-3-yl)-1H-pyrazol-5-yl]-6-[3,5-dimethyl-4-(trifluoromethyl)-1H-pyrazol-1-yl]pyrimidin-4-amine

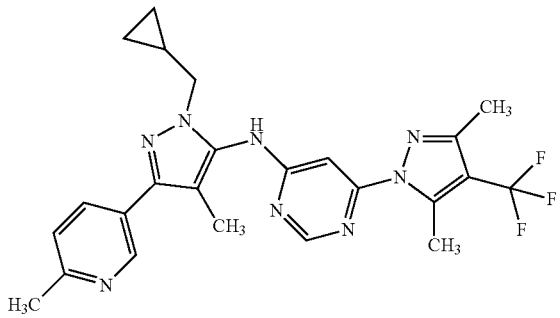 [SMILES: Cc1ccc(-c2nn(CC3CC3)c(Nc3cc(-n4nc(C)c(C(F)(F)F)c4C)ncn3)c2C)cn1]

In a sealed microwave tube under argon, 1-(cyclopropylmethyl)-4-methyl-3-(6-methylpyridin-3-yl)-1H-pyrazol-5-amine (60.0 mg, 248 μmol), 4-chloro-6-[3,5-dimethyl-4-(trifluoromethyl)-1H-pyrazol-1-yl]pyrimidine (75.3 mg, 272 μmol), (31.6 mg, 272 μmol), (6.80 mg, 7.43 μmol), (7.85 mg, 14.9 μmol) were dissolved in 1,4-dioxane (1.2 ml). The reaction mixture was heated at 90° C. for 30 minutes. The cooled reaction mixture was diluted with ethylacetate, washed with a saturated aqueous solution of sodium hydrogen carbonate and the aqueous phase then extracted twice with ethylacetate. The combined organic phase s were dried with sodium sulfate and concentrated in vacuo. The crude product was purified by flash-chromatography on silica gel (gradient 18% to 100% ethylacetate in cyclohexane, column: Biotage SNAP Ultra 10 g) to yield 72.8 mg (100% purity, 61% yield) of the desired product.

LC-MS (Method 10): $R_t$=1.84 min; MS (ESIpos): m/z=483 [M+H]$^+$ $^1$H-NMR (500 MHz, CHLOROFORM-d) δ [ppm]: 0.330 (0.68), 0.340 (2.77), 0.351 (2.74), 0.361 (0.73), 0.555 (0.77), 0.564 (2.30), 0.566 (2.26), 0.570 (1.05), 0.580 (2.37), 0.582 (2.16), 0.592 (0.59), 1.255 (0.46), 1.264 (0.63), 1.271 (0.58), 1.274 (0.47), 1.280 (0.94), 1.290 (0.57), 1.294 (0.55), 2.110 (16.00), 2.309 (7.02), 2.311 (6.83), 2.604 (15.69), 2.804 (8.27), 2.806 (7.96), 3.946 (3.39), 3.960 (3.31), 6.599 (0.64), 6.849 (0.54), 7.224 (2.11), 7.240 (2.24), 7.951 (1.75), 7.956 (1.73), 7.967 (1.66), 7.972 (1.64), 8.572 (4.18), 8.574 (4.15), 8.850 (2.31), 8.854 (2.22).

Example 456

1-[1-(6-{[5-(4-fluorophenyl)-1,4-dimethyl-1H-pyrazol-3-yl]amino}pyrimidin-4-yl)-3,5-dimethyl-1H-pyrazol-4-yl]-3-methylbutan-1-ol

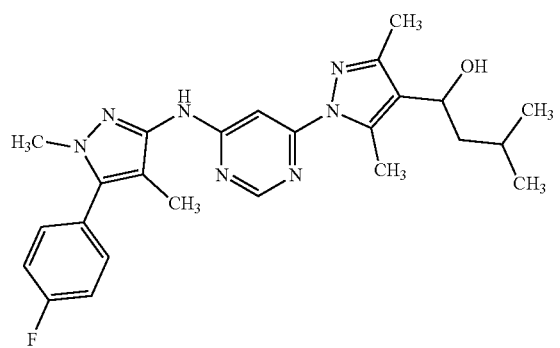 [SMILES: Cc1nn(-c2cc(Nc3nn(C)c(-c4ccc(F)cc4)c3C)ncn2)c(C)c1C(O)CC(C)C]

Under an argon atmosphere, ethyl 1-(6-{[5-(4-fluorophenyl)-1,4-dimethyl-1H-pyrazol-3-yl]amino}pyrimidin-4-yl)-3,5-dimethyl-1H-pyrazole-4-carboxylate (32.0 mg, 71.2 μmol) was dissolved in tetrahydrofuran (0.7 mL) and the solution cooled to 0° C. Titanium isopropoxide (46 μl, 160 μmol) was added, followed by a solution of isobutyl magnesium chloride (250 μl, 2.0 M in tetrahydrofuran, 500 μmol). The reaction mixture was stirred for 3 h at 0° C. and overnight at ambient temperature. The reaction mixture was carefully quenched by addition of aqueous saturated ammonium chloride solution and extracted with ethyl acetate (3×). The combined organic phase extracts were washed with brine, dried over sodium sulfate and concentrated. The residue was purified by preparative HPLC (column: Chromatorex C18; 200*40 mm, 10 μM, flow 100 mL/min, gradient acetonitrile/water (containing 0.1% trifluoroacetic acid) 10/90 to 95/5) was added to yield the desired compound LC-MS (method 11): $R_t$=1.42 min; MS (ESIpos): m/z=464 [M+H]$^+$ $^1$H-NMR (400 MHz, dimethylsulfoxide-d6) δ [ppm]: −0.149 (0.25), −0.008 (2.29), 0.008 (2.00), 0.146 (0.27), 0.875 (8.29), 0.888 (10.54), 0.891 (10.59), 0.904 (9.12), 1.235 (0.54), 1.364 (0.54), 1.381 (1.06), 1.397 (1.28), 1.413 (1.26), 1.430 (0.74), 1.540 (0.56), 1.557 (1.00), 1.573 (1.22), 1.590 (1.00), 1.606 (0.54), 1.623 (0.25), 1.644 (0.86), 1.664 (1.04), 1.678 (0.96), 1.697 (0.79), 1.713 (0.54), 1.816 (0.40), 1.849 (15.01), 1.967 (0.33), 1.985 (0.35), 2.073 (0.33), 2.142 (0.28), 2.233 (15.48), 2.262 (0.46), 2.328 (0.47), 2.366 (0.49), 2.389 (0.24), 2.614 (16.00), 2.670 (0.44), 2.710 (0.44), 3.472 (4.07), 4.610 (1.18), 4.630 (1.61), 4.646 (1.13), 7.356 (3.73), 7.379 (5.20), 7.401 (3.13), 7.508 (3.01), 7.514 (1.44), 7.522 (3.37), 7.530 (2.69), 7.544 (2.18), 8.441 (4.03), 9.371 (3.08).

Example 457

N-(4-chloro-1-methyl-3-phenyl-1H-pyrazol-5-yl)-6-(3,5-dimethyl-1H-pyrazol-1-yl)pyrimidin-4-amine

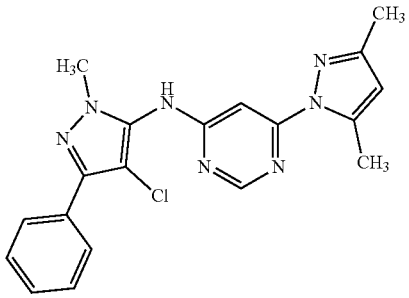 [SMILES: Cc1cc(C)n(-c2cc(Nc3c(Cl)c(-c4ccccc4)nn3C)ncn2)n1]

A microwave vial was charged with 4-chloro-1-methyl-3-phenyl-1H-pyrazol-5-amine (109 mg, 527 μmol) and sodium phenolate (83.5 mg, 719 μmol) and the contents were suspended in 1,4-dioxane (1.2 mL). The reaction mixture was degassed with Ar for 3 min. 4-chloro-6-(3,5-dimethyl-1H-pyrazol-1-yl)pyrimidine (100 mg, 479 μmol), tris(dibenzylideneacetone)dipalladium (5.71 mg, 6.23 μmol) and XantPhos (8.32 mg, 14.4 μmol) were added and the reaction mixture was degassed again for 1 min. The vial was sealed and heated at 80° C. overnight while vigorously shaking. After cooling to ambient temperature, the reaction mixture was filtered, diluted with dimethylsulfoxide and purified by preparative HPLC (method 4) to yield the desired product (15 mg, 8% yield).

LC-MS (method 10): R$_t$=2.14 min; MS (ESIpos): m/z=380 [M+H]$^+$ $^1$H-NMR (400 MHz, dimethylsulfoxide-d6) δ [ppm]: −0.008 (1.38), 0.008 (1.29), 1.646 (0.50), 2.189 (10.90), 2.328 (0.17), 2.524 (0.66), 2.638 (15.99), 2.665 (0.23), 2.670 (0.24), 2.710 (0.16), 3.734 (16.00), 6.162 (3.96), 7.101 (0.20), 7.169 (0.16), 7.368 (0.42), 7.384 (1.09), 7.402 (2.45), 7.421 (1.75), 7.466 (3.19), 7.486 (4.98), 7.504 (2.18), 7.857 (4.04), 7.875 (3.86), 7.878 (2.88), 8.502 (2.69), 9.680 (4.25).

Example 458

2-[1-(6-{[1-(cyclopropylmethyl)-3-(5-fluoropyridin-2-yl)-4-methyl-1H-pyrazol-5-yl]amino}pyrimidin-4-yl)-3,5-dimethyl-1H-pyrazol-4-yl]propan-2-ol

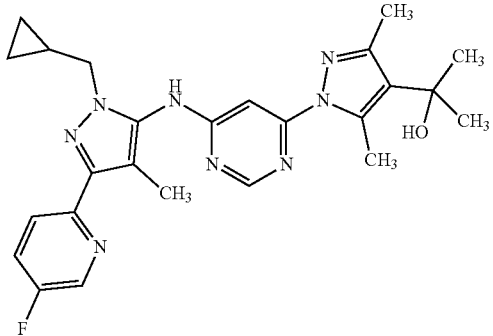 [SMILES: Cc1nn(-c2cc(Nc3c(C)c(-c4ccc(F)cn4)nn3CC3CC3)ncn2)c(C)c1C(C)(C)O]

A solution of ethyl 1-(6-{[1-(cyclopropylmethyl)-3-(5-fluoropyridin-2-yl)-4-methyl-1H-pyrazol-5-yl]amino}pyrimidin-4-yl)-3,5-dimethyl-1H-pyrazole-4-carboxylate (52.0 mg, 106 μmol) in tetrahydrofuran (2.0 ml, 25 mmol) was treated at 0° C. with chloro(methyl)magnesium (120 μl, 3.0 M, 370 μmol) and stirred overnight at ambient temperature. No full conversion was observed. Therefore additional chloro(methyl)magnesium (120 μl, 3.0 M, 370 μmol) was added at 0° C. and the mixture was stirred three hours at ambient temperature. The mixture was diluted with potassium sodium tartrate solution and water and extracted with ethyl acetate. The combined organic phases were dried over Extrelut NT3 and concentrated under reduced pressure. The crude product was purified using preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 30.2 mg (60%) of the desired product.

LC-MS (method 9): R$_t$=1.00 min; MS (ESIpos): m/z=477 [M+H]$^+$ $^1$H-NMR (500 MHz, dimethylsulfoxide-d6) δ [ppm]: −0.006 (1.44), 0.007 (0.80), 0.307 (2.23), 0.317 (2.31), 0.436 (2.29), 0.452 (2.35), 1.023 (0.45), 1.036 (0.45), 1.195 (0.68), 1.200 (0.64), 1.209 (0.99), 1.219 (0.58), 1.224 (0.60), 1.461 (13.86), 1.491 (0.54), 1.969 (0.43), 2.146 (16.00), 2.264 (1.88), 2.725 (0.70), 2.740 (14.95), 3.856 (1.79), 3.869 (1.77), 4.839 (0.47), 4.852 (3.15), 7.751 (0.66), 7.757 (0.74), 7.769 (1.40), 7.775 (1.48), 7.786 (0.78), 7.792 (0.82), 7.985 (0.95), 7.994 (1.01), 8.003 (0.93), 8.012 (0.82), 8.463 (0.54), 8.590 (2.76), 8.595 (2.76), 9.381 (0.62).

Example 459

(±)-4-{3-[(6-{4-[cyclopropyl(hydroxy)methyl]-3,5-dimethyl-1H-pyrazol-1-yl}pyrimidin-4-yl)amino]-4-methoxy-1-methyl-1H-pyrazol-5-yl}benzonitrile (Racemic)

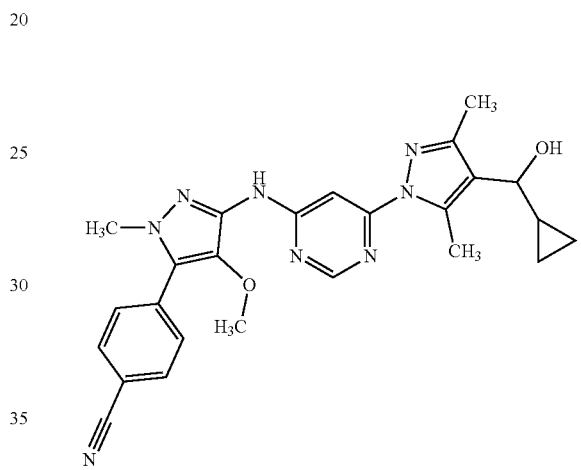

Under an argon atmosphere a solution of 4-(3-{[6-(4-formyl-3,5-dimethyl-1H-pyrazol-1-yl)pyrimidin-4-yl]amino}-4-methoxy-1-methyl-1H-pyrazol-5-yl)benzonitrile (19.0 mg, 44.3 μmol) in tetrahydrofuran (1.0 ml, 12 mmol) was treated with bromo(cyclopropyl)magnesium (440 μl, 0.50 M in tetrahydrofuran, 220 μmol) at 0° C. The resulting mixture was stirred one hour at ambient temperature. The mixture was purified by preparative HPLC (method: column: Reprosil C18; 10 μm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 9.8 mg (47%) of the desired product.

LC-MS (method 9): R$_t$=0.89 min; MS (ESIpos): m/z=471 [M+H]$^+$ $^1$H-NMR (500 MHz, dimethylsulfoxide-d6) δ [ppm]: 0.128 (0.60), 0.139 (0.68), 0.146 (0.49), 0.338 (0.44), 0.347 (0.61), 0.354 (0.89), 0.364 (0.78), 0.369 (1.06), 0.374 (0.74), 0.384 (0.57), 0.499 (0.57), 0.504 (0.52), 0.507 (0.45), 0.515 (0.44), 1.191 (0.63), 1.197 (0.41), 1.201 (0.41), 1.207 (0.62), 2.247 (0.95), 2.258 (9.62), 2.617 (10.75), 2.627 (0.73), 2.662 (0.41), 3.564 (16.00), 3.784 (12.22), 3.953 (0.88), 3.960 (0.88), 3.969 (0.86), 3.975 (0.82), 4.947 (2.16), 4.953 (2.12), 5.753 (1.93), 7.185 (3.07), 7.186 (3.02), 7.773 (3.25), 7.777 (1.22), 7.787 (1.36), 7.790 (3.67), 8.004 (3.82), 8.007 (1.30), 8.017 (1.25), 8.021 (3.24), 8.449 (2.33), 8.450 (2.30), 9.411 (1.19).

Example 460

(±)-cyclopropyl {1-[6-({1-(cyclopropylmethyl)-3-[4-(difluoromethyl)phenyl]-4-methyl-1H-pyrazol-5-yl}amino)pyrimidin-4-yl]-3,5-dimethyl-1H-pyrazol-4-yl}methanol (Racemate)

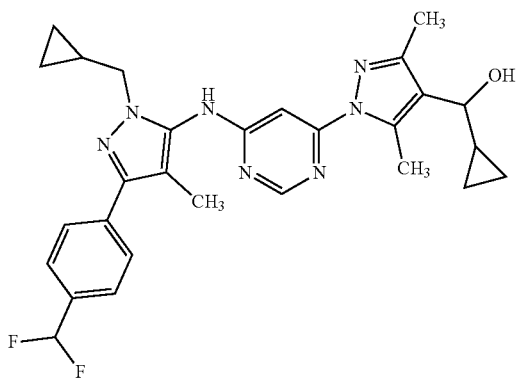 [SMILES: Cc1nn(-c2cc(Nc3c(C)c(-c4ccc(C(F)F)cc4)nn3CC3CC3)ncn2)c(C)c1C(O)C1CC1]

A solution of 1-[6-{1-(cyclopropylmethyl)-3-[4-(difluoromethyl)phenyl]-4-methyl-1H-pyrazol-5-yl}amino)pyrimidin-4-yl]-3,5-dimethyl-1H-pyrazole-4-carbaldehyde (165 mg, 346 µmol) on tetrahydrofuran (7.8 ml, 96 mmol) was treated at 0° C. with bromo(cyclopropyl)magnesium (3.5 ml, 0.50 M in tetrahydrofuran, 1.7 mmol). The mixture was stirred one hour at ambient temperature. The mixture was diluted with saturated potassium sodium tartrate solution and water and extracted with ethyl acetate (2×). The combined organic phases were dried over Extrelut NT3 and concentrated under reduced pressure. The crude product was purified by preparative HPLC (method: column: Reprosil C18; 10 µm; 125×30 mm/flow: 50 mL/min/solvent: A=water (0.01% formic acid), B=acetonitrile/gradient: 0.00-5.00 min=10% B, 6.50 min=20% B, 17.0-19.75 min=100% B, 19.75-23.00 min=90% B) to yield 139 mg (78%) of the desired product.

LC-MS (method 9): $R_t$=1.10 min; MS (ESIpos): m/z=520 [M+H]$^+$ $^1$H-NMR (500 MHz, dimethylsulfoxide-d6) δ [ppm]: 0.118 (0.50), 0.127 (0.70), 0.137 (0.78), 0.145 (0.58), 0.308 (2.08), 0.317 (2.28), 0.327 (0.98), 0.335 (0.76), 0.345 (0.78), 0.353 (0.96), 0.368 (1.15), 0.375 (0.95), 0.384 (0.79), 0.393 (0.55), 0.436 (2.15), 0.452 (2.18), 0.489 (0.48), 0.499 (0.75), 0.505 (0.71), 0.515 (0.61), 1.035 (0.54), 1.048 (0.55), 1.190 (0.93), 1.199 (1.11), 1.205 (1.16), 1.215 (1.28), 1.224 (0.68), 1.230 (0.66), 2.053 (13.14), 2.257 (1.65), 2.633 (16.00), 3.860 (1.66), 3.873 (1.61), 3.965 (0.76), 3.976 (0.75), 4.969 (1.35), 4.974 (1.34), 5.754 (2.74), 6.966 (1.27), 7.078 (2.78), 7.190 (1.14), 7.641 (2.59), 7.657 (3.05), 7.851 (2.18), 7.867 (1.91), 8.466 (0.48), 9.382 (0.48).

Example 461

N-[5-(5-fluoropyridin-2-yl)-1,4-dimethyl-1H-pyrazol-3-yl]-6-(4-methoxy-3,5-dimethyl-1H-pyrazol-1-yl)pyrimidin-4-amine

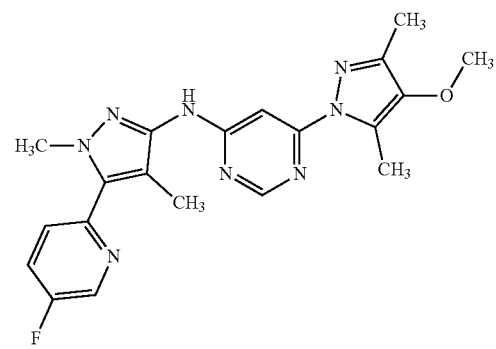 [SMILES: COc1c(C)nn(-c2cc(Nc3nn(C)c(-c4ccc(F)cn4)c3C)ncn2)c1C]

A microwave vial was charged 4-chloro-6-(4-methoxy-3,5-dimethyl-1H-pyrazol-1-yl)pyrimidine (75.0 mg, 314 µmol) and 5-(5-fluoropyridin-2-yl)-1,4-dimethyl-1H-pyrazol-3-amine (71.3 mg, 346 µmol) and the contents were suspended in 1,4-dioxane (1.2 ml, 14 mmol). The reaction mixture was degassed with Ar for 3 min. Tris(dibenzylidenaceton)dipalladium (8.63 mg, 9.43 µmol) and Xantphos (10.9 mg, 18.9 mol) were added and the reaction mixture was degassed again for 1 min and heated to 85° C. At this temperature and sodium phenolate (40.1 mg, 346 µmol) was added. The vial was sealed and heated at 85° C. for 90 minutes while vigorously stirring. The mixture was left overnight, the reaction mixture was diluted with water and extracted with dichloromethane (2×). The remaining residue was suspended in a mixture of tetrahydrofuran/water/dimethylsulfoxide, the occurring precipitate was collected by filtration, washed with tetrahydrofuran and dried to yield 72.1 mg (52%) of the desired product.

LC-MS (method 10): $R_t$=1.79 min; MS (ESIpos): m/z=409 [M+H]$^+$ $^1$H-NMR (500 MHz, CHLOROFORM-d) δ [ppm]: −0.007 (0.55), 2.224 (6.27), 2.309 (11.70), 3.782 (16.00), 3.977 (11.28), 7.444 (0.70), 7.453 (0.72), 7.462 (0.95), 7.470 (0.96), 7.554 (0.64), 7.559 (0.67), 7.570 (0.82), 7.575 (0.84), 7.587 (0.49), 7.593 (0.49), 8.414 (1.30), 8.425 (2.30), 8.626 (1.65), 8.631 (1.63).

Example 462

4-(4-methoxy-5-{[6-(4-methoxy-3,5-dimethyl-1H-pyrazol-1-yl)pyrimidin-4-yl]amino}-1-methyl-1H-pyrazol-3-yl)benzonitrile

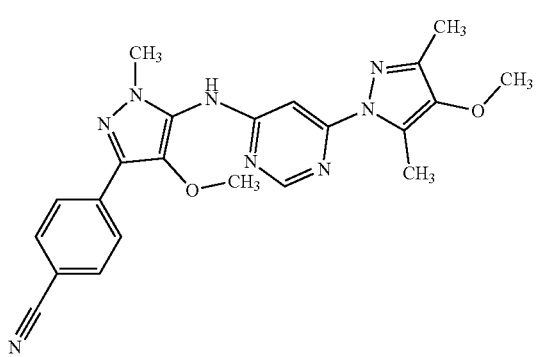 [SMILES: COc1c(-c2ccc(C#N)cc2)nn(C)c1Nc1cc(-n2nc(C)c(OC)c2C)ncn1]

A microwave vial was charged with 4-chloro-6-(4-methoxy-3,5-dimethyl-1H-pyrazol-1-yl)pyrimidine (100 mg, 100% purity, 419 μmol) and 4-(5-amino-4-methoxy-1-methyl-1H-pyrazol-3-yl)benzonitrile (105 mg, 100% purity, 461 μmol), and the contents were suspended in 1,4-dioxane (1.5 mL). The reaction mixture was degassed with Ar for 3 min. Tris(dibenzylideneacetone)dipalladium (11.5 mg, 12.6 μmol) and XantPhos (14.5 mg, 25.1 μmol) were added and the reaction mixture was degassed again for 1 min. Finally, sodium phenolate (53.5 mg, 461 μmol) was added and the vial was sealed and heated at 85° C. overnight while vigorously shaking. After cooling to ambient temperature, the reaction mixture was diluted with dimethylsulfoxide, filtered and purified by preparative HPLC (method 3) to yield the desired product (55 mg, 30% yield).

LC-MS (method 10): R$_t$=1.96 min; MS (ESIpos): m/z=431 [M+H]$^+$ $^1$H-NMR (500 MHz, dimethylsulfoxide-d6) δ [ppm]: 1.343 (0.19), 1.530 (0.30), 1.647 (0.52), 2.188 (2.14), 2.213 (0.46), 3.650 (5.99), 3.703 (9.16), 3.714 (0.78), 3.725 (16.00), 7.372 (0.34), 7.385 (0.35), 7.395 (0.38), 7.871 (2.63), 7.875 (0.97), 7.885 (1.16), 7.889 (3.12), 8.034 (2.80), 8.038 (0.98), 8.051 (2.15), 8.481 (0.86), 9.501 (0.76).

Example 463

N-[1-(4-fluorophenyl)-3,5-dimethyl-1H-pyrazol-4-yl]-6-(4-methoxy-3,5-dimethyl-1H-pyrazol-1-yl)pyrimidin-4-amine

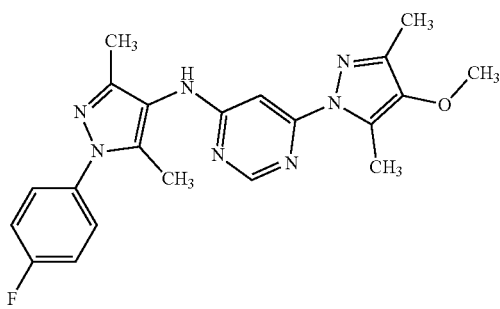 [SMILES: COc1c(C)nn(-c2cc(Nc3c(C)nn(-c4ccc(F)cc4)c3C)ncn2)c1C]

A microwave vial was charged with 4-chloro-6-(4-methoxy-3,5-dimethyl-1H-pyrazol-1-yl)pyrimidine (90.0 mg, 100% purity, 377 μmol) and 1-(4-fluorophenyl)-3,5-dimethyl-1H-pyrazol-4-amine (100 mg, 85% purity, 415 μmol) and the contents were suspended in 1,4-dioxane (1.4 mL). The reaction mixture was degassed with Ar for 3 min. Tris(dibenzylideneacetone)dipalladium (10.4 mg, 11.3 μmol) and XantPhos (13.1 mg, 22.6 μmol) were added and the reaction mixture was degassed again for 1 min. Finally, sodium phenolate (48.2 mg, 415 μmol) was added and the vial was sealed and heated at 85° C. overnight while vigorously shaking. After cooling to ambient temperature, the reaction mixture was diluted with dimethylsulfoxide, filtered and purified by preparative HPLC (method 3) to yield the desired product (13.5 mg, 9% yield).

LC-MS (method 10): R$_t$=1.91 min; MS (ESIpos): m/z=408 [M+H]$^+$ $^1$H-NMR (500 MHz, dimethylsulfoxide-d6) δ [ppm]: 1.544 (0.57), 2.072 (16.00), 2.159 (1.40), 2.174 (8.65), 2.520 (0.32), 3.692 (4.70), 7.339 (1.20), 7.357 (2.44), 7.374 (1.45), 7.591 (1.03), 8.381 (0.35), 8.844 (1.80).

Example 464

4-[1-(cyclopropylmethyl)-5-{[6-(4-methoxy-3,5-dimethyl-1H-pyrazol-1-yl)pyrimidin-4-yl]amino}-4-methyl-1H-pyrazol-3-yl]benzonitrile

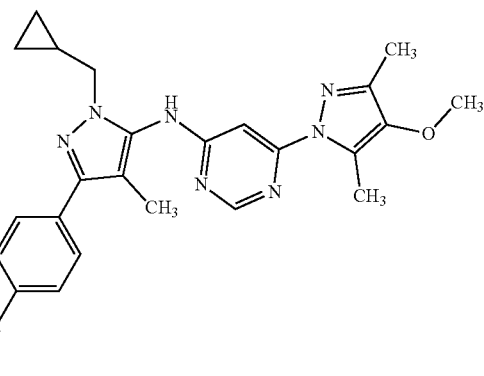

A microwave vial was charged with 4-chloro-6-(4-methoxy-3,5-dimethyl-1H-pyrazol-1-yl)pyrimidine (100 mg, 419 μmol) and 4-[5-amino-1-(cyclopropylmethyl)-4-methyl-1H-pyrazol-3-yl]benzonitrile (116 mg, 461 μmol), and the contents were suspended in 1,4-dioxane (1.3 mL). The reaction mixture was degassed with Ar for 3 min. Tris(dibenzylideneacetone)dipalladium (11.5 mg, 12.6 μmol) and XantPhos (14.5 mg, 25.1 μmol) were added and the reaction mixture was degassed again for 1 min. Finally, sodium phenolate (53.5 mg, 461 μmol) was added and the vial was sealed and heated at 85° C. overnight while vigorously shaking. After cooling to ambient temperature, the reaction mixture was diluted with dimethylsulfoxide, filtered and purified by preparative HPLC (method 4) and further by column chromatography (SNAP Ultra 10 g, cyclohexane/ethyl acetate gradient 90/10 to 30/70) to yield the desired product after lyophilisation (85 mg, 44% yield).

LC-MS (method 11): R$_t$=1.45 min; MS (ESIpos): m/z=455 [M+H]$^+$ $^1$H-NMR (500 MHz, dimethylsulfoxide-d6) δ [ppm]: −0.007 (0.81), 0.006 (0.48), 0.305 (2.08), 0.315 (2.15), 0.433 (2.21), 0.449 (2.25), 1.162 (0.40), 1.176 (0.96), 1.181 (0.36), 1.191 (0.97), 1.197 (0.62), 1.207 (0.95), 1.216 (0.57), 1.221 (0.57), 1.231 (0.32), 1.236 (0.22), 1.397 (6.06), 1.990 (1.35), 2.061 (16.00), 2.075 (0.89), 2.181 (1.89), 3.699 (8.28), 3.861 (1.79), 3.875 (1.71), 4.024 (0.32), 4.038 (0.31), 7.888 (1.33), 7.892 (1.01), 7.905 (7.63), 7.912 (4.86), 7.929 (0.95), 8.443 (0.48), 9.411 (0.47).

Example 465

6-[5-(difluoromethyl)-3-methyl-1H-pyrazol-1-yl]-N-[3-(5-fluoropyridin-2-yl)-1,4-dimethyl-1H-pyrazol-5-yl]pyrimidin-4-amine

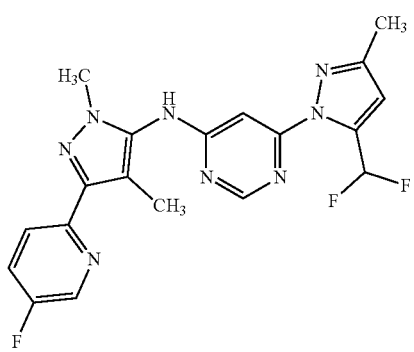 [SMILES: Cc1cc(C(F)F)n(-c2cc(Nc3c(C)c(-c4ccc(F)cn4)nn3C)ncn2)n1]

A microwave vial was charged 4-chloro-6-[5-(difluoromethyl)-3-methyl-H-pyrazol-1-yl]pyrimidine (108 mg, 441 µmol) and 3-(5-fluoropyridin-2-yl)-1,4-dimethyl-1H-pyrazol-5-amine (100 mg, 485 µmol) and the contents were suspended in 1,4-dioxane (1.7 ml, 20 mmol). The reaction mixture was degassed with Ar for 3 min. Tris(dibenzylidenaceton)dipalladium (12.1 mg, 13.2 µmol) and Xantphos (15.3 mg, 26.4 µmol) were added and the reaction mixture was degassed again for 1 min and heated to 85° C. At this temperature and sodium phenolate (56.3 mg, 485 µmol) was added. The vial was sealed and heated at 85° C. for 90 minutes while vigorously stirring. The mixture was left overnight at ambient temperature.

The reaction mixture was diluted with water and extracted with dichloromethane (2×). The combined organic phases were dried over sodium sulfate and concentrated under reduced pressure. The crude product was purified by preparative HPLC (method 3) and further flash-chromatography (column: SNAP KP-Sil 10 g, solvent: 88% dichloromethane/12% ethyl acetate to 100% ethyl acetate) to yield the desired product (51.1 mg, 28%).

LC-MS (method 10): $R_t$=2.03 min; MS (ESIpos): m/z=415 [M+H]$^+$ $^1$H-NMR (500 MHz, dimethylsulfoxide-d6) δ [ppm]: 1.162 (0.44), 1.176 (0.90), 1.191 (0.46), 1.990 (1.64), 2.166 (16.00), 2.281 (1.04), 3.701 (3.94), 6.784 (1.57), 7.710 (1.06), 7.753 (0.41), 7.759 (0.45), 7.771 (0.85), 7.777 (0.87), 7.789 (0.50), 7.794 (0.49), 7.819 (2.12), 7.927 (0.95), 7.978 (0.55), 7.986 (0.62), 7.994 (0.56), 8.003 (0.47), 8.590 (1.74), 8.596 (1.68), 9.617 (0.60).

Example 466

N-[1-(cyclopropylmethyl)-3-(4-fluorophenyl)-4-methyl-1H-pyrazol-5-yl]-6-(3,5-dimethyl-4-nitro-1H-pyrazol-1-yl)pyrimidin-4-amine

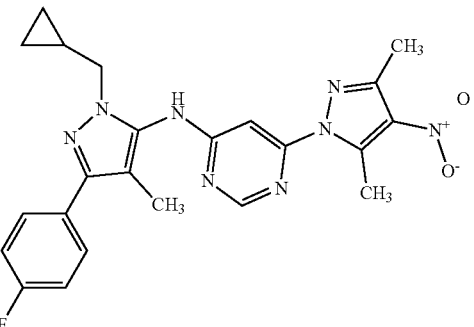

Under an argon atmosphere, 4-chloro-6-(3,5-dimethyl-4-nitro-1H-pyrazol-1-yl)pyrimidine (500 mg, 100% purity, 1.97 mmol) and 1-(cyclopropylmethyl)-3-(4-fluorophenyl)-4-methyl-1H-pyrazol-5-amine (532 mg, 2.17 mmol) were suspended in 1,4-dioxane (6.3 mL). The reaction mixture was degassed with Ar for 3 min. Tris(dibenzylideneacetone)dipalladium (54.2 mg, 59.1 µmol) and XantPhos (68.4 mg, 118 mol) were added and the reaction mixture was degassed again for 1 min. Finally, sodium phenolate (252 mg, 2.17 mmol) was added and the reaction mixture was heated at 85° C. overnight while vigorously stirring. After cooling to ambient temperature, the reaction mixture was diluted with ethyl acetate and washed with brine. The organic phase extract was dried over sodium sulfate and concentrated. The residue was purified by flash column chromatography (SNAP Ultra 25 g, cyclohexane/ethyl acetate 90/10 to 0/100) to yield the desired product (62 mg, 7% yield) and a slightly impure product fraction (281 mg, 95% purity, 29% yield).

LC-MS (method 11): $R_t$=1.51 min; MS (ESIpos): m/z=463 [M+H]$^+$ $^1$H-NMR (500 MHz, dimethylsulfoxide-d6) δ [ppm]: −0.007 (0.82), 0.006 (0.48), 0.296 (2.21), 0.305 (2.24), 0.430 (2.48), 0.446 (2.55), 1.161 (0.54), 1.175 (1.15), 1.181 (0.75), 1.189 (1.02), 1.196 (1.05), 1.211 (0.68), 1.221 (0.37), 1.237 (0.24), 1.398 (10.29), 1.988 (1.73), 2.011 (16.00), 2.119 (0.34), 2.368 (0.51), 2.636 (0.27), 2.993 (5.30), 3.029 (0.27), 3.089 (0.27), 3.568 (5.03), 3.838 (1.60), 4.023 (0.37), 4.037 (0.37), 7.257 (2.31), 7.274 (4.69), 7.292 (2.62), 7.727 (1.83), 8.574 (0.27), 9.619 (0.20).

Example 467

6-(3,5-dimethyl-1H-pyrazol-1-yl)-N-[3-(5-fluoropyridin-2-yl)-1,4-dimethyl-1H-pyrazol-5-yl]pyrimidin-4-amine

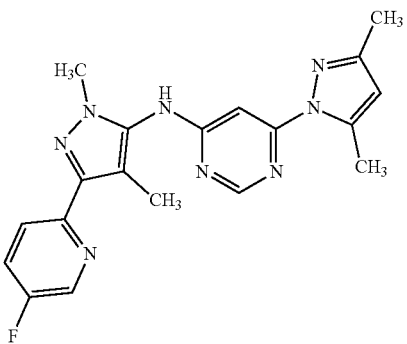 [SMILES: Cc1cc(C)n(-c2cc(Nc3c(C)c(-c4ccc(F)cn4)nn3C)ncn2)n1]

A microwave vial was charged 4-chloro-6-(3,5-dimethyl-1H-pyrazol-1-yl)pyrimidine (92.0 mg, 441 μmol) and 3-(5-fluoropyridin-2-yl)-1,4-dimethyl-1H-pyrazol-5-amine (100 mg, 485 μmol) and the contents were suspended in 1,4-dioxane (1.7 ml, 20 mmol). The reaction mixture was degassed with Ar for 3 min. Tris(dibenzylidenaceton)dipalladium (12.1 mg, 13.2 μmol) and Xantphos (15.3 mg, 26.4 μmol) were added and the reaction mixture was degassed again for 1 min and heated to 85° C. At this temperature and sodium phenolate (56.3 mg, 485 μmol) was added. The vial was sealed and heated at 85° C. for 90 minutes while vigorously stirring. The mixture was left overnight at ambient temperature.

The reaction mixture was diluted with water and extracted with dichloromethane (2×). The combined organic phases were dried over sodium sulfate and concentrated under reduced pressure. The crude product was purified by preparative HPLC (method 7) and further flash-chromatography to yield the desired product (35.4 mg, 21%).

LC-MS (method 10): $R_f$=1.91 min; MS (ESIpos): m/z=379 [M+H]$^+$ $^1$H-NMR (500 MHz, dimethylsulfoxide-d6) δ [ppm]: 1.078 (0.76), 1.092 (1.53), 1.106 (0.76), 2.163 (16.00), 2.228 (0.75), 2.630 (11.81), 2.662 (0.53), 3.377 (0.77), 3.391 (0.76), 3.694 (7.29), 6.141 (2.18), 7.749 (0.52), 7.755 (0.57), 7.767 (1.11), 7.773 (1.16), 7.785 (0.63), 7.791 (0.63), 7.974 (0.82), 7.983 (0.87), 7.992 (0.76), 8.001 (0.69), 8.471 (0.55), 8.587 (2.14), 8.592 (2.11), 9.427 (1.90).

Example 468

N-[3-(5-fluoropyridin-2-yl)-1,4-dimethyl-1H-pyrazol-5-yl]-6-(4-methoxy-3,5-dimethyl-1H-pyrazol-1-yl)pyrimidin-4-amine

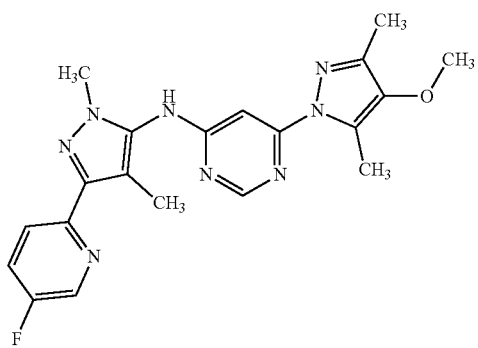 [SMILES: COc1c(C)nn(-c2cc(Nc3c(C)c(-c4ccc(F)cn4)nn3C)ncn2)c1C]

A microwave vial was charged 4-chloro-6-(4-methoxy-3,5-dimethyl-1H-pyrazol-1-yl)pyrimidine (75.0 mg, 314 μmol) and 3-(5-fluoropyridin-2-yl)-1,4-dimethyl-1H-pyrazol-5-amine (71.3 mg, 346 μmol) and the contents were suspended in 1,4-dioxane (1.2 ml, 14 mmol). The reaction mixture was degassed with Ar for 3 min. Tris(dibenzylidenaceton)dipalladium (8.63 mg, 9.43 μmol) and Xantphos (10.9 mg, 18.9 μmol) were added and the reaction mixture was degassed again for 1 min and heated to 85° C. At this temperature and sodium phenolate (40.1 mg, 346 μmol) was added. The vial was sealed and heated at 85° C. for 90 minutes while vigorously stirring. The mixture was left overnight. The reaction mixture was diluted with water and extracted with dichloromethane (2×). The combined organic phases were dried over sodium sulfate and concentrated under reduced pressure. The crude product was purified by preparative HPLC (method 7) and further flash-chromatography (column: SNAP KP-Sil 10 g, solvent: 88% dichloromethane/12% ethyl acetate to 100% ethyl acetate) to yield the desired product (18.7 mg, 15%).

LC-MS (method 10): $R_f$=1.91 min; MS (ESIpos): m/z=409 [M+H]$^+$ $^1$H-NMR (500 MHz, dimethylsulfoxide-d6) δ [ppm]: 1.079 (1.92), 1.093 (3.88), 1.107 (1.92), 2.161 (16.00), 2.177 (2.10), 3.363 (0.67), 3.377 (1.91), 3.391 (1.88), 3.405 (0.62), 3.692 (8.83), 3.699 (9.77), 7.749 (0.55), 7.755 (0.61), 7.766 (1.18), 7.772 (1.25), 7.784 (0.69), 7.790 (0.70), 7.975 (0.84), 7.984 (0.91), 7.992 (0.81), 8.001 (0.73), 8.456 (0.57), 8.586 (2.25), 8.592 (2.25), 9.415 (1.91).

Example 469

N-[4-(difluoromethoxy)-5-(4-fluorophenyl)-1-methyl-1H-pyrazol-3-yl]-6-[3,5-dimethyl-4-(trifluoromethyl)-1H-pyrazol-1-yl]pyrimidin-4-amine

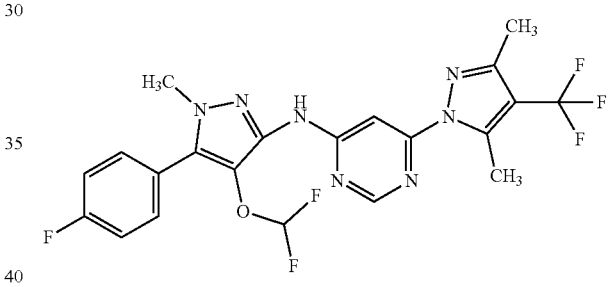

A microwave vial was charged with 4-(difluoromethoxy)-5-(4-fluorophenyl)-1-methyl-1H-pyrazol-3-amine (120 mg, 467 μmol), 4-chloro-6-[3,5-dimethyl-4-(trifluoromethyl)-1H-pyrazol-1-yl]pyrimidine (142 mg, 513 μmol) and sodium phenolate (59.6 mg, 513 μmol) and the contents were suspended in 1,4-dioxane (1.5 mL). The reaction mixture was degassed with Ar for 3 min. Tris(dibenzylideneacetone)dipalladium (12.8 mg, 14.0 μmol) and XantPhos (16.2 mg, 28.0 μmol) were added and the reaction mixture was degassed again for 1 min. The vial was sealed and heated at 85° C. overnight while vigorously shaking. After cooling to ambient temperature, the suspension was diluted with ethyl acetate and filter over celite. The filtrate was concentrated, the residue was redissolved in dimethylsulfoxide and purified by preparative HPLC (method 4) to yield the desired product (84 mg, 36% yield).

LC-MS (method 11): Rt=1.55 min; MS (ESIpos): m/z=498 [M+H]$^+$ $^1$H-NMR (500 MHz, dimethylsulfoxide-d6) δ [ppm]: −0.007 (1.49), 0.007 (1.00), 2.321 (6.57), 2.324 (6.32), 2.748 (6.75), 2.751 (6.47), 3.729 (16.00), 6.651 (1.28), 6.798 (2.49), 6.945 (1.06), 7.378 (1.06), 7.387 (2.33), 7.391 (0.84), 7.400 (0.96), 7.404 (4.39), 7.409 (0.84), 7.418 (0.78), 7.422 (2.37), 7.589 (2.33), 7.593 (0.96), 7.599 (2.52), 7.606 (2.18), 7.613 (0.84), 7.617 (1.93), 8.551 (2.65), 9.746 (1.21).

Example 470

N-[4-(difluoromethoxy)-5-(4-fluorophenyl)-1-methyl-1H-pyrazol-3-yl]-6-(4-methoxy-3,5-dimethyl-1H-pyrazol-1-yl)pyrimidin-4-amine

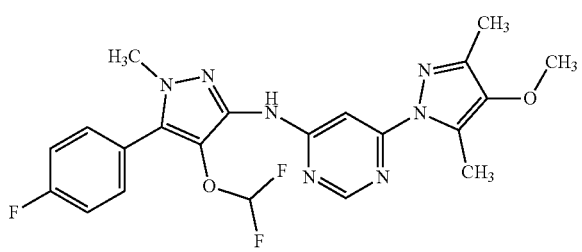 [SMILES: COc1c(C)nn(-c2cc(Nc3nn(C)c(-c4ccc(F)cc4)c3OC(F)F)ncn2)c1C]

A microwave vial was charged with 4-(difluoromethoxy)-5-(4-fluorophenyl)-1-methyl-1H-pyrazol-3-amine (100 mg, 389 μmol), 4-chloro-6-(4-methoxy-3,5-dimethyl-1H-pyrazol-1-yl)pyrimidine (102 mg, 428 μmol) and sodium phenolate (49.6 mg, 428 μmol) and the contents were suspended in 1,4-dioxane (1.5 mL). The reaction mixture was degassed with Ar for 3 min. Tris(dibenzylideneacetone)dipalladium (10.7 mg, 11.7 μmol) and XantPhos (13.5 mg, 23.3 μmol) were added and the reaction mixture was degassed again for 1 min. The vial was sealed and heated at 85° C. overnight while vigorously shaking. After cooling to ambient temperature, the suspension was diluted with ethyl acetate and filter over celite. The filtrate was concentrated, the residue was redissolved in dimethylsulfoxide and purified by preparative HPLC (method 3) to yield the desired product (75 mg, 40% yield).

LC-MS (method 11): $R_t$=1.39 min; MS (ESIpos): m/z=460 [M+H]$^+$ $^1$H-NMR (500 MHz, dimethylsulfoxide-d6) δ [ppm]: −0.007 (1.06), 0.006 (0.63), 2.205 (10.36), 3.707 (16.00), 3.727 (10.73), 6.643 (0.88), 6.790 (1.71), 6.938 (0.73), 7.310 (1.39), 7.385 (1.41), 7.389 (0.53), 7.403 (2.95), 7.407 (0.63), 7.416 (0.55), 7.421 (1.59), 7.587 (1.61), 7.591 (0.71), 7.597 (1.76), 7.604 (1.49), 7.611 (0.63), 7.615 (1.31), 8.440 (2.32), 8.442 (2.22), 9.470 (1.94).

Example 471

1-(6-{[4-(difluoromethoxy)-5-(4-fluorophenyl)-1-methyl-1H-pyrazol-3-yl]amino}pyrimidin-4-yl)-3,5-dimethyl-1H-pyrazole-4-carbonitrile

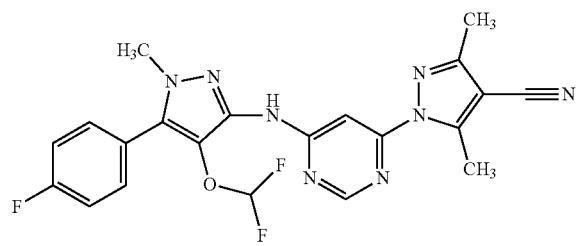 [SMILES: Cc1nn(-c2cc(Nc3nn(C)c(-c4ccc(F)cc4)c3OC(F)F)ncn2)c(C)c1C#N]

A microwave vial was charged with 4-(difluoromethoxy)-5-(4-fluorophenyl)-1-methyl-1H-pyrazol-3-amine (100 mg, 389 μmol), 1-(6-chloropyrimidin-4-yl)-3,5-dimethyl-1H-pyrazole-4-carbonitrile (99.9 mg, 428 μmol) and sodium phenolate (49.6 mg, 428 μmol) and the contents were suspended in 1,4-dioxane (1.5 mL). The reaction mixture was degassed with Ar for 3 min. Tris(dibenzylideneacetone)dipalladium (10.7 mg, 11.7 μmol) and XantPhos (13.5 mg, 23.3 μmol) were added and the reaction mixture was degassed again for 1 min. The vial was sealed and heated at 85° C. overnight while vigorously shaking. After cooling to ambient temperature, the suspension was diluted with ethyl acetate and filter over celite. The filtrate was concentrated, the residue was redissolved in dimethylsulfoxide and purified by preparative HPLC (method 3) to yield the desired product (36 mg, 20% yield).

LC-MS (method 11): $R_t$=1.39 min; MS (ESIpos): m/z=455 [M+H]$^+$ $^1$H-NMR (500 MHz, dimethylsulfoxide-d6) δ [ppm]: −0.007 (1.40), 0.007 (0.93), 2.349 (14.87), 2.793 (16.00), 3.730 (14.77), 6.646 (1.20), 6.794 (2.33), 6.941 (1.00), 7.387 (2.26), 7.391 (1.23), 7.400 (1.53), 7.404 (4.46), 7.409 (0.96), 7.418 (0.80), 7.422 (2.30), 7.587 (2.20), 7.592 (0.93), 7.598 (2.40), 7.605 (2.10), 7.612 (0.83), 7.616 (1.83), 8.549 (2.43), 9.766 (1.06).

Example 472

4-(1,4-dimethyl-5-{[6-(3-oxo-1,3,4,5,6,7-hexahydro-2H-indazol-2-yl)pyrimidin-4-yl]amino}-1H-pyrazol-3-yl)benzonitrile

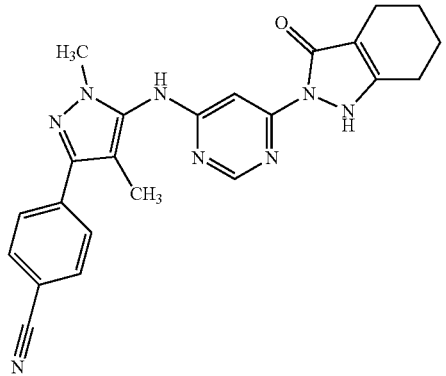 [SMILES: Cc1c(-c2ccc(C#N)cc2)nn(C)c1Nc1cc(-n2[nH]c3c(c2=O)CCCC3)ncn1]

A solution of 4-{5-[(6-hydrazinylpyrimidin-4-yl)amino]-1,4-dimethyl-1H-pyrazol-3-yl}benzonitrile (90.0 mg, 281 μmol) in methanol (3.0 ml, 74 mmol) was treated with methyl 2-oxocyclohexanecarboxylate (41 μl, 280 μmol) and stirred for 4 hours at 80° C. The mixture was concentrated under reduced pressure and purified by preparative HPLC (method 7) to yield 33.0 mg (28%) of the desired product.

LC-MS (method 10): $R_t$=1.68 min; MS (ESIpos): m/z=427 [M+H]$^+$ $^1$H-NMR (500 MHz, dimethylsulfoxide-d6) δ [ppm]: −0.007 (0.98), 0.007 (0.81), 1.635 (1.21), 1.645 (1.30), 1.694 (1.30), 1.704 (1.25), 2.059 (12.99), 2.073 (0.66), 2.078 (0.65), 2.130 (1.44), 2.455 (1.17), 2.466 (2.10), 2.477 (1.22), 3.666 (0.43), 3.687 (8.59), 7.870 (0.78), 7.888 (16.00), 7.900 (1.16), 8.433 (0.91), 9.495 (2.25), 11.428 (1.72).

Example 473

N-{3-[6-(difluoromethyl)pyridin-3-yl]-1,4-dimethyl-1H-pyrazol-5-yl}-6-[3,5-dimethyl-4-(trifluoromethyl)-1H-pyrazol-1-yl]pyrimidin-4-amine

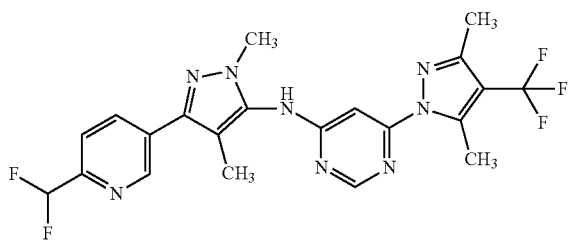 [SMILES: Cc1nn(-c2cc(Nc3c(C)c(-c4ccc(C(F)F)nc4)nn3C)ncn2)c(C)c1C(F)(F)F]

A microwave vial was charged with 3-[6-(difluoromethyl)pyridin-3-yl]-1,4-dimethyl-1H-pyrazol-5-amine (80.0 mg, 336 µmol) and 4-chloro-6-[3,5-dimethyl-4-(trifluoromethyl)-1H-pyrazol-1-yl]pyrimidine (102 mg, 369 µmol) and the contents were suspended in 1,4-dioxane (1.2 mL). The reaction mixture was degassed with Ar for 3 min. Tris(dibenzylideneacetone)dipalladium (9.22 mg, 10.1 µmol), XantPhos (11.7 mg, 20.1 µmol) and sodium phenolate (42.9 mg, 369 µmol) were added and the reaction mixture was degassed again for 1 min. The vial was sealed and heated at 85° C. overnight while vigorously shaking. After cooling to ambient temperature, the reaction mixture was diluted with ethyl acetate, filtered and concentrated. The residue was redissolved in dimethylsulfoxide and purified by preparative HPLC (method 4) to yield the desired product (64 mg, 37% yield).

LC-MS (method 11): $R_t$=1.47 min; MS (ESIpos): m/z=479 [M+H]$^+$ $^1$H-NMR (500 MHz, dimethylsulfoxide-d6) δ [ppm]: 1.567 (0.33), 1.915 (0.61), 2.088 (16.00), 2.315 (2.25), 2.744 (0.62), 2.747 (0.66), 2.762 (6.37), 3.718 (6.95), 3.758 (1.12), 6.894 (1.28), 7.004 (2.83), 7.064 (0.20), 7.115 (1.11), 7.346 (0.59), 7.378 (0.67), 7.457 (0.22), 7.463 (0.84), 7.466 (0.82), 7.471 (0.34), 7.478 (0.51), 7.767 (1.91), 7.783 (2.18), 7.793 (0.47), 7.796 (0.49), 7.807 (0.37), 7.812 (0.42), 7.818 (0.44), 8.255 (0.98), 8.259 (0.98), 8.272 (0.92), 8.275 (0.91), 8.551 (0.41), 8.563 (0.46), 9.003 (1.81), 9.687 (0.58).

Example 474

6-(4-chloro-3,5-dimethyl-1H-pyrazol-1-yl)-N-{3-[6-(difluoromethyl)pyridin-3-yl]-1,4-dimethyl-1H-pyrazol-5-yl}pyrimidin-4-amine

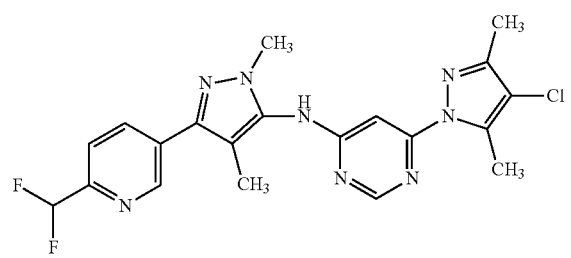 [SMILES: Cc1nn(-c2cc(Nc3c(C)c(-c4ccc(C(F)F)nc4)nn3C)ncn2)c(C)c1Cl]

A microwave vial was charged with 3-[6-(difluoromethyl)pyridin-3-yl]-1,4-dimethyl-1H-pyrazol-5-amine (80.0 mg, 336 µmol), 4-chloro-6-(4-chloro-3,5-dimethyl-1H-pyrazol-1-yl)pyrimidine (89.8 mg, 369 µmol) and the contents were suspended in 1,4-dioxane (1.2 mL). The reaction mixture was degassed with Ar for 3 min. Tris(dibenzylideneacetone)dipalladium (9.22 mg, 10.1 µmol), XantPhos (11.7 mg, 20.1 µmol) and sodium phenolate (42.9 mg, 369 µmol) were added and the reaction mixture was degassed again for 1 min. The vial was sealed and heated at 85° C. overnight while vigorously shaking. After cooling to ambient temperature, the reaction mixture was diluted with ethyl acetate, filtered through Celite and concentrated. The residue was redissolved in dimethylsulfoxide and purified by preparative HPLC (method 4) to yield the desired product (18.6 mg, 12% yield).

LC-MS (method 11): $R_t$=1.44 min; MS (ESIpos): m/z=445 [M+H]$^+$ $^1$H-NMR (500 MHz, dimethylsulfoxide-d6) δ [ppm]: −0.007 (0.49), 0.007 (0.30), 2.081 (16.00), 2.221 (2.13), 2.363 (0.19), 2.651 (15.28), 3.708 (7.33), 3.757 (0.15), 6.893 (1.14), 7.003 (2.51), 7.113 (0.99), 7.345 (0.23), 7.377 (0.27), 7.463 (0.30), 7.465 (0.30), 7.477 (0.19), 7.765 (1.67), 7.781 (1.82), 7.796 (0.19), 7.811 (0.19), 7.816 (0.19), 8.254 (0.84), 8.271 (0.80), 8.512 (0.53), 9.001 (1.56), 9.576 (0.68).

Example 475

N-{1-(cyclopropylmethyl)-3-[4-(difluoromethoxy)phenyl]-4-methyl-1H-pyrazol-5-yl}-6-[5-(difluoromethyl)-3-methyl-1H-pyrazol-1-yl]pyrimidin-4-amine

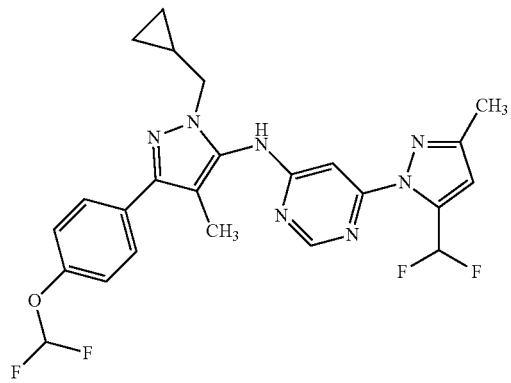 [SMILES: Cc1cc(C(F)F)n(-c2cc(Nc3c(C)c(-c4ccc(OC(F)F)cc4)nn3CC3CC3)ncn2)n1]

In a sealed microwave tube under argon, 1-(cyclopropylmethyl)-3-[4-(difluoromethoxy)phenyl]-4-methyl-1H-pyrazol-5-amine (60.0 mg, 205 µmol), 4-chloro-6-[5-(difluoromethyl)-3-methyl-1H-pyrazol-1-yl]pyrimidine (55.0 mg, 225 µmol), sodium phenolate (26.1 mg, 225 µmol), tris(dibenzylidenaceton)dipalladium (5.62 mg, 6.14 µmol), Xantphos (6.49 mg, 12.3 µmol) were dissolved in 1,4-dioxane (980 µl). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 7% to 60% ethylacetate in cyclohexane, column: Biotage SNAP Ultra 25 g) to yield 63.5 mg (100% purity, 62% yield) of the desired product.

LC-MS (Method 10): R$_t$=2.33 min; MS (ESIpos): m/z=502 [M+H]$^+$ $^1$H-NMR (500 MHz, dimethylsulfoxide-d6) δ [ppm]: 0.300 (2.78), 0.423 (3.08), 0.439 (3.10), 1.193 (1.40), 2.017 (16.00), 2.282 (1.58), 2.700 (0.55), 3.838 (2.05), 6.781 (2.11), 7.130 (2.76), 7.247 (4.44), 7.264 (4.66), 7.278 (5.92), 7.426 (2.64), 7.709 (1.87), 7.744 (1.97), 7.817 (3.69), 7.926 (1.52), 8.487 (0.37), 9.521 (0.26).

Example 476

N-{1-(cyclopropylmethyl)-3-[4-(difluoromethoxy)phenyl]-4-methyl-1H-pyrazol-5-yl}-6-(3,5-dimethyl-1H-pyrazol-1-yl)pyrimidin-4-amine

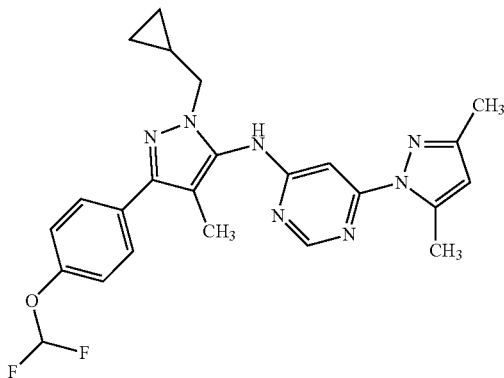 [SMILES: Cc1cc(C)n(-c2cc(Nc3c(C)c(-c4ccc(OC(F)F)cc4)nn3CC3CC3)ncn2)n1]

In a sealed microwave tube under argon, 1-(cyclopropylmethyl)-3-[4-(difluoromethoxy)phenyl]-4-methyl-1H-pyrazol-5-amine (60.0 mg, 205 μmol), 4-chloro-6-(3,5-dimethyl-1H-pyrazol-1-yl)pyrimidine (46.9 mg, 225 μmol), sodium phenolate (26.1 mg, 225 μmol), tris(dibenzylidenaceton)dipalladium (5.62 mg, 6.14 μmol), Xantphos (6.49 mg, 12.3 μmol) were dissolved in 1,4-dioxane (980 μl). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 7% to 60% ethylacetate in cyclohexane, column: Biotage SNAP Ultra 25 g) to yield 60.0 mg (100% purity, 63% yield) of the desired product.

LC-MS (Method 10): R$_t$=2.29 min; MS (ESIpos): m/z=466 [M+H]$^+$ $^1$H-NMR (500 MHz, dimethylsulfoxide-d6) δ [ppm]: 0.296 (2.41), 0.305 (2.48), 0.425 (2.54), 0.441 (2.60), 1.183 (0.71), 1.189 (0.71), 1.199 (1.11), 1.208 (0.65), 1.214 (0.66), 2.016 (16.00), 2.169 (2.29), 2.630 (15.40), 3.833 (2.08), 3.846 (2.02), 6.140 (2.47), 7.130 (2.15), 7.246 (4.35), 7.264 (4.54), 7.278 (4.53), 7.427 (2.04), 7.742 (2.52), 7.759 (2.35), 8.464 (0.55), 9.370 (0.53).

Example 477

1-[6-({1-(cyclopropylmethyl)-3-[4-(difluoromethoxy)phenyl]-4-methyl-1H-pyrazol-5-yl}amino)pyrimidin-4-yl]-3,5-dimethyl-1H-pyrazole-4-carbonitrile

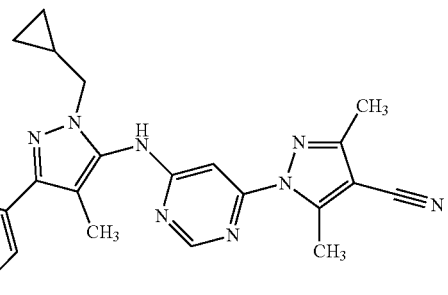

In a sealed microwave tube under argon, 1-(cyclopropylmethyl)-3-[4-(difluoromethoxy)phenyl]-4-methyl-1H-pyrazol-5-amine (60.0 mg, 205 μmol), 1-(6-chloropyrimidin-4-yl)-3,5-dimethyl-1H-pyrazole-4-carbonitrile (52.6 mg, 225 μmol), sodium phenolate (26.1 mg, 225 μmol), tris(dibenzylidenaceton)dipalladium (5.62 mg, 6.14 μmol), Xantphos (6.49 mg, 12.3 μmol) were dissolved in 1,4-dioxane (980 μl). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (gradient 7% to 60% ethylacetate in cyclohexane, column: Biotage SNAP Ultra 25 g) and then by preparative TLC (cyclohexane:ethylacetate 7:3) to yield 38.4 mg (100% purity, 38% yield) of the desired product.

LC-MS (Method 10): R$_t$=2.24 min; MS (ESIpos): m/z=491 [M+H]$^+$ $^1$H-NMR (500 MHz, dimethylsulfoxide-d6) δ [ppm]: −0.008 (10.09), 0.006 (6.62), 0.298 (2.05), 0.422 (2.31), 0.438 (2.33), 1.188 (1.01), 2.010 (15.46), 2.328 (1.18), 2.404 (1.08), 2.795 (16.00), 2.870 (0.99), 3.833 (1.56), 7.129 (2.26), 7.244 (3.72), 7.261 (3.86), 7.277 (4.88), 7.425 (2.12), 7.735 (1.77), 7.750 (1.67), 8.534 (0.26), 9.549 (0.19).

Example 478

N-{1-(cyclopropylmethyl)-3-[4-(difluoromethoxy)phenyl]-4-methyl-1H-pyrazol-5-yl}-6-[3,5-dimethyl-4-(trifluoromethyl)-1H-pyrazol-1-yl]pyrimidin-4-amine

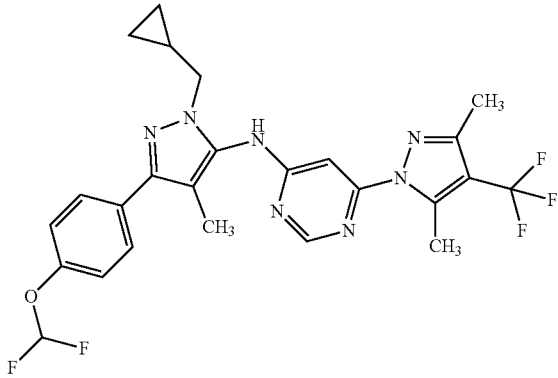 [SMILES: Cc1nn(-c2cc(Nc3c(C)c(-c4ccc(OC(F)F)cc4)nn3CC3CC3)ncn2)c(C)c1C(F)(F)F]

In a sealed microwave tube under argon, 1-(cyclopropylmethyl)-3-[4-(difluoromethoxy)phenyl]-4-methyl-1H-pyrazol-5-amine (60.0 mg, 205 μmol), 4-chloro-6-[3,5-dimethyl-4-(trifluoromethyl)-1H-pyrazol-1-yl]pyrimidine (62.2 mg, 225 μmol), sodium phenolate (26.1 mg, 225 μmol), tris(dibenzylidenaceton)dipalladium (5.62 mg, 6.14 μmol), Xantphos (6.49 mg, 12.3 μmol) were dissolved in 1,4-dioxane (980 μl). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 7% to 60% ethylacetate in cyclohexane, column: Biotage SNAP Ultra 25 g) and then by preparative HPLC (Method 19) to yield 49.3 mg (100% purity, 45% yield) of the desired product.

LC-MS (Method 10): $R_t$=2.52 min; MS (ESIpos): m/z=534 [M+H]$^+$ $^1$H-NMR (500 MHz, dimethylsulfoxide-d6) δ [ppm]: 0.296 (2.26), 0.305 (2.29), 0.429 (2.51), 0.445 (2.54), 1.172 (0.41), 1.181 (0.73), 1.188 (0.73), 1.197 (1.11), 1.207 (0.67), 1.211 (0.69), 2.016 (16.00), 2.303 (1.34), 2.760 (7.73), 3.838 (1.72), 3.851 (1.68), 7.130 (2.39), 7.245 (4.32), 7.263 (4.55), 7.278 (5.18), 7.426 (2.26), 7.737 (2.28), 7.753 (2.17).

Example 479

6-(4-chloro-3,5-dimethyl-1H-pyrazol-1-yl)-N-[5-(5-fluoropyridin-2-yl)-1,4-dimethyl-1H-pyrazol-3-yl]pyrimidin-4-amine

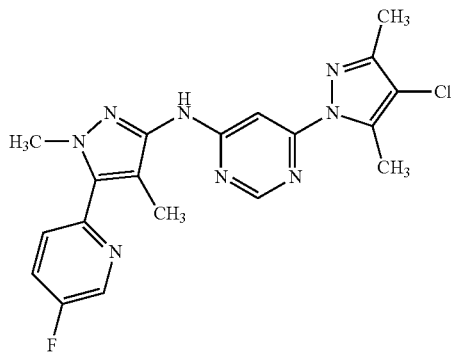 [SMILES: Cc1nn(-c2cc(Nc3nn(C)c(-c4ccc(F)cn4)c3C)ncn2)c(C)c1Cl]

A microwave vial was charged 4-chloro-6-(4-chloro-3,5-dimethyl-1H-pyrazol-1-yl)pyrimidine (108 mg, 444 μmol) and 5-(5-fluoropyridin-2-yl)-1,4-dimethyl-1H-pyrazol-3-amine (101 mg, 488 μmol) and the contents were suspended in 1,4-dioxane (1.7 ml, 20 mmol). The reaction mixture was degassed with Ar for 3 min. Tris(dibenzylidenaceton)dipalladium (12.2 mg, 13.3 μmol) and Xantphos (15.4 mg, 26.6 μmol) were added and the reaction mixture was degassed again for 1 min and heated to 85° C. At this temperature and sodium phenolate (56.6 mg, 488 μmol) was added. The vial was sealed and heated at 85° C. for 90 minutes while vigorously stirring. The mixture was left at ambient temperature overnight. The reaction mixture was diluted with water and extracted with dichloromethane (2×). The combined organic phases were dried over sodium sulfate and concentrated under reduced pressure. The crude product was purified by preparative HPLC (method: column: Reprosil C18; 10 μm; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75-23.00 min=90% B) to yield the desired product (54.7 mg, 30%).

LC-MS (method 10): $R_t$=2.17 min; MS (ESIpos): m/z=413 [M+H]$^+$ $^1$H-NMR (500 MHz, dimethylsulfoxide-d6) δ [ppm]: 1.956 (13.71), 2.219 (15.24), 2.640 (16.00), 3.571 (0.70), 3.853 (15.82), 7.307 (3.21), 7.709 (1.68), 7.717 (2.01), 7.725 (2.25), 7.734 (2.01), 7.905 (1.42), 7.917 (2.12), 7.922 (2.21), 7.934 (1.24), 8.482 (4.09), 8.778 (3.70), 9.510 (3.78).

Example 480

N-{1-(cyclopropylmethyl)-4-methyl-3-[4-(methylamino)phenyl]-1H-pyrazol-5-yl}-6-(3,5-dimethyl-1H-pyrazol-1-yl)pyrimidin-4-amine

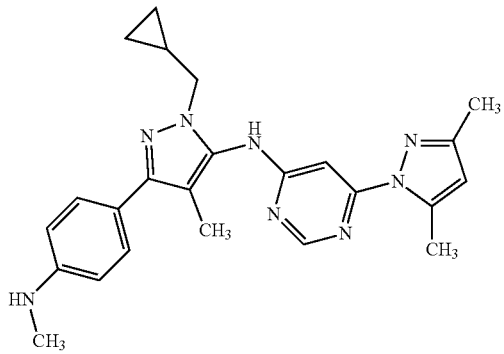 [SMILES: CNc1ccc(-c2nn(CC3CC3)c(Nc3cc(-n4nc(C)cc4C)ncn3)c2C)cc1]

In a sealed microwave tube under argon, 1-(cyclopropylmethyl)-4-methyl-3-[4-(methylamino)phenyl]-1H-pyrazol-5-amine (60.0 mg, 234 μmol), 4-chloro-6-(3,5-dimethyl-1H-pyrazol-1-yl)pyrimidine (53.7 mg, 257 μmol), sodium phenolate (29.9 mg, 257 μmol), tris(dibenzylidenaceton)dipalladium (6.43 mg, 7.02 μmol), Xantphos (7.42 mg, 14.0 μmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 10% to 80% ethylacetate in cyclohexane, column: Biotage SNAP Ultra 10 g) to yield 77.5 mg (100% purity, 77% yield) of the desired product.

LC-MS (Method 10): $R_t$=1.99 min; MS (ESIpos): m/z=429 [M+H]$^+$ $^1$H-NMR (500 MHz, dimethylsulfoxide-d6) δ [ppm]: 0.275 (2.31), 0.284 (2.34), 0.408 (2.55), 0.424 (2.62), 1.151 (0.42), 1.161 (0.77), 1.167 (0.77), 1.176 (1.19), 1.186 (0.73), 1.190 (0.70), 1.963 (15.55), 2.161 (2.20), 2.627 (16.00), 2.703 (11.56), 2.713 (11.35), 3.355 (0.45), 3.783 (2.06), 3.795 (1.99), 5.725 (1.12), 5.734 (1.08), 6.131 (2.34), 6.590 (5.24), 6.607 (5.24), 7.432 (2.41), 7.448 (2.24), 8.456 (0.49), 9.302 (0.52).

Example 481

6-[5-(difluoromethyl)-3-methyl-1H-pyrazol-1-yl]-N-{3-[6-(difluoromethyl)pyridin-3-yl]-1,4-dimethyl-1H-pyrazol-5-yl}pyrimidin-4-amine

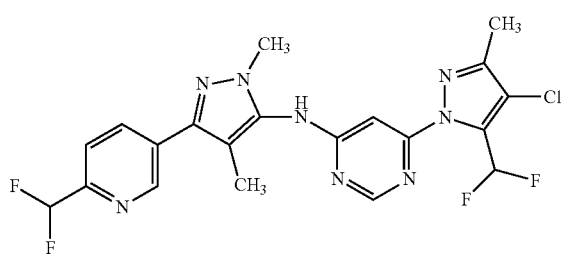 [SMILES: Cc1nn(-c2cc(Nc3c(C)c(-c4ccc(C(F)F)nc4)nn3C)ncn2)c(C(F)F)c1Cl]

A microwave vial was charged with 3-[6-(difluoromethyl) pyridin-3-yl]-1,4-dimethyl-1H-pyrazol-5-amine (80.0 mg, 336 µmol) and 4-chloro-6-[5-(difluoromethyl)-3-methyl-1H-pyrazol-1-yl]pyrimidine (90.4 mg, 369 µmol) and the contents were suspended in 1,4-dioxane (1.2 mL). The reaction mixture was degassed with Ar for 3 min. Tris(dibenzylideneacetone)dipalladium (9.22 mg, 10.1 µmol), XantPhos (11.7 mg, 20.1 µmol) and sodium phenolate (42.9 mg, 369 µmol) were added and the reaction mixture was degassed again for 1 min. The vial was sealed and heated at 85° C. overnight while vigorously shaking. After cooling to ambient temperature, the reaction mixture was filtered and concentrated. The residue was redissolved in dimethylsulfoxide and purified by preparative HPLC (method 4) to yield the desired product (55 mg, 35% yield).

LC-MS (method 11): $R_t$=1.34 min; MS (ESIpos): m/z=447 [M+H]$^+$ $^1$H-NMR (500 MHz, dimethylsulfoxide-d6) δ [ppm]: −0.007 (0.44), 1.908 (0.92), 2.086 (16.00), 2.300 (2.64), 2.336 (0.78), 3.715 (5.80), 3.768 (1.59), 6.776 (0.41), 6.794 (2.03), 6.895 (1.22), 7.005 (2.64), 7.115 (1.05), 7.712 (1.02), 7.767 (1.73), 7.784 (1.83), 7.821 (2.07), 7.930 (0.92), 8.261 (0.78), 8.278 (0.75), 8.490 (0.41), 8.511 (0.44), 9.007 (1.46), 9.656 (0.71).

Example 482

6-(4-chloro-3,5-dimethyl-1H-pyrazol-1-yl)-N-[1-(cyclopropylmethyl)-3-(4-methoxyphenyl)-4-methyl-1H-pyrazol-5-yl]pyrimidin-4-amine

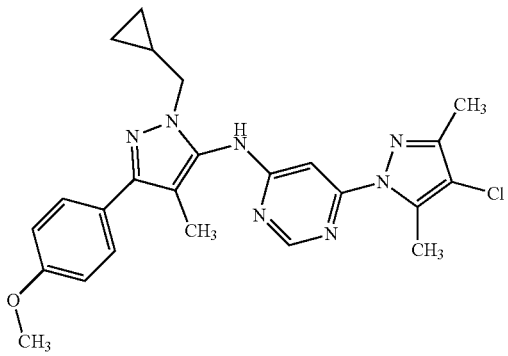 [SMILES: COc1ccc(-c2nn(CC3CC3)c(Nc3cc(-n4nc(C)c(Cl)c4C)ncn3)c2C)cc1]

In a sealed microwave tube under argon, 1-(cyclopropylmethyl)-3-(4-methoxyphenyl)-4-methyl-1H-pyrazol-5-amine (60.0 mg, 233 µmol), 4-chloro-6-(4-chloro-3,5-dimethyl-1H-pyrazol-1-yl)pyrimidine (68.0 mg, 280 µmol), sodium phenolate (29.8 mg, 256 µmol), tris(dibenzylidenaceton)dipalladium (6.41 mg, 6.99 µmol), Xantphos (7.40 mg, 14.0 µmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 7% to 60% ethylacetate in cyclohexane, column: Biotage SNAP Ultra 10 g) to yield 61.3 mg (100% purity, 57% yield) of the desired product.

LC-MS (Method 10): $R_t$=2.48 min; MS (ESIpos): m/z=464 [M+H]$^+$ $^1$H-NMR (500 MHz, dimethylsulfoxide-d6) δ [ppm]: 0.291 (1.20), 0.415 (1.29), 0.431 (1.31), 1.184 (0.58), 1.987 (8.04), 2.202 (0.91), 2.644 (10.66), 3.794 (16.00), 3.810 (1.06), 3.823 (1.00), 6.999 (2.41), 7.017 (2.50), 7.613 (1.12), 7.629 (1.07), 8.498 (0.19), 9.435 (0.15).

Example 483

1-(6-{[1-(cyclopropylmethyl)-3-(4-methoxyphenyl)-4-methyl-1H-pyrazol-5-yl]amino}pyrimidin-4-yl)-3,5-dimethyl-1H-pyrazole-4-carbonitrile

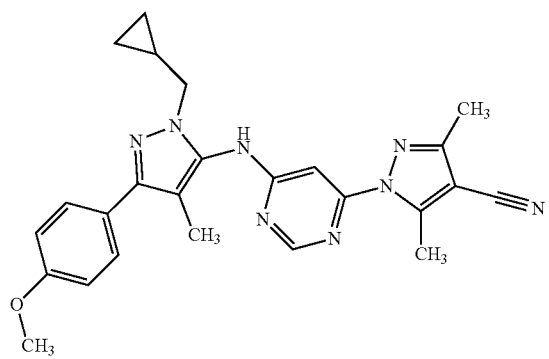 [SMILES: COc1ccc(-c2nn(CC3CC3)c(Nc3cc(-n4nc(C)c(C#N)c4C)ncn3)c2C)cc1]

In a sealed microwave tube under argon, 1-(cyclopropylmethyl)-3-(4-methoxyphenyl)-4-methyl-1H-pyrazol-5-amine (60.0 mg, 233 μmol), 1-(6-chloropyrimidin-4-yl)-3,5-dimethyl-1H-pyrazole-4-carbonitrile (65.4 mg, 280 μmol), sodium phenolate (29.8 mg, 256 μmol), tris(dibenzylideneaceton)dipalladium (6.41 mg, 6.99 μmol), Xantphos (7.40 mg, 14.0 μmol) were dissolved in 1,4-dioxane (1.1 ml). The reaction mixture was heated at 90° C. for 60 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 7% to 60% ethylacetate in cyclohexane, column: Biotage SNAP Ultra 10 g) and then by preparative TLC (cyclohexane:ethylacetate 6:4) to yield 50.0 mg (100% purity, 47% yield) of the desired product.

LC-MS (Method 10): R$_t$=2.14 min; MS (ESIpos): m/z=455 [M+H]$^+$ $^1$H-NMR (500 MHz, dimethylsulfoxide-d6) δ [ppm]: 0.288 (0.98), 0.415 (1.11), 0.431 (1.12), 1.180 (0.49), 1.986 (7.44), 2.324 (0.52), 2.402 (0.38), 2.792 (8.06), 2.868 (0.33), 3.793 (16.00), 3.811 (0.77), 6.501 (0.04), 6.999 (2.03), 7.016 (2.09), 7.292 (0.06), 7.611 (0.83), 7.626 (0.80), 8.539 (0.11), 9.524 (0.08), 9.630 (0.06).

Example 484

6-(4-amino-3,5-dimethyl-1H-pyrazol-1-yl)-N-[1-(cyclopropylmethyl)-3-(4-fluorophenyl)-4-methyl-1H-pyrazol-5-yl]pyrimidin-4-amine trifluoroacetate

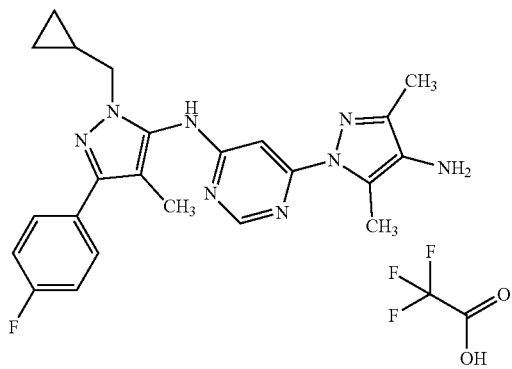

tert-butyl [6-(4-amino-3,5-dimethyl-1H-pyrazol-1-yl)pyrimidin-4-yl][1-(cyclopropylmethyl)-3-(4-fluorophenyl)-4-methyl-1H-pyrazol-5-yl]carbamate (24.0 mg, 45.1 μmol) was dissolved in dichloromethane (800 μL) and trifluoroacetic acid (800 μL) was added. The reaction mixture was stirred at ambient temperature for 15 min. The reaction mixture was concentrated and the residue redissolved in dichloromethane and concentrated (3 cycles). The residue was then redissolved in acetonitrile/water and lyophilized to yield the desired product as the TFA salt (25 mg, 93% yield).

LC-MS (method 11): R$_t$=1.16 min; MS (ESIpos): m/z=433 [M+H]$^+$ $^1$H-NMR (600 MHz, dimethylsulfoxide-d6) δ [ppm]: 0.295 (2.65), 0.424 (3.05), 0.437 (3.05), 0.854 (0.18), 1.191 (1.53), 1.235 (0.95), 1.649 (0.25), 2.005 (15.34), 2.241 (1.48), 2.388 (0.66), 2.616 (0.84), 2.661 (16.00), 2.709 (0.50), 2.868 (0.34), 3.828 (2.63), 7.018 (0.48), 7.103 (0.50), 7.188 (0.55), 7.268 (2.40), 7.282 (4.35), 7.297 (2.44), 7.730 (2.11), 8.500 (0.34), 9.463 (0.38).

Example 485

N-{3-[6-(difluoromethyl)pyridin-3-yl]-1,4-dimethyl-1H-pyrazol-5-yl}-6-(4-fluoro-3,5-dimethyl-1H-pyrazol-1-yl)pyrimidin-4-amine

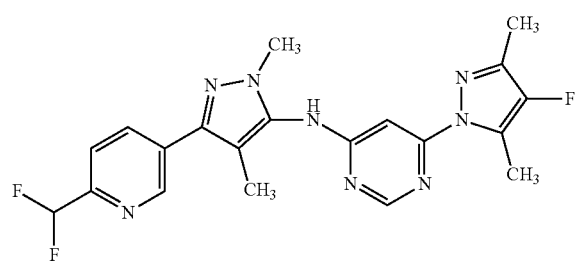 [SMILES: Cc1nn(-c2cc(Nc3c(C)c(-c4ccc(C(F)F)nc4)nn3C)ncn2)c(C)c1F]

A microwave vial was charged with 3-[6-(difluoromethyl)pyridin-3-yl]-1,4-dimethyl-1H-pyrazol-5-amine (80.0 mg, 336 μmol) and 4-chloro-6-(4-fluoro-3,5-dimethyl-1H-pyrazol-1-yl)pyrimidine (83.7 mg, 369 μmol), and the contents were suspended in 1,4-dioxane (1.2 mL). The reaction mixture was degassed with Ar for 3 min. Tris(dibenzylideneacetone)dipalladium (9.22 mg, 10.1 μmol), XantPhos (11.7 mg, 20.1 μmol) and sodium phenolate (42.9 mg, 369 μmol) were added and the reaction mixture was degassed again for 1 min. The vial was sealed and heated at 85° C. overnight while vigorously shaking. After cooling to ambient temperature, the reaction mixture was diluted with ethyl acetate, filtered over Celite and concentrated. The residue was redissolved in dimethylsulfoxide and purified by preparative HPLC (method 4) to yield the desired product (33 mg, 23% yield).

LC-MS (method 11): Rt=1.37 min; MS (ESIneg): m/z=427 [M−H]$^-$ $^1$H NMR (500 MHz, dimethylsulfoxide-d6) δ ppm: 2.05-2.12 (s, 3H), 2.15-2.28 (br s, 3H), 2.60 (d, J=1.66 Hz, 3H), 3.66-3.81 (s, 3H), 6.99 (t, J=55.1 Hz, 1H), 7.01-7.53 (br s, 1H), 7.70-7.85 (m, 1H), 8.18-8.29 (m, 1H), 8.37-8.62 (m, 1H), 9.00 (s, 1H), 9.54 (br s, 1H).

Example 486

N-[1-(cyclopropylmethyl)-3-(4-methoxyphenyl)-4-methyl-1H-pyrazol-5-yl]-6-[3,5-dimethyl-4-(trifluoromethyl)-1H-pyrazol-1-yl]pyrimidin-4-amine

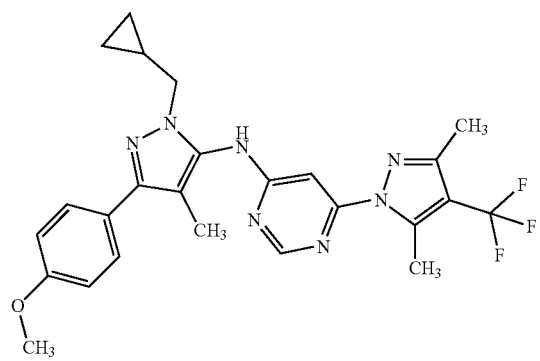 [SMILES: COc1ccc(-c2nn(CC3CC3)c(Nc3cc(-n4nc(C)c(C(F)(F)F)c4C)ncn3)c2C)cc1]

In a sealed microwave tube under argon, 1-(cyclopropylmethyl)-3-(4-methoxyphenyl)-4-methyl-1H-pyrazol-5-amine (60.0 mg, 233 µmol), 4-chloro-6-[3,5-dimethyl-4-(trifluoromethyl)-1H-pyrazol-1-yl]pyrimidine (77.4 mg, 280 µmol), sodium phenolate (29.8 mg, 256 µmol), tris(dibenzylidenaceton)dipalladium (6.41 mg, 6.99 µmol), Xantphos (7.40 mg, 14.0 µmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (gradient 7% to 60% ethylacetate in cyclohexane, column: Biotage SNAP Ultra 10 g) to yield 73.6 mg (100% purity, 63% yield) of the desired product.

LC-MS (Method 9): $R_t$=1.29 min; MS (ESIpos): m/z=498 [M+H]$^+$ $^1$H-NMR (500 MHz, dimethylsulfoxide-d6) δ [ppm]: 0.294 (1.10), 0.420 (1.21), 0.436 (1.23), 1.187 (0.55), 1.991 (7.54), 2.296 (0.62), 2.756 (3.92), 3.793 (16.00), 3.816 (0.87), 6.471 (0.02), 6.999 (2.40), 7.016 (2.50), 7.305 (0.06), 7.610 (1.08), 7.626 (1.02), 8.537 (0.13), 9.517 (0.09).

Example 487

N-{1-(cyclopropylmethyl)-4-methyl-3-[4-(methylamino)phenyl]-1H-pyrazol-5-yl}-6-[5-(difluoromethyl)-3-methyl-1H-pyrazol-1-yl]pyrimidin-4-amine

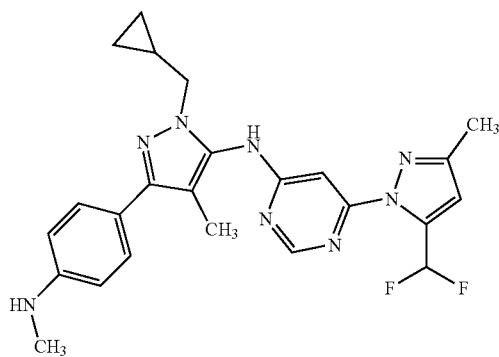 [SMILES: CNc1ccc(-c2nn(CC3CC3)c(Nc3cc(-n4nc(C)cc4C(F)F)ncn3)c2C)cc1]

In a sealed microwave tube under argon, 1-(cyclopropylmethyl)-4-methyl-3-[4-(methylamino)phenyl]-1H-pyrazol-5-amine (60.0 mg, 234 µmol), 4-chloro-6-[5-(difluoromethyl)-3-methyl-1H-pyrazol-1-yl]pyrimidine (63.0 mg, 257 µmol), sodium phenolate (29.9 mg, 257 µmol), tris(dibenzylidenaceton)dipalladium (6.43 mg, 7.02 µmol), Xantphos (7.42 mg, 14.0 µmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 8% to 60% ethyl-acetate in cyclohexane, column: Biotage SNAP Ultra 10 g) and then by preparative TLC (dichloromethane:ethylacetate 7:3). The resultant residue was dissolved in dichloromethane and washed with a saturated aqueous solution of sodium bicarbonate. The aqueous phase was extracted with dichloromethane and the combined organic phase s dried with sodium sulfate and concentrated in vacuo to yield 63.2 mg (97% purity, 56% yield) of the desired product.

LC-MS (Method 10): $R_t$=2.07 min; MS (ESIpos): m/z=465 [M+H]$^+$ $^1$H-NMR (500 MHz, dimethylsulfoxide-d6) δ [ppm]: 0.278 (2.61), 0.405 (3.07), 0.421 (3.08), 1.171 (1.65), 1.232 (0.47), 1.408 (0.61), 1.421 (0.32), 1.965 (15.86), 2.269 (1.43), 2.701 (16.00), 2.711 (15.62), 3.792 (2.14), 3.837 (0.62), 5.736 (1.13), 6.464 (0.13), 6.589 (5.54), 6.606 (5.50), 6.771 (1.89), 7.288 (0.18), 7.437 (1.99), 7.708 (1.85), 7.817 (4.02), 7.925 (1.65), 8.472 (0.30), 9.432 (0.23), 9.544 (0.23).

Example 488

N-{1-(cyclopropylmethyl)-4-methyl-3-[4-(methylamino)phenyl]-1H-pyrazol-5-yl}-6-[3,5-dimethyl-4-(trifluoromethyl)-1H-pyrazol-1-yl]pyrimidin-4-amine

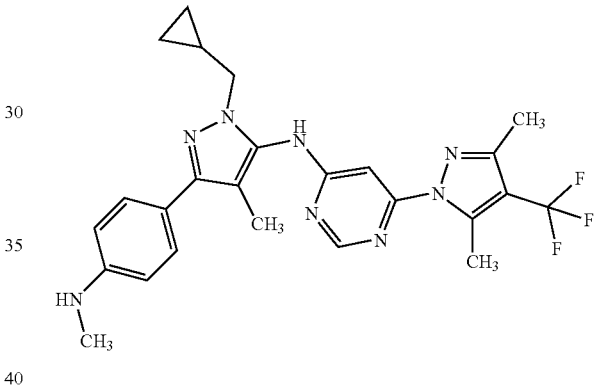

In a sealed microwave tube under argon, 1-(cyclopropylmethyl)-4-methyl-3-[4-(methylamino)phenyl]-1H-pyrazol-5-amine (60.0 mg, 234 µmol), 4-chloro-6-[3,5-dimethyl-4-(trifluoromethyl)-1H-pyrazol-1-yl]pyrimidine (71.2 mg, 257 µmol), sodium phenolate (29.9 mg, 257 µmol), tris(dibenzylidenaceton)dipalladium (6.43 mg, 7.02 µmol), Xantphos (7.42 mg, 14.0 µmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 8% to 60% ethyl-acetate in cyclohexane, column: Biotage SNAP Ultra 10 g) and then by preparative HPLC (Method 19) to yield 63.0 mg (96% purity, 52% yield) of the desired product.

LC-MS (Method 9): $R_t$=1.18 min; MS (ESIpos): m/z=497 [M+H]$^+$ $^1$H-NMR (500 MHz, dimethylsulfoxide-d6) δ [ppm]: 0.273 (2.73), 0.411 (3.10), 0.426 (3.03), 1.033 (0.62), 1.174 (1.72), 1.233 (0.96), 1.962 (16.00), 2.288 (1.55), 2.699 (12.12), 2.709 (11.76), 2.754 (10.12), 3.788 (2.24), 5.732 (1.24), 6.474 (0.13), 6.585 (5.65), 6.602 (5.62), 7.279 (0.18), 7.424 (2.72), 7.440 (2.46), 8.531 (0.34), 9.502 (0.27).

Example 489

N-[1-(cyclopropylmethyl)-3-(4-methoxyphenyl)-4-methyl-1H-pyrazol-5-yl]-6-[5-(difluoromethyl)-3-methyl-1H-pyrazol-1-yl]pyrimidin-4-amine

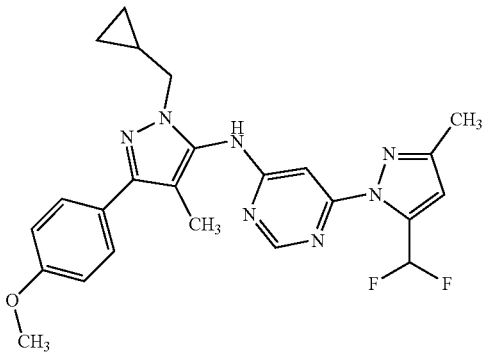 [SMILES: COc1ccc(-c2nn(CC3CC3)c(Nc3cc(-n4nc(C)cc4C(F)F)ncn3)c2C)cc1]

In a sealed microwave tube under argon, 1-(cyclopropylmethyl)-3-(4-methoxyphenyl)-4-methyl-1H-pyrazol-5-amine (60.0 mg, 233 µmol), 4-chloro-6-[5-(difluoromethyl)-3-methyl-1H-pyrazol-1-yl]pyrimidine (68.4 mg, 280 µmol), sodium phenolate (29.8 mg, 256 µmol), tris(dibenzylidenaceton)dipalladium (6.41 mg, 6.99 µmol), Xantphos (7.40 mg, 14.0 µmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 7% to 60% ethylacetate in cyclohexane, column: Biotage SNAP Ultra 10 g) and then by preparative HPLC (Method 19) to yield 65.0 mg (97% purity, 58% yield) of the desired product.

LC-MS (Method 10): $R_t$=2.24 min; MS (ESIpos): m/z=466 [M+H]$^+$ $^1$H-NMR (500 MHz, dimethylsulfoxide-d6) δ [ppm]: 0.291 (1.08), 0.416 (1.22), 0.432 (1.23), 1.169 (0.39), 1.185 (0.57), 1.993 (6.20), 2.281 (0.60), 2.699 (0.24), 3.795 (16.00), 3.818 (0.85), 6.777 (0.80), 7.002 (1.91), 7.020 (1.96), 7.621 (0.76), 7.708 (0.72), 7.817 (1.50), 7.926 (0.63), 8.489 (0.13), 9.492 (0.09).

Example 490

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]propan-2-one

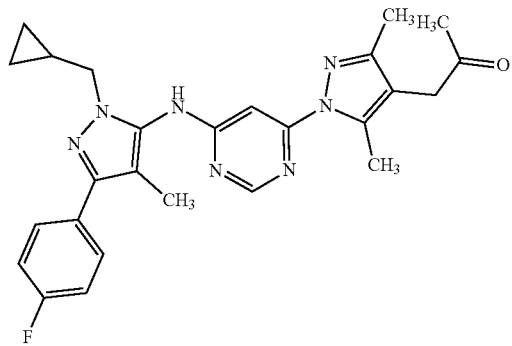 [SMILES: CC(=O)Cc1c(C)nn(-c2cc(Nc3c(C)c(-c4ccc(F)cc4)nn3CC3CC3)ncn2)c1C]

A solution ethyl [1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]acetate (570 mg, 1.13 mmol) in tetrahydrofuran (12 ml, 140 mmol) was treated with chloro(methyl)magnesium (1.3 ml, 3.0 M, 4.0 mmol) at 0° C. and stirred for 2 hours at ambient temperature. The mixture was diluted with potassium sodium tartrate and water, and extracted with ethyl acetate (3×). The combined organic phases were washed with water, dried over sodium sulfate and concentrated under reduced pressure. The crude product was purified by flash-chromatography on silica gel (column: Biotage SNAP Ultra 25 g, solvent: dichloromethane/methanol 20:1) and subsequently by preparative HPLC (column: 250×20 mm YMC Chiralart Cellulose SC, 5 µM, flow: 15 mL/min, solvent: n-heptane 30%/ethanol 70%) to yield 22.0 mg (4%) of the described product along with 1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-2-methylpropan-2-ol.

LC-MS (method 10): $R_t$=2.06 min; MS (ESIpos): m/z=474 [M+H]$^+$ $^1$H-NMR (500 MHz, dimethylsulfoxide-d6) δ [ppm]: −0.007 (1.30), 0.007 (0.93), 0.294 (2.45), 0.303 (2.54), 0.424 (2.59), 0.440 (2.68), 1.086 (0.83), 1.119 (0.77), 1.133 (1.41), 1.147 (0.72), 1.171 (0.43), 1.180 (0.74), 1.186 (0.75), 1.195 (1.11), 1.205 (0.69), 1.210 (0.69), 2.008 (16.00), 2.068 (2.10), 2.142 (13.82), 2.576 (0.81), 2.650 (0.58), 2.858 (0.42), 3.589 (4.74), 3.830 (2.03), 3.843 (1.97), 7.255 (2.48), 7.273 (4.88), 7.291 (2.54), 7.719 (1.47), 7.730 (1.96), 7.746 (1.30), 8.460 (0.55), 9.358 (0.43).

Example 491

N-[1-(cyclopropylmethyl)-3-(4-methoxyphenyl)-4-methyl-1H-pyrazol-5-yl]-6-(3,5-dimethyl-1H-pyrazol-1-yl)pyrimidin-4-amine

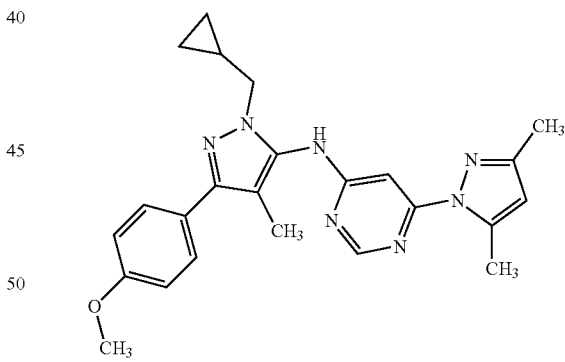

In a sealed microwave tube under argon, 1-(cyclopropylmethyl)-3-(4-methoxyphenyl)-4-methyl-1H-pyrazol-5-amine (60.0 mg, 233 µmol), 4-chloro-6-(3,5-dimethyl-1H-pyrazol-1-yl)pyrimidine (58.4 mg, 280 µmol), sodium phenolate (29.8 mg, 256 µmol), tris(dibenzylidenaceton)dipalladium (6.41 mg, 6.99 µmol), Xantphos (7.40 mg, 14.0 µmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 7% to 60% ethylacetate in cyclohexane, column: Biotage SNAP Ultra 10 g) and then by preparative HPLC (Method 19) to yield 78.0 mg (100% purity, 78% yield) of the desired product.

LC-MS (Method 10): $R_t$=2.18 min; MS (ESIpos): m/z=430 [M+H]$^+$ $^1$H-NMR (500 MHz, dimethylsulfoxide-d6) δ [ppm]: 0.285 (1.11), 0.295 (1.13), 0.416 (1.20), 0.432 (1.22), 1.163 (0.19), 1.173 (0.38), 1.179 (0.35), 1.188 (0.55), 1.198 (0.31), 1.203 (0.31), 1.213 (0.16), 1.990 (8.05), 2.163 (1.03), 2.626 (7.44), 3.647 (0.07), 3.794 (16.00), 3.810 (1.00), 3.823 (0.94), 3.936 (0.08), 6.134 (1.12), 7.000 (2.45), 7.017 (2.52), 7.615 (1.15), 7.632 (1.07), 8.458 (0.24), 9.336 (0.23).

Example 492 ethyl [1-(6-{[5-(4-cyanophenyl)-4-methoxy-1-methyl-1H-pyrazol-3-yl]amino}pyrimidin-4-yl)-3,5-dimethyl-1H-pyrazol-4-yl]acetate

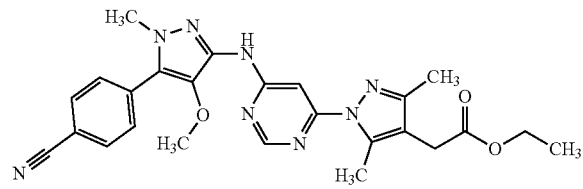 [SMILES: CCOC(=O)Cc1c(C)nn(-c2cc(Nc3nn(C)c(-c4ccc(C#N)cc4)c3OC)ncn2)c1C]

A microwave vial was charged ethyl [1-(6-chloropyrimidin-4-yl)-3,5-dimethyl-1H-pyrazol-4-yl]acetate (252 mg, 856 µmol) and 4-(3-amino-4-methoxy-1-methyl-1H-pyrazol-5-yl)benzonitrile (215 mg, 942 µmol) and the contents were suspended in 1,4-dioxane (13 ml, 150 mmol). The reaction mixture was degassed with Ar for 3 min. Tris(dibenzylideneaceton)dipalladium (23.5 mg, 25.7 µmol) and Xantphos (29.7 mg, 51.4 µmol) were added and the reaction mixture was degassed again for 1 min and heated to 85° C. At this temperature and sodium phenolate (109 mg, 942 µmol) was added. The vial was sealed and heated at 85° C. for 120 minutes while vigorously stirring. After cooling to ambient temperature, the reaction mixture was filtered and preparative HPLC (method: column: Reprosil C18; 10 µm; 125×40 mm/flow: 75 ml/min/eluent: A=water (0.1% formic acid), B=acetonitrile/gradient: 0.00-5.50 min=10% B, 17.65-19.48 min=95% B, 19.66 min=10% B) and further flash-chromatography (column; SNAP Ultra 25 g, solvent: dichloromethane/ethyl acetate 1:1) to yield the desired product (190 mg, 46%).

LC-MS (method 9): $R_t$=0.99 min; MS (ESIpos): m/z=487 [M+H]$^+$ $^1$H-NMR (600 MHz, dimethylsulfoxide-d6) δ [ppm]: 1.175 (4.47), 1.187 (9.06), 1.199 (4.30), 1.992 (0.43), 2.140 (10.65), 2.572 (12.28), 3.482 (6.07), 3.566 (16.00), 3.791 (13.16), 4.060 (1.23), 4.072 (3.80), 4.084 (3.81), 4.095 (1.21), 7.198 (3.47), 7.199 (3.37), 7.780 (3.43), 7.783 (1.20), 7.791 (1.30), 7.794 (3.75), 8.011 (3.91), 8.014 (1.23), 8.022 (1.23), 8.025 (3.35), 8.463 (2.38), 9.470 (0.82).

Example 493

4-(4-methoxy-3-{[6-(4-methoxy-3,5-dimethyl-1H-pyrazol-1-yl)pyrimidin-4-yl]amino}-1-methyl-1H-pyrazol-5-yl)benzonitrile

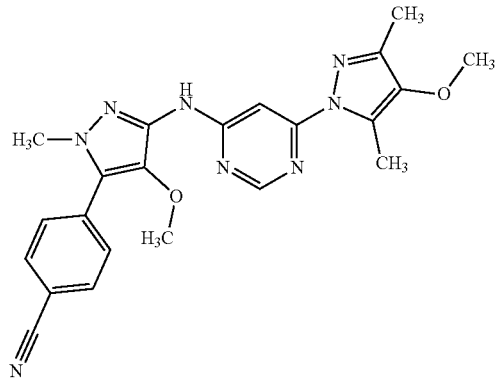 [SMILES: COc1c(Nc2cc(-n3nc(C)c(OC)c3C)ncn2)nn(C)c1-c1ccc(C#N)cc1]

A microwave vial was charged 4-chloro-6-(4-methoxy-3,5-dimethyl-1H-pyrazol-1-yl)pyrimidine (143 mg, 597 µmol) and 4-(3-amino-4-methoxy-1-methyl-1H-pyrazol-5-yl)benzonitrile (150 mg, 657 µmol) and the contents were suspended in 1,4-dioxane (2.2 ml, 25 mmol). The reaction mixture was degassed with Ar for 3 min. Tris(dibenzylideneaceton)dipalladium (16.4 mg, 17.9 µmol) and Xantphos (20.7 mg, 35.8 µmol) were added and the reaction mixture was degassed again for 1 min and heated to 85° C. At this temperature and sodium phenolate (76.3 mg, 657 µmol) was added. The vial was sealed and heated at 85° C. for 90 minutes while vigorously stirring. The mixture was left overnight at ambient temperature. The reaction mixture was filtered and purified by preparative HPLC (method: column: Reprosil C18; 10 m; 125×30 mm/flow: 50 ml/min/eluent: A=water (0.01% formic acid), B=acetonitrile/gradient: 0.00-5.00 min=10% B, 6.50 min=20% B, 17.0-19.75 min=100% B, 19.75-23.00 min=90% B) and further flash-chromatography (column: KP-Sil 10 g, solvent: dichloromethane/ethylacetate 1:1 to yield the desired product (47 mg, 18%).

LC-MS (method 10): $R_t$=1.83 min; MS (ESIpos): m/z=431 [M+H]$^+$ $^1$H-NMR (600 MHz, dimethylsulfoxide-d6) δ [ppm]: 0.005 (0.73), 2.187 (10.69), 3.560 (14.60), 3.699 (16.00), 3.788 (12.42), 7.175 (3.54), 7.778 (3.30), 7.792 (3.62), 8.012 (3.73), 8.025 (3.21), 8.439 (2.52), 9.443 (0.97).

Example 494

6-[3,5-dimethyl-4-(trifluoromethyl)-1H-pyrazol-1-yl]-N-[3-(6-methoxypyridin-3-yl)-1,4-dimethyl-1H-pyrazol-5-yl]pyrimidin-4-amine

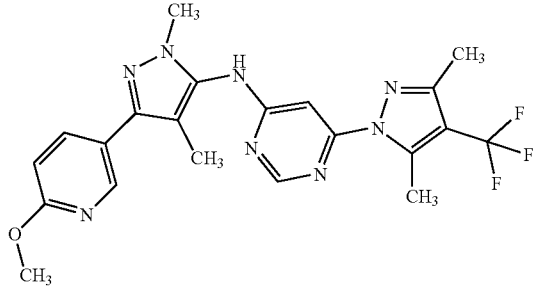 [SMILES: COc1ccc(-c2nn(C)c(Nc3cc(-n4nc(C)c(C(F)(F)F)c4C)ncn3)c2C)cn1]

In a sealed microwave tube under argon, 3-(6-methoxypyridin-3-yl)-1,4-dimethyl-1H-pyrazol-5-amine (50.0 mg, 229 µmol), 4-chloro-6-[3,5-dimethyl-4-(trifluoromethyl)-1H-pyrazol-1-yl]pyrimidine (76.1 mg, 275 µmol), sodium phenolate (29.3 mg, 252 µmol), tris(dibenzylidenaceton) dipalladium (6.29 mg, 6.87 µmol), Xantphos (7.27 mg, 13.7 µmol) were dissolved in 1,4-dioxane (1.1 ml). The reaction mixture was heated at 90° C. for 60 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (gradient 12% to 100% ethylacetate in cyclohexane, column: Biotage SNAP Ultra 10 g) and then by preparative TLC (cyclohexane:ethylacetate 1:1) to yield 30.0 mg (100% purity, 29% yield) of the desired product.

LC-MS (Method 9): $R_t$=1.13 min; MS (ESIpos): m/z=459 [M+H]$^+$ $^1$H-NMR (500 MHz, dimethylsulfoxide-d6) δ [ppm]: 2.010 (10.85), 2.071 (2.91), 2.308 (1.10), 2.756 (3.97), 3.163 (0.42), 3.173 (0.45), 3.664 (3.97), 3.891 (16.00), 3.926 (0.14), 6.890 (1.36), 6.907 (1.39), 7.977 (0.56), 7.981 (0.61), 7.994 (0.56), 7.999 (0.56), 8.435 (1.03), 8.439 (1.03), 8.553 (0.26), 9.626 (0.28).

Example 495

Cyclopropyl {1-[6-({1-(cyclopropylmethyl)-3-[4-(difluoromethyl)phenyl]-4-methyl-1H-pyrazol-5-yl}amino)pyrimidin-4-yl]-3,5-dimethyl-1H-pyrazol-4-yl}methanol

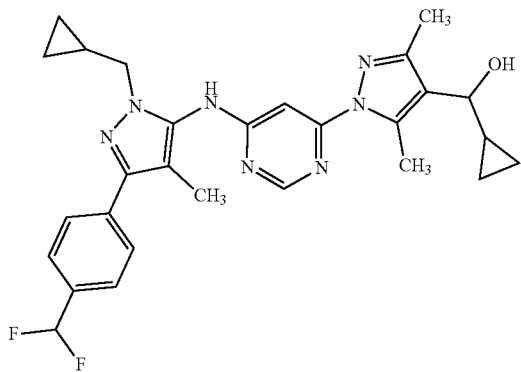 [SMILES: Cc1nn(-c2cc(Nc3c(C)c(-c4ccc(C(F)F)cc4)nn3CC3CC3)ncn2)c(C)c1C(O)C1CC1]

A sample of racemic cyclopropyl {1-[6-({1-(cyclopropylmethyl)-3-[4-(difluoromethyl)phenyl]-4-methyl-1H-pyrazol-5-yl}amino)pyrimidin-4-yl]-3,5-dimethyl-1H-pyrazol-4-yl}methanol (139.2 mg, 270 µMol) was separated using chiral SFC (column: AD-H 5µ250×20 mm, temperature: 40° C., flow: 80 mL/min, wavelength: 210 nM, solvent: 87% carbon dioxide/13% ethanol) to yield 35.80 mg of the second eluting enantiomer which was further purified by preparative HPLC (method 6) to yield 25.3 mg of the desired product (18% from racemate).

LC-MS (method 10): $R_t$=2.02 min; MS (ESIpos): m/z=520 [M+H]$^+$

Chiral SFC (Daicel AD, isocratic carbon dioxide/ethanol 80/20): Rt=2.82 min, 96.8% ee $^1$H-NMR (500 MHz, dimethylsulfoxide-d6) δ [ppm]: −0.007 (2.26), 0.006 (1.45), 0.116 (0.66), 0.123 (0.68), 0.133 (0.75), 0.141 (0.56), 0.304 (1.99), 0.314 (2.18), 0.332 (0.71), 0.342 (0.77), 0.350 (1.00), 0.364 (1.14), 0.370 (0.95), 0.380 (0.77), 0.389 (0.53), 0.432 (2.06), 0.449 (2.09), 0.485 (0.49), 0.496 (0.75), 0.502 (0.70), 0.512 (0.61), 1.077 (0.54), 1.091 (1.07), 1.105 (0.53), 1.185 (0.92), 1.194 (1.09), 1.200 (1.16), 1.210 (1.24), 1.224 (0.65), 2.047 (13.70), 2.252 (1.62), 2.628 (16.00), 3.325 (0.60), 3.377 (0.54), 3.390 (0.53), 3.854 (1.62), 3.868 (1.53), 3.960 (0.75), 3.969 (0.73), 4.962 (1.58), 4.968 (1.53), 6.964 (1.23), 7.076 (2.67), 7.188 (1.09), 7.637 (2.52), 7.654 (2.89), 7.846 (2.11), 7.862 (1.79), 8.458 (0.46), 9.374 (0.44).

Example 496

Cyclopropyl {1-[6-({1-(cyclopropylmethyl)-3-[4-(difluoromethyl)phenyl]-4-methyl-1H-pyrazol-5-yl}amino)pyrimidin-4-yl]-3,5-dimethyl-1H-pyrazol-4-yl}methanol

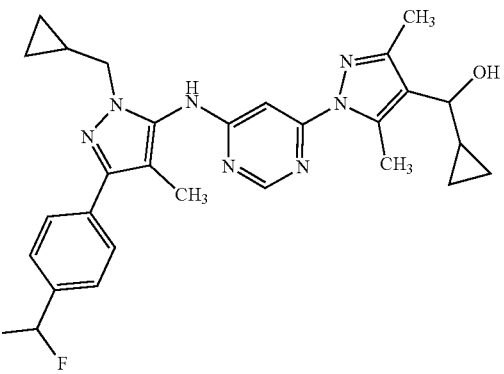

A sample of racemic cyclopropyl {1-[6-({1-(cyclopropylmethyl)-3-[4-(difluoromethyl)phenyl]-4-methyl-1H-pyrazol-5-yl}amino)pyrimidin-4-yl]-3,5-dimethyl-1H-pyrazol-4-yl}methanol (139.2 mg, 270 Mol) was separated using chiral SFC (column: AD-H 5 250×20 mm, temperature: 40° C., flow: 80 mL/min, wavelength: 210 nM, solvent: 87% carbon dioxide/13% ethanol) to yield 35.80 mg of the first eluting enantiomer which was further purified by preparative HPLC (method 6) to yield 19.2 mg of the desired product (14% from racemate).

LC-MS (method 10): $R_t$=2.02 min; MS (ESIpos): m/z=520 [M+H]$^+$

Chiral SFC (Daicel AD, isocratic carbon dioxide/ethanol 80/20): Rt=2.48 min, >99.5% ee $^1$H-NMR (500 MHz, dimethylsulfoxide-d6) δ [ppm]: −0.007 (2.01), 0.006 (1.31), 0.116 (0.64), 0.123 (0.65), 0.133 (0.76), 0.141 (0.55), 0.304 (1.96), 0.314 (2.17), 0.332 (0.71), 0.342 (0.76), 0.350 (1.01), 0.364 (1.16), 0.370 (0.96), 0.380 (0.76), 0.389 (0.52), 0.433 (2.05), 0.449 (2.10), 0.485 (0.49), 0.496 (0.72), 0.502 (0.69), 0.513 (0.60), 1.185 (0.89), 1.194 (1.07), 1.200 (1.12), 1.210 (1.24), 1.225 (0.64), 2.047 (13.30), 2.251 (1.59), 2.629 (16.00), 2.690 (1.11), 3.855 (1.58), 3.868 (1.54), 3.960 (0.74), 3.970 (0.72), 4.962 (1.61), 4.968 (1.56), 6.964 (1.24), 7.076 (2.70), 7.188 (1.11), 7.637 (2.50), 7.654 (2.90), 7.846 (2.08), 7.862 (1.80), 8.459 (0.47), 9.373 (0.44).

Example 497

1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl acetate

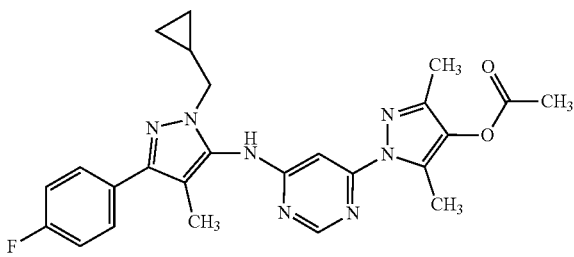 [SMILES: CC(=O)Oc1c(C)nn(-c2cc(Nc3c(C)c(-c4ccc(F)cc4)nn3CC3CC3)ncn2)c1C]

Under an argon atmosphere, 1-(cyclopropylmethyl)-3-(4-fluorophenyl)-4-methyl-1H-pyrazol-5-amine (418 mg, 1.70 mmol), 1-(6-chloropyrimidin-4-yl)-3,5-dimethyl-1H-pyrazol-4-yl acetate (500 mg, 1.87 mmol), tris(dibenzylideneacetone)dipalladium (46.8 mg, 51.1 μmol) and XantPhos (59.2 mg, 102 μmol) and were suspended in 1,4-dioxane (4 mL). The reaction mixture was degassed with Ar for 5 min. Sodium phenolate (218 mg, 1.87 mmol) was added and the reaction mixture was degassed again for 1 min. The reaction mixture was heated at 85° C. overnight while vigorously stirring. After cooling to ambient temperature, the reaction mixture was diluted with ethyl acetate, filtered over Celite and concentrated. The residue was purified by preparative HPLC (column: Chromatorex C18; 125*30 mm, 10 μM, flow 75 mL/min, gradient acetonitrile/water (containing 0.1% trifluoroacetic acid) 10/90 to 95/5) to yield the desired product (118 mg, 14% yield).

LC-MS (method 11): $R_t$=1.47 min; MS (ESIpos): m/z=476 [M+H]$^+$ $^1$H-NMR (500 MHz, dimethylsulfoxide-d6) δ [ppm]: −0.120 (0.43), −0.007 (4.19), 0.007 (3.01), 0.116 (0.43), 0.300 (1.18), 0.424 (1.29), 0.440 (1.40), 1.190 (0.54), 2.008 (7.73), 2.072 (8.59), 2.220 (0.43), 2.321 (6.87), 2.358 (1.18), 2.362 (1.18), 2.486 (16.00), 2.635 (1.07), 3.830 (0.86), 7.256 (1.18), 7.274 (2.47), 7.291 (1.29), 7.732 (0.97).

Example 498

6-(4-chloro-3,5-dimethyl-1H-pyrazol-1-yl)-N-[1-(cyclopropylmethyl)-3-(6-methoxypyridin-3-yl)-4-methyl-1H-pyrazol-5-yl]pyrimidin-4-amine

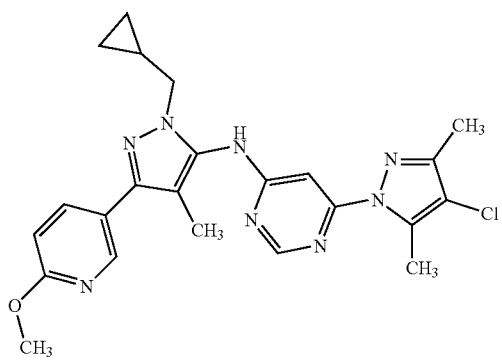 [SMILES: COc1ccc(-c2nn(CC3CC3)c(Nc3cc(-n4nc(C)c(Cl)c4C)ncn3)c2C)cn1]

In a sealed microwave tube under argon, 1-(cyclopropylmethyl)-3-(6-methoxypyridin-3-yl)-4-methyl-1H-pyrazol-5-amine (50.0 mg, 194 μmol), 4-chloro-6-(4-chloro-3,5-dimethyl-1H-pyrazol-1-yl)pyrimidine (56.5 mg, 232 μmol), sodium phenolate (24.7 mg, 213 μmol), tris(dibenzylidenaceton)dipalladium (5.32 mg, 5.81 μmol), Xantphos (6.14 mg, 11.6 μmol) were dissolved in 1,4-dioxane (920 μl). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phases were dried with sodium sulfate and concentrated in vacuo. The crude product was purified by flash-chromatography on silica gel (gradient 7% to 60% ethylacetate in cyclohexane, column: Biotage SNAP Ultra 10 g) to yield 61.1 mg (100% purity, 68% yield) of the desired product.

LC-MS (Method 10): $R_t$=2.40 min; MS (ESIpos): m/z=465 [M+H]$^+$ $^1$H-NMR (500 MHz, dimethylsulfoxide-d6) δ [ppm]: −0.122 (0.10), −0.009 (1.05), 0.114 (0.10), 0.289 (1.11), 0.299 (1.15), 0.421 (1.19), 0.437 (1.22), 1.176 (0.34), 1.182 (0.33), 1.191 (0.52), 1.205 (0.32), 1.999 (7.55), 2.208 (0.99), 2.645 (10.17), 3.826 (0.94), 3.839 (0.91), 3.895 (16.00), 6.898 (1.33), 6.915 (1.37), 8.003 (0.46),

Example 499

6-[5-(difluoromethyl)-3-methyl-1H-pyrazol-1-yl]-N-[3-(6-methoxypyridin-3-yl)-1,4-dimethyl-1H-pyrazol-5-yl]pyrimidin-4-amine

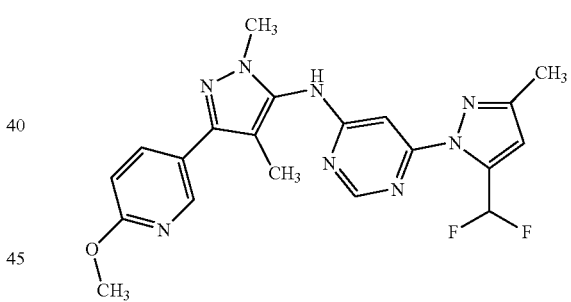

In a sealed microwave tube under argon, 3-(6-methoxypyridin-3-yl)-1,4-dimethyl-1H-pyrazol-5-amine (50.0 mg, 229 μmol), 4-chloro-6-[5-(difluoromethyl)-3-methyl-1H-pyrazol-1-yl]pyrimidine (67.2 mg, 275 μmol), sodium phenolate (29.3 mg, 252 μmol), tris(dibenzylidenaceton)dipalladium (6.29 mg, 6.87 μmol), Xantphos (7.27 mg, 13.7 μmol) were dissolved in 1,4-dioxane (1.1 ml). The reaction mixture was heated at 90° C. for 60 minutes. The cooled reaction mixture was diluted with dichloromethane, washed with a saturated aqueous solution of sodium hydrogen carbonate and the aqueous phase then extracted twice with dichloromethane. The combined organic phases were dried with sodium sulfate and concentrated in vacuo. The crude product was purified by flash-chromatography on silica gel (gradient 12% to 100% ethylacetate in cyclohexane, column: Biotage SNAP Ultra 10 g) to yield 60.5 mg (90% purity, 56% yield) of the desired product.

LC-MS (Method 10): $R_t$=1.94 min; MS (ESIpos): m/z=427 [M+H]$^+$

¹H-NMR (500 MHz, dimethylsulfoxide-d6) δ [ppm]: −0.008 (0.51), 2.012 (9.87), 2.288 (1.10), 2.700 (0.24), 3.664 (3.61), 3.704 (0.27), 3.894 (16.00), 3.928 (0.36), 6.787 (1.36), 6.894 (1.28), 6.911 (1.32), 7.709 (0.68), 7.818 (1.38), 7.926 (0.60), 7.988 (0.47), 8.004 (0.46), 8.444 (0.89), 8.503 (0.26), 9.594 (0.36).

Example 500

2-[1-(6-{[4-(difluoromethoxy)-5-(4-fluorophenyl)-1-methyl-1H-pyrazol-3-yl]amino}pyrimidin-4-yl)-3,5-dimethyl-1H-pyrazol-4-yl]propan-2-ol

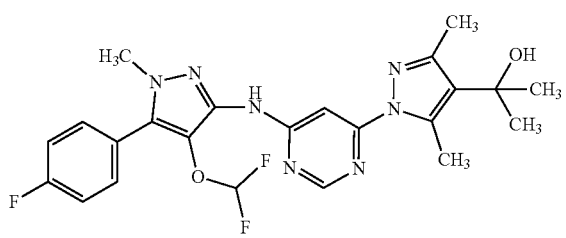 [SMILES: Cc1nn(-c2cc(Nc3nn(C)c(-c4ccc(F)cc4)c3OC(F)F)ncn2)c(C)c1C(C)(C)O]

Under an argon atmosphere, ethyl 1-(6-{[4-(difluoromethoxy)-5-(4-fluorophenyl)-1-methyl-1H-pyrazol-3-yl]amino}pyrimidin-4-yl)-3,5-dimethyl-1H-pyrazole-4-carboxylate (119 mg, 237 μmol) was dissolved in tetrahydrofuran and the solution cooled to 0° C. A solution of chloro(methyl)magnesium (395 μl, 3.0 M, 1.2 mmol) was added dropwise over 15 min and the reaction mixture was stirred for 6 h at ambient temperature. Another aliquot of chloro(methyl)magnesium (395 μl, 3.0 M, 1.2 mmol) was added and the reaction mixture was allowed to stir overnight. The reaction mixture was carefully quenched by addition of water and aqueous hydrochloric acid solution (0.5 mL, 2 N). It was extracted with ethyl acetate (3×) and the combined organic phase extracts were washed with brine, dried over sodium sulfate and concentrated. The residue was purified by flash column chromatography (SNAP Ultra 10 g, cyclohexane/ethyl acetate gradient 100/0 to 0/100) to yield the desired product (19 mg, 16% yield) after lyophilization from acetonitrile/water.

LC-MS (method 11): R$_t$=1.27 min; MS (ESIneg): m/z=486 [M−H]⁻

¹H-NMR (500 MHz, dimethylsulfoxide-d6) δ [ppm]: −0.007 (0.47), 1.475 (16.00), 2.289 (8.05), 2.726 (8.49), 3.696 (0.63), 3.721 (9.06), 4.852 (2.05), 6.647 (0.71), 6.795 (1.36), 6.942 (0.59), 7.286 (1.03), 7.383 (1.17), 7.387 (0.42), 7.401 (2.41), 7.405 (0.51), 7.415 (0.47), 7.419 (1.31), 7.584 (1.34), 7.588 (0.62), 7.595 (1.49), 7.601 (1.27), 7.608 (0.53), 7.612 (1.11), 8.463 (1.90), 8.465 (1.78), 9.494 (0.78).

Example 501

N-[1-(cyclopropylmethyl)-3-(4-fluorophenyl)-4-methyl-1H-pyrazol-5-yl]-6-[4-(ethylamino)-3,5-dimethyl-1H-pyrazol-1-yl]pyrimidin-4-amine trifluoroacetate

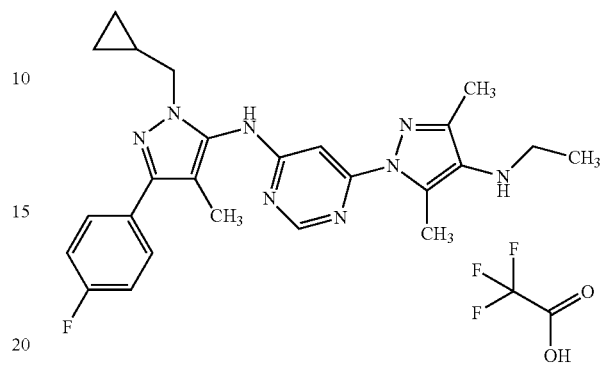

tert-butyl [1-(cyclopropylmethyl)-3-(4-fluorophenyl)-4-methyl-1H-pyrazol-5-yl]{6-[4-(ethylamino)-3,5-dimethyl-1H-pyrazol-1-yl]pyrimidin-4-yl}carbamate (24.0 mg, 42.8 μmol) was dissolved in dichloromethane (760 μL) and trifluoroacetic acid (760 μL) was added. The reaction mixture was stirred at ambient temperature for 20 min. The reaction mixture was concentrated and the residue redissolved in dichloromethane and concentrated (3 cycles). The residue was then redissolved in acetonitrile/water and lyophilized to yield the desired product as the TFA salt (26 mg, 94% yield).

LC-MS (method 11): R$_t$=1.20 min; MS (ESIpos): m/z=461 [M+H]⁺

¹H-NMR (500 MHz, dimethylsulfoxide-d6) δ [ppm]: −0.007 (0.84), 0.006 (0.39), 0.297 (2.61), 0.424 (2.83), 0.440 (2.81), 0.852 (0.19), 1.122 (0.40), 1.136 (0.79), 1.161 (2.69), 1.175 (5.17), 1.190 (3.20), 1.235 (0.82), 1.322 (0.21), 1.649 (0.70), 2.005 (16.00), 2.069 (0.31), 2.280 (1.57), 2.363 (0.45), 2.371 (0.43), 2.428 (0.31), 2.637 (0.42), 2.651 (0.79), 2.698 (11.97), 2.969 (0.31), 2.995 (0.20), 3.207 (1.43), 3.829 (2.41), 3.842 (2.28), 6.994 (0.50), 7.096 (0.61), 7.198 (0.59), 7.260 (2.25), 7.278 (4.59), 7.295 (2.65), 7.729 (2.20), 8.513 (0.39), 9.493 (0.31).

Example 502

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]ethanone

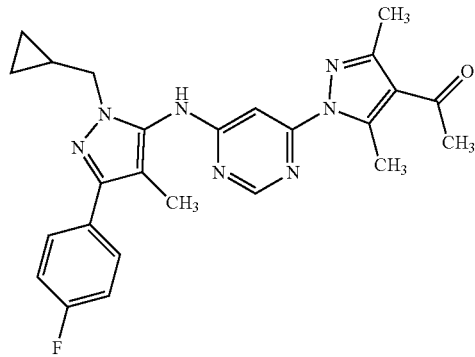 [SMILES: CC(=O)c1c(C)nn(-c2cc(Nc3c(C)c(-c4ccc(F)cc4)nn3CC3CC3)ncn2)c1C]

Ethyl 1-(6-{[1-(cyclopropylmethyl)-3-(4-fluorophenyl)-4-methyl-1H-pyrazol-5-yl]amino}pyrimidin-4-yl)-3,5-dimethyl-1H-pyrazole-4-carboxylate (375 mg, 766 µmol) was dissolved in tetrahydrofuran (3.0 ml, 37 mmol) under an argon atmosphere and the resulting solution was cooled to 0° C. A solution of bromo(methyl)magnesium (890 µl, 3.0 M in diethyl ether, 2.7 mmol) was added dropwise and the reaction mixture was stirred 2 hours at ambient temperature. Additional 3.5 equivalents of bromo(methyl)magnesium (890 µl, 3.0 M in diethyl ether, 2.7 mmol) were added and it was stirred another hour. The mixture was diluted with water and extracted with ethyl acetate (2×). The combined organic phases were dried over Extrelut NT3 and the residue was purified by flash-chromatography (column: SNAP Ultra 10 g, solvent: 90% dichloromethane/10% ethyl acetate to 100% ethyl acetate) to yield 61.1 mg (17%) of the described product as a by-product of 2-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]propan-2-ol.

LC-MS (method 10): $R_t$=2.09 min; MS (ESIpos): m/z=460 [M+H]$^+$ $^1$H-NMR (400 MHz, dimethylsulfoxide-d6) δ [ppm]: −0.008 (0.58), 0.008 (0.60), 0.296 (1.18), 0.308 (1.25), 0.427 (1.23), 0.447 (1.24), 1.074 (0.48), 1.091 (0.97), 1.109 (0.49), 1.200 (0.50), 1.276 (3.67), 1.293 (3.71), 1.459 (16.00), 1.475 (1.33), 1.994 (0.42), 2.010 (6.96), 2.273 (8.60), 2.283 (0.89), 2.421 (1.02), 2.435 (1.01), 2.464 (4.05), 2.639 (8.80), 2.770 (0.64), 2.889 (4.72), 3.375 (0.50), 3.392 (0.48), 3.544 (1.18), 3.557 (1.25), 3.565 (1.24), 3.580 (1.18), 3.834 (1.07), 3.851 (1.01), 4.826 (3.29), 5.334 (0.60), 5.350 (0.58), 7.149 (1.69), 7.168 (2.05), 7.171 (1.91), 7.194 (1.31), 7.212 (0.71), 7.251 (1.27), 7.274 (2.31), 7.296 (1.20), 7.368 (1.51), 7.389 (1.89), 7.408 (1.03), 7.711 (0.79), 7.725 (1.00), 7.746 (0.71).

Example 503

N-[1-(cyclopropylmethyl)-3-(4-fluorophenyl)-4-methyl-1H-pyrazol-5-yl]-6-[4-(methoxymethyl)-3,5-dimethyl-1H-pyrazol-1-yl]pyrimidin-4-amine

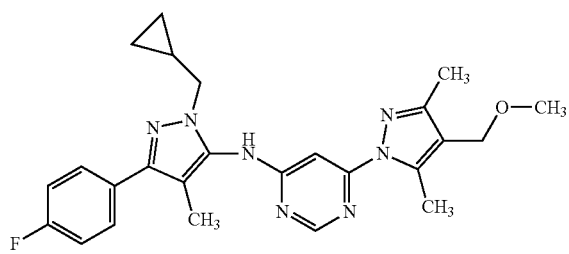 [SMILES: COCc1c(C)nn(-c2cc(Nc3c(C)c(-c4ccc(F)cc4)nn3CC3CC3)ncn2)c1C]

A microwave vial was charged with 1-(cyclopropylmethyl)-3-(4-fluorophenyl)-4-methyl-1H-pyrazol-5-amine (52.9 mg, 216 µmol) and 4-chloro-6-[4-(methoxymethyl)-3,5-dimethyl-1H-pyrazol-1-yl]pyrimidine (60.0 mg, 237 µmol) and the contents were suspended in 1,4-dioxane (0.86 mL). The reaction mixture was degassed with Ar for 3 min. Tris(dibenzylideneacetone)dipalladium (5.93 mg, 6.48 µmol) and XantPhos (7.49 mg, 13.0 µmol) were added and the reaction mixture was degassed again for 1 min. Finally, sodium phenolate (27.6 mg, 237 µmol) was added, the vial was sealed and heated at 85° C. overnight while vigorously shaking. After cooling to ambient temperature, the reaction mixture was filtered and concentrated. The residue was redissolved in dimethylsulfoxide and purified by preparative HPLC (column: Chromatorex C18; 125*30 mm, 10 µM, flow 75 mL/min, gradient acetonitrile/water (containing 0.1% trifluoroacetic acid) 10/90 to 95/5) and further by flash column chromatography (SNAP Ultra 10 g, cyclohexane/ethyl acetate gradient) to yield the desired product (44 mg, 44% yield).

LC-MS (method 10): $R_t$=2.20 min; MS (ESIpos): m/z=462 [M+H]$^+$ $^1$H-NMR (500 MHz, dimethylsulfoxide-d6) δ [ppm]: 0.295 (2.29), 0.304 (2.32), 0.425 (2.42), 0.441 (2.42), 1.161 (0.89), 1.176 (1.81), 1.183 (0.73), 1.190 (1.34), 1.198 (1.02), 1.207 (0.60), 1.212 (0.60), 1.989 (3.02), 2.009 (13.46), 2.184 (2.04), 2.632 (16.00), 2.664 (0.41), 3.216 (11.51), 3.354 (0.51), 3.830 (2.00), 3.843 (1.91), 4.023 (0.64), 4.038 (0.64), 4.250 (4.36), 7.256 (2.10), 7.274 (4.20), 7.292 (2.23), 7.719 (1.34), 7.730 (1.81), 7.746 (1.24), 8.473 (0.51), 9.387 (0.48).

Example 504

N-[1-(cyclopropylmethyl)-3-(4-fluorophenyl)-4-methyl-1H-pyrazol-5-yl]-6-{4-[(±)-1-(dimethylamino)-2,2,2-trifluoroethyl]-3,5-dimethyl-1H-pyrazol-1-yl}pyrimidin-4-amine (Racemate)

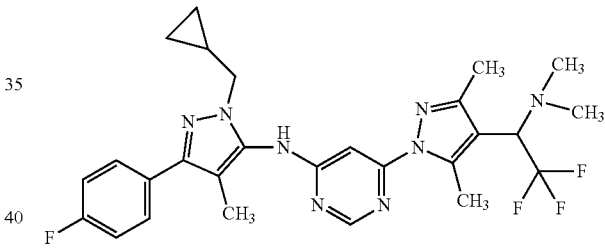

A microwave vial was charged with 1-(cyclopropylmethyl)-3-(4-fluorophenyl)-4-methyl-1H-pyrazol-5-amine (5.14 mg, 21.0 µmol) and (±)-1-[1-(6-chloropyrimidin-4-yl)-3,5-dimethyl-1H-pyrazol-4-yl]-2,2,2-trifluoro-N,N-dimethylethanamine (racemate, 7.00 mg, 21.0 µmol) and the contents were suspended in 1,4-dioxane (0.5 mL). The reaction mixture was degassed with Ar for 3 min. Tris(dibenzylideneacetone)dipalladium (580 µg, 0.63 µmol) and XantPhos (730 µg, 1.3 µmol) were added and the reaction mixture was degassed again for 1 min. Finally, sodium phenolate (2.68 mg, 23.1 µmol) was added, the vial was sealed and heated at 85° C. overnight while vigorously shaking. After cooling to ambient temperature, the reaction mixture was concentrated. The residue was purified by flash column chromatography (KP Sil 10 g, cyclohexane/ethyl acetate 95/5 to 20/80) to yield the desired product (1.9 mg, 15% yield).

LC-MS (method 11): $R_t$=1.64 min; MS (ESIneg): m/z=541 [M−H]$^-$ $^1$H NMR (600 MHz, dimethylsulfoxide-d$_6$) δ ppm: 0.30 (br d, J=2.93 Hz, 2H), 0.44 (br d, J=7.89 Hz, 2H), 1.16-1.23 (m, 1H), 2.01 (s, 3H), 2.16-2.29 (m, 9H), 2.70 (s, 3H), 3.84 (br s, 2H), 3.99-4.19 (m, 1H), 7.21-7.36 (m, 3H), 7.70-7.78 (m, 2H), 8.34-8.69 (br s, 1H) 9.29-9.71 (br s, 1H).

Example 505

6-(4-chloro-3,5-dimethyl-1H-pyrazol-1-yl)-N-[3-(6-methoxypyridin-3-yl)-1,4-dimethyl-1H-pyrazol-5-yl]pyrimidin-4-amine

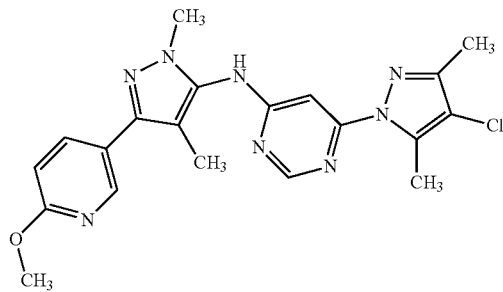 [SMILES: COc1ccc(-c2nn(C)c(Nc3cc(-n4nc(C)c(Cl)c4C)ncn3)c2C)cn1]

In a sealed microwave tube under argon, 3-(6-methoxypyridin-3-yl)-1,4-dimethyl-1H-pyrazol-5-amine (50.0 mg, 229 µmol), 4-chloro-6-(4-chloro-3,5-dimethyl-1H-pyrazol-1-yl)pyrimidine (66.8 mg, 275 µmol), sodium phenolate (29.3 mg, 252 µmol), tris(dibenzylidenaceton)dipalladium (6.29 mg, 6.87 µmol), Xantphos (7.27 mg, 13.7 µmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phase s were dried with sodium sulfate and concentrated in vacuo. The crude product was purified by flash-chromatography on silica gel (Gradient 12% to 100% ethylacetate in cyclohexane, column: Biotage SNAP Ultra 10 g) and then by preparative HPLC (Method 1) to yield 44.8 mg (100% purity, 46% yield) of the desired product.

LC-MS (Method 10): $R_t$=2.14 min; MS (ESIpos): m/z=425 $[M+H]^+$ $^1$H-NMR (500 MHz, DIMETHYLSULFOXIDE-d6) δ [ppm]: −0.007 (1.47), 0.006 (0.98), 2.008 (11.85), 2.216 (1.62), 2.648 (11.45), 3.660 (5.35), 3.894 (16.00), 5.754 (1.20), 6.892 (1.51), 6.909 (1.54), 7.981 (0.62), 7.985 (0.63), 7.998 (0.61), 8.003 (0.59), 8.439 (1.17), 8.443 (1.14), 9.513 (0.46).

Example 506

{[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]oxy}acetonitrile

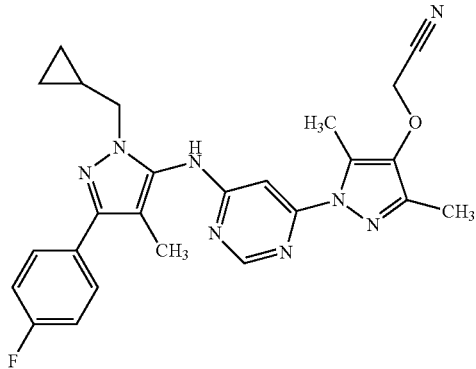 [SMILES: Cc1nn(-c2cc(Nc3c(C)c(-c4ccc(F)cc4)nn3CC3CC3)ncn2)c(C)c1OCC#N]

A microwave vial was charged with 1-(cyclopropylmethyl)-3-(4-fluorophenyl)-4-methyl-1H-pyrazol-5-amine (100 mg, 408 µmol), {[1-(6-chloropyrimidin-4-yl)-3,5-dimethyl-1H-pyrazol-4-yl]oxy}acetonitrile (118 mg, 448 µmol) and sodium phenolate (52.1 mg, 448 µmol) and the contents were suspended in dioxane (1.3 mL). The reaction mixture was degassed with Ar for 3 min. Tris(dibenzylideneacetone)dipalladium (11.2 mg, 12.2 µmol) and XantPhos (14.2 mg, 24.5 µmol) were added and the reaction mixture was degassed again for 1 min. The vial was sealed and heated at 85° C. overnight while vigorously shaking. After cooling to ambient temperature, the reaction mixture was diluted with ethyl acetate, filtered over Celite and concentrated. The residue was redissolved in dimethylsulfoxide and purified by preparative HPLC (method 3) to yield the desired product (81 mg, 40% yield).

LC-MS (method 10): $R_t$=2.15 min; MS (ESIpos): m/z=473 $[M+H]^+$ $^1$H-NMR (500 MHz, DIMETHYLSULFOXIDE-d6) δ [ppm]: 0.291 (1.98), 0.300 (2.04), 0.423 (2.14), 0.439 (2.19), 1.167 (0.33), 1.176 (0.59), 1.182 (0.59), 1.191 (0.88), 1.201 (0.54), 1.206 (0.57), 1.216 (0.28), 2.006 (12.47), 2.215 (1.62), 2.363 (0.21), 2.598 (16.00), 2.637 (0.21), 3.828 (1.62), 3.841 (1.57), 4.949 (4.66), 7.257 (1.80), 7.275 (3.50), 7.293 (1.88), 7.345 (0.70), 7.378 (0.77), 7.463 (1.11), 7.465 (1.06), 7.477 (0.67), 7.720 (1.16), 7.731 (1.55), 7.784 (0.70), 7.792 (0.59), 7.796 (0.64), 7.806 (0.54), 7.811 (0.59), 7.816 (0.59), 8.472 (0.39), 9.415 (0.33).

Example 507

1-[1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]-1,1-difluoro-2-methyl-propan-2-ol

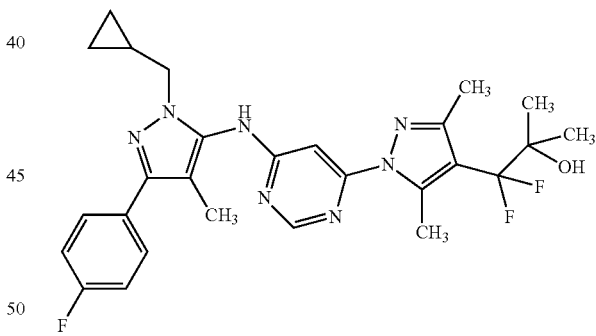

Under an argon atmosphere, ethyl [1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl](difluoro)acetate (30.0 mg, 55.6 µmol) was dissolved in tetrahydrofuran and the solution cooled to 0° C. A solution of bromido(methyl)magnesium (280 µl, 1.0 M, 280 µmol) was added dropwise and the reaction mixture was stirred for 35 min at ambient temperature. The reaction mixture was carefully quenched by addition of aqueous Na$_2$EDTA solution (10%) and extracted with ethyl acetate (3×). The combined organic extracts were dried over sodium sulfate and concentrated. The residue was dissolved standing overnight, the organic phase was decanted and concentrated. The residue was dissolved in tetrahydrofuran and the solution cooled to 0° C. A solution of bromido(methyl)magnesium (280 µl, 1.0 M, 280 µmol) was added dropwise and the reaction mixture was stirred for 20 min at ambient temperature. The reaction mixture was carefully quenched by addition of aqueous Na$_2$EDTA solution (10%) and extracted with ethyl acetate (3×). The combined organic extracts were dried over sodium sulfate and concentrated. The residue was purified by preparative HPLC (column: Chromatorex C18; 125*30 mm, 10 µM, flow 75 mL/min, gradient acetonitrile/water (containing 0.1% trifluoroacetic acid) 10/90 to 95/5) to yield the desired product (8 mg, 26% yield).

LC-MS (method 9): R$_t$=1.15 min; MS (ESIpos): m/z=526 [M+H]$^+$ $^1$H-NMR (600 MHz, DIMETHYLSULFOXIDE-d6) δ [ppm]: 0.298 (3.18), 0.431 (3.65), 0.444 (3.68), 0.853 (0.30), 1.119 (0.44), 1.162 (1.09), 1.176 (1.81), 1.188 (2.04), 1.197 (2.63), 1.219 (15.64), 1.258 (0.89), 1.299 (0.36), 1.500 (0.17), 1.645 (0.23), 1.991 (1.89), 2.011 (16.00), 2.116 (0.17), 2.176 (0.58), 2.254 (1.50), 2.388 (0.20), 2.618 (0.20), 2.687 (13.68), 3.838 (2.24), 4.023 (0.44), 4.035 (0.44), 4.047 (0.17), 5.324 (2.56), 5.762 (0.59), 7.265 (2.62), 7.279 (5.14), 7.293 (2.88), 7.731 (2.51), 8.492 (0.34), 9.452 (0.30), 11.232 (0.30).

Example 508

6-[4-(cyclopropylmethoxy)-3,5-dimethyl-1H-pyrazol-1-yl]-N-[1-(cyclopropylmethyl)-3-(4-fluorophenyl)-4-methyl-1H-pyrazol-5-yl]pyrimidin-4-amine

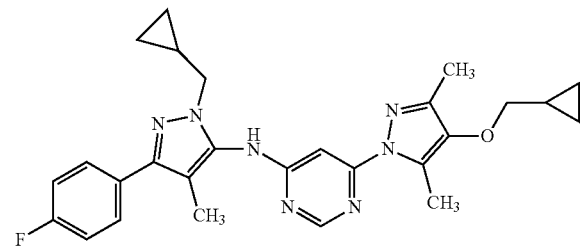 [SMILES: Cc1nn(-c2cc(Nc3c(C)c(-c4ccc(F)cc4)nn3CC3CC3)ncn2)c(C)c1OCC1CC1]

A microwave vial was charged with 1-(cyclopropylmethyl)-3-(4-fluorophenyl)-4-methyl-1H-pyrazol-5-amine (16.0 mg, 65.2 µmol) and 4-chloro-6-[4-(cyclopropylmethoxy)-3,5-dimethyl-1H-pyrazol-1-yl]pyrimidine (20.0 mg, 71.8 µmol) and the contents were suspended in dioxane (0.5 mL). The reaction mixture was degassed with Ar for 3 min. Tris(dibenzylideneacetone)dipalladium (1.79 mg, 1.96 µmol) and XantPhos (2.26 mg, 3.91 µmol) were added and the reaction mixture was degassed again for 1 min. Lastly, sodium phenolate (8.33 mg, 71.8 µmol) was added, the vial was sealed and heated at 85° C. overnight while vigorously shaking. After cooling to ambient temperature, the reaction mixture was diluted with ethyl acetate, filtered and concentrated. The residue was redissolved in dimethylsulfoxide and purified by preparative HPLC (method 6) to yield the desired product (2 mg, 5% yield).

LC-MS (method 11): R$_t$=1.61 min; MS (ESIpos): m/z=488 [M+H]$^+$ $^1$H-NMR (600 MHz, DIMETHYLSULFOXIDE-d6) δ [ppm]: 0.247 (4.98), 0.261 (0.90), 0.291 (2.70), 0.298 (2.77), 0.421 (2.92), 0.434 (3.01), 0.527 (3.45), 0.530 (3.16), 0.537 (3.51), 0.543 (2.33), 0.550 (0.69), 1.135 (1.21), 1.143 (1.25), 1.155 (0.82), 1.164 (0.59), 1.168 (0.67), 1.176 (0.94), 1.181 (0.85), 1.189 (1.28), 1.197 (0.84), 1.201 (0.85), 1.233 (0.40), 2.000 (16.00), 2.161 (1.42), 2.181 (11.17), 2.388 (0.25), 2.579 (10.35), 2.616 (0.27), 3.509 (0.18), 3.653 (2.31), 3.664 (2.31), 3.678 (3.89), 3.690 (3.62), 3.831 (1.90), 7.166 (2.91), 7.254 (2.20), 7.263 (2.58), 7.266 (3.26), 7.277 (4.08), 7.292 (2.18), 7.318 (0.59), 7.331 (1.29), 7.343 (0.77), 7.486 (1.55), 7.500 (2.15), 7.512 (1.22), 7.731 (1.87), 8.436 (0.35), 8.656 (2.69), 9.366 (0.16).

Example 509

N-[1-(cyclopropylmethyl)-3-(4-fluorophenyl)-4-methyl-1H-pyrazol-5-yl]-6-[4-(difluoromethoxy)-3,5-dimethyl-1H-pyrazol-1-yl]pyrimidin-4-amine

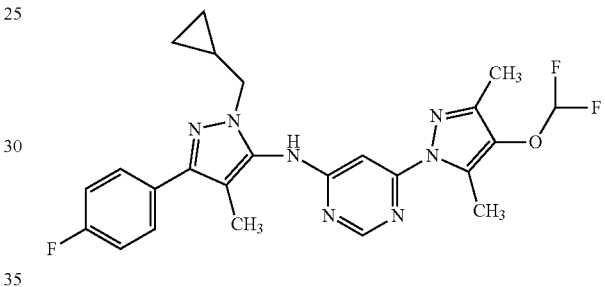

A microwave vial was charged with 1-(cyclopropylmethyl)-3-(4-fluorophenyl)-4-methyl-1H-pyrazol-5-amine (110 mg, 447 µmol) and 4-chloro-6-[4-(difluoromethoxy)-3,5-dimethyl-1H-pyrazol-1-yl]pyrimidine (135 mg, 492 µmol) and the contents were suspended in dioxane (1.7 mL). The reaction mixture was degassed with Ar for 3 min. Tris(dibenzylideneacetone)dipalladium (12.3 mg, 13.4 µmol) and XantPhos (15.5 mg, 26.8 µmol) were added and the reaction mixture was degassed again for 1 min. Lastly, sodium phenolate (57.1 mg, 492 µmol) was added, the vial was sealed and heated at 85° C. overnight while vigorously shaking. After cooling to ambient temperature, the reaction mixture was filtered and concentrated. The residue was redissolved in dimethylsulfoxide and purified by preparative HPLC (method 4) to yield the desired product (93 mg, 41% yield).

LC-MS (method 10): R$_t$=2.32 min; MS (ESIpos): m/z=484 [M+H]$^+$ $^1$H-NMR (500 MHz, DIMETHYLSULFOXIDE-d6) δ [ppm]: −0.007 (0.85), 0.007 (0.54), 0.292 (2.08), 0.301 (2.14), 0.424 (2.29), 0.440 (2.33), 1.163 (0.25), 1.168 (0.35), 1.177 (0.66), 1.183 (0.64), 1.193 (1.00), 1.202 (0.59), 1.208 (0.60), 1.217 (0.30), 1.223 (0.20), 2.008 (14.36), 2.175 (1.62), 2.196 (2.64), 2.577 (16.00), 2.600 (2.14), 3.831 (1.70), 3.844 (1.64), 6.873 (0.58), 6.901 (0.23), 7.020 (1.13), 7.048 (0.46), 7.166 (0.58), 7.194 (0.22), 7.239 (0.77), 7.241 (0.75), 7.257 (2.14), 7.261 (1.37), 7.275 (4.36), 7.292 (2.16), 7.320 (0.19), 7.335 (0.35), 7.350 (0.22), 7.487 (0.42), 7.502 (0.48), 7.519 (0.28), 7.720 (1.19), 7.732 (1.63), 7.747 (1.12), 8.491 (0.37), 8.707 (0.63), 8.709 (0.61), 9.454 (0.29).

Example 510

N-{1-(cyclopropylmethyl)-3-[6-(difluoromethyl)pyridin-3-yl]-4-methyl-1H-pyrazol-5-yl}-6-(4-methoxy-3,5-dimethyl-1H-pyrazol-1-yl)pyrimidin-4-amine

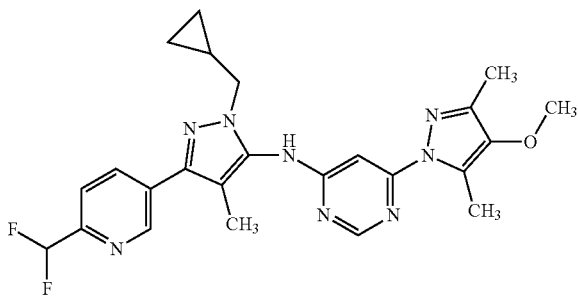 [SMILES: COc1c(C)nn(-c2cc(Nc3c(C)c(-c4ccc(C(F)F)nc4)nn3CC3CC3)ncn2)c1C]

A microwave vial was charged with 1-(cyclopropylmethyl)-3-[6-(difluoromethyl)pyridin-3-yl]-4-methyl-1H-pyrazol-5-amine (100 mg, 359 µmol) and 4-chloro-6-(4-methoxy-3,5-dimethyl-1H-pyrazol-1-yl)pyrimidine (94.3 mg, 395 µmol) and the contents were suspended in dioxane (1.5 mL). The reaction mixture was degassed with Ar for 3 min. Tris(dibenzylideneacetone)dipalladium (9.87 mg, 10.8 µmol) and XantPhos (12.5 mg, 21.6 µmol) were added and the reaction mixture was degassed again for 1 min. Finally, sodium phenolate (45.9 mg, 395 µmol) was added and the vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (47.6 mg, 28% yield).

LC-MS (method 10): $R_t$=2.10 min; MS (ESIpos): m/z=481 [M+H]$^+$ $^1$H-NMR (500 MHz, DIMETHYLSULFOXIDE-d6) δ [ppm]: −0.007 (0.58), 0.312 (2.35), 0.322 (2.47), 0.332 (0.71), 0.439 (2.47), 0.455 (2.54), 1.203 (0.68), 1.209 (0.66), 1.219 (1.05), 1.228 (0.61), 1.233 (0.62), 2.071 (16.00), 2.187 (2.44), 3.316 (15.94), 3.877 (2.10), 3.890 (2.03), 6.899 (1.56), 7.009 (3.41), 7.119 (1.36), 7.773 (2.37), 7.790 (2.51), 8.273 (1.11), 8.289 (1.06), 8.453 (0.66), 9.017 (2.11), 9.420 (0.60).

Example 511

6-(4-chloro-3,5-dimethyl-1H-pyrazol-1-yl)-N-{1-(cyclopropylmethyl)-3-[6-(difluoromethyl)pyridin-3-yl]-4-methyl-1H-pyrazol-5-yl}pyrimidin-4-amine

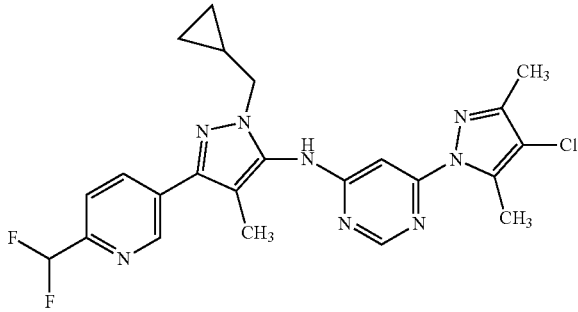 [SMILES: Cc1nn(-c2cc(Nc3c(C)c(-c4ccc(C(F)F)nc4)nn3CC3CC3)ncn2)c(C)c1Cl]

A microwave vial was charged with 1-(cyclopropylmethyl)-3-[6-(difluoromethyl)pyridin-3-yl]-4-methyl-1H-pyrazol-5-amine (100 mg, 359 µmol) and 4-chloro-6-(4-chloro-3,5-dimethyl-1H-pyrazol-1-yl)pyrimidine (96.1 mg, 395 µmol) and the contents were suspended in dioxane (1.5 mL). The reaction mixture was degassed with Ar for 3 min. Tris(dibenzylideneacetone)dipalladium (9.87 mg, 10.8 µmol) and XantPhos (12.5 mg, 21.6 µmol) were added and the reaction mixture was degassed again for 1 min. Lastly, sodium phenolate (45.9 mg, 395 µmol) was added, the vial was sealed and heated at 85° C. overnight while vigorously shaking. After cooling to ambient temperature, the reaction mixture was filtered and concentrated. The residue was redissolved in dimethylsulfoxide and purified by preparative HPLC (method 4) to yield the desired product (78 mg, 45% yield).

LC-MS (method 10): $R_t$=2.41 min; MS (ESIpos): m/z=485 [M+H]$^+$ $^1$H-NMR (500 MHz, DIMETHYLSULFOXIDE-d6) δ [ppm]: −0.006 (0.50), 0.007 (0.27), 0.314 (2.03), 0.324 (2.10), 0.441 (2.14), 0.457 (2.18), 1.191 (0.22), 1.196 (0.32), 1.206 (0.60), 1.211 (0.58), 1.221 (0.90), 1.231 (0.53), 1.236 (0.55), 1.245 (0.27), 1.251 (0.18), 2.074 (13.29), 2.216 (1.75), 2.264 (0.22), 2.650 (16.00), 3.880 (1.74), 3.894 (1.68), 6.899 (1.32), 7.009 (2.88), 7.119 (1.16), 7.774 (2.03), 7.790 (2.16), 8.273 (0.93), 8.289 (0.88), 8.503 (0.41), 9.017 (1.77), 9.528 (0.31).

Example 512

1-[6-({1-(cyclopropylmethyl)-3-[6-(difluoromethyl)pyridin-3-yl]-4-methyl-1H-pyrazol-5-yl}amino)pyrimidin-4-yl]-3,5-dimethyl-1H-pyrazole-4-carbonitrile

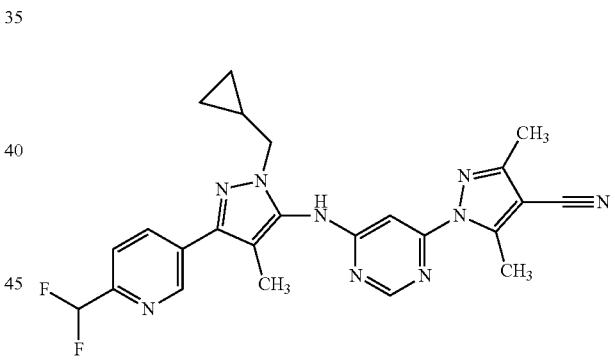

A microwave vial was charged with 1-(cyclopropylmethyl)-3-[6-(difluoromethyl)pyridin-3-yl]-4-methyl-1H-pyrazol-5-amine (100 mg, 359 µmol) and 1-(6-chloropyrimidin-4-yl)-3,5-dimethyl-1H-pyrazole-4-carbonitrile (120 mg, 77% purity, 395 µmol) and the contents were suspended in dioxane (1.5 mL). The reaction mixture was degassed with Ar for 3 min. Tris(dibenzylideneacetone)dipalladium (9.87 mg, 10.8 µmol) and XantPhos (12.5 mg, 21.6 µmol) were added and the reaction mixture was degassed again for 1 min. Lastly, sodium phenolate (45.9 mg, 395 µmol) was added, the vial was sealed and heated at 85° C. overnight while vigorously shaking. After cooling to ambient temperature, the reaction mixture was filtered and concentrated. The residue was redissolved in dimethylsulfoxide and purified by preparative HPLC (method 3) to yield the desired product (11 mg, 6% yield).

LC-MS (method 10): $R_t$=2.07 min; MS (ESIpos): m/z=476 [M+H]$^+$

¹H-NMR (500 MHz, DIMETHYLSULFOXIDE-d6) δ [ppm]: −0.007 (0.83), 0.007 (0.48), 0.311 (2.33), 0.320 (2.38), 0.440 (2.52), 0.456 (2.56), 1.191 (0.39), 1.200 (0.72), 1.206 (0.70), 1.216 (1.06), 1.225 (0.65), 1.231 (0.65), 1.240 (0.33), 1.647 (0.52), 2.071 (15.87), 2.337 (1.50), 2.799 (16.00), 3.880 (1.78), 3.893 (1.72), 6.898 (1.60), 7.008 (3.50), 7.118 (1.39), 7.371 (0.41), 7.384 (0.41), 7.395 (0.43), 7.773 (2.37), 7.789 (2.50), 8.271 (1.03), 8.286 (0.97), 8.548 (0.34), 9.013 (1.94), 9.630 (0.22).

Example 513

4-[5-{[6-(4-chloro-3,5-dimethyl-1H-pyrazol-1-yl)pyrimidin-4-yl]amino}-1-(cyclopropylmethyl)-4-methyl-1H-pyrazol-3-yl]cubane-1-carbonitrile

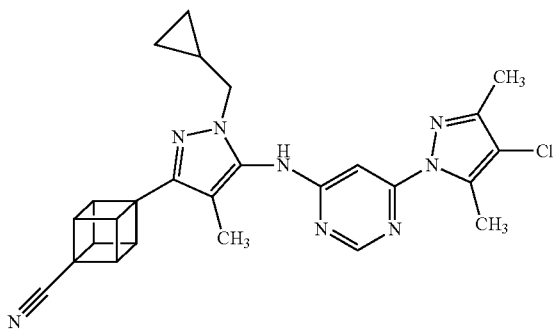 [SMILES: Cc1nn(-c2cc(Nc3c(C)c(C45C6C7C4C4C5C6C74C#N)nn3CC3CC3)ncn2)c(C)c1Cl]

A microwave vial was charged with 4-[5-amino-1-(cyclopropylmethyl)-4-methyl-1H-pyrazol-3-yl]cubane-1-carbonitrile (60.0 mg, 216 µmol) and 4-chloro-6-(4-chloro-3,5-dimethyl-1H-pyrazol-1-yl)pyrimidine (57.6 mg, 237 µmol) and the contents were suspended in dioxane (1.2 mL). The reaction mixture was degassed with Ar for 3 min. Tris(dibenzylideneacetone)dipalladium (5.92 mg, 6.47 µmol) and XantPhos (7.48 mg, 12.9 µmol) were added and the reaction mixture was degassed again for 1 min. Lastly, sodium phenolate (27.5 mg, 237 µmol) was added and the vial was sealed and heated at 85° C. overnight while vigorously shaking. After cooling to ambient temperature, the reaction mixture was filtered and concentrated. The residue was redissolved in dimethylsulfoxide and purified by preparative HPLC (method 1) to yield the desired product (28 mg, 27% yield).

LC-MS (method 11): R$_t$=1.55 min; MS (ESIpos): m/z=485 [M+H]⁺

¹H NMR (500 MHz, DIMETHYLSULFOXIDE-d$_6$) δ ppm: 0.18-0.27 (m, 2H), 0.35-0.43 (m, 2H), 1.07-1.17 (m, 1H), 1.77 (s, 3H), 2.22 (s, 3H), 2.63 (s, 3H), 3.72 (d, J=6.86 Hz, 2H), 4.25-4.35 (m, 3H), 4.36-4.45 (m, 3H), 8.47 (br s, 1H), 9.18-9.60 (br s, 1H).

Example 514

4-[1-(cyclopropylmethyl)-5-{[6-(4-methoxy-3,5-dimethyl-1H-pyrazol-1-yl)pyrimidin-4-yl]amino}-4-methyl-1H-pyrazol-3-yl]cubane-1-carbonitrile

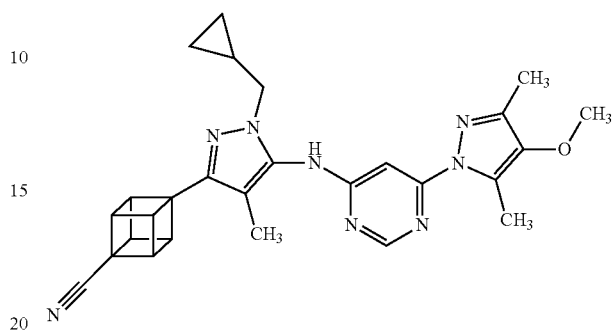

A microwave vial was charged with 4-[5-amino-1-(cyclopropylmethyl)-4-methyl-1H-pyrazol-3-yl]cubane-1-carbonitrile (50.0 mg, 180 µmol) and 4-chloro-6-(4-methoxy-3,5-dimethyl-1H-pyrazol-1-yl)pyrimidine (47.2 mg, 198 µmol) and the contents were suspended in dioxane (1.0 mL). The reaction mixture was degassed with Ar for 3 min. Tris(dibenzylideneacetone)dipalladium (4.93 mg, 5.39 µmol) and XantPhos (6.24 mg, 10.8 µmol) were added and the reaction mixture was degassed again for 1 min. Lastly, sodium phenolate (22.9 mg, 198 µmol) was added, the vial was sealed and heated at 85° C. overnight while vigorously shaking. After cooling to ambient temperature, the reaction mixture was filtered and concentrated. The residue was redissolved in dimethylsulfoxide and purified by preparative HPLC (method 1) to yield the desired product (28 mg, 33% yield).

LC-MS (method 11): R$_t$=1.39 min; MS (ESIpos): m/z=481 [M+H]⁺

¹H NMR (500 MHz, DIMETHYLSULFOXIDE-d$_6$) δ ppm: 0.22 (q, J=4.83 Hz, 2H), 0.36-0.41 (m, 2H), 1.08-1.16 (m, 1H), 1.77 (s, 3H), 2.18 (s, 3H), 2.53 (s, 3H), 3.67-3.73 (m, 5H), 4.29-4.33 (m, 3H), 4.38-4.43 (m, 3H), 8.42 (br s, 1H), 9.24 (br s, 1H).

Example 515

2-(6-{[1-(cyclopropylmethyl)-3-(4-fluorophenyl)-4-methyl-1H-pyrazol-5-yl]amino}pyrimidin-4-yl)-3,4-dimethyl-2,4,5,6-tetrahydrocyclopenta[c]pyrazol-4-ol

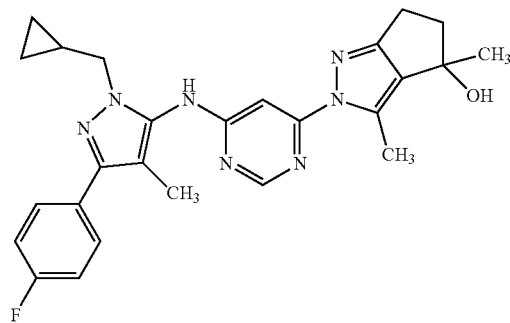 [SMILES: Cc1c(-c2ccc(F)cc2)nn(CC2CC2)c1Nc1cc(-n2nc3c(c2C)C(C)(O)CC3)ncn1]

Obtained from separation of the enantiomers of a racemic sample of 2-(6-{[1-(cyclopropylmethyl)-3-(4-fluorophenyl)-4-methyl-1H-pyrazol-5-yl]amino}pyrimidin-4-yl)-3,4-dimethyl-2,4,5,6-tetrahydrocyclopenta[c]pyrazol-4-ol (racemate 293 mg dissolved in ethanol/acetonitrile 5:2, 7 mL) by preparative HPLC (Daicel Chiralpak IA 5 m, 250×20 mm, 50° C., flow: 15 mL/min, isocratic ethanol/n-heptane 80/20+ 0.2% diethylamine, injections of 0.15 mL every 13 min) to yield the title compound as the first eluting enantiomer (133 mg, 45% from racemate). As partial elimination was observed during concentration, the compound was repurified by flash column chromatography (SNAP Ultra 10 g, cyclohexane/ethyl acetate gradient 80/20 to 0/100) to yield the desired product (70 mg, 24% yield based on racemate).

LC (Daicel Chiralpak IA-3 3 μm, 50 mm×4.6 mm, 1 mL/min n-heptane/EtOH 80/20+0.2% diethylamine): $R_t$=1.42 min, enantiomeric excess=93.4%

LC-MS (method 11): $R_t$=1.33 min; MS (ESIneg): m/z=472 [M−H]⁻

¹H-NMR (500 MHz, DIMETHYLSULFOXIDE-d6) δ [ppm]: −0.120 (0.41), −0.007 (4.38), 0.006 (3.18), 0.116 (0.41), 0.285 (1.47), 0.293 (1.52), 0.415 (1.65), 0.430 (1.68), 1.167 (0.48), 1.175 (0.53), 1.181 (0.72), 1.189 (0.47), 1.196 (0.46), 1.470 (5.78), 1.988 (0.36), 2.006 (13.90), 2.304 (1.23), 2.362 (0.22), 2.519 (0.59), 2.523 (0.55), 2.635 (0.34), 2.655 (16.00), 2.690 (0.37), 3.828 (1.58), 3.842 (1.53), 5.027 (2.54), 7.255 (1.98), 7.259 (0.77), 7.273 (4.05), 7.287 (0.82), 7.291 (2.12), 7.724 (1.08), 7.736 (1.45), 7.752 (1.03), 8.469 (0.43), 9.359 (0.53).

Example 516

2-(6-{[1-(cyclopropylmethyl)-3-(4-fluorophenyl)-4-methyl-1H-pyrazol-5-yl]amino}pyrimidin-4-yl)-3,4-dimethyl-2,4,5,6-tetrahydrocyclopenta[c]pyrazol-4-ol

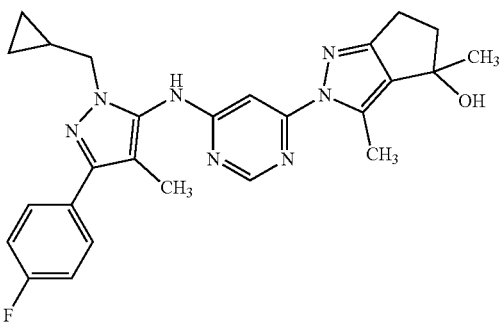 [SMILES: Cc1c(-c2ccc(F)cc2)nn(CC2CC2)c1Nc1cc(-n2nc3c(c2C)C(C)(O)CC3)ncn1]

Obtained from separation of the enantiomers of a racemic sample of 2-(6-{[1-(cyclopropylmethyl)-3-(4-fluorophenyl)-4-methyl-1H-pyrazol-5-yl]amino}pyrimidin-4-yl)-3,4-dimethyl-2,4,5,6-tetrahydrocyclopenta[c]pyrazol-4-ol (racemate 293 mg dissolved in ethanol/acetonitrile 5:2, 7 mL) by preparative HPLC (Daicel Chiralpak IA 5 m, 250×20 mm, 50° C., flow: 15 mL/min, isocratic ethanol/n-heptane 80/20+ 0.2% diethylamine, injections of 0.15 mL every 13 min) to yield the title compound as the second eluting enantiomer (130 mg, 44% from racemate). As partial elimination was observed during concentration, the compound was repurified by flash column chromatography (SNAP Ultra 10 g, cyclohexane/ethyl acetate gradient 80/20 to 0/100) to yield the desired product (60 mg, 20% yield based on racemate).

LC (Daicel Chiralpak IA-3 3 μm, 50 mm×4.6 mm, 1 mL/min n-heptane/EtOH 80/20+0.2% diethylamine): $R_t$=2.72 min, enantiomeric excess=90.2%

LC-MS (method 11): $R_t$=1.32 min; MS (ESIpos): m/z=474 [M+H]⁺

¹H-NMR (500 MHz, DIMETHYLSULFOXIDE-d6) δ [ppm]: −0.120 (0.29), −0.007 (3.73), 0.006 (1.95), 0.117 (0.29), 0.285 (1.69), 0.293 (1.71), 0.415 (1.85), 0.431 (1.87), 1.161 (0.37), 1.167 (0.56), 1.175 (0.73), 1.182 (0.79), 1.189 (0.60), 1.196 (0.51), 1.398 (0.21), 1.470 (6.30), 1.988 (0.67), 2.007 (14.73), 2.304 (1.39), 2.362 (0.16), 2.523 (0.51), 2.655 (16.00), 2.689 (0.41), 3.829 (1.79), 3.842 (1.71), 5.028 (2.72), 7.255 (2.08), 7.273 (4.20), 7.291 (2.19), 7.725 (1.24), 7.737 (1.65), 7.753 (1.15), 8.467 (0.49), 9.361 (0.58).

Example 517

N-[1-(cyclopropylmethyl)-3-(4-fluorophenyl)-4-methyl-1H-pyrazol-5-yl]-6-{3,5-dimethyl-4-[2-(trifluoromethyl)-1,3-dioxolan-2-yl]-1H-pyrazol-1-yl}pyrimidin-4-amine

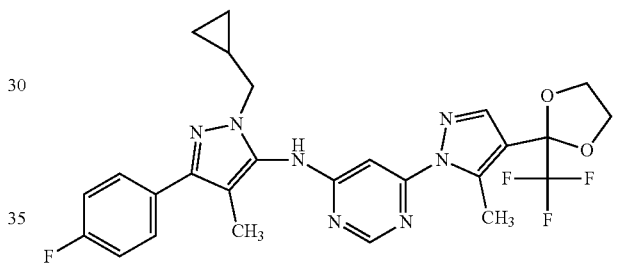

Under an argon atmosphere, 4-chloro-6-{3,5-dimethyl-4-[2-(trifluoromethyl)-1,3-dioxolan-2-yl]-1H-pyrazol-1-yl}pyrimidine (1.50 g, 90% purity, 3.87 mmol) and 1-(cyclopropylmethyl)-3-(4-fluorophenyl)-4-methyl-1H-pyrazol-5-amine (1.14 g, 4.65 mmol) were suspended in dioxane (25 mL). The reaction mixture was degassed with Ar for 3 min. Tris(dibenzylideneacetone)dipalladium (124 mg, 135 μmol) and XantPhos (146 mg, 252 μmol) were added and the reaction mixture was degassed again for 1 min. Lastly, sodium phenolate (517 mg, 4.45 mmol) was added and the reaction mixture heated at 85° C. overnight while vigorously stirring. After cooling to ambient temperature, the reaction mixture was diluted with water and extracted with ethyl acetate (2×). The combined organic extracts were dried over sodium sulfate and concentrated. The residue was purified by flash column chromatography (SNAP Ultra 50 g, cyclohexane/ethyl acetate gradient 90/10 to 20/80) to yield the desired product (1.24 g, 57% yield).

LC-MS (method 11): $R_t$=1.61 min; MS (ESIpos): m/z=558 [M+H]⁺

¹H-NMR (400 MHz, DIMETHYLSULFOXIDE-d6) δ [ppm]: −0.149 (0.16), −0.008 (1.22), 0.008 (1.31), 0.145 (0.16), 0.290 (0.95), 0.300 (1.02), 0.423 (0.92), 0.442 (1.02), 1.192 (0.41), 1.398 (16.00), 2.004 (5.83), 2.254 (0.90), 2.327 (0.86), 2.366 (0.40), 2.523 (2.64), 2.669 (0.92), 2.674 (0.71), 2.710 (0.49), 2.729 (5.38), 3.568 (0.20), 3.825 (0.82), 3.842 (0.80), 4.087 (1.05), 4.223 (1.22), 4.240 (0.32), 7.250

(0.90), 7.272 (1.83), 7.294 (0.98), 7.708 (0.61), 7.723 (0.80), 7.744 (0.56), 8.500 (0.21), 9.459 (0.17).

Example 518

1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl methyl carbonate

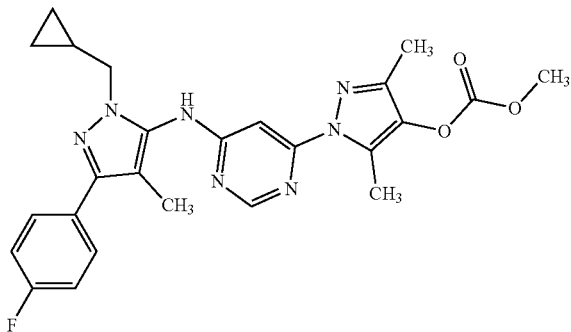 [SMILES: COC(=O)Oc1c(C)nn(-c2cc(Nc3c(C)c(-c4ccc(F)cc4)nn3CC3CC3)ncn2)c1C]

A microwave vial was charged with 1-(6-chloropyrimidin-4-yl)-3,5-dimethyl-1H-pyrazol-4-yl methyl carbonate (100 mg, 100% purity, 354 µmol) and 1-(cyclopropylmethyl)-3-(4-fluorophenyl)-4-methyl-1H-pyrazol-5-amine (95.5 mg, 389 µmol) and the contents were suspended in dioxane (1.1 mL). The reaction mixture was degassed with Ar for 3 min. Tris(dibenzylideneacetone)dipalladium (6.10 mg, 10.6 µmol) and XantPhos (12.3 mg, 21.2 µmol) were added and the reaction mixture was degassed again for 1 min. The vial was heated at 85° C. when sodium phenolate (45.2 mg, 389 µmol) was added. The vial was sealed and heated at 85° C. overnight while vigorously shaking. After cooling to ambient temperature, the reaction mixture was diluted with aqueous saturated sodium hydrogencarbonate solution and extracted with ethyl acetate (2×). The combined organic extracts were washed with brine, dried over sodium sulfate and concentrated. The residue was redissolved in dimethylsulfoxide and purified by preparative HPLC (method 4) to yield the desired product (12 mg, 7% yield).

LC-MS (method 11): $R_t$=1.49 min; MS (ESIpos): m/z=492 [M+H]$^+$ $^1$H NMR (400 MHz, DIMETHYLSULFOXIDE-d$_6$) δ ppm: 0.25-0.35 (m, 2H), 0.39-0.48 (m, 2H), 1.15-1.25 (m, 1H), 2.01 (s, 3H), 2.06-2.18 (br s, 3H), 2.53 (s, 3H), 3.81-3.88 (m, 5H), 7.24-7.32 (m, 2H), 7.66-7.82 (m, 2H), 8.41-8.62 (br s, 1H), 9.36-9.55 (br s, 1H).

Example 519

1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl methylcarbamate

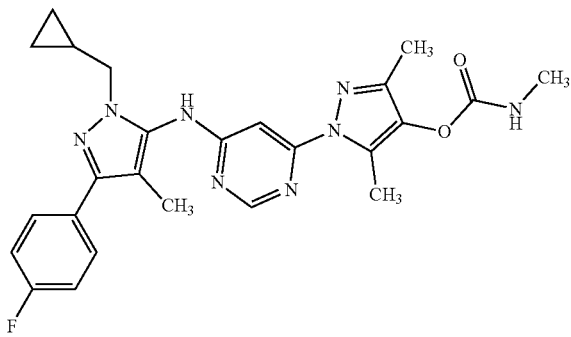 [SMILES: CNC(=O)Oc1c(C)nn(-c2cc(Nc3c(C)c(-c4ccc(F)cc4)nn3CC3CC3)ncn2)c1C]

A microwave vial was charged with 1-(6-chloropyrimidin-4-yl)-3,5-dimethyl-1H-pyrazol-4-yl methylcarbamate (100 mg, 100% purity, 355 µmol) and 1-(cyclopropylmethyl)-3-(4-fluorophenyl)-4-methyl-1H-pyrazol-5-amine (95.8 mg, 390 µmol) and the contents were suspended in dioxane (1.1 mL). The reaction mixture was degassed with Ar for 3 min. Tris(dibenzylideneacetone)dipalladium (6.12 mg, 10.6 µmol) and XantPhos (12.3 mg, 21.3 µmol) were added and the reaction mixture was degassed again for 1 min. The vial was heated at 85° C. when sodium phenolate (45.3 mg, 390 µmol) was added. The vial was sealed and heated at 85° C. overnight while vigorously shaking. After cooling to ambient temperature, the reaction mixture was diluted with aqueous saturated sodium hydrogencarbonate solution and extracted with ethyl acetate (2×). The combined organic extracts were washed with brine, dried over sodium sulfate and concentrated. The residue was redissolved in dimethylsulfoxide and purified by preparative HPLC (method 3) to yield the desired product (14 mg, 7% yield).

LC-MS (method 11): $R_t$=1.34 min; MS (ESIpos): m/z=491 [M+H]$^+$ $^1$H-NMR (400 MHz, DIMETHYLSULFOXIDE-d6) δ [ppm]: −0.149 (0.52), −0.008 (4.20), 0.008 (4.20), 0.146 (0.54), 0.289 (2.45), 0.302 (2.70), 0.423 (2.53), 0.442 (2.66), 1.191 (1.08), 1.647 (1.33), 2.009 (15.09), 2.065 (2.74), 2.328 (0.67), 2.366 (0.69), 2.476 (16.00), 2.665 (7.00), 2.676 (6.88), 2.710 (0.64), 2.794 (0.42), 3.830 (2.12), 3.845 (2.04), 7.252 (2.45), 7.274 (4.84), 7.296 (2.60), 7.368 (1.00), 7.385 (0.96), 7.397 (1.21), 7.724 (2.62), 8.467 (0.69), 9.405 (0.62).

Example 520

1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl dimethylcarbamate

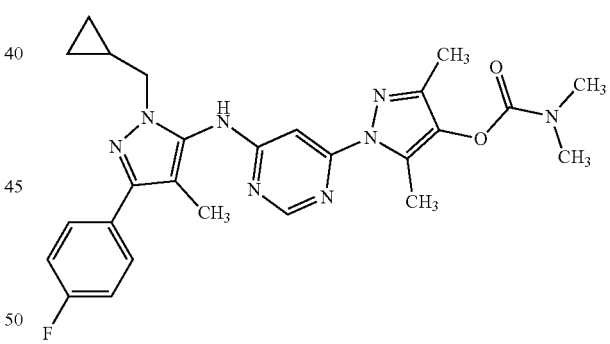

A microwave vial was charged with 1-(6-chloropyrimidin-4-yl)-3,5-dimethyl-1H-pyrazol-4-yl dimethylcarbamate (100 mg, 100% purity, 338 µmol) and 1-(cyclopropylmethyl)-3-(4-fluorophenyl)-4-methyl-1H-pyrazol-5-amine (91.2 mg, 372 µmol) and the contents were suspended in dioxane (1.1 mL). The reaction mixture was degassed with Ar for 3 min. Tris(dibenzylideneacetone)dipalladium (5.83 mg, 10.1 µmol) and XantPhos (11.7 mg, 20.3 µmol) were added and the reaction mixture was degassed again for 1 min. The vial was heated at 85° C. when sodium phenolate (43.2 mg, 372 µmol) was added. The vial was sealed and heated at 85° C. overnight while vigorously shaking. After cooling to ambient temperature, the reaction mixture was diluted with aqueous saturated sodium hydrogencarbonate solution and extracted with ethyl acetate (2×). The combined organic extracts were washed with brine, dried over sodium sulfate and concentrated. The residue was redissolved in acetonitrile and purified by preparative HPLC (column: Chromatorex C18; 125*30 mm, 10 µM, flow 75 mL/min, gradient acetonitrile/water (containing 0.1% trifluoroacetic acid) 10/90 to 95/5) and further by flash column chromatography (SNAP Ultra 10 g, cyclohexane/ethyl acetate gradient 90/10 to 20/80) to yield the desired product (61 mg, 35% yield).

LC-MS (method 10): R$_t$=2.20 min; MS (ESIpos): m/z=505 [M+H]$^+$ $^1$H-NMR (400 MHz, DIMETHYLSULFOXIDE-d6) δ [ppm]: 0.304 (2.88), 0.422 (2.71), 0.442 (2.88), 1.193 (1.22), 1.398 (1.90), 2.009 (16.00), 2.068 (2.92), 2.328 (1.86), 2.366 (0.75), 2.523 (5.63), 2.669 (2.00), 2.711 (0.68), 2.919 (8.95), 3.067 (9.05), 3.830 (2.24), 3.846 (2.27), 7.252 (2.44), 7.274 (5.08), 7.296 (2.78), 7.732 (2.07), 8.468 (0.85), 9.407 (0.64).

Example 521

6-(4-chloro-3,5-dimethyl-1H-pyrazol-1-yl)-N-{1-(2-methoxyethyl)-4-methyl-3-[4-(methylamino)phenyl]-1H-pyrazol-5-yl}pyrimidin-4-amine

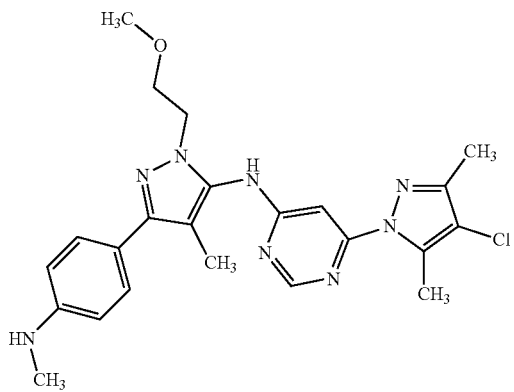 [SMILES: CNc1ccc(-c2nn(CCOC)c(Nc3cc(-n4nc(C)c(Cl)c4C)ncn3)c2C)cc1]

In a sealed microwave tube under argon, 1-(2-methoxyethyl)-4-methyl-3-[4-(methylamino)phenyl]-1H-pyrazol-5-amine (50.0 mg, 192 µmol), 4-chloro-6-(4-chloro-3,5-dimethyl-1H-pyrazol-1-yl)pyrimidine (56.0 mg, 230 µmol), sodium phenolate (24.5 mg, 211 µmol), tris(dibenzylidenaceton)dipalladium (5.28 mg, 5.76 µmol), Xantphos (6.09 mg, 11.5 µmol) were dissolved in 1,4-dioxane (1.0 ml). The reaction mixture was heated at 90° C. for 45 minutes. The cooled reaction mixture was diluted with ethylacetate, washed with a saturated aqueous solution of sodium bicarbonate and the aqueous phase then extracted twice with ethylacetate. The combined organic phases were dried with sodium sulfate and concentrated in vacuo. The crude product was purified by preparative HPLC (Method 19) and then flash-chromatography on silica gel (gradient of ethylacetate in cyclohexane, column: Biotage SNAP Ultra) to yield 38.6 mg (100% purity, 43% yield) of the desired product.

LC-MS (Method 9): R$_t$=1.14 min; MS (ESIneg): m/z=465 [M−H]$^−$ $^1$H-NMR (500 MHz, DMSO-d6) δ [ppm]: 1.954 (15.46), 2.197 (1.54), 2.643 (16.00), 2.700 (8.26), 2.710 (8.15), 3.133 (2.50), 3.620 (1.54), 3.631 (3.04), 3.643 (1.57), 4.061 (0.87), 5.738 (0.75), 5.748 (0.75), 6.585 (3.65), 6.602 (3.76), 7.425 (1.65), 7.441 (1.62), 8.497 (0.41), 9.346 (0.80).

Example 522

N-[1-(cyclopropylmethyl)-3-(4-fluorophenyl)-4-methyl-1H-pyrazol-5-yl]-6-(5-propyl-5,6-dihydropyrrolo[3,4-c]pyrazol-1(4H)-yl)pyrimidin-4-amine

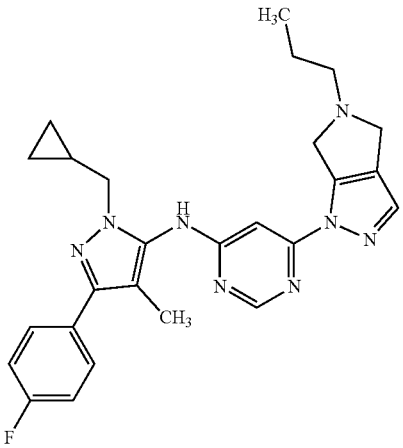 [SMILES: CCCN1Cc2cnn(-c3cc(Nc4c(C)c(-c5ccc(F)cc5)nn4CC4CC4)ncn3)c2C1]

To N-[1-(cyclopropylmethyl)-3-(4-fluorophenyl)-4-methyl-1H-pyrazol-5-yl]-6-(5,6-dihydropyrrolo[3,4-c]pyrazol-1(4H)-yl)pyrimidin-4-amine (23.8 mg, 55.3 µmol) and propanal (4.0 µl, 55 µmol) in tetrahydrofuran (500 µl) under an atmosphere of argon was added sodium triacetoxyborhydride (16.4 mg, 77.4 µmol) and the reaction stirred overnight at room temperature. To the reaction was then added sodium triacetoxyborhydride (16.4 mg, 77.4 µmol), propanal (20 µl, 275 µmol) and 2 drops of acetic acid and the reaction then stirred overnight at room temperature. The reaction was quenched with a saturated aqueous solution of ammonium chloride, extracted with ethylacetate and the organic phase then washed with a saturated aqueous solution of sodium bicarbonate, dried with sodium sulfate and concentrated in vacuo. The crude product was purified by preparative TLC (10:1 dichloromethane:MeOH) to yield 22.9 mg (100% purity, 88% yield) of the desired product.

LC-MS (Method 10): R$_t$=1.43 min; MS (ESIpos): m/z=473 [M+H]$^+$ $^1$H-NMR (500 MHz, DMSO-d6) δ [ppm]: 0.288 (3.03), 0.412 (3.15), 0.427 (3.10), 0.897 (4.60), 0.912 (8.68), 0.926 (4.37), 1.181 (1.27), 1.234 (1.94), 1.479 (1.60), 1.493 (2.74), 1.508 (2.64), 1.523 (1.39), 2.006 (16.00), 2.076 (0.54), 2.676 (2.32), 2.691 (3.65), 2.705 (2.17), 3.689 (3.60), 3.846 (2.72), 4.127 (5.05), 7.258 (2.44), 7.276 (4.65), 7.293 (2.59), 7.561 (0.54), 7.735 (2.90), 8.464 (0.58), 9.527 (0.62).

Example 523

N-[1-(cyclopropylmethyl)-3-(4-fluorophenyl)-4-methyl-1H-pyrazol-5-yl]-6-(5-propyl-5,6-dihydropyrrolo[3,4-c]pyrazol-2(4H)-yl)pyrimidin-4-amine

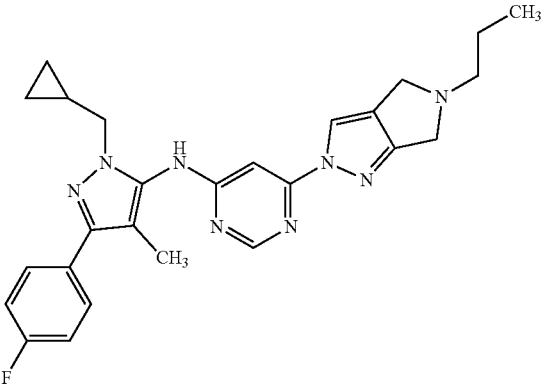 [SMILES: CCCN1Cc2cn(-c3cc(Nc4c(C)c(-c5ccc(F)cc5)nn4CC4CC4)ncn3)nc2C1]

To N-[1-(cyclopropylmethyl)-3-(4-fluorophenyl)-4-methyl-1H-pyrazol-5-yl]-6-(5,6-dihydropyrrolo[3,4-c]pyrazol-2(4H)-yl)pyrimidin-4-amine (23.3 mg, 54.1 µmol) and propanal (3.9 µl, 54 µmol) in tetrahydrofuran (500 µl) under an atmosphere of argon was added sodium triacetoxyborhydride (16.1 mg, 75.8 µmol) and the reaction stirred overnight at room temperature. To the reaction was then added sodium triacetoxyborhydride (16.4 mg, 77.4 µmol), propanal (20 µl, 275 µmol) and 2 drops of acetic acid and the reaction then stirred overnight at room temperature. The reaction was quenched with a saturated aqueous solution of ammonium chloride, extracted with ethylacetate and the organic phase then washed with a saturated aqueous solution of sodium bicarbonate, dried with sodium sulfate and concentrated in vacuo. The crude product was purified by preparative TLC (10:1 dichloromethane:MeOH) to yield 16.2 mg (100% purity, 63% yield) of the desired product.

LC-MS (Method 10): $R_t$=1.38 min; MS (ESIneg): m/z=471 [M−H]⁻

¹H-NMR (500 MHz, DMSO-d6) δ [ppm]: 0.285 (1.91), 0.410 (2.15), 0.425 (2.10), 0.889 (2.29), 0.903 (4.20), 0.918 (2.25), 1.179 (0.86), 1.231 (1.16), 1.497 (1.32), 2.011 (16.00), 2.659 (1.67), 3.672 (4.33), 3.833 (2.06), 7.258 (1.99), 7.276 (3.96), 7.293 (2.09), 7.742 (1.86), 8.252 (4.32), 8.473 (0.32), 9.475 (0.48).

Example 524

6-[3,5-dimethyl-4-(trifluoromethyl)-1H-pyrazol-1-yl]-N-[3-(4-fluorophenyl)-1-(2-methoxyethyl)-4-methyl-1H-pyrazol-5-yl]pyrimidin-4-amine

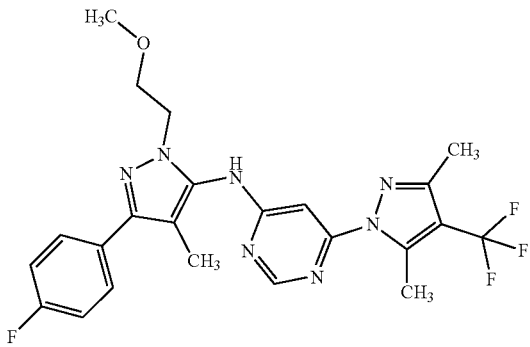 [SMILES: COCCn1nc(-c2ccc(F)cc2)c(C)c1Nc1cc(-n2nc(C)c(C(F)(F)F)c2C)ncn1]

In a sealed microwave tube under argon, 3-(4-fluorophenyl)-1-(2-methoxyethyl)-4-methyl-1H-pyrazol-5-amine (50.0 mg, 201 µmol), 4-chloro-6-[3,5-dimethyl-4-(trifluoromethyl)-1H-pyrazol-1-yl]pyrimidine (66.6 mg, 241 µmol), sodium phenolate (25.6 mg, 221 µmol), tris(dibenzylidenaceton)dipalladium (5.51 mg, 6.02 µmol), Xantphos (6.36 mg, 12.0 µmol) were dissolved in 1,4-dioxane (1.0 ml). The reaction mixture was heated at 90° C. for 45 minutes. The cooled reaction mixture was purified directly by flash-chromatography on silica gel (gradient 2:1 to 1:1 cyclohexane:ethyl acetate, column: Biotage SNAP Ultra) to yield 46.8 mg (100% purity, 48% yield) of the desired product.

LC-MS (Method 10): $R_t$=2.44 min; MS (ESIpos): m/z=490 [M+H]⁺

¹H-NMR (500 MHz, DMSO-d6) δ [ppm]: 2.006 (16.00), 2.298 (1.65), 2.755 (7.55), 3.144 (3.16), 3.649 (1.81), 3.660 (3.48), 3.671 (1.83), 4.117 (1.12), 7.257 (2.11), 7.274 (4.19), 7.292 (2.23), 7.714 (1.33), 7.726 (1.79), 7.741 (1.23), 8.554 (0.44), 9.529 (0.57).

Example 525

6-(3,5-dimethyl-1H-pyrazol-1-yl)-N-[3-(4-fluorophenyl)-1-(2-methoxyethyl)-4-methyl-1H-pyrazol-5-yl]pyrimidin-4-amine

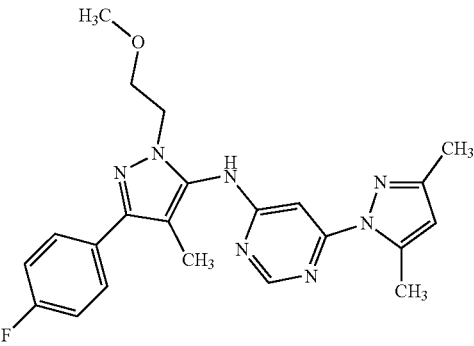 [SMILES: COCCn1nc(-c2ccc(F)cc2)c(C)c1Nc1cc(-n2nc(C)cc2C)ncn1]

In a sealed microwave tube under argon, 3-(4-fluorophenyl)-1-(2-methoxyethyl)-4-methyl-1H-pyrazol-5-amine (50.0 mg, 201 µmol), 4-chloro-6-(3,5-dimethyl-1H-pyrazol-1-yl)pyrimidine (50.2 mg, 241 µmol), sodium phenolate (25.6 mg, 221 µmol), tris(dibenzylidenaceton)dipalladium (5.51 mg, 6.02 µmol), Xantphos (6.36 mg, 12.0 µmol) were dissolved in 1,4-dioxane (1.0 ml). The reaction mixture was heated at 90° C. for 45 minutes. The cooled reaction mixture was purified directly by flash-chromatography on silica gel (gradient 2:1 to 1:1 cyclohexane:ethyl acetate, column: Biotage SNAP Ultra) to yield 31.3 mg (100% purity, 37% yield) of the desired product.

LC-MS (Method 10): $R_t$=2.14 min; MS (ESIpos): m/z=422 [M+H]⁺

¹H-NMR (500 MHz, DMSO-d6) δ [ppm]: 2.005 (16.00), 2.167 (3.34), 2.629 (14.36), 3.150 (7.07), 3.651 (2.24), 3.663 (4.46), 3.674 (2.30), 4.112 (1.64), 6.138 (2.81), 7.257 (2.22), 7.275 (4.40), 7.292 (2.33), 7.718 (1.62), 7.729 (2.12), 7.745 (1.46), 8.467 (0.97), 9.316 (2.53).

Example 526

N-[3-(4-fluorophenyl)-1-(2-methoxyethyl)-4-methyl-1H-pyrazol-5-yl]-6-(4-methoxy-3,5-dimethyl-1H-pyrazol-1-yl)pyrimidin-4-amine

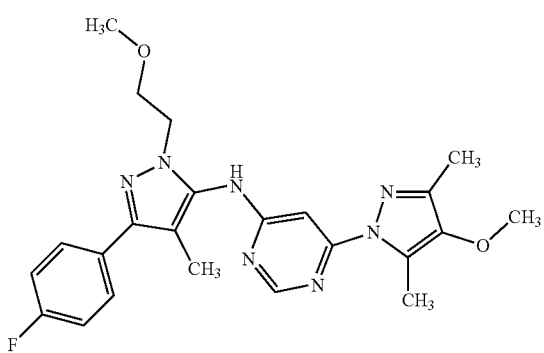 [SMILES: COCCn1nc(-c2ccc(F)cc2)c(C)c1Nc1cc(-n2nc(C)c(OC)c2C)ncn1]

In a sealed microwave tube under argon, 3-(4-fluorophenyl)-1-(2-methoxyethyl)-4-methyl-1H-pyrazol-5-amine (50.0 mg, 201 µmol), 4-chloro-6-(4-methoxy-3,5-dimethyl-1H-pyrazol-1-yl)pyrimidine (57.4 mg, 241 µmol), sodium phenolate (25.6 mg, 221 µmol), tris(dibenzylidenaceton)dipalladium (5.51 mg, 6.02 µmol), Xantphos (6.36 mg, 12.0 µmol) were dissolved in 1,4-dioxane (1.0 ml). The reaction mixture was heated at 90° C. for 45 minutes. The cooled reaction mixture was purified directly by flash-chromatography on silica gel (gradient 2:1 to 1:1 cyclohexane:ethyl acetate, column: Biotage SNAP Ultra) to yield 45.7 mg (100% purity, 50% yield) of the desired product.

LC-MS (Method 10): $R_t$=2.13 min; MS (ESIpos): m/z=452 [M+H]$^+$ $^1$H-NMR (500 MHz, DMSO-d6) δ [ppm]: 1.525 (0.57), 2.000 (16.00), 2.177 (2.85), 3.149 (6.83), 3.648 (1.99), 3.660 (4.04), 3.671 (2.19), 3.697 (10.54), 4.110 (1.42), 7.257 (1.91), 7.274 (3.94), 7.292 (2.14), 7.716 (1.39), 7.728 (1.89), 7.744 (1.37), 8.451 (0.86), 9.304 (1.98).

Example 527

6-[5-(difluoromethyl)-3-methyl-1H-pyrazol-1-yl]-N-[3-(4-fluorophenyl)-1-(2-methoxyethyl)-4-methyl-1H-pyrazol-5-yl]pyrimidin-4-amine

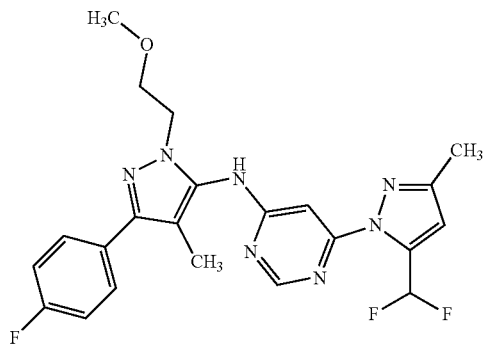 [SMILES: COCCn1nc(-c2ccc(F)cc2)c(C)c1Nc1cc(-n2nc(C)cc2C(F)F)ncn1]

In a sealed microwave tube under argon, 3-(4-fluorophenyl)-1-(2-methoxyethyl)-4-methyl-1H-pyrazol-5-amine (50.0 mg, 201 µmol), 4-chloro-6-[5-(difluoromethyl)-3-methyl-1H-pyrazol-1-yl]pyrimidine (58.9 mg, 241 µmol), sodium phenolate (25.6 mg, 221 µmol), tris(dibenzylidenaceton)dipalladium (5.51 mg, 6.02 µmol), Xantphos (6.36 mg, 12.0 µmol) were dissolved in 1,4-dioxane (1.0 ml). The reaction mixture was heated at 90° C. for 45 minutes. The cooled reaction mixture was purified directly by flash-chromatography on silica gel (gradient 2:1 to 1:1 cyclohexane:ethyl acetate, column: Biotage SNAP Ultra) to yield 58.5 mg (100% purity, 64% yield) of the desired product.

LC-MS (Method 10): $R_t$=2.22 min; MS (ESIpos): m/z=458 [M+H]$^+$ $^1$H-NMR (500 MHz, DMSO-d6) δ [ppm]: 2.009 (16.00), 2.277 (1.64), 3.137 (2.46), 3.649 (1.96), 3.660 (3.71), 3.671 (1.97), 4.118 (1.15), 6.779 (1.98), 7.260 (1.96), 7.278 (3.80), 7.296 (2.09), 7.714 (1.79), 7.736 (1.61), 7.822 (2.70), 7.931 (1.19), 8.502 (0.48), 9.503 (0.83).

Example 528 ethyl 1-(6-{[3-(4-fluorophenyl)-1-(2-methoxyethyl)-4-methyl-1H-pyrazol-5-yl]amino}pyrimidin-4-yl)-3,5-dimethyl-1H-pyrazole-4-carboxylate

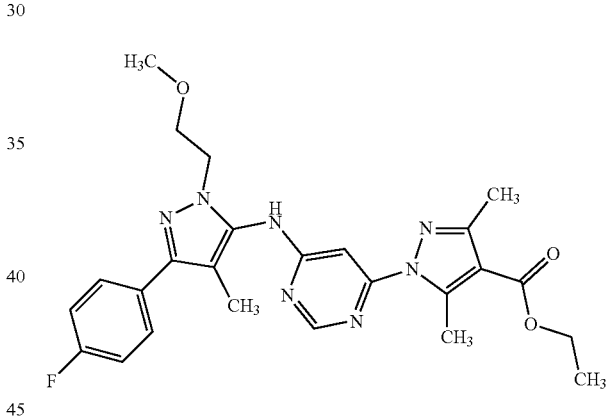

In a sealed microwave tube under argon, 3-(4-fluorophenyl)-1-(2-methoxyethyl)-4-methyl-1H-pyrazol-5-amine (100 mg, 401 µmol), ethyl 1-(6-chloropyrimidin-4-yl)-3,5-dimethyl-1H-pyrazole-4-carboxylate (135 mg, 481 µmol), sodium phenolate (51.2 mg, 441 µmol), tris(dibenzylidenaceton)dipalladium (11.0 mg, 12.0 µmol), Xantphos (12.7 mg, 24.1 µmol) were dissolved in 1,4-dioxane (2.0 ml). The reaction mixture was heated at 90° C. for 45 minutes. The cooled reaction mixture was purified directly by flash-chromatography on silica gel (gradient 2:1 to 1:1 cyclohexane:ethyl acetate, column: Biotage SNAP Ultra) to yield 110 mg (100% purity, 56% yield) of the desired product.

LC-MS (Method 10): $R_t$=2.29 min; MS (ESIpos): m/z=494 [M+H]$^+$ $^1$H-NMR (500 MHz, DMSO-d6) δ [ppm]: 1.290 (3.34), 1.304 (6.43), 1.318 (3.18), 2.008 (16.00), 2.368 (2.06), 2.905 (11.73), 3.146 (3.49), 3.651 (2.03), 3.662 (3.88), 3.673 (2.06), 4.116 (1.39), 4.232 (1.07), 4.246 (2.94), 4.260 (2.89), 4.274 (1.01), 7.256 (2.17), 7.274 (4.38), 7.292 (2.38), 7.715 (1.47), 7.727 (2.02), 7.743 (1.44), 8.544 (0.54), 9.493 (0.86).

Example 529

N-[1-(cyclopropylmethyl)-4-methyl-3-(6-methylpyridin-3-yl)-1H-pyrazol-5-yl]-6-(3,5-dimethyl-1H-pyrazol-1-yl)pyrimidin-4-amine

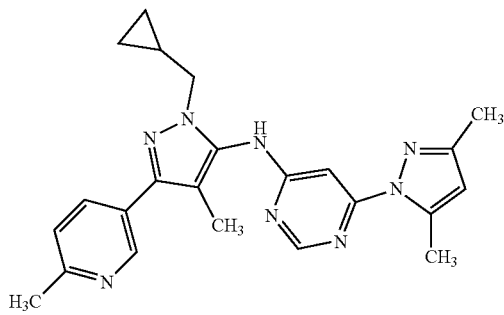

In a sealed microwave tube under argon, 1-(cyclopropylmethyl)-4-methyl-3-(6-methylpyridin-3-yl)-1H-pyrazol-5-amine (60.0 mg, 248 µmol), 4-chloro-6-(3,5-dimethyl-1H-pyrazol-1-yl)pyrimidine (56.8 mg, 272 µmol), (31.6 mg, 272 µmol), (6.80 mg, 7.43 µmol), (7.85 mg, 14.9 µmol) were dissolved in 1,4-dioxane (1.2 ml). The reaction mixture was heated at 90° C. for 30 minutes. The cooled reaction mixture was diluted with ethylacetate, washed with a saturated aqueous solution of sodium hydrogen carbonate and the aqueous phase then extracted twice with ethylacetate. The combined organic phases were dried with sodium sulfate and concentrated in vacuo. The crude product was purified by flash-chromatography on silica gel (Gradient 20% to 100% ethylacetate in cyclohexane, column: Biotage SNAP Ultra 10 g) to yield the desired product 53.9 mg (100% purity, 53% yield).

LC-MS (Method 10): $R_t$=1.45 min; MS (ESIpos): m/z=415 [M+H]$^+$ $^1$H-NMR (500 MHz, CHLOROFORM-d) δ [ppm]: 0.328 (0.64), 0.338 (2.58), 0.350 (2.58), 0.359 (0.73), 0.543 (0.78), 0.553 (2.09), 0.555 (2.10), 0.559 (1.02), 0.569 (2.21), 0.571 (2.01), 0.581 (0.62), 1.270 (0.53), 1.272 (0.49), 1.277 (0.51), 1.286 (0.88), 1.296 (0.48), 1.301 (0.47), 1.302 (0.47), 2.110 (16.00), 2.219 (13.40), 2.601 (15.07), 2.676 (11.82), 2.678 (11.67), 3.940 (3.06), 3.954 (3.01), 5.968 (3.03), 6.615 (0.47), 6.872 (0.69), 7.218 (1.99), 7.234 (2.08), 7.950 (1.68), 7.955 (1.68), 7.966 (1.58), 7.971 (1.59), 8.514 (4.06), 8.516 (3.98), 8.851 (2.11), 8.855 (2.07).

Example 530

N-[1,4-dimethyl-3-(6-methylpyridin-3-yl)-1H-pyrazol-5-yl]-6-[3,5-dimethyl-4-(trifluoromethyl)-1H-pyrazol-1-yl]pyrimidin-4-amine

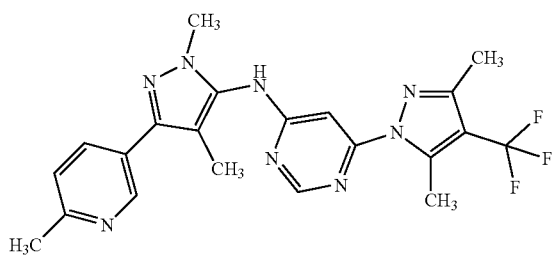 [SMILES: Cc1ccc(-c2nn(C)c(Nc3cc(-n4nc(C)c(C(F)(F)F)c4C)ncn3)c2C)cn1]

In a sealed microwave tube under argon, 1,4-dimethyl-3-(6-methylpyridin-3-yl)-1H-pyrazol-5-amine (45.0 mg, 222 µmol), 4-chloro-6-[3,5-dimethyl-4-(trifluoromethyl)-1H-pyrazol-1-yl]pyrimidine (73.9 mg, 267 µmol), sodium phenolate (28.4 mg, 245 µmol), tris(dibenzylidenaceton)dipalladium (6.11 mg, 6.67 µmol), Xantphos (7.06 mg, 13.3 µmol) were dissolved in 1,4-dioxane (1.1 ml). The reaction mixture was heated at 90° C. for 45 minutes. The cooled reaction mixture was diluted with dichloromethane, washed with a saturated aqueous solution of sodium hydrogen carbonate and the aqueous phase then extracted twice with dichloromethane. The combined organic phases were dried with sodium sulfate and concentrated in vacuo. The crude product was purified by flash-chromatography on silica gel (Gradient 25% to 100% ethylacetate in cyclohexane, column: Biotage SNAP Ultra 10 g) and then recrystallized from acetonitrile to yield 49.7 mg (100% purity, 50% yield) of the desired product.

LC-MS (Method 9): $R_t$=0.84 min; MS (ESIpos): m/z=443 [M+H]$^+$ $^1$H-NMR (500 MHz, DMSO-d6) δ [ppm]: 1.161 (1.11), 1.175 (2.26), 1.190 (1.15), 1.989 (4.22), 2.029 (16.00), 2.309 (1.59), 2.759 (6.00), 3.351 (0.41), 3.680 (6.11), 4.023 (0.93), 4.037 (0.93), 7.316 (1.78), 7.332 (1.85), 7.925 (0.89), 7.929 (0.93), 7.941 (0.89), 7.945 (0.85), 8.741 (1.59), 8.745 (1.59), 9.640 (0.44).

Example 531

4-[3-({6-[4-(2-hydroxy-2-methylpropyl)-3,5-dimethyl-1H-pyrazol-1-yl]pyrimidin-4-yl}amino)-4-methoxy-1-methyl-1H-pyrazol-5-yl]benzonitrile

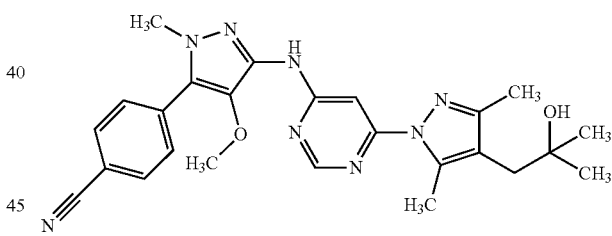

A solution of ethyl [1-(6-{[5-(4-cyanophenyl)-4-methoxy-1-methyl-1H-pyrazol-3-yl]amino}pyrimidin-4-yl)-3,5-dimethyl-1H-pyrazol-4-yl]acetate (177 mg, 364 µmol) in tetrahydrofuran (14 ml, 170 mmol) was treated with chlorido(methyl)magnesium (420 µl, 3.0 M, 1.3 mmol) at 0° C. The mixture was left overnight at ambient temperature. The mixture was diluted with saturated potassium sodium tartrate solution and water and extracted with ethyl acetate (3×). The combined organics were dried over magnesium sulfate, concentrated under reduced pressure and purified by preparative HPLC (method 7) to yield 70.0 mg (40%) of the desired product.

LC-MS (method 10): $R_t$=1.67 min; MS (ESIpos): m/z=473 [M+H]$^+$ $^1$H-NMR (400 MHz, DMSO-d6) δ [ppm]: 1.090 (16.00), 2.166 (10.42), 2.432 (4.44), 2.519 (1.24), 2.524 (0.95), 2.569 (10.76), 3.565 (15.37), 3.785 (11.96), 4.237 (4.37), 7.195 (3.11), 7.197 (3.24), 7.771 (3.04), 7.792 (3.70), 8.001 (3.60), 8.022 (2.97), 8.440 (2.36), 9.371 (1.94).

Example 532

N-{1-(cyclopropylmethyl)-4-methyl-3-[6-(trifluoromethyl)pyridin-3-yl]-1H-pyrazol-5-yl}-6-[5-(difluoromethyl)-3-methyl-1H-pyrazol-1-yl]pyrimidin-4-amine

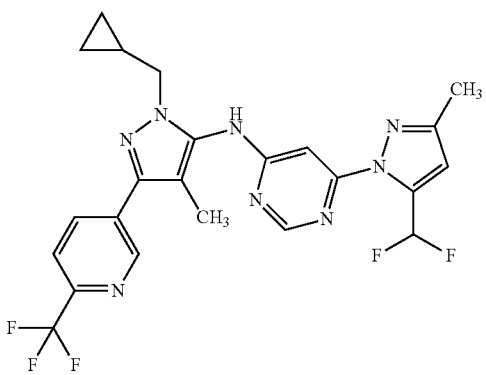 [SMILES: Cc1cc(C(F)F)n(-c2cc(Nc3c(C)c(-c4ccc(C(F)(F)F)nc4)nn3CC3CC3)ncn2)n1]

A microwave vial was charged 4-chloro-6-[5-(difluoromethyl)-3-methyl-H-pyrazol-1-yl]pyrimidine (105 mg, 430 µmol) and 1-(cyclopropylmethyl)-4-methyl-3-[6-(trifluoromethyl)pyridin-3-yl]-1H-pyrazol-5-amine (140 mg, 472 µmol) and the contents were suspended in 1,4-dioxane (2.2 ml, 26 mmol). The reaction mixture was degassed with Ar for 3 min. Tris(dibenzylidenaceton)dipalladium (11.8 mg, 12.9 µmol) and Xantphos (14.9 mg, 25.8 µmol) were added and the reaction mixture was degassed again for 1 min and heated to 85° C. At this temperature and sodium phenolate (54.9 mg, 472 µmol) was added. The vial was sealed and heated at 85° C. for 120 minutes while vigorously stirring. After cooling to ambient temperature, the reaction mixture was diluted with water and extracted with dichloromethane (2×). The combined organics were filtered over a column Chromabond PTS and concentrated under reduced pressure. The crude product was purified by preparative HPLC (method 4) to yield the desired product (80.0 mg, 36%).

LC-MS (Method 10): $R_t$=2.30 min; MS (ESIpos): m/z=505 [M+H]$^+$ $^1$H-NMR (400 MHz, DMSO-d6) δ [ppm]: −0.008 (1.17), 0.008 (1.02), 0.316 (2.83), 0.327 (3.09), 0.440 (2.90), 0.460 (3.07), 1.191 (0.43), 1.203 (0.77), 1.210 (0.75), 1.222 (1.17), 1.234 (0.81), 1.240 (0.78), 1.356 (0.40), 2.093 (16.00), 2.292 (2.54), 2.300 (2.43), 2.322 (1.50), 2.328 (1.50), 2.367 (0.67), 2.524 (3.48), 2.665 (0.85), 2.670 (1.13), 2.705 (0.54), 2.710 (0.66), 3.893 (2.43), 3.909 (2.40), 6.792 (2.74), 7.684 (1.53), 7.819 (3.21), 7.955 (1.45), 7.967 (2.68), 7.987 (2.94), 8.352 (1.15), 8.372 (1.09), 8.502 (0.52), 9.107 (2.00), 9.621 (0.43).

Example 533

N-{1-(cyclopropylmethyl)-4-methyl-3-[6-(trifluoromethyl)pyridin-3-yl]-1H-pyrazol-5-yl}-6-(3,5-dimethyl-1H-pyrazol-1-yl)pyrimidin-4-amine

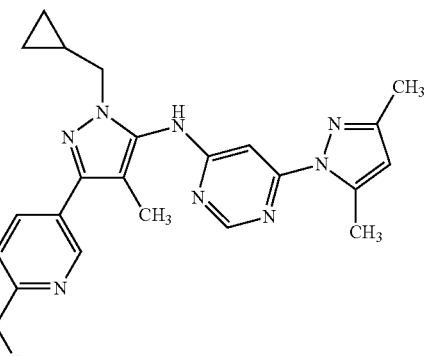

A microwave vial was charged 4-chloro-6-(3,5-dimethyl-1H-pyrazol-1-yl)pyrimidine (84.5 mg, 405 µmol) and 1-(cyclopropylmethyl)-4-methyl-3-[6-(trifluoromethyl)pyridin-3-yl]-1H-pyrazol-5-amine (132 mg, 445 µmol) and the contents were suspended in 1,4-dioxane (2.1 ml, 25 mmol). The reaction mixture was degassed with Ar for 3 min. Tris(dibenzylidenaceton)dipalladium (11.1 mg, 12.1 µmol) and Xantphos (14.1 mg, 24.3 µmol) were added and the reaction mixture was degassed again for 1 min and heated to 85° C. At this temperature and sodium phenolate (51.7 mg, 445 µmol) was added. The vial was sealed and heated at 85° C. for 90 minutes while vigorously stirring. After cooling to ambient temperature, the reaction mixture was diluted with water and extracted with dichloromethane (2×). The combined organics were filtered over a column Chromabond PTS and concentrated under reduced pressure. The crude product was purified by preparative HPLC (method 4) to yield the desired product (80.0 mg, 42%).

LC-MS (Method 10): $R_t$=2.25 min; MS (ESIpos): m/z=469 [M+H]$^+$ $^1$H-NMR (400 MHz, DMSO-d6) δ [ppm]: −0.008 (0.59), 0.008 (0.59), 0.305 (0.60), 0.317 (2.52), 0.330 (2.85), 0.342 (0.85), 0.441 (2.48), 0.461 (2.69), 1.206 (0.67), 1.213 (0.65), 1.225 (1.05), 1.237 (0.63), 1.244 (0.63), 2.090 (16.00), 2.178 (3.82), 2.328 (0.55), 2.333 (0.40), 2.524 (1.77), 2.633 (15.04), 2.666 (0.52), 2.670 (0.67), 2.675 (0.53), 3.887 (2.67), 3.904 (2.62), 6.150 (3.09), 7.963 (2.57), 7.984 (2.87), 8.350 (1.27), 8.370 (1.17), 8.469 (0.92), 9.106 (2.29), 9.447 (0.93).

Example 534

6-(4-chloro-3,5-dimethyl-1H-pyrazol-1-yl)-N-{1-(cyclopropylmethyl)-4-methyl-3-[6-(trifluoromethyl)pyridin-3-yl]-1H-pyrazol-5-yl}pyrimidin-4-amine

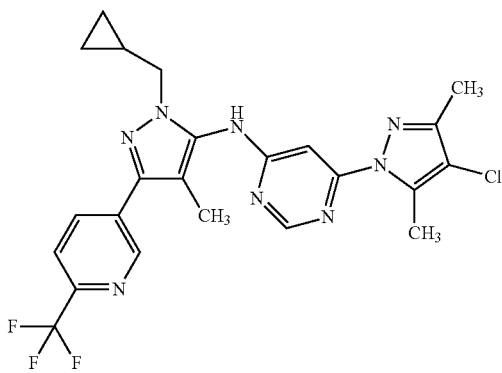 [SMILES: Cc1nn(-c2cc(Nc3c(C)c(-c4ccc(C(F)(F)F)nc4)nn3CC3CC3)ncn2)c(C)c1Cl]

A microwave vial was charged 4-chloro-6-(4-chloro-3,5-dimethyl-1H-pyrazol-1-yl)pyrimidine (95.5 mg, 393 µmol) and 1-(cyclopropylmethyl)-4-methyl-3-[6-(trifluoromethyl)pyridin-3-yl]-1H-pyrazol-5-amine (128 mg, 432 µmol) and the contents were suspended in 1,4-dioxane (2.0 ml, 24 mmol). The reaction mixture was degassed with Ar for 3 min. Tris(dibenzylidenaceton)dipalladium (10.8 mg, 11.8 µmol) and Xantphos (13.6 mg, 23.6 µmol) were added and the reaction mixture was degassed again for 1 min and heated to 85° C. At this temperature and sodium phenolate (50.2 mg, 432 µmol) was added. The vial was sealed and heated at 85° C. for 90 minutes while vigorously stirring. After cooling to ambient temperature, the reaction mixture was diluted with water and extracted with dichloromethane (2×). The combined organics were filtered over a column Chromabond PTS and concentrated under reduced pressure. The crude product was purified by preparative HPLC (method 5) to yield the desired product (115 mg, 54%).

LC-MS (Method 10): $R_t$=2.52 min; MS (ESIpos): m/z=503 [M+H]$^+$ $^1$H-NMR (400 MHz, DMSO-d6) δ [ppm]: 0.314 (2.13), 0.327 (2.32), 0.440 (2.09), 0.460 (2.26), 1.203 (0.63), 1.222 (0.89), 1.241 (0.58), 2.089 (13.43), 2.218 (2.71), 2.229 (3.23), 2.266 (0.74), 2.329 (0.67), 2.651 (16.00), 2.671 (2.69), 2.679 (0.96), 3.886 (2.06), 3.904 (2.09), 7.237 (0.54), 7.259 (0.41), 7.278 (0.48), 7.964 (2.18), 7.985 (2.48), 8.347 (1.10), 8.367 (1.02), 8.502 (0.70), 8.719 (0.47), 9.103 (2.10), 9.549 (0.50).

Example 535

N-{1-(cyclopropylmethyl)-4-methyl-3-[6-(trifluoromethyl)pyridin-3-yl]-1H-pyrazol-5-yl}-6-(4-methoxy-3,5-dimethyl-1H-pyrazol-1-yl)pyrimidin-4-amine

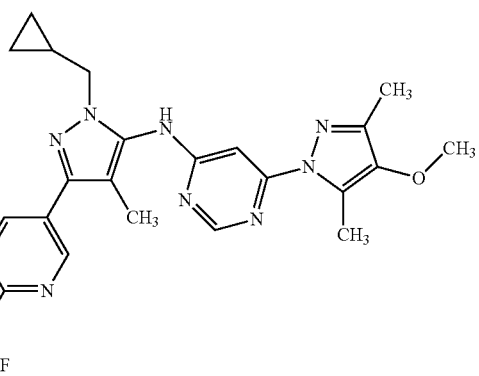

A microwave vial was charged 4-chloro-6-(4-methoxy-3,5-dimethyl-1H-pyrazol-1-yl)pyrimidine (100 mg, 420 µmol) and 1-(cyclopropylmethyl)-4-methyl-3-[6-(trifluoromethyl)pyridin-3-yl]-1H-pyrazol-5-amine (137 mg, 462 µmol) and the contents were suspended in 1,4-dioxane (2.2 ml, 26 mmol). The reaction mixture was degassed with Ar for 3 min. Tris(dibenzylidenaceton)dipalladium (11.5 mg, 12.6 mol) and Xantphos (14.6 mg, 25.2 µmol) were added and the reaction mixture was degassed again for 1 min and heated to 85° C. At this temperature and sodium phenolate (53.7 mg, 462 µmol) was added. The vial was sealed and heated at 85° C. for 90 minutes while vigorously stirring. After cooling to ambient temperature, the reaction mixture was diluted with water and extracted with dichloromethane (2×). The combined organics were filtered over a column Chromabond PTS and concentrated under reduced pressure. The crude product was purified by preparative HPLC (method 4) to yield the desired product (92.0 mg, 44%).

LC-MS (Method 10): $R_t$=2.24 min; MS (ESIpos): m/z=499 [M+H]$^+$ $^1$H-NMR (400 MHz, DMSO-d6) δ [ppm]: 0.008 (0.47), 0.314 (2.40), 0.325 (2.70), 0.438 (2.40), 0.458 (2.60), 1.202 (0.66), 1.209 (0.63), 1.220 (0.98), 1.238 (0.63), 2.086 (16.00), 2.187 (3.69), 2.329 (0.52), 2.524 (1.60), 2.671 (0.56), 3.702 (14.04), 3.883 (2.51), 3.901 (2.45), 7.963 (2.55), 7.984 (2.81), 8.346 (1.28), 8.367 (1.17), 8.454 (1.03), 9.105 (2.42), 9.435 (0.89).

Example 536

N-{3-[4-(difluoromethyl)phenyl]-1-(2-methoxyethyl)-4-methyl-1H-pyrazol-5-yl}-6-(3,5-dimethyl-1H-pyrazol-1-yl)pyrimidin-4-amine

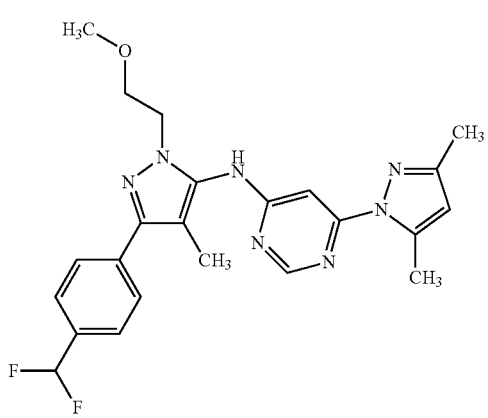 [SMILES: COCCn1nc(-c2ccc(C(F)F)cc2)c(C)c1Nc1cc(-n2nc(C)cc2C)ncn1]

A microwave vial was charged 4-chloro-6-(3,5-dimethyl-1H-pyrazol-1-yl)pyrimidine (67.4 mg, 323 µmol) and 3-[4-(difluoromethyl)phenyl]-1-(2-methoxyethyl)-4-methyl-1H-pyrazol-5-amine (100 mg, 355 µmol) and the contents were suspended in 1,4-dioxane (1.8 ml, 22 mmol). The reaction mixture was degassed with Ar for 3 min. Tris(dibenzylidenaceton)dipalladium (8.88 mg, 9.69 µmol) and Xantphos (11.2 mg, 19.4 µmol) were added and the reaction mixture was degassed again for 1 min and heated to 85° C. At this temperature and sodium phenolate (41.3 mg, 355 µmol) was added. The vial was sealed and heated at 85° C. for 60 minutes while vigorously stirring. After cooling to ambient temperature, the reaction mixture was diluted with water and extracted with dichloromethane (2×). The combined organics were dried over sodium sulfate and concentrated under reduced pressure. The crude product was purified by preparative HPLC (Method 3) to yield the desired product (66.7 mg, 46%).

LC-MS (Method 10): $R_t$=2.15 min; MS (ESIpos): m/z=454 [M+H]$^+$ $^1$H-NMR (400 MHz, DMSO-d6) δ [ppm]: −0.008 (0.40), 2.044 (16.00), 2.168 (3.74), 2.188 (1.35), 2.328 (0.50), 2.524 (1.34), 2.630 (14.36), 2.653 (0.65), 2.670 (0.54), 2.675 (0.58), 3.153 (8.78), 3.171 (0.64), 3.660 (2.03), 3.674 (4.36), 3.688 (2.26), 4.136 (1.63), 6.141 (3.03), 6.937 (1.44), 7.077 (3.02), 7.217 (1.26), 7.636 (2.88), 7.656 (3.51), 7.844 (2.99), 7.863 (2.50), 8.471 (1.23), 9.339 (2.78).

Example 537

6-(4-chloro-3,5-dimethyl-1H-pyrazol-1-yl)-N-{3-[4-(difluoromethyl)phenyl]-1-(2-methoxyethyl)-4-methyl-1H-pyrazol-5-yl}pyrimidin-4-amine

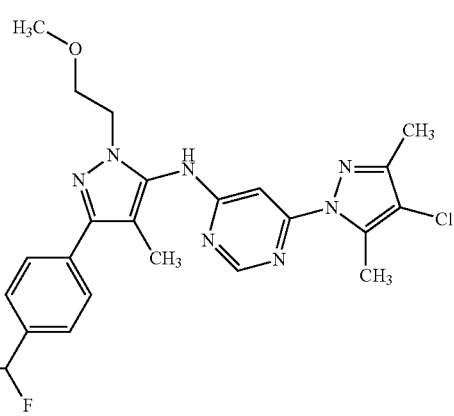

A microwave vial was charged 4-chloro-6-(4-chloro-3,5-dimethyl-1H-pyrazol-1-yl)pyrimidine (78.6 mg, 323 µmol) and 3-[4-(difluoromethyl)phenyl]-1-(2-methoxyethyl)-4-methyl-1H-pyrazol-5-amine (100 mg, 355 µmol) and the contents were suspended in 1,4-dioxane (1.7 ml, 20 mmol). The reaction mixture was degassed with Ar for 3 min. Tris(dibenzylidenaceton)dipalladium (8.88 mg, 9.69 µmol) and Xantphos (11.2 mg, 19.4 µmol) were added and the reaction mixture was degassed again for 1 min and heated to 85° C. At this temperature and sodium phenolate (41.3 mg, 355 µmol) was added. The vial was sealed and heated at 85° C. for 90 minutes while vigorously stirring. After cooling to ambient temperature, the reaction mixture was diluted with water and extracted with dichloromethane (2×). The combined organics were dried over sodium sulfate and concentrated under reduced pressure. The crude product was purified by preparative HPLC (Method 4) to yield the desired product (101 mg, 64%).

LC-MS (Method 10): $R_t$=2.44 min; MS (ESIpos): m/z=488 [M+H]$^+$ $^1$H-NMR (400 MHz, DMSO-d6) δ [ppm]: 1.074 (0.64), 1.091 (1.30), 1.109 (0.65), 2.043 (14.92), 2.207 (2.62), 2.524 (0.62), 2.648 (16.00), 3.146 (4.92), 3.168 (0.58), 3.375 (0.65), 3.392 (0.63), 3.658 (1.76), 3.672 (3.72), 3.685 (1.95), 4.139 (1.36), 6.938 (1.28), 7.078 (2.66), 7.218 (1.15), 7.636 (2.55), 7.657 (3.21), 7.843 (2.52), 7.863 (2.16), 8.507 (0.71), 9.443 (1.50).

Example 538

6-[5-(difluoromethyl)-3-methyl-1H-pyrazol-1-yl]-N-{3-[4-(difluoromethyl)phenyl]-1-(2-methoxyethyl)-4-methyl-1H-pyrazol-5-yl}pyrimidin-4-amine

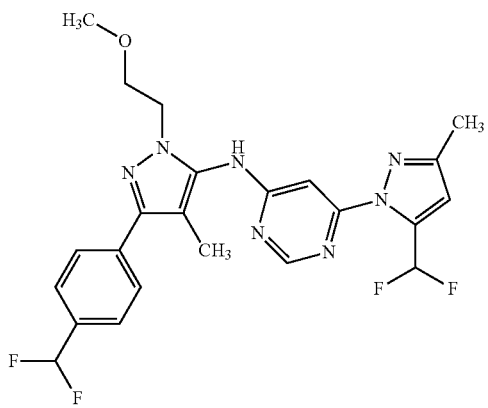 [SMILES: COCCn1nc(-c2ccc(C(F)F)cc2)c(C)c1Nc1cc(-n2nc(C)cc2C(F)F)ncn1]

A microwave vial was charged 4-chloro-6-[5-(difluoromethyl)-3-methyl-H-pyrazol-1-yl]pyrimidine (85.9 mg, 351 µmol) and 3-[4-(difluoromethyl)phenyl]-1-(2-methoxyethyl)-4-methyl-1H-pyrazol-5-amine (150 mg, 72% purity, 386 µmol) and the contents were suspended in 1,4-dioxane (1.8 ml, 21 mmol). The reaction mixture was degassed with Ar for 3 min. Tris(dibenzylidenaceton)dipalladium (9.64 mg, 10.5 µmol) and Xantphos (12.2 mg, 21.1 µmol) were added and the reaction mixture was degassed again for 1 min and heated to 85° C. At this temperature and sodium phenolate (44.8 mg, 386 µmol) was added. The vial was sealed and heated at 85° C. for 90 minutes while vigorously stirring. As the conversion was not completed the mixture was again treated with (9.64 mg, 10.5 µmol) and (12.2 mg, 21.1 µmol) and stirred for 2 hours at 85° C. After cooling to ambient temperature 20 mg of sodium phenolate were added (0.17 mmol) and the mixture was stirred further for 2 hours at 85° C. The mixture was purified by preparative HPLC (method: column: Reprosil C18; 10 µm; 125×30 mm/flow: 50 ml/min/eluent: A=H2O (0.01% HCOOH), B=acetonitrile/gradient: 0.00-5.00 min=10% B, 6.50 min=20% B, 17.0-19.75 min=100% B, 19.75-23.00 min=90% B) and subsequent flash-chromatography (column: SNAP KP-Sil 10 g, solvent: dichloromethane/ethyl acetate 88/12 to 100% ethyl acetate) to yield 30.2 mg (17%) of the desired product.

LC-MS (Method 10): $R_t$=2.22 min; MS (ESIpos): m/z=490 [M+H]$^+$ $^1$H-NMR (400 MHz, DMSO-d6) δ [ppm]: −0.008 (1.22), 0.008 (1.02), 1.988 (0.53), 2.047 (16.00), 2.278 (2.04), 2.328 (0.45), 3.139 (3.27), 3.182 (0.43), 3.568 (0.65), 3.657 (1.92), 3.671 (3.86), 3.685 (2.05), 4.143 (1.34), 6.781 (2.22), 6.939 (1.44), 7.079 (2.97), 7.219 (1.31), 7.639 (2.83), 7.659 (3.49), 7.687 (1.42), 7.823 (2.93), 7.848 (2.16), 7.868 (1.85), 7.959 (1.25), 8.503 (0.57), 9.525 (1.16).

Example 539

N-{3-[4-(difluoromethyl)phenyl]-1-(2-methoxyethyl)-4-methyl-1H-pyrazol-5-yl}-6-(4-methoxy-3,5-dimethyl-1H-pyrazol-1-yl)pyrimidin-4-amine

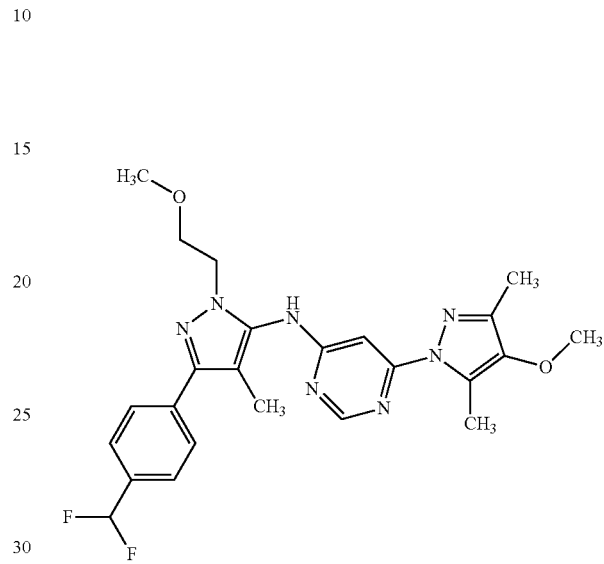

A microwave vial was charged 4-chloro-6-(4-methoxy-3,5-dimethyl-1H-pyrazol-1-yl)pyrimidine (77.1 mg, 323 µmol) and 3-[4-(difluoromethyl)phenyl]-1-(2-methoxyethyl)-4-methyl-1H-pyrazol-5-amine (100 mg, 355 µmol) and the contents were suspended in 1,4-dioxane (1.7 ml, 20 mmol). The reaction mixture was degassed with Ar for 3 min. Tris(dibenzylidenaceton)dipalladium (8.88 mg, 9.69 µmol) and Xantphos (11.2 mg, 19.4 µmol) were added and the reaction mixture was degassed again for 1 min and heated to 85° C. At this temperature and sodium phenolate (41.3 mg, 355 µmol) was added. The vial was sealed and heated at 85° C. for 120 minutes while vigorously stirring. After cooling to ambient temperature, the reaction mixture was diluted with water and extracted with dichloromethane (2×). The combined organics were dried over sodium sulfate and concentrated under reduced pressure. The crude product was purified by preparative HPLC (method 3) and subsequent by flash-chromatography (column: SNAP KP-Sil 10 g, solvent: dichloromethane/ethyl acetate 88/12 to 100% ethyl acetate) to yield the desired product (55.75 mg, 36%).

LC-MS (Method 10): $R_t$=2.11 min; MS (ESIpos): m/z=484 [M+H]$^+$ $^1$H-NMR (400 MHz, DMSO-d6) δ [ppm]: −0.008 (0.51), 0.008 (0.48), 1.525 (0.68), 2.038 (16.00), 2.177 (3.56), 2.328 (0.59), 2.523 (1.69), 2.670 (0.61), 3.151 (9.11), 3.171 (0.53), 3.656 (2.05), 3.670 (4.37), 3.684 (2.60), 3.697 (13.32), 4.134 (1.63), 6.936 (1.39), 7.076 (2.91), 7.217 (1.22), 7.635 (2.91), 7.655 (3.50), 7.841 (3.05), 7.861 (2.49), 8.452 (1.15), 9.325 (2.70).

Example 540

4-(3-{[6-(4-chloro-3,5-dimethyl-1H-pyrazol-1-yl)pyrimidin-4-yl]amino}-4-methoxy-1-methyl-1H-pyrazol-5-yl)benzonitrile

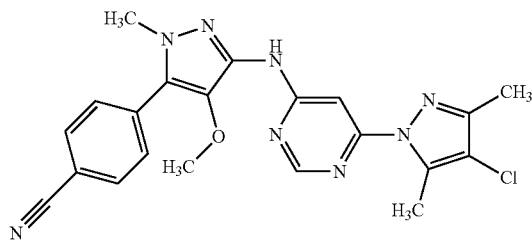

A microwave vial was charged 4-chloro-6-(4-chloro-3,5-dimethyl-1H-pyrazol-1-yl)pyrimidine (96.8 mg, 398 µmol) and 4-(3-amino-4-methoxy-1-methyl-1H-pyrazol-5-yl)benzonitrile (100 mg, 438 µmol) and the contents were suspended in 1,4-dioxane (6.0 ml, 70 mmol). The reaction mixture was degassed with Ar for 3 min. Tris(dibenzylidenaceton)dipalladium (10.9 mg, 11.9 µmol) and Xantphos (13.8 mg, 23.9 µmol) were added and the reaction mixture was degassed again for 1 min and heated to 85° C. At this temperature and sodium phenolate (50.9 mg, 438 µmol) was added. The vial was sealed and heated at 85° C. for 90 minutes while vigorously stirring. After cooling to ambient temperature, the reaction mixture was diluted with water and extracted with dichloromethane (2×). The combined organics were filtered over a column Chromabond PTS and concentrated under reduced pressure. The crude product was purified by preparative HPLC (method 3) to yield the desired product (90.0 mg, 49%).

LC-MS (Method 10): $R_t$=2.14 min; MS (ESIpos): m/z=435 [M+H]$^+$ $^1$H-NMR (400 MHz, DMSO-d6) δ [ppm]: 2.074 (0.97), 2.215 (11.60), 2.328 (0.53), 2.642 (12.80), 2.670 (0.55), 3.560 (16.00), 3.785 (12.67), 7.226 (3.39), 7.341 (0.53), 7.382 (0.66), 7.461 (0.93), 7.465 (0.93), 7.478 (0.56), 7.772 (3.27), 7.793 (4.37), 7.814 (0.48), 7.820 (0.50), 8.004 (3.92), 8.025 (3.22), 8.490 (3.00), 9.550 (1.37).

Example 541

4-[3-({6-[3,5-dimethyl-4-(trifluoromethyl)-1H-pyrazol-1-yl]pyrimidin-4-yl}amino)-4-methoxy-1-methyl-1H-pyrazol-5-yl]benzonitrile

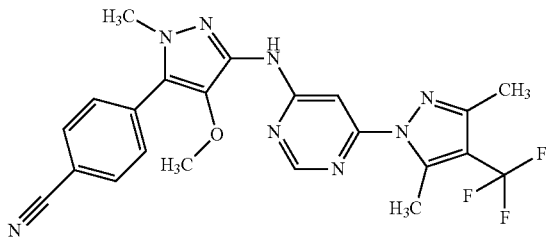 [SMILES: COc1c(Nc2cc(-n3nc(C)c(C(F)(F)F)c3C)ncn2)nn(C)c1-c1ccc(C#N)cc1]

A microwave vial was charged 4-chloro-6-[3,5-dimethyl-4-(trifluoromethyl)-1H-pyrazol-1-yl]pyrimidine (110 mg, 398 µmol) and 4-(3-amino-4-methoxy-1-methyl-1H-pyrazol-5-yl)benzonitrile (100 mg, 438 µmol) and the contents were suspended in 1,4-dioxane (6.0 ml, 70 mmol). The reaction mixture was degassed with Ar for 3 min. Tris(dibenzylidenaceton)dipalladium (10.9 mg, 11.9 µmol) and Xantphos (13.8 mg, 23.9 µmol) were added and the reaction mixture was degassed again for 1 min and heated to 85° C. At this temperature and sodium phenolate (50.9 mg, 438 µmol) was added. The vial was sealed and heated at 85° C. for 120 minutes while vigorously stirring. After cooling to ambient temperature, the reaction mixture was diluted with water and extracted with dichloromethane (2×). The combined organics were filtered over a column Chromabond PTS and concentrated under reduced pressure. The crude product was purified by preparative HPLC (method 3) to yield the desired product (45.0 mg, 24%).

LC-MS (Method 10): $R_t$=2.15 min; MS (ESIpos): m/z=469 [M+H]$^+$ $^1$H-NMR (400 MHz, DMSO-d6) δ [ppm]: 2.074 (1.99), 2.304 (6.31), 2.328 (0.51), 2.671 (0.40), 2.744 (6.56), 3.564 (16.00), 3.782 (13.19), 7.251 (3.38), 7.772 (3.38), 7.793 (4.07), 8.005 (4.00), 8.026 (3.27), 8.544 (2.94), 9.686 (0.91).

Example 542

6-(3,5-dimethyl-1H-pyrazol-1-yl)-N-[3-(5-fluoropyridin-2-yl)-1-(2-methoxyethyl)-4-methyl-1H-pyrazol-5-yl]pyrimidin-4-amine

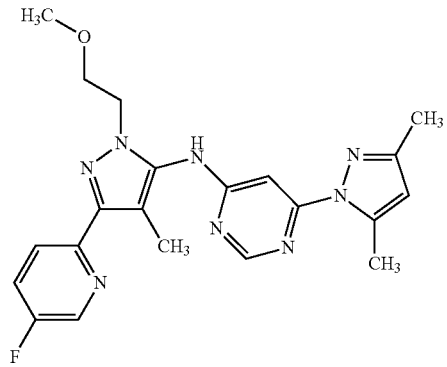 [SMILES: COCCn1nc(-c2ccc(F)cn2)c(C)c1Nc1cc(-n2nc(C)cc2C)ncn1]

A microwave vial was charged 4-chloro-6-(3,5-dimethyl-1H-pyrazol-1-yl)pyrimidine (79.6 mg, 381 µmol) and 3-(5-fluoropyridin-2-yl)-1-(2-methoxyethyl)-4-methyl-1H-pyrazol-5-amine (105 mg, 420 µmol) and the contents were suspended in 1,4-dioxane (2.5 ml, 29 mmol). The reaction mixture was degassed with Ar for 3 min. Tris(dibenzylidenaceton)dipalladium (10.5 mg, 11.4 µmol) and Xantphos (13.2 mg, 22.9 µmol) were added and the reaction mixture was degassed again for 1 min and heated to 85° C. At this temperature and sodium phenolate (48.7 mg, 420 µmol) was added. The vial was sealed and heated at 85° C. for 60 minutes while vigorously stirring. After cooling to ambient temperature, the reaction mixture was diluted with water and extracted with dichloromethane (2×). The combined organics were dried over sodium sulfate and concentrated under reduced pressure. The crude product was purified by preparative HPLC (method 3) to yield the desired product (48.6 mg, 29%).

LC-MS (Method 10): $R_t$=2.01 min; MS (ESIpos): m/z=423 [M+H]$^+$ $^1$H-NMR (400 MHz, DMSO-d6) δ [ppm]: −0.008 (0.49), 0.008 (0.43), 2.142 (16.00), 2.156 (2.93), 2.228 (1.41), 2.328 (0.41), 2.524 (1.12), 2.626 (13.06), 2.664 (1.25), 2.670 (0.46), 3.146 (5.91), 3.659 (1.79), 3.673 (3.75), 3.686 (1.94), 4.147 (1.33), 6.135 (2.31), 7.752 (0.61), 7.759 (0.65), 7.774 (1.32), 7.781 (1.39), 7.796 (0.75), 7.803 (0.77), 7.982 (0.94), 7.994 (1.00), 8.004 (0.85), 8.016 (0.77), 8.464 (0.70), 8.594 (2.23), 8.601 (2.22), 9.333 (2.75).

Example 543

6-[5-(difluoromethyl)-3-methyl-1H-pyrazol-1-yl]-N-[3-(5-fluoropyridin-2-yl)-1-(2-methoxyethyl)-4-methyl-1H-pyrazol-5-yl]pyrimidin-4-amine

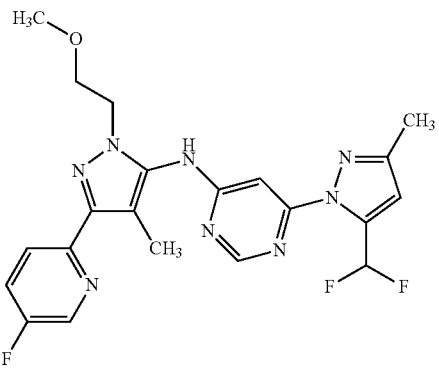 [SMILES: COCCn1nc(-c2ccc(F)cn2)c(C)c1Nc1cc(-n2nc(C)cc2C(F)F)ncn1]

A microwave vial was charged 4-chloro-6-[5-(difluoromethyl)-3-methyl-H-pyrazol-1-yl]pyrimidine (93.3 mg, 381 µmol) and 3-(5-fluoropyridin-2-yl)-1-(2-methoxyethyl)-4-methyl-1H-pyrazol-5-amine (105 mg, 420 µmol) and the contents were suspended in 1,4-dioxane (2.5 ml, 29 mmol). The reaction mixture was degassed with Ar for 3 min. Tris(dibenzylidenaceton)dipalladium (10.5 mg, 11.4 µmol) and Xantphos (13.2 mg, 22.9 µmol) were added and the reaction mixture was degassed again for 1 min and heated to 85° C. At this temperature and sodium phenolate (48.7 mg, 420 µmol) was added. The vial was sealed and heated at 85° C. for 60 minutes while vigorously stirring. After cooling to ambient temperature, the reaction mixture was diluted with water and extracted with dichloromethane (2×). The combined organics were filtered over a column Chromabond PTS and concentrated under reduced pressure. The crude product was purified by preparative HPLC (method 3) to yield the desired product (32.1 mg, 18%).

LC-MS (Method 10): $R_t$=2.12 min; MS (ESIpos): m/z=459 [M+H]$^+$ $^1$H-NMR (400 MHz, DMSO-d6) δ [ppm]: −0.008 (0.85), 0.008 (0.66), 2.145 (16.00), 2.266 (1.41), 2.323 (0.67), 2.328 (0.82), 2.332 (0.65), 2.523 (1.95), 2.665 (0.54), 2.670 (0.74), 2.675 (0.54), 2.697 (0.51), 3.131 (2.15), 3.656 (1.57), 3.670 (3.12), 3.683 (1.69), 4.152 (1.01), 6.775 (1.77), 7.683 (1.27), 7.757 (0.44), 7.764 (0.52), 7.779 (1.04), 7.787 (1.13), 7.801 (0.66), 7.809 (0.68), 7.819 (2.62), 7.955 (1.15), 7.987 (0.66), 7.999 (0.75), 8.009 (0.70), 8.599 (1.99), 8.606 (2.02), 9.524 (1.07).

Example 544

N-[3-(5-fluoropyridin-2-yl)-1-(2-methoxyethyl)-4-methyl-1H-pyrazol-5-yl]-6-(4-methoxy-3,5-dimethyl-1H-pyrazol-1-yl)pyrimidin-4-amine

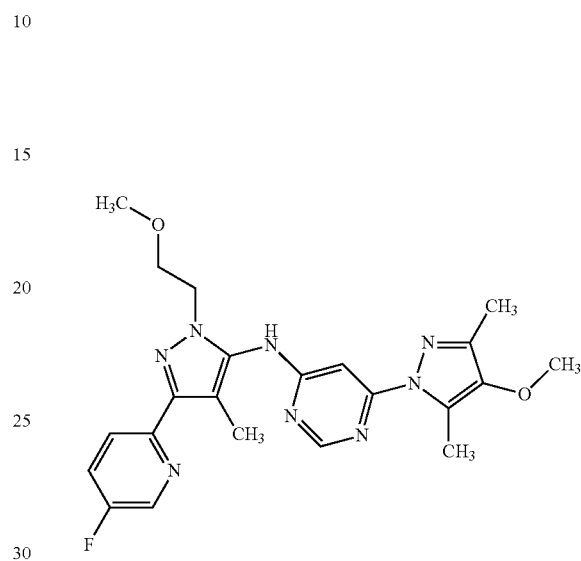

A microwave vial was charged 4-chloro-6-(4-methoxy-3,5-dimethyl-1H-pyrazol-1-yl)pyrimidine (91.0 mg, 381 µmol) and 3-(5-fluoropyridin-2-yl)-1-(2-methoxyethyl)-4-methyl-1H-pyrazol-5-amine (105 mg, 420 µmol) and the contents were suspended in 1,4-dioxane (2.5 ml, 29 mmol). The reaction mixture was degassed with Ar for 3 min. Tris(dibenzylidenaceton)dipalladium (10.5 mg, 11.4 µmol) and Xantphos (13.2 mg, 22.9 µmol) were added and the reaction mixture was degassed again for 1 min and heated to 85° C. At this temperature and sodium phenolate (48.7 mg, 420 µmol) was added. The vial was sealed and heated at 85° C. for 120 minutes while vigorously stirring. After cooling to ambient temperature, the reaction mixture was diluted with water and extracted with dichloromethane (2×). The combined organics were dried over sodium sulfate and concentrated under reduced pressure. The crude product was purified by preparative HPLC (method 3) and subsequent flash-chromatography (column: SNAP KP_Sil 10 g, solvent: dichloromethane/ethyl acetate 88/12 to 0/100) to yield the desired product (70.0 mg, 41%).

LC-MS (Method 10): $R_t$=1.96 min; MS (ESIpos): m/z=453 [M+H]$^+$ $^1$H-NMR (400 MHz, DMSO-d6) δ [ppm]: −0.008 (0.48), 2.041 (0.40), 2.137 (16.00), 2.166 (2.74), 2.328 (0.48), 2.524 (1.29), 2.671 (0.45), 3.145 (6.73), 3.655 (1.80), 3.670 (3.83), 3.693 (11.51), 4.143 (1.33), 7.751 (0.61), 7.759 (0.66), 7.774 (1.36), 7.781 (1.44), 7.796 (0.79), 7.803 (0.77), 7.981 (0.99), 7.993 (1.07), 8.004 (0.91), 8.015 (0.82), 8.448 (0.88), 8.594 (2.54), 8.601 (2.51), 9.320 (2.68).

Example 545 ethyl 1-(6-{[3-(5-fluoropyridin-2-yl)-1-(2-methoxy-ethyl)-4-methyl-1H-pyrazol-5-yl]amino}pyrimidin-4-yl)-3,5-dimethyl-1H-pyrazole-4-carboxylate

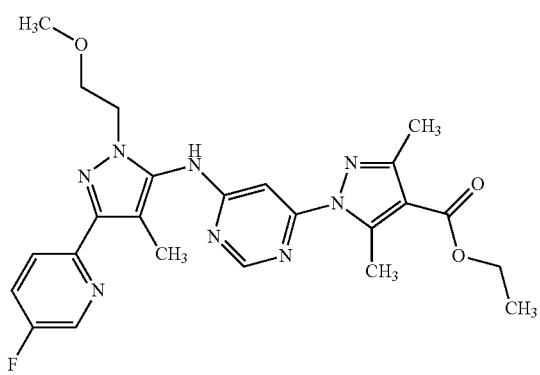 [SMILES: CCOC(=O)c1c(C)nn(-c2cc(Nc3c(C)c(-c4ccc(F)cn4)nn3CCOC)ncn2)c1C]

A microwave vial was charged ethyl 1-(6-chloropyrimidin-4-yl)-3,5-dimethyl-1H-pyrazole-4-carboxylate (107 mg, 381 µmol) and 3-(5-fluoropyridin-2-yl)-1-(2-methoxy-ethyl)-4-methyl-1H-pyrazol-5-amine (105 mg, 420 µmol) and the contents were suspended in 1,4-dioxane (2.5 ml, 29 mmol). The reaction mixture was degassed with Ar for 3 min. Tris(dibenzylidenaceton)dipalladium (10.5 mg, 11.4 µmol) and Xantphos (13.2 mg, 22.9 µmol) were added and the reaction mixture was degassed again for 1 min and heated to 85° C. At this temperature and sodium phenolate (48.7 mg, 420 µmol) was added. The vial was sealed and heated at 85° C. for 60 minutes while vigorously stirring. After cooling to ambient temperature, the reaction mixture was diluted with water and extracted with dichloromethane (2×). The combined organics were dried over sodium sulfate and concentrated under reduced pressure. The crude product was purified by preparative HPLC (method 3) to yield the desired product (82.5 mg, 44%).

LC-MS (Method 10): $R_t$=2.18 min; MS (ESIpos): m/z=495 [M+H]$^+$ $^1$H-NMR (400 MHz, DMSO-d6) δ [ppm]: 1.283 (2.98), 1.301 (6.03), 1.319 (3.03), 2.145 (16.00), 2.358 (1.75), 2.524 (1.24), 2.671 (0.44), 2.904 (12.52), 3.143 (3.24), 3.659 (1.66), 3.672 (3.33), 3.686 (1.77), 4.146 (1.24), 4.224 (0.97), 4.241 (2.70), 4.259 (2.66), 4.277 (0.92), 7.751 (0.58), 7.758 (0.66), 7.773 (1.29), 7.781 (1.38), 7.795 (0.76), 7.803 (0.74), 7.980 (0.95), 7.991 (1.03), 8.001 (0.91), 8.013 (0.80), 8.538 (0.54), 8.593 (2.56), 8.600 (2.57), 9.512 (1.17).

Example 546 ethyl 1-[6-({3-[4-(difluoromethyl)phenyl]-1-(2-methoxyethyl)-4-methyl-1H-pyrazol-5-yl}amino)pyrimidin-4-yl]-3,5-dimethyl-1H-pyrazole-4-carboxylate

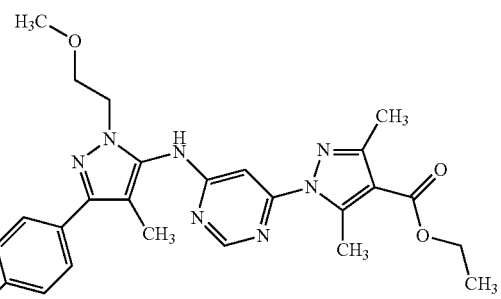

A microwave vial was charged ethyl 1-(6-chloropyrimidin-4-yl)-3,5-dimethyl-1H-pyrazole-4-carboxylate (227 mg, 808 µmol) and 3-[4-(difluoromethyl)phenyl]-1-(2-methoxy-ethyl)-4-methyl-1H-pyrazol-5-amine (250 mg, 889 µmol) and the contents were suspended in 1,4-dioxane (4.6 ml, 54 mmol). The reaction mixture was degassed with Ar for 3 min. Tris(dibenzylidenaceton)dipalladium (22.2 mg, 24.2 µmol) and Xantphos (28.0 mg, 48.5 µmol) were added and the reaction mixture was degassed again for 1 min and heated to 85° C. At this temperature and sodium phenolate (103 mg, 889 µmol) was added. The vial was sealed and heated at 85° C. for 60 minutes while vigorously stirring. After cooling to ambient temperature, the reaction mixture was diluted with water and extracted with dichloromethane (2×). The combined organics were dried over sodium sulfate and concentrated under reduced pressure. The crude product was purified by preparative HPLC (method 4) to yield the desired product (153 mg, 34%).

LC-MS (Method 10): $R_t$=2.29 min; MS (ESIpos): m/z=526 [M+H]$^+$ $^1$H-NMR (400 MHz, DMSO-d6) δ [ppm]: −0.008 (0.46), 1.287 (3.51), 1.304 (7.18), 1.322 (3.57), 2.046 (16.00), 2.329 (0.74), 2.333 (0.68), 2.368 (2.55), 2.524 (1.47), 2.671 (0.51), 2.908 (13.13), 3.148 (4.42), 3.651 (2.04), 3.659 (2.02), 3.673 (3.92), 3.687 (2.07), 4.143 (1.45), 4.228 (1.11), 4.245 (3.20), 4.263 (3.17), 4.281 (1.05), 6.938 (1.40), 7.077 (3.07), 7.217 (1.30), 7.342 (1.44), 7.382 (1.62), 7.461 (2.27), 7.465 (2.43), 7.478 (1.44), 7.636 (2.97), 7.656 (3.64), 7.781 (1.39), 7.790 (1.12), 7.794 (1.31), 7.807 (0.98), 7.814 (1.16), 7.821 (1.33), 7.841 (2.92), 7.861 (2.49), 8.548 (0.72), 9.518 (1.09).

Example 547

4-[5-({6-[3,5-dimethyl-4-(trifluoromethyl)-1H-pyrazol-1-yl]pyrimidin-4-yl}amino)-1,4-dimethyl-1H-pyrazol-3-yl]benzonitrile

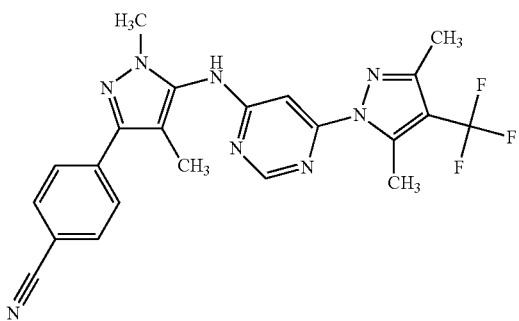 [SMILES: Cc1nn(-c2cc(Nc3c(C)c(-c4ccc(C#N)cc4)nn3C)ncn2)c(C)c1C(F)(F)F]

A microwave vial was charged with 4-chloro-6-[3,5-dimethyl-4-(trifluoromethyl)-1H-pyrazol-1-yl]pyrimidine (112 mg, 95% purity, 385 μmol) and 4-(5-amino-1,4-dimethyl-1H-pyrazol-3-yl)benzonitrile (100 mg, 90% purity, 424 μmol) and the contents were suspended in dioxane (1.2 mL). The reaction mixture was degassed with Ar for 3 min. Tris(dibenzylideneacetone)dipalladium (7.06 mg, 7.71 μmol) and XantPhos (8.92 mg, 15.4 μmol) were added and the reaction mixture was degassed again for 1 min. Lastly, sodium phenolate (49.2 mg, 424 μmol) was added, the vial was sealed and heated at 85° C. overnight while vigorously shaking. After cooling to ambient temperature, the reaction mixture was diluted with dimethylsulfoxide and the precipitated solid was collected by filtration. The solid was redissolved in dichloromethane and purified by flash column chromatography (SNAP Ultra 10 g, cyclohexane/EtOAc gradient) to yield the desired product (16 mg, 9% yield).

LC-MS (method 11): $R_t$=1.51 min; MS (ESIpos): m/z=453 [M+H]$^+$ $^1$H-NMR (400 MHz, DMSO-d6) δ [ppm]: −0.008 (1.01), 0.008 (1.04), 1.235 (1.57), 1.489 (0.41), 2.076 (13.10), 2.193 (0.92), 2.285 (1.24), 2.309 (2.21), 2.759 (6.27), 3.702 (7.50), 7.896 (16.00), 8.554 (0.49), 9.670 (0.77).

Example 548

6-[5-(difluoromethyl)-3-methyl-1H-pyrazol-1-yl]-N-{1,4-dimethyl-3-[6-(trifluoromethyl)pyridin-3-yl]-1H-pyrazol-5-yl}pyrimidin-4-amine

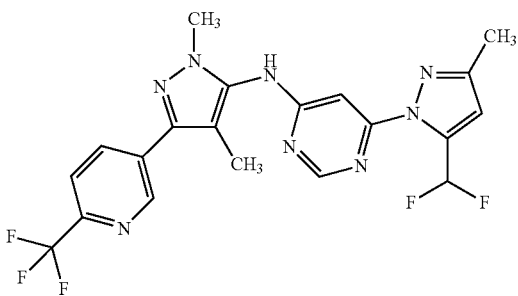 [SMILES: Cc1cc(C(F)F)n(-c2cc(Nc3c(C)c(-c4ccc(C(F)(F)F)nc4)nn3C)ncn2)n1]

A microwave vial was charged 4-chloro-6-[5-(difluoromethyl)-3-methyl-H-pyrazol-1-yl]pyrimidine (108 mg, 443 μmol) and 1,4-dimethyl-3-[6-(trifluoromethyl)pyridin-3-yl]-1H-pyrazol-5-amine (125 mg, 488 μmol) and the contents were suspended in 1,4-dioxane (2.3 ml, 27 mmol). The reaction mixture was degassed with Ar for 3 min. Tris(dibenzylideneaceton)dipalladium (12.2 mg, 13.3 μmol) and Xantphos (15.4 mg, 26.6 μmol) were added and the reaction mixture was degassed again for 1 min and heated to 85° C. At this temperature and sodium phenolate (56.6 mg, 488 μmol) was added. The vial was sealed and heated at 85° C. for 120 minutes while vigorously stirring. After cooling to ambient temperature, the reaction mixture was diluted with water and extracted with DCM (2×). The combined organics were filtered over a column Chromabond PTS and concentrated under reduced pressure. The crude product was purified by preparative HPLC (method 4) to yield the desired product (83.0 mg, 36%).

LC-MS (Method 10): $R_t$=2.15 min; MS (ESIpos): m/z=465 [M+H]$^+$ $^1$H-NMR (400 MHz, DMSO-d6) δ [ppm]: −0.008 (0.64), 0.008 (0.57), 1.091 (0.54), 1.647 (0.82), 2.104 (16.00), 2.295 (2.73), 3.727 (8.48), 6.796 (2.66), 7.369 (0.64), 7.385 (0.60), 7.399 (0.76), 7.685 (1.20), 7.821 (2.45), 7.959 (2.68), 7.980 (2.34), 8.337 (1.02), 8.358 (0.94), 8.512 (0.61), 9.097 (1.76), 9.673 (1.14).

Example 549

6-(3,5-dimethyl-H-pyrazol-1-yl)-N-{1,4-dimethyl-3-[6-(trifluoromethyl)pyridin-3-yl]-1H-pyrazol-5-yl}pyrimidin-4-amine

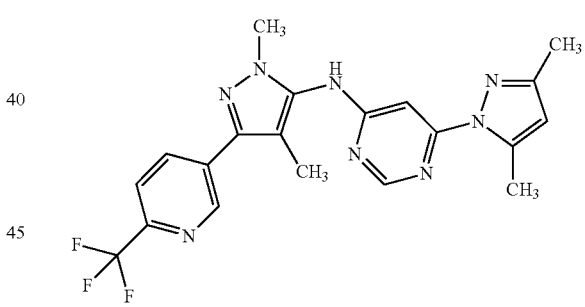

A microwave vial was charged 4-chloro-6-(3,5-dimethyl-1H-pyrazol-1-yl)pyrimidine (94.0 mg, 451 μmol) and 1,4-dimethyl-3-[6-(trifluoromethyl)pyridin-3-yl]-1H-pyrazol-5-amine (127 mg, 496 μmol) and the contents were suspended in 1,4-dioxane (2.3 ml, 27 mmol). The reaction mixture was degassed with Ar for 3 min. Tris(dibenzylidenaceton)dipalladium (12.4 mg, 13.5 μmol) and Xantphos (15.6 mg, 27.0 μmol) were added and the reaction mixture was degassed again for 1 min and heated to 85° C. At this temperature and sodium phenolate (57.5 mg, 496 μmol) was added. The vial was sealed and heated at 85° C. for 120 minutes while vigorously stirring. After cooling to ambient temperature, the reaction mixture was diluted with water and extracted with DCM (2×). The combined organics were filtered over a column Chromabond PTS and concentrated under reduced pressure. The crude product was purified by preparative HPLC (method 3) to yield the desired product (90.0 mg, 47%).

LC-MS (Method 10): $R_t$=2.06 min; MS (ESIpos): m/z=429 [M+H]$^+$ $^1$H-NMR (400 MHz, DMSO-d6) δ [ppm]: −0.008 (0.71), 0.008 (0.69), 1.074 (0.73), 1.091 (1.48), 1.109 (0.74), 2.101 (16.00), 2.183 (4.74), 2.635 (13.30), 3.375 (0.75), 3.392 (0.74), 3.720 (12.00), 6.154 (2.94), 7.957 (2.23), 7.978 (2.51), 8.332 (1.18), 8.353 (1.08), 8.479 (1.08), 9.096 (1.96), 9.491 (2.40).

Example 550

6-(4-chloro-3,5-dimethyl-1H-pyrazol-1-yl)-N-{1,4-dimethyl-3-[6-(trifluoromethyl)pyridin-3-yl]-1H-pyrazol-5-yl}pyrimidin-4-amine

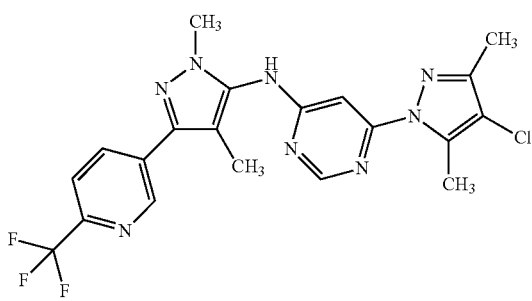 [SMILES: Cc1nn(-c2cc(Nc3c(C)c(-c4ccc(C(F)(F)F)nc4)nn3C)ncn2)c(C)c1Cl]

A microwave vial was charged 4-chloro-6-(4-chloro-3,5-dimethyl-1H-pyrazol-1-yl)pyrimidine (110 mg, 454 μmol) and 1,4-dimethyl-3-[6-(trifluoromethyl)pyridin-3-yl]-1H-pyrazol-5-amine (128 mg, 500 μmol) and the contents were suspended in 1,4-dioxane (2.4 ml, 28 mmol). The reaction mixture was degassed with Ar for 3 min. Tris(dibenzylidenaceton)dipalladium (12.5 mg, 13.6 μmol) and Xantphos (15.8 mg, 27.2 μmol) were added and the reaction mixture was degassed again for 1 min and heated to 85° C. At this temperature and sodium phenolate (58.0 mg, 500 μmol) was added. The vial was sealed and heated at 85° C. for 120 minutes while vigorously stirring. After cooling to ambient temperature, the reaction mixture was diluted with water and extracted with DCM (2×). The combined organics were filtered over a column Chromabond PTS and concentrated under reduced pressure. The crude product was purified by preparative HPLC (method 4) to yield the desired product (90.0 mg, 43%).

LC-MS (Method 10): $R_t$=2.36 min; MS (ESIpos): m/z=463 [M+H]$^+$ $^1$H-NMR (400 MHz, DMSO-d6) δ [ppm]: −0.008 (0.68), 0.008 (0.65), 1.074 (1.20), 1.091 (2.45), 1.109 (1.23), 2.086 (2.01), 2.099 (15.27), 2.222 (3.70), 2.265 (0.77), 2.652 (16.00), 2.678 (0.78), 3.357 (0.44), 3.375 (1.22), 3.392 (1.19), 3.721 (10.57), 7.957 (2.14), 7.978 (2.37), 8.331 (1.10), 8.354 (1.01), 8.515 (0.97), 9.094 (2.06), 9.593 (1.41).

Example 551

N-{1,4-dimethyl-3-[6-(trifluoromethyl)pyridin-3-yl]-1H-pyrazol-5-yl}-6-(4-methoxy-3,5-dimethyl-1H-pyrazol-1-yl)pyrimidin-4-amine

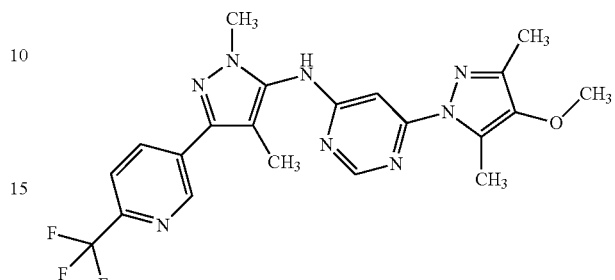

A microwave vial was charged 4-chloro-6-(4-methoxy-3,5-dimethyl-1H-pyrazol-1-yl)pyrimidine (108 mg, 454 μmol) and 1,4-dimethyl-3-[6-(trifluoromethyl)pyridin-3-yl]-1H-pyrazol-5-amine (128 mg, 500 μmol) and the contents were suspended in 1,4-dioxane (2.4 ml, 28 mmol). The reaction mixture was degassed with Ar for 3 min. Tris(dibenzylidenaceton)dipalladium (12.5 mg, 13.6 μmol) and Xantphos (15.8 mg, 27.2 μmol) were added and the reaction mixture was degassed again for 1 min and heated to 85° C. At this temperature and sodium phenolate (58.0 mg, 500 μmol) was added. The vial was sealed and heated at 85° C. for 120 minutes while vigorously stirring. After cooling to ambient temperature, the reaction mixture was diluted with water and extracted with DCM (2×). The combined organics were filtered over a column Chromabond PTS and concentrated under reduced pressure. The crude product was purified by preparative HPLC (method 3) to yield the desired product (128.0 mg, 61%).

LC-MS (Method 10): $R_t$=2.06 min; MS (ESIpos): m/z=459 [M+H]$^+$ $^1$H-NMR (400 MHz, DMSO-d6) δ [ppm]: −0.008 (0.62), 0.008 (0.57), 1.074 (0.62), 1.091 (1.28), 1.109 (0.64), 2.096 (16.00), 2.193 (4.52), 3.375 (0.64), 3.392 (0.63), 3.706 (15.37), 3.716 (12.45), 7.957 (2.16), 7.978 (2.44), 8.331 (1.17), 8.335 (1.15), 8.351 (1.06), 8.462 (1.05), 9.091 (1.92), 9.478 (2.36).

Example 552

6-[5-(difluoromethyl)-3-methyl-1H-pyrazol-1-yl]-N-{1,4-dimethyl-5-[6-(trifluoromethyl)pyridin-3-yl]-1H-pyrazol-3-yl}pyrimidin-4-amine

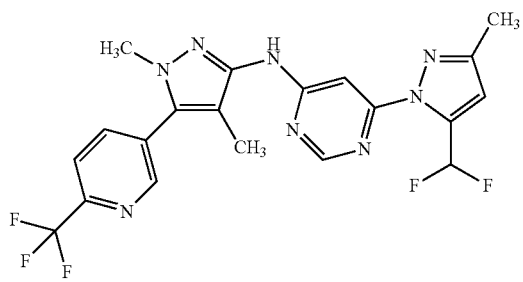 [SMILES: Cc1cc(C(F)F)n(-c2cc(Nc3nn(C)c(-c4ccc(C(F)(F)F)nc4)c3C)ncn2)n1]

A microwave vial was charged 4-chloro-6-[5-(difluoromethyl)-3-methyl-H-pyrazol-1-yl]pyrimidine (104 mg, 426 µmol) and 1,4-dimethyl-5-[6-(trifluoromethyl)pyridin-3-yl]-1H-pyrazol-3-amine (120 mg, 468 µmol) and the contents were suspended in 1,4-dioxane (2.5 ml, 29 mmol). The reaction mixture was degassed with Ar for 3 min. Tris(dibenzylideneaceton)dipalladium (11.7 mg, 12.8 µmol) and Xantphos (14.8 mg, 25.5 µmol) were added and the reaction mixture was degassed again for 1 min and heated to 85° C. At this temperature and sodium phenolate (54.4 mg, 468 µmol) was added. The vial was sealed and heated at 85° C. for 120 minutes while vigorously stirring. After cooling to ambient temperature, the reaction mixture was diluted with water and extracted with DCM (2×). The combined organics were filtered over a column Chromabond PTS and concentrated under reduced pressure. The crude product was purified by preparative HPLC (method 3) to yield the desired product (45.0 mg, 23%).

LC-MS (Method 10): $R_t$=2.13 min; MS (ESIpos): m/z=465 [M+H]$^+$ $^1$H-NMR (400 MHz, DMSO-d6) δ [ppm]: 1.921 (11.83), 2.300 (13.63), 3.775 (0.75), 3.787 (16.00), 6.777 (3.73), 7.462 (0.88), 7.694 (1.18), 7.830 (2.44), 7.966 (1.05), 8.078 (2.14), 8.098 (2.63), 8.262 (1.47), 8.267 (1.40), 8.283 (1.19), 8.287 (1.15), 8.491 (2.74), 8.929 (2.27), 8.934 (2.19), 9.680 (1.90).

Example 553

6-(4-chloro-3,5-dimethyl-1H-pyrazol-1-yl)-N-{1,4-dimethyl-5-[6-(trifluoromethyl)pyridin-3-yl]-1H-pyrazol-3-yl}pyrimidin-4-amine

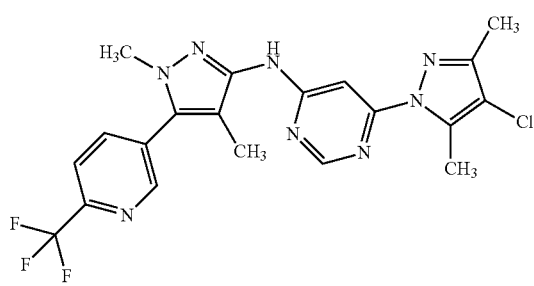 [SMILES: Cc1nn(-c2cc(Nc3nn(C)c(-c4ccc(C(F)(F)F)nc4)c3C)ncn2)c(C)c1Cl]

A microwave vial was charged 4-chloro-6-(4-chloro-3,5-dimethyl-1H-pyrazol-1-yl)pyrimidine (103 mg, 426 µmol) and 1,4-dimethyl-5-[6-(trifluoromethyl)pyridin-3-yl]-1H-pyrazol-3-amine (120 mg, 468 µmol) and the contents were suspended in 1,4-dioxane (2.5 ml, 29 mmol). The reaction mixture was degassed with Ar for 3 min. Tris(dibenzylidenaceton)dipalladium (11.7 mg, 12.8 µmol) and Xantphos (14.8 mg, 25.5 µmol) were added and the reaction mixture was degassed again for 1 min and heated to 85° C. At this temperature and sodium phenolate (54.4 mg, 468 µmol) was added. The vial was sealed and heated at 85° C. for 120 minutes while vigorously stirring. After cooling to ambient temperature, the reaction mixture was diluted with water and extracted with DCM (2×). The combined organics were filtered over a column Chromabond PTS and concentrated under reduced pressure. The crude product was purified by preparative HPLC (method 4) to yield the desired product (45.0 mg, 23%).

LC-MS (Method 10): $R_t$=2.32 min; MS (ESIpos): m/z=463 [M+H]$^+$ $^1$H-NMR (400 MHz, DMSO-d6) δ [ppm]: 0.008 (0.48), 1.917 (13.01), 2.227 (14.26), 2.645 (15.36), 3.776 (16.00), 7.433 (1.18), 8.074 (2.10), 8.095 (2.54), 8.256 (1.52), 8.260 (1.44), 8.276 (1.19), 8.280 (1.14), 8.496 (2.78), 8.923 (2.28), 9.592 (2.31).

Example 554

4-[5-({6-[5-(difluoromethyl)-3-methyl-1H-pyrazol-1-yl]pyrimidin-4-yl}amino)-1-(2-methoxyethyl)-4-methyl-1H-pyrazol-3-yl]benzonitrile

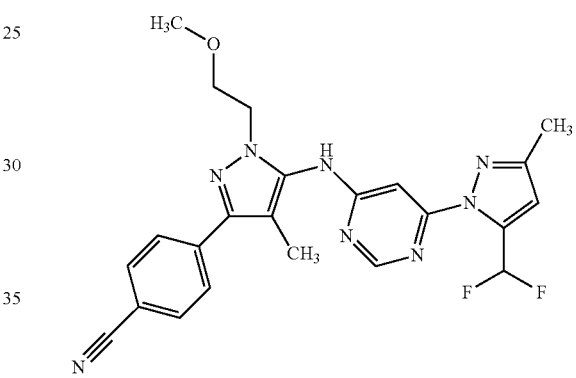

A microwave vial was charged 4-chloro-6-[5-(difluoromethyl)-3-methyl-H-pyrazol-1-yl]pyrimidine (104 mg, 426 µmol) and 4-[5-amino-1-(2-methoxyethyl)-4-methyl-1H-pyrazol-3-yl]benzonitrile (120 mg, 468 µmol) and the contents were suspended in 1,4-dioxane (2.5 ml, 29 mmol). The reaction mixture was degassed with Ar for 3 min. Tris(dibenzylidenaceton)dipalladium (11.7 mg, 12.8 µmol) and Xantphos (14.8 mg, 25.5 µmol) were added and the reaction mixture was degassed again for 1 min and heated to 85° C. At this temperature and sodium phenolate (54.4 mg, 468 µmol) was added. The vial was sealed and heated at 85° C. for 120 minutes while vigorously stirring. After cooling to ambient temperature, the reaction mixture was diluted with water and extracted with DCM (2×). The combined organics were filtered over a column Chromabond PTS and concentrated under reduced pressure. The crude product was purified by preparative HPLC (method 3) to yield the desired product (55.0 mg, 27%).

LC-MS (Method 10): $R_t$=2.12 min; MS (ESIpos): m/z=465 [M+H]$^+$ $^1$H-NMR (400 MHz, DMSO-d6) δ [ppm]: −0.008 (1.66), 0.008 (1.01), 2.061 (16.00), 2.284 (2.35), 2.699 (0.46), 3.138 (3.50), 3.177 (0.72), 3.660 (1.89), 3.674 (3.65), 3.687 (1.95), 4.154 (1.33), 6.783 (2.35), 7.684 (1.33), 7.819 (2.70), 7.911 (10.45), 7.956 (1.33), 8.500 (0.74), 9.552 (1.20).

Example 555

4-[5-{[6-(3,5-dimethyl-1H-pyrazol-1-yl)pyrimidin-4-yl]amino}-1-(2-methoxyethyl)-4-methyl-1H-pyrazol-3-yl]benzonitrile

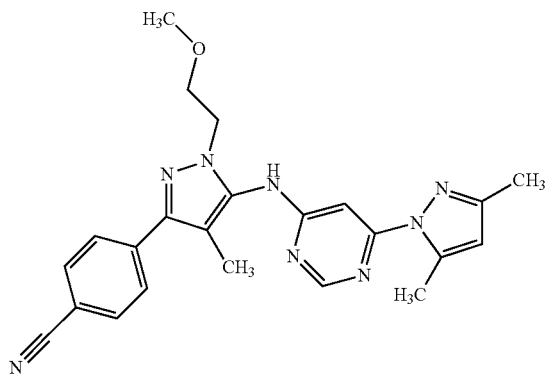 [SMILES: COCCn1nc(-c2ccc(C#N)cc2)c(C)c1Nc1cc(-n2nc(C)cc2C)ncn1]

A microwave vial was charged 4-chloro-6-(3,5-dimethyl-1H-pyrazol-1-yl)pyrimidine (88.8 mg, 426 µmol) and 4-[5-amino-1-(2-methoxyethyl)-4-methyl-1H-pyrazol-3-yl]benzonitrile (120 mg, 468 µmol) and the contents were suspended in 1,4-dioxane (2.5 ml, 29 mmol). The reaction mixture was degassed with Ar for 3 min. Tris(dibenzylidenaceton)dipalladium (11.7 mg, 12.8 µmol) and Xantphos (14.8 mg, 25.5 µmol) were added and the reaction mixture was degassed again for 1 min and heated to 85° C. At this temperature and sodium phenolate (54.4 mg, 468 µmol) was added. The vial was sealed and heated at 85° C. for 120 minutes while vigorously stirring. After cooling to ambient temperature, the reaction mixture was diluted with water and extracted with DCM (2×). The combined organics were filtered over a column Chromabond PTS and concentrated under reduced pressure. The crude product was purified by preparative HPLC (method 2) to yield the desired product (94.0 mg, 49%).

LC-MS (Method 10): $R_t$=2.03 min; MS (ESIpos): m/z=429 [M+H]$^+$ $^1$H-NMR (400 MHz, DMSO-d6) δ [ppm]: −0.008 (0.79), 0.008 (0.71), 1.646 (0.74), 2.059 (16.00), 2.169 (3.65), 2.628 (13.61), 3.150 (8.75), 3.663 (1.95), 3.677 (4.13), 3.691 (2.14), 4.147 (1.58), 6.143 (2.93), 7.369 (0.53), 7.385 (0.52), 7.398 (0.65), 7.885 (0.71), 7.907 (13.16), 7.932 (0.63), 8.466 (1.11), 9.367 (2.73).

Example 556 methyl [1-(6-{[1-(cyclopropylmethyl)-3-(4-fluorophenyl)-4-methyl-1H-pyrazol-5-yl]amino}pyrimidin-4-yl)-3,5-dimethyl-1H-pyrazol-4-yl]carbamate

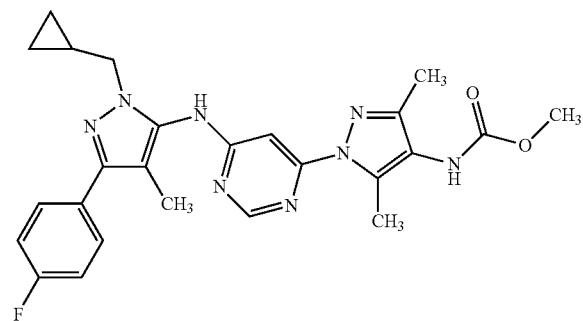 [SMILES: COC(=O)Nc1c(C)nn(-c2cc(Nc3c(C)c(-c4ccc(F)cc4)nn3CC3CC3)ncn2)c1C]

A solution of tert-butyl [6-(4-amino-3,5-dimethyl-1H-pyrazol-1-yl)pyrimidin-4-yl][1-(cyclopropylmethyl)-3-(4-fluorophenyl)-4-methyl-1H-pyrazol-5-yl]carbamate (125 mg, 235 µmol) and methyl carbonochloridate (33.3 mg, 352 µmol) in dichloromethane (2.5 mL) was treated with triethylamine (65 µl, 470 µmol) and stirred for 3 hours at ambient temperature. The mixture was diluted with dichloromethane. The organic phase was dried over Chromabond PTS and concentrated under reduced pressure. The residue was resolved in 4M hydrochloric acid in dioxane and stirred for 30 min at ambient temperature. The mixture was concentrated under reduced pressure and the crude product was purified by preparative HPLC (method 3) to yield 36.1 mg (31%) of the desired product.

LC-MS (Method 10): $R_t$=1.91 min; MS (ESIpos): m/z=491 [M+H]$^+$ $^1$H-NMR (400 MHz, DMSO-d6) δ [ppm]: −0.008 (0.43), 0.291 (2.21), 0.304 (2.41), 0.422 (2.29), 0.442 (2.44), 1.073 (1.12), 1.091 (2.32), 1.109 (1.16), 1.175 (0.62), 1.182 (0.60), 1.194 (0.95), 1.206 (0.57), 1.213 (0.58), 2.009 (14.04), 2.075 (2.58), 2.488 (16.00), 3.357 (0.40), 3.375 (1.15), 3.392 (1.11), 3.631 (3.56), 3.829 (2.05), 3.846 (2.01), 7.251 (2.19), 7.274 (4.44), 7.296 (2.36), 7.717 (1.37), 7.731 (1.81), 7.751 (1.26), 8.468 (0.63), 8.694 (0.76), 9.394 (0.55).

Example 557

1-(6-{[3-(5-fluoropyridin-2-yl)-1-(2-methoxyethyl)-4-methyl-1H-pyrazol-5-yl]amino}pyrimidin-4-yl)-N,N,3,5-tetramethyl-1H-pyrazole-4-carboxamide

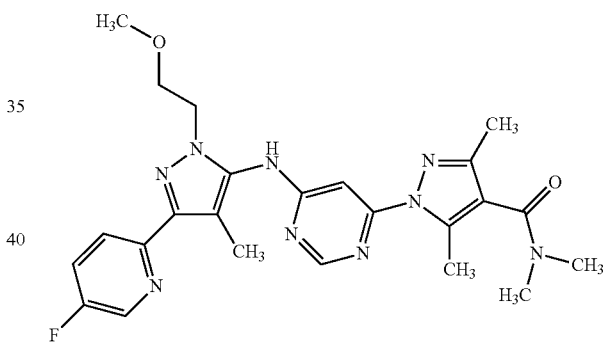

A solution of 1-(6-{[3-(5-fluoropyridin-2-yl)-1-(2-methoxyethyl)-4-methyl-1H-pyrazol-5-yl]amino}pyrimidin-4-yl)-3,5-dimethyl-1H-pyrazole-4-carboxylic acid (26.6 mg, 57.0 µmol) and N-methylmethanamine (57 µl, 2.0 M in tetrahydrofuran, 110 µmol) in dimethylformamide (1.0 ml, 13 mmol) was treated with N,N-diisopropylethylamine (30 µl, 170 µmol) and (1-[Bis(dimethylamino)methylene]-1H-1,2,3-triazolo[4,5-b]pyridinium 3-oxid hexafluorophosphate) (32.5 mg, 85.5 µmol) and the mixture was stirred 30 min at ambient temperature. The mixture was diluted with water and extracted with DCM. The organic phase was filtered over Chromabond PTS concentrated under reduced pressure. The crude product was purified by preparative HPLC (method 7) to yield 19.3 mg (68%) of the desired product.

LC-MS (Method 10): $R_t$=1.56 min; MS (ESIpos): m/z=494 [M+H]$^+$ $^1$H-NMR (400 MHz, DMSO-d6) δ [ppm]: −0.008 (0.50), 1.073 (0.55), 1.091 (1.10), 1.109 (0.55), 2.146 (16.00), 2.583 (15.20), 2.902 (2.60), 2.975 (2.87), 3.148 (4.51), 3.375 (0.55), 3.392 (0.55), 3.661 (1.62), 3.675 (3.35), 3.688 (1.76), 4.151 (1.10), 7.754 (0.54), 7.761 (0.60), 7.776 (1.20), 7.783 (1.30), 7.798 (0.71), 7.805 (0.74), 7.984 (0.81), 7.995 (0.86), 8.006 (0.76), 8.017 (0.69), 8.500 (0.52), 8.595 (2.23), 8.602 (2.24), 9.416 (1.72).

Example 558

1-[6-({3-[4-(difluoromethyl)phenyl]-1-(2-methoxyethyl)-4-methyl-1H-pyrazol-5-yl}amino)pyrimidin-4-yl]-N,N,3,5-tetramethyl-1H-pyrazole-4-carboxamide

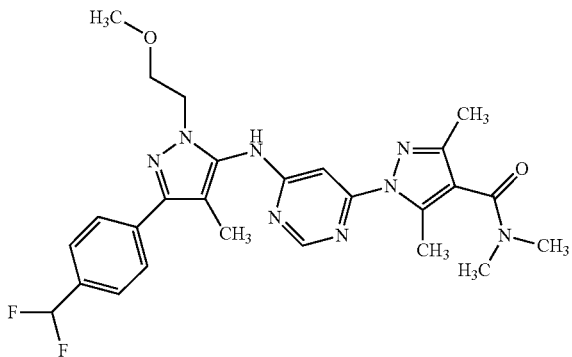 [SMILES: COCCn1nc(-c2ccc(C(F)F)cc2)c(C)c1Nc1cc(-n2nc(C)c(C(=O)N(C)C)c2C)ncn1]

A solution of 1-[6-({3-[4-(difluoromethyl)phenyl]-1-(2-methoxyethyl)-4-methyl-1H-pyrazol-5-yl}amino)pyrimidin-4-yl]-3,5-dimethyl-1H-pyrazole-4-carboxylic acid (57.7 mg, 116 µmol) and N-methylmethanamine (120 µl, 2.0 M, 230 µmol) in dimethylformamide (1.0 ml, 13 mmol) was treated with N,N-diisopropylethylamine (61 µl, 350 µmol) and (1-[Bis(dimethylamino)methylene]-1H-1,2,3-triazolo[4,5-b]pyridinium 3-oxid hexafluorophosphate) (66.1 mg, 174 µmol) and the mixture was stirred overnight at ambient temperature. The mixture was diluted with water and extracted with DCM. The combined organics were washed the with brine, dried over sodium sulfate and concentrated under reduced pressure. The crude product was purified by preparative HPLC (method 7) to yield 41.0 mg (67%) of the desired product.

LC-MS (Method 10): $R_t$=1.75 min; MS (ESIpos): m/z=525 [M+H]$^+$ $^1$H-NMR (400 MHz, DMSO-d6) δ [ppm]: −0.008 (0.55), 0.008 (0.42), 1.074 (0.58), 1.091 (1.19), 1.109 (0.60), 2.047 (14.98), 2.149 (2.50), 2.586 (16.00), 2.907 (2.88), 2.977 (3.11), 3.155 (6.39), 3.375 (0.60), 3.392 (0.58), 3.662 (1.87), 3.676 (3.98), 3.690 (2.07), 4.142 (1.36), 6.938 (1.35), 7.078 (2.85), 7.218 (1.21), 7.636 (2.62), 7.657 (3.25), 7.844 (2.54), 7.864 (2.13), 8.505 (0.69), 9.421 (1.68).

Example 559

6-(3,5-dimethyl-1H-pyrazol-1-yl)-N-{1,4-dimethyl-5-[6-(trifluoromethyl)pyridin-3-yl]-1H-pyrazol-3-yl}pyrimidin-4-amine

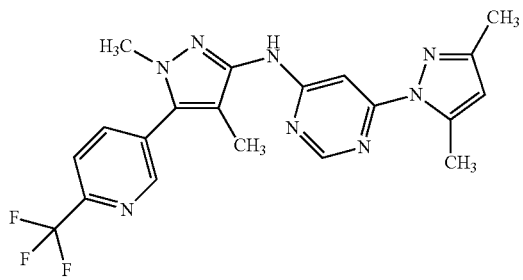 [SMILES: Cc1cc(C)n(-c2cc(Nc3nn(C)c(-c4ccc(C(F)(F)F)nc4)c3C)ncn2)n1]

A microwave vial was charged 4-chloro-6-(3,5-dimethyl-1H-pyrazol-1-yl)pyrimidine (88.8 mg, 426 µmol) and 1,4-dimethyl-5-[6-(trifluoromethyl)pyridin-3-yl]-1H-pyrazol-3-amine (120 mg, 468 µmol) and the contents were suspended in 1,4-dioxane (2.5 ml, 29 mmol). The reaction mixture was degassed with Ar for 3 min. Tris(dibenzylidenaceton)dipalladium (11.7 mg, 12.8 µmol) and Xantphos (14.8 mg, 25.5 µmol) were added and the reaction mixture was degassed again for 1 min and heated to 85° C. At this temperature and sodium phenolate (54.4 mg, 468 µmol) was added. The vial was sealed and heated at 85° C. for 120 minutes while vigorously stirring. After cooling to ambient temperature, the reaction mixture was diluted with water and extracted with DCM (2×). The combined organics were filtered over a column Chromabond PTS and concentrated under reduced pressure. The crude product was purified by preparative HPLC (method 7) and subsequently by flash-chromatography on silica gel (column: Kp Sil 10 g, solvent: dichloromethane/ethyl acetate 1:1). The pure product was resolved in DCM and dried to yield the desired product (56.0 mg, 31%).

LC-MS (Method 10): $R_t$=1.98 min; MS (ESIpos): m/z=429 [M+H]$^+$ $^1$H-NMR (400 MHz, DMSO-d6) δ [ppm]: 1.915 (13.61), 2.189 (14.40), 2.626 (12.12), 3.776 (16.00), 5.754 (0.95), 6.137 (3.54), 7.403 (1.84), 8.074 (2.01), 8.094 (2.46), 8.256 (1.36), 8.260 (1.34), 8.276 (1.07), 8.281 (1.09), 8.461 (3.43), 8.923 (2.26), 8.928 (2.24), 9.469 (2.72).

Experimental Section—Biological Assays

Biological Investigations

The example testing experiments described herein serve to illustrate the present invention and the invention is not limited to the examples given.

The following assays can be used to illustrate the commercial utility of the compounds according to the present invention.

Examples were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

The in vitro activity of the compounds of the present invention can be demonstrated in the following assays:

Biological Assays:

For measuring Npt2a activity in a cell based assay, a stable CHO cell line with inducible Npt2a expression was generated. Therefore, CHO T-Rex cells (life technologies cat. R718-07) were stably transfected with doxycycline-inducible human NPT2a (pcDNA5TO-hNpt2a). The obtained CHO T-REx hNpt2a cells were routinely cultured in Dulbecco's MEM/F12 (4.5 g/l Glucose, Gibco cat. 21331-020; 500 mL) supplemented with 10 ml Glutamax 100×, Sodium pyruvate (7 mL of 100 mM solution), HEPES (10 mL of 1 M solution), Sodium bicarbonate (10 mL of 7.5% solution), 10% Fetal Bovine Serum Tetracycline free (Clontech cat. 631106, 500 ml), Penicillin-Streptomycin (5 mL of 100× Solution), Blasticidin 10 µg/mL and 400 µg/mL Hygromycin.

Activity of Npt2a was detected by following depolarization of cellular membrane potential by influx of sodium phosphate using fluorescent membrane potential dye kit BLUE (Molecular devices cat. R8034). For Npt2a activity measurements, CHO T-Rex hNpt2a cells were seeded into 1536 well microtiter plates (GREINER Bio-One cat. 782092) with 750 cells/well in 7 µL/w of complete medium (2% Tetracycline-free FBS, 2% Poly-D-Lysine) without selective agents+Doxycycline 0.5 µg/mL to induce Npt2a gene expression, and grown for 24 h at 37° C., 5% carbon dioxide.

On the day of experiment a 1×MPdye Loading Solution was freshly prepared by re-suspending 15 mg of Blue MPdye powder in 10 mL of NHE buffer sodium-free (140 mM N-Methyl-D-glucamine, 5.4 mM KCl, 1 mM CaCl2, 11 mM D(±)-Glucose water free, 1.2 mM MgCl2, 10 mM HEPES; pH 7.4 (adjusted with hydrochloric acid); sterile filtered). 5 µl medium was removed from plates by robotic manipulation, then 5 µL/well of sodium-free NHE buffer was added. After incubation for 2 min, this washing step was repeated once. Then, 5 µL/w of buffer was removed from plates and cells were incubated for 5 min at room temperature with 5 µL/w of MPdye Loading Solution (1× in Sodium-free NHE Buffer). Test compounds were added to the cells at final test concentrations between 50 µM and 1 nM (0.6 µL/well, final DMSO 0.6%, prepared in MPDye Loading Solution) and incubated for 5 min at room temperature.

Plates were analyzed with an in house CCD camera device using a λexc 510-545 nm/λem 565-625 nm filter. Fluorescence was detected for 15 sec (background measurement M1). Activity of Npt2a was triggered by addition of 2 µL/well of 30 mM Na+ and 1 mM phosphate (prepared in a mixture of NHE Buffer Na+ free and NHE Buffer 140 mM Na+). Fluorescence was followed for 2-3 min (depolarization measurement M2). Data was normalized to cell number and dye loading efficiency by calculating M2/M1. This quotient was plotted against test compound concentration. Graph Pad Prism or equivalent in house software was used to create sigmoidal dose-response curves (variable slope) and determine $IC_{50}$ values.

TABLE 1

Assay results on activity on human Npt2a

| Example No | Npt2a, human $IC_{50}$ [nM] |
|---|---|
| Example 1 | 4.48 |
| Example 2 | 12 |
| Example 3 | 13 |
| Example 4 | 28.3 |
| Example 5 | 27.5 |
| Example 6 | 49 |
| Example 7 | 36 |
| Example 8 | 38 |
| Example 9 | 40 |
| Example 10 | 33.7 |
| Example 11 | 50.3 |
| Example 12 | 50 |
| Example 13 | 61.9 |
| Example 14 | 70 |
| Example 15 | 72 |
| Example 16 | 81 |
| Example 17 | 100 |
| Example 18 | 110 |
| Example 19 | 110 |
| Example 20 | 120 |
| Example 21 | 140 |
| Example 22 | 150 |
| Example 23 | 315 |
| Example 24 | 310 |
| Example 25 | 1070 |
| Example 26 | 460 |
| Example 27 | 460 |
| Example 28 | 490 |
| Example 29 | 1420 |
| Example 30 | 620 |
| Example 31 | 670 |
| Example 32 | 690 |
| Example 33 | 1000 |
| Example 34 | 1000 |
| Example 35 | 1400 |
| Example 36 | 1700 |
| Example 37 | 1700 |
| Example 38 | 2350 |
| Example 39 | 3.2 |
| Example 40 | 2760 |
| Example 41 | 11 |
| Example 42 | 7.67 |
| Example 43 | 144 |
| Example 44 | 5.35 |
| Example 45 | 29 |
| Example 46 | 6.5 |
| Example 47 | 89 |
| Example 48 | 310 |
| Example 49 | 310 |
| Example 50 | 160 |
| Example 51 | 100 |
| Example 52 | 83 |
| Example 53 | 11.3 |
| Example 54 | 90.3 |
| Example 55 | 133 |
| Example 56 | 20.5 |
| Example 57 | 117 |
| Example 58 | 760 |
| Example 59 | 12 |
| Example 60 | 43 |
| Example 61 | 4.4 |
| Example 62 | 135 |
| Example 63 | 7.65 |
| Example 64 | 6.25 |
| Example 65 | 130 |
| Example 66 | 87 |
| Example 67 | 3.45 |
| Example 68 | 31.5 |
| Example 69 | 8.4 |
| Example 70 | 36 |
| Example 71 | 50 |
| Example 72 | 15.4 |
| Example 73 | 15.7 |
| Example 74 | 1260 |
| Example 75 | 42 |
| Example 76 | 190 |
| Example 77 | 2230 |
| Example 78 | 247 |
| Example 79 | 31 |
| Example 80 | 44 |
| Example 81 | 11 |
| Example 82 | 1500 |
| Example 83 | 1300 |
| Example 84 | 75.5 |
| Example 85 | 130 |
| Example 86 | 50 |
| Example 87 | 32 |
| Example 88 | 28.5 |
| Example 89 | 4.8 |
| Example 90 | 133 |
| Example 91 | 5.73 |
| Example 92 | 820 |
| Example 93 | 29 |
| Example 94 | 2500 |
| Example 95 | 63.5 |

TABLE 1-continued

Assay results on activity on human Npt2a

| Example No | Npt2a, human IC$_{50}$ [nM] |
|---|---|
| Example 96 | 110 |
| Example 97 | 75 |
| Example 98 | 51 |
| Example 99 | 50 |
| Example 100 | 360 |
| Example 101 | 11.5 |
| Example 102 | 7.3 |
| Example 103 | 64 |
| Example 104 | 150 |
| Example 105 | 235 |
| Example 106 | 120 |
| Example 107 | 293 |
| Example 108 | 94 |
| Example 109 | 50.3 |
| Example 110 | 22 |
| Example 111 | 360 |
| Example 112 | 59.5 |
| Example 113 | 32 |
| Example 114 | 290 |
| Example 115 | <1.6 |
| Example 116 | 92.5 |
| Example 117 | 19 |
| Example 118 | 7.0 |
| Example 119 | 870 |
| Example 120 | 1450 |
| Example 121 | <1.6 |
| Example 122 | 25 |
| Example 123 | 395 |
| Example 124 | 155 |
| Example 125 | 20.3 |
| Example 126 | 975 |
| Example 127 | 1200 |
| Example 128 | 1300 |
| Example 129 | 78 |
| Example 130 | 28 |
| Example 131 | 1600 |
| Example 132 | 39 |
| Example 133 | 57 |
| Example 134 | 180 |
| Example 135 | 700 |
| Example 136 | 360 |
| Example 137 | 71 |
| Example 138 | 150 |
| Example 139 | 130 |
| Example 140 | 23 |
| Example 141 | 3 |
| Example 142 | 3 |
| Example 143 | 415 |
| Example 144 | 520 |
| Example 145 | 170 |
| Example 146 | 126 |
| Example 147 | 3 |
| Example 148 | 80 |
| Example 149 | 7 |
| Example 150 | 3 |
| Example 151 | 390 |
| Example 152 | 6 |
| Example 153 | 410 |
| Example 154 | 3 |
| Example 155 | 9 |
| Example 156 | 2 |
| Example 157 | 6 |
| Example 158 | 4 |
| Example 159 | 8 |
| Example 160 | 1110 |
| Example 161 | 2 |
| Example 162 | 97 |
| Example 163 | 71 |
| Example 164 | 11 |
| Example 165 | 3 |
| Example 166 | 9 |
| Example 167 | 550 |
| Example 168 | 15 |
| Example 169 | 690 |
| Example 170 | 440 |
| Example 171 | 12 |
| Example 172 | 57 |
| Example 173 | 16 |
| Example 174 | 33 |
| Example 175 | 14 |
| Example 176 | 13 |
| Example 177 | 41 |
| Example 178 | 26 |
| Example 179 | 170 |
| Example 180 | 47 |
| Example 181 | 1500 |
| Example 182 | 106 |
| Example 183 | 930 |
| Example 184 | 1200 |
| Example 185 | 27 |
| Example 186 | 60 |
| Example 187 | 10 |
| Example 188 | 710 |
| Example 189 | 74 |
| Example 190 | 210 |
| Example 191 | 3 |
| Example 192 | 16 |
| Example 193 | 51 |
| Example 194 | 1300 |
| Example 195 | 3 |
| Example 196 | 2 |
| Example 197 | 28 |
| Example 198 | 12 |
| Example 199 | 36 |
| Example 200 | 8 |
| Example 201 | 6 |
| Example 202 | 13 |
| Example 203 | 1400 |
| Example 204 | 3 |
| Example 205 | 20 |
| Example 206 | 9 |
| Example 207 | 18 |
| Example 208 | 465 |
| Example 209 | 18 |
| Example 210 | 13 |
| Example 211 | 200 |
| Example 212 | 1170 |
| Example 213 | 2 |
| Example 214 | 86 |
| Example 215 | 250 |
| Example 216 | 12 |
| Example 217 | 2 |
| Example 218 | 32 |
| Example 219 | <1.6 |
| Example 220 | 320 |
| Example 221 | 6 |
| Example 222 | 44 |
| Example 223 | 36 |
| Example 224 | 47 |
| Example 225 | 8 |
| Example 226 | 190 |
| Example 227 | 16 |
| Example 228 | 210 |
| Example 229 | 350 |
| Example 230 | 830 |
| Example 231 | 2 |
| Example 232 | 6 |
| Example 233 | 29 |
| Example 234 | 28 |
| Example 235 | 3 |
| Example 236 | 3 |
| Example 237 | 15 |
| Example 238 | 83 |
| Example 239 | 290 |
| Example 240 | 18 |
| Example 241 | 7 |
| Example 242 | 21 |
| Example 243 | 28 |
| Example 244 | 8 |
| Example 245 | 660 |

TABLE 1-continued

Assay results on activity on human Npt2a

| Example No | Npt2a, human IC$_{50}$ [nM] |
|---|---|
| Example 246 | 340 |
| Example 247 | 29 |
| Example 248 | 182 |
| Example 249 | 22 |
| Example 250 | 21 |
| Example 251 | 14 |
| Example 252 | 48 |
| Example 253 | 67 |
| Example 254 | 150 |
| Example 255 | 2 |
| Example 256 | 35 |
| Example 257 | 74 |
| Example 258 | 2800 |
| Example 259 | 50 |
| Example 260 | 140 |
| Example 261 | 20 |
| Example 262 | 33 |
| Example 263 | 111 |
| Example 264 | 500 |
| Example 265 | 180 |
| Example 266 | 410 |
| Example 267 | 27 |
| Example 268 | 8 |
| Example 269 | 53 |
| Example 270 | 12 |
| Example 271 | 39 |
| Example 272 | 340 |
| Example 273 | 120 |
| Example 274 | 44 |
| Example 275 | 1050 |
| Example 276 | 25 |
| Example 277 | 150 |
| Example 278 | 86 |
| Example 279 | 11 |
| Example 280 | 16 |
| Example 281 | 16 |
| Example 282 | 73 |
| Example 283 | 21 |
| Example 284 | 25 |
| Example 285 | 140 |
| Example 286 | 93 |
| Example 287 | 5 |
| Example 288 | 16 |
| Example 289 | 23 |
| Example 290 | 170 |
| Example 291 | 110 |
| Example 292 | 240 |
| Example 293 | 570 |
| Example 294 | 1400 |
| Example 295 | 13 |
| Example 296 | 117 |
| Example 297 | 1430 |
| Example 298 | 17 |
| Example 299 | 5 |
| Example 300 | 88 |
| Example 301 | 92 |
| Example 302 | 9 |
| Example 303 | 47 |
| Example 304 | 6 |
| Example 305 | 27 |
| Example 306 | 60 |
| Example 307 | 560 |
| Example 308 | 23 |
| Example 309 | 44 |
| Example 310 | 21 |
| Example 311 | 340 |
| Example 312 | 10 |
| Example 313 | 36 |
| Example 314 | 9 |
| Example 315 | 99 |
| Example 316 | 81 |
| Example 317 | 450 |
| Example 318 | 790 |
| Example 319 | 82 |
| Example 320 | 71 |
| Example 321 | 16 |
| Example 322 | 4 |
| Example 323 | 660 |
| Example 324 | 270 |
| Example 325 | 1100 |
| Example 326 | 4 |
| Example 327 | 4 |
| Example 328 | 4 |
| Example 329 | 67 |
| Example 330 | 22 |
| Example 331 | 2800 |
| Example 332 | 1900 |
| Example 333 | 54 |
| Example 334 | 41 |
| Example 335 | 51 |
| Example 336 | 1650 |
| Example 337 | 66 |
| Example 338 | 7 |
| Example 339 | 8 |
| Example 340 | 12 |
| Example 341 | 17 |
| Example 342 | 2 |
| Example 343 | 6 |
| Example 344 | 5 |
| Example 345 | 7 |
| Example 346 | 4 |
| Example 347 | 23 |
| Example 348 | 15 |
| Example 349 | 49 |
| Example 350 | 1300 |
| Example 351 | 65 |
| Example 352 | 25 |
| Example 353 | 5 |
| Example 354 | 135 |
| Example 355 | 20 |
| Example 356 | 2 |
| Example 357 | 32 |
| Example 358 | 10 |
| Example 359 | 15 |
| Example 360 | 6 |
| Example 361 | 31 |
| Example 362 | 220 |
| Example 363 | 150 |
| Example 364 | 5 |
| Example 365 | 61 |
| Example 366 | 150 |
| Example 367 | 40 |
| Example 368 | 7 |
| Example 369 | 420 |
| Example 370 | 2400 |
| Example 371 | 240 |
| Example 372 | 7 |
| Example 373 | 5 |
| Example 374 | 63 |
| Example 375 | 40 |
| Example 376 | 8 |
| Example 377 | 205 |
| Example 378 | 2550 |
| Example 379 | 880 |
| Example 380 | 170 |
| Example 381 | 8 |
| Example 382 | 35 |
| Example 383 | 5 |
| Example 384 | 30 |
| Example 385 | 4 |
| Example 386 | 12 |
| Example 387 | 70 |
| Example 388 | 64 |
| Example 389 | 130 |
| Example 390 | 25 |
| Example 391 | 13 |
| Example 392 | 18 |
| Example 393 | 180 |
| Example 394 | 71 |
| Example 395 | 19 |

TABLE 1-continued

Assay results on activity on human Npt2a

| Example No | Npt2a, human IC$_{50}$ [nM] |
|---|---|
| Example 396 | 16 |
| Example 397 | 92 |
| Example 398 | 25 |
| Example 399 | 6 |
| Example 400 | 6 |
| Example 401 | 1400 |
| Example 402 | 55 |
| Example 403 | 12 |
| Example 404 | 13 |
| Example 405 | 14 |
| Example 406 | 3 |
| Example 407 | 29 |
| Example 408 | 6 |
| Example 409 | 140 |
| Example 410 | 2 |
| Example 411 | 150 |
| Example 412 | 12 |
| Example 413 | 4 |
| Example 414 | 3 |
| Example 415 | 1150 |
| Example 416 | 1150 |
| Example 417 | 27 |
| Example 418 | 65 |
| Example 419 | 14 |
| Example 420 | 24 |
| Example 421 | 410 |
| Example 422 | 240 |
| Example 423 | 55 |
| Example 424 | 370 |
| Example 425 | 415 |
| Example 426 | 59 |
| Example 427 | 15 |
| Example 428 | 550 |
| Example 429 | 17 |
| Example 430 | 45 |
| Example 431 | 69 |
| Example 432 | 320 |
| Example 433 | 1500 |
| Example 434 | 7 |
| Example 435 | 5 |
| Example 436 | 10 |
| Example 437 | 21 |
| Example 438 | 16 |
| Example 439 | 39 |
| Example 440 | 97 |
| Example 441 | 21 |
| Example 442 | 8 |
| Example 443 | 11 |
| Example 444 | 120 |
| Example 445 | 12 |
| Example 446 | 12 |
| Example 447 | 560 |
| Example 448 | 440 |
| Example 449 | 8 |
| Example 450 | 660 |
| Example 451 | 78 |
| Example 452 | 16 |
| Example 453 | 18 |
| Example 454 | 11 |
| Example 455 | 165 |
| Example 456 | 41 |
| Example 457 | 130 |
| Example 458 | 1550 |
| Example 459 | 46 |
| Example 460 | 98 |
| Example 461 | 170 |
| Example 462 | 25 |
| Example 463 | 34 |
| Example 464 | 2 |
| Example 465 | 170 |
| Example 466 | 11 |
| Example 467 | 69 |
| Example 468 | 300 |
| Example 469 | 5 |
| Example 470 | 3 |
| Example 471 | 7 |
| Example 472 | 880 |
| Example 473 | 160 |
| Example 474 | 234 |
| Example 475 | 215 |
| Example 476 | 29 |
| Example 477 | 98 |
| Example 478 | 45 |
| Example 479 | 18 |
| Example 480 | 375 |
| Example 481 | 1400 |
| Example 482 | 52 |
| Example 483 | 1250 |
| Example 484 | 36 |
| Example 485 | 1350 |
| Example 486 | 59 |
| Example 487 | 150 |
| Example 488 | 65 |
| Example 489 | 270 |
| Example 490 | 6 |
| Example 491 | 220 |
| Example 492 | 13 |
| Example 493 | 625 |
| Example 494 | 190 |
| Example 495 | 11 |
| Example 496 | 230 |
| Example 497 | 3 |
| Example 498 | 1310 |
| Example 499 | 3150 |
| Example 500 | 52 |
| Example 501 | 5 |
| Example 502 | 5 |
| Example 503 | 4 |
| Example 504 | 5 |
| Example 505 | 1200 |
| Example 506 | 28 |
| Example 497 | 3 |
| Example 498 | 1310 |
| Example 499 | 3150 |
| Example 500 | 52 |
| Example 501 | 5 |
| Example 502 | 5 |
| Example 503 | 4 |
| Example 504 | 5 |
| Example 505 | 1200 |
| Example 506 | 28 |
| Example 509 | 10 |
| Example 510 | 190 |
| Example 511 | 120 |
| Example 512 | 1400 |
| Example 513 | 7 |
| Example 514 | 9 |
| Example 515 | 110 |
| Example 516 | 31 |
| Example 517 | 29 |
| Example 518 | 14 |
| Example 519 | 230 |
| Example 520 | 1600 |
| Example 521 | 8 |
| Example 522 | 910 |
| Example 523 | 690 |
| Example 524 | 8 |
| Example 525 | 4 |
| Example 526 | 17 |
| Example 527 | 9 |
| Example 528 | 4 |
| Example 529 | 2700 |
| Example 530 | 33 |
| Example 531 | 1500 |
| Example 532 | 2800 |
| Example 533 | 2000 |
| Example 534 | 1500 |
| Example 535 | 26 |
| Example 536 | 17 |
| Example 537 | 26 |

TABLE 1-continued

Assay results on activity on human Npt2a

| Example No | Npt2a, human IC$_{50}$ [nM] |
|---|---|
| Example 538 | 12 |
| Example 539 | 20 |
| Example 540 | 17 |
| Example 541 | 260 |
| Example 542 | 28 |
| Example 543 | 480 |
| Example 544 | 11 |
| Example 545 | 14 |
| Example 546 | 14 |
| Example 547 | 29 |
| Example 548 | 790 |
| Example 549 | 2600 |
| Example 550 | 500 |
| Example 551 | 1900 |
| Example 552 | 15 |
| Example 553 | 7.2 |
| Example 554 | 1.9 |
| Example 555 | 1.6 |
| Example 556 | 810 |
| Example 557 | 1000 |
| Example 558 | 80 |
| Example 559 | 110 |

Biological In Vivo Assays

The in vivo activity of the compounds of the present invention can be demonstrated in the following assays:

FGFR Induced Calcification Model (Rat)

The aim of this study was to test the effect of Npt2a antagonists on vascular and soft tissue calcification and plasma levels of FGF-23, parathyroid hormone and phosphate in FGFR inhibitor induced calcification model in rats.

All rat experiments were conducted in accordance with European guidelines for the use of experimental animals and in accordance with the German Animal Protection Act (Deutsches Tierschutzgesetz).

Briefly, male Wistar Unilever (WU) rats were housed under normal conditions for laboratory rats in a 12:12-h light:dark cycle. Vascular and soft tissue calcification was induced by application of a FGFR inhibitor by once daily oral gavage for up to 2 weeks. The respective Npt2a inhibitor was also applied as indicated in the respective graph once or twice daily (QD or BID) by oral gavage for the same duration as the FGFR inhibitor. Blood samples were withdrawn during the study period and at the end of the study to determine the plasma levels of FGF-23, parathyroid hormone and phosphate with commercial available assay systems according to the manufactures protocols (e.g. FGF-23: Mouse/Rat FGF-23(C-Term) ELISA Kit; Immuntopics; phosphate: Pentra400 system, parathyroid hormone: PTH 1-84 Bioactive, rat).

At the end of the study animals were sacrificed and the organs (e.g. heart, aorta, kidney, stomach) withdrawn. To determine the calcification of the respective organs either von Kossa staining or H&E staining was done on histological preparations of the organs or an ashing of the organs was done followed by flame photometry to determine the calcium content in the organ proportionally to the wet weight of the organ.

The invention claimed is:

1. A compound of formula (I):

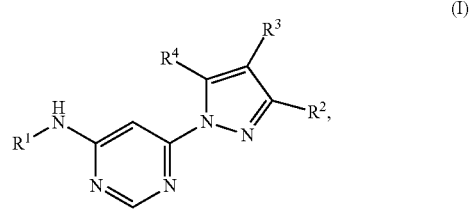

wherein

R$^1$ is a group of the formula

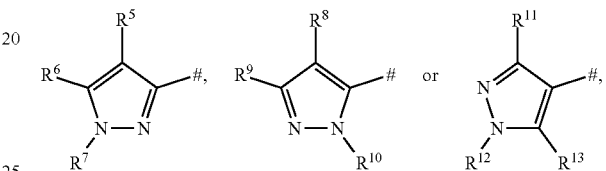

wherein # is the point of attachment to the amino group,

R$^5$ is a group selected from a halogen atom, cyano, (C$_1$-C$_4$)-alkyl, (C$_1$-C$_4$)-alkoxy, (C$_3$-C$_6$)-cycloalkyl, 4- to 6-membered heterocycle and (C$_1$-C$_4$)-alkylcarbonyl, wherein said (C$_1$-C$_4$)-alkyl is optionally substituted, identically or differently, with one or two groups selected from —NR$^{14}$R$^{15}$, (C$_1$-C$_4$)-alkoxy and cyclopropyl and optionally up to five fluorine atoms, wherein said cyclopropyl is optionally substituted with up to four fluorine atoms, wherein R$^{14}$ is a hydrogen atom or (C$_1$-C$_4$)-alkyl, R$^{15}$ is a hydrogen atom or (C$_1$-C$_4$)-alkyl, or R$^{14}$ and R$^{15}$ together with the nitrogen atom they are attached form a 4- to 5-membered heterocycle wherein said 4- to 5-membered heterocycle is optionally substituted, identically or differently, with one, two or three groups selected from (C1-C$_4$)-alkyl trifluormethyl, difluoromethyl and optionally up to five fluorine atoms, wherein said (C$_1$-C$_4$)-alkoxy is optionally substituted with up to three fluorine atoms, wherein said 4- to 6-membered heterocycle is optionally substituted, identically or differently, with one or two groups selected from (C$_1$-C$_4$)-alkyl and optionally up to five fluorine atoms, wherein said (C$_3$-C$_6$)-cycloalkyl is optionally substituted, identically or differently, with one or two groups selected from (C$_1$-C$_4$)-alkyl and optionally up to five fluorine atoms, R$^6$ is 6-membered heteroaryl, 2-oxopyridin-1(2H)-yl, a 4- to 8-membered heterocycle or (C$_4$-C$_8$)-cycloalkyl, or
is a group of the formula

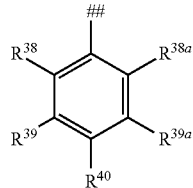

wherein
## is the point of attachment to the pyrazole ring,
$R^{38}$ is a hydrogen atom, halogen or methyl,
$R^{38a}$ is a hydrogen atom, halogen or methyl,
$R^{39}$ is a hydrogen atom, cyano, fluorine or $(C_1-C_4)$-alkylsulfanyl,
$R^{39a}$ is a hydrogen atom, cyano, fluorine or $(C_1-C_4)$-alkylsulfanyl,
$R^{40}$ is a hydrogen atom, halogen, cyano, hydroxy, —$(CH_2)_n NR^{16}R^{17}$, $(C_1-C_4)$-alkyl, $(C_1-C_4)$-alkoxy or $(C_1-C_4)$-alkoxycarbonyl,
  wherein said $(C_1-C_4)$-alkyl is optionally substituted with cyano and optionally with up to five fluorine atoms,
  wherein said $(C_1-C_4)$-alkoxy is optionally substituted with up to five fluorine atoms,
  wherein
  n is 0 or 1,
  $R^{16}$ is a hydrogen atom or $(C_1-C_4)$-alkyl,
    wherein said $(C_1-C_4)$-alkyl is optionally substituted with up to five fluorine atoms,
  $R^{17}$ is a hydrogen atom or $(C_1-C_4)$-alkyl,
    wherein said $(C_1-C_4)$-alkyl is optionally substituted with up to five fluorine atoms,
  or
  $R^{16}$ and $R^{17}$ together with the nitrogen atom they are attached form a
  4- to 8-membered heterocycle
    wherein said 4- to 8-membered heterocycle is optionally substituted, identically or differently, with one, two or three groups selected from $(C_1-C_4)$-alkyl and optionally up to five fluorine atoms,
wherein said 6-membered heteroaryl group is optionally substituted, identically or differently, with one or two groups selected from a halogen atom, cyano, $(C_1-C_4)$-alkyl, and $(C_1-C_4)$-alkoxy,
  wherein said $(C_1-C_4)$-alkyl is optionally substituted with up to five fluorine atoms,
  wherein said $(C_1-C_4)$-alkoxy is optionally substituted with up to three fluorine atoms,
wherein said 2-oxopyridin-1(2H)-yl is optionally substituted, identically or differently, with one or two groups selected from a halogen atom, cyano, $(C_1-C_4)$-alkyl and $(C_1-C_4)$-alkoxy,
  wherein said $(C_1-C_4)$-alkyl is optionally substituted with up to five luorine atoms,
  wherein said $(C_1-C_4)$-alkoxy is optionally substituted with up to three fluorine atoms,
wherein said 4- to 8-membered heterocycle is optionally substituted, identically or differently, with one, two or three groups selected from $(C_1-C_4)$-alkyl, cyano, $(C_1-C_4)$-alkoxycarbonyl and optionally up to five fluorine atoms,
  wherein said $(C_1-C_4)$-alkyl is optionally substituted with up to five fluorine atoms,
  wherein said $(C_4-C_8)$-cycloalkyl is optionally substituted, identically or differently, with one or two groups selected from $(C_1-C_4)$-alkyl, cyano and optionally up to five fluorine atoms,
  wherein said $(C_1-C_4)$-alkyl is optionally substituted with $(C_3-C_6)$-cycloalkyl and optionally up to five fluorine atoms,
$R^7$ is a hydrogen atom, $(C_1-C_4)$-alkyl, a phenyl group, a 5- to 6-membered heteroaryl group or $(C_1-C_4)$-alkylsulfonyl,
  wherein any phenyl group and any 5- to 6-membered heteroaryl are each optionally substituted, identically or differently, with one, two or three groups selected from a halogen atom, $(C_1-C_4)$-alkyl, trifluoromethyl, $(C_1-C_4)$-alkoxy and trifluoromethoxy,
  wherein said $(C_1-C_4)$-alkyl is optionally substituted with a group selected from $(C_3-C_6)$-cycloalkyl, 4- to 6-membered heterocycle, hydroxy, —$NR^{20}R^{21}$, $(C_1-C_4)$-alkoxy or benzyloxy and optionally with up to five fluorine atoms,
    wherein said $(C_3-C_6)$-cycloalkyl is optionally substituted, identically or differently, with one or two groups selected from $(C_1-C_4)$-alkyl, hydroxy and up to five fluorine atoms,
    wherein said 4- to 6-membered heterocycle is optionally substituted, identically or differently, with one or two groups selected from $(C_1-C_4)$-alkyl and optionally up to five fluorine atoms,
    and
    wherein
    $R^{20}$ is a hydrogen atom or $(C_1-C_4)$-alkyl,
    $R^{21}$ is a hydrogen atom or $(C_1-C_4)$-alkyl,
    or
    $R^{20}$ and $R^{21}$ together with the nitrogen atom they are attached form a 4- to 6-membered heterocycle
      wherein said 4- to 6-membered heterocycle is optionally substituted, identically or differently, with one, two or three groups selected from $(C_1-C_4)$-alkyl and optionally up to five fluorine atoms,
with the proviso that if $R^5$ is $(C_1-C_4)$-alkoxy then $R^7$ is different from hydrogen,
with the proviso that if $R^6$ is 6-membered heteroaryl then $R^7$ is different from hydrogen,
with the proviso that if $R^6$ is 2-oxopyridin-1(2H)-yl then $R^7$ is different from hydrogen,
with the proviso that if $R^6$ is a 4- to 8-membered heterocycle then $R^7$ is different from hydrogen,
$R^8$ is a group selected from a halogen atom, cyano, $(C_1-C_4)$-alkyl, $(C_1-C_4)$-alkoxy, $(C_3-C_6)$-cycloalkyl, 4- to 6-membered heterocycle, $(C_1-C_4)$-alkylcarbonyl and a phenyl group,
  wherein said $(C_1-C_4)$-alkyl is optionally substituted, identically or differently, with one or two groups selected from —$NR^{22}R^{23}$ $(C_1-C_4)$-alkoxy and cyclopropyl and optionally up to five fluorine atoms,
    wherein said cyclopropyl is optionally substituted with up to four fluorine atoms,
    wherein said $(C_1-C_4)$-alkoxy is optionally substituted with up to five fluorine atoms, wherein
R$^{22}$ is a hydrogen atom or (C$_1$-C$_4$)-alkyl,
R$^{23}$ is a hydrogen atom or (C$_1$-C$_4$)-alkyl,
or
R$^{22}$ and R$^{23}$ together with the nitrogen atom they are attached form a 4- to 6-membered heterocycle
wherein said 4- to 6-membered heterocycle is optionally substituted, identically or differently, with one, two or three groups selected from (C$_1$-C$_4$)-alkyl and optionally up to five fluorine atoms,
wherein said (C$_1$-C$_4$)-alkoxy is optionally substituted with up to five fluorine atoms,
wherein said (C$_3$-C$_6$)-cycloalkyl is optionally substituted, identically or differently, with one or two groups selected from (C$_1$-C$_4$)-alkyl and optionally up to five fluorine atoms,
wherein said 4- to 6-membered heterocycle is optionally substituted, identically or differently, with one or two groups selected from (C$_1$-C$_4$)-alkyl and optionally up to five fluorine atoms,
and
wherein said phenyl group is optionally substituted, identically or differently, with one, two or three groups selected from a halogen atom, cyano, (C$_1$-C$_4$)-alkyl, trifluoromethyl, (C$_1$-C$_4$)-alkoxy and trifluoromethoxy,
R$^9$ is 6-membered heteroaryl, 2-oxopyridin-1(2H)-yl, (C$_3$-C$_8$)-cycloalkyl, a 4- to 8-membered heterocycle or (C$_1$-C$_4$)-alkyl,
or
is a group of the formula

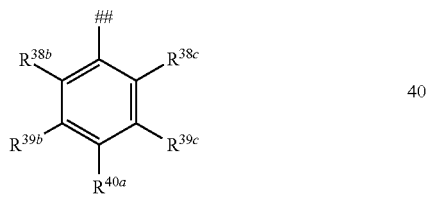

wherein
## is the point of attachment to the pyrazole ring,
R$^{38b}$ is a hydrogen atom, halogen or methyl,
R$^{38c}$ is a hydrogen atom, halogen or methyl,
R$^{39b}$ is a hydrogen atom, cyano, fluorine or (C$_1$-C$_4$)-alkylsulfanyl,
R$^{39c}$ is a hydrogen atom, cyano, fluorine or (C$_1$-C$_4$)-alkylsulfanyl,
R$^{40a}$ is a hydrogen atom, halogen, cyano, hydroxy, —(CH$_2$)$_n$NR$^{16a}$R$^{17a}$, (C$_1$-C$_4$)-alkyl, (C$_1$-C$_4$)-alkoxy, (C$_1$-C$_4$)-alkoxycarbonyl, a 4- to 6-membered heterocycle, cyclopropyl or cyclobutyl,
wherein said (C$_1$-C$_4$)-alkyl is optionally substituted with cyano and optionally with up to five fluorine atoms,
wherein said (C$_1$-C$_4$)-alkoxy is optionally substituted with up to five fluorine atoms,
wherein said 4- to 6-membered heterocycle is optionally substituted, identically or differently, with one, two or three groups selected from (C$_1$-C$_4$)-alkyl and optionally up to five fluorine atoms,
wherein
n is 0 or 1,
R$^{16a}$ is a hydrogen atom or (C$_1$-C$_4$)-alkyl,
wherein said (C$_1$-C$_4$)-alkyl is optionally substituted with up to five fluorine atoms,
R$^{17a}$ is a hydrogen atom or (C$_1$-C$_4$)-alkyl,
wherein said (C$_1$-C$_4$)-alkyl is optionally substituted with up to five fluorine atoms,
or
R$^{16a}$ and R$^{17a}$ together with the nitrogen atom they are attached form a 4- to 8-membered heterocycle
wherein said 4- to 8-membered heterocycle is optionally substituted, identically or differently, with one, two or three groups selected from (C$_1$-C$_4$)-alkyl and optionally up to five fluorine atoms,
wherein said (C$_1$-C$_4$)-alkyl is optionally substituted with up to five fluorine atoms,
wherein said 6-membered heteroaryl group is optionally substituted, identically or differently, with one or two groups selected from a halogen atom, cyano, (C$_1$-C$_4$)-alkyl, and (C$_1$-C$_4$)-alkoxy,
wherein said (C$_1$-C$_4$)-alkyl is optionally substituted with up to five fluorine atoms,
wherein said (C$_1$-C$_4$)-alkoxy is optionally substituted with up to three fluorine atoms,
wherein said 2-oxopyridin-1(2H)-yl is optionally substituted, identically or differently, with one or two groups selected from a halogen atom, cyano, (C$_1$-C$_4$)-alkyl, and (C$_1$-C$_4$)-alkoxy,
wherein said (C$_1$-C$_4$)-alkyl is optionally substituted with up to five fluorine atoms,
wherein said (C$_1$-C$_4$)-alkoxy is optionally substituted with up to three fluorine atoms,
wherein said (C$_3$-C$_8$)-cycloalkyl is optionally substituted, identically or differently, with one or two groups selected from (C$_1$-C$_4$)-alkyl, cyano and optionally up to five fluorine atoms,
wherein said (C$_1$-C$_4$)-alkyl is optionally substituted with (C$_3$-C$_6$)-cycloalkyl and optionally up to five fluorine atoms,
wherein said 4- to 8-membered heterocycle is optionally substituted identically or differently, with one or two groups selected from (C$_1$-C$_4$)-alkyl, cyano, (C$_1$-C$_4$)-alkoxycarbonyl and optionally up to five fluorine atoms,
wherein said (C$_1$-C$_4$)-alkyl is optionally substituted with up to five fluorine atoms,
R$^{10}$ is a hydrogen atom, (C$_1$-C$_4$)-alkyl, (C$_3$-C$_8$)-cycloalkyl, (C$_1$-C$_4$)-alkoxycarbonyl, mono-(C$_1$-C$_4$)-alkylamino, a phenyl group or a 5- to 6-membered heteroaryl group,
wherein any phenyl group and any 5- to 6-membered heteroaryl are each optionally substituted, identically or differently, with one, two or three groups selected from a halogen atom, (C$_1$-C$_4$)-alkyl, trifluoromethyl, (C$_1$-C$_4$)-alkoxy and trifluoromethoxy,
wherein said (C$_1$-C$_4$)-alkyl is optionally substituted with a group selected from (C$_3$-C$_6$)-cycloalkyl, 5-membered heteroaryl, —NR$^{28}$R$^{29}$, (C$_1$-C$_4$)-alkoxy or benzyloxy and optionally with up to five fluorine atoms and is optionally additionally substituted with hydroxy,
wherein said (C$_3$-C$_6$)-cycloalkyl is optionally substituted, identically or differently, with hydroxy or one or two groups $(C_1\text{-}C_4)$-alkyl and optionally up to five fluorine atoms,
and
wherein
$R^{28}$ is a hydrogen atom or $(C_1\text{-}C_4)$-alkyl,
$R^{29}$ is a hydrogen atom or $(C_1\text{-}C_4)$-alkyl,
or
$R^{28}$ and $R^{29}$ together with the nitrogen atom they are attached form a 4- to 6-membered heterocycle
wherein said 4- to 6-membered heterocycle is optionally substituted, identically or differently, with one, two or three groups selected from $(C_1\text{-}C_4)$-alkyl and optionally up to five fluorine atoms,
wherein said 5-membered heteroaryl is optionally substituted with $(C_1\text{-}C_4)$-alkyl,
with the proviso that if $R^9$ is 6-membered heterorayl then $R^{10}$ is different from hydrogen,
with the proviso that if $R^9$ is 2-oxopyridin-1(2H)-yl then $R^{10}$ is different from hydrogen,
with the proviso that if $R^9$ is a 4- to 8-membered heterocycle then $R^{10}$ is different from hydrogen,
with the proviso that if $R^8$ is $(C_1\text{-}C_4)$-alkoxy then $R^{10}$ is different from hydrogen,
$R^{11}$ is a group selected from a hydrogen atom, a fluorine atom, a chlorine atom, $(C_1\text{-}C_4)$-alkyl and cyclopropyl,
wherein said $(C_1\text{-}C_4)$-alkyl is optionally substituted with cyclopropyl and optionally up to five fluorine atoms,
$R^{12}$ is a 6-membered heteroaryl group, 2-oxopyridin-1(2H)-yl, $(C_4\text{-}C_8)$-cycloalkyl or $(C_1\text{-}C_4)$-alkyl,
or
is a group of the formula

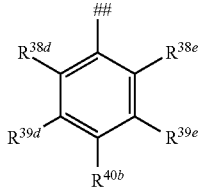

wherein
## is the point of attachment to the pyrazole ring,
$R^{38d}$ is a hydrogen atom, halogen or methyl,
$R^{38e}$ is a hydrogen atom, halogen or methyl,
$R^{39d}$ is a hydrogen atom, cyano, fluorine or $(C_1\text{-}C_4)$-alkylsulfanyl,
$R^{39e}$ is a hydrogen atom, cyano, fluorine or $(C_1\text{-}C_4)$-alkylsulfanyl,
$R^{40b}$ is a hydrogen atom, halogen, cyano, hydroxy, —$(CH_2)_n NR^{16a}R^{17a}$, $(C_1\text{-}C_4)$-alkyl, $(C_1\text{-}C_4)$-alkoxy, $(C_1\text{-}C_4)$-alkoxycarbonyl, a 4- to 6-membered heterocycle, cyclopropyl or cyclobutyl,
wherein said $(C_1\text{-}C_4)$-alkyl is optionally substituted with cyano and optionally with up to five fluorine atoms,
wherein said $(C_1\text{-}C_4)$-alkoxy is optionally substituted with up to five fluorine atoms,
wherein said 4- to 6-membered heterocycle is optionally substituted, identically or differently, with one, two or three groups selected from $(C_1\text{-}C_4)$-alkyl and optionally up to five fluorine atoms,
wherein
n is 0 or 1,
$R^{16a}$ is a hydrogen atom or $(C_1\text{-}C_4)$-alkyl,
wherein said $(C_1\text{-}C_4)$-alkyl is optionally substituted with up to five fluorine atoms,
$R^{17a}$ is a hydrogen atom or $(C_1\text{-}C_4)$-alkyl,
wherein said $(C_1\text{-}C_4)$-alkyl is optionally substituted with up to five fluorine atoms,
or
$R^{16a}$ and $R^{17a}$ together with the nitrogen atom they are attached form a 4- to 8-membered heterocycle
wherein said 4- to 8-membered heterocycle is optionally substituted, identically or differently, with one, two or three groups selected from $(C_1\text{-}C_4)$-alkyl and optionally up to five fluorine atoms,
wherein said 6-membered heteroaryl group is optionally substituted, identically or differently, with one or two groups selected from a halogen atom, cyano, $(C_1\text{-}C_4)$-alkyl, and $(C_1\text{-}C_4)$-alkoxy,
wherein said $(C_1\text{-}C_4)$-alkyl is optionally substituted with up to five fluorine atoms,
wherein said $(C_1\text{-}C_4)$-alkoxy is optionally substituted with up to three fluorine atoms,
wherein said 2-oxopyridin-1(2H)-yl is optionally substituted, identically or differently, with one or two groups selected from a halogen atom, cyano, $(C_1\text{-}C_4)$-alkyl, and $(C_1\text{-}C_4)$-alkoxy,
wherein said $(C_1\text{-}C_4)$-alkyl is optionally substituted with up to five fluorine atoms,
wherein said $(C_1\text{-}C_4)$-alkoxy is optionally substituted with up to three fluorine atoms,
wherein said $(C_4\text{-}C_8)$-cycloalkyl is optionally substituted, identically or differently, with one or two groups selected from $(C_1\text{-}C_4)$-alkyl or cyano and optionally up to five fluorine atoms,
$R^{13}$ is a group selected from a hydrogen atom, a fluorine atom, a chlorine atom, $(C_1\text{-}C_4)$-alkyl and cyclopropyl,
wherein said $(C_1\text{-}C_4)$-alkyl is optionally substituted with cyclopropyl and up to five fluorine atoms,
$R^2$ is a group selected from a hydrogen atom, $(C_1\text{-}C_4)$-alkyl, $(C_3\text{-}C_6)$-cycloalkyl and $(C_1\text{-}C_4)$-alkoxycarbonyl,
wherein said $(C_1\text{-}C_4)$-alkyl is optionally substituted, identically or differently, with one or two groups selected from hydroxy, $(C_1\text{-}C_4)$-alkoxy, cyclopropyl and optionally up to five fluorine atoms,
$R^3$ is a group selected from a hydrogen atom, a halogen atom, cyano, hydroxy, nitro, amino, mono-$(C_1\text{-}C_4)$-alkylamino, di-$(C_1\text{-}C_4)$-alkylamino, $(C_1\text{-}C_4)$-alkylsulfanyl, $(C_1\text{-}C_4)$-alkylsulfinyl, $(C_1\text{-}C_4)$-alkylsulfonyl, $(C_1\text{-}C_6)$-alkyl, $(C_1\text{-}C_4)$-alkoxy, $(C_3\text{-}C_6)$-cycloalkyl, 4- to 6-membered heterocycle, 5- to 6-membered heteroaryl, —$(CH_2)_q C(=O)$—$NR^{34}R^{35}$, —O—C$(=O)$—$NR^{36}R^{37}$, —O—C$(=O)$—$OR^{37a}$, —NH—C$(=O)$—$NR^{36}R^{37}$, —N$(CH_3)$—C$(=O)$—$NR^{36}R^{37}$, —NH—C$(=O)$—$OR^{37a}$, —N$(CH_3)$—C$(=O)$—$OR^{37a}$—NH—C$(=O)$—$R^{37}$, —N$(CH_3)$—C$(=O)$—$R^{37}$, $(C_1\text{-}C_4)$-alkylcarbonyl, $(C_1\text{-}C_4)$-alkylcarbonyloxy and $(C_1\text{-}C_4)$-alkoxycarbonyl,
wherein said $(C_1\text{-}C_6)$-alkyl is optionally substituted, identically or differently, with one or two groups selected from hydroxy, amino, mono-$(C_1\text{-}C_4)$-alkylamino, di-($C_1$-$C_4$)-alkylamino, cyano, ($C_1$-$C_4$)-alkoxy, 4- to 6-membered heterocycle, ($C_1$-$C_4$)-alkoxycarbonyl and cyclopropyl and optionally up to six fluorine atoms,
   wherein said 4- to 6-membered heterocycle is optionally substituted with ($C_1$-$C_4$)-alkyl or cyclopropyl and optionally up to two fluorine atoms,
wherein said ($C_1$-$C_4$)-alkoxy is optionally substituted with cyano, cyclopropyl and optionally up to five fluorine atoms,
wherein said ($C_1$-$C_4$)-alkyl of mono-($C_1$-$C_4$)-alkylamino is optionally substituted with cyano, cyclopropyl and optionally up to five fluorine atoms,
wherein said di-($C_1$-$C_4$)-alkylamino is optionally substituted with cyano, cyclopropyl and optionally up to five fluorine atoms,
wherein said ($C_3$-$C_6$)-cycloalkyl is optionally substituted, identically or differently, with one or two groups selected from ($C_1$-$C_4$)-alkyl, ($C_1$-$C_4$)-alkoxy, hydroxy and cyclopropyl and optionally up to five fluorine atoms,
wherein said 4- to 6-membered heterocycle is optionally substituted, identically or differently, with one or two groups selected from ($C_1$-$C_4$)-alkyl, trifluoromethyl, difluoromethyl, ($C_1$-$C_4$)-alkoxy, ($C_1$-$C_4$)-alkoxycarbonyl, mono-($C_1$-$C_4$)-alkylaminocarbonyl, di-($C_1$-$C_4$)-alkylaminocarbonyl, ($C_1$-$C_4$)-alkylcarbonyl, hydroxy and cyclopropyl and optionally up to five fluorine atoms,
wherein said 5- to 6-membered heteroaryl is optionally substituted, identically or differently, with one or two groups selected from ($C_1$-$C_4$)-alkyl, ($C_1$-$C_4$)-alkoxy, and cyclopropyl and optionally up to five fluorine atoms,
wherein
q is 0 or 1,
$R^{34}$ is a hydrogen atom or ($C_1$-$C_4$)-alkyl,
$R^{35}$ is a hydrogen atom, ($C_1$-$C_4$)-alkyl or phenyl,
or
$R^{34}$ and $R^{35}$ together with the nitrogen atom they are attached form a 4- to 7-membered heterocyclyl ring
   wherein said 4- to 7-membered heterocyclyl ring is optionally substituted, identically or differently, with one, two or three groups selected from a fluorine atom, hydroxy, ($C_1$-$C_4$)-alkyl, ($C_1$-$C_4$)-alkoxy, cyclopropyl, difluoromethyl, trifluoromethyl and trifluoromethoxy,
wherein
$R^{36}$ is a hydrogen atom or methyl,
$R^{37}$ is a hydrogen atom, methyl, difluoromethyl, trifluoromethyl or cyclopropyl,
$R^{37a}$ is methyl, difluoromethyl, trifluoromethyl or cyclopropyl,
with the proviso that if $R^3$ is —(CH$_2$)$_q$C(=O)—NR$^{34}$R$^{35}$, —O—C(=O)—NR$^{36}$R$^{37}$, —O—C(=O)—OR$^{37a}$, —N(CH$_3$)—C(=O)—NR$^{36}$R$^{37}$, —NH—C(=O)—OR$^{37a}$, —NH—C(=O)—NR$^{36}$R$^{37}$, —N(CH$_3$)—C(=O)—OR$^{37a}$—NH—C(=O)—R$^{37}$ or —N(CH$_3$)—C(=O)—R$^{37}$, then $R^7$ and $R^{10}$ are different from hydrogen,
with the proviso that if $R^3$ is cyano then $R^2$ and $R^4$ are different from hydrogen,
with the proviso that if $R^3$ is cyano then $R^6$ and $R^9$ are different from 6-membered heteroaryl,
or
$R^2$ and $R^3$ together with the carbon atoms they are attached form a 4- to 6-membered carbocycle, a 4- to 7-membered azaheterocycle, a 4- to 7-membered oxaheterocycle, a 5- to 6-membered heteroaryl group or a phenyl ring,
   wherein said 4- to 7-membered azaheterocycle is optionally substituted, identically or differently, with one or two groups selected from hydroxy, oxo, ($C_1$-$C_4$)-alkyl, trifluoromethyl, ($C_1$-$C_4$)-alkylcarbonyl and ($C_1$-$C_4$)-alkoxycarbonyl and optionally up to five fluorine atoms,
   wherein said 4- to 7-membered oxaheterocycle is optionally substituted, identically or differently, with one or two groups selected from hydroxy, oxo, ($C_1$-$C_4$)-alkyl, trifluoromethyl, ($C_1$-$C_4$)-alkylcarbonyl and ($C_1$-$C_4$)-alkoxycarbonyl and optionally up to five fluorine atoms,
   wherein said 4- to 6-membered carbocycle is optionally substituted, identically or differently, with one or two groups selected from hydroxy, oxo, amino, mono-($C_1$-$C_4$)-alkylamino, di-($C_1$-$C_4$)-alkylamino, ($C_1$-$C_4$)-alkyl, trifluoromethyl, ($C_1$-$C_4$)-alkylcarbonyl and ($C_1$-$C_4$)-alkoxycarbonyl and optionally up to five fluorine atoms,
and
wherein any phenyl group and any 5- to 6-membered heteroaryl group are each optionally substituted, identically or differently, with one, two or three groups selected from a halogen atom, ($C_1$-$C_4$)-alkyl, trifluoromethyl, ($C_1$-$C_4$)-alkoxy and trifluoromethoxy,
with the proviso that if $R^2$ and $R^3$ together with the carbon atoms they are attached to form a 4- to 7-membered azaheterocycle with a non-substituted nitrogen atom which is not directly attached to the pyrazole, then $R^7$ and $R^{10}$ are different from hydrogen,
with the proviso that if $R^7$ and $R^{10}$ are hydrogen then the nitrogen atom of the 4- to 7-membered azaheterocycle formed by $R^2$ and $R^3$ together with the carbon atoms they are attached to is substituted with ($C_1$-$C_4$)-alkyl or ($C_1$-$C_4$)-alkoxycarbonyl,
$R^4$ is a group selected from a hydrogen atom, ($C_1$-$C_4$)-alkyl, ($C_3$-$C_6$)-cycloalkyl and ($C_1$-$C_4$)-alkoxycarbonyl and hydroxy,
   wherein said ($C_1$-$C_4$)-alkyl is optionally substituted, identically or differently, with one or two groups selected from hydroxy, ($C_1$-$C_4$)-alkoxy and cyclopropyl and optionally up to five fluorine atoms,
or
$R^3$ and $R^4$ together with the carbon atoms they are attached form a 4- to 6-membered carbocycle, a 4- to 7-membered heterocycle, a 5- to 6-membered heteroaryl group or a phenyl ring,
   wherein said 4- to 7-membered heterocycle is optionally substituted, identically or differently, with one or two groups selected from a fluorine atom, hydroxy, oxo, ($C_1$-$C_4$)-alkyl, trifluoromethyl, ($C_1$-$C_4$)-alkylcarbonyl and ($C_1$-$C_4$)-alkoxycarbonyl and optionally up to five fluorine atoms,
   wherein said 4- to 6-membered carbocycle is optionally substituted, identically or differently, with one or two groups selected from a fluorine atom, hydroxy, oxo, ($C_1$-$C_4$)-alkyl, trifluoromethyl, ($C_1$-$C_4$)-alkylcarbonyl and ($C_1$-$C_4$)-alkoxycarbonyl and optionally up to five fluorine atoms,
and
wherein any phenyl group and any 5- to 6-membered heteroaryl group are each optionally substituted, identically or differently, with one, two or three groups selected from a halogen atom, $(C_1-C_4)$-alkyl, trifluoromethyl, $(C_1-C_4)$-alkoxy and trifluoromethoxy, with the proviso that if $R^3$ and $R^4$ together with the carbon atoms they are attached form a 4- to 7-membered heterocycle with a non-substituted nitrogen atom which is not directly attached to the pyrazole, then $R^7$ and $R^{10}$ is different from hydrogen, with the proviso that if $R^7$ and $R^{10}$ are hydrogen then the nitrogen atom of the 4- to 7-membered heterocycle formed by $R^3$ and $R^4$ together with the carbon atoms they are attached to is substituted with $(C_1-C_4)$-alkyl or $(C_1-C_4)$-alkoxycarbonyl, or a stereoisomer, a tautomer, an N-oxide, a hydrate, a solvate, or a salt thereof, or a mixture of same.

2. The compound of formula (I) according to claim 1, wherein $R^1$ is a group of the formula

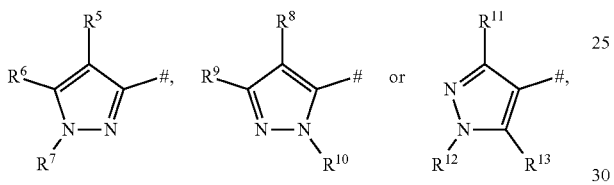

wherein

\# is the point of attachment to the amino group, $R^5$ is a group selected from fluorine, chlorine, cyano, $(C_1-C_4)$-alkyl, methoxy, ethoxy, $(C_3-C_5)$-cycloalkyl, methylcarbonyl and ethylcarbonyl, wherein said $(C_1-C_4)$-alkyl is optionally substituted, identically or differently, with one or two groups selected from $-NR^{14}R^{15}$, methoxy, ethoxy, difluoromethoxy, trifluoromethoxy and cyclopropyl and optionally up to five fluorine atoms, wherein said cyclopropyl is optionally substituted with up to four fluorine atoms, wherein $R^{14}$ is a hydrogen atom or $(C_1-C_4)$-alkyl, $R^{15}$ is a hydrogen atom or $(C_1-C_4)$-alkyl, or $R^{14}$ and $R^{15}$ together with the nitrogen atom they are attached form a 4- to 5-membered heterocycle wherein said 4- to 5-membered heterocycle is optionally substituted, identically or differently, with one or two groups selected from $(C_1-C_4)$-alkyl, trifluormethyl, difluoromethyl and optionally up to five fluorine atoms, wherein said methoxy and ethoxy are optionally substituted with up to three fluorine atoms, wherein said $(C_3-C_5)$-cycloalkyl is optionally substituted with up to four fluorine atoms, $R^6$ is pyridyl, pyrimidyl, 2-oxopyridin-1(2H)-yl, $(C_5-C_8)$-cycloalkyl or a 6- to 8-membered heterocycle or is a group of the formula

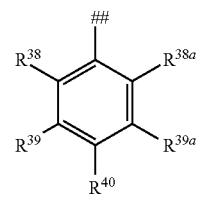

wherein

\#\# is the point of attachment to the pyrazole ring, $R^{38}$ is a hydrogen atom, halogen or methyl, $R^{38a}$ is a hydrogen atom, halogen or methyl, $R^{39}$ is a hydrogen atom, cyano, fluorine or $(C_1-C_4)$-alkylsulfanyl, $R^{39a}$ is a hydrogen atom, cyano, fluorine or $(C_1-C_4)$-alkylsulfanyl, $R^{40}$ is a hydrogen atom, fluorine, chlorine, cyano, hydroxy, $-(CH_2)_nNR^{16}R^{17}$, $(C_1-C_3)$-alkyl, $(C_1-C_3)$-alkoxy or $(C_1-C_4)$-alkoxycarbonyl, wherein said $(C_1-C_3)$-alkyl is optionally substituted with cyano and optionally with up to five fluorine atoms, wherein said $(C_1-C_3)$-alkoxy is optionally substituted with up to five fluorine atoms, wherein n is 0 or 1, $R^{16}$ is a hydrogen atom or $(C_1-C_4)$-alkyl, $R^{17}$ is a hydrogen atom or $(C_1-C_4)$-alkyl, or $R^{16}$ and $R^{17}$ together with the nitrogen atom they are attached form a 4- to 6-membered heterocycle wherein said 4- to 6-membered heterocycle is optionally substituted, identically or differently, with one, two or three groups selected from $(C_1-C_4)$-alkyl and optionally up to five fluorine atoms, wherein said pyridyl and pyrimidyl are optionally substituted, identically or differently, with one or two groups selected from a halogen atom, cyano, methyl, ethyl, methoxy and ethoxy, wherein said $(C_1-C_4)$-alkyl is optionally substituted with up to five fluorine atoms, wherein said methoxy and ethoxy are optionally substituted with up to three fluorine atoms, wherein said 2-oxopyridin-1(2H)-yl is optionally substituted, identically or differently, with one or two groups selected from fluorine, cyano, methyl, ethyl, methoxy and ethoxy, wherein said methyl and ethyl are optionally substituted with up to three fluorine atoms, wherein said methoxy and ethoxy are optionally substituted with up to three fluorine atoms, wherein said 6- to 8-membered heterocycle is optionally substituted, identically or differently, with one or two groups selected from $(C_1-C_4)$-alkyl, cyano, $(C_1-C_4)$-alkoxycarbonyl and optionally up to five fluorine atoms, wherein said $(C_1-C_4)$-alkyl is optionally substituted with up to three fluorine atoms, wherein said $(C_5-C_8)$-cycloalkyl is optionally substituted, identically or differently, with one or two groups selected from $(C_1-C_4)$-alkyl and cyano, and optionally up to five fluorine atoms, wherein said $(C_1-C_4)$-alkyl is optionally substituted with up to three fluorine atoms,
$R^7$ is a hydrogen atom, $(C_1-C_4)$-alkyl, methylsulfonyl or ethylsulfonyl,
  wherein said $(C_1-C_4)$-alkyl is optionally substituted with a group selected from $(C_3-C_6)$-cycloalkyl, hydroxy, —$NR^{20}R^{21}$, methoxy, ethoxy or benzyloxy and optionally with up to five fluorine atoms,
    wherein said $(C_3-C_6)$-cycloalkyl is optionally substituted with hydroxy and optionally up to four fluorine atoms,
    and
    wherein
      $R^{20}$ is a hydrogen atom or $(C_1-C_4)$-alkyl,
      $R^{21}$ is a hydrogen atom or $(C_1-C_4)$-alkyl,
with the proviso that if $R^5$ is methoxy or ethoxy then $R^7$ is different from hydrogen,
with the proviso that if $R^6$ is pyridyl or pyrimidyl then $R^7$ is different from hydrogen,
with the proviso that if $R^6$ is 2-oxopyridin-1(2H)-yl then $R^7$ is different from hydrogen,
with the proviso that if $R^6$ is a 6- to 8-membered heterocycle then $R^7$ is different from hydrogen,
$R^8$ is a group selected from fluorine, chlorine, cyano, $(C_1-C_4)$-alkyl, methoxy, ethoxy, methylcarbonyl, ethylcarbonyl and $(C_3-C_8)$-cycloalkyl,
  wherein said $(C_1-C_4)$-alkyl is optionally substituted with methoxy, —$NR^{22}R^{23}$ and cyclopropyl and optionally up to five fluorine atoms,
    wherein said cyclopropyl is optionally substituted with up to four fluorine atoms,
    wherein said methoxy is optionally substituted with up to three fluorine atoms,
    wherein
      $R^{22}$ is a hydrogen atom or $(C_1-C_4)$-alkyl,
      $R^{23}$ is a hydrogen atom or $(C_1-C_4)$-alkyl,
      or
      $R^{22}$ and $R^{23}$ together with the nitrogen atom they are attached form a 4- to 6-membered heterocycle
        wherein said 4- to 6-membered heterocycle is optionally substituted, identically or differently, with one, two or three groups selected from $(C_1-C_4)$-alkyl and optionally up to five fluorine atoms,
      wherein said methoxy and ethoxy are optionally substituted with up to three fluorine atoms,
    and
    wherein said $(C_3-C_8)$-cycloalkyl is optionally substituted with up to four fluorine atoms,
$R^9$ is pyridyl, pyrimidyl, 2-oxopyridin-1(2H)-yl, $(C_5-C_8)$-cycloalkyl or a 6- to 8-membered heterocycle or $(C_1-C_4)$-alkyl,
  or
  is a group of the formula

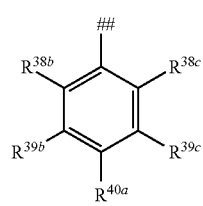

wherein
## is the point of attachment to the pyrazole ring,
$R^{38b}$ is a hydrogen atom, halogen or methyl,
$R^{38c}$ is a hydrogen atom, halogen or methyl,
$R^{39b}$ is a hydrogen atom, cyano, fluorine or $(C_1-C_4)$-alkylsulfanyl,
$R^{39c}$ is a hydrogen atom, cyano, fluorine or $(C_1-C_4)$-alkylsulfanyl,
$R^{40a}$ is a hydrogen atom, fluorine, chlorine, cyano, hydroxy, —$(CH_2)_nNR^{16a}R^{17a}$, $(C_1-C_3)$-alkyl, $(C_1-C_3)$-alkoxy, $(C_1-C_4)$-alkoxycarbonyl, a 4- to 6-membered heterocycle, cyclopropyl or cyclobutyl,
  wherein said $(C_1-C_3)$-alkyl is optionally substituted with cyano and optionally with up to five fluorine atoms,
  wherein said $(C_1-C_3)$-alkoxy is optionally substituted with up to five fluorine atoms,
  wherein said 4- to 6-membered heterocycle is optionally substituted, identically or differently, with one, two or three groups selected from $(C_1-C_4)$-alkyl and optionally up to five fluorine atoms,
  wherein
    n is 0 or 1,
    $R^{16a}$ is a hydrogen atom or $(C_1-C_4)$-alkyl,
    $R^{17a}$ is a hydrogen atom or $(C_1-C_4)$-alkyl,
    or
    $R^{16a}$ and $R^{17a}$ together with the nitrogen atom they are attached form a 4- to 6-membered heterocycle
      wherein said 4- to 6-membered heterocycle is optionally substituted, identically or differently, with one, two or three groups selected from $(C_1-C_4)$-alkyl and optionally up to five fluorine atoms,
wherein said $(C_1-C_4)$-alkyl is optionally substituted with up to five fluorine atoms,
wherein said pyridyl and pyrimidyl are optionally substituted, identically or differently, with one or two groups selected from a halogen atom, cyano, methyl, ethyl, methoxy and ethoxy,
  wherein said methyl and ethyl is optionally substituted with up to three fluorine atoms,
  wherein said methoxy and ethoxy are optionally substituted with up to three fluorine atoms,
wherein said 2-oxopyridin-1(2H)-yl is optionally substituted, identically or differently, with one or two groups selected from fluorine, cyano, methyl, ethyl, methoxy and ethoxy,
  wherein said methyl and ethyl are optionally substituted with up to three fluorine atoms,
  wherein said methoxy and ethoxy are optionally substituted with up to three fluorine atoms,
wherein said 6- to 8-membered heterocycle is optionally substituted, identically or differently, with one or two groups selected from methyl, ethyl, cyano and $(C_1-C_4)$-alkoxycarbonyl and optionally up to five fluorine atoms,
  wherein said methyl is optionally substituted with up to three fluorine atoms,
wherein said $(C_5-C_8)$-cycloalkyl is optionally substituted, identically or differently, with one or two groups selected from methyl, ethyl and cyano, and optionally up to five fluorine atoms,
  wherein said methyl is optionally substituted with up to three fluorine atoms, $R^{10}$ is a hydrogen atom, $(C_1-C_4)$-alkyl or $(C_3-C_8)$-cycloalkyl,
  wherein said $(C_1-C_4)$-alkyl is optionally substituted with a group selected from $(C_3-C_6)$-cycloalkyl, 2-methyl-2H-tetrazol-5-yl, 1-methyl-1H-tetrazol-5-yl, —$NR^{28}R^{29}$ methoxy, ethoxy or benzyloxy and optionally with up to five fluorine atoms optionally with up to five fluorine atoms and is optionally additionally substituted with hydroxy,
  wherein said $(C_3-C_6)$-cycloalkyl is optionally substituted with up to four fluorine atoms,
  and
  wherein
    $R^{28}$ is a hydrogen atom or $(C_1-C_4)$-alkyl,
    $R^{29}$ is a hydrogen atom or $(C_1-C_4)$-alkyl,
with the proviso that if $R^9$ is pyridyl or pyrimidyl then $R^{10}$ is different from hydrogen,
with the proviso that if $R^9$ is 2-oxopyridin-1(2H)-yl then $R^{10}$ is different from hydrogen,
with the proviso that if $R^9$ is a 6- to 8-membered heterocycle then $R^{10}$ is different from hydrogen,
with the proviso that if $R^8$ is methoxy or ethoxy then $R^{10}$ is different from hydrogen,
$R^{11}$ is a group selected from a hydrogen atom, $(C_1-C_4)$-alkyl and cyclopropyl,
  wherein said $(C_1-C_4)$-alkyl is optionally substituted with cyclopropyl and optionally with up to five fluorine atoms,
$R^{12}$ is pyridyl or 2-oxopyridin-1(2H)-yl,
  or
  is a group of the formula

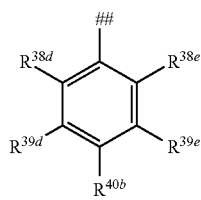

wherein
## is the point of attachment to the pyrazole ring,
$R^{38d}$ is a hydrogen atom, fluorine or methyl,
$R^{38e}$ is a hydrogen atom, fluorine or methyl,
$R^{39d}$ is a hydrogen atom, cyano or fluorine,
$R^{39e}$ is a hydrogen atom,
$R^{40b}$ is a hydrogen atom, fluorine, chlorine, cyano, hydroxy, methyl, trifluoromethyl, methoxy, trifluoromethoxy or methoxycarbonyl,
  wherein said pyridyl is optionally substituted, identically or differently, with one or two groups selected from fluorine, cyano, methyl and methoxy,
    wherein said methyl is optionally substituted with up to three fluorine atoms,
    wherein said methoxy is optionally substituted with up to three fluorine atoms,
  wherein said 2-oxopyridin-1(2H)-yl is optionally substituted, identically or differently, with one or two groups selected from fluorine, cyano, methyl and methoxy,
    wherein said methyl is optionally substituted with up to three fluorine atoms,
    wherein said methoxy is optionally substituted with up to three fluorine atoms, $R^{13}$ is a group selected from a hydrogen atom, $(C_1-C_4)$-alkyl and cyclopropyl,
  wherein said $(C_1-C_4)$-alkyl is optionally substituted with cyclopropyl and optionally with up to five fluorine atoms,
$R^2$ is a group selected from a hydrogen atom, $(C_1-C_4)$-alkyl, cyclopropyl, methoxycarbonyl and ethoxycarbonyl,
  wherein said $(C_1-C_4)$-alkyl is optionally substituted, identically or differently, with one or two groups selected from hydroxy, methoxy, ethoxy, cyclopropyl and optionally up to five fluorine atoms,
$R^3$ is a group selected from a hydrogen atom, fluorine, chlorine, bromine, cyano, hydroxy, nitro, amino, mono-$(C_1-C_4)$-alkylamino, di-$(C_1-C_4)$-alkylamino, $(C_1-C_4)$-alkylsulfanyl, $(C_1-C_4)$-alkylsulfinyl, $(C_1-C_4)$-alkylsulfonyl, $(C_1-C_6)$-alkyl, $(C_1-C_4)$-alkoxy, —O—C(=O)—$NR^{36}R^{37}$, —O—C(=O)—$OR^{37a}$, —NH—C(=O)—$NR^{36}R^{37}$, —N(CH$_3$)—C(=O)—$NR^{36}R^{37}$, —NH—C(=O)—$OR^{37a}$, —N(CH$_3$)—C(=O)—$OR^{37a}$, —NH—C(=O)—$R^{37}$, —N(CH$_3$)—C(=O)—$R^{37}$, $(C_3-C_8)$-cycloalkyl, 4- to 6-membered heterocycle, 5- to 6-membered heteroaryl, —(CH$_2$)$_q$—C(=O)—$NR^{34}R^{35}$, methylcarbonyl, ethylcarbonyl, $(C_1-C_4)$-alkylcarbonyloxy and $(C_1-C_4)$-alkoxycarbonyl,
  wherein said $(C_1-C_6)$-alkyl is optionally substituted, identically or differently, with one or two groups selected from hydroxy, amino, mono-$(C_1-C_4)$-alkylamino, di-$(C_1-C_4)$-alkylamino, cyano, methoxy, ethoxy, methoxycarbonyl, ethoxycarbony, 4- to 6-membered heterocycle, 1 and cyclopropyl and optionally up to five fluorine atoms,
    wherein said 4- to 6-membered heterocycle is optionally substituted with methyl, ethyl or cyclopropyl and optionally up to two fluorine atoms,
  wherein said $(C_1-C_4)$-alkoxy is optionally substituted with cyano, cyclopropyl and optionally up to five fluorine atoms,
  wherein said $(C_3-C_5)$-cycloalkyl is optionally substituted with hydroxyl, methoxy, ethoxy and optionally up to four fluorine atoms,
  wherein said 4- to 6-membered heterocycle is optionally substituted with hydroxyl, trifluoromethyl, methoxy, ethoxy and optionally up to four fluorine atoms,
  wherein said 5- to 6-membered heteroaryl is optionally substituted, identically or differently, with one or two groups selected from methyl, ethyl and methoxy and optionally up to four fluorine atoms,
wherein
q is 0,
$R^{34}$ is a hydrogen atom or $(C_1-C_4)$-alkyl,
$R^{35}$ is a hydrogen atom or $(C_1-C_4)$-alkyl,
or
$R^{34}$ and $R^{35}$ together with the nitrogen atom they are attached form a 4- to 7-membered heterocycle,
  wherein said 4- to 7-membered heterocycle ring is optionally substituted, identically or differently, with one, two or three groups selected from a fluorine atom, hydroxy, methyl, ethyl, methoxy, ethoxy, cyclopropyl, difluoromethyl, trifluoromethyl and trifluoromethoxy,
wherein
$R^{36}$ is a hydrogen atom or methyl,
$R^{37}$ is a hydrogen atom, methyl, difluoromethyl, trifluoromethyl or cyclopropyl, $R^{37a}$ is methyl, difluoromethyl, trifluoromethyl or cyclopropyl, with the proviso that if $R^3$ is —$(CH_2)_qC(\!\!=\!\!O)$—$NR^{34}R^{35}$, —O—C(=O)—$NR^{36}R^{37}$, —O—C(=O)—$OR^{37a}$, —N($CH_3$)—C(=O)—$NR^{36}R^{37}$, —NH—C(=O)—$OR^{37a}$, —NH—C(=O)—$NR^{36}R^{37}$, —N($CH_3$)—C(=O)—$OR^{37a}$, —NH—C(=O)—$R^{37}$ or —N($CH_3$)—C(=O)—$R^{37}$, then $R^7$ and $R^{10}$ are different from hydrogen, with the proviso that if $R^3$ is cyano then $R^2$ and $R^4$ are different from hydrogen, with the proviso that if $R^3$ is cyano then $R^6$ and $R^9$ are different from 6-membered heteroaryl, or $R^2$ and $R^3$ together with the carbon atoms they are attached form a 5- to 6-membered carbocycle, a 5- to 7-membered azaheterocycle, a 5- to 7-membered oxaheterocycle, a 5- to 6-membered heteroaryl group or a phenyl ring, wherein said 5- to 7-membered azaheterocycle is optionally substituted, identically or differently, with one or two groups selected from oxo, methyl, ethyl, propyl, trifluoromethyl and $(C_1\text{-}C_4)$-alkoxycarbonyl and optionally up to four fluorine atoms, wherein said 5- to 7-membered oxaheterocycle is optionally substituted, identically or differently, with one or two groups selected from oxo, methyl, ethyl, trifluoromethyl and $(C_1\text{-}C_4)$-alkoxycarbonyl and optionally up to four fluorine atoms, wherein said 5- to 6-membered carbocycle is optionally substituted, identically or differently, with one or two groups selected from hydroxy, oxo, amino, mono-$(C_1\text{-}C_4)$-alkylamino, di-$(C_1\text{-}C_4)$-alkylamino, methyl, ethyl, trifluoromethyl and $(C_1\text{-}C_4)$-alkoxycarbonyl and optionally up to four fluorine atoms, and wherein any phenyl group and any 5- to 6-membered heteroaryl group are each optionally substituted, identically or differently, with one or two groups selected from fluorine, chlorine, methyl, ethyl, trifluoromethyl, methoxy and trifluoromethoxy, with the proviso that if $R^2$ and $R^3$ together with the carbon atoms they are attached to form a 5- to 7-membered azaheterocycle with a non-substituted nitrogen atom which is not directly attached to the pyrazole, then $R^7$ and $R^{10}$ are different from hydrogen, with the proviso that if $R^7$ and $R^{10}$ are hydrogen then the nitrogen atom of the 5- to 7-membered azaheterocycle formed by $R^2$ and $R^3$ together with the carbon atoms they are attached to is substituted with methyl, ethyl or $(C_1\text{-}C_4)$-alkoxycarbonyl, $R^4$ is a group selected from a hydrogen atom, $(C_1\text{-}C_4)$-alkyl, cyclopropyl, methoxycarbonyl, ethoxycarbonyl and hydroxy, wherein said $(C_1\text{-}C_4)$-alkyl is optionally substituted, identically or differently, with one or two groups selected from hydroxy, methoxy and cyclopropyl and optionally up to five fluorine atoms, or $R^3$ and $R^4$ together with the carbon atoms they are attached form a 5- to 6-membered carbocycle, a 5- to 7-membered heterocycle, a 5- to 6-membered heteroaryl group or a phenyl ring, wherein said 5- to 7-membered heterocycle is optionally substituted, identically or differently, with one or two groups selected from oxo, methyl, ethyl, propyl, trifluoromethyl and $(C_1\text{-}C_4)$-alkoxycarbonyl and optionally up to four fluorine atoms, wherein said 5- to 6-membered carbocycle is optionally substituted, identically or differently, with one or two groups selected from oxo, hydroxyl, methyl, ethyl, trifluoromethyl and $(C_1\text{-}C_4)$-alkoxycarbonyl and optionally up to four fluorine atoms, and wherein any phenyl group and any 5- to 6-membered heteroaryl group are each optionally substituted, identically or differently, with one or two groups selected from fluorine, chlorine, methyl, ethyl, trifluoromethyl, methoxy and trifluoromethoxy, with the proviso that if $R^3$ and $R^4$ together with the carbon atoms they are attached form a 5- to 7-membered heterocycle with a non-substituted nitrogen atom which is not directly attached to the pyrazole, then $R^7$ and $R^{10}$ is different from hydrogen, with the proviso that if $R^7$ and $R^{10}$ are hydrogen then the nitrogen atom of the 5- to 7-membered heterocycle formed by $R^3$ and $R^4$ together with the carbon atoms they are attached to is substituted with methyl, ethyl or $(C_1\text{-}C_4)$-alkoxycarbonyl, or a stereoisomer, a tautomer, an N-oxide, a hydrate, a solvate, or a salt thereof, or a mixture of same.

3. The compound of formula (I) according to claim 1, wherein:

$R^1$ is a group of the formula

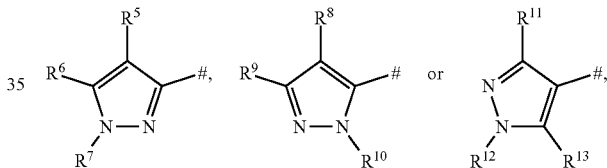

wherein # is the point of attachment to the amino group, $R^5$ is a group selected from chlorine, $(C_1\text{-}C_4)$-alkyl, methoxy, ethoxy and $(C_3\text{-}C_5)$-cycloalkyl, wherein said $(C_1\text{-}C_4)$-alkyl is optionally substituted with a group selected from methoxy, difluoromethoxy, trifluoromethoxy, —$NR^{14}R^{15}$, cyclopropyl or optionally with up to three fluorine atoms, wherein $R^{14}$ is $(C_1\text{-}C_4)$-alkyl, $R^{15}$ is $(C_1\text{-}C_4)$-alkyl, or $R^{14}$ and $R^{15}$ together with the nitrogen atom they are attached form a 4- to 6-membered heterocycle wherein said 4- to 6-membered heterocycle is optionally substituted with methyl or trifluoromethyl or optionally with up to four fluorine atoms, wherein said methoxy and ethoxy are optionally substituted with up to three fluorine atoms, wherein said $(C_3\text{-}C_5)$-cycloalkyl is optionally substituted with up to four fluorine atoms, $R^6$ is pyridyl or $(C_5-C_8)$-cycloalkyl,
or
is a group of the formula

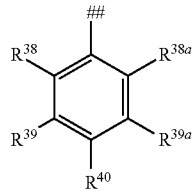

wherein
## is the point of attachment to the pyrazole ring,
$R^{38}$ is a hydrogen atom, methyl or fluorine,
$R^{38a}$ is a hydrogen atom,
$R^{39}$ is a hydrogen atom, cyano or fluorine,
$R^{39a}$ is a hydrogen atom, cyano, fluorine or methylsulfanyl,
$R^{40}$ is a hydrogen atom, fluorine, chlorine, cyano, hydroxy, $-(CH_2)_n NR^{16}R^{17}$, methyl, methoxy, ethoxy, difluoromethoxy, trifluoromethoxy, methoxycarbonyl or ethoxycarbonyl,
  wherein said methyl is optionally substituted with cyano or optionally with up to three fluorine atoms,
  wherein
  n is 0,
  $R^{16}$ is a hydrogen atom or $(C_1-C_4)$-alkyl,
  $R^{17}$ is $(C_1-C_4)$-alkyl,
  wherein said pyridyl is optionally substituted, identically or differently, with one or two groups selected from fluorine, cyano, methyl, methoxy and ethoxy,
    wherein said methyl is optionally substituted with up to three fluorine atoms,
    wherein said methoxy is optionally substituted with up to three fluorine atoms,
  wherein said $(C_5-C_8)$-cycloalkyl is optionally substituted, identically or differently, with one or two groups selected from $(C_1-C_4)$-alkyl and cyano, or optionally with up to five fluorine atoms,
    wherein said $(C_1-C_4)$-alkyl is optionally substituted with up to three fluorine atoms,
$R^7$ is a hydrogen atom or $(C_1-C_4)$-alkyl,
  wherein said $(C_1-C_4)$-alkyl is optionally substituted with $(C_3-C_6)$-cycloalkyl, methoxy or ethoxy or optionally with up to three fluorine atoms,
with the proviso that if $R^5$ is methoxy, ethoxy, difluoromethoxy or trifluoromethoxy then $R^7$ is different from hydrogen,
with the proviso that if $R^6$ is pyridyl then $R^7$ is different from hydrogen,
$R^8$ is a group selected from chlorine, $(C_1-C_4)$-alkyl, methoxy, ethoxy and $(C_3-C_8)$-cycloalkyl,
  wherein said $(C_1-C_4)$-alkyl is optionally substituted with a group selected from methoxy $-NR^{22}R^{23}$, cyclopropyl or optionally with up to three fluorine atoms,
    wherein said methoxy is optionally substituted with up to three fluorine atoms,
    wherein
    $R^{22}$ is $(C_1-C_4)$-alkyl,
    $R^{23}$ is $(C_1-C_4)$-alkyl,
    wherein said methoxy and ethoxy are optionally substituted with up to three fluorine atoms,
    and
    wherein said $(C_3-C_8)$-cycloalkyl is optionally substituted with up to four fluorine atoms,
$R^9$ is pyridyl or $(C_5-C_8)$-cycloalkyl,
or
is a group of the formula

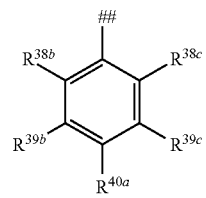

wherein
## is the point of attachment to the pyrazole ring,
$R^{38b}$ is a hydrogen atom, methyl or fluorine,
$R^{38c}$ is a hydrogen atom or fluorine,
$R^{39b}$ is a hydrogen atom, cyano or fluorine,
$R^{39c}$ is a hydrogen atom, cyano or fluorine,
$R^{40a}$ is a hydrogen atom, fluorine, chlorine, cyano, hydroxy, $-(CH_2)_n NR^{16a}R^{17a}$, methyl, methoxy, ethoxy, difluoromethoxy, trifluoromethoxy, methoxycarbonyl or ethoxycarbonyl, a 4- to 6-membered heterocycle, cyclopropyl or cyclobutyl,
  wherein said methyl is optionally substituted with cyano or optionally with up to three fluorine atoms,
  wherein
  n is 0,
  $R^{16a}$ is a hydrogen atom,
  $R^{17a}$ is $(C_1-C_4)$-alkyl,
  wherein said 4- to 6-membered heterocycle is optionally substituted, with methyl or optionally with up to five fluorine atoms,
wherein said pyridyl is optionally substituted, identically or differently, with one or two groups selected from fluorine, cyano, methyl, methoxy and ethoxy,
  wherein said methyl is optionally substituted with up to three fluorine atoms,
  wherein said methoxy and ethoxy are optionally substituted with up to three fluorine atoms,
wherein said $(C_5-C_8)$-cycloalkyl is optionally substituted, identically or differently, with one or two groups selected from methyl, ethyl, cyano or optionally with up to five fluorine atoms,
  wherein said methyl is optionally substituted with up to three fluorine atoms,
$R^{10}$ is a hydrogen atom, $(C_1-C_4)$-alkyl or cyclopropyl,
  wherein said $(C_1-C_4)$-alkyl is optionally substituted with a group selected from $(C_3-C_6)$-cycloalkyl, methoxy, ethoxy, 2-methyl-2H-tetrazol-5-yl, 1-methyl-1H-tetrazol-5-yl, $-NR^{28}R^{29}$ or optionally with up to three fluorine atoms and is optionally additionally substituted with hydroxy,
    wherein said $(C_3-C_6)$-cycloalkyl is optionally substituted with up to four fluorine atoms,
    and
    wherein
    $R^{28}$ is a hydrogen atom or $(C_1-C_4)$-alkyl,
    $R^{29}$ is $(C_1-C_4)$-alkyl, with the proviso that if $R^9$ is pyridyl then $R^{10}$ is different from hydrogen,
with the proviso that if $R^8$ is methoxy, ethoxy, difluoromethoxy or trifluoromethoxy then $R^{10}$ is different from hydrogen,
$R^{10}$ is cyclopropyl, methyl or ethyl,
  wherein said methyl or ethyl are optionally substituted with cyclopropyl or optionally with up to three fluorine atoms,
$R^{12}$ is a group of the formula

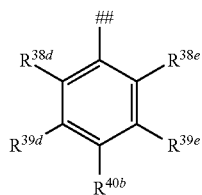

wherein
## is the point of attachment to the pyrazole ring,
$R^{38d}$ is a hydrogen atom or fluorine,
$R^{38e}$ is a hydrogen atom,
$R^{39d}$ is a hydrogen atom or fluorine,
$R^{39e}$ is a hydrogen atom,
$R^{40b}$ is a hydrogen atom, fluorine, chlorine or cyano,
$R^{13}$ is a group selected from a hydrogen atom, methyl and cyclopropyl,
  wherein said methyl is optionally substituted with cyclopropyl or optionally with up to three fluorine atoms,
$R^2$ is a hydrogen atom or methyl,
  wherein said methyl is optionally substituted with up to three fluorine atoms,
$R^3$ is a group selected from a hydrogen atom, fluorine, chlorine, bromine, cyano, hydroxy, nitro, amino, mono-$(C_1-C_4)$-alkylamino, di-$(C_1-C_4)$-alkylamino, methylsulfanyl, ethylsulfanyl, methylsulfinyl, ethylsulfinyl, methylsulfonyl, ethylsulfonyl, —O—C(=O)—OR$^{37a}$, —NH—C(=O)—NR$^{36}$R$^{37}$, —N(CH$_3$)—C(=O)—NR$^{36}$R$^{37}$, —NH—C(=O)—OR$^{37a}$, $(C_1-C_4)$-alkyl, methoxy, ethoxy, $(C_3-C_5)$-cycloalkyl, 4- to 6-membered heterocycle, 5-membered heteroaryl, —(CH$_2$)$_q$—C(=O)—NR$^{34}$R$^{35}$, methoxycarbonyl and ethoxycarbonyl,
  wherein said $(C_1-C_4)$-alkyl is optionally substituted, identically or differently, with one or two groups selected from hydroxy, cyano, methoxy, ethoxy, methoxycarbonyl, ethoxycarbonyl, methylamino, ethylamino, dimethylamino, diethylamino, a 4- to 6-membered heterocycle and cyclopropyl and optionally up to three fluorine atoms,
    wherein said 4- to 6-membered heterocycle is optionally substituted with methyl, ethyl or cyclopropyl and optionally up to two fluorine atoms,
  wherein said methoxy and ethoxy are optionally substituted with cyano, cyclopropyl or optionally up to three fluorine atoms,
  wherein said $(C_3-C_5)$-cycloalkyl is optionally substituted with hydroxy or optionally with up to four fluorine atoms,
  wherein said 4- to 6-membered heterocycle is optionally substituted with hydroxyl or trifluoromethyl or optionally with up to four fluorine atoms,
  wherein said 5-membered heteroaryl is optionally substituted, identically or differently, with one or two groups selected from methyl and methoxy
wherein
q is 0,
$R^{34}$ is a hydrogen atom or $(C_1-C_4)$-alkyl,
$R^{35}$ is $(C_1-C_4)$-alkyl,
or
$R^{34}$ and $R^{35}$ together with the nitrogen atom they are attached form a 4- to 6-membered heterocycle ring wherein said 4- to 6-membered heterocycle ring is optionally substituted, identically or differently, with one or two groups selected from a fluorine atom, methyl, difluoromethyl, trifluoromethyl and trifluoromethoxy,
wherein
$R^{36}$ is a hydrogen atom or methyl,
$R^{37}$ is a hydrogen atom, methyl, difluoromethyl, trifluoromethyl or cyclopropyl,
$R^{37a}$ is methyl, difluoromethyl, trifluoromethyl or cyclopropyl,
with the proviso that if $R^3$ is —(CH$_2$)$_q$C(=O)—NR$^{34}$R$^{35}$, —O—C(=O)—OR$^{37a}$, —NH—C(=O)—NR$^{36}$R$^{37}$, —N(CH$_3$)—C(=O)—NR$^{36}$R$^{37}$ or —NH—C(=O)—OR$^{37a}$, then $R^7$ and $R^{10}$ are different from hydrogen,
with the proviso that if $R^3$ is cyano then $R^2$ and $R^4$ are different from hydrogen,
with the proviso that if $R^3$ is cyano then $R^6$ and $R^9$ are different from pyridyl or pyrimidyl,
or
$R^2$ and $R^3$ together with the carbon atoms they are attached form a 4- to 6-membered carbocycle, a 5- to 6-membered azaheterocycle, a 5- to 6-membered oxaheterocycle, a 6-membered heteroaryl group or a phenyl ring,
  wherein said phenyl group is optionally substituted, identically or differently, with one or two groups selected from fluorine, chlorine, methyl, trifluoromethyl, methoxy and trifluoromethoxy,
  wherein said 5- to 6-membered carbocycle is optionally substituted, identically or differently, with one or two groups selected from hydroxy, oxo, methyl, ethyl, trifluoromethyl and $(C_1-C_4)$-alkoxycarbonyl or optionally with up to four fluorine atoms,
  wherein said 5- to 6-membered azaheterocycle is optionally substituted with oxo, methyl, ethyl, propyl, trifluoromethyl, tert.-butoxycarbonyl or optionally with up to four fluorine atoms,
  wherein said 5- to 6-membered oxaheterocycle is optionally substituted with oxo, methyl, ethyl, trifluoromethyl, methoxycarbonyl and ethoxycarbonyl or optionally with up to four fluorine atoms,
with the proviso that if $R^2$ and $R^3$ together with the carbon atoms they are attached to form a 5- to 6-membered azaheterocycle with a non-substituted nitrogen atom which is not directly attached to the pyrazole, then $R^7$ and $R^{10}$ are different from hydrogen,
with the proviso that if $R^7$ and $R^{10}$ are hydrogen then the nitrogen atom of the 5- to 6-membered azaheterocycle formed by $R^2$ and $R^3$ together with the carbon atoms they are attached to is substituted with methyl, ethyl, methoxycarbonyl or ethoxycarbonyl,
$R^4$ is a group selected from a hydrogen atom, $(C_1-C_4)$-alkyl, cyclopropyl, methoxycarbonyl, ethoxycarbonyl and hydroxy, wherein said $(C_1\text{-}C_4)$-alkyl is optionally substituted with a group selected from hydroxy, methoxy and cyclopropyl or optionally with up to three fluorine atoms,
or $R^3$ and $R^4$ together with the carbon atoms they are attached form a 5- to 6-membered carbocycle, a 5- to 6-membered heterocycle, a 6-membered heteroaryl group or a phenyl ring, wherein said 5- to 6-membered heterocycle is optionally substituted, identically or differently, with one or two groups selected from oxo, methyl, ethyl, propyl trifluoromethyl, methoxycarbonyl, ethoxycarbonyl, tert.-butoxycarbonyl or optionally with up to four fluorine atoms, wherein said 5- to 6-membered carbocycle is optionally substituted, identically or differently, with one or two groups selected from oxo, hydroxy, methyl, ethyl, trifluoromethyl methoxycarbonyl and ethoxycarbonyl or optionally with up to four fluorine atoms, and wherein any phenyl group and any 6-membered heteroaryl group are each optionally substituted, identically or differently, with one or two groups selected from fluorine, chlorine, methyl, ethyl, trifluoromethyl, methoxy and trifluoromethoxy, with the proviso that if $R^3$ and $R^4$ together with the carbon atoms they are attached form a 5- to 6-membered heterocycle with a non-substituted nitrogen atom which is not directly attached to the pyrazole, then $R^7$ and $R^{10}$ is different from hydrogen, with the proviso that if $R^7$ and $R^{10}$ are hydrogen then the nitrogen atom of the 5- to 6-membered heterocycle formed by $R^3$ and $R^4$ together with the carbon atoms they are attached to is substituted with methyl, ethyl, methoxycarbonyl or ethoxycarbonyl, or a stereoisomer, a tautomer, an N-oxide, a hydrate, a solvate, or a salt thereof, or a mixture of same.

4. The compound of formula (I) according to claim 1, wherein:

$R^1$ is a group of the formula

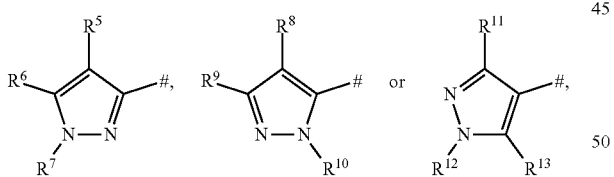

wherein

\# is the point of attachment to the amino group, $R^5$ is a group selected from chlorine, methyl, ethyl, methoxy or cyclopropyl, wherein said methyl and ethyl are optionally substituted with methoxy or optionally with up to three fluorine atoms, wherein said methoxy is optionally substituted with up to three fluorine atoms, $R^6$ is 5-fluoropyridin-2-yl, 6-trifluoromethylpyridin-3-yl or cyclohexyl, or is a group of the formula

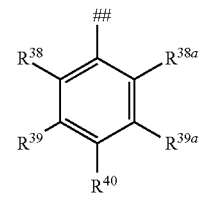

wherein

\#\# is the point of attachment to the pyrazole ring, $R^{38}$ is a hydrogen atom or fluorine, $R^{38a}$ is a hydrogen atom, $R^{39}$ is a hydrogen atom, $R^{39a}$ is a hydrogen atom or cyano, $R^{40}$ is a hydrogen atom, fluorine, chlorine, cyano, methyl, difluoromethyl, trifluoromethyl, methoxy, ethoxy, difluoromethoxy, trifluoromethoxy, methoxycarbonyl or ethoxycarbonyl, $R^7$ is a hydrogen atom, methyl, ethyl, cyclopropylmethyl, 2-cyclopropylethyl or 2,2-difluoroethyl, with the proviso that if R is methoxy, difluoromethoxy or trifluoromethoxy then $R^7$ is different from hydrogen, with the proviso that if $R^6$ is 5-fluoropyridin-2-yl or 6-trifluoromethylpyridin-3-yl then $R^7$ is different from hydrogen, $R^8$ is a group selected from chlorine, methyl, ethyl, methoxy and cylcopropyl, $R^9$ is pyridyl or 4-cyanopentacyclo[4.2.0.0$^{2,5}$.0$^{3,8}$.0$^{4,7}$]octan-1-yl, or is a group of the formula

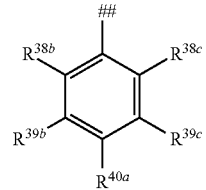

wherein

\#\# is the point of attachment to the pyrazole ring, $R^{38b}$ is a hydrogen atom or fluorine, $R^{38c}$ is a hydrogen atom, $R^{39b}$ is a hydrogen atom, $R^{39c}$ is a hydrogen atom, $R^{40a}$ is a hydrogen atom, fluorine, chlorine, cyano, methyl, difluoromethyl, trifluoromethyl, methylamino, methoxy, difluoromethoxy, trifluoromethoxy or cyclopropyl, wherein said pyridyl is optionally substituted with fluorine, methyl, difluoromethyl, trifluoromethyl or methoxy, $R^{10}$ is a hydrogen atom, methyl, ethyl, 2,2-difluoroethyl, cyclopropylmethyl, cyclobutylmethyl, 2-cyclopropylethyl, 2-cyclopropyl-2-hydroxypropyl, 2-cyclopropyl-2-hydroxyethyl, 2-methoxyethyl, or cyclopropyl, wherein said methyl and ethyl are optionally substituted with a group selected from cyclopropyl, methoxy or optionally up to three fluorine atoms and is optionally additionally substituted with hydroxy, with the proviso that if $R^9$ is pyridyl then $R^{10}$ is different from hydrogen, with the proviso that if $R^8$ is methoxy then $R^{10}$ is different from hydrogen, $R^{11}$ is methyl, $R^{12}$ is a group of the formula

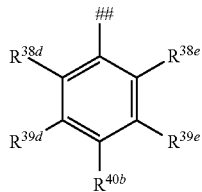

wherein ## is the point of attachment to the pyrazole ring, $R^{38d}$ is a hydrogen atom, $R^{38e}$ is a hydrogen atom, $R^{39d}$ is a hydrogen atom, $R^{39e}$ is a hydrogen atom, $R^{40b}$ is fluorine or cyano, $R^{13}$ is a group selected from a hydrogen atom or methyl, $R^2$ is a hydrogen atom, methyl or difluoromethyl, $R^3$ is a group selected from a hydrogen atom, fluorine, chlorine, bromine, cyano, hydroxy, nitro, amino, ethylamino, dimethylamino, —O—C(=O)—NR$^{36}$R$^{37}$, —O—C(=O)—OR$^{37a}$, —NH—C(=O)—OR$^{37a}$, (C$_1$-C$_4$)-alkyl, methoxy, cyclopropyl, cyclobutyl, 4-membered heterocycle, 1,3,4-oxadiazol-2-yl, 2-(trifluoromethyl)-1,3-dioxolan-2-yl, —(CH$_2$)$_q$—C(=O)—NR$^{34}$R$^{35}$, methoxycarbonyl and ethoxycarbonyl, wherein said (C$_1$-C$_4$)-alkyl is optionally substituted, identically or differently, with one or two groups selected from hydroxy, methoxy, methoxycarbonyl, ethoxycarbonyl, dimethylamino, a 4-membered azaheterocycle and cyclopropyl and optionally up to three fluorine atoms, wherein said 4-membered azaheterocycle is optionally substituted with up to two fluorine atoms, wherein said methoxy is optionally substituted with cyano, cyclopropyl and optionally up to three fluorine atoms, wherein said cyclopropyl and cyclobutyl are optionally substituted with hydroxy, wherein said 4-membered heterocycle is optionally substituted with hydroxy, wherein said 1,3,4-oxadiazol-2-yl is optionally substituted with methyl, wherein q is 0, $R^{34}$ is methyl, $R^{35}$ is methyl, or $R^{34}$ and $R^{35}$ together with the nitrogen atom they are attached form a 4- to 6-membered heterocycle ring wherein said 4- to 6-membered heterocycle ring is optionally substituted, identically or differently, with one or two groups selected from a fluorine atom, methyl, difluoromethyl and trifluoromethyl, wherein $R^{36}$ is a methyl atom, $R^{37}$ is a hydrogen atom or methyl, $R^{37a}$ is methyl, with the proviso that if $R^3$ is —(CH$_2$)$_q$C(=O)—NR$^{34}$R$^{35}$ O—C(=O)—NR$^{36}$R$^{37}$, —O—C(=O)—OR$^{37a}$ or —NH—C(=O)—OR$^{37a}$, then $R^7$ and $R^{10}$ are different from hydrogen, with the proviso that if $R^3$ is cyano then $R^2$ and $R^4$ are different from hydrogen, with the proviso that if $R^3$ is cyano then $R^6$ and $R^9$ are different from pyridyl, or $R^2$ and $R^3$ together with the carbon atoms they are attached form a 5- to 6-membered carbocycle, a pyrrolidinyl, a pyridyl or a phenyl ring, wherein said 5- to 6-membered carbocycle is optionally substituted, identically or differently, with one or two groups selected from oxo, methyl, trifluoromethyl and hydroxy, wherein said pyrrolidinyl is substituted with propyl or tert-butoxycarbonyl, $R^4$ is a group selected from a hydrogen atom, methyl, 2-hydroxypropan-2-yl, fluoromethyl, difluoromethyl, methoxycarbonyl, ethoxycarbonyl and hydroxy, or $R^3$ and $R^4$ together with the carbon atoms they are attached form a 5- to 6-membered carbocycle, a pyrrolidinyl ring or a piperidinyl ring, a pyridyl group or a phenyl ring, wherein said pyrrolidinyl ring is substituted with propyl or tert-butoxycarbonyl, wherein said piperidinyl ring is substituted with propyl or tert-butoxycarbonyl, wherein said 5- to 6-membered carbocycle is optionally substituted, identically or differently, with one or two groups selected from oxo, hydroxy and methyl, or a stereoisomer, a tautomer, an N-oxide, a hydrate, a solvate, or a salt thereof, or a mixture of same.

5. A method of preparing a compound of formula (I) according to claim 1, said method comprising the step

[A] reacting an intermediate compound of formula (II-A), (II-B) or (II-C):

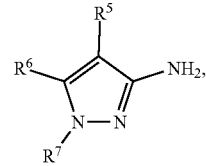
(II-A)

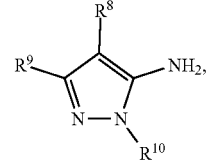
(II-B)

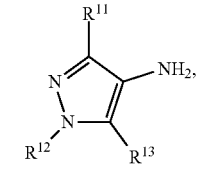
(II-C)

wherein $R^5$, $R^6$, $R^7$, $R^8$, $R^9$, $R^{10}$, $R^{11}$, $R^{12}$ and $R^{13}$ are as defined for the compound of formula (I) as defined supra, a) in the presence of sodium iodide and a suitable base, with 4,6-dichloropyrimidine (III),
or
b) in the presence of a suitable Broenstedt acid or Lewis acid with 4,6-dichloropyrimidine (III),
or
c) in the presence of a suitable base with a 4,6-dichloropyrimidine of formula (III),
or
d) in the presence of a suitable base and in the presence of a suitable catalyst and a suitable ligand with a 4,6-dichloropyrimidine of formula (III),

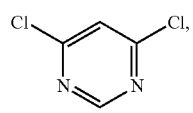
(III)

thereby giving a compound of formula (IV-A), (IV-B) and (IV-C), respectively:

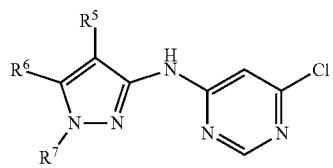
(IV-A)

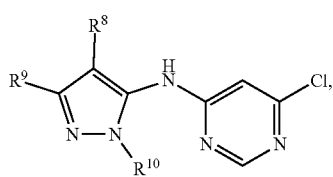
(IV-B)

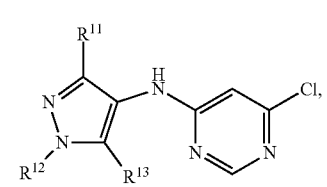
(IV-C)

wherein $R^5$, $R^6$, $R^7$, $R^8$, $R^9$, $R^{10}$, $R^{11}$, $R^{12}$ and $R^{13}$ are as defined for the compound of formula (I) as defined supra,
and reacting the compound of formula (IV-A), (IV-B) or (IV-C) in the presence of a suitable base and where appropriate in the presence of a suitable catalyst, with a pyrazole of formula (V),

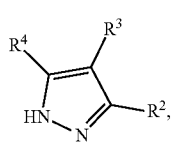
(V)

wherein $R^2$, $R^3$ and $R^4$ are as defined for the compound of formula (I) as defined supra,
thereby giving a compound of formula (I-A), (I-B) and (I-C), respectively,

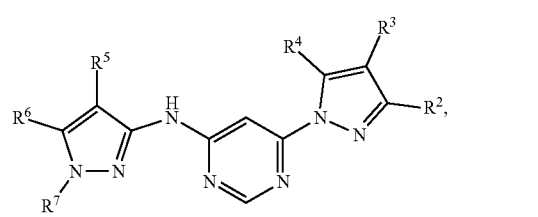
(I-A)

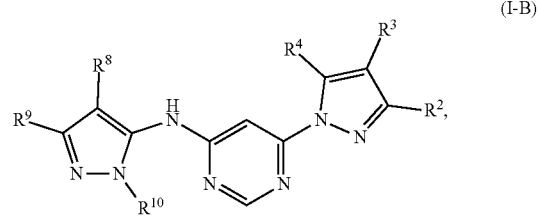
(I-B)

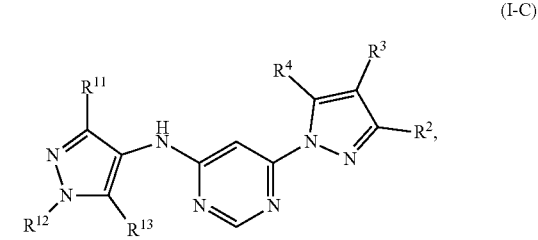
(I-C)

wherein $R^2$, $R^3$, $R^4$, $R^5$, $R^6$, $R^7$, $R^8$, $R^9$, $R^{10}$, $R^{11}$, $R^{12}$ and $R^{13}$ are as defined for the compound of formula (I) as defined supra,
then optionally converting said compound of formula (I-A), (I-B) or (I-C) into a solvate, a salt, or a solvate of the salt thereof using the corresponding (i) solvents and/or (ii) bases or acids;
or
[B] reacting an intermediate compound of formula (IV-A), (IV-B) or (IV-C):

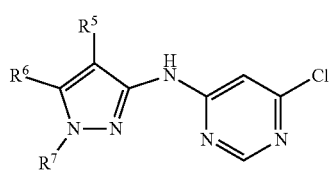
(IV-A)

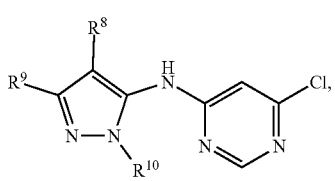
(IV-B)

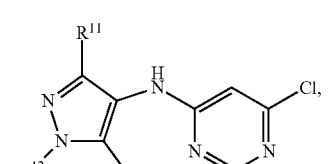
(IV-C)

wherein $R^5$, $R^6$, $R^7$, $R^8$, $R^9$, $R^{10}$, $R^{11}$, $R^{12}$ and $R^{13}$ are as defined for the compound of formula (I) as defined supra, with a hydrazine equivalent,
thereby giving a compound of formula (V-A), (V-B) and (V-C), respectively,

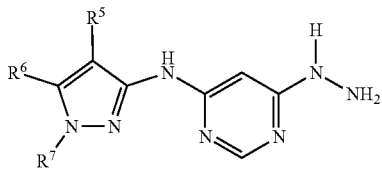
(V-A)

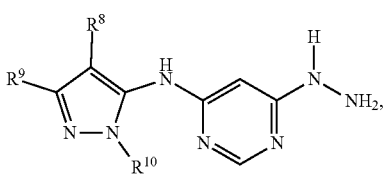
(V-B)

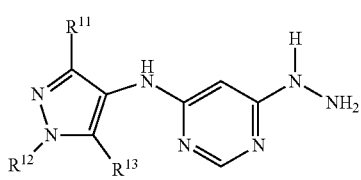
(V-C)

and reacting the compound of formula (V-A), (V-B), or (V-C) with a 1,3 dicarbonyl compound of formula (VI),

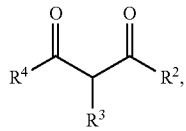
(VI)

wherein $R^2$, $R^3$ and $R^4$ are as defined for the compound of formula (I) as defined supra, thereby giving a compound of formula (I-A), (I-B) and (I-C), respectively,

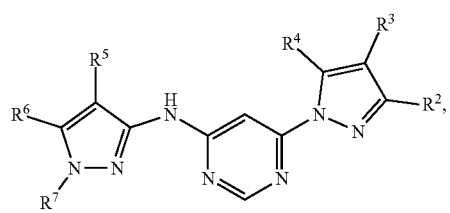
(I-A)

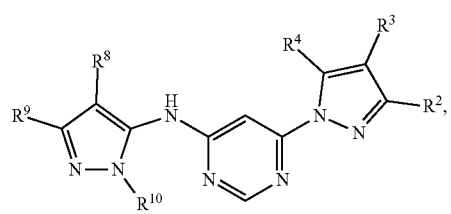
(I-B)

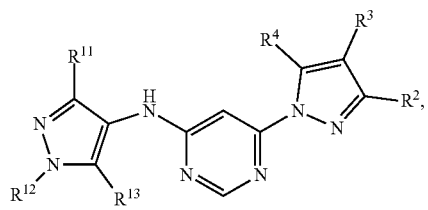
(I-C)

wherein $R^2$, $R^3$, $R^4$, $R^5$, $R^6$, $R^7$, $R^8$, $R^9$, $R^{10}$, $R^{11}$, $R^{12}$ and $R^{13}$ are as defined for the compound of formula (I) as defined supra, then optionally converting said compound of formula (I-A), (I-B) or (I-C) into a solvate, a salt, or a solvate of the salt thereof, using the corresponding (i) solvents and/or (ii) bases or acid;

or

[C] reacting an intermediate compound of formula (IV-A), (IV-B) or (IV-C):

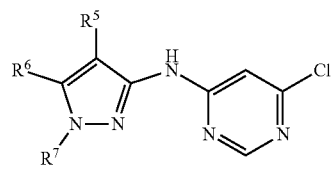
(IV-A)

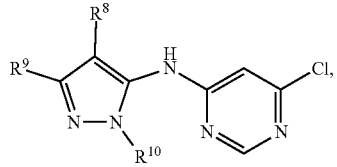
(IV-B)

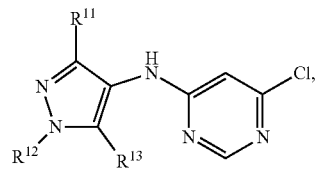
(IV-C)

wherein $R^5$, $R^6$, $R^7$, $R^8$, $R^9$, $R^{10}$, $R^{11}$, $R^{12}$ and $R^{13}$ are as defined for the compound of formula (I) as defined supra, with a hydrazine equivalent, thereby giving a compound of formula (V-A), (V-B) and (V-C), respectively,

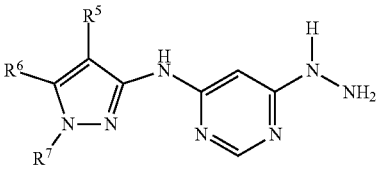
(V-A)

-continued

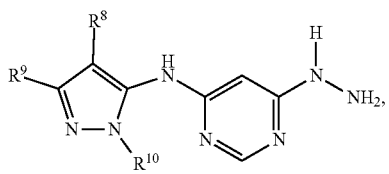
(V-B)

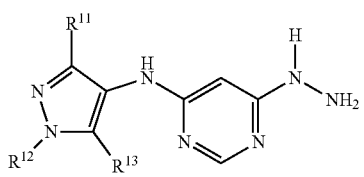
(V-C)

and reacting the compound of formula (V-A), (V-B), or (V-C) with a 1,3 dicarbonyl compound of formula (VII),

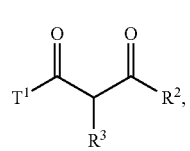
(VII)

wherein $R^2$ and $R^3$ are as defined for the compound of formula (I) as defined supra, and
$T^1$ is methoxy or ethoxy,
thereby giving a compound of formula (I-D), (I-E) and (I-F), respectively,

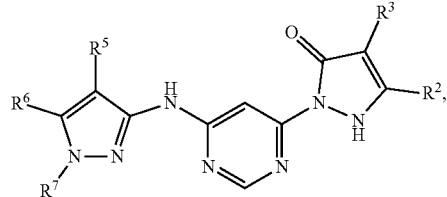
(I-D)

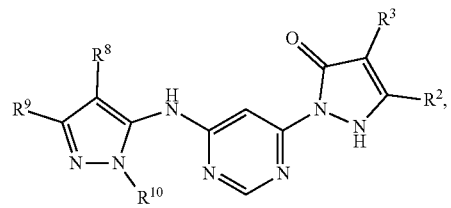
(I-E)

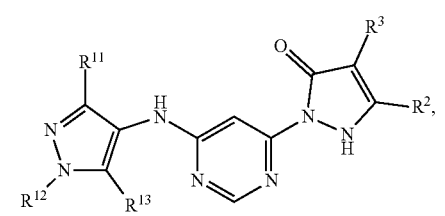
(I-F)

wherein $R^2$, $R^3$, $R^4$, $R^5$, $R^6$, $R^7$, $R^8$, $R^9$, $R^{10}$, $R^{11}$, $R^{12}$ and $R^{13}$ are as defined for the compound of formula (I) as defined supra,
then optionally converting said compound of formula (I-D), (I-E) or (I-F) into a solvate, a salt, or a solvate of the salt thereof, using the corresponding (i) solvents and/or (ii) bases or acids;

or

[D] reacting an intermediate compound of formula (VIII):

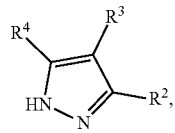
(VIII)

wherein $R^2$, $R^3$ and $R^4$ are as defined for the compound of formula (I) as defined supra,
in the presence of a suitable base with 4,6-dichloropyrimidine (III),

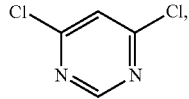
(III)

thereby giving a compound of formula (IX),

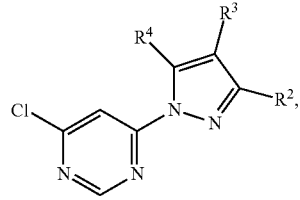
(IX)

wherein $R^1$, $R^2$, $R^3$ and $R^4$ are as defined for the compound of formula (I) as defined supra, and reacting the compound of formula (IX)

b) in the presence of a suitable Broenstedt acid or Lewis acid with an intermediate compound of formula (II-A), (II-B) or (II-C), or c) in the presence of a suitable base with an intermediate compound of formula (II-A), (II-B) or (II-C), or d) in the presence of a suitable base and in the presence of a suitable catalyst, and a suitable ligand with an intermediate compound of formula (II-A), (II-B) or (II-C),

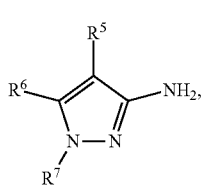
(II-A)

-continued

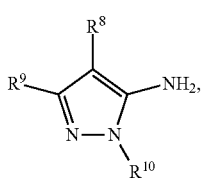
(II-B)

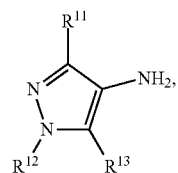
(II-C)

wherein $R^5$, $R^6$, $R^7$, $R^8$, $R^9$, $R^{10}$, $R^{11}$, $R^{12}$ and $R^{13}$ are as defined for the compound of formula (I) as defined supra, and thereby giving a compound of formula (I-A), (I-B) and (I-C), respectively,

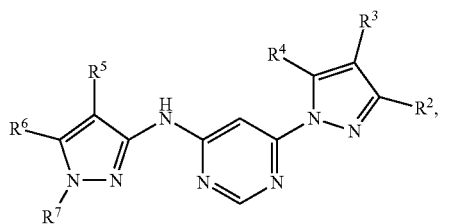
(I-A)

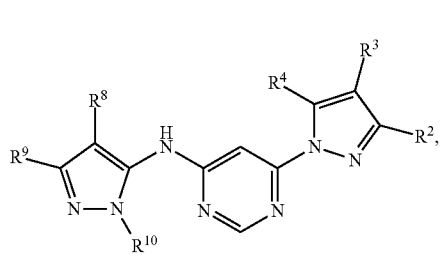
(I-B)

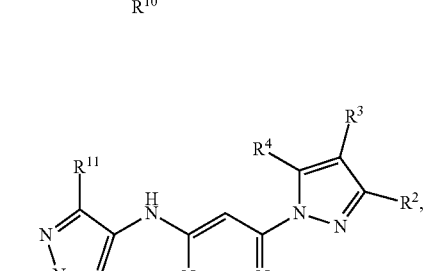
(I-C)

wherein $R^2$, $R^3$, $R^5$, $R^6$, $R^7$, $R^8$, $R^9$, $R^{10}$, $R^{11}$, $R^{12}$ and $R^{13}$ are as defined for the compound of formula (I) as defined supra, then optionally converting said compound of formula (I-A), (I-B), or (I-C) into a solvate, a salt, or a solvate of the salt thereof, using the corresponding (i) solvents and/or (ii) bases or acids;

or

[E] reacting a 4,6-dichloropyrimidine of formula (III),

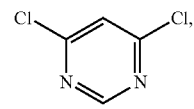
(III)

with a hydrazine equivalent, thereby giving a compound of formula (X),

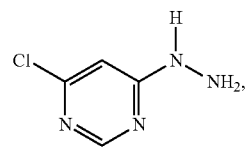
(X)

reacting the compound of formula (X) with a 1,3 dicarbonyl compound of formula (VI),

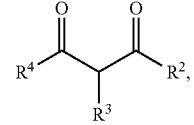
(VI)

wherein $R^2$, $R^3$ and $R^4$ are as defined for the compound of formula (I) as defined supra, thereby giving a compound of formula (VII),

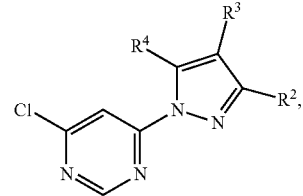
(IX)

wherein $R^1$, $R^2$, $R^3$ and $R^4$ are as defined for the compound of formula (I) as defined supra, and reacting the compound of formula (VII)

b) in the presence of a suitable Broenstedt acid with an intermediate compound of formula (II-A), (II-B) or (II-C), or c) in the presence of a suitable base with an intermediate compound of formula (II-A), (II-B) or (II-C), or d) in the presence of a suitable base and in the presence of a suitable catalyst, and a suitable ligand with an intermediate compound of formula (II-A), (II-B) or (II-C), (II-A)

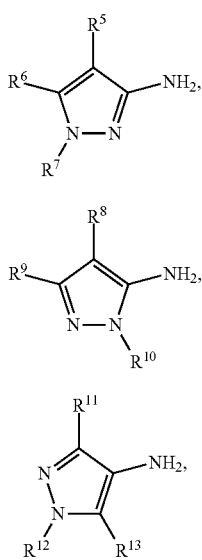

(II-B)

(II-C)

wherein $R^5$, $R^6$, $R^7$, $R^8$, $R^9$, $R^{10}$, $R^{11}$, $R^{12}$ and $R^{13}$ are as defined for the compound of formula (I) as defined supra, and
thereby giving a compound of formula (I-A), (I-B) and (I-C), respectively,

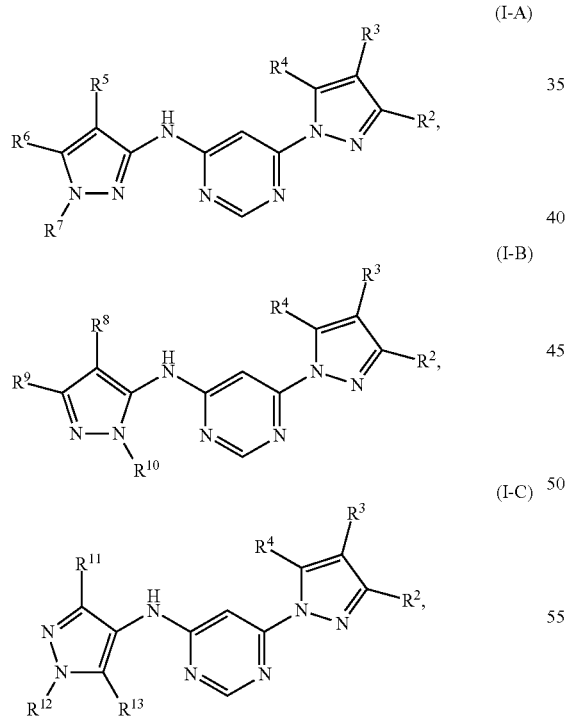

(I-A)

(I-B)

(I-C)

wherein $R^2$, $R^3$, $R^4$, $R^5$, $R^6$, $R^7$, $R^8$, $R^9$, $R^{10}$, $R^{11}$, $R^{12}$ and $R^{13}$ are as defined for the compound of formula (I) as defined supra,
then optionally converting said compound of formula (I-A), (I-B), or (I-C) into a solvate, a salt, or a solvate of the salt thereof, using the corresponding (i) solvents and/or (ii) bases or acids;

or
[F] reacting a compound of formula (IX),

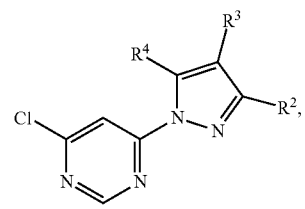

(IX)

wherein $R^2$, R and $R^4$ are as defined for the compound of formula (I) as defined supra,
b) in the presence of a suitable Broenstedt acid or a suitable base with an intermediate compound of formula (X),
or
c) in the presence of a suitable base with an intermediate compound of formula (X)
or
d) in the presence of a suitable base and in the presence of a suitable catalyst, and a suitable ligand with an intermediate compound of formula (X),

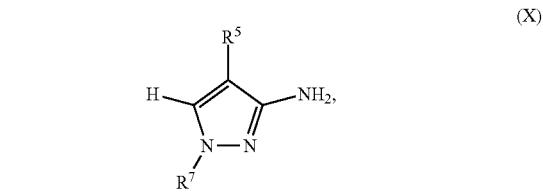

(X)

wherein $R^5$, and $R^7$ are as defined for the compound of formula (I) as defined supra, and
thereby giving a compound of formula (XI),

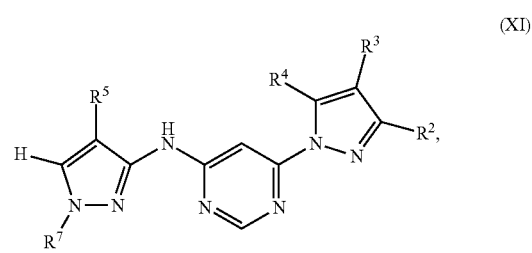

(XI)

wherein $R^2$, $R^3$, $R^4$, $R^5$ and $R^7$ are as defined for the compound of formula (I) as defined supra,
reacting the compound of formula (XI) in the presence of a suitable base and in the presence of a suitable palladium catalyst with a compound of formula (XII),

(XII)

wherein R⁶ is as defined for the compound of formula (I) as defined supra, and
X is chlorine, bromine, iodine or triflate,
thereby giving a compound of formula (I-A),

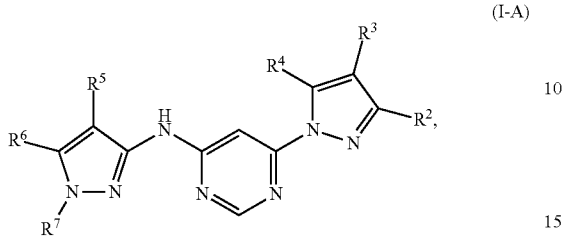

(I-A)

wherein R², R³, R⁴, R⁵, R⁶ and R⁷ are as defined for the compound of formula (I) as defined supra,
then optionally converting said compound of formula (I-A) a solvate, a salt, or a solvate of the salt thereof using the corresponding (i) solvents and/or (ii) bases or acids.

6. A method for treatment of a disease or condition associated with soft tissue calcification, comprising administering to a patient in need thereof an effective amount of at least one compound of formula (I) according to claim 1.

7. A pharmaceutical composition comprising a compound of the formula (I) as defined in any of claim 1 in combination with an inert, non-toxic, pharmaceutically suitable auxiliary.

8. A pharmaceutical combination comprising a compound of the formula (I) as defined in claim 1 in combination with a further active compound selected from the group consisting of the hypotensive active compounds, of the antiinflammatory agents/immunosuppressive agents, the phosphate binders, the sodium-phosphate co-transporters, NHE3 inhibitors, antiarrhythmic agents, agents that alter lipid metabolism and the active compounds which modulate vitamin D metabolism.

9. A method for treatment of a cardiovascular or renal disorder, comprising administering to a patient in need thereof an effective amount of a pharmaceutical composition according to claim 7, wherein the cardiovascular or renal disorder is a disease or condition associated with soft tissue calcification.

10. A method for treatment of a cardiovascular or renal disorder, comprising administering to a patient in need thereof an effective amount of a pharmaceutical combination according to claim 8, wherein the cardiovascular or renal disorder is a disease or condition associated with soft tissue calcification.

11. The method of claim 6, wherein the disease or condition associated with soft tissue calcification is selected from the group consisting of chronic kidney disease associated calcification, non-chronic kidney disease associated calcification, and chronic renal disease.

12. The method of claim 9, wherein the disease or condition associated with soft tissue calcification is selected from the group consisting of chronic kidney disease associated calcification and non-chronic kidney disease associated calcification, and chronic renal disease.

13. The method of claim 10, wherein the disease or condition associated with soft tissue calcification is selected from the group consisting of chronic kidney disease associated calcification, non-chronic kidney disease associated calcification, and chronic renal disease.

14. The compound of claim 1, wherein the compound is

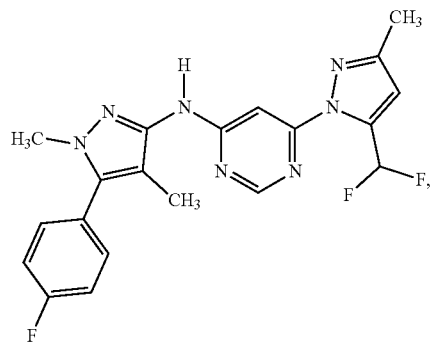 [SMILES: Cc1cc(C(F)F)n(-c2cc(Nc3nn(C)c(-c4ccc(F)cc4)c3C)ncn2)n1]

or a stereoisomer, a tautomer, an N-oxide, a hydrate, a solvate, or a salt thereof, or a mixture of same.

15. The compound of claim 1, wherein the compound is

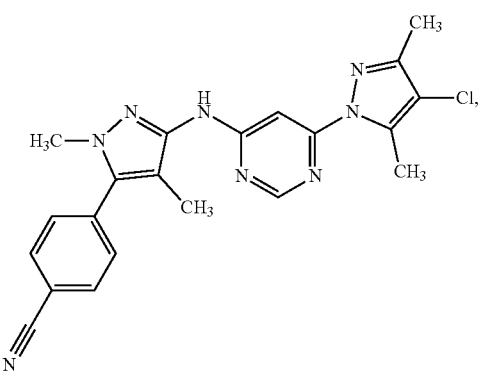 [SMILES: Cc1nn(-c2cc(Nc3nn(C)c(-c4ccc(C#N)cc4)c3C)ncn2)c(C)c1Cl]

or a stereoisomer, a tautomer, an N-oxide, a hydrate, a solvate, or a salt thereof, or a mixture of same.

16. The compound of claim 1, wherein the compound is

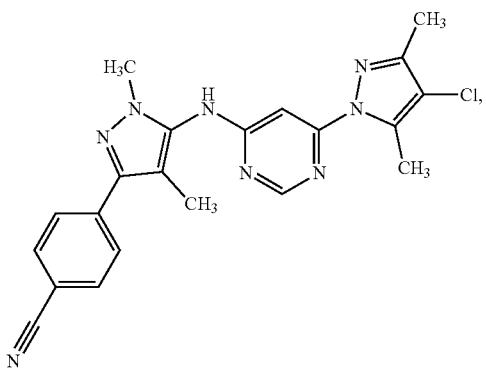 [SMILES: Cc1nn(-c2cc(Nc3c(C)c(-c4ccc(C#N)cc4)nn3C)ncn2)c(C)c1Cl]

or a stereoisomer, a tautomer, an N-oxide, a hydrate, a solvate, or a salt thereof, or a mixture of same.

17. The compound of claim 1, wherein the compound is
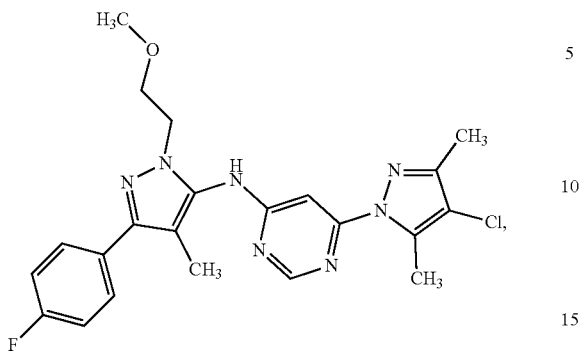
or a stereoisomer, a tautomer, an N-oxide, a hydrate, a solvate, or a salt thereof, or a mixture of same.
* * * * *